US010968230B2

(12) United States Patent
Cha et al.

(10) Patent No.: US 10,968,230 B2
(45) Date of Patent: Apr. 6, 2021

(54) SPIRO-STRUCTURED COMPOUND AND ORGANIC ELECTRONIC DEVICE COMPRISING SAME

(71) Applicant: LG Chem, Ltd., Seoul (KR)

(72) Inventors: Yongbum Cha, Daejeon (KR); Sung Kil Hong, Daejeon (KR); Jungbum Kim, Daejeon (KR); Dong Uk Heo, Daejeon (KR); Sung Jae Lee, Daejeon (KR)

(73) Assignee: LG Chem, Ltd.

( * ) Notice: Subject to any disclaimer, the term of this patent is extended or adjusted under 35 U.S.C. 154(b) by 286 days.

(21) Appl. No.: 16/069,694

(22) PCT Filed: Jan. 26, 2017

(86) PCT No.: PCT/KR2017/000982
§ 371 (c)(1),
(2) Date: Jul. 12, 2018

(87) PCT Pub. No.: WO2017/131483
PCT Pub. Date: Aug. 3, 2017

(65) Prior Publication Data
US 2019/0010164 A1    Jan. 10, 2019

(30) Foreign Application Priority Data
Jan. 27, 2016 (KR) .......................... 10-2016-0010112

(51) Int. Cl.
*H01L 51/50* (2006.01)
*C07D 491/052* (2006.01)
(Continued)

(52) U.S. Cl.
CPC ....... *C07D 491/052* (2013.01); *C07D 209/82* (2013.01); *C07D 405/04* (2013.01);
(Continued)

(58) Field of Classification Search
None
See application file for complete search history.

(56) References Cited

U.S. PATENT DOCUMENTS

2002/0172420 A1    11/2002   Nicolas
2006/0286405 A1*  12/2006   Begley ............... H05B 33/14
                                                              428/690
(Continued)

FOREIGN PATENT DOCUMENTS

EP    2902463 A1    8/2015
EP    3305764 A2    4/2018
(Continued)

OTHER PUBLICATIONS

Bhanuchandra et al., Synthesis of Spirocyclic Diarylfluorenes by One-Pot Twofold SNAr Reactions of Diaryl Sulfones with Diarylmethanes; Organic Letters (2016), 18(3), 384-387 (Year: 2016).*

(Continued)

*Primary Examiner* — Gregory D Clark
(74) *Attorney, Agent, or Firm* — Lerner, David, Littenberg, Krumholz & Mentlik, LLP

(57) ABSTRACT

The present specification relates to a spiro compound and an organic electronic device including the same.

19 Claims, 1 Drawing Sheet

(51) Int. Cl.
  *H01L 51/00*  (2006.01)
  *C07D 209/82* (2006.01)
  *C09K 11/06*  (2006.01)
  *C07D 405/04* (2006.01)
  *C07D 407/04* (2006.01)
  *C07D 409/04* (2006.01)
  *C07D 493/04* (2006.01)
  *C07D 495/04* (2006.01)

(52) U.S. Cl.
  CPC ......... *C07D 407/04* (2013.01); *C07D 409/04* (2013.01); *C07D 493/04* (2013.01); *C07D 495/04* (2013.01); *C09K 11/06* (2013.01); *H01L 51/00* (2013.01); *H01L 51/0039* (2013.01); *H01L 51/0067* (2013.01); *H01L 51/0071* (2013.01); *H01L 51/0072* (2013.01); *H01L 51/0073* (2013.01); *H01L 51/0074* (2013.01); *H01L 51/50* (2013.01); *H01L 51/5012* (2013.01); *H01L 51/5016* (2013.01); *H01L 51/5056* (2013.01); *H01L 51/5072* (2013.01); *H01L 51/5096* (2013.01)

(56) References Cited

U.S. PATENT DOCUMENTS

| | | | |
|---|---|---|---|
| 2007/0018569 A1* | 1/2007 | Kawamura | H05B 33/14 313/504 |
| 2014/0027757 A1* | 1/2014 | Yamada | H01L 51/0073 257/40 |
| 2014/0225040 A1 | 8/2014 | Parham et al. | |
| 2015/0137111 A1 | 5/2015 | Ryu et al. | |
| 2017/0217992 A1 | 8/2017 | Jun et al. | |
| 2018/0148640 A1 | 5/2018 | Cha et al. | |

FOREIGN PATENT DOCUMENTS

| | | |
|---|---|---|
| JP | 2012229195 A | 11/2012 |
| JP | 2014527522 A | 10/2014 |
| JP | 2017523970 A | 8/2017 |
| JP | 2018518471 A | 7/2018 |
| KR | 20030012890 A | 2/2003 |
| KR | 20110084508 A | 7/2011 |
| KR | 20130140303 A | 12/2013 |
| KR | 20140054132 A | 5/2014 |
| KR | 20150010016 A | 1/2015 |
| KR | 20170016703 A | 2/2017 |
| WO | 2010047551 A2 | 4/2010 |
| WO | 2014051232 A1 | 4/2014 |
| WO | 2015009076 A1 | 1/2015 |
| WO | 2016021989 A1 | 2/2016 |

OTHER PUBLICATIONS

Search report from International Application No. PCT/KR2017/000982, dated May 11, 2017.
Bhanuchandra, M. et. al, "Synthesis of Spirocyclic Diarylfluorenes by One-Pot Twofold SNAr Reactions of Diaryl Sulfones with Diarylmethanes." Organic Letters, Jan. 8, 2016, vol. 18, No. 3, pp. 384-387.
Chemical Abstract Compound, STN express, RNs 1975175-35-9, 1975175-280, 1975174-94-7, 1975174-17-4, 1975173-92-2, 1975173-90-0 (Entered Aug. 18, 2016).
Extended European Search Report including Written Opinion for Application No. EP17744604.4 dated Dec. 7, 2018.

* cited by examiner

[Figure 1]
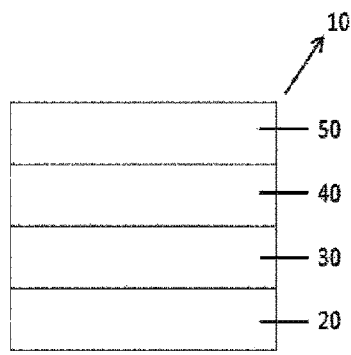
[Figure 2]
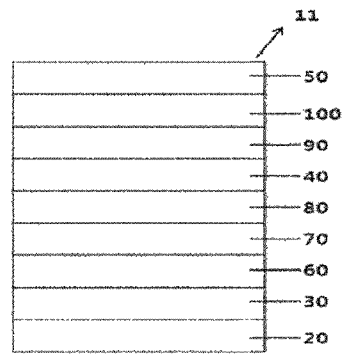

SPIRO-STRUCTURED COMPOUND AND ORGANIC ELECTRONIC DEVICE COMPRISING SAME

CROSS-REFERENCE TO RELATED APPLICATIONS

The present application is a national phase entry under 35 U.S.C. § 371 of International Application No. PCT/KR2017/000982 filed on Jan. 26, 2017, which claims priority from Korean Patent Application No. 10-2016-0010112 filed in the Korean Intellectual Property Office on Jan. 27, 2016, the entire contents of which are incorporated herein by reference.

TECHNICAL FIELD

The present specification relates to a spiro compound and an organic electronic device including the same.

BACKGROUND ART

Representative examples of an organic electronic device include an organic light emitting device. In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

International Publication No. 2003-012890

DISCLOSURE

Technical Problem

The present specification has been made in an effort to provide a spiro compound and an organic electronic device including the same.

Technical Solution

The present specification provides a spiro compound represented by the following Chemical Formula 1.

[Chemical Formula 1]

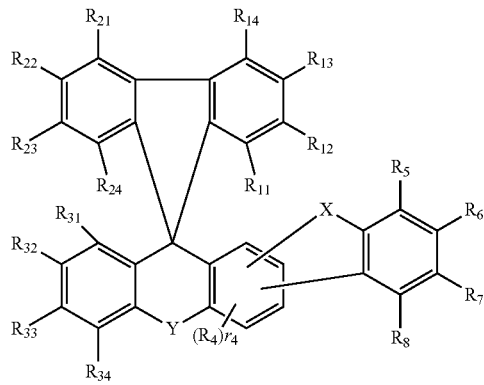

In Chemical Formula 1,
X is $NR_9$, O, S or $CR_{101}R_{102}$,
Y is O, S, $CR_{103}R_{104}$ or $SiR_{105}R_{106}$,
$R_9$ is $-L_1Ar_1$,
$L_1$ is a direct bond; a substituted or unsubstituted arylene group; or a substituted or unsubstituted heteroarylene group,
$R_4$ to $R_8$, $R_{11}$ to $R_{14}$, $R_{21}$ to $R_{24}$, $R_{31}$ to $R_{34}$, $R_{101}$ to $R_{106}$, and $Ar_1$ are the same as or different from each other, and are each independently hydrogen; deuterium; a halogen group; a cyano group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted amine group; a substituted or unsubstituted alkylamine group; a substituted or unsubstituted arylamine group; a substituted or unsubstituted heteroarylamine group; a substituted or unsubstituted phosphine oxide group; a substituted or unsubstituted aryl group; or a substituted or unsubstituted heteroaryl group, or may be bonded to an adjacent group to form a ring,
$r_4$ is an integer of 1 or 2, and
when $r_4$ is 2, $R_4$s are the same as or different from each other.

Further, the present specification provides an organic electronic device including: a first electrode; a second electrode disposed to face the first electrode; and an organic material layer having one or more layers disposed between the first electrode and the second electrode, in which one or more layers of the organic material layer include the above-described spiro compound.

Advantageous Effects

The spiro compound according to an exemplary embodiment of the present specification is used for an organic electronic device including an organic light emitting device, and thus may lower the driving voltage of the organic electronic device and improve the light efficiency thereof, and enhance service life characteristics of the device due to thermal stability of the compound.

DESCRIPTION OF DRAWINGS

FIG. 1 illustrates an organic light emitting device 10 according to an exemplary embodiment of the present specification.

FIG. 2 illustrates an organic light emitting device 11 according to another exemplary embodiment of the present specification.

MODE FOR INVENTION

Hereinafter, the present specification will be described in more detail.

The present specification provides the spiro compound represented by Chemical Formula 1.

The spiro compound of Chemical Formula 1 may have characteristics suitable for use in an organic material layer used in an organic light emitting device by introducing various substitutes into a core structure.

Examples of the substituents in the present specification will be described below, but are not limited thereto.

In the present specification,

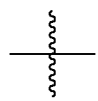

means a moiety to be linked.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group; a nitro group; a hydroxy group; a carbonyl group; an ester group; an imide group; an amino group; an alkyl group; a cycloalkyl group; an alkenyl group; an amine group; a phosphine oxide group; an aryl group; a silyl group; and a heterocyclic group including one or more of N, O, S, Se, and Si atoms, being substituted with a substituent to which two or more substituents among the substituents exemplified are linked, or having no substituent.

In the present specification, the number of carbon atoms of a carbonyl group is not particularly limited, but is preferably 1 to 50. Specifically, the carbonyl group may be a compound having the following structures, but is not limited thereto.

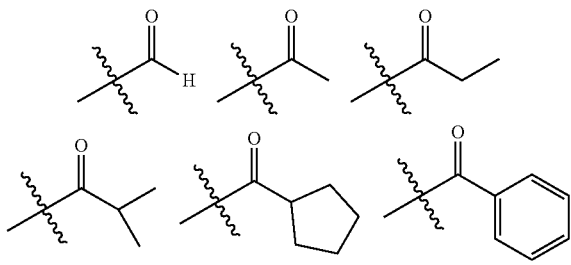

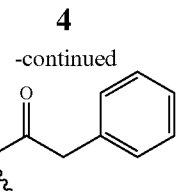

In the present specification, the number of carbon atoms of an ester group is not particularly limited, but is preferably 1 to 50. Specifically, the ester group may be a compound having the following structural formulae, but is not limited thereto.

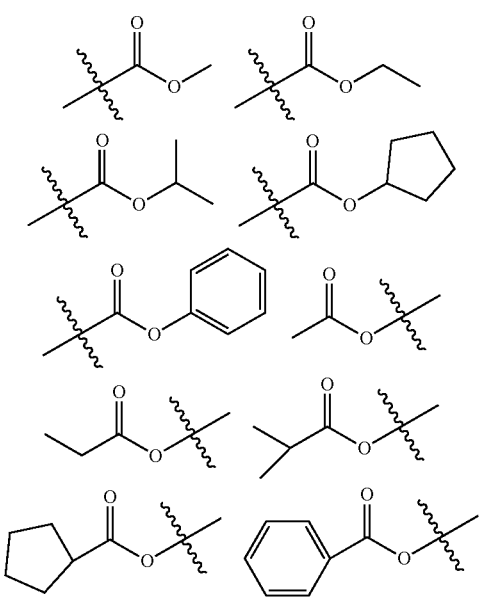

In the present specification, the number of carbon atoms of an imide group is not particularly limited, but is preferably 1 to 50. Specifically, the imide group may be a compound having the following structures, but is not limited thereto.

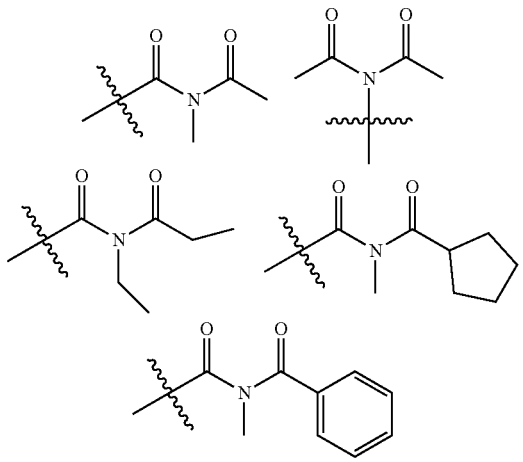

In the present specification, for an amino group, the nitrogen of the amino group may be substituted with hydrogen, a straight, branched, or cyclic alkyl group having 1 to 30 carbon atoms, or an aryl group having 6 to 30 carbon atoms. Specifically, the amino group may be a compound having the following structural formulae, but is not limited thereto.

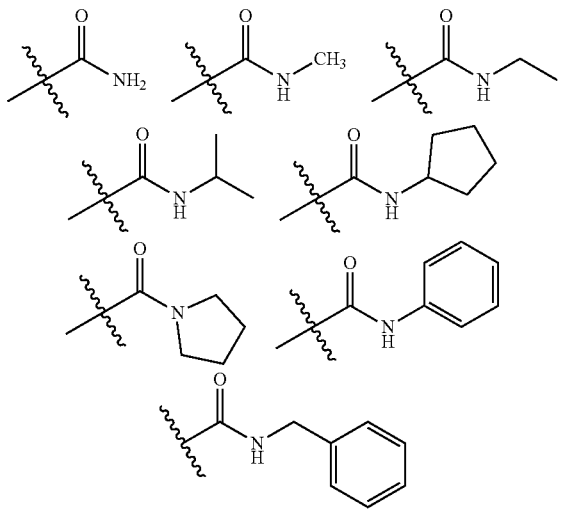

In the present specification, an alkyl group may be straight or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an alkoxy group may be straight, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, an alkenyl group may be straight or branched, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a silyl group includes Si and is a substituent to which the Si atom is directly linked as a radical, and is represented by $-SiR_{201}R_{202}R_{203}$, and $R_{201}$ to $R_{203}$ are the same as or different from each other, and may be each independently a substituent composed of at least one of hydrogen; deuterium; a halogen group; an alkyl group; an alkenyl group; an alkoxy group; a cycloalkyl group; an aryl group; and a heterocyclic group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be $-BR_{204}R_{205}$, and $R_{204}$ and $R_{205}$ are the same as or different from each other, and may be each independently selected from the group consisting of hydrogen; deuterium; halogen; a substituted or unsubstituted monocyclic or polycyclic cycloalkyl group having 3 to 30 carbon atoms; a substituted or unsubstituted straight or branched alkyl group having 1 to 30 carbon atoms; a substituted or unsubstituted monocyclic or polycyclic aryl group having 6 to 30 carbon atoms; and a substituted or unsubstituted monocyclic or polycyclic heterocyclic group having 2 to 30 carbon atoms.

In the present specification, when an aryl group is a monocyclic aryl group, the number of carbon atoms thereof is not particularly limited, but is preferably 6 to 50. Specific examples of the monocyclic aryl group include a phenyl group, a biphenyl group, a terphenyl group, a quarterphenyl group, and the like, but are not limited thereto.

When the aryl group is a polycyclic aryl group, the number of carbon atoms thereof is not particularly limited, but is preferably 10 to 50. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may be bonded to each other to form a ring.

When the fluorenyl group is substituted, the group may be

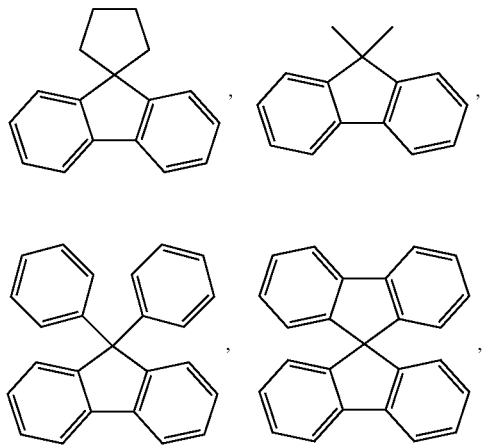

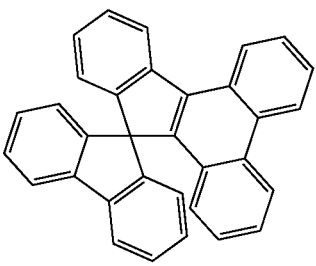

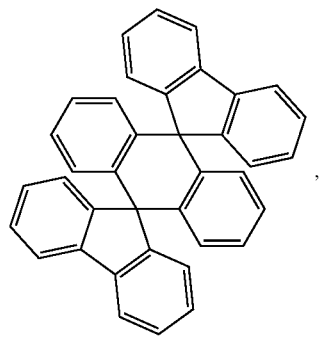

and the like, but is not limited thereto.

In the present specification, a heteroaryl group is a heterocyclic group including one or more of N, O, S, Si, and Se as a heteroatom, and the number of carbon atoms thereof is not particularly limited, but is preferably 2 to 60. Examples of the heteroaryl group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a dibenzofuranyl group, and the like, but are not limited thereto.

In the present specification, the fused structure may be a structure in which an aromatic hydrocarbon ring is fused with the corresponding substituent. Examples of a fused ring of benzimidazole include

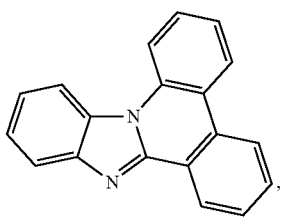

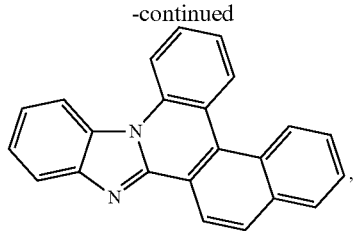

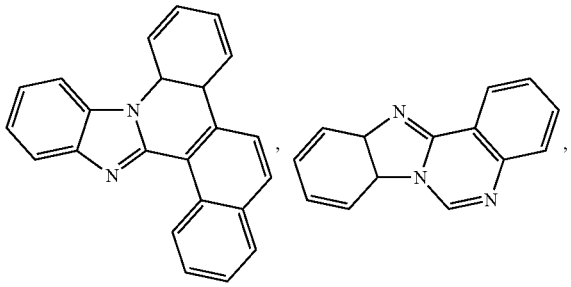

and the like, but are not limited thereto.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the case where adjacent groups are bonded to each other to form a ring means that adjacent groups are bonded to each other to form a 5-membered to 8-membered hydrocarbon ring or a 5-membered to 8-membered hetero ring as described above, and the ring may be monocyclic or polycyclic, may be an aliphatic ring, an aromatic ring, or a fused form thereof, and is not limited thereto.

In the present specification, a hydrocarbon ring or a hetero ring may be selected among the above-described examples of the cycloalkyl group, the aryl group, or the heteroaryl group, except for being a monovalent group, and the hydrocarbon ring or the hetero ring may be monocyclic or polycyclic, an aliphatic ring or an aromatic ring or a fused form thereof, but is not limited thereto.

In the present specification, an amine group means a monovalent amine in which at least one hydrogen atom of an amino group (—NH$_2$) is substituted with another substitute, and is represented by —NR$_{107}$R$_{108}$, and R$_{107}$ and R$_{108}$ are the same as or different from each other, and may be each independently a substituent composed of at least one among hydrogen; deuterium; a halogen group; an alkyl group; an alkenyl group; an alkoxy group; a cycloalkyl group; an aryl group; and a heterocyclic group (however, at least one of R$_{107}$ and R$_{108}$ is not hydrogen). For example, the amine group may be selected from the group consisting of —NH$_2$; a monoalkylamine group; a dialkylamine group; an N-alkylarylamine group; a monoarylamine group; a diarylamine group; an N-arylheteroarylamine group; an N-alkylheteroarylamine group, a monoheteroarylamine group, and a diheteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group, and the like, but are not limited thereto.

In the present specification, specific examples of a phosphine oxide group include a diphenylphosphine oxide group, dinaphthylphosphine oxide group, and the like, but are not limited thereto.

In the present specification, the aryl group in the aryloxy group, the arylthioxy group, the arylsulfoxy group, the N-arylalkylamine group, and the N-arylheteroarylamine group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthracenyloxy group, a 2-anthracenyloxy group, a 9-anthracenyloxy group, a 1-phenanthryloxy group, a 3-phenanthryloxy group, a 9-phenanthryloxy group, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples thereof are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group. For example, the aryl group in the arylamine group may be selected from the above-described examples of the aryl group.

In the present specification, examples of a heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include a monocyclic heteroaryl group, a polycyclic heteroaryl group, or both a monocyclic heteroaryl group and a polycyclic heteroaryl group. For example, the heteroaryl group in the heteroarylamine group may be selected from the above-described examples of the heteroaryl group.

In the present specification, an aromatic ring group may be monocyclic or polycyclic, and may be selected from the examples of the aryl group, except for the aromatic ring group which is not monovalent.

In the present specification, a divalent to tetravalent aromatic ring group may be monocyclic or polycyclic, and means a group having two to four bonding positions in the aryl group, that is, a divalent to tetravalent group. The above-described description on the aryl group may be applied to the aromatic ring group, except for a divalent to tetravalent aromatic ring group In the present specification, an arylene group means a group having two bonding positions in an aryl group, that is, a divalent group. The above-described description on the aryl group may be applied to the arylene group, except for a divalent arylene group.

In the present specification, the heteroarylene group means a group having two bonding positions in a heteroaryl group, that is, a divalent group. The above-described description on the heteroaryl group may be applied to the heteroarylene group, except for a divalent heteroarylene group.

In an exemplary embodiment of the present specification, X is $NR_9$, O, S, or $CR_{101}R_{102}$.

In an exemplary embodiment of the present specification, X is $NR_9$.

In an exemplary embodiment of the present specification, X is O.

In an exemplary embodiment of the present specification, X is S.

In an exemplary embodiment of the present specification, X is $CR_{101}R_{102}$.

In an exemplary embodiment of the present specification, Y is O, S, $CR_{103}R_{104}$, or $SiR_{105}R_{106}$.

In an exemplary embodiment of the present specification, Y is O.

In an exemplary embodiment of the present specification, Y is S.

In an exemplary embodiment of the present specification, Y is $CR_{103}R_{104}$.

In an exemplary embodiment of the present specification, Y is $SiR_{105}R_{106}$.

In an exemplary embodiment of the present specification, $R_9$ is $-L_1Ar_1$.

In an exemplary embodiment of the present invention, $L_1$ is a direct bond; a substituted or unsubstituted arylene group; or a substituted or unsubstituted heteroarylene group.

In an exemplary embodiment of the present specification, $L_1$ is a direct bond.

In an exemplary embodiment of the present specification, $L_1$ is a substituted or unsubstituted arylene group.

In an exemplary embodiment of the present specification, $L_1$ is a substituted or unsubstituted phenylene group, a substituted or unsubstituted biphenylene group, a substituted or unsubstituted naphthylene group, a substituted or unsubstituted terphenylene group, a substituted or unsubstituted phenanthrylene group, a substituted or unsubstituted triphenylene group, or a substituted or unsubstituted fluorenylene group.

In an exemplary embodiment of the present specification, $L_1$ is a phenylene group.

In an exemplary embodiment of the present specification, $L_1$ is a biphenylene group.

In an exemplary embodiment of the present specification, $L_1$ is a naphthylene group.

In an exemplary embodiment of the present specification, $L_1$ is a terphenylene group.

In an exemplary embodiment of the present specification, $L_1$ is a substituted or unsubstituted heteroarylene group.

In an exemplary embodiment of the present specification, $L_1$ is a substituted or unsubstituted divalent pyridine group, a substituted or unsubstituted divalent pyrimidine group, a substituted or unsubstituted divalent triazine group, a substituted or unsubstituted divalent carbazole group, a substituted or unsubstituted divalent dibenzocarbazole group, a substituted or unsubstituted divalent dibenzothiophene group, a substituted or unsubstituted divalent dibenzofuran group, a substituted or unsubstituted divalent quinoline group, a substituted or unsubstituted divalent quinazoline group, or a substituted or unsubstituted divalent quinoxaline group.

In an exemplary embodiment of the present specification, $L_1$ is a divalent pyridine group, a divalent pyrimidine group, a divalent triazine group, a divalent carbazole group, a divalent dibenzocarbazole group, a divalent dibenzothiophene group, a divalent dibenzofuran group, a divalent quinoline group, a divalent quinazoline group, or a divalent quinoxaline group.

In an exemplary embodiment of the present specification, $L_1$ is a substituted or unsubstituted divalent

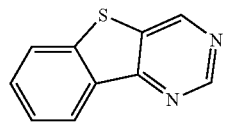 [SMILES: c1ccc2c(c1)sc1cncnc12]

or a substituted unsubstituted divalent

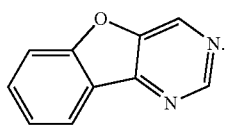 [SMILES: c1ccc2c(c1)oc1cncnc12]

In an exemplary embodiment of the present specification, $R_4$ to $R_8$, $R_{11}$ to $R_{14}$, $R_{21}$ to $R_{24}$, $R_{31}$ to $R_{34}$, $R_{101}$ to $R_{106}$, and $Ar_1$ are the same as or different from each other, and are each independently hydrogen; deuterium; a halogen group; a cyano group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted amine group; a substituted or unsubstituted alkylamine group; a substituted or unsubstituted arylamine group; a substituted or unsubstituted heteroarylamine group; a substituted or unsubstituted phosphine oxide group; a substituted or unsubstituted aryl group; or a substituted or unsubstituted heteroaryl group, or may be bonded to an adjacent group to form a ring.

In an exemplary embodiment of the present specification, $Ar_1$ is an unsubstituted aryl group having 6 to 50 carbon atoms.

In an exemplary embodiment of the present specification, $Ar_1$ is a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthryl group, a substituted or unsubstituted triphenyl group, or a substituted or unsubstituted fluorenyl group.

In an exemplary embodiment of the present specification, $Ar_1$ is a halogen group, a cyano group, an alkyl group, or a phenyl group which is unsubstituted or substituted with an aryl group.

In an exemplary embodiment of the present specification, $Ar_1$ is a halogen group, a cyano group, a methyl group, an ethyl group, a tert-butyl group, an isopropyl group, a phenyl group, a biphenyl group, or a phenyl group which is unsubstituted or substituted with a naphthyl group.

In an exemplary embodiment of the present specification, $Ar_1$ is a phenyl group.

In an exemplary embodiment of the present specification, $Ar_1$ is a halogen group, a cyano group, an alkyl group, or a biphenyl group which is unsubstituted or substituted with an aryl group.

In an exemplary embodiment of the present specification, $Ar_1$ is a halogen group, a cyano group, a methyl group, an ethyl group, a tert-butyl group, an isopropyl group, a phenyl group, a biphenyl group, or a biphenyl group which is unsubstituted or substituted with a naphthyl group.

In an exemplary embodiment of the present specification, $Ar_1$ is a biphenyl group.

In an exemplary embodiment of the present specification, $Ar_1$ is a halogen group, a cyano group, an alkyl group, or a terphenyl group which is unsubstituted or substituted with an aryl group.

In an exemplary embodiment of the present specification, $Ar_1$ is a halogen group, a cyano group, a methyl group, an ethyl group, a tert-butyl group, an isopropyl group, a phenyl group, a biphenyl group, or a terphenyl group which is unsubstituted or substituted with a naphthyl group.

In an exemplary embodiment of the present specification, $Ar_1$ is a terphenyl group.

In an exemplary embodiment of the present specification, $Ar_1$ is a halogen group, a cyano group, an alkyl group, or a naphthyl group which is unsubstituted or substituted with an aryl group.

In an exemplary embodiment of the present specification, $Ar_1$ is a halogen group, a cyano group, a methyl group, an ethyl group, a tert-butyl group, an isopropyl group, a phenyl group, a biphenyl group, or a naphthyl group which is unsubstituted or substituted with a naphthyl group.

In an exemplary embodiment of the present specification, $Ar_1$ is a naphthyl group.

In an exemplary embodiment of the present specification, $Ar_1$ is a halogen group, a cyano group, an alkyl group, or a triphenyl group which is unsubstituted or substituted with an aryl group.

In an exemplary embodiment of the present specification, $Ar_1$ is a halogen group, a cyano group, a methyl group, an ethyl group, a tert-butyl group, an isopropyl group, a phenyl group, a biphenyl group, or a triphenyl group which is unsubstituted or substituted with a naphthyl group.

In an exemplary embodiment of the present specification, $Ar_1$ is a triphenyl group.

In an exemplary embodiment of the present specification, $Ar_1$ is a halogen group, a cyano group, an alkyl group, or a fluorenyl group which is unsubstituted or substituted with an aryl group.

In an exemplary embodiment of the present specification, $Ar_1$ is a halogen group, a cyano group, a methyl group, an ethyl group, a tert-butyl group, an isopropyl group, a phenyl group, a biphenyl group, or a fluorenyl group which is unsubstituted or substituted with a naphthyl group.

In an exemplary embodiment of the present specification, $Ar_1$ is a fluorenyl group.

In an exemplary embodiment of the present specification, $Ar_1$ is a substituted or unsubstituted heteroaryl group having 6 to 50 carbon atoms.

In an exemplary embodiment of the present specification, $Ar_1$ is a substituted or unsubstituted pyridine group, a substituted or unsubstituted pyrimidine group, a substituted or unsubstituted triazine group, a substituted or unsubstituted carbazole group, a substituted or unsubstituted dibenzocarbazole group, a substituted or unsubstituted dibenzofuran group, a substituted or unsubstituted dibenzothiophene group, a substituted or unsubstituted quinoline group, a substituted or unsubstituted quinazoline group, or a substituted or unsubstituted quinoxaline group.

In an exemplary embodiment of the present specification, $Ar_1$ is a substituted or unsubstituted pyridine group.

In an exemplary embodiment of the present specification, $Ar_1$ is a phenyl group, a biphenyl group, a terphenyl group, a naphthyl group, a triphenyl group, a phenanthryl group, or a pyridine group in which a fluorenyl group is substituted or unsubstituted.

In an exemplary embodiment of the present specification, $Ar_1$ is a pyridine group.

In an exemplary embodiment of the present specification, $Ar_1$ is a pyrimidine group in which an aryl group is substituted or unsubstituted.

In an exemplary embodiment of the present specification, $Ar_1$ is a phenyl group, a biphenyl group, a terphenyl group, a naphthyl group, a triphenyl group, a phenanthryl group, or a pyrimidine group in which a fluorenyl group is substituted or unsubstituted.

In an exemplary embodiment of the present specification, $Ar_1$ is a pyrimidine group.

In an exemplary embodiment of the present specification, $Ar_1$ is a triazine group in which an aryl group is substituted or unsubstituted.

In an exemplary embodiment of the present specification, $Ar_1$ is a phenyl group, a biphenyl group, a terphenyl group, a naphthyl group, a triphenyl group, a phenanthryl group, or a triazine group in which a fluorenyl group is substituted or unsubstituted.

In an exemplary embodiment of the present specification, $Ar_1$ is a triazine group.

In an exemplary embodiment of the present specification, $Ar_1$ is a carbazole group in which an aryl group is substituted or unsubstituted.

In an exemplary embodiment of the present specification, $Ar_1$ is a phenyl group, a biphenyl group, a terphenyl group, a naphthyl group, a triphenyl group, a phenanthryl group, or a carbazole group in which a fluorenyl group is substituted or unsubstituted.

In an exemplary embodiment of the present specification, $Ar_1$ is a carbazole group.

In an exemplary embodiment of the present specification, $Ar_1$ is a dibenzocarbazole group in which an aryl group is substituted or unsubstituted.

In an exemplary embodiment of the present specification, $Ar_1$ is a phenyl group, a biphenyl group, a terphenyl group, a naphthyl group, a triphenyl group, a phenanthryl group, or a dibenzocarbazole group in which a fluorenyl group is substituted or unsubstituted.

In an exemplary embodiment of the present specification, $Ar_1$ is a dibenzocarbazole group.

In an exemplary embodiment of the present specification, $Ar_1$ is a dibenzothiophene group in which an aryl group is substituted or unsubstituted.

In an exemplary embodiment of the present specification, $Ar_1$ is a phenyl group, a biphenyl group, a terphenyl group, a naphthyl group, a triphenyl group, a phenanthryl group, or a dibenzothiophene group in which a fluorenyl group is substituted or unsubstituted.

In an exemplary embodiment of the present specification, $Ar_1$ is a dibenzothiophene group.

In an exemplary embodiment of the present specification, $Ar_1$ is a dibenzofuran group in which an aryl group is substituted or unsubstituted.

In an exemplary embodiment of the present specification, $Ar_1$ is a phenyl group, a biphenyl group, a terphenyl group, a naphthyl group, a triphenyl group, a phenanthryl group, or a dibenzofuran group in which a fluorenyl group is substituted or unsubstituted.

In an exemplary embodiment of the present specification, $Ar_1$ is a dibenzofuran group.

In an exemplary embodiment of the present specification, $Ar_1$ is a quinoline group in which an aryl group is substituted or unsubstituted.

In an exemplary embodiment of the present specification, $Ar_1$ is a phenyl group, a biphenyl group, a terphenyl group, a naphthyl group, a triphenyl group, a phenanthryl group, or a quinoline group in which a fluorenyl group is substituted or unsubstituted.

In an exemplary embodiment of the present specification, $Ar_1$ is a quinoline group.

In an exemplary embodiment of the present specification, $Ar_1$ is a quinazoline group in which an aryl group is substituted or unsubstituted.

In an exemplary embodiment of the present specification, $Ar_1$ is a phenyl group, a biphenyl group, a terphenyl group, a naphthyl group, a triphenyl group, a phenanthryl group, or a quinazoline group in which a fluorenyl group is substituted or unsubstituted.

In an exemplary embodiment of the present specification, $Ar_1$ is a quinazoline group.

In an exemplary embodiment of the present specification, $Ar_1$ is a quinoxaline group in which an aryl group is substituted or unsubstituted.

In an exemplary embodiment of the present specification, $Ar_1$ is a phenyl group, a biphenyl group, a terphenyl group, a naphthyl group, a triphenyl group, a phenanthryl group, or a quinoxaline group in which a fluorenyl group is substituted or unsubstituted.

In an exemplary embodiment of the present specification, $Ar_1$ is a quinoxaline group.

In an exemplary embodiment of the present specification, $Ar_1$ is a substituted or unsubstituted or a substituted unsubstituted In an exemplary embodiment of the present specification, $Ar_1$ is in which an aryl group is substituted or unsubstituted.

In an exemplary embodiment of the present specification, $Ar_1$ is a phenyl group, a biphenyl group, a terphenyl group, a naphthyl group, a triphenyl group, a phenanthryl group, or

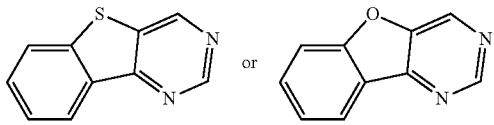 [SMILES: c1ccc2c(c1)sc1cncnc12 ; c1ccc2c(c1)oc1cncnc12]

in which a fluorenyl group is substituted or unsubstituted.

In an exemplary embodiment of the present specification, $Ar_1$ is

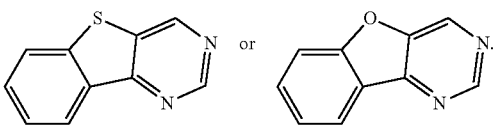 [SMILES: c1ccc2c(c1)sc1cncnc12 ; "or" ; c1ccc2c(c1)oc1cncnc12]

In an exemplary embodiment of the present specification, $Ar_1$ is a substituted or unsubstituted amine group having 6 to 40 carbon atoms.

In an exemplary embodiment of the present specification, $Ar_1$ is an amine group which is unsubstituted or substituted with an aryl group or a heteroaryl group.

In an exemplary embodiment of the present specification, $Ar_1$ is a phenyl group, a biphenyl group, a terphenyl group, a naphthyl group, a carbazole group, a dibenzothiophene group, or an amine group which is unsubstituted or substituted with a dibenzofuran group.

In an exemplary embodiment of the present specification, $Ar_1$ is a phosphine oxide group which is substituted or unsubstituted with an aryl group.

In an exemplary embodiment of the present specification, $Ar_1$ is a phenyl group, a biphenyl group, or a phosphine oxide group which is unsubstituted or substituted with a naphthyl group.

In an exemplary embodiment of the present specification, $Ar_1$ is a phosphine oxide group.

In an exemplary embodiment of the present specification, $Ar_1$ is a halogen group.

In an exemplary embodiment of the present specification, $Ar_1$ is a cyano group.

In an exemplary embodiment of the present specification, $Ar_1$ is a substituted or unsubstituted alkyl group having 1 to 30 carbon atoms.

In an exemplary embodiment of the present specification, $Ar_1$ is a substituted or unsubstituted methyl group, a substituted or unsubstituted ethyl group, a substituted or unsubstituted tert-butyl group, or a substituted or unsubstituted isopropyl group.

In an exemplary embodiment of the present specification, $Ar_1$ is a methyl group.

In an exemplary embodiment of the present specification, $Ar_1$ is an ethyl group.

In an exemplary embodiment of the present specification, $Ar_1$ is a tert-butyl group.

In an exemplary embodiment of the present specification, $Ar_1$ is an isopropyl group.

In an exemplary embodiment of the present specification, $R_4$ to $R_8$, $R_{11}$ to $R_{14}$, $R_{21}$ to $R_{24}$, $R_{31}$ to $R_{34}$, and $R_{101}$ to $R_{106}$ are the same as or different from each other, and are each independently an amine group having 6 to 30 carbon atoms.

In an exemplary embodiment of the present specification, $R_4$ to $R_8$, $R_{11}$ to $R_{14}$, $R_{21}$ to $R_{24}$, $R_{31}$ to $R_{34}$, and $R_{101}$ to $R_{106}$ are the same as or different from each other, and are each independently an amine group which is unsubstituted or substituted with an aryl group or a heteroaryl group.

In an exemplary embodiment of the present specification, $R_4$ to $R_8$, $R_{11}$ to $R_{14}$, $R_{21}$ to $R_{24}$, $R_{31}$ to $R_{34}$, and $R_{101}$ to $R_{106}$ are the same as or different from each other, and are each independently a phenyl group, a phenyl group substituted with a methyl group, a biphenyl group, a naphthyl group, a carbazole group, a dibenzothiophene group, or an amine group which is unsubstituted or substituted with a dibenzofuran group.

In an exemplary embodiment of the present specification, $R_{33}$ or $R_{23}$ is an amine group substituted with an aryl group or a heteroaryl group.

In an exemplary embodiment of the present specification, $R_{33}$ or $R_{23}$ is a phenyl group, a phenyl group substituted with a methyl group, a biphenyl group, a naphthyl group, a carbazole group, a dibenzothiophene group, or an amine group which is unsubstituted or substituted with a dibenzofuran group.

In an exemplary embodiment of the present specification, $R_4$ to $R_8$, $R_{11}$ to $R_{14}$, $R_{21}$ to $R_{24}$, $R_{31}$ to $R_{34}$, and $R_{101}$ to $R_{106}$ are the same as or different from each other, and are each independently a substituted or unsubstituted heteroaryl group having 6 to 50 carbon atoms.

In an exemplary embodiment of the present specification, $R_4$ to $R_8$, $R_{11}$ to $R_{14}$, $R_{21}$ to $R_{24}$, $R_{31}$ to $R_{34}$, and $R_{101}$ to $R_{106}$ are the same as or different from each other, and are each independently a substituted or unsubstituted pyridine group, a substituted or unsubstituted pyrimidine group, or a substituted or unsubstituted triazine group.

In an exemplary embodiment of the present specification, $R_4$ to $R_8$, $R_{11}$ to $R_{14}$, $R_{21}$ to $R_{24}$, $R_{31}$ to $R_{34}$, and $R_{101}$ to $R_{106}$ are the same as or different from each other, and are each independently a pyridine group in which an aryl group is substituted or unsubstituted.

In an exemplary embodiment of the present specification, $R_4$ to $R_8$, $R_{11}$ to $R_{14}$, $R_{21}$ to $R_{24}$, $R_{31}$ to $R_{34}$, and $R_{101}$ to $R_{106}$ are the same as or different from each other, and are each independently a pyridine group which is unsubstituted or substituted with a phenyl group or a biphenyl group.

In an exemplary embodiment of the present specification, $R_4$ to $R_8$, $R_{11}$ to $R_{14}$, $R_{21}$ to $R_{24}$, $R_{31}$ to $R_{34}$, and $R_{101}$ to $R_{106}$ are the same as or different from each other, and are each independently a pyrimidine group in which an aryl group is substituted or unsubstituted.

In an exemplary embodiment of the present specification, $R_4$ to $R_8$, $R_{11}$ to $R_{14}$, $R_{21}$ to $R_{24}$, $R_{31}$ to $R_{34}$, and $R_{101}$ to $R_{106}$ are the same as or different from each other, and are each independently a pyrimidine group which is unsubstituted or substituted with a phenyl group or a biphenyl group.

In an exemplary embodiment of the present specification, $R_4$ to $R_8$, $R_{11}$ to $R_{14}$, $R_{21}$ to $R_{24}$, $R_{31}$ to $R_{34}$, and $R_{101}$ to $R_{106}$ are the same as or different from each other, and are each independently a triazine group in which an aryl group is substituted or unsubstituted.

In an exemplary embodiment of the present specification, $R_4$ to $R_8$, $R_{11}$ to $R_{14}$, $R_{21}$ to $R_{24}$, $R_{31}$ to $R_{34}$, and $R_{101}$ to $R_{106}$ are the same as or different from each other, and are each independently a triazine group which is unsubstituted or substituted with a phenyl group or a biphenyl group.

In an exemplary embodiment of the present specification, $R_8$ is a substituted or unsubstituted pyridine group, a substituted or unsubstituted pyrimidine group, or a substituted or unsubstituted triazine group.

In an exemplary embodiment of the present specification, $R_8$ is a pyridine group which is unsubstituted or substituted with an aryl group.

In an exemplary embodiment of the present specification, $R_8$ is a pyridine group which is unsubstituted or substituted with a phenyl group or a biphenyl group.

In an exemplary embodiment of the present specification, $R_8$ is a pyrimidine group which is unsubstituted or substituted with an aryl group.

In an exemplary embodiment of the present specification, $R_8$ is a pyrimidine group which is unsubstituted or substituted with a phenyl group or a biphenyl group.

In an exemplary embodiment of the present specification, $R_8$ is a triazine group which is unsubstituted or substituted with an aryl group.

In an exemplary embodiment of the present specification, $R_8$ is a triazine group which is unsubstituted or substituted with a phenyl group or a biphenyl group.

In an exemplary embodiment of the present specification, $R_{101}$ to $R_{104}$ are the same as or different from each other, and are each independently a substituted or unsubstituted alkyl group.

In an exemplary embodiment of the present specification, $R_{101}$ to $R_{104}$ are the same as or different from each other, and are each independently a substituted or unsubstituted methyl group, a substituted or unsubstituted ethyl group, or a substituted or unsubstituted isopropyl group.

In an exemplary embodiment of the present specification, $R_{101}$ to $R_{104}$ are a methyl group.

In an exemplary embodiment of the present specification, $R_{101}$ to $R_{104}$ are an ethyl group.

In an exemplary embodiment of the present specification, $R_{101}$ to $R_{104}$ are an isopropyl group.

In an exemplary embodiment of the present specification, $R_{105}$ and $R_{106}$ are hydrogen.

In an exemplary embodiment of the present specification, $R_4$ to $R_8$, $R_{11}$ to $R_{14}$, $R_{21}$ to $R_{24}$, $R_{31}$ to $R_{34}$, and $R_{101}$ to $R_{106}$ are hydrogen.

In an exemplary embodiment of the present specification, Chemical Formula 1 may be represented by any one of the following Chemical Formulae 2 to 5.

[Chemical Formula 2]

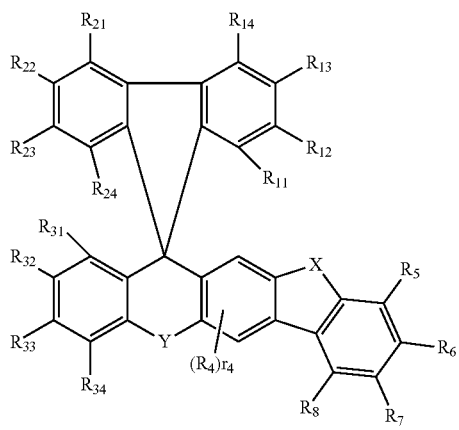

[Chemical Formula 3]

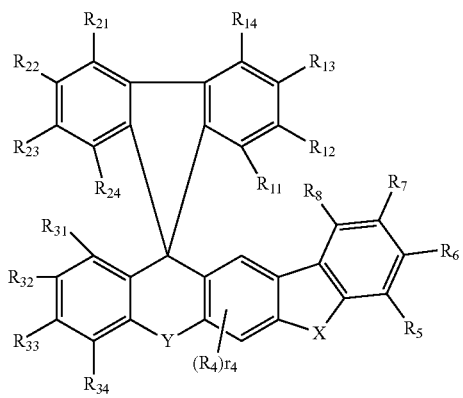

[Chemical Formula 4]

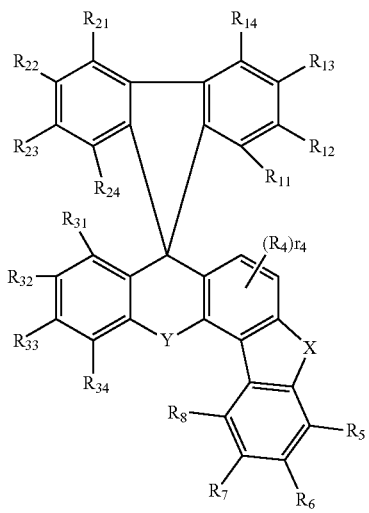

[Chemical Formula 5]

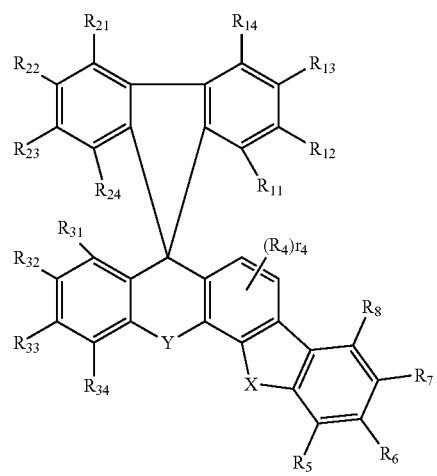

In Chemical Formulae 2 to 5, the definitions of X, Y, $R_4$ to $R_9$, $R_{11}$ to $R_{14}$, $R_{21}$ to $R_{24}$, $R_{31}$ to $R_{34}$, $R_{101}$ to $R_{106}$, and $r_4$ are the same as those defined in Chemical Formula 1.

In an exemplary embodiment of the present specification, Chemical Formula 1 may be represented by any one of the following Chemical Formulae 6 to 17.

[Chemical Formula 6]
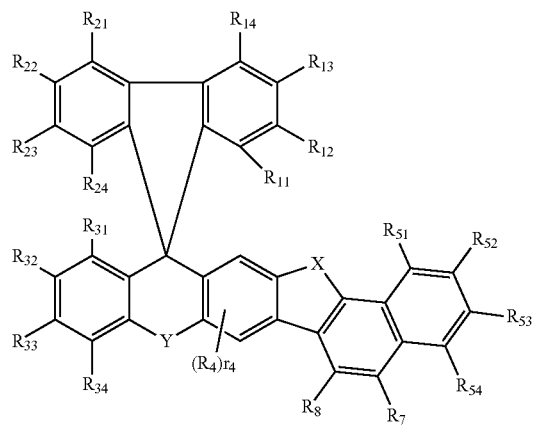
[Chemical Formula 7]
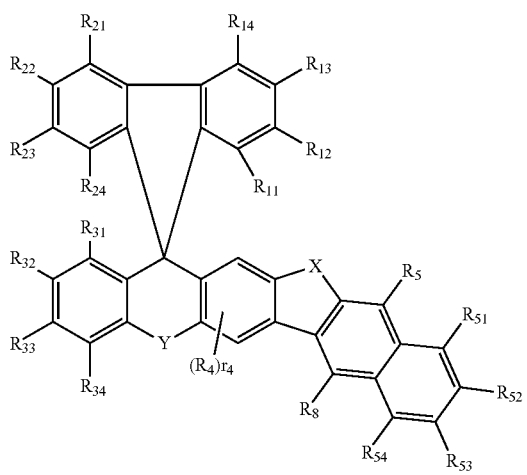
[Chemical Formula 8]
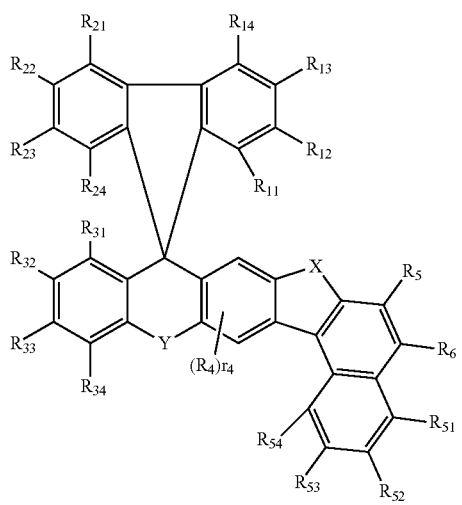
[Chemical Formula 9]
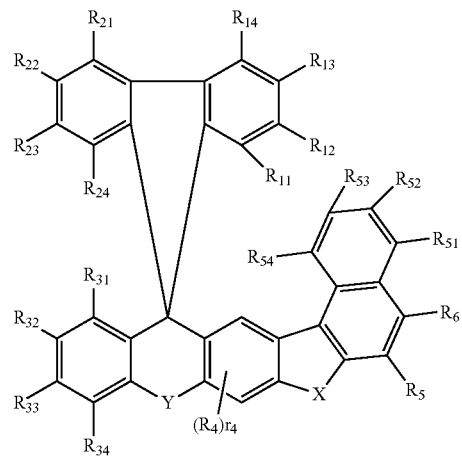
[Chemical Formula 10]
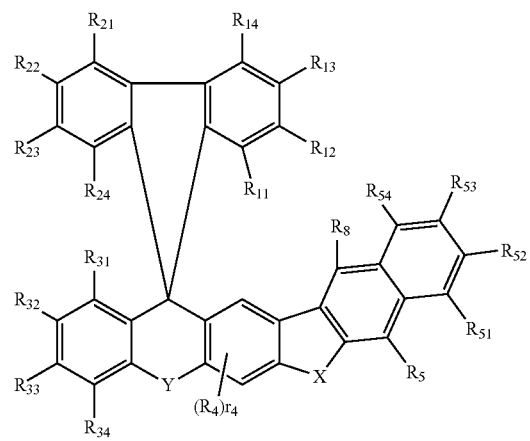
[Chemical Formula 11]
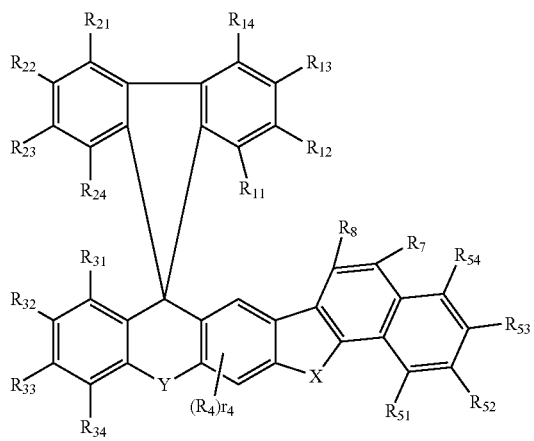

[Chemical Formula 12]
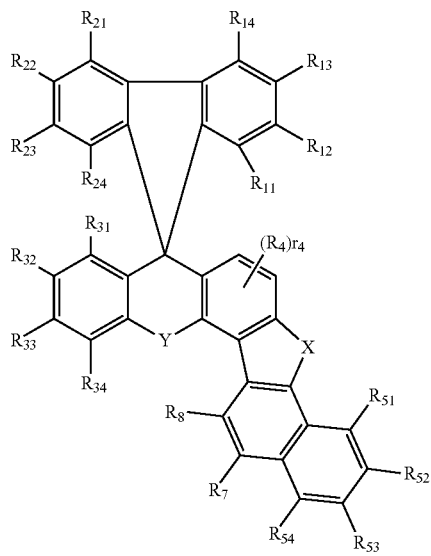
[Chemical Formula 13]
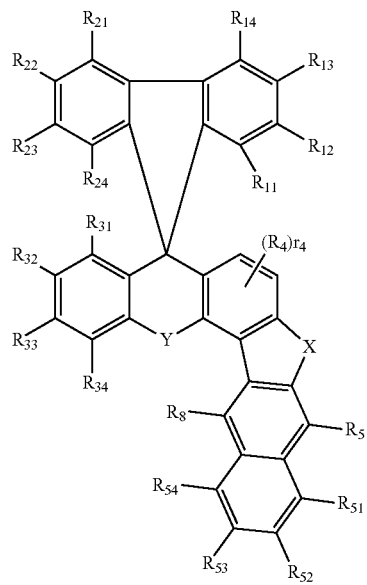
[Chemical Formula 14]
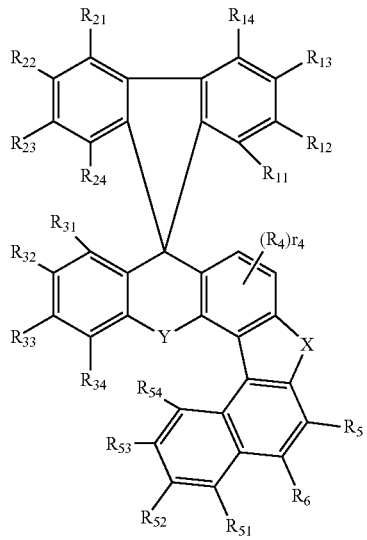
[Chemical Formula 15]
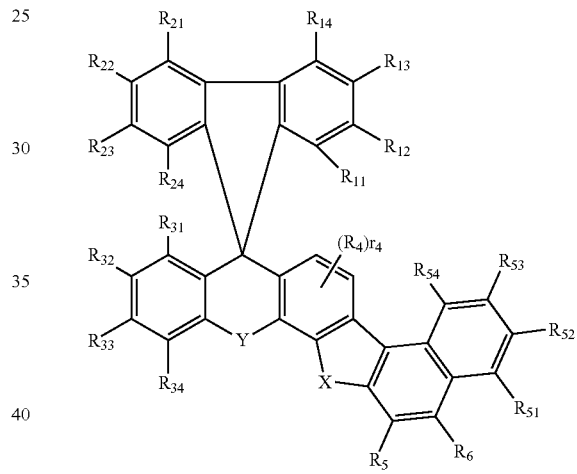
[Chemical Formula 16]
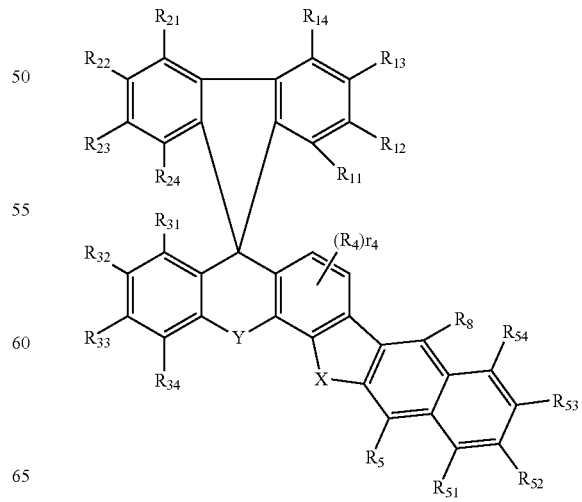

[Chemical Formula 17]

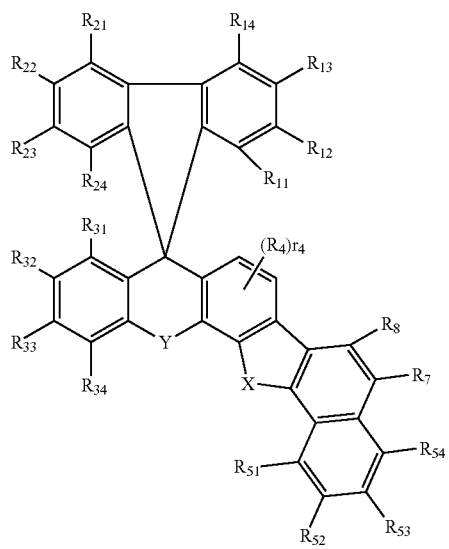

In Chemical Formulae 6 to 17, the definitions of X, Y, $R_4$ to $R_9$, $R_{11}$ to $R_{14}$, $R_{21}$ to $R_{24}$, $R_{31}$ to $R_{34}$, $R_{101}$ to $R_{106}$, and $r_4$ are the same as those defined in Chemical Formula 1, and $R_{51}$ to $R_{54}$ are hydrogen; deuterium; a halogen group; a cyano group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted amine group; a substituted or unsubstituted alkylamine group; a substituted or unsubstituted arylamine group; a substituted or unsubstituted heteroarylamine group; a substituted or unsubstituted phosphine oxide group; a substituted or unsubstituted aryl group; or a substituted or unsubstituted heteroaryl group, or may be bonded to an adjacent group to form a ring.

In an exemplary embodiment of the present specification, $R_{51}$ to $R_{54}$ are hydrogen.

In an exemplary embodiment of the present specification, $-L_1Ar_1$ may be any one of the substituents of the following [A-1] to [A-4], but is not limited thereto.

[A-1]

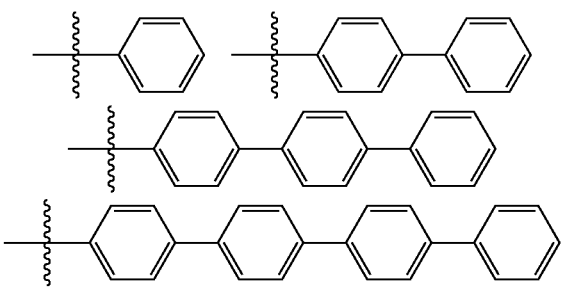

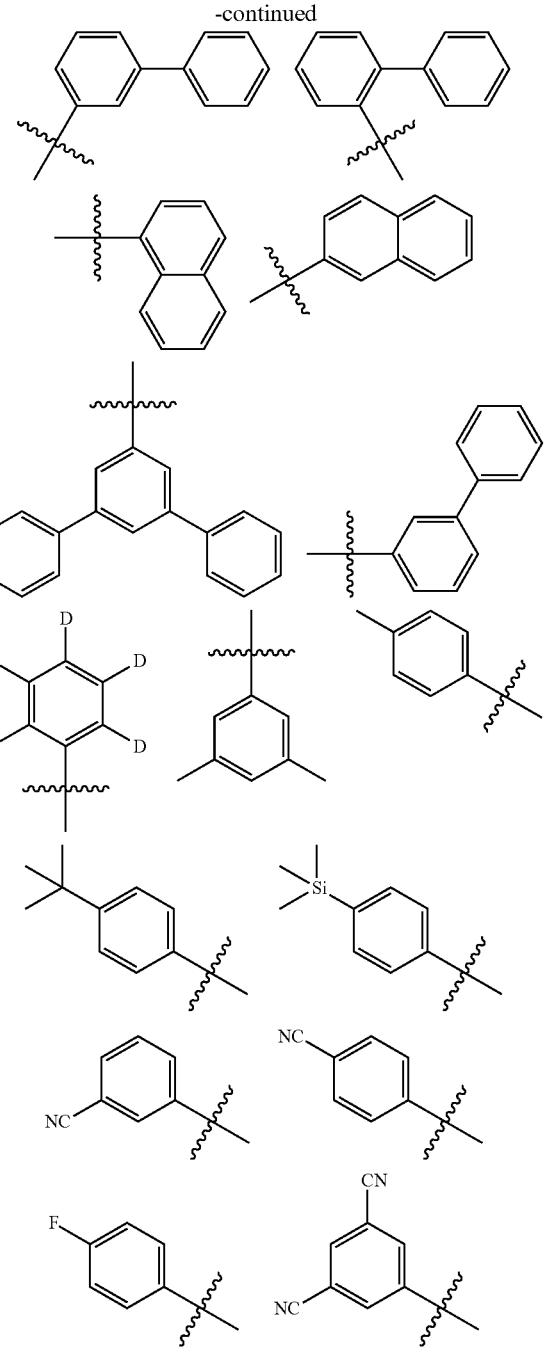

-continued
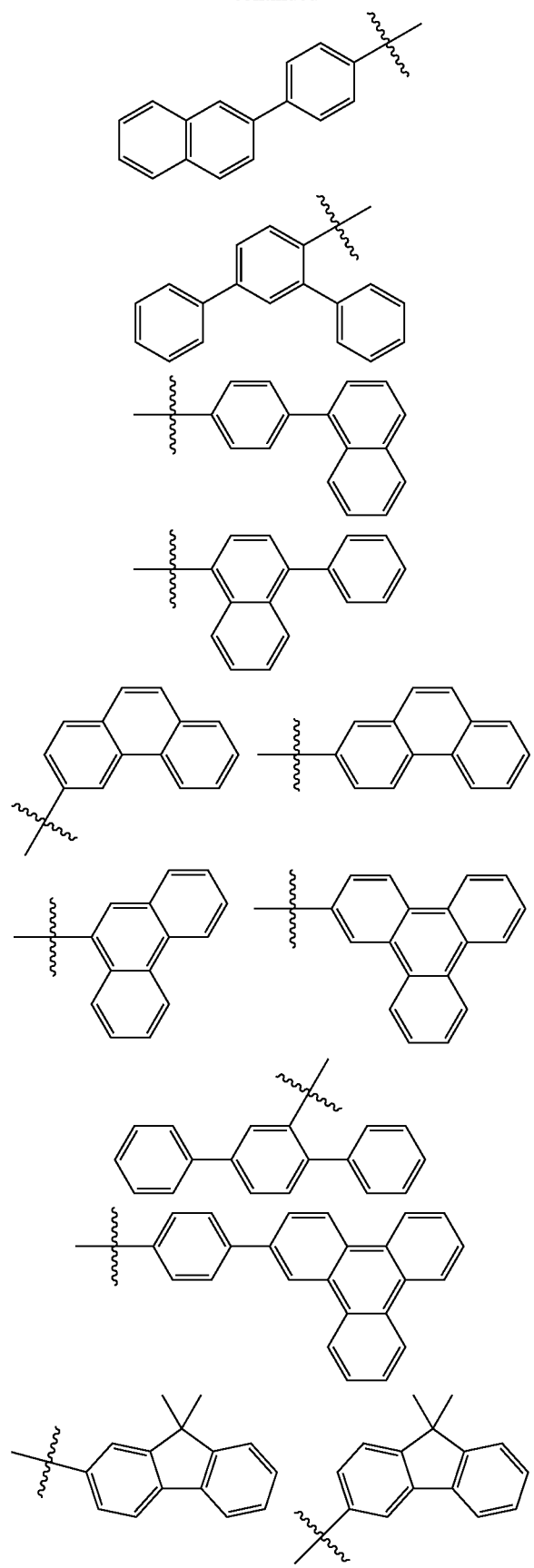
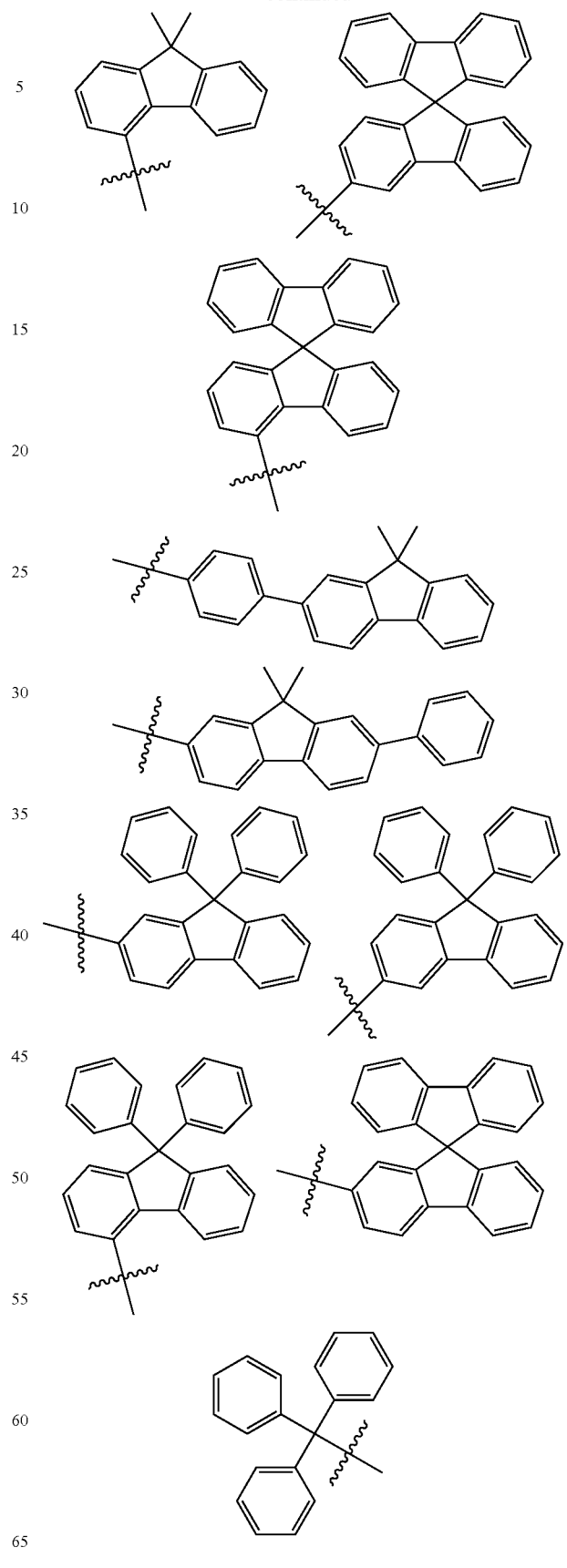

[A-2]
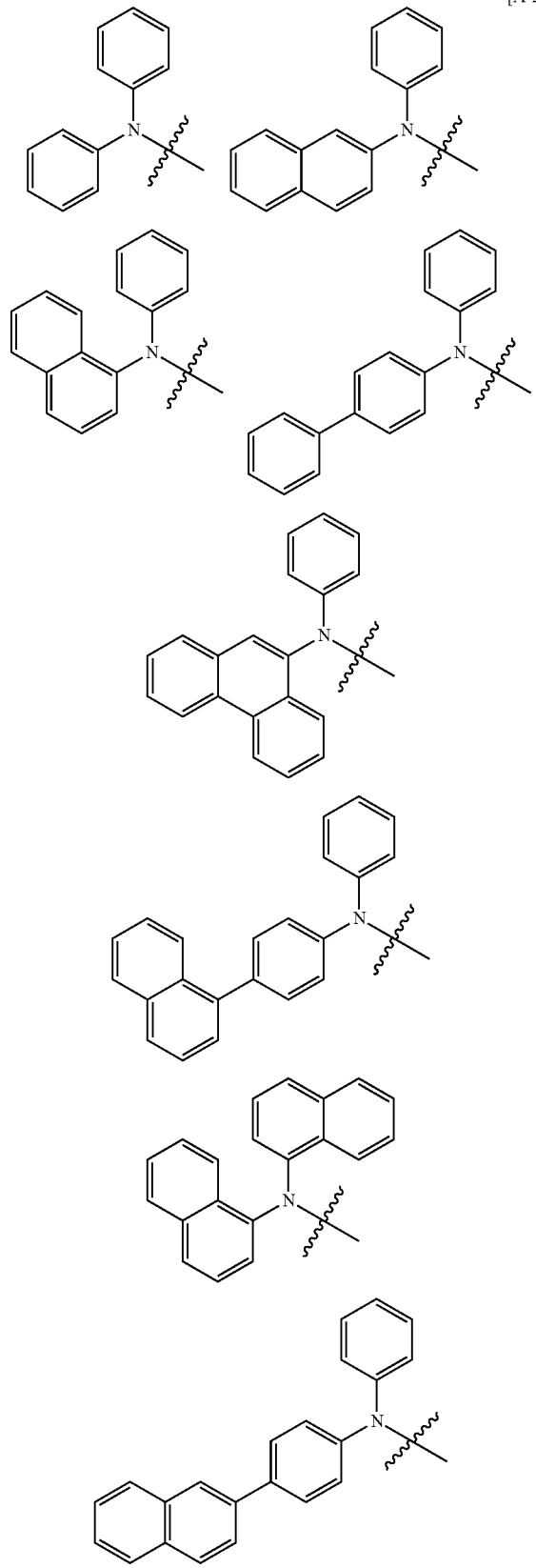
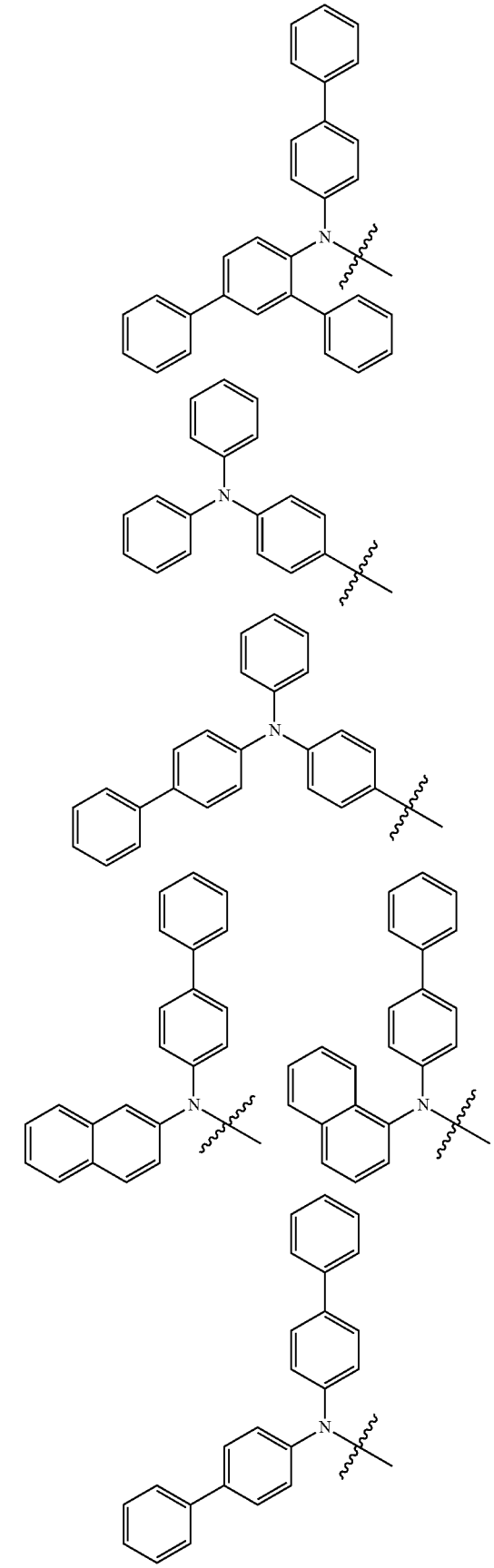

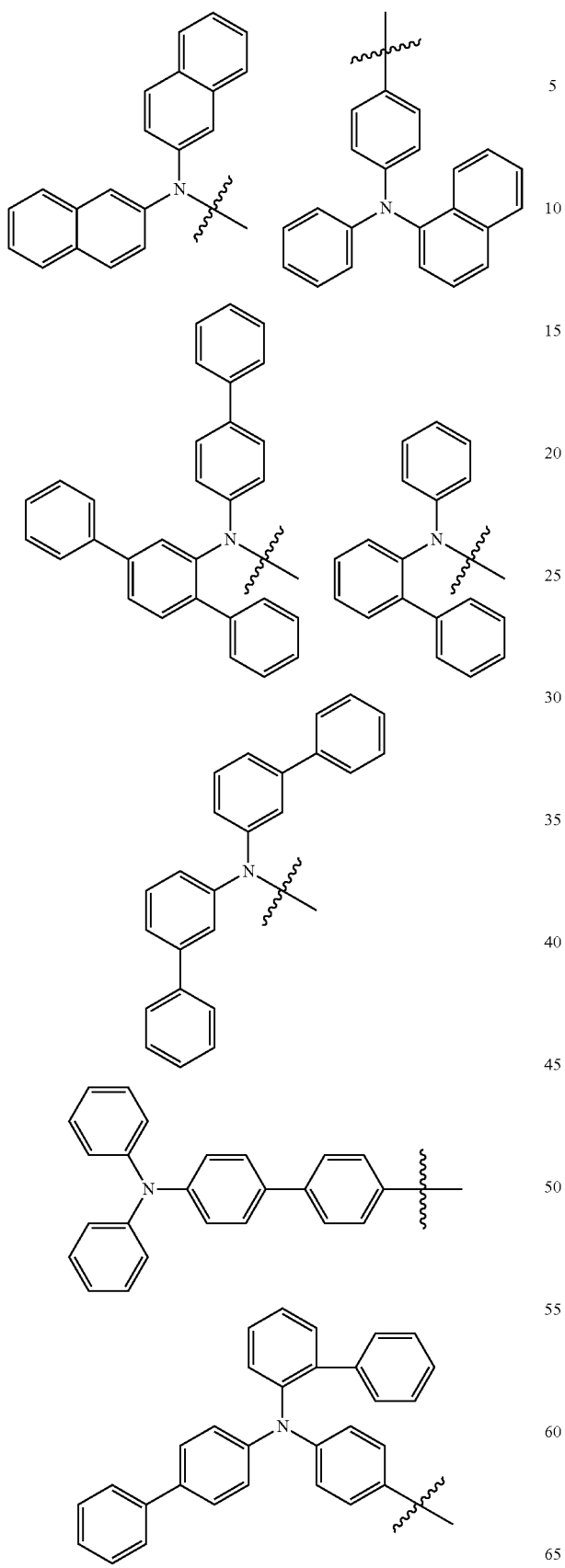
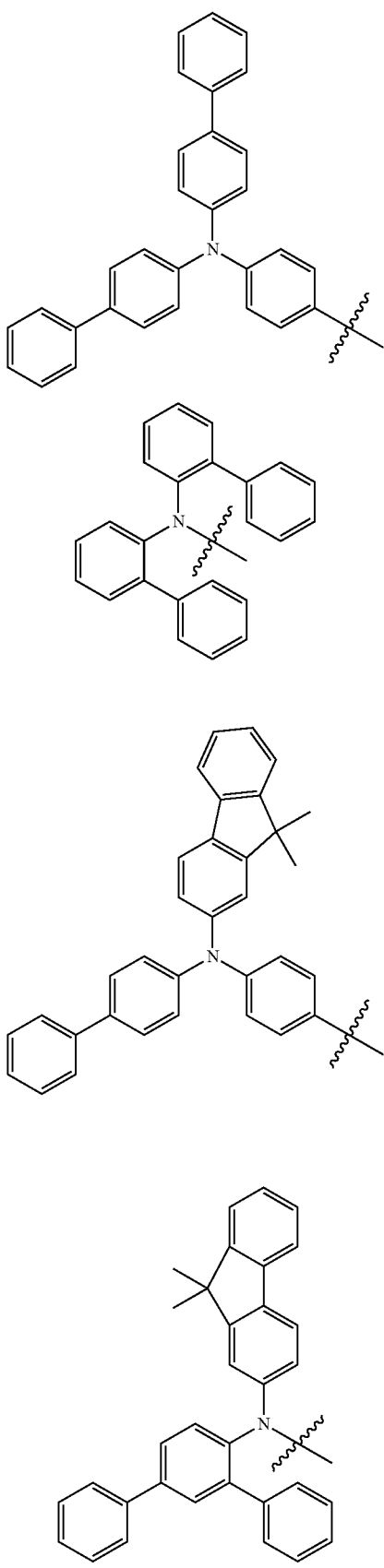

31
-continued
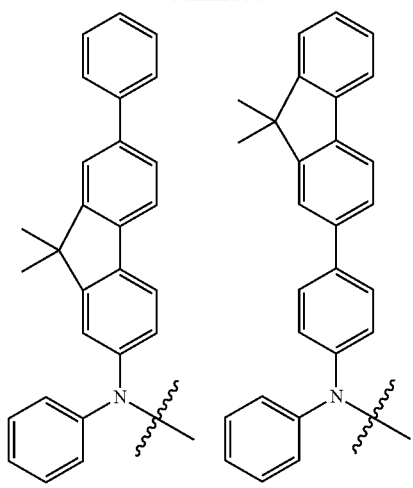
32
-continued
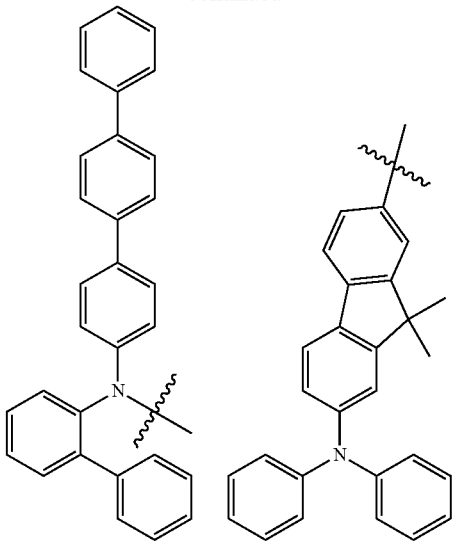
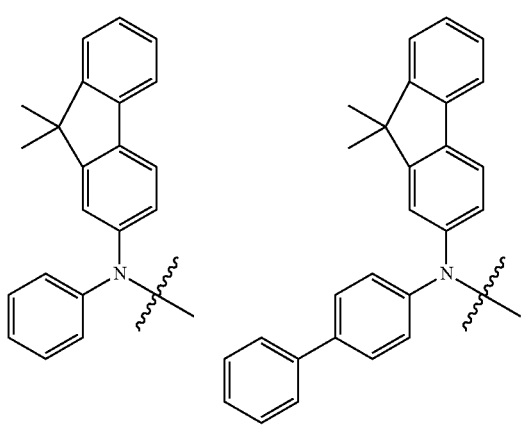
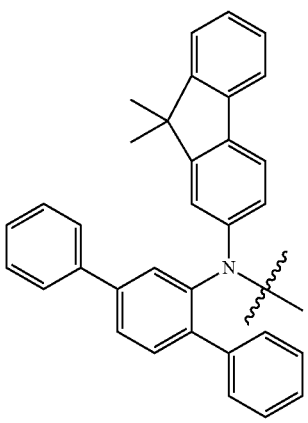
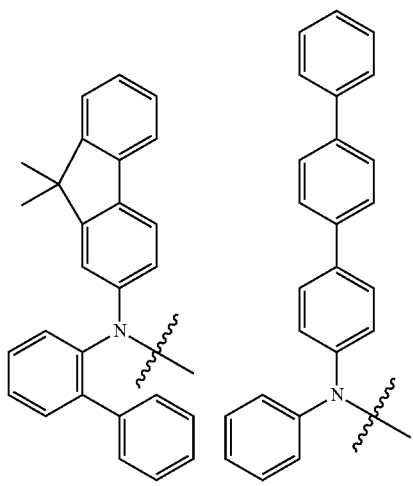
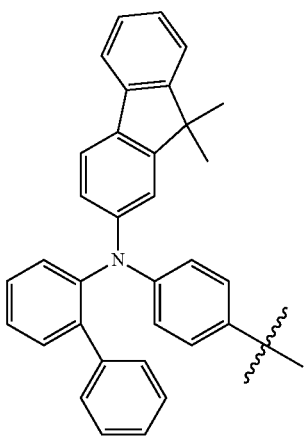

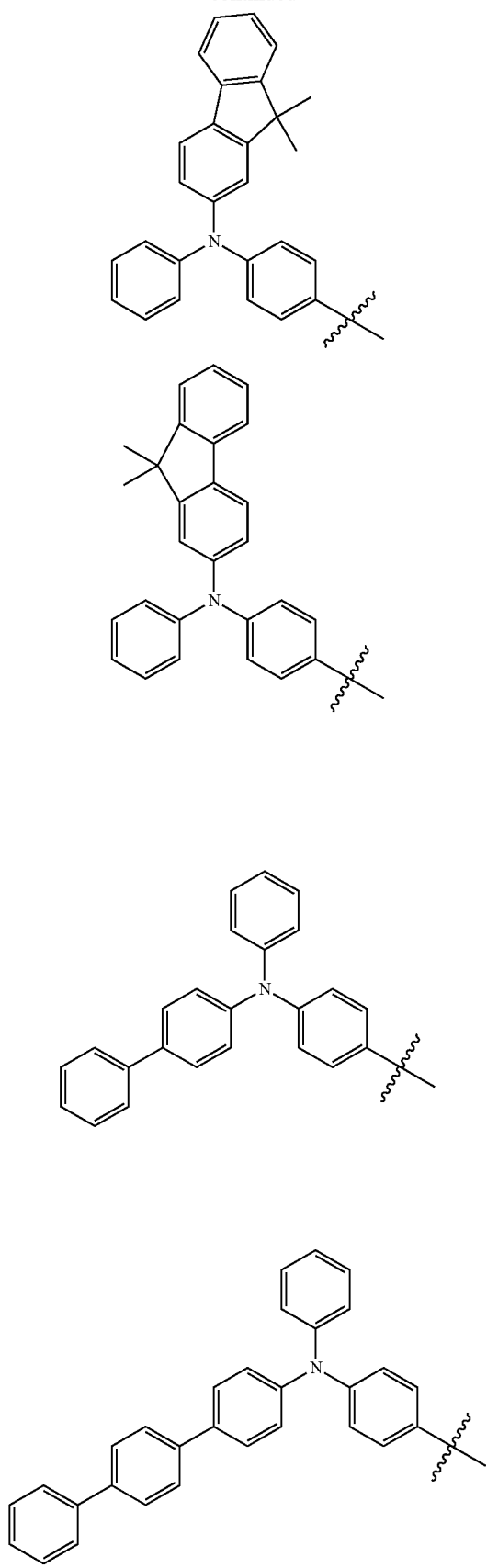
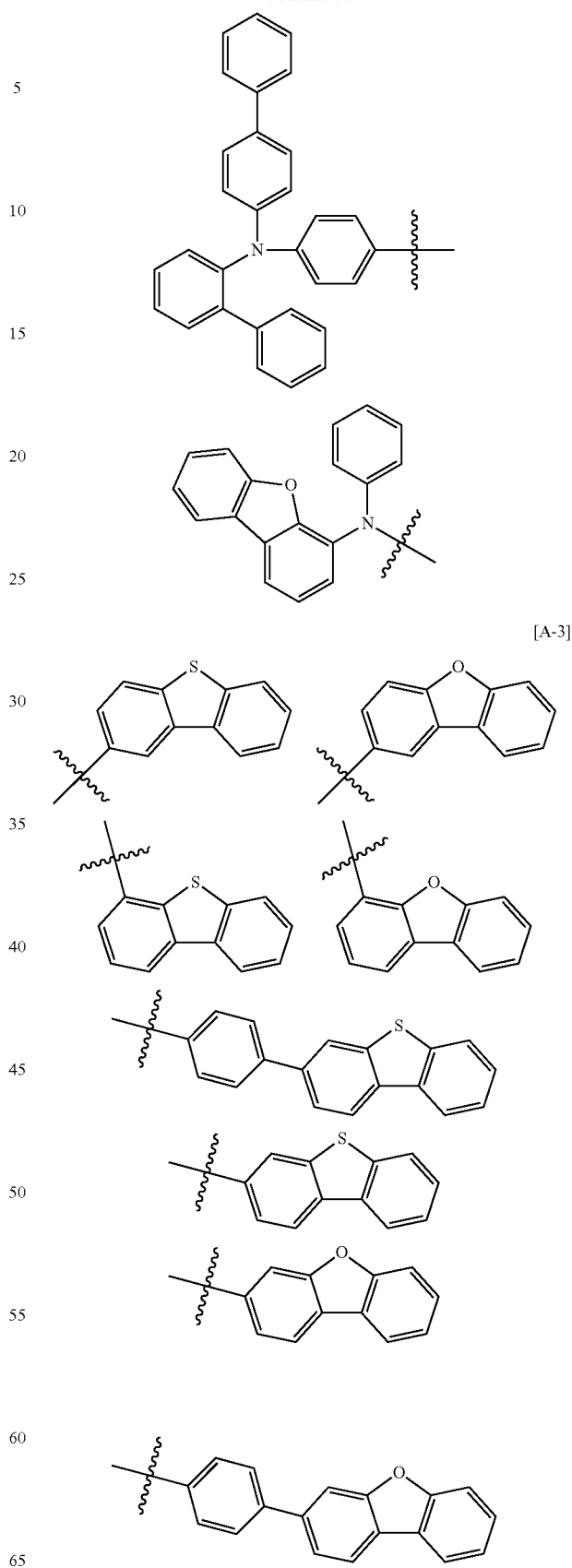
[A-3]

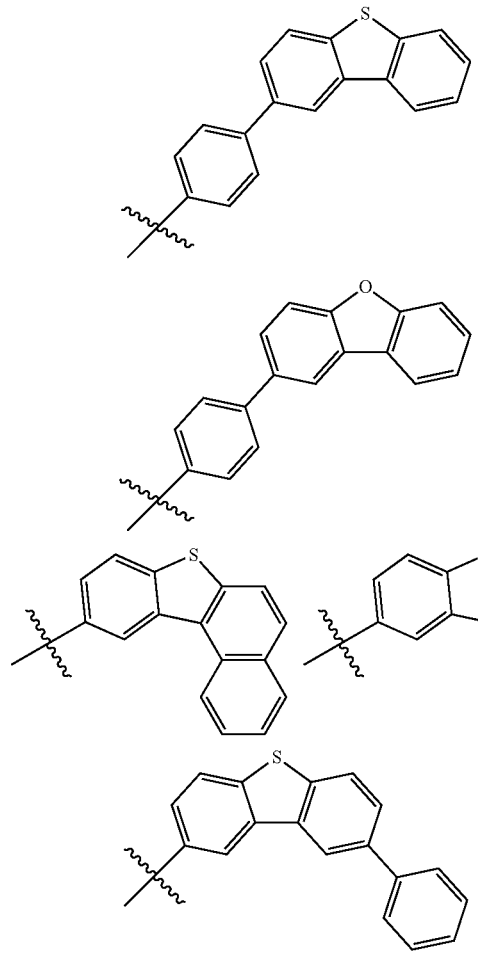
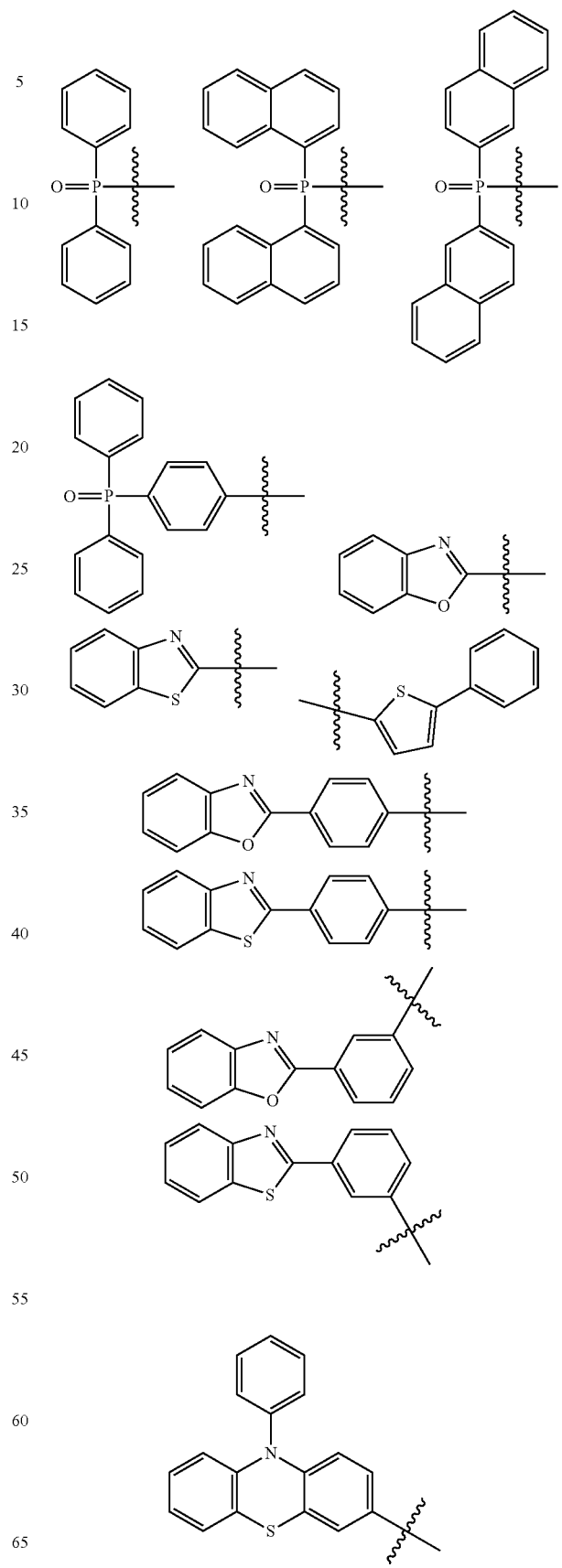

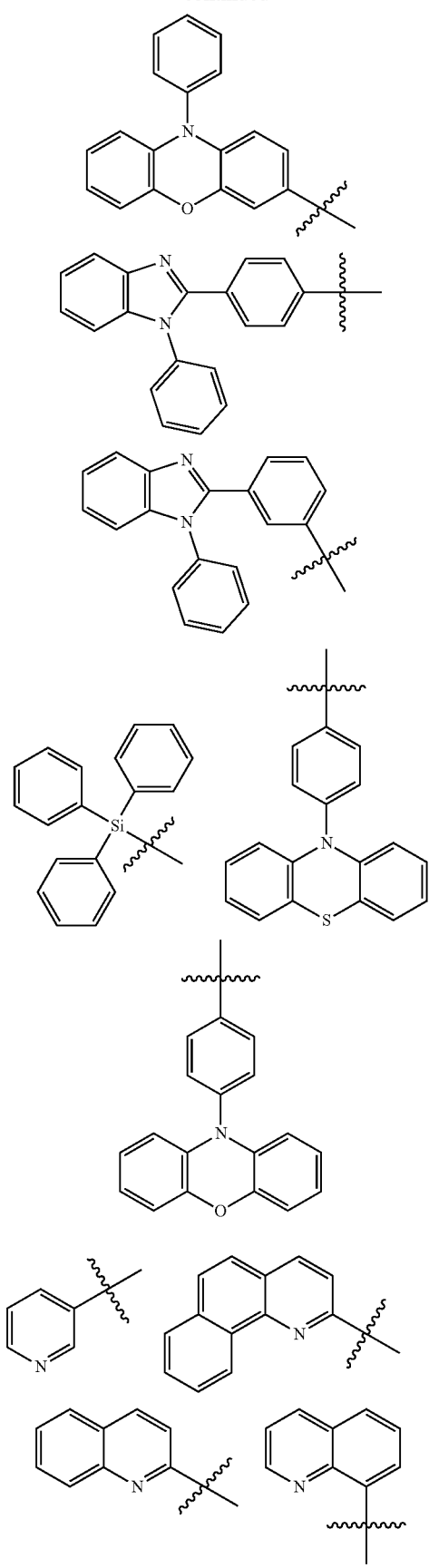

-continued
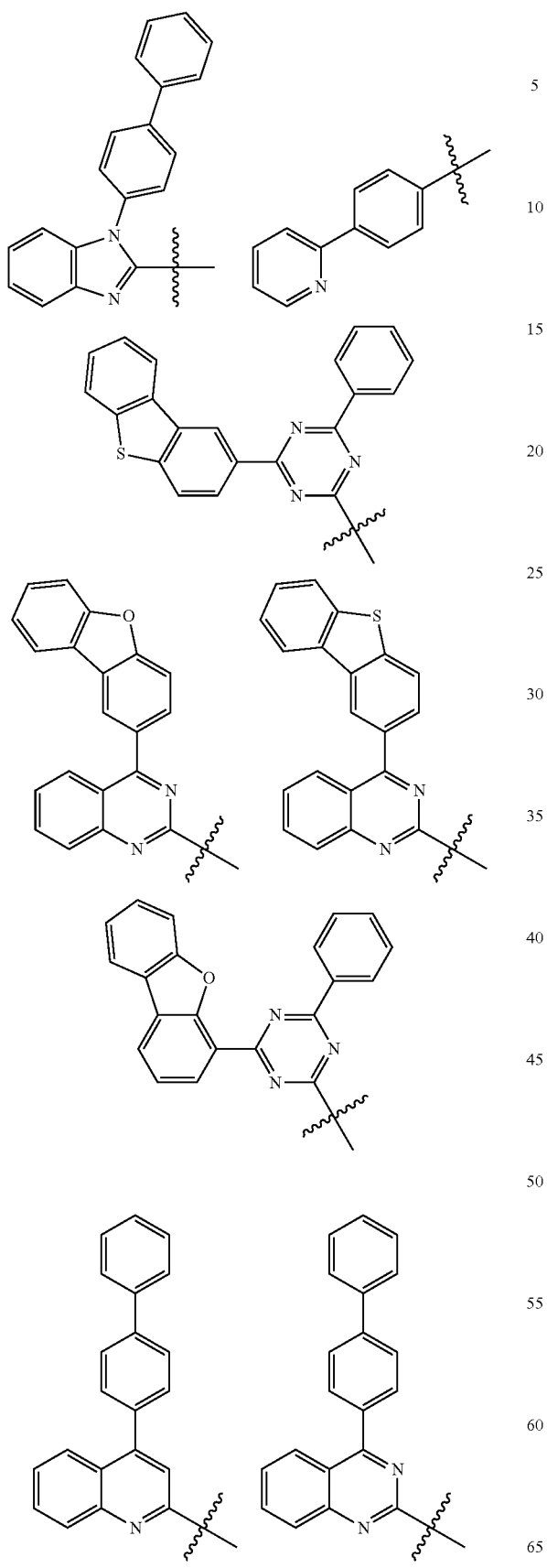
-continued
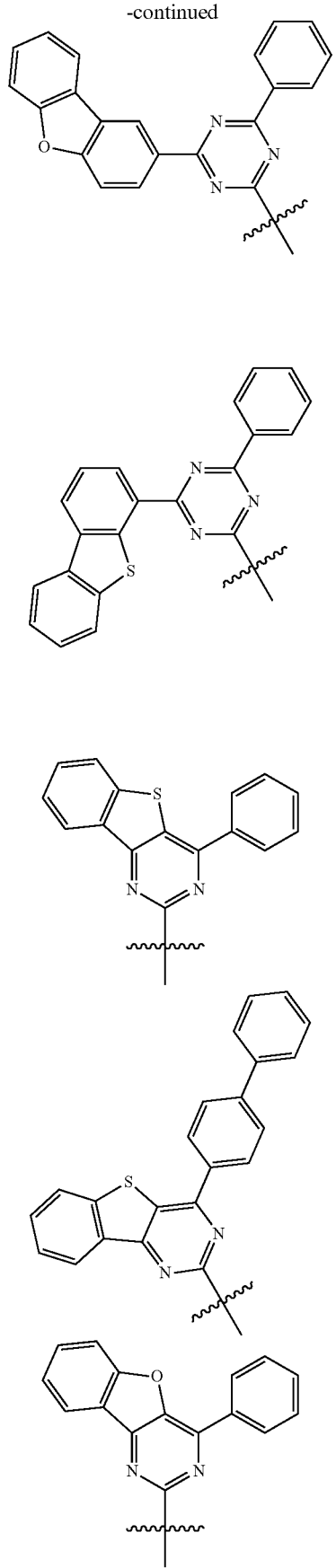

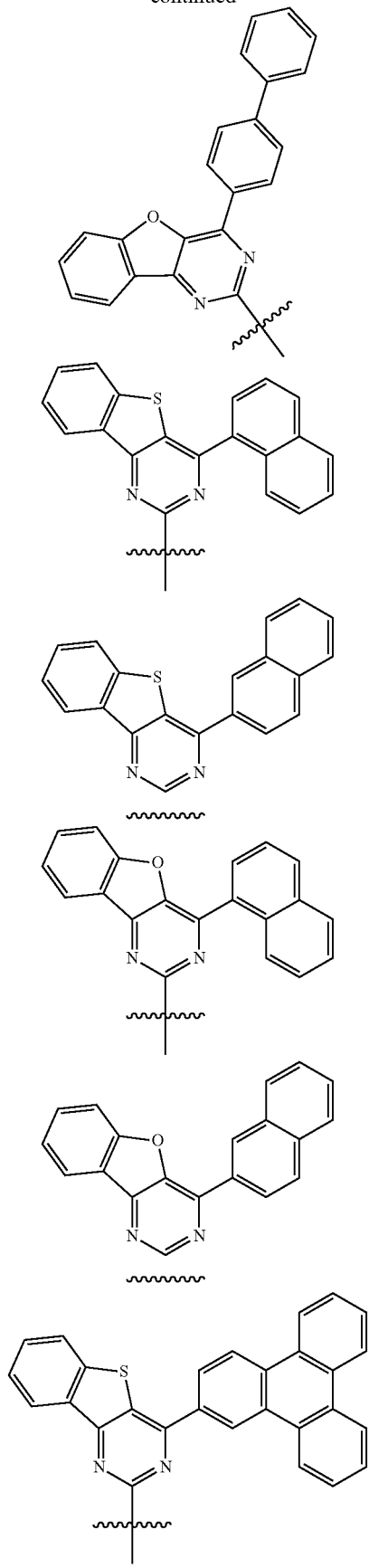
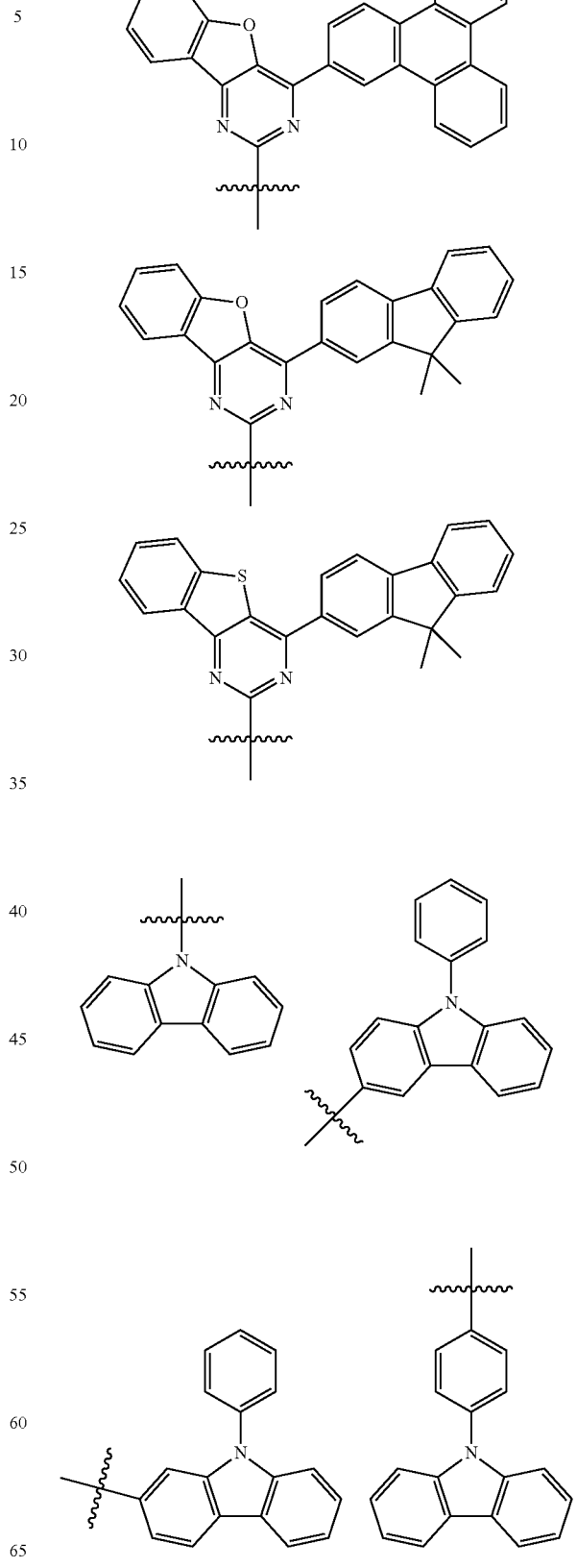

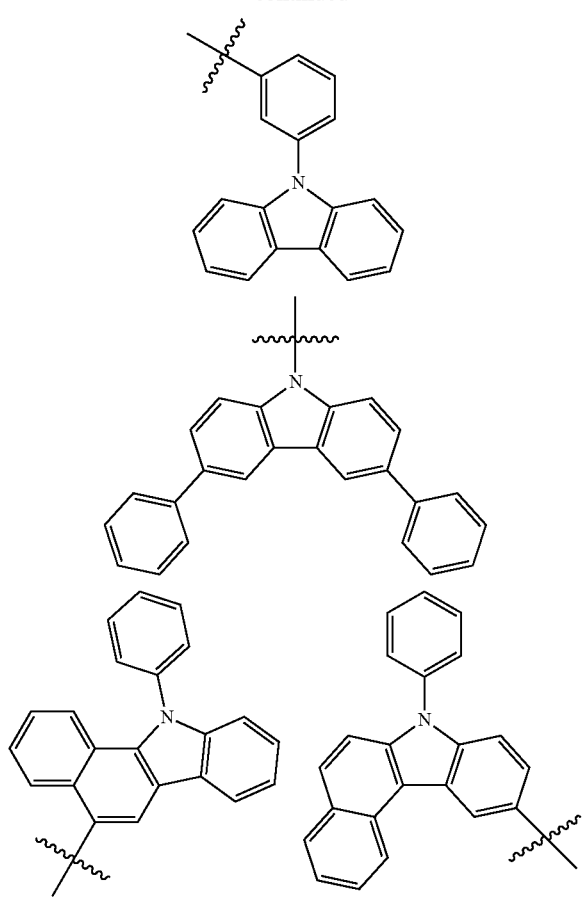
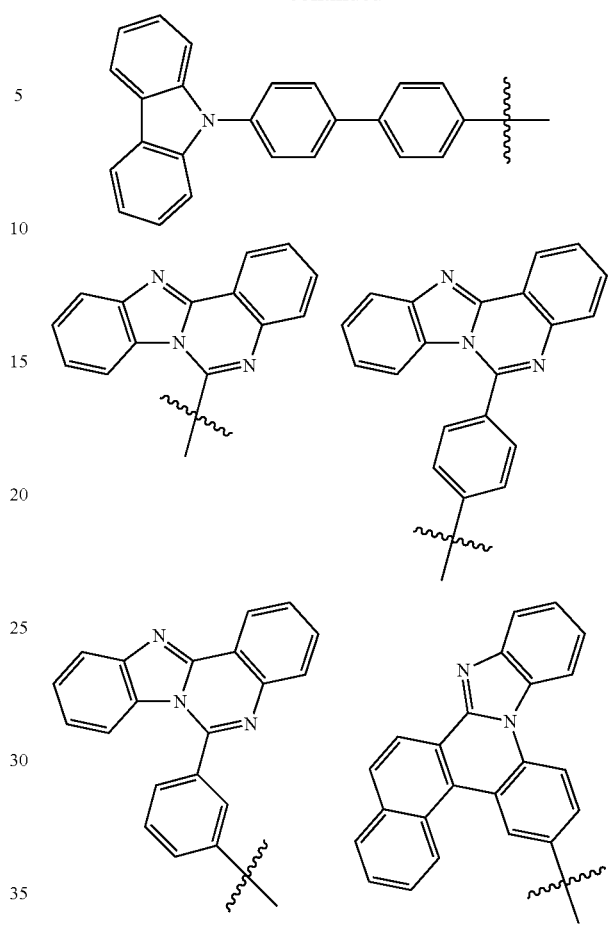
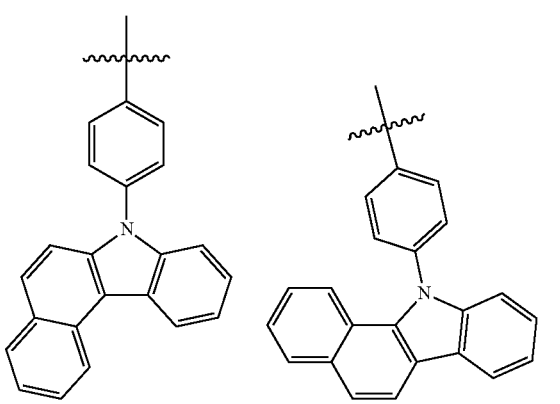
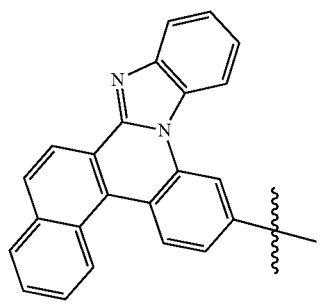
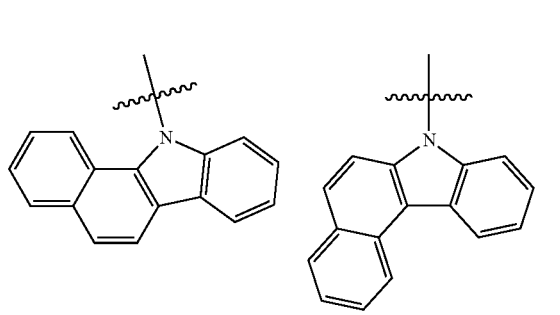
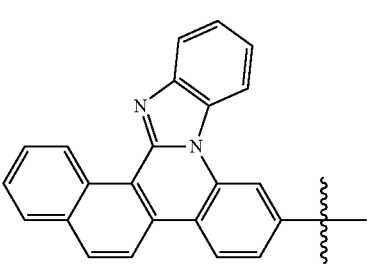

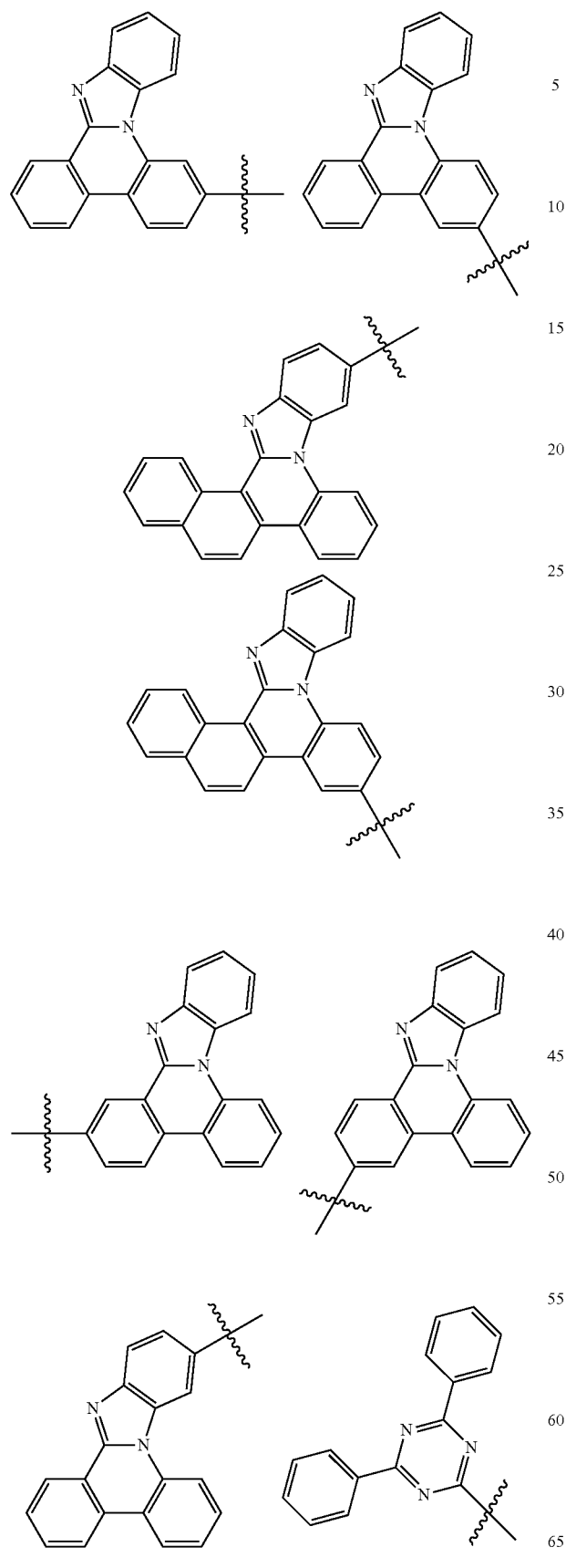
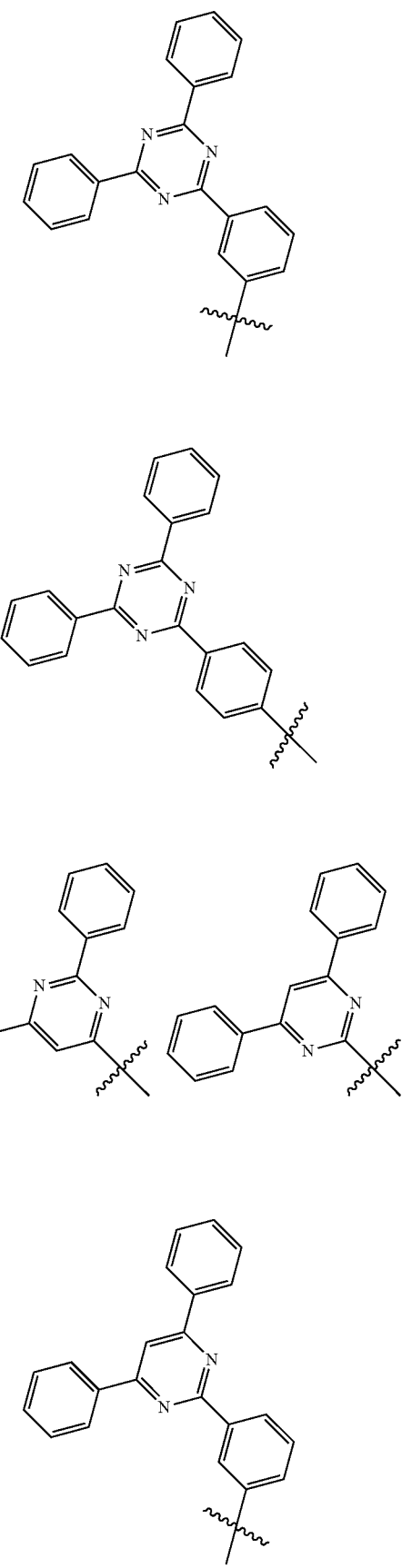

-continued
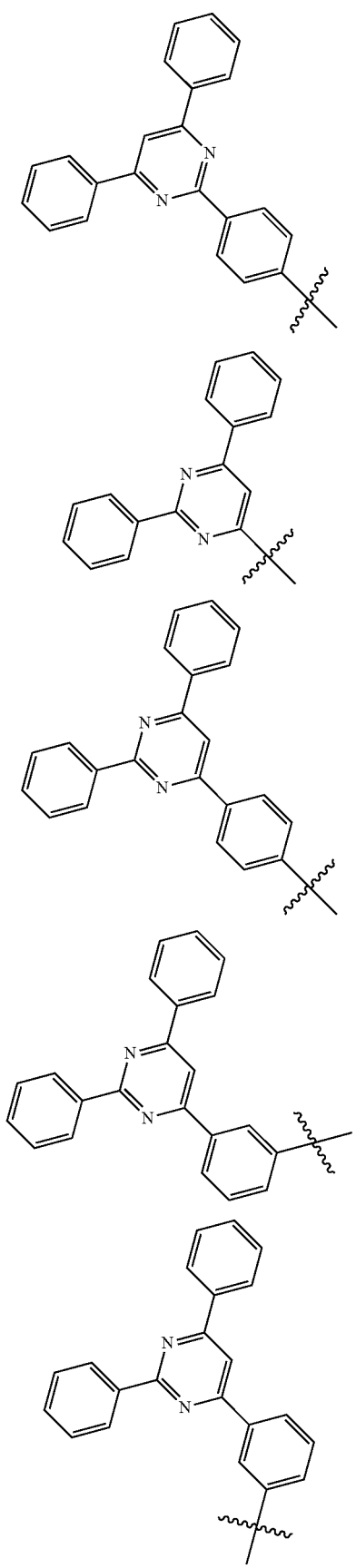
-continued
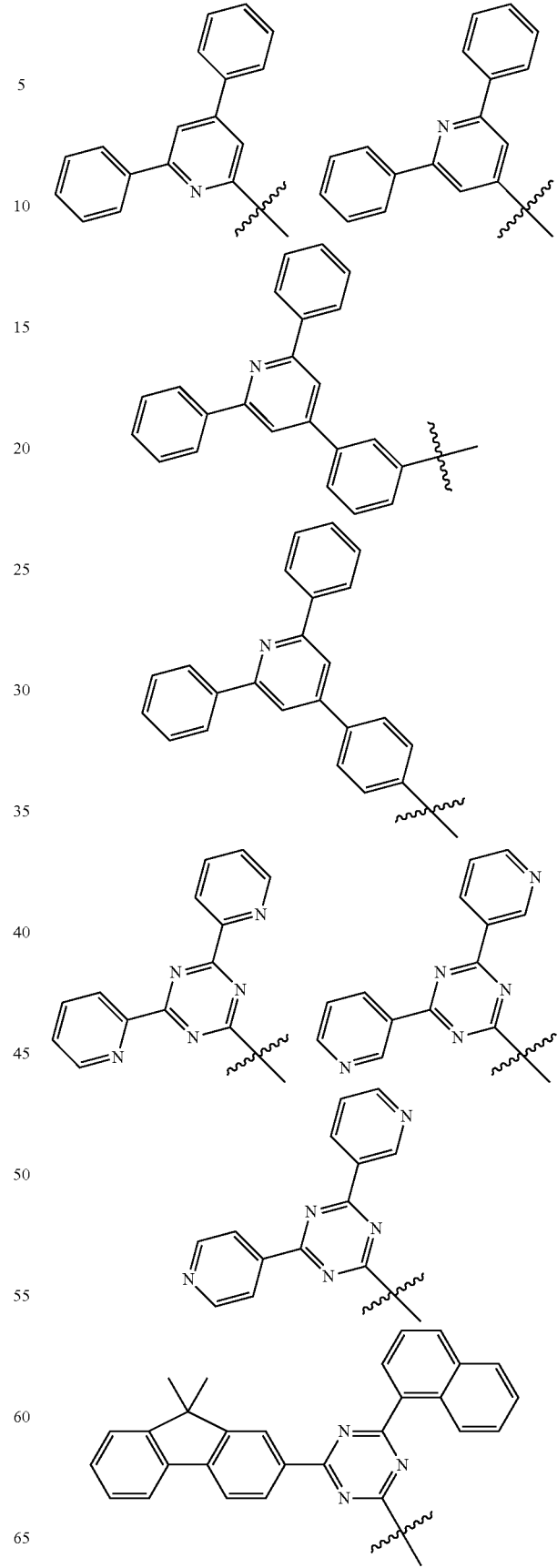

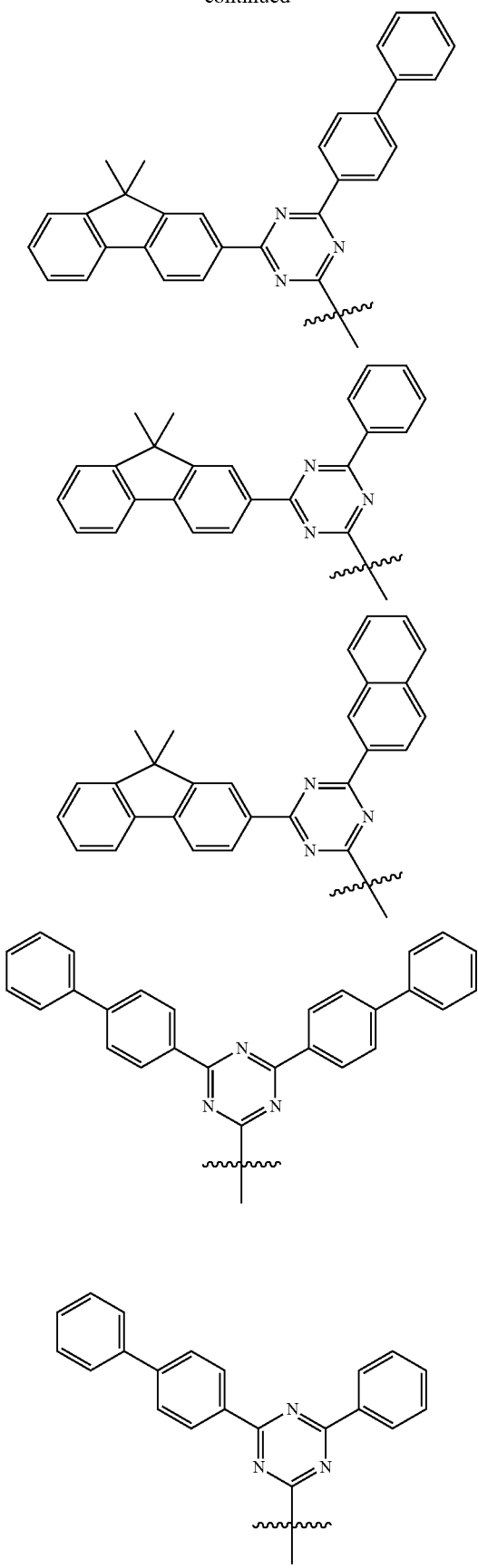
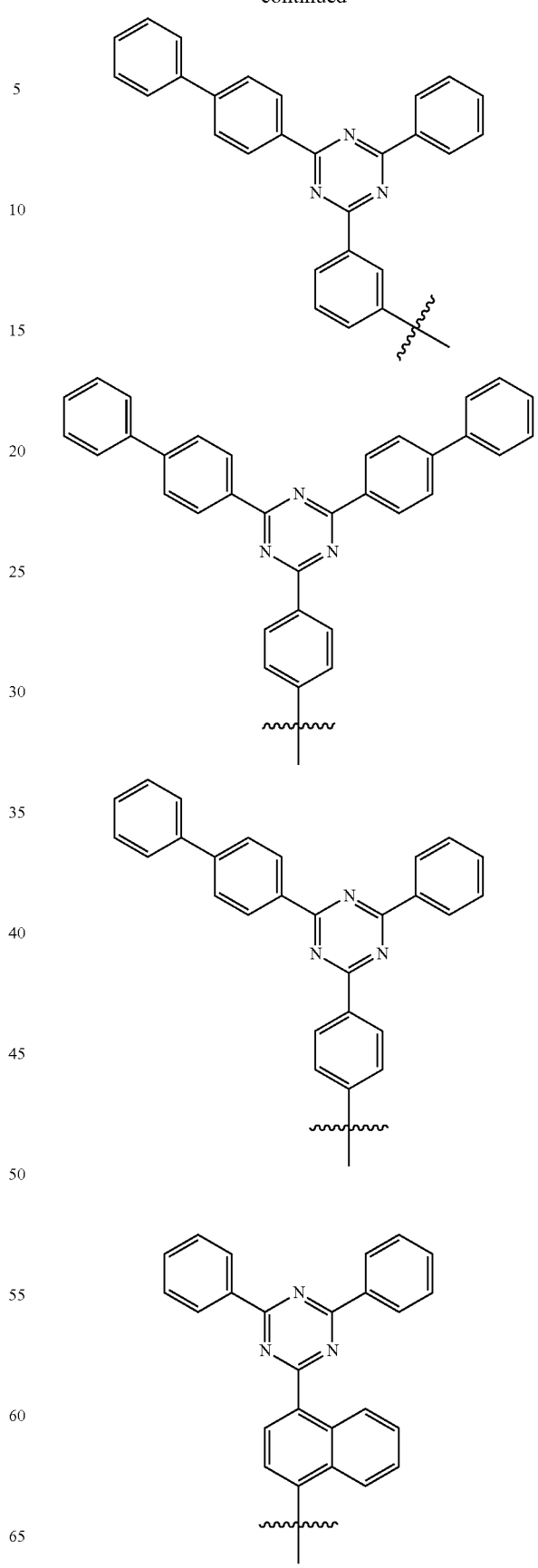

51
-continued
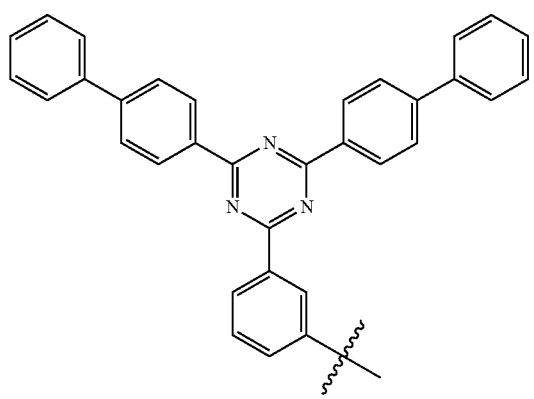
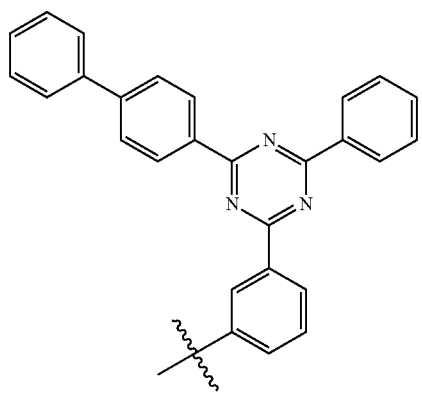
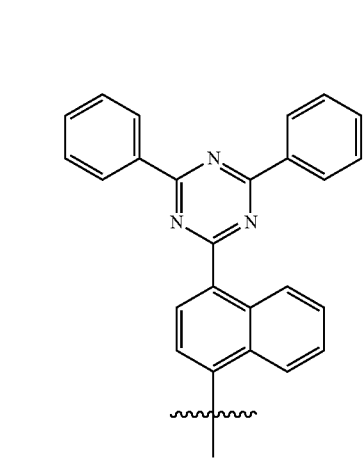
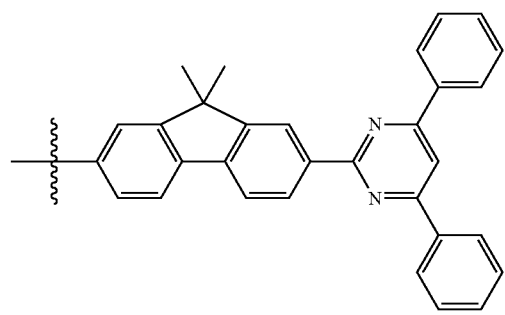
52
-continued
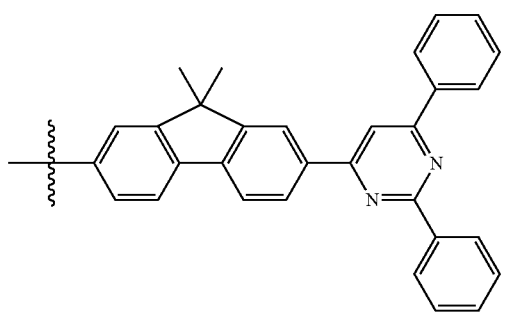
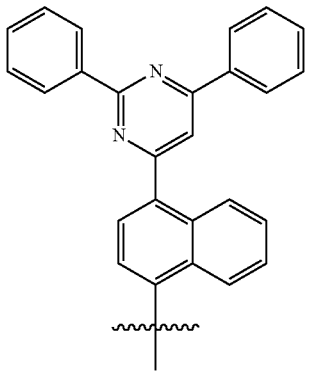
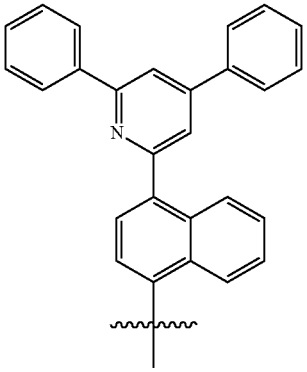
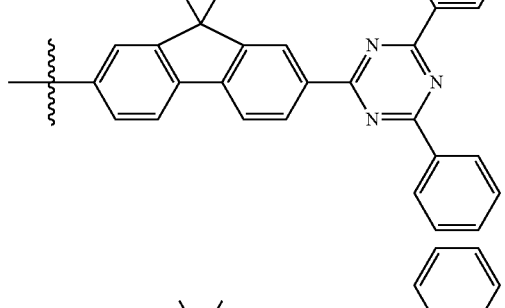
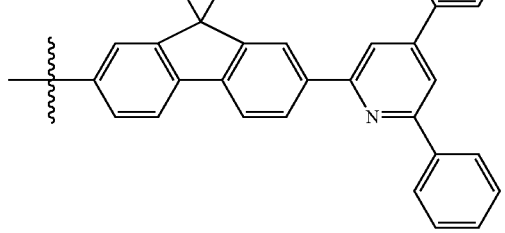

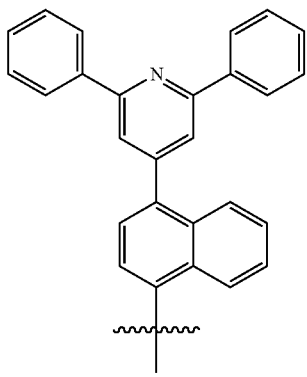
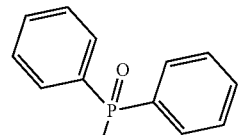
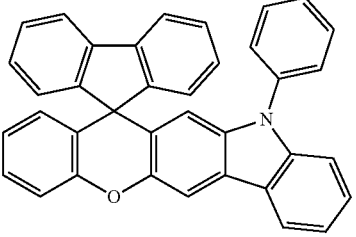
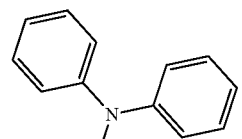
According to an exemplary embodiment of the present specification, the spiro compound of Chemical Formula 1 may be any one selected from the following structures.
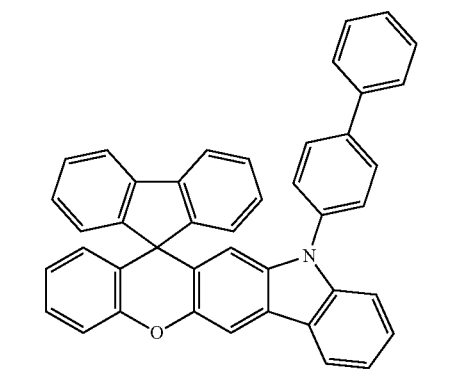
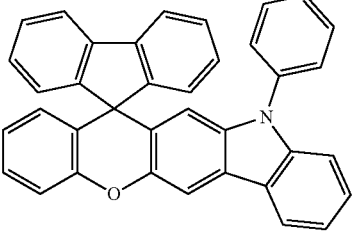
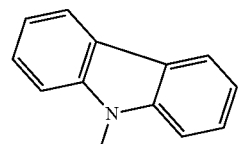
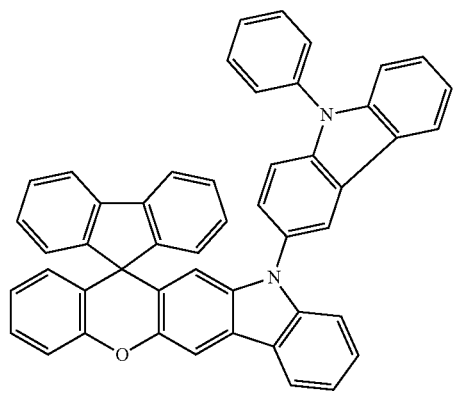
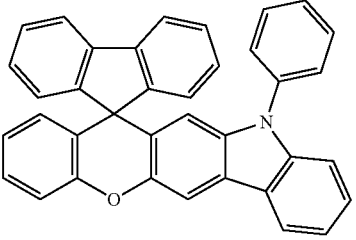
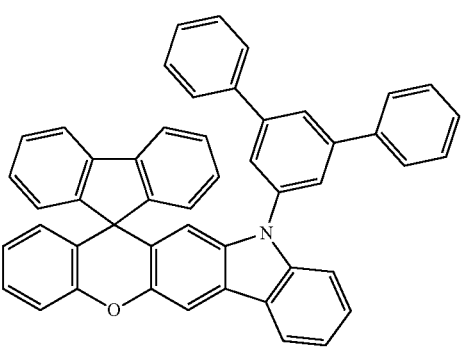
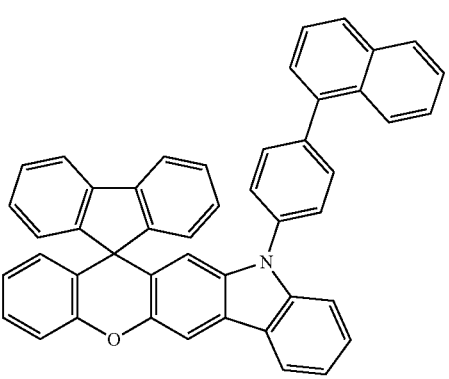

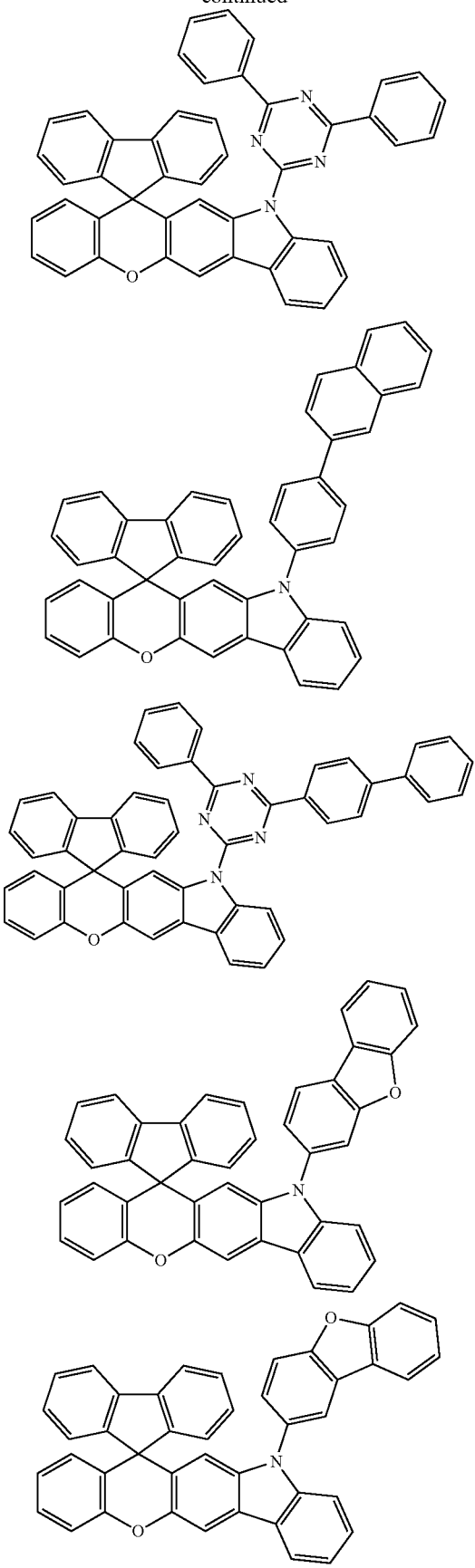
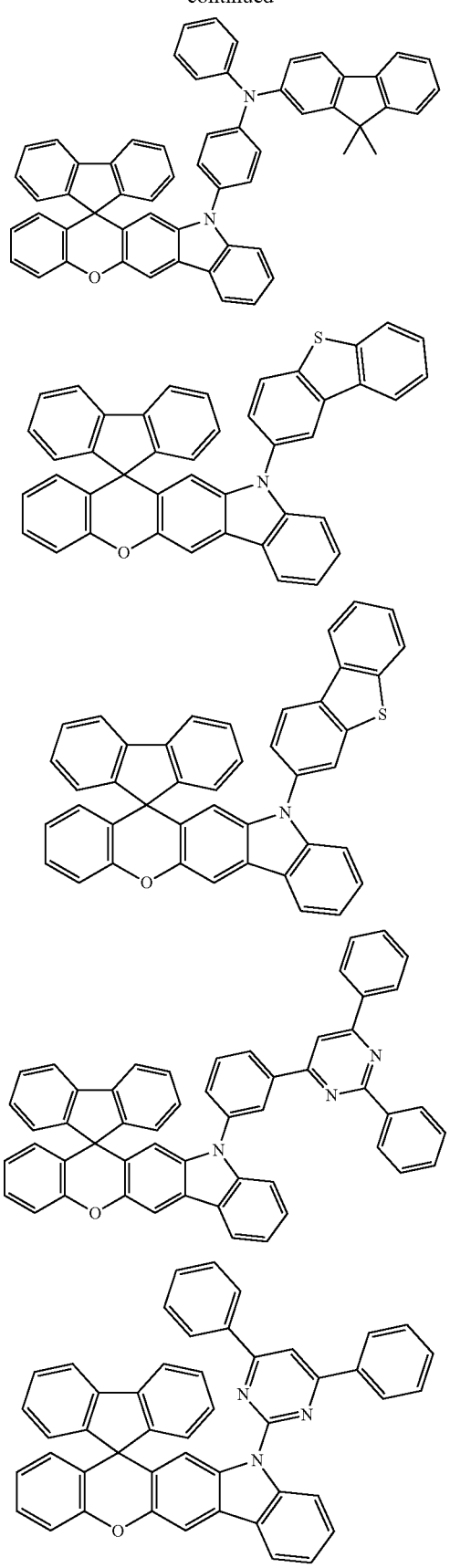

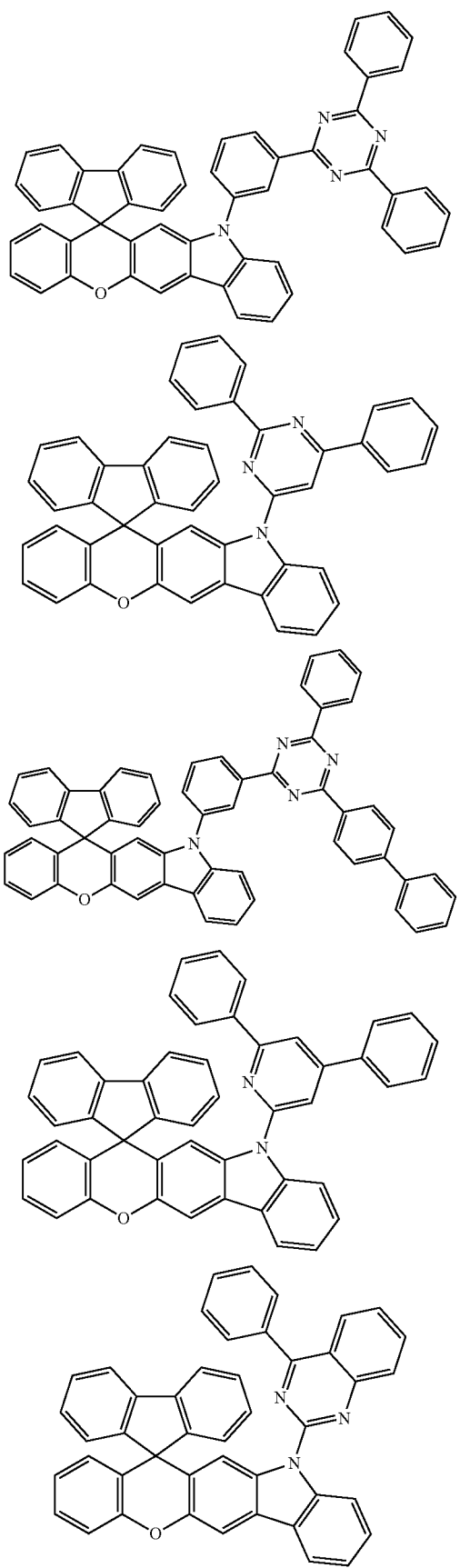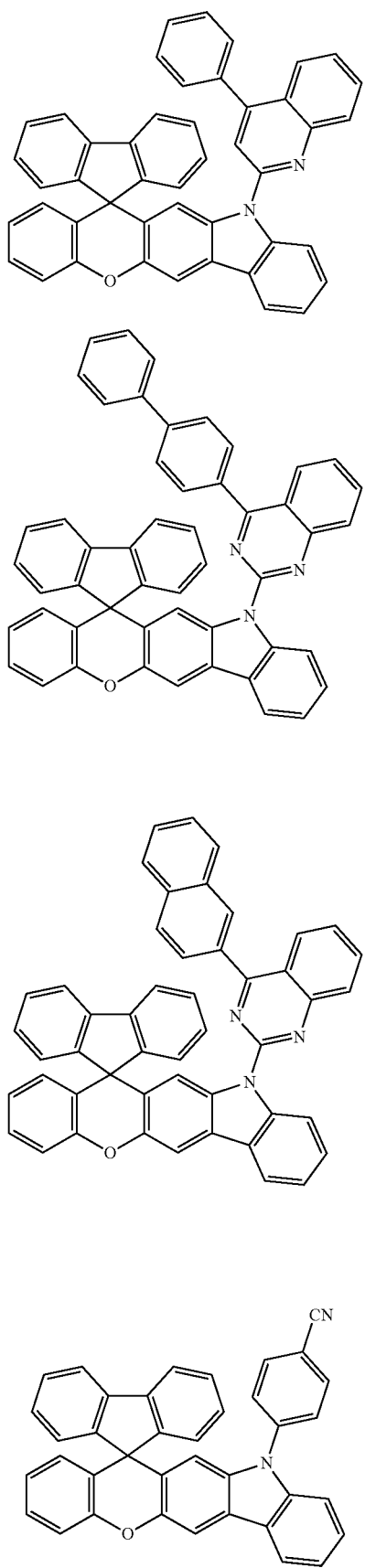

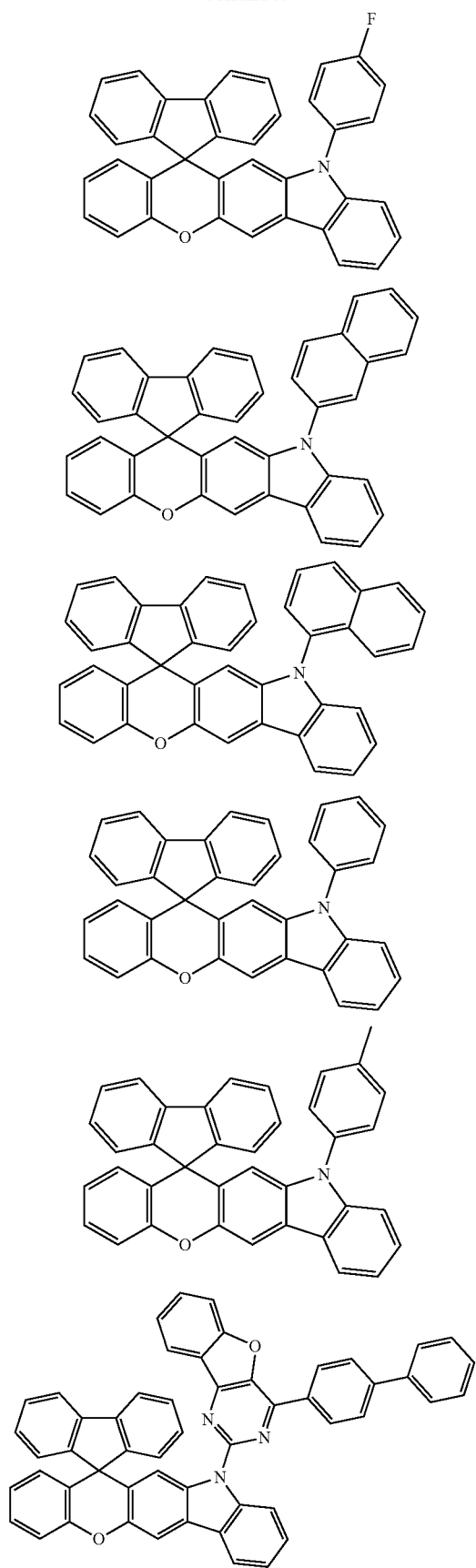
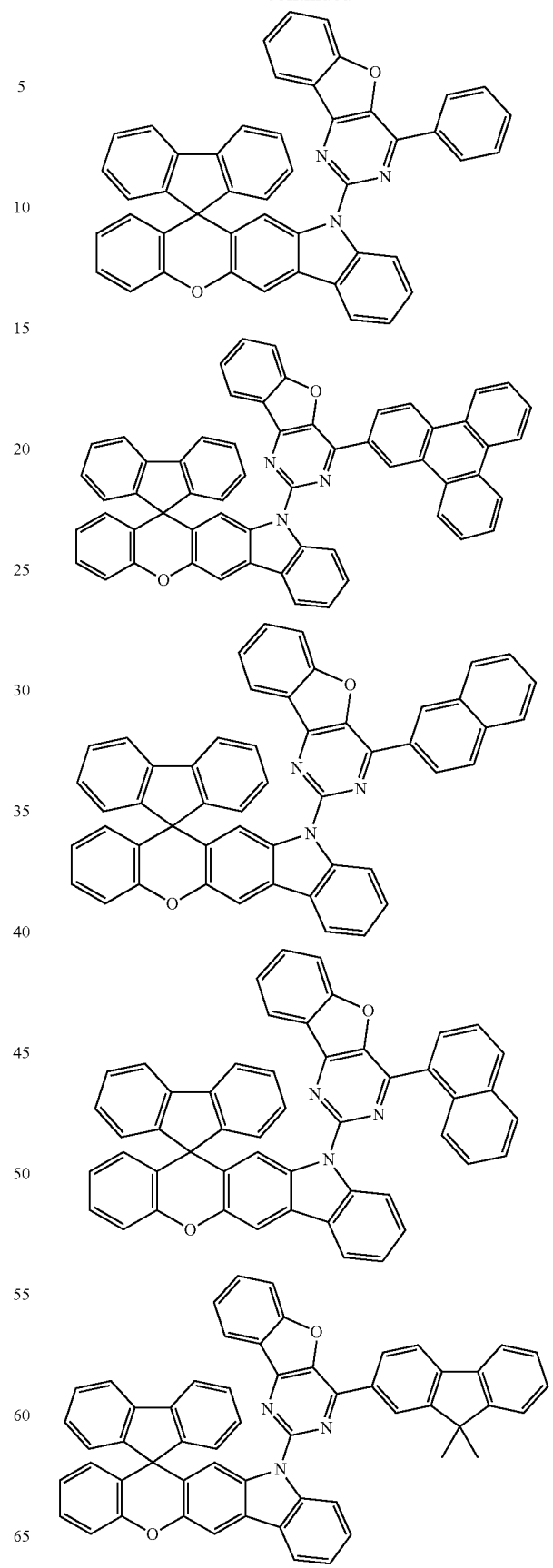

-continued
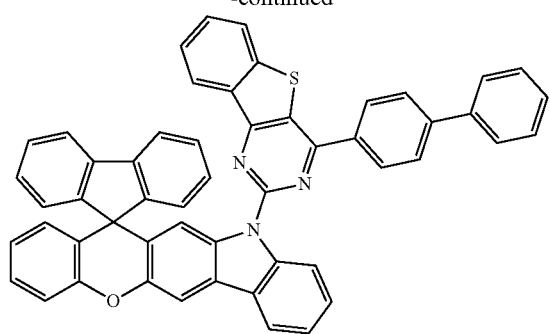
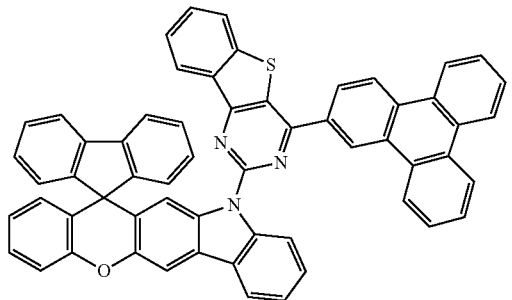
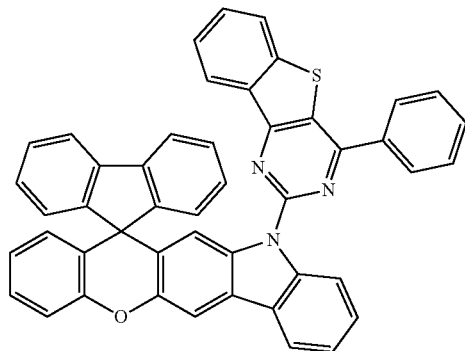
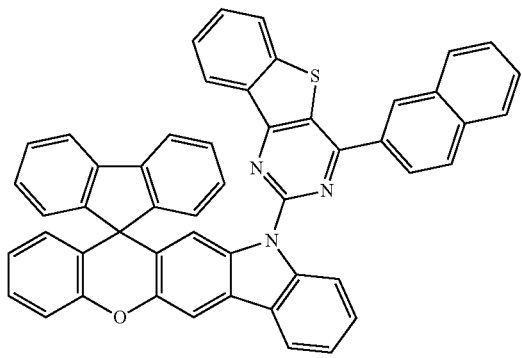
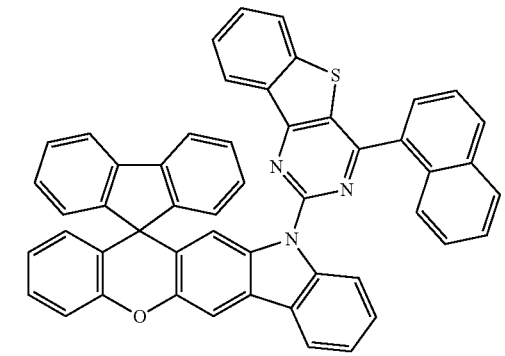
-continued
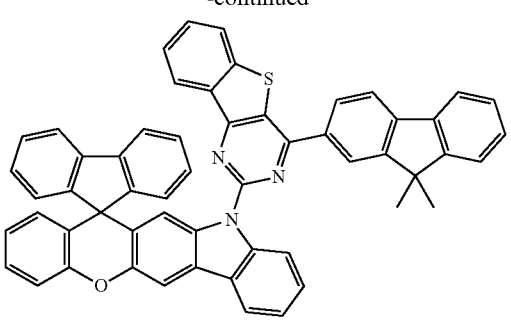
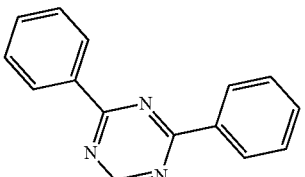
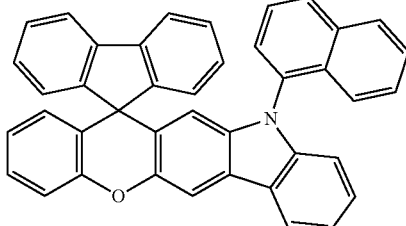
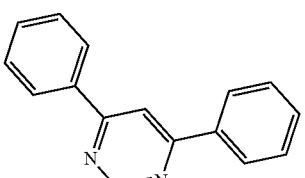
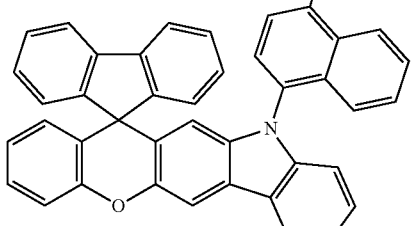
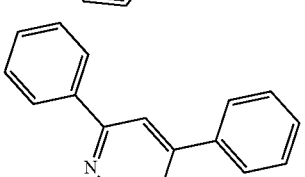
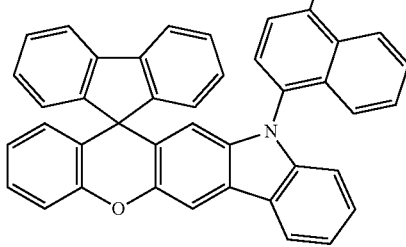

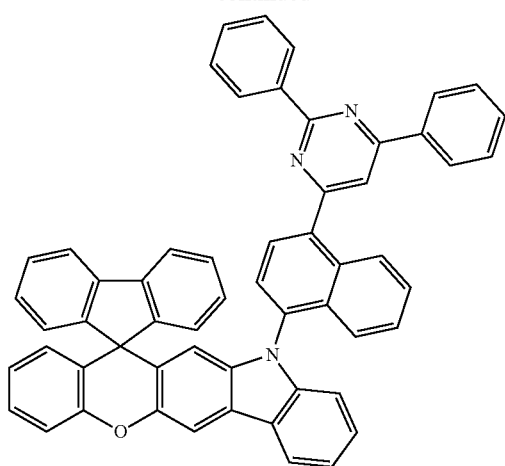
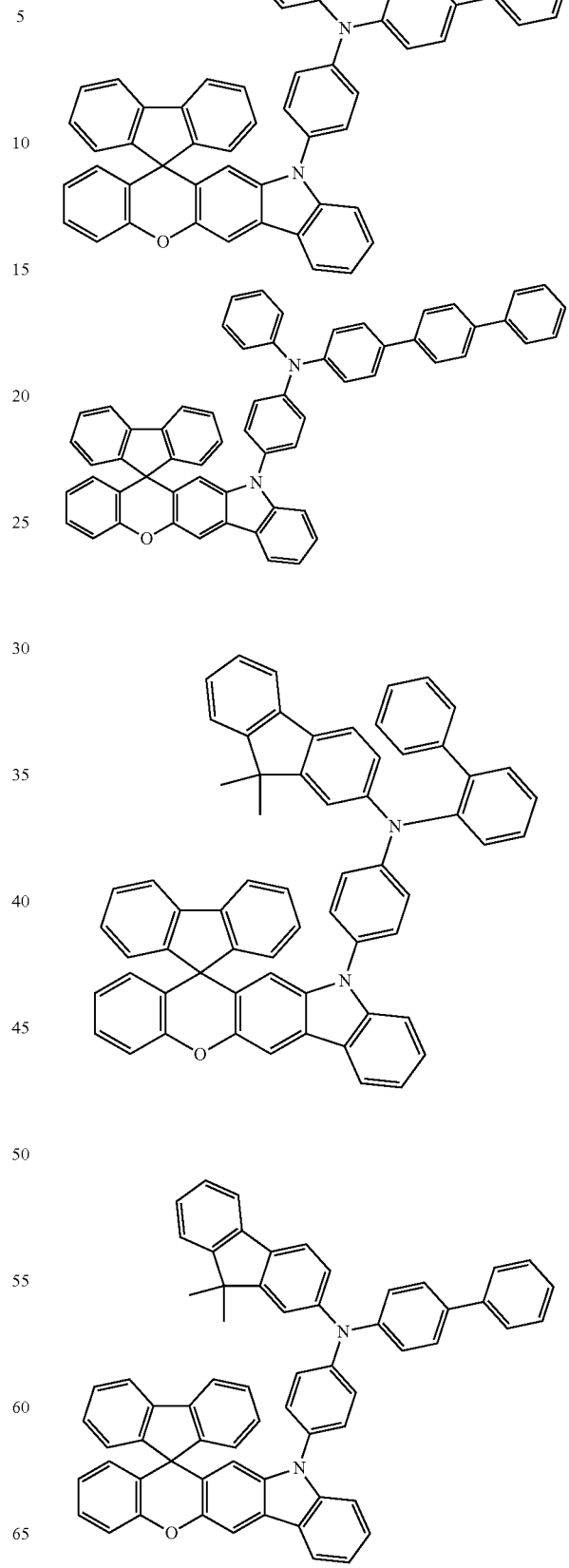

65
-continued
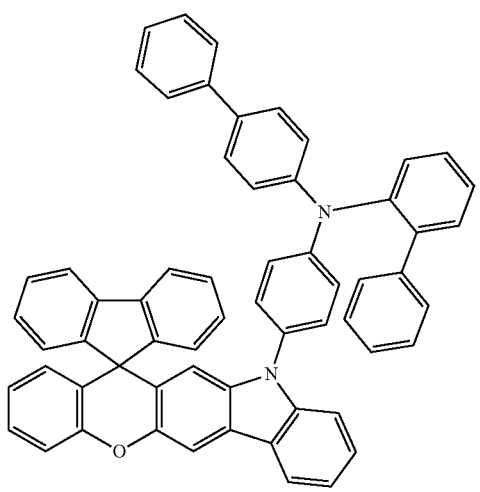
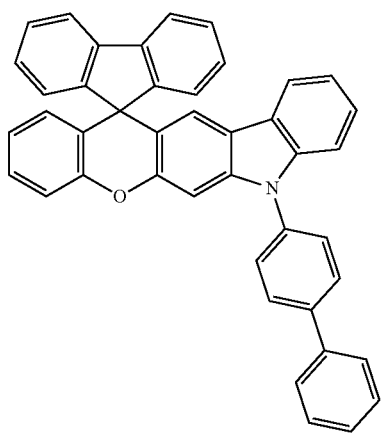
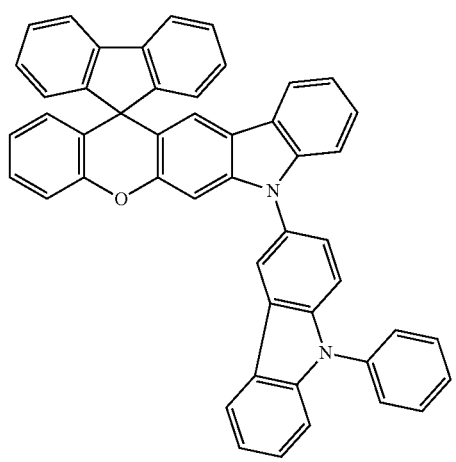
66
-continued
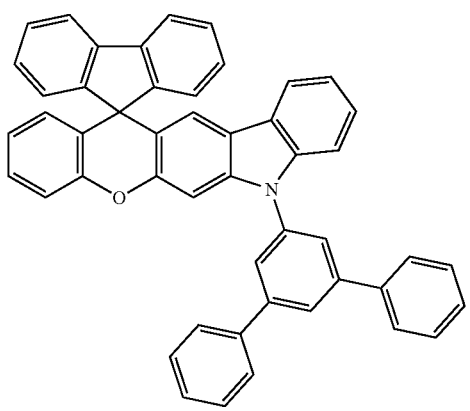
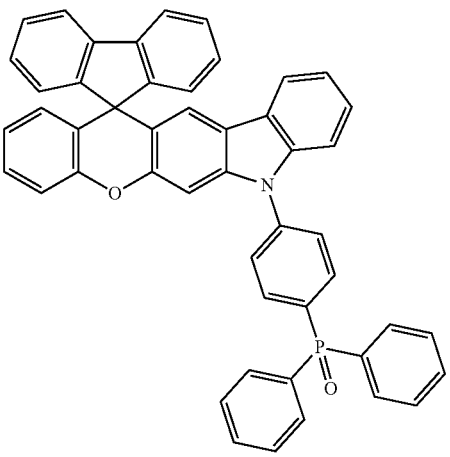
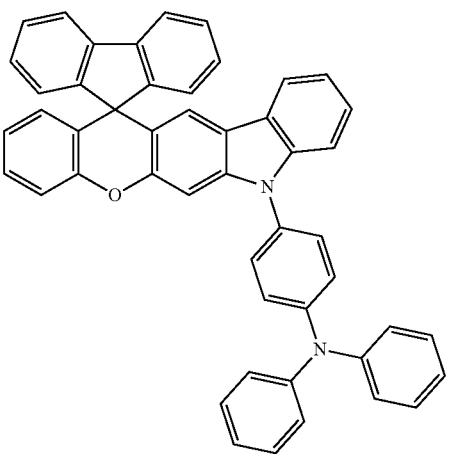

-continued
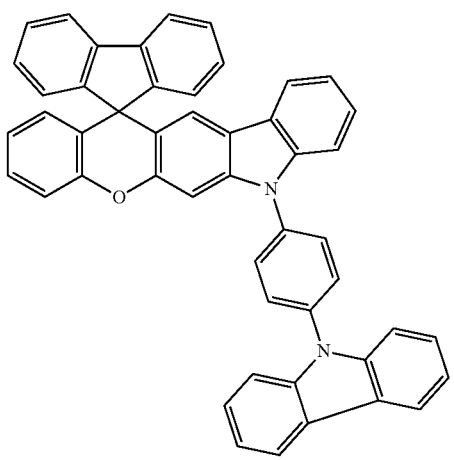
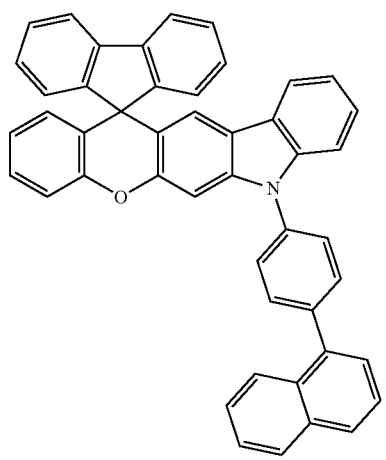
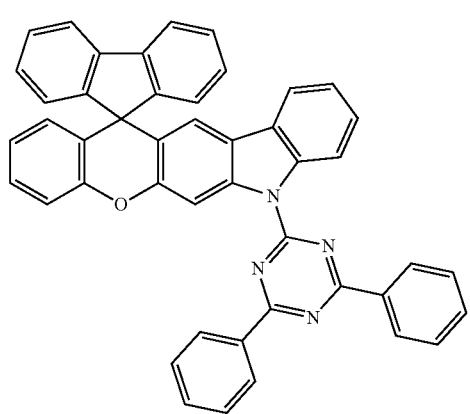
-continued
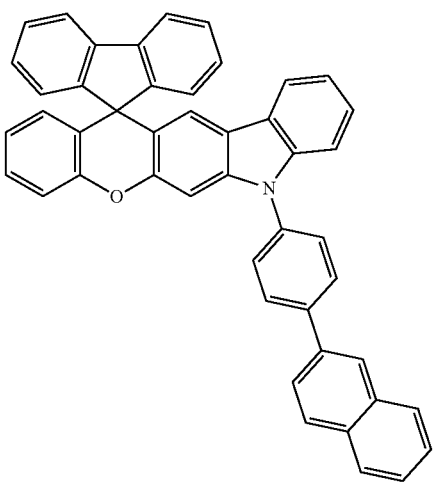
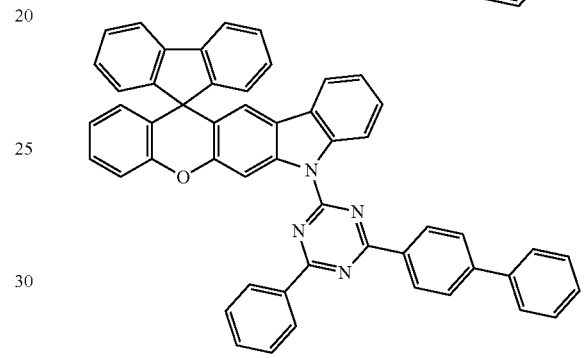
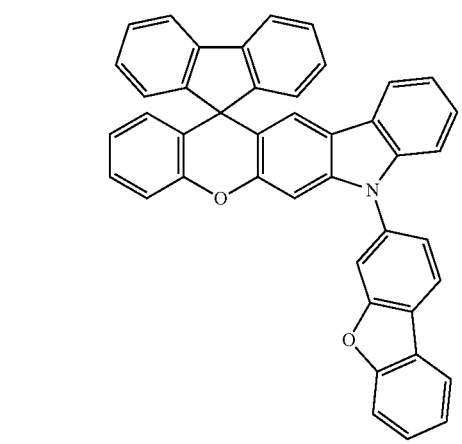
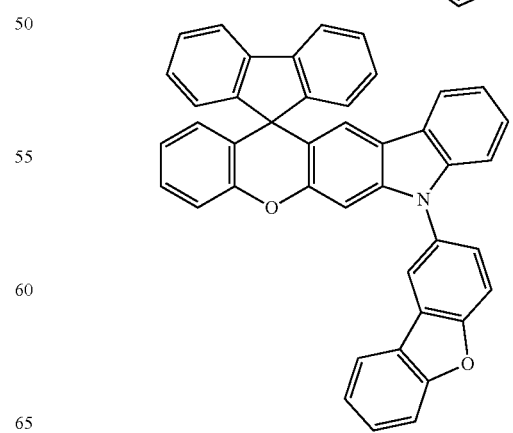

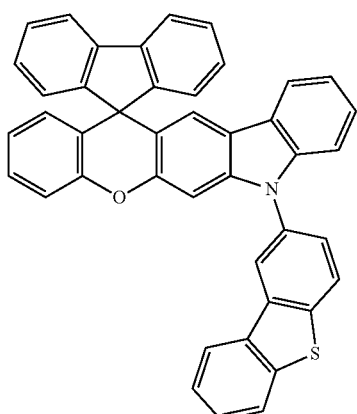
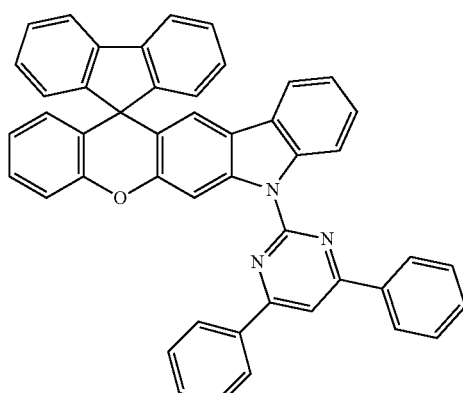
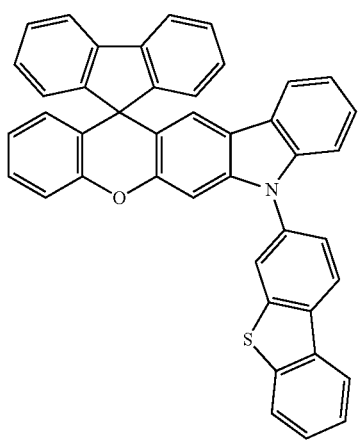
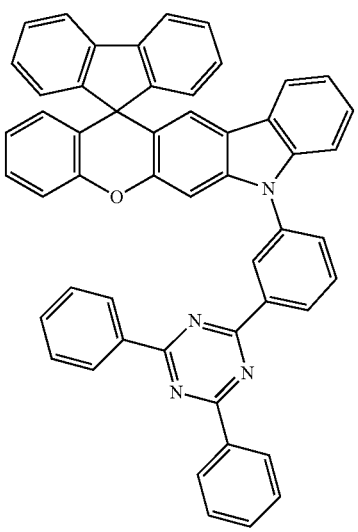
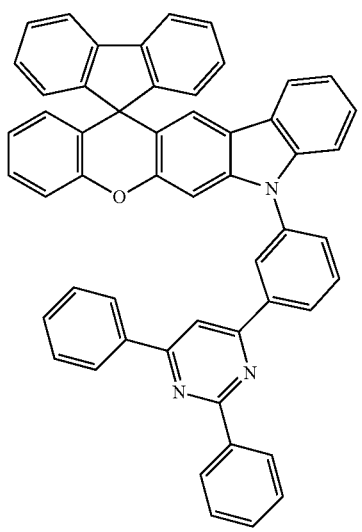
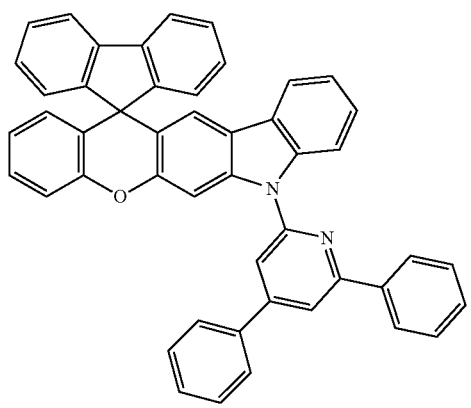

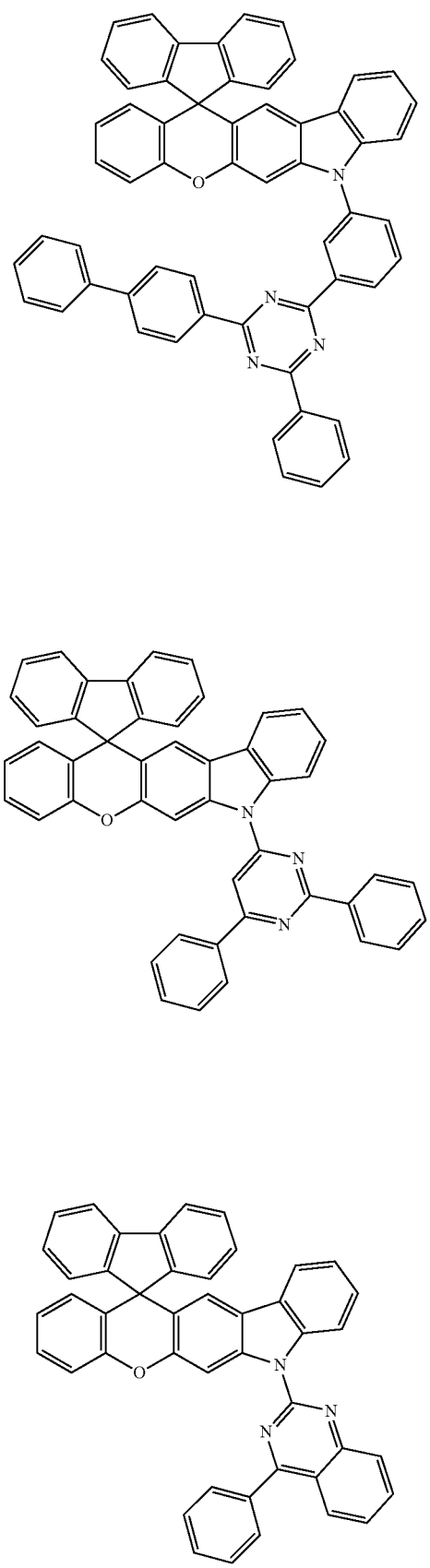
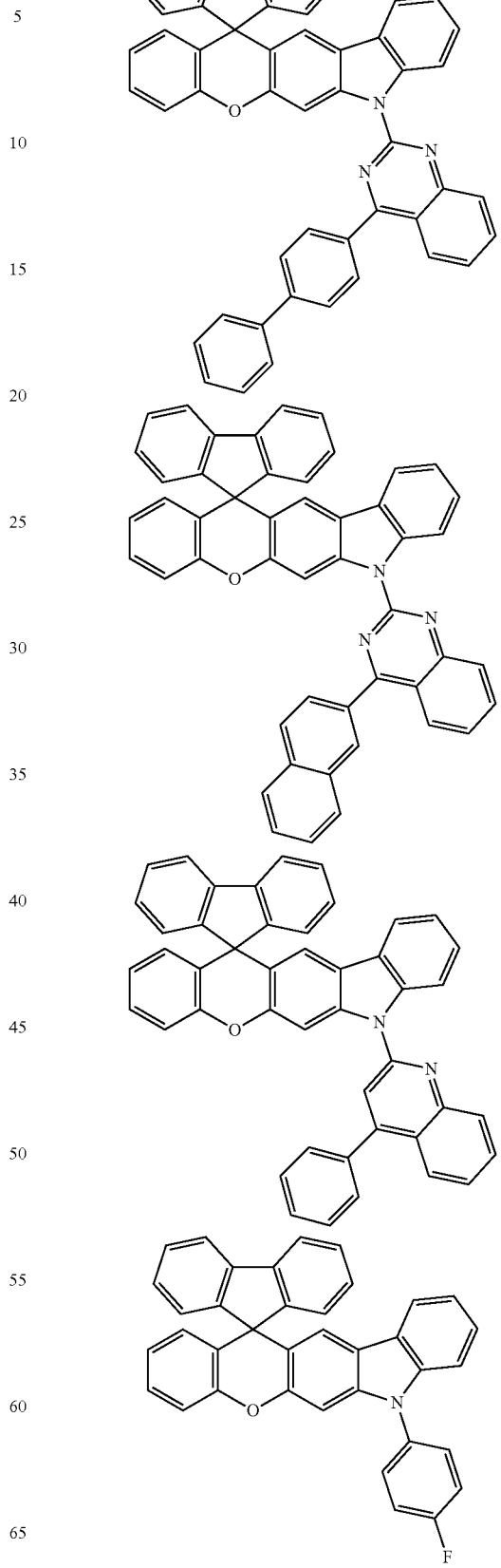

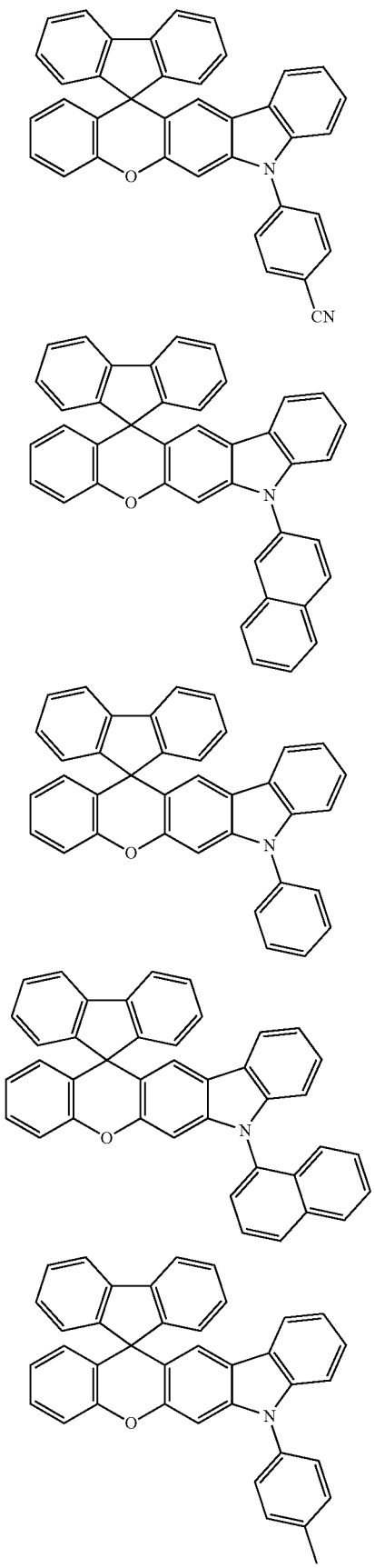
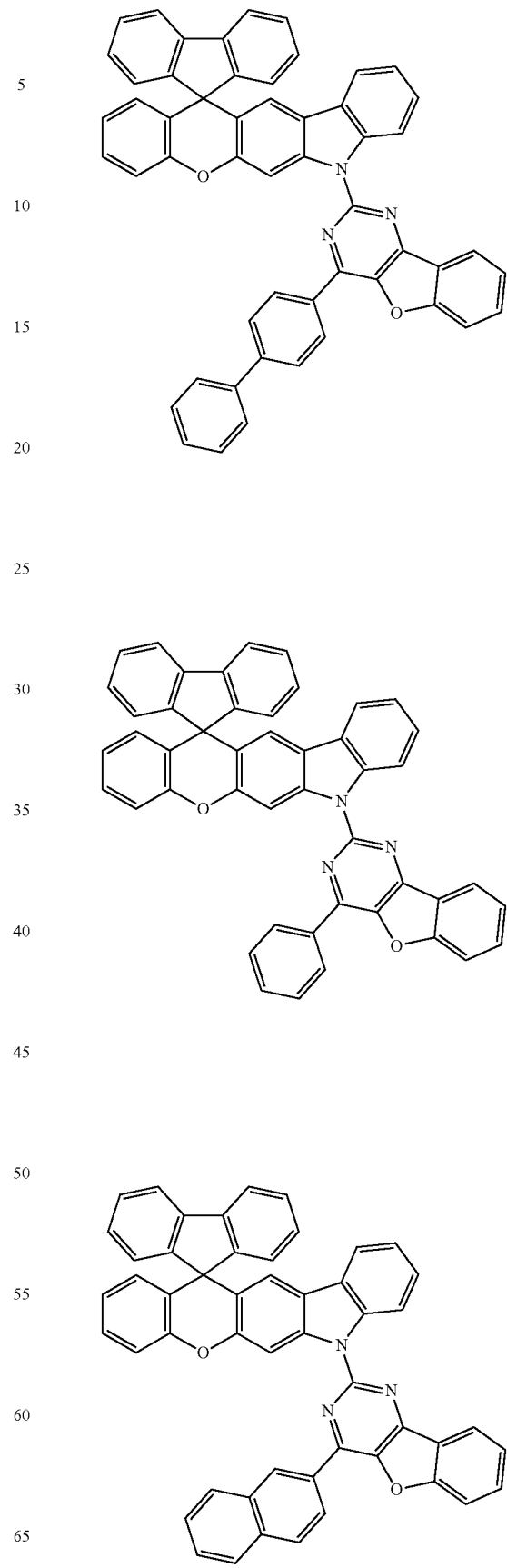

75
-continued
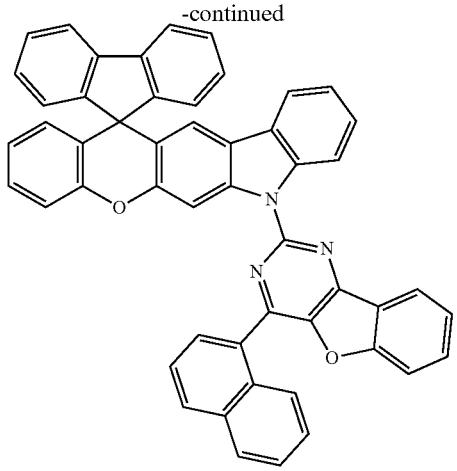
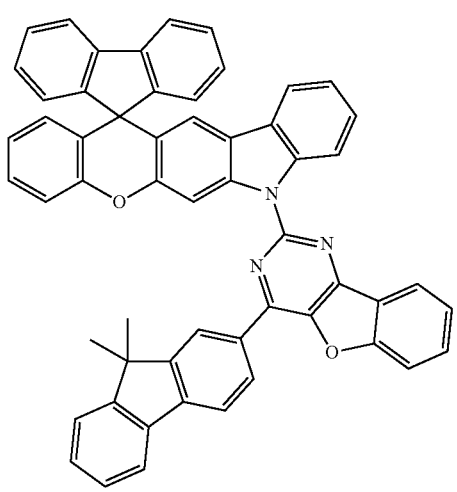
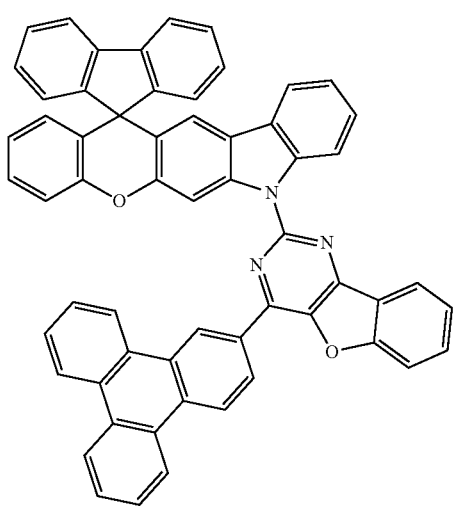
76
-continued
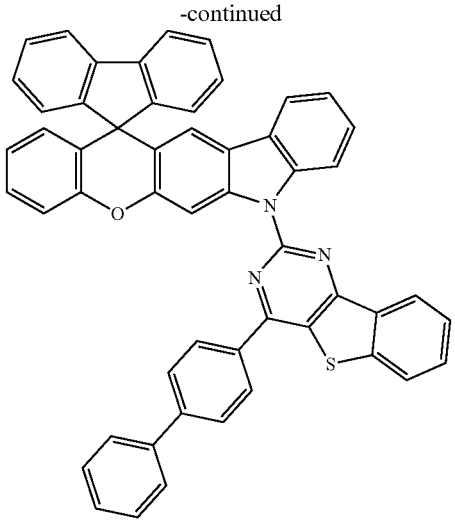
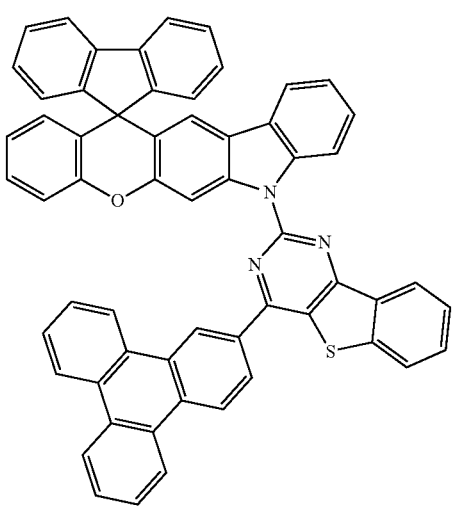
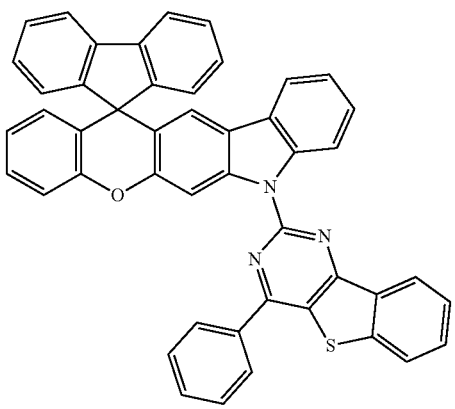

77
-continued
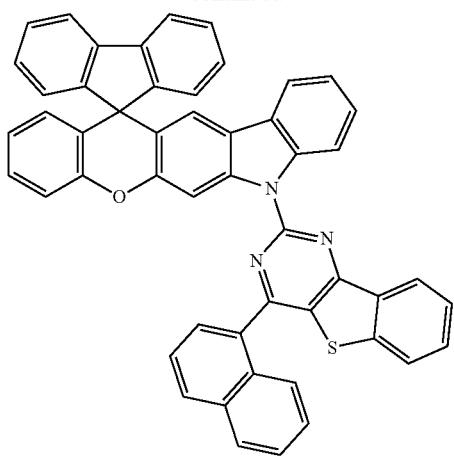
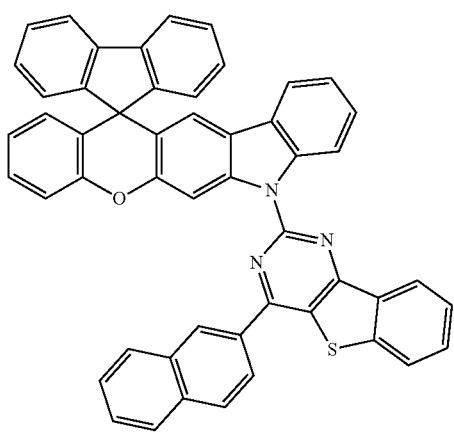
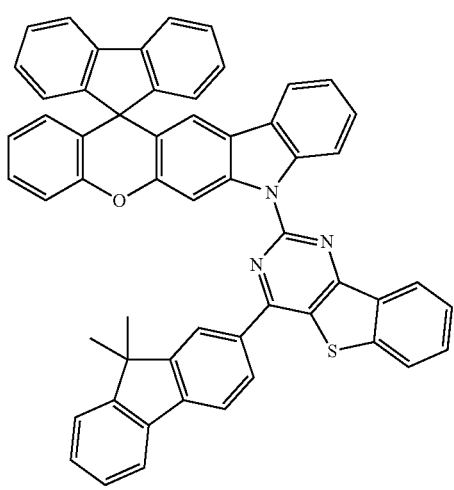
78
-continued
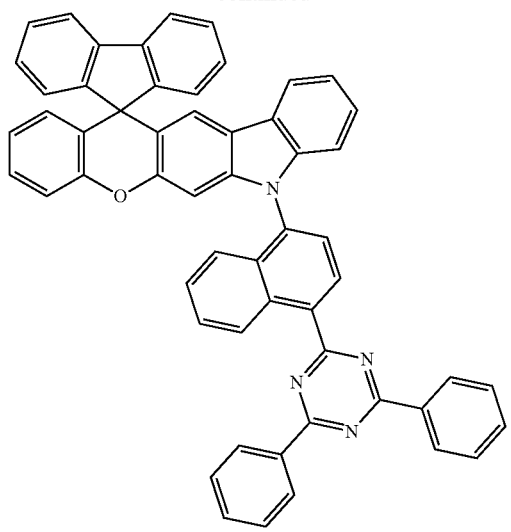
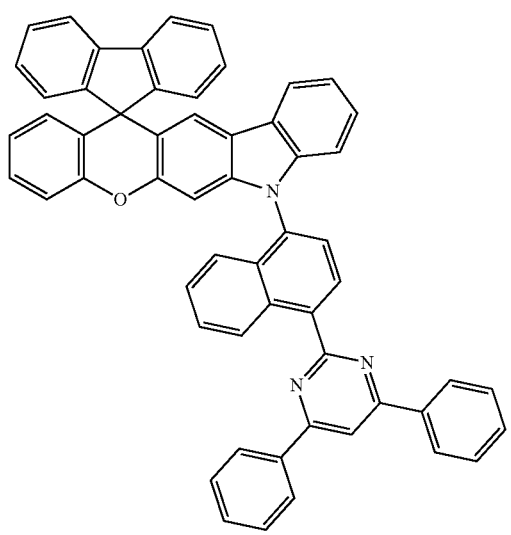
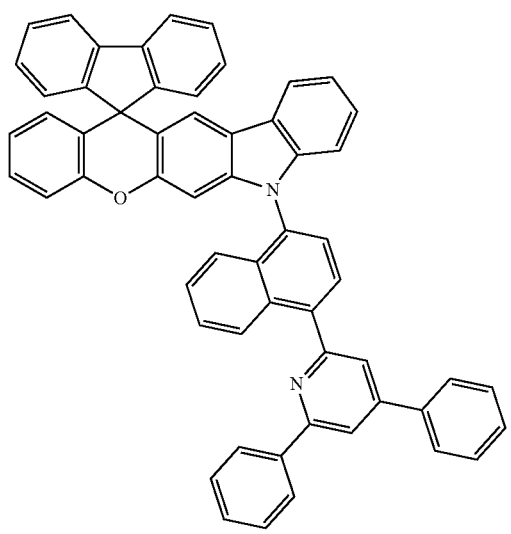

79
-continued
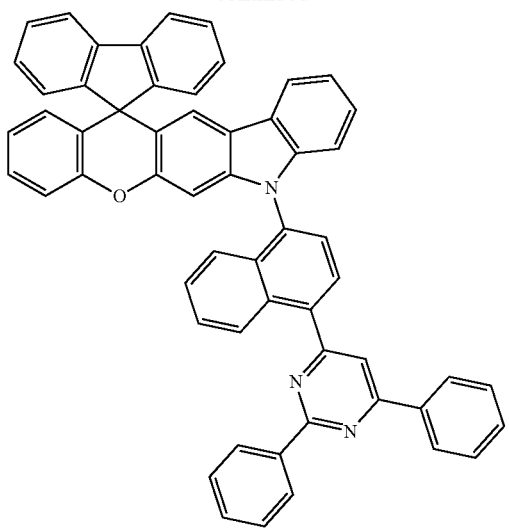
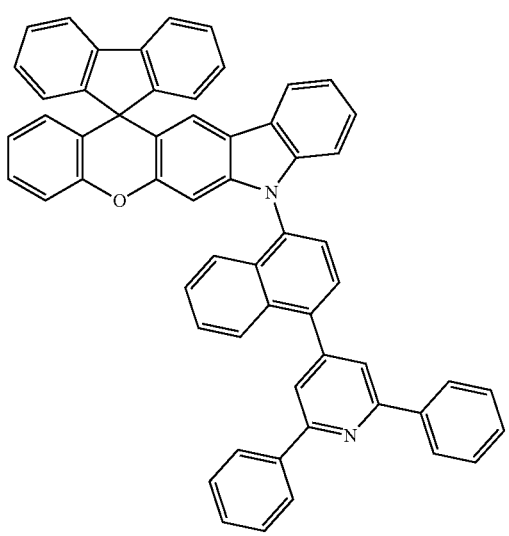
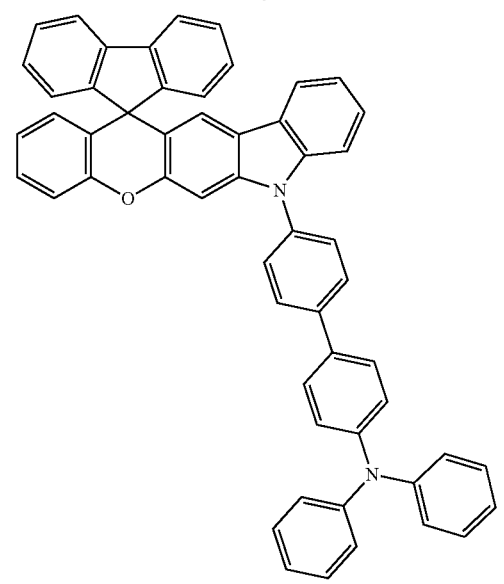
80
-continued
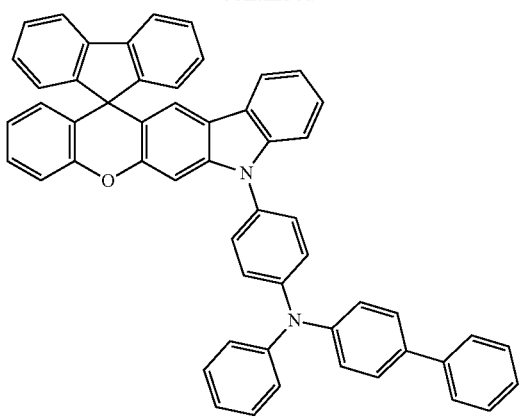
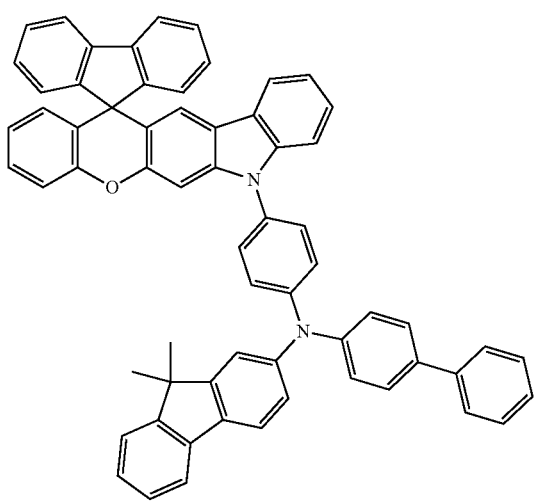
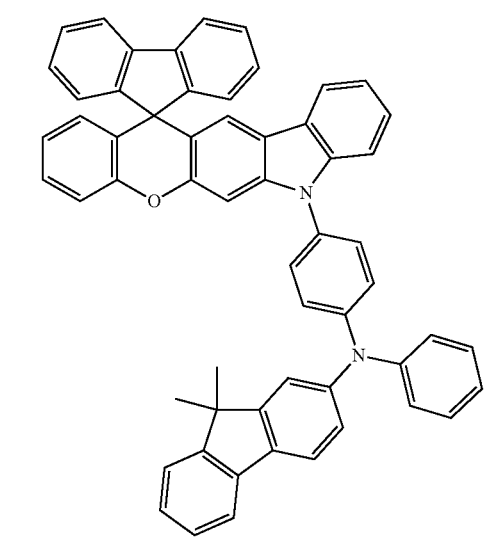

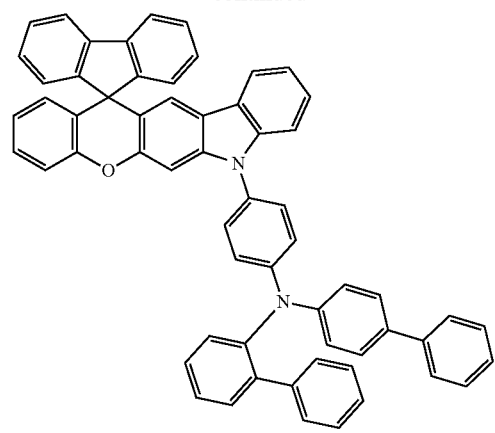
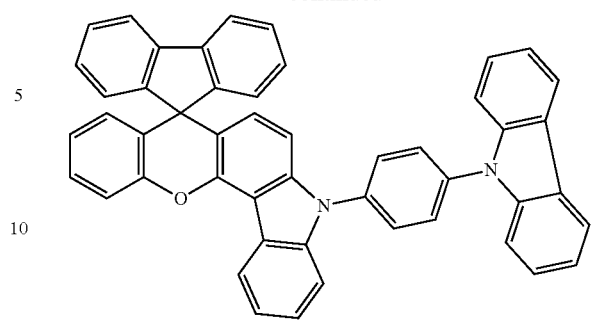
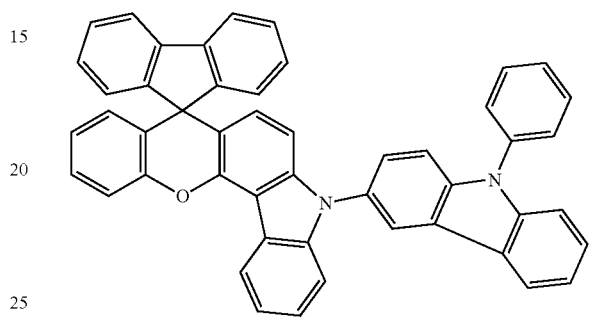
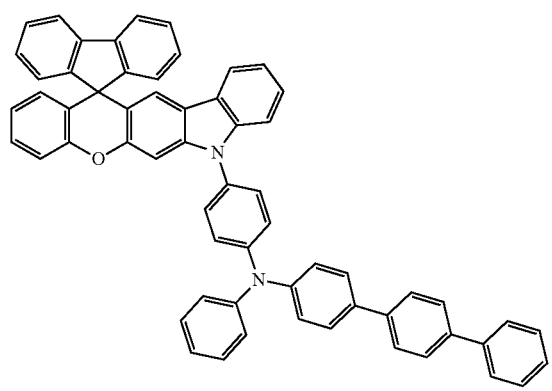
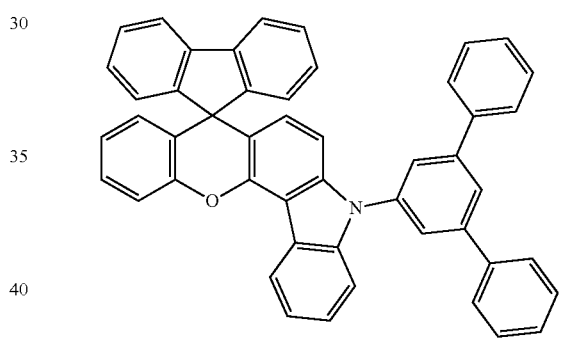
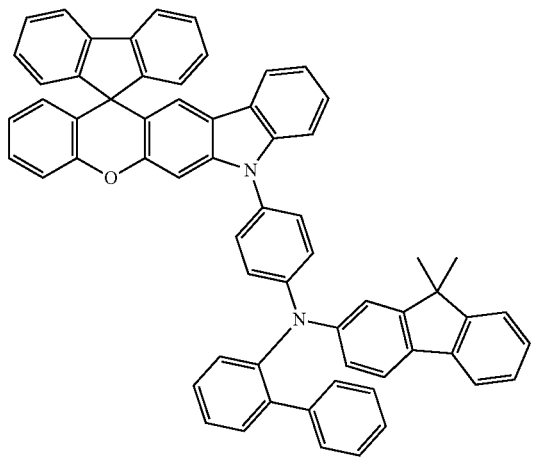
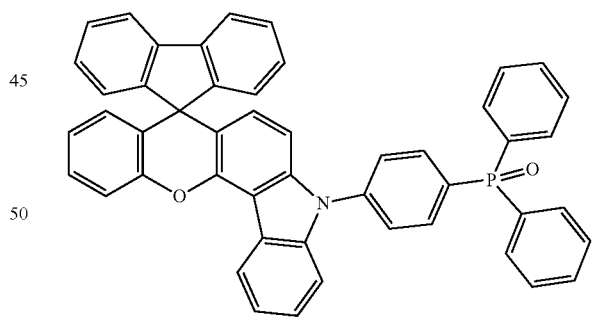
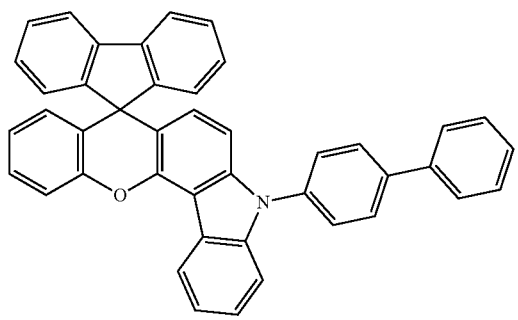
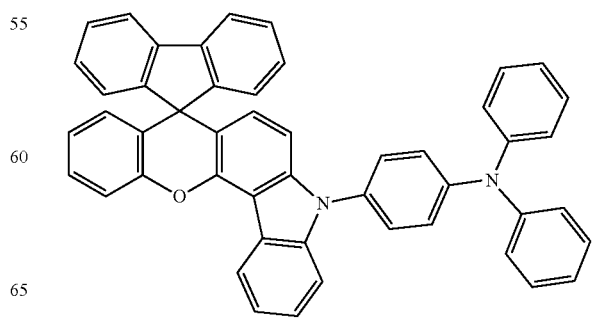

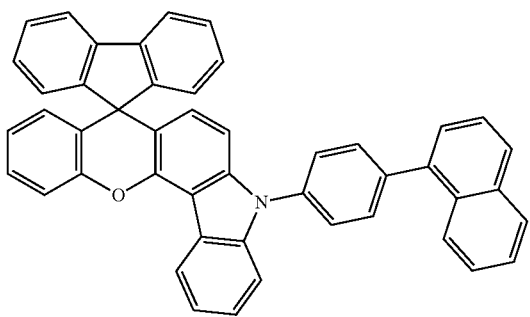
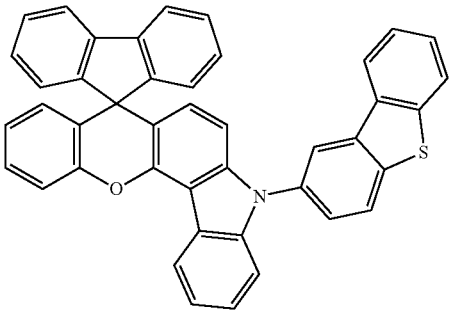
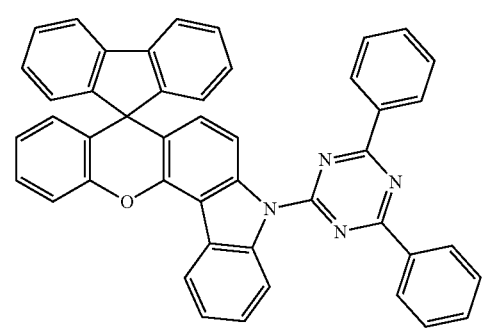
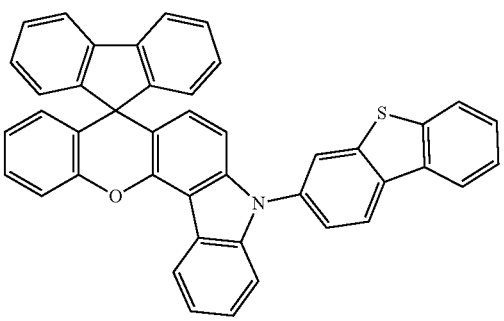
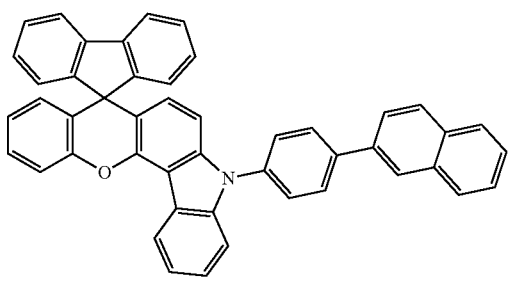
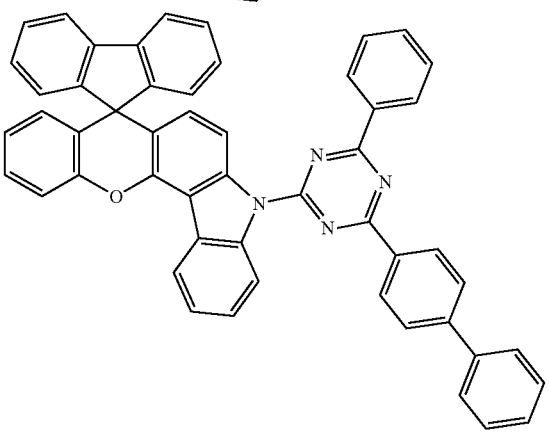
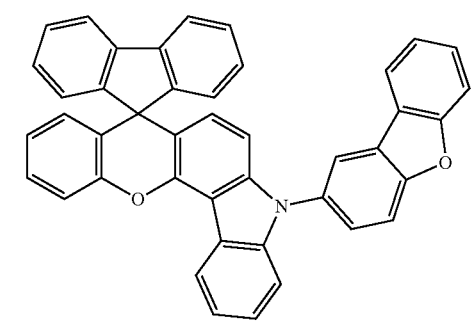
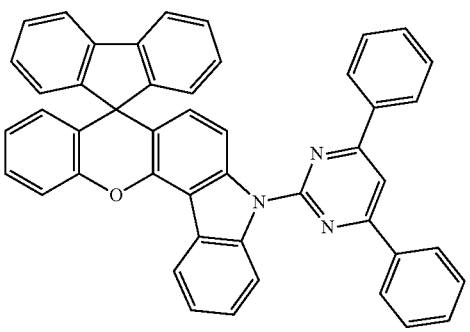
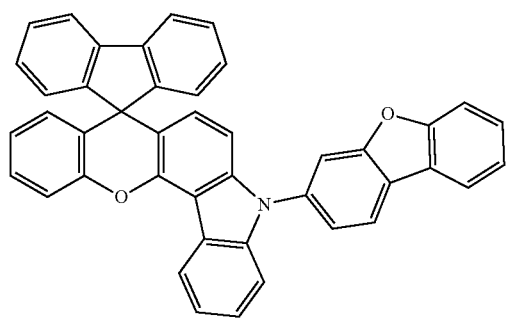
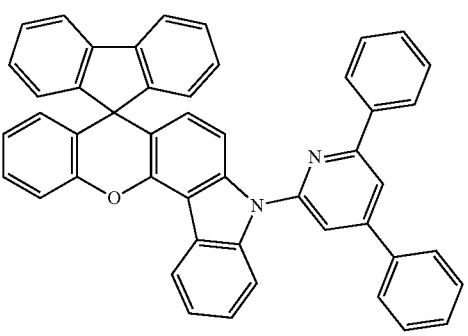

85
-continued
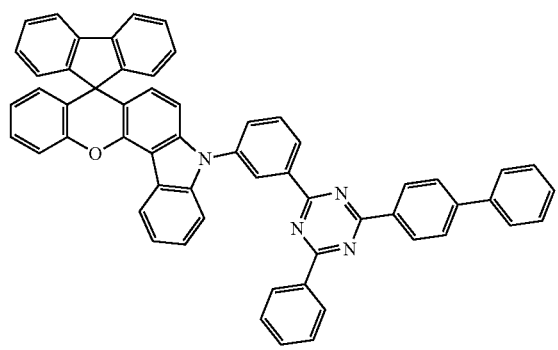
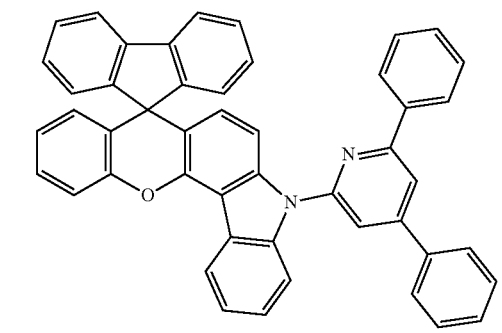
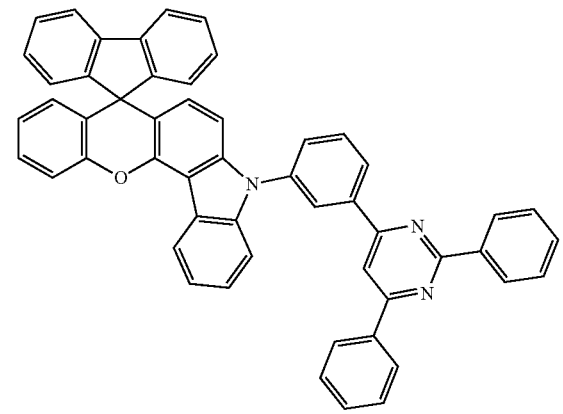
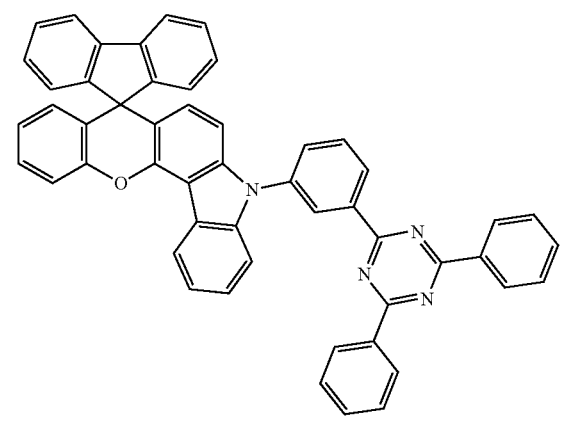
86
-continued
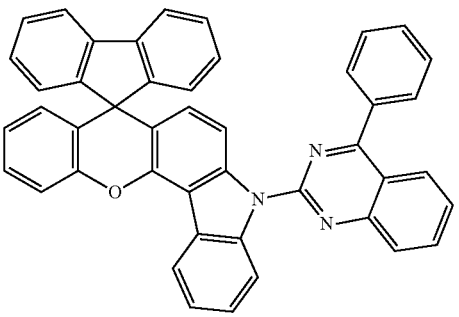
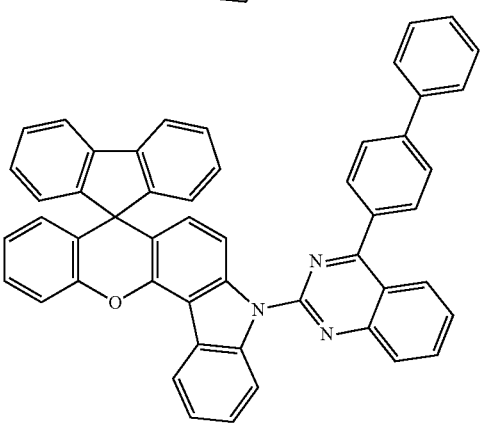
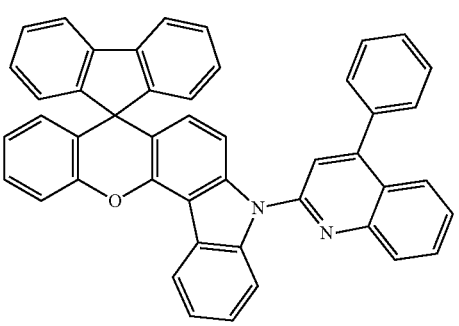
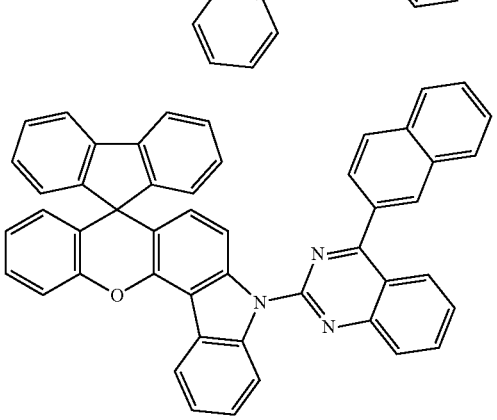
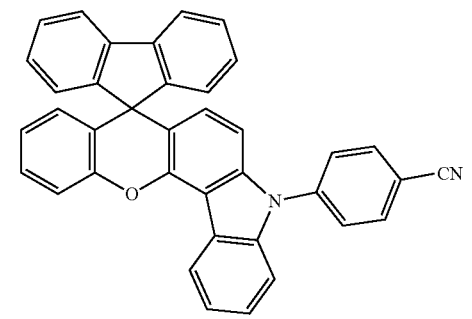

87
-continued
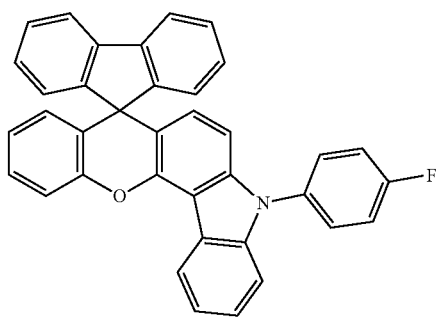
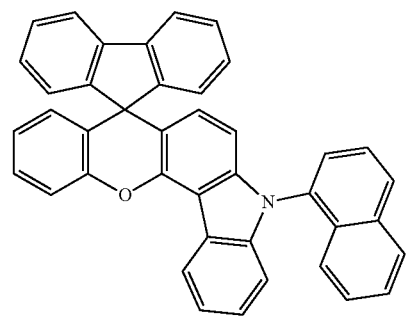
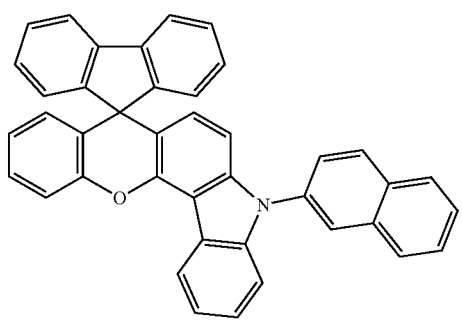
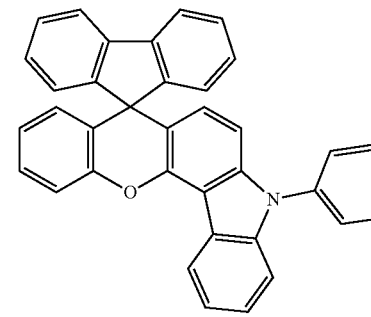
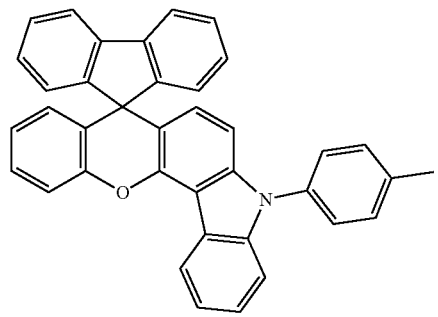
88
-continued
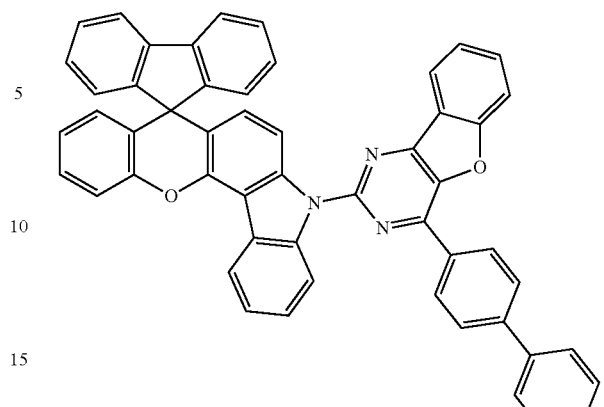
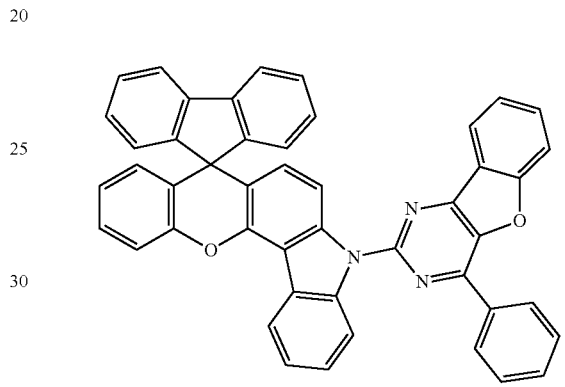
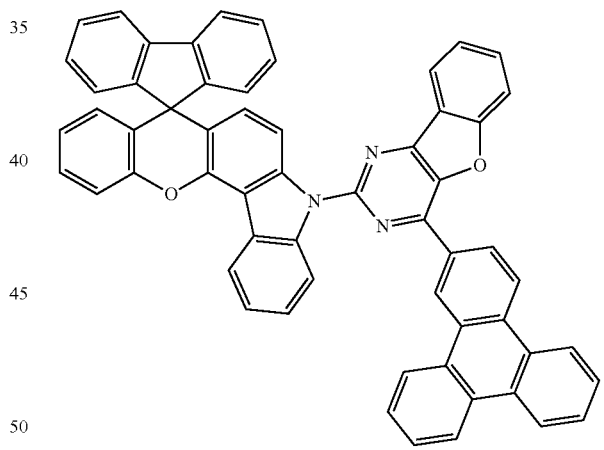
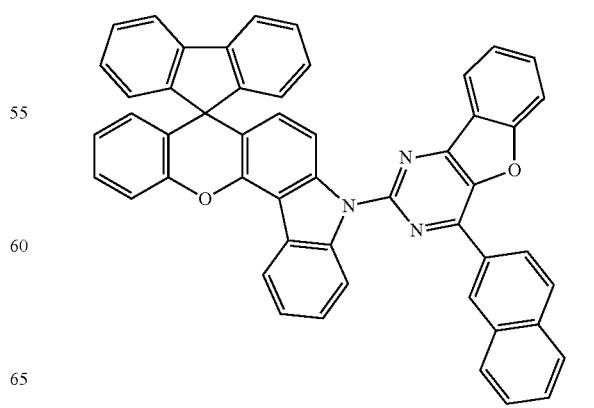

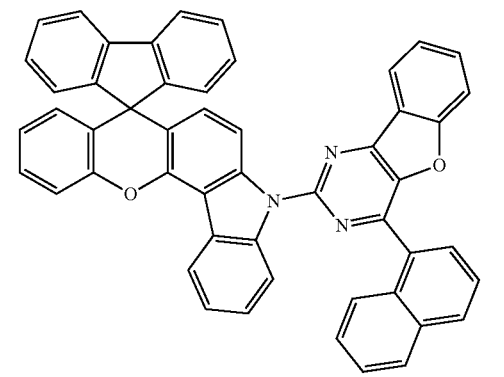
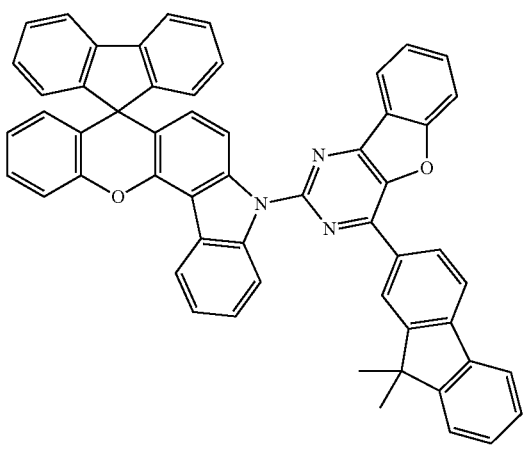
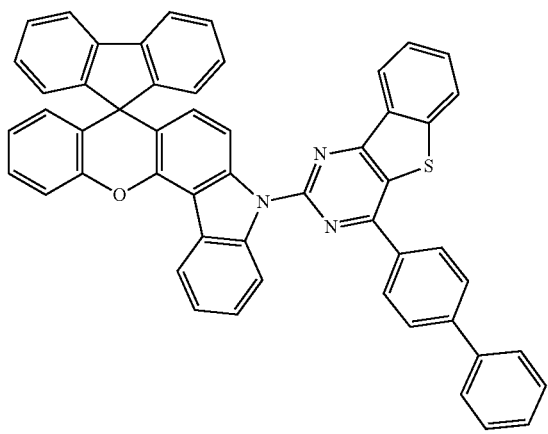
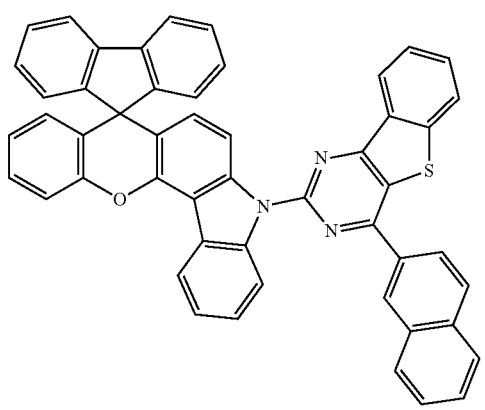
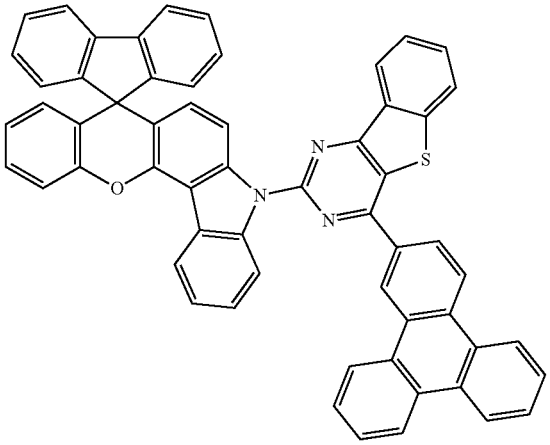
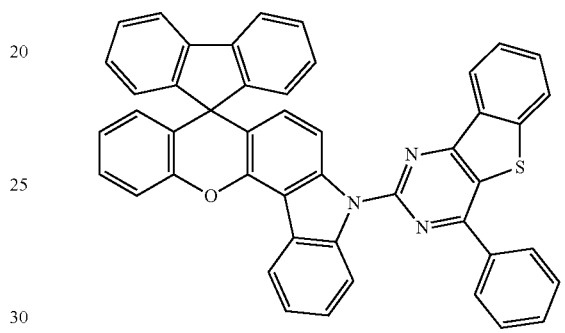
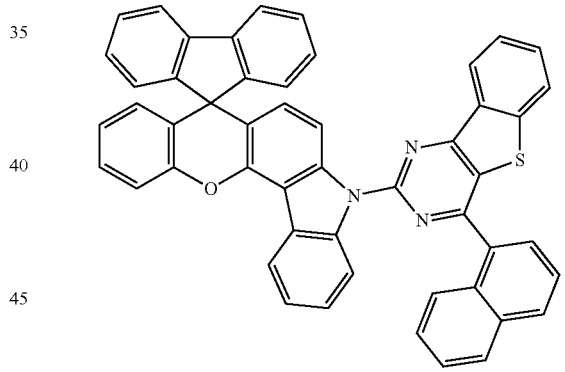
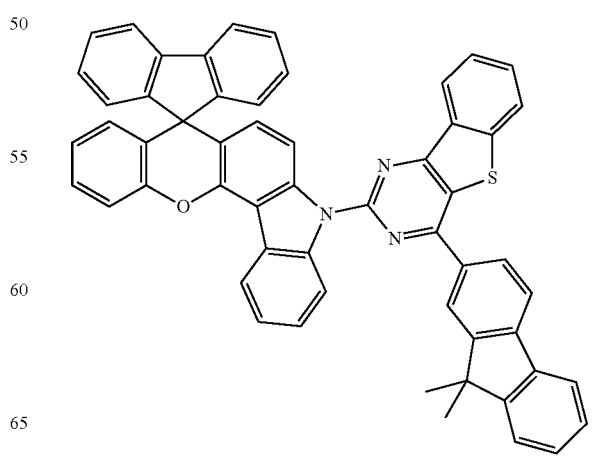

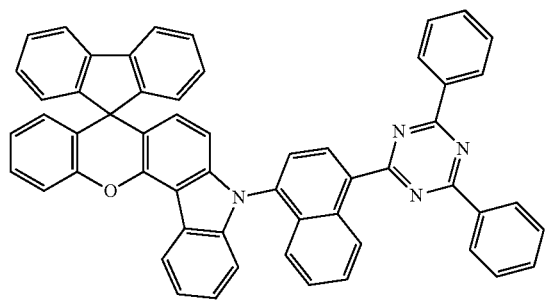
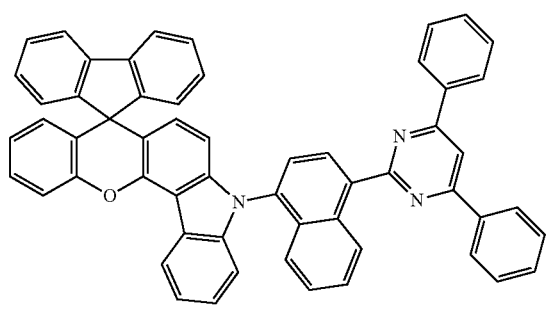
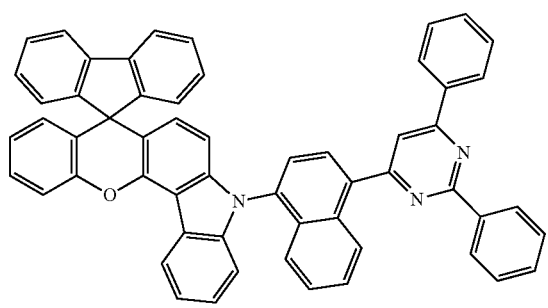
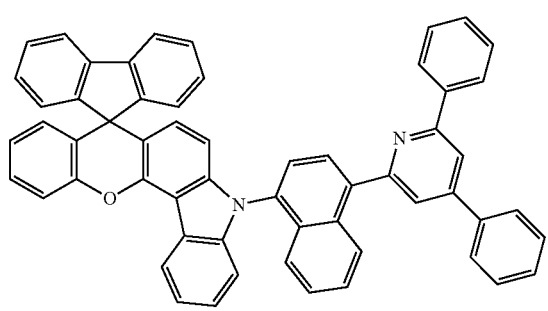
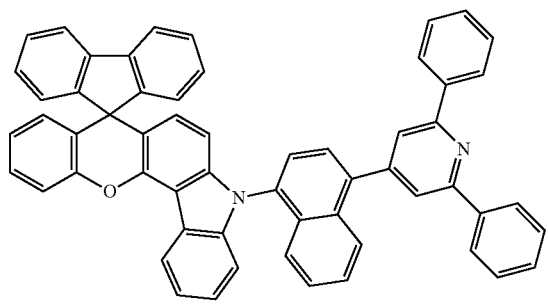
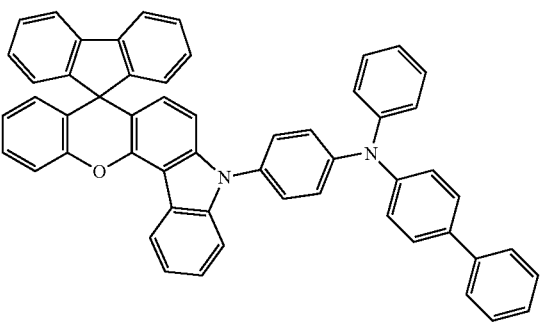
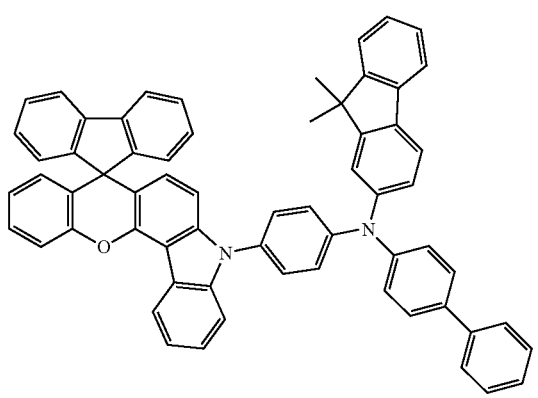
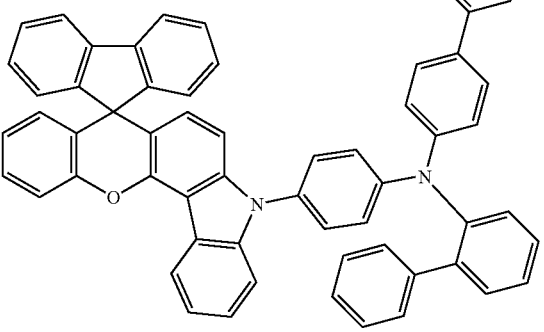
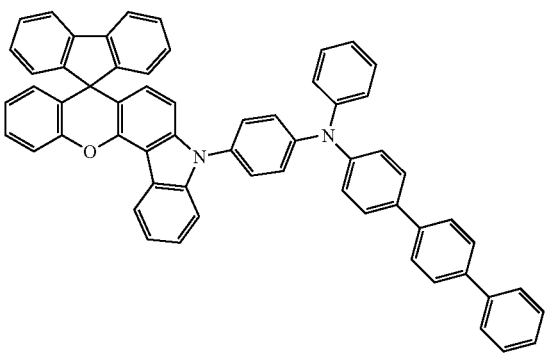

93
-continued
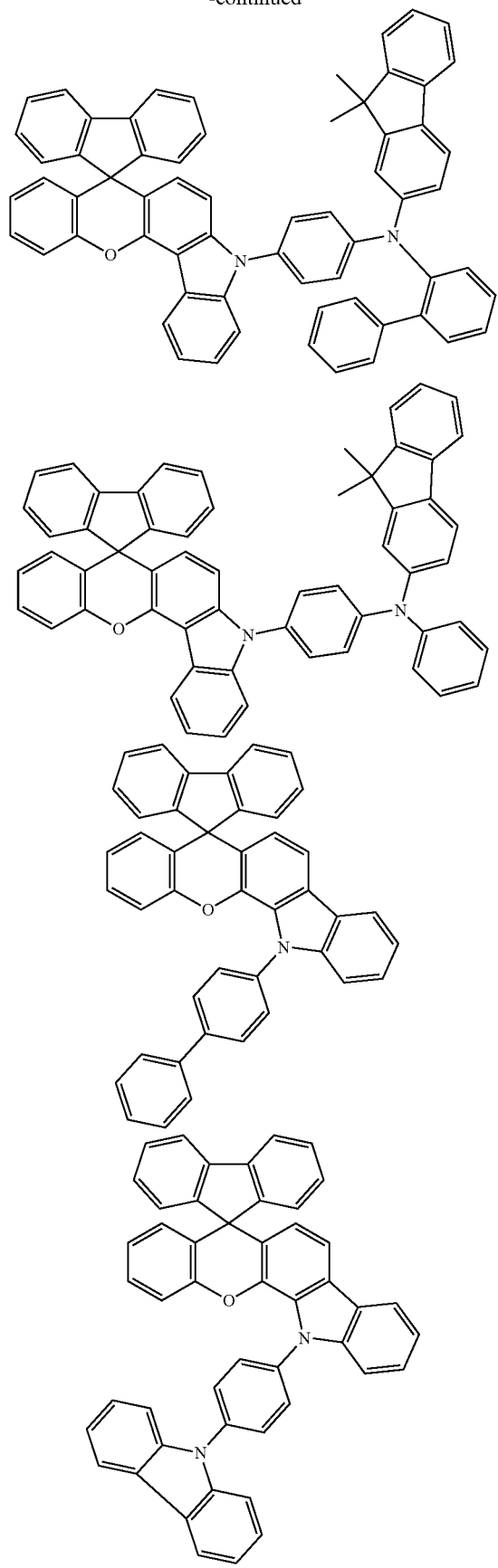
94
-continued
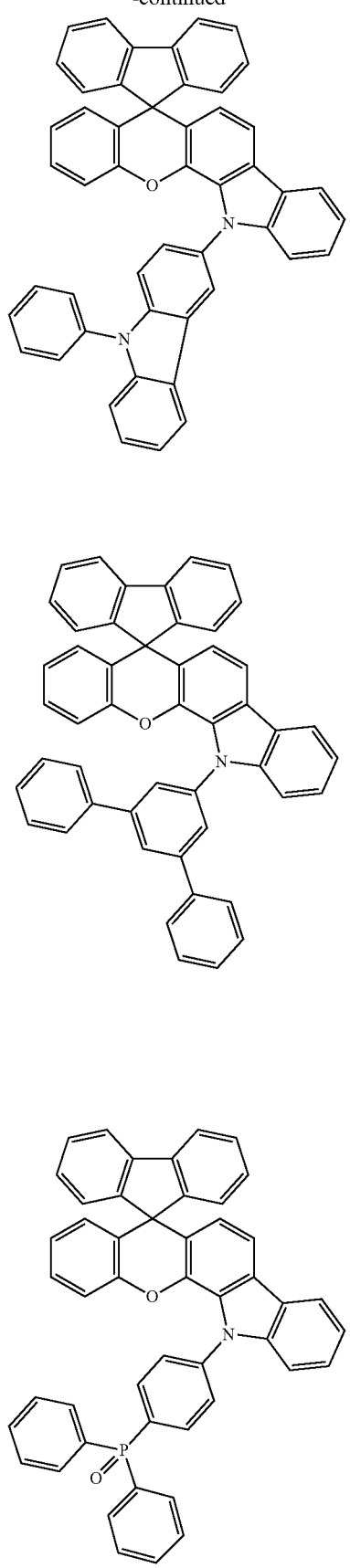

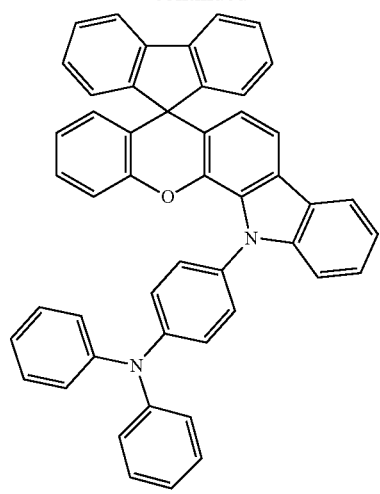
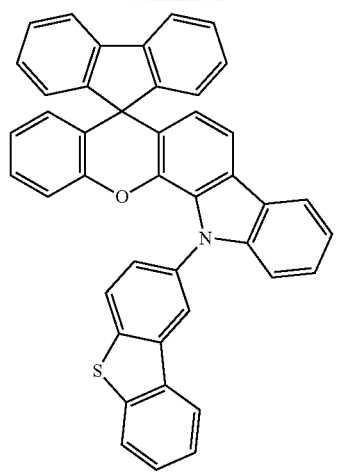
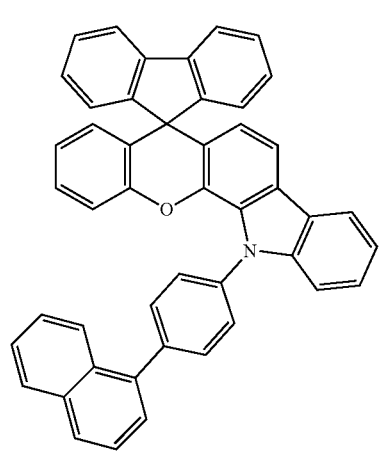
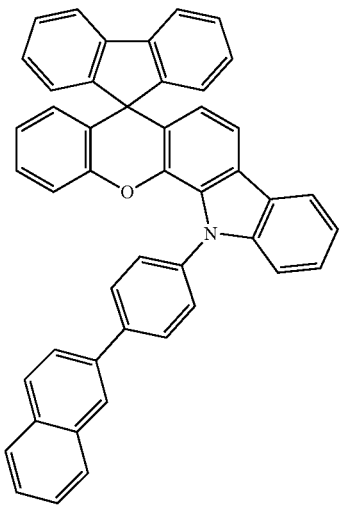
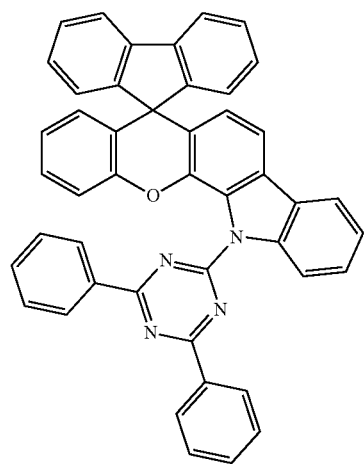
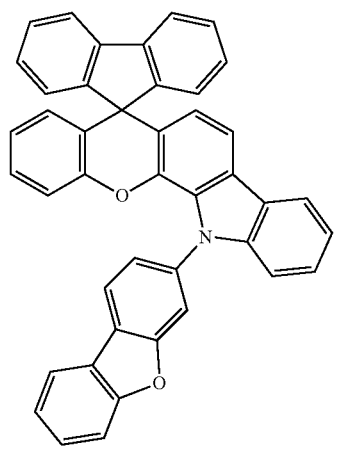

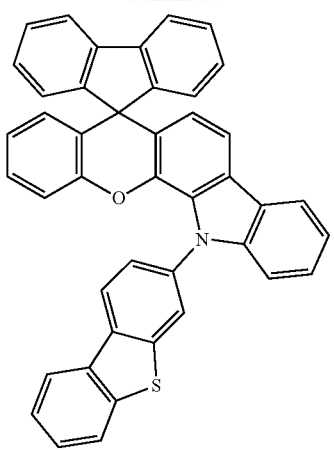
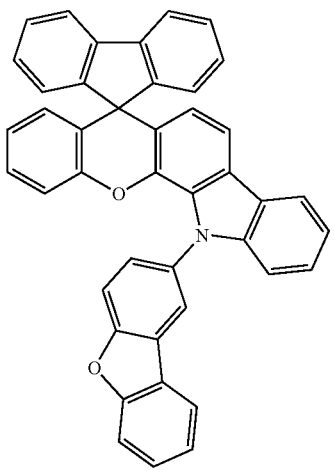
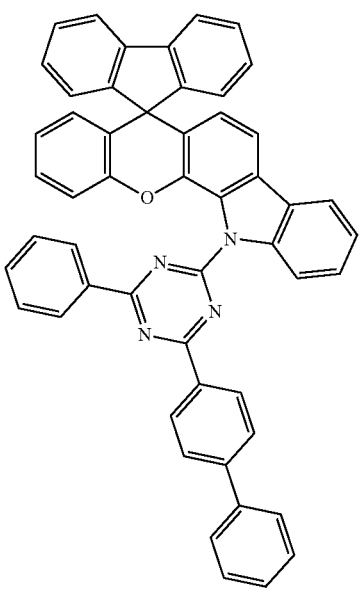
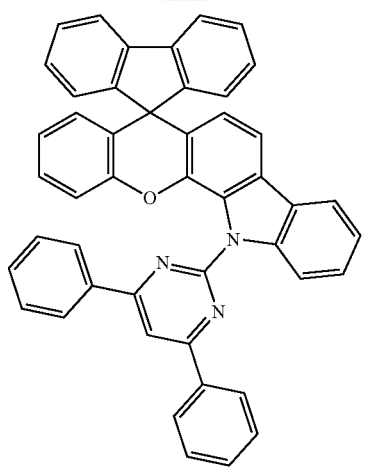
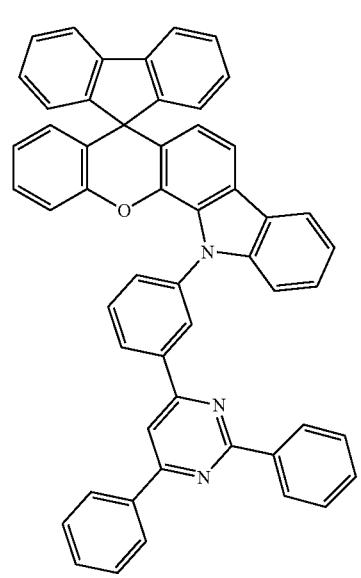
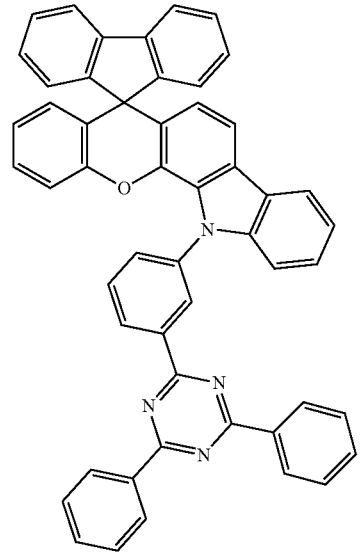

99
-continued
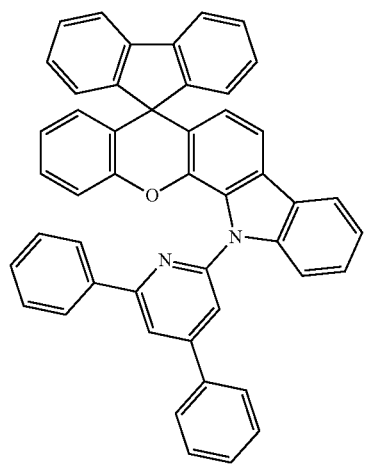
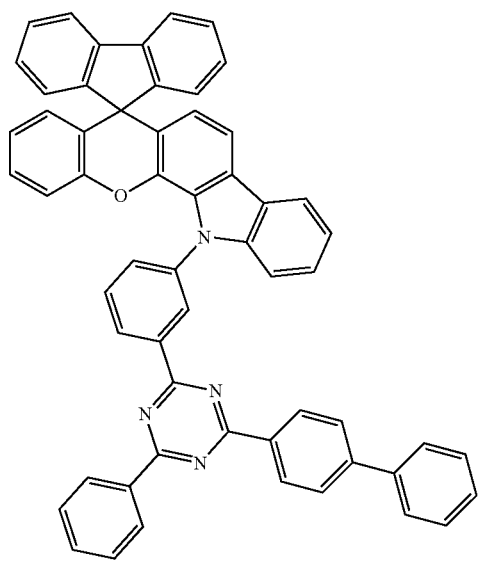
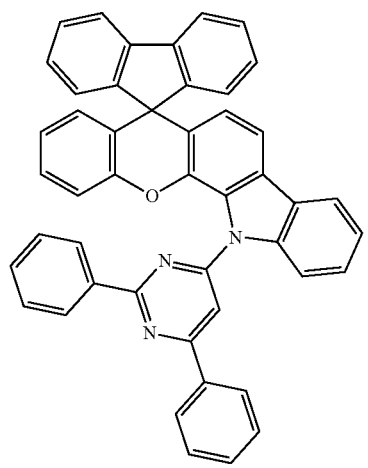
100
-continued
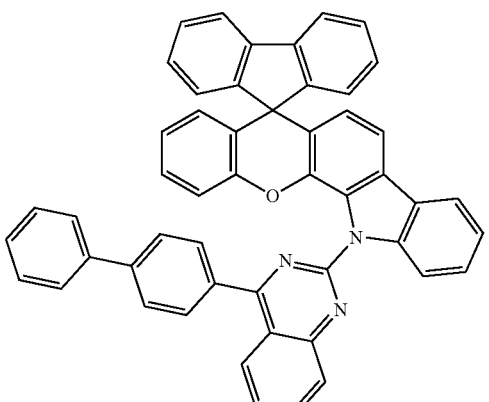
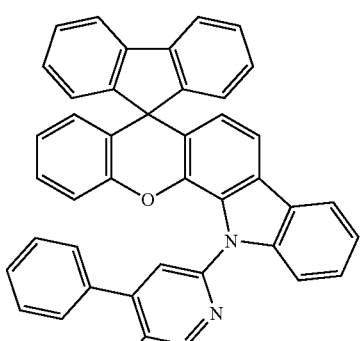
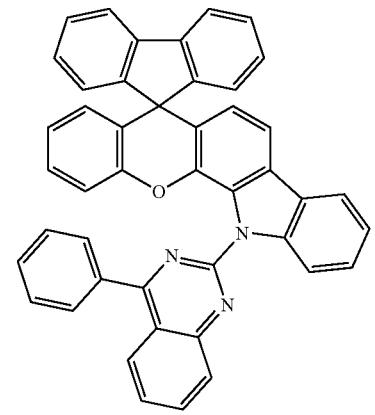
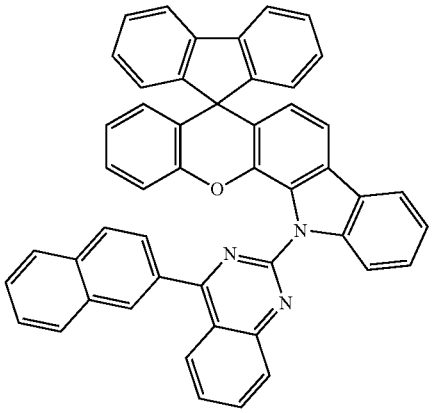

101
-continued
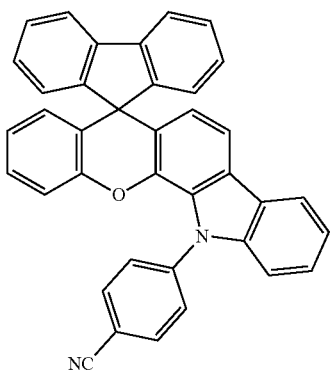
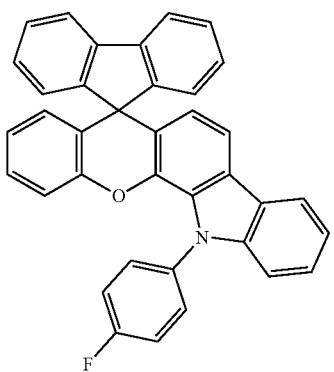
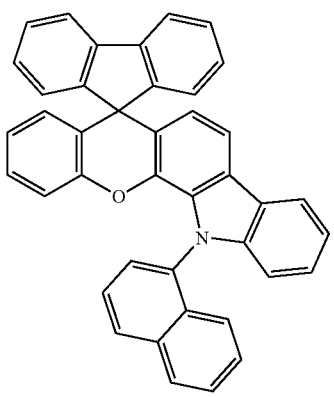
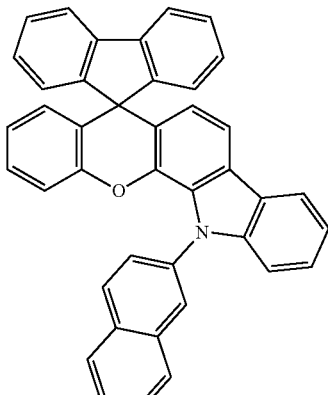
102
-continued
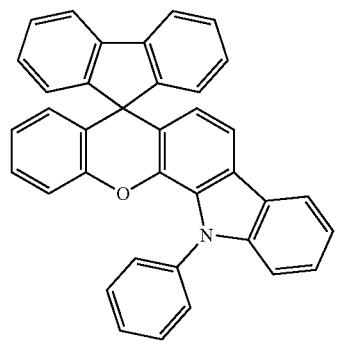
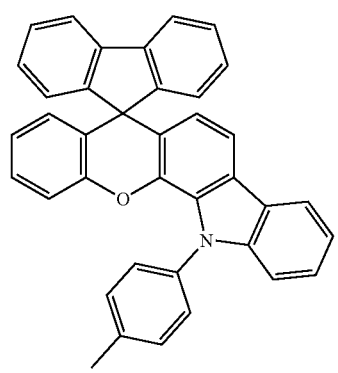
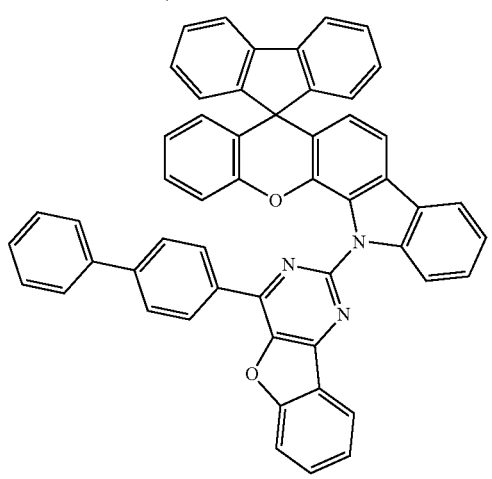
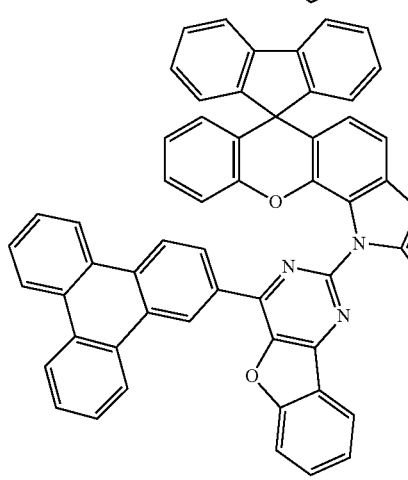

103
-continued
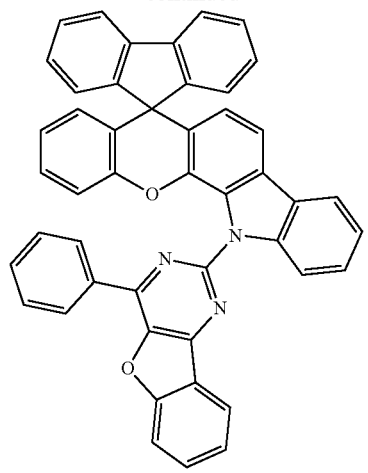
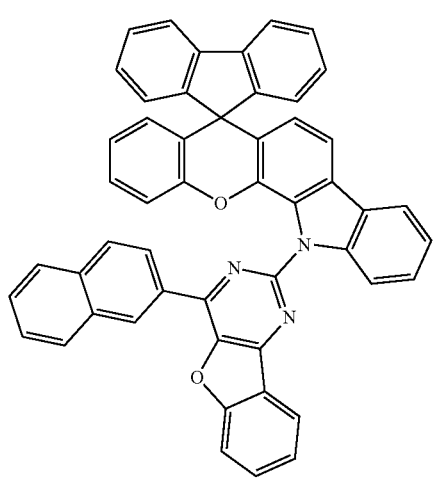
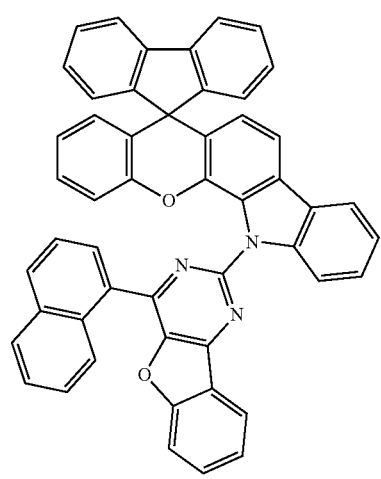
104
-continued
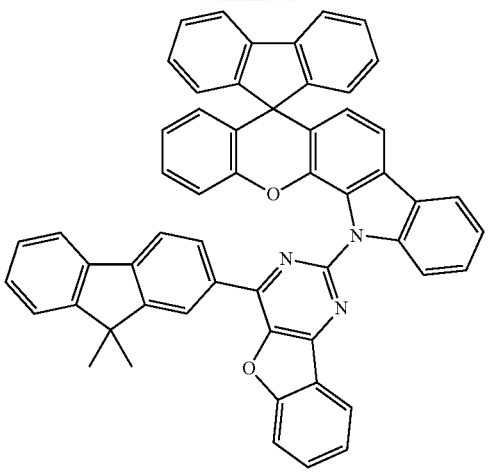
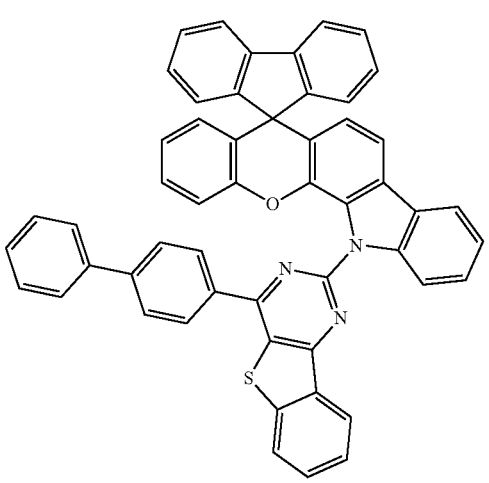
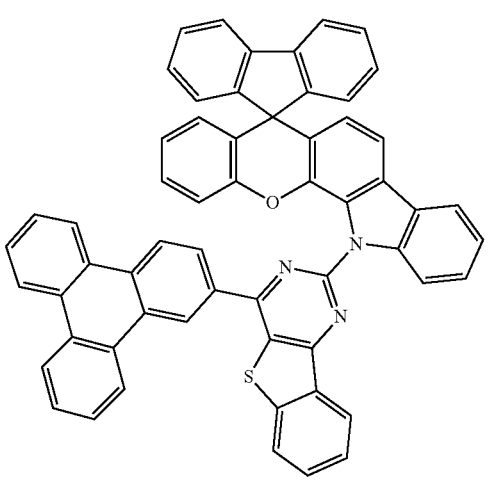

105
-continued
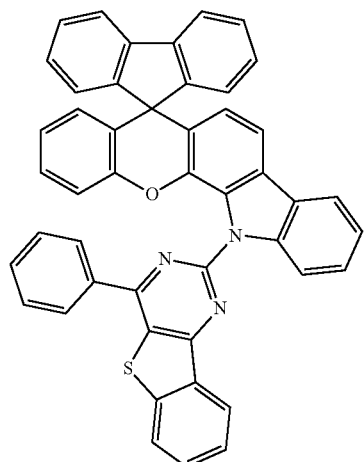
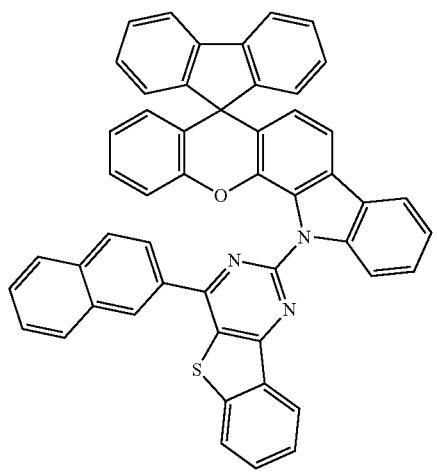
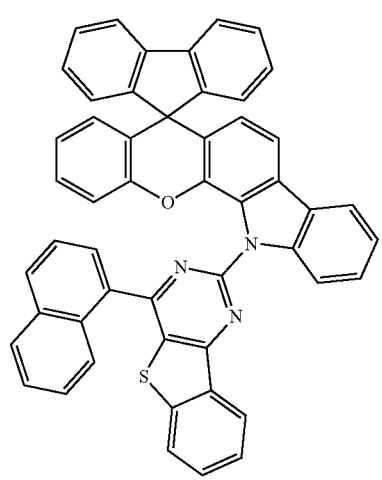
106
-continued
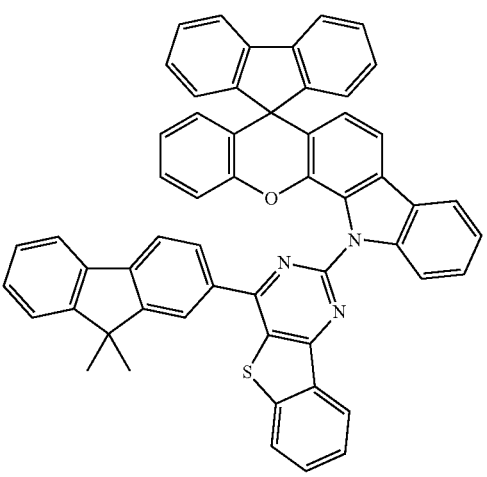
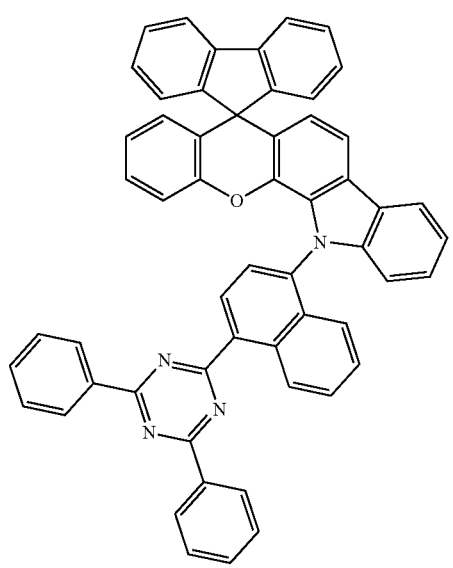
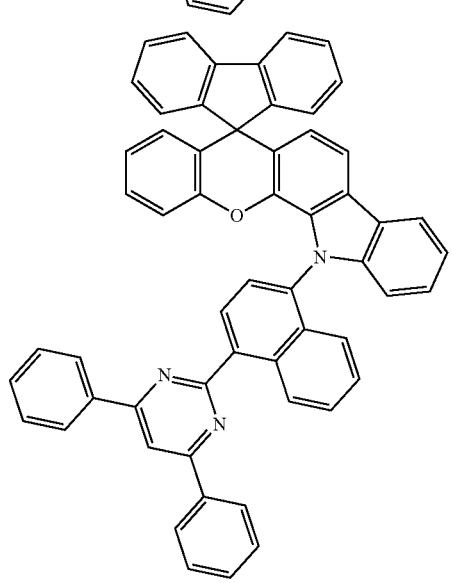

107
-continued
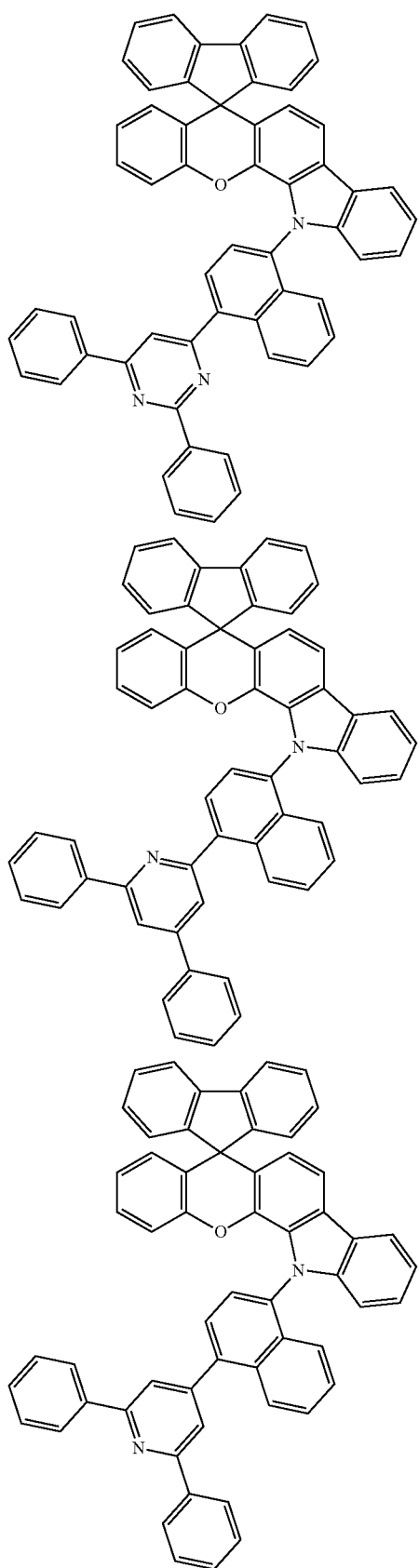
108
-continued
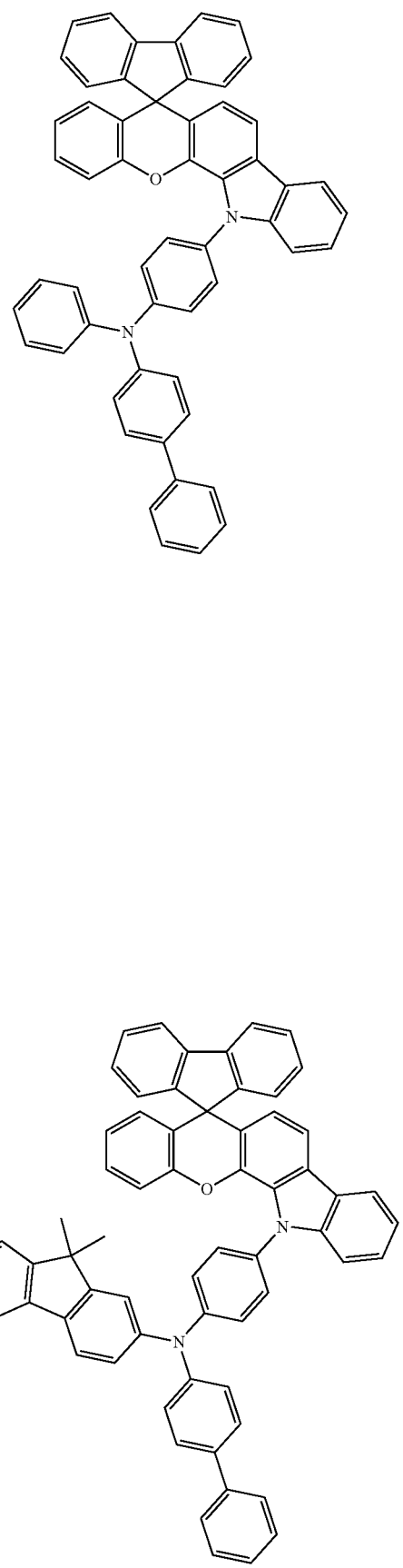

109
-continued

110
-continued
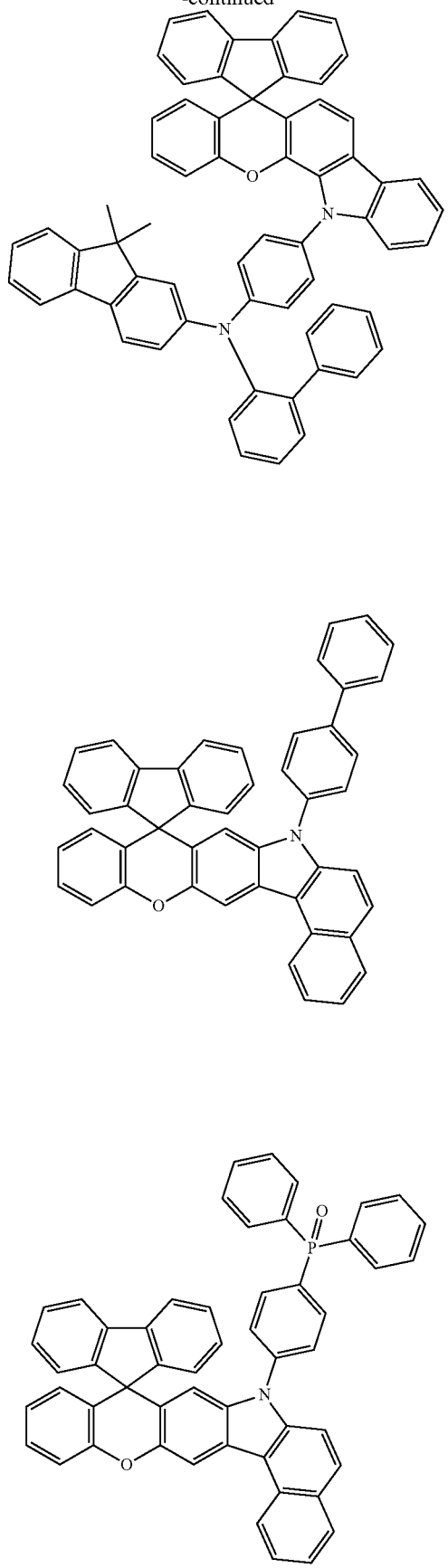

111
-continued
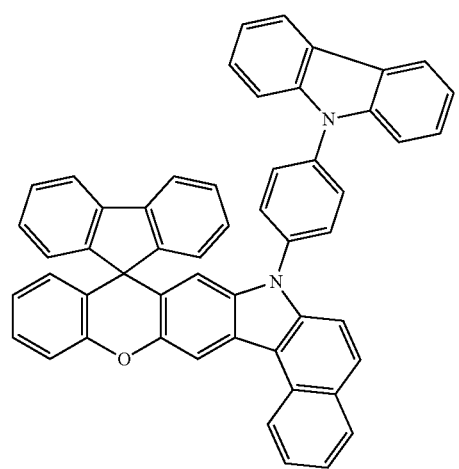
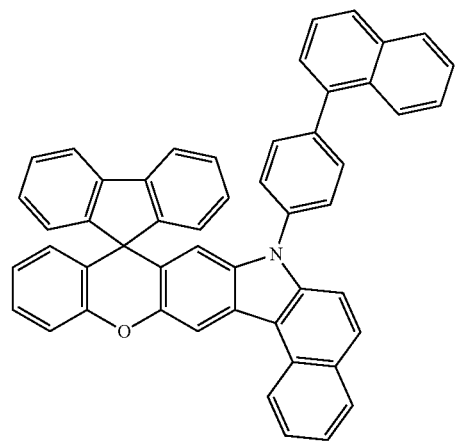
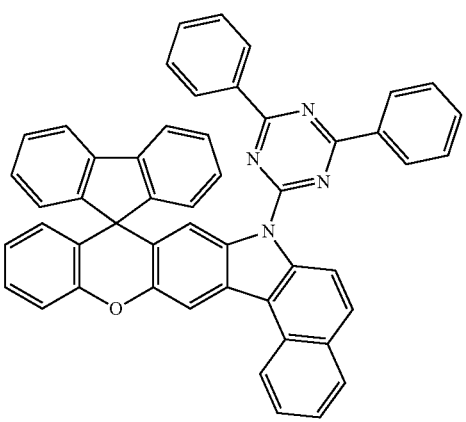
112
-continued
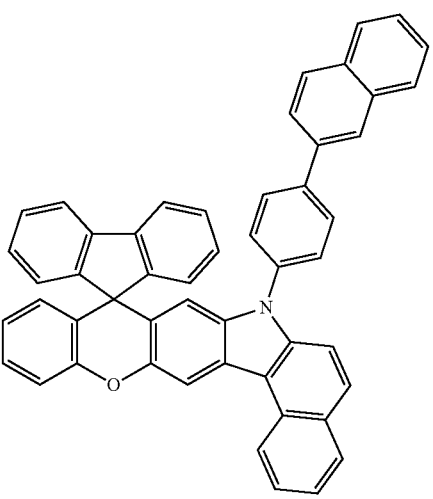
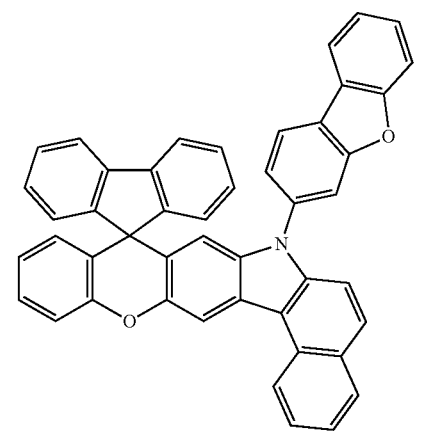

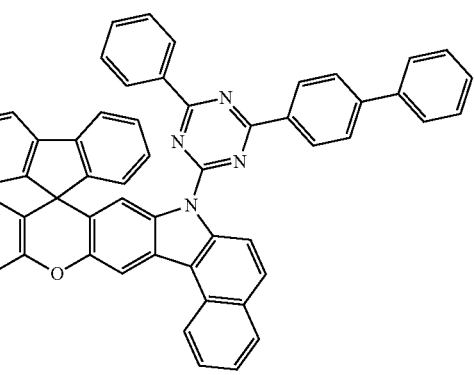

-continued
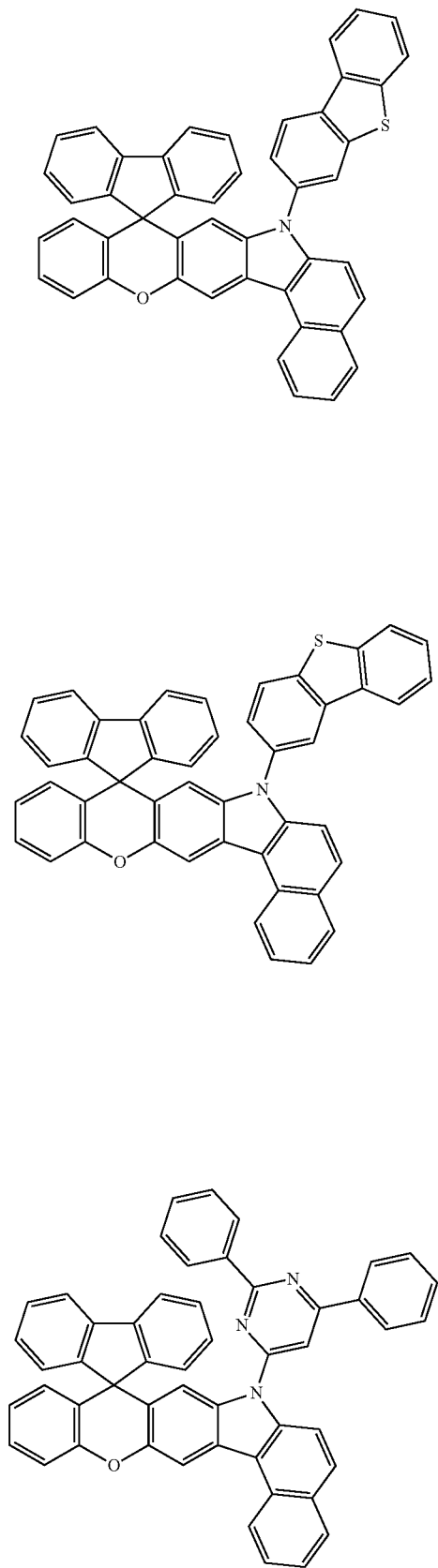
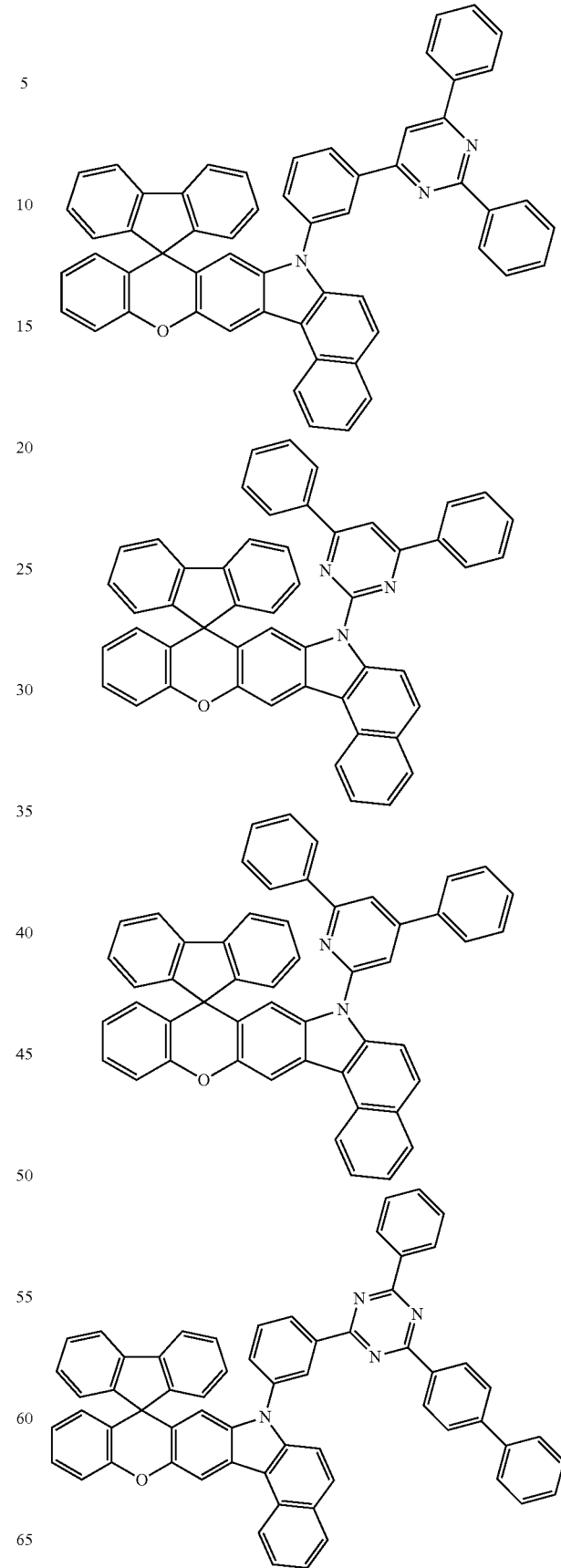

115
-continued
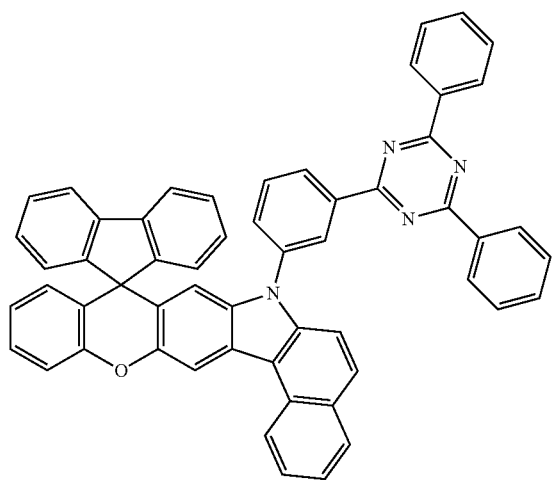
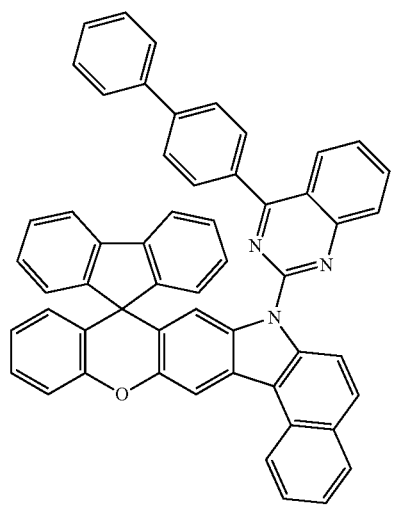
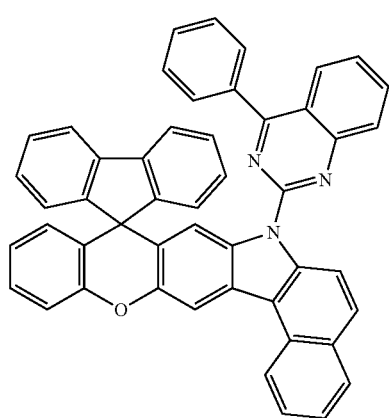
116
-continued
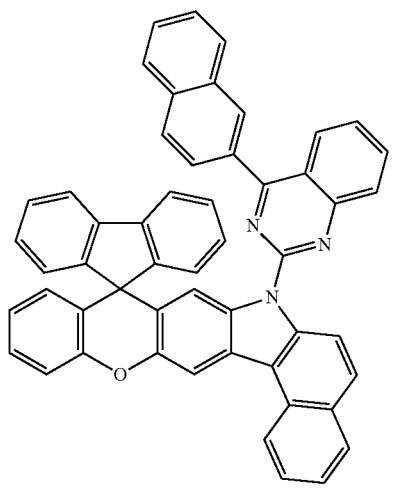
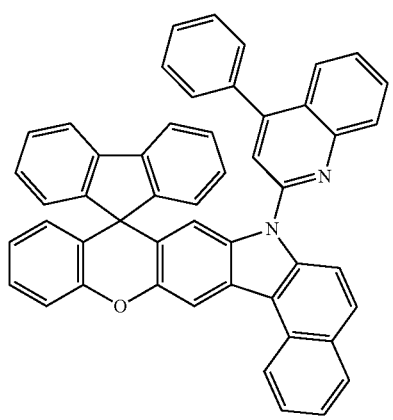
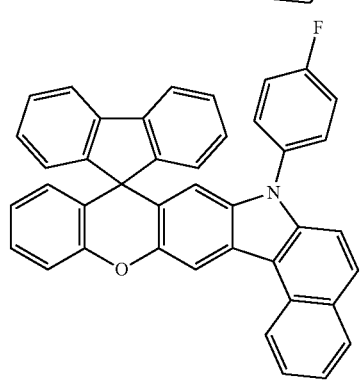
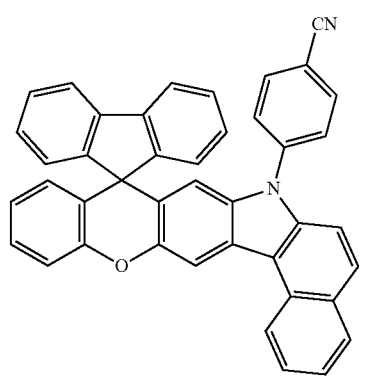

117
-continued
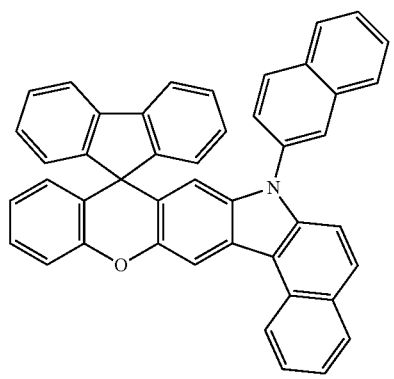
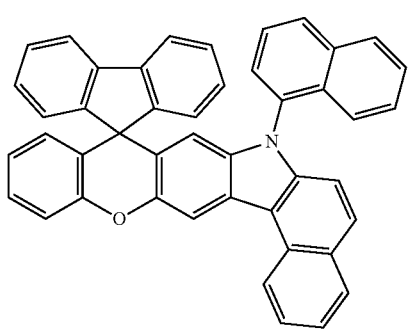
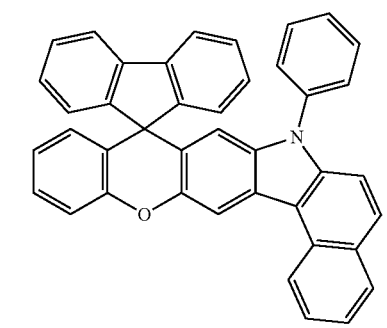
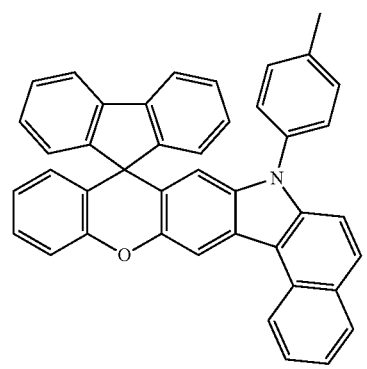
118
-continued
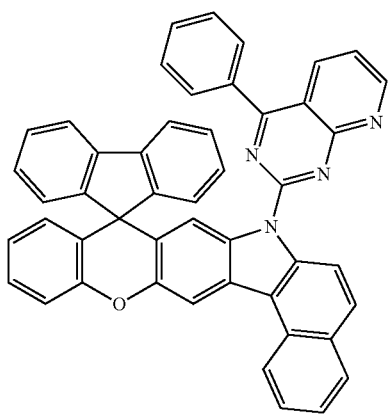
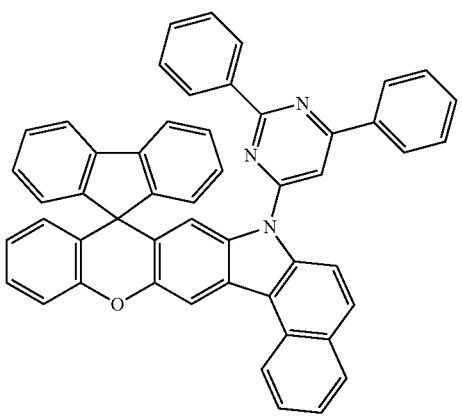
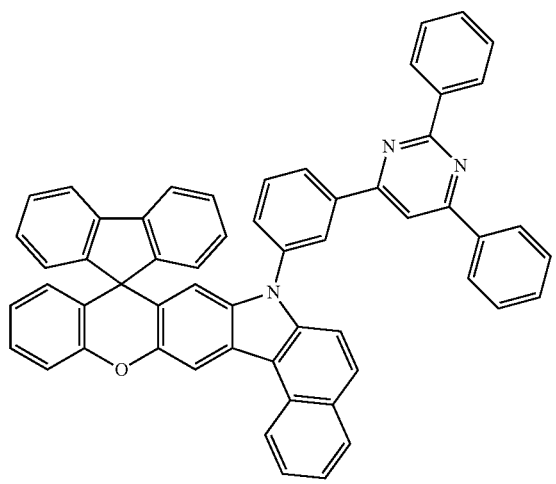

119
-continued
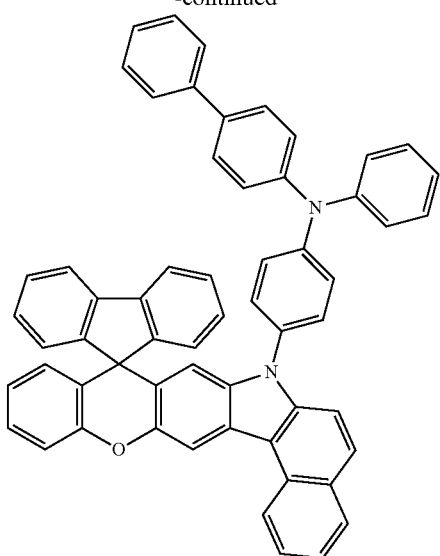
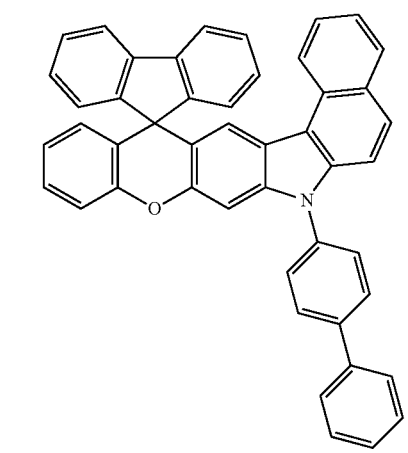
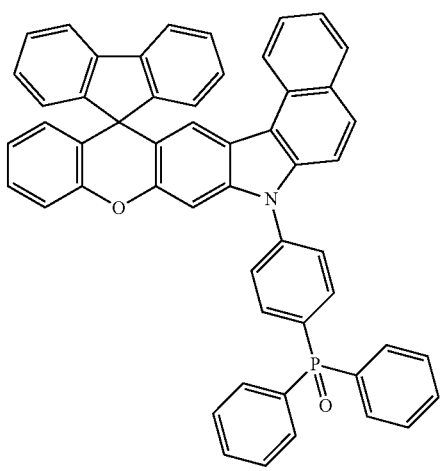
120
-continued
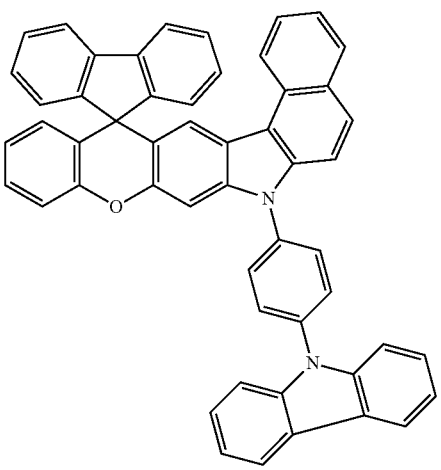
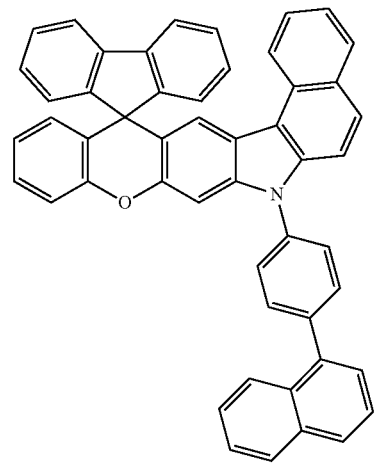
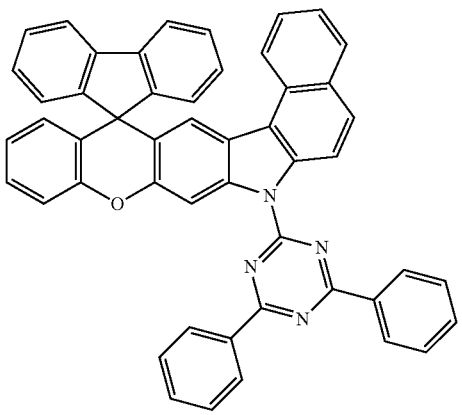

121
-continued
122
-continued
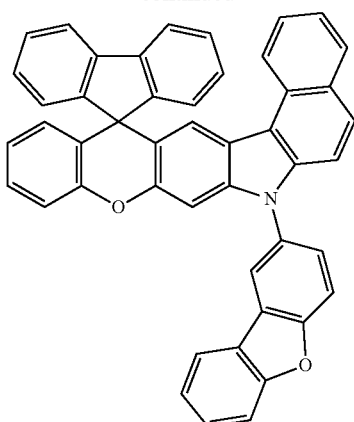
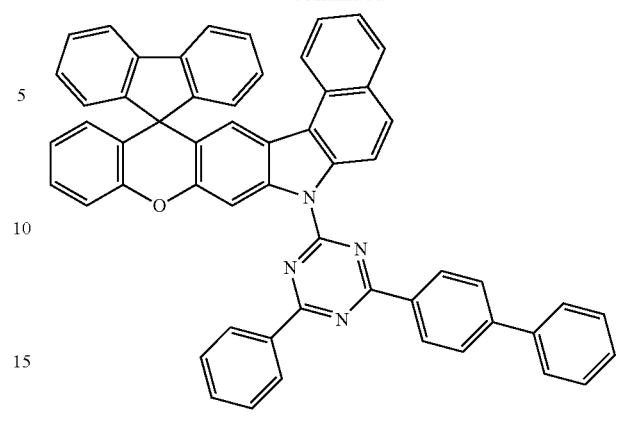
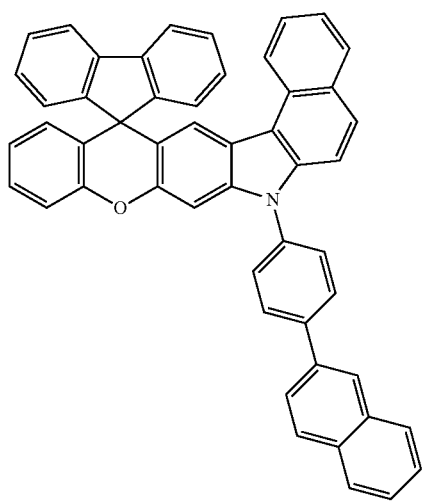
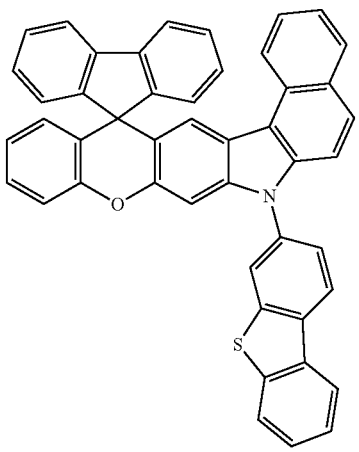
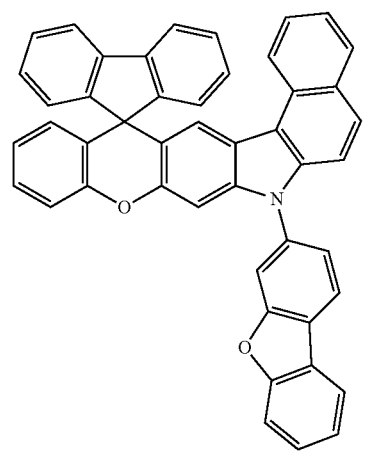
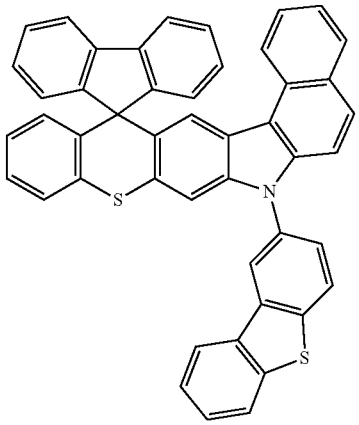

123
-continued
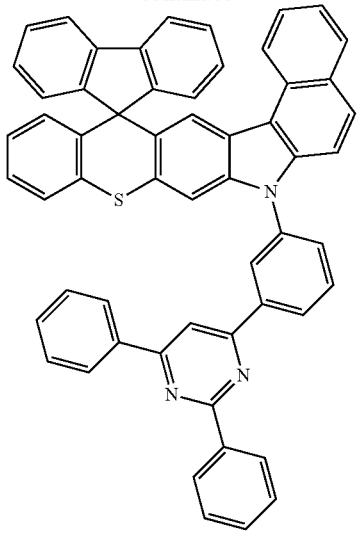
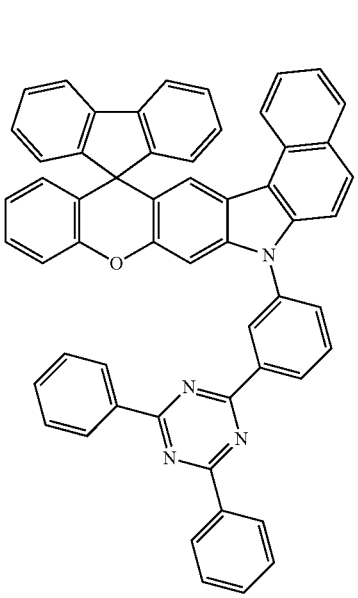
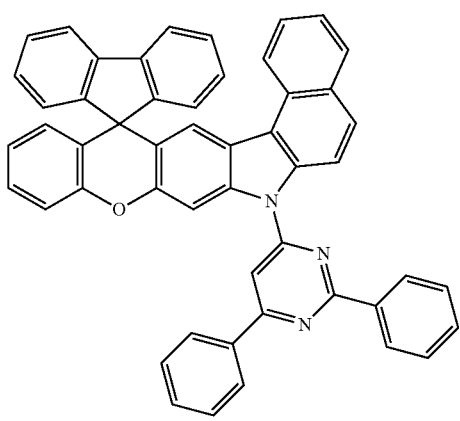
124
-continued
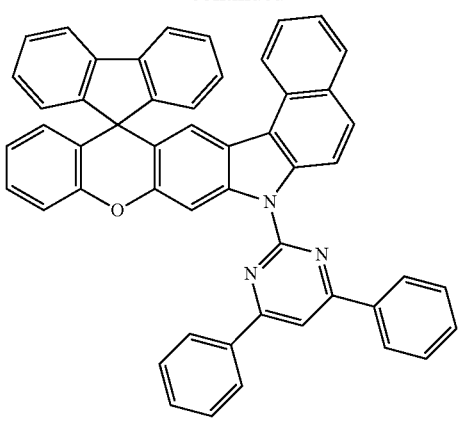
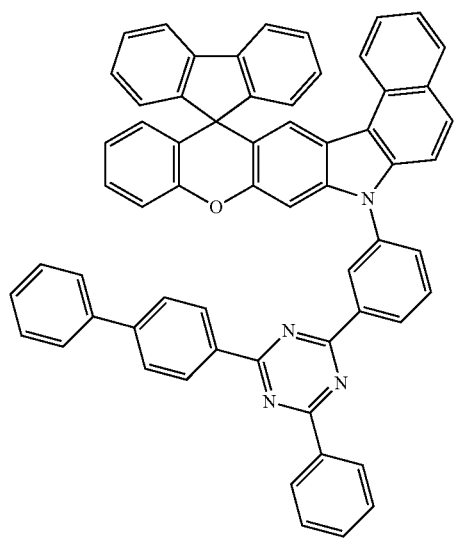
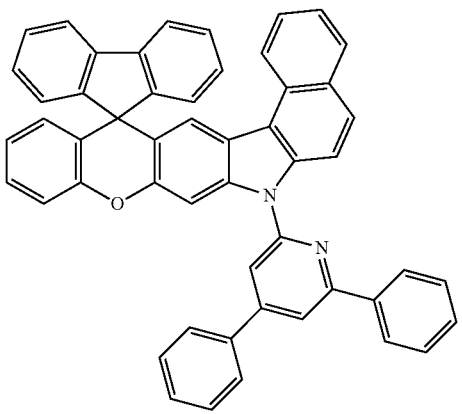

125
-continued
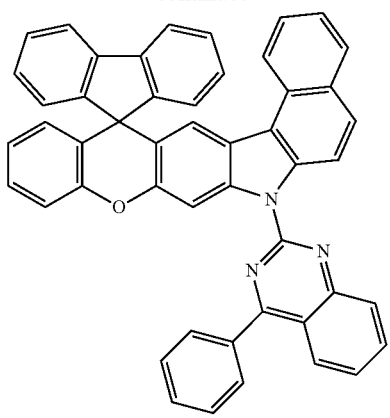
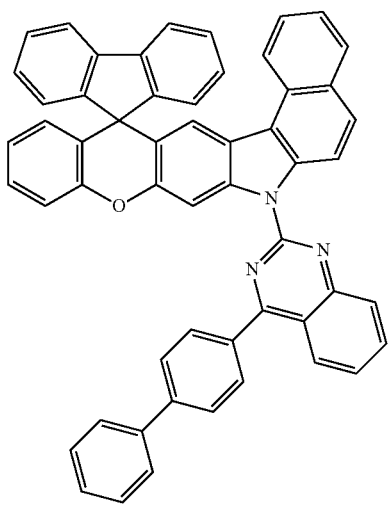
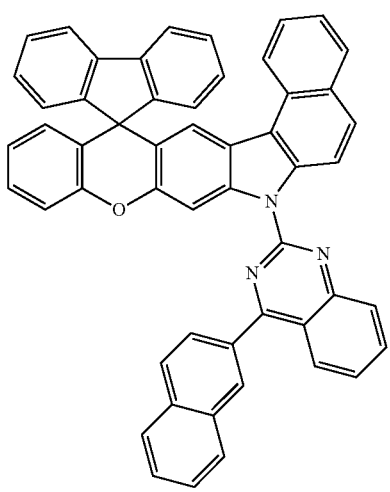
126
-continued
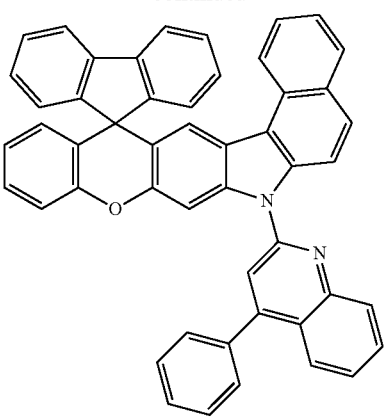
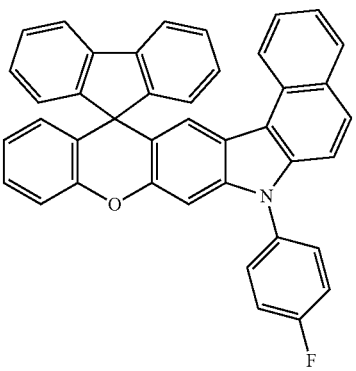
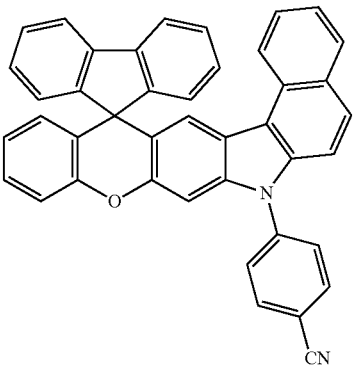
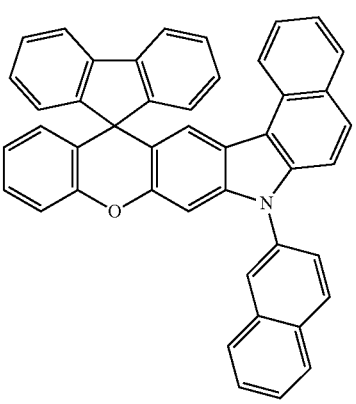

127
-continued
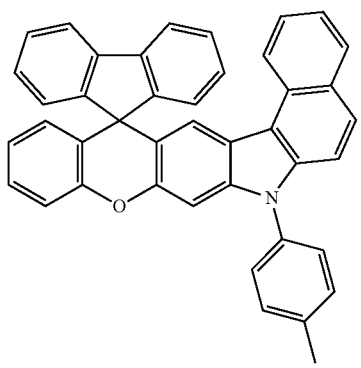
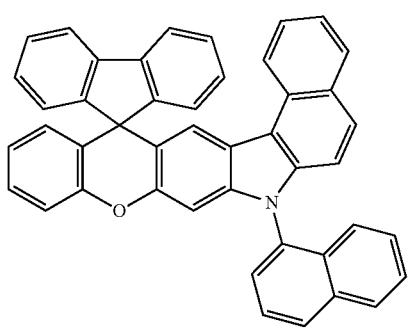
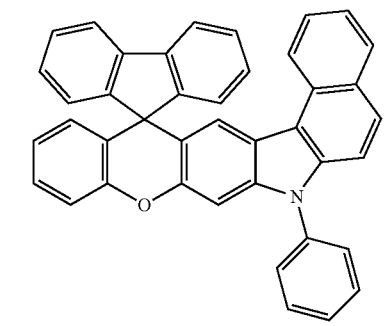
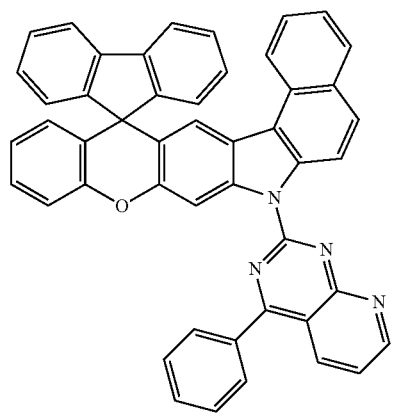
128
-continued
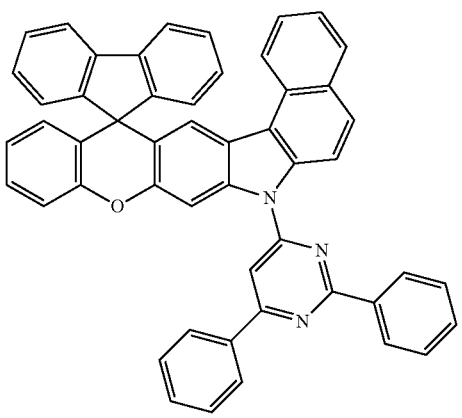
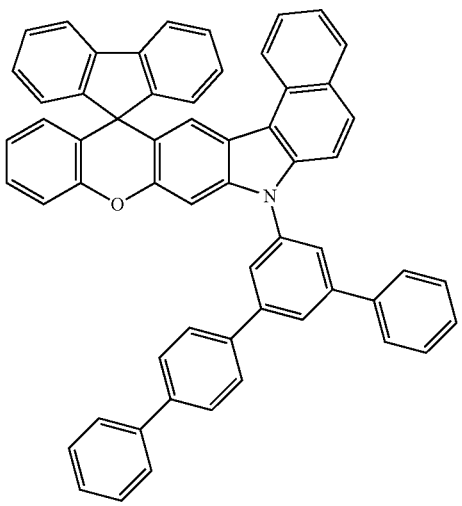
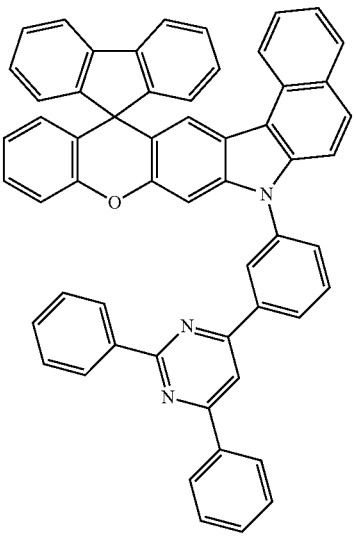

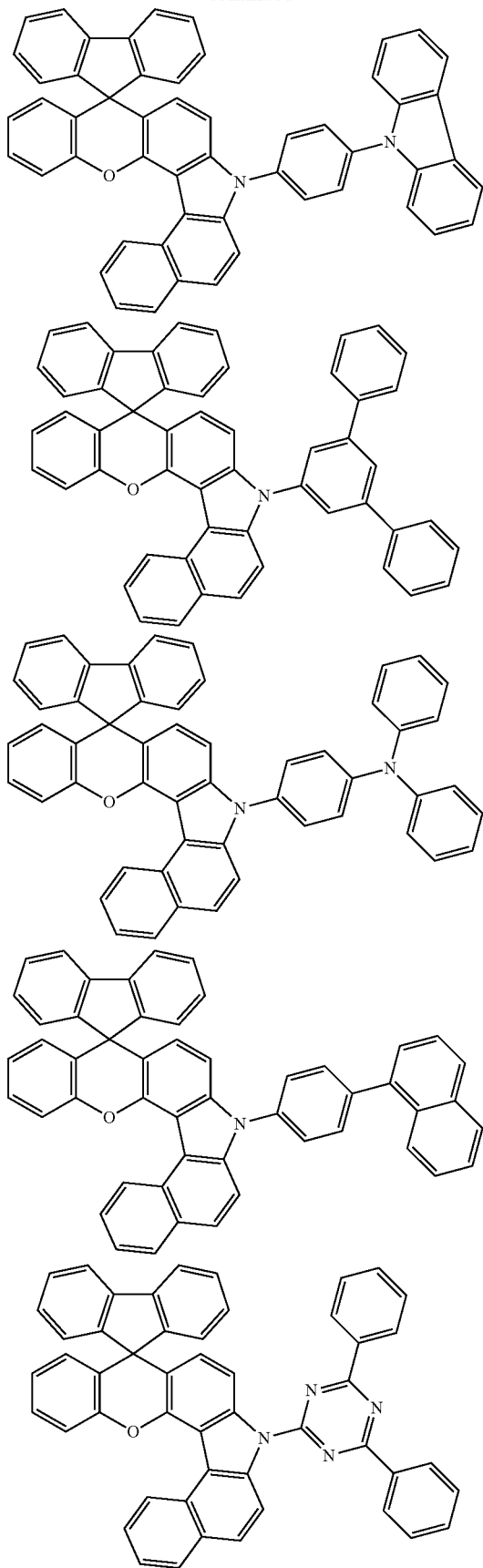
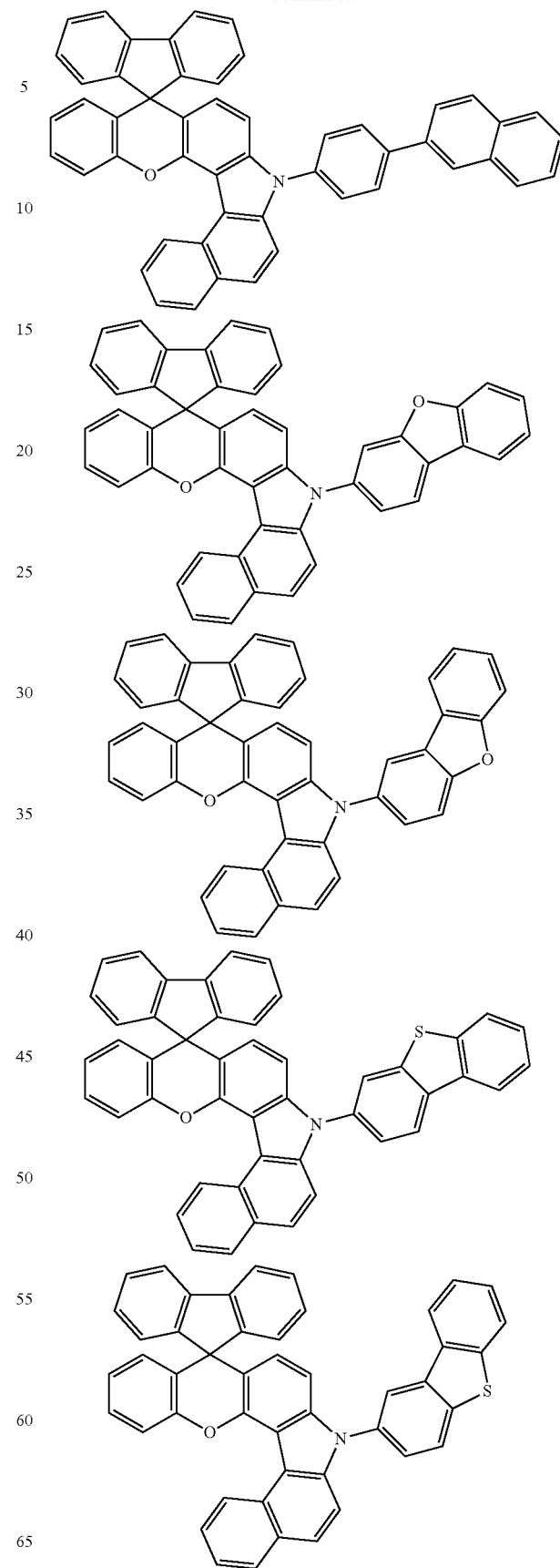

131
-continued
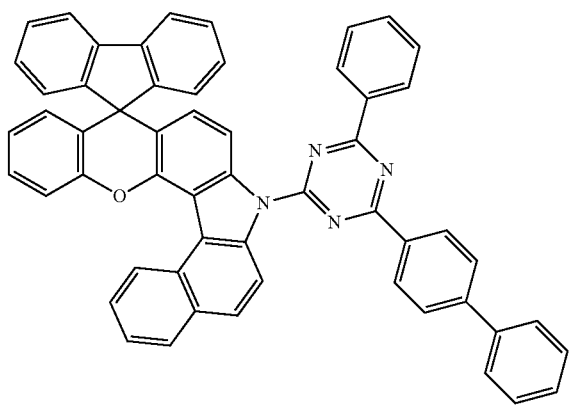
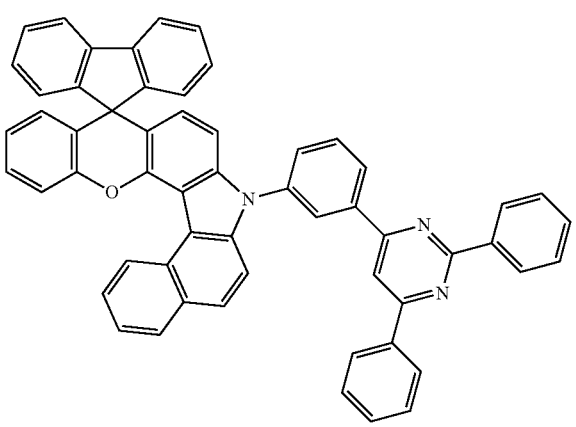
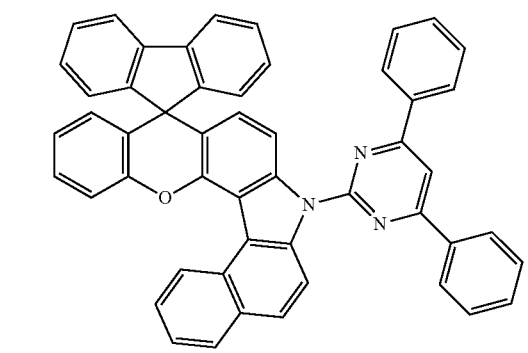
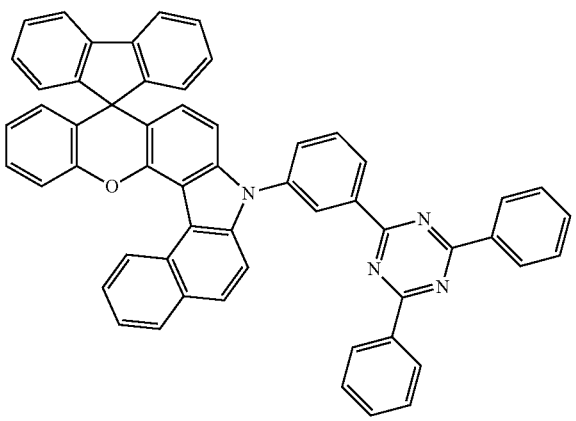
132
-continued
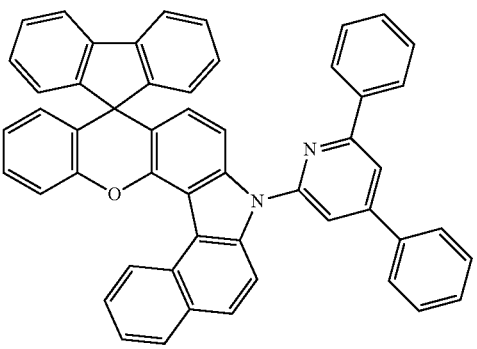
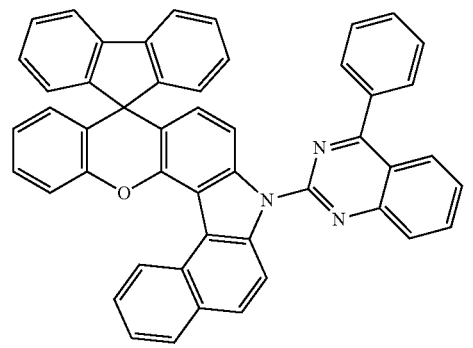
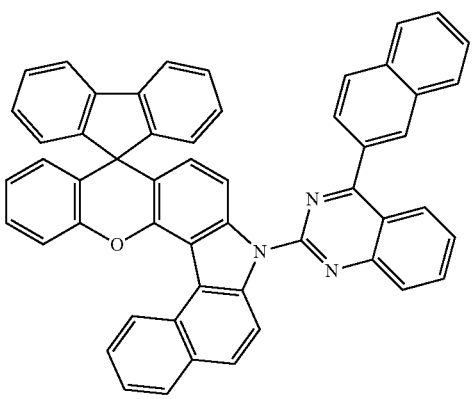

-continued
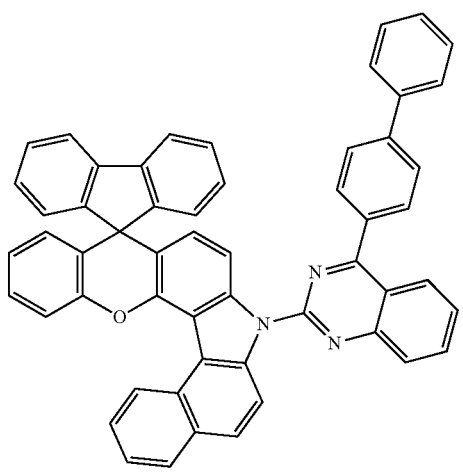
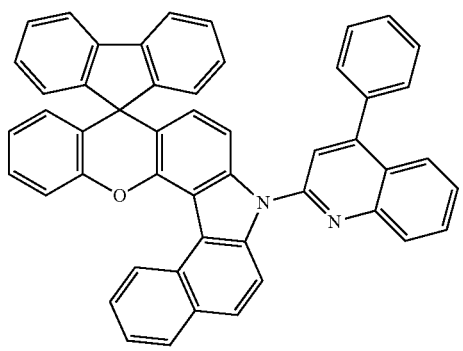
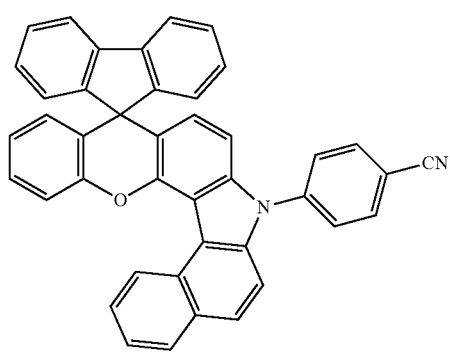
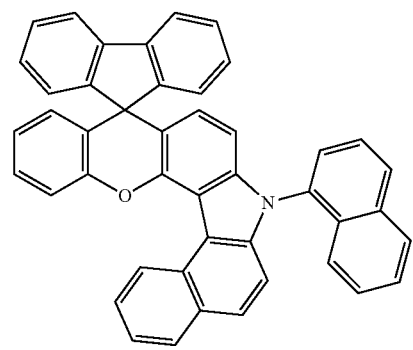
-continued
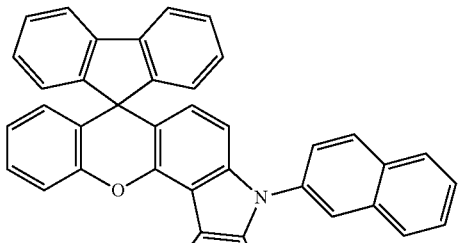
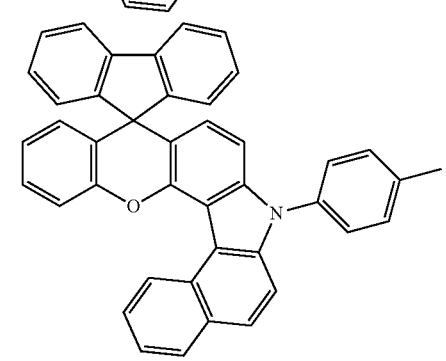
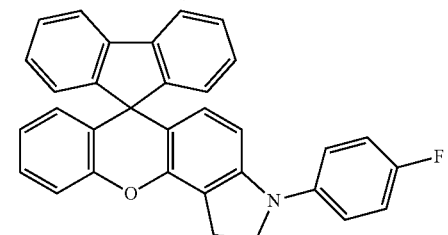
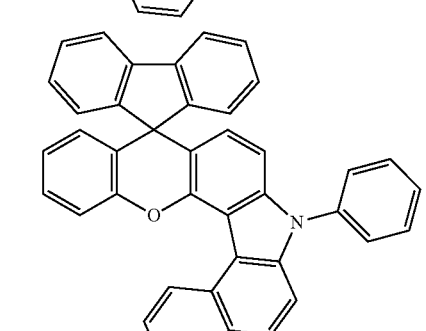
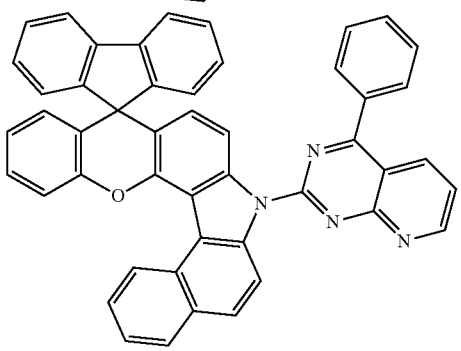

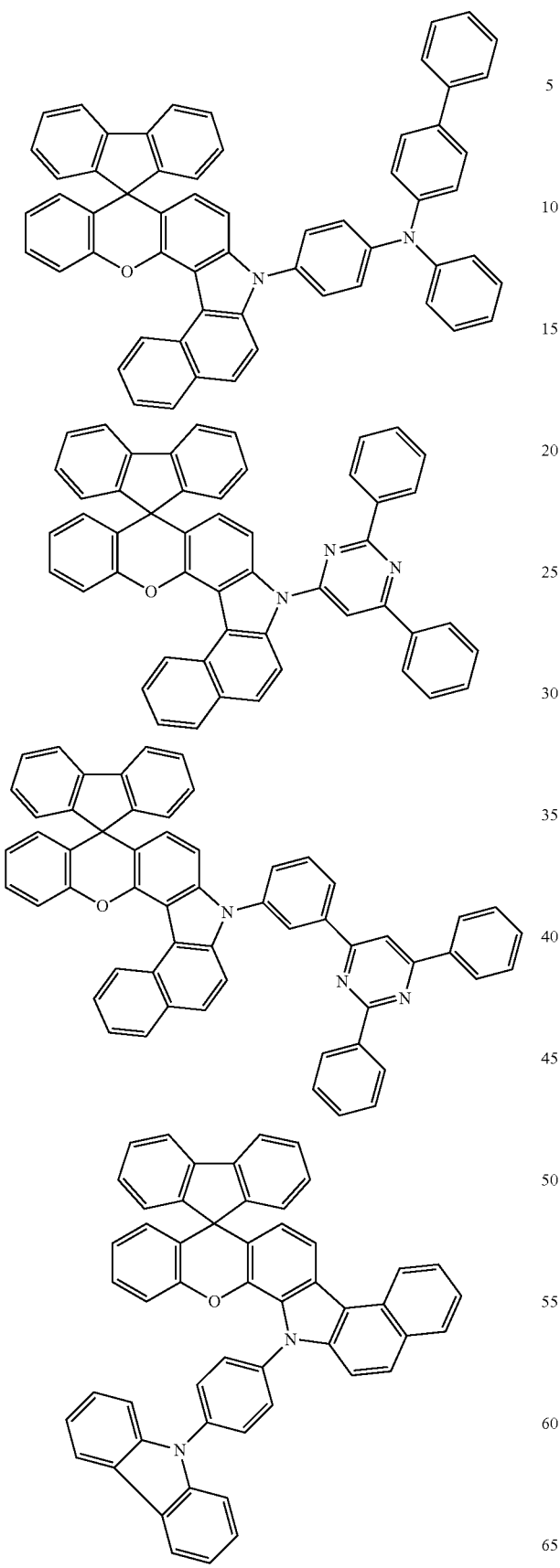
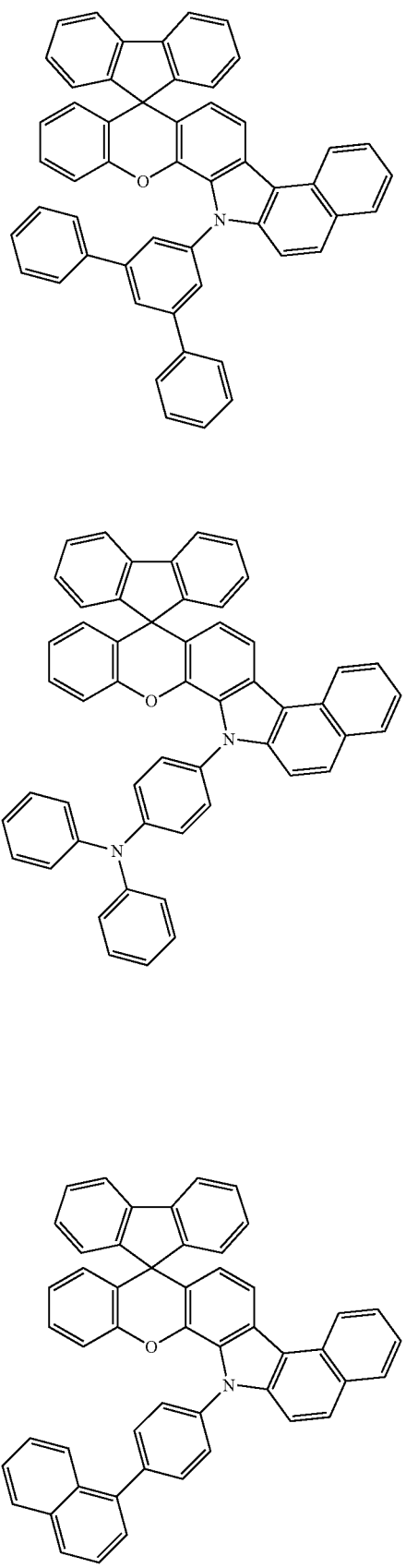

137
-continued
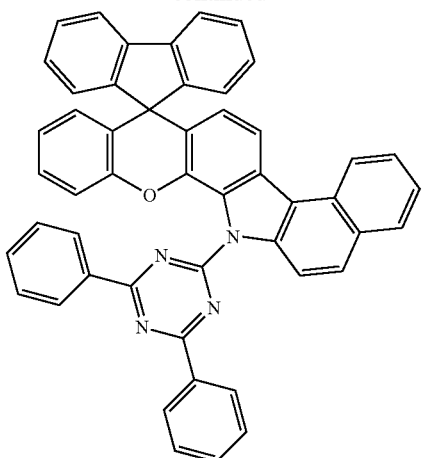
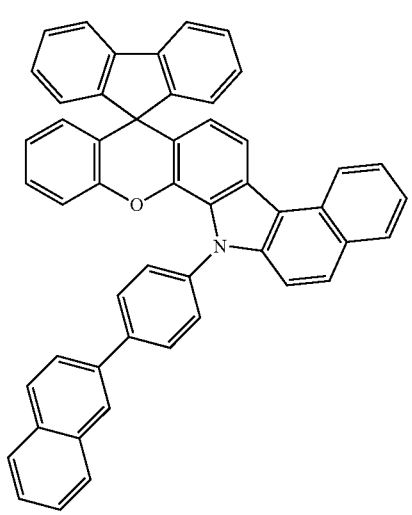
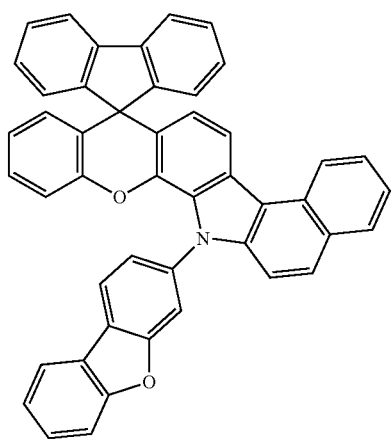
138
-continued
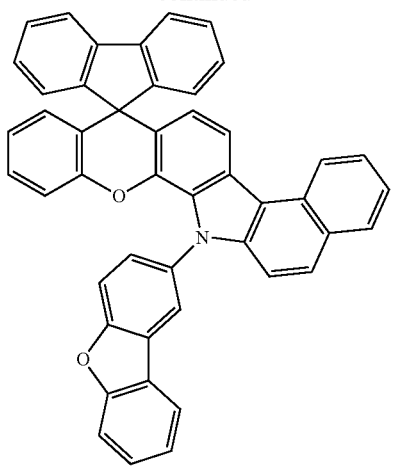
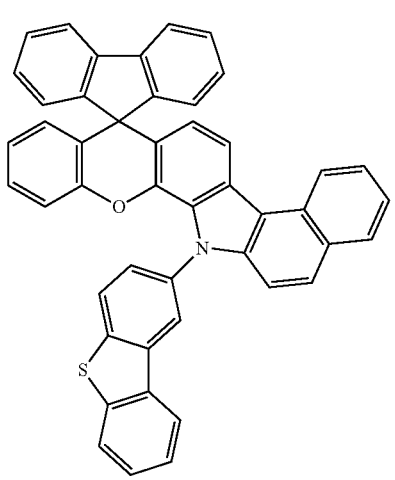
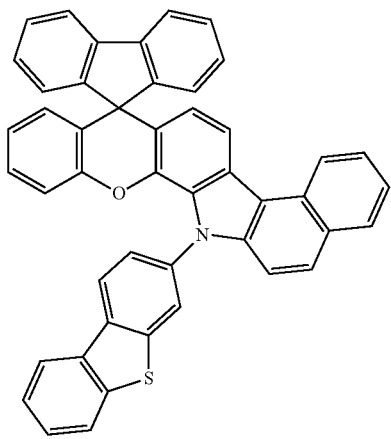

139
-continued
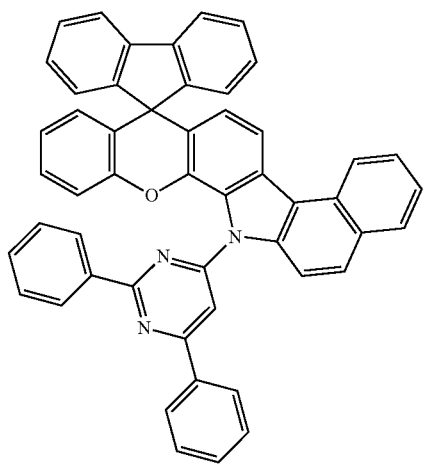
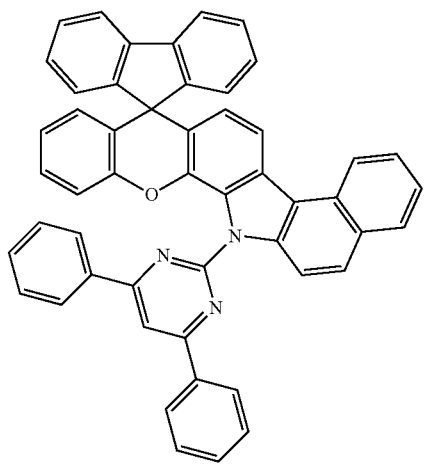
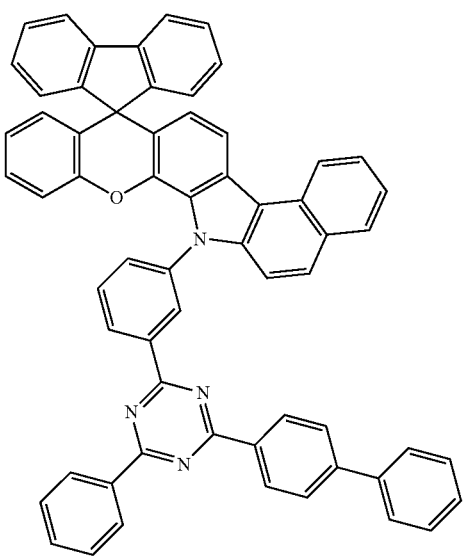
140
-continued
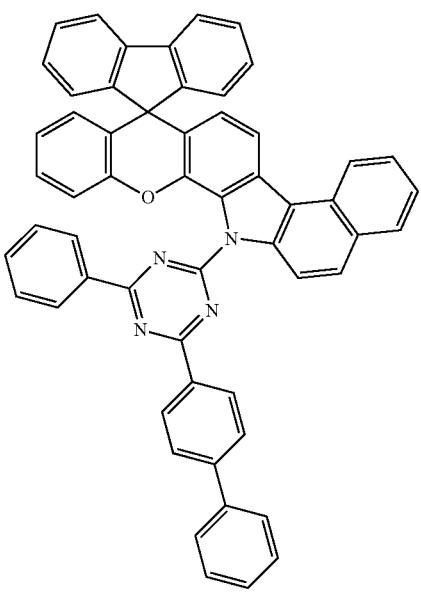
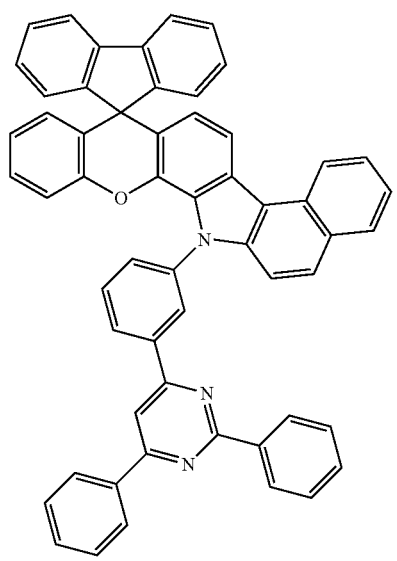
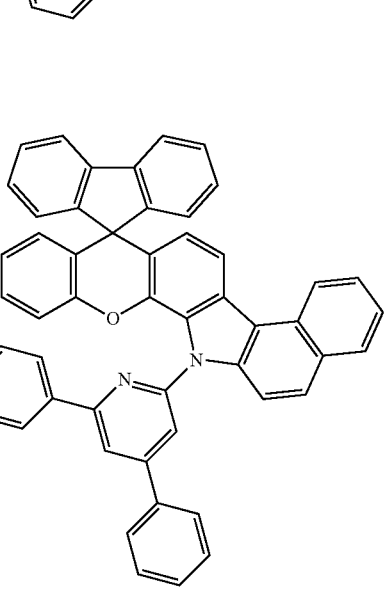

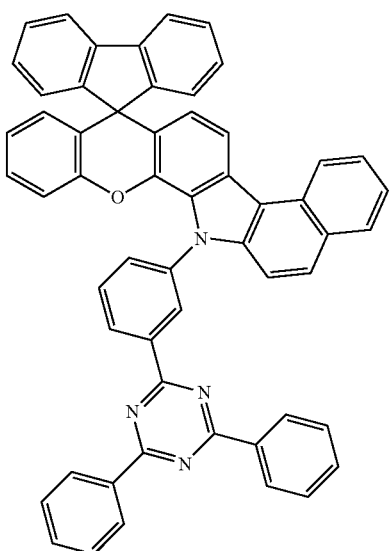
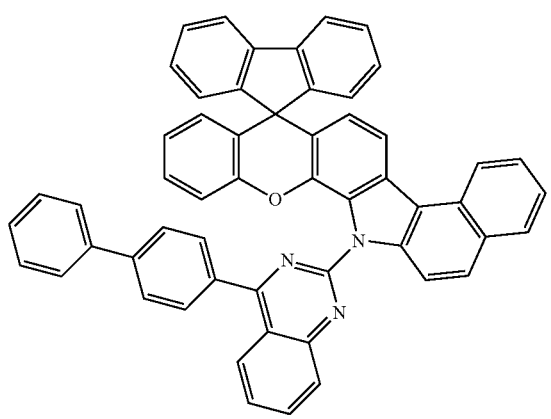
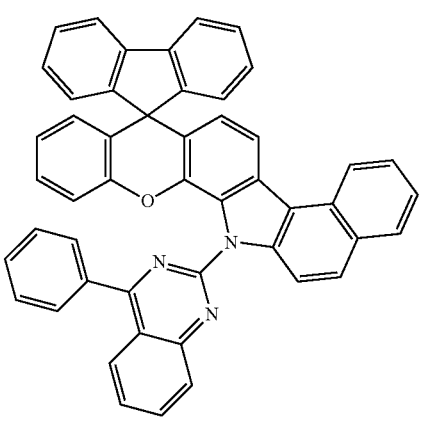
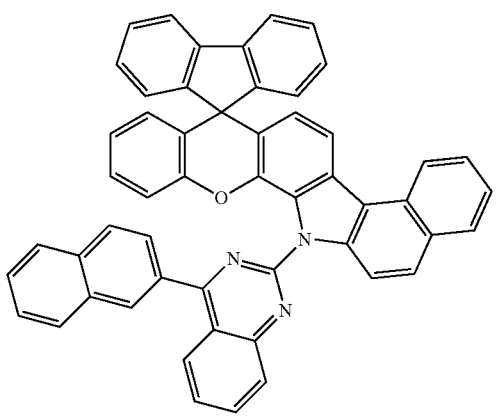
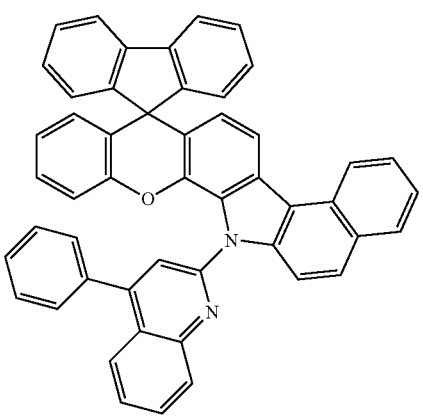
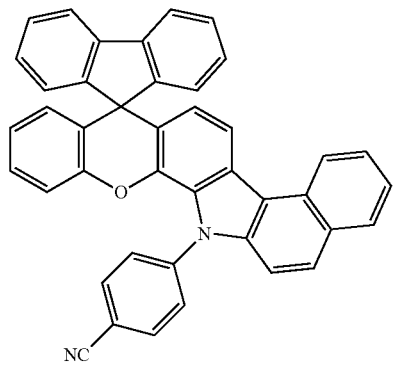
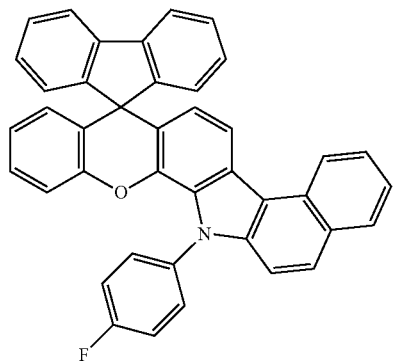

143
-continued
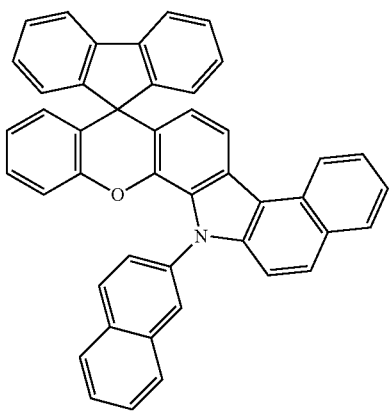
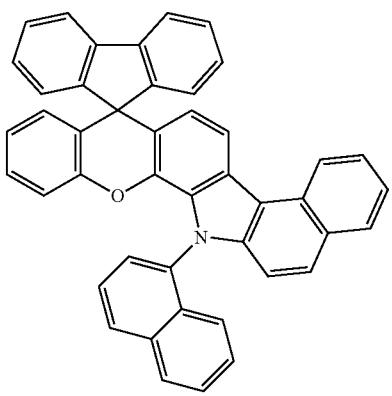
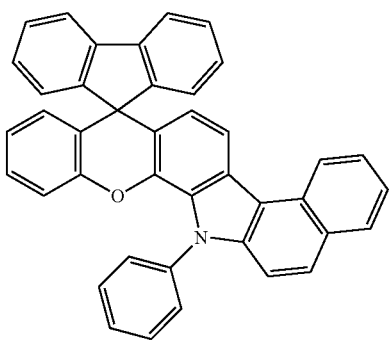
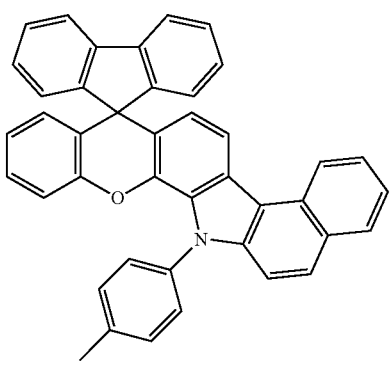
144
-continued
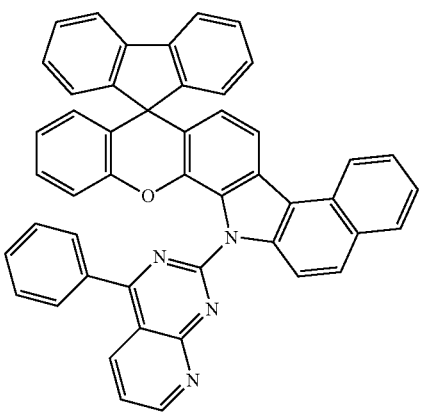
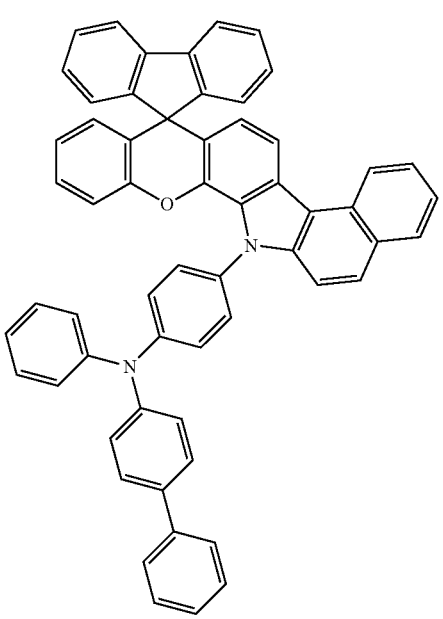
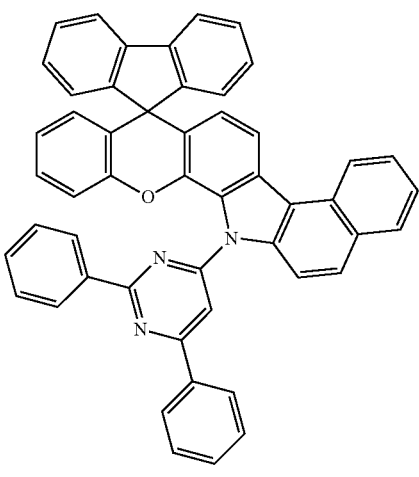

145
-continued
146
-continued
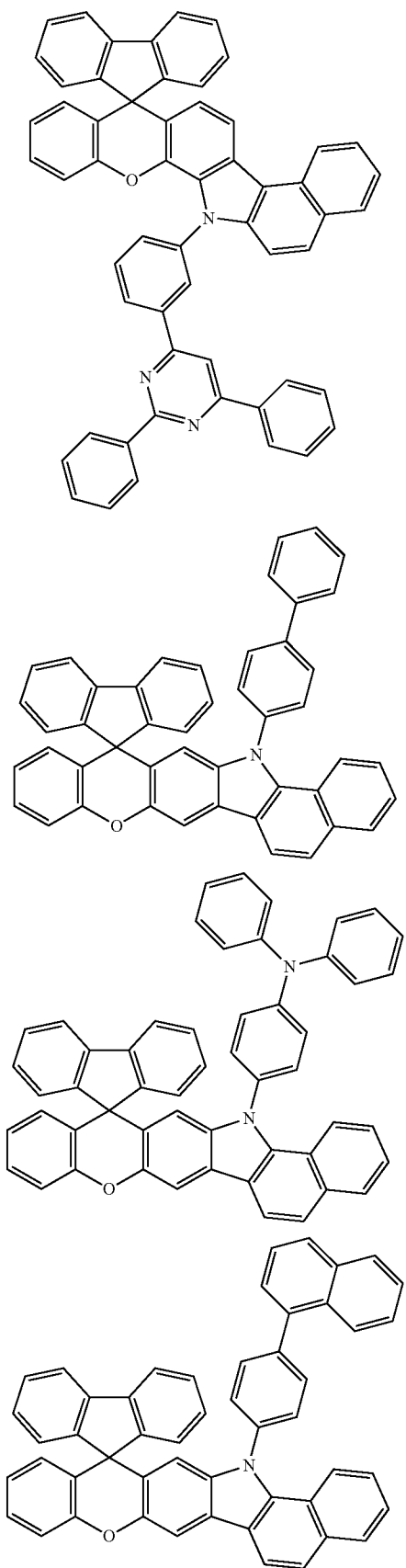
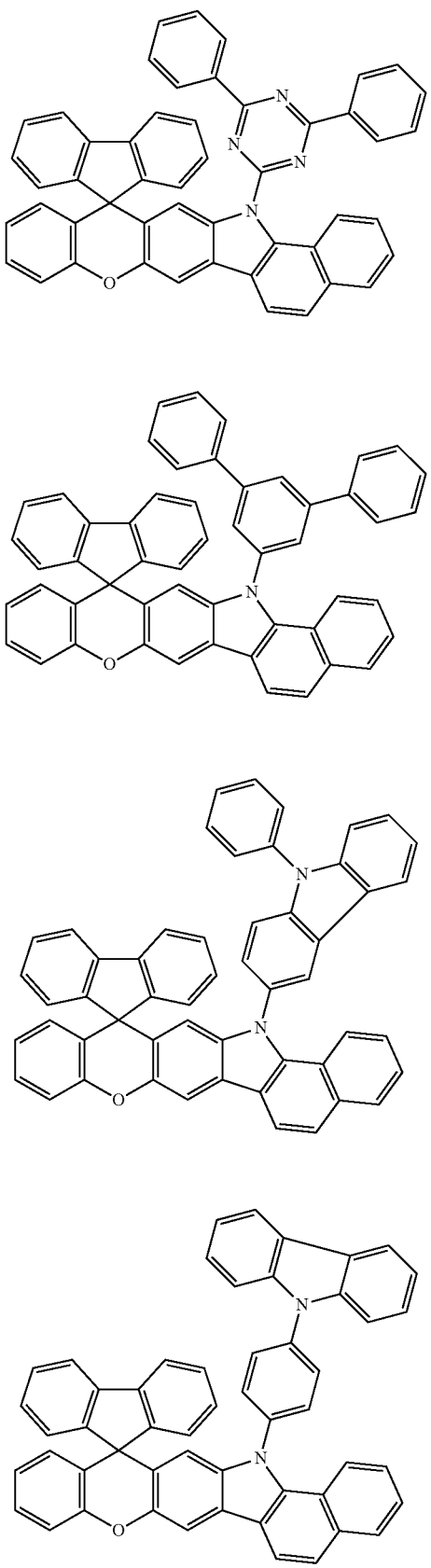

147
-continued
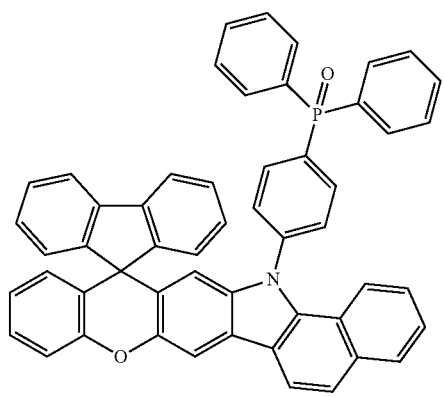
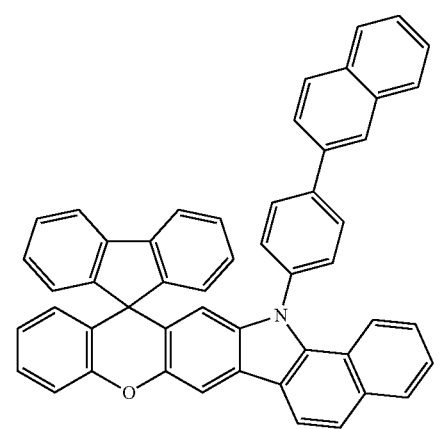
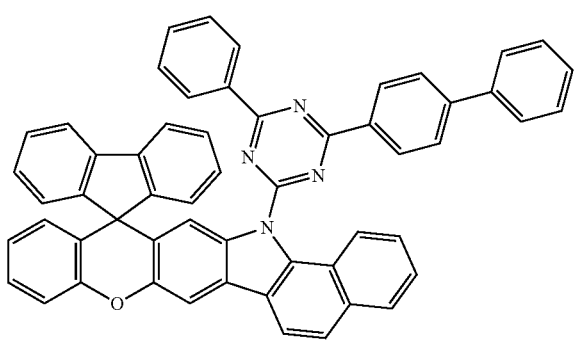
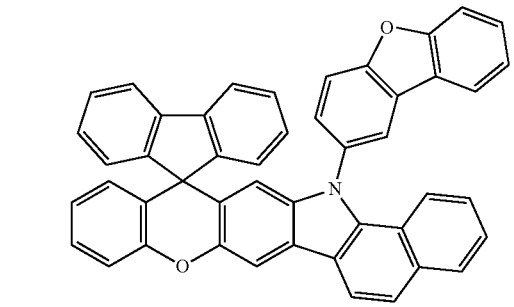
148
-continued
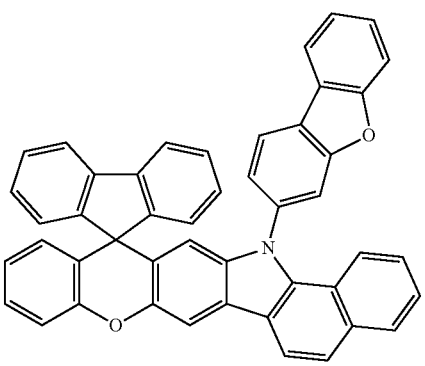
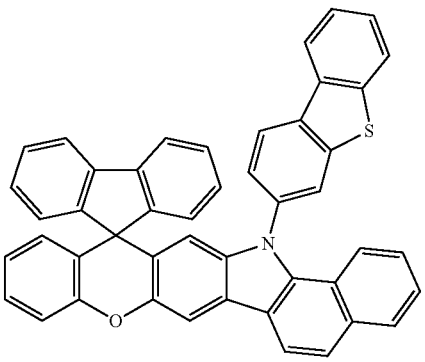
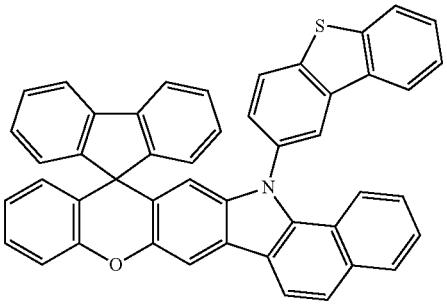
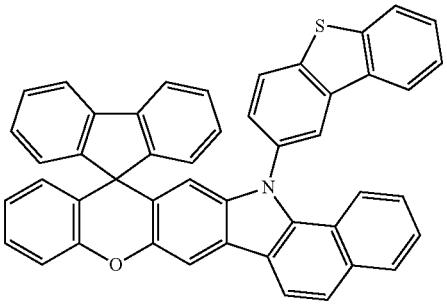

149
-continued

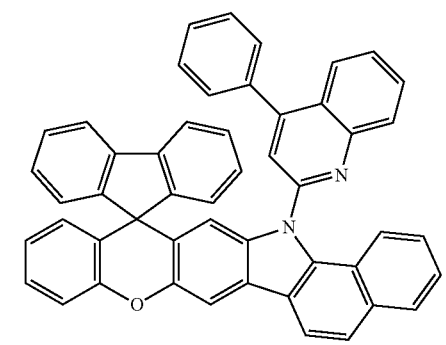
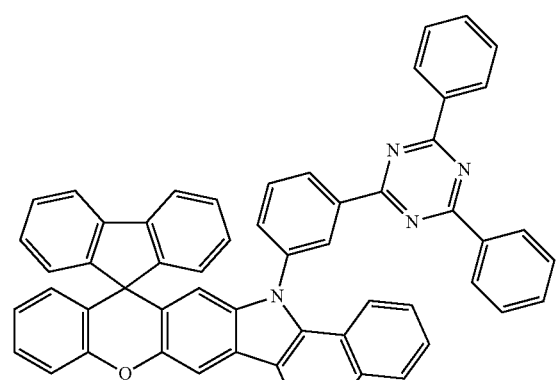
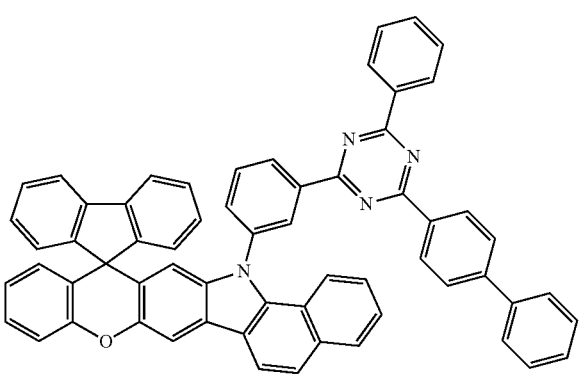
150
-continued
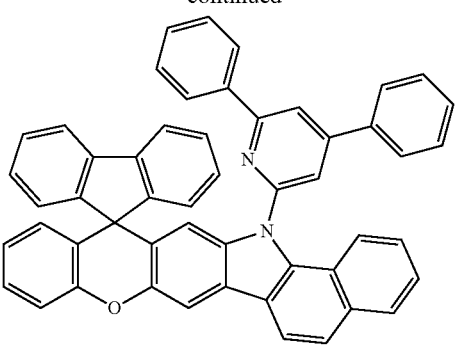
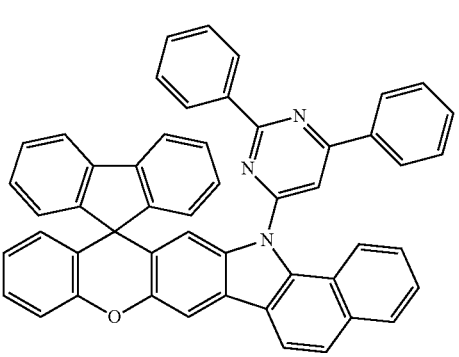
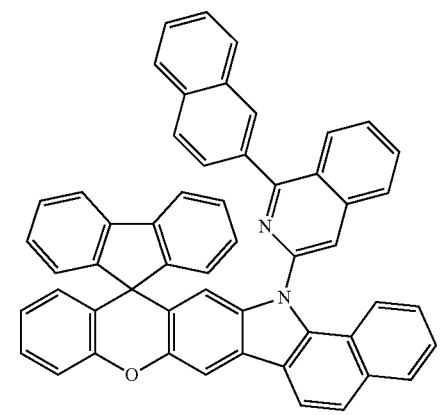
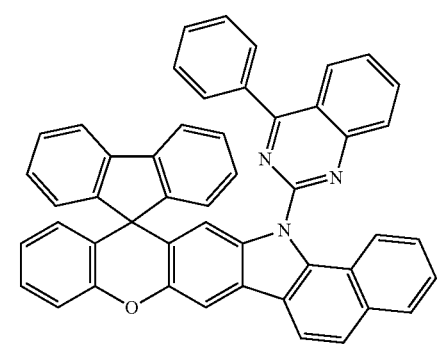

151
-continued
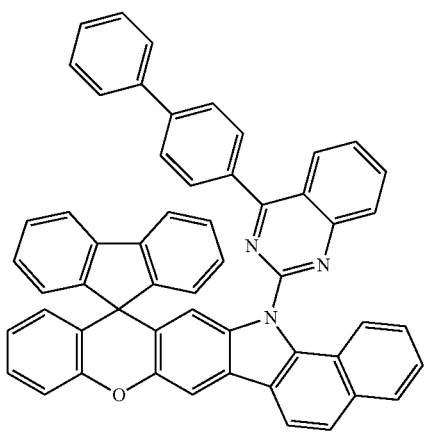
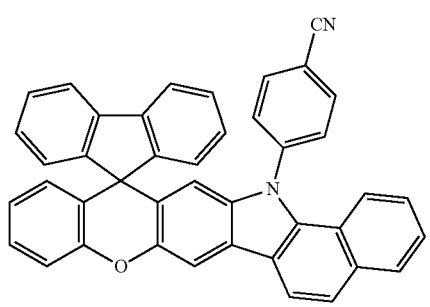
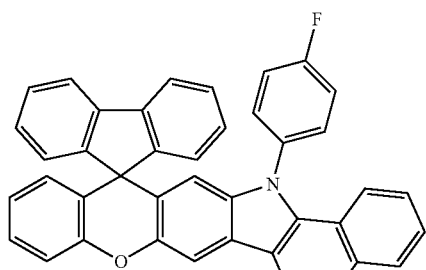
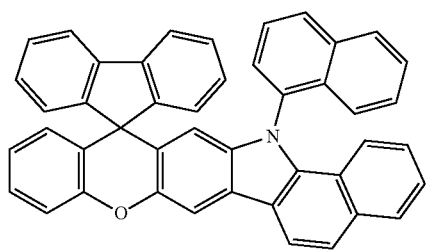
152
-continued
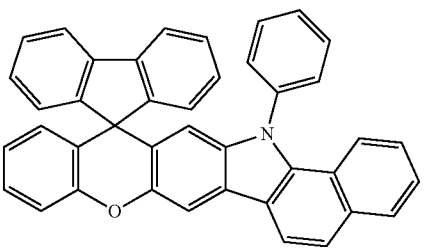
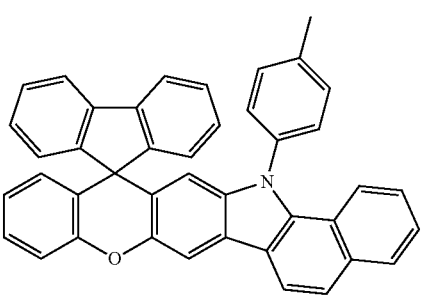
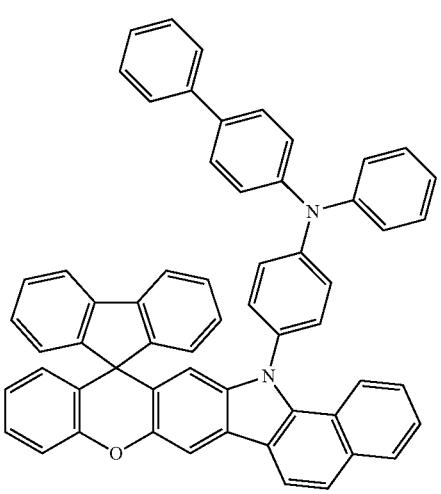
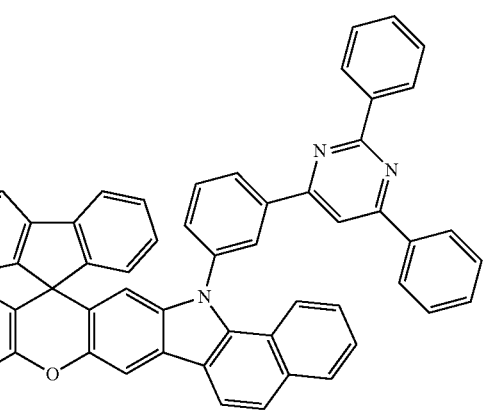

153
-continued
154
-continued
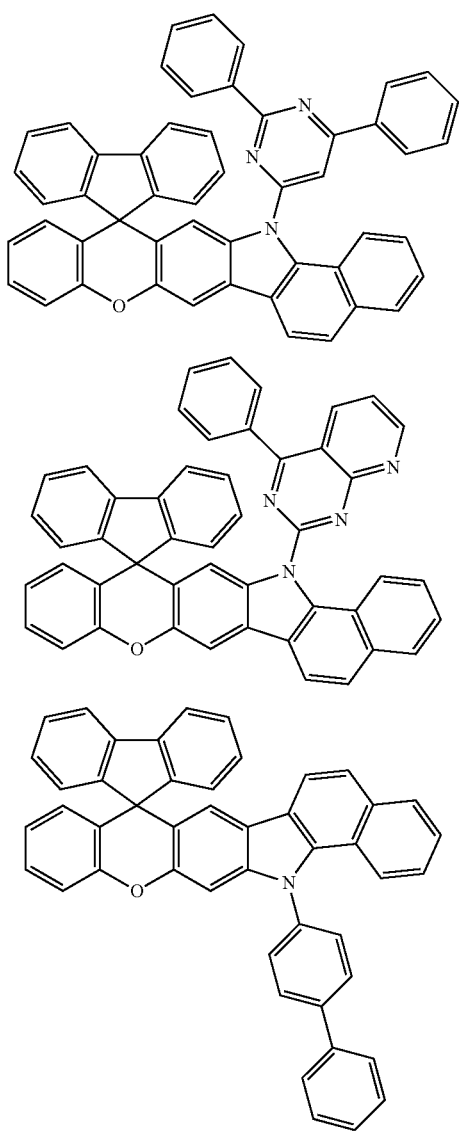
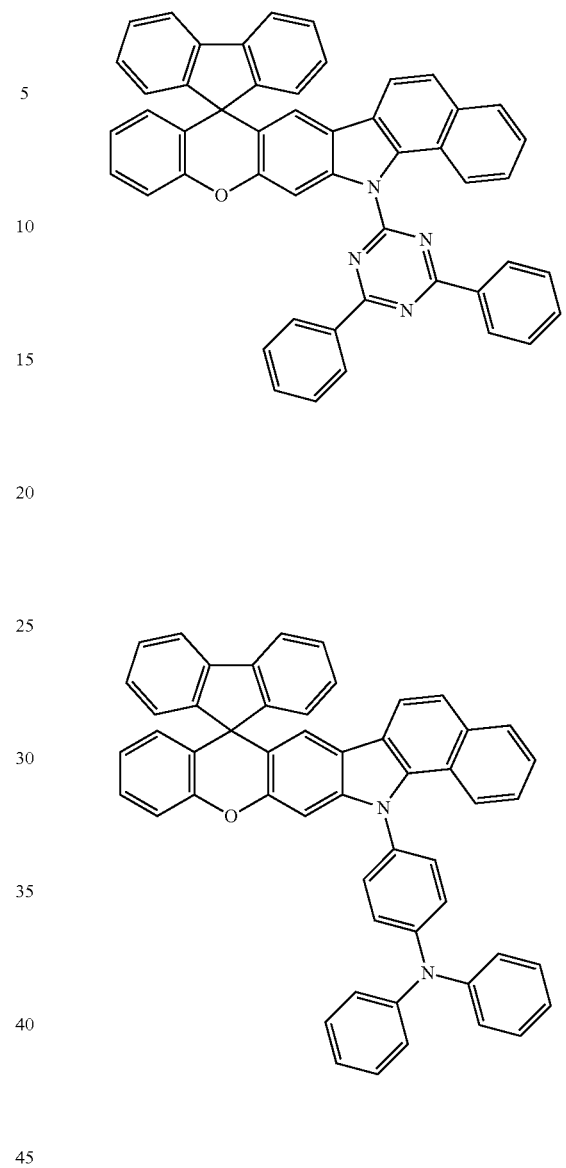
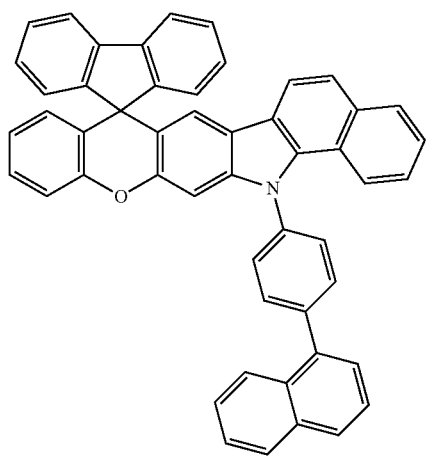

155
-continued
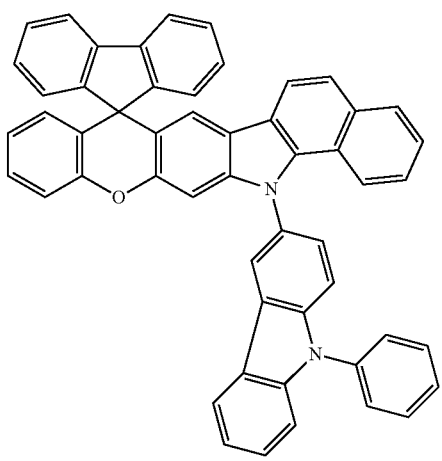
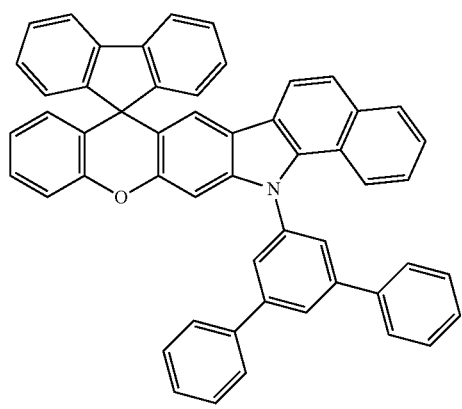
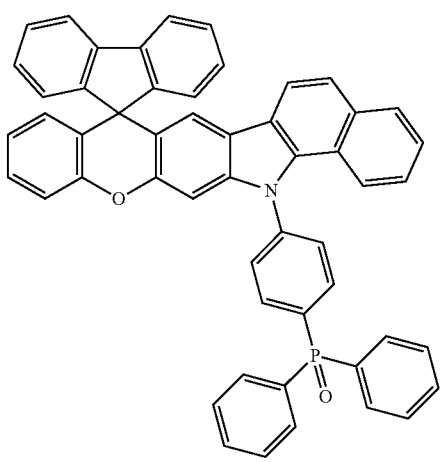
156
-continued
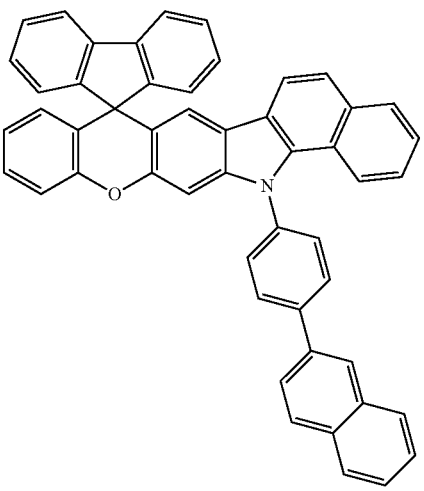
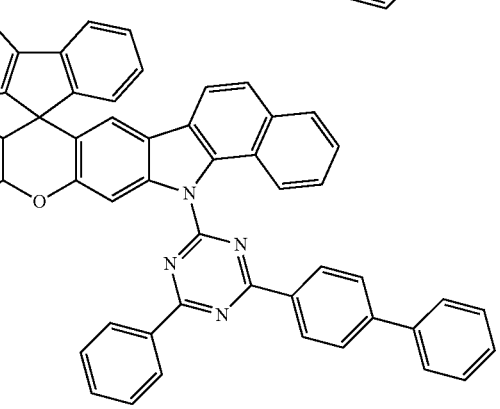
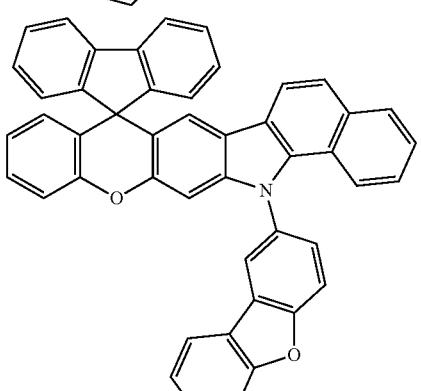
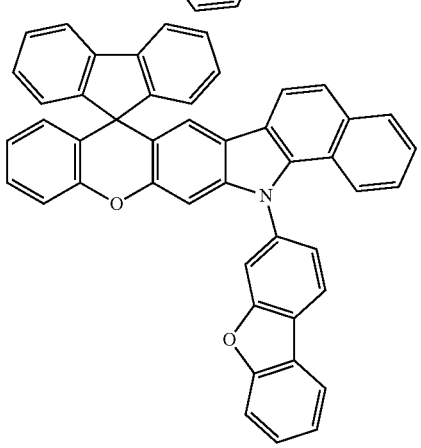

157
-continued
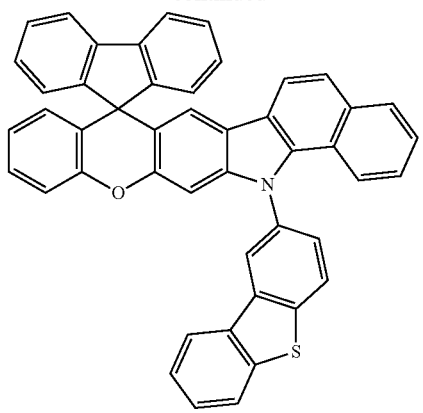
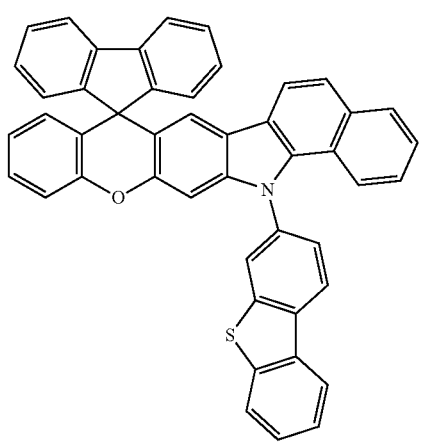
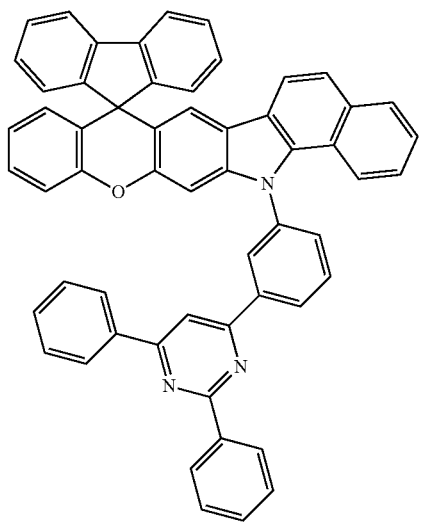
158
-continued
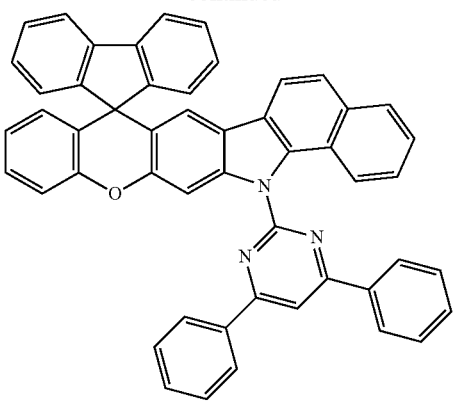
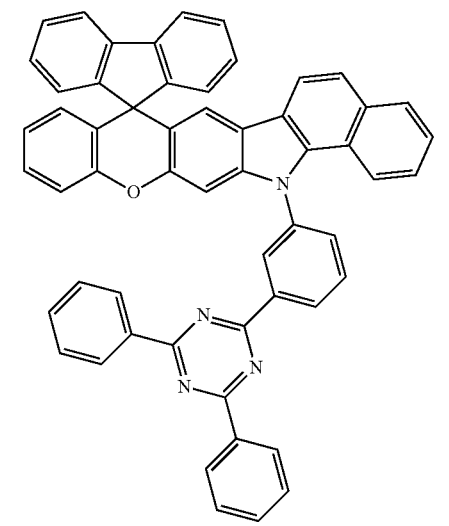
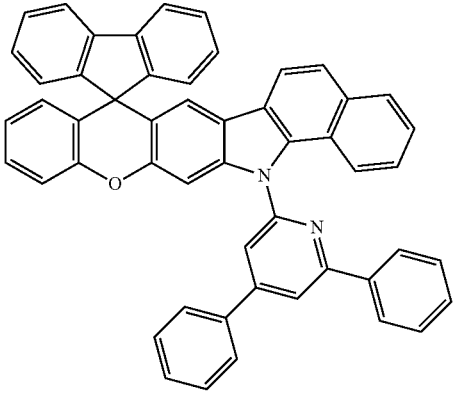

159
-continued
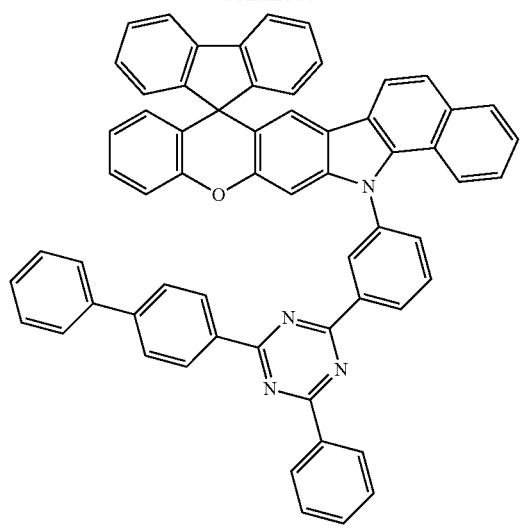
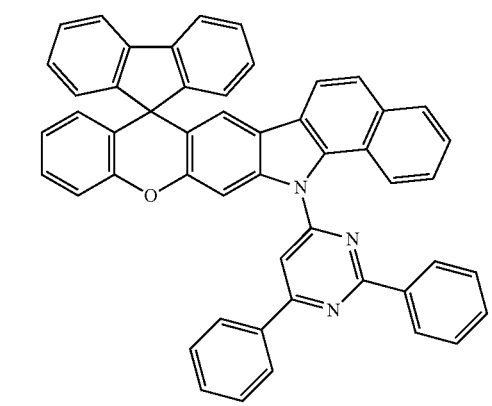
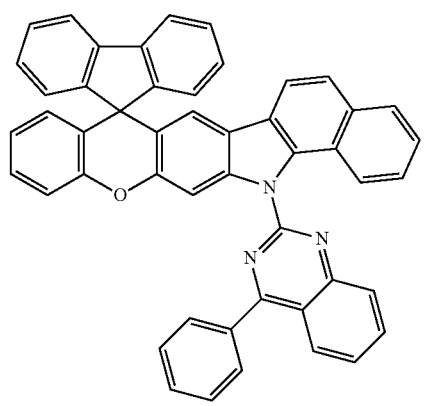
160
-continued
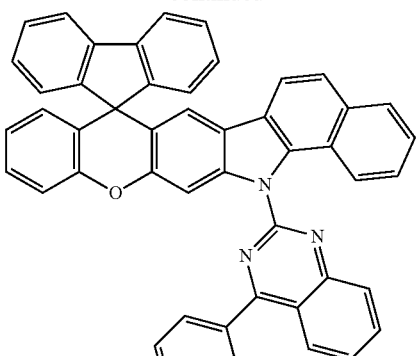
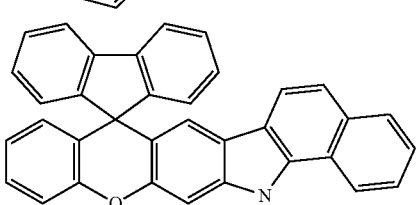
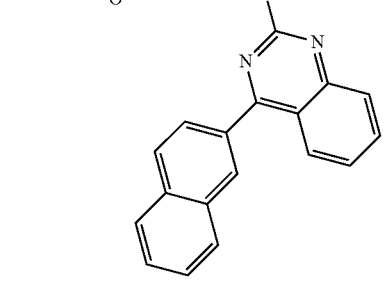
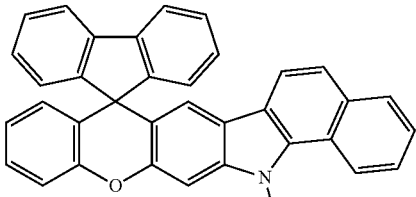
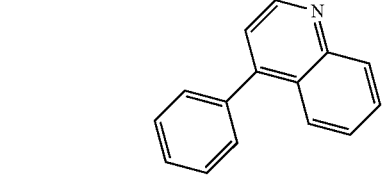
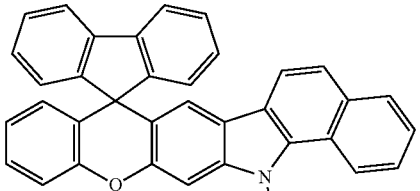
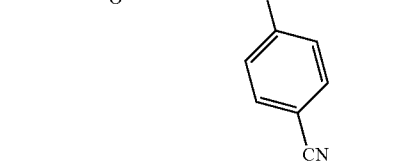

-continued
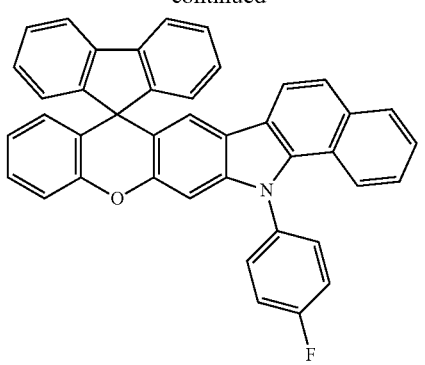
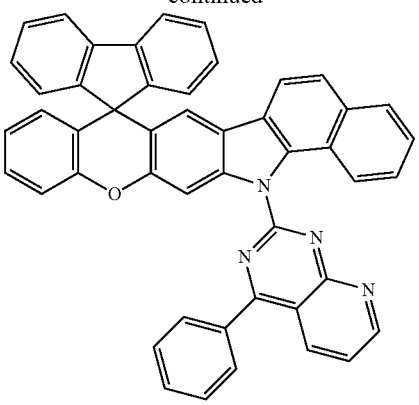

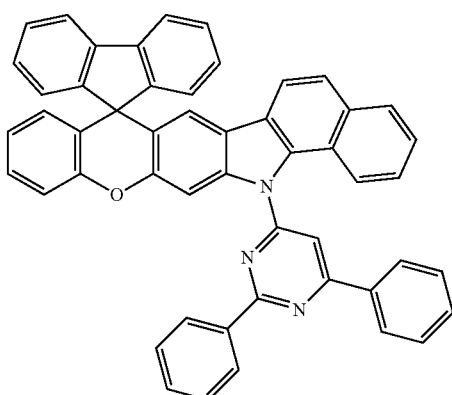
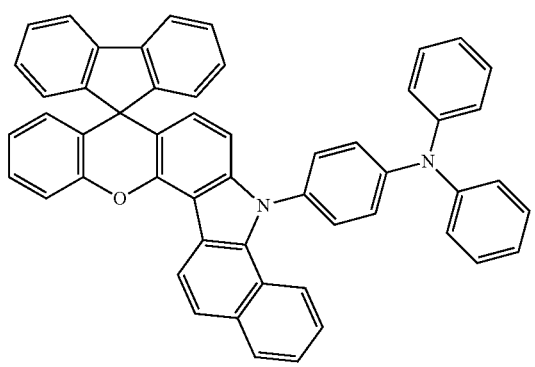
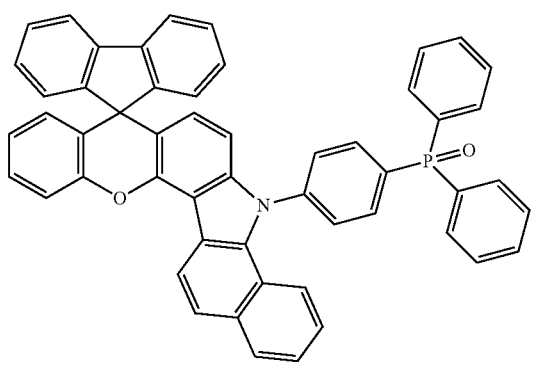
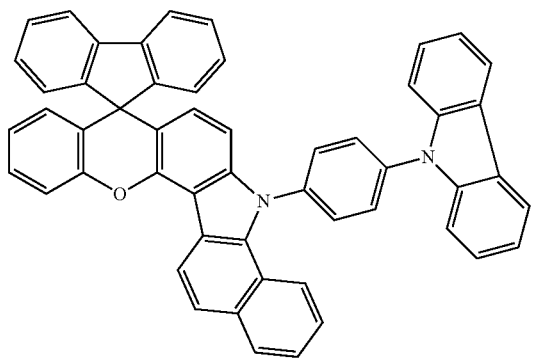
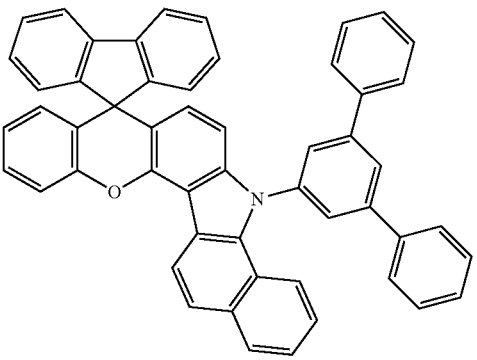
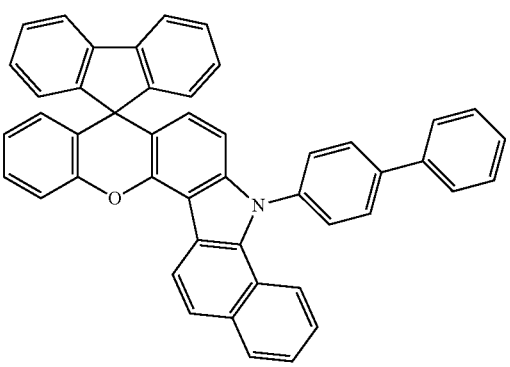
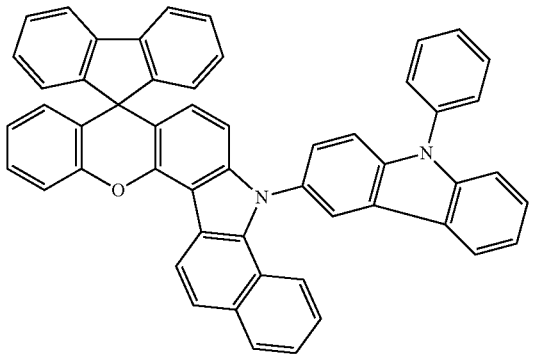
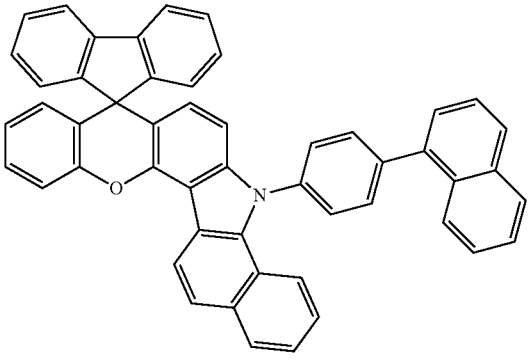

165
-continued
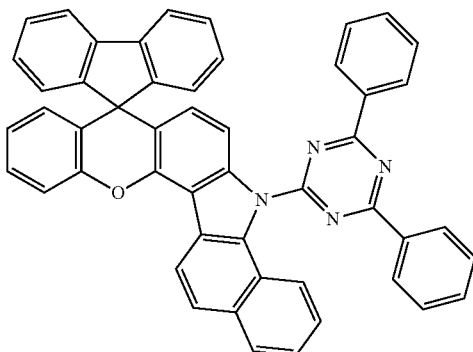
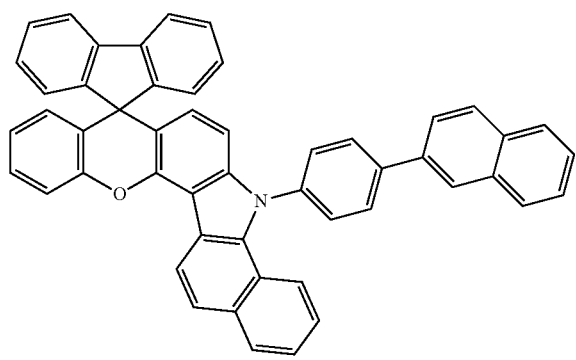
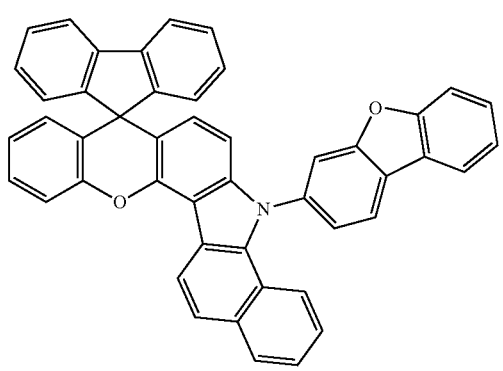
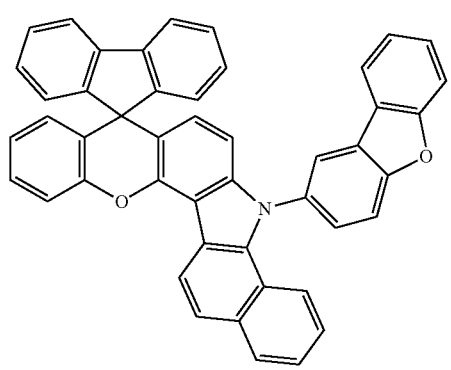
166
-continued
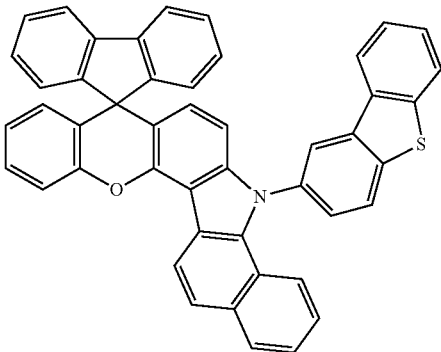
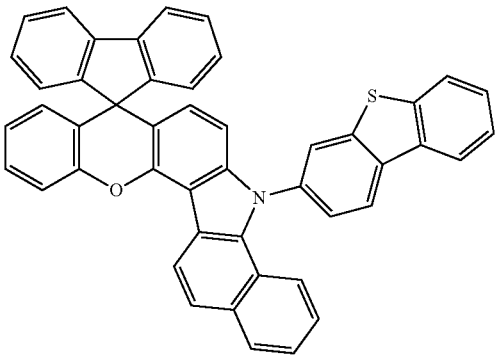
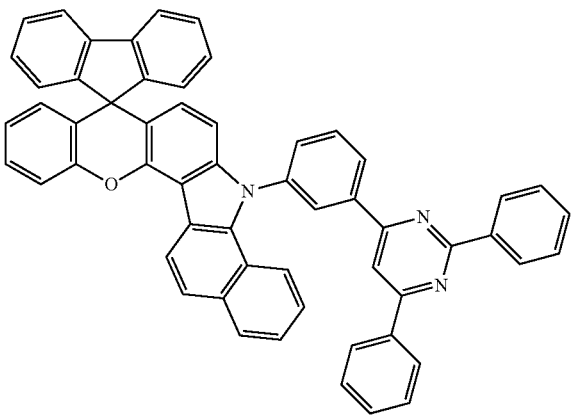
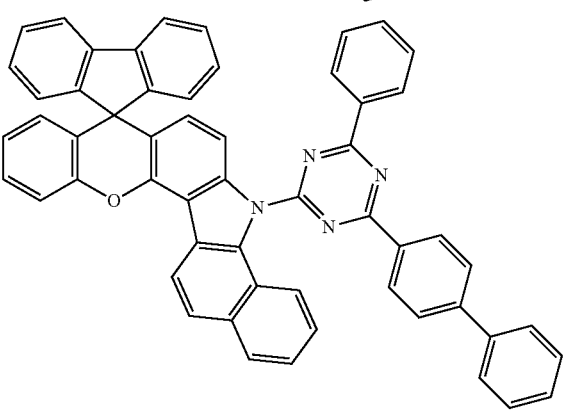

167
-continued
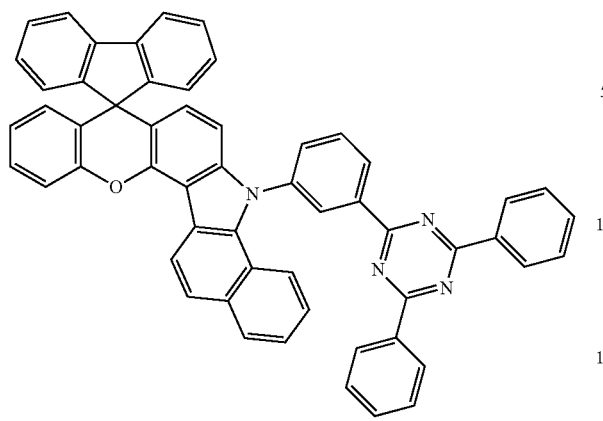
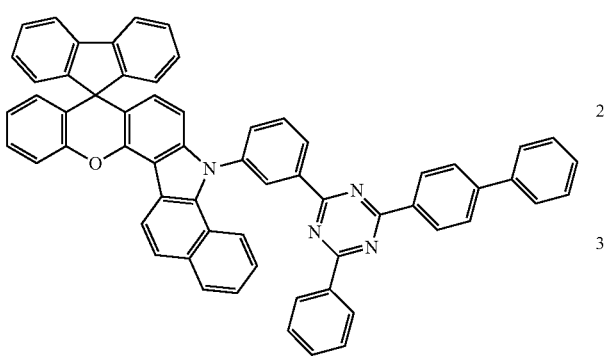
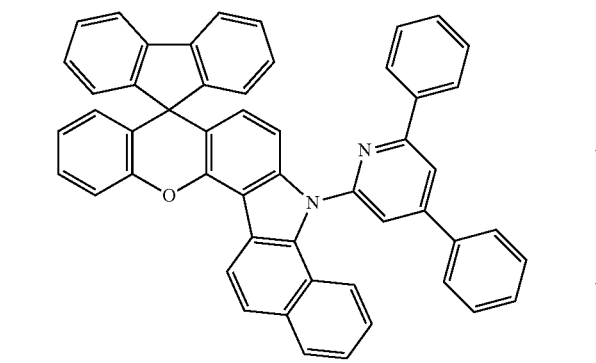
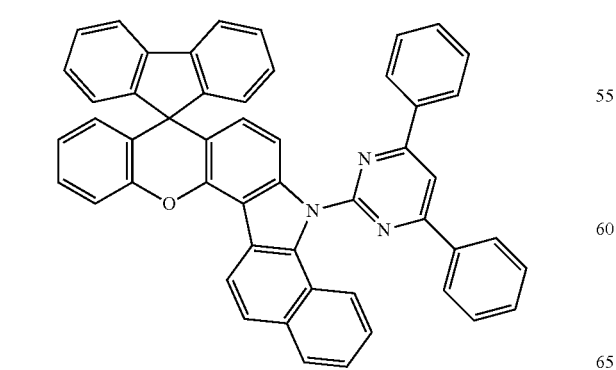
168
-continued
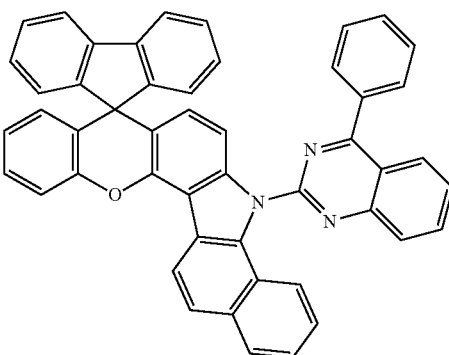
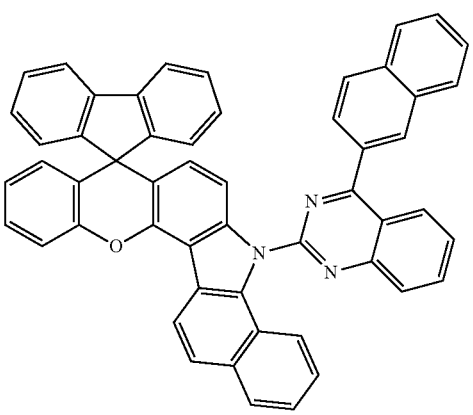
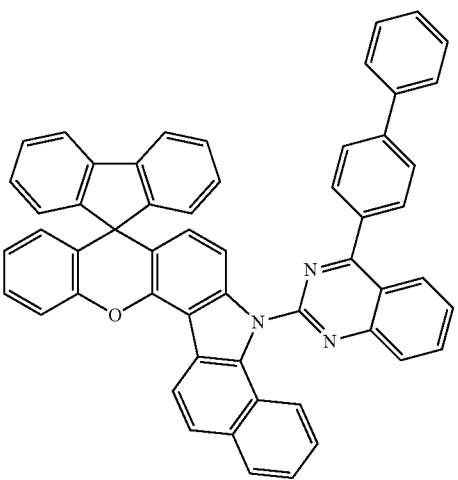
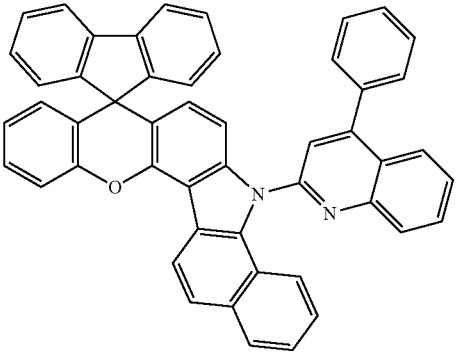

169
-continued
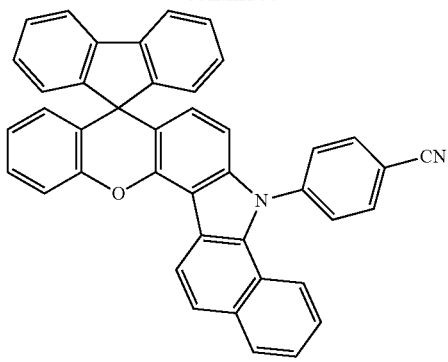
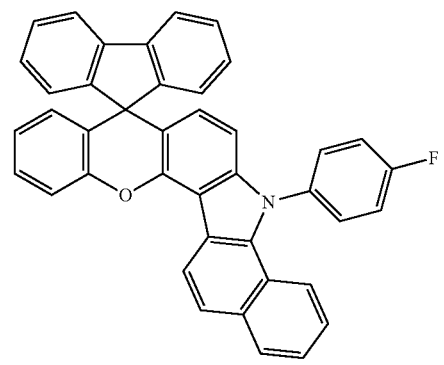
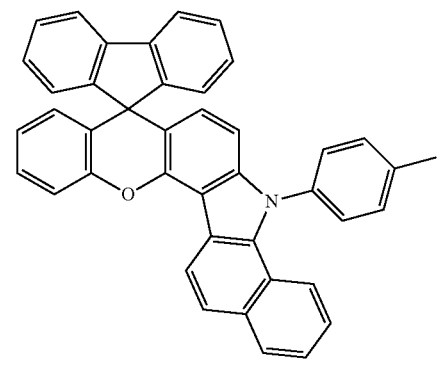
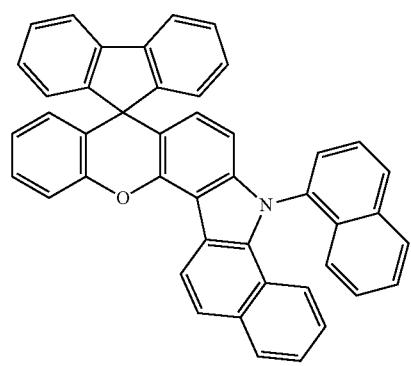
170
-continued
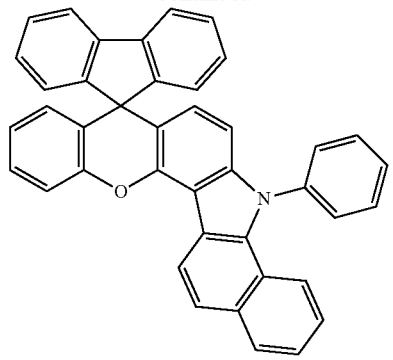
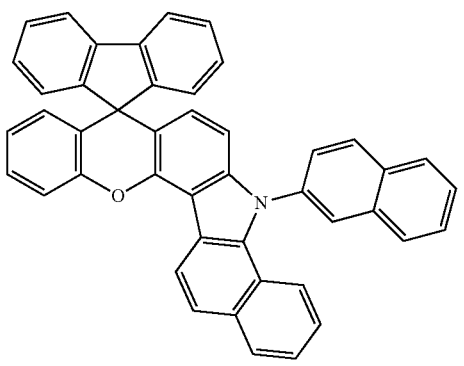
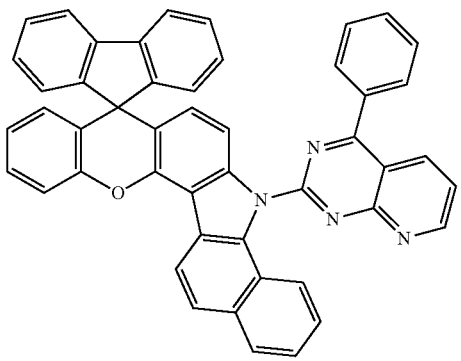
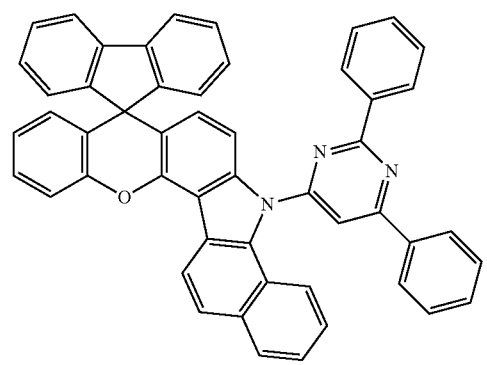

171
-continued
172
-continued
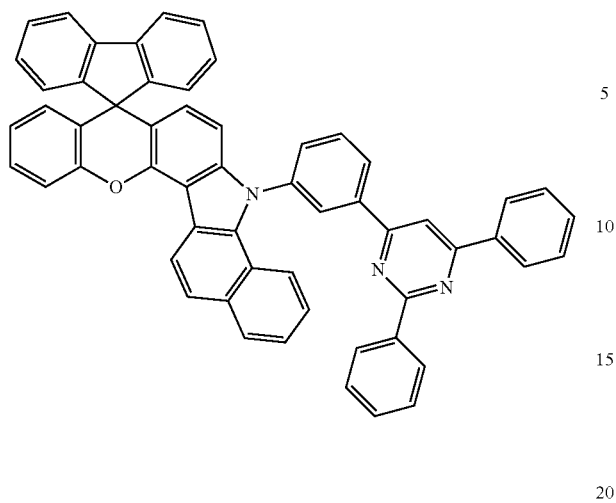
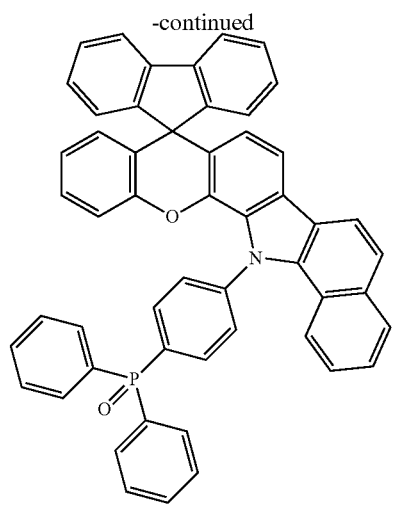
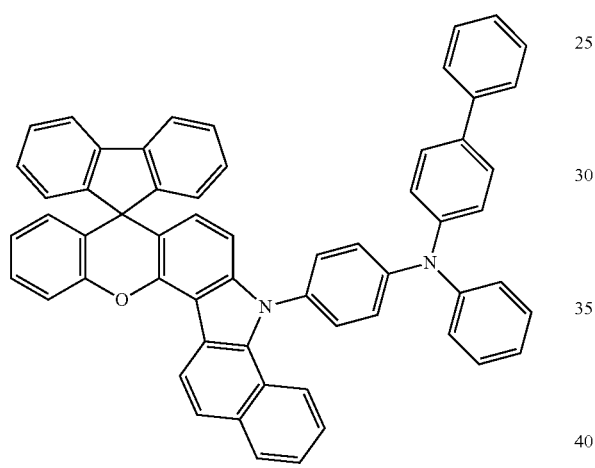
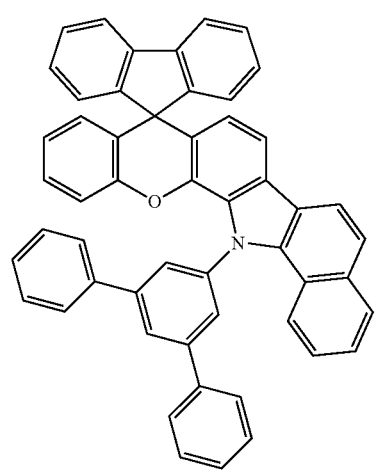
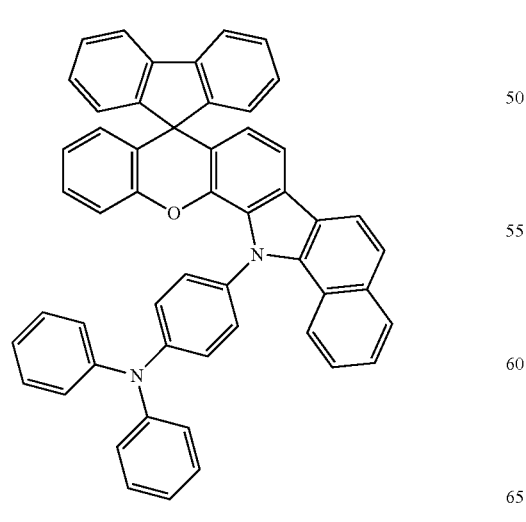
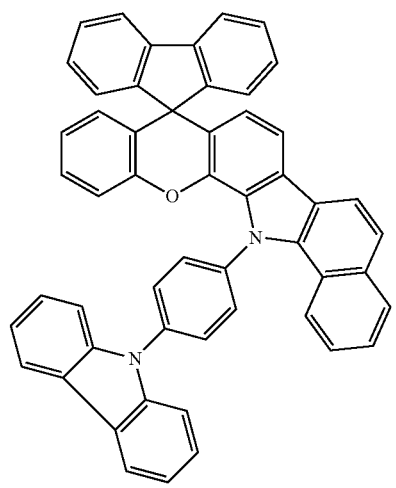

173
-continued
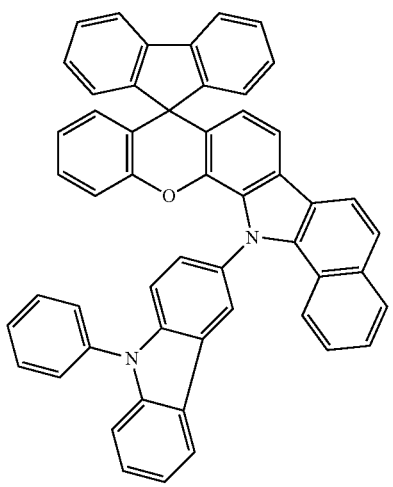
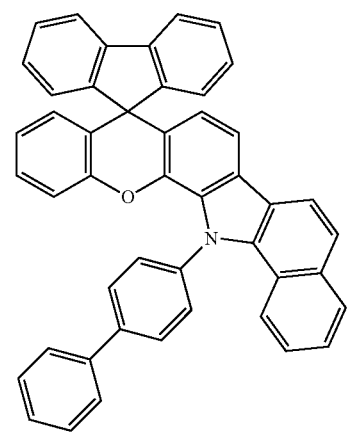
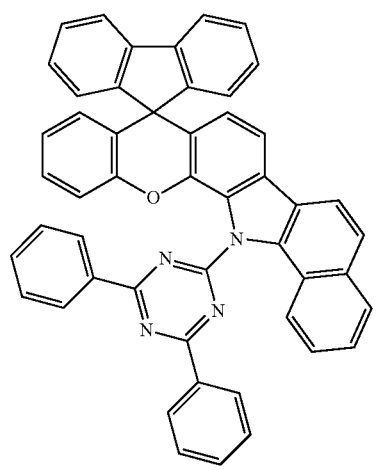
174
-continued
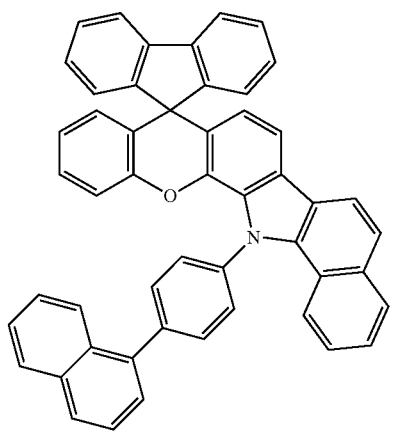
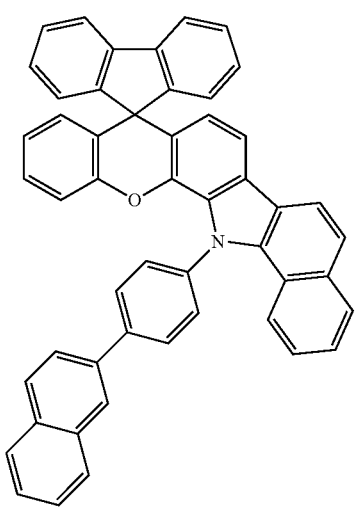
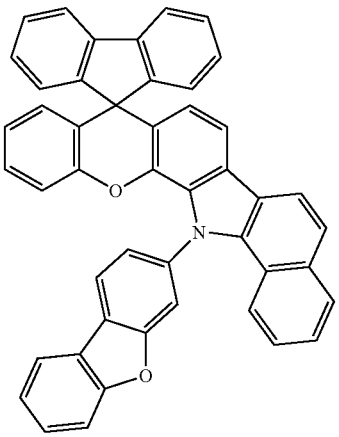

175
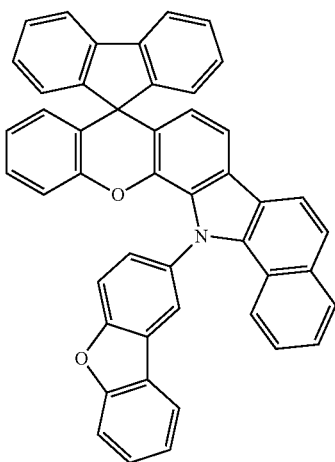
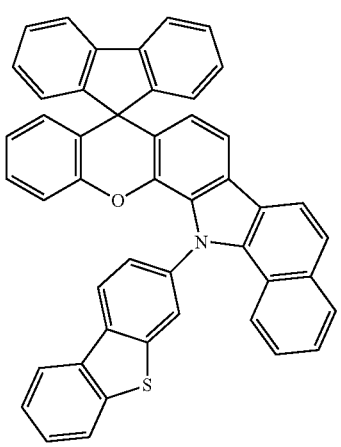
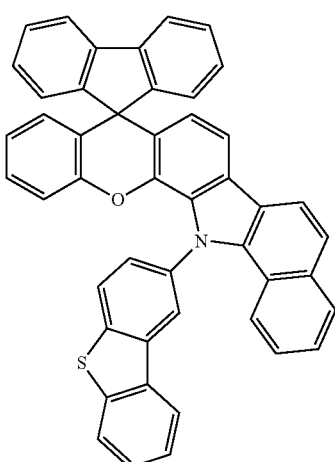
176
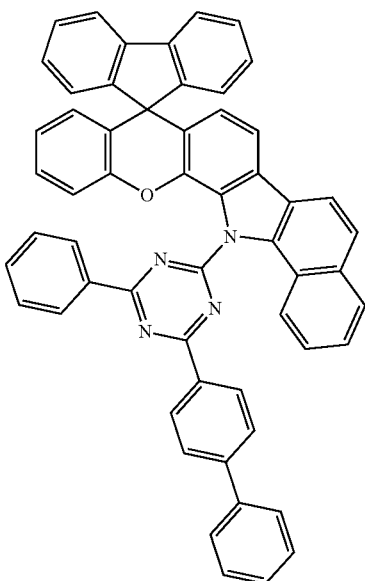
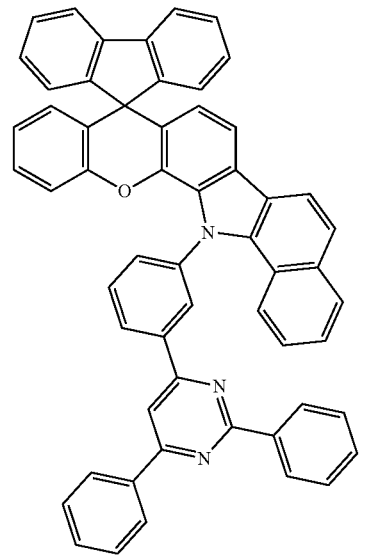

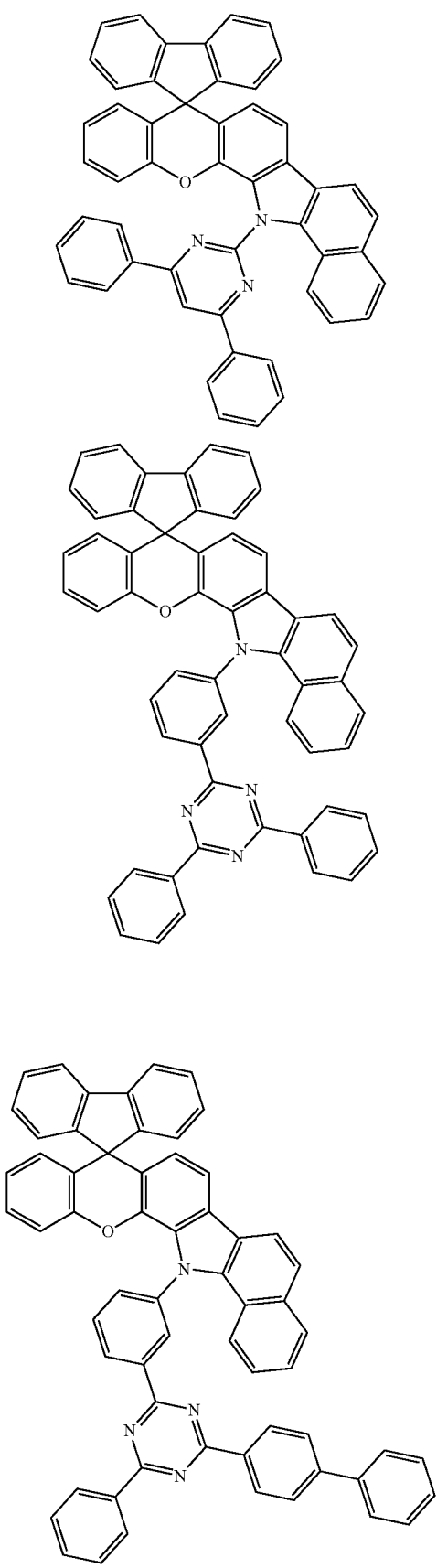
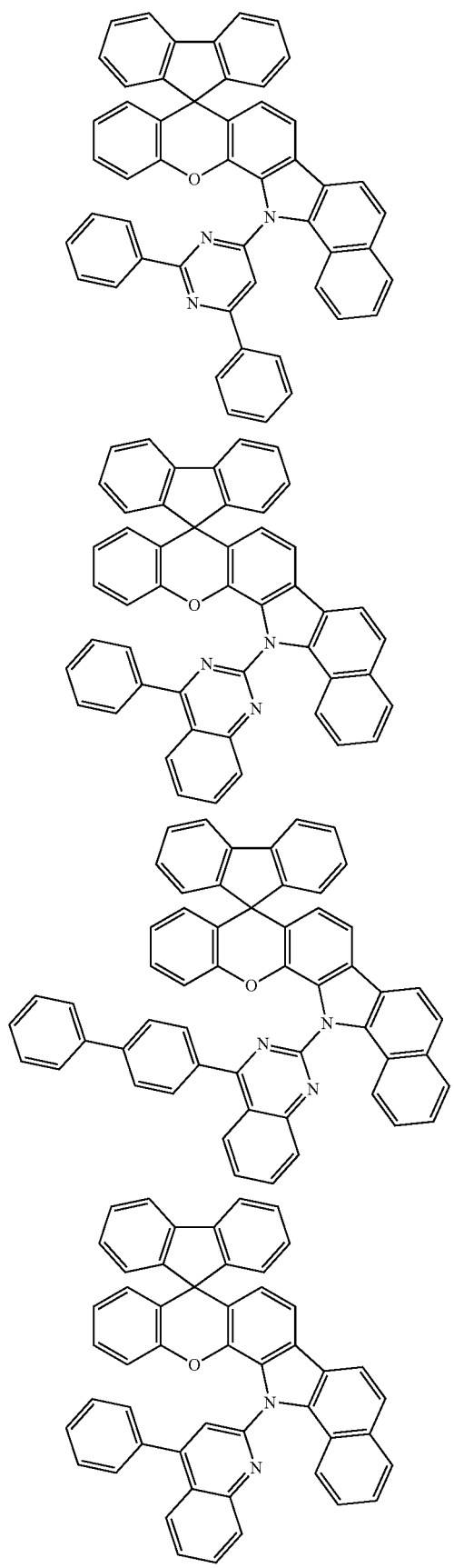

179
-continued
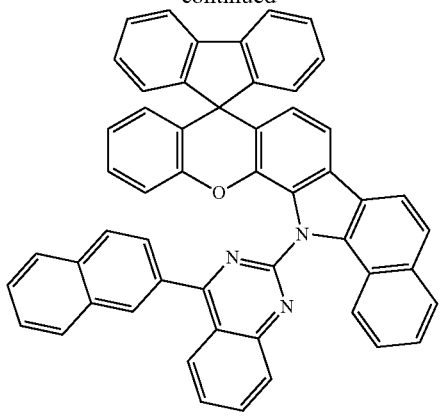
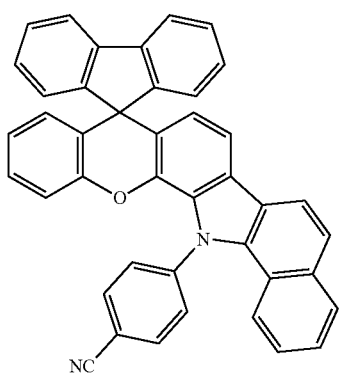
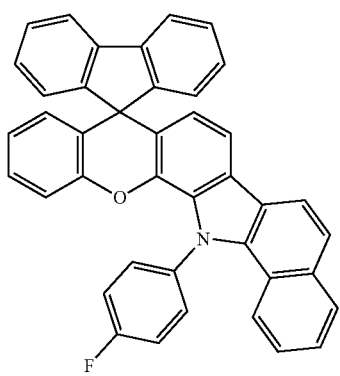
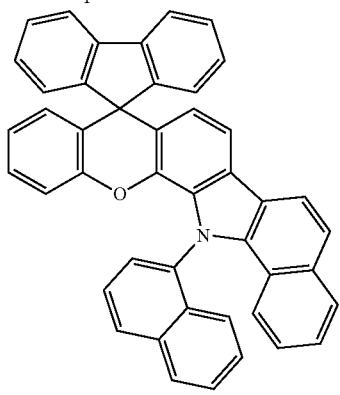
180
-continued
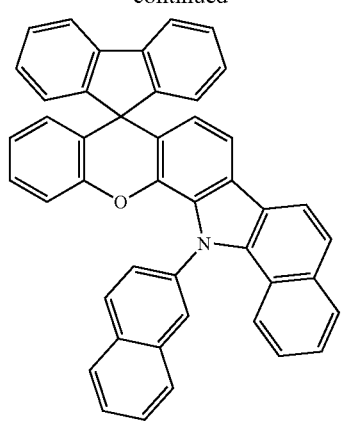
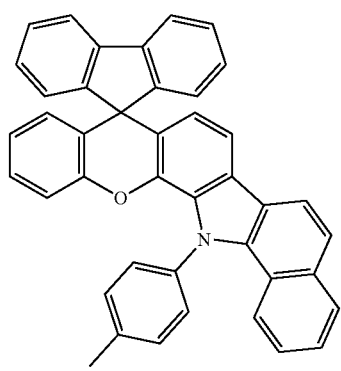
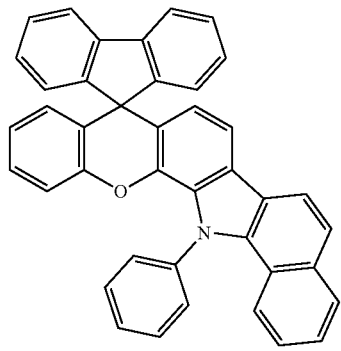
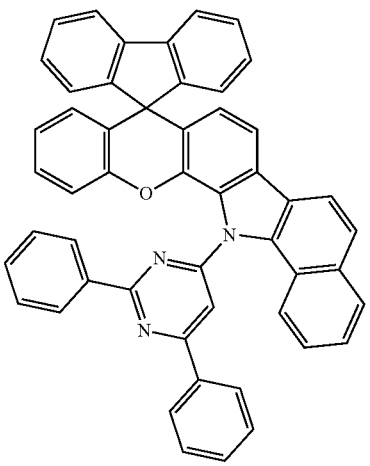

181
-continued
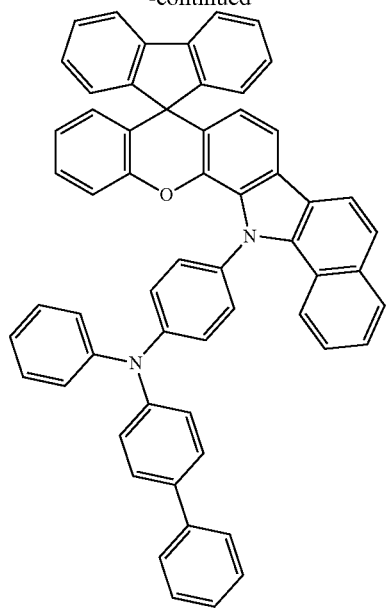
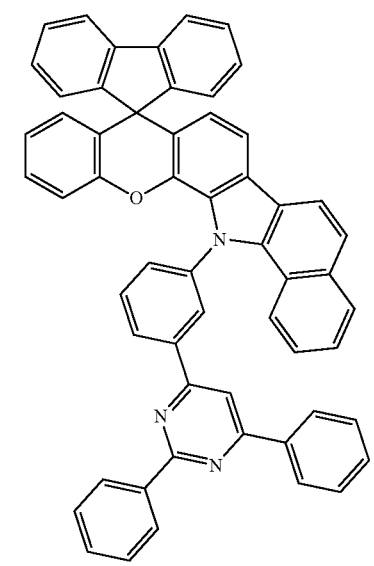
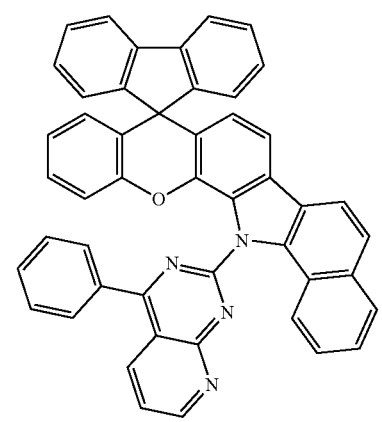
182
-continued
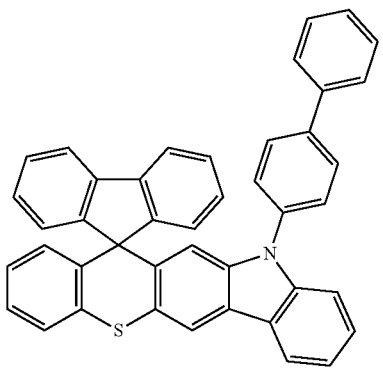
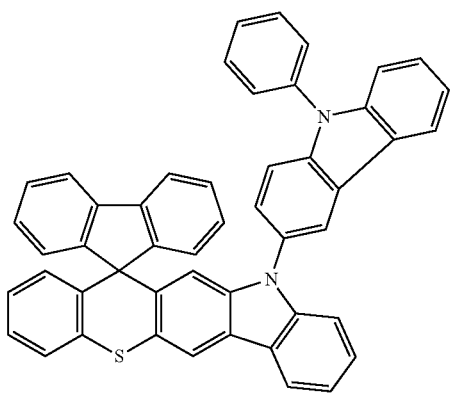
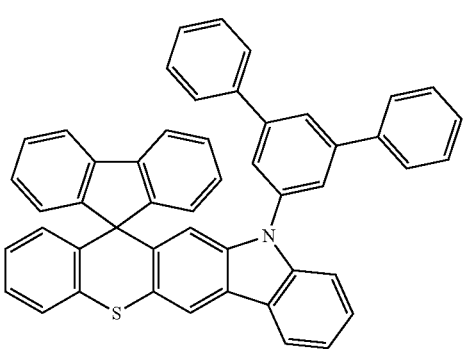
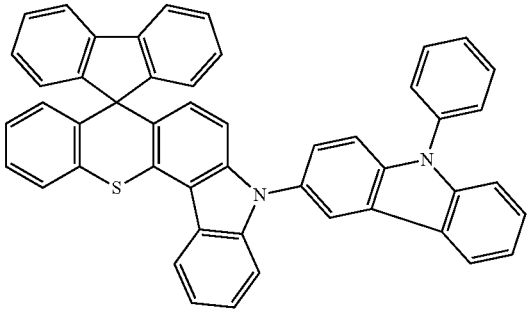

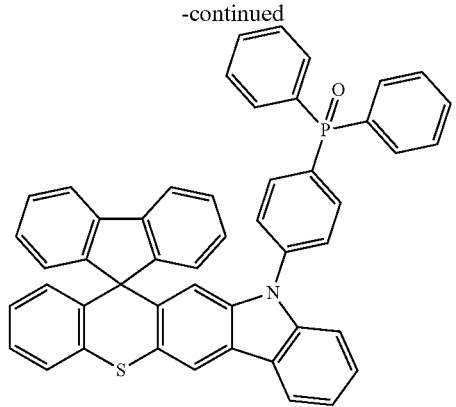
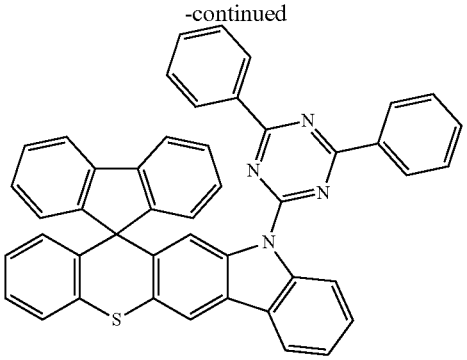
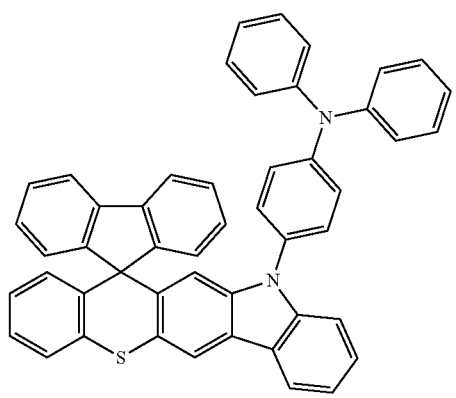
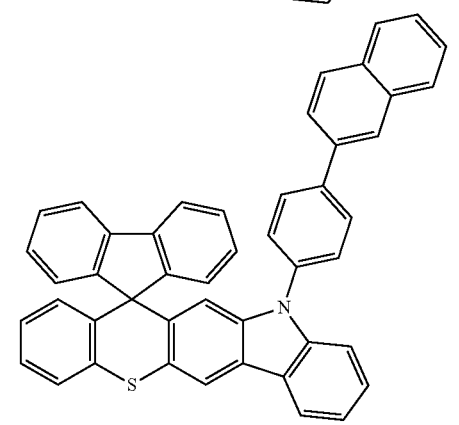
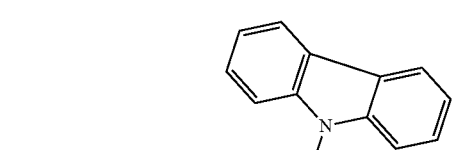
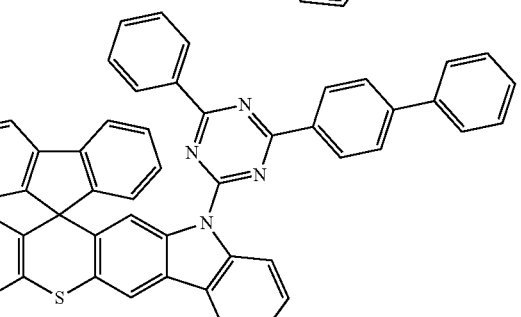
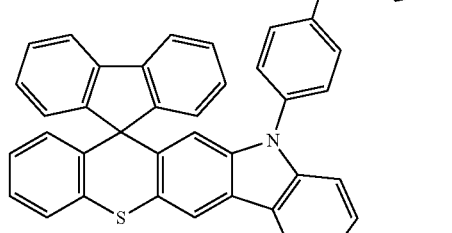
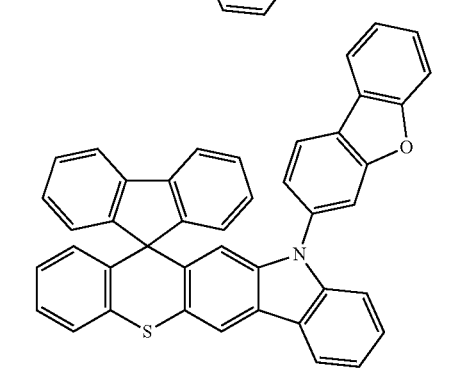
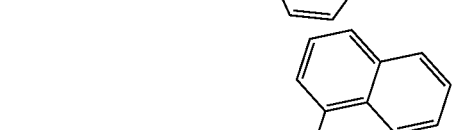
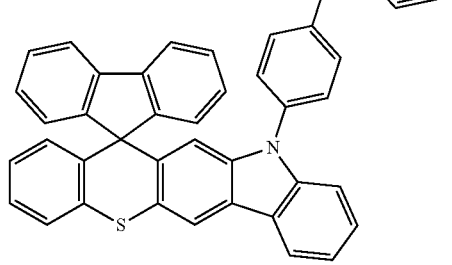
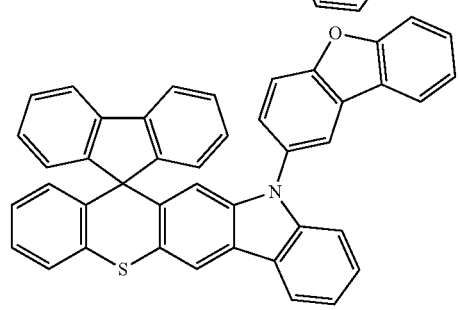

-continued
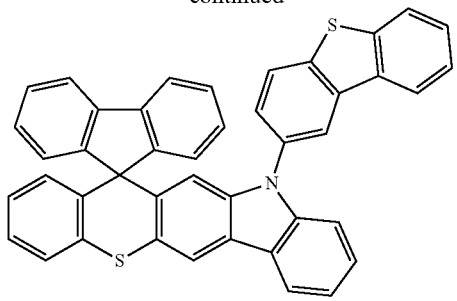
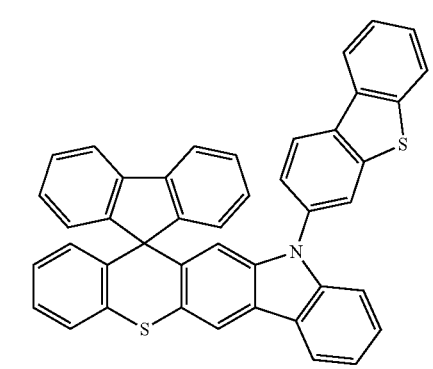
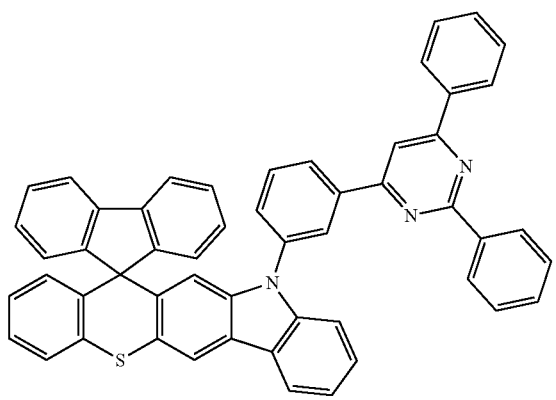
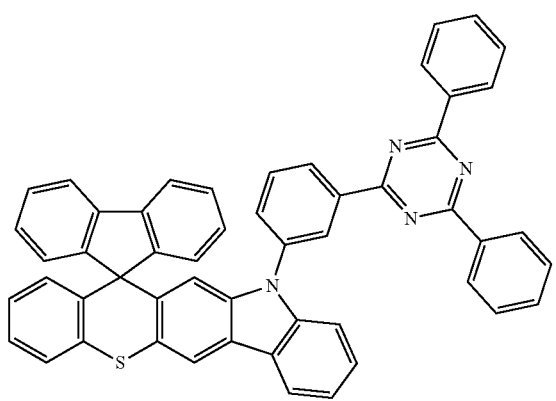
-continued
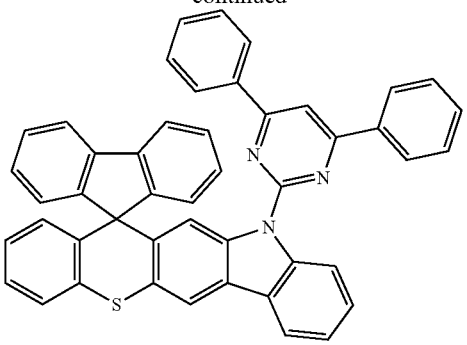
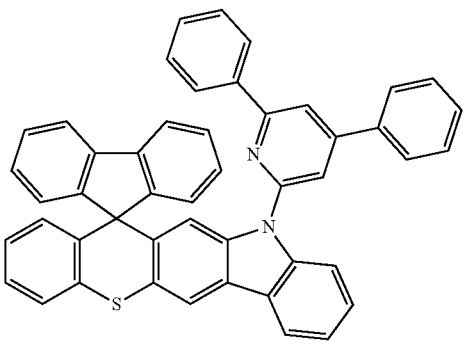
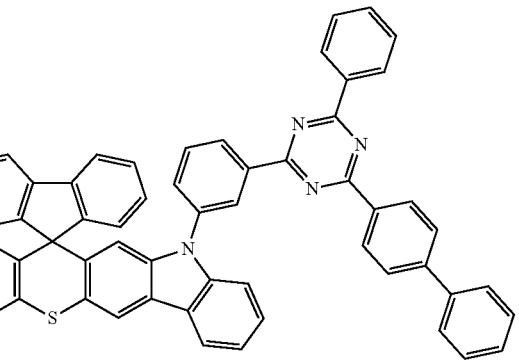
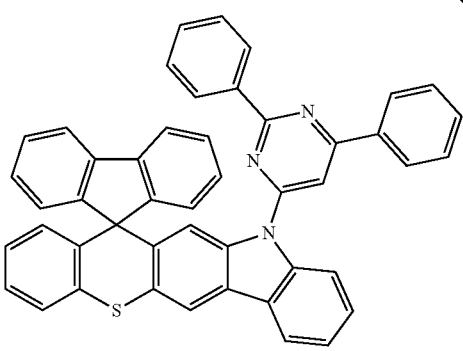
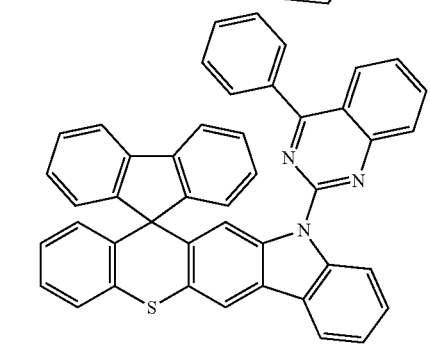

187
-continued
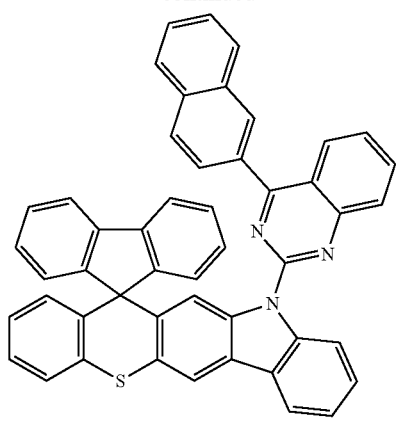
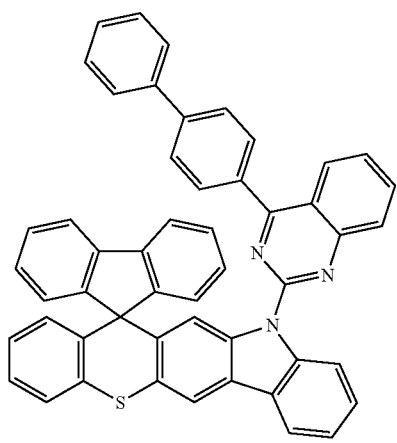
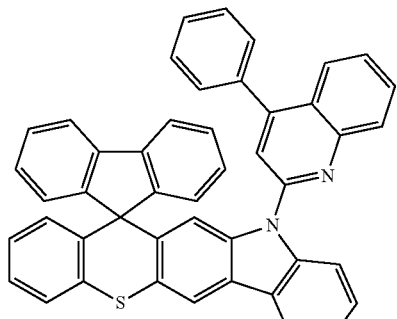
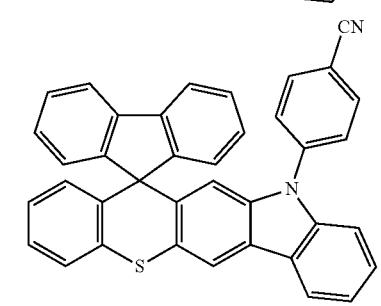
188
-continued
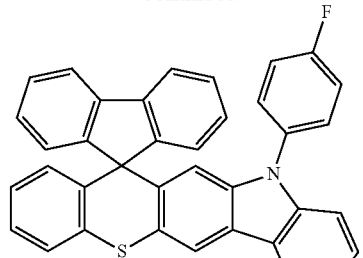
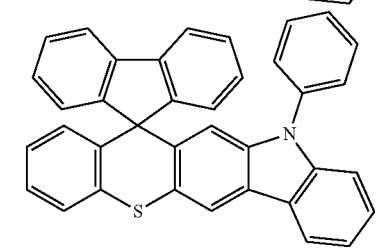
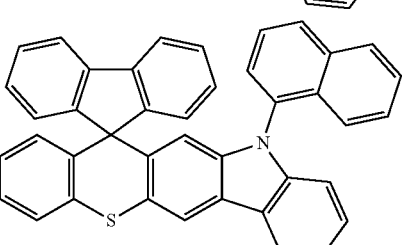
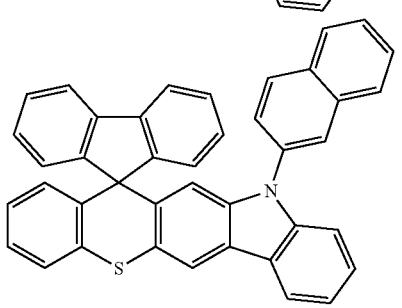
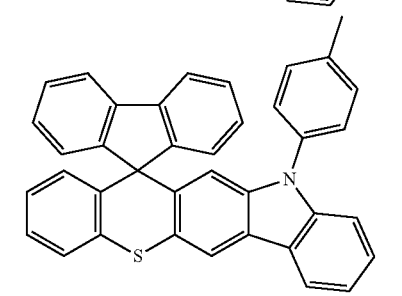
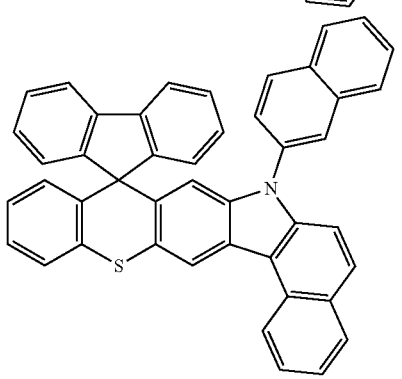

189
-continued
190
-continued
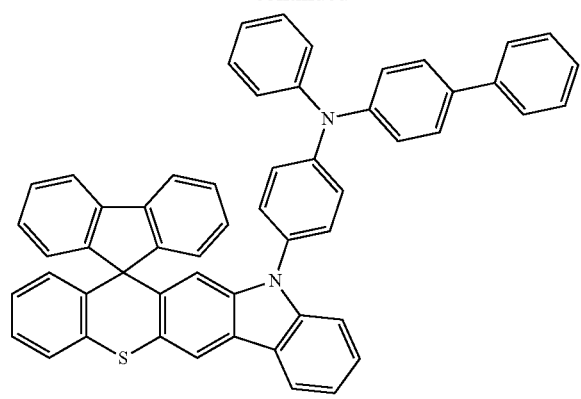
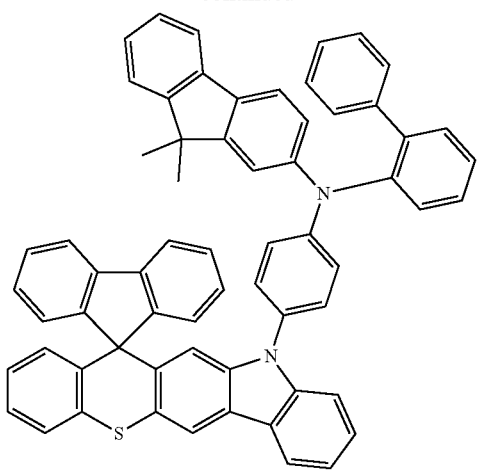
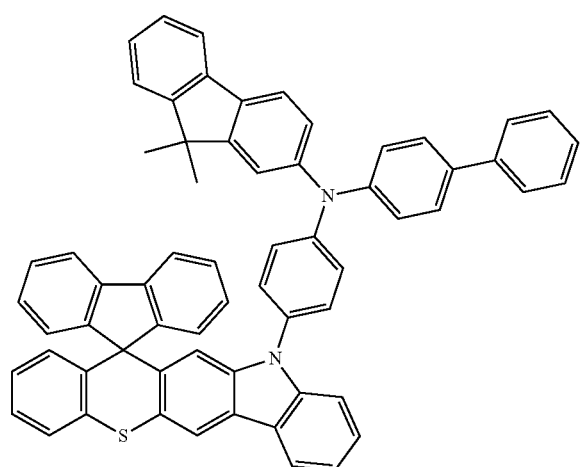
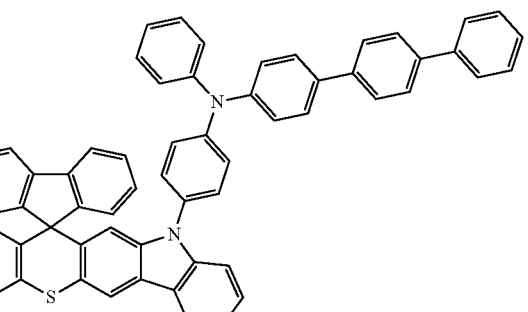
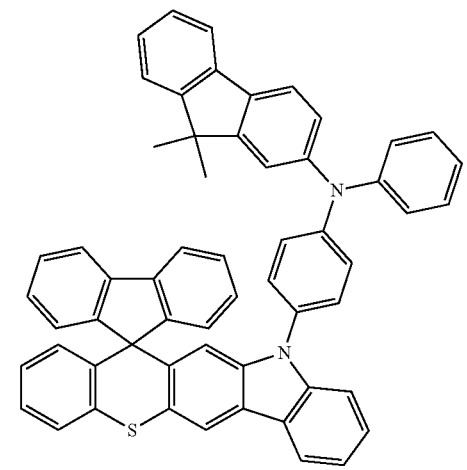
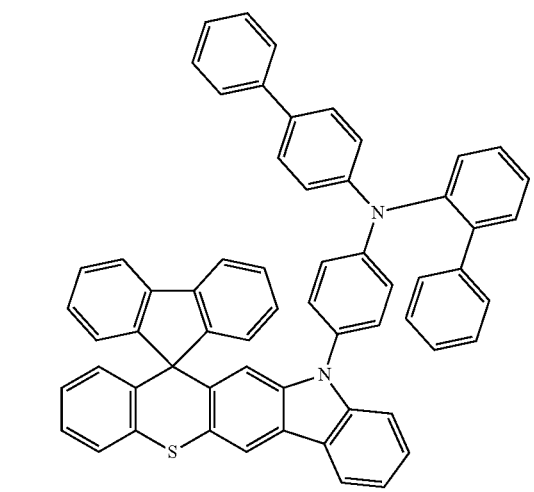
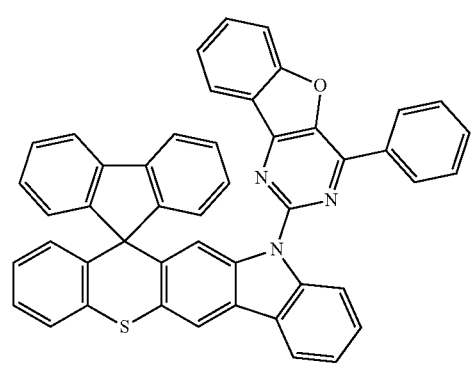

191
-continued
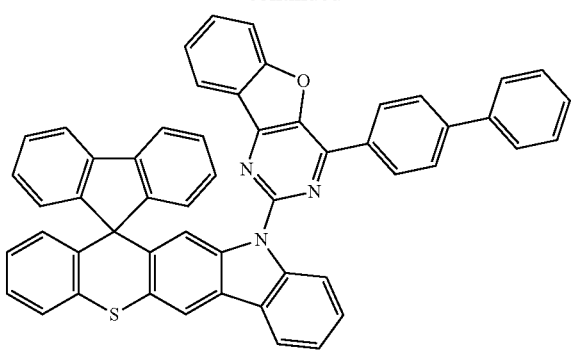
192
-continued
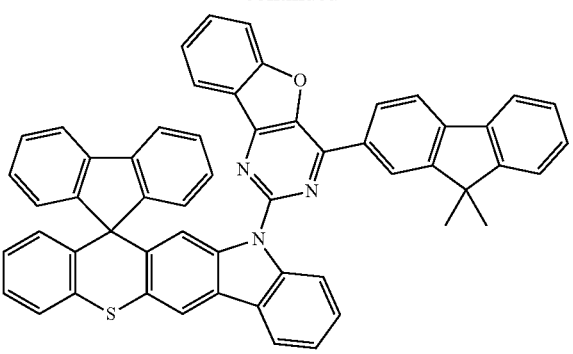
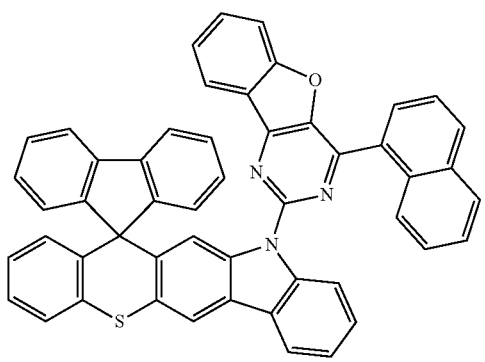
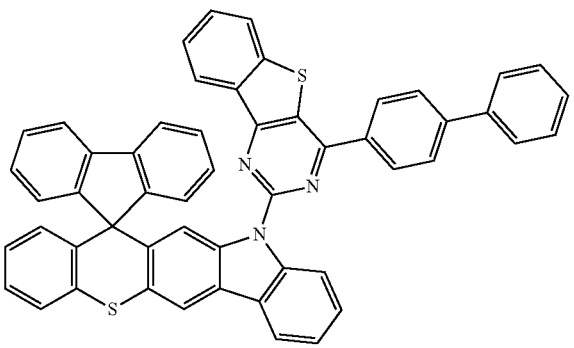
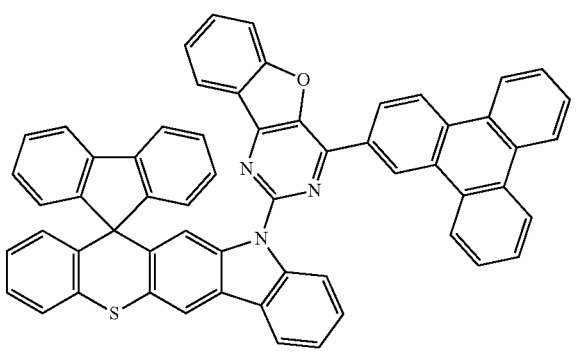
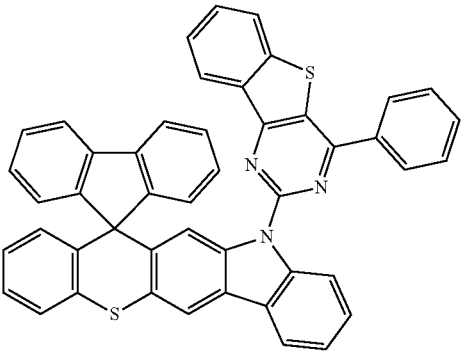
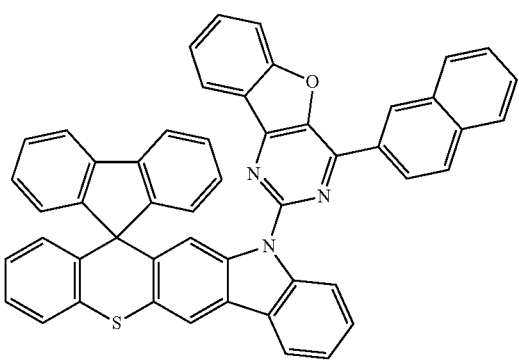
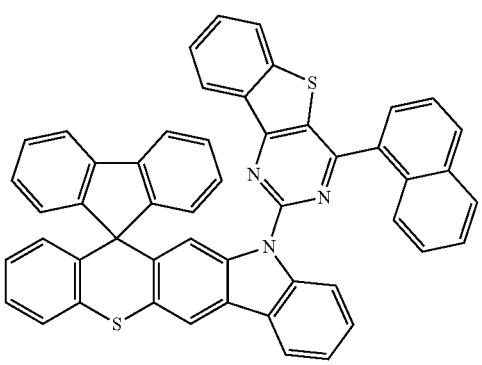

193
-continued
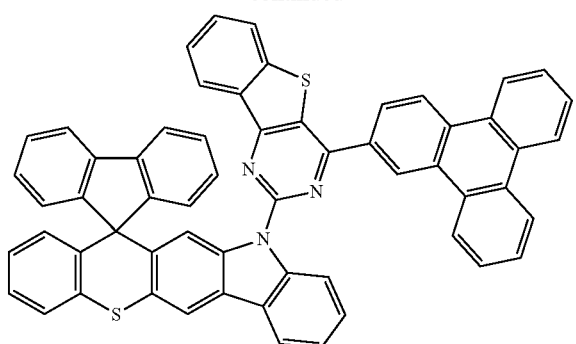
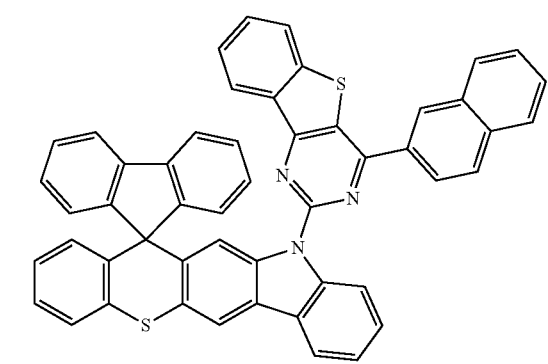
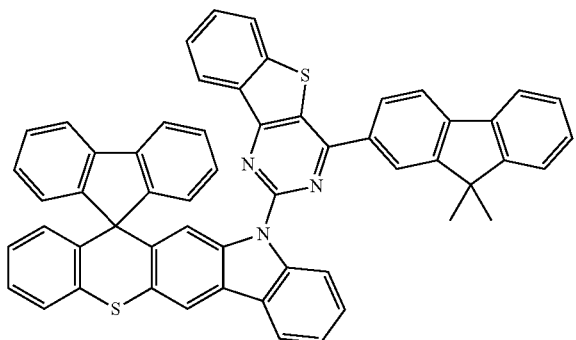
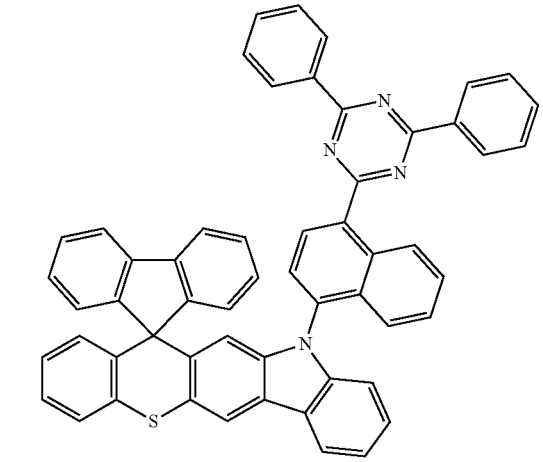
194
-continued
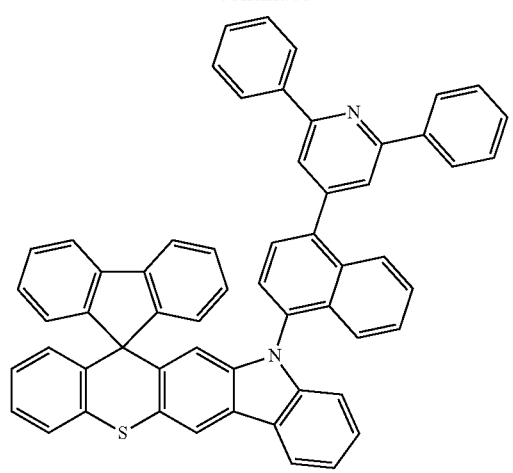
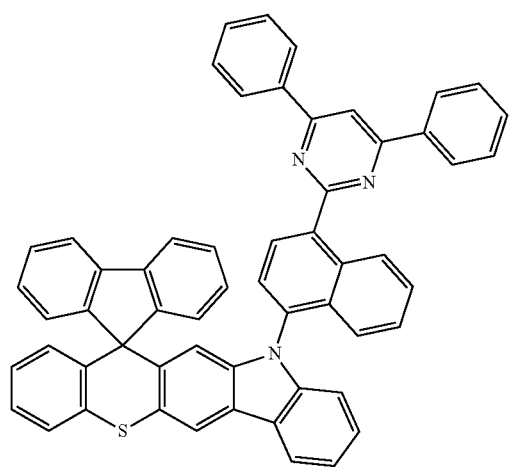
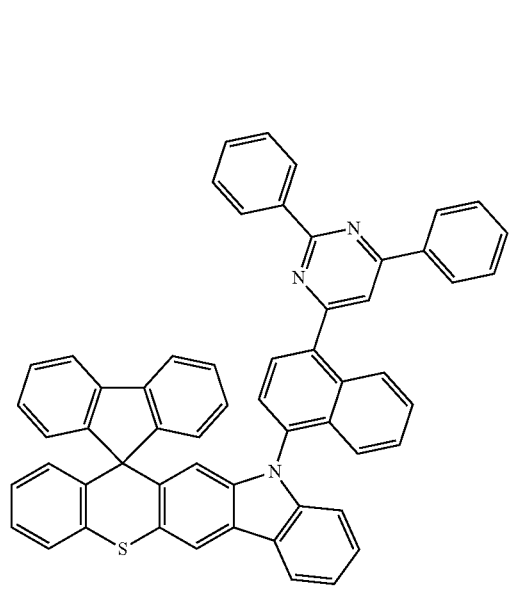

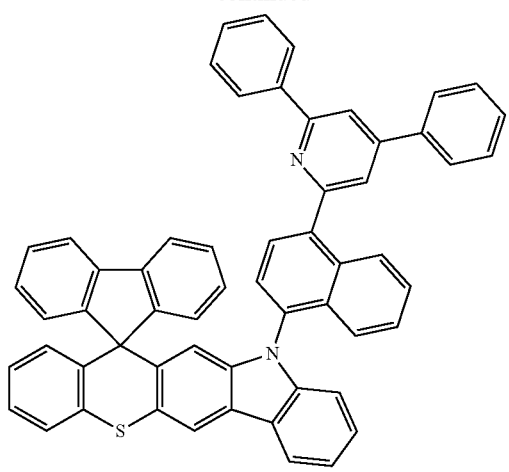
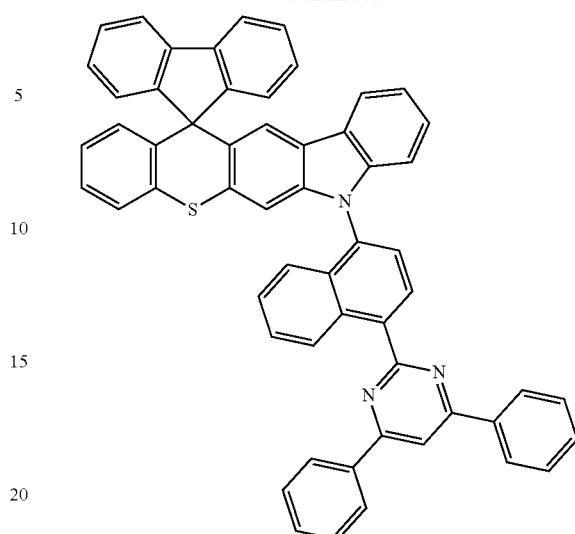
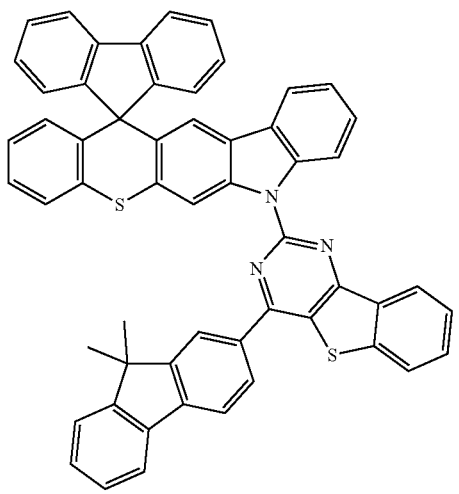
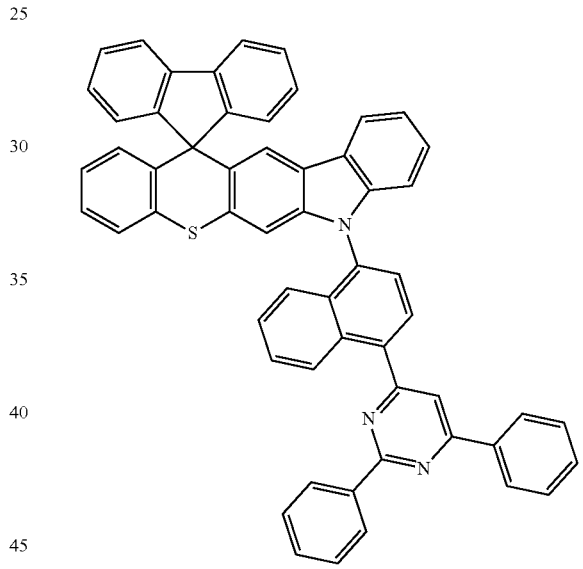
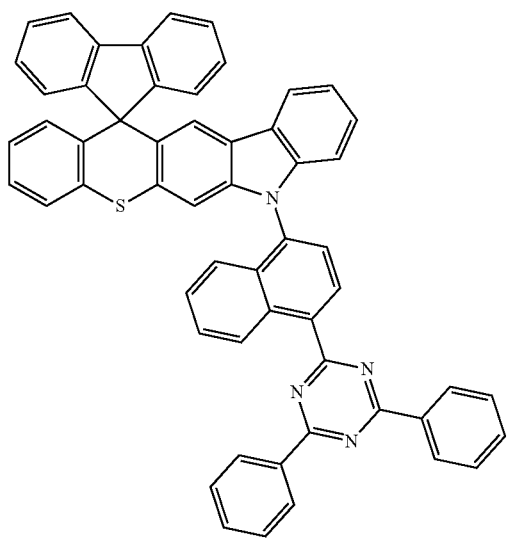
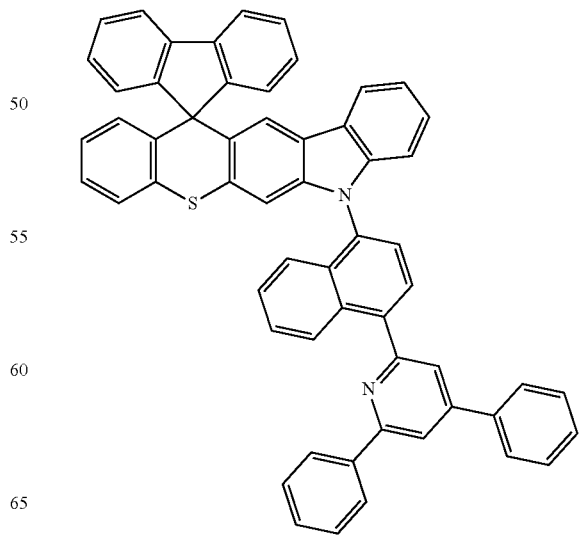

197
-continued
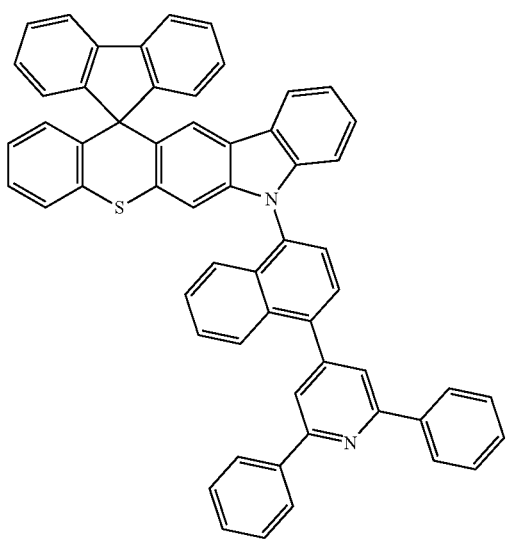
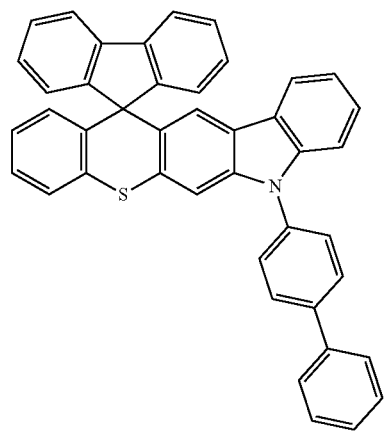
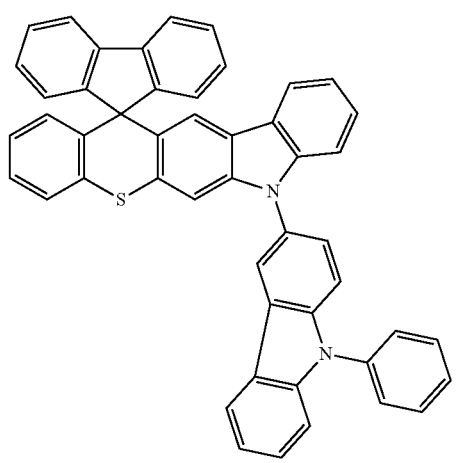
198
-continued
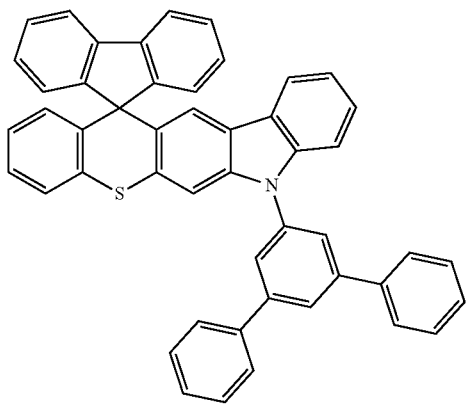
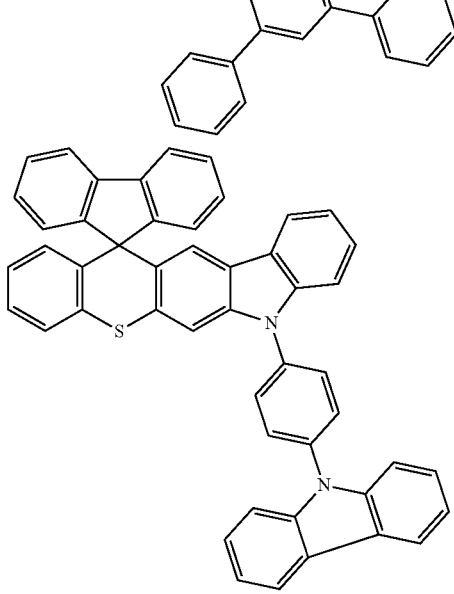
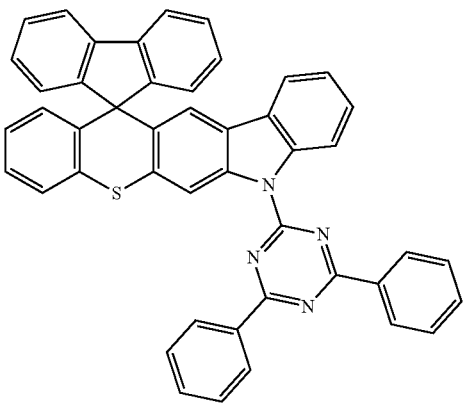
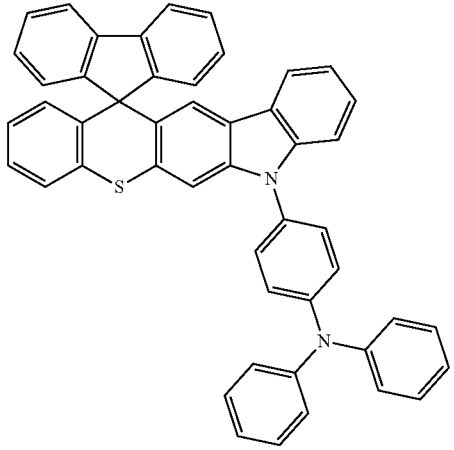

199
-continued
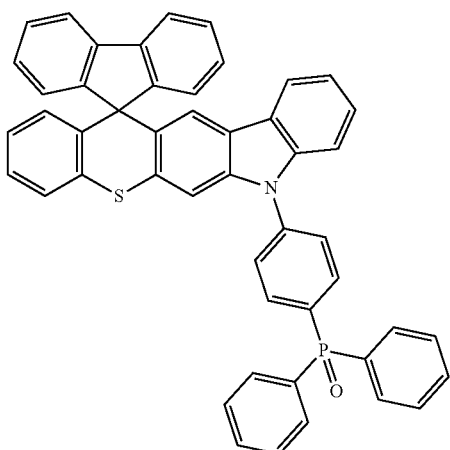
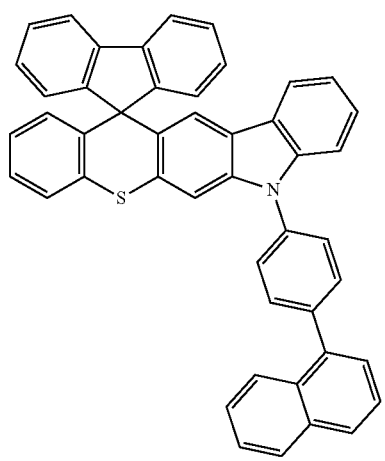
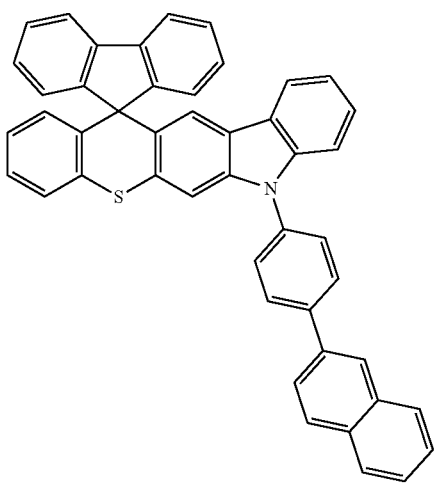
200
-continued
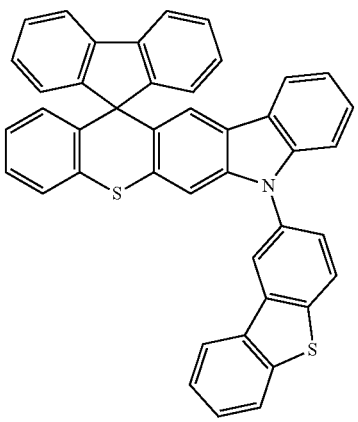
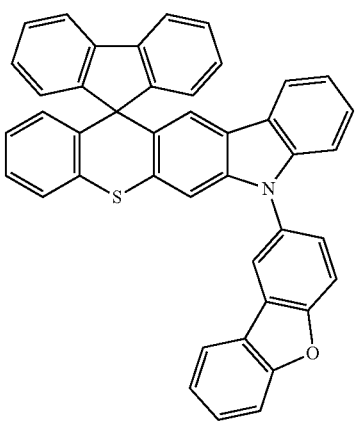
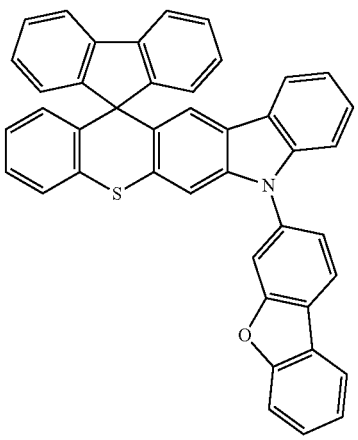
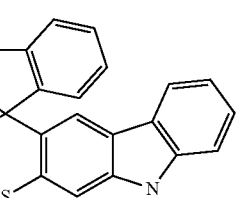
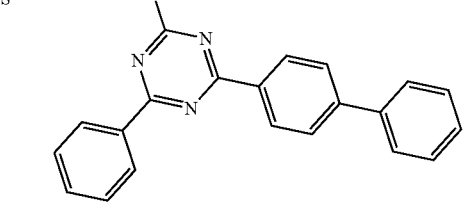

201
-continued
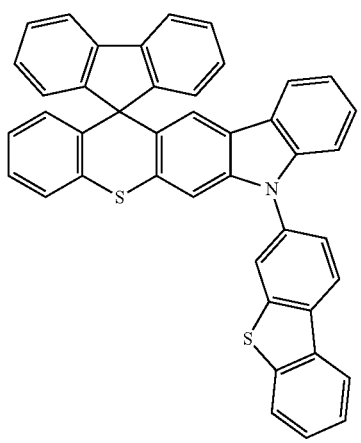
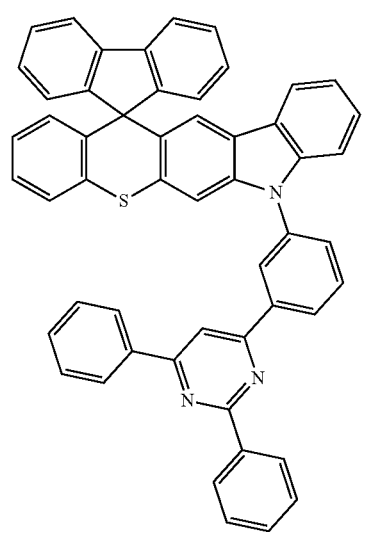
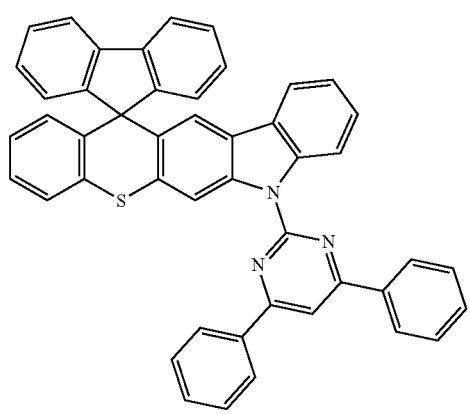
202
-continued
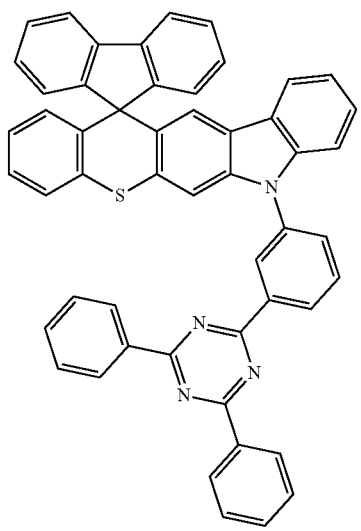
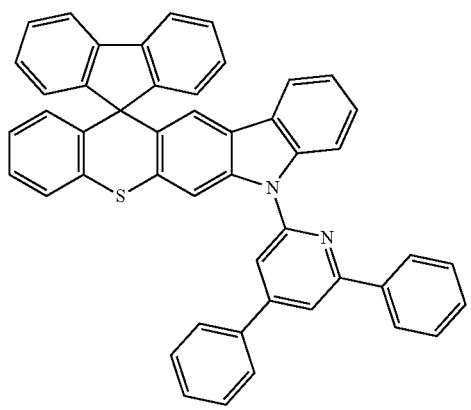
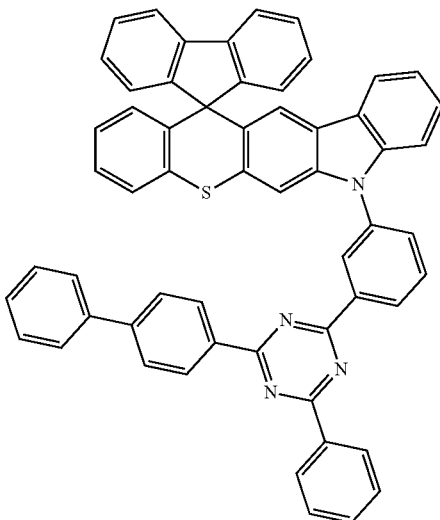

203
-continued
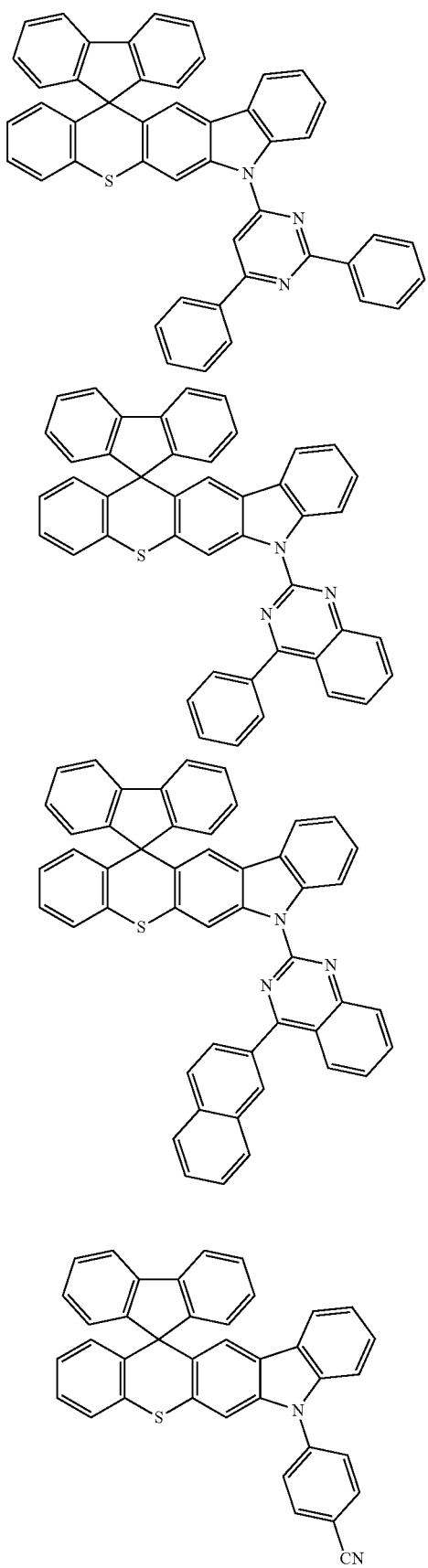
204
-continued
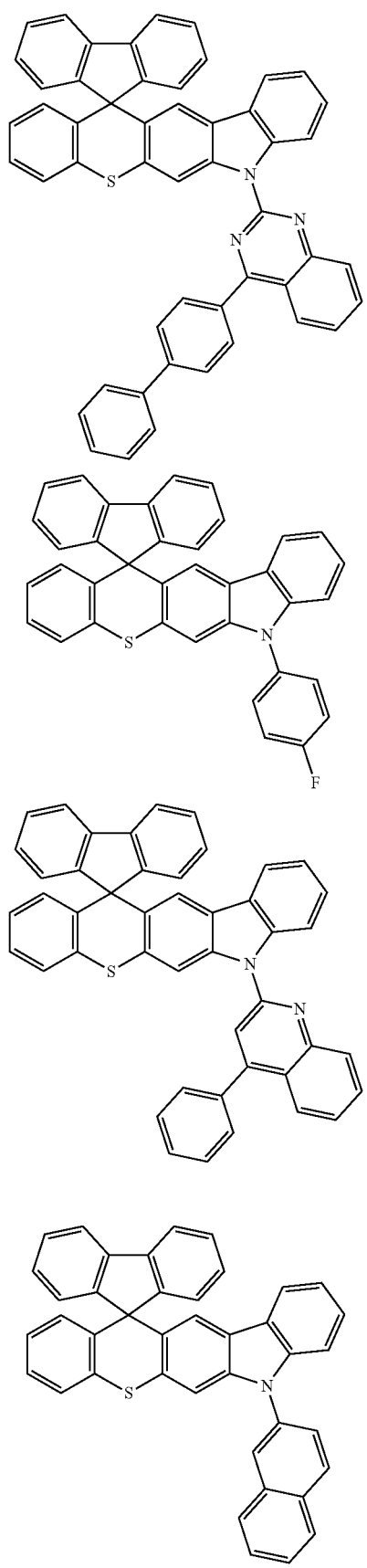

205
-continued
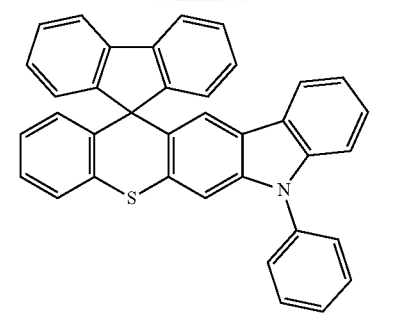
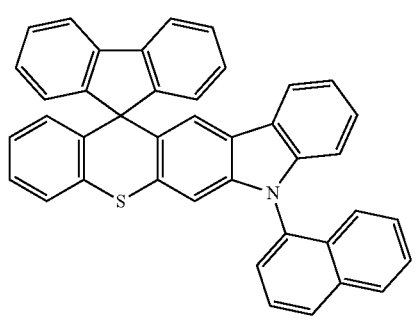
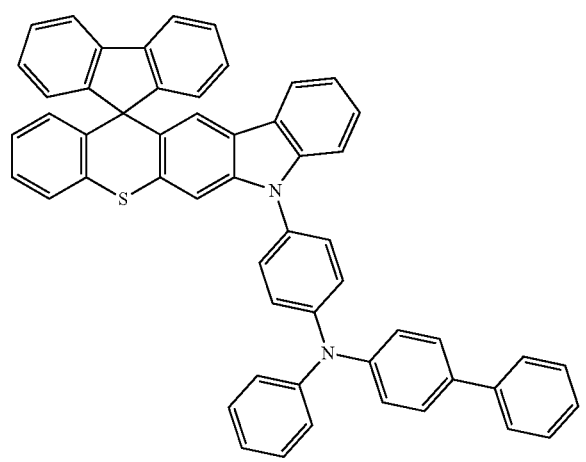
206
-continued
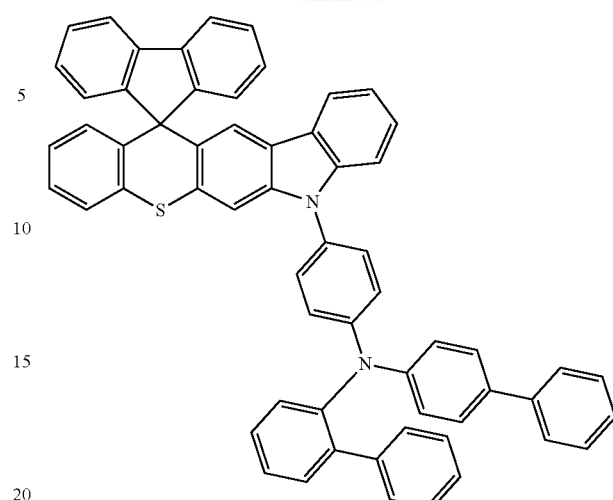
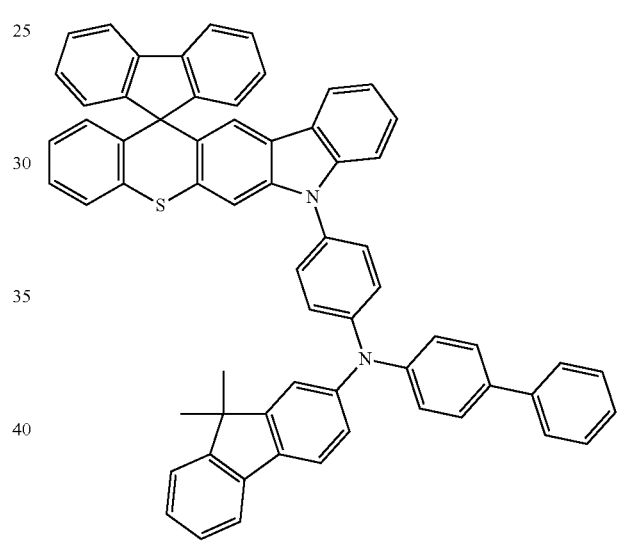
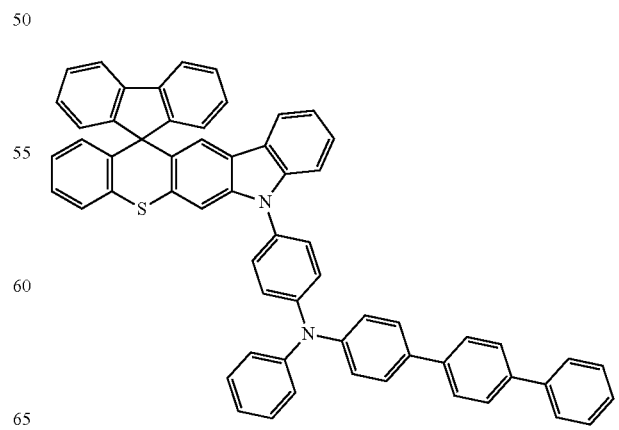

207
-continued
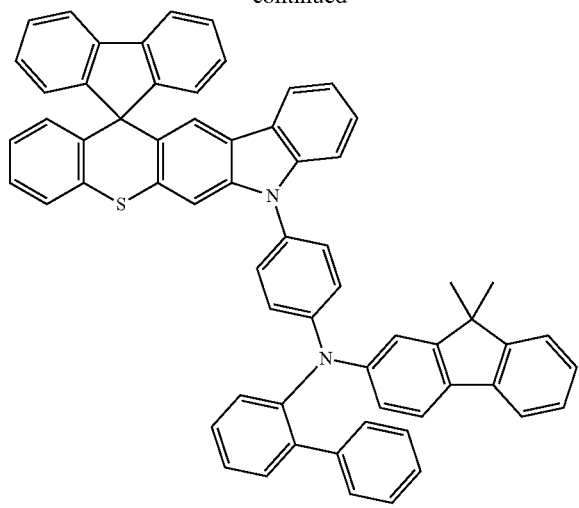
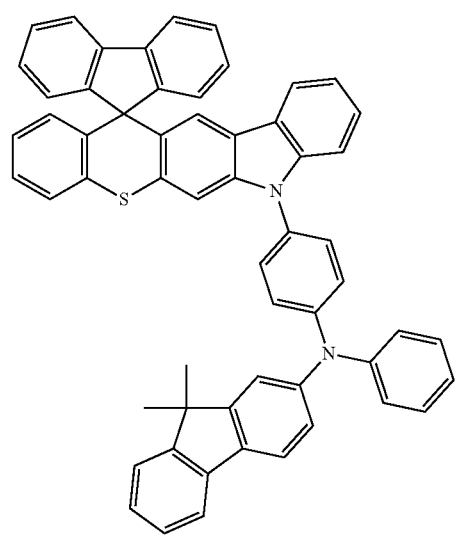
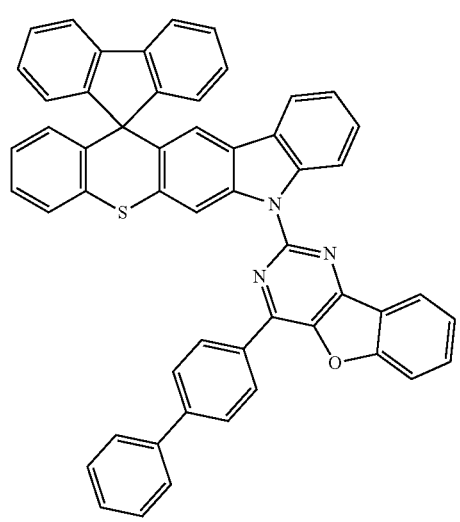
208
-continued
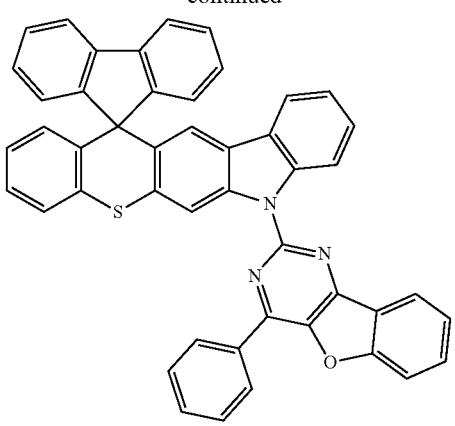
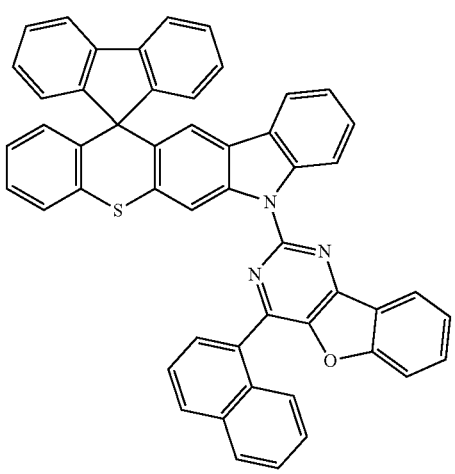
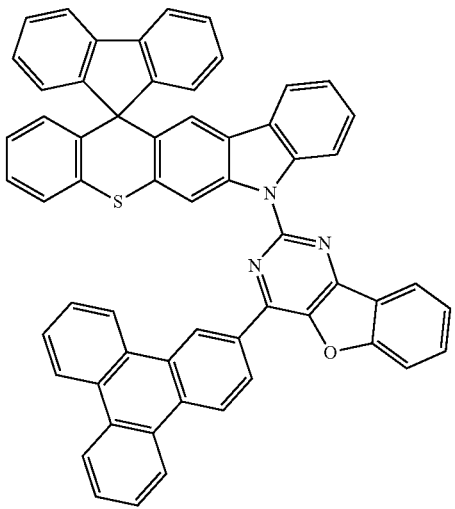

209
-continued
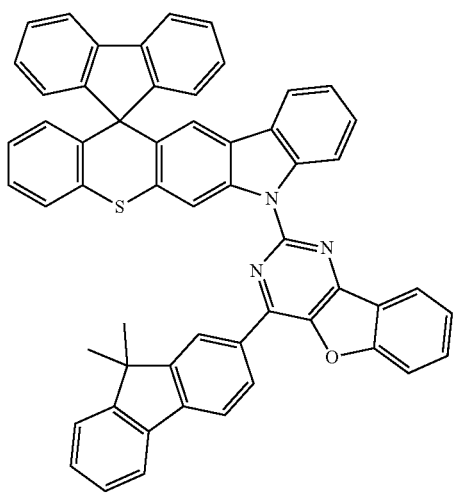
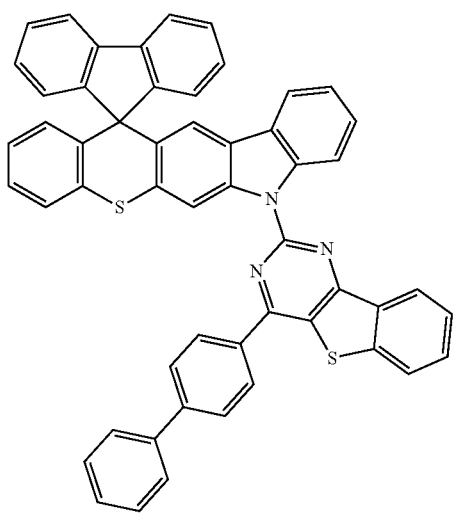
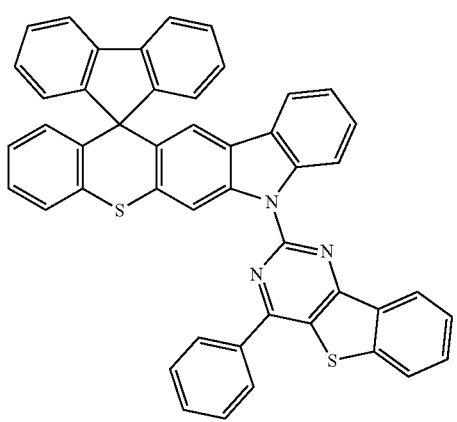
210
-continued
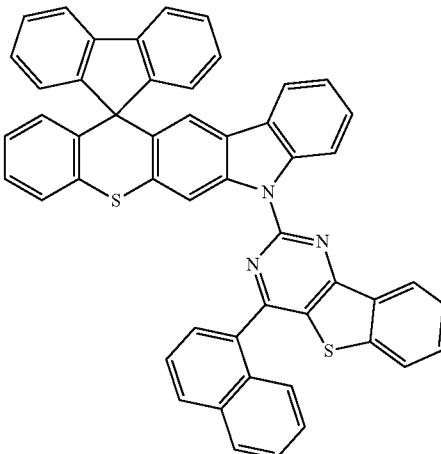
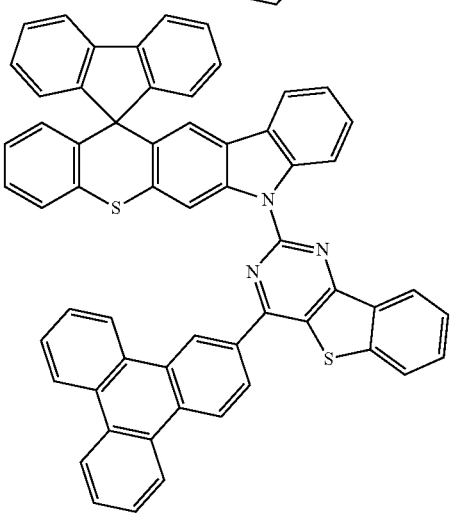
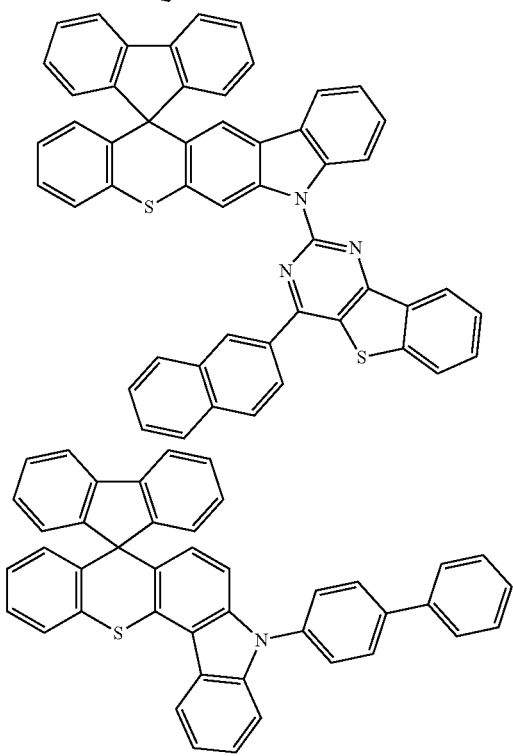

211
-continued
212
-continued
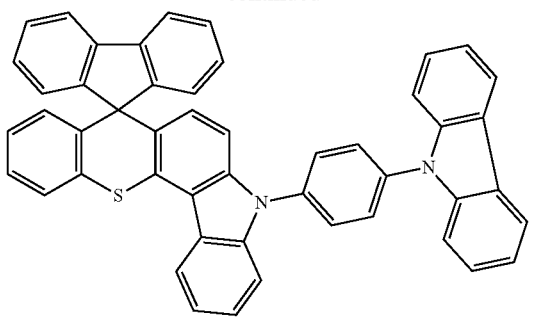
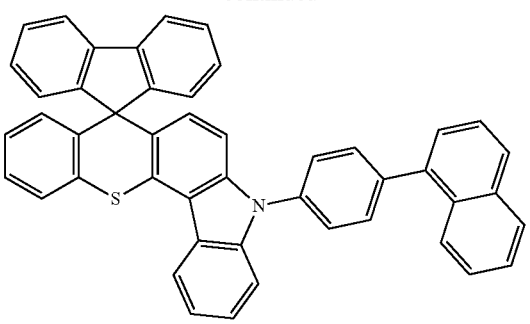

213
-continued
214
-continued
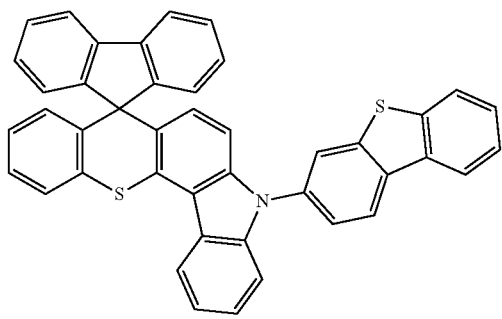
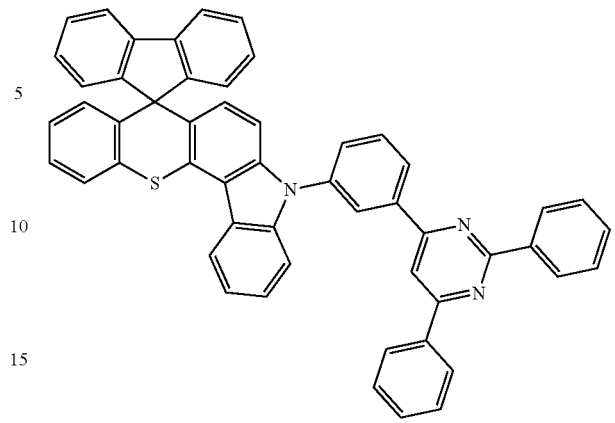
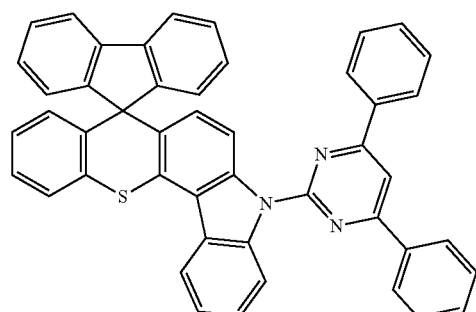
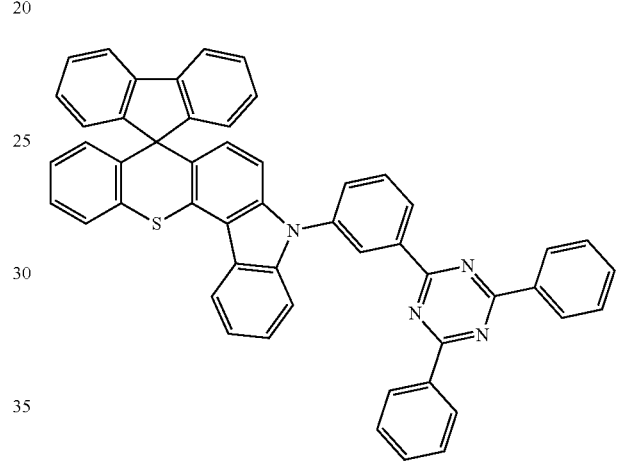
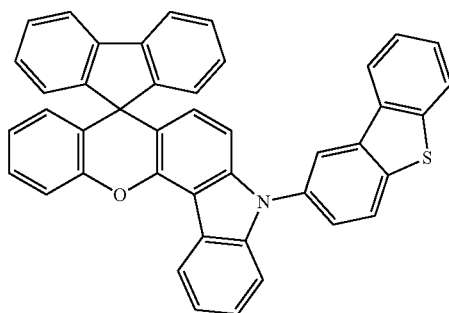
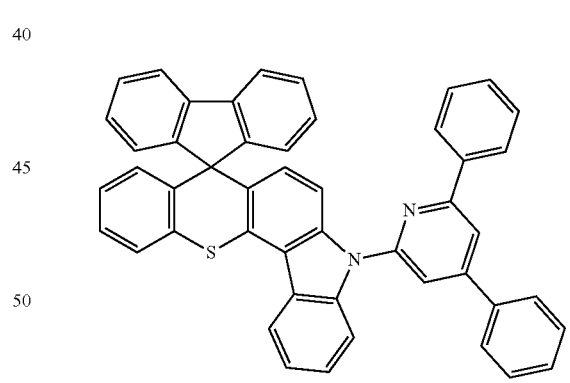
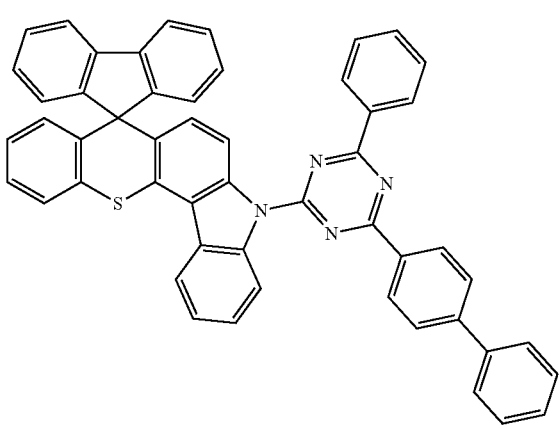
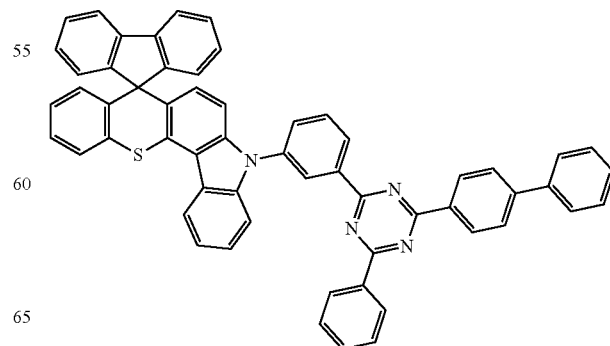

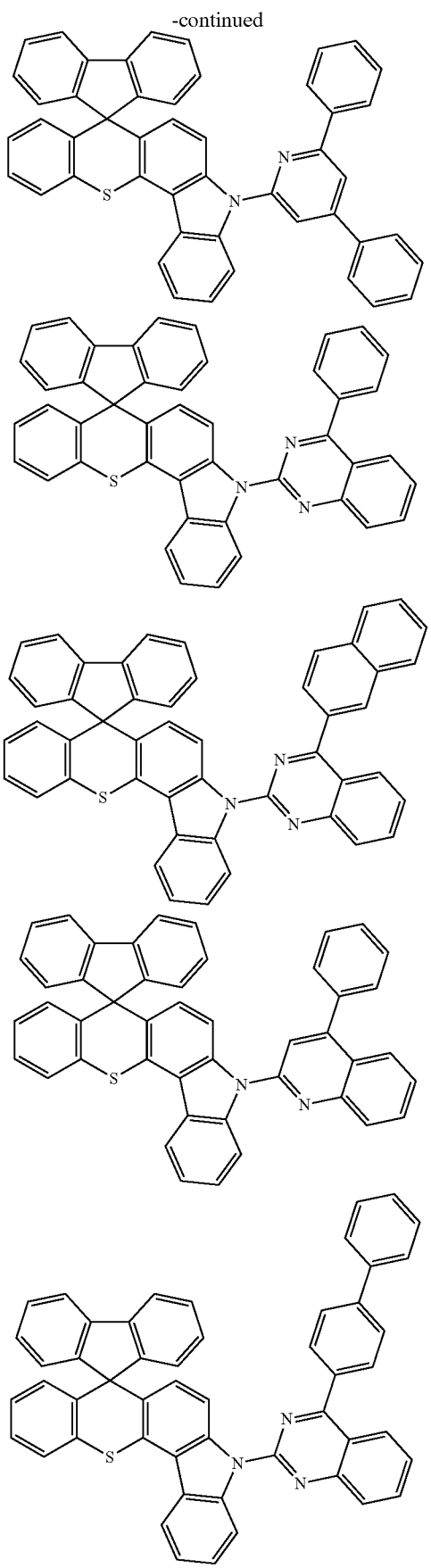
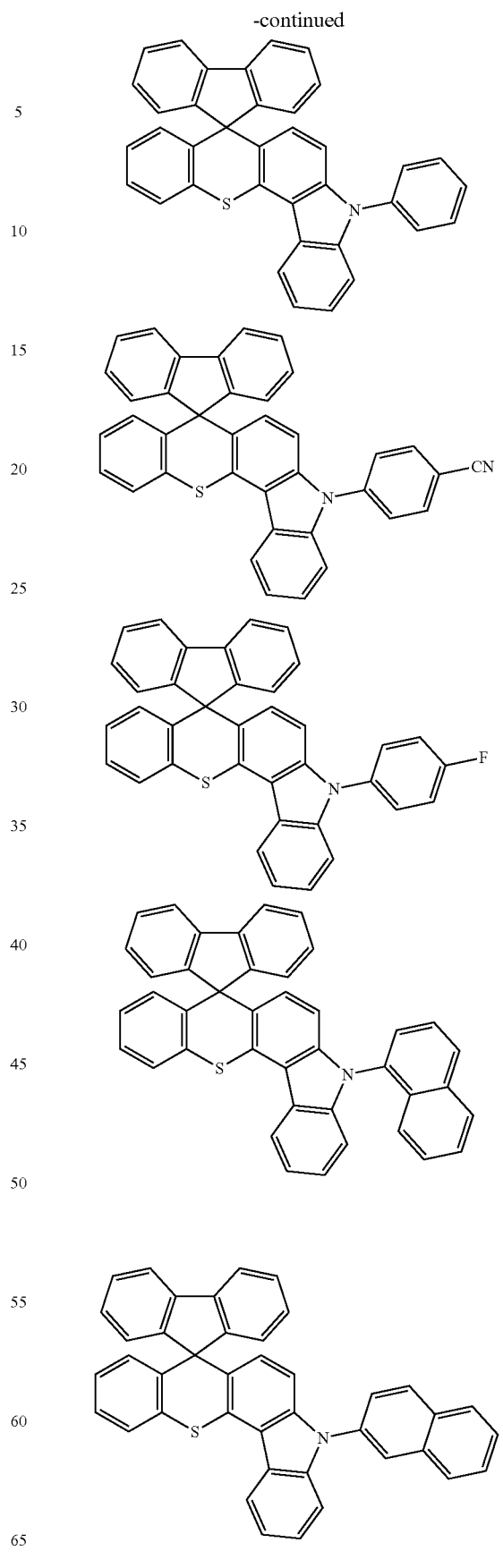

217
-continued
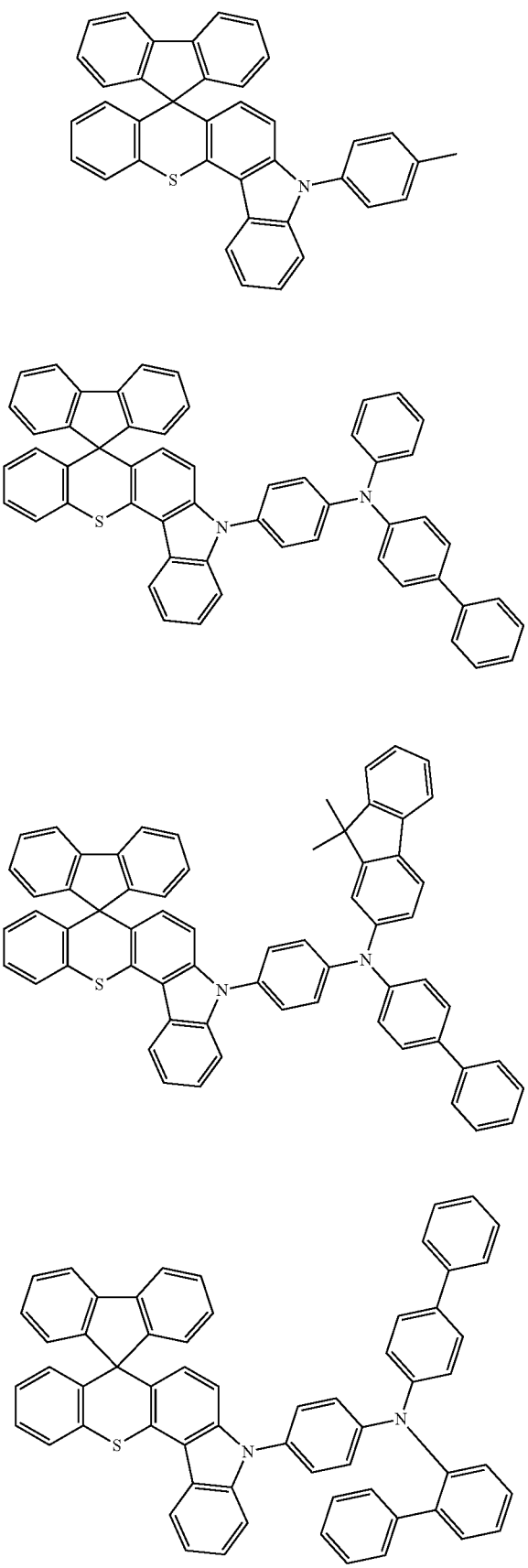
218
-continued
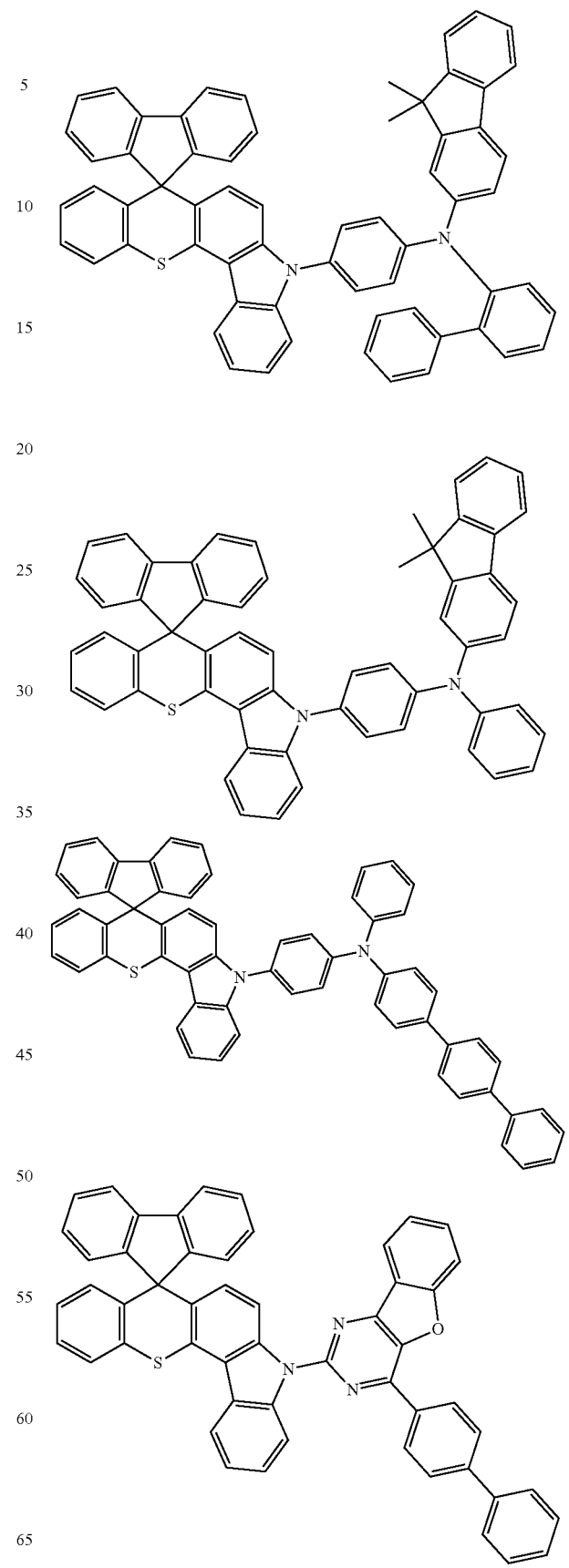

219
-continued
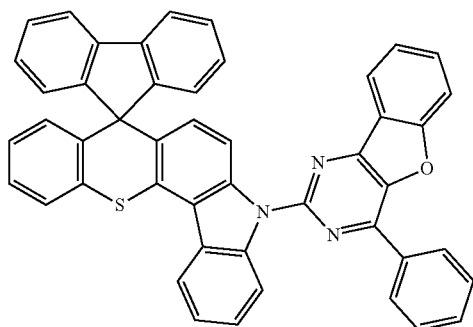
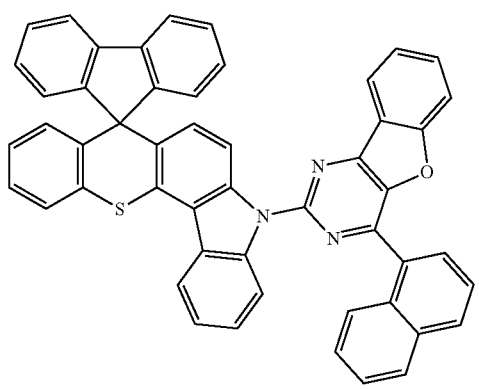
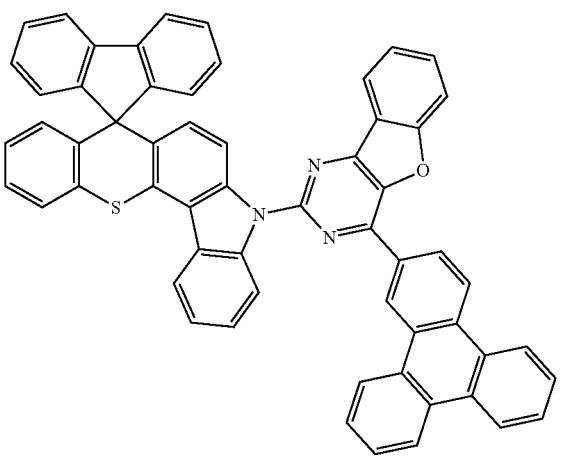
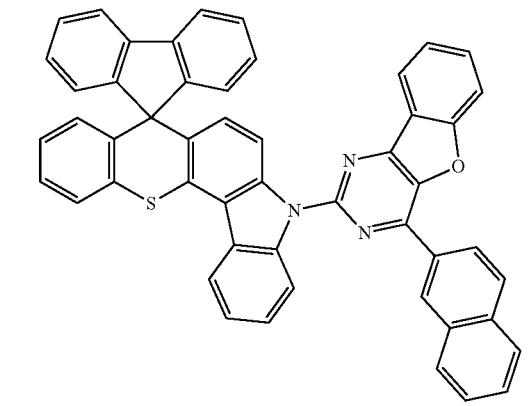
220
-continued
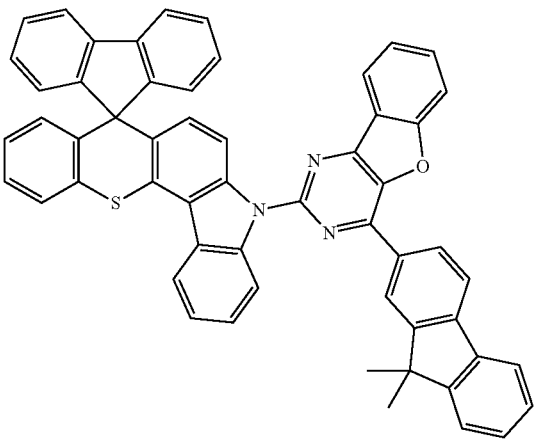
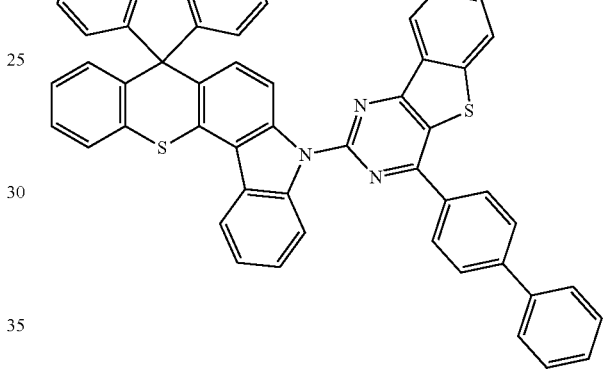
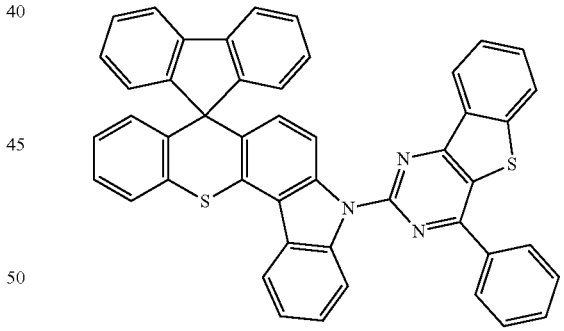
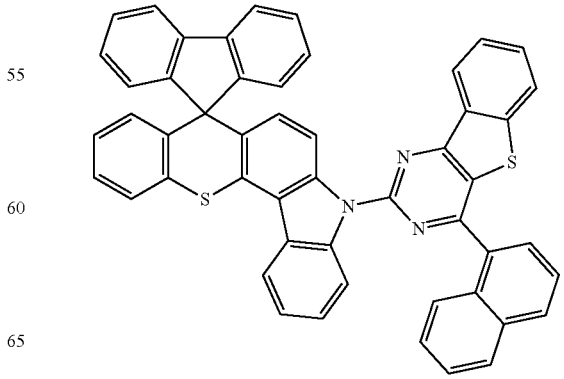

221
-continued
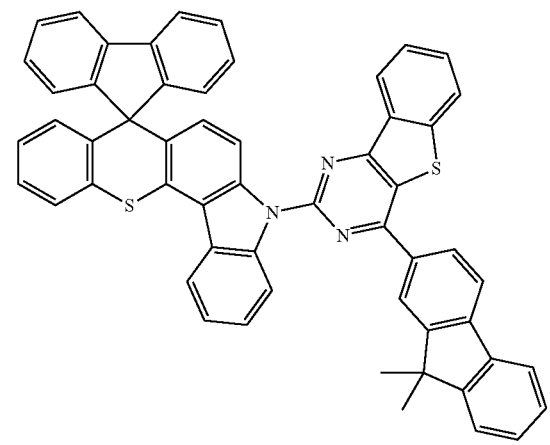
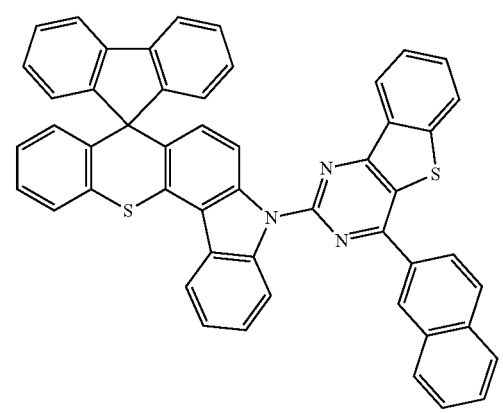
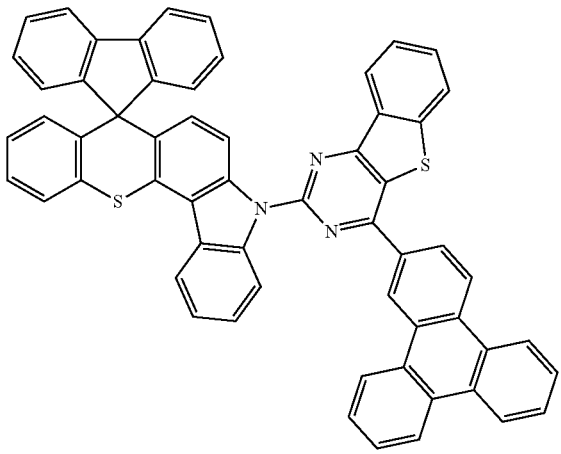
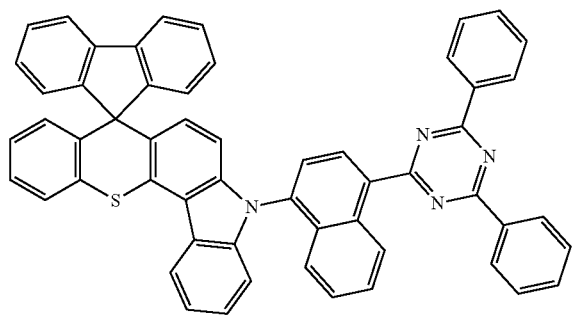
222
-continued
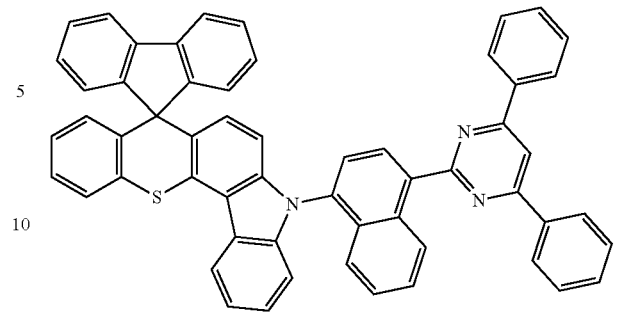
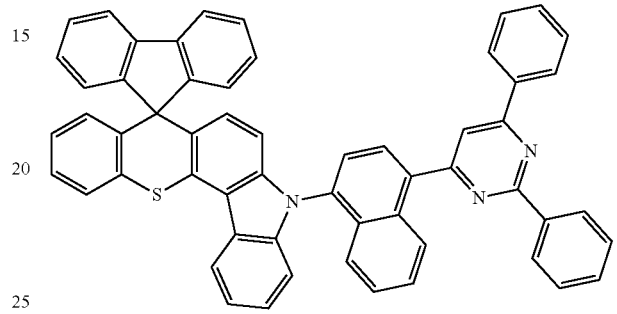
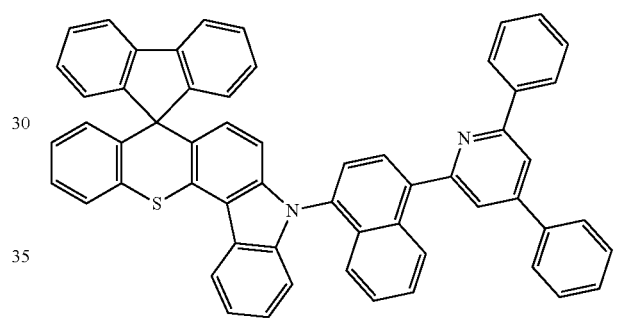
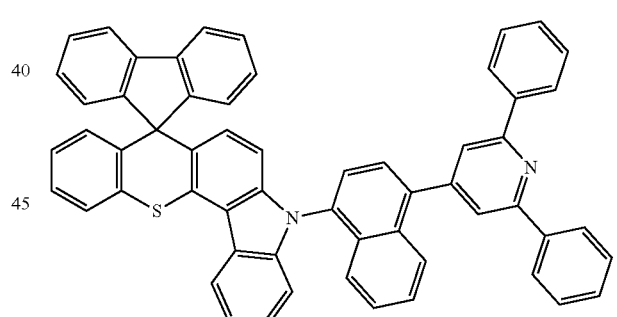
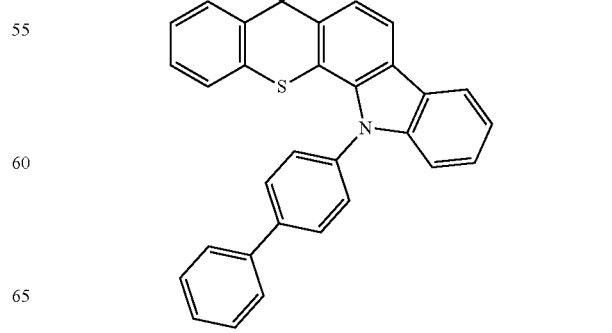

223
-continued
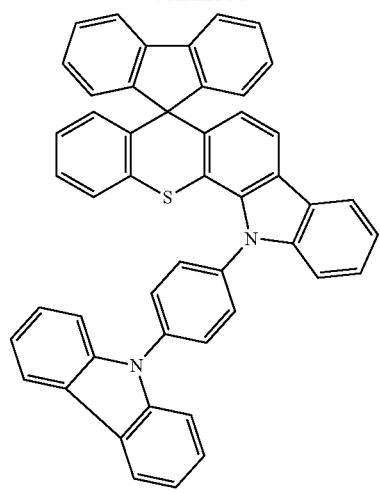
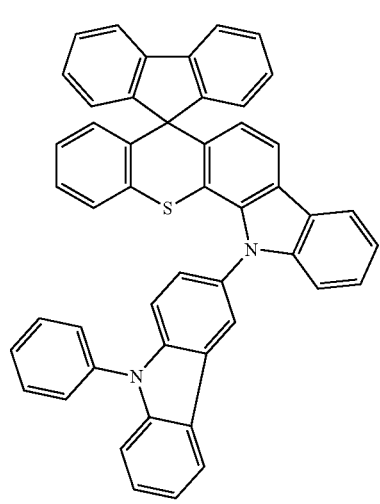
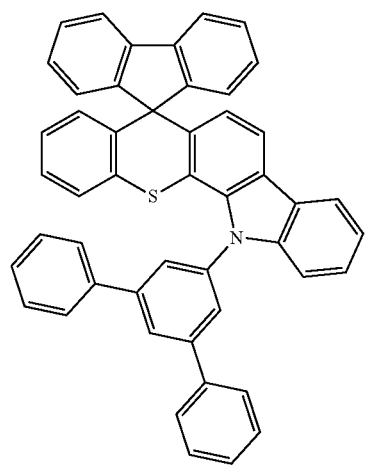
224
-continued
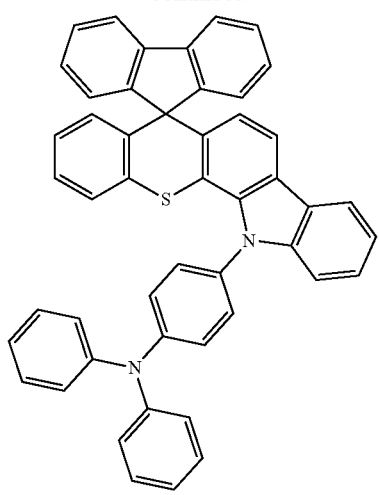
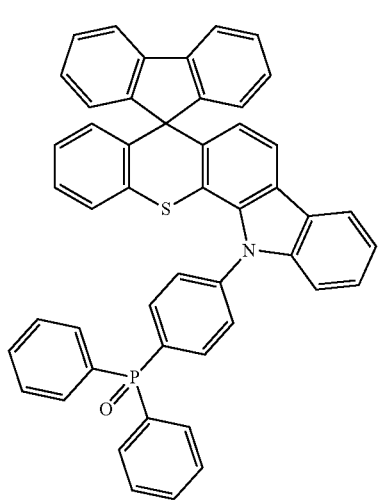
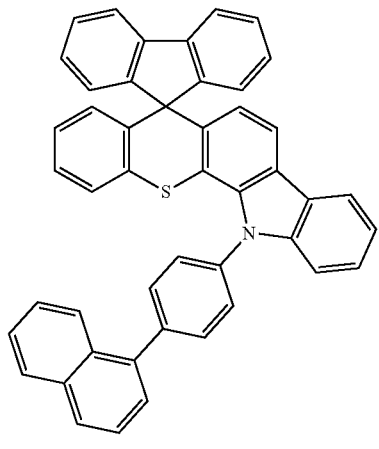

225
-continued
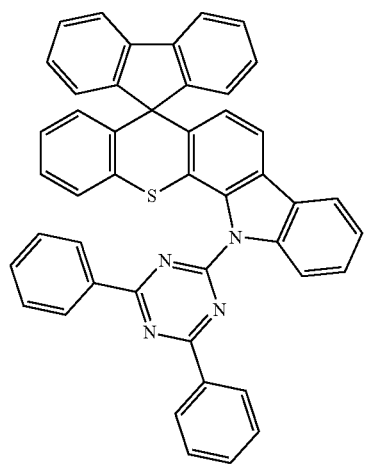
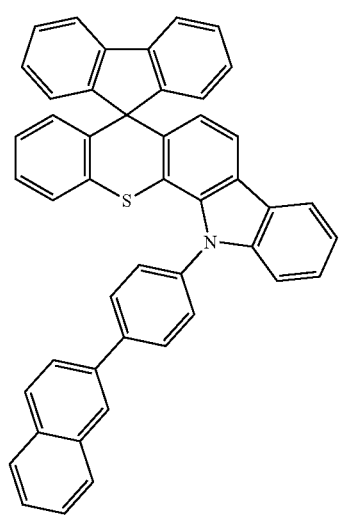
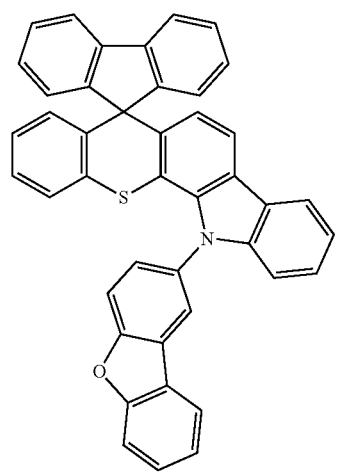
226
-continued
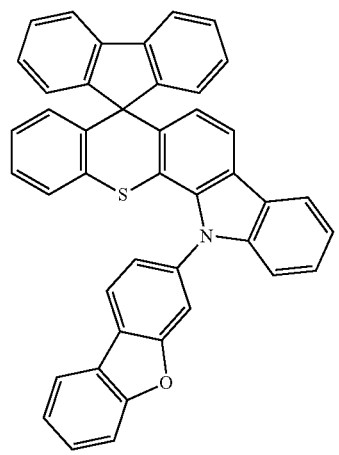
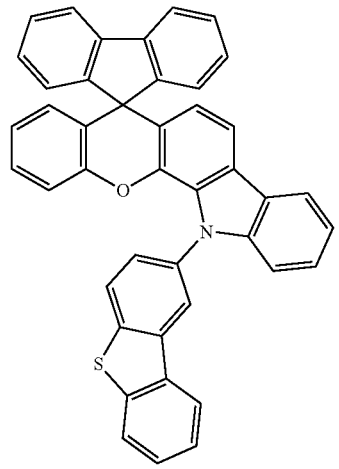
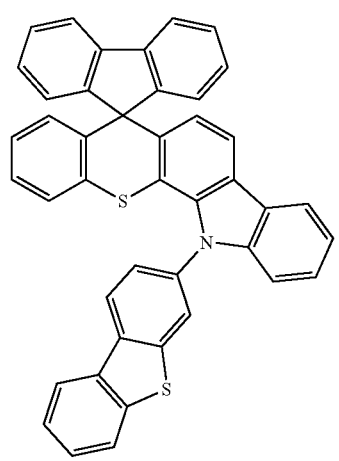

227
-continued
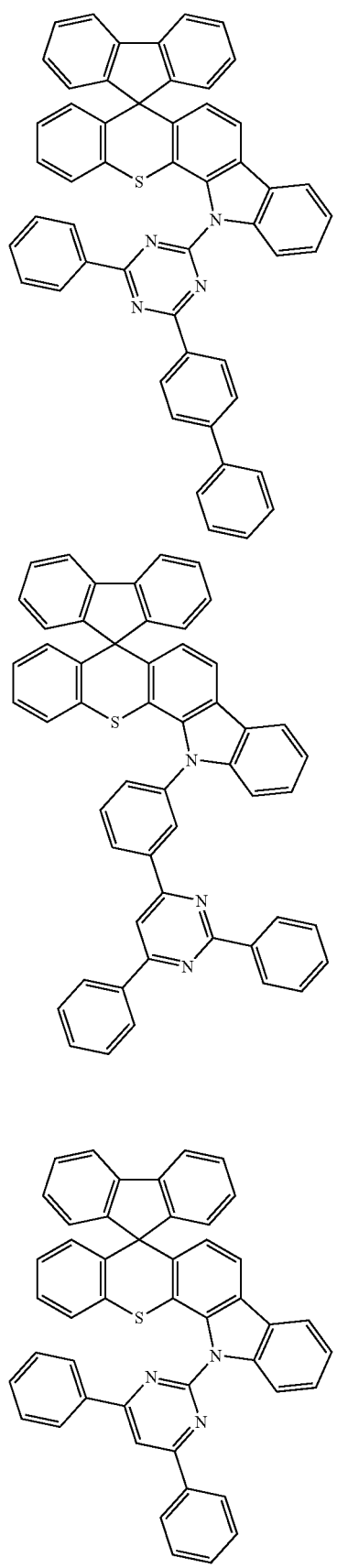
228
-continued
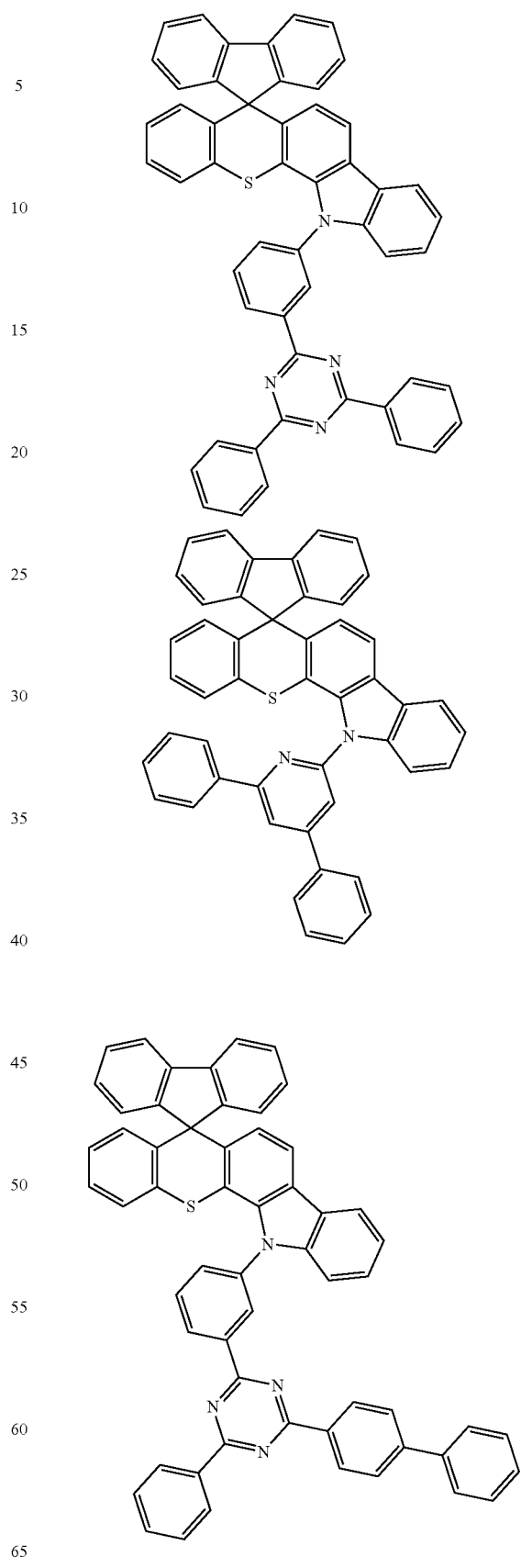

229
-continued
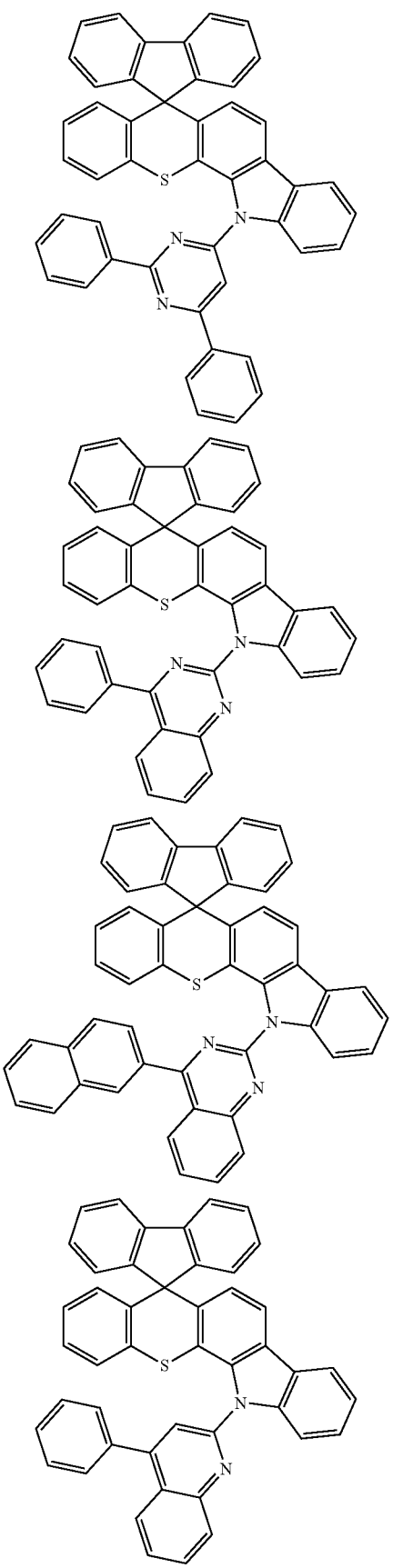
230
-continued
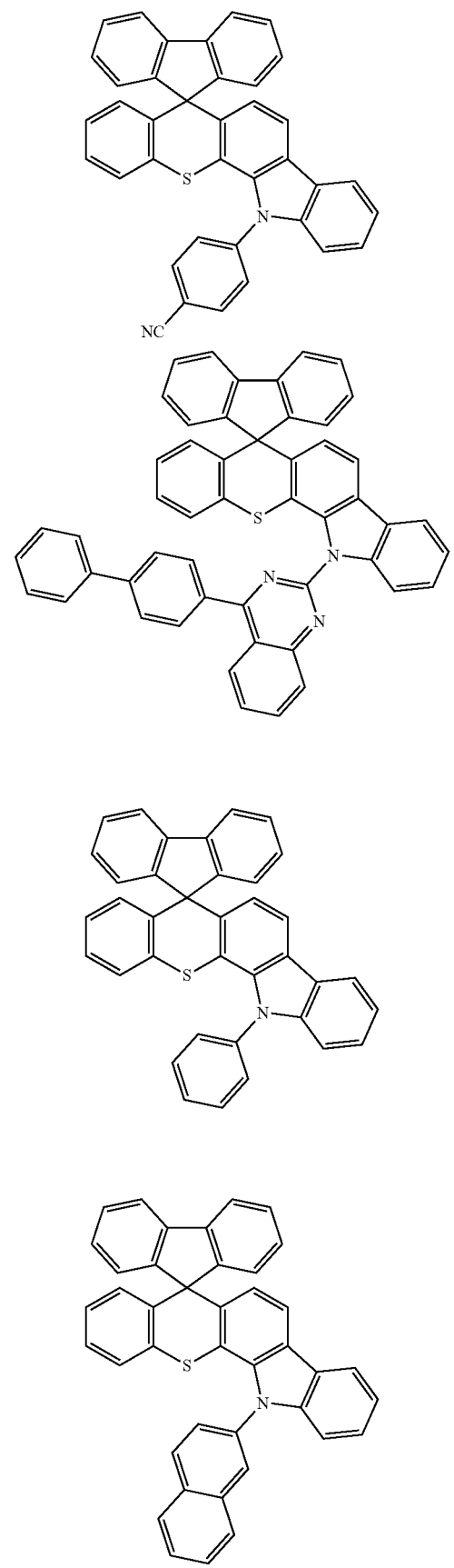

231
-continued
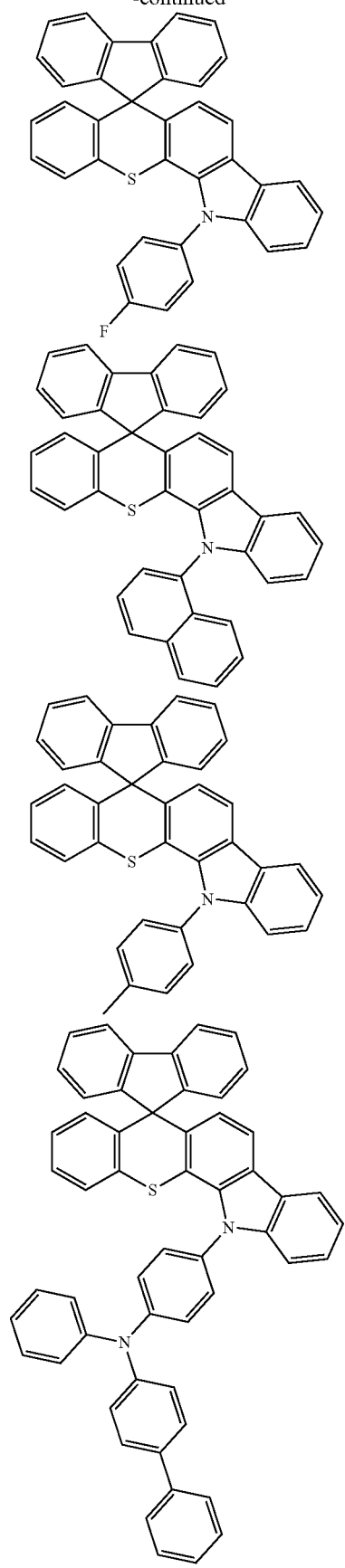
232
-continued
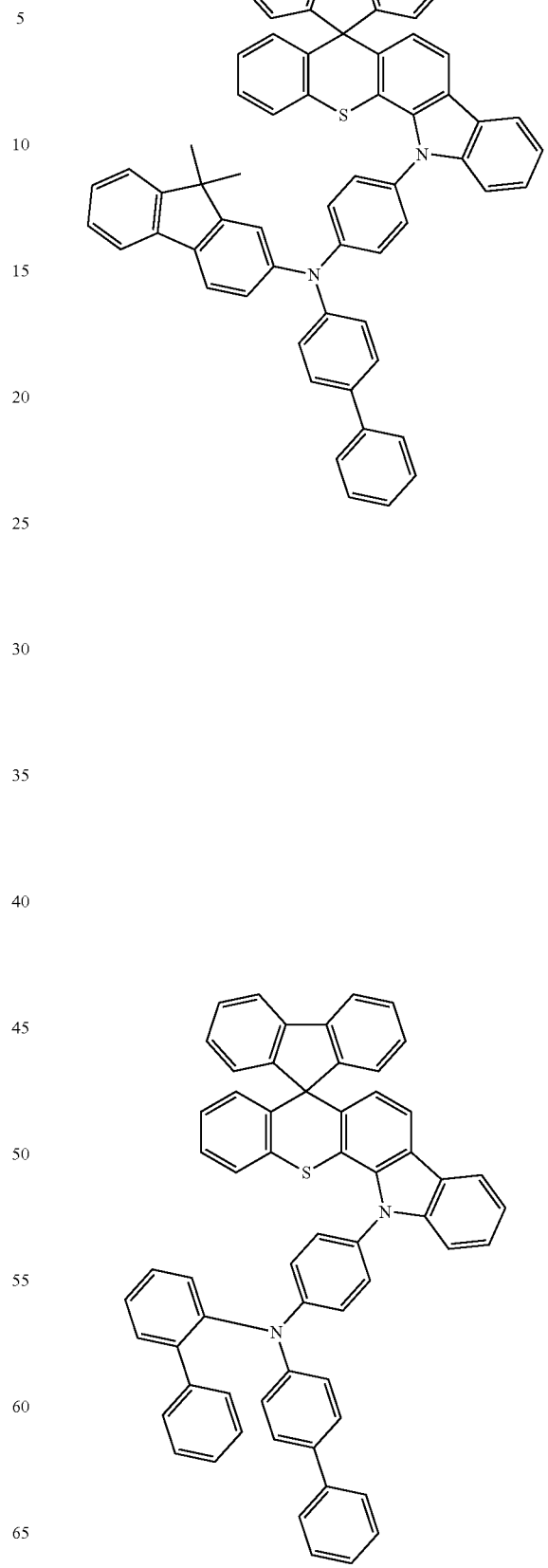

233
-continued
234
-continued
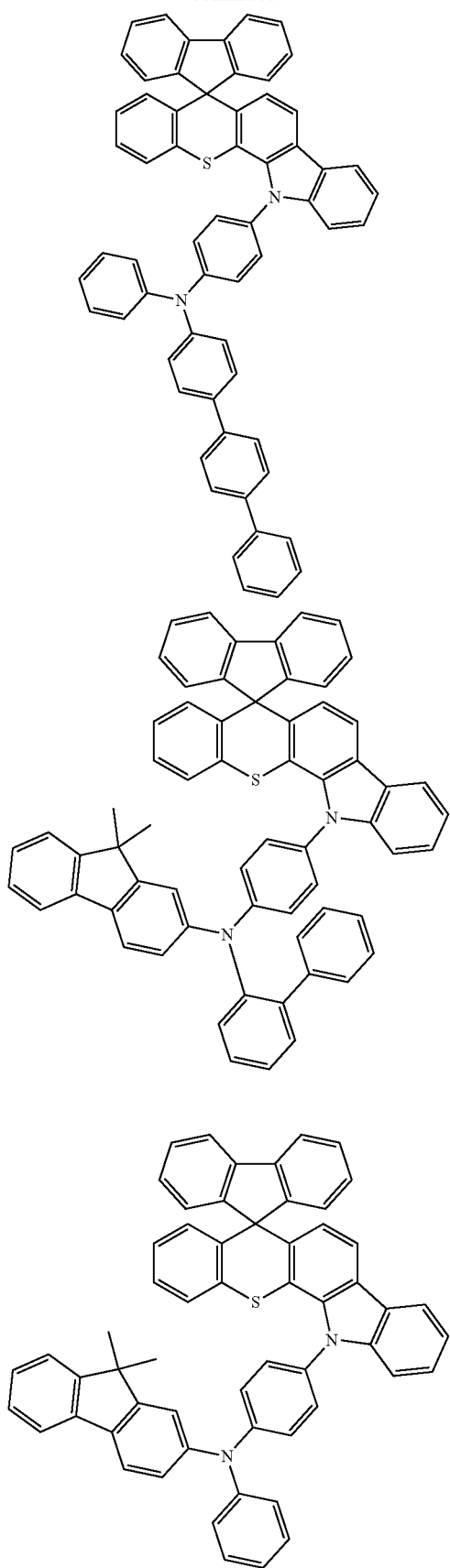
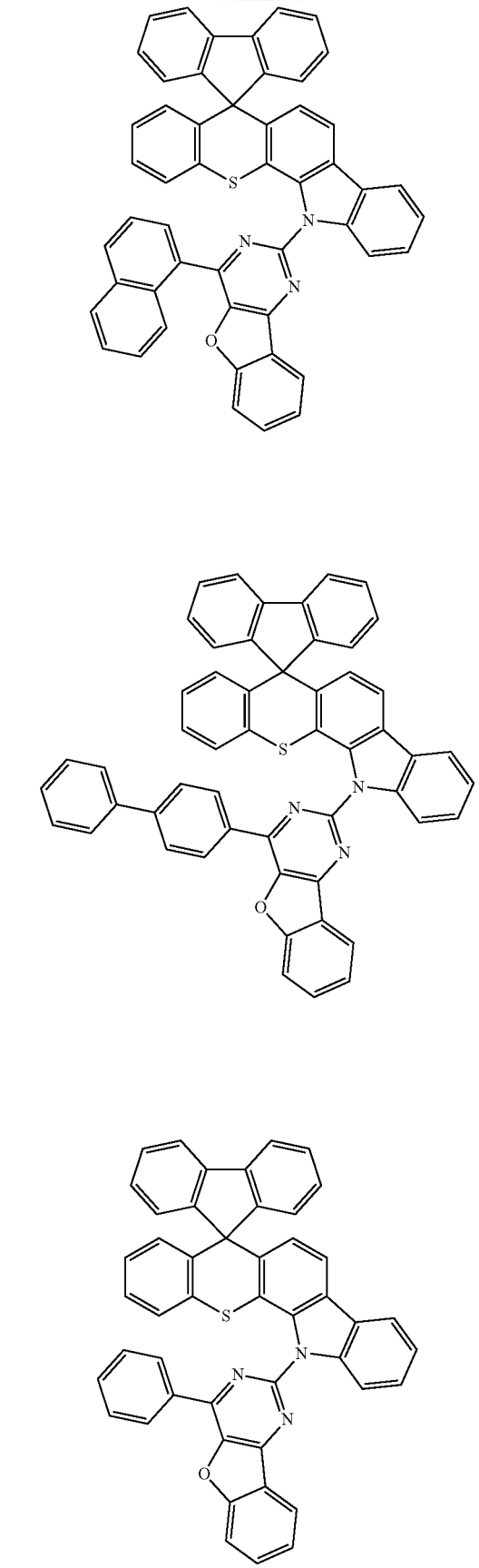

-continued
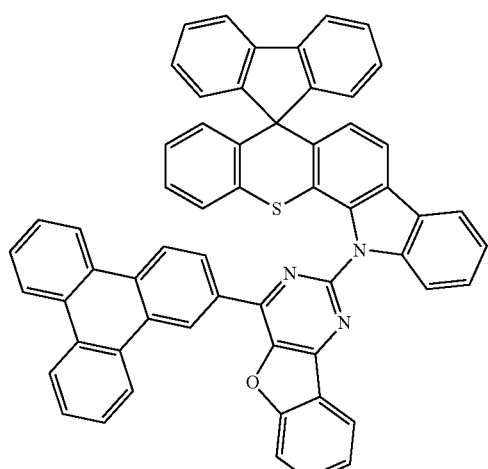
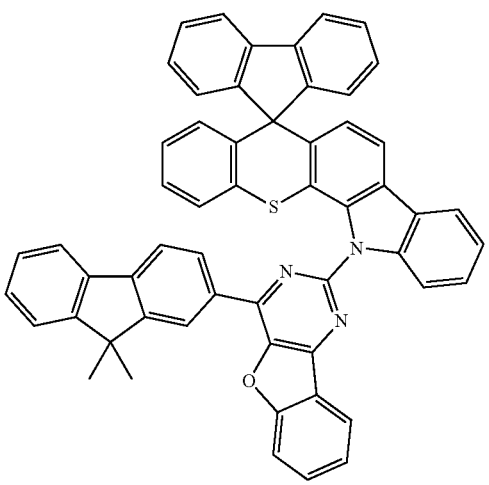
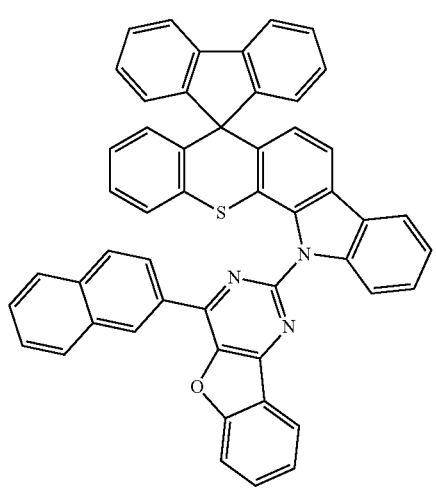
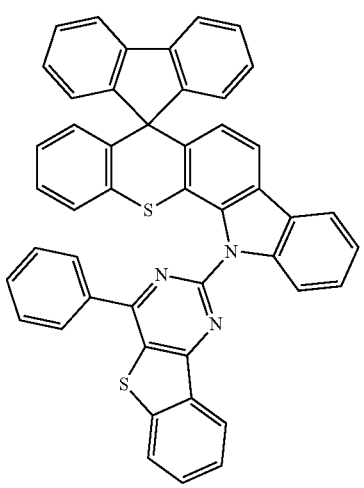
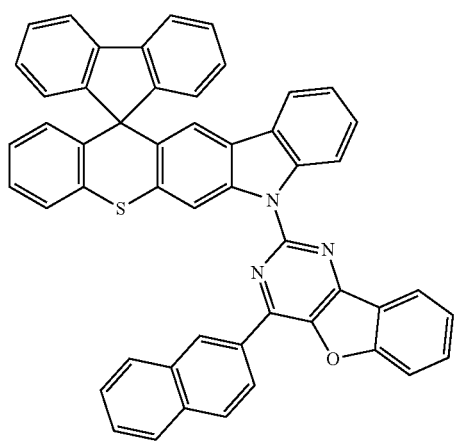
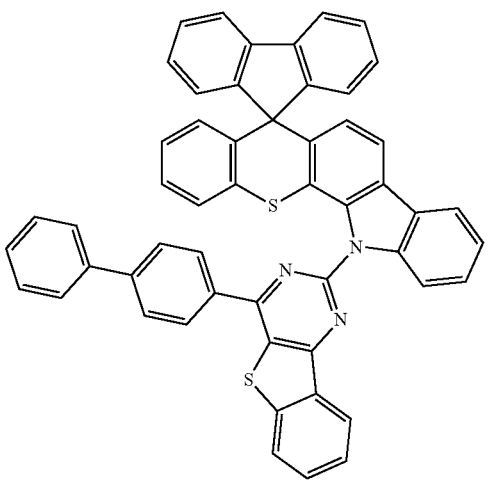

237
-continued
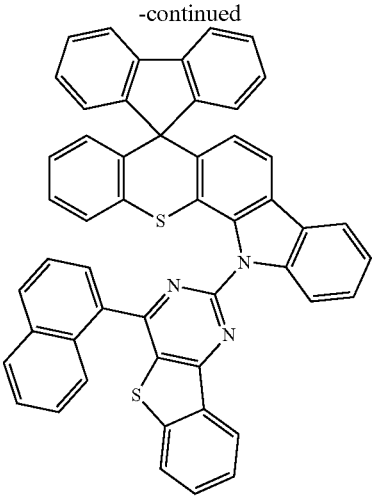
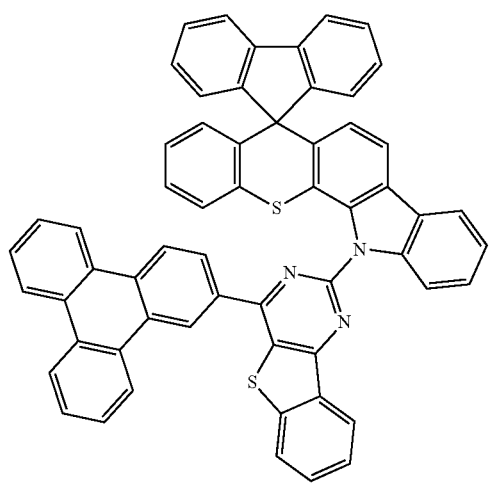
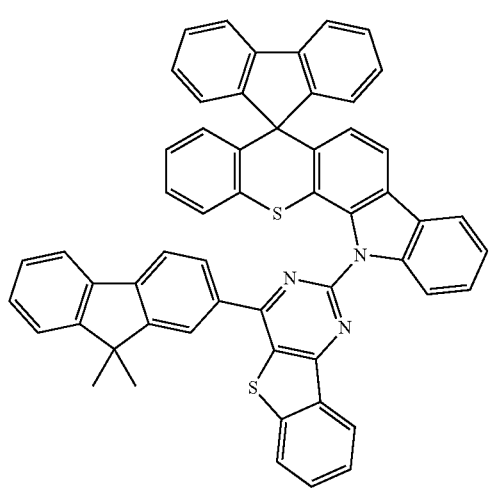
238
-continued
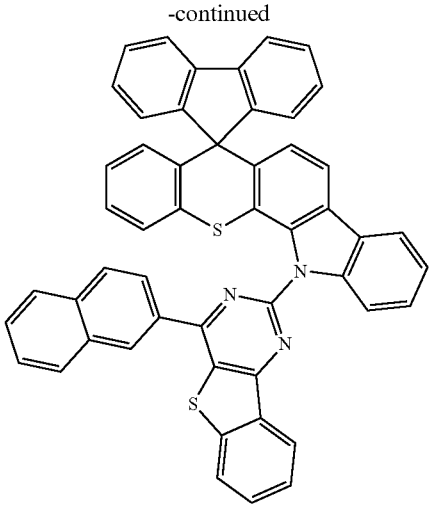
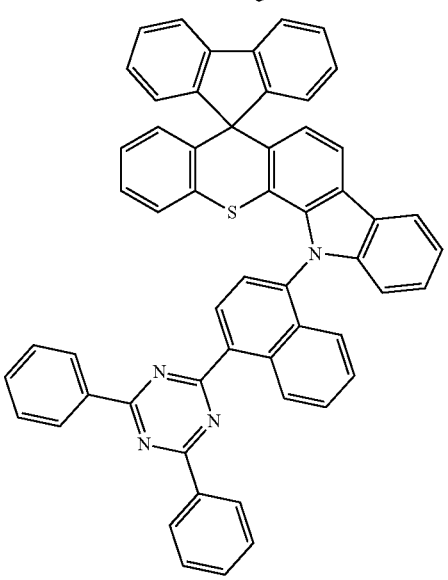
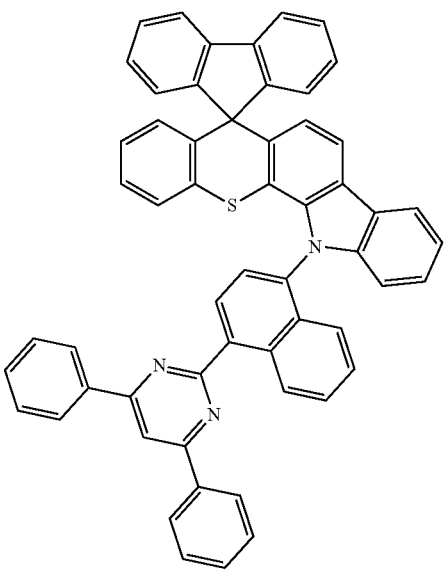

239
-continued
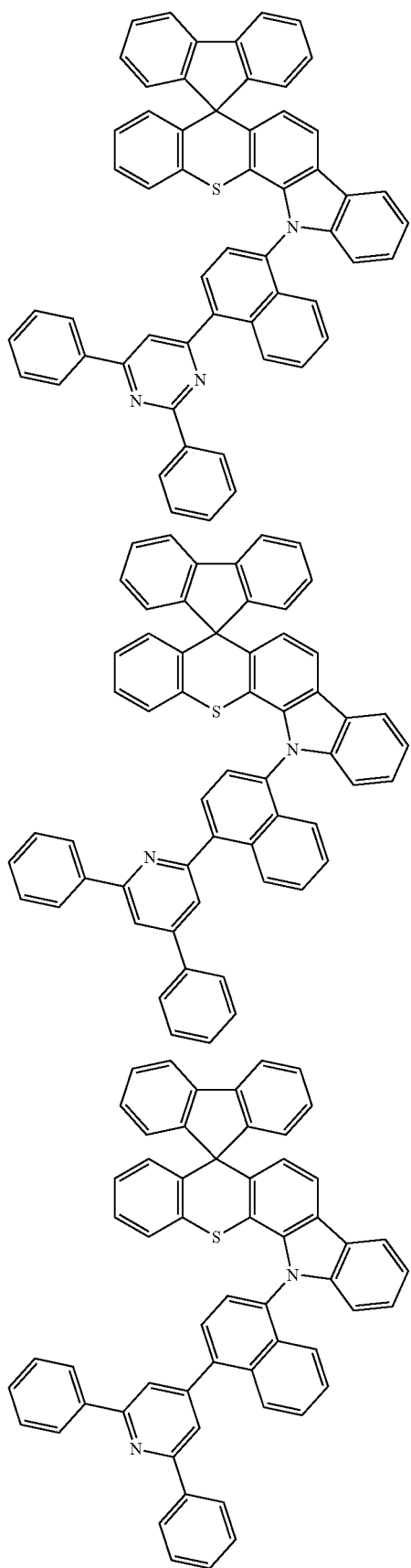
240
-continued
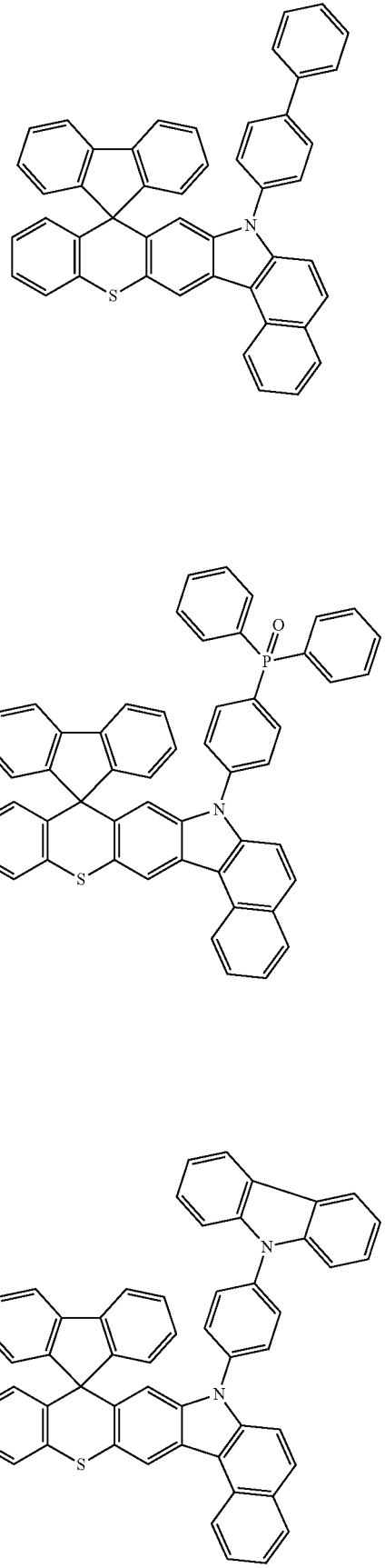

241
-continued
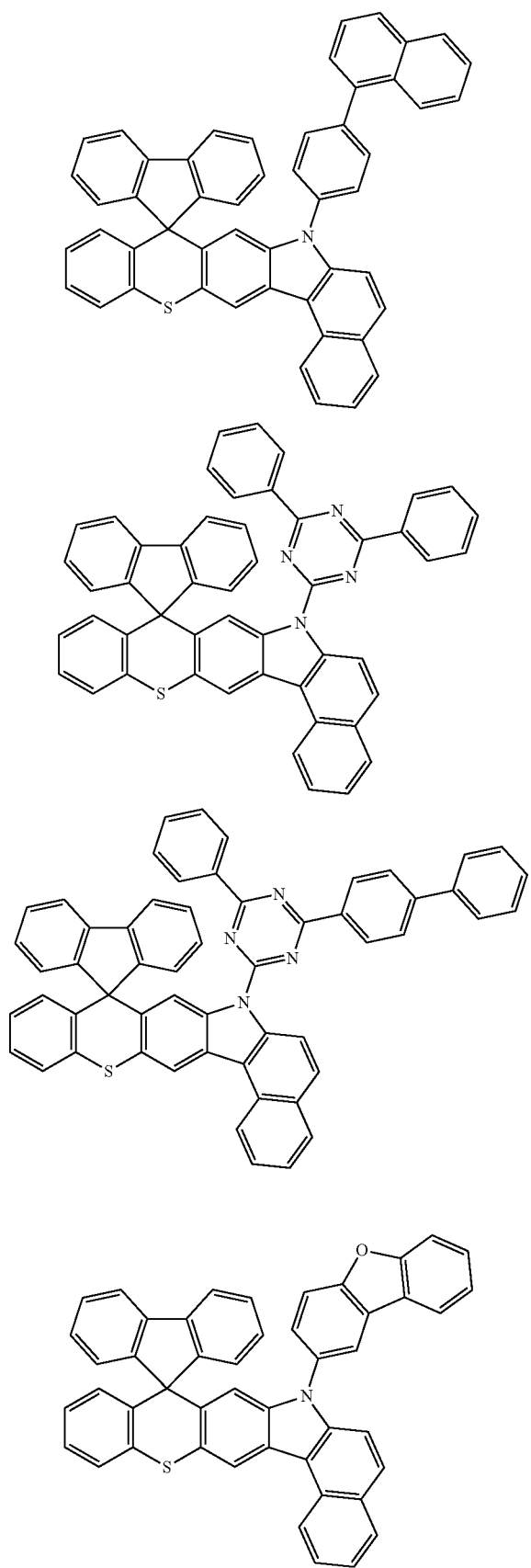
242
-continued
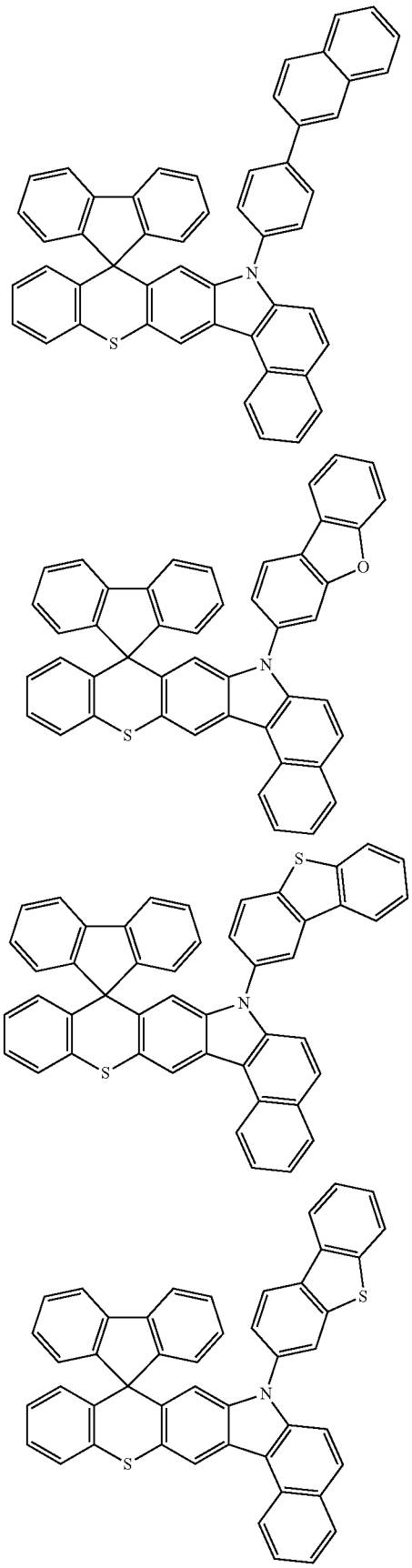

243
-continued
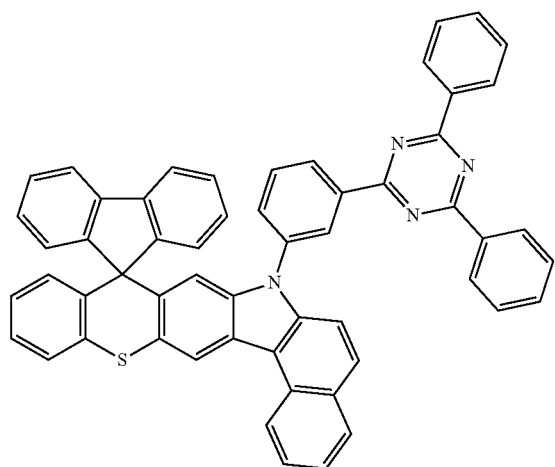 [SMILES: c1ccc(-c2nc(-c3ccccc3)nc(-c3cccc(-n4c5cc6c(cc5c5c7ccccc7ccc54)Sc4ccccc4C64c5ccccc5-c5ccccc54)c3)n2)cc1]
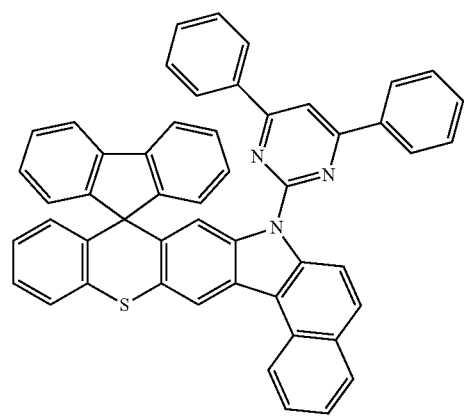
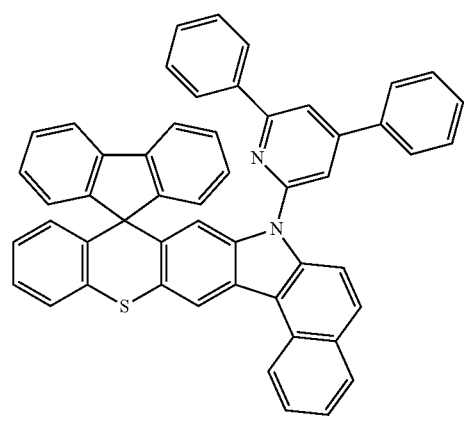
244
-continued
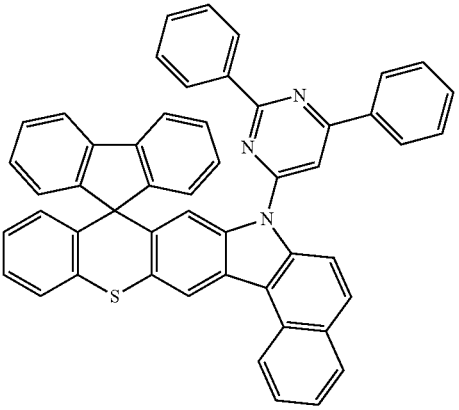
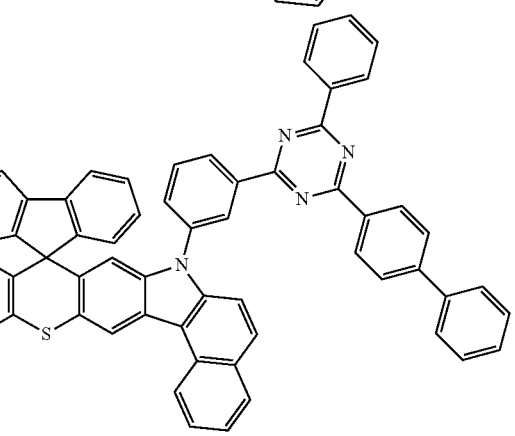
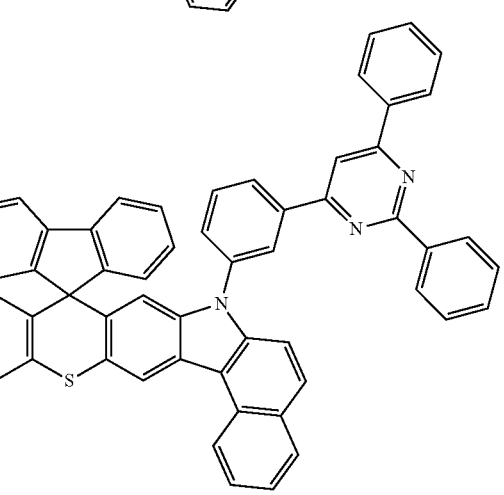
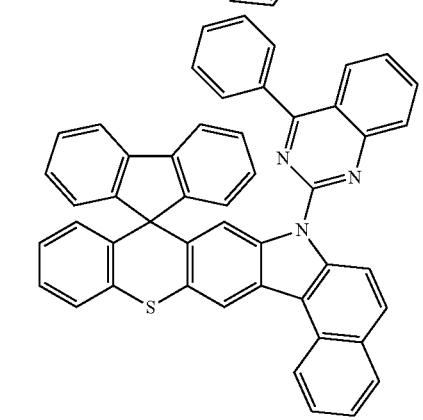

245
-continued
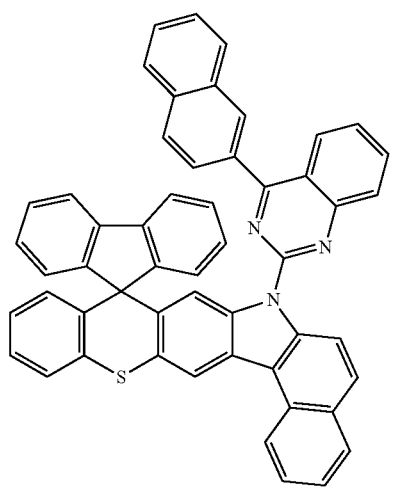
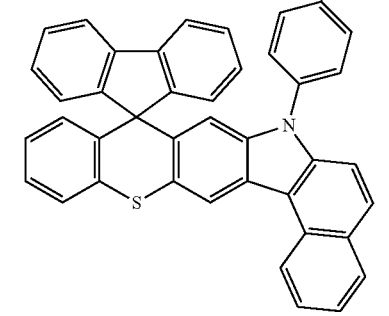
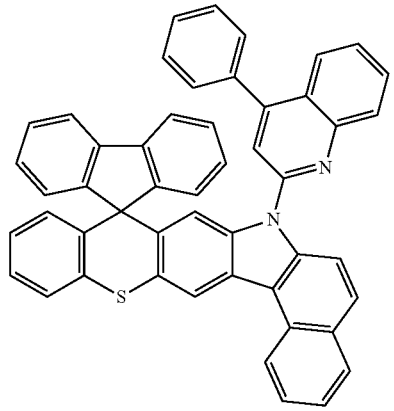
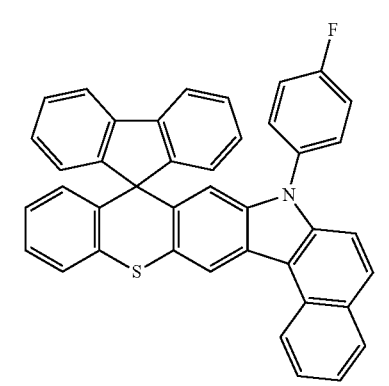
246
-continued
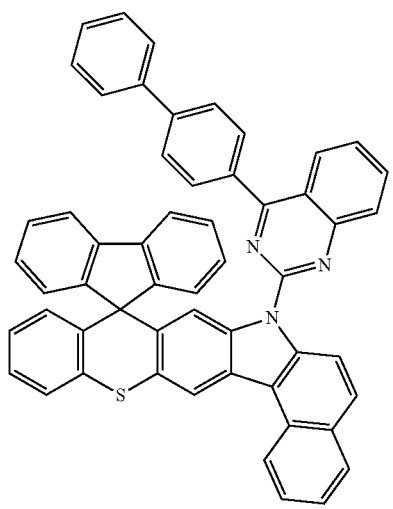
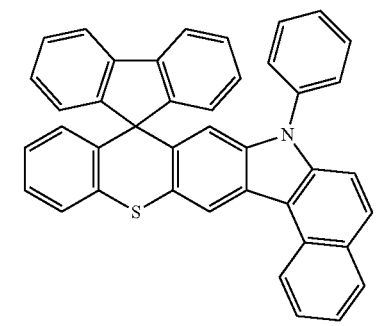
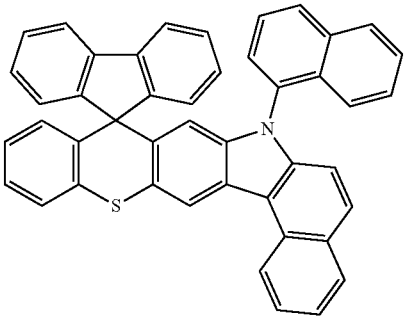
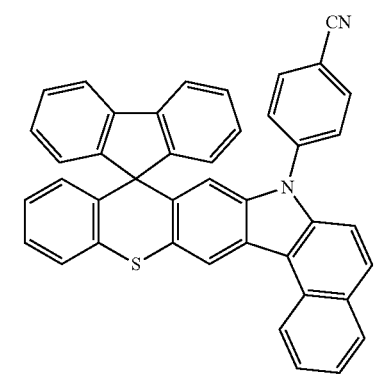

247
-continued
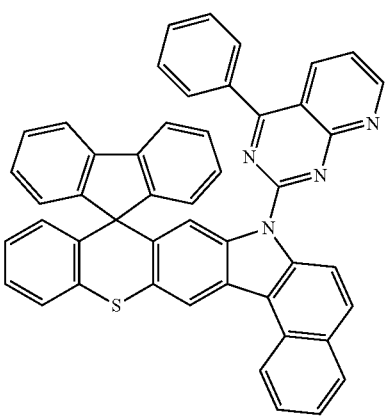
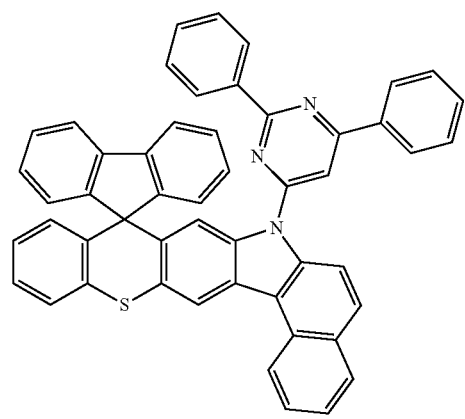
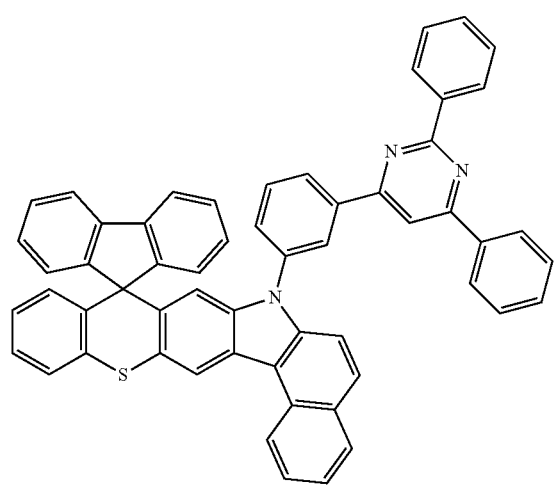
248
-continued
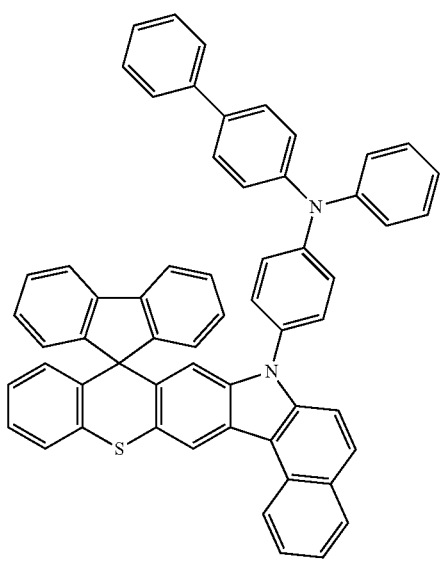
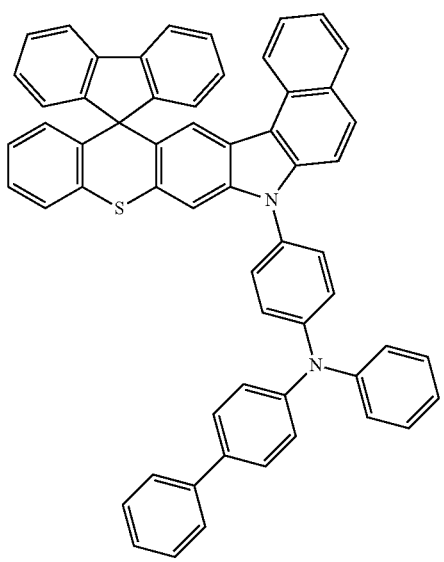
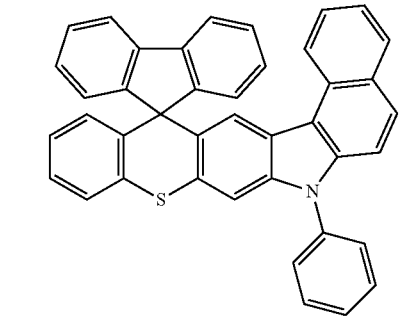

249
-continued
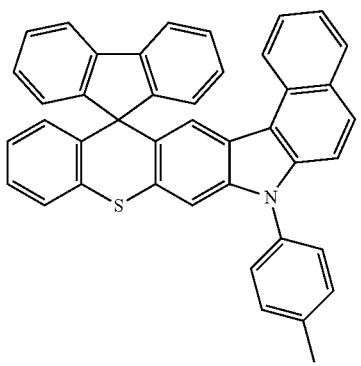
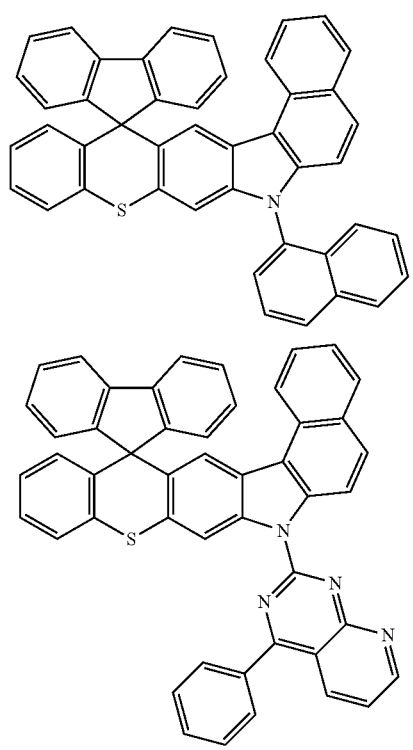
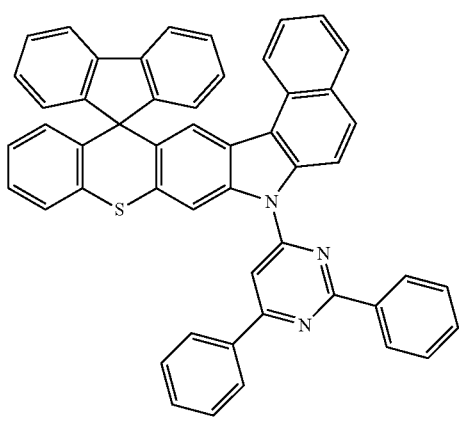
250
-continued
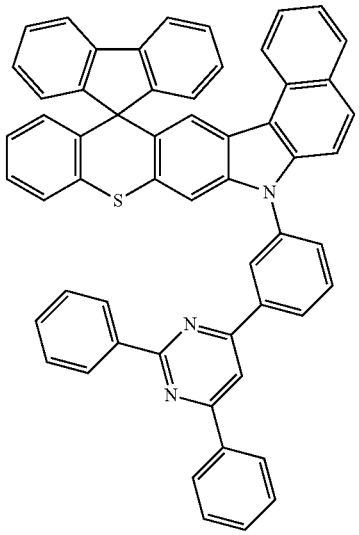
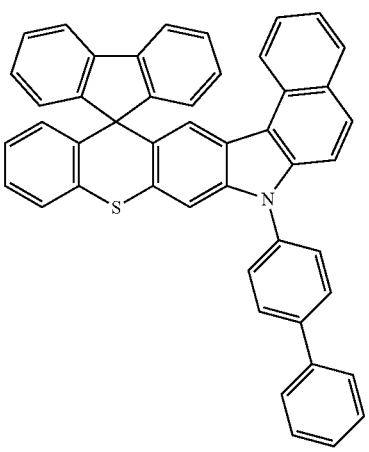
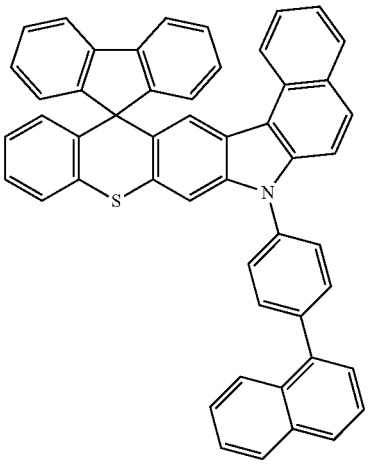

251
-continued
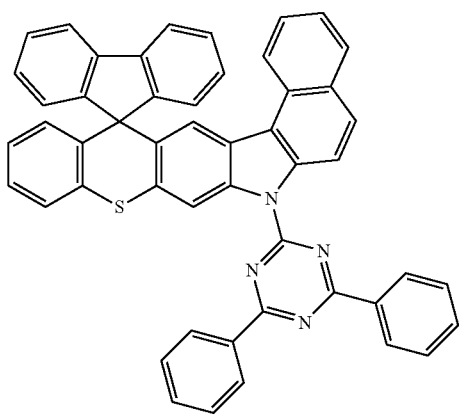
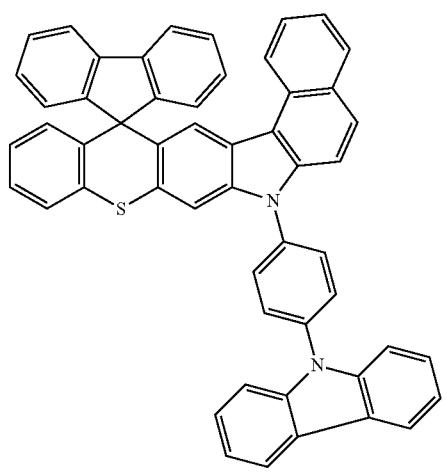
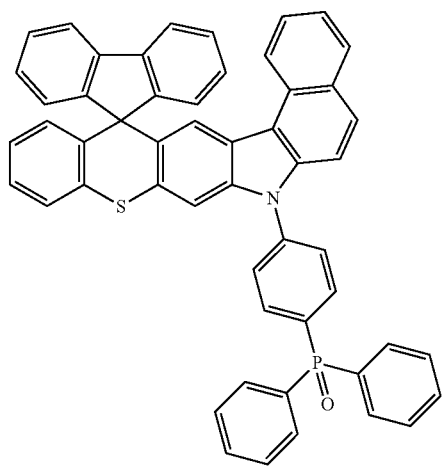
252
-continued
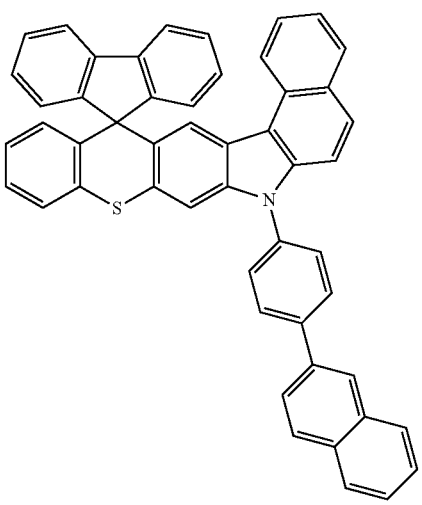
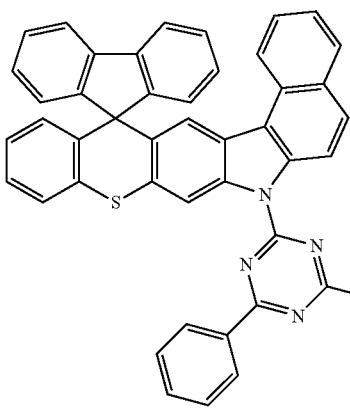
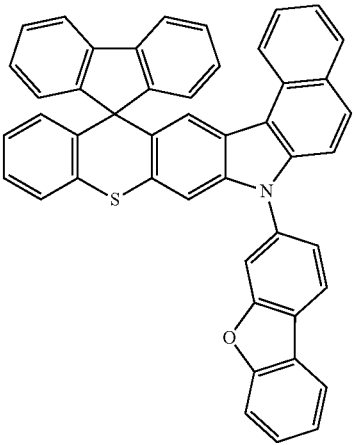

253
-continued
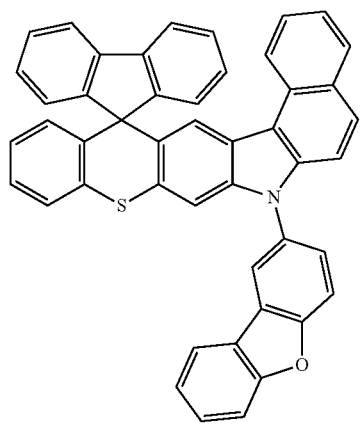
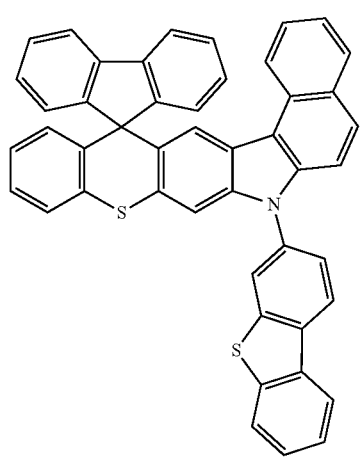
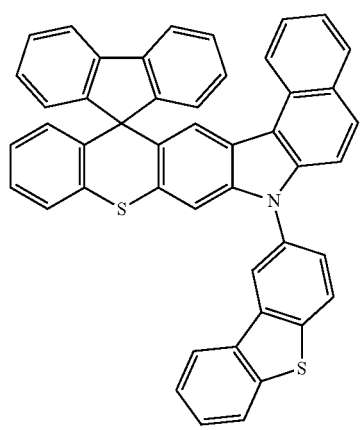
254
-continued
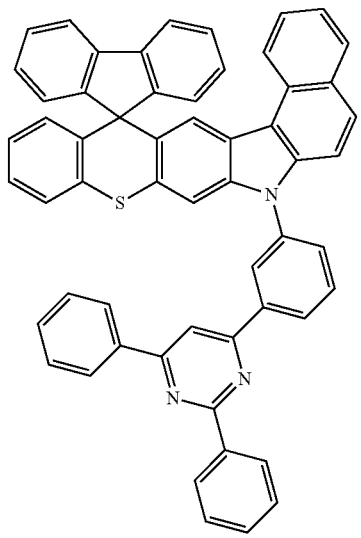
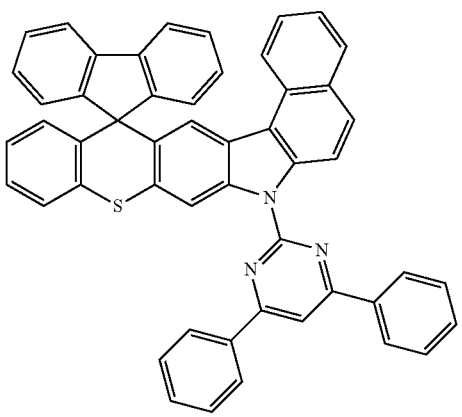
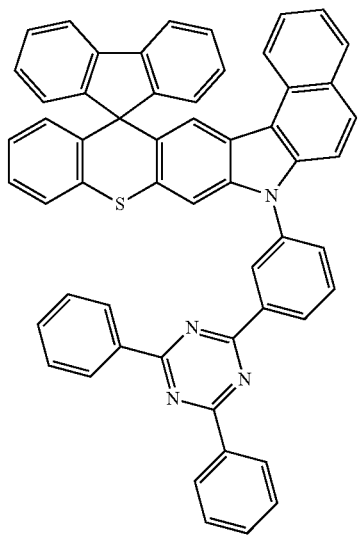

255
-continued
256
-continued
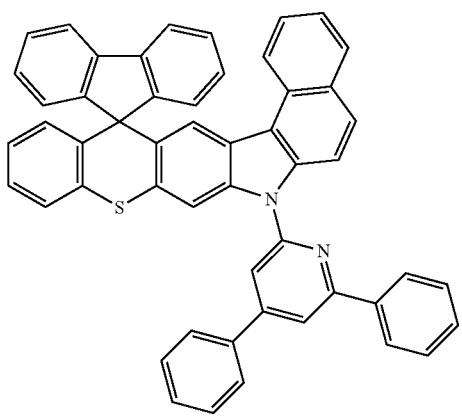
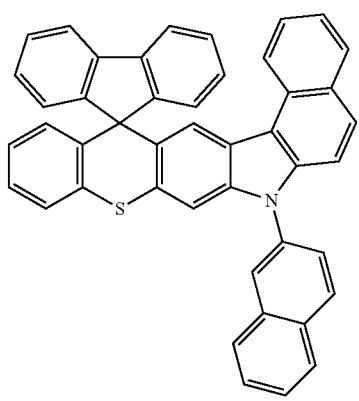

257
-continued
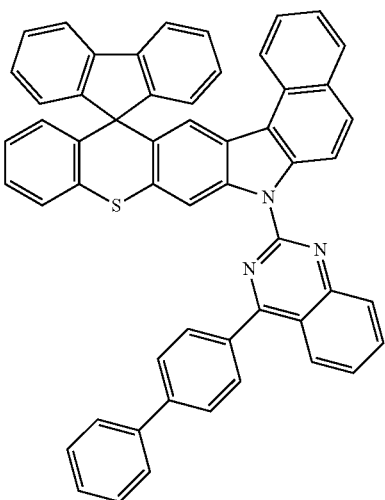
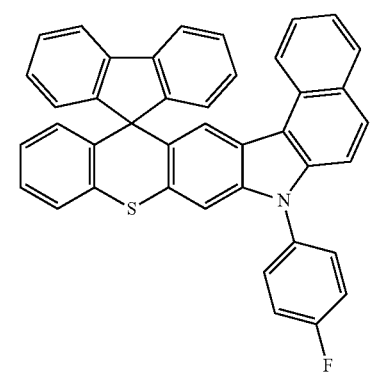
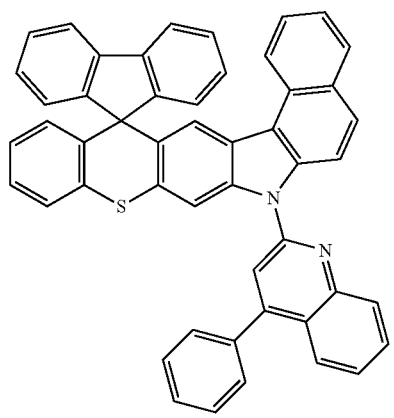
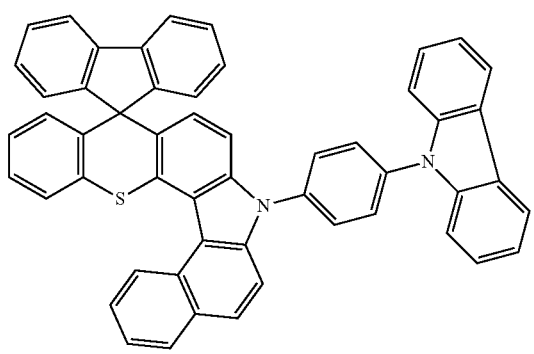
258
-continued
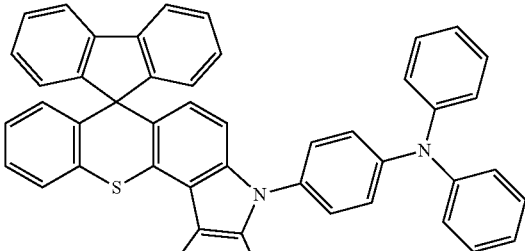
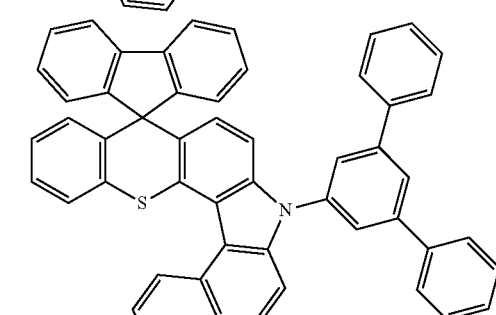
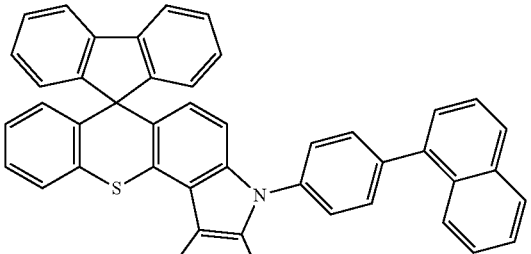
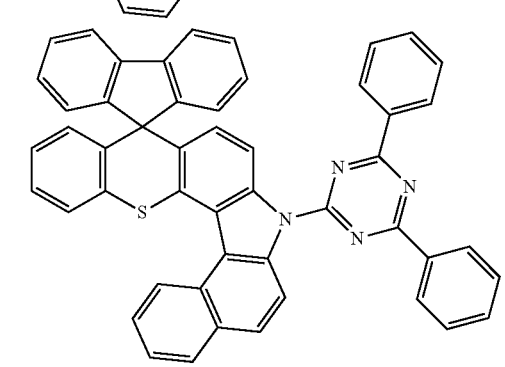
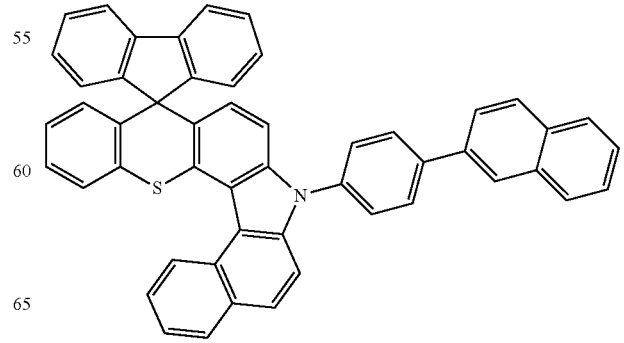

259
-continued
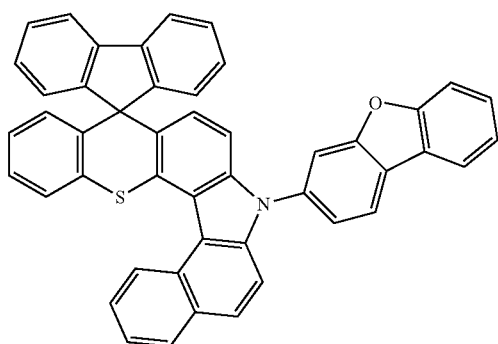
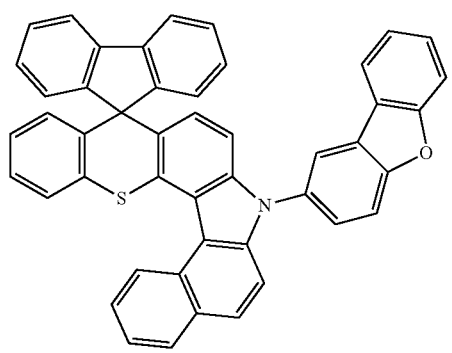
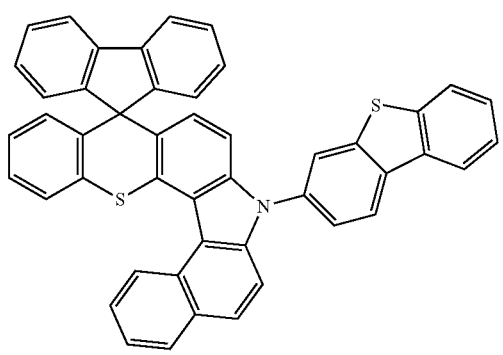
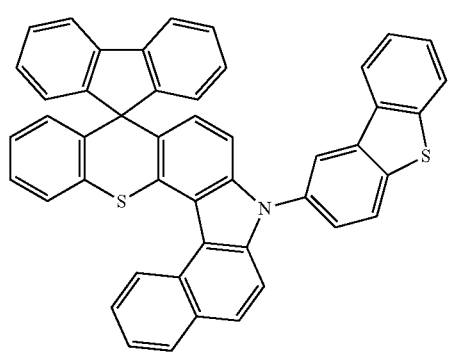
260
-continued
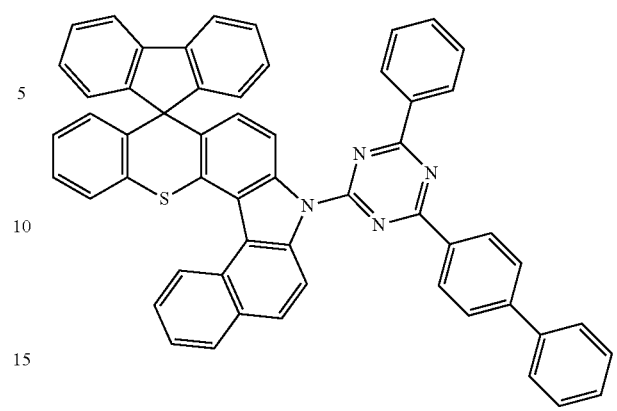
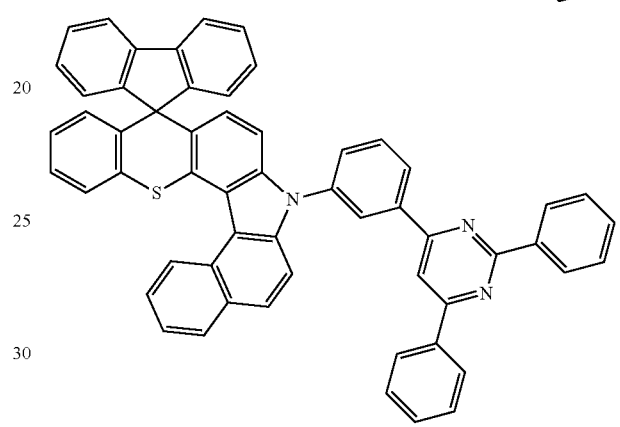
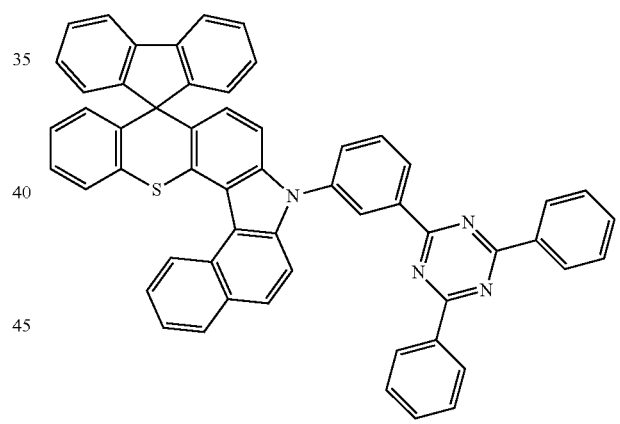
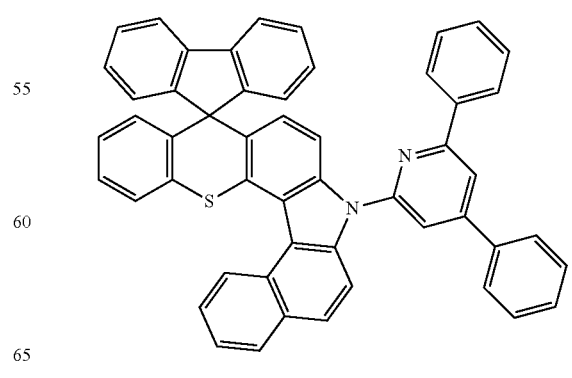

261
-continued
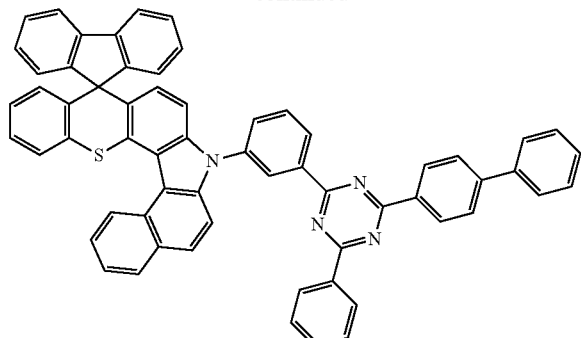

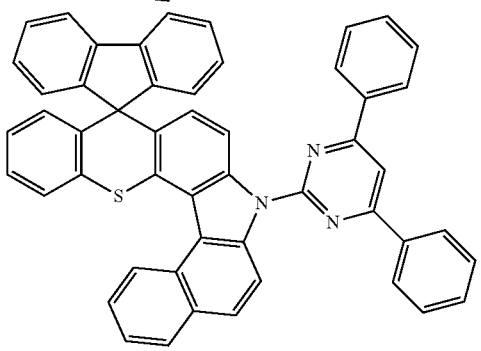
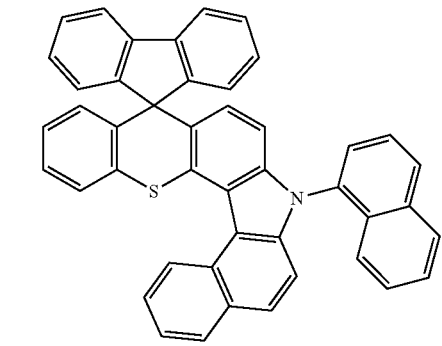
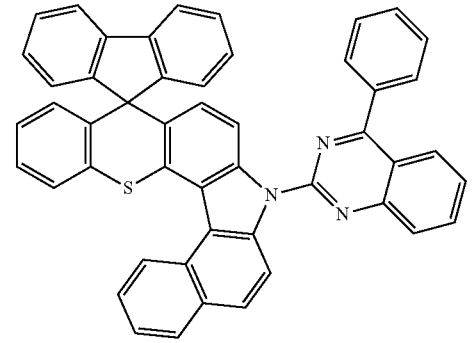
262
-continued
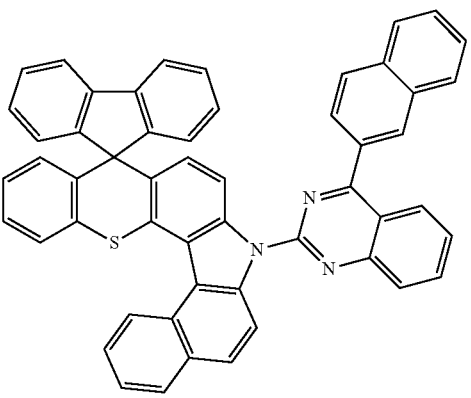
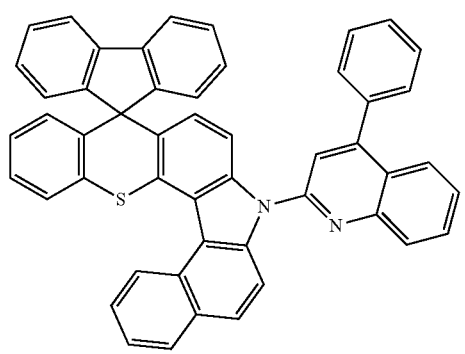
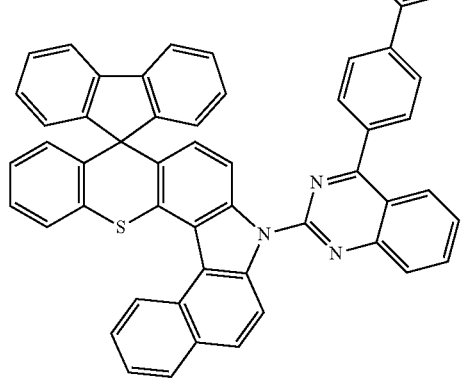
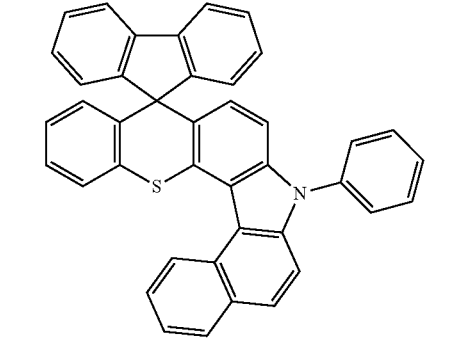

263
-continued
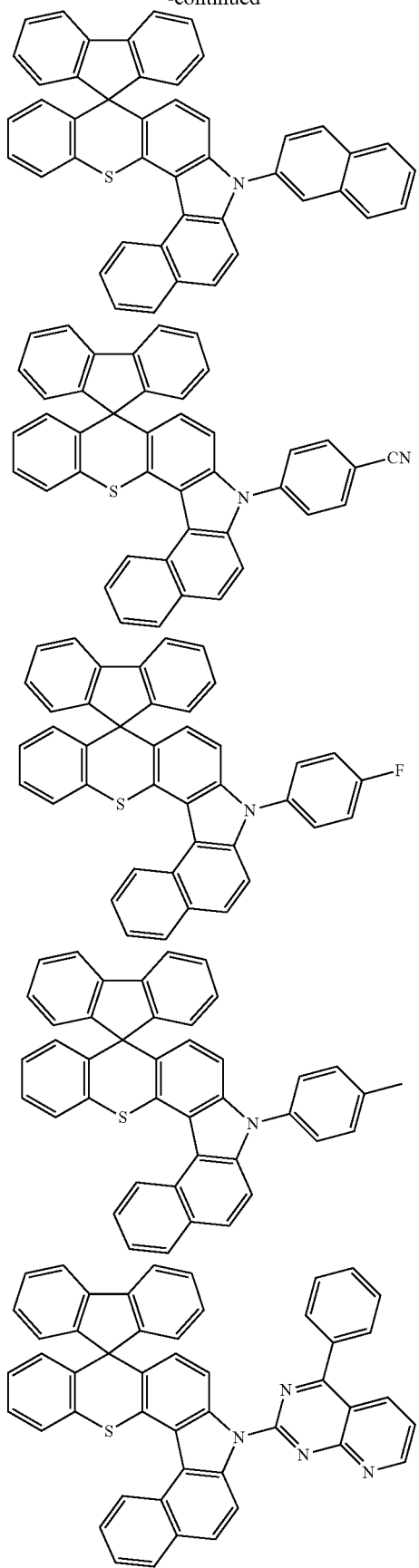
264
-continued
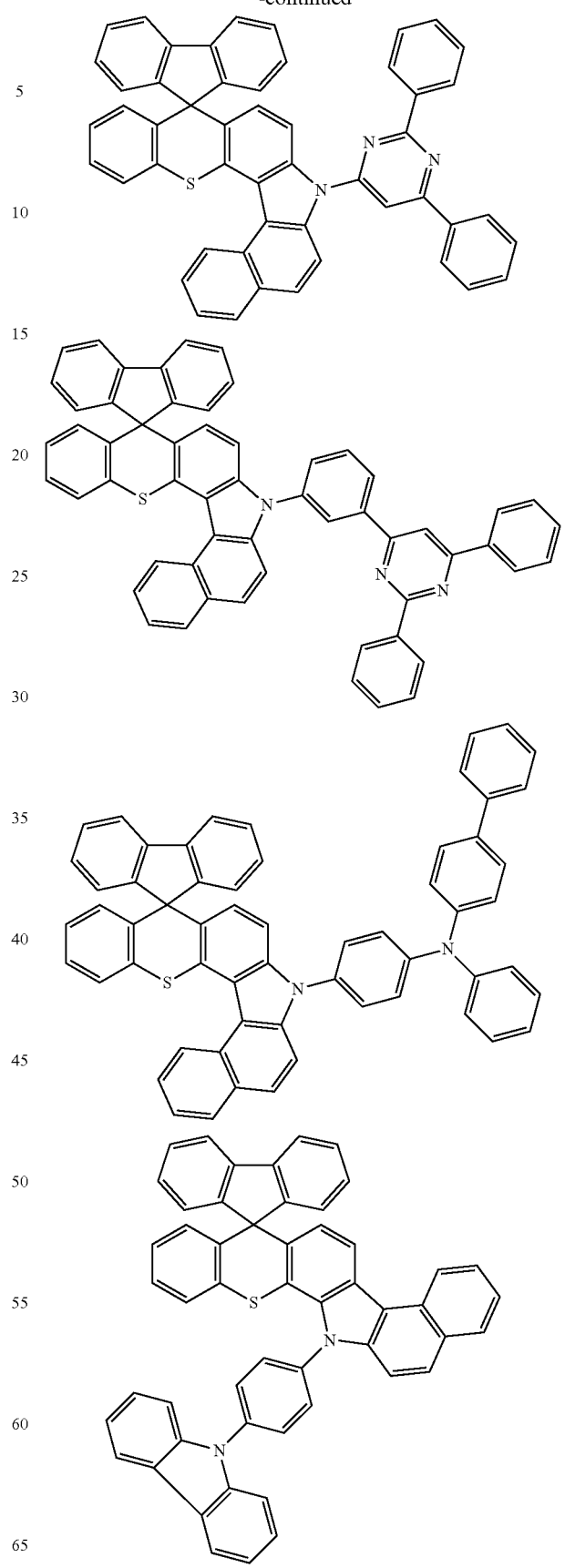

265
-continued
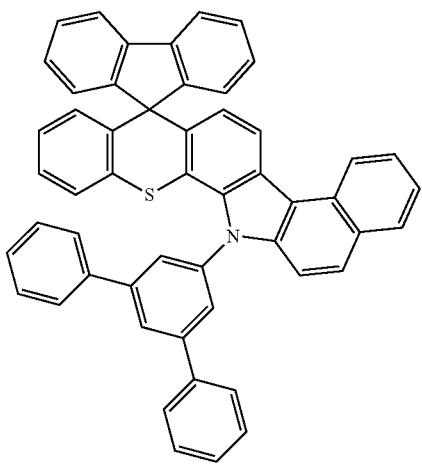
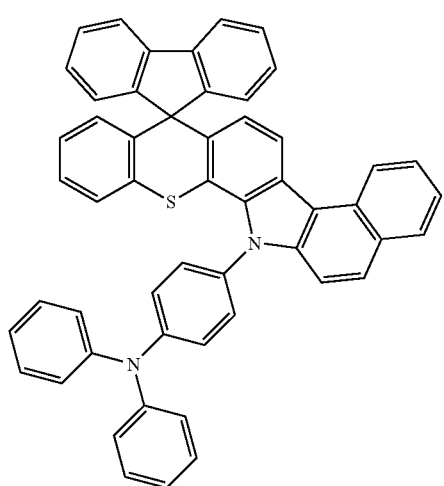
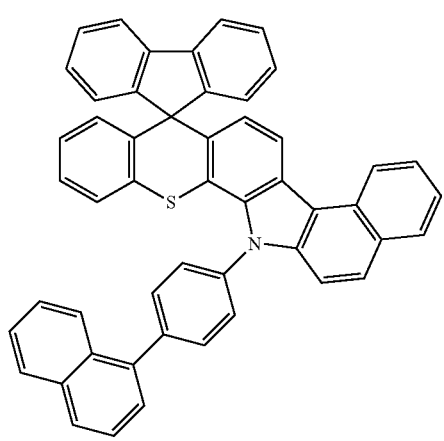
266
-continued
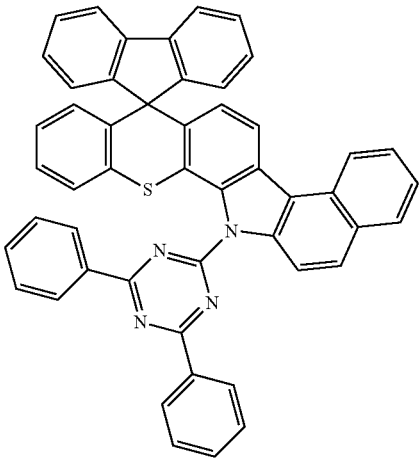
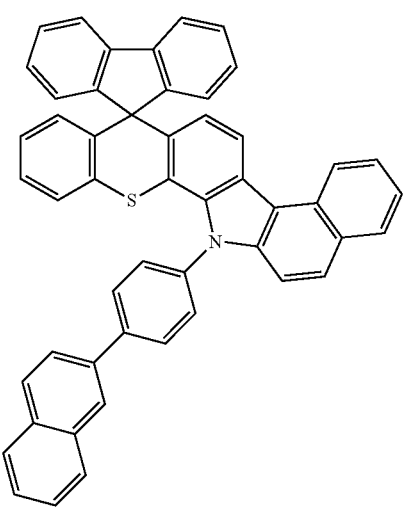
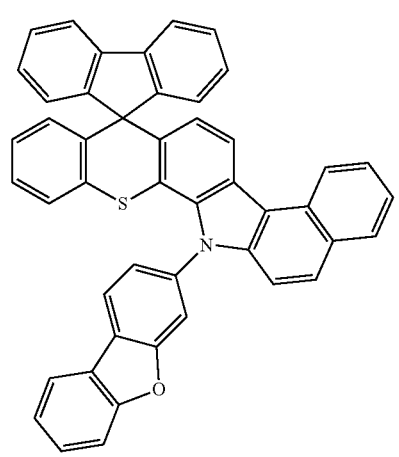

267
-continued
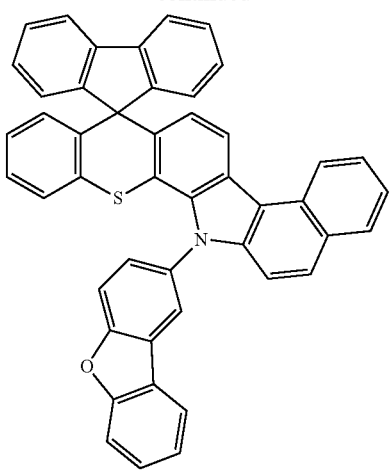
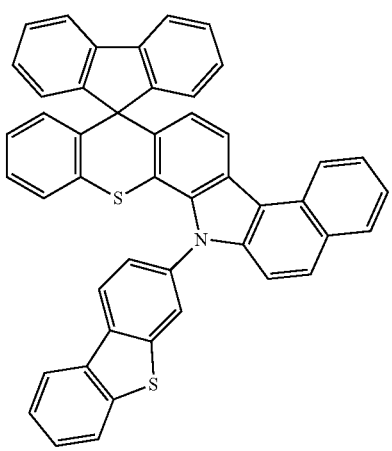
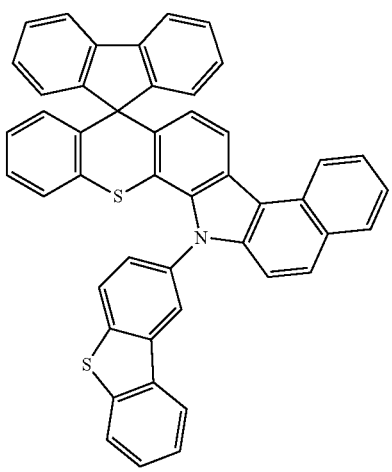
268
-continued
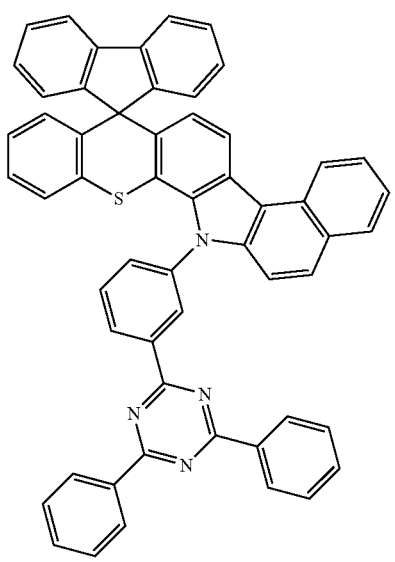
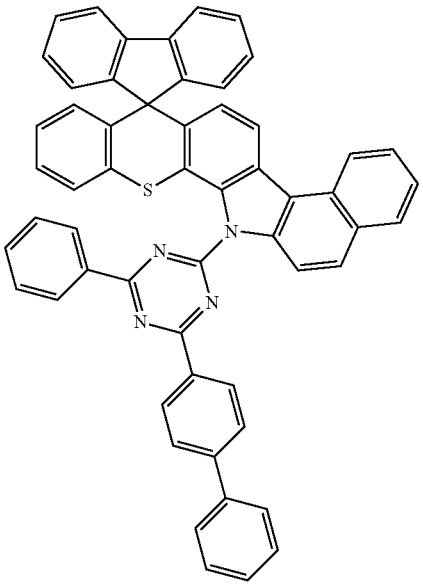
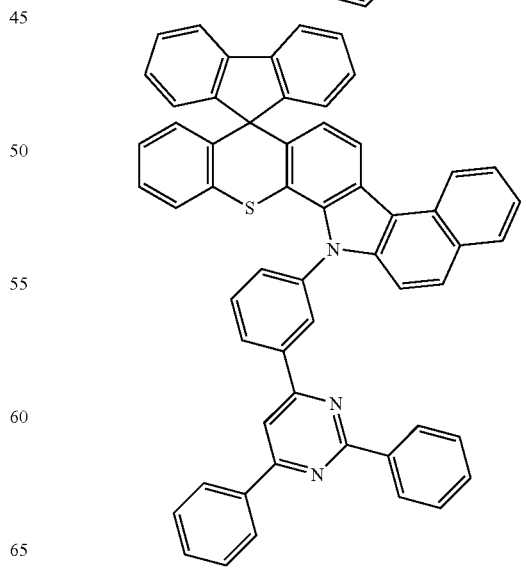

269
-continued
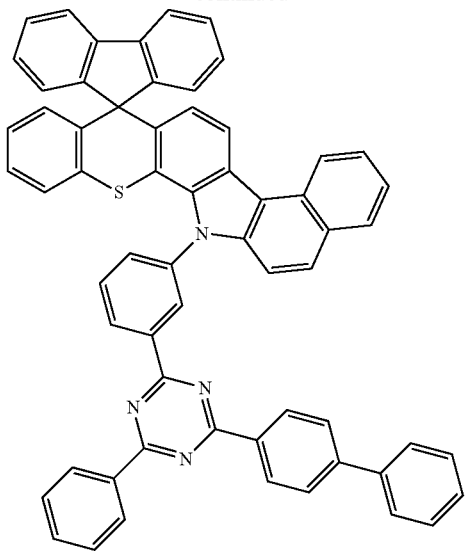
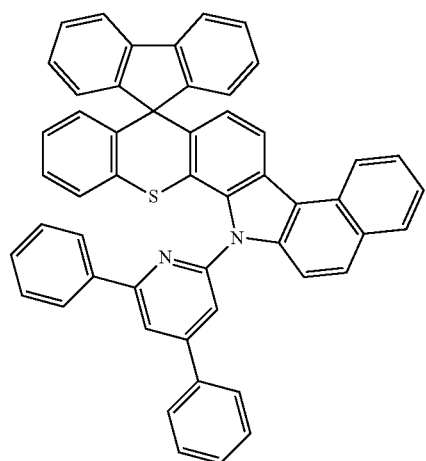
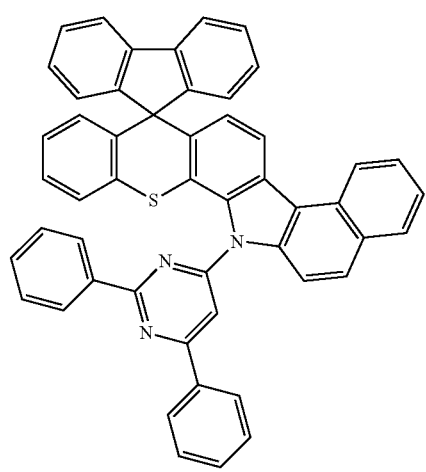
270
-continued
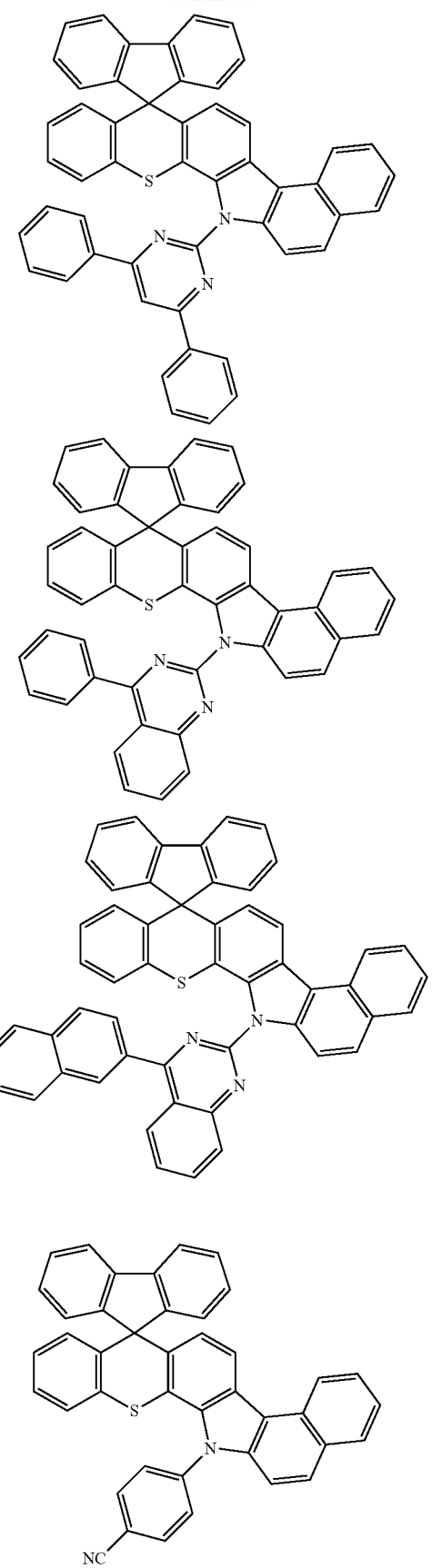

271
-continued
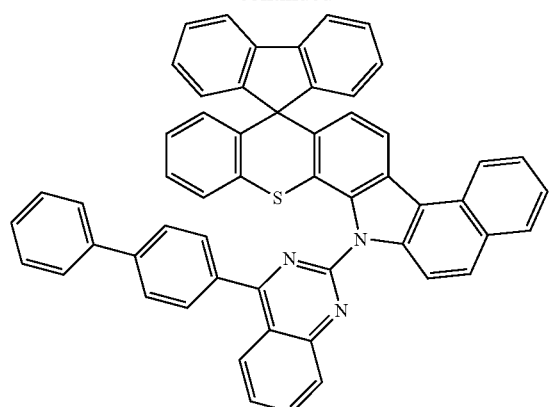
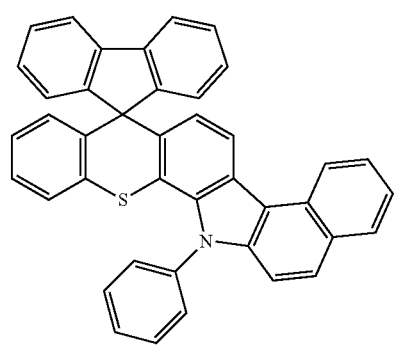
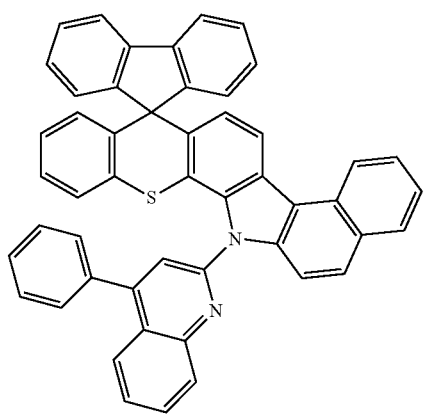
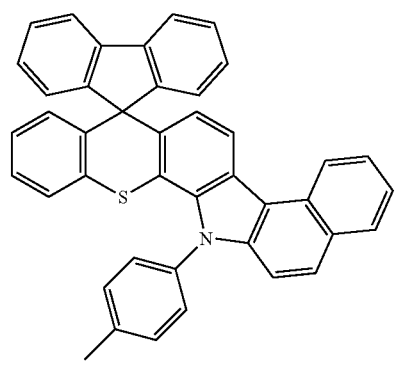
272
-continued
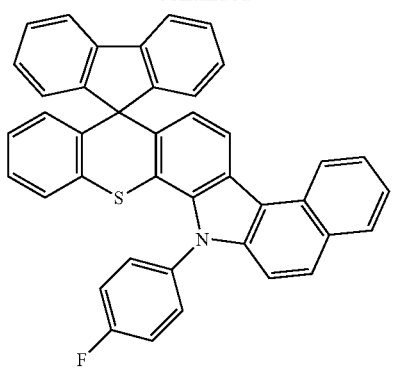
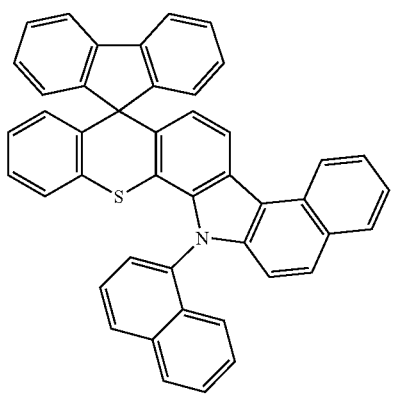
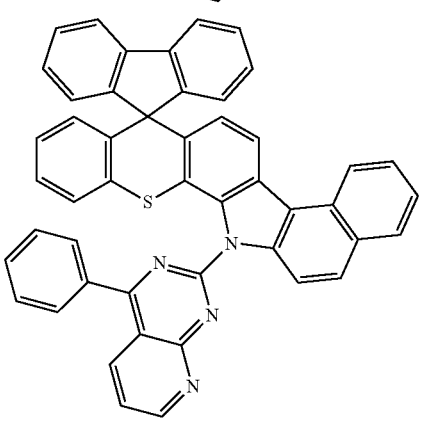
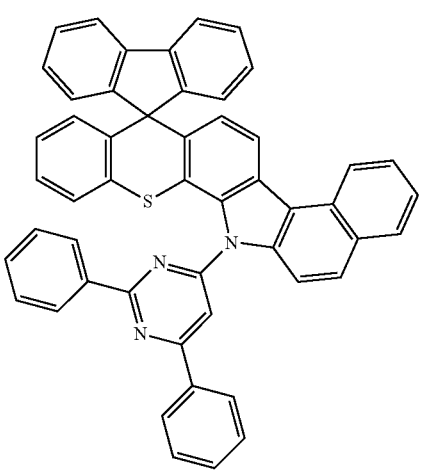

273
-continued
274
-continued
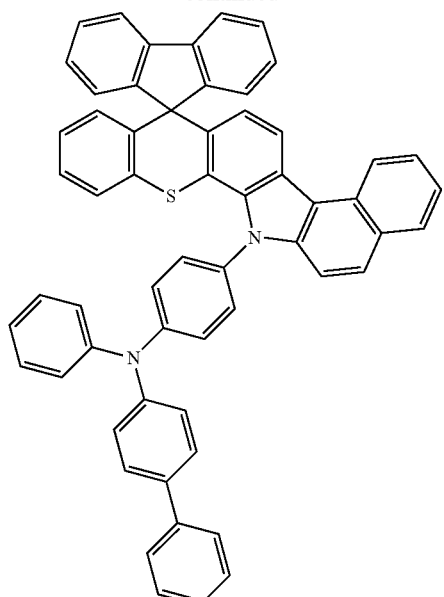
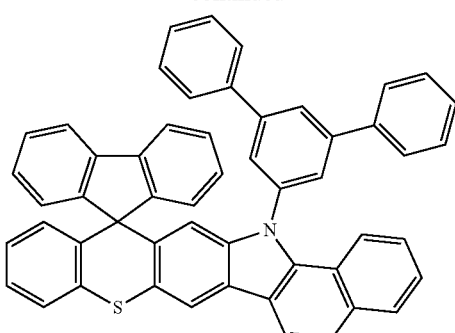
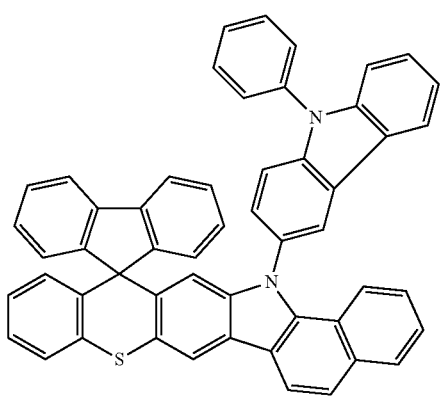
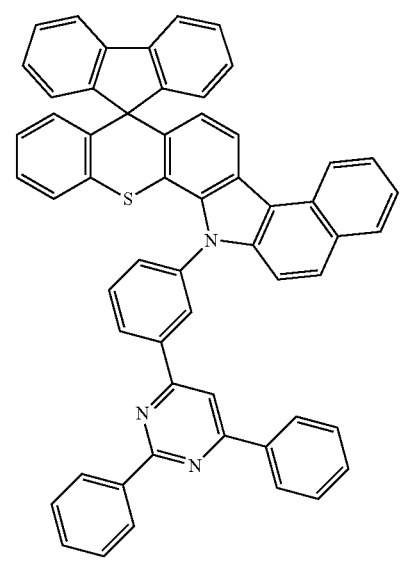
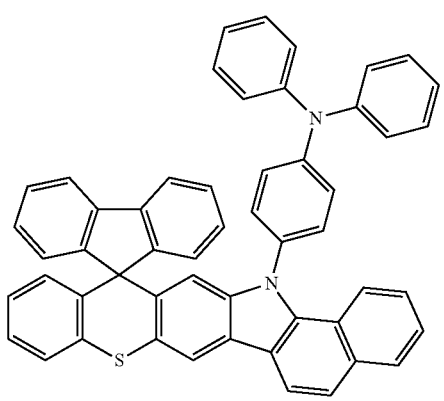
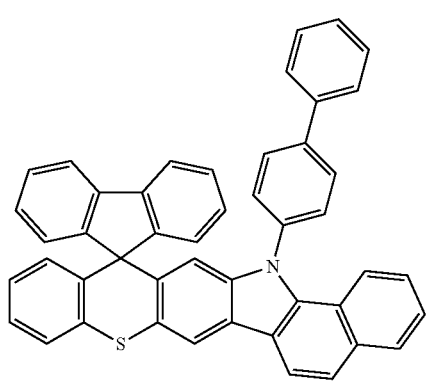
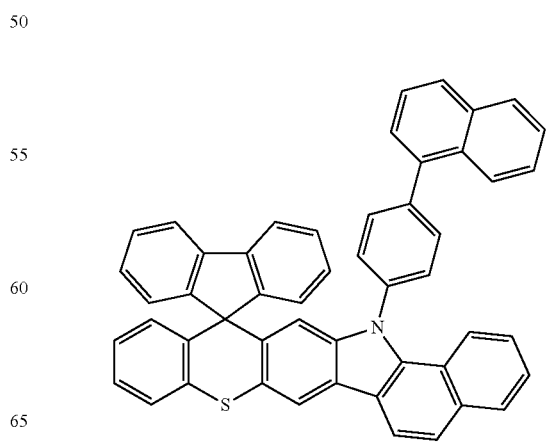

275
-continued
276
-continued
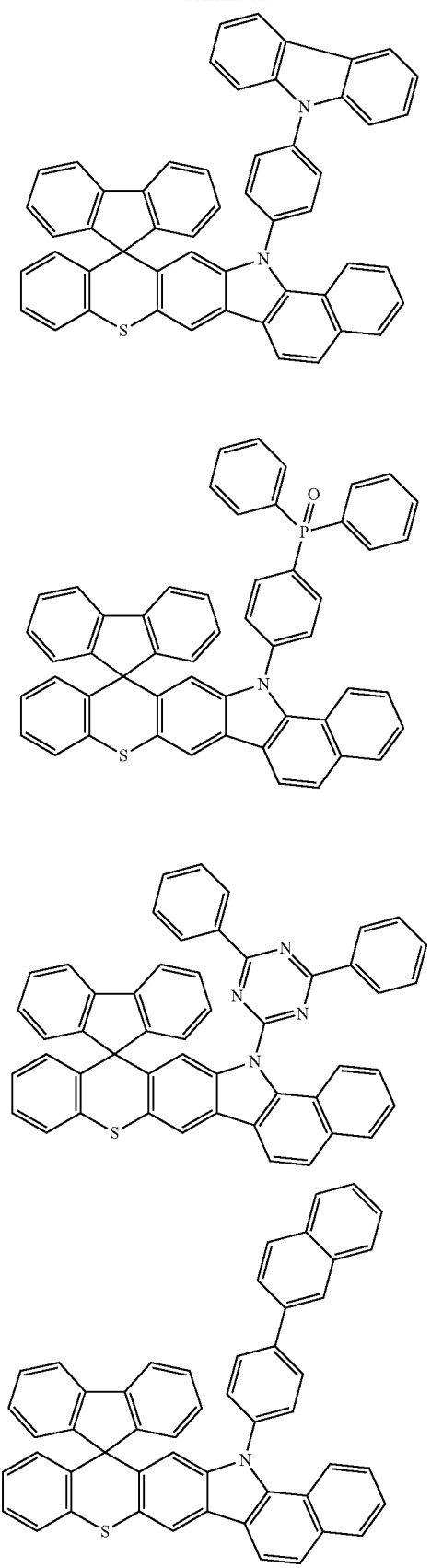
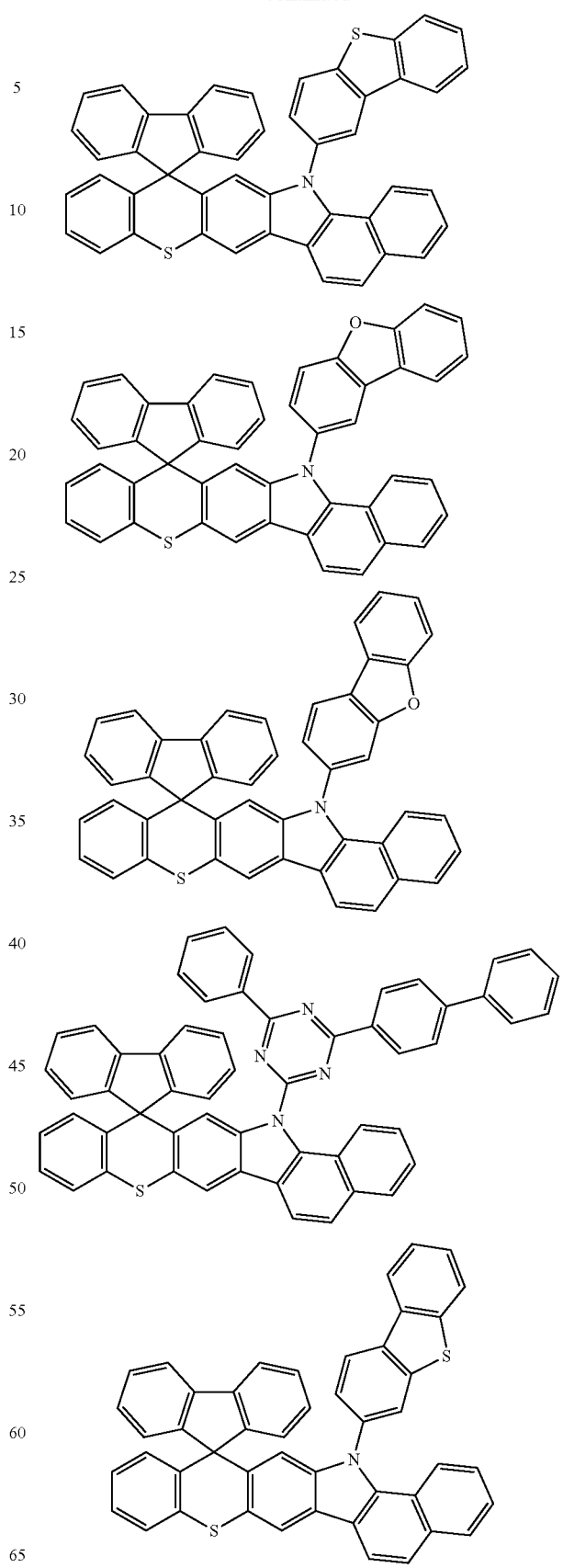

277
-continued
278
-continued
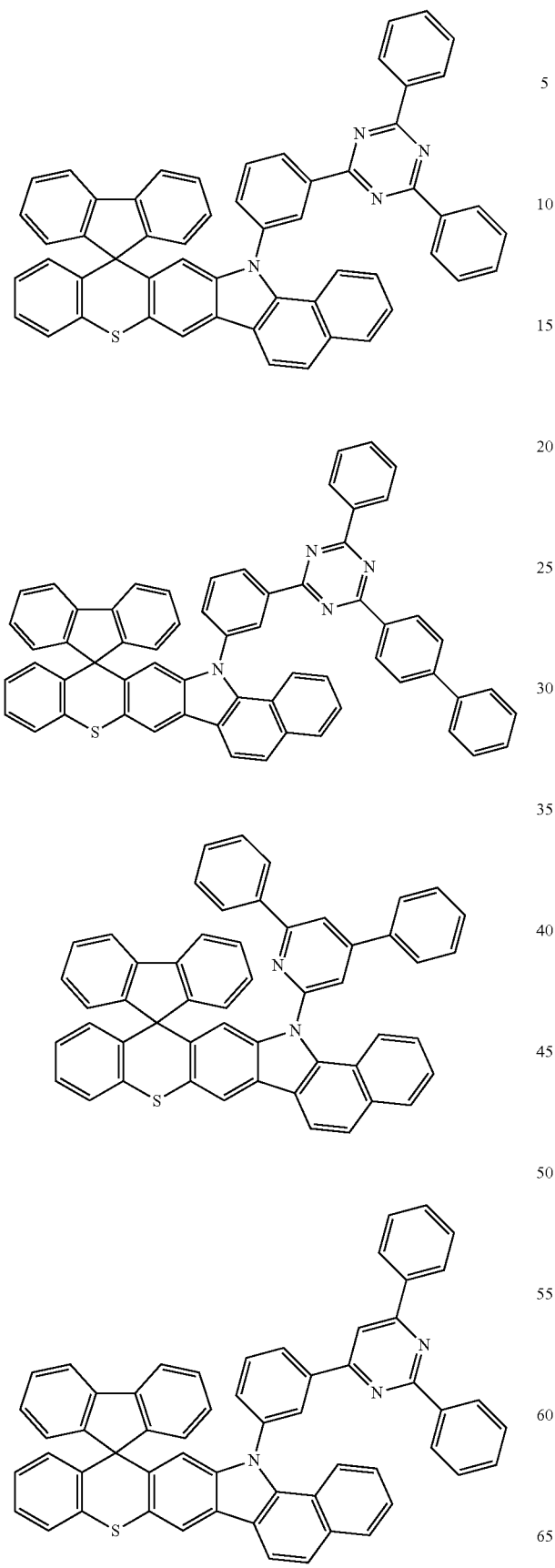
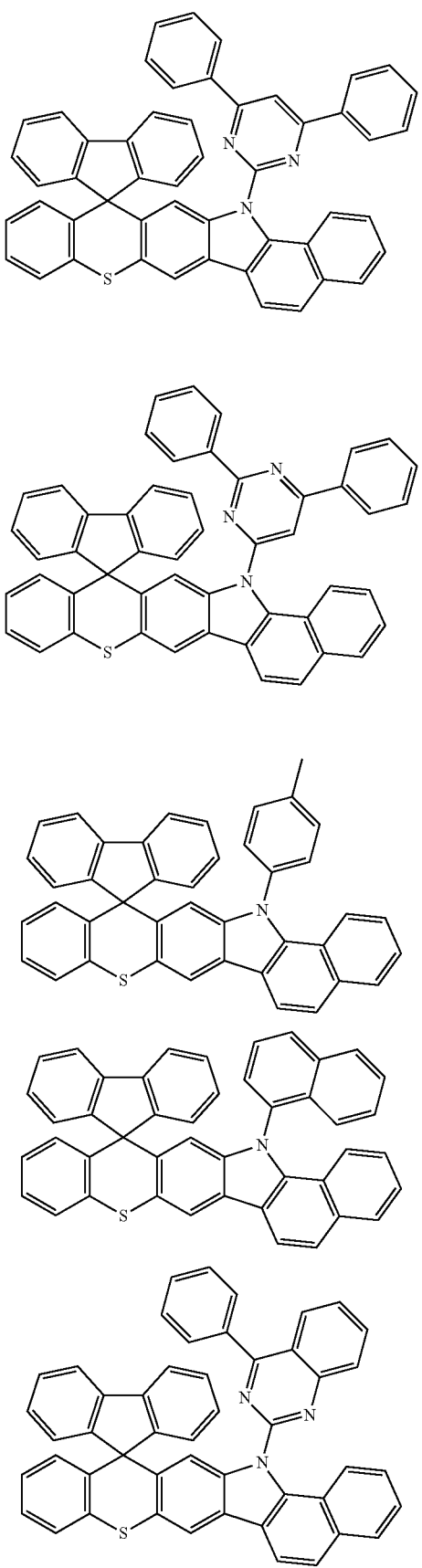

279
-continued
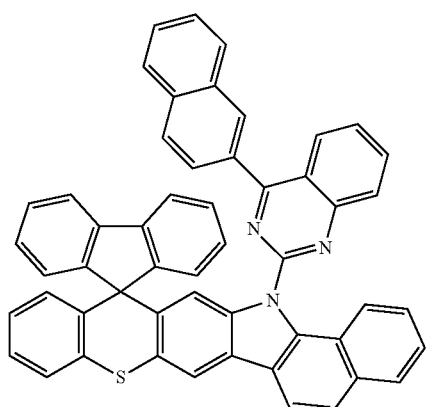
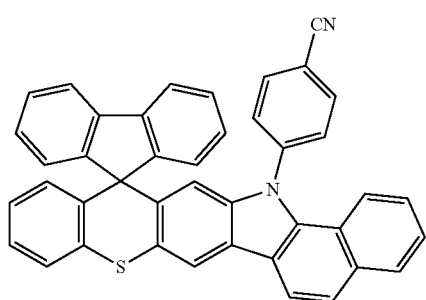
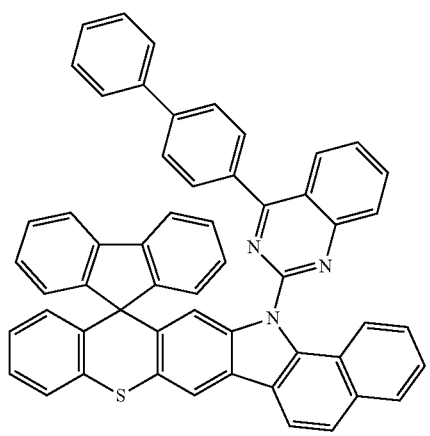
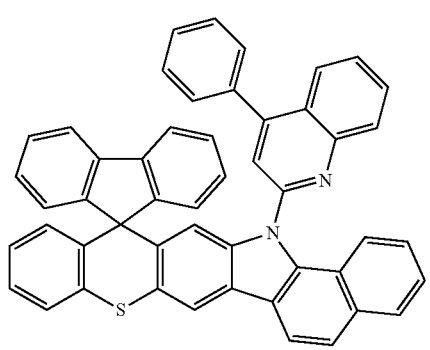
280
-continued
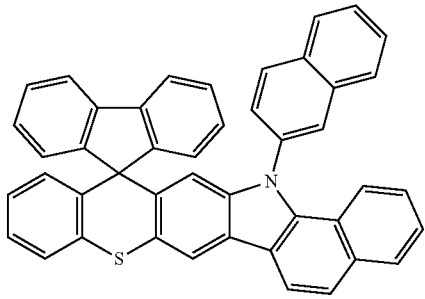
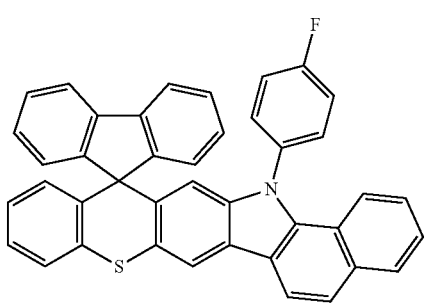
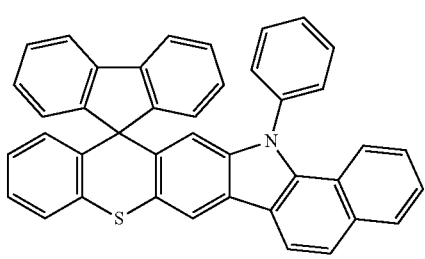
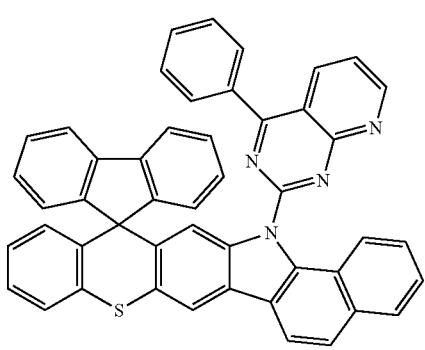
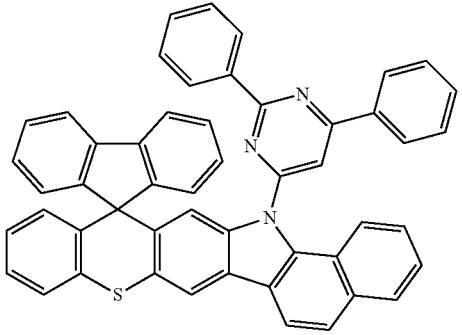

-continued
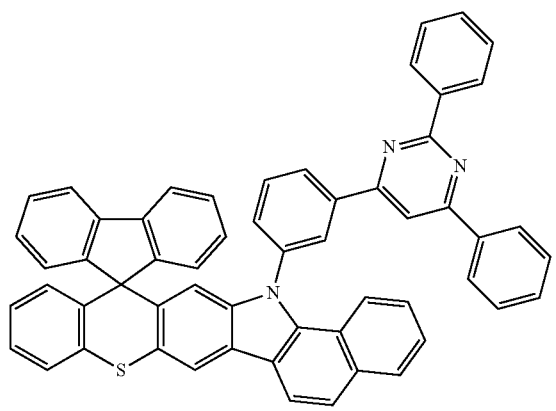
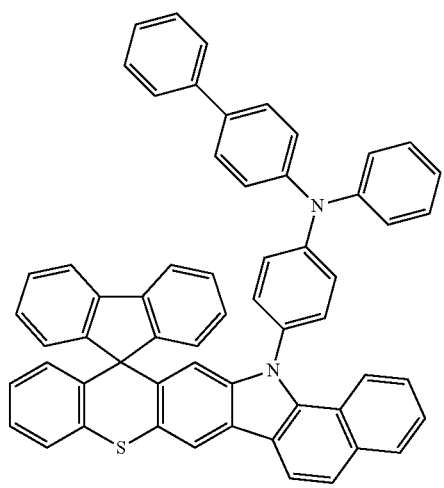
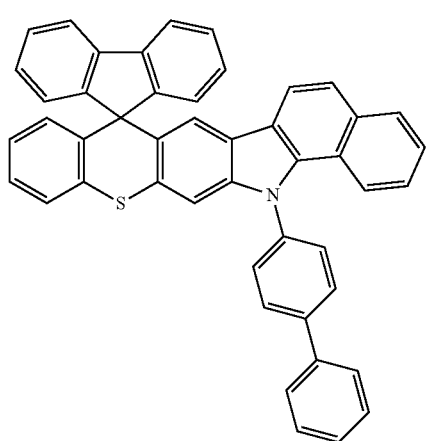
-continued
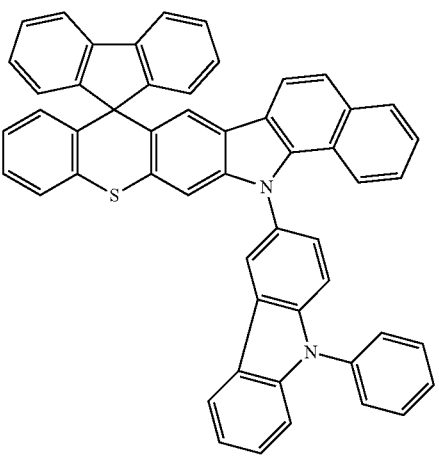
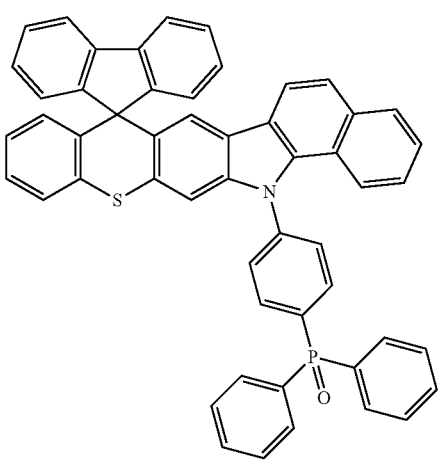

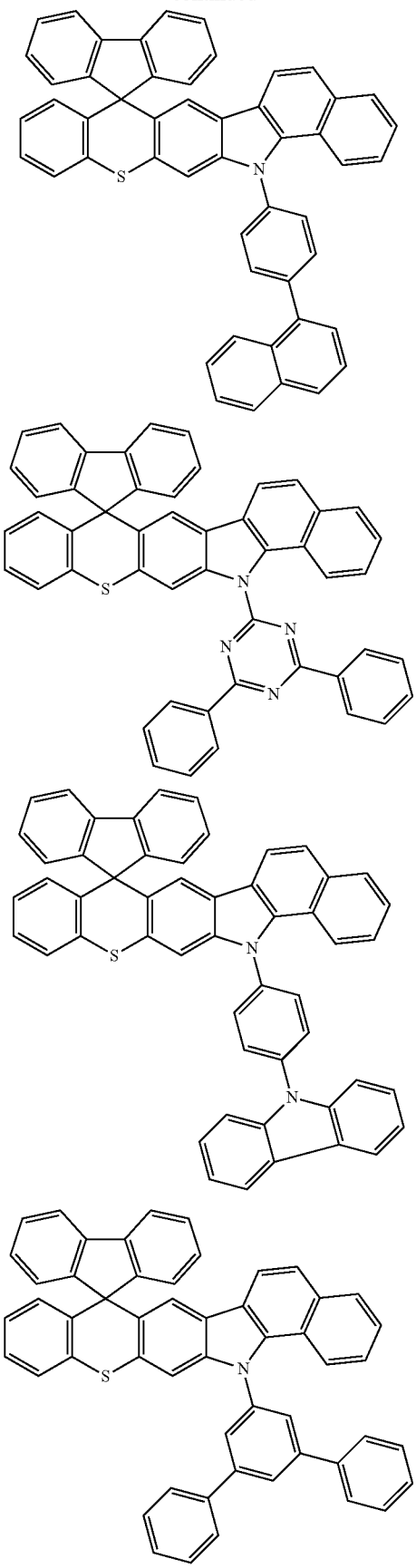
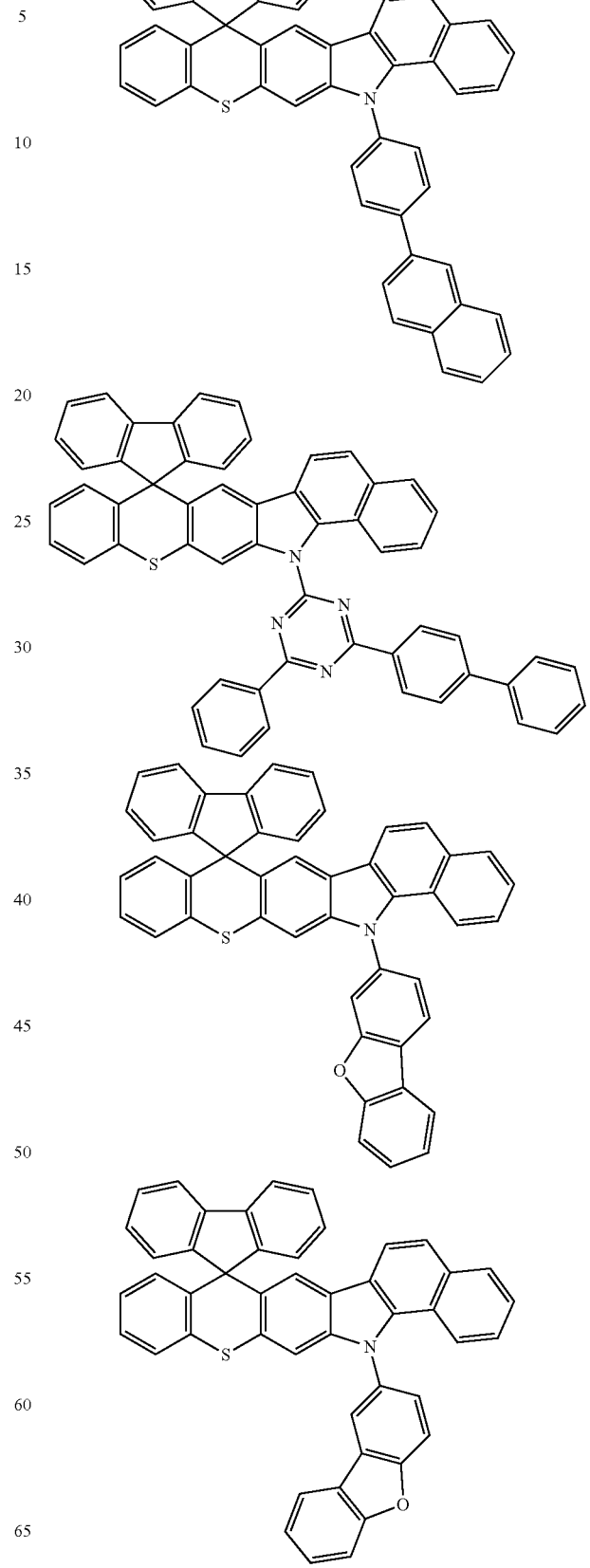

285
-continued
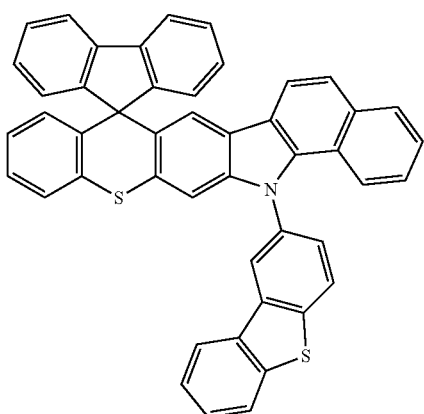
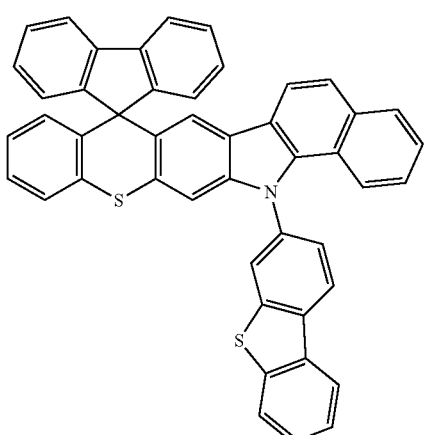
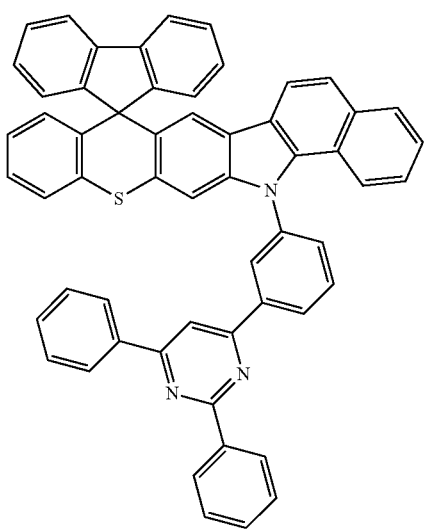
286
-continued
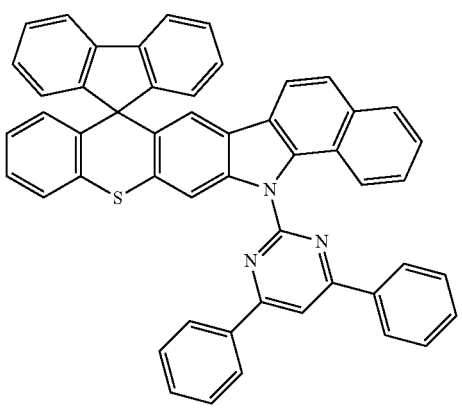
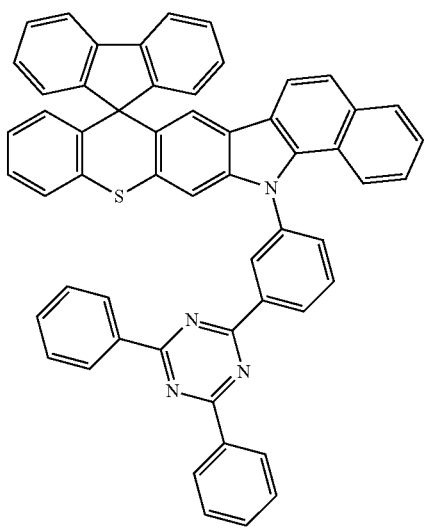
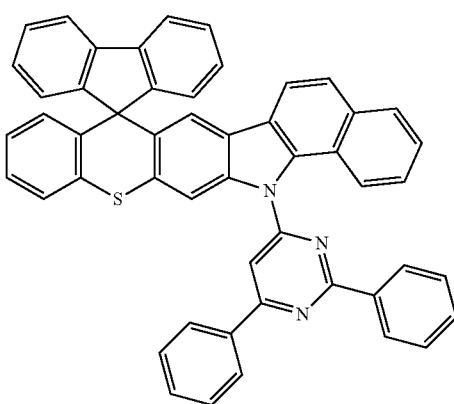

287
-continued
288
-continued
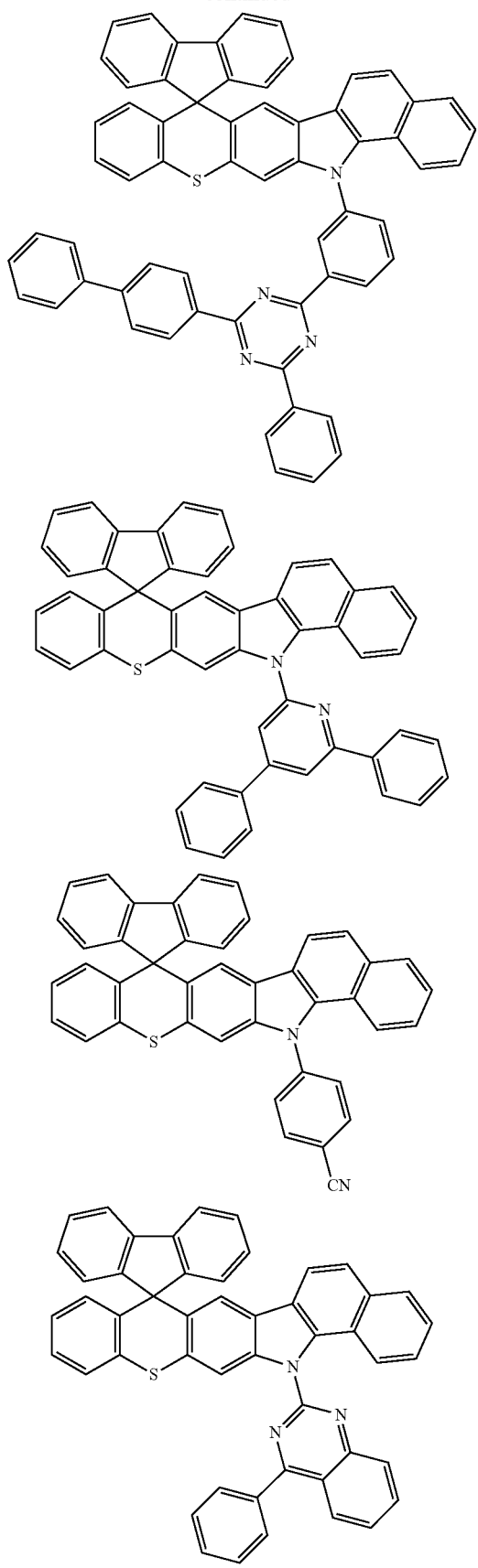
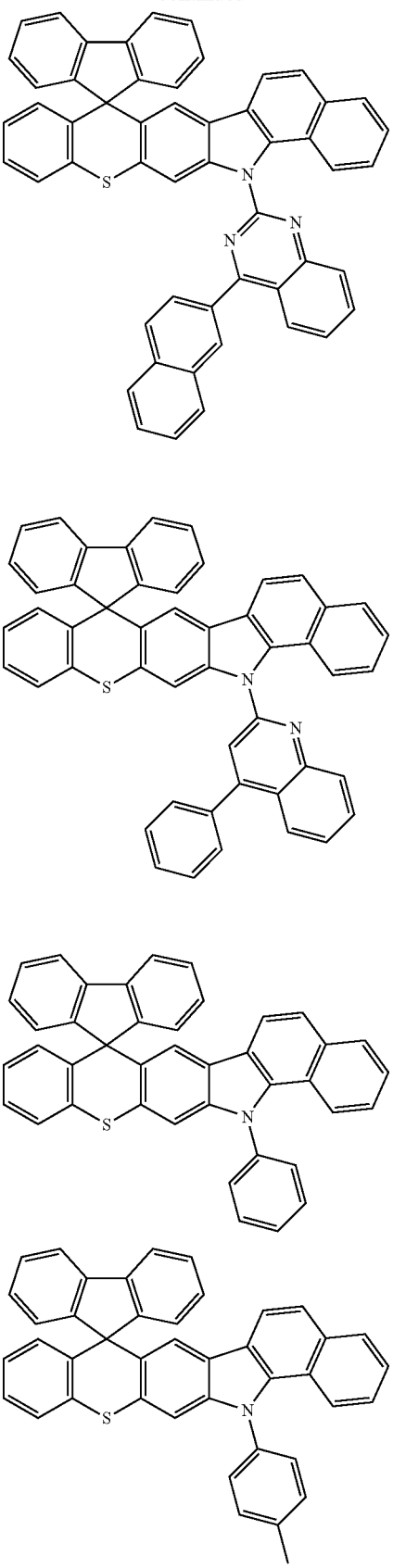

289
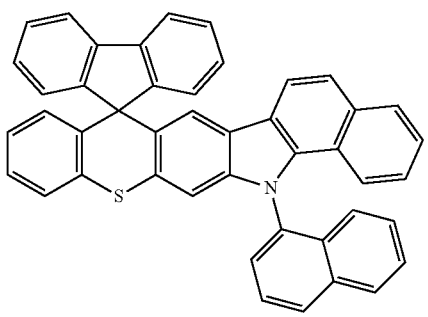
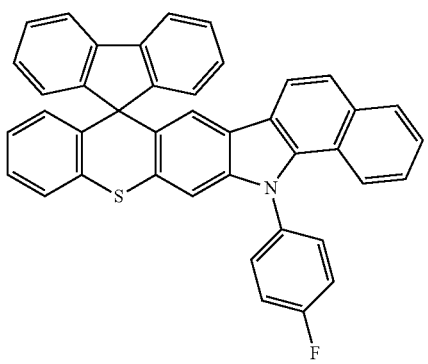
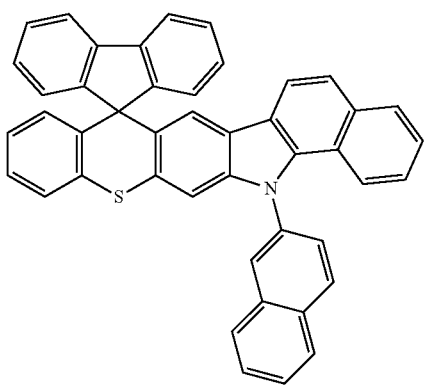
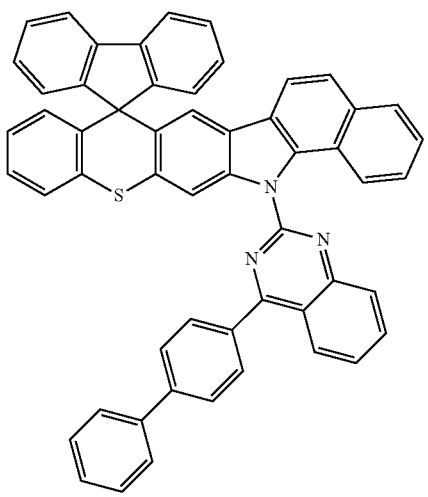
290
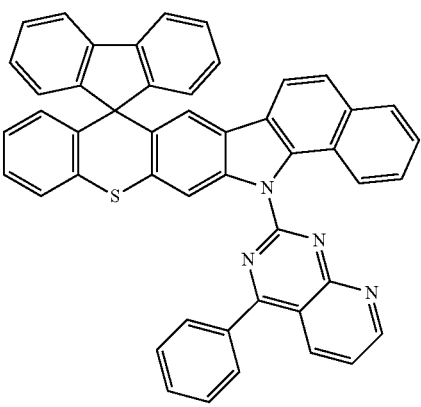
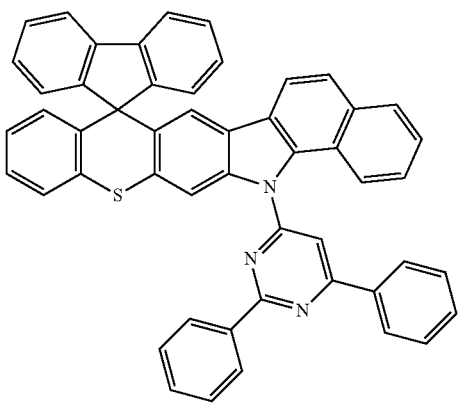
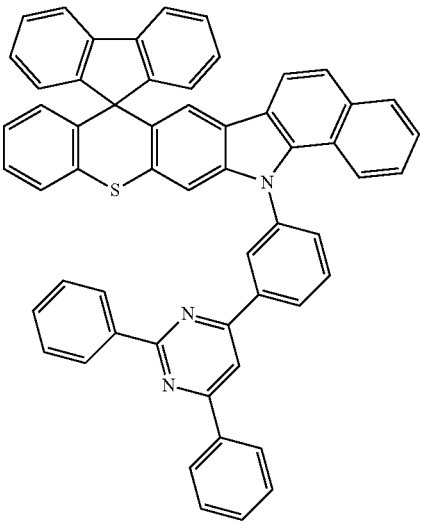

291
-continued
292
-continued
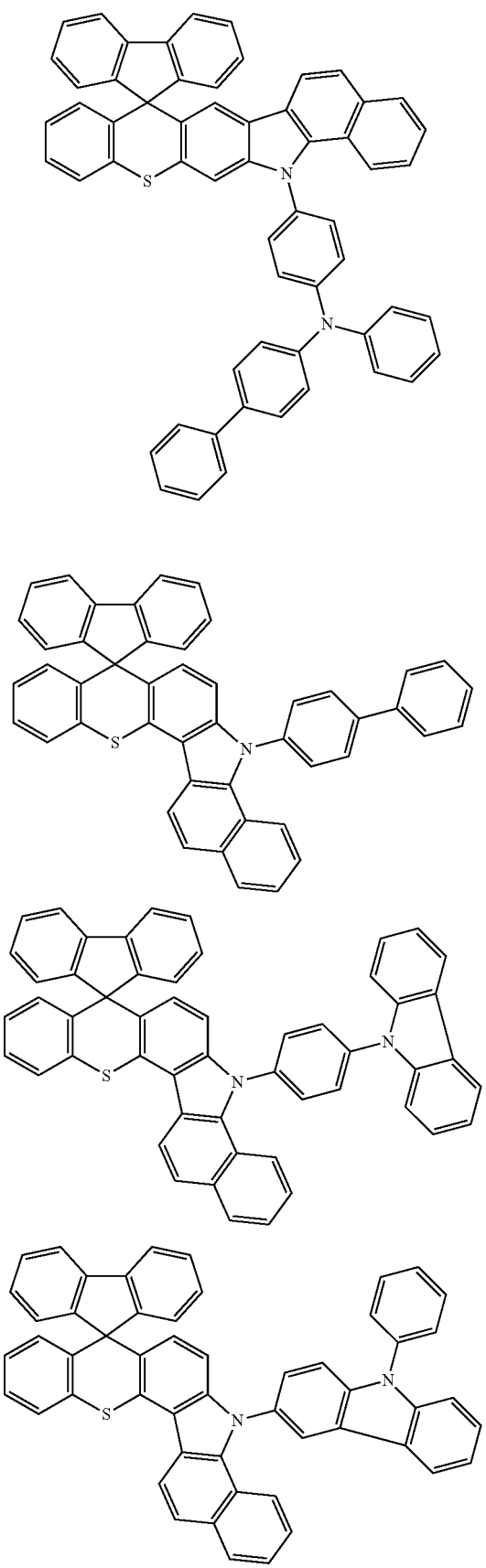
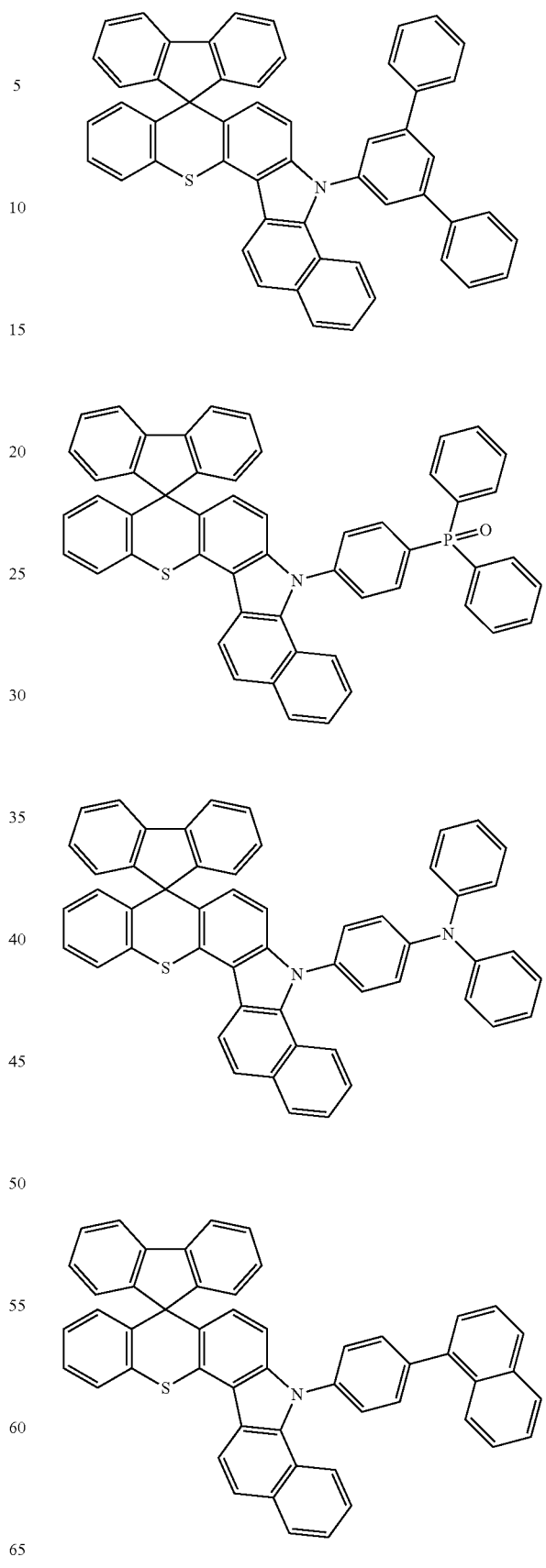

293
-continued
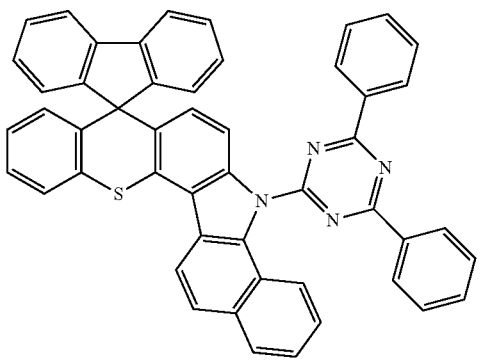
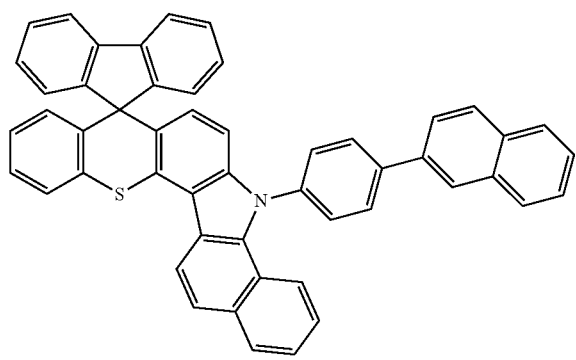
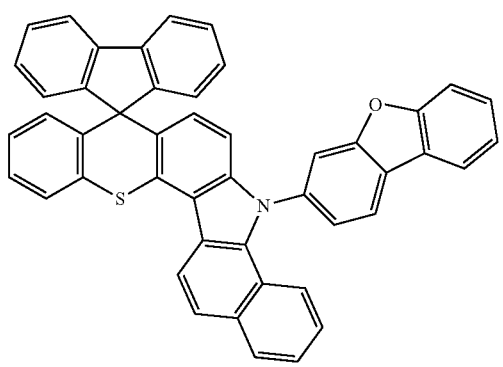
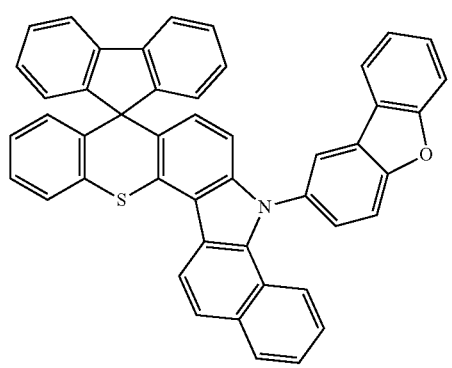
294
-continued
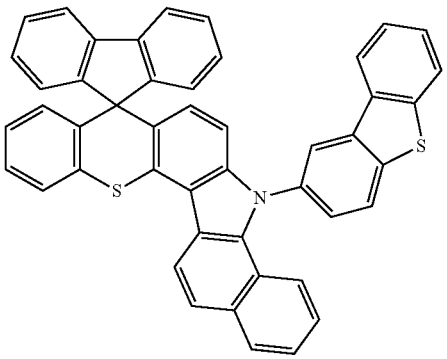
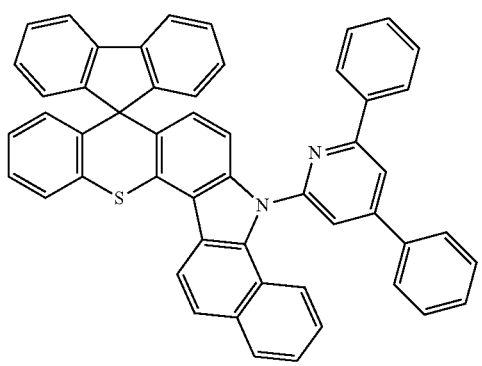
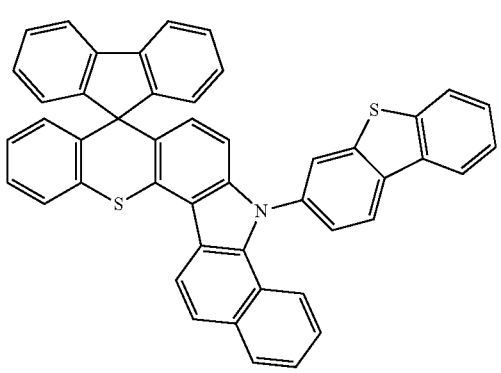
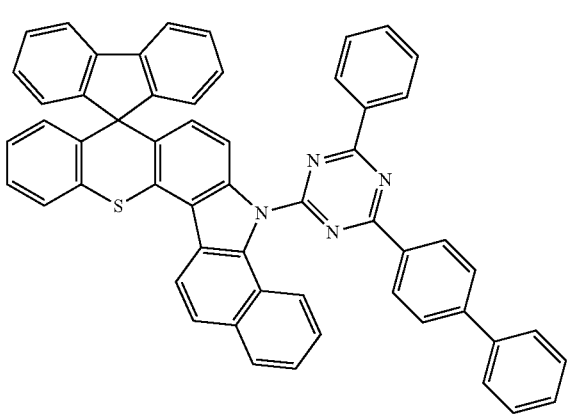

295
-continued
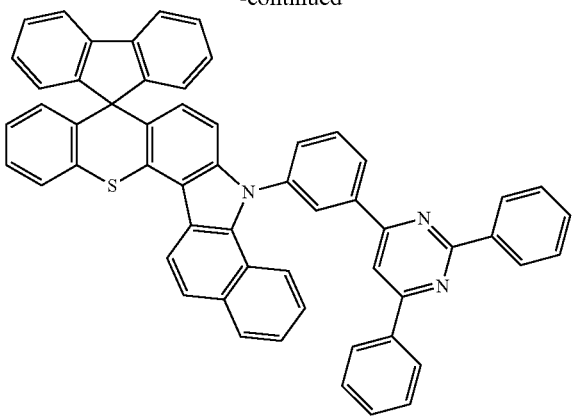
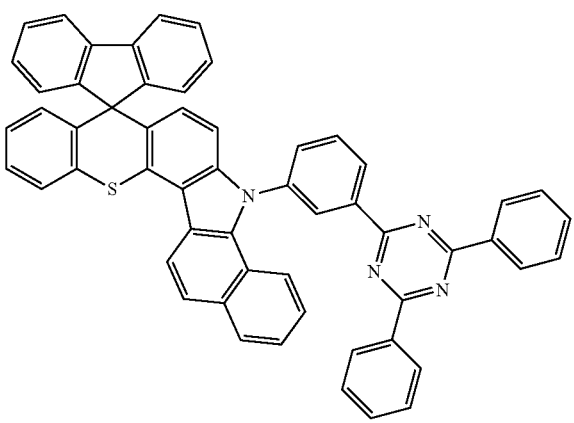
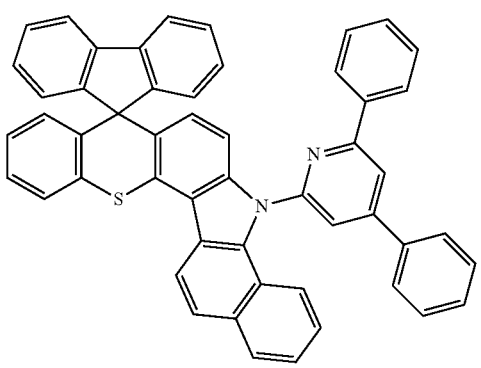
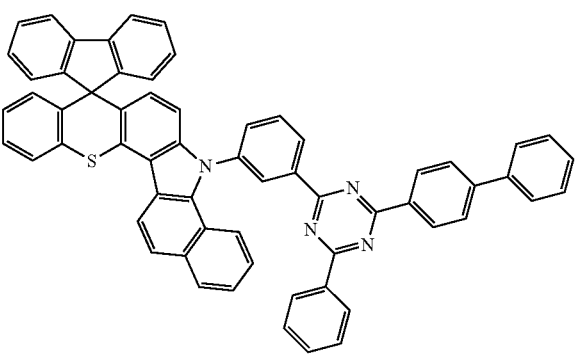
296
-continued
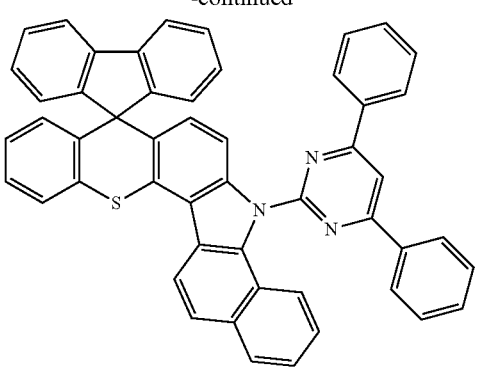
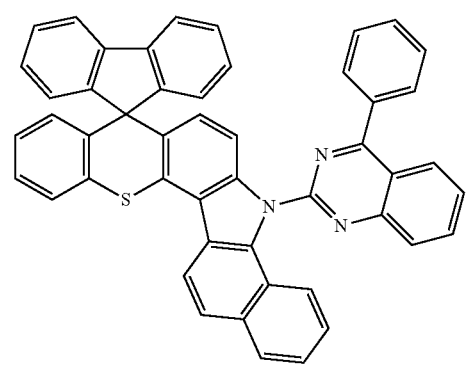
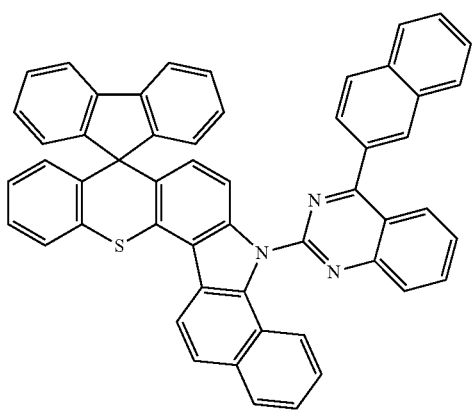
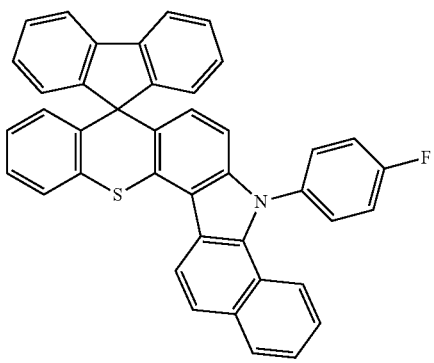

297
-continued
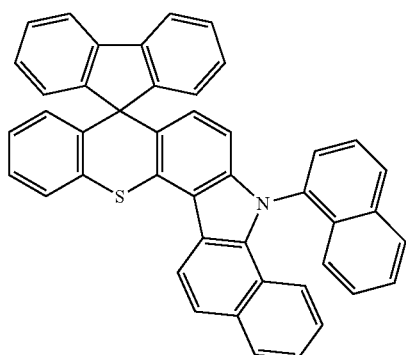
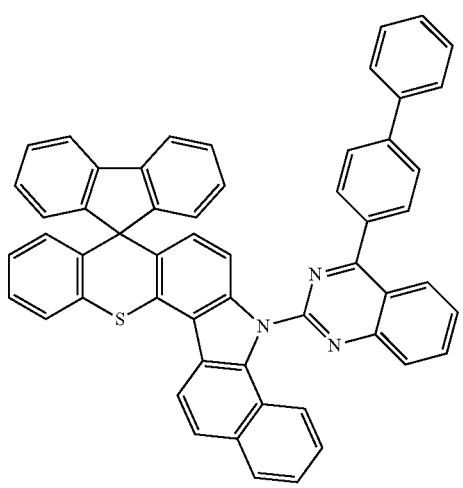
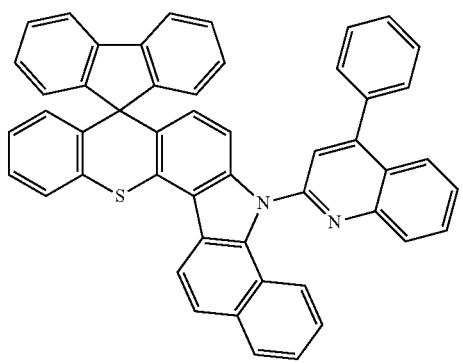
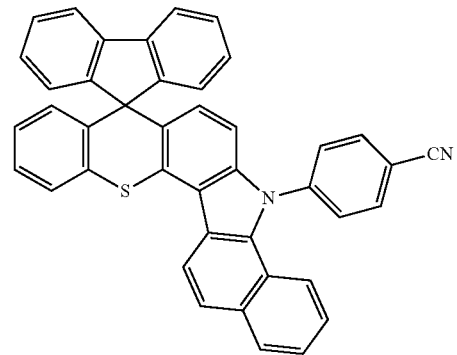
298
-continued
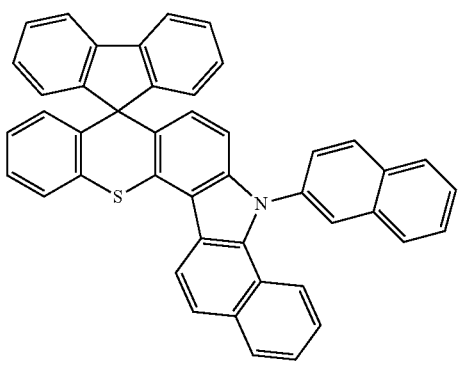
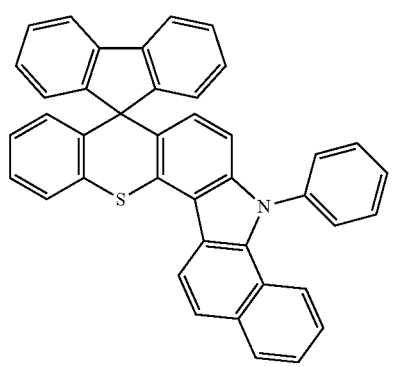
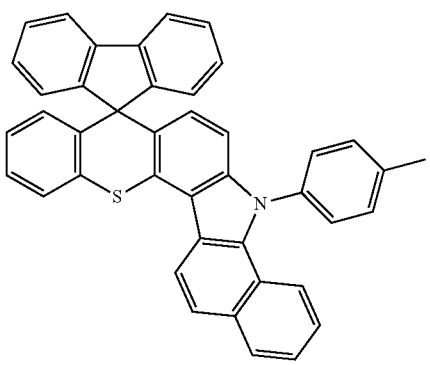
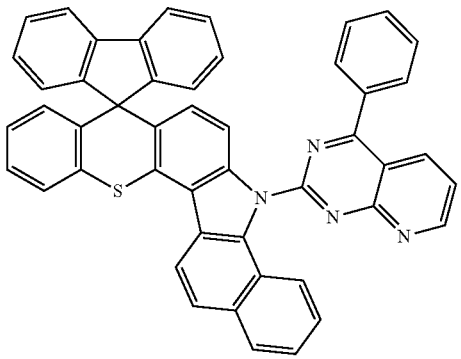

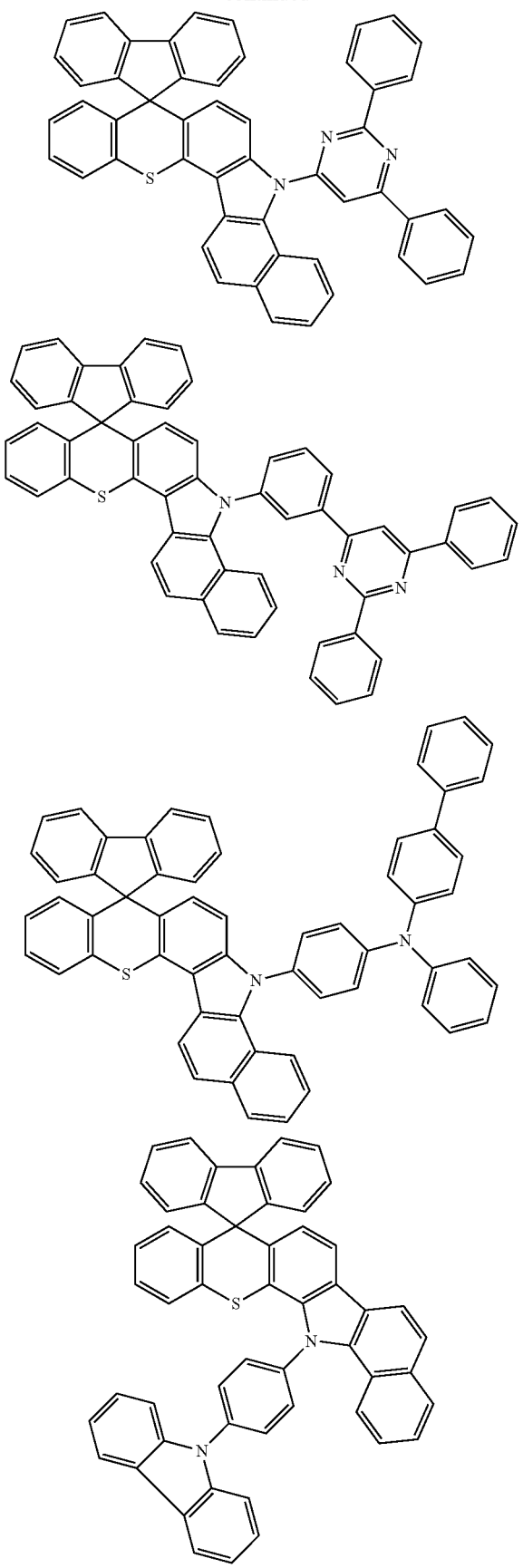

US 10,968,230 B2
301
-continued
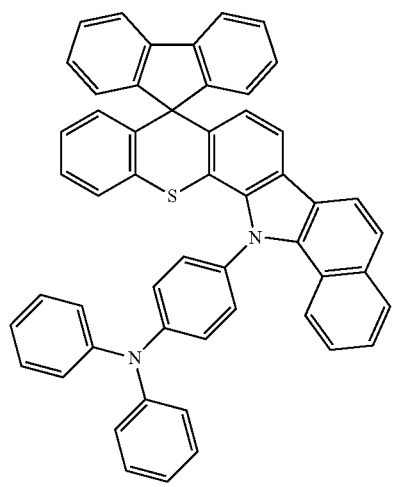
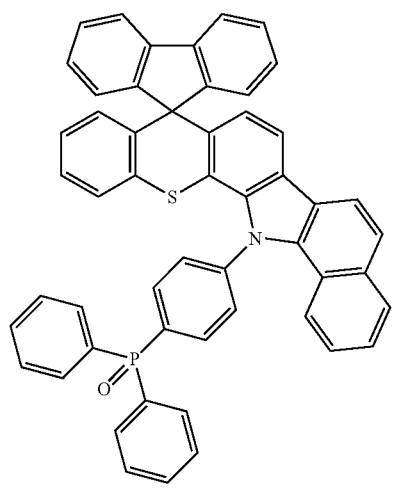
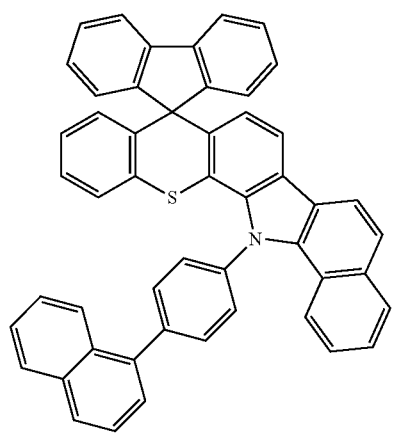
302
-continued
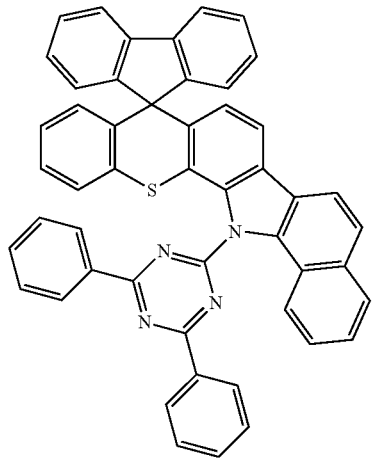
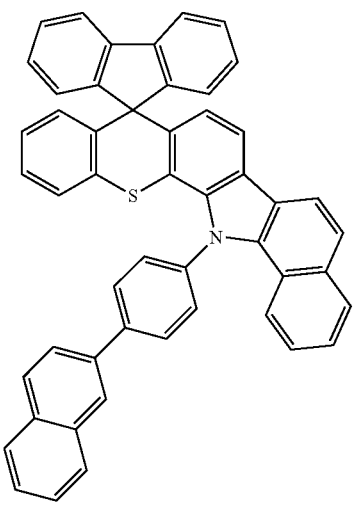
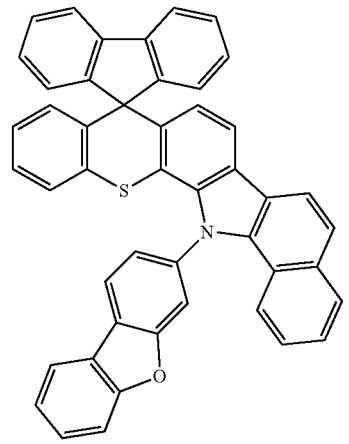

303
-continued
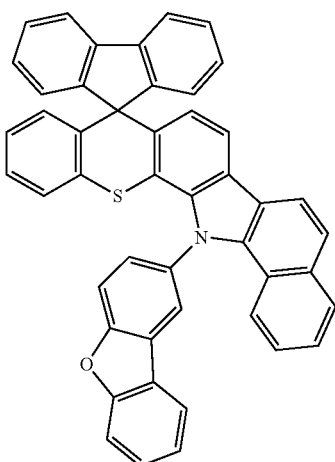
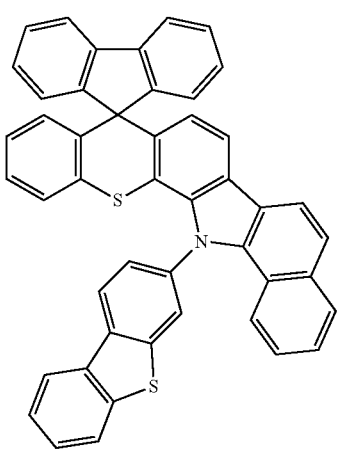
304
-continued
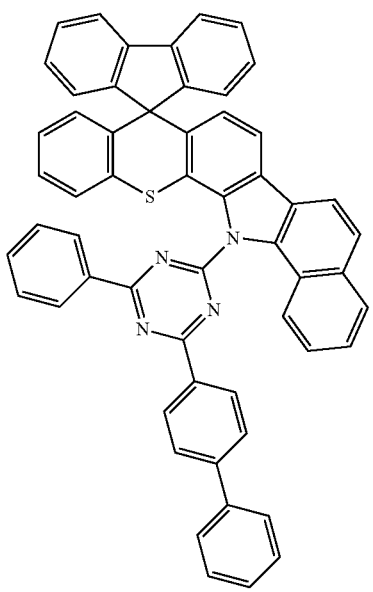
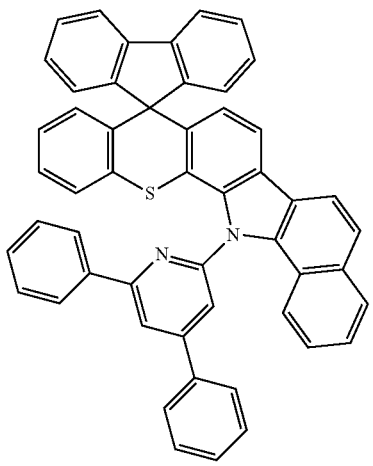
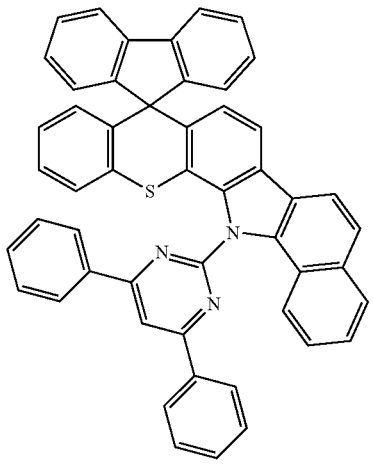

305
-continued
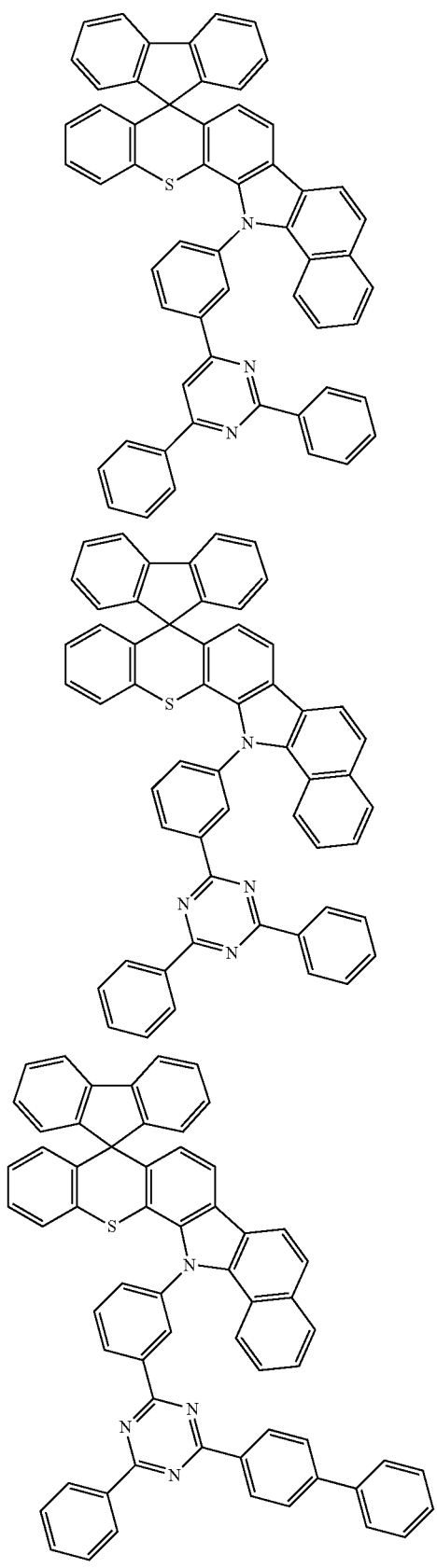
306
-continued
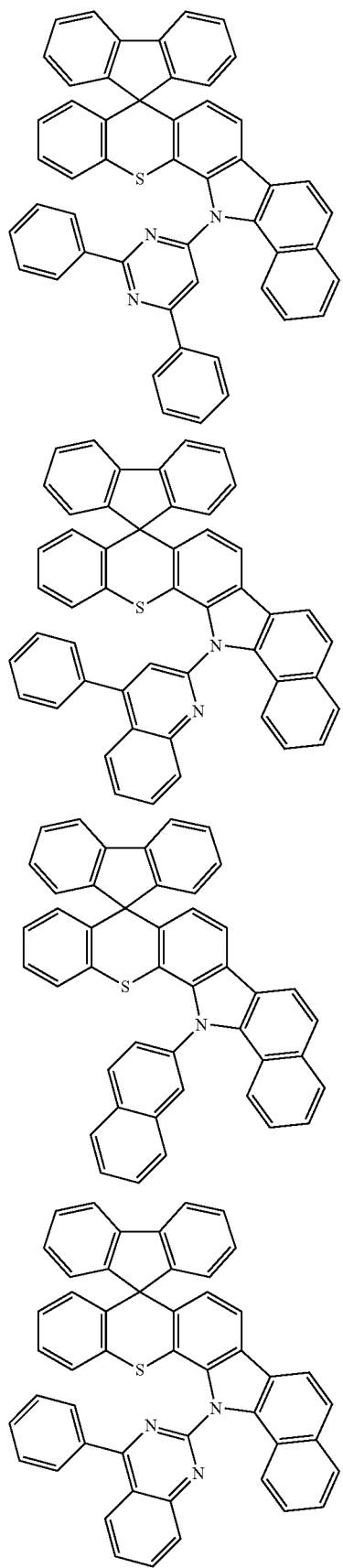

307
-continued
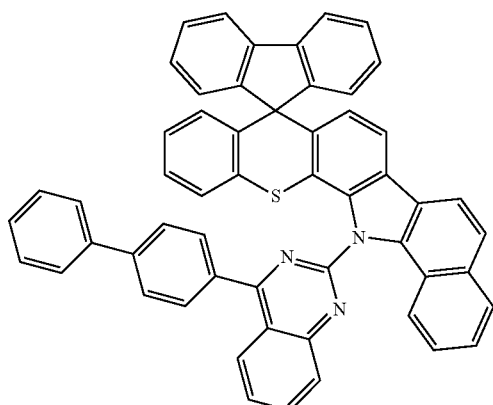
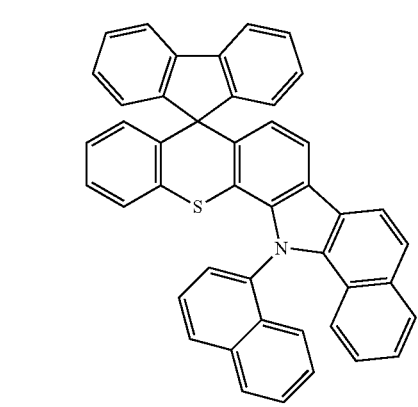
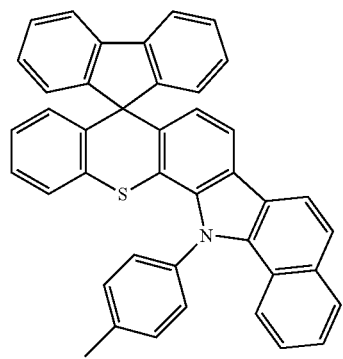
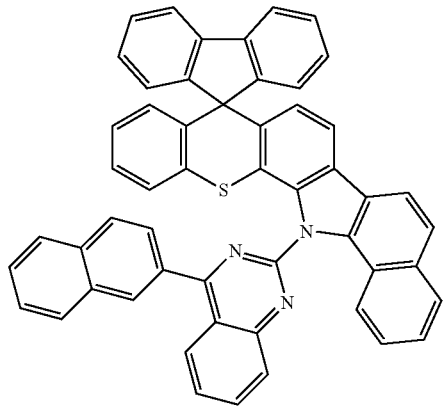
308
-continued
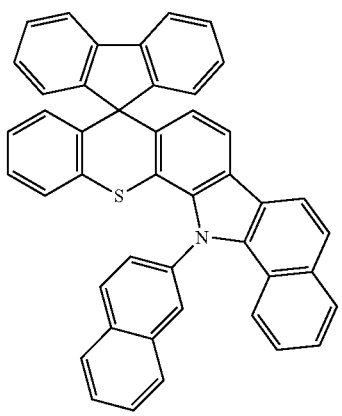
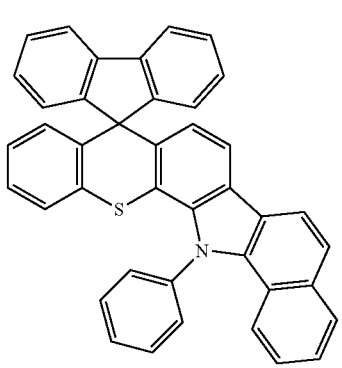
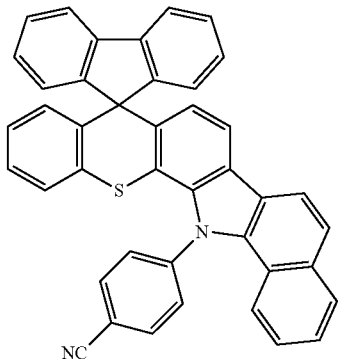
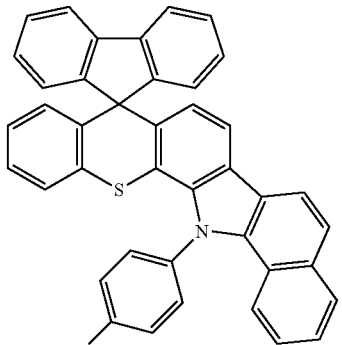

309
-continued
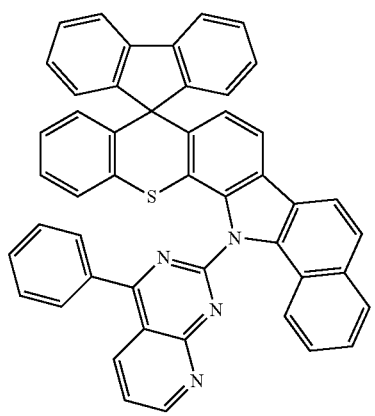
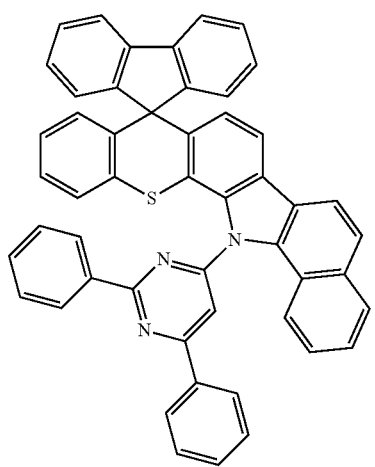

310
-continued
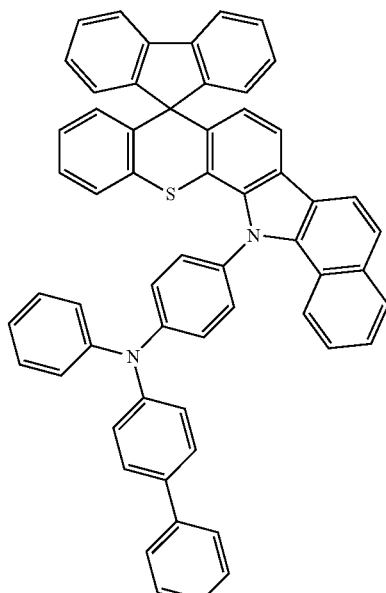
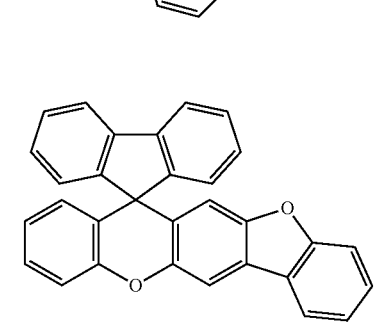
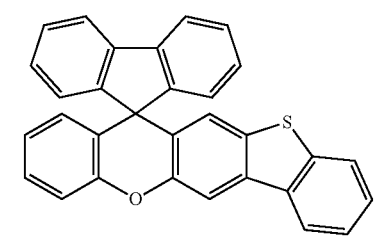
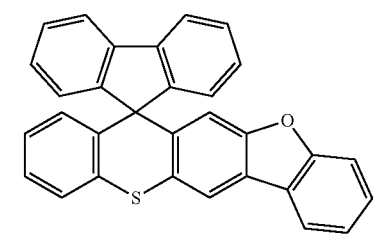
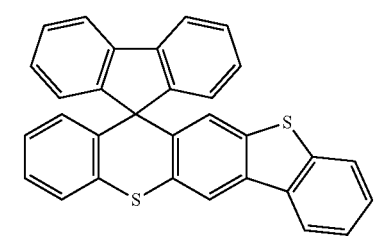

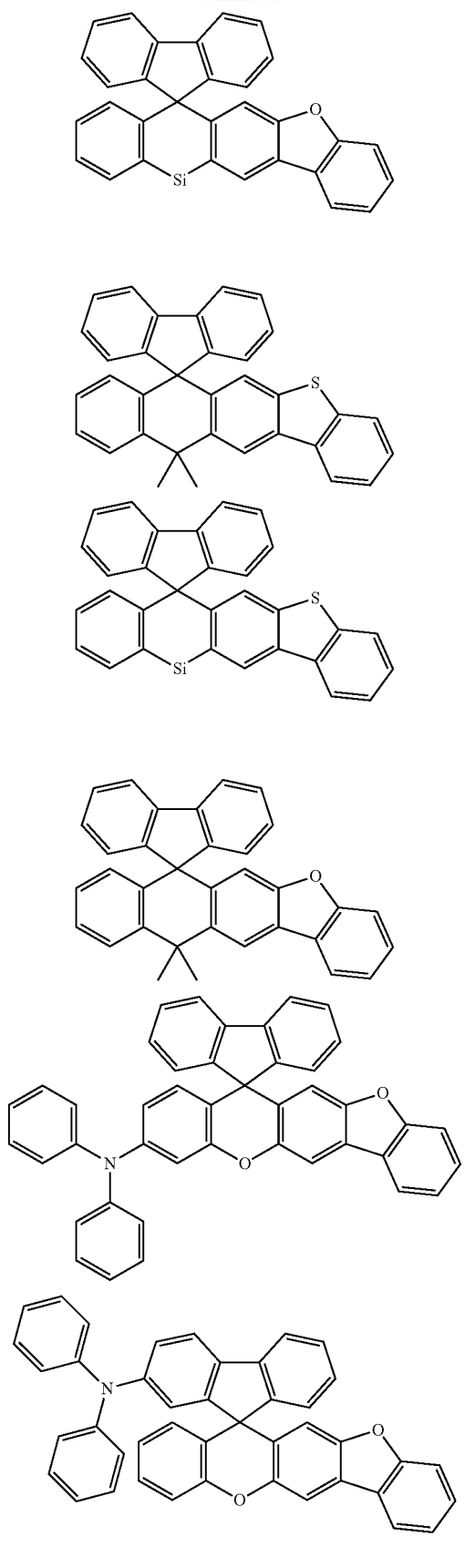

313
-continued
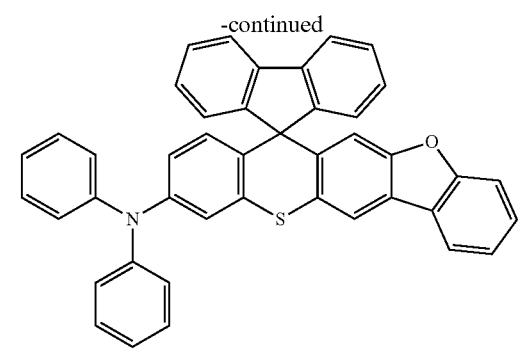
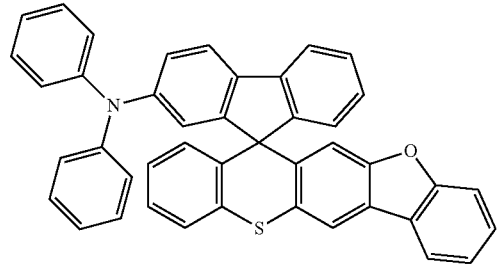
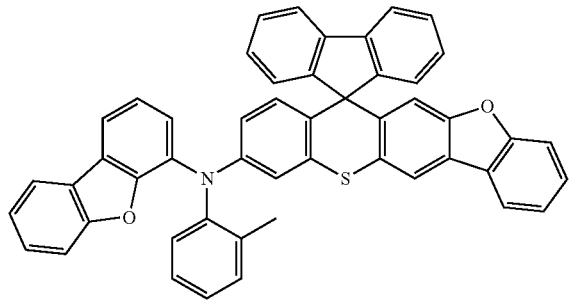
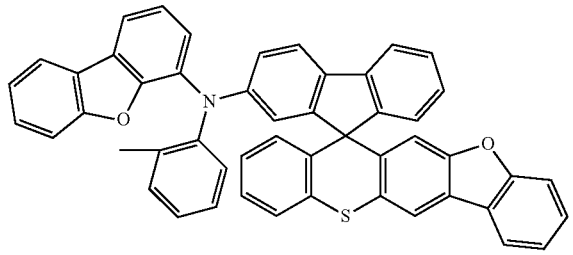
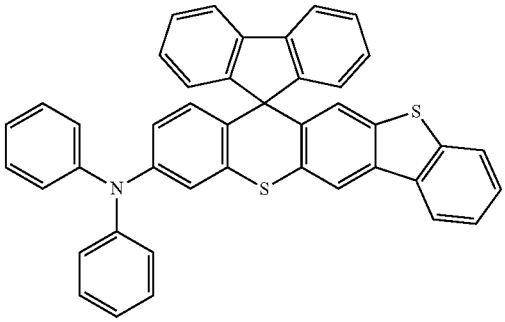
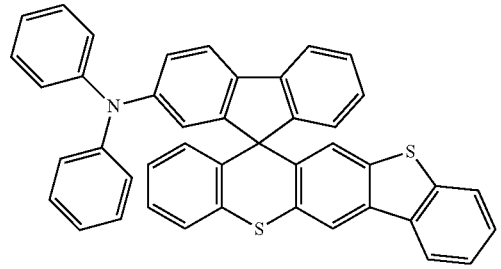
314
-continued
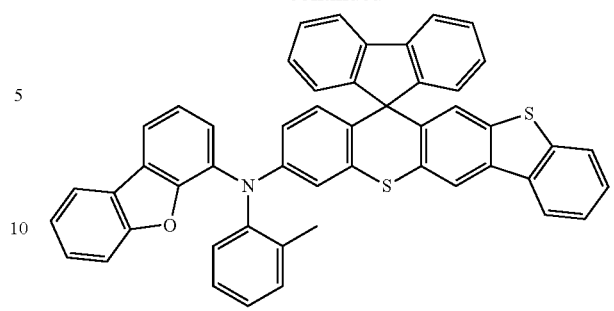
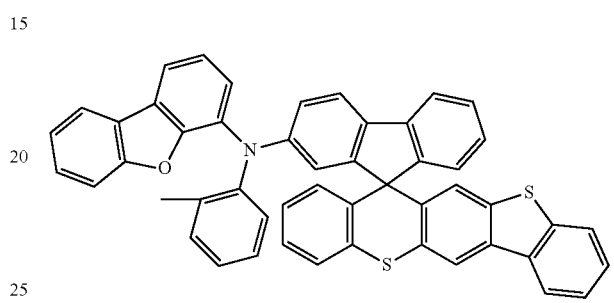
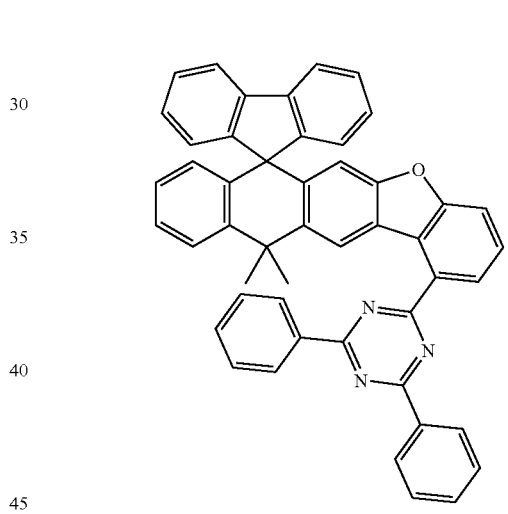

315
-continued
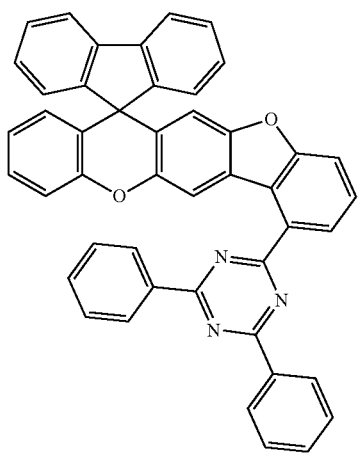
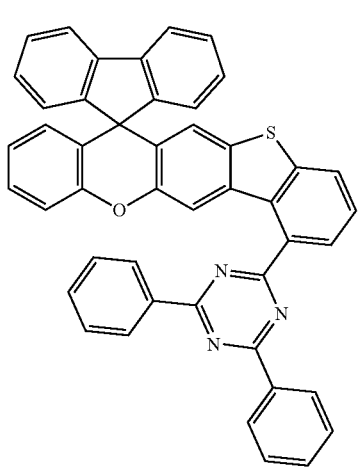
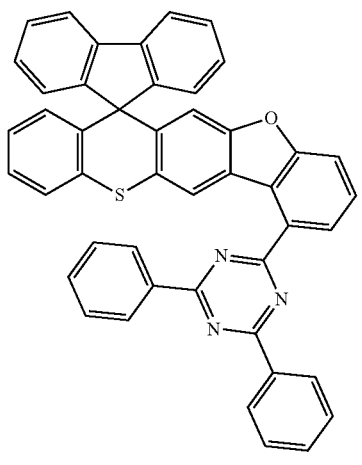
316
-continued
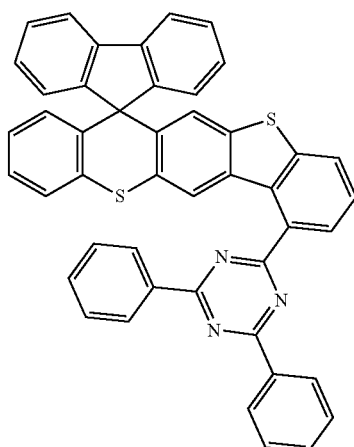
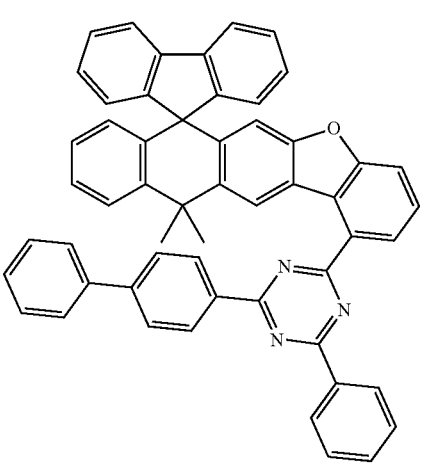
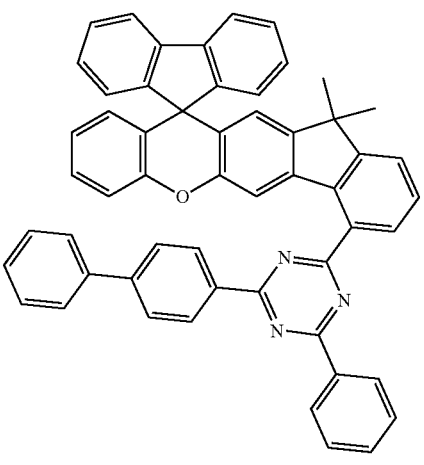

317
-continued
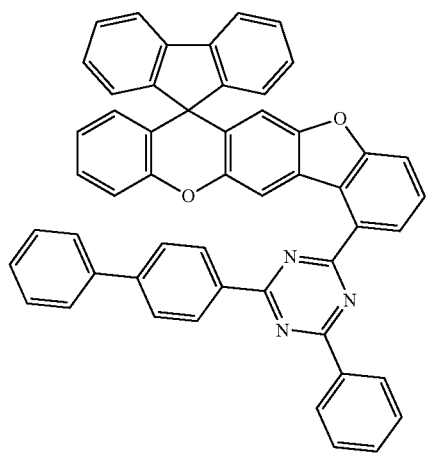
318
-continued
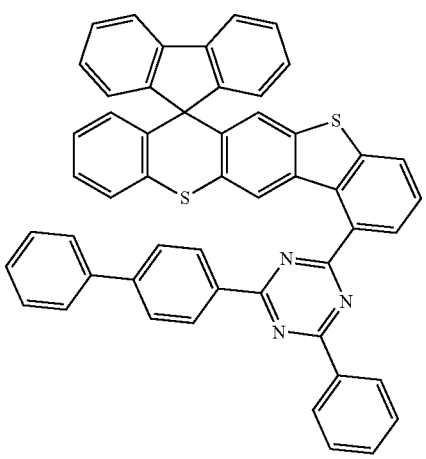
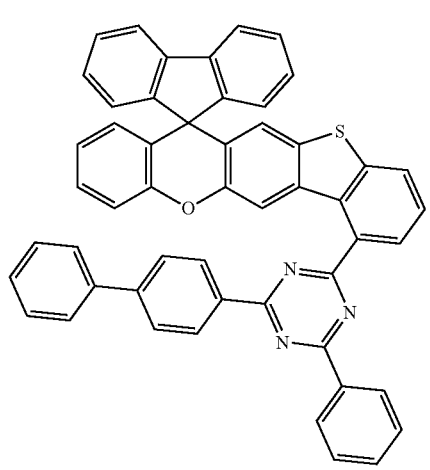
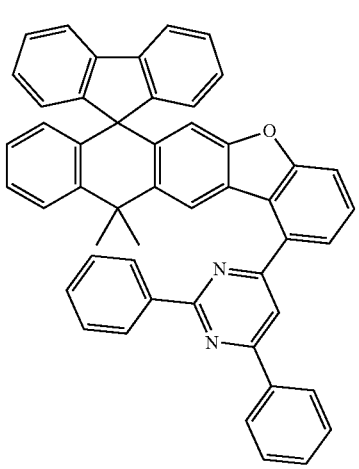
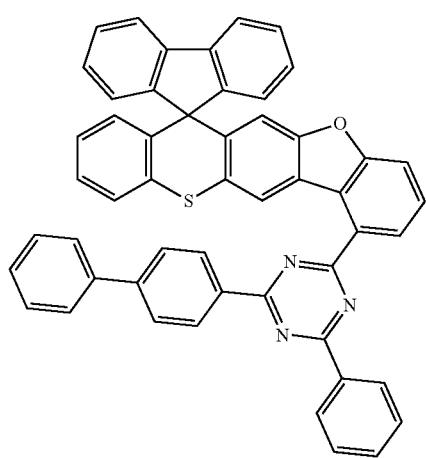
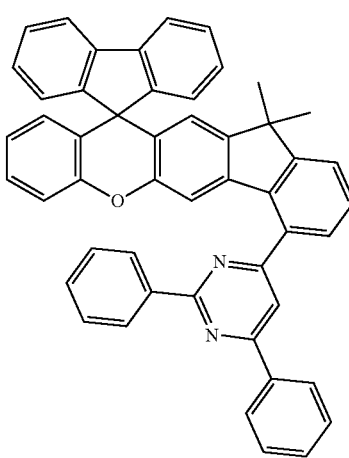

319
-continued
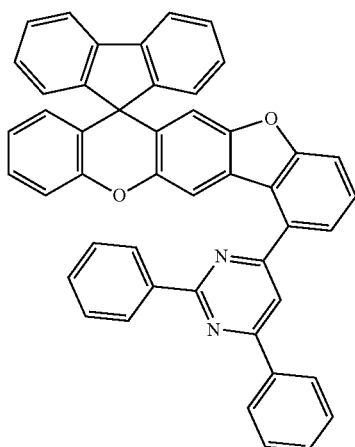
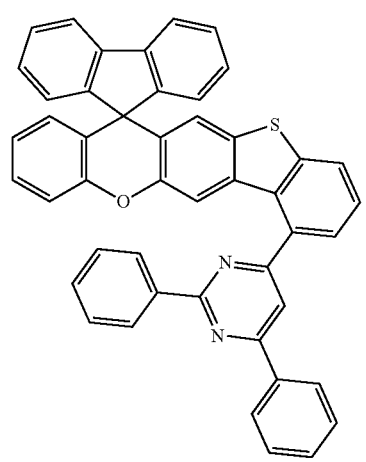
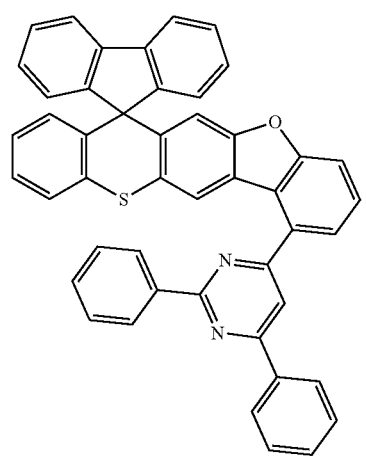
320
-continued
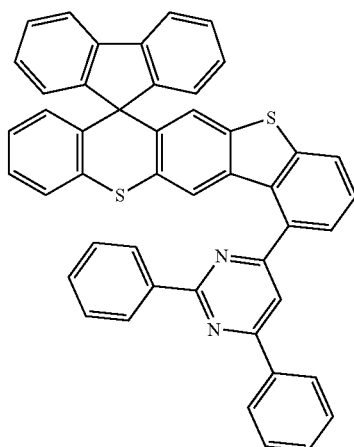
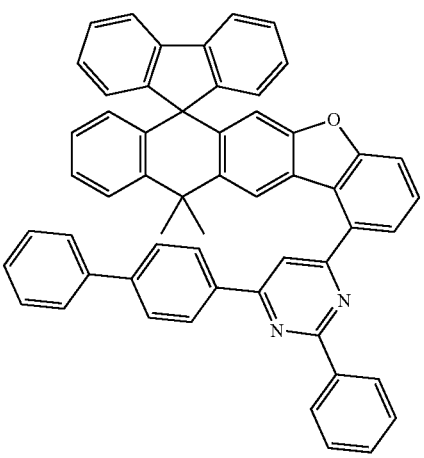
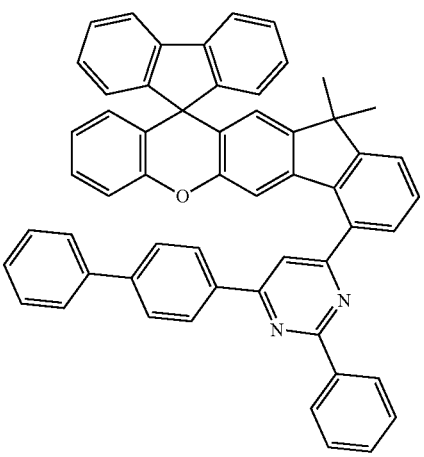

| 321 | 322 |
|---|---|
| -continued | -continued |
| 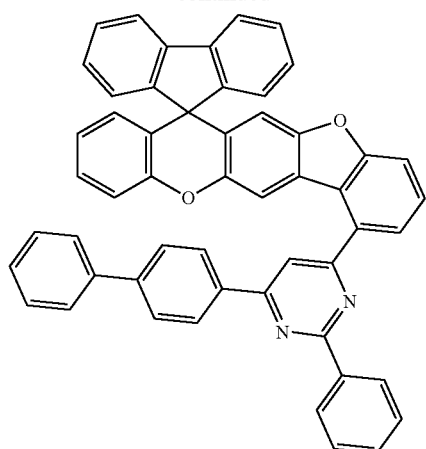 | 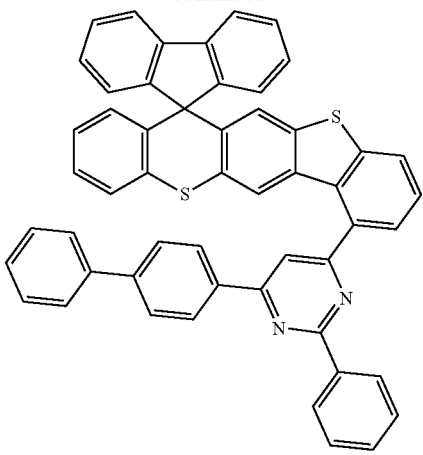 |
| 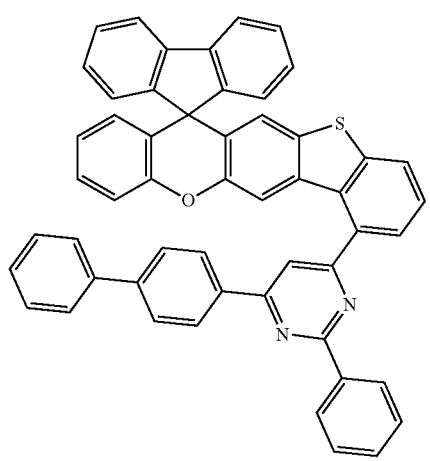 | 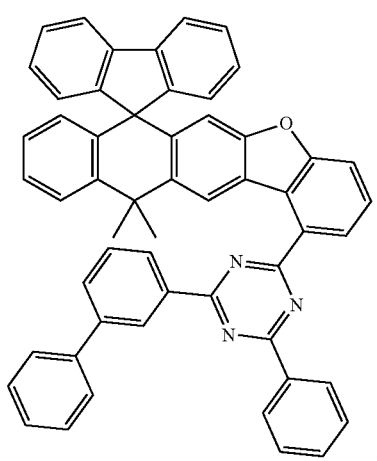 |
| 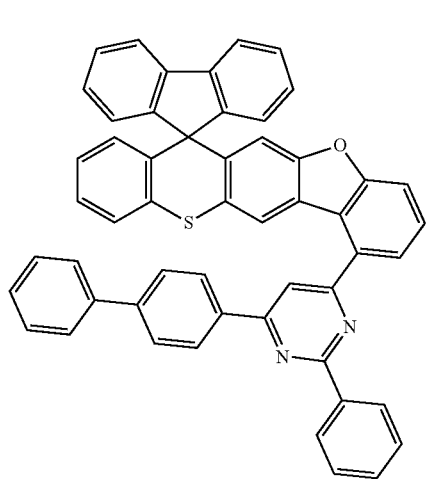 | 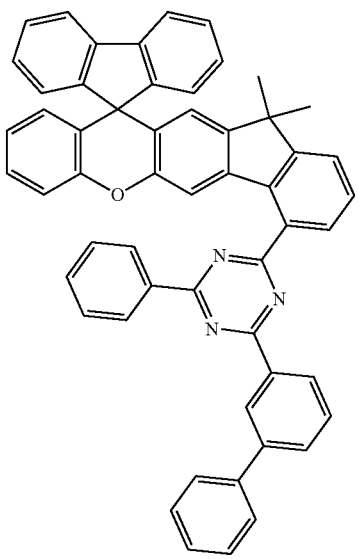 |

323
-continued
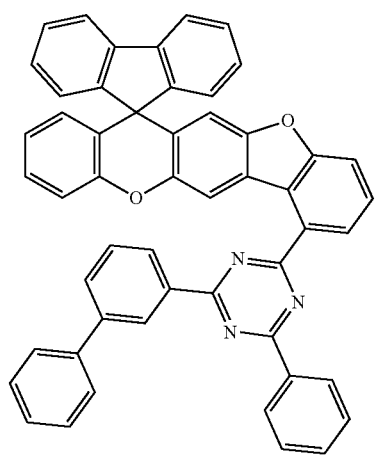
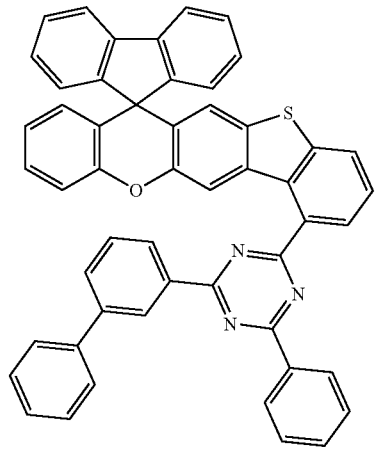
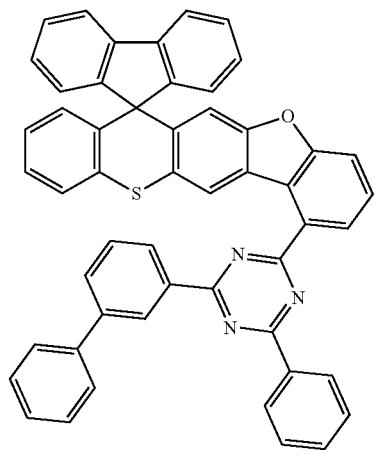
324
-continued
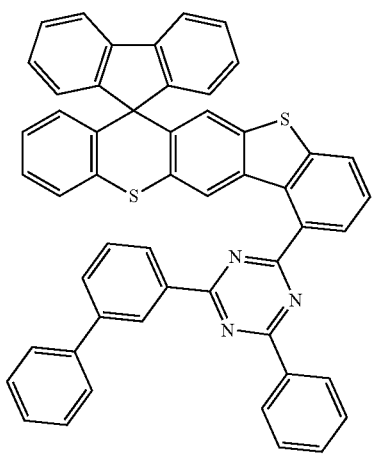
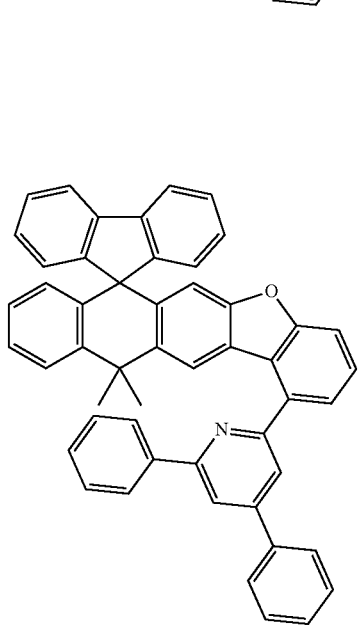
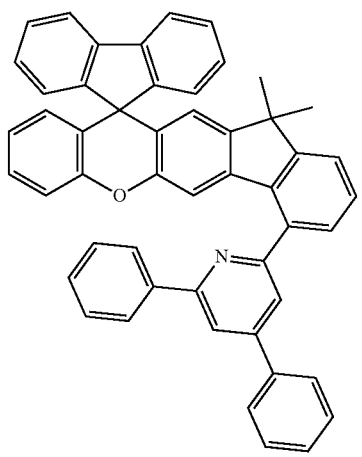

325
-continued
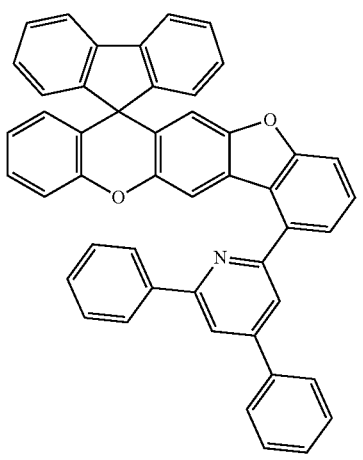
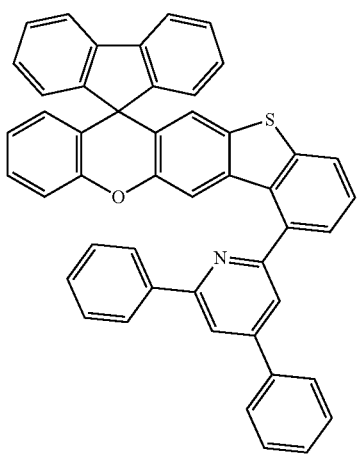
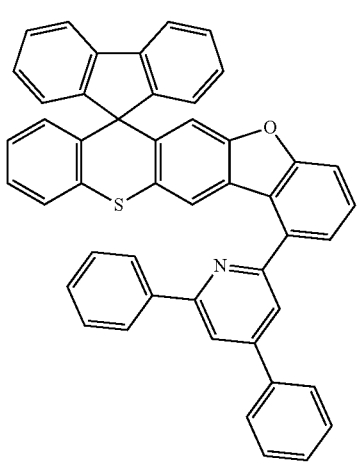
326
-continued
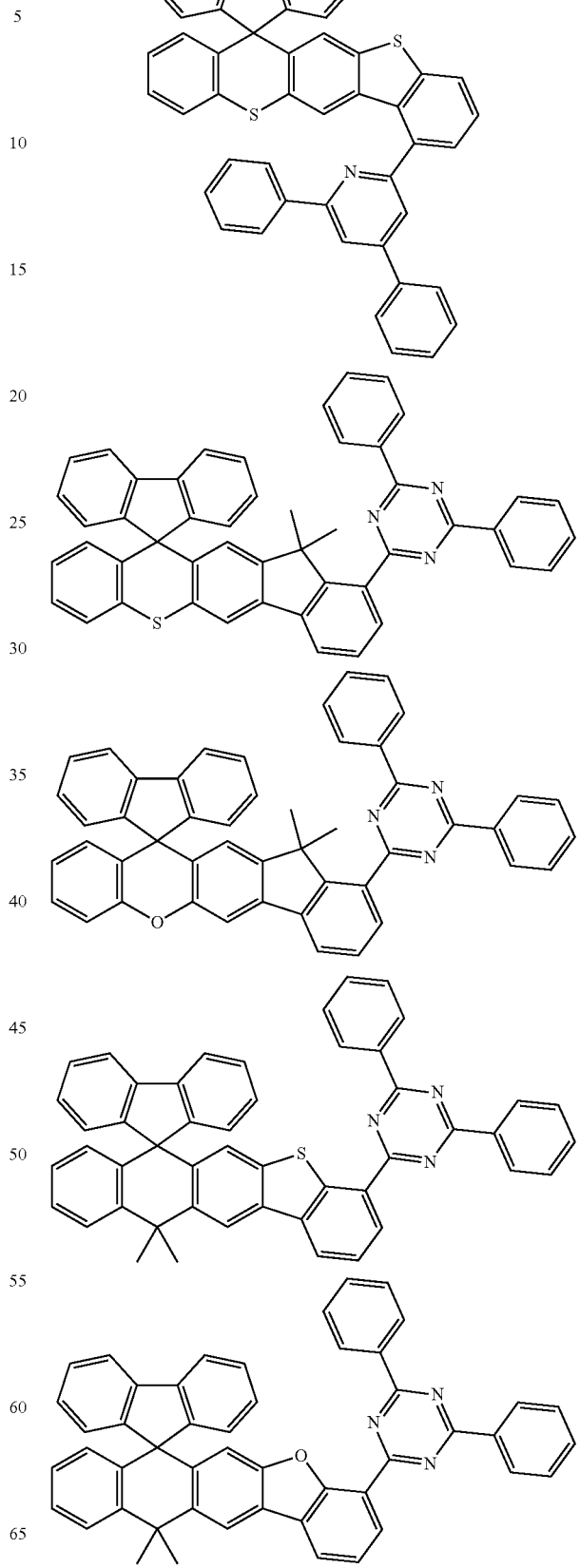

327
-continued
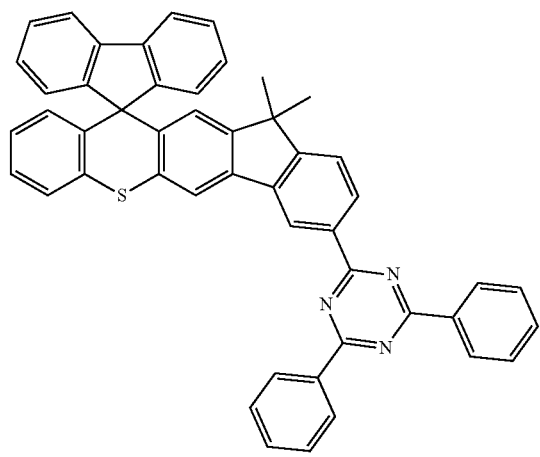
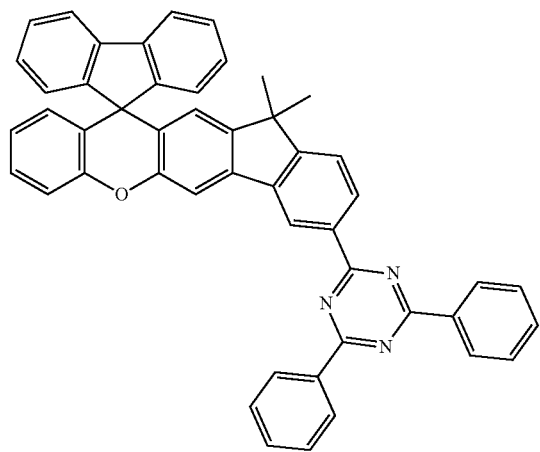
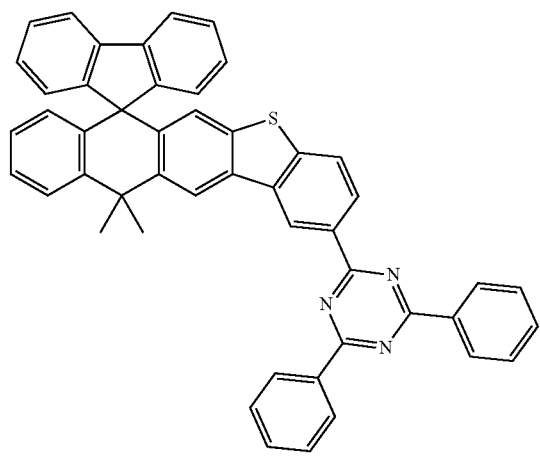
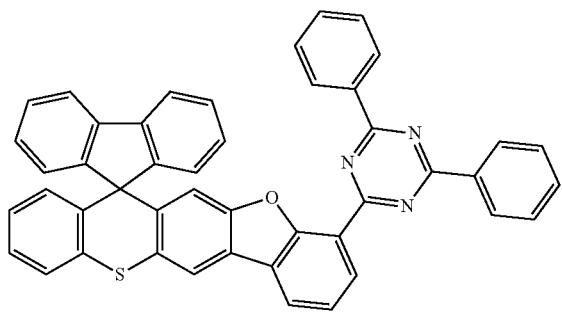
328
-continued
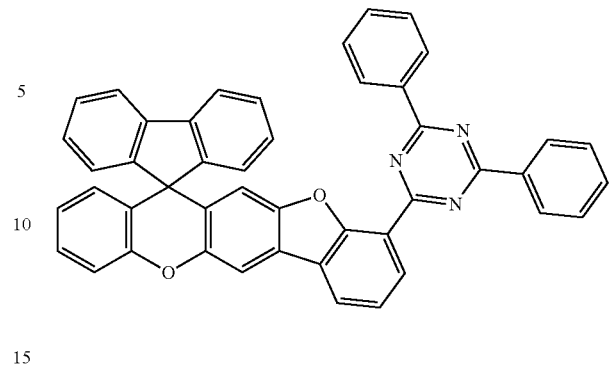
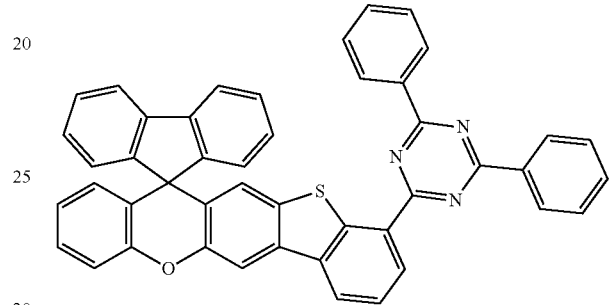
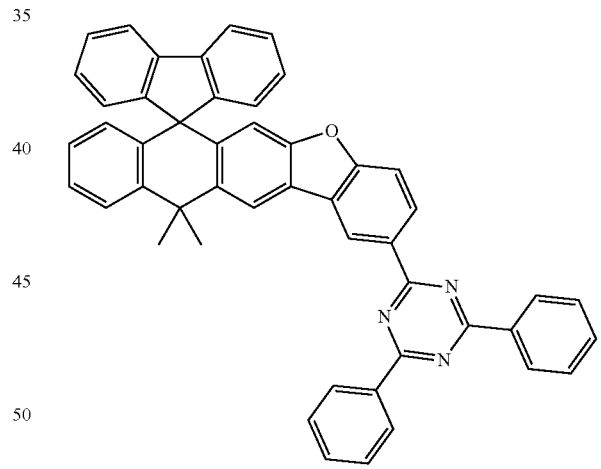
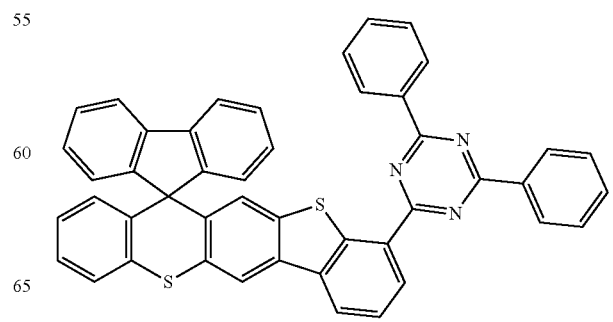

329
-continued
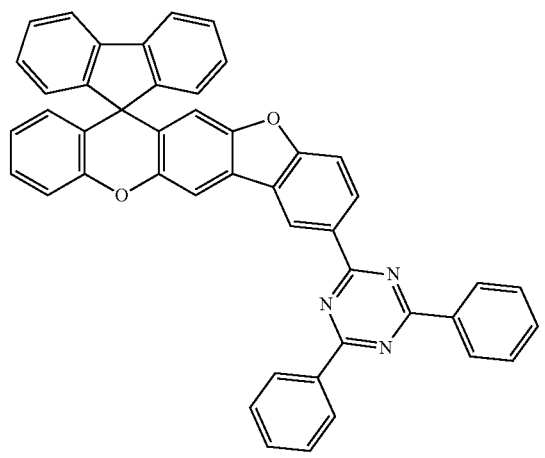
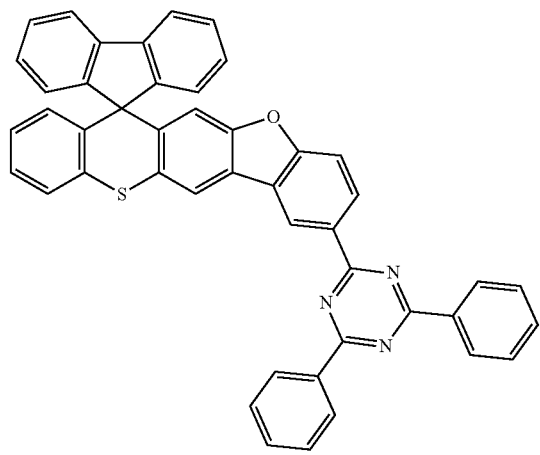
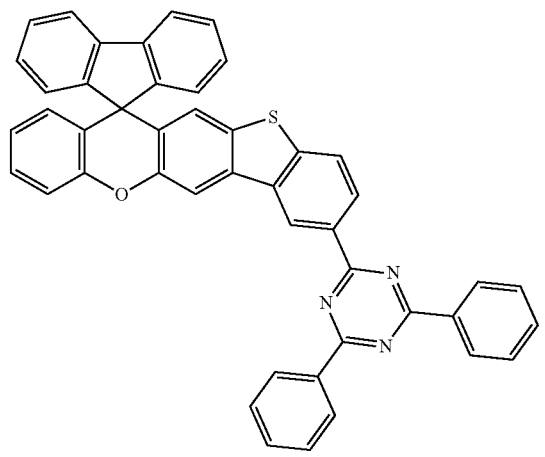
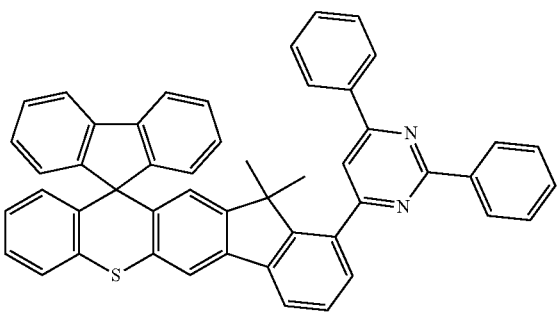
330
-continued
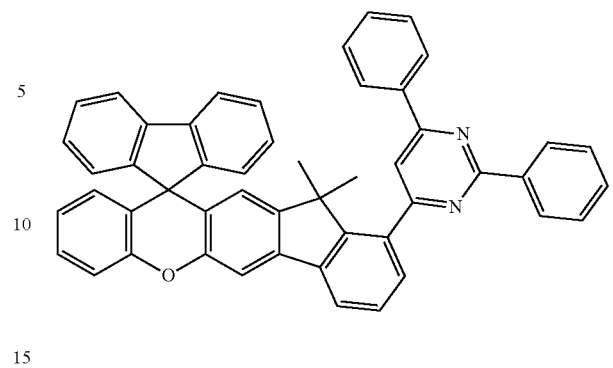
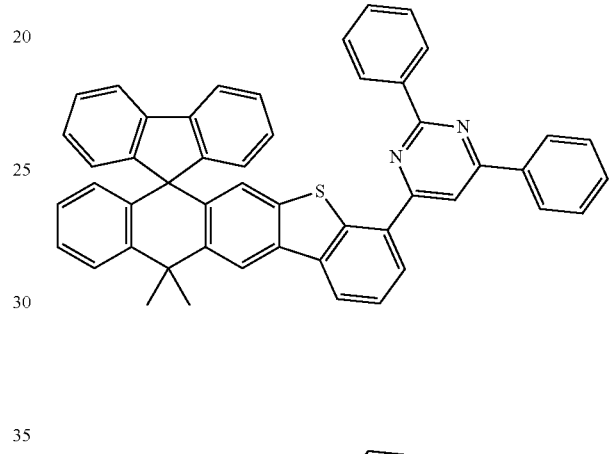
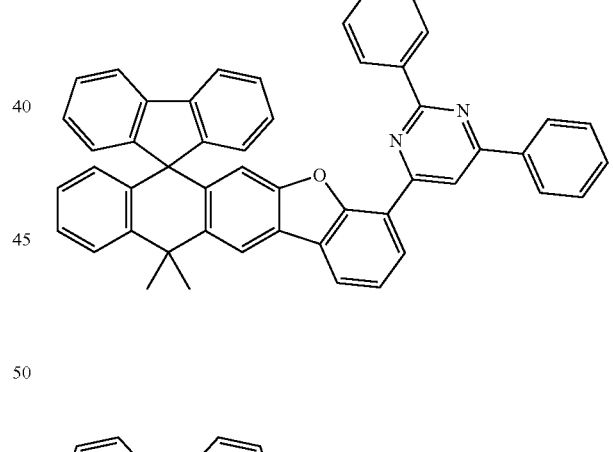
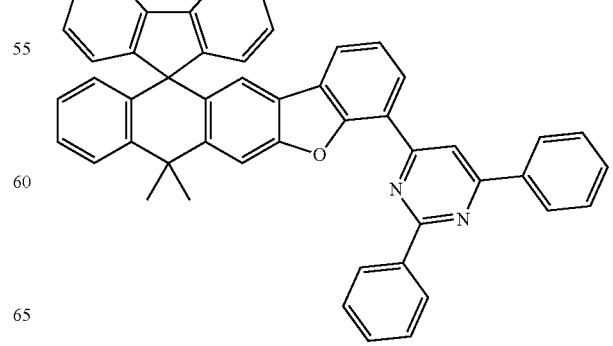

331
-continued
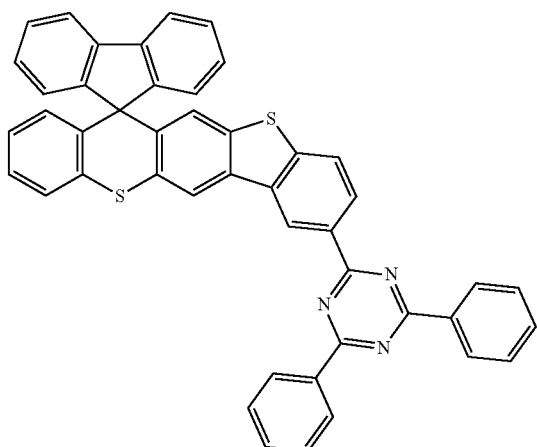
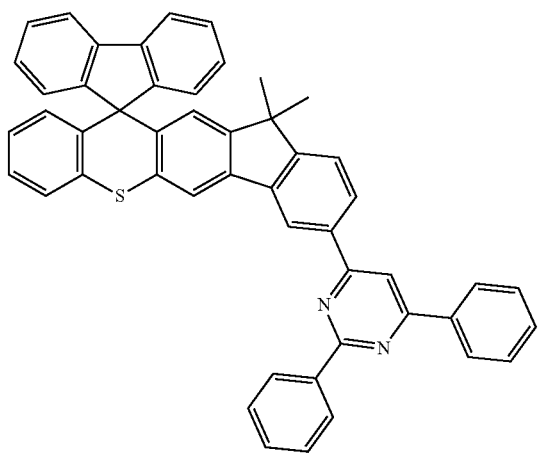
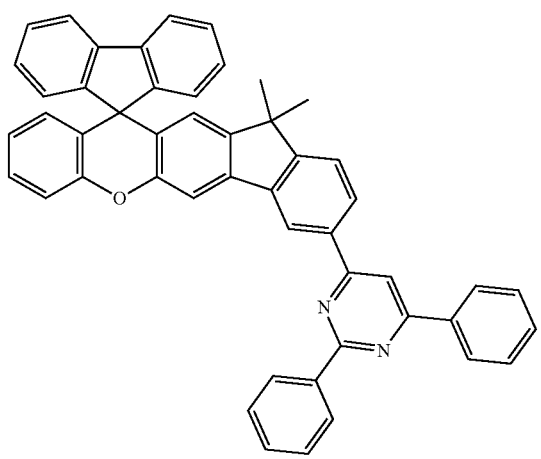
332
-continued
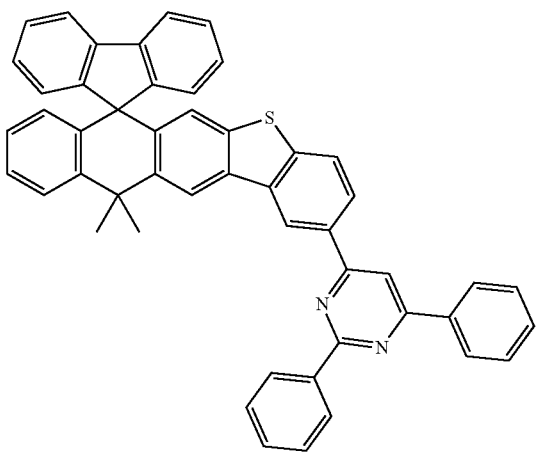
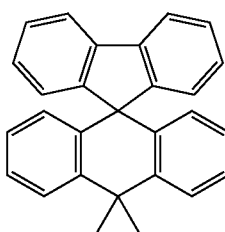
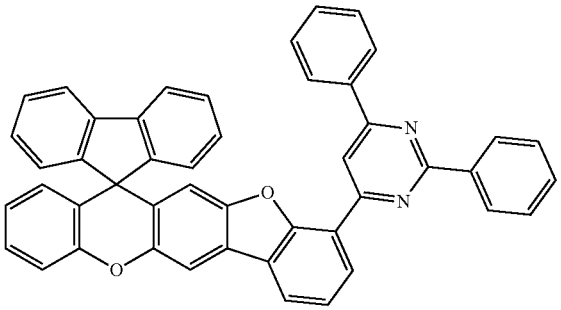
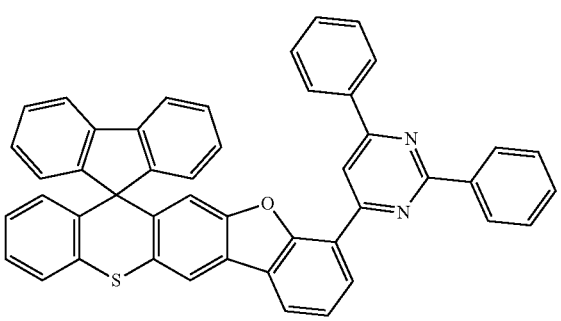

333
-continued
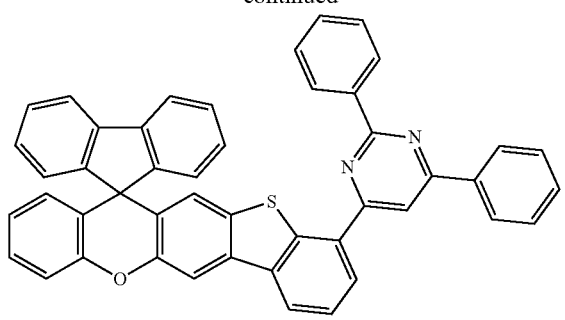
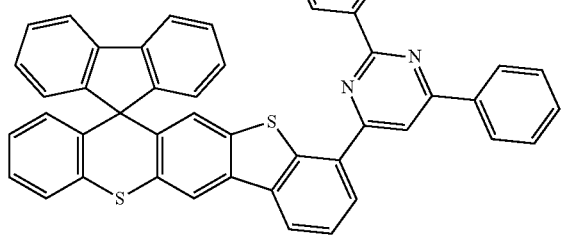
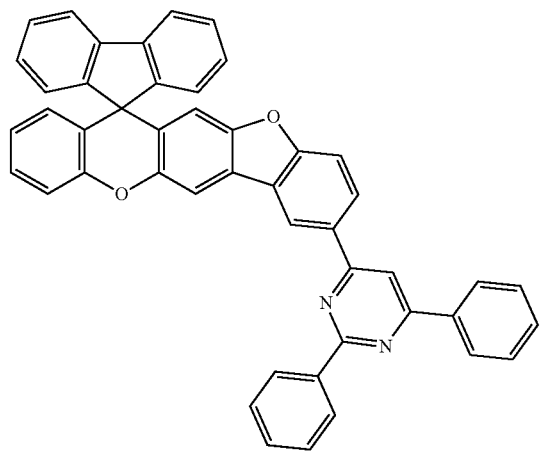
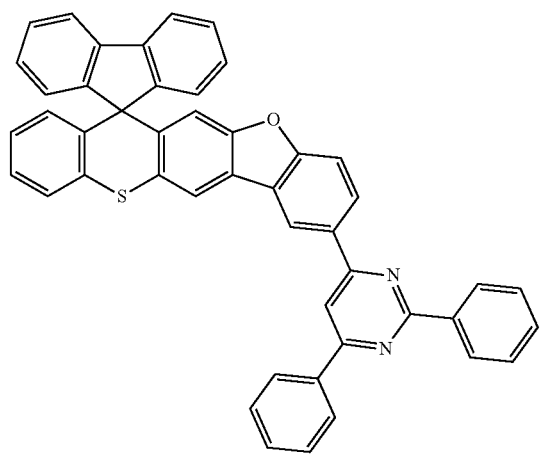
334
-continued
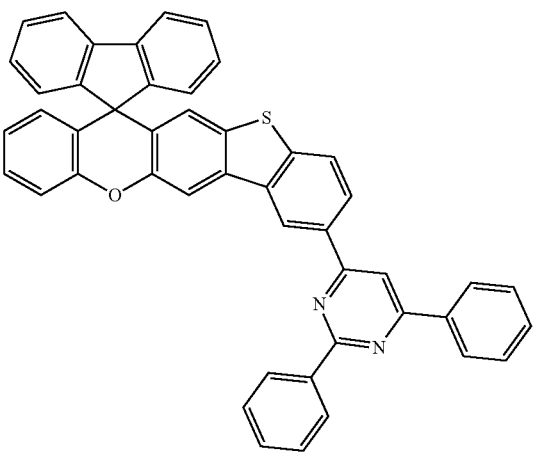
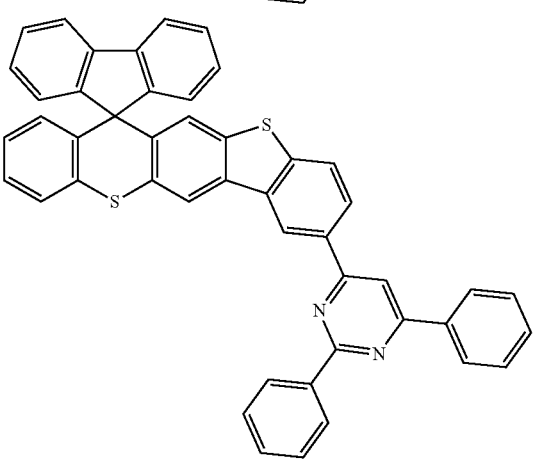
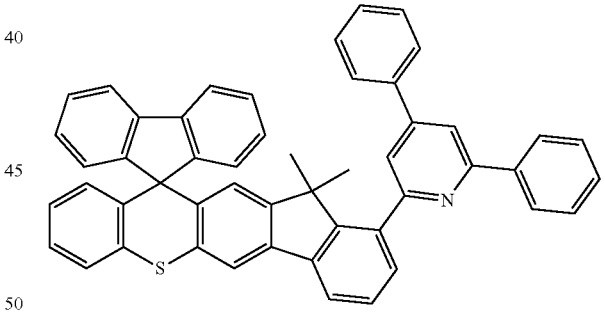

335
-continued
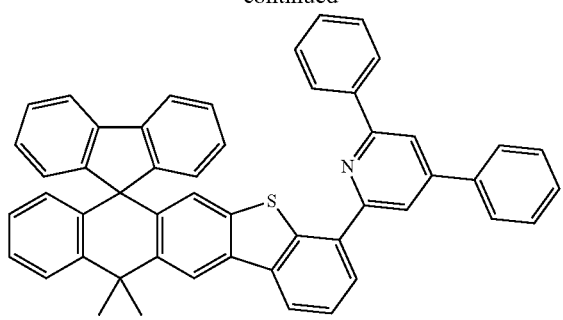
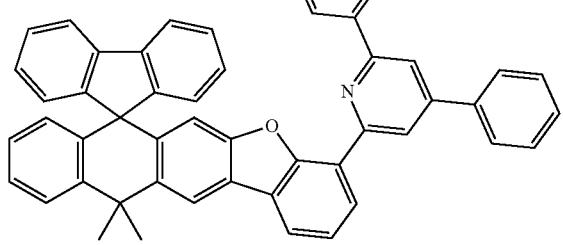
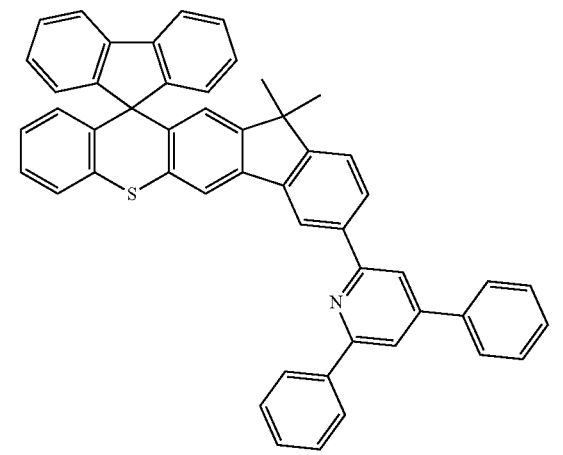
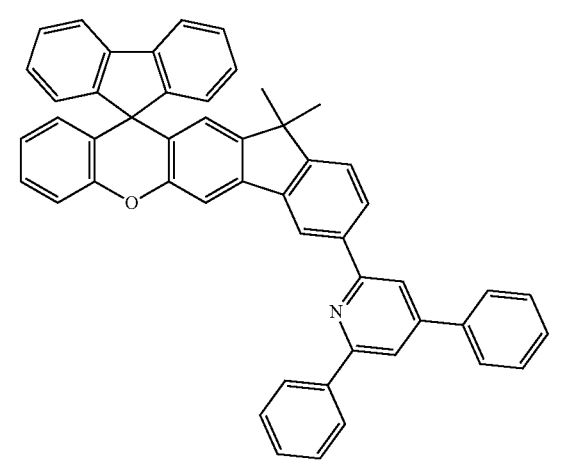
336
-continued
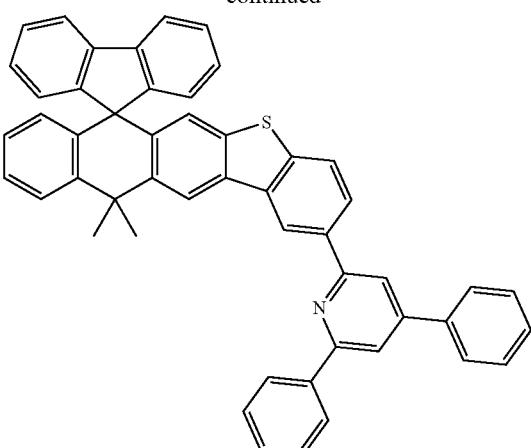
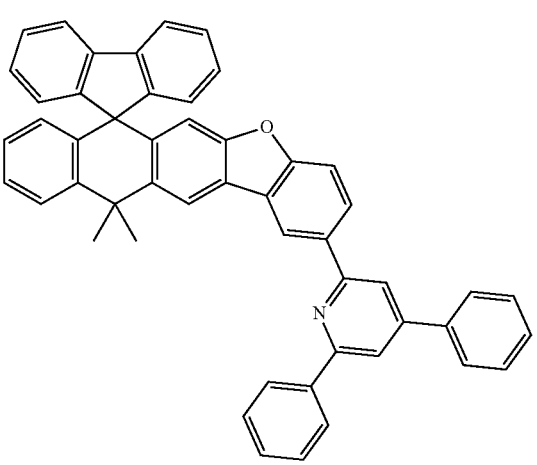
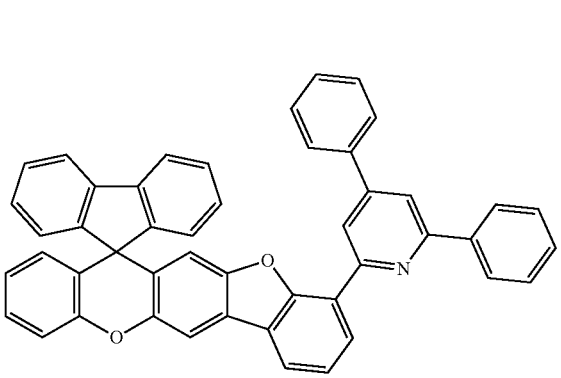
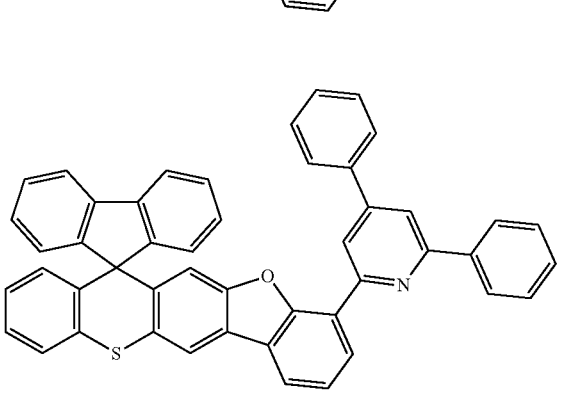

337
-continued

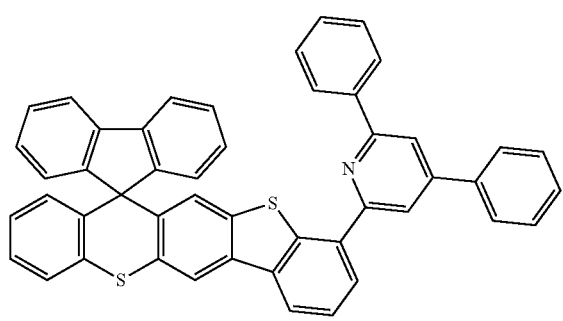
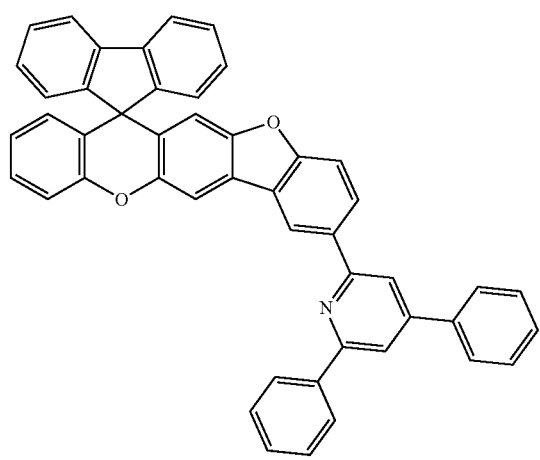
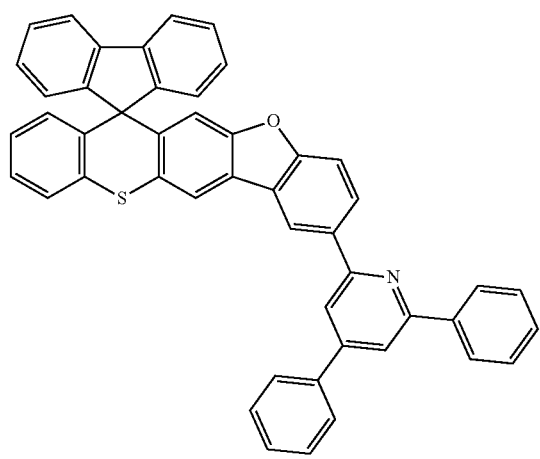
338
-continued
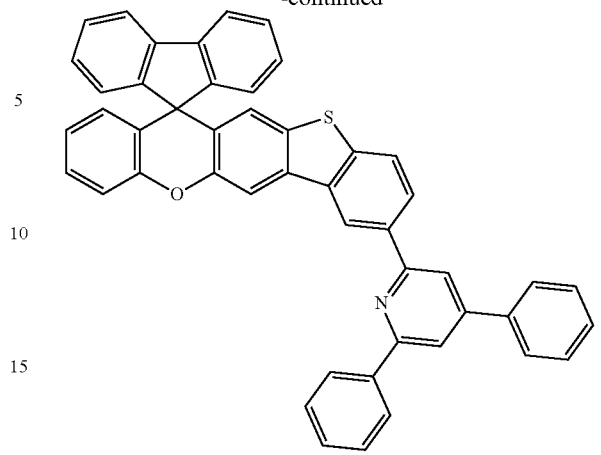
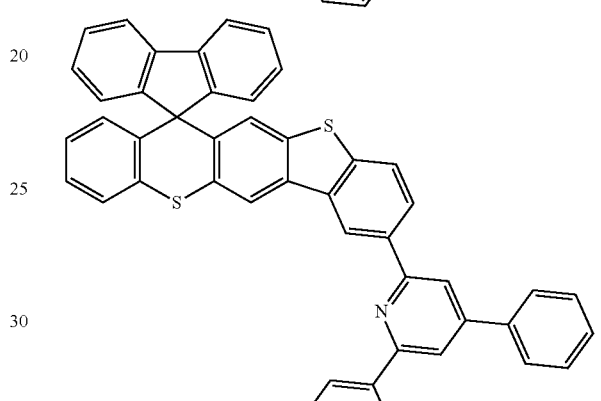
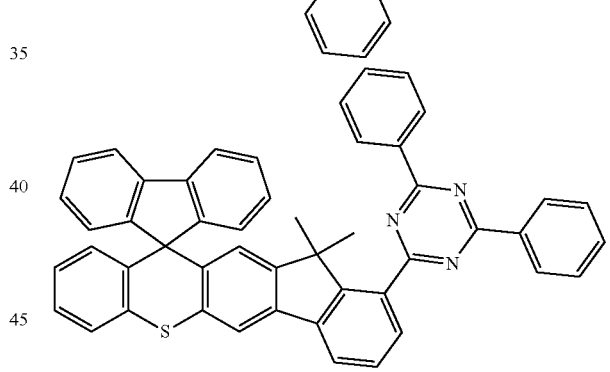
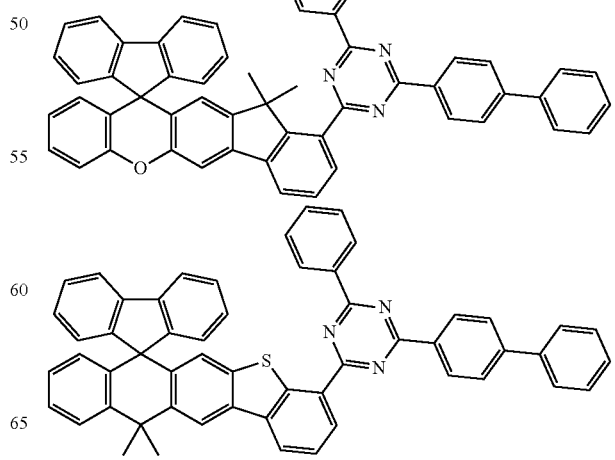

339
-continued
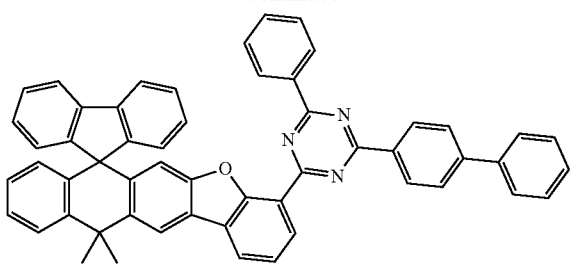
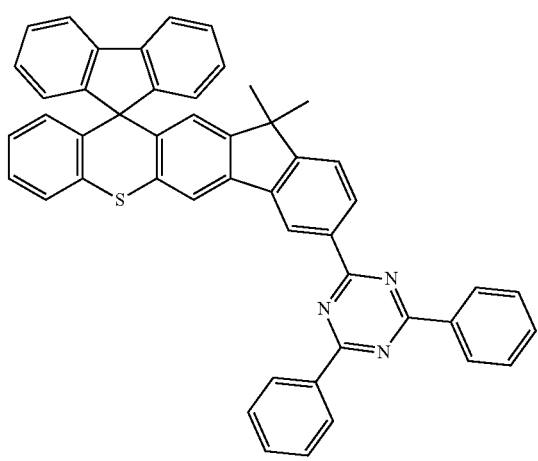
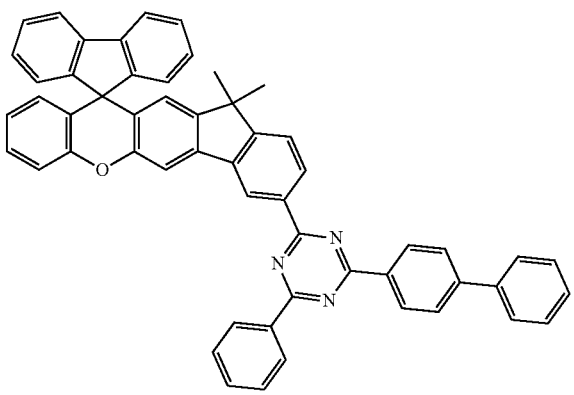
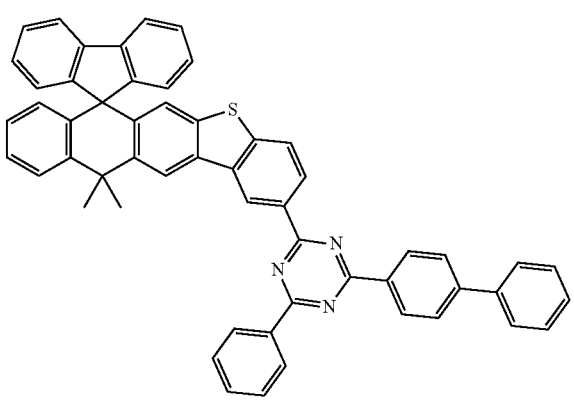
340
-continued
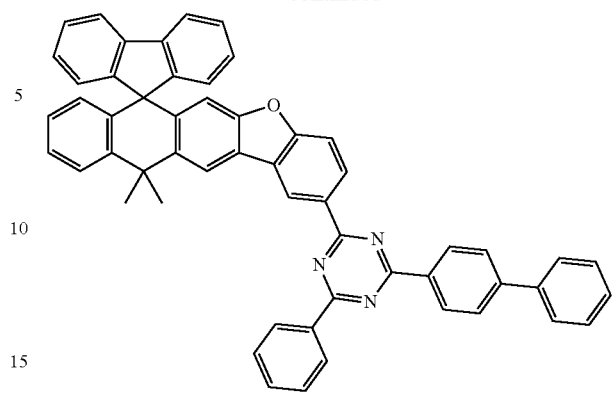
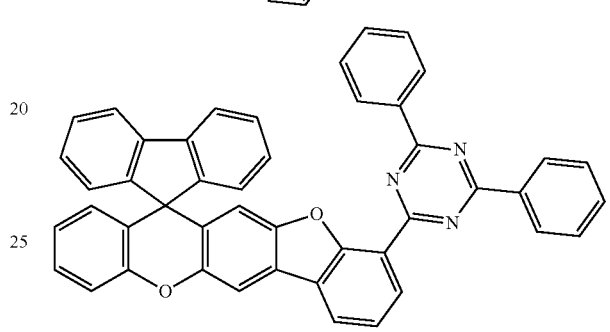
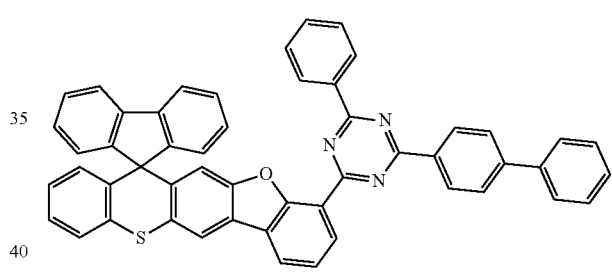
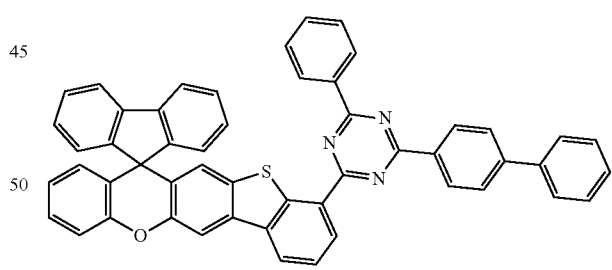
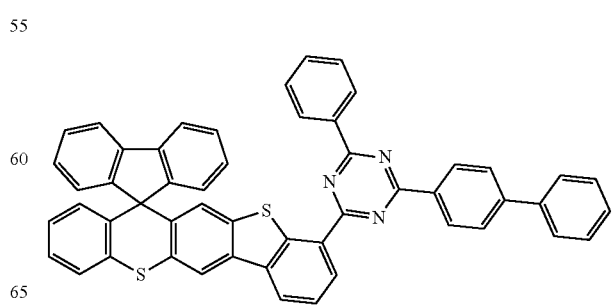

341
-continued
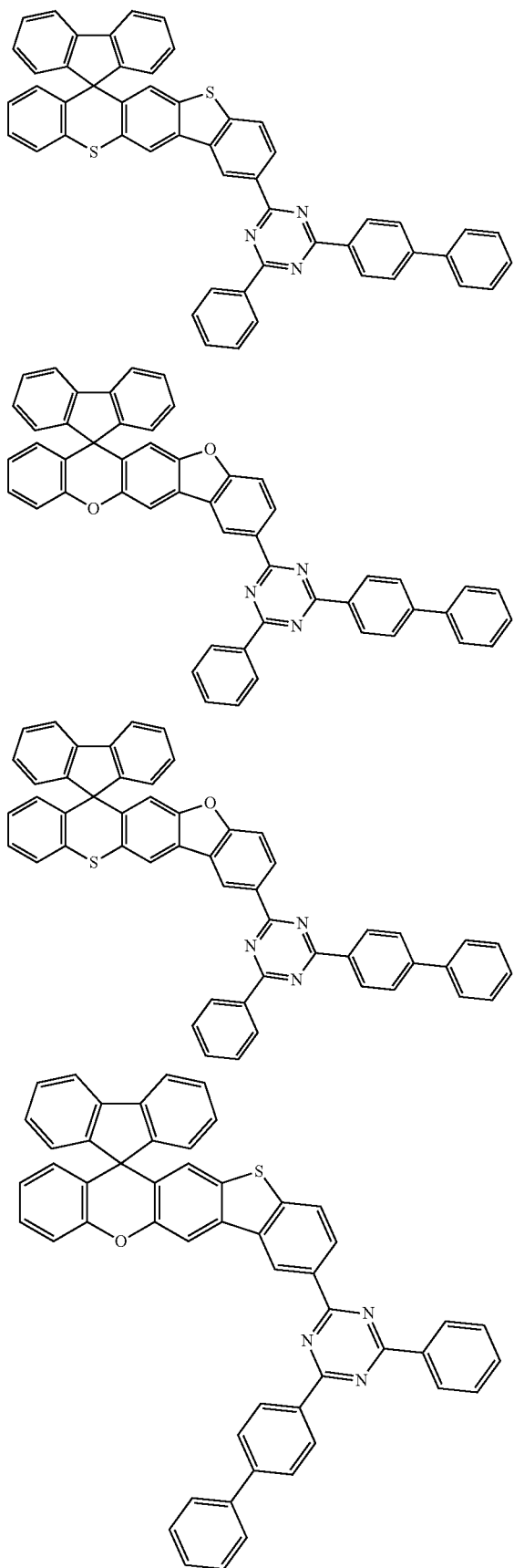
342
-continued
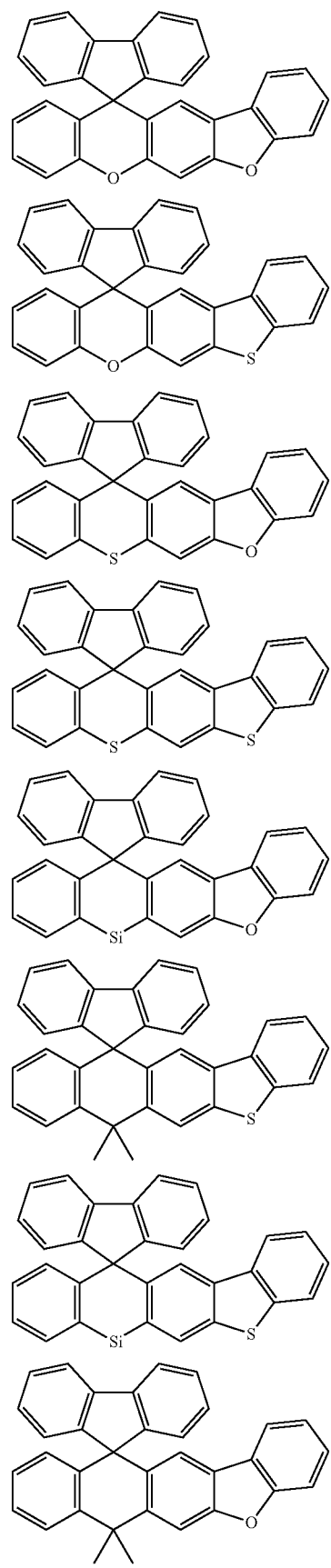

343
-continued
344
-continued
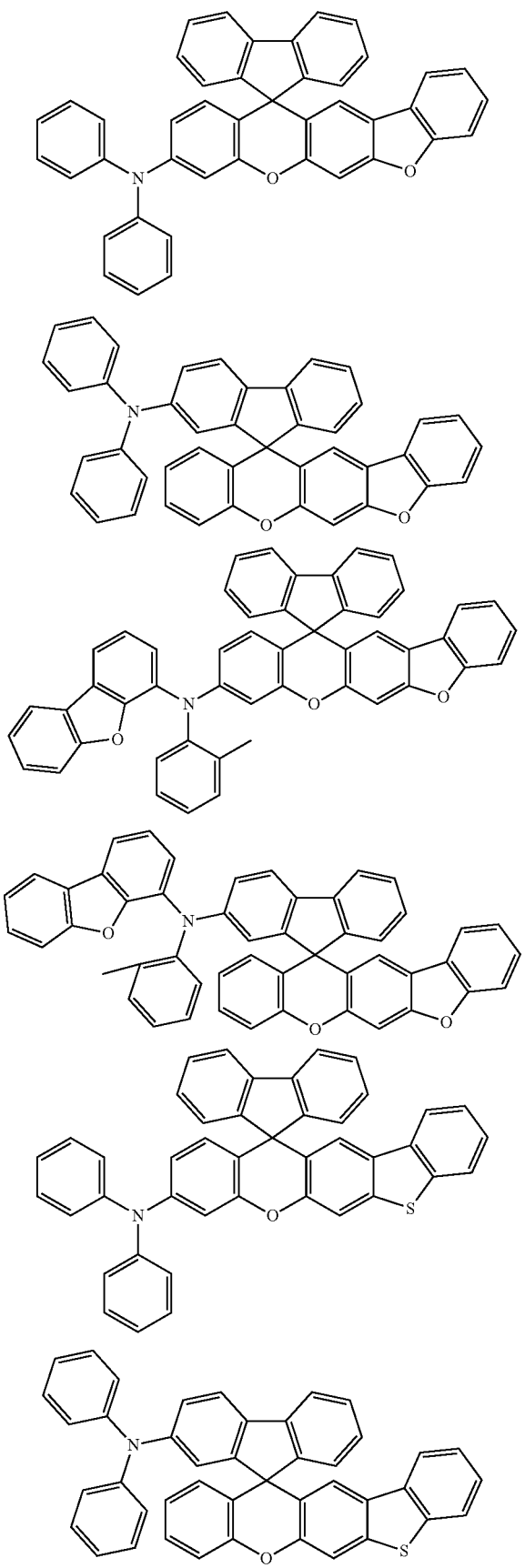
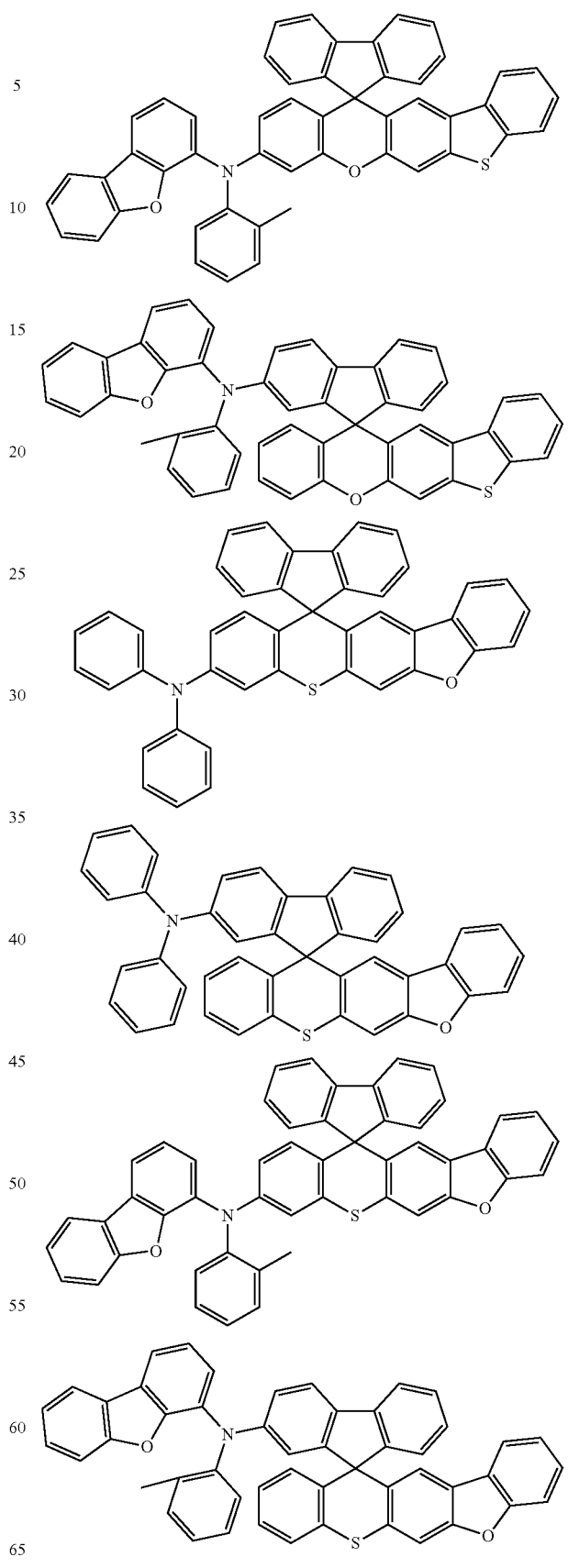

345
-continued
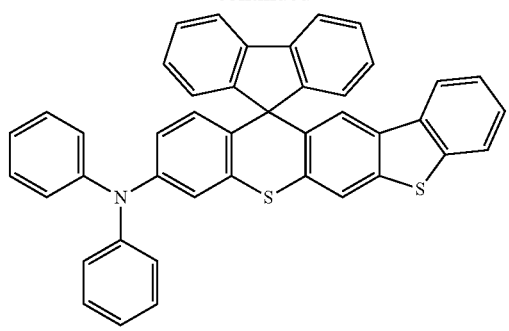
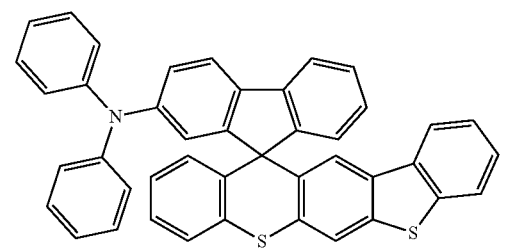
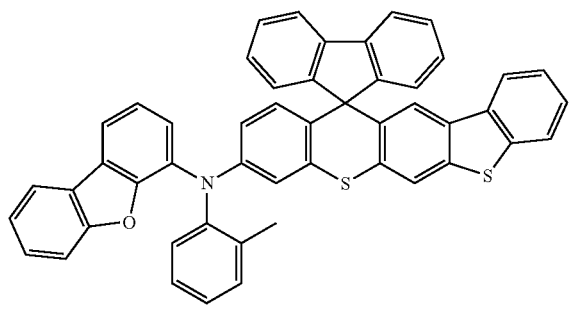
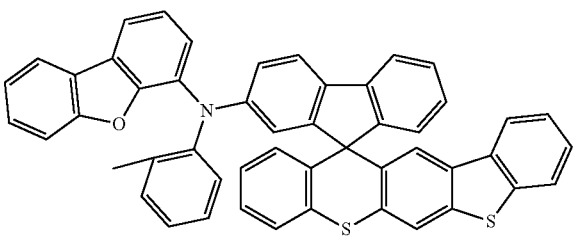
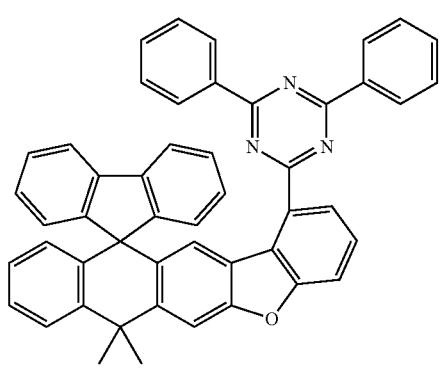
346
-continued
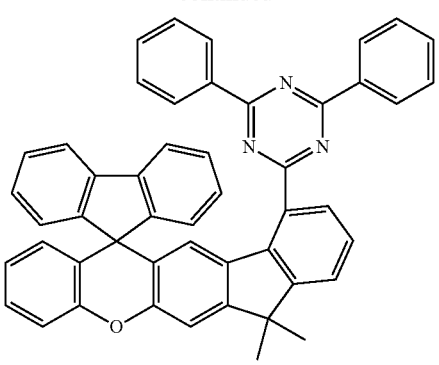
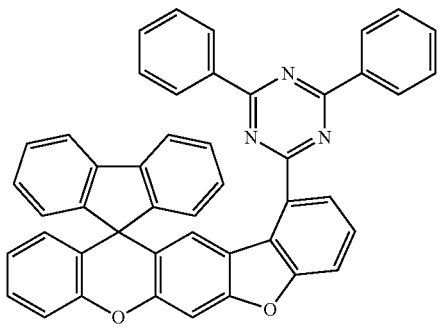
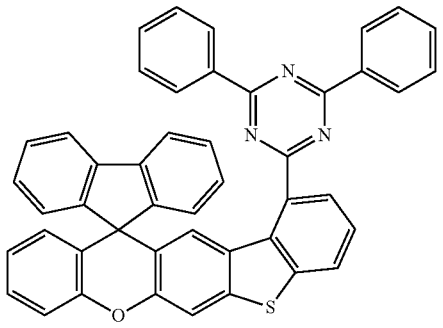
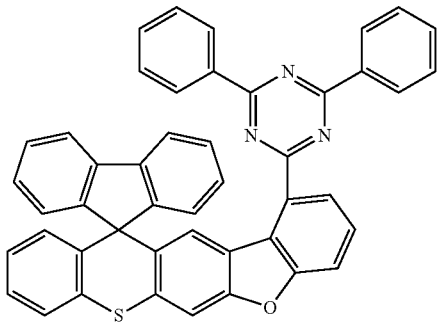
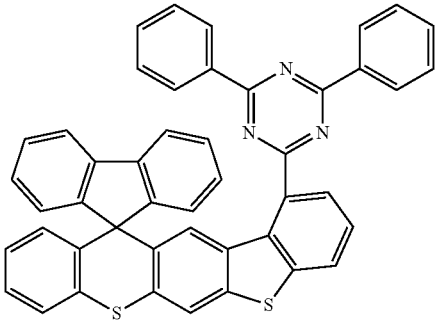

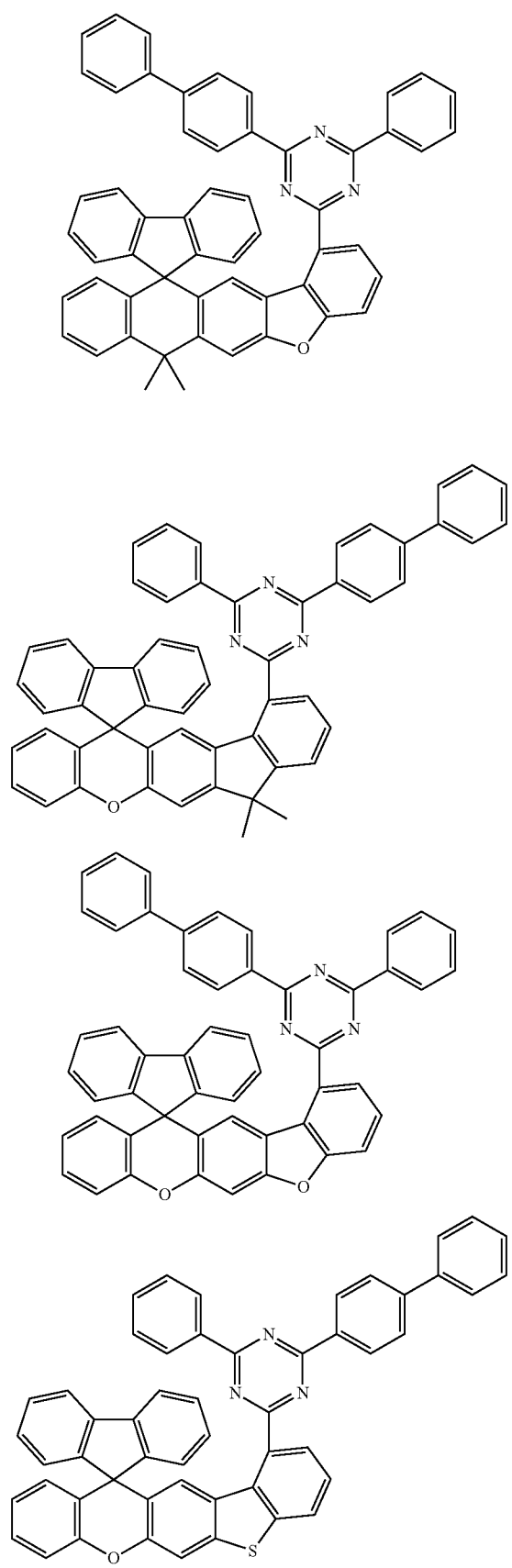
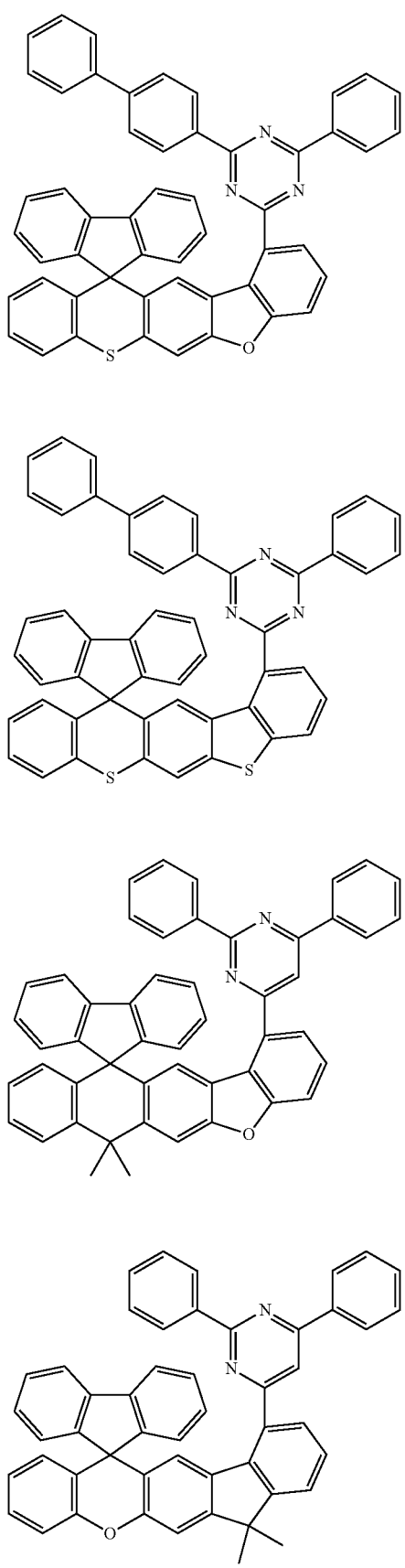

349
-continued
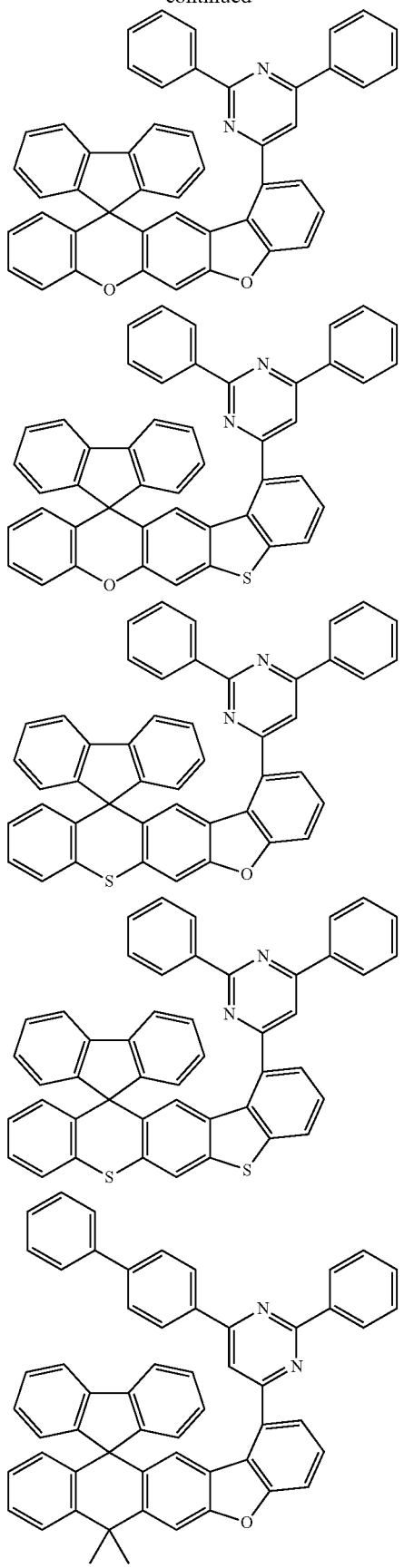
350
-continued
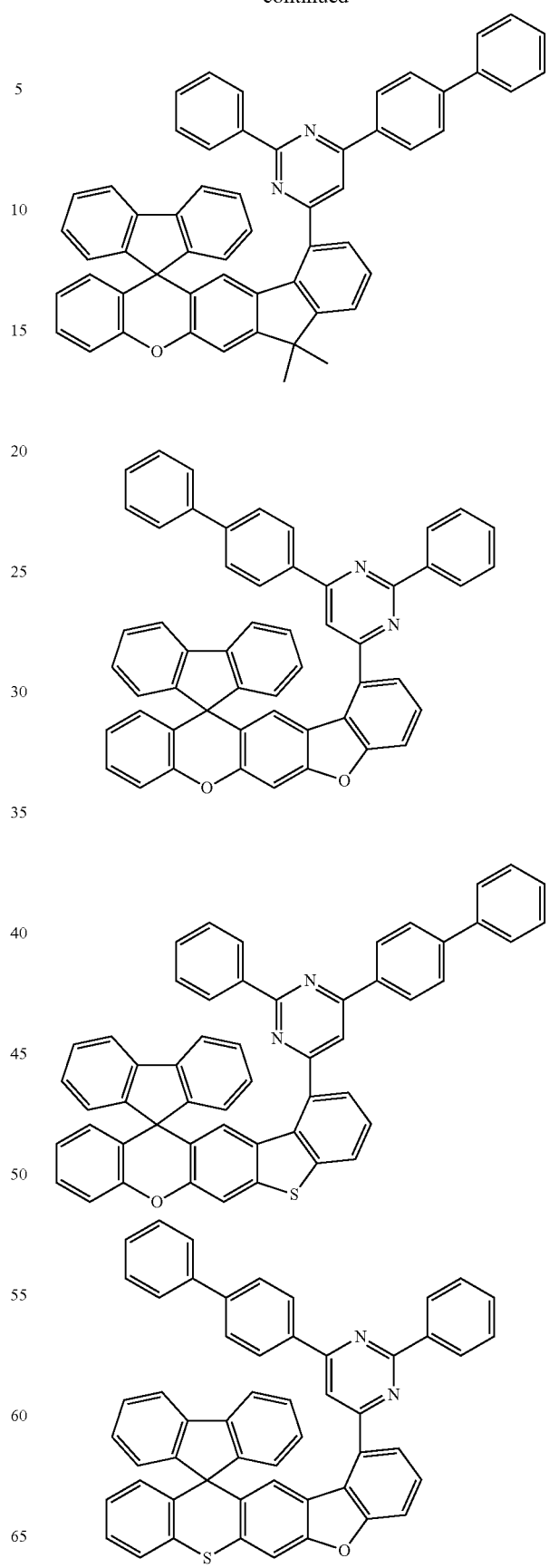

351
-continued
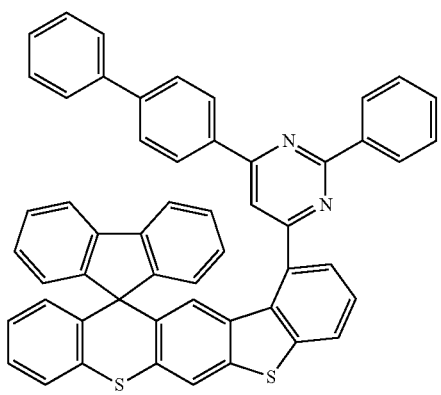
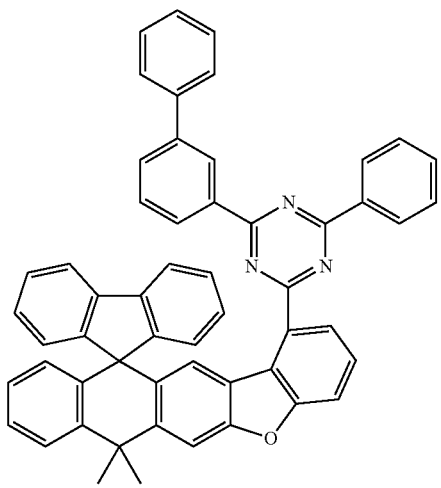
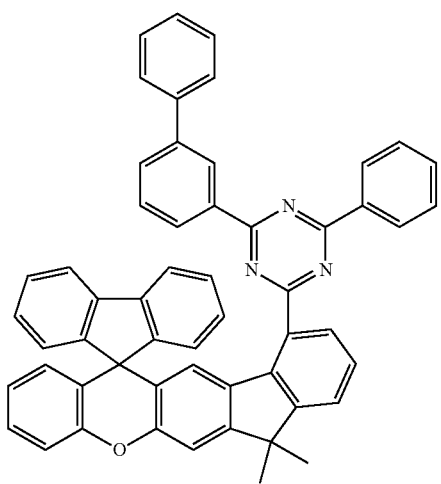
352
-continued
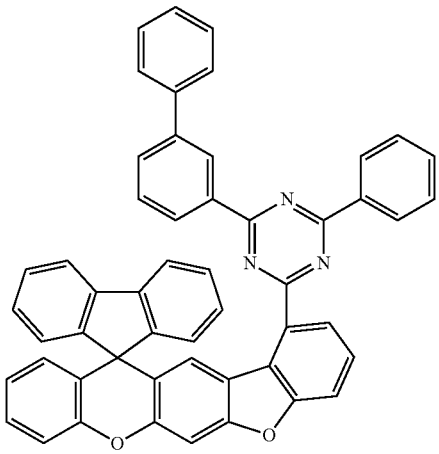
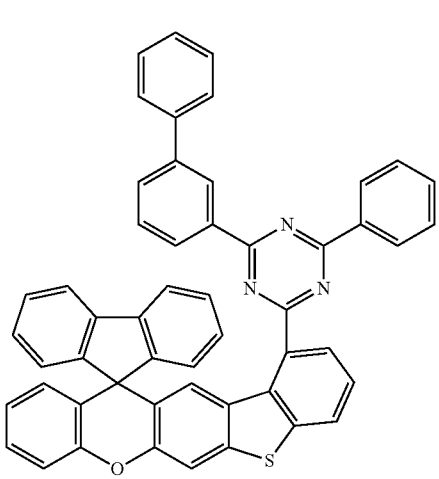
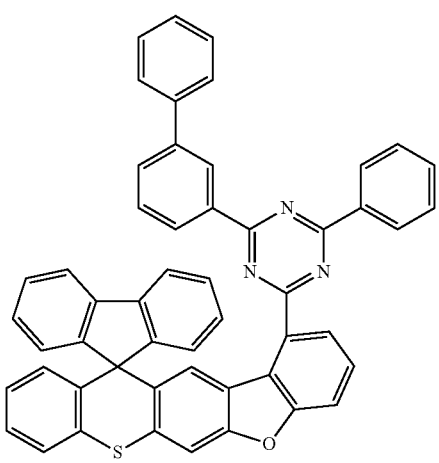

353
-continued
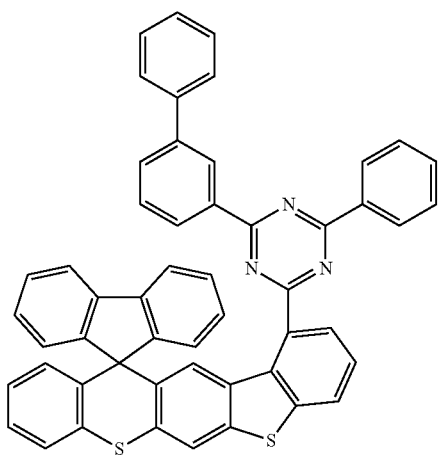
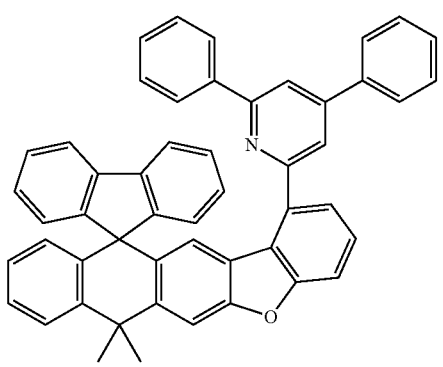
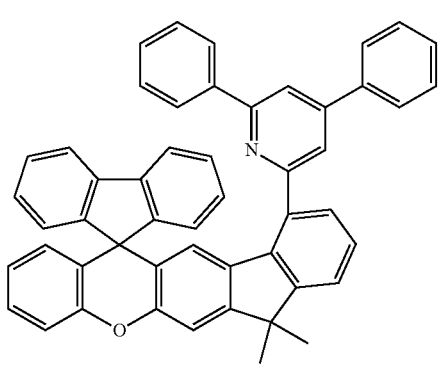
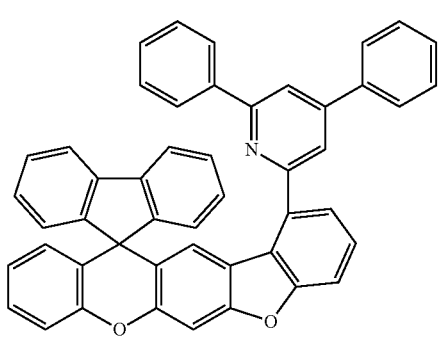
354
-continued
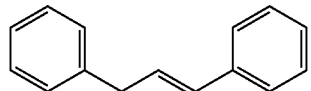
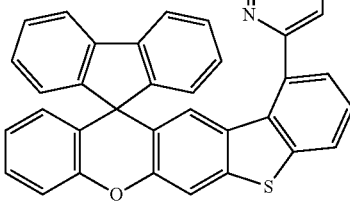
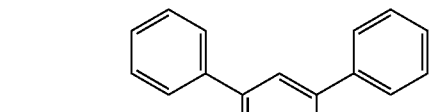
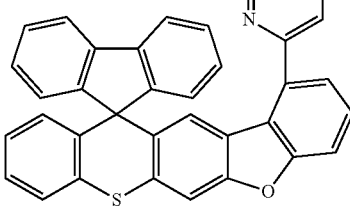
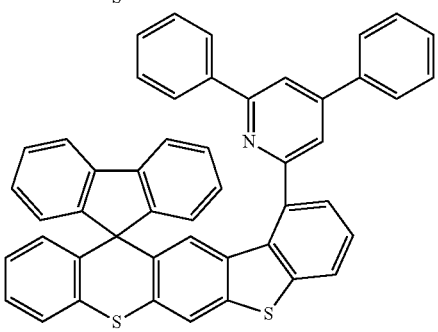
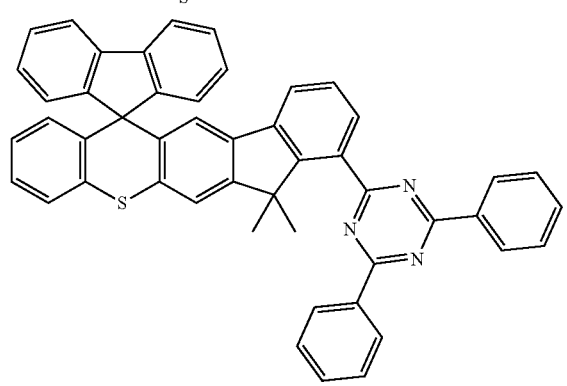
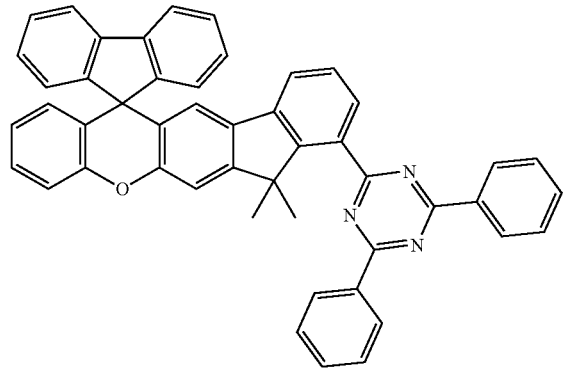

355
-continued
356
-continued
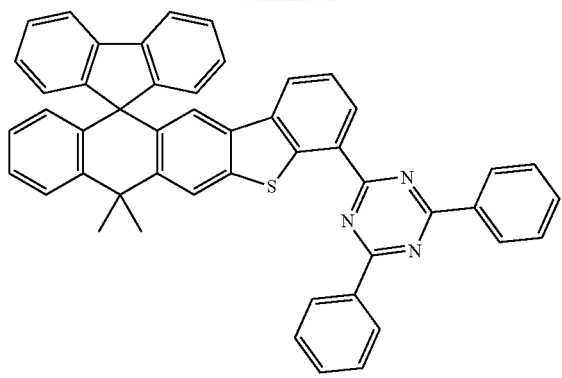
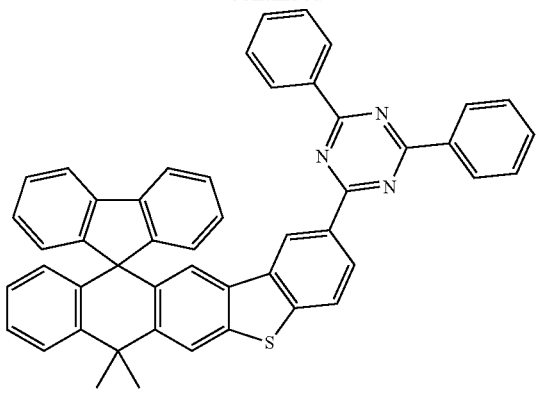
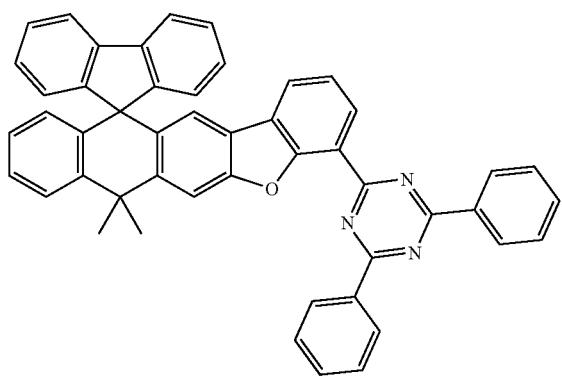
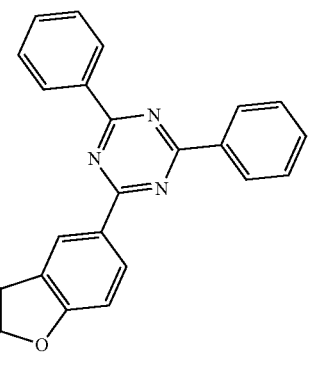
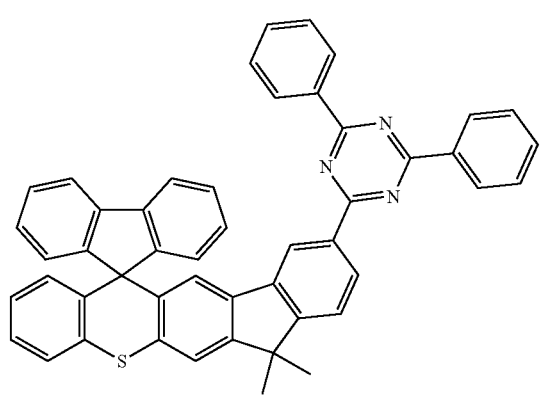
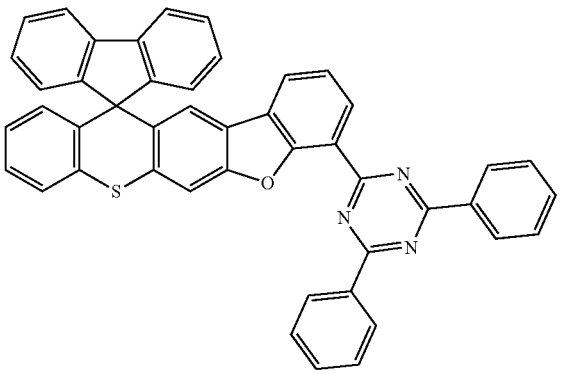
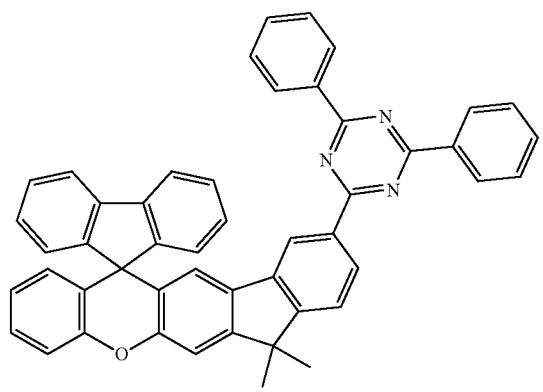
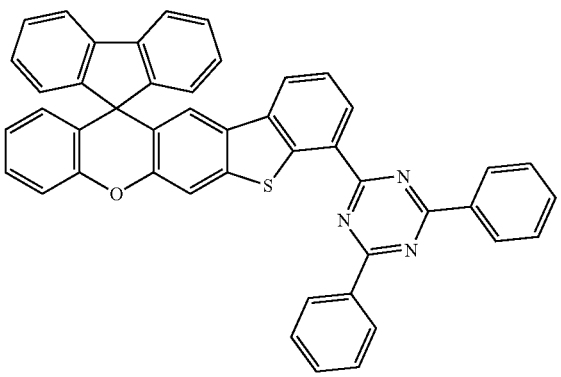

357
-continued
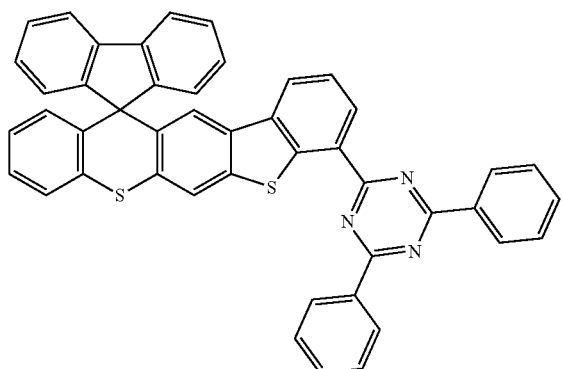
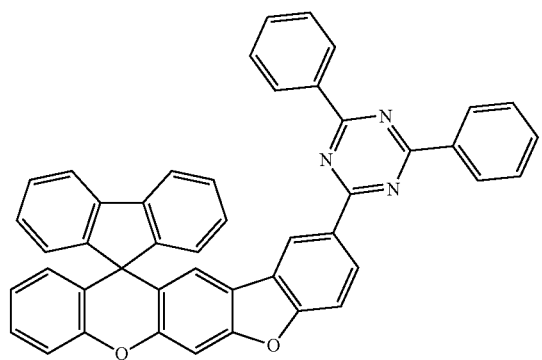
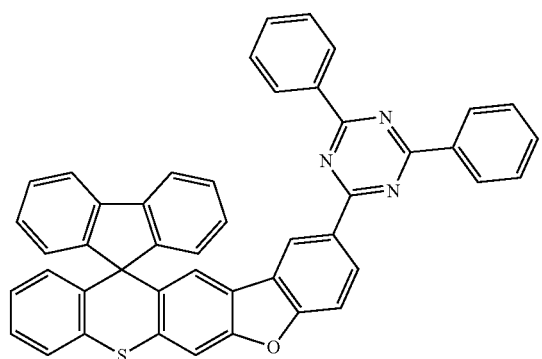
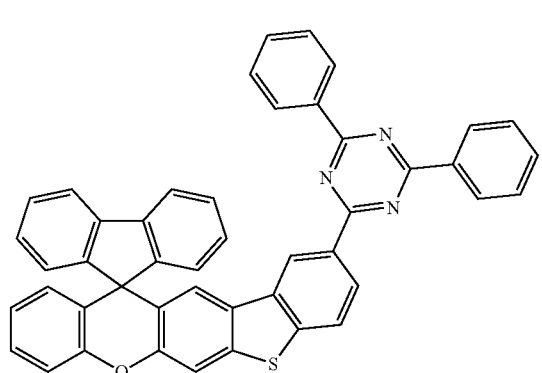
358
-continued
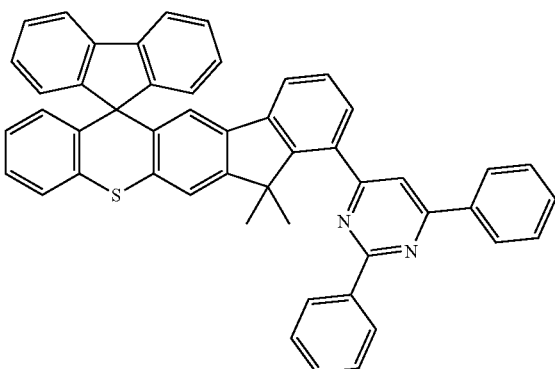
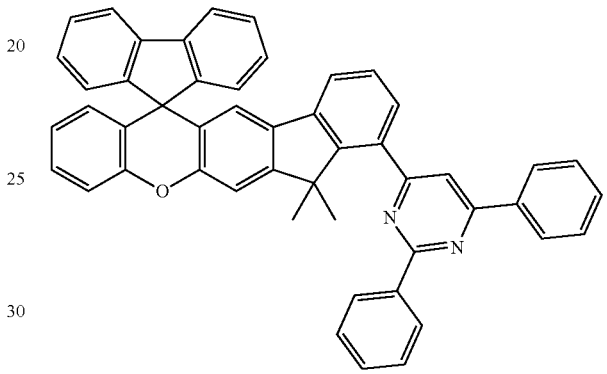
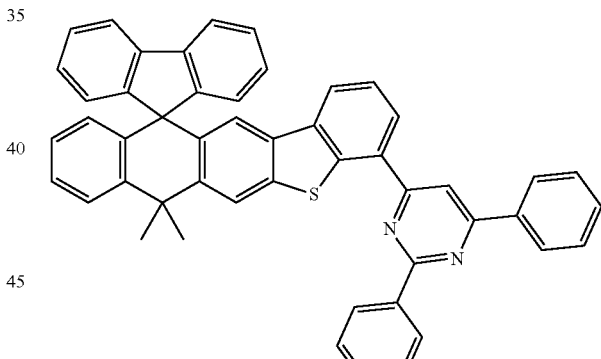
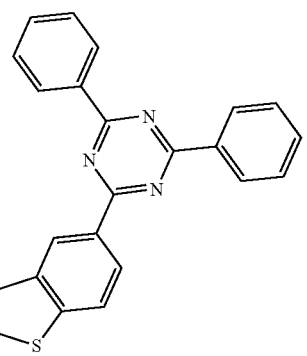

359
-continued
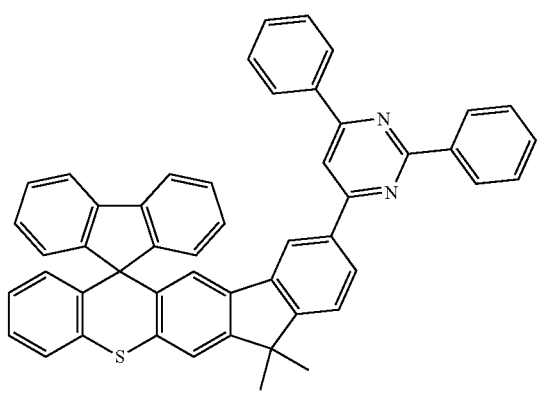
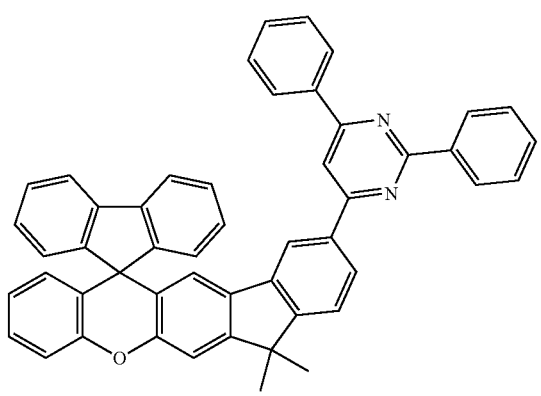
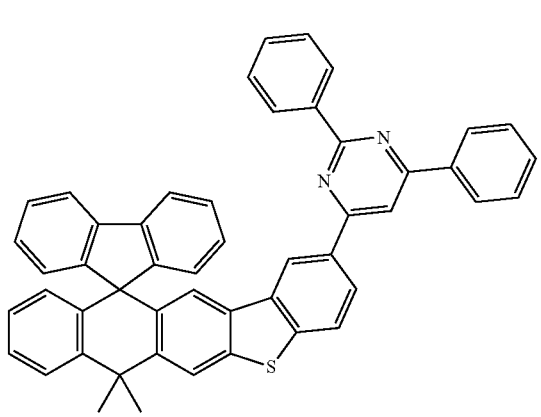
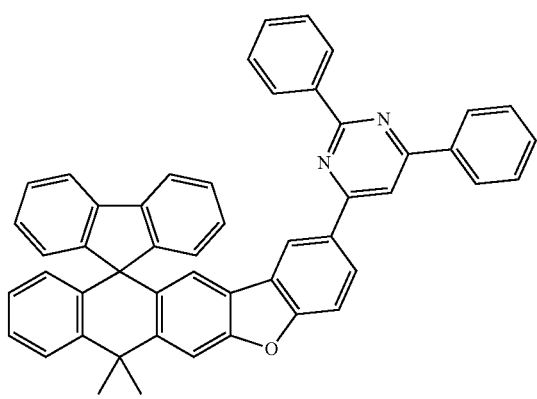
360
-continued
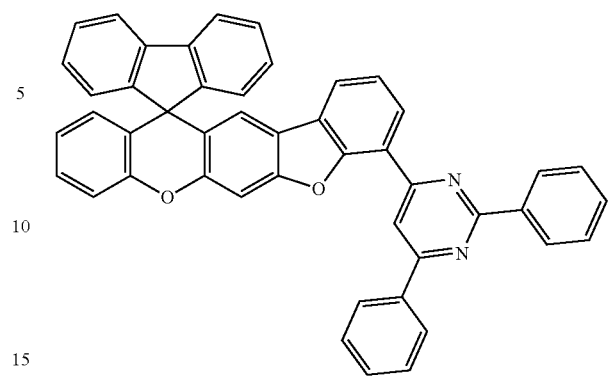
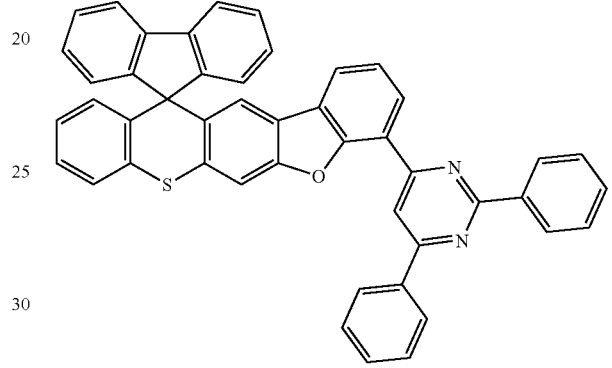
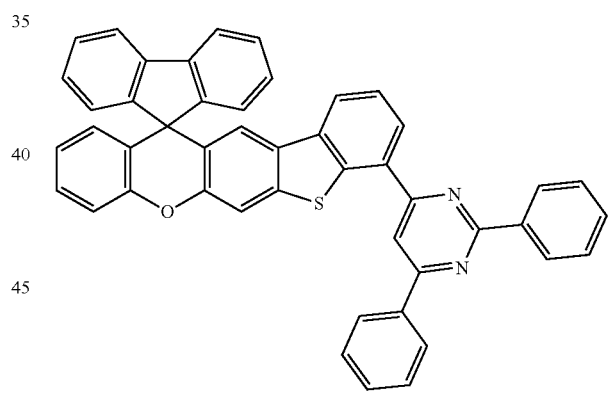
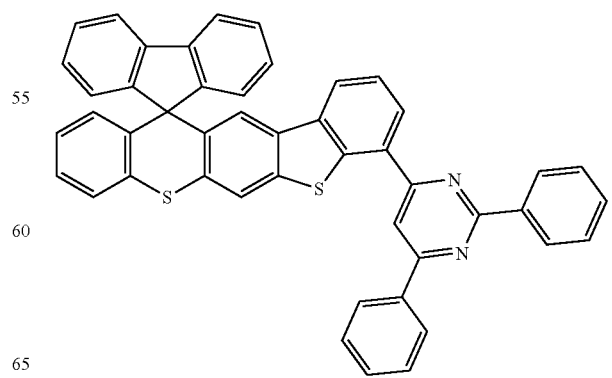

361
-continued
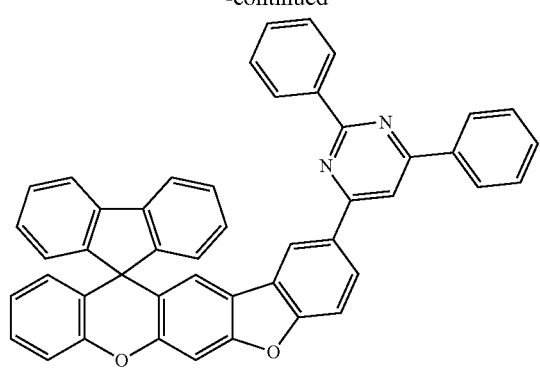
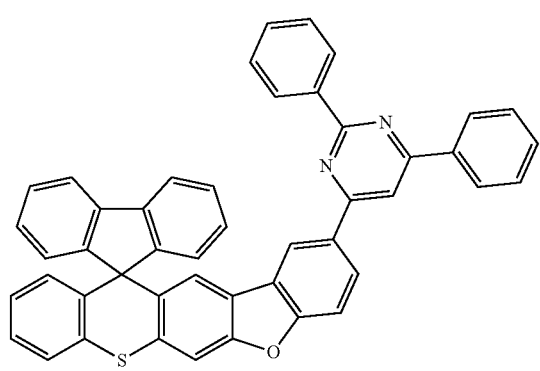
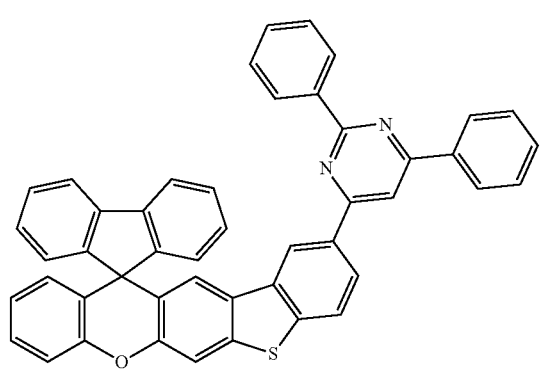
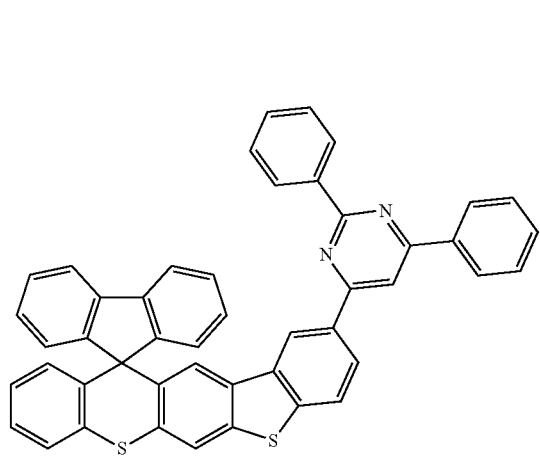
362
-continued
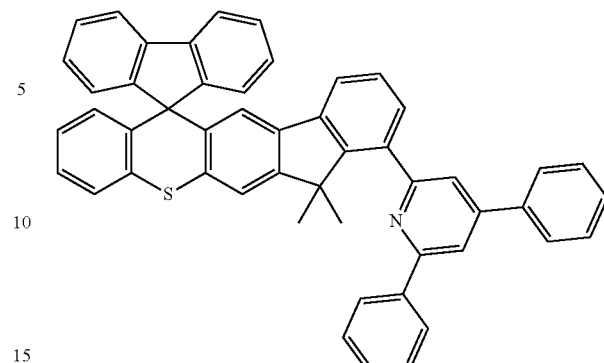
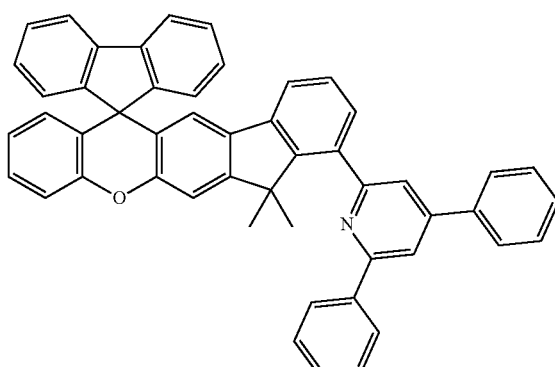
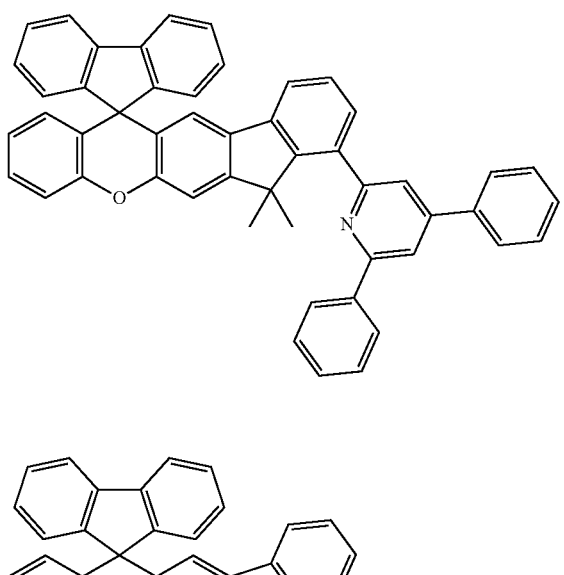
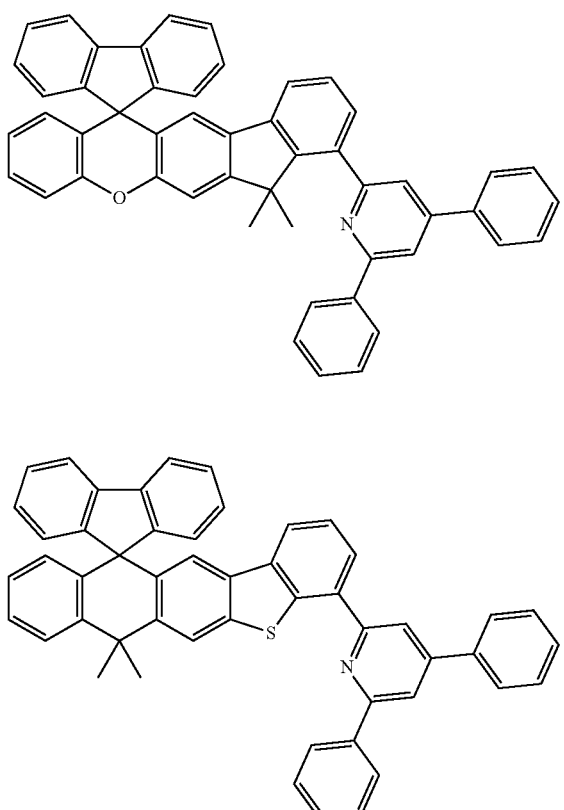

363
-continued
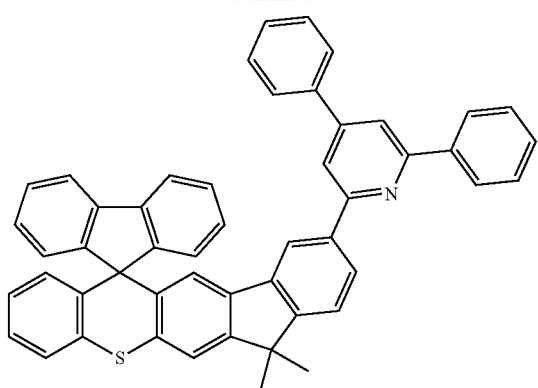
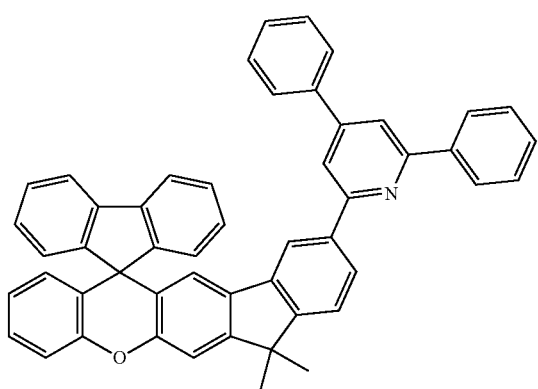
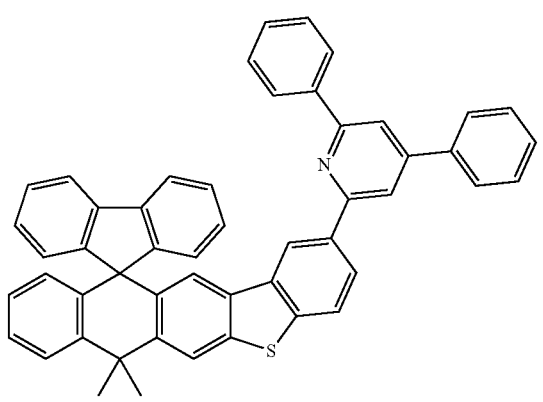
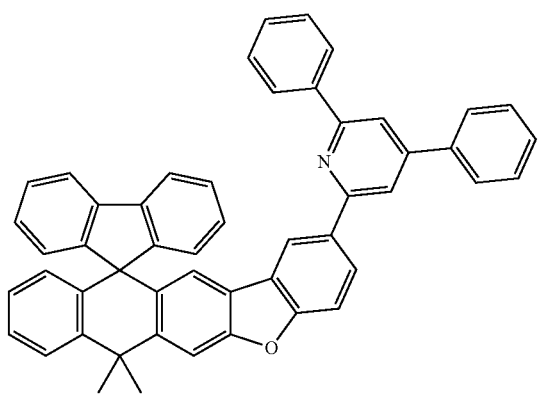
364
-continued
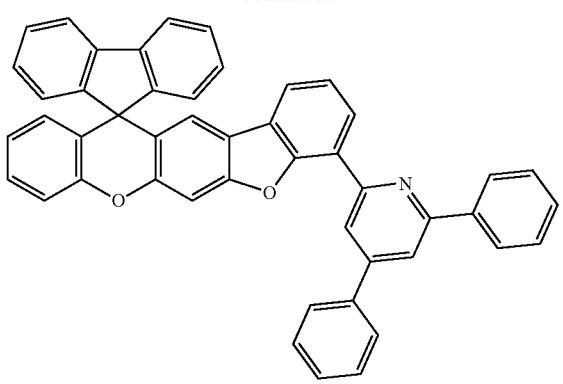
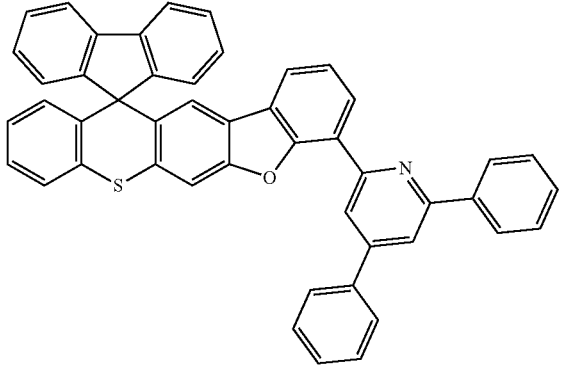
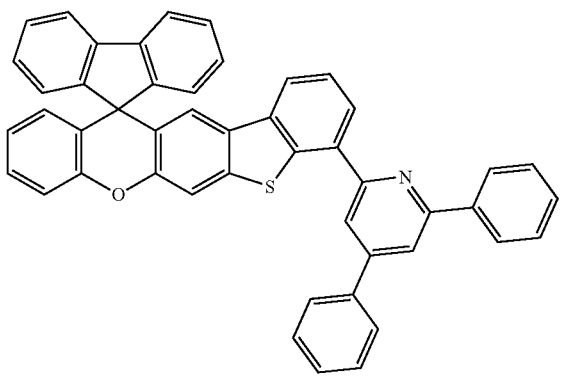
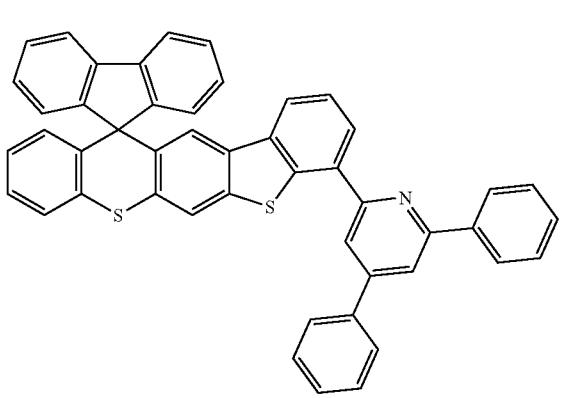

-continued
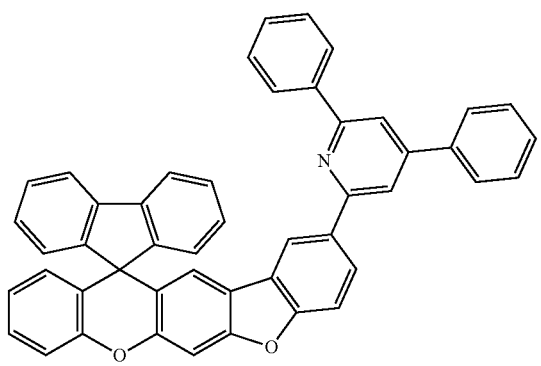
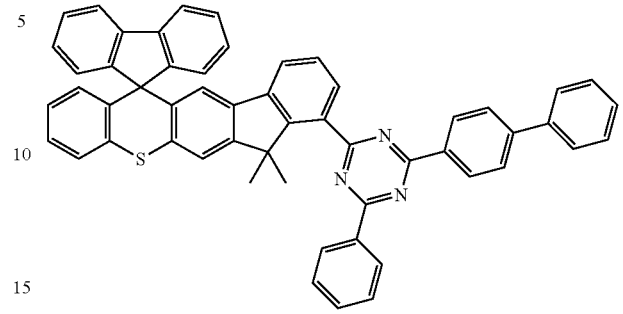
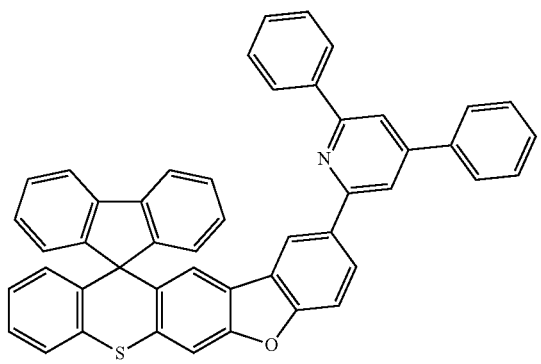
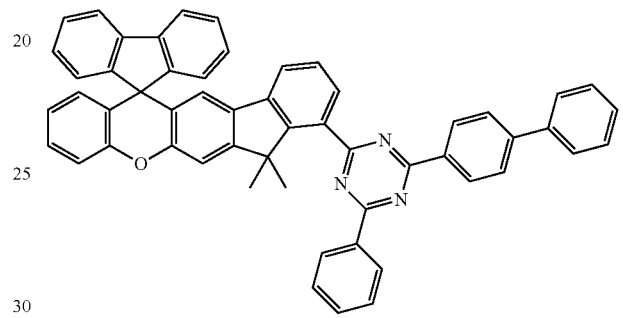
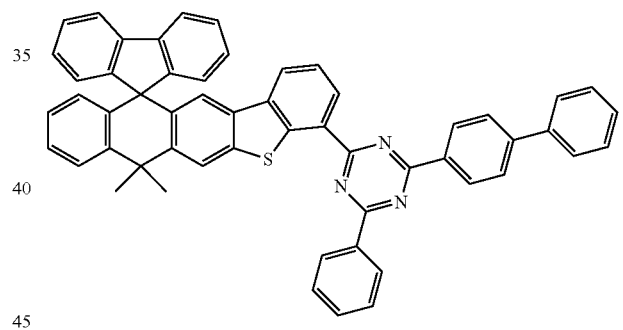
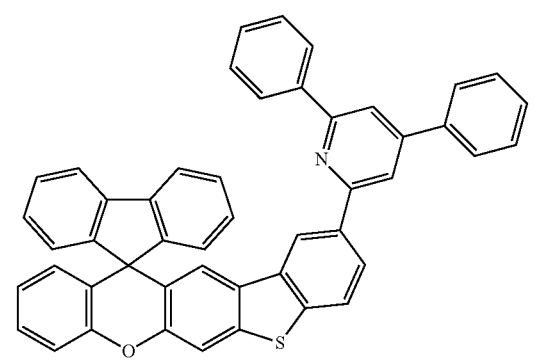
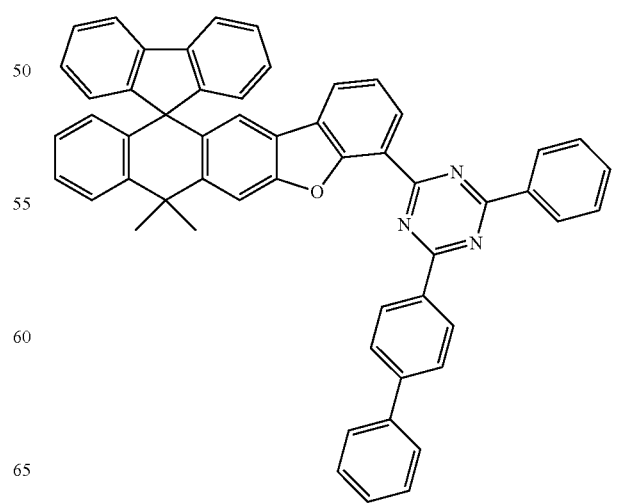
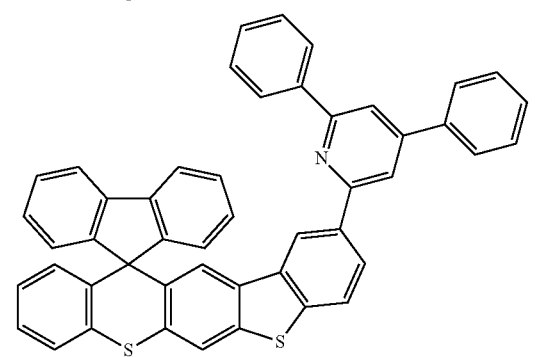

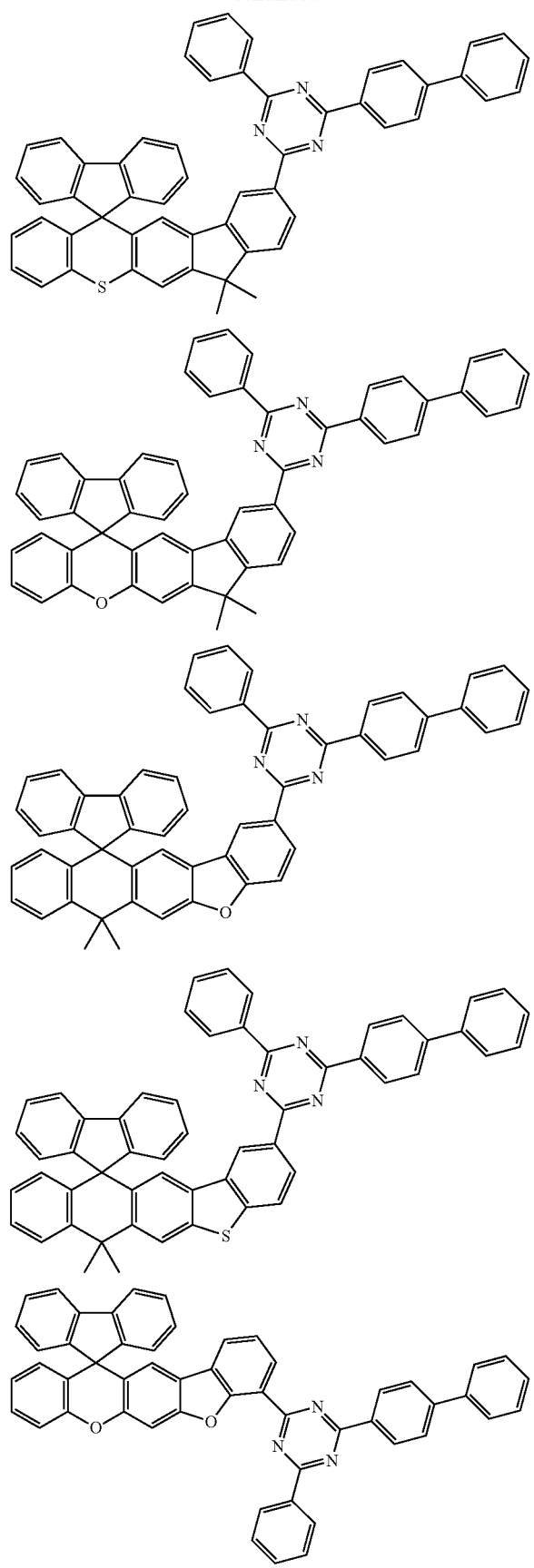
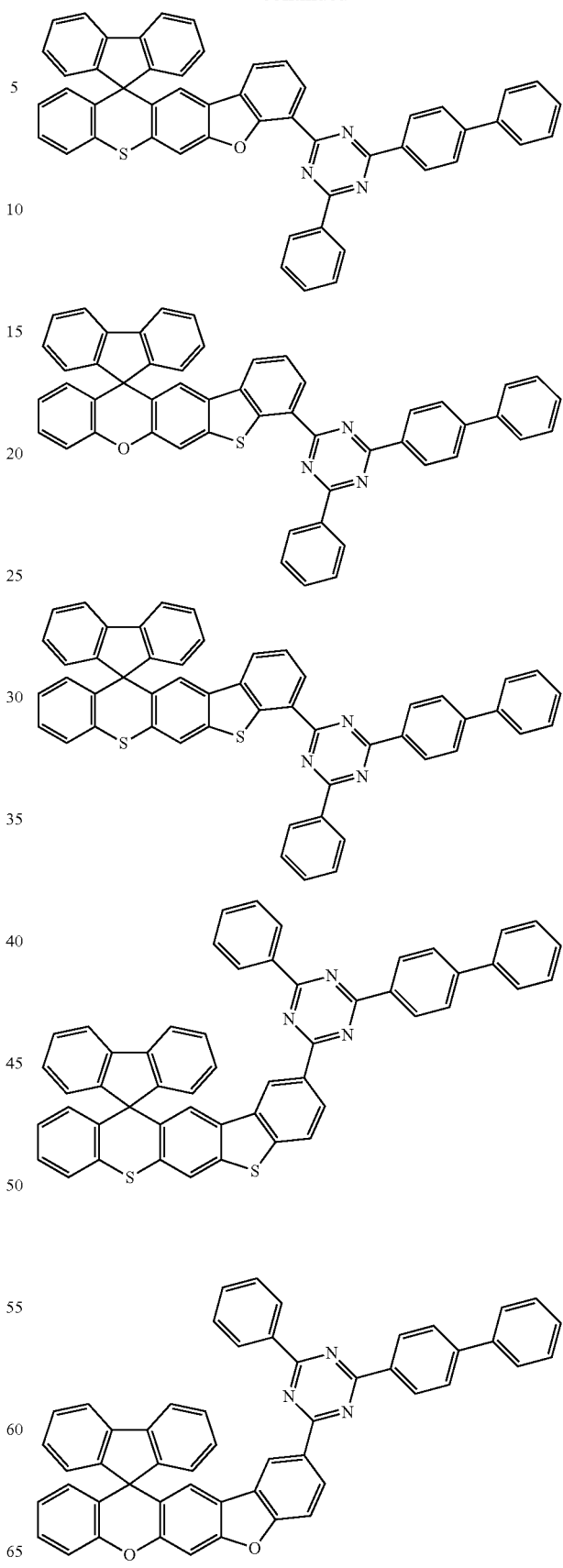

369
-continued
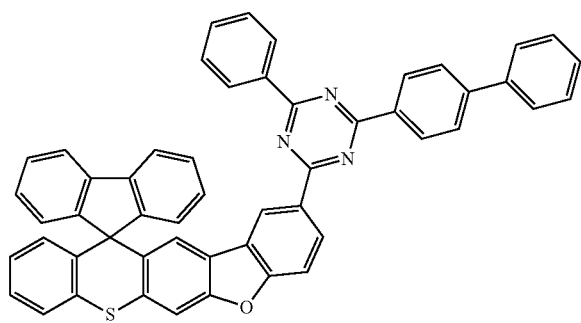
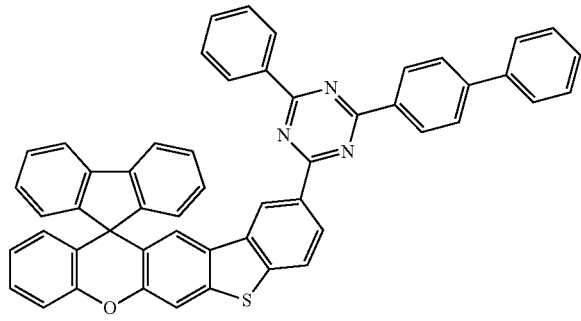
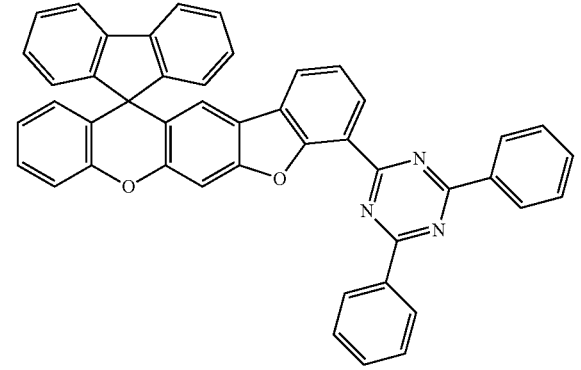
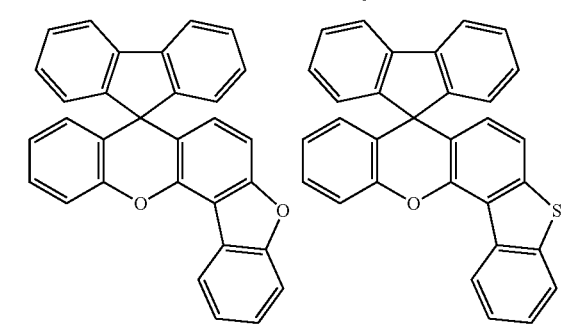
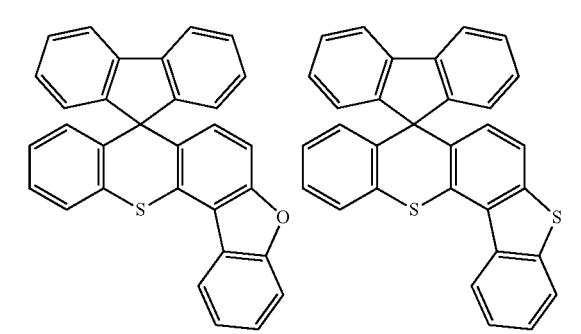
370
-continued
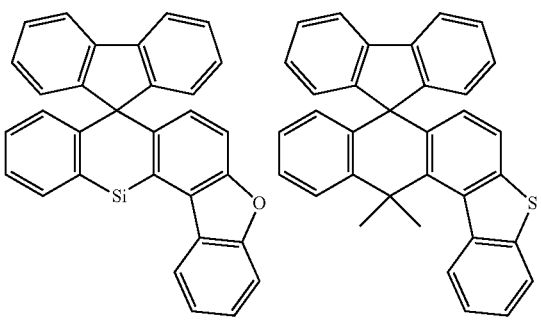
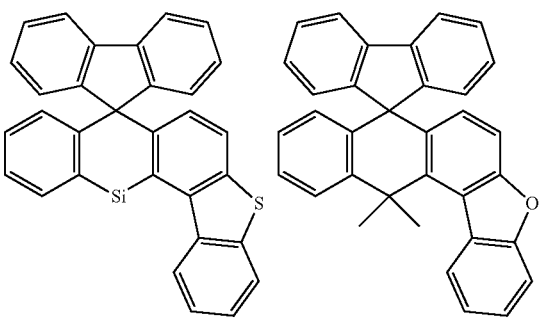
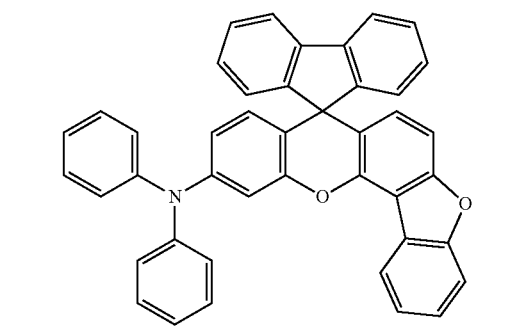
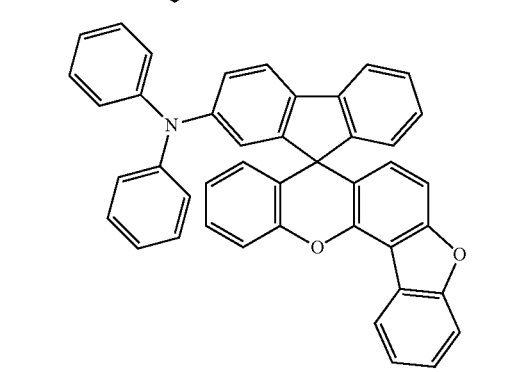
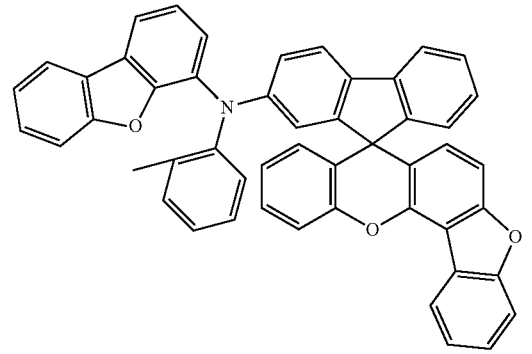

-continued
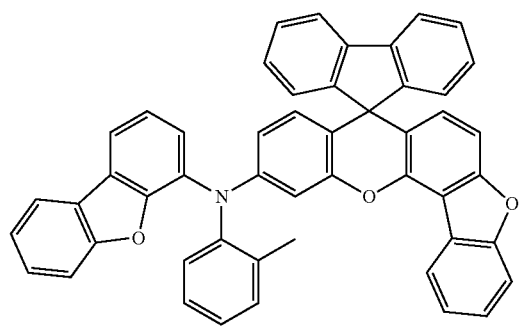
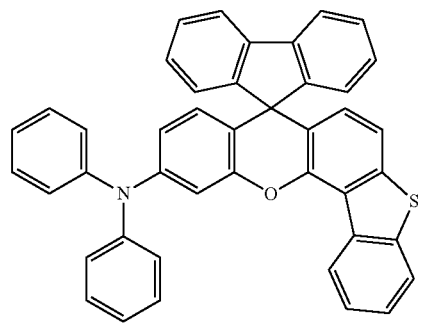
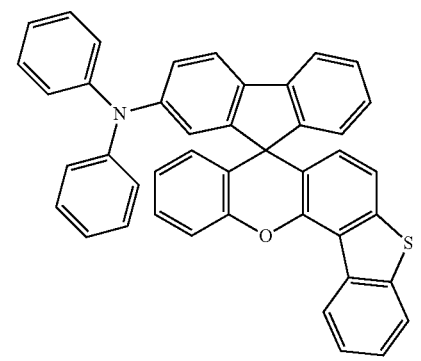
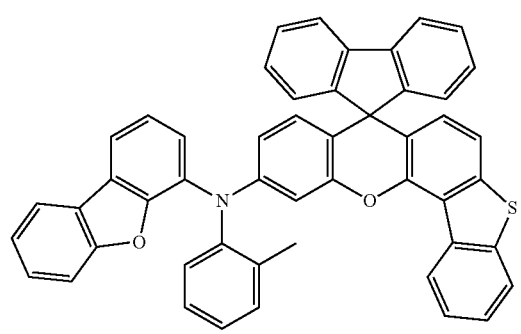
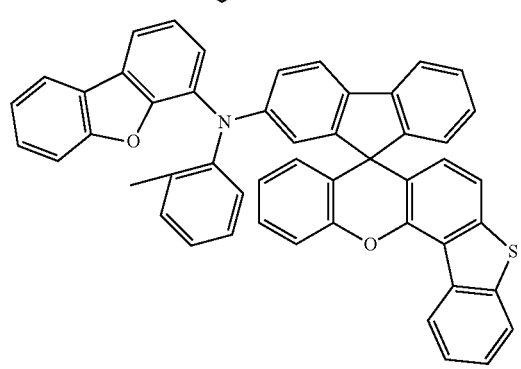
-continued
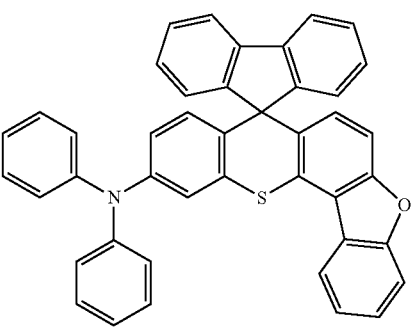
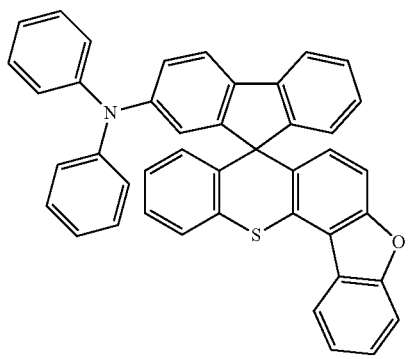
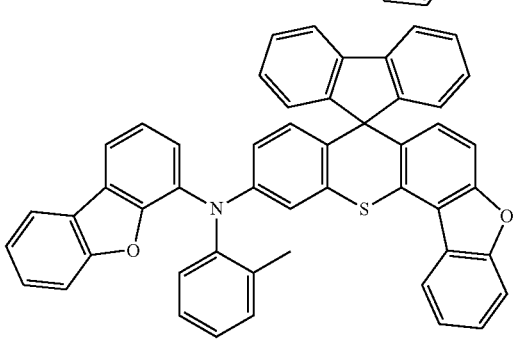
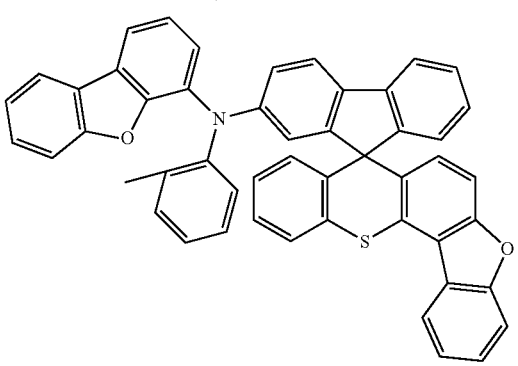
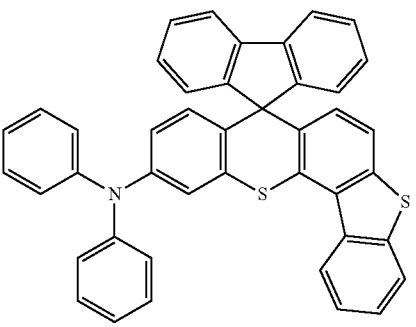

373
-continued
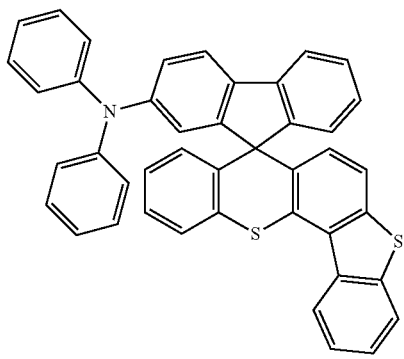
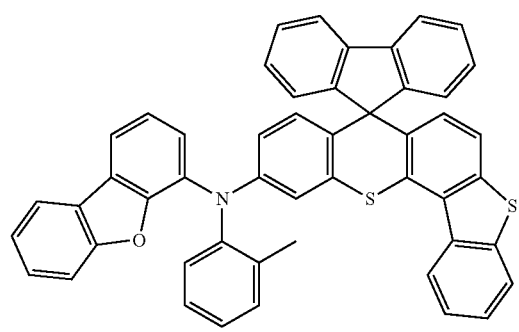
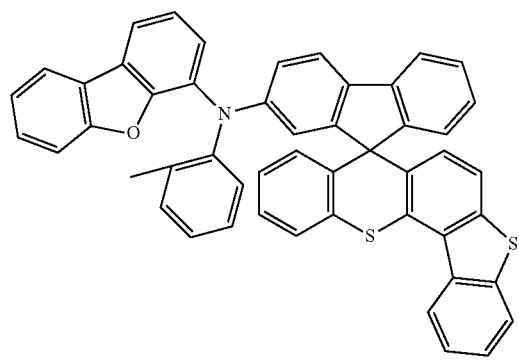
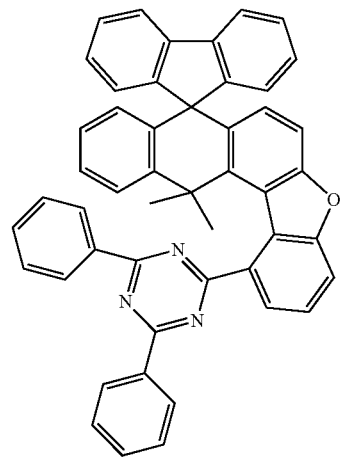
374
-continued
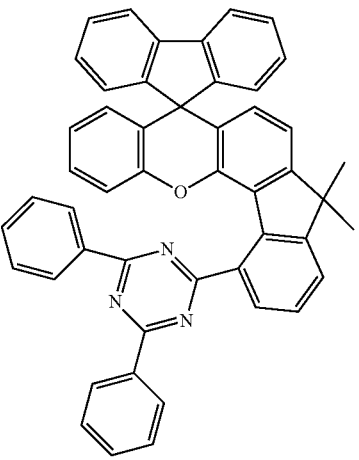
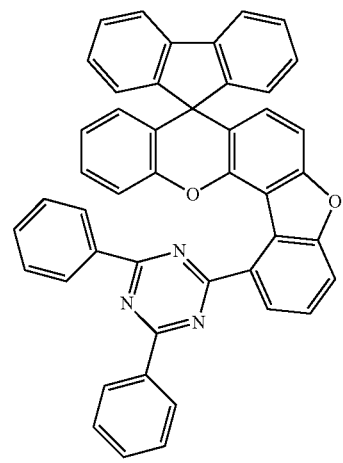
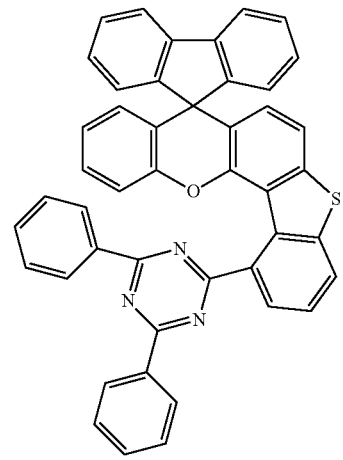

375
-continued
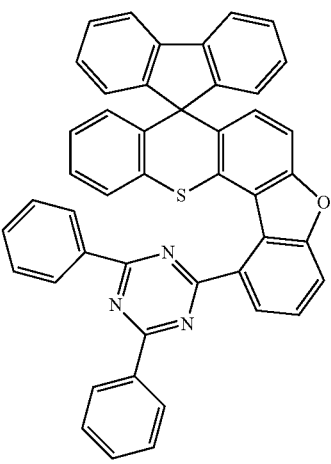
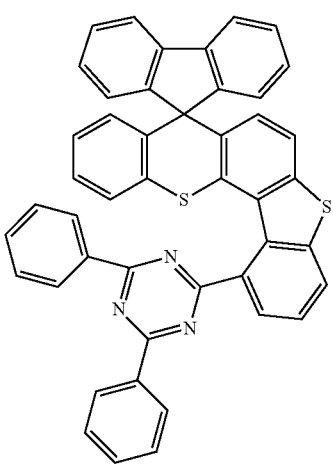
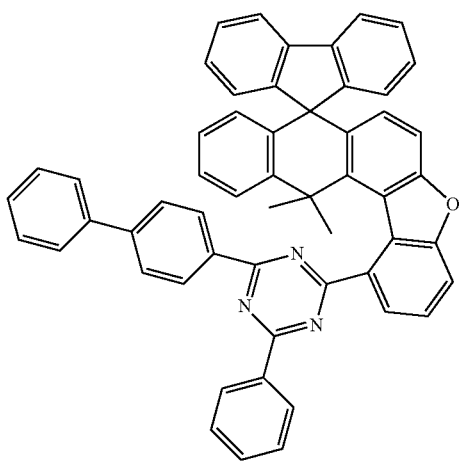
376
-continued
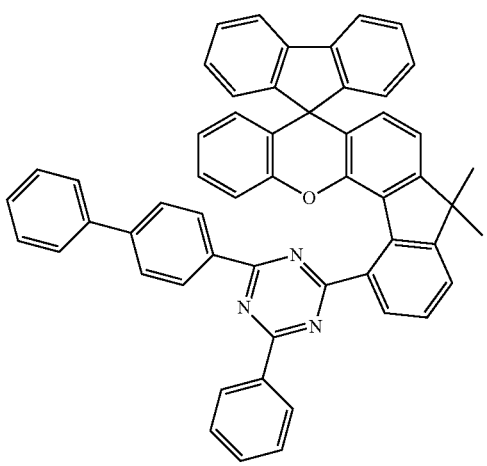
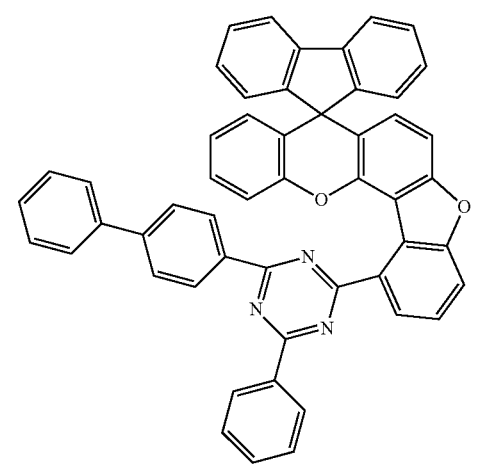
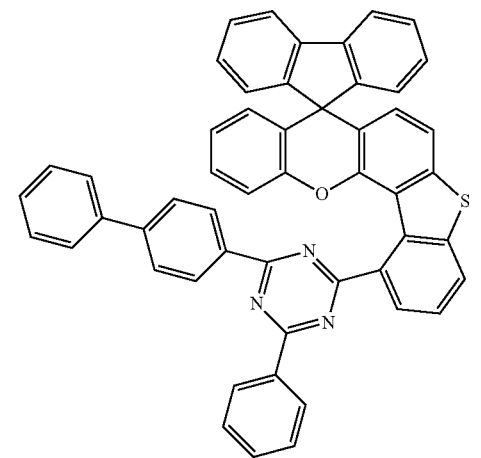

377
-continued
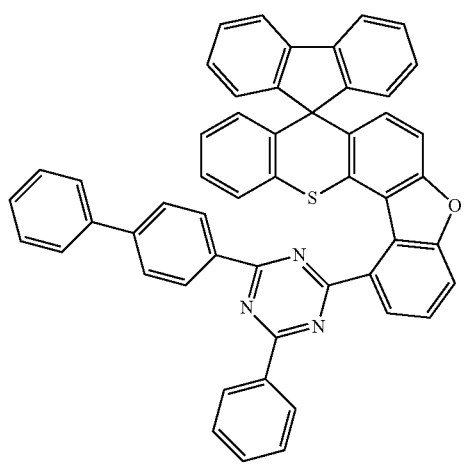
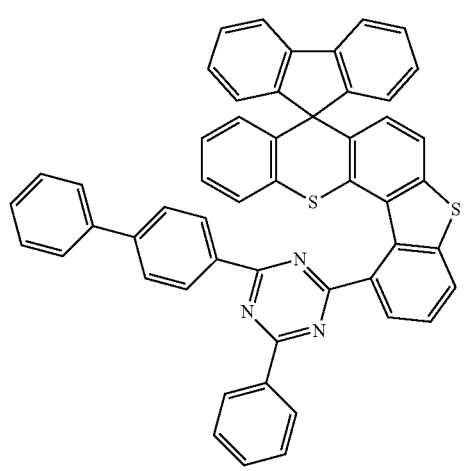
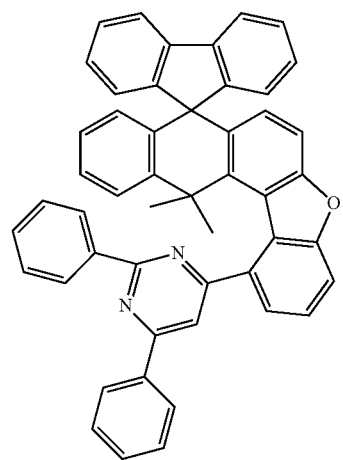
378
-continued
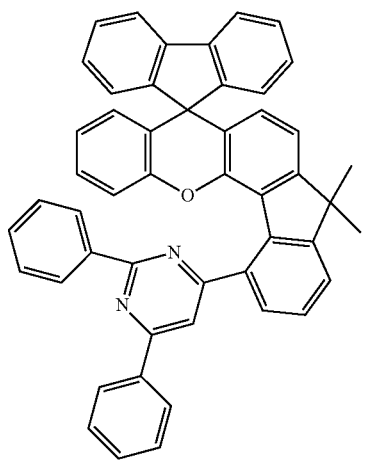
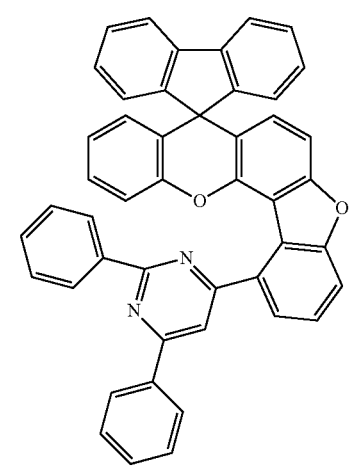
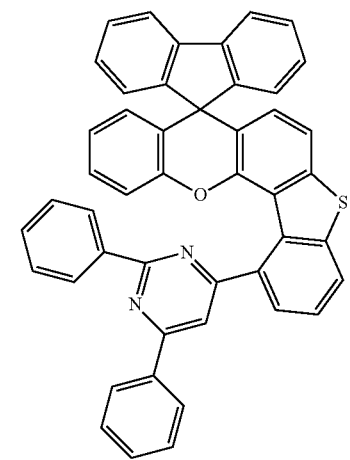

-continued
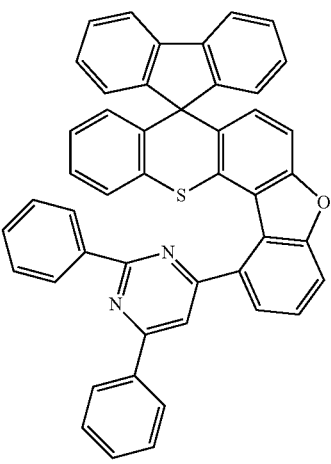
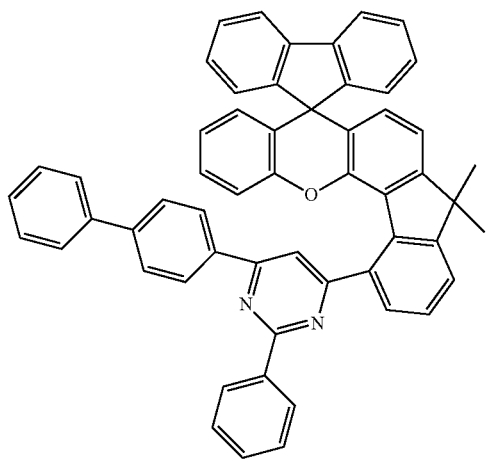
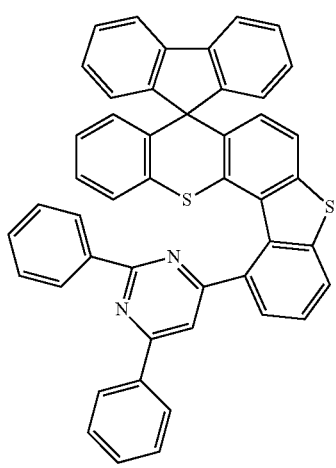
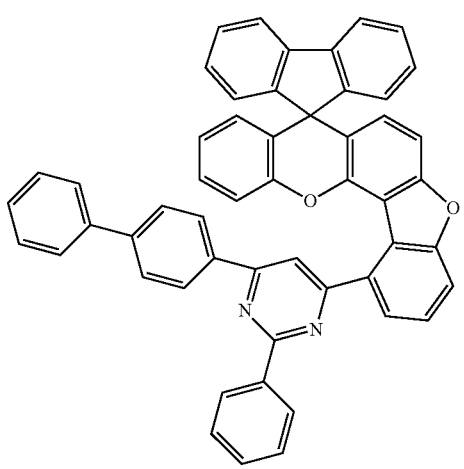
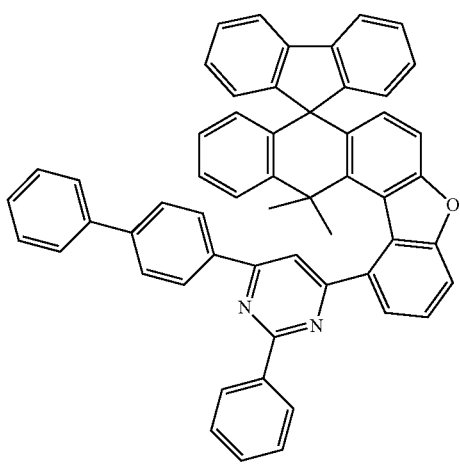
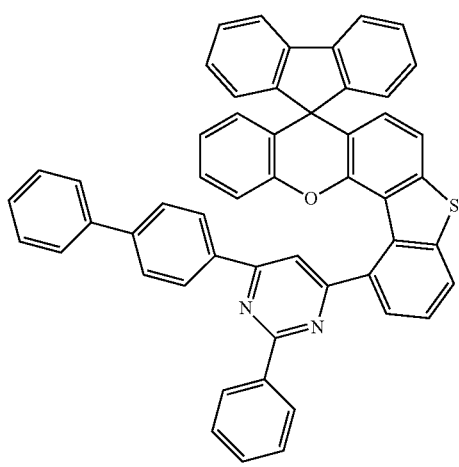

381
-continued
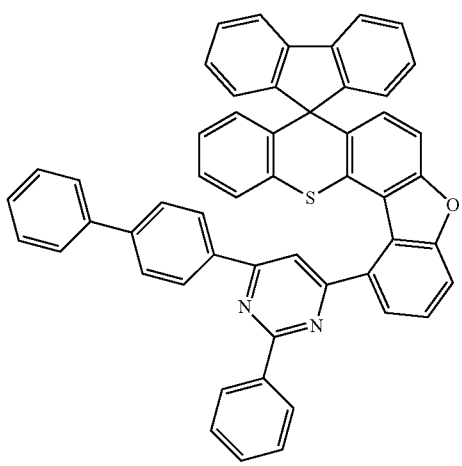
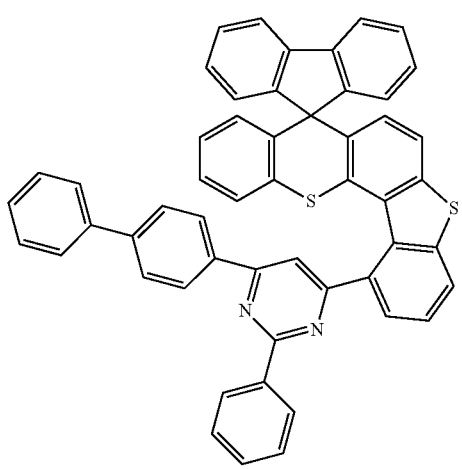
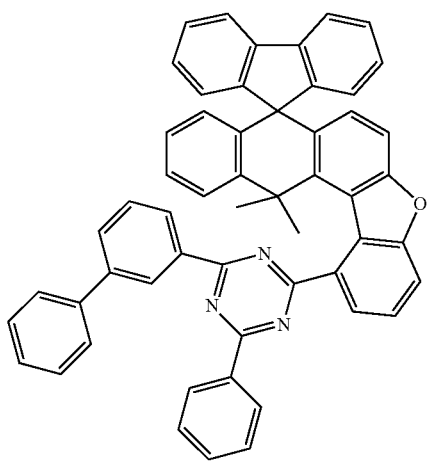
382
-continued
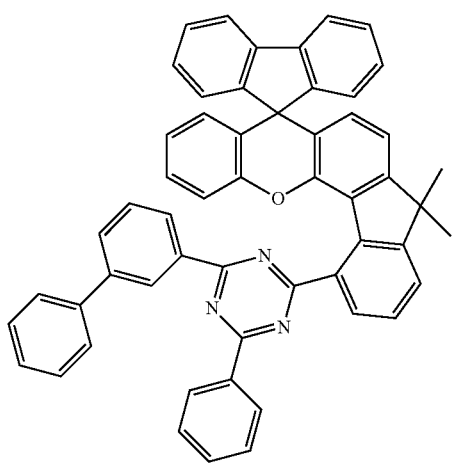
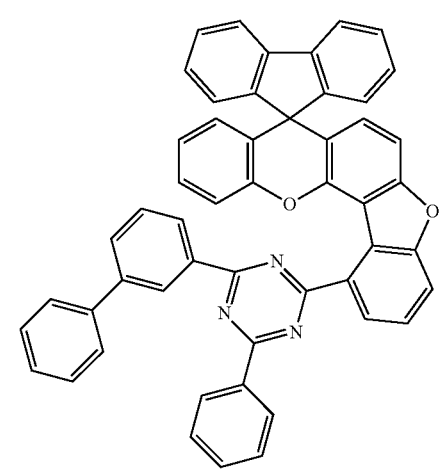
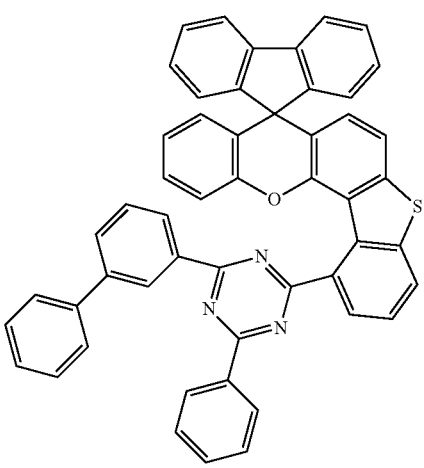

383
-continued
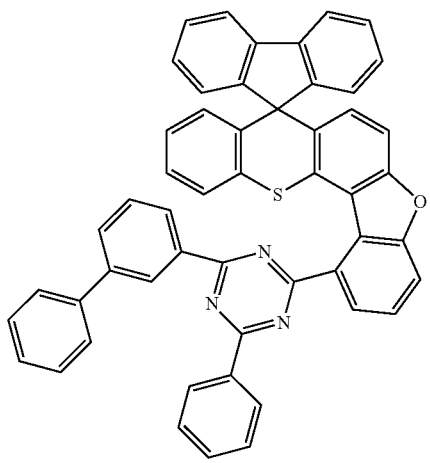
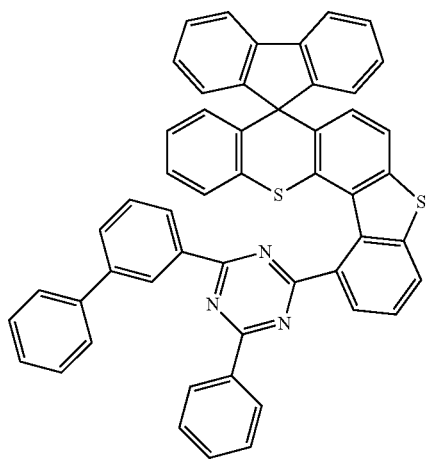
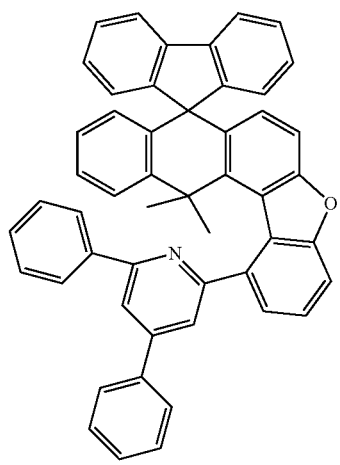
384
-continued
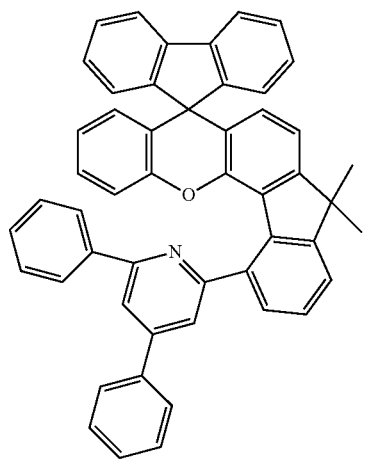
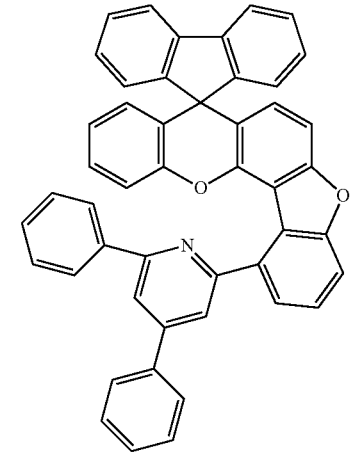
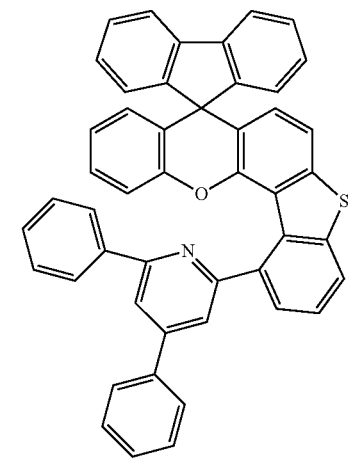

385
-continued
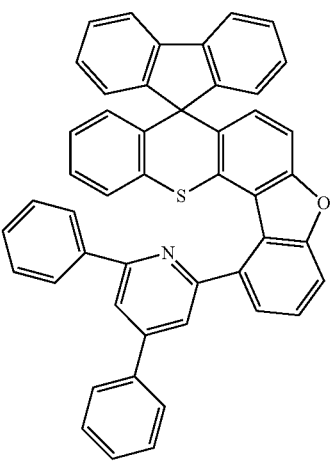
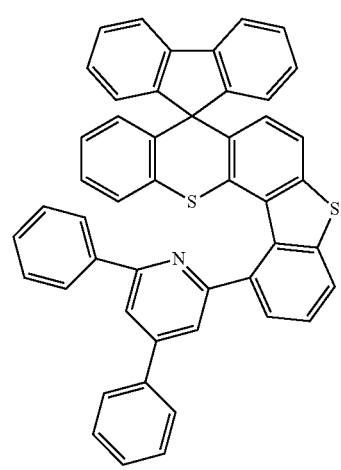
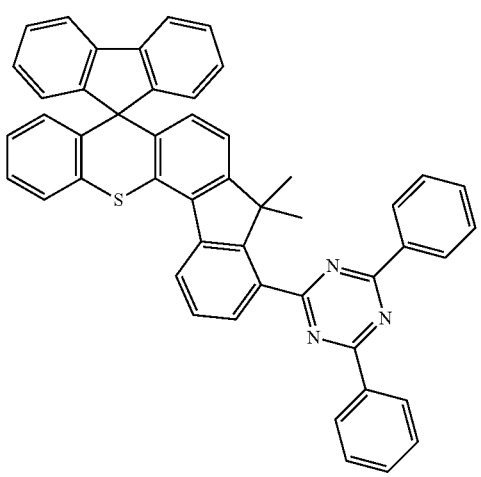
386
-continued
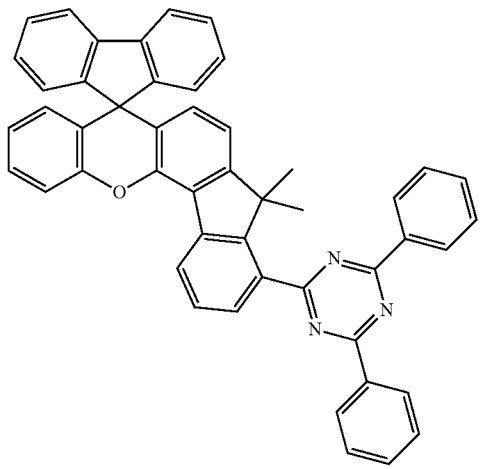
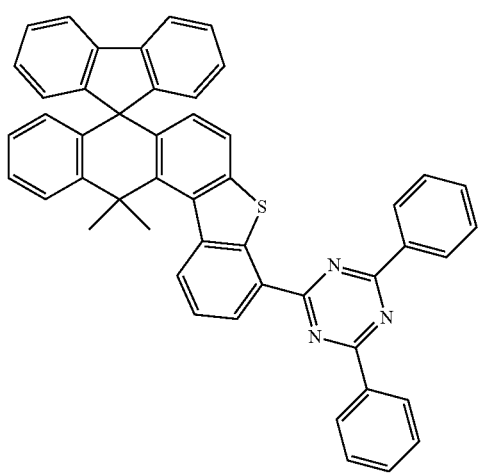
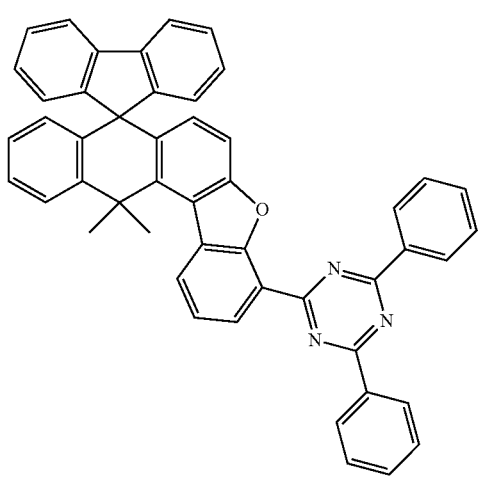

387
-continued
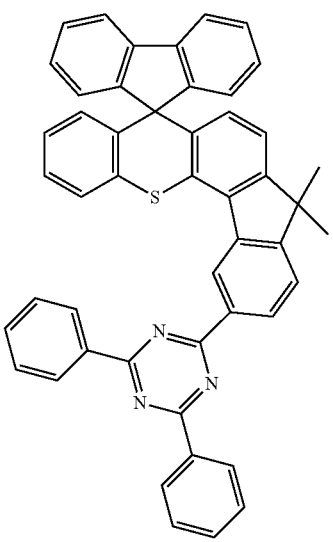
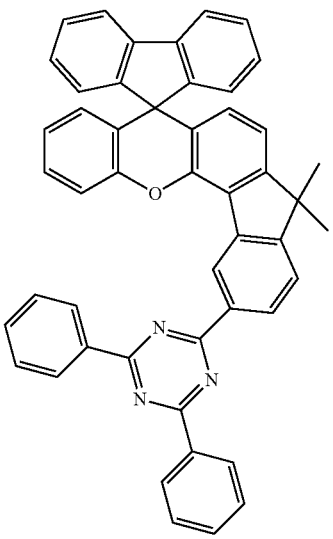
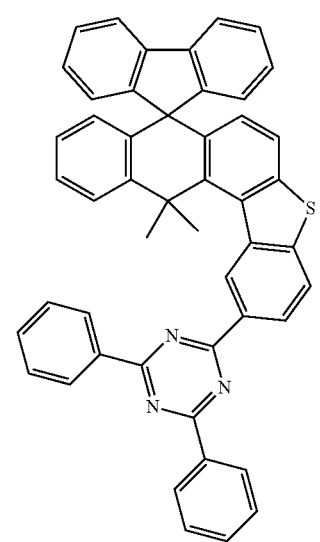
388
-continued
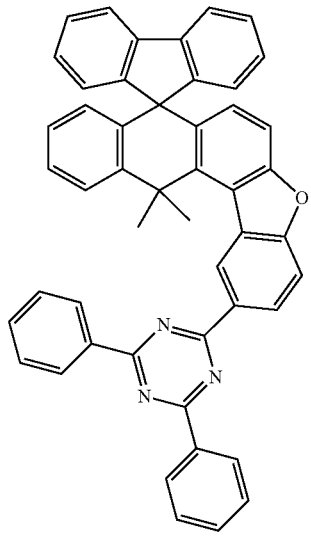
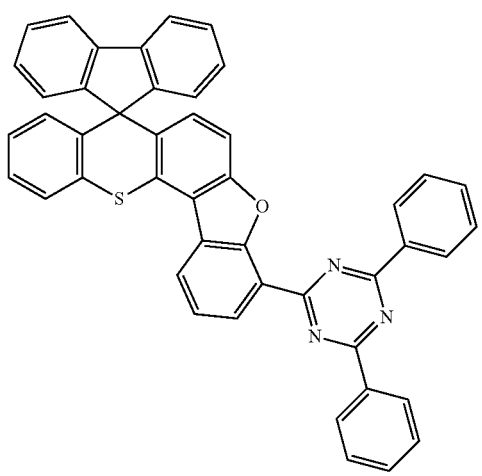
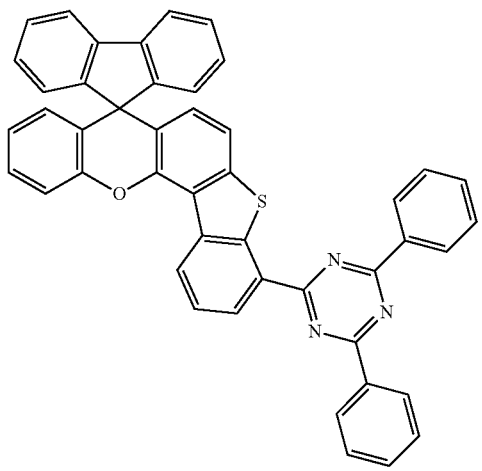

389
-continued
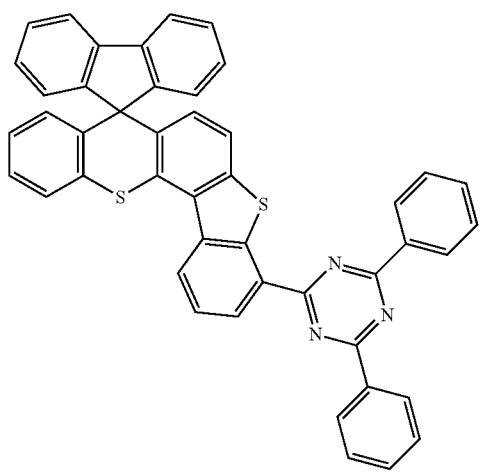
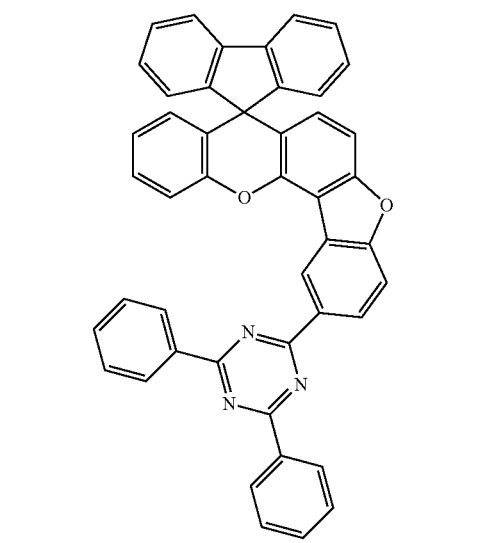
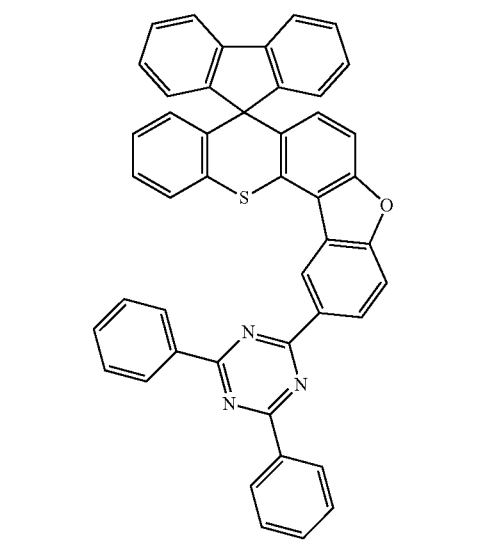
390
-continued
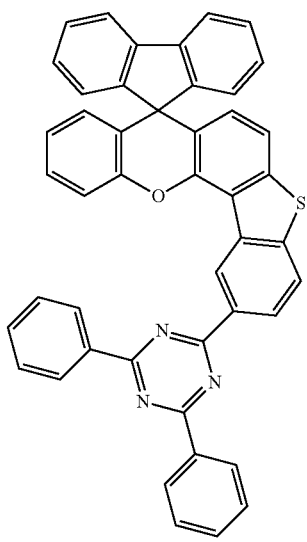
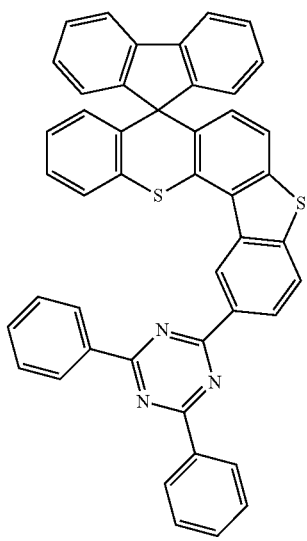
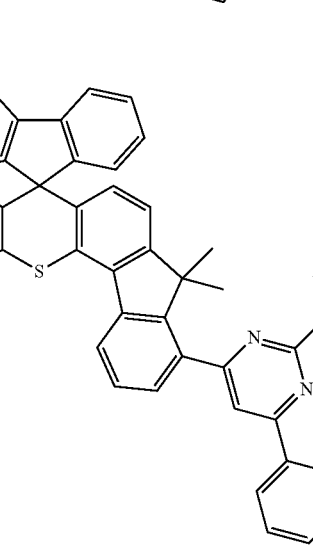

391
-continued
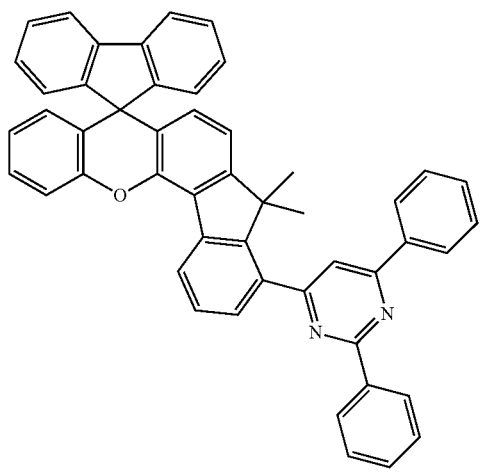
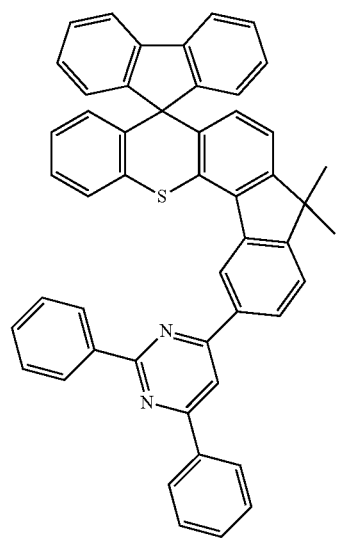
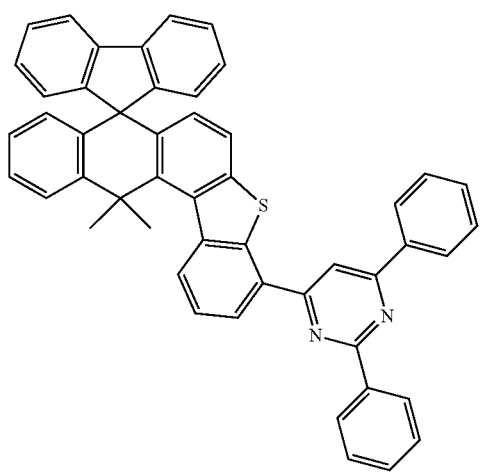
392
-continued
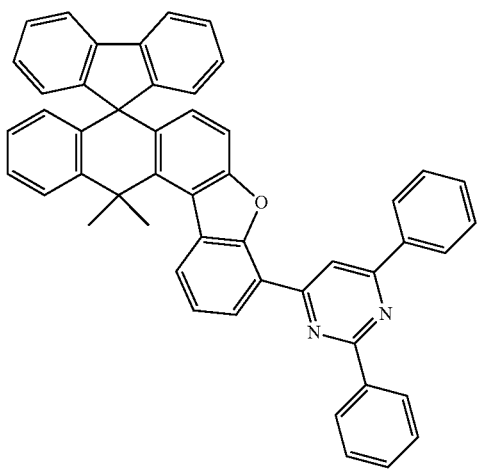
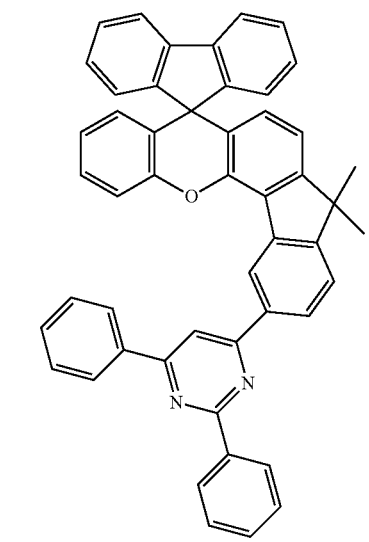
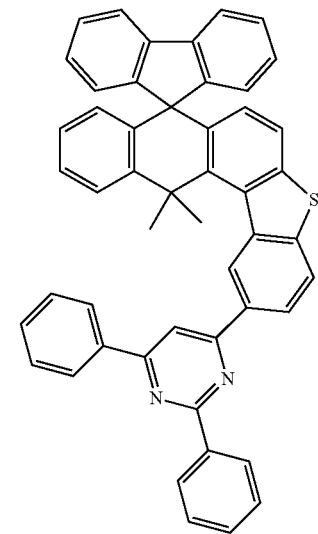

393
-continued
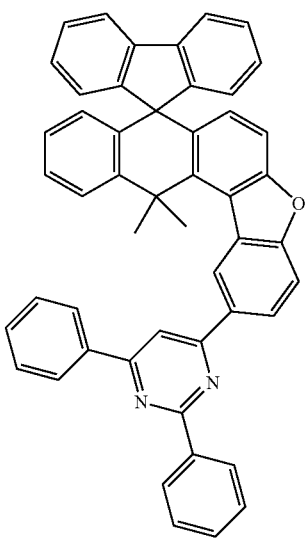
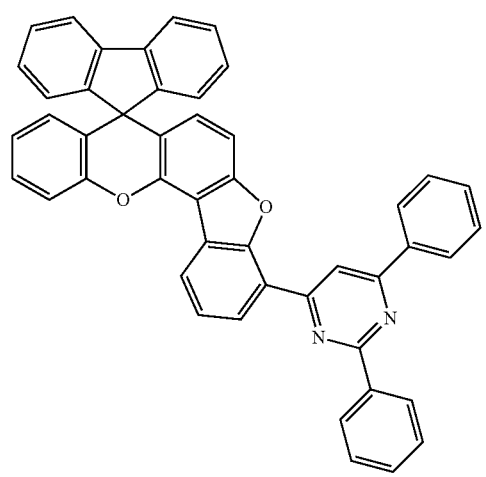
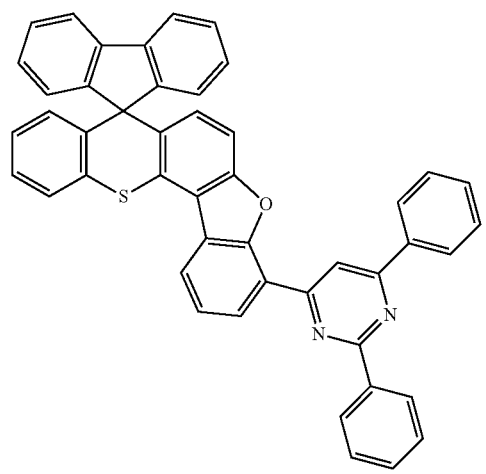
394
-continued
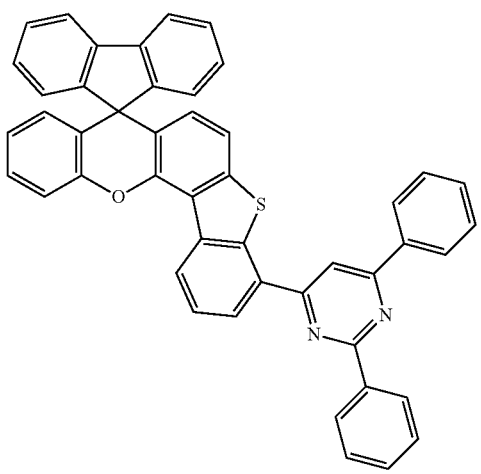
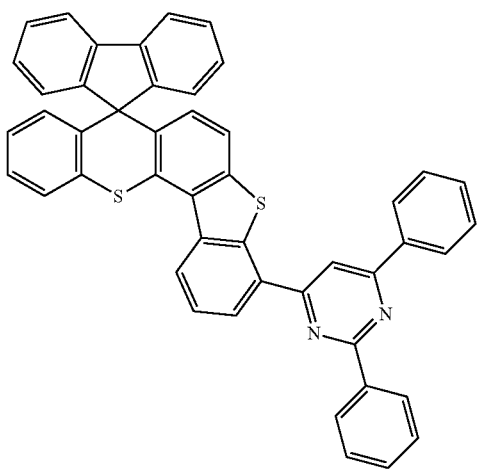
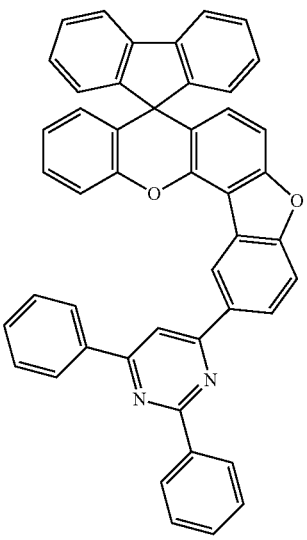

395
-continued
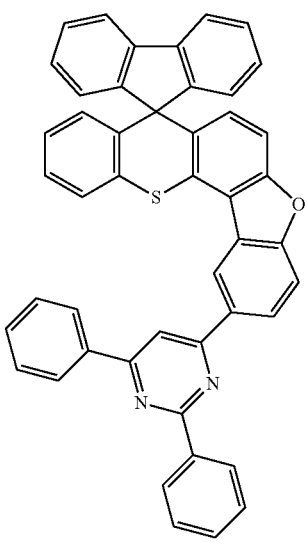
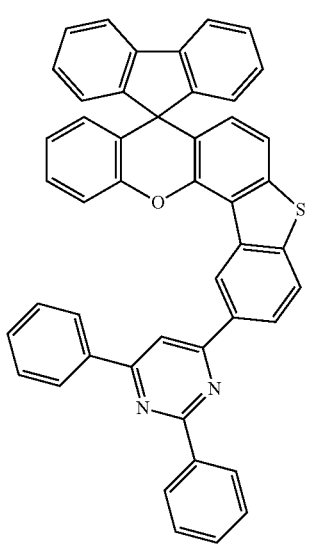
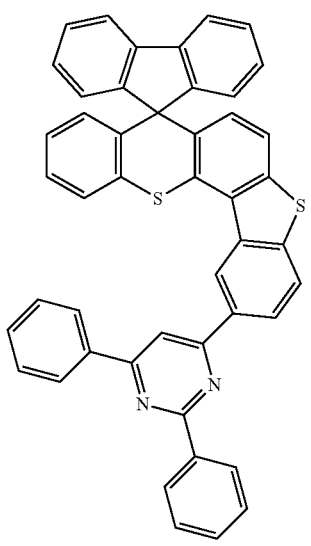
396
-continued
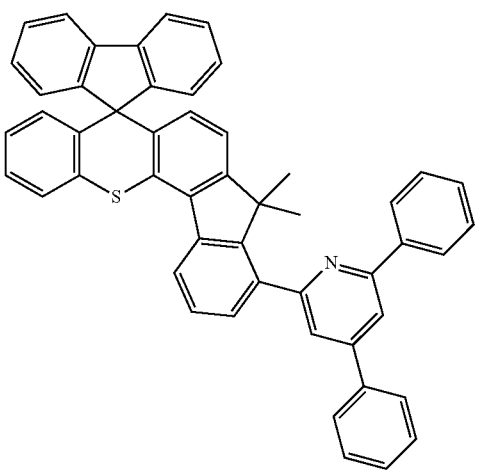
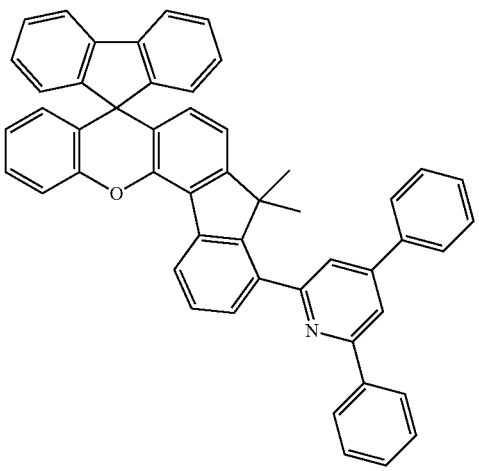
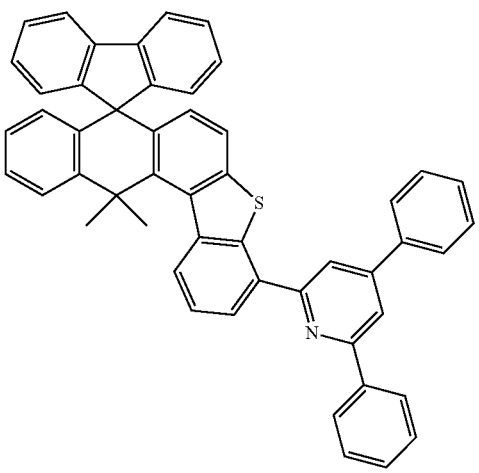

397
-continued
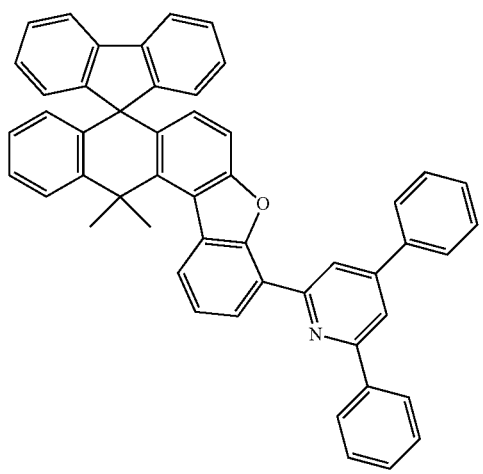
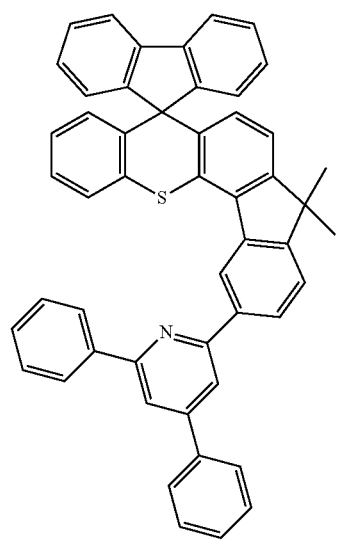
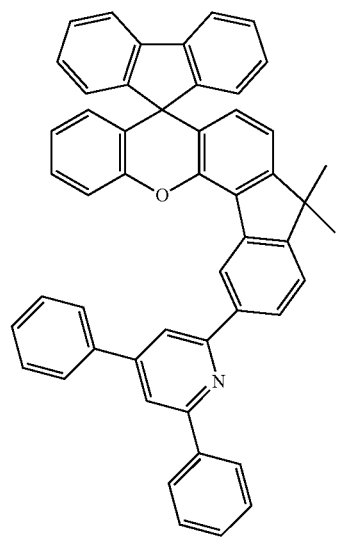
398
-continued
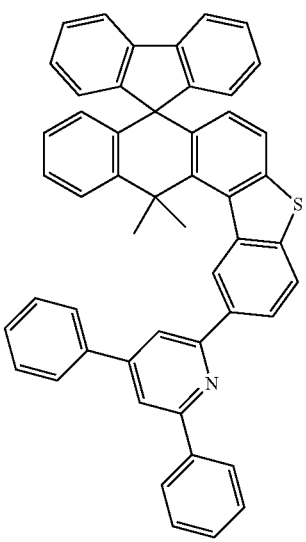
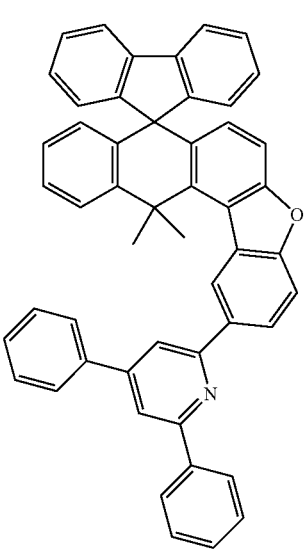
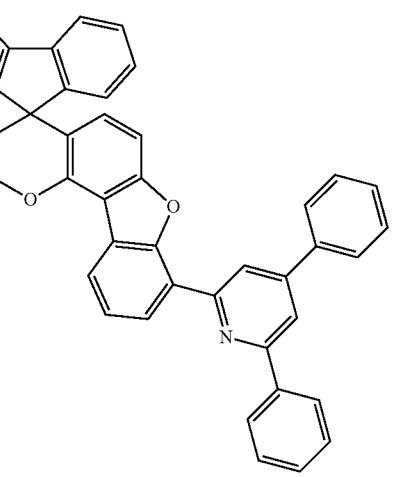

399
-continued
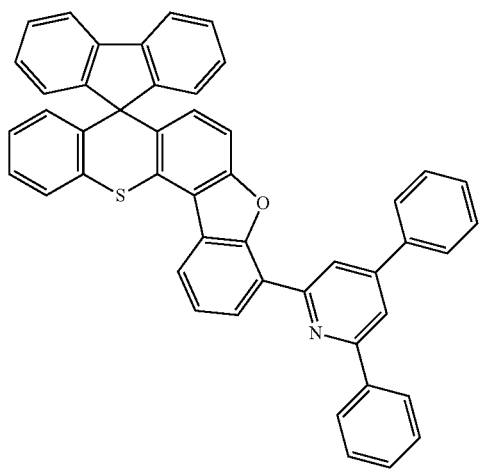
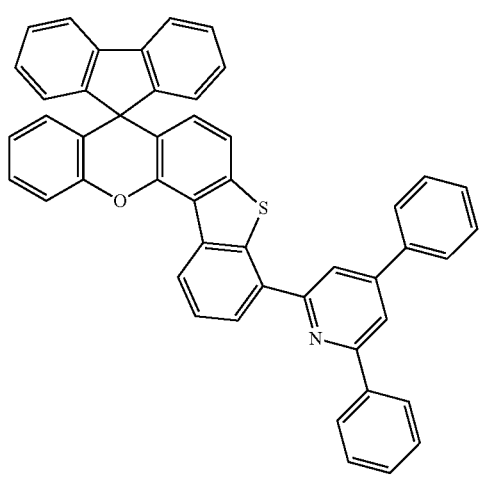
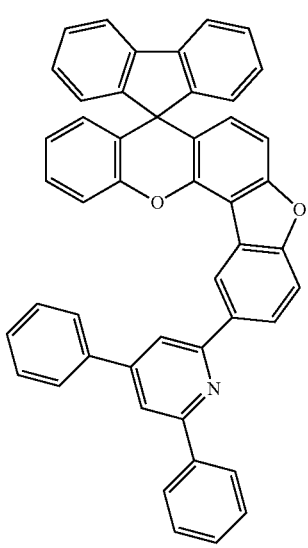
400
-continued
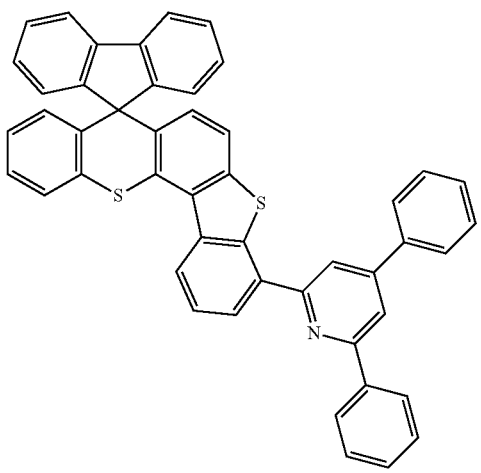
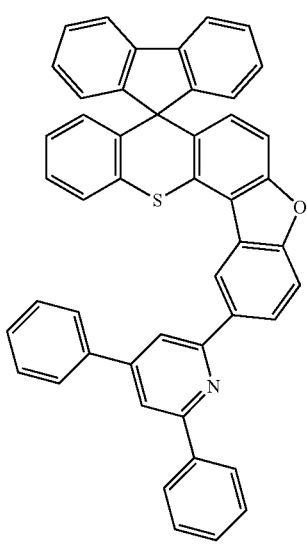
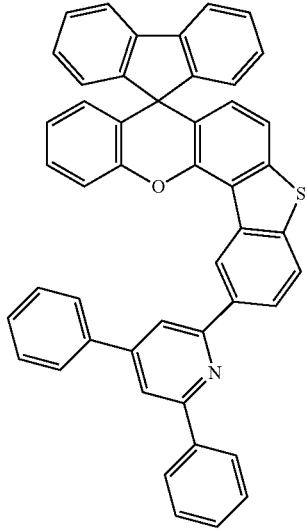

401
-continued
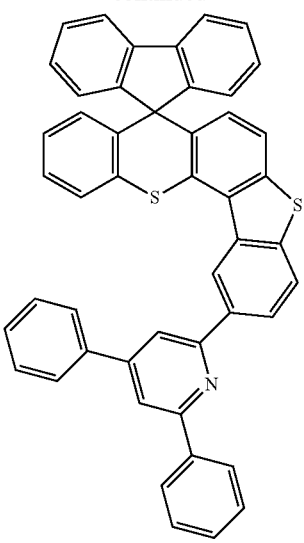
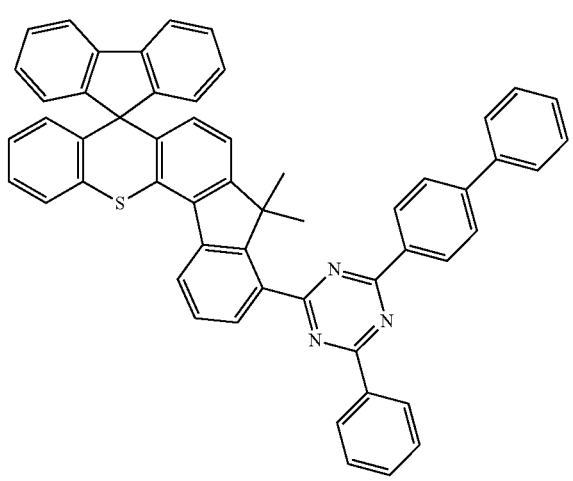
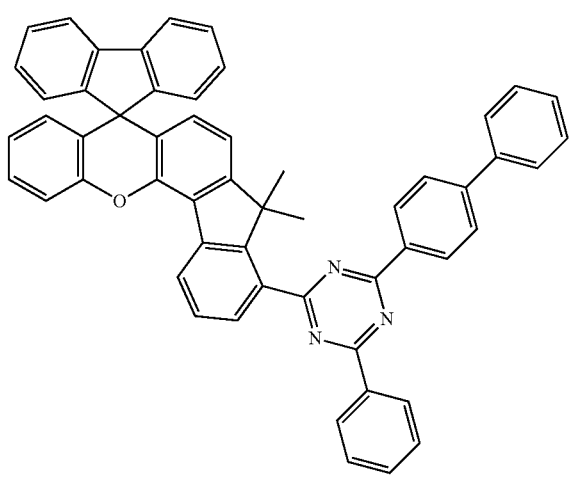
402
-continued
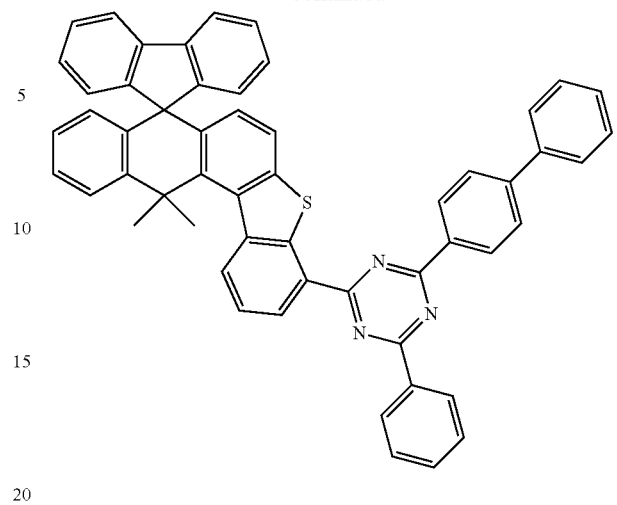
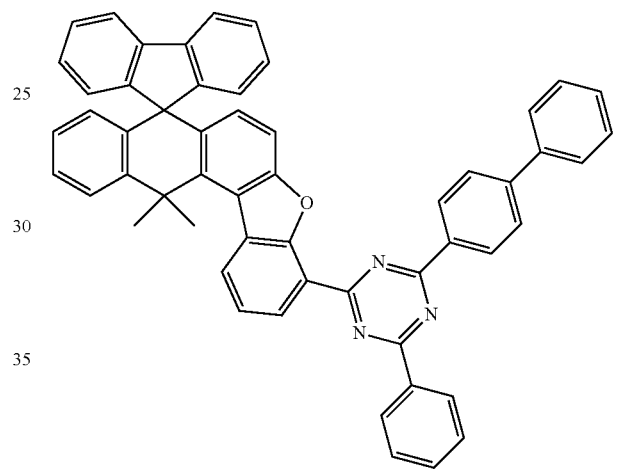
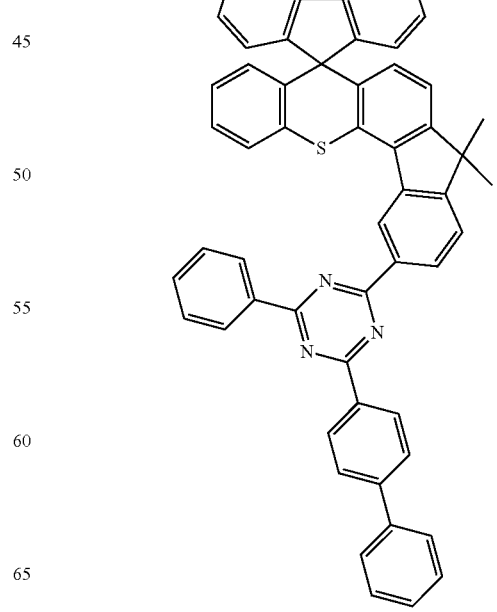

403
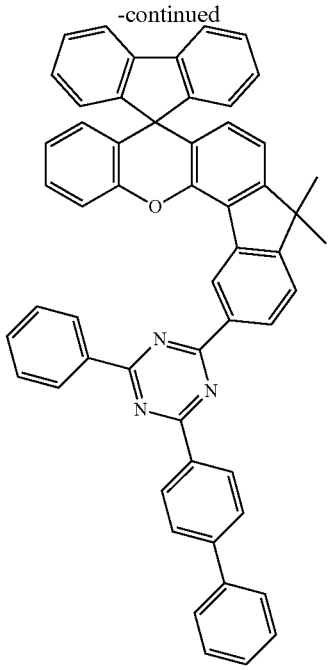
404
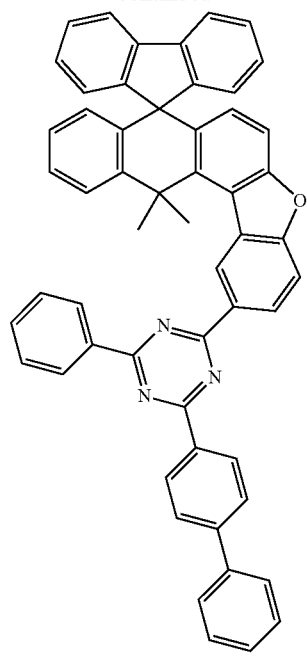
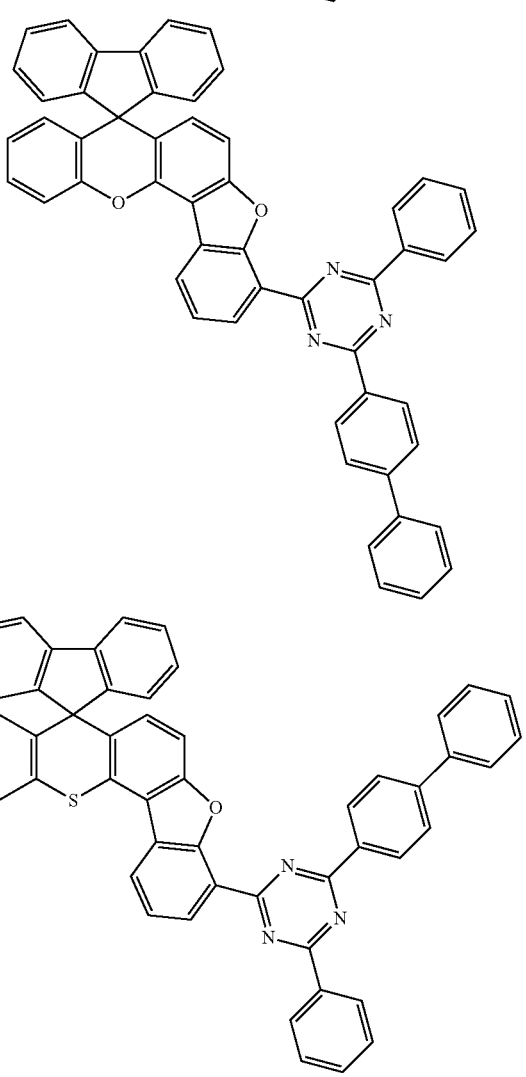
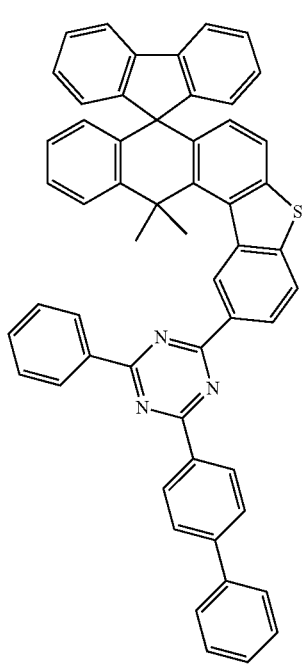

405
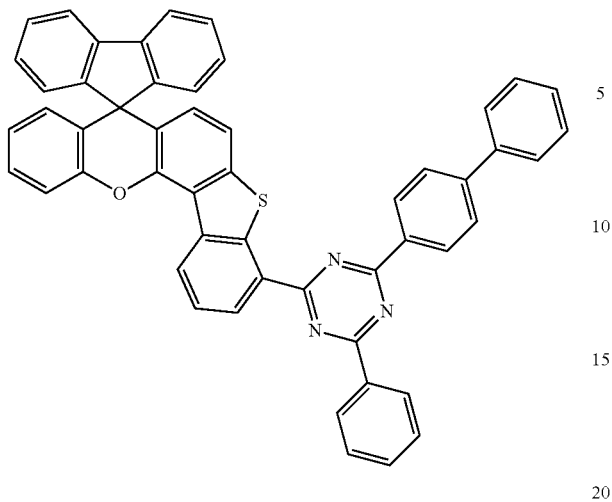
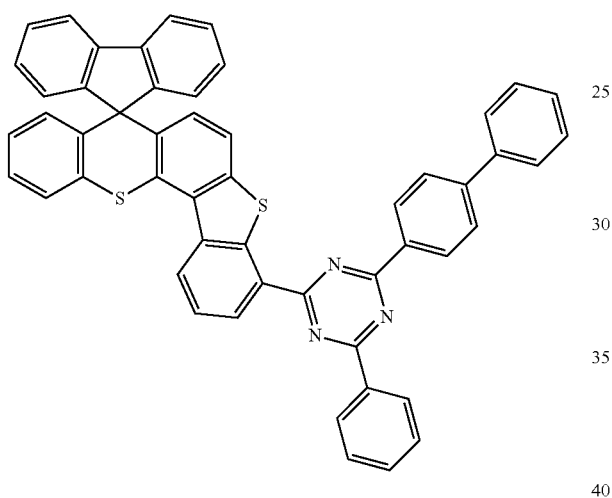
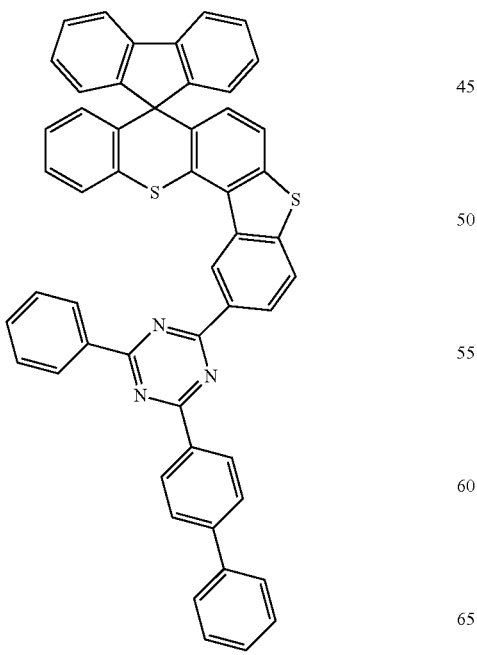
406
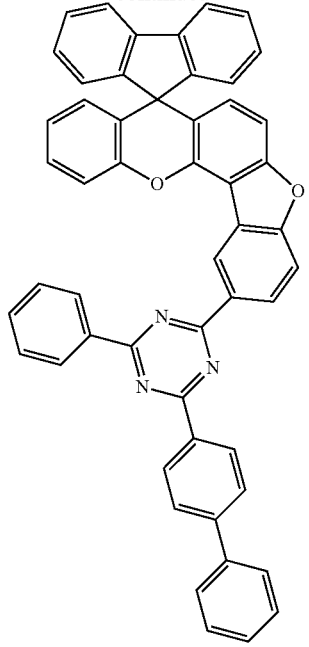
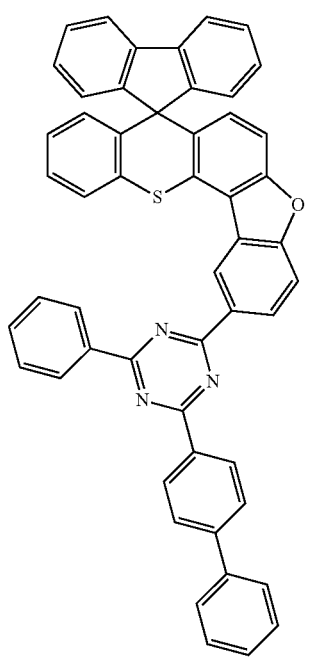

407
-continued
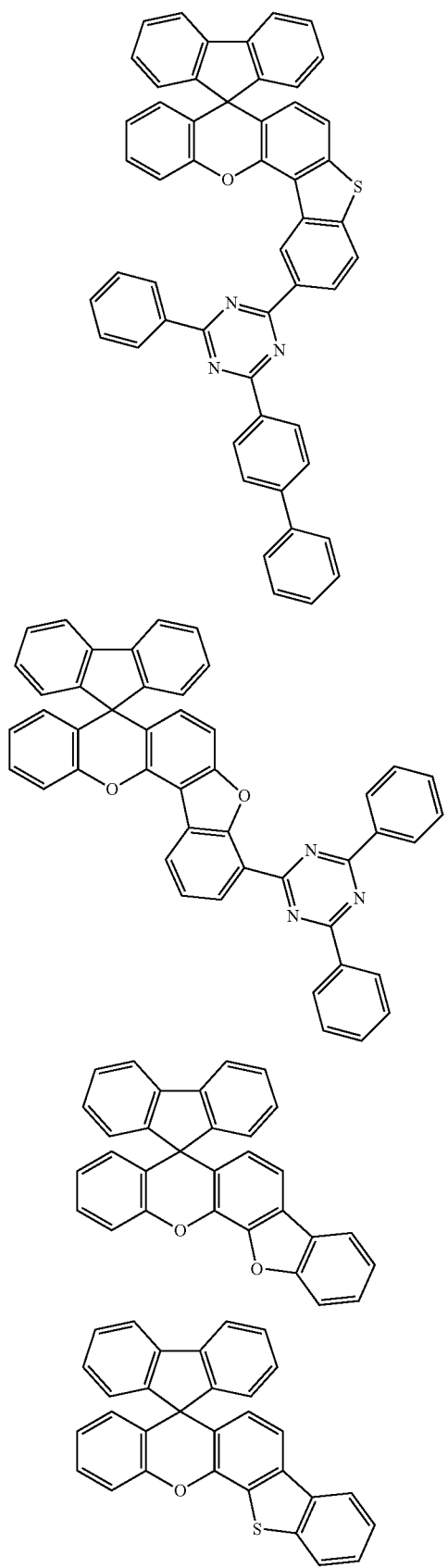
408
-continued
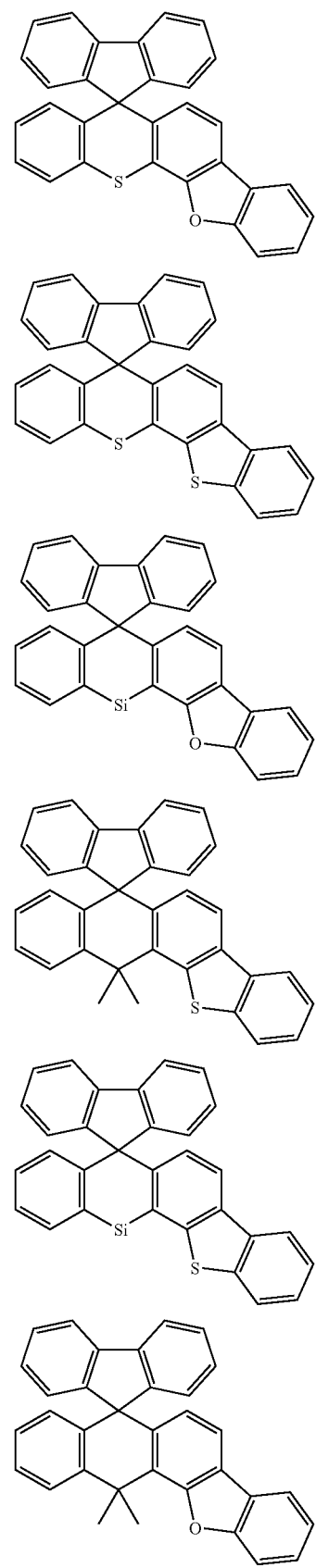

409
-continued
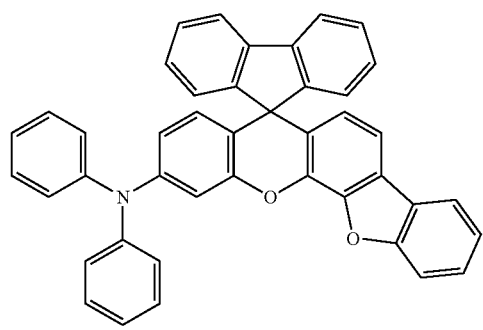
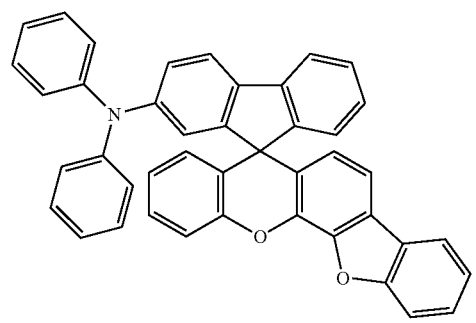
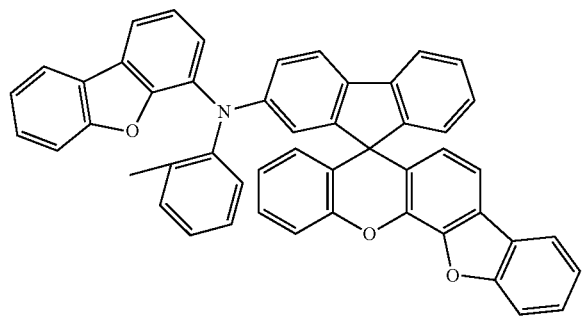
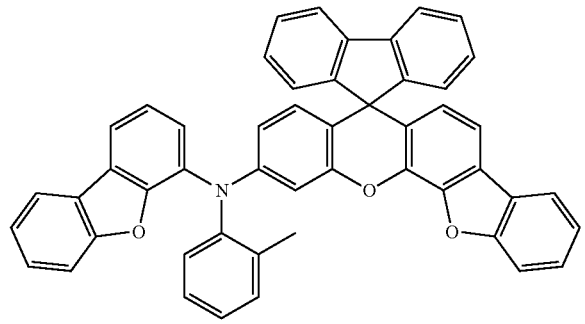
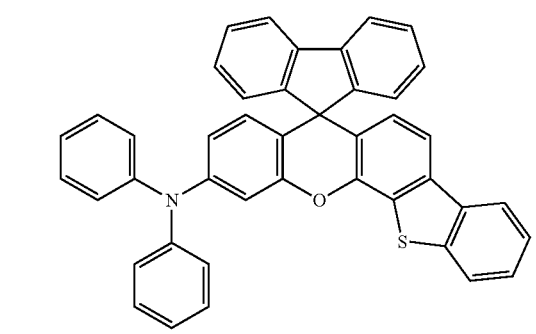
410
-continued
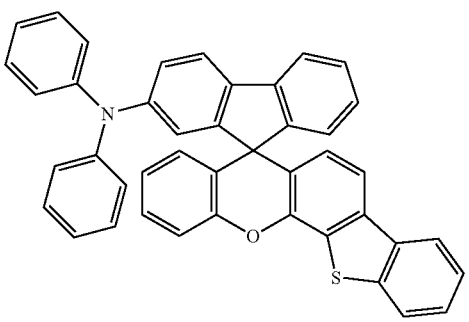
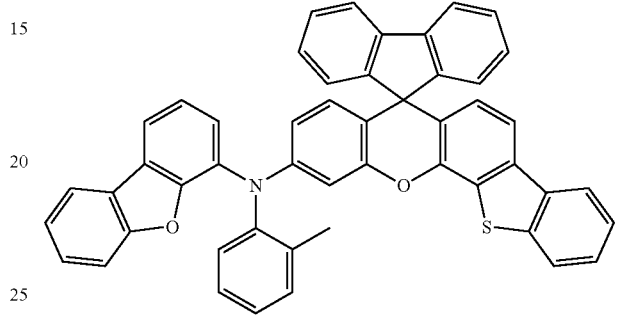
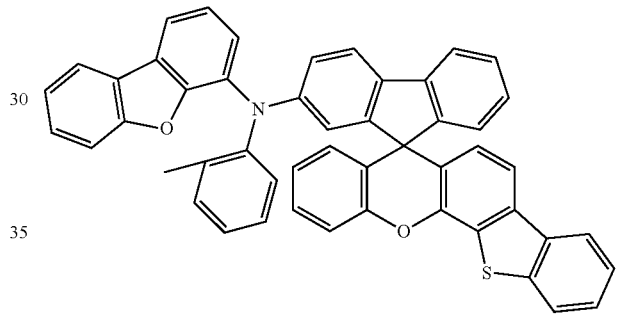
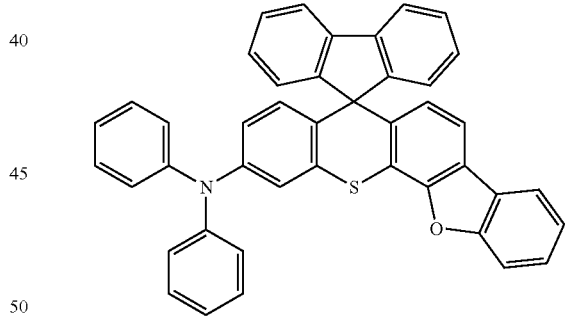
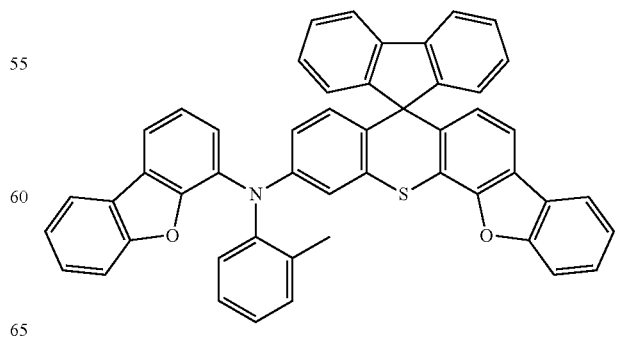

411
-continued
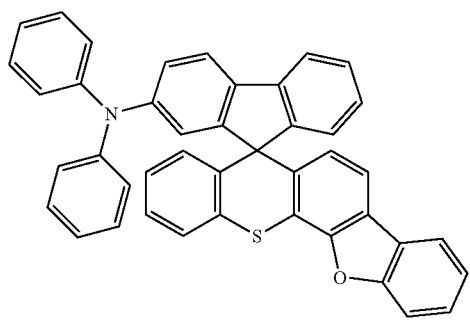
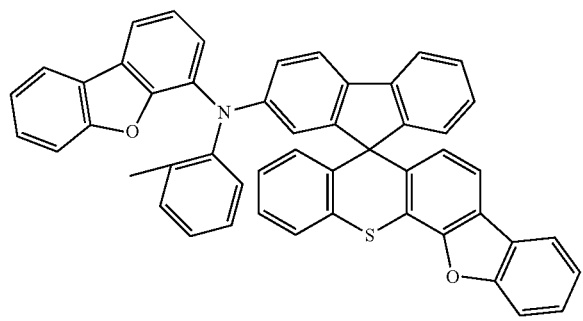
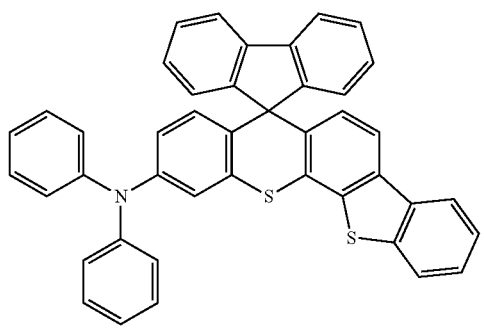
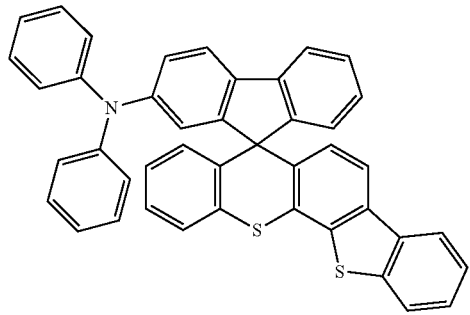
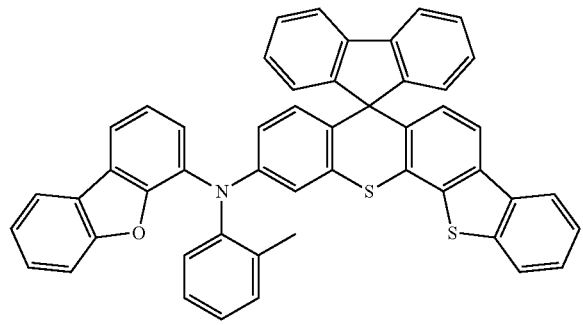
412
-continued
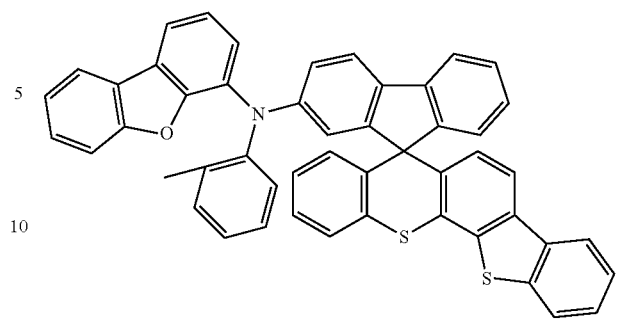
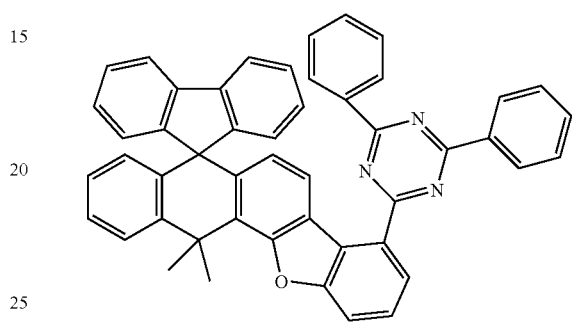
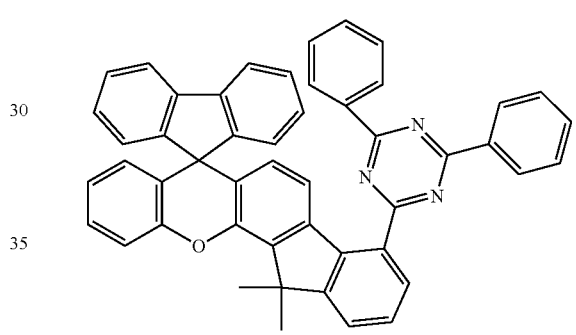
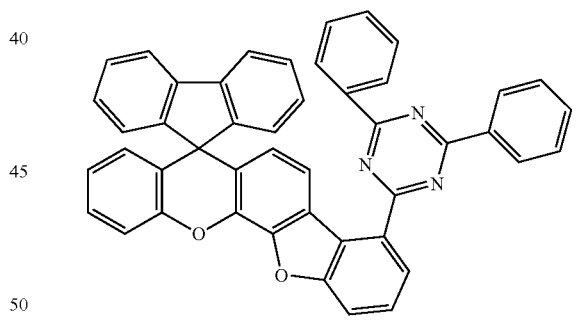
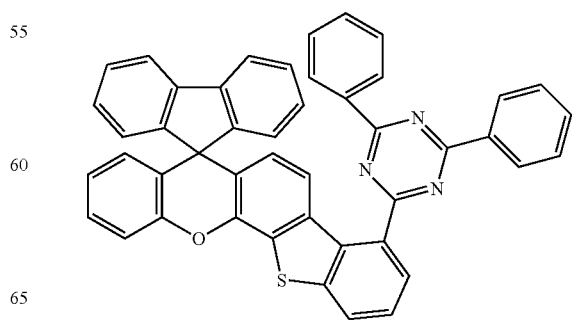

413
-continued
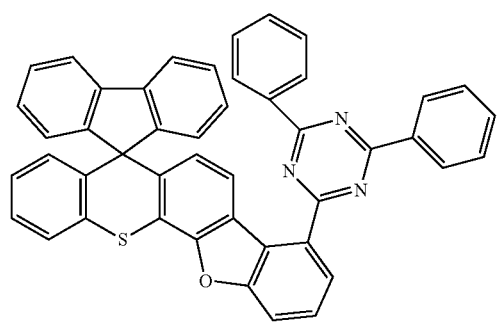
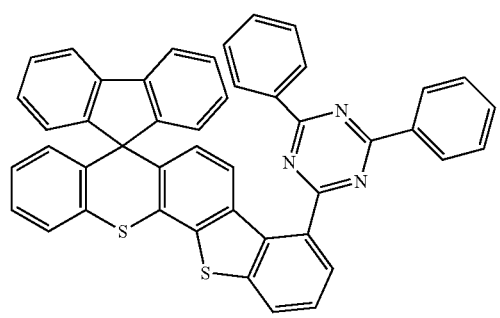
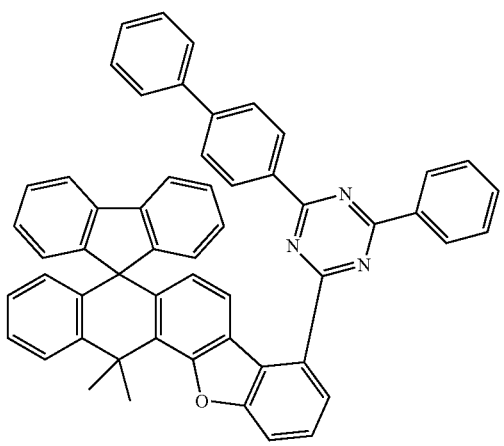
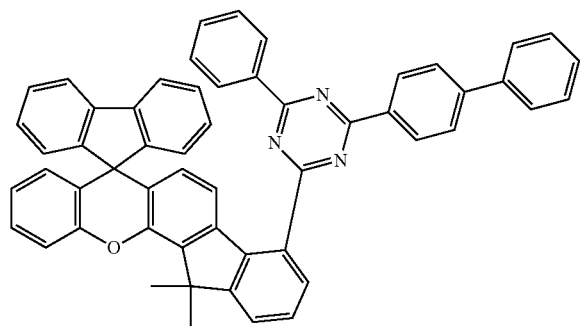
414
-continued
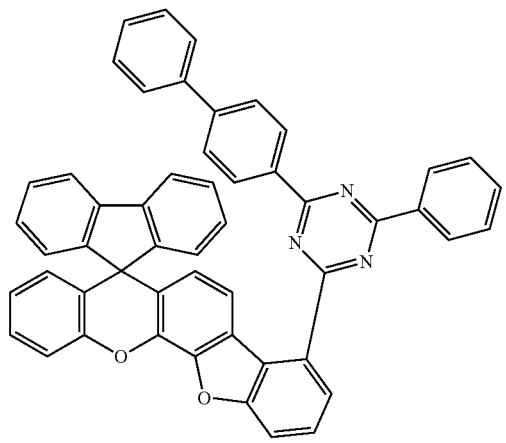
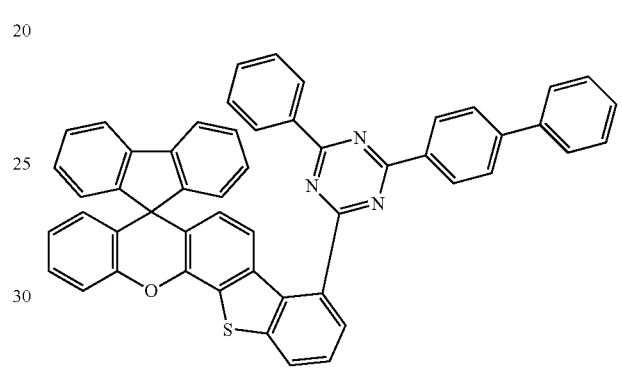
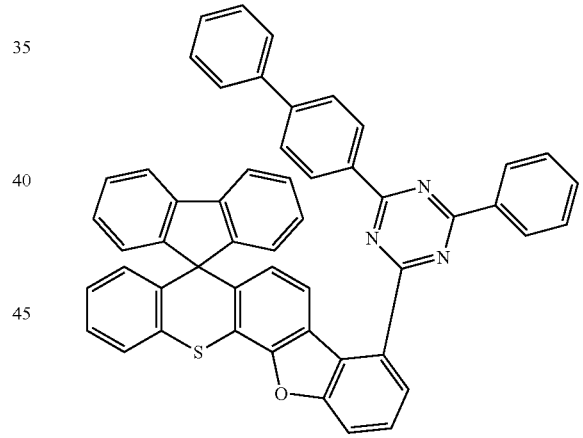
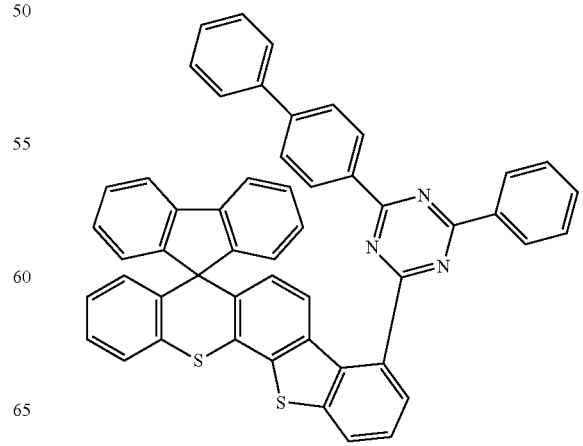

415
-continued
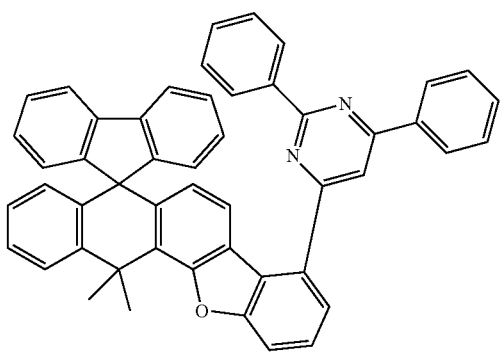
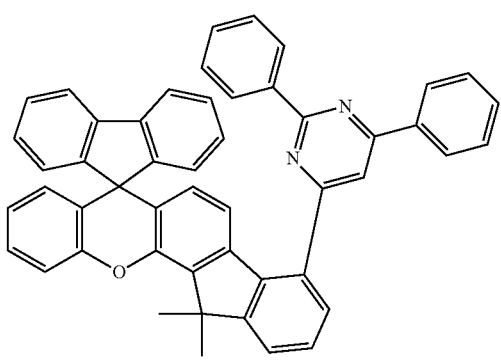
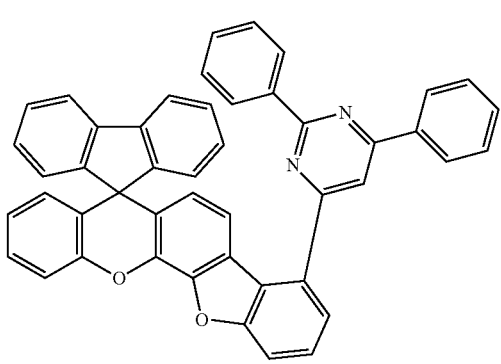
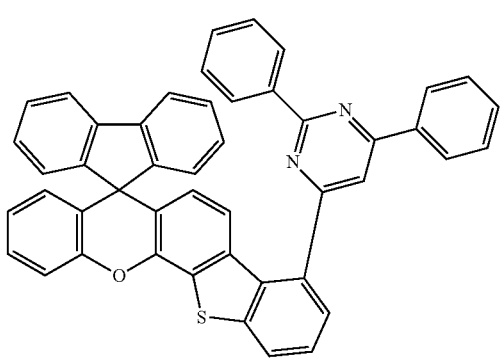
416
-continued
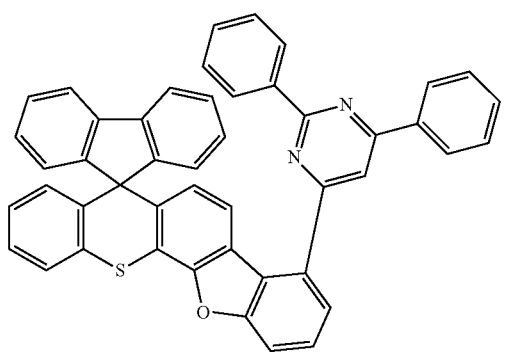
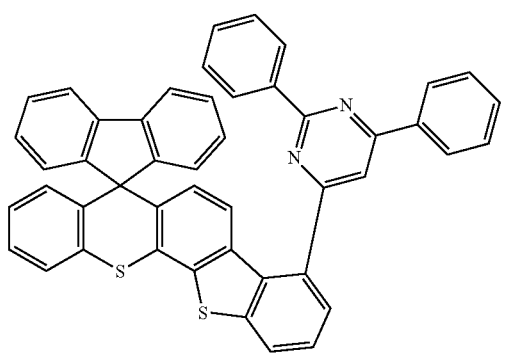
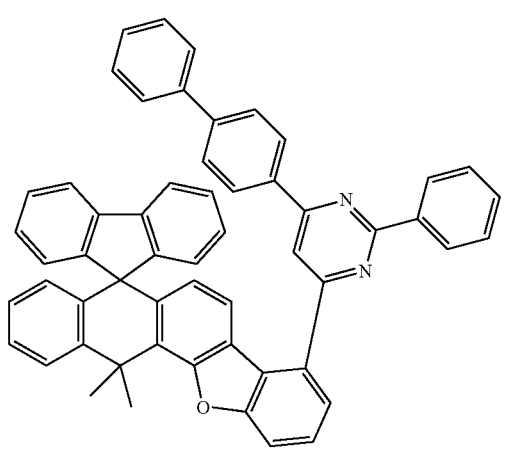
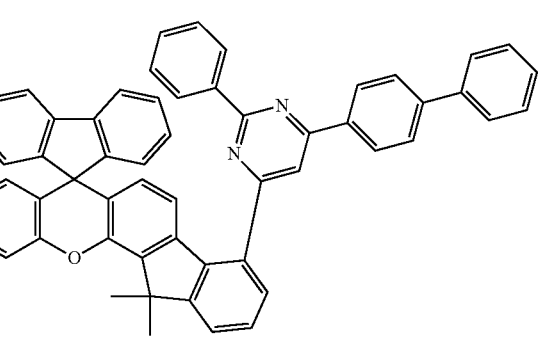

417
-continued
418
-continued
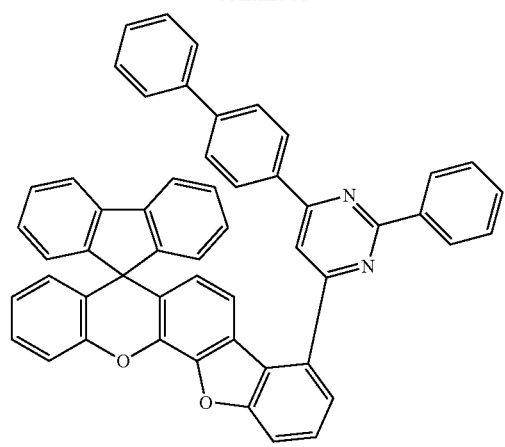
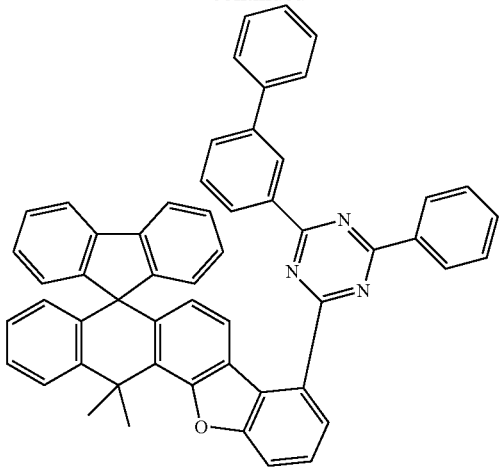

419
-continued
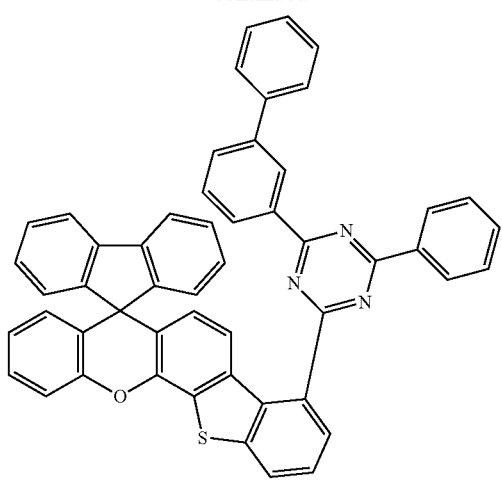
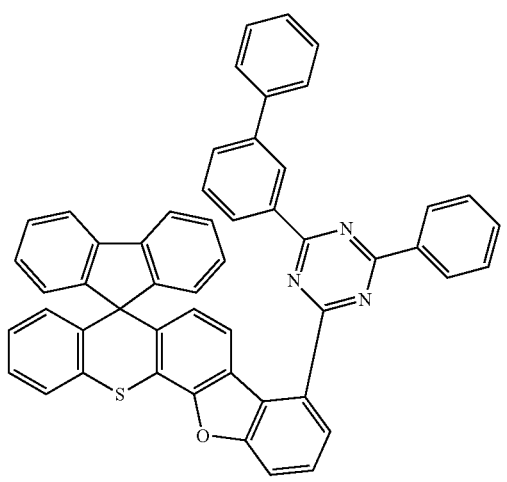
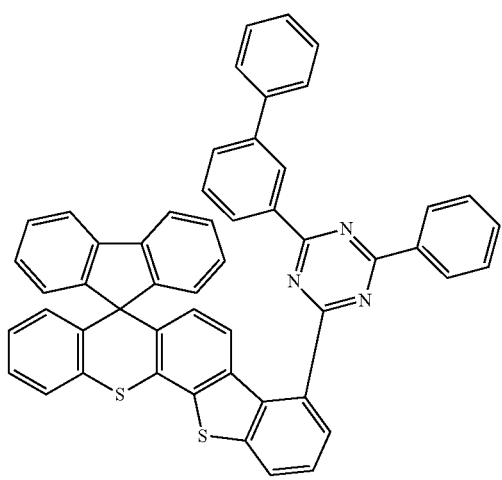
420
-continued
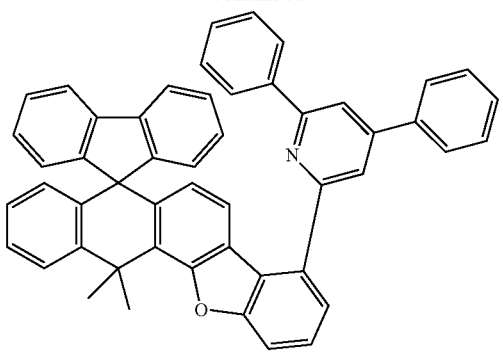
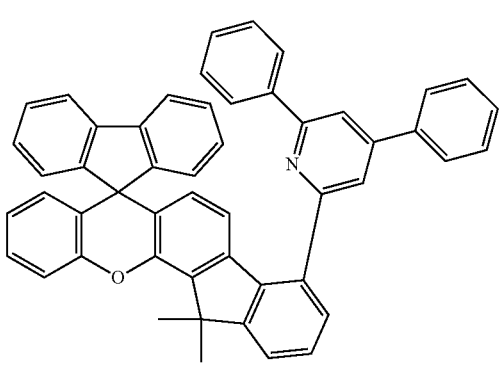
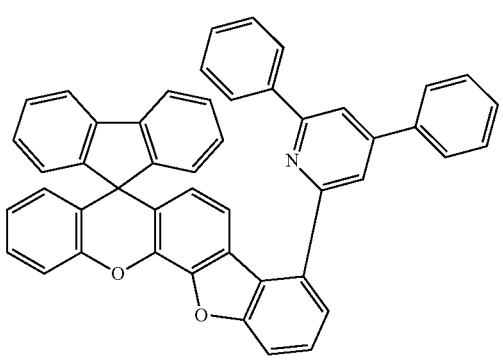
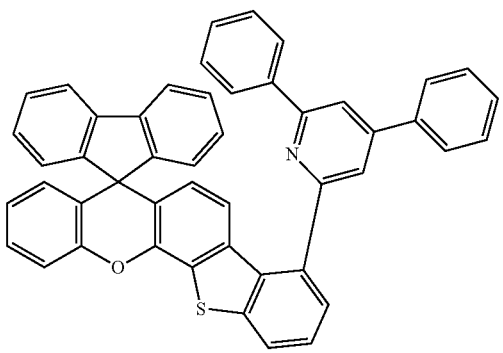

421
-continued
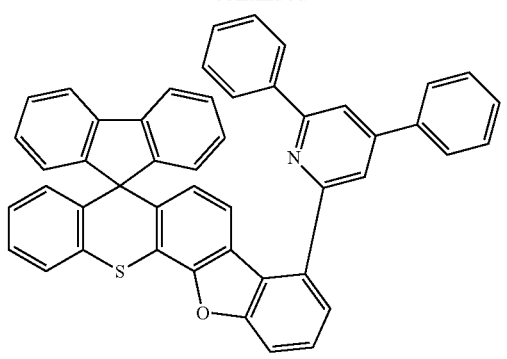
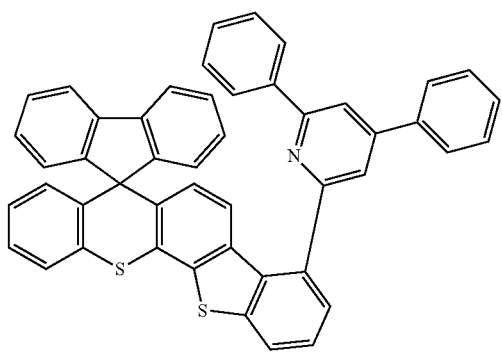
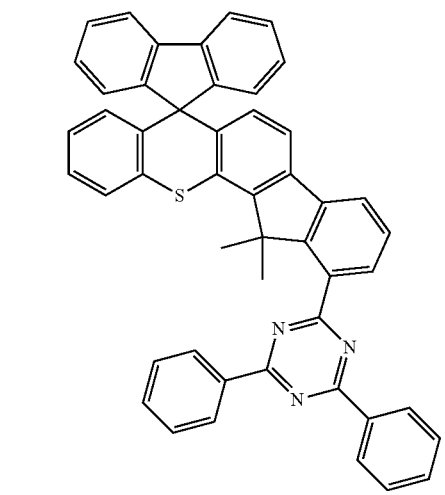
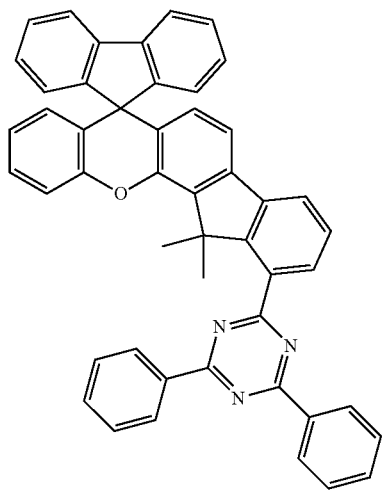
422
-continued
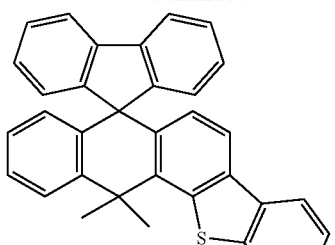
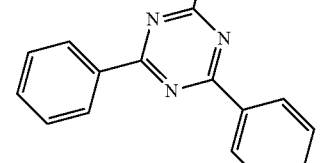
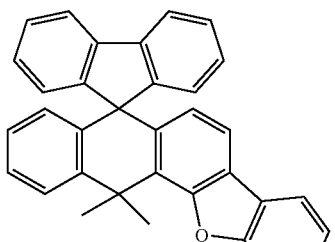
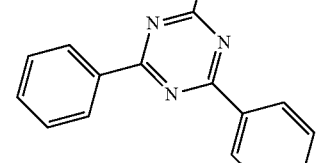
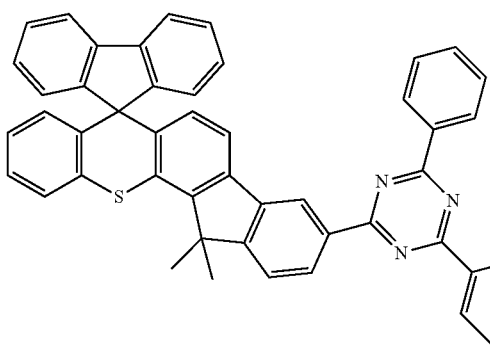
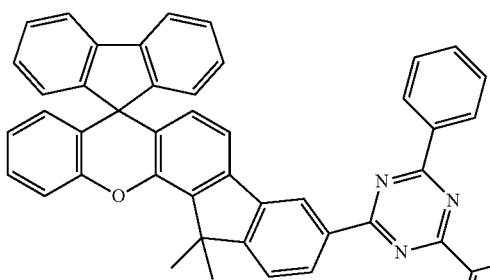

423
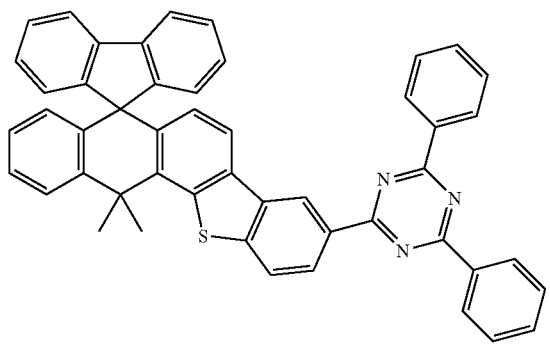
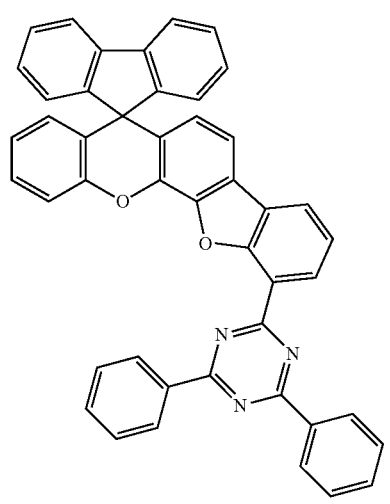
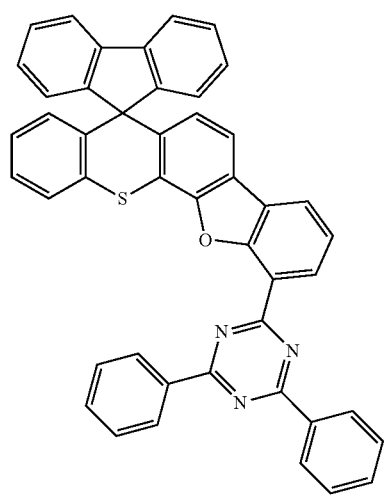
424
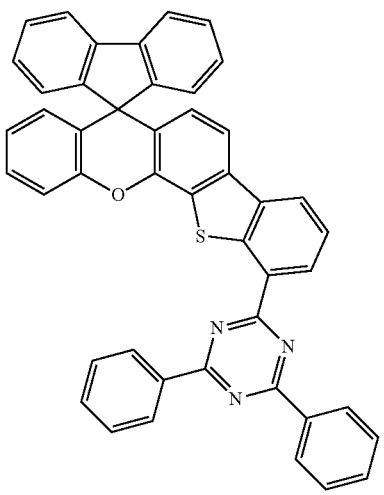
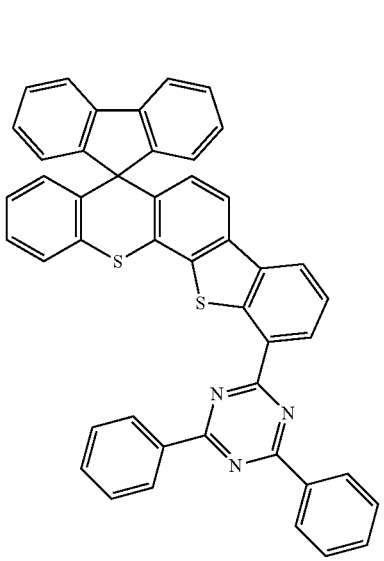
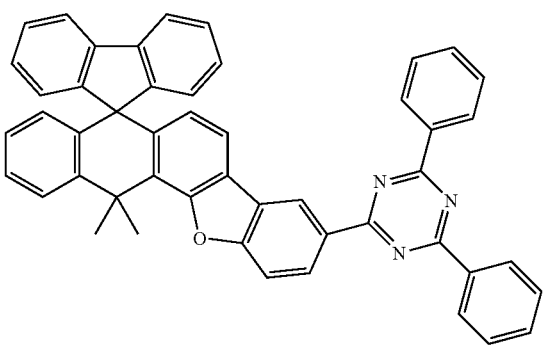

425
-continued
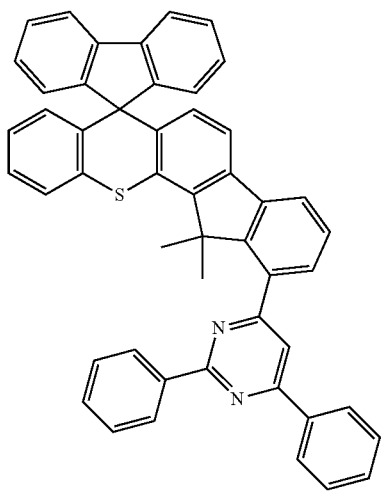
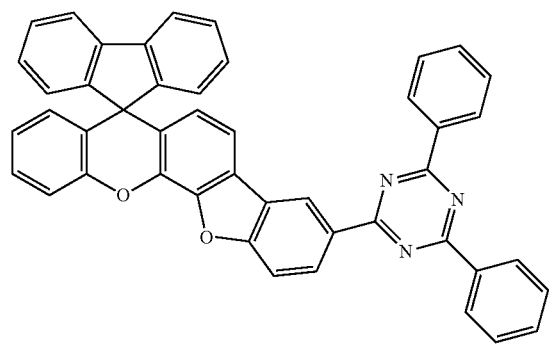
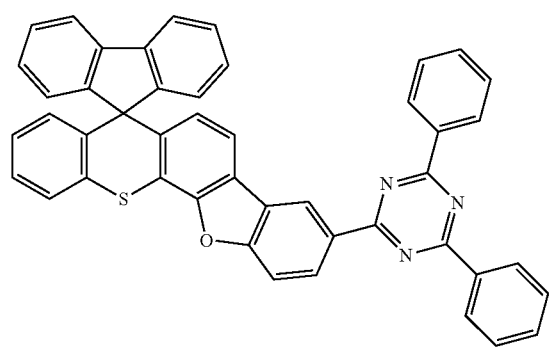
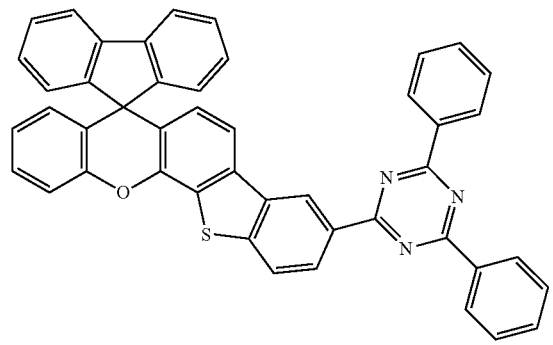
426
-continued
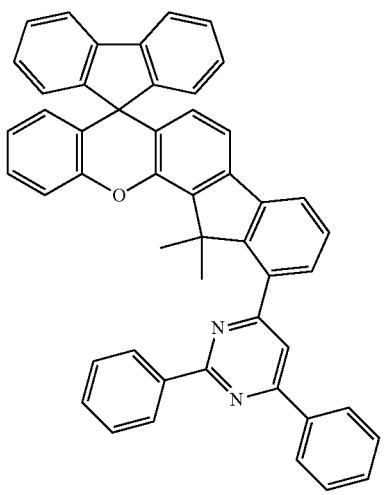
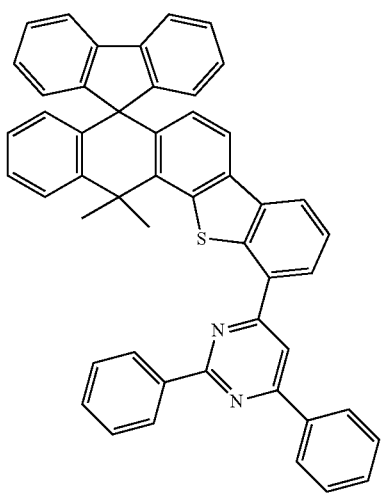
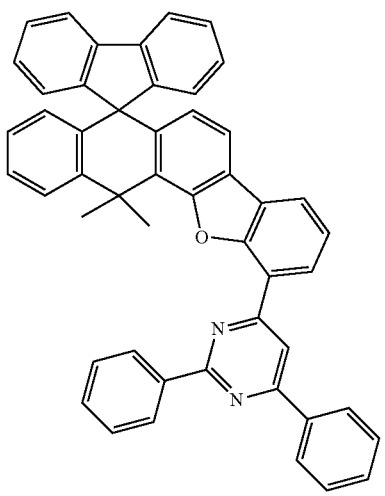

427
-continued
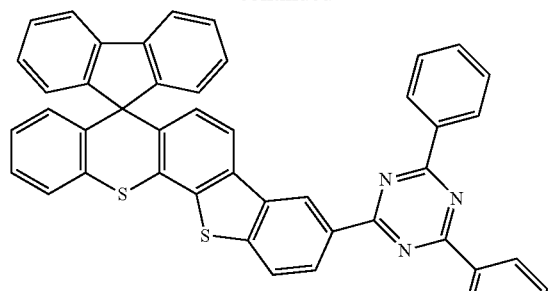
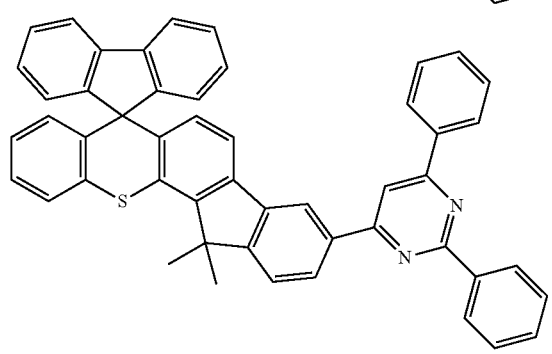
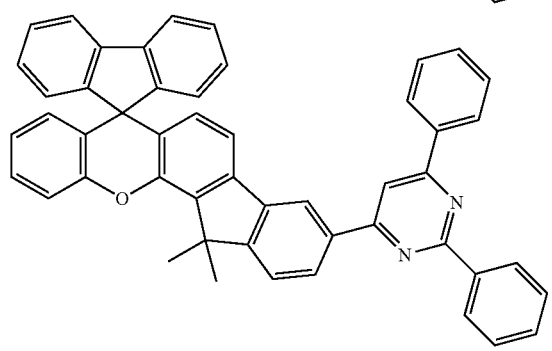
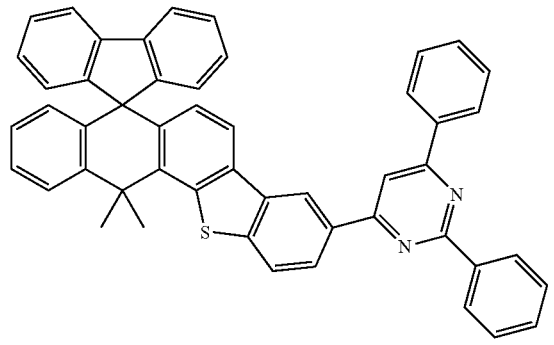
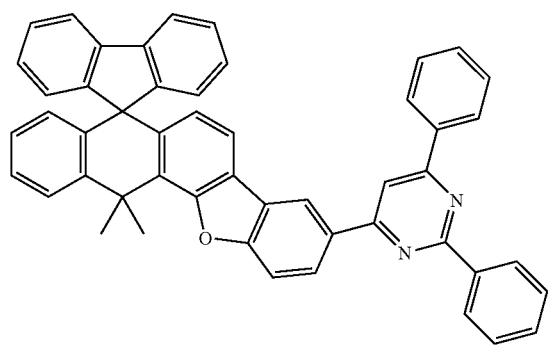
428
-continued
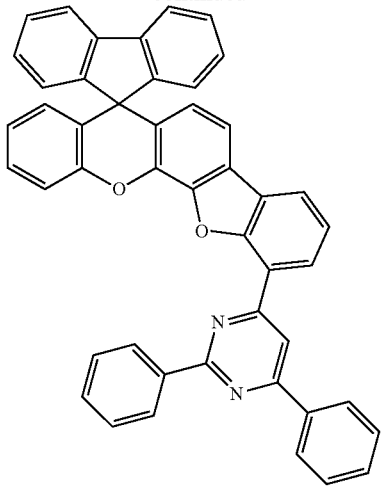
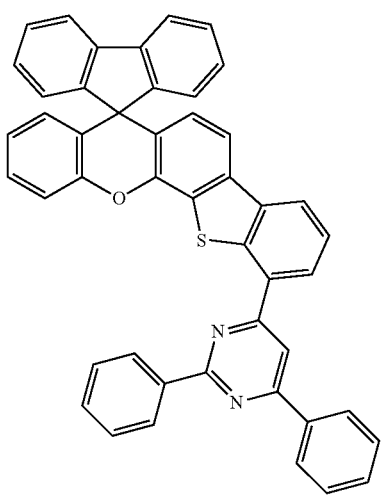
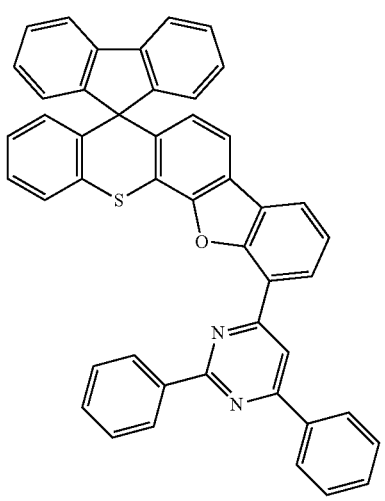

429
-continued
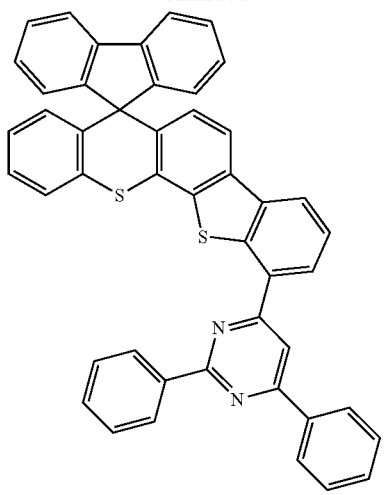
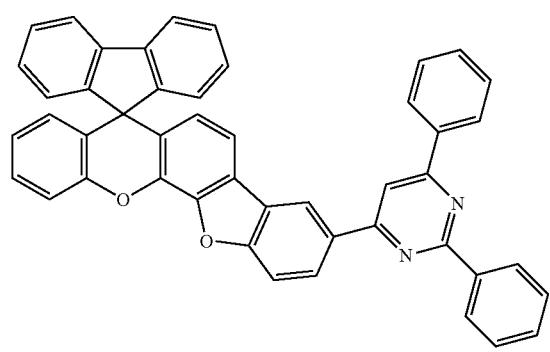
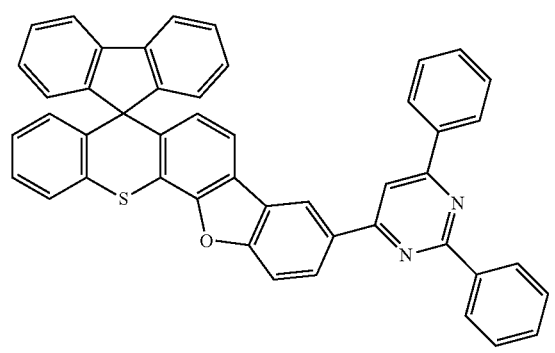
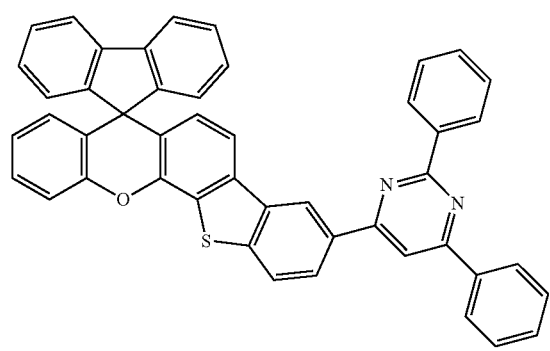
430
-continued
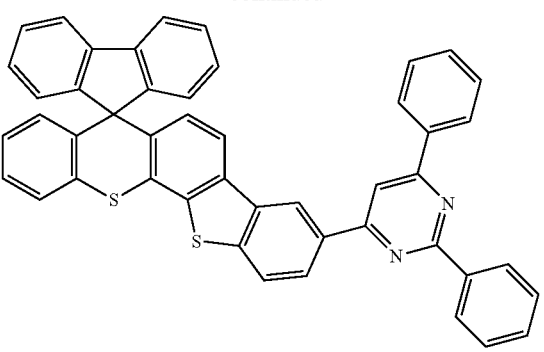
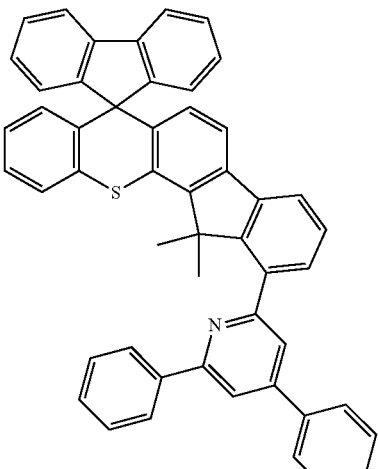
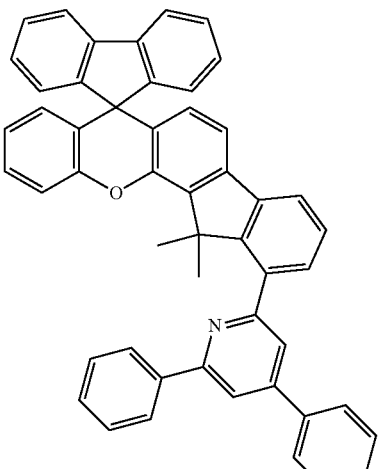

431
-continued
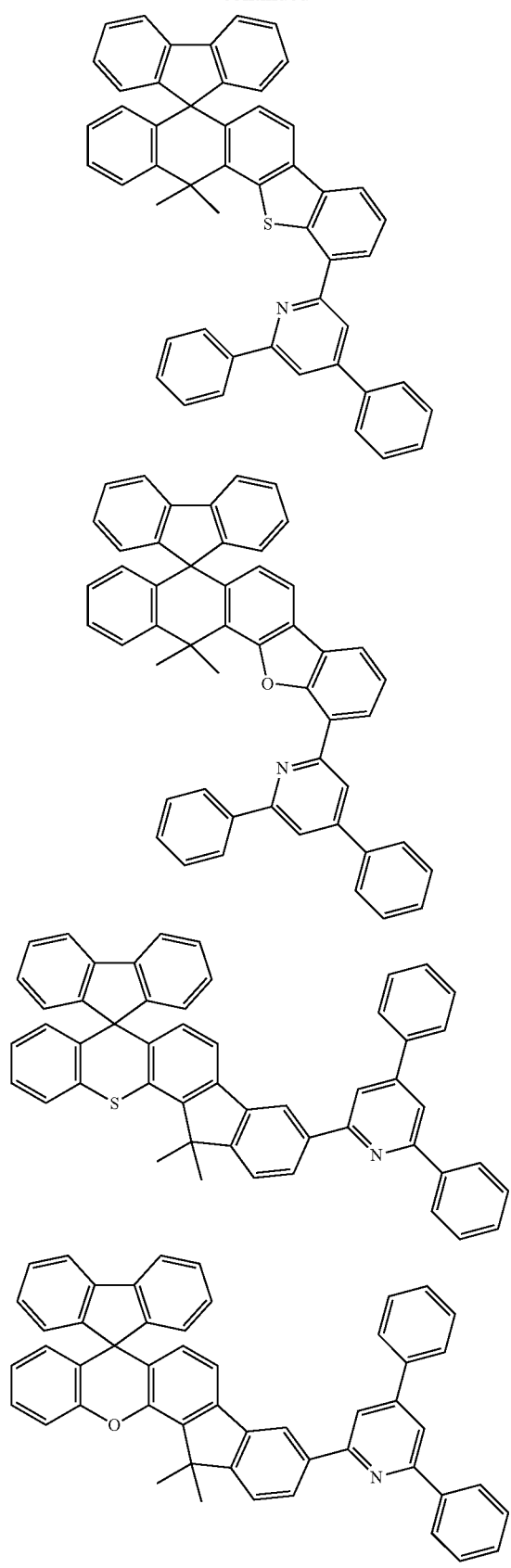
432
-continued
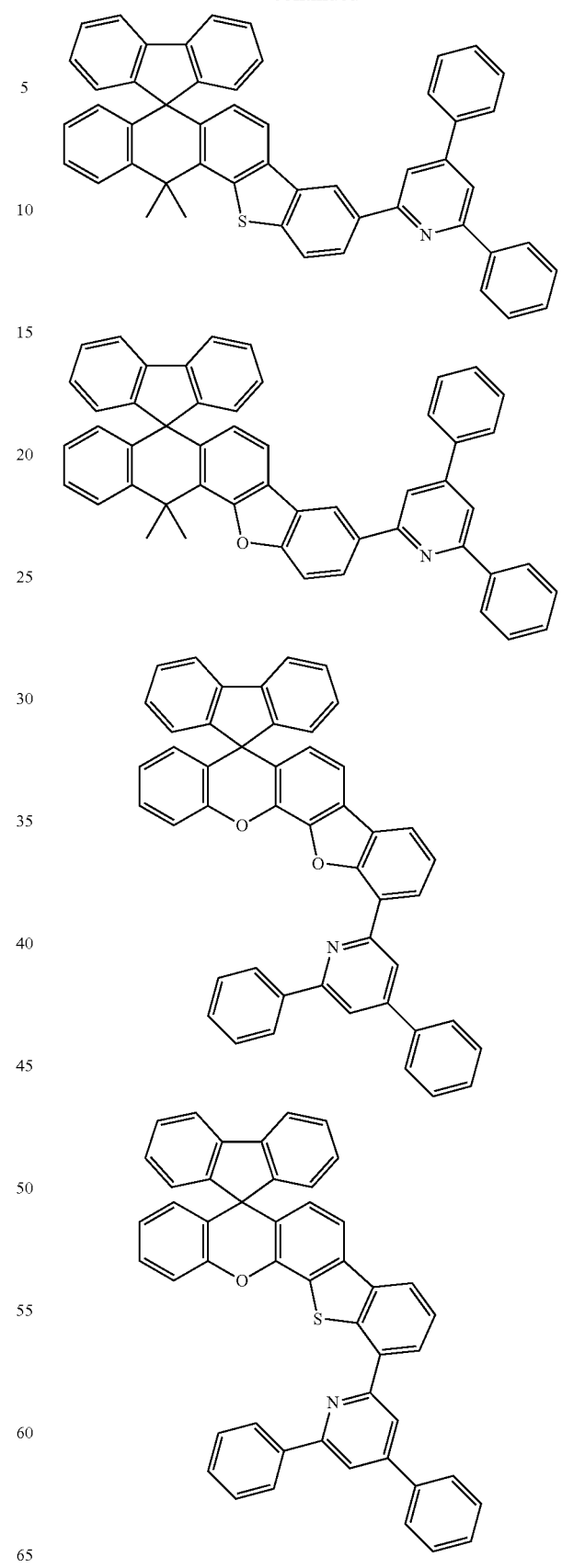

433
-continued
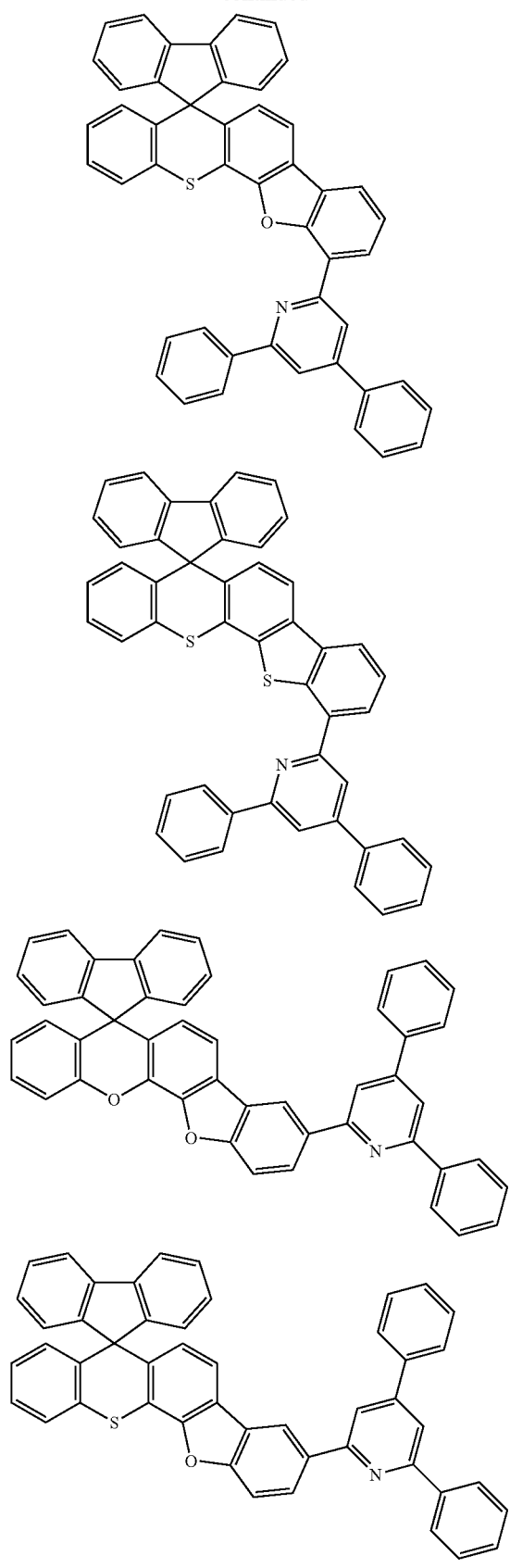
434
-continued
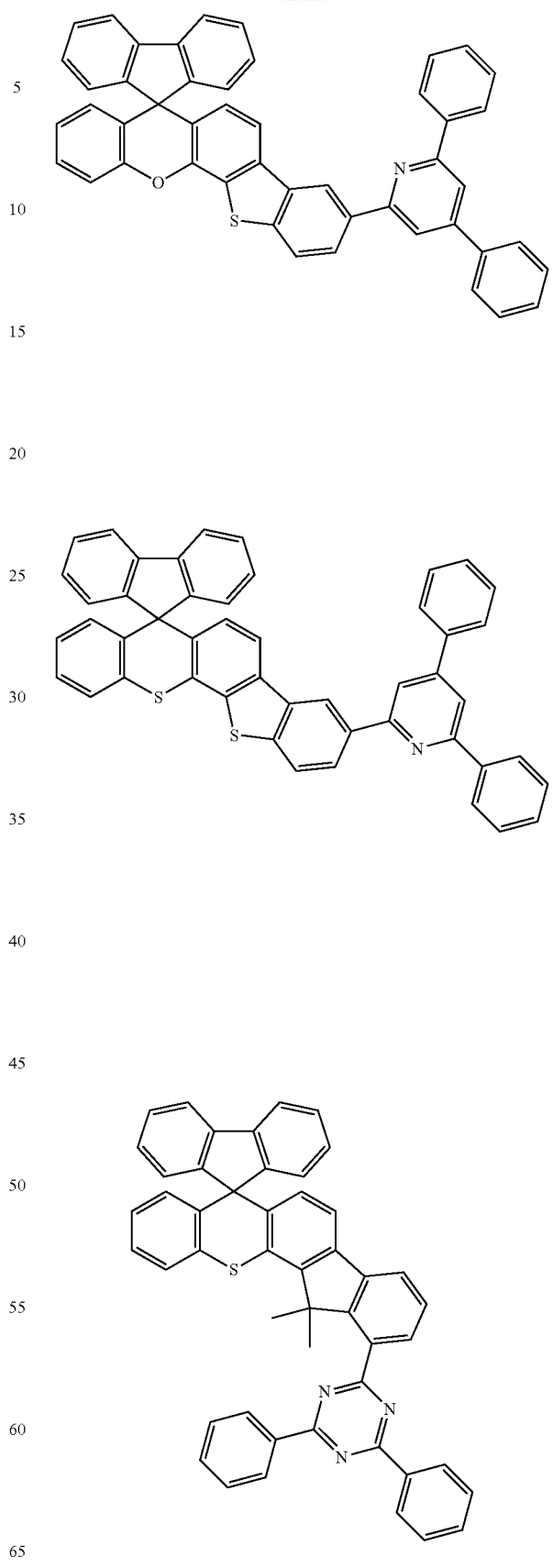

435
-continued
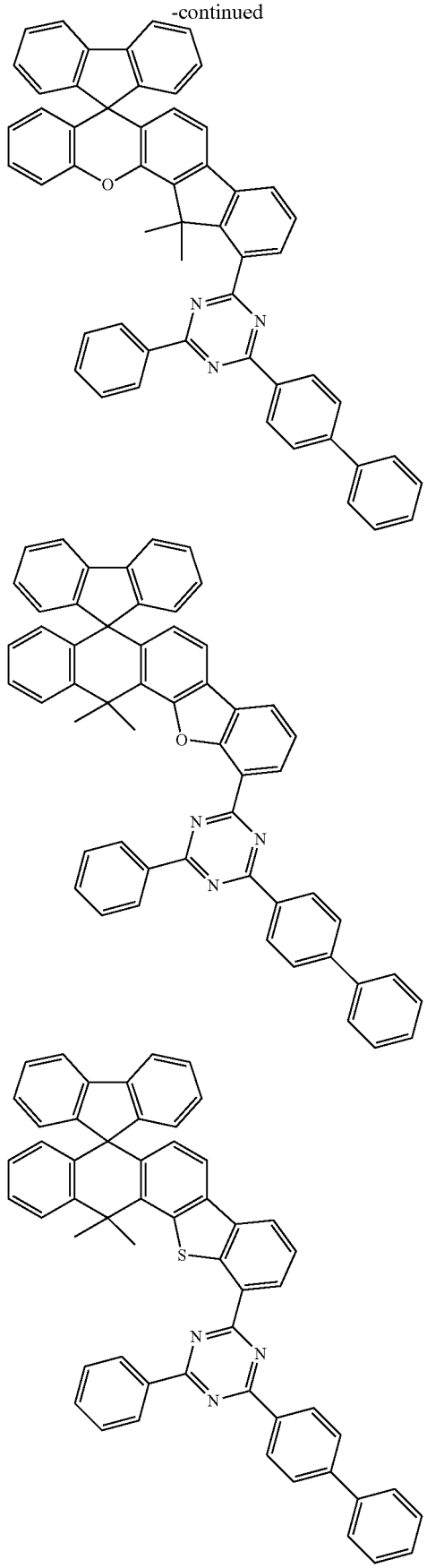
436
-continued
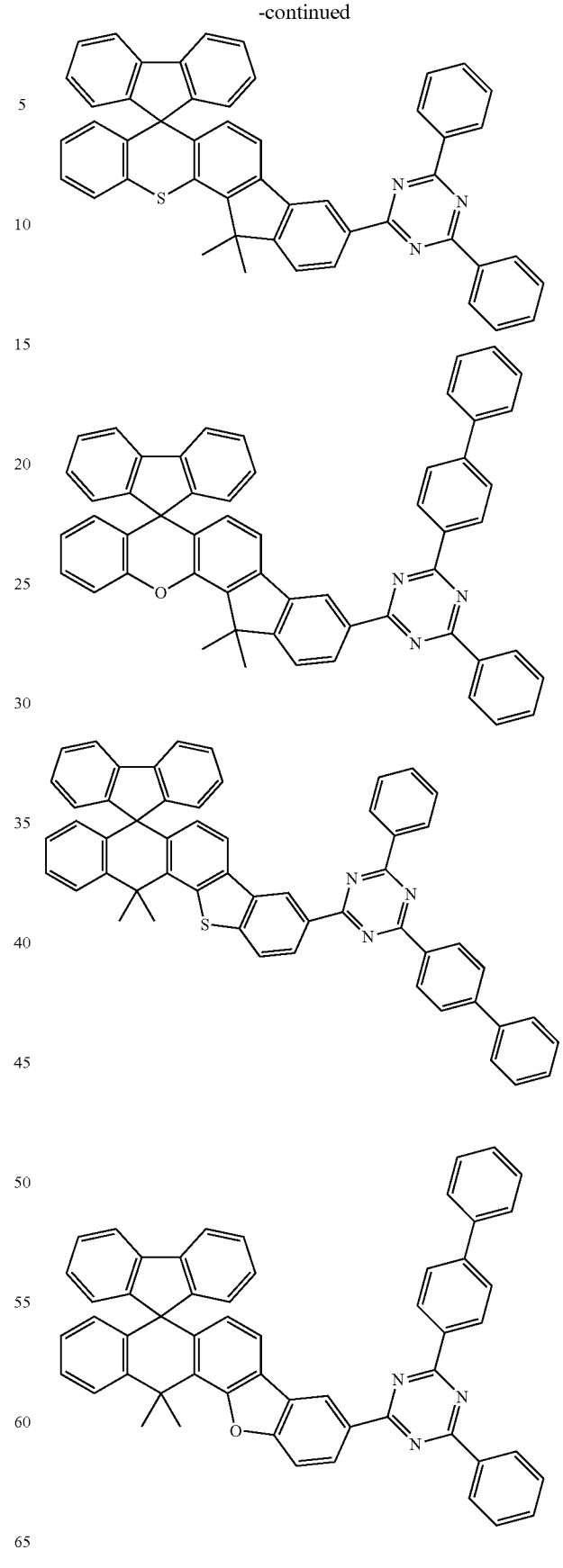

437
-continued
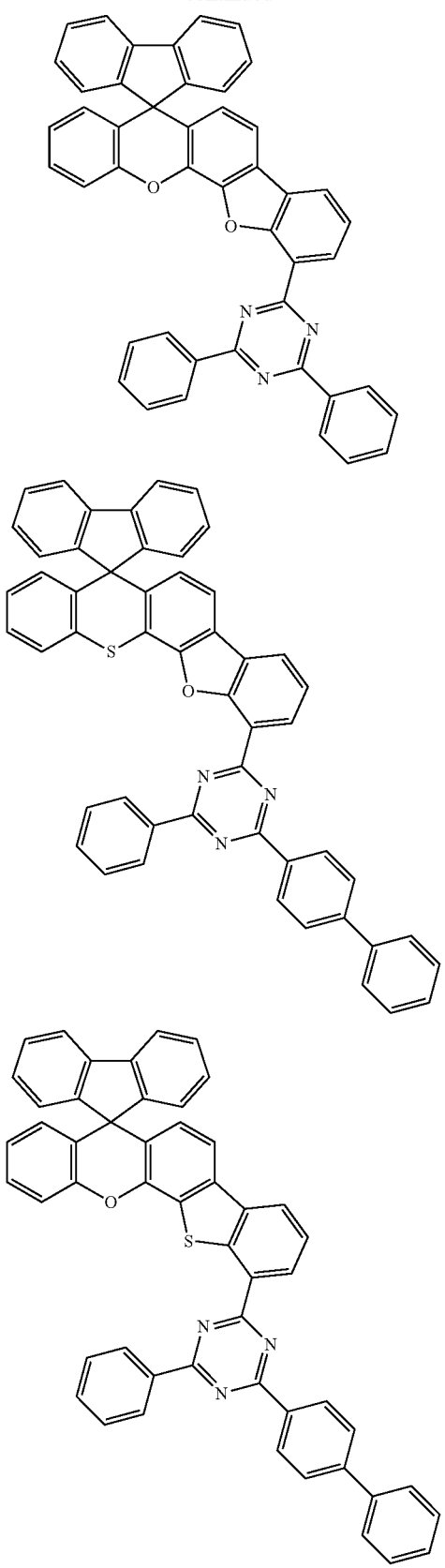
438
-continued
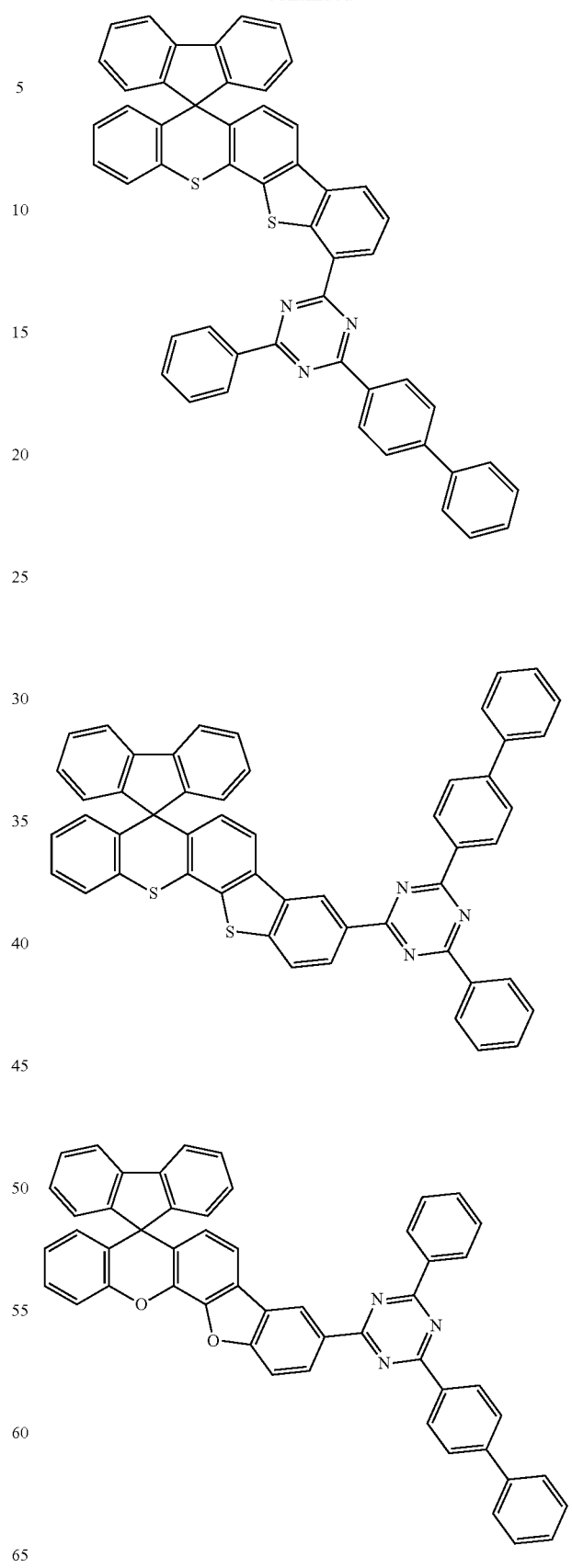

-continued

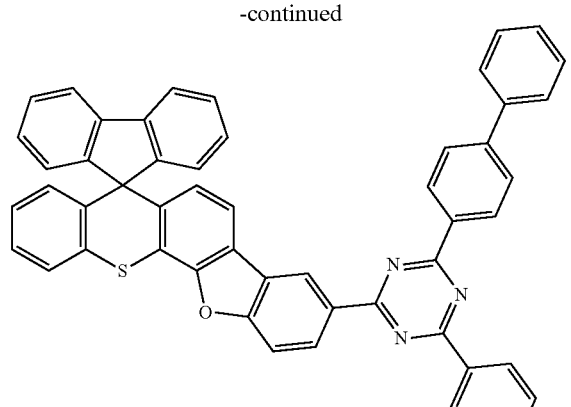

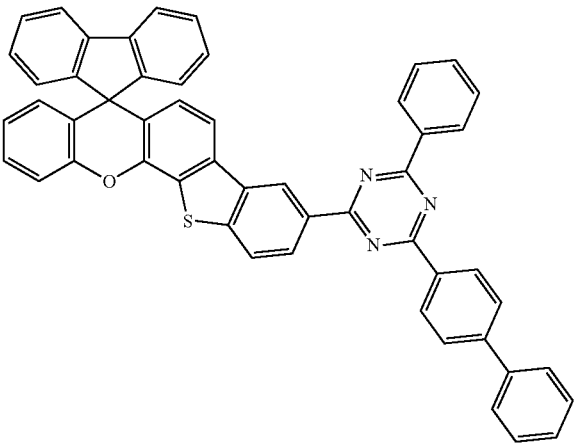

[Reaction Formula 1]

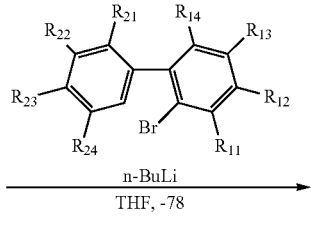

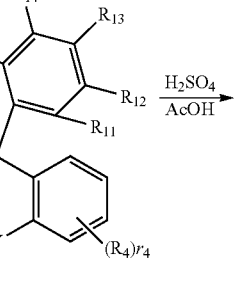

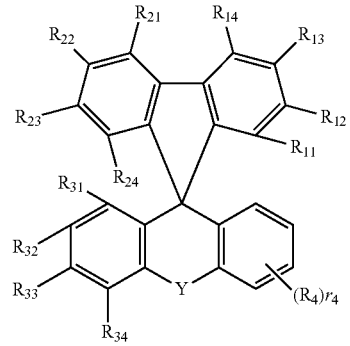

$Y = O, S, CR_{103}R_{104}, SiR_{105}R_{106}$

[Reaction Formula 2]

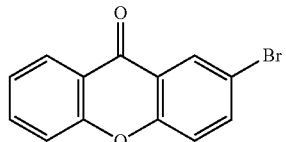

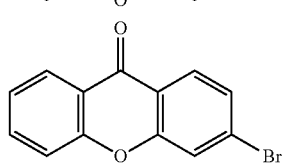

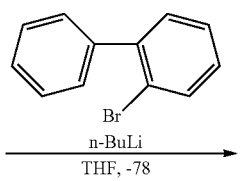

The spiro compound according to an exemplary embodiment of the present specification may be prepared by a preparation method described below. Representative examples will be described in the Preparation Examples described below, but if necessary, a substituent may be added or excluded, and the position of the substituent may be changed. Further, a starting material, a reactant, reaction conditions, and the like may be changed based on the technology known in the art.

For example, for the spiro compound of Chemical Formula 1, a core structure may be prepared as in the following Reaction Formula 1 or 2, and specifically, the spiro compound of Chemical Formula 1 may be prepared via the reactions such as Reaction Formulae 4 to 6. The substituent may be bonded by a method known in the art, and the kind and position of the substituent or the number of substituents may be changed according to the technology known in the art. The specific preparation method will be described below.

441
-continued
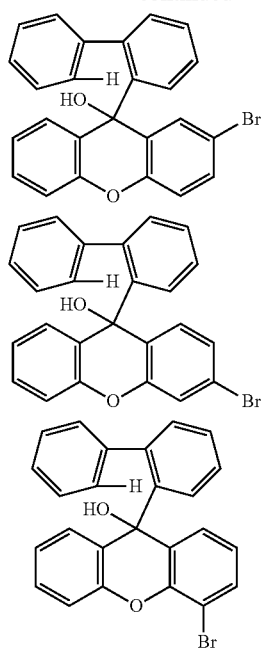
H₂SO₄ / AcOH →
[Reaction Formula 3]
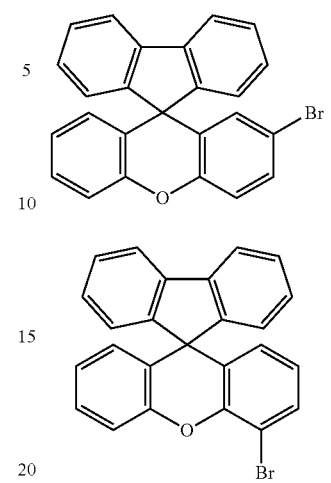
+
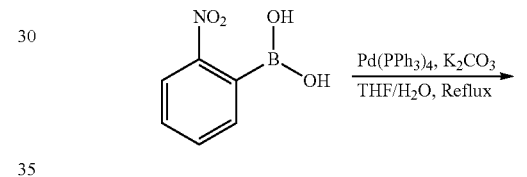
Pd(PPh₃)₄, K₂CO₃ / THF/H₂O, Reflux →
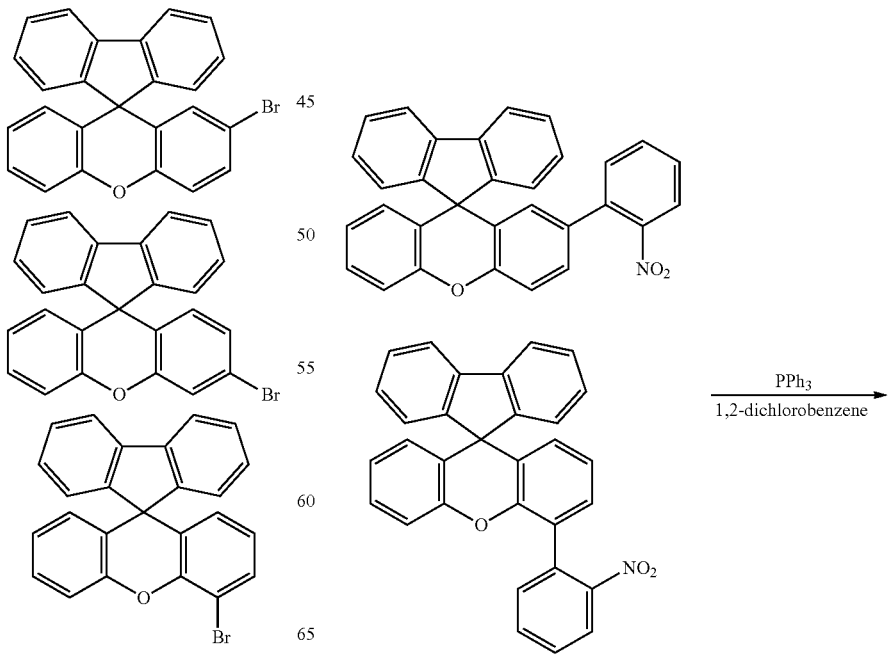
PPh₃ / 1,2-dichlorobenzene →

443
-continued
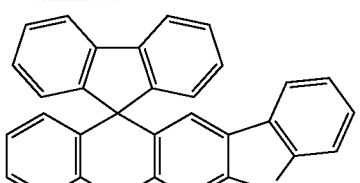
A
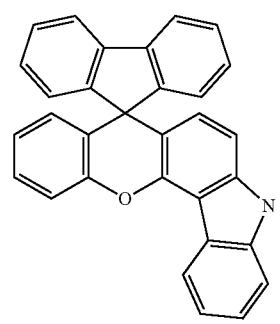
C
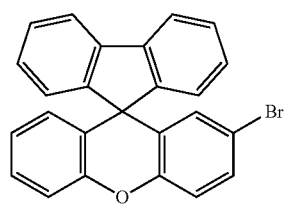
+
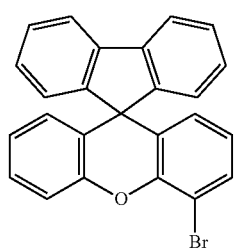
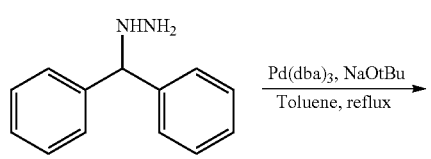
444
-continued
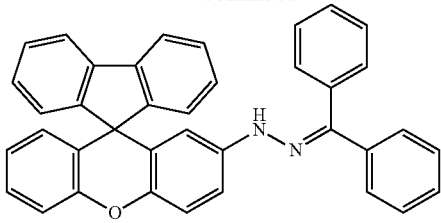
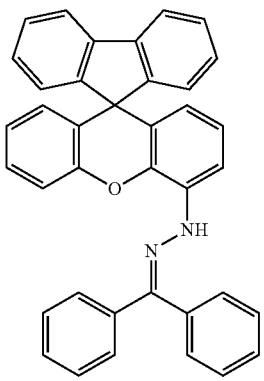
+
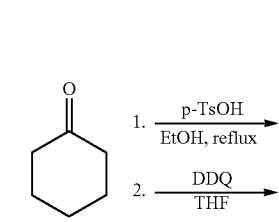
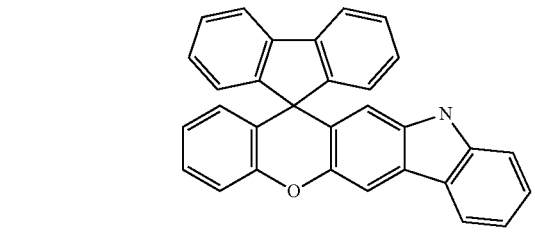
B
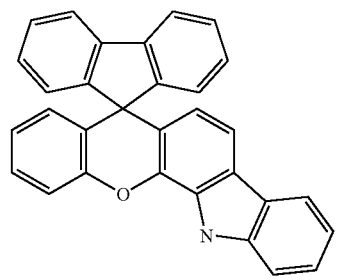
D

[Reaction Formula 4]
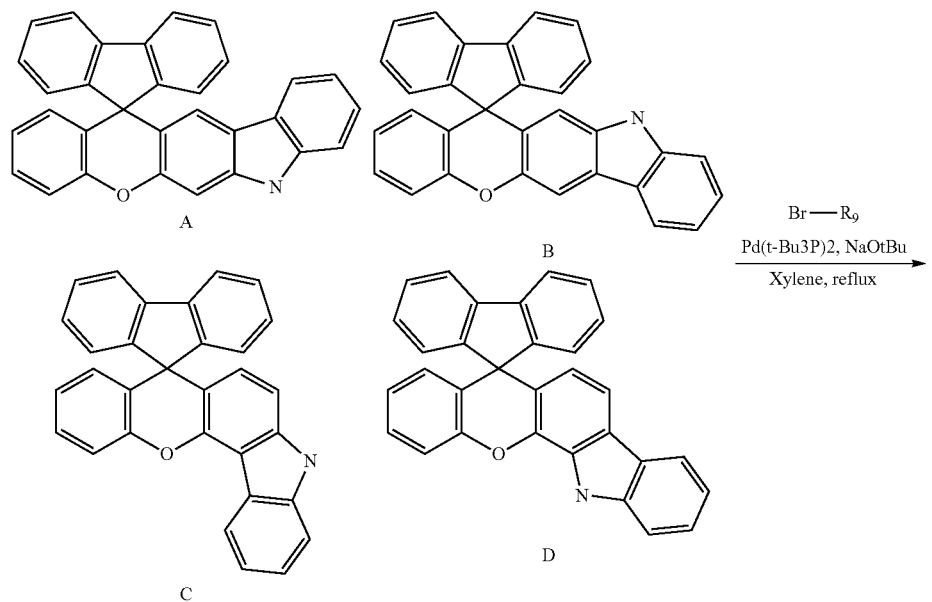
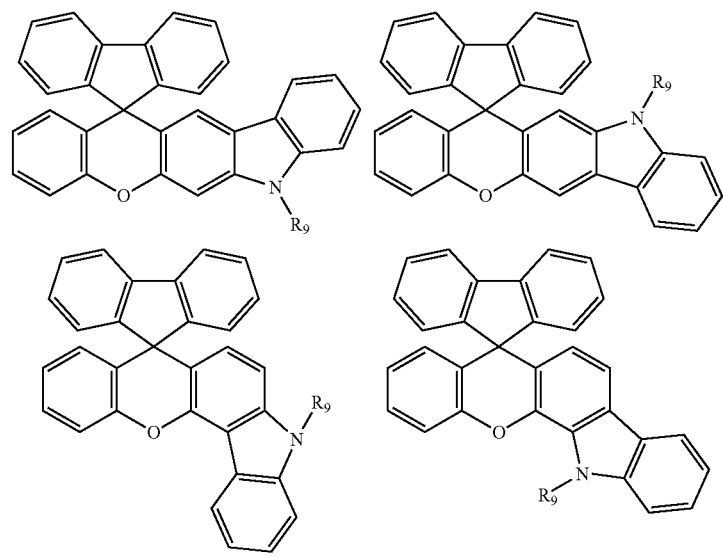

[Reaction Formula 5]
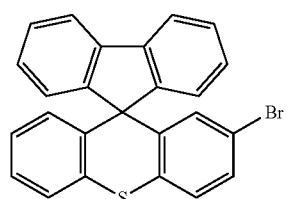
+
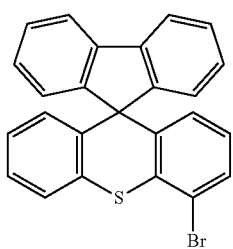
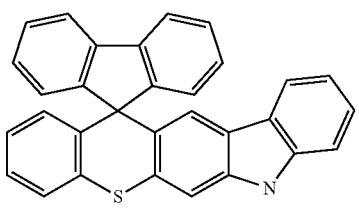
E
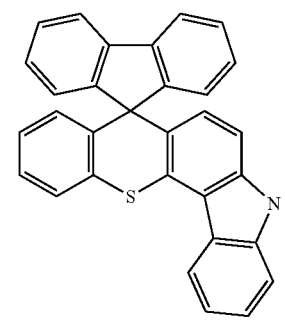
G
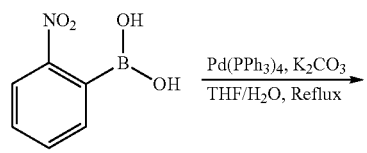 $\xrightarrow{\text{Pd(PPh}_3)_4, \text{K}_2\text{CO}_3}{\text{THF/H}_2\text{O, Reflux}}$
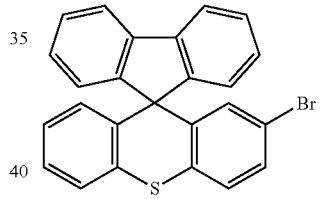
+
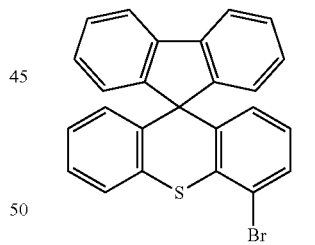
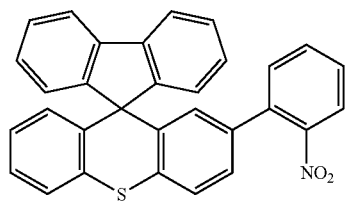 $\xrightarrow{\text{PPh}_3}{\text{1,2-dichlorobenzene}}$
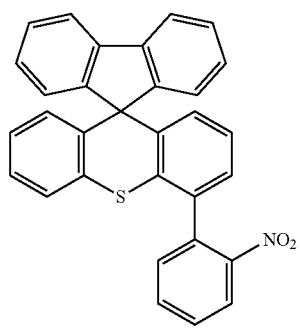
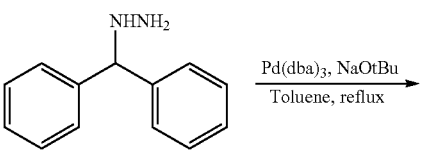 $\xrightarrow{\text{Pd(dba)}_3, \text{NaOtBu}}{\text{Toluene, reflux}}$ 449
-continued
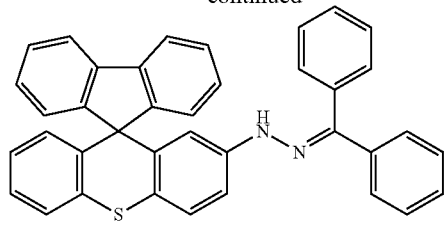
+
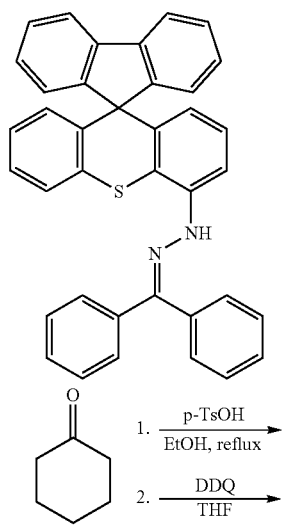
450
-continued
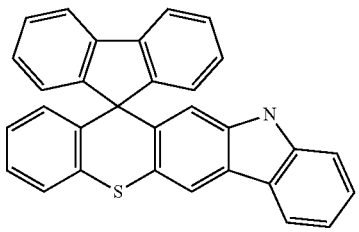
F
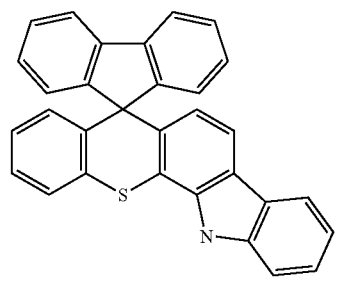
H
[Reaction Formula 6]
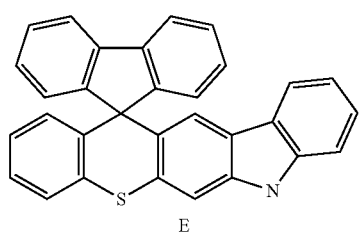
E
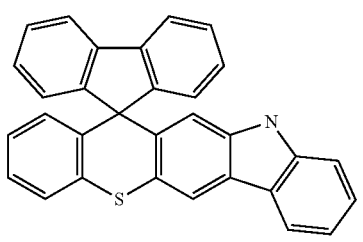
F
Br—R$_9$
Pd(t-Bu$_3$P)$_2$, NaOtBu
Xylene, reflux
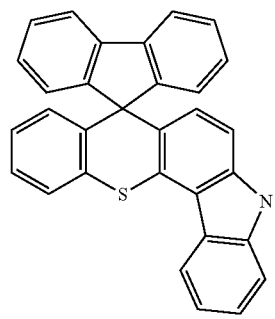
G
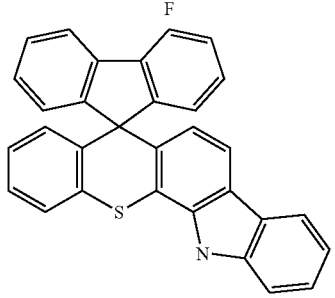
H -continued

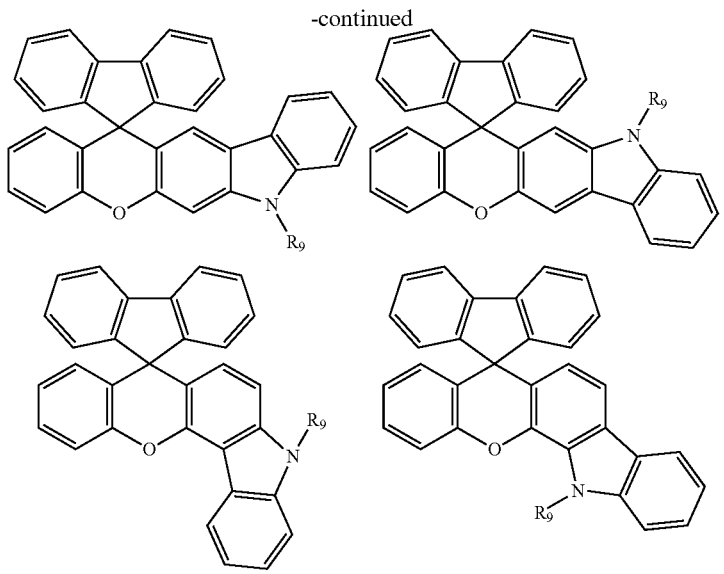

Reaction Formulae 1 to 6 only describe an example of a method for synthesizing the core of Chemical Formula 1, but the method is not limited thereto.

In Reaction Formulae 1 to 6, the definitions of Y, R11 to R14, R21 to R24, R31 to R34, R4, r4, and R9 are the same as those defined in Chemical Formula 1. The specific preparation method will be described below.

Further, the present specification provides an organic electronic device including the above-described compound.

An exemplary embodiment of the present specification provides an organic electronic device including: a first electrode; a second electrode disposed to face the first electrode; and an organic material layer having one or more layers disposed between the first electrode and the second electrode, in which one or more layers of the organic material layer include the compound.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element may be further included.

The organic material layer of the organic electronic device of the present specification may also be composed of a single-layered structure, but may be composed of a multi-layered structure in which an organic material layer having two or more layers is stacked. For example, as a representative example of the organic electronic device of the present invention, an organic light emitting device may have a structure including a hole injection layer, a hole transporting layer, a light emitting layer, an electron transporting layer, an electron injection layer, an electron blocking layer, a hole blocking layer, and the like as organic material layers. However, the structure of the organic electronic device is not limited thereto, and may include a fewer number of organic layers.

According to an exemplary embodiment of the present specification, the organic electronic device may be selected from the group consisting of an organic light emitting device, an organic phosphorescent device, an organic solar cell, an organic photoconductor (OPC), and an organic transistor.

Hereinafter, an organic light emitting device will be exemplified.

In an exemplary embodiment of the present specification, the organic material layer includes a light emitting layer, and the light emitting layer includes the spiro compound represented by Chemical Formula 1.

In an exemplary embodiment of the present specification, the organic material layer includes a light emitting layer, and the light emitting layer includes the compound represented by Chemical Formula 1 as a host of the light emitting layer.

According to an exemplary embodiment of the present specification, the organic material layer includes a light emitting layer, and the light emitting layer includes the spiro compound represented by Chemical Formula 1 as a phosphorescent host or a fluorescent host of the light emitting layer.

In an exemplary embodiment of the present specification, the organic material layer includes the spiro compound represented by Chemical Formula 1 as a host of the light emitting layer, and includes another organic compound, a metal or a metal compound as a dopant.

In an exemplary embodiment of the present specification, the organic material layer includes the spiro compound represented by Chemical Formula 1 as a host of the light emitting layer, and includes an iridium complex as a dopant.

In an exemplary embodiment of the present specification, the organic material layer includes a hole injection layer or a hole transporting layer, and the hole injection layer or the hole transporting layer includes the spiro compound represented by Chemical Formula 1.

In an exemplary embodiment of the present specification, the organic material layer includes an electron transporting layer or an electron injection layer, and the electron transporting layer or the electron injection layer includes the spiro compound represented by Chemical Formula 1.

In an exemplary embodiment of the present specification, the organic material layer includes an electron blocking layer, and the electron blocking layer includes the spiro compound represented by Chemical Formula 1.

In an exemplary embodiment of the present specification, the organic light emitting device further includes one or two or more layers selected from the group consisting of a hole injection layer, a hole transporting layer, a light emitting layer, an electron transporting layer, an electron injection layer, a hole blocking layer, and an electron blocking layer.

In an exemplary embodiment of the present specification, the organic light emitting device includes: a first electrode; a second electrode disposed to face the first electrode; a light emitting layer disposed between the first electrode and the second electrode; and an organic material layer having two or more layers disposed between the light emitting layer and the first electrode, or between the light emitting layer and the second electrode, in which at least one of the organic material layer having two or more layers includes the spiro compound. In an exemplary embodiment of the present specification, as the organic material layer having two or more layers, two or more may be selected from the group consisting of an electron transporting layer, an electron injection layer, a layer which transports and injects electrons simultaneously, and a hole blocking layer.

In an exemplary embodiment of the present specification, the organic material layer includes an electron transporting layer having two or more layers, and at least one of the electron transporting layer having two or more layers includes the spiro compound. Specifically, in an exemplary embodiment of the present specification, the spiro compound may also be included in one layer of the electron transporting layer having two or more layers, and may be included in each layer of the electron transporting layer having two or more layers.

In addition, in an exemplary embodiment of the present specification, when the spiro compound is included in each of the electron transporting layer having two or more layers, the other materials except for the spiro compound may be the same as or different from each other.

In an exemplary embodiment of the present specification, the organic material layer further includes a hole injection layer or a hole transporting layer, which includes a compound including an arylamino group, a carbazolyl group, or a benzocarbazolyl group, in addition to the organic material layer including the spiro compound.

In another exemplary embodiment, the organic light emitting device may be an organic light emitting device having a structure (normal type) in which a positive electrode, an organic material layer having one or more layers, and a negative electrode are sequentially stacked on a substrate.

When the organic material layer including the spiro compound of Chemical Formula 1 is an electron transporting layer, the electron transporting layer may further include an n-type dopant. As the n-type dopant, those known in the art may be used, and for example, a metal or a metal complex may be used. According to an example, the electron transporting layer including the compound of Chemical Formula 1 may further include LiQ.

In still another exemplary embodiment, the organic light emitting device may be an organic light emitting device having a reverse-direction structure (inverted type) in which a negative electrode, an organic material layer having one or more layers, and a positive electrode are sequentially stacked on a substrate.

In an exemplary embodiment of the present specification, the organic material layer includes a light emitting layer, and the light emitting layer includes a compound represented by the following Chemical Formula A-1.

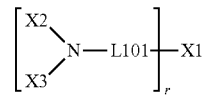

[Chemical Formula A-1]

In Chemical Formula A-1,

X1 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L101 is a direct bond; a substituted or unsubstituted arylene group; or a substituted or unsubstituted heteroarylene group, X2 and X3 are the same as or different from each other, and are each independently a substituted or unsubstituted aryl group; a substituted or unsubstituted silyl group; a substituted or unsubstituted alkyl group; a substituted or unsubstituted aralkyl group; or a substituted or unsubstituted heteroaryl group, or may be bonded to each other to form a substituted or unsubstituted ring, r is an integer of 1 or more, and when r is 2 or more, substituents in the parenthesis are the same as or different from each other.

According to an exemplary embodiment of the present specification, the organic material layer includes a light emitting layer, and the light emitting layer includes the compound represented by Chemical Formula A-1 as a dopant of the light emitting layer.

In an exemplary embodiment of the present specification, L101 is a direct bond.

In an exemplary embodiment of the present specification, r is 2.

According to an exemplary embodiment of the present specification, X1 is a substituted or unsubstituted divalent pyrene group.

In another exemplary embodiment, X1 is a divalent pyrene group which is unsubstituted or substituted with an alkyl group.

In still another exemplary embodiment, X1 is a divalent pyrene group.

In an exemplary embodiment of the present specification, x2 and X3 are the same as or different from each other, and are each independently a substituted or unsubstituted aryl group having 6 to 30 carbon atoms; a substituted or unsubstituted alkyl group having 1 to 30 carbon atoms; or a substituted or unsubstituted heteroaryl group having 2 to 30 carbon atoms.

According to an exemplary embodiment of the present specification, X2 and X3 are the same as or different from each other, and are each independently a substituted or unsubstituted aryl group having 6 to 30 carbon atoms.

In an exemplary embodiment of the present specification, X2 and X3 are the same as or different from each other, and are each independently an aryl group having 6 to 30 carbon atoms, which is unsubstituted or substituted with a germanium group.

In an exemplary embodiment of the present specification, X2 and X3 are a phenyl group which is unsubstituted or substituted with a trimethylgermanium group.

In an exemplary embodiment of the present specification, the organic material layer includes a light emitting layer, and the light emitting layer includes a compound represented by the following Chemical Formula A-2.

[Chemical Formula A-2]

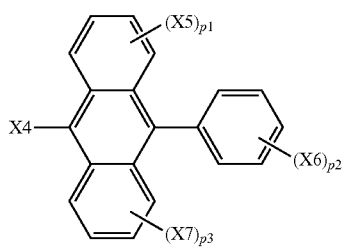

In Chemical Formula A-2,

X4 is a 1-naphthyl group, a 2-naphthyl group, a 1-anthracenyl group, a 2-anthracenyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

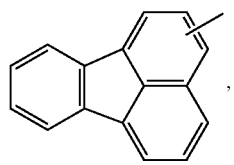

,

X6 is a phenyl group, a 1-naphtyl group, a 2-naphtyl group, a 1-anthracenyl group, a 2-anthracenyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthracenyl group, a 4'-methylbiphenylyl group, a 4"-t-butyl-p-terphenyl-4-yl group, or a 3-fluoranthenyl group, X5 and X7 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, p2 is an integer from 1 to 5, p1 and p3 are each an integer from 1 to 4, and when p1 to p3 are each 2 or more, substituents in the parenthesis are the same as or different from each other.

According to an exemplary embodiment of the present specification, the organic material layer includes a light emitting layer, and the light emitting layer includes the compound represented by Chemical Formula A-2 as a host of the light emitting layer.

In an exemplary embodiment of the present specification, X4 is a 1-naphthyl group, a 2-naphthyl group, a 1-anthracenyl group, a 2-anthracenyl group, a 1-phenanthryl group, a 2-phenanthryl group, a 4-phenanthryl group, a 1-naphthacenyl group, or a 1-pyrenyl group.

In an exemplary embodiment of the present specification, X4 is a 1-naphthyl group, a 2-naphthyl group, or a 1-anthracenyl group.

In an exemplary embodiment of the present specification, X4 is a 1-naphthyl group.

In an exemplary embodiment of the present specification, X6 is a phenyl group, a 1-naphthyl group, a 2-naphthyl group, a 1-anthracenyl group, a 2-anthracenyl group, a 1-phenanthryl group, a 2-phenanthryl group, a 4-phenanthryl group, a 1-naphthacenyl group, or a 1-pyrenyl group.

In an exemplary embodiment of the present specification, X6 is a phenyl group, a 1-naphthyl group, a 2-naphthyl group, or a 1-anthracenyl group.

According to an exemplary embodiment of the present specification, X6 is a 2-naphthyl group, and p2 is 1. In an exemplary embodiment of the present specification, X5 and X7 are hydrogen.

For example, the structure of the organic light emitting device of the present specification may have a structure as illustrated in FIGS. 1 and 2, but is not limited thereto.

FIG. 1 exemplifies the structure of an organic light emitting device 10 in which a first electrode 30, a light emitting layer 40, and a second electrode 50 are sequentially stacked on a substrate 20. FIG. 1 is an exemplified structure of the organic light emitting device according to an exemplary embodiment of the present specification, and may further include other organic material layers.

FIG. 2 exemplifies the structure of an organic light emitting device in which a first electrode 30, a hole injection layer 60, a hole transporting layer 70, an electron blocking layer 80, a light emitting layer 40, an electron transporting layer 90, an electron injection layer 100, and a second electrode 50 are sequentially stacked on a substrate 20. FIG. 2 is an exemplified structure according to exemplary embodiments of the present specification, and may further include other organic material layers.

The organic light emitting device of the present specification may be manufactured by the materials and methods known in the art, except that one or more layers of the organic material layer include the compound of the present specification, that is, the compound.

When the organic light emitting device includes a plurality of organic material layers, the organic material layers may be formed of the same material or different materials.

The organic light emitting device of the present specification may be manufactured by the materials and methods known in the art, except that one or more layers of the organic material layer include the compound, that is, the compound represented by Chemical Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transporting layer, a light emitting layer, and an electron transporting layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto.

In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, materials having a large work function are usually preferred so as to facilitate the injection of holes into an organic material layer. Specific examples of the positive electrode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnO_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

As the negative electrode material, materials having a small work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material such as LiF/Al or $LiO_2$/Al; and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transporting layer is a layer which accepts holes from a hole injection layer and transports the holes to a light emitting layer, and a hole transporting material is suitably a material having high hole mobility which may accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The electron blocking layer is a layer which may improve the service life and efficiency of the device by preventing holes injected from a hole injection layer from passing through a light emitting layer and entering an electron injection layer, and may be formed at an appropriate portion between the light emitting layer and the electron injection layer using publicly-known materials, if necessary.

In the present specification, when the compound represented by Chemical Formula 1 is included in an organic material layer other than a light emitting layer or an additional light emitting layer is provided, a light emitting material of the light emitting layer is a material which may emit light in a visible light region by accepting and combining holes and electrons from a hole transporting layer and an electron transporting layer, respectively, and preferably a material having high quantum efficiency for fluorescence or phosphorescence. Specific examples thereof include: an 8-hydroxy-quinoline aluminum complex ($Alq_3$); carbazole-based compounds; dimerized styryl compounds; BAlq; 10-hydroxybenzoquinoline-metal compounds; benzoxazole-based, benzthiazole-based and benzimidazole-based compounds; poly(p-phenylenevinylene) (PPV)-based polymers; spiro compounds; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a compound, a dibenzofuran derivative, a ladder-type furan compound, a pyrimidine derivative, and the like, but the examples are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting layer is a layer which accepts electrons from an electron injection layer and transports the electrons to a light emitting layer, and an electron transporting material is suitably a material having high electron mobility which may proficiently accept electrons from a negative electrode and transfer the electrons to a light emitting layer. Specific examples thereof include: Al complexes of 8-hydroxyquinoline; complexes including Alq₃; organic radical compounds; hydroxyflavone-metal complexes, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h] quinolinato) beryllium, bis(10-hydroxybenzo[h] quinolinato) zinc, bis(2-methyl-8-quinolinato) chlorogallium, bis(2-methyl-8-quinolinato)(o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a negative electrode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the materials to be used.

In an exemplary embodiment of the present specification, the compound represented by Chemical Formula 1 may be included in an organic solar cell or an organic transistor in addition to the organic light emitting device.

The compound according to the present specification may act even in organic electronic devices including organic phosphorescent devices, organic solar cells, organic photoconductors, organic transistors, and the like, based on the principle similar to those applied to organic light emitting devices.

Hereinafter, the present invention will be described in detail with reference to Examples, Comparative Examples, and the like for specifically describing the present specification. However, the Examples and the Comparative Examples according to the present specification may be modified in various forms, and it is not interpreted that the scope of the present specification is limited to the Examples and the Comparative Examples described below in detail. The Examples and the Comparative Examples of the present specification are provided to more completely explain the present specification to a person with ordinary skill in the art.

EXAMPLES

Preparation Example 1

Synthesis of Compound 1

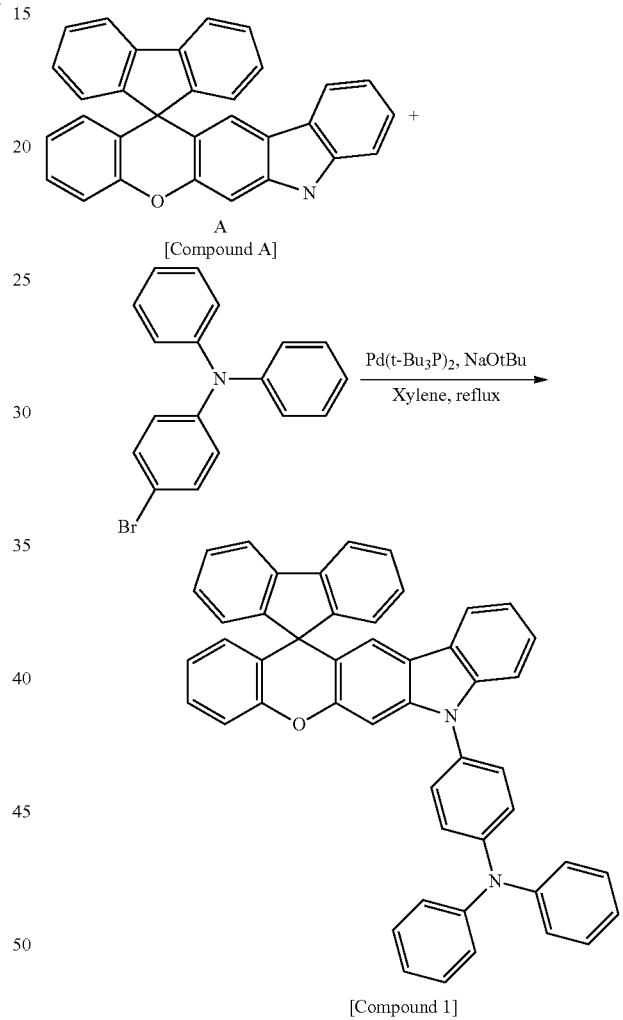

Under a nitrogen atmosphere, Compound A (10.0 g, 23.75 mmol) and 4-bromo-N,N-diphenylaniline (8.06 g, 24.94 mmol) were completely dissolved in 150 ml of xylene in a 500 ml-round bottom flask, and then sodium-tert-butoxide (2.97 g, 30.88 mol) was added thereto, bis(tri-tert-butylphosphine) palladium (0.12 g, 0.24 mmol) was put thereinto, and then the resulting mixture was heated and stirred for 2 hours. The temperature was lowered to normal temperature, the resulting mixture was filtered to remove the salt, and then xylene was concentrated under reduced pressure, and the residue was recrystallized with 120 ml of ethyl acetate to prepare Compound 1 (12.16 g, yield: 77%).

MS[M+H]⁺=665

Preparation Example 2

Synthesis of Compound 2

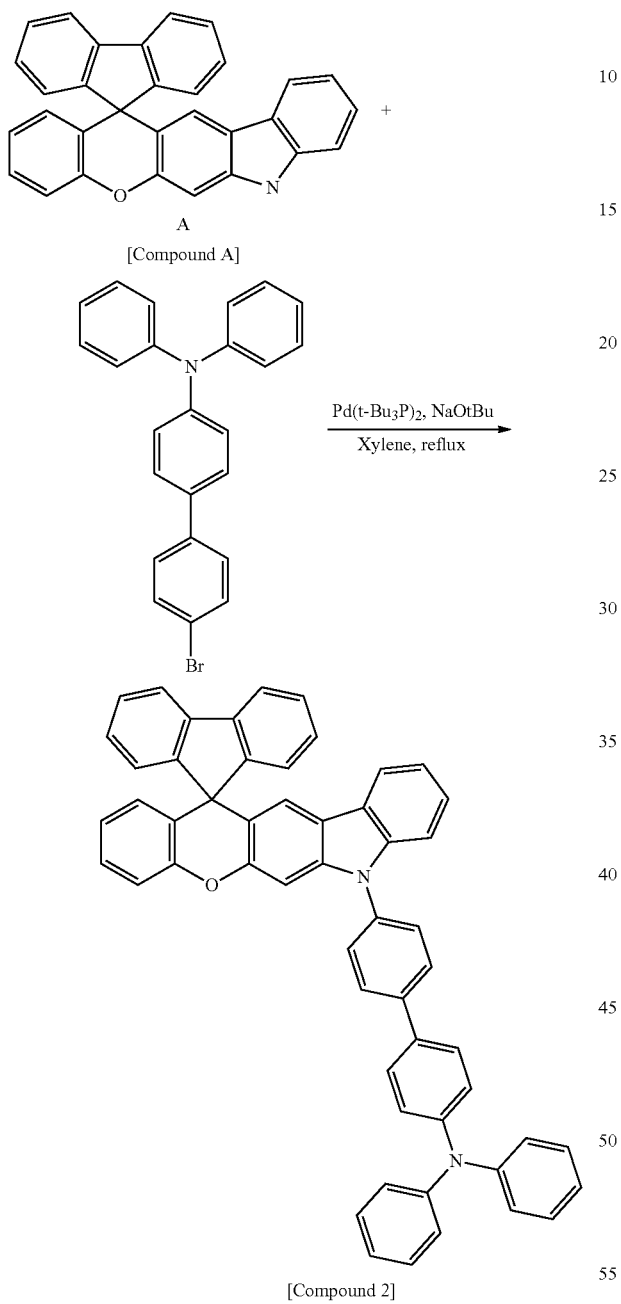

[Compound 2]

Under a nitrogen atmosphere, Compound A (10.0 g, 23.75 mmol) and 4'-bromo-N,N-diphenybiphenyl-4-amine (9.98 g, 24.94 mmol) were completely dissolved in 190 ml of xylene in a 500 ml-round bottom flask, and then sodium-tert-butoxide (2.97 g, 30.88 mol) was added thereto, bis(tri-tert-butylphosphine) palladium (0.12 g, 0.24 mmol) was put thereinto, and then the resulting mixture was heated and stirred for 5 hours. The temperature was lowered to normal temperature, the resulting mixture was filtered to remove the salt, and then xylene was concentrated under reduced pressure, and the residue was recrystallized with 160 ml of ethyl acetate to prepare Compound 2 (15.68 g, yield: 89%).

MS[M+H]$^+$=741

Preparation Example 3

Synthesis of Compound 3

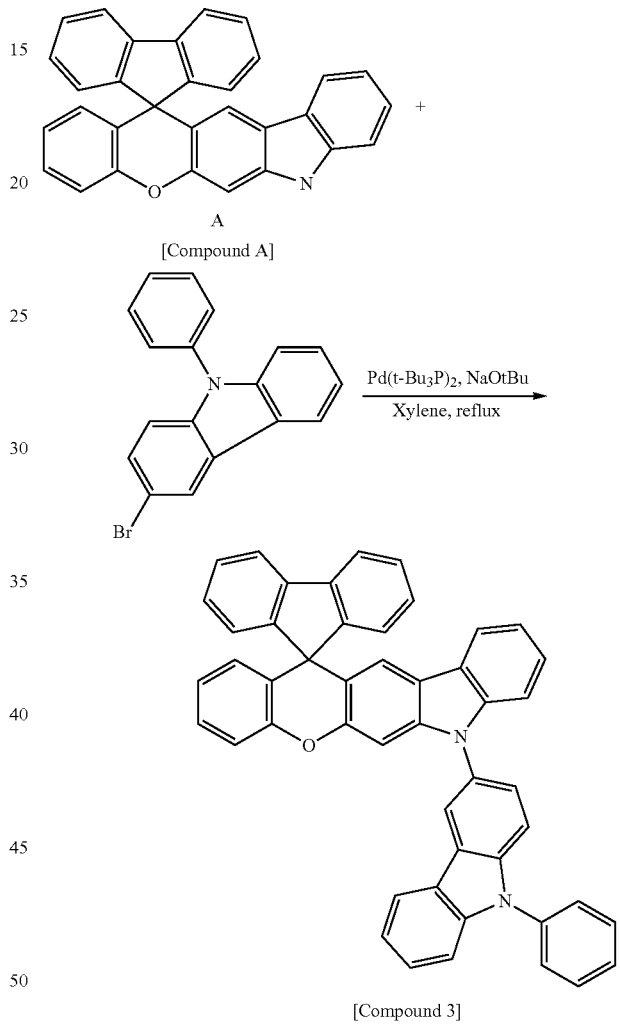

[Compound 3]

Under a nitrogen atmosphere, Compound A (10.0 g, 23.75 mmol) and 3-bromo-9-phenyl-9H-carbazole (8.01 g, 24.94 mmol) were completely dissolved in 180 ml of xylene in a 500 ml-round bottom flask, and then sodium-tert-butoxide (2.97 g, 30.88 mol) was added thereto, bis(tri-tert-butylphosphine) palladium (0.12 g, 0.24 mmol) was put thereinto, and then the resulting mixture was heated and stirred for 2 hours. The temperature was lowered to normal temperature, the resulting mixture was filtered to remove the salt, and then xylene was concentrated under reduced pressure, and the residue was recrystallized with 140 ml of ethyl acetate to prepare Compound 3 (9.49 g, yield: 60%).

MS[M+H]$^+$=663

Preparation Example 4

Synthesis of Compound 4

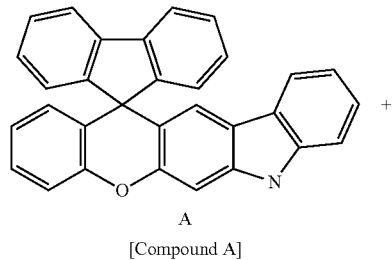

[Compound A]

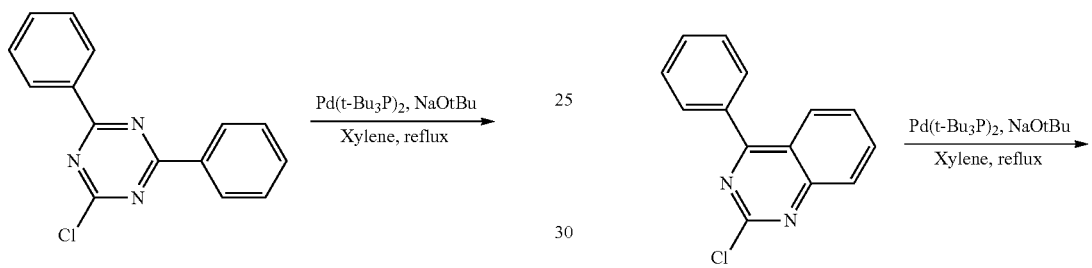

[Compound 4]

Under a nitrogen atmosphere, Compound A (10.0 g, 23.75 mmol) and 2-chloro-4,6-diphenyl-1,3,5-triazine (6.66 g, 24.94 mmol) were completely dissolved in 210 ml of xylene in a 500 ml-round bottom flask, and then sodium-tert-butoxide (2.97 g, 30.88 mol) was added thereto, bis(tri-tert-butylphosphine) palladium (0.12 g, 0.24 mmol) was put thereinto, and then the resulting mixture was heated and stirred for 4 hours. The temperature was lowered to normal temperature, the resulting mixture was filtered to remove the salt, and then xylene was concentrated under reduced pressure, and the residue was recrystallized with 240 ml of ethyl acetate to prepare Compound 4 (14.47 g, yield: 93%).

MS[M+H]$^+$=653

Preparation Example 5

Synthesis of Compound 5

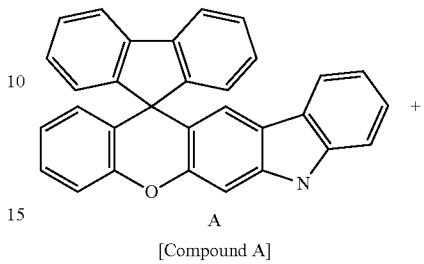

[Compound A]

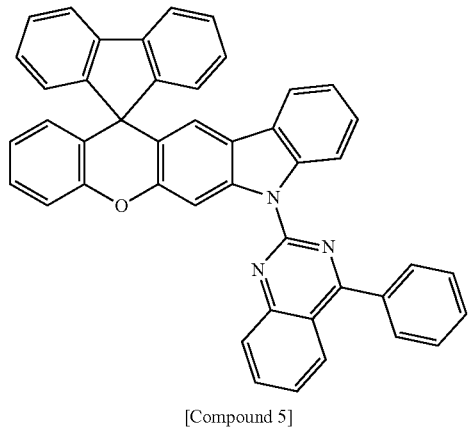

[Compound 5]

Under a nitrogen atmosphere, Compound A (10.0 g, 23.75 mmol) and 2-chloro-4-phenylquinazoline (6.66 g, 24.94 mmol) were completely dissolved in 250 ml of xylene in a 500 ml-round bottom flask, and then sodium-tert-butoxide (2.97 g, 30.88 mol) was added thereto, bis(tri-tert-butylphosphine) palladium (0.12 g, 0.24 mmol) was put thereinto, and then the resulting mixture was heated and stirred for 7 hours. The temperature was lowered to normal temperature, the resulting mixture was filtered to remove the salt, and then xylene was concentrated under reduced pressure, and the residue was recrystallized with 210 ml of ethyl acetate to prepare Compound 5 (12.10 g, yield: 81%).

MS[M+H]$^+$=626

Preparation Example 6

Synthesis of Compound 6

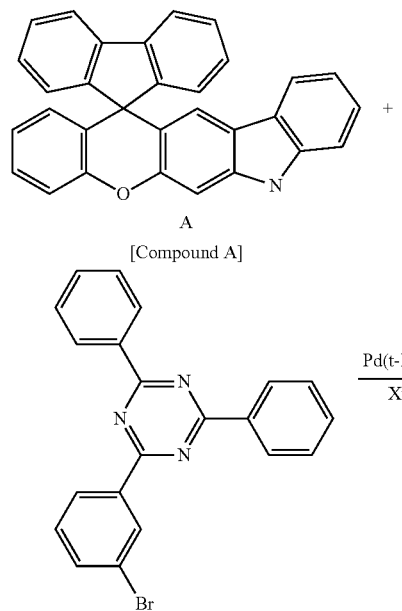

Preparation Example 7

Synthesis of Compound 7

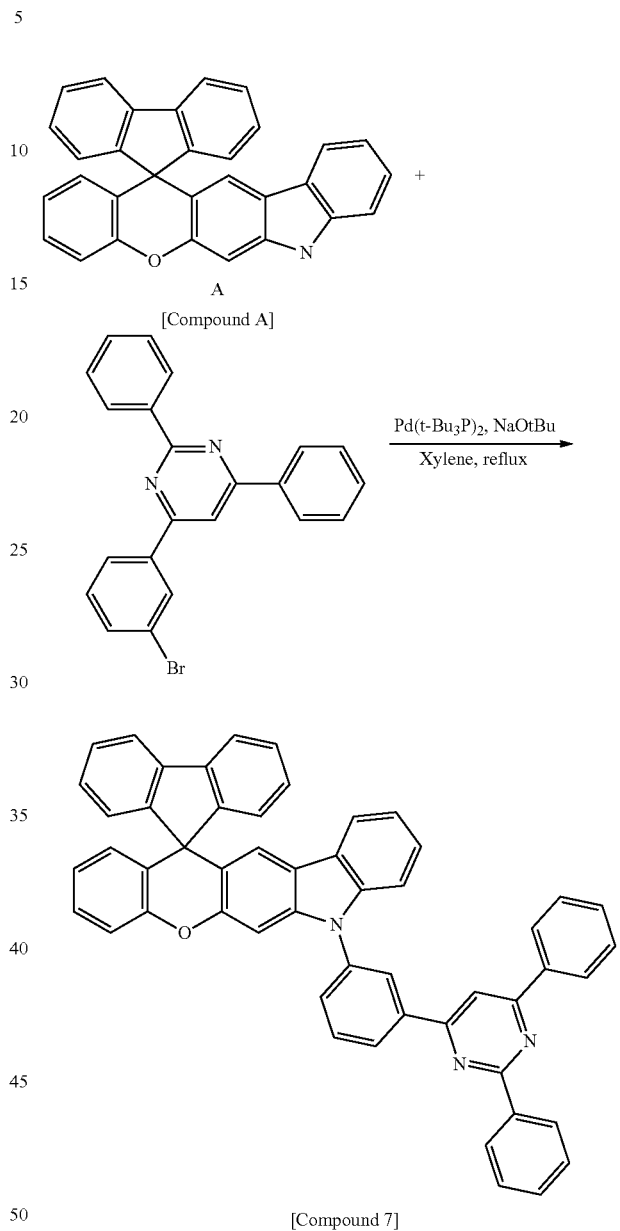

Under a nitrogen atmosphere, Compound A (10.0 g, 23.75 mmol) and 2-(3-bromophenyl)-4,6-diphenyl-1,3,5-triazine (9.65 g, 24.94 mmol) were completely dissolved in 330 ml of xylene in a 500 ml-round bottom flask, and then sodium-tert-butoxide (2.97 g, 30.88 mol) was added thereto, bis(tri-tert-butylphosphine) palladium (0.12 g, 0.24 mmol) was put thereinto, and then the resulting mixture was heated and stirred for 4 hours. The temperature was lowered to normal temperature, the resulting mixture was filtered to remove the salt, and then xylene was concentrated under reduced pressure, and the residue was recrystallized with 340 ml of tetrahydrofuran to prepare Compound 6 (15.54 g, yield: 90%).

MS[M+H]$^+$=729

Under a nitrogen atmosphere, Compound A (10.0 g, 23.75 mmol) and 4-(3-bromophenyl)-2,6-diphenylpyrimidine (9.65 g, 24.94 mmol) were completely dissolved in 330 ml of xylene in a 500 ml-round bottom flask, and then sodium-tert-butoxide (2.97 g, 30.88 mol) was added thereto, bis(tri-tert-butylphosphine) palladium (0.12 g, 0.24 mmol) was put thereinto, and then the resulting mixture was heated and stirred for 4 hours. The temperature was lowered to normal temperature, the resulting mixture was filtered to remove the salt, and then xylene was concentrated under reduced pressure, and the residue was recrystallized with 340 ml of tetrahydrofuran to prepare Compound 7 (15.54 g, yield: 90%).

MS[M+H]$^+$=729

467

Preparation Example 8

Synthesis of Compound 8

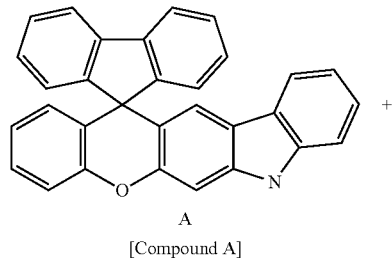

[Compound A]

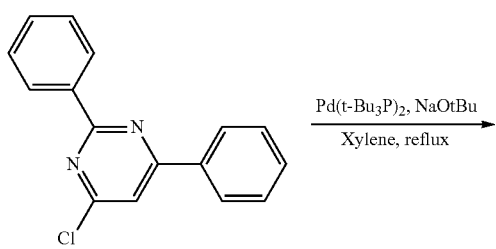

Pd(t-Bu₃P)₂, NaOtBu
———————→
Xylene, reflux

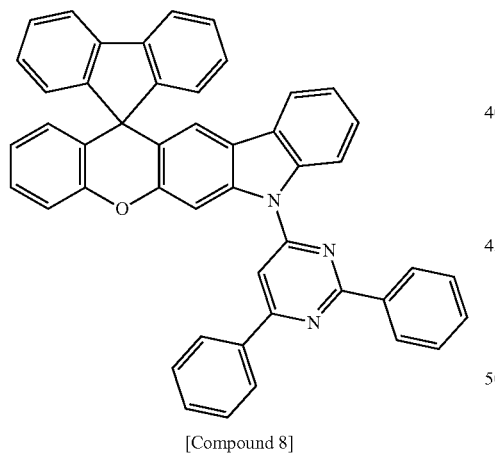

[Compound 8]

Under a nitrogen atmosphere, Compound A (10.0 g, 23.75 mmol) and 4-chloro-2,6-diphenylpyrimidine (6.66 g, 24.94 mmol) were completely dissolved in 210 ml of xylene in a 500 ml-round bottom flask, and then sodium-tert-butoxide (2.97 g, 30.88 mol) was added thereto, bis(tri-tert-butylphosphine) palladium (0.12 g, 0.24 mmol) was put thereinto, and then the resulting mixture was heated and stirred for 3 hours. The temperature was lowered to normal temperature, the resulting mixture was filtered to remove the salt, and then xylene was concentrated under reduced pressure, and the residue was recrystallized with 190 ml of ethyl acetate to prepare Compound 8 (14.47 g, yield: 93%).

MS[M+H]⁺=652

468

Preparation Example 9

Synthesis of Compound 9

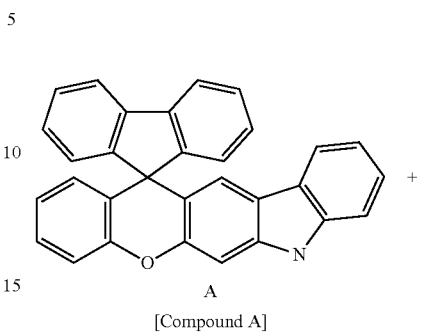

[Compound A]

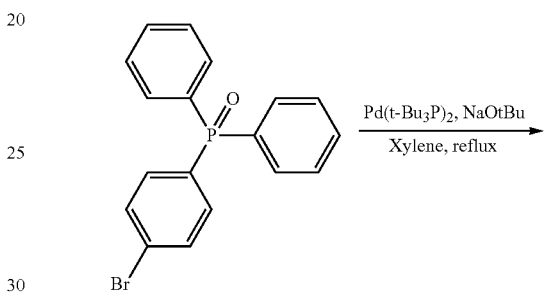

Pd(t-Bu₃P)₂, NaOtBu
———————→
Xylene, reflux

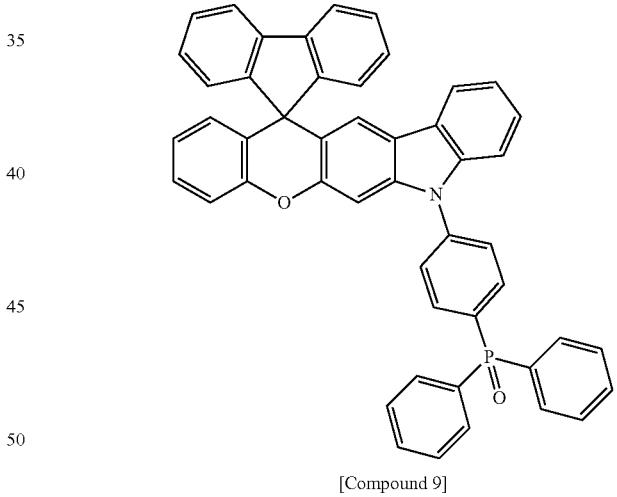

[Compound 9]

Under a nitrogen atmosphere, Compound A (10.0 g, 23.75 mmol) and (4-bromophenyl)diphenylphosphine oxide (8.88 g, 24.94 mmol) were completely dissolved in 230 ml of xylene in a 500 ml-round bottom flask, and then sodium-tert-butoxide (2.97 g, 30.88 mol) was added thereto, bis(tri-tert-butylphosphine) palladium (0.12 g, 0.24 mmol) was put thereinto, and then the resulting mixture was heated and stirred for 6 hours. The temperature was lowered to normal temperature, the resulting mixture was filtered to remove the salt, and then xylene was concentrated under reduced pressure, and the residue was recrystallized with 120 ml of ethyl acetate to prepare Compound 9 (13.34 g, yield: 81%).

MS[M+H]⁺=698

Preparation Example 10

Synthesis of Compound 10

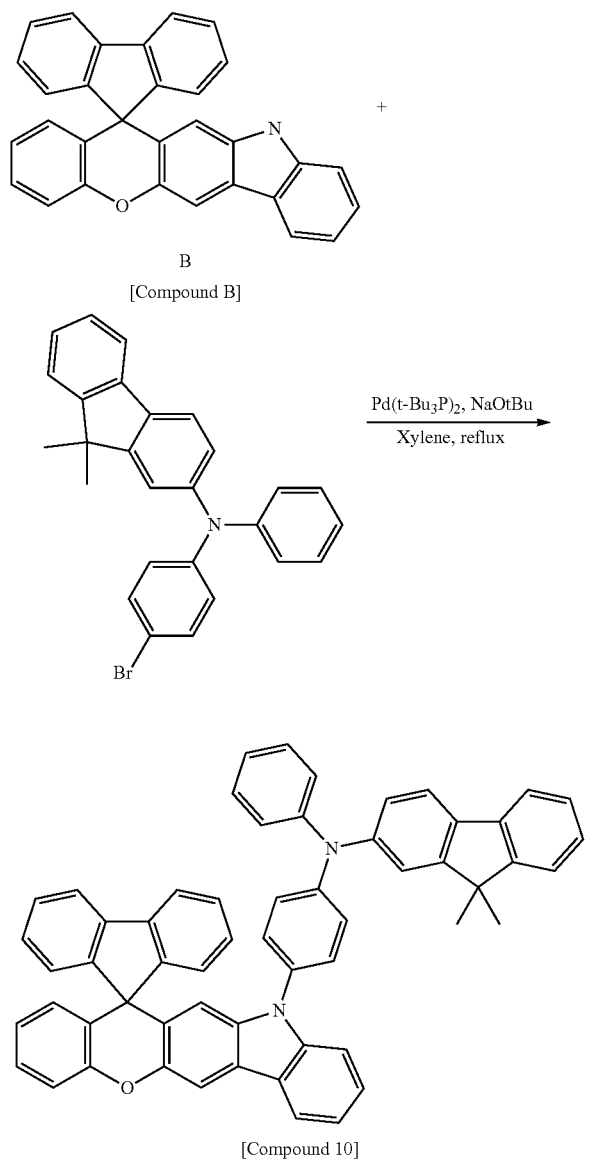

[Compound 10]

Under a nitrogen atmosphere, Compound B (10.0 g, 23.75 mmol) and N-(4-bromophenyl)-9,9-dimethyl-N-phenyl-9H-fluoren-2-amine (10.97 g, 24.94 mmol) were completely dissolved in 170 ml of xylene in a 500 ml-round bottom flask, and then sodium-tert-butoxide (2.97 g, 30.88 mol) was added thereto, bis(tri-tert-butylphosphine) palladium (0.12 g, 0.24 mmol) was put thereinto, and then the resulting mixture was heated and stirred for 5 hours. The temperature was lowered to normal temperature, the resulting mixture was filtered to remove the salt, and then xylene was concentrated under reduced pressure, and the residue was recrystallized with 160 ml of ethyl acetate to prepare Compound 10 (14.29 g, yield: 77%).

MS[M+H]$^+$=781

Preparation Example 11

Synthesis of Compound 11

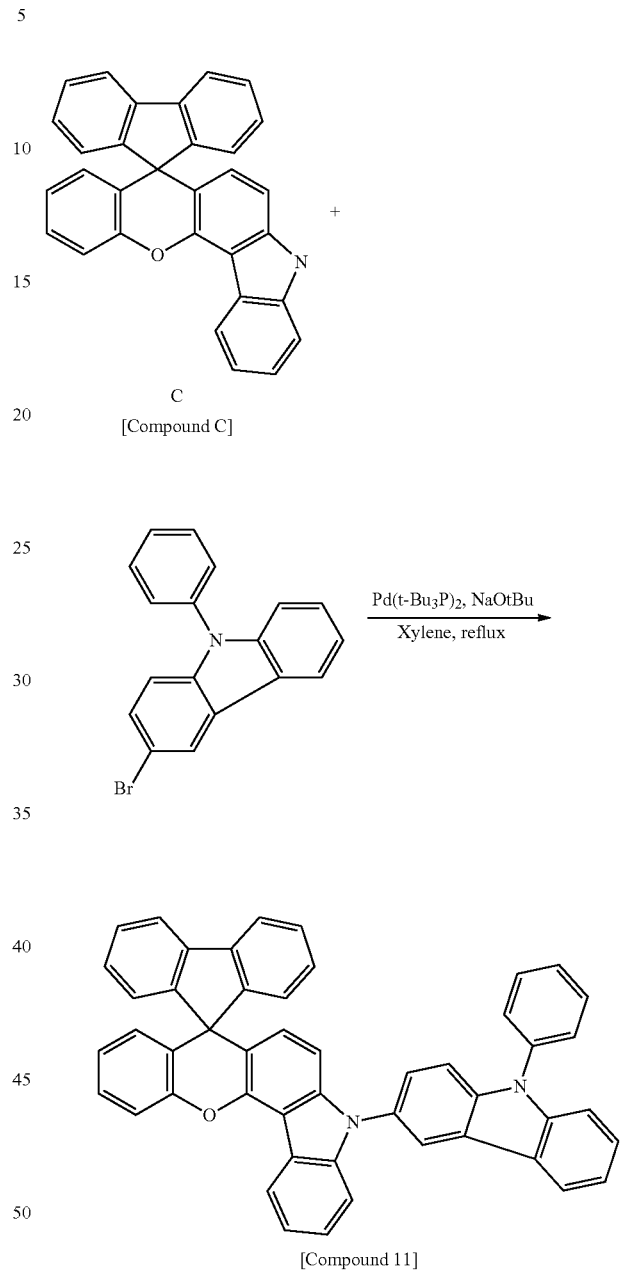

[Compound 11]

Under a nitrogen atmosphere, Compound C (10.0 g, 23.75 mmol) and 3-bromo-9-phenyl-9H-carbazole (8.01 g, 24.94 mmol) were completely dissolved in 180 ml of xylene in a 500 ml-round bottom flask, and then sodium-tert-butoxide (2.97 g, 30.88 mol) was added thereto, bis(tri-tert-butylphosphine) palladium (0.12 g, 0.24 mmol) was put thereinto, and then the resulting mixture was heated and stirred for 2 hours. The temperature was lowered to normal temperature, the resulting mixture was filtered to remove the salt, and then xylene was concentrated under reduced pressure, and the residue was recrystallized with 140 ml of ethyl acetate to prepare Compound 11 (12.11 g, yield: 77%).

MS[M+H]$^+$=663

Preparation Example 12

Synthesis of Compound 12

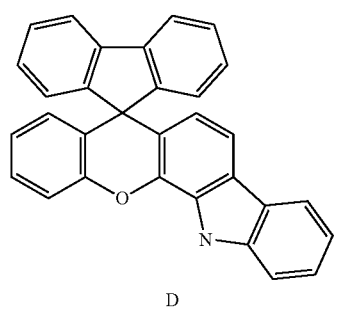

[Compound D]

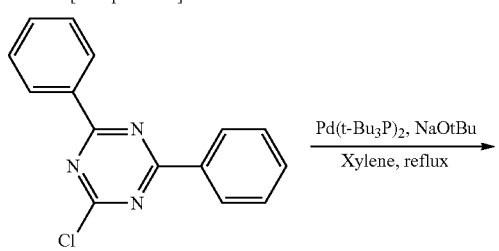

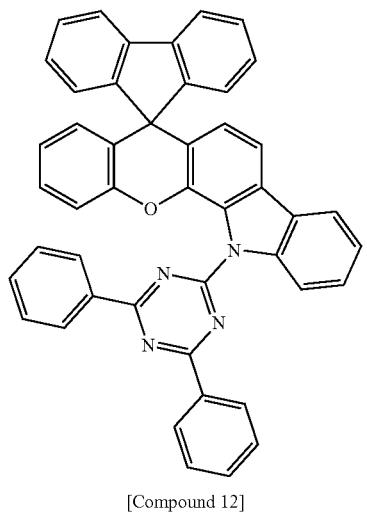

[Compound 12]

Under a nitrogen atmosphere, Compound D (10.0 g, 23.75 mmol) and 2-chloro-4,6-diphenyl-1,3,5-triazine (6.66 g, 24.94 mmol) were completely dissolved in 210 ml of xylene in a 500 ml-round bottom flask, and then sodium-tert-butoxide (2.97 g, 30.88 mol) was added thereto, bis(tri-tert-butylphosphine) palladium (0.12 g, 0.24 mmol) was put thereinto, and then the resulting mixture was heated and stirred for 4 hours. The temperature was lowered to normal temperature, the resulting mixture was filtered to remove the salt, and then xylene was concentrated under reduced pressure, and the residue was recrystallized with 240 ml of ethyl acetate to prepare Compound 12 (10.86 g, yield: 70%).

MS[M+H]$^+$=653

Preparation Example 13

Synthesis of Compound 13

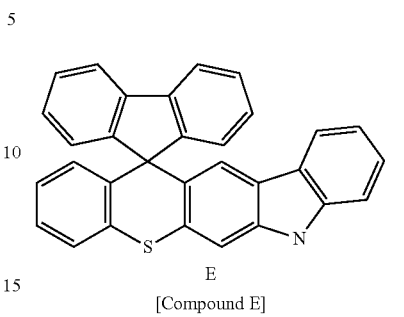

[Compound E]

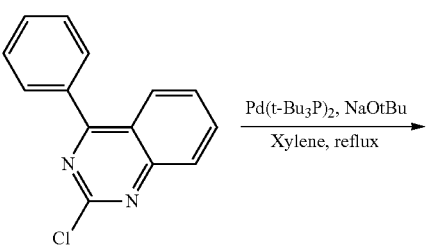

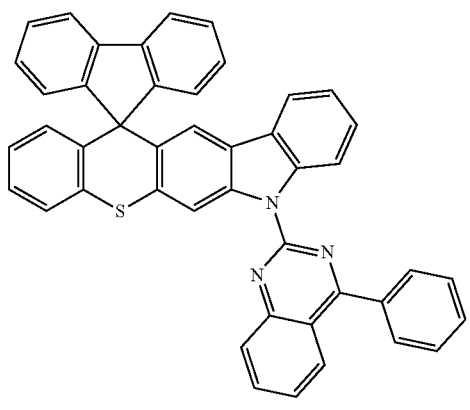

[Compound 13]

Under a nitrogen atmosphere, Compound E (10.0 g, 22.88 mmol) and 2-chloro-4-phenylquinazoline (5.77 g, 24.03 mmol) were completely dissolved in 210 ml of xylene in a 500 ml-round bottom flask, and then sodium-tert-butoxide (2.86 g, 29.75 mol) was added thereto, bis(tri-tert-butylphosphine) palladium (0.12 g, 0.23 mmol) was put thereinto, and then the resulting mixture was heated and stirred for 5 hours. The temperature was lowered to normal temperature, the resulting mixture was filtered to remove the salt, and then xylene was concentrated under reduced pressure, and the residue was recrystallized with 260 ml of ethyl acetate to prepare Compound 13 (9.92 g, yield: 68%).

MS[M+H]$^+$=642

Preparation Example 14

Synthesis of Compound 14

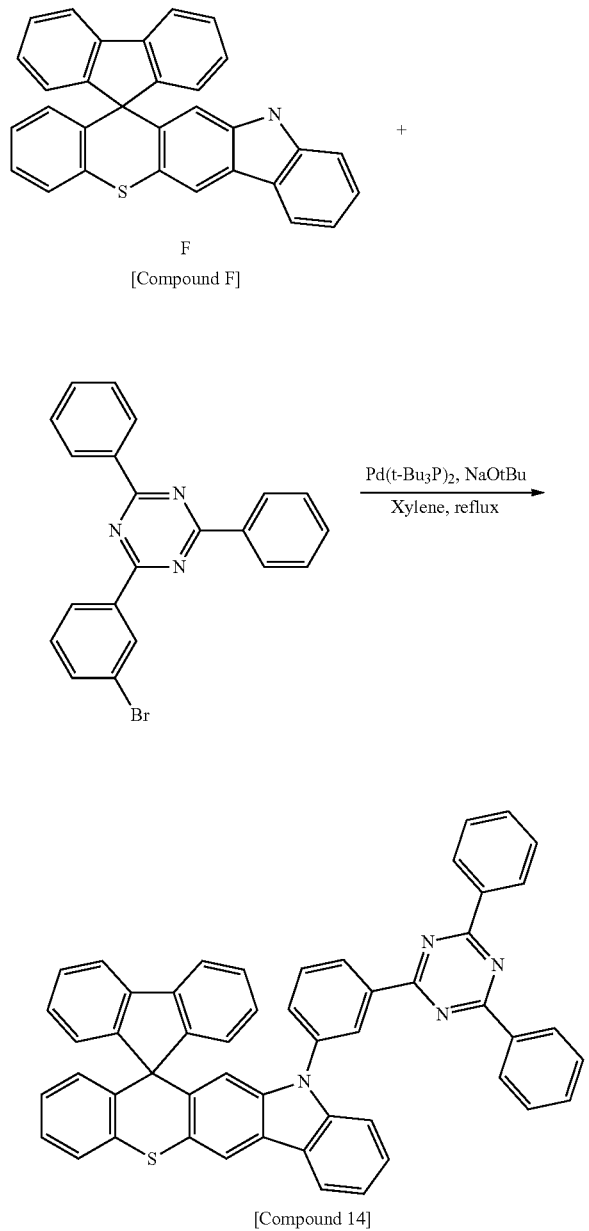

[Compound 14]

Under a nitrogen atmosphere, Compound F (10.0 g, 22.88 mmol) and 2-(3-bromophenyl)-4,6-diphenyl-1,3,5-triazine (9.30 g, 24.03 mmol) were completely dissolved in 250 ml of xylene in a 500 ml-round bottom flask, and then sodium-tert-butoxide (2.86 g, 29.75 mol) was added thereto, bis(tri-tert-butylphosphine) palladium (0.12 g, 0.23 mmol) was put thereinto, and then the resulting mixture was heated and stirred for 5 hours. The temperature was lowered to normal temperature, the resulting mixture was filtered to remove the salt, and then xylene was concentrated under reduced pressure, and the residue was recrystallized with 280 ml of ethyl acetate to prepare Compound 14 (12.45 g, yield: 72%).

MS[M+H]$^+$=745

Preparation Example 15

Synthesis of Compound 15

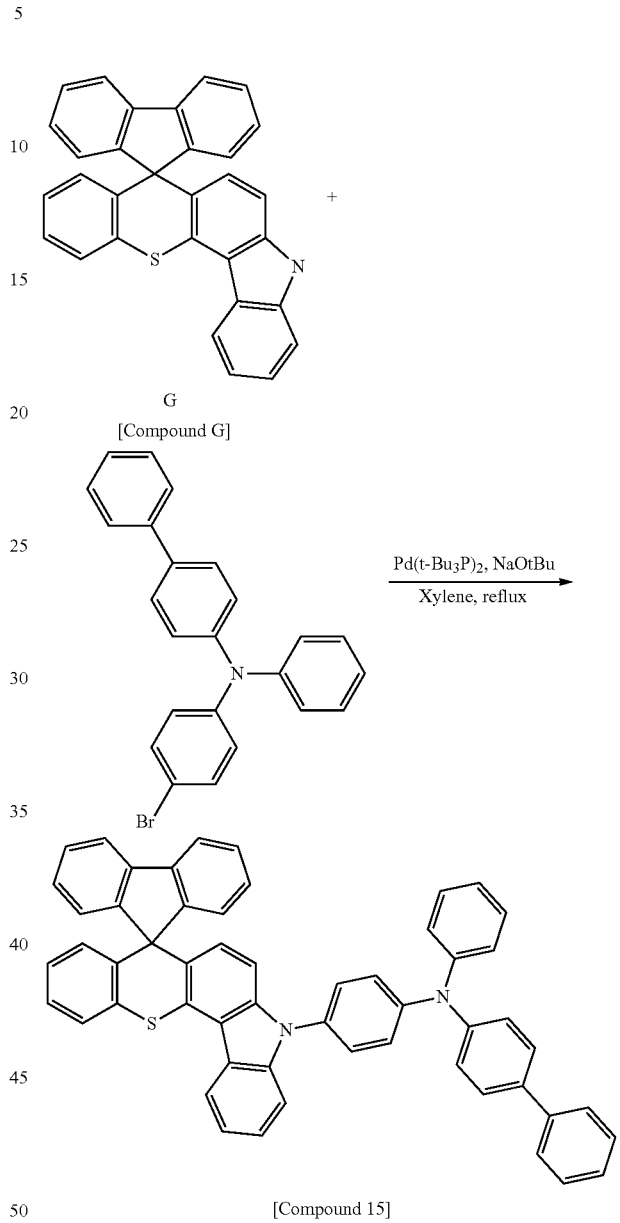

[Compound 15]

Under a nitrogen atmosphere, Compound G (10.0 g, 22.88 mmol) and N-(4-bromophenyl)-4-phenylbiphenyl-4-amine (9.61 g, 24.03 mmol) were completely dissolved in 150 ml of xylene in a 500 ml-round bottom flask, and then sodium-tert-butoxide (2.86 g, 29.75 mol) was added thereto, bis(tri-tert-butylphosphine) palladium (0.12 g, 0.23 mmol) was put thereinto, and then the resulting mixture was heated and stirred for 4 hours. The temperature was lowered to normal temperature, the resulting mixture was filtered to remove the salt, and then xylene was concentrated under reduced pressure, and the residue was recrystallized with 180 ml of ethyl acetate to prepare Compound 15 (13.39 g, yield: 77%).

MS[M+H]$^+$=757

Preparation Example 16

Synthesis of Compound 16

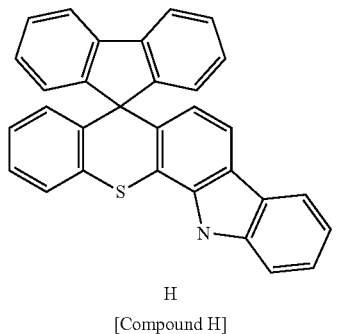

[Compound H]

+

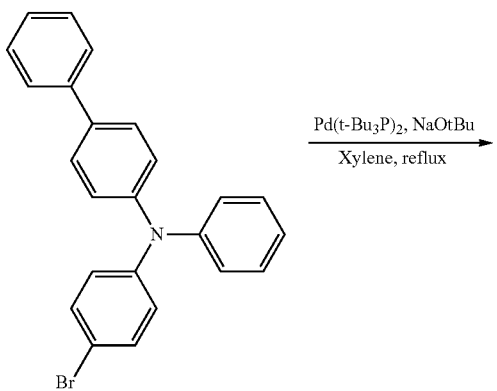

$\xrightarrow{\text{Pd(t-Bu}_3\text{P)}_2\text{, NaOtBu}}_{\text{Xylene, reflux}}$

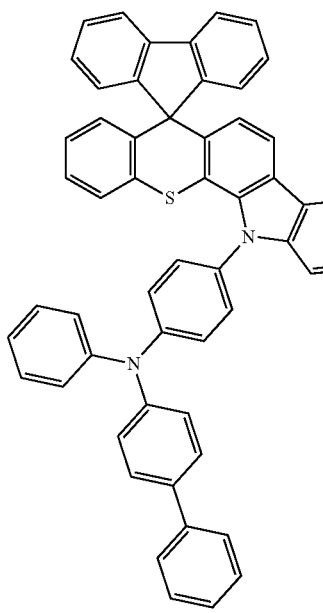

[Compound 16]

Under a nitrogen atmosphere, Compound H (10.0 g, 22.88 mmol) and N-(4-bromophenyl)-N-phenylbiphenyl-4-amine (9.61 g, 24.03 mmol) were completely dissolved in 150 ml of xylene in a 500 ml-round bottom flask, and then sodium-tert-butoxide (2.86 g, 29.75 mol) was added thereto, bis(tri-tert-butylphosphine) palladium (0.12 g, 0.23 mmol) was put thereinto, and then the resulting mixture was heated and stirred for 4 hours. The temperature was lowered to normal temperature, the resulting mixture was filtered to remove the salt, and then xylene was concentrated under reduced pressure, and the residue was recrystallized with 130 ml of ethyl acetate to prepare Compound 16 (12.24 g, yield: 71%).

MS[M+H]$^+$=757

Experimental Example 1

Experimental Example 1-1

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

Hexanitrile hexaazatriphenylene (HAT) of the following Chemical Formula was thermally vacuum deposited to have a thickness of 150 Å on the transparent ITO electrode, which was thus prepared, thereby forming a hole injection layer.

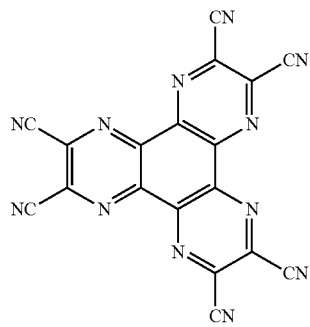

[HAT]

The following Compound HT (850 Å) being a material which transports holes was vacuum deposited on the hole injection layer, thereby forming a hole transporting layer.

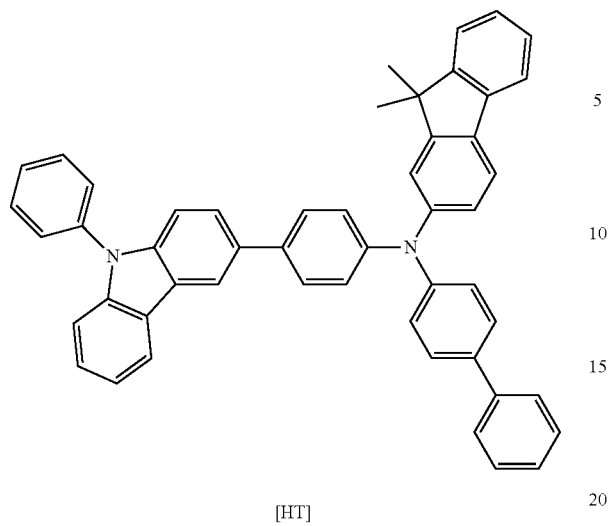

[HT]

Subsequently, the following Compound 1 was vacuum deposited to have a film thickness of 150 Å on the hole transporting layer, thereby forming an electron blocking layer.

[Compound 1]

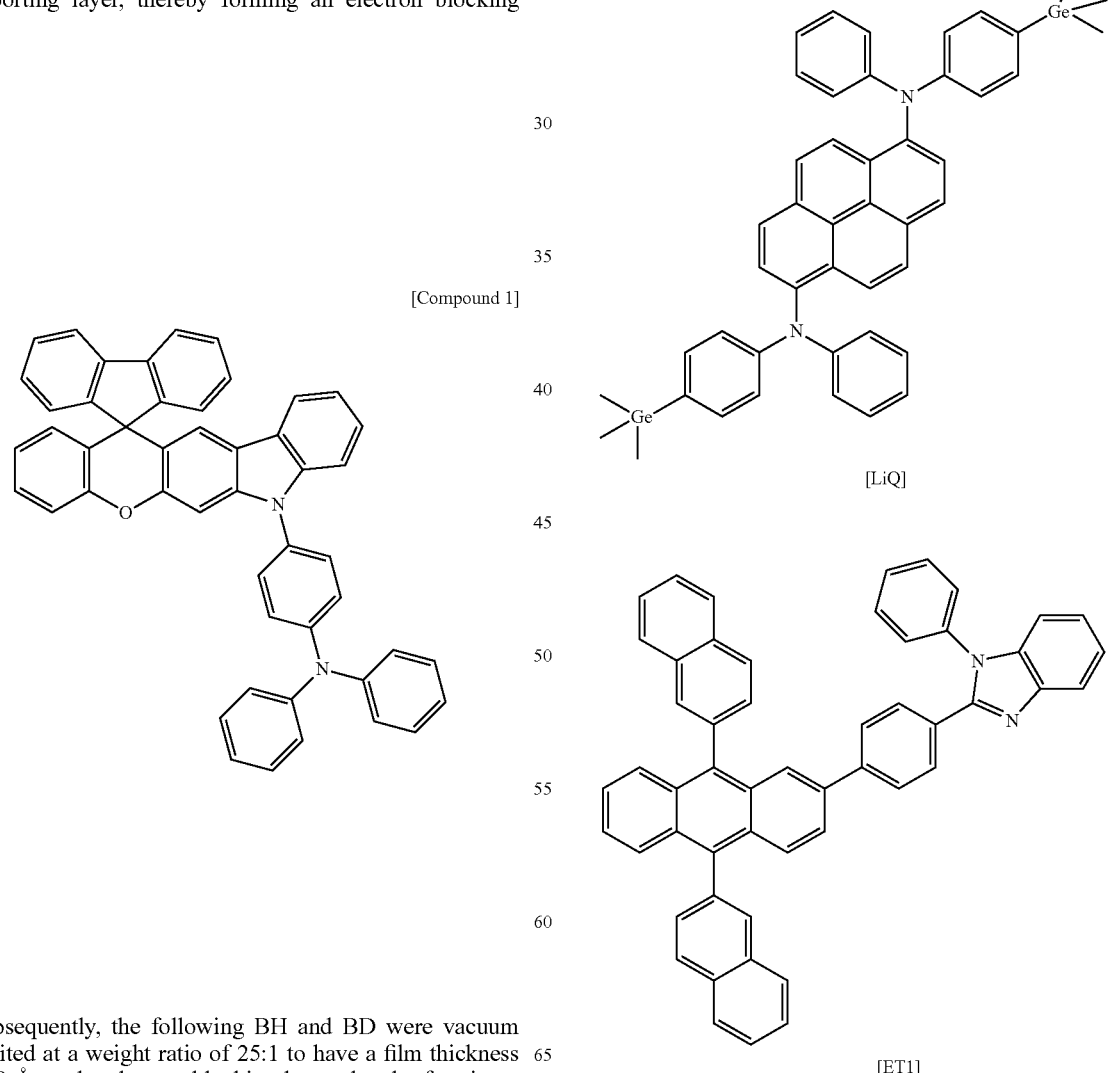

Subsequently, the following BH and BD were vacuum deposited at a weight ratio of 25:1 to have a film thickness of 300 Å on the electron blocking layer, thereby forming a light emitting layer.

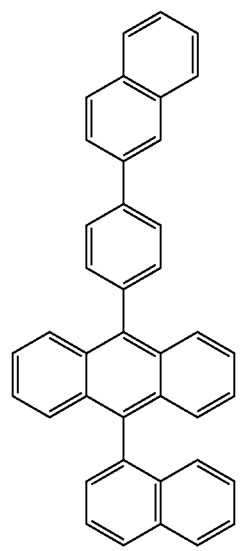

[BH]

[LiQ]

[ET1]

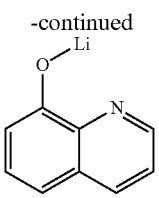

[LiQ]

Compound ET1 and Compound LiQ (lithium quinolate) were vacuum deposited at a weight ratio of 1:1 on the light emitting layer, thereby forming an electron injection and transporting layer having a thickness of 360 Å. Lithium fluoride (LiF) and aluminum were sequentially deposited on the electron injection and transporting layer to have a thickness of 12 Å and 2,000 Å, respectively, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

Experimental Example 1-2

An organic light emitting device was manufactured in the same manner as in Experimental Example 1-1, except that Compound 2 was used instead of Compound 1 in Experimental Example 1-1.

Experimental Example 1-3

An organic light emitting device was manufactured in the same manner as in Experimental Example 1-1, except that Compound 3 was used instead of Compound 1 in Experimental Example 1-1.

Experimental Example 1-4

An organic light emitting device was manufactured in the same manner as in Experimental Example 1-1, except that Compound 10 was used instead of Compound 1 in Experimental Example 1-1.

Experimental Example 1-5

An organic light emitting device was manufactured in the same manner as in Experimental Example 1-1, except that Compound 11 was used instead of Compound 1 in Experimental Example 1-1.

Experimental Example 1-6

An organic light emitting device was manufactured in the same manner as in Experimental Example 1-1, except that Compound 15 was used instead of Compound 1 in Experimental Example 1-1.

Experimental Example 1-7

An organic light emitting device was manufactured in the same manner as in Experimental Example 1-1, except that Compound 16 was used instead of Compound 1 in Experimental Example 1-1.

Comparative Example 1-1

An organic light emitting device was manufactured in the same manner as in Experimental Example 1-1, except that the following EB 1 (TCTA) was used instead of Compound 1 in Experimental Example 1-1.

[EB 1]

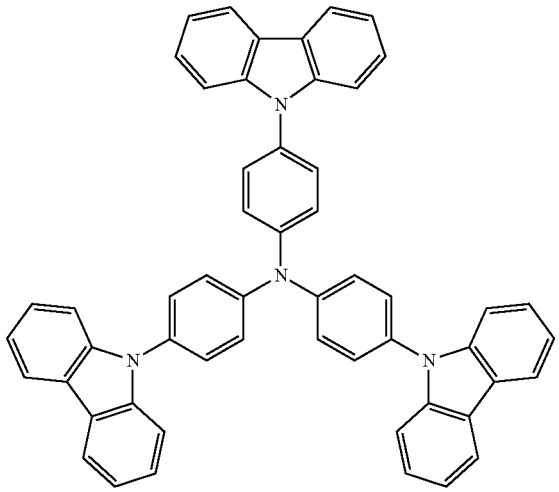

Comparative Example 1-2

An organic light emitting device was manufactured in the same manner as in Experimental Example 1-1, except that the following EB 2 was used instead of Compound 1 in Experimental Example 1-1.

[EB 2]

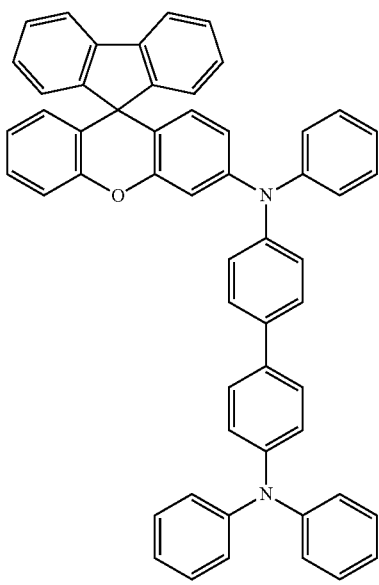

Comparative Example 1-3

An organic light emitting device was manufactured in the same manner as in Experimental Example 1-1, except that the following EB 3 was used instead of Compound 1 in Experimental Example 1-1.

[EB 3]

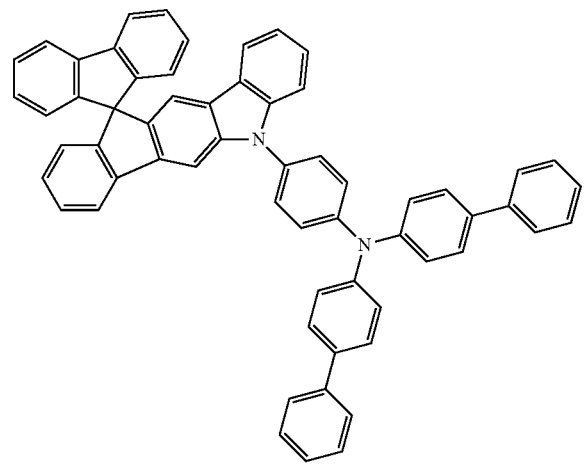

When current was applied to the organic light emitting devices manufactured in Experimental Examples 1-1 to 1-7 and Comparative Examples 1-1 to 1-3, the results of Table 1 were obtained.

TABLE 1

| Classification | Compound (Electron blocking layer) | Voltage (V@10 mA/cm$^2$) | Efficiency (cd/A@10 mA/cm$^2$) | Color coordinate (x, y) |
|---|---|---|---|---|
| Experimental Example 1-1 | Compound 1 | 3.70 | 5.30 | (0.138, 0.125) |
| Experimental Example 1-2 | Compound 2 | 3.62 | 5.38 | (0.137, 0.126) |
| Experimental Example 1-3 | Compound 3 | 3.59 | 5.41 | (0.137, 0.126) |
| Experimental Example 1-4 | Compound 10 | 3.52 | 5.46 | (0.138, 0.126) |
| Experimental Example 1-5 | Compound 11 | 3.53 | 5.44 | (0.137, 0.126) |
| Experimental Example 1-6 | Compound 15 | 3.61 | 5.39 | (0.138, 0.126) |
| Experimental Example 1-7 | Compound 16 | 3.68 | 5.49 | (0.138, 0.127) |
| Comparative Example 1-1 | EB 1 (TCTA) | 4.13 | 4.71 | (0.137, 0.126) |
| Comparative Example 1-2 | EB 2 | 4.04 | 4.85 | (0.139, 0.125) |
| Comparative Example 1-3 | EB 3 | 4.25 | 4.56 | (0.138, 0.124) |

As observed in Table 1, it can be seen that Experimental Examples 1-1 to 1-7 in which the spiro compound represented by Chemical Formula 1 according to the present specification is used as an electron blocking layer exhibit low voltage and high efficiency characteristics as compared to Comparative Example 1-1 in which EB1 (TCTA) in the related art is used and Comparative Examples 1-2 and 1-3 in which the compound has a core structure similar to Chemical Formula 1 of the present specification.

It could be confirmed that the compound derivatives according to the present specification have excellent electron blocking capability and thus exhibit low voltage and high efficiency characteristics, and may be applied to an organic electronic device.

Experimental Example 2

Experimental Example 2-1

The compounds synthesized in the Preparation Examples were subjected to high-purity sublimation purification by a typically known method, and then green organic light emitting devices were manufactured by the following method.

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

An organic electronic device was manufactured by configuring a light emitting device in the order of m-MTDATA (60 nm)/TCTA (80 nm)/Compound 4+10% Ir(ppy)$_3$ (300 nm)/BCP (10 nm)/Alq$_3$ (30 nm)/LiF (1 nm)/Al (200 nm) on the thus prepared ITO transparent electrode by using Compound 4 as a host.

The structures of m-MTDATA, TCTA, Ir(ppy)$_3$, and BCP are as follows.

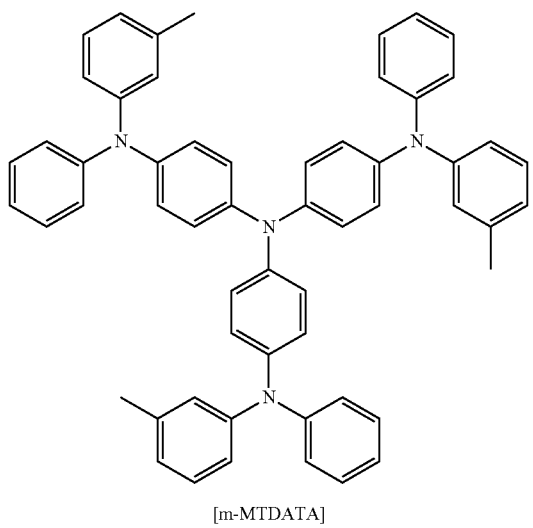

[m-MTDATA]

-continued

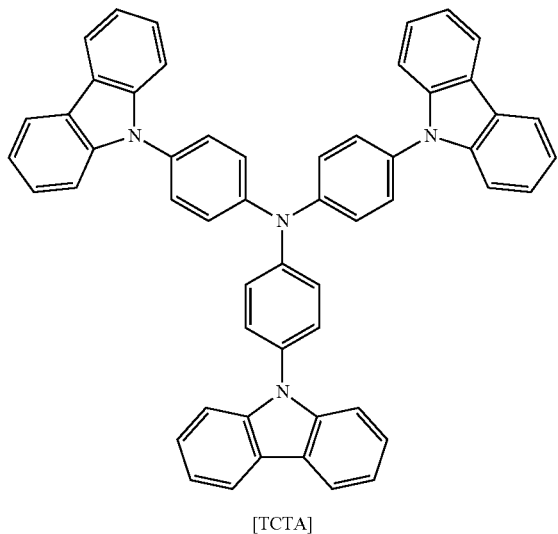

[TCTA]

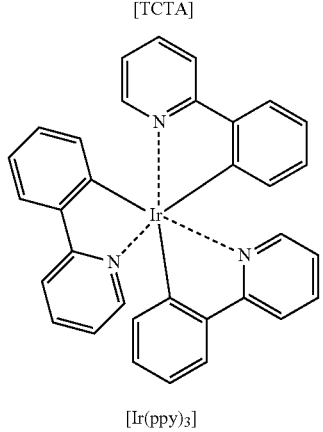

[Ir(ppy)₃]

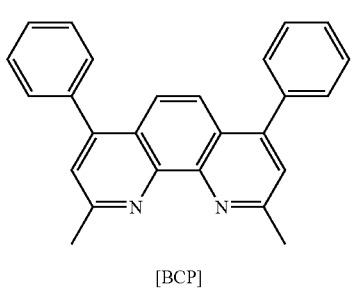

[BCP]

[Compound 4]

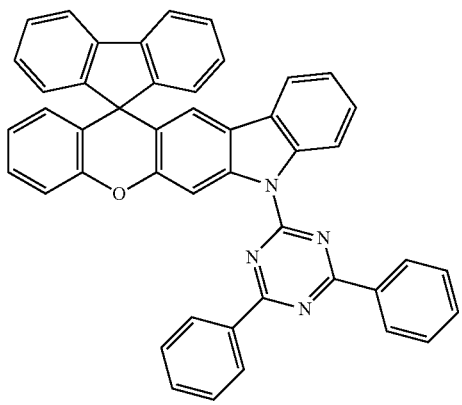

Experimental Example 2-2

An organic light emitting device was manufactured in the same manner as in Experimental Example 2-1, except that Compound 6 was used instead of Compound 4 in Experimental Example 2-1.

Experimental Example 2-3

An organic light emitting device was manufactured in the same manner as in Experimental Example 2-1, except that Compound 7 was used instead of Compound 4 in Experimental Example 2-1.

Experimental Example 2-4

An organic light emitting device was manufactured in the same manner as in Experimental Example 2-1, except that Compound 8 was used instead of Compound 4 in Experimental Example 2-1.

Experimental Example 2-5

An organic light emitting device was manufactured in the same manner as in Experimental Example 2-1, except that Compound 12 was used instead of Compound 4 in Experimental Example 2-1.

Experimental Example 2-6

An organic light emitting device was manufactured in the same manner as in Experimental Example 2-1, except that Compound 14 was used instead of Compound 4 in Experimental Example 2-1.

Comparative Example 2-1

An organic light emitting device was manufactured in the same manner as in Experimental Example 2-1, except that the following GH 1 (CBP) was used instead of Compound 4 in Experimental Example 2-1.

[GH 1]

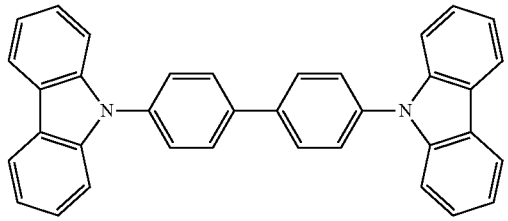

Comparative Example 2-2

An organic light emitting device was manufactured in the same manner as in Experimental Example 2-1, except that the following GH 2 was used instead of Compound 4 in Experimental Example 2-1.

[GH 2]

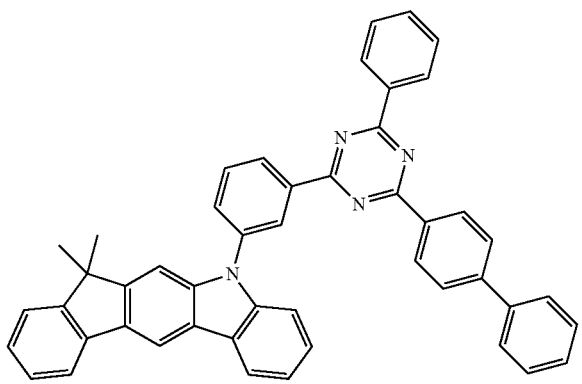

Comparative Example 2-3

An organic light emitting device was manufactured in the same manner as in Experimental Example 2-1, except that the following GH 3 was used instead of Compound 4 in Experimental Example 2-1.

[GH 3]

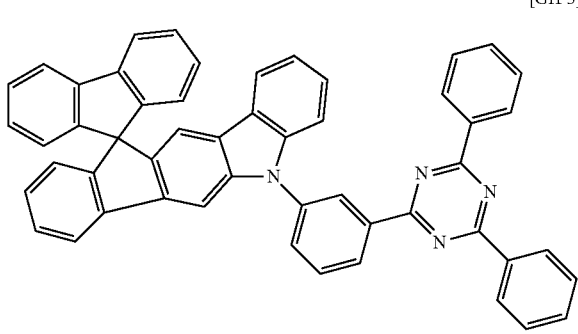

When current was applied to the organic light emitting devices manufactured in Experimental Examples 2-1 to 2-6 and Comparative Examples 2-1 to 2-3, the results of the following Table 2 were obtained.

TABLE 2

| Classification | Compound (Host) | Voltage (V@10 mA/cm$^2$) | Efficiency (cd/A@10 mA/cm$^2$) | EL peak (nm) |
|---|---|---|---|---|
| Experimental Example 2-1 | Compound 4 | 5.38 | 45.31 | 517 |
| Experimental Example 2-2 | Compound 6 | 5.43 | 44.93 | 516 |
| Experimental Example 2-3 | Compound 7 | 5.55 | 44.34 | 518 |
| Experimental Example 2-4 | Compound 8 | 5.49 | 44.25 | 517 |
| Experimental Example 2-5 | Compound 12 | 5.44 | 44.88 | 518 |
| Experimental Example 2-6 | Compound 14 | 5.39 | 45.30 | 517 |
| Comparative Example 2-1 | GH 1 (CBP) | 6.12 | 39.41 | 517 |
| Comparative Example 2-2 | GH 2 | 5.75 | 41.35 | 518 |
| Comparative Example 2-3 | GH 3 | 5.92 | 40.25 | 519 |

As observed in Table 2, it could be confirmed that the green organic light emitting devices of Experimental Examples 2-1 to 2-6 in which the spiro compound represented by Chemical Formula 1 according to the present specification was used as a host material of the green light emitting layer exhibited better performances in terms of current efficiency and driving voltage than the green organic EL devices of Comparative Examples 2-1 to 2-3 in which CBP in the related art was used.

Experimental Example 3

Experimental Example 3-1

The compounds synthesized in the Preparation Examples were subjected to high-purity sublimation purification by a typically known method, and then red organic light emitting devices were manufactured by the following method.

An ITO glass was patterned and then washed, such that the light emitting area of the ITO glass became 2 mm×2 mm. The substrate was mounted on a vacuum chamber, and then the base pressure was allowed to be 1×10$^{-6}$ torr, and then for the organic material, DNTPD (700 Å), α-NPB (300 Å), and Compound 5 were used as hosts (90 wt %) on the ITO, the following (piq)$_2$Ir(acac) (10 wt %) was vacuum deposited (300 Å) as a dopant, films were formed in the order of Alq$_3$ (350 Å), LiF (5 Å), and Al (1,000 Å), and measurements were made at 0.4 mA.

The structures of DNTPD, α-NPB, (piq)$_2$Ir(acac), and Alq$_3$ are as follows.

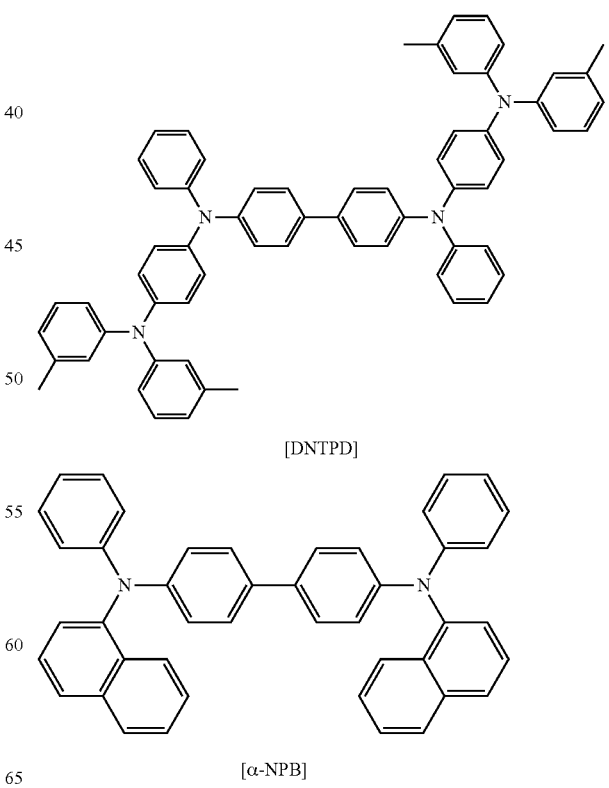

[DNTPD]

[α-NPB]

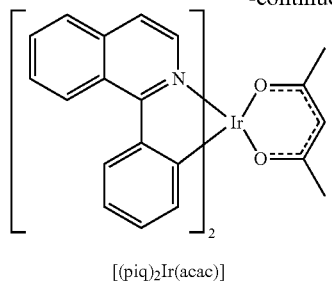

[(piq)₂Ir(acac)]

[Alq₃]

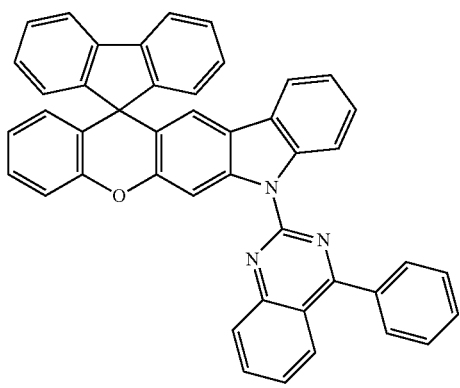

[Compound 5]

Experimental Example 3-2

An organic light emitting device was manufactured in the same manner as in Experimental Example 3-1, except that Compound 13 was used instead of Compound 5 in Experimental Example 3-1.

Comparative Example 3-1

An organic light emitting device was manufactured in the same manner as in Experimental Example 3-1, except that the following Compound RH 1 (CBP) was used instead of Compound 5 in Experimental Example 3-1.

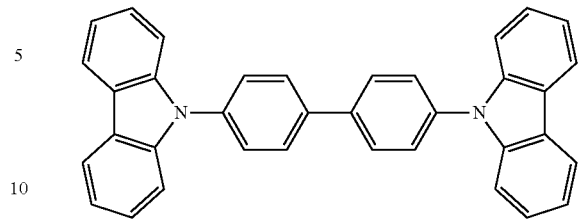

[RH 1]

For the organic light emitting devices manufactured according to Experimental Examples 3-1 and 3-2 and Comparative Example 3-1, the voltages, current densities, luminances, color coordinates, and service lives were measured, and the results are shown in the following [Table 3]. T95 means the time taken for the luminance to be reduced to 95% of the initial luminance (5,000 nit).

TABLE 3

| Classification | Compound (Host) | Voltage (V) | Luminance (cd/m²) | Color coordinate (x, y) | T95 (hr) |
|---|---|---|---|---|---|
| Experimental Example 3-1 | Compound 5 | 4.3 | 1860 | (0.670, 0.329) | 465 |
| Experimental Example 3-2 | Compound 13 | 4.2 | 1920 | (0.674, 0.325) | 435 |
| Comparative Example 3-1 | RH 1 (CBP) | 5.4 | 1350 | (0.671, 0.327) | 355 |

As observed in Table 3, it could be confirmed that the red organic light emitting devices of Experimental Examples 3-1 and 3-2 in which the spiro compound according to the present specification was used as a host material of the light emitting layer exhibited better performances in terms of current efficiency, driving voltage, and service life than the red organic EL device of Comparative Example 3-1 in which CBP in the related art was used.

Although the preferred exemplary embodiments (an electron blocking layer, a green light emitting layer, and a red light emitting layer) of the present specification have been described above, the present specification is not limited thereto, and can be variously modified and carried out within the scope of the claims and the detailed description of the invention, and the modifications also fall within the scope of the specification.

EXPLANATION OF REFERENCE NUMERALS AND SYMBOLS

10, 11: Organic light emitting device
20: Substrate
30: First electrode
40: Light emitting layer
50: Second electrode
60: Hole injection layer
70: Hole transporting layer
80: Electron blocking layer
90: Electron transporting layer
100: Electron injection layer

The invention claimed is:

1. A spiro compound represented by the following Chemical Formula 1:

[Chemical Formula 1]

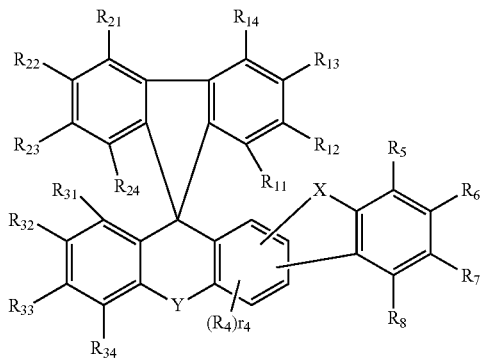

in Chemical Formula 1,

X is $NR_9$, O, S or $CR_{101}R_{102}$,

Y is O, S, $CR_{103}R_{104}$ or $SiR_{105}R_{106}$, $R_9$ is $-L_1Ar_1$, $L_1$ is a direct bond; a substituted or unsubstituted arylene group; or a substituted or unsubstituted heteroarylene group, $R_4$ to $R_8$, $R_{11}$ to $R_{14}$, $R_{21}$ to $R_{24}$, $R_{31}$ to $R_{34}$, $R_{101}$ to $R_{106}$, and $Ar_1$ are the same as or different from each other, and are each independently hydrogen; deuterium; a halogen group; a cyano group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted amine group; a substituted or unsubstituted alkylamine group; a substituted or unsubstituted arylamine group; a substituted or unsubstituted heteroarylamine group; a substituted or unsubstituted phosphine oxide group; a substituted or unsubstituted aryl group; or a substituted or unsubstituted heteroaryl group, or are optionally bonded to an adjacent group to form a ring provided that when $R_{103}$ and $R_{104}$ are phenyl, $R_{103}$ and $R_{104}$ are not bonded to each other to form a ring, $r_4$ is an integer of 1 or 2, and when $r_4$ is 2, $R_4$s are the same as or different from each other;

with the proviso that the following compound is excluded from the derivatives of Chemical Formula 1:

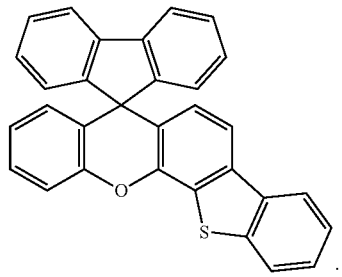 [SMILES: c1ccc2c(c1)Oc1c(ccc3c1sc1ccccc13)C21c2ccccc2-c2ccccc21]

2. The spiro compound of claim 1, wherein Chemical Formula 1 is represented by any one of the following Chemical Formulae 2 to 5:

[Chemical Formula 2]

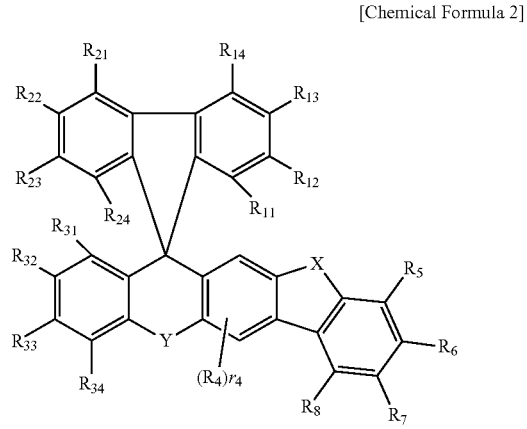

[Chemical Formula 3]

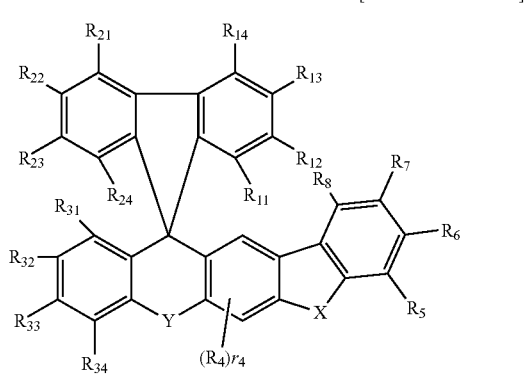

[Chemical Formula 4]
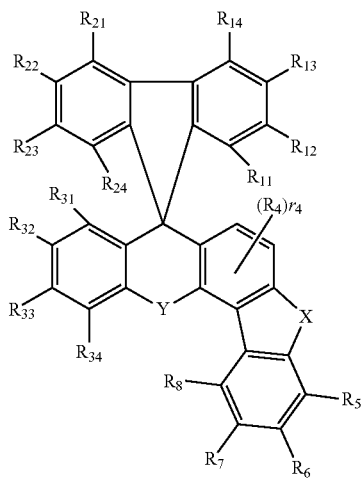
[Chemical Formula 5]
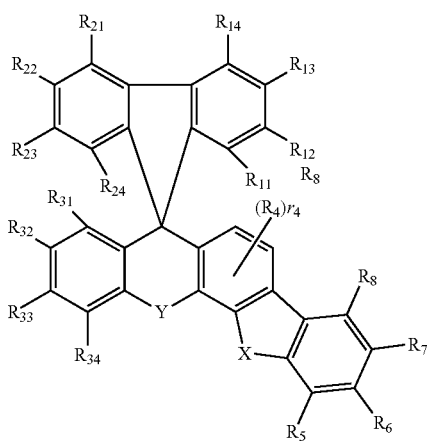
in Chemical Formulae 2 to 5,
the definitions of X, Y, $R_4$ to $R_8$, $R_{11}$ to $R_{14}$, $R_{21}$ to $R_{24}$, $R_{31}$ to $R_{34}$, and $r_4$ are the same as those defined in Chemical Formula 1.
3. A spiro compound represented by any one of the following Chemical Formulae 6 to 17:
[Chemical Formula 6]
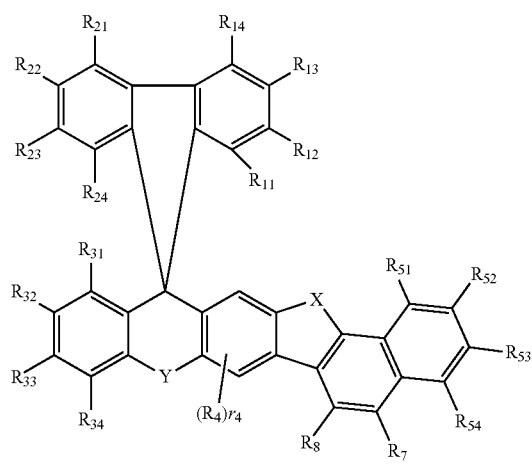
[Chemical Formula 7]
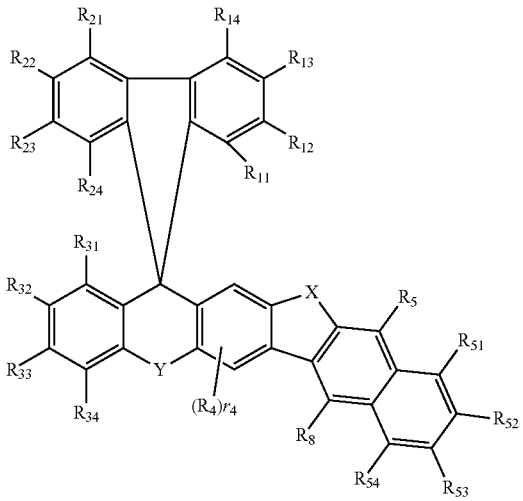
[Chemical Formula 8]
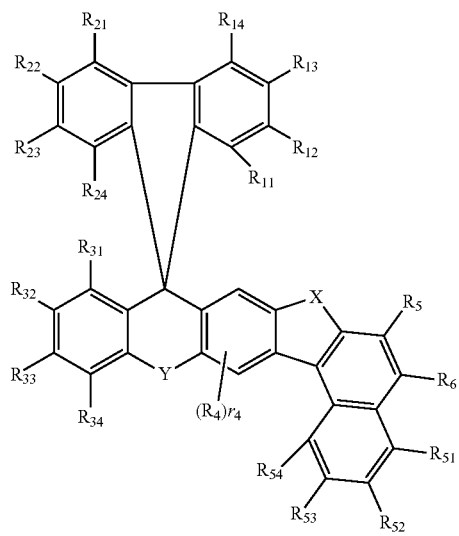
[Chemical Formula 9]
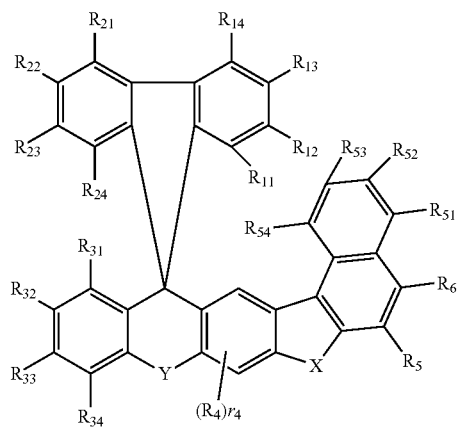

[Chemical Formula 10]
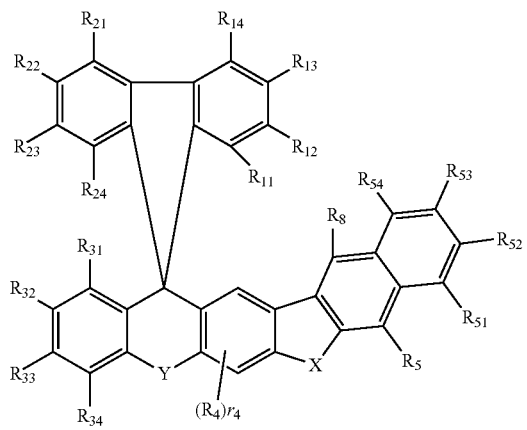
[Chemical Formula 11]
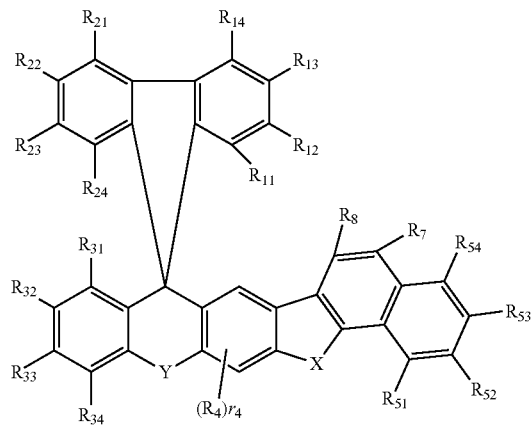
[Chemical Formula 12]
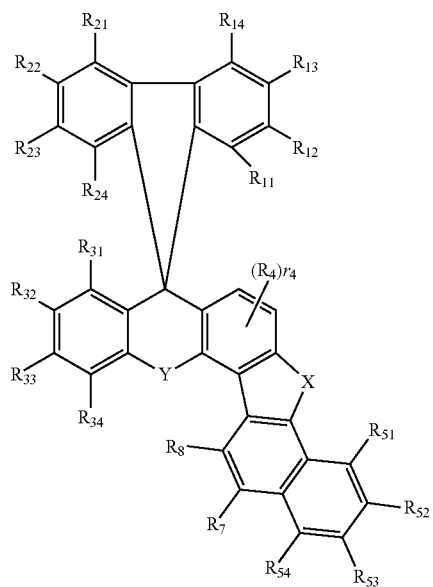
[Chemical Formula 13]
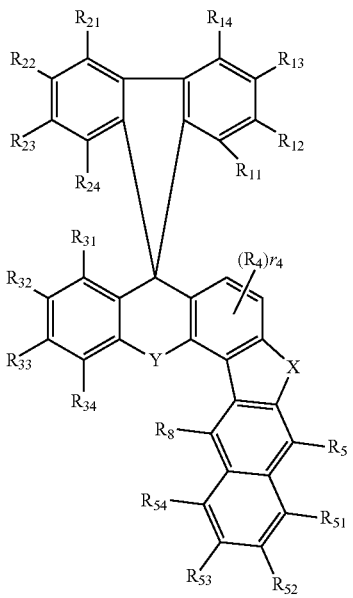
[Chemical Formula 14]
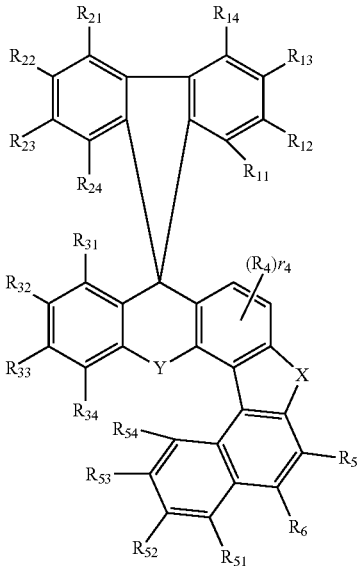

[Chemical Formula 15]

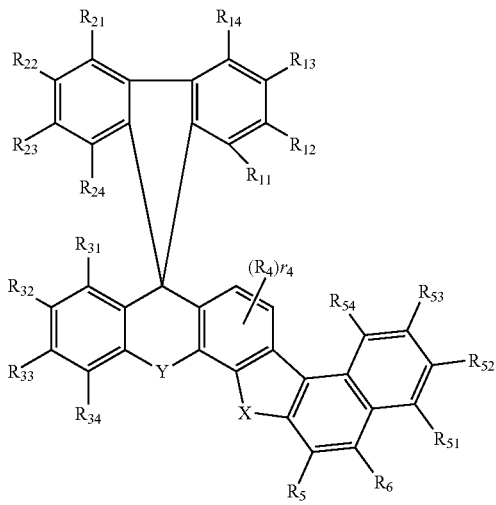

[Chemical Formula 16]

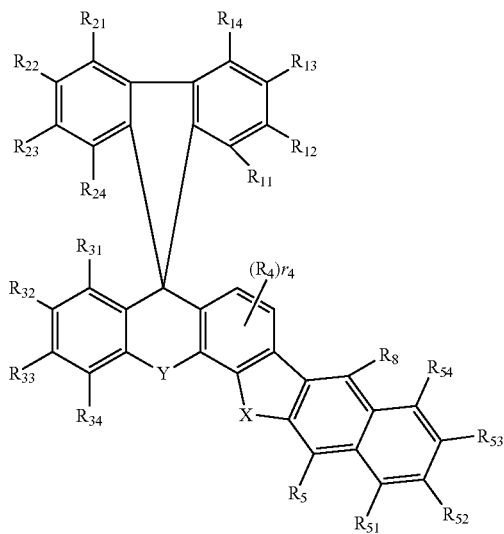

[Chemical Formula 17]

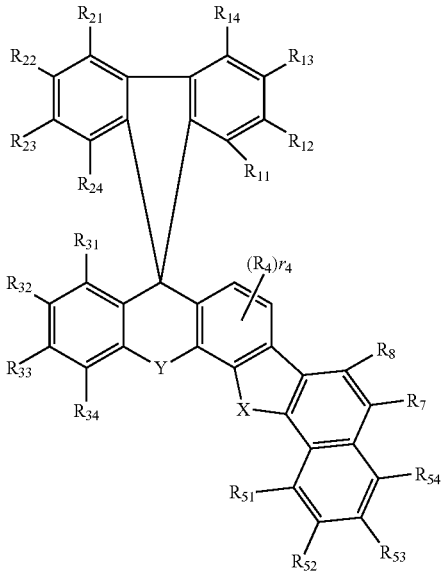

in Chemical Formulae 6 to 17,

X is $NR_9$, O, S or $CR_{101}R_{102}$,

Y is O, S, $CR_{103}R_{104}$ or $SiR_{105}R_{106}$, $R_9$ is $-L_1Ar_1$, $L_1$ is a direct bond; a substituted or unsubstituted arylene group; or a substituted or unsubstituted heteroarylene group, $R_4$ to $R_8$, $R_{11}$ to $R_{14}$, $R_{21}$ to $R_{24}$, $R_{31}$ to $R_{34}$, $R_{101}$ to $R_{106}$, and $Ar_1$ are the same as or different from each other, and are each independently hydrogen; deuterium; a halogen group; a cyano group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted amine group; a substituted or unsubstituted alkylamine group; a substituted or unsubstituted arylamine group; a substituted or unsubstituted heteroarylamine group; a substituted or unsubstituted phosphine oxide group; a substituted or unsubstituted aryl group; or a substituted or unsubstituted heteroaryl group, or are optionally bonded to an adjacent group to form a ring, $r_4$ is an integer of 1 or 2, and when $r_4$ is 2, $R_4$s are the same as or different from each other, $R_{51}$ to $R_{54}$ are the same as or different from each other, and are each independently hydrogen; deuterium; a halogen group; a cyano group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted amine group; a substituted or unsubstituted alkylamine group; a substituted or unsubstituted arylamine group; a substituted or unsubstituted heteroarylamine group; a substituted or unsubstituted phosphine oxide group; a substituted or unsubstituted aryl group; or a substituted or unsubstituted heteroaryl group, or are optionally bonded to an adjacent group to form a ring.

4. The spiro compound of claim 1, wherein Chemical Formula 1 is selected from the following compounds:

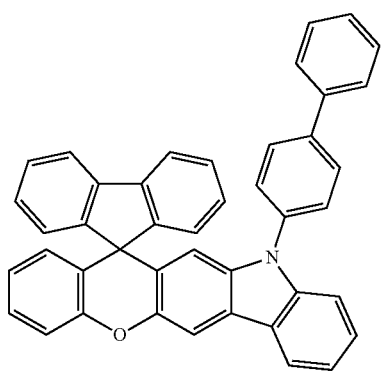

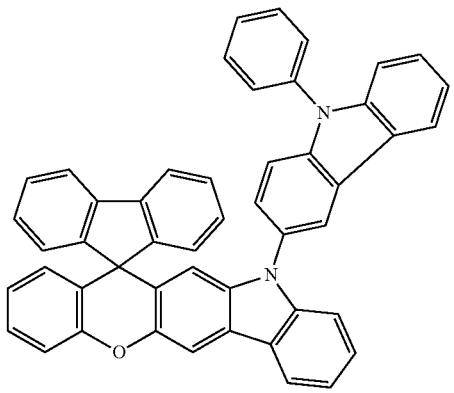

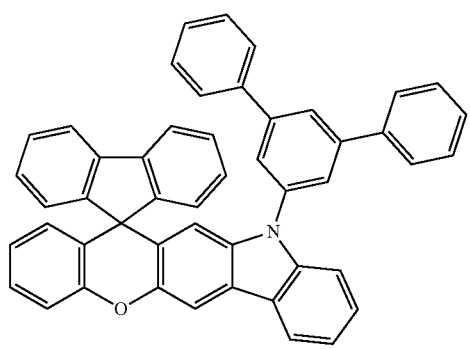

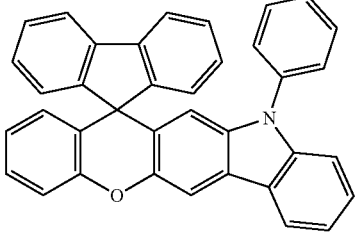

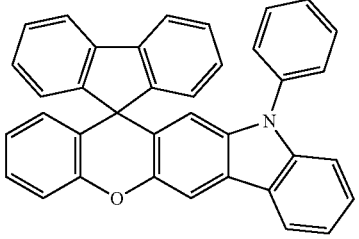

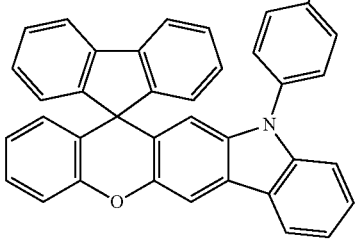

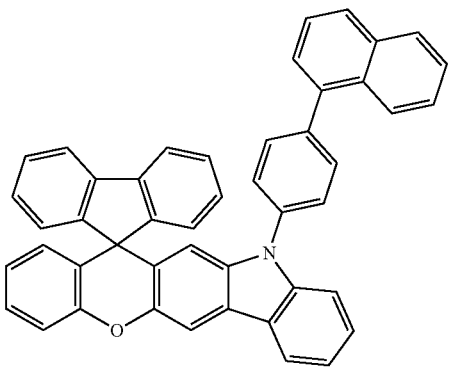

499
-continued
500
-continued
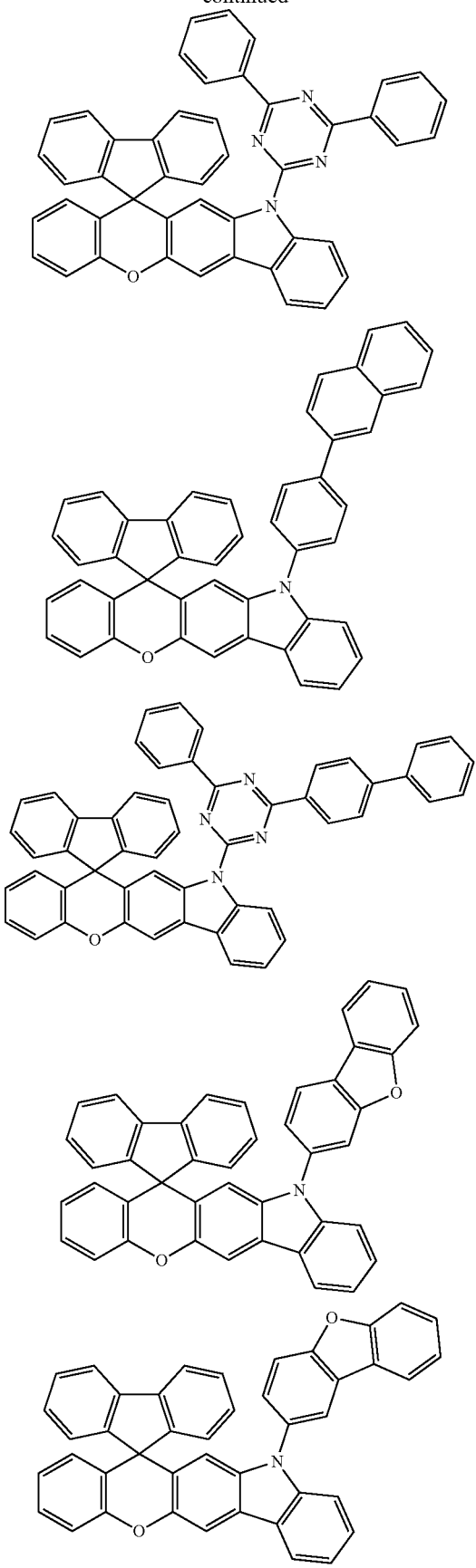
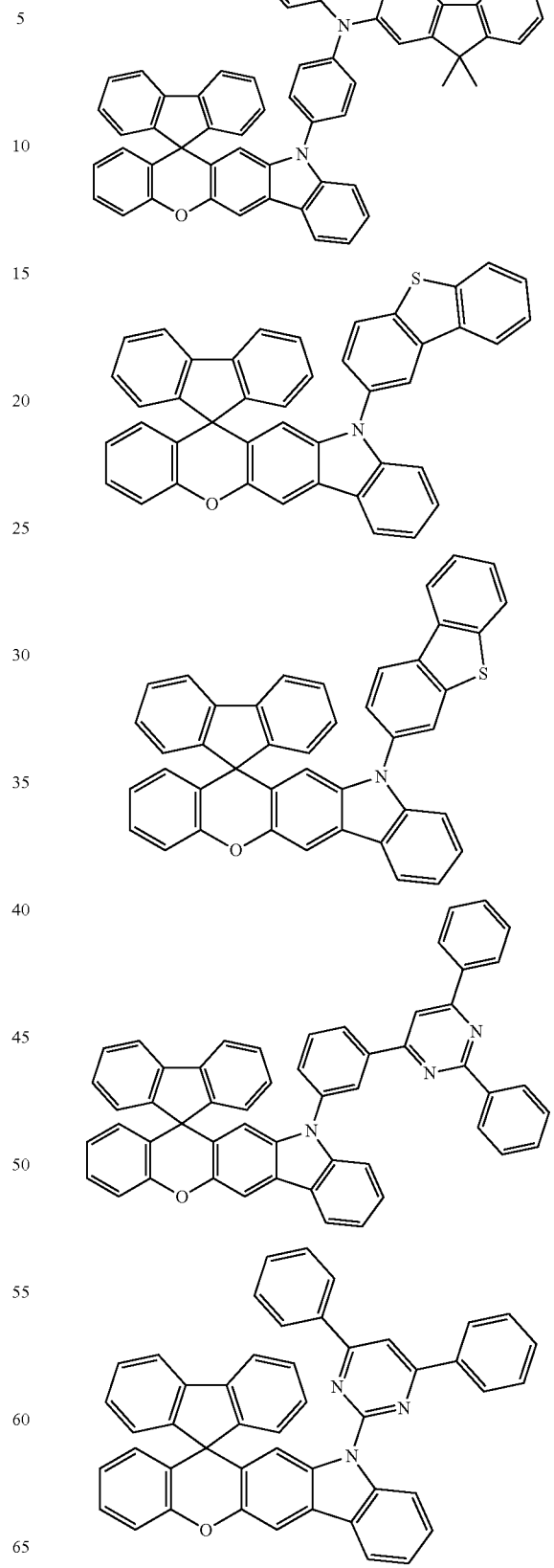

501
-continued
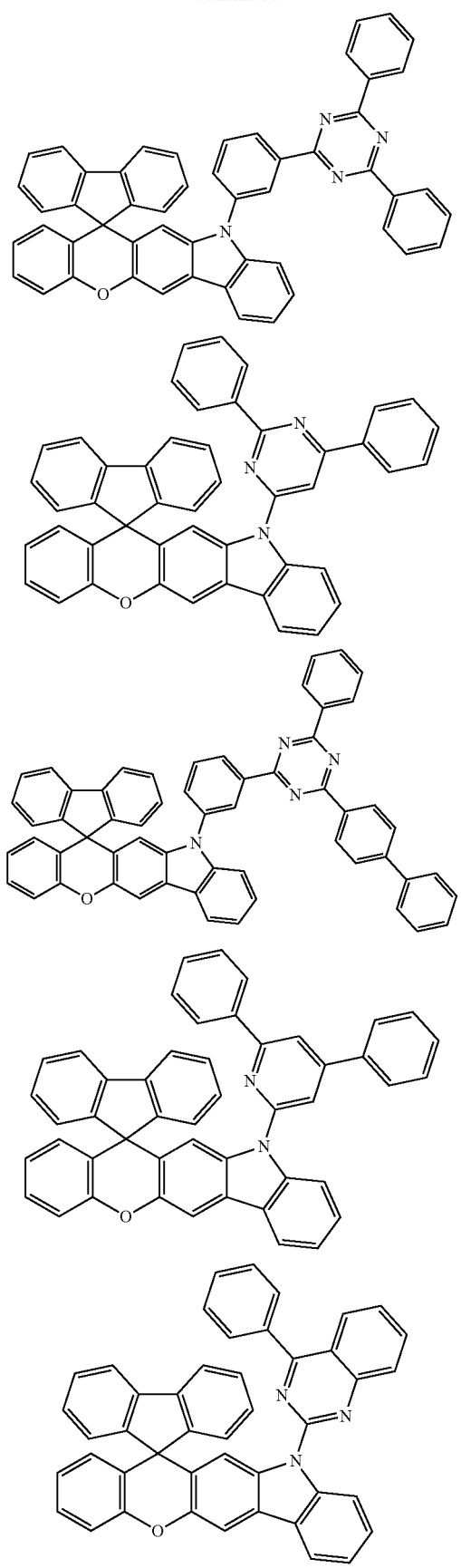
502
-continued
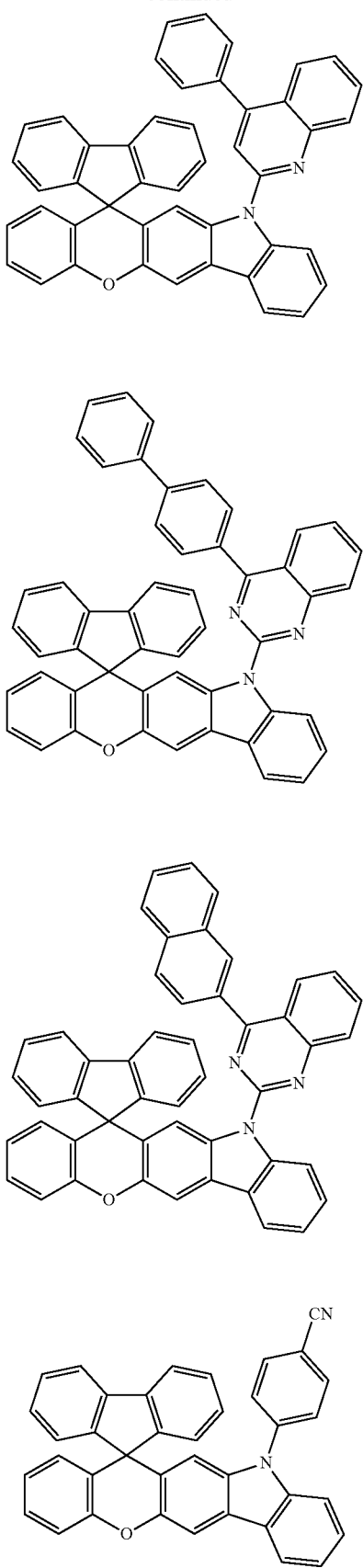

503
-continued
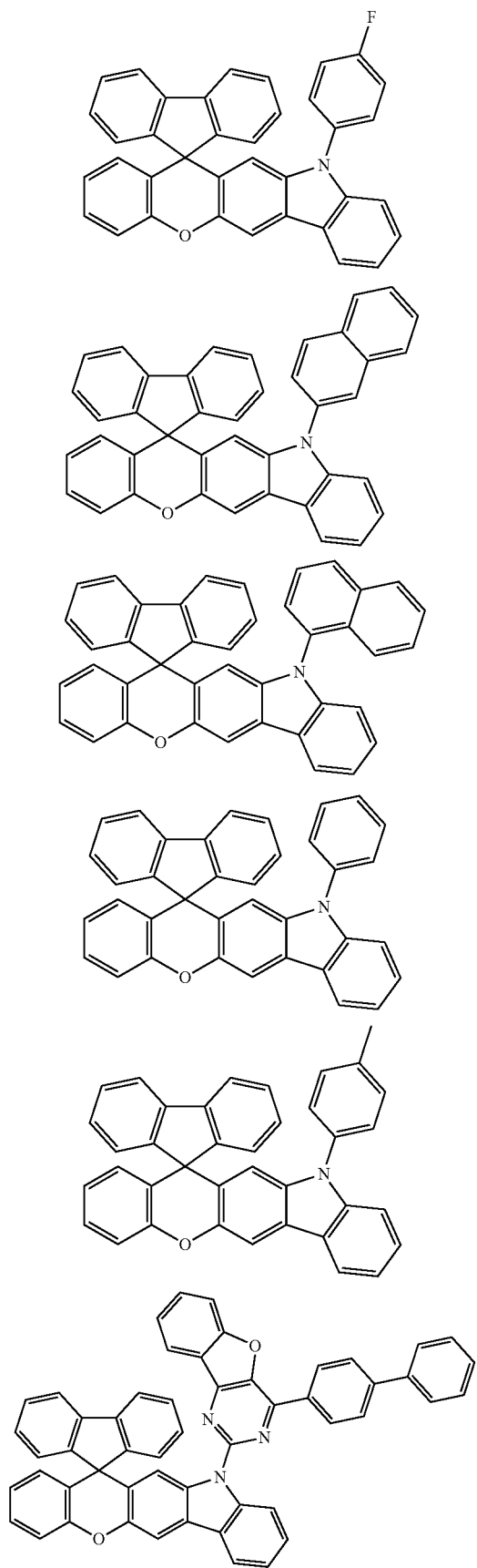
504
-continued
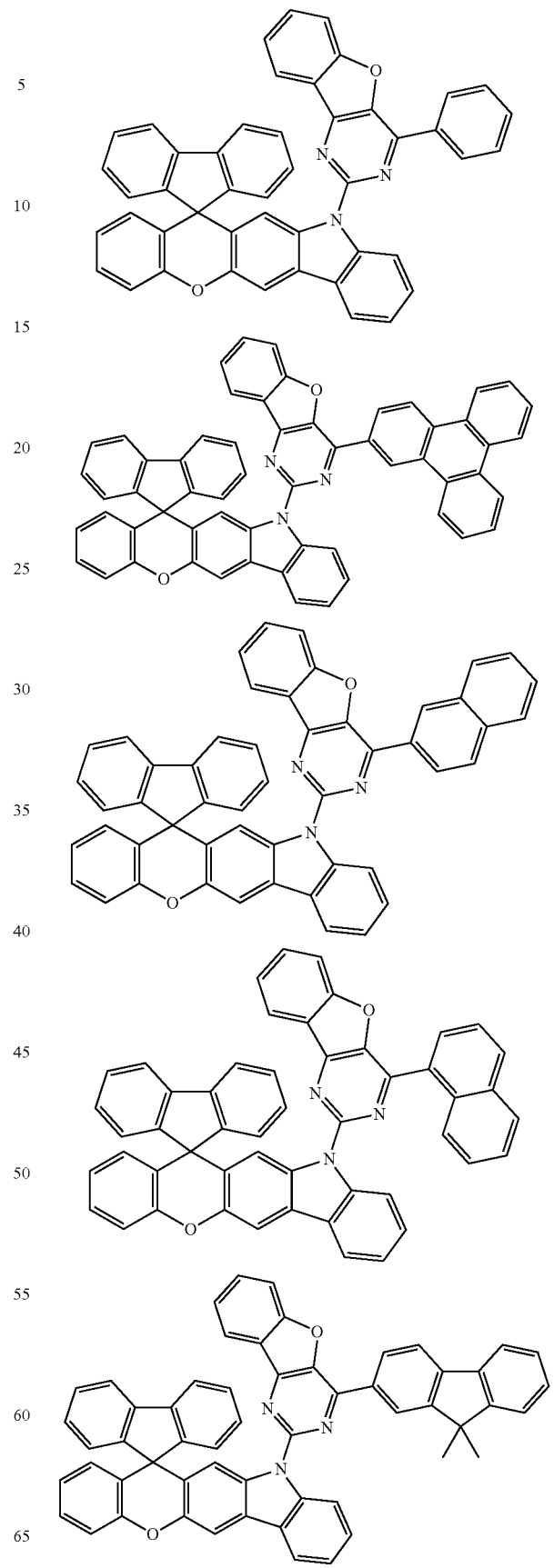

505
-continued
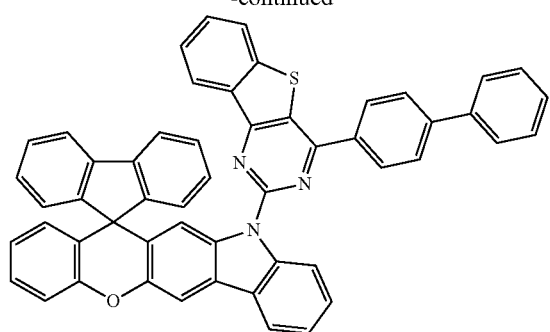
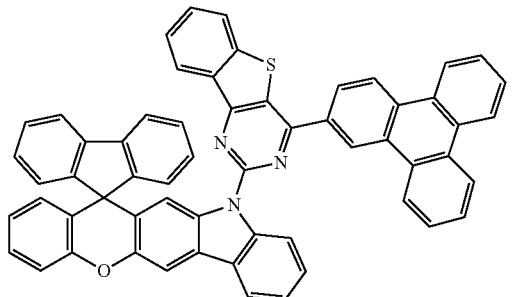
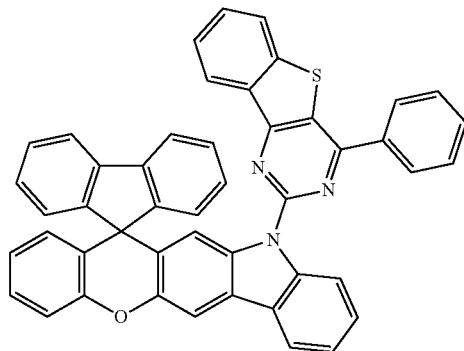
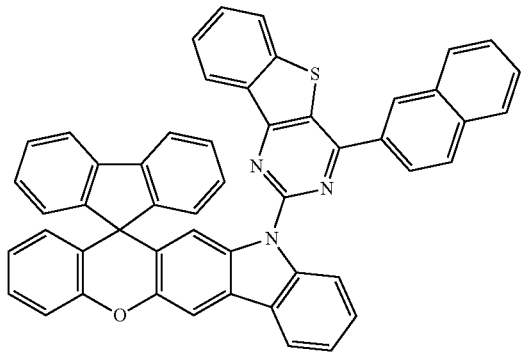
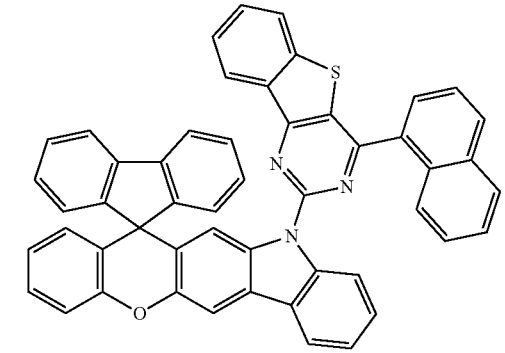
506
-continued
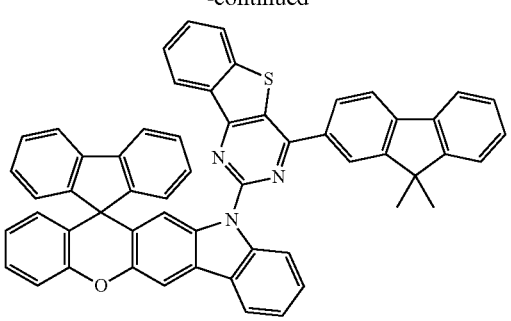
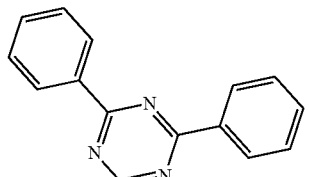
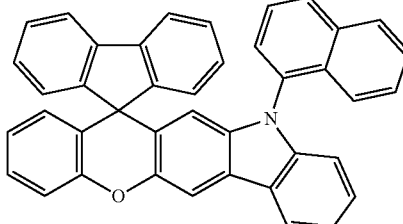
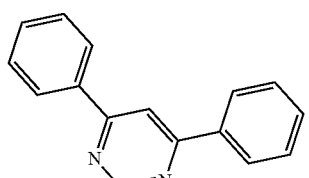
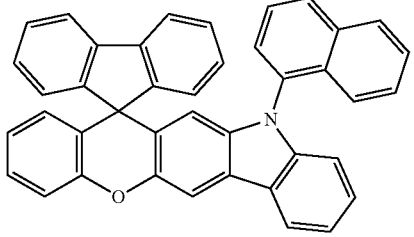
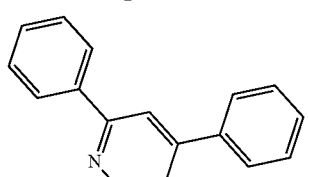
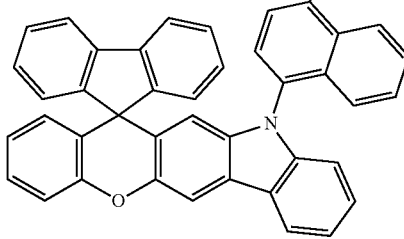

507
-continued
508
-continued
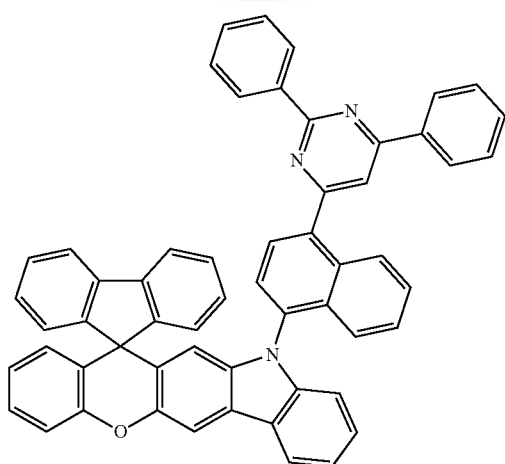
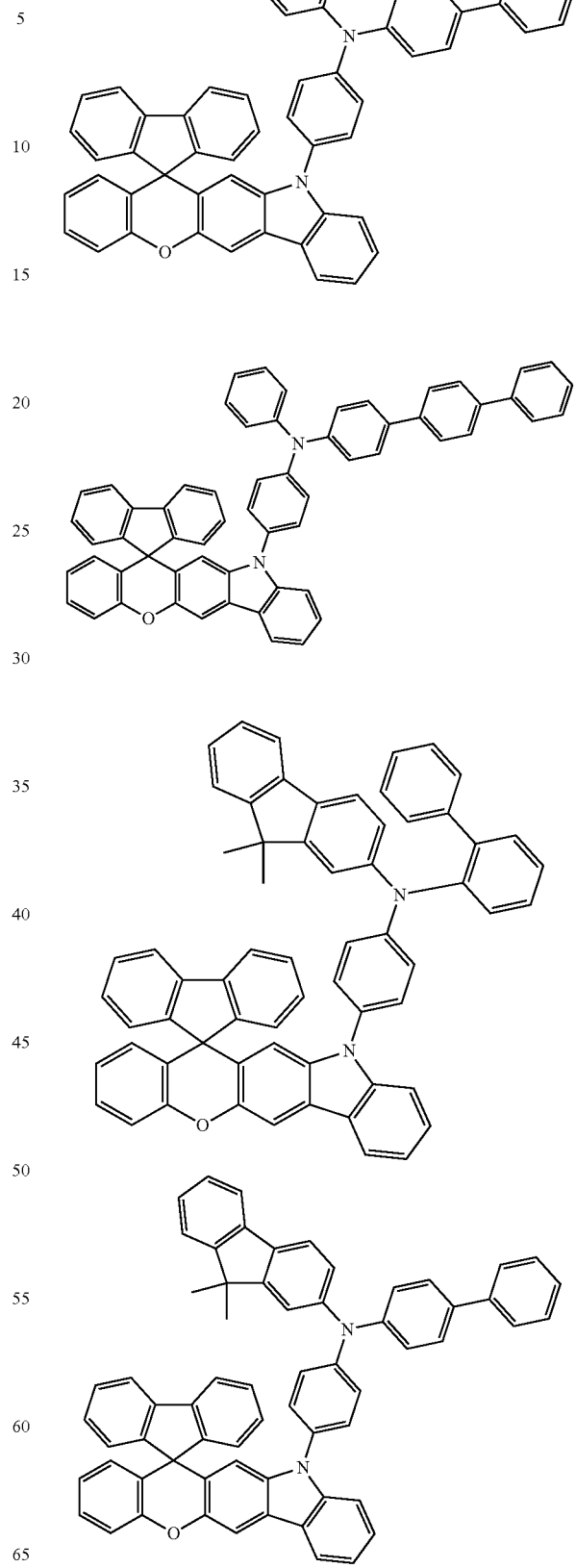

509
-continued
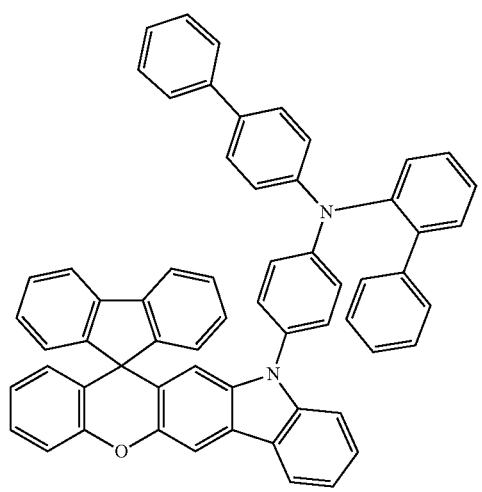
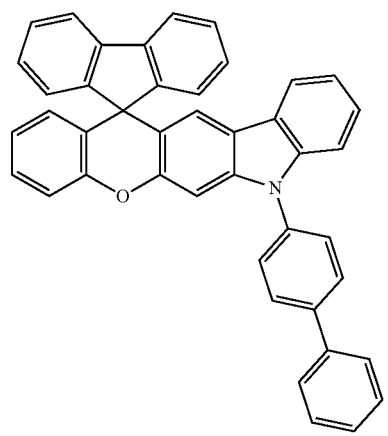
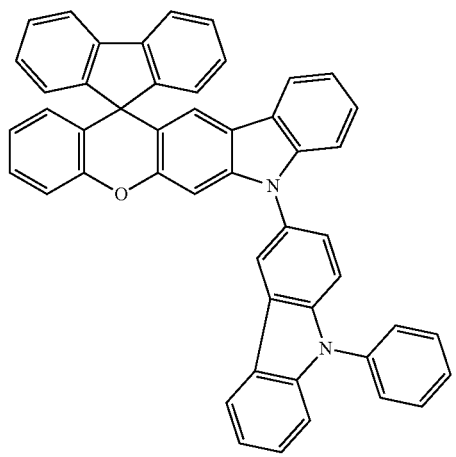
510
-continued
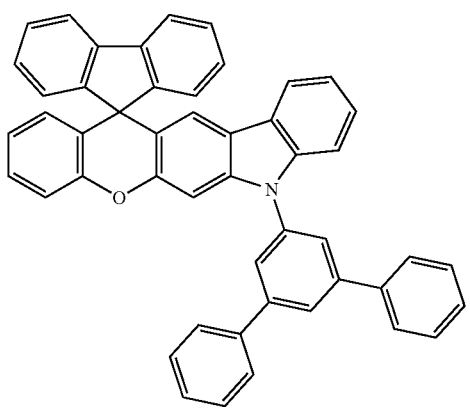
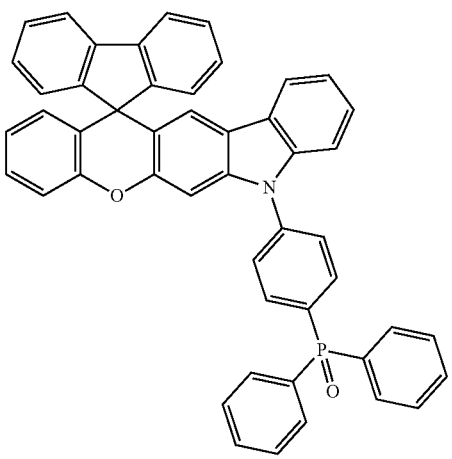
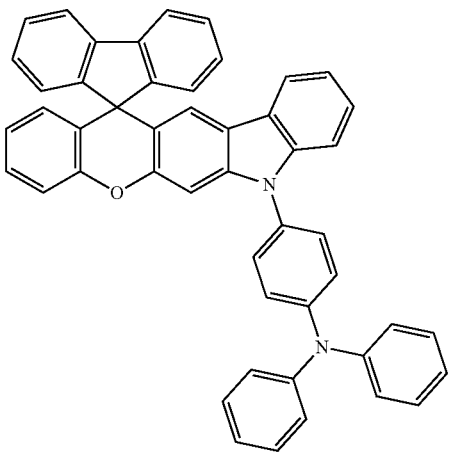

511
-continued
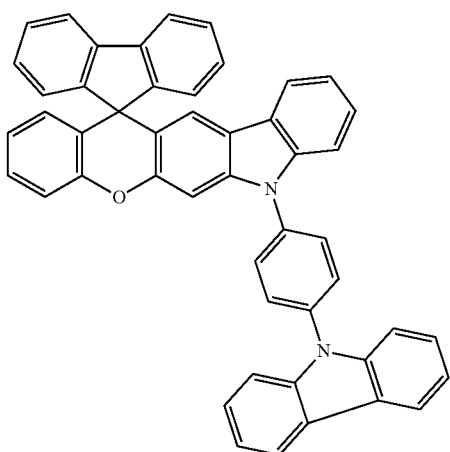
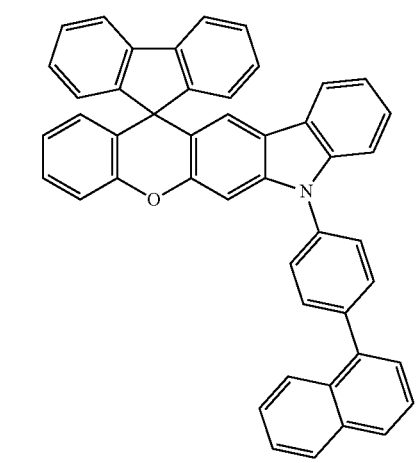
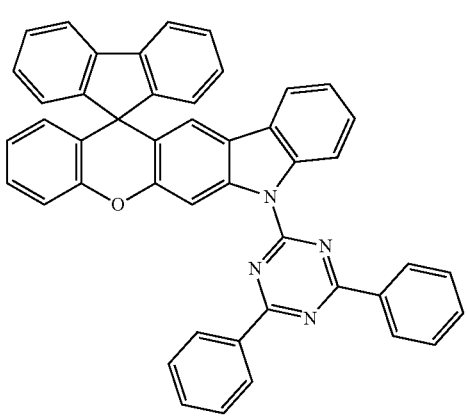
512
-continued
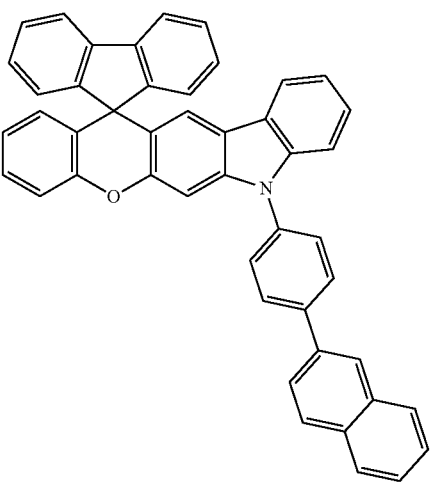
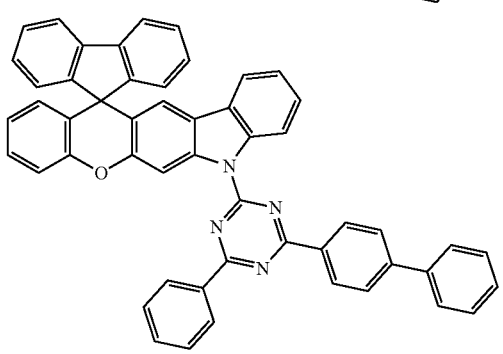
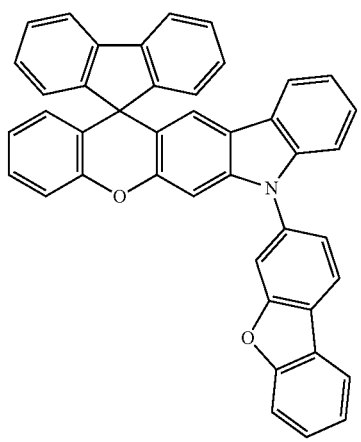
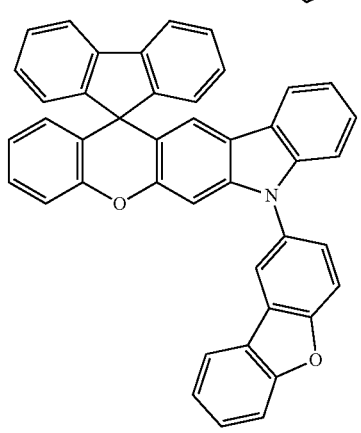

513
-continued
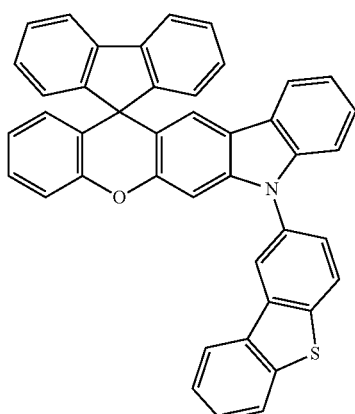
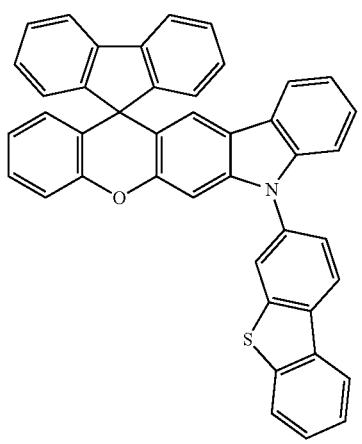
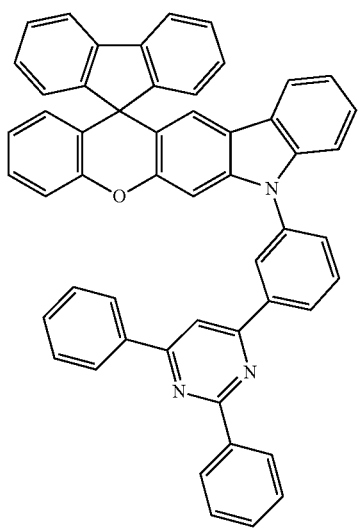
514
-continued
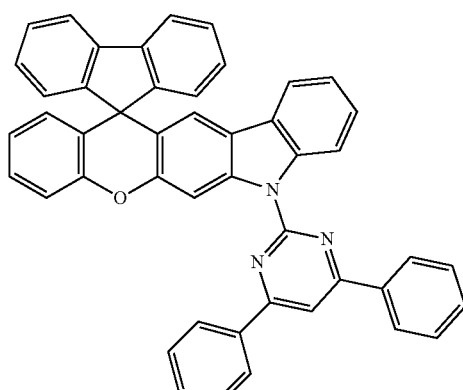
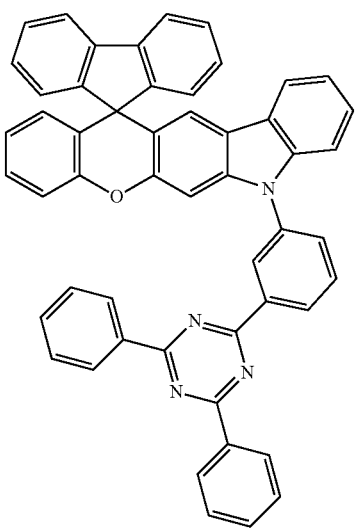
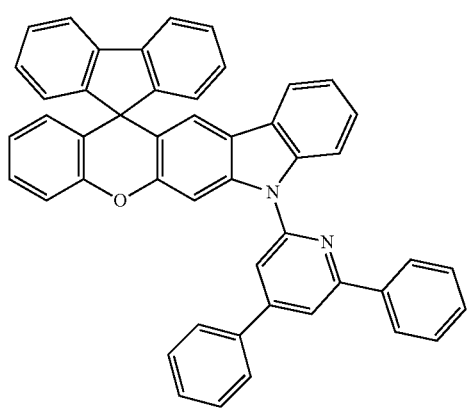

515
-continued
516
-continued
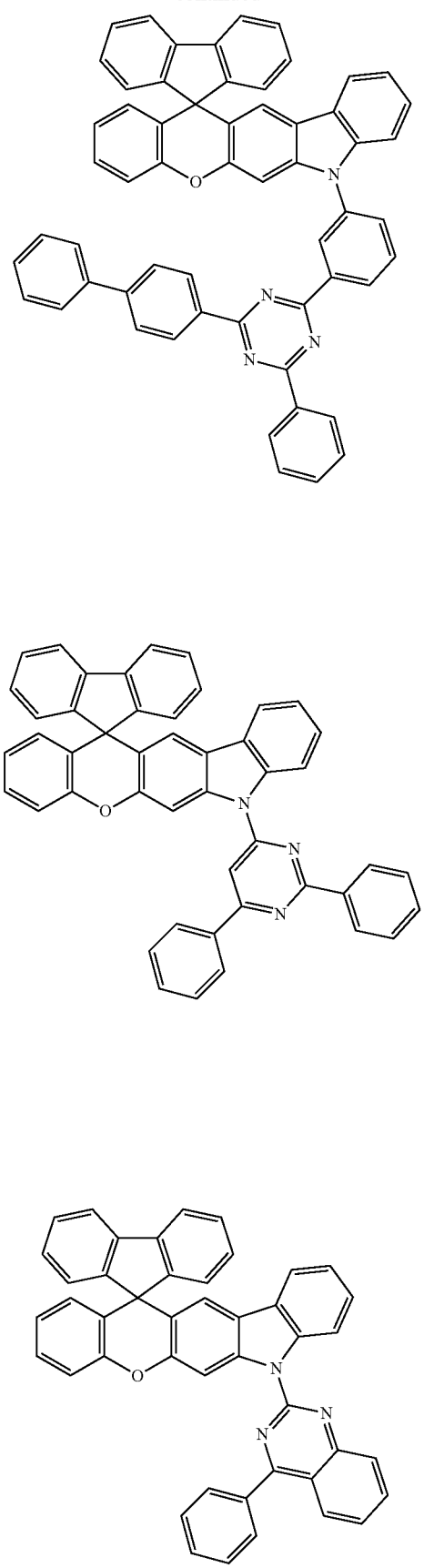
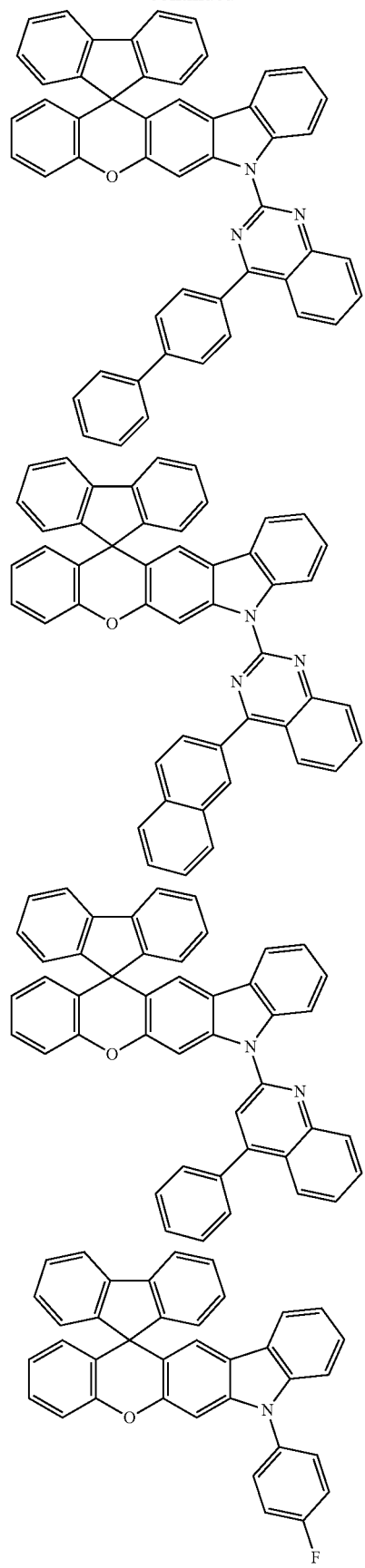

517
-continued
518
-continued
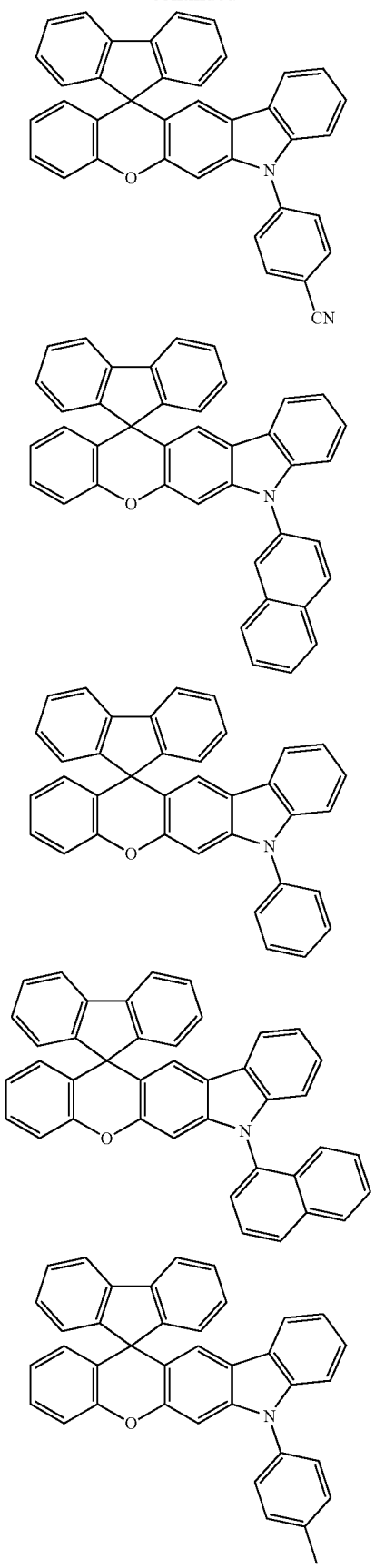
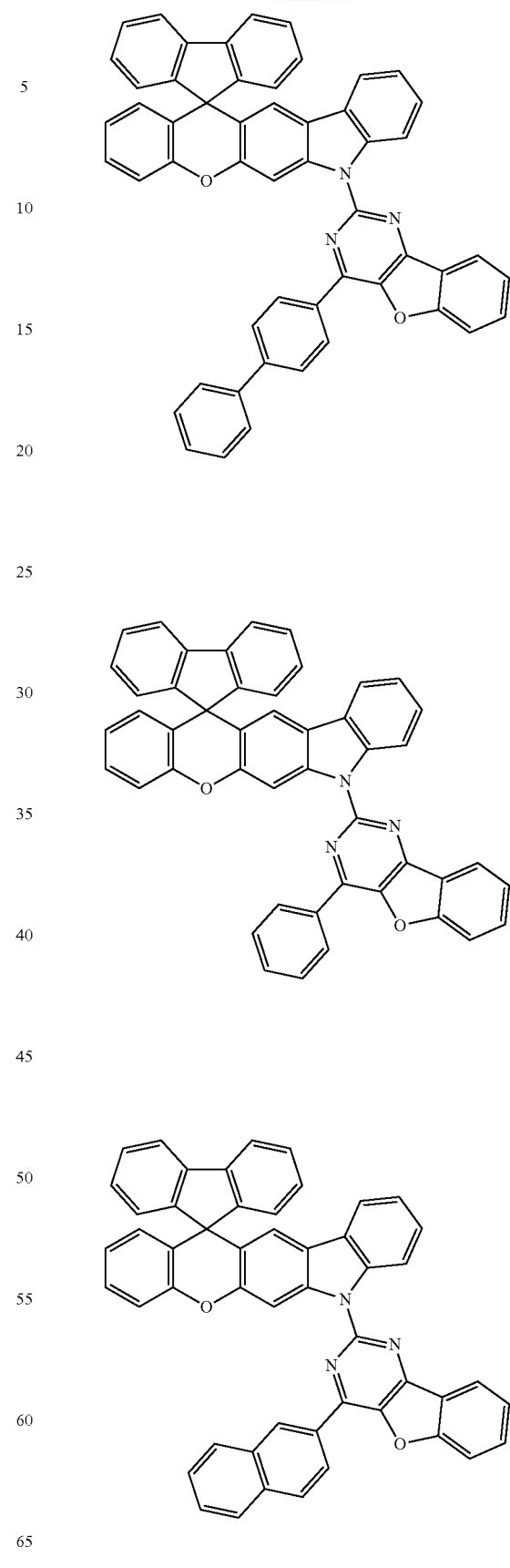

519
-continued
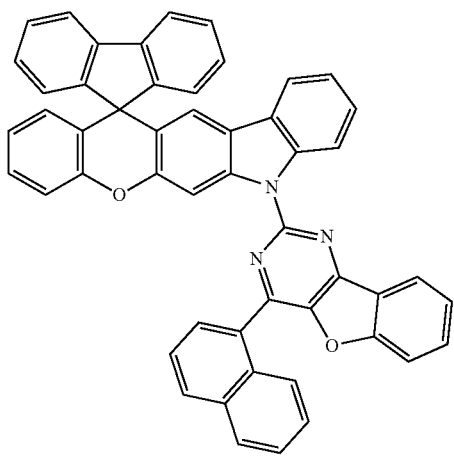
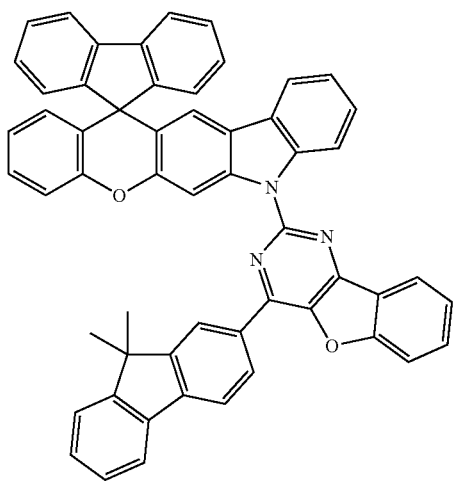
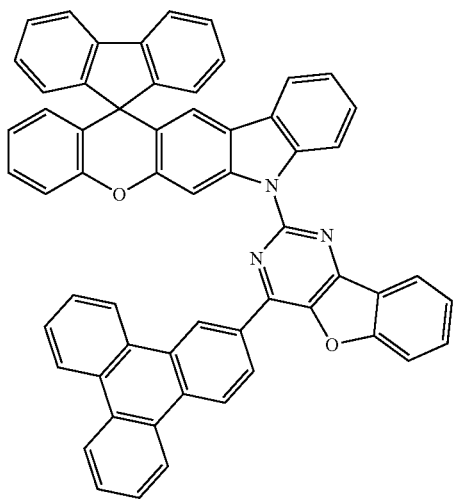
520
-continued
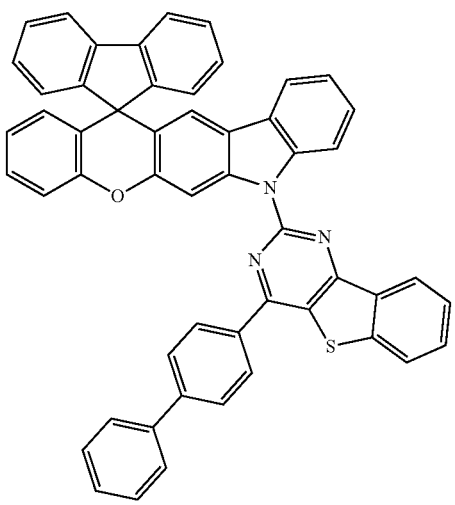
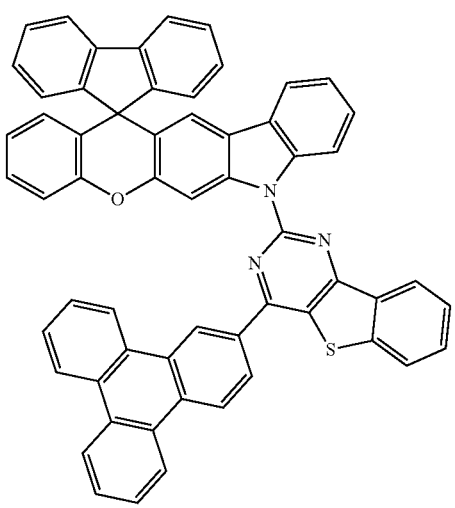
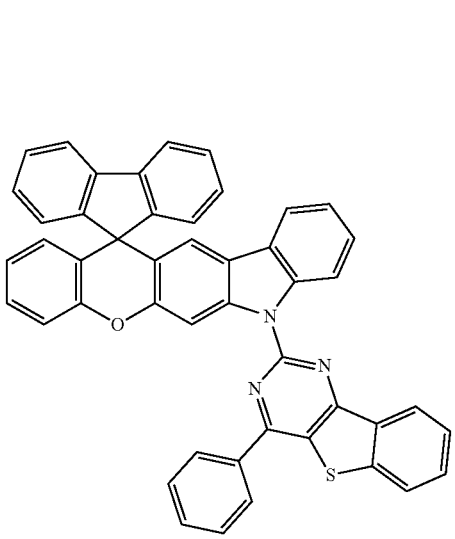

521
-continued
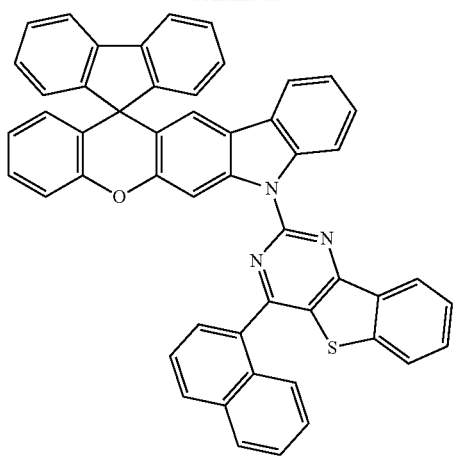
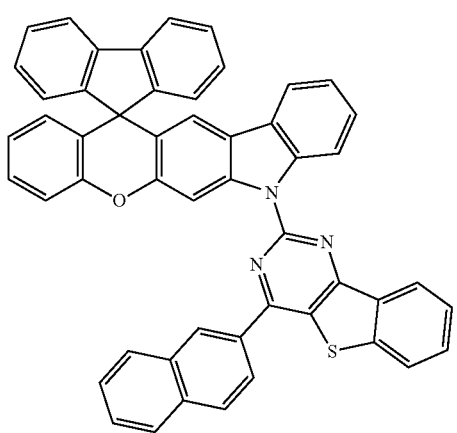
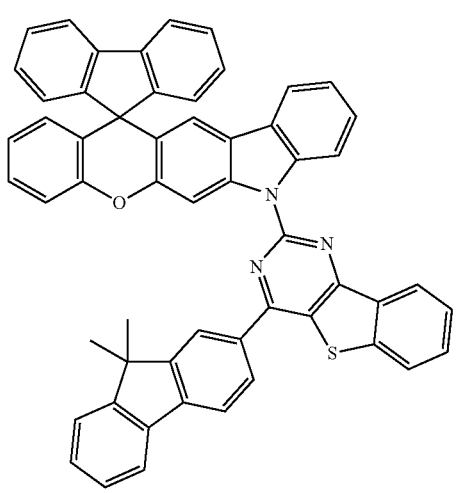
522
-continued
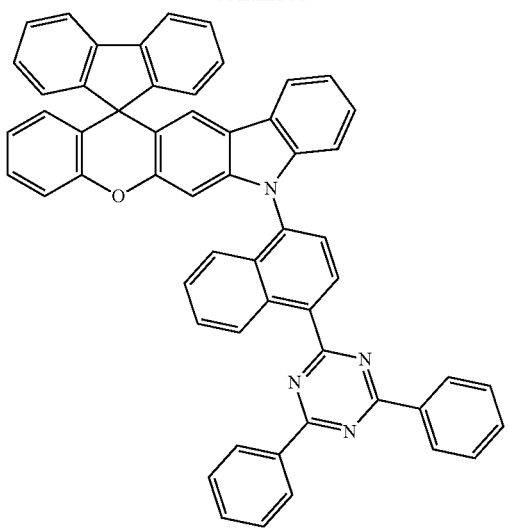
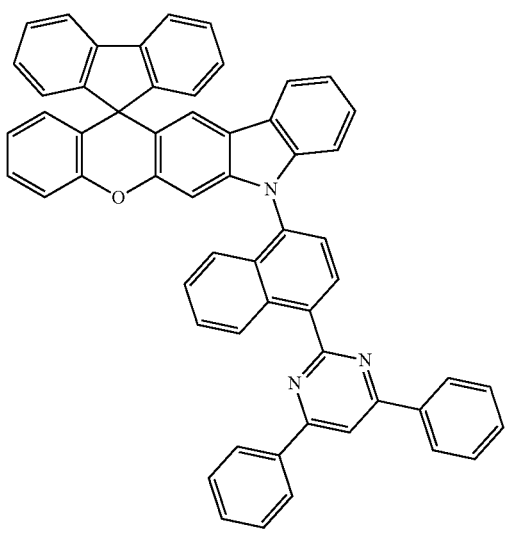
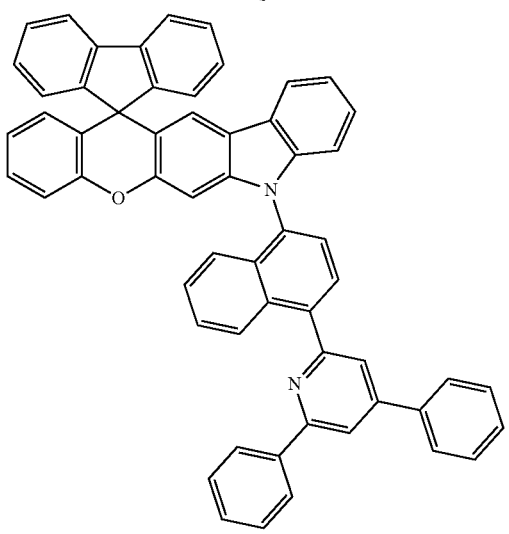

523
-continued
524
-continued
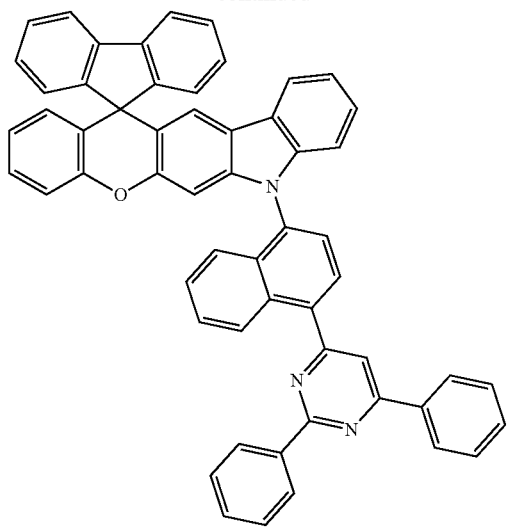
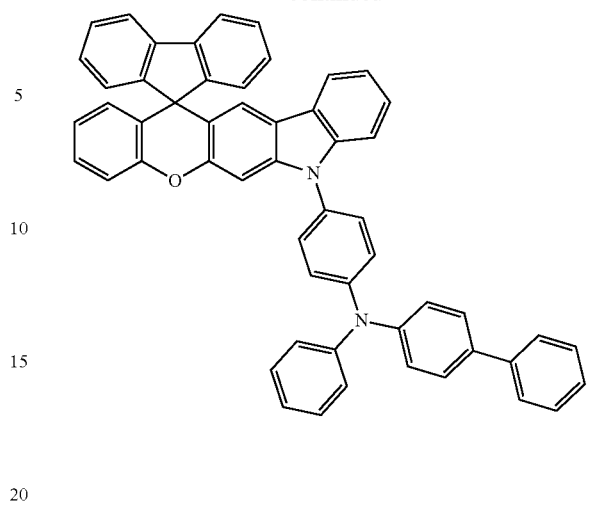
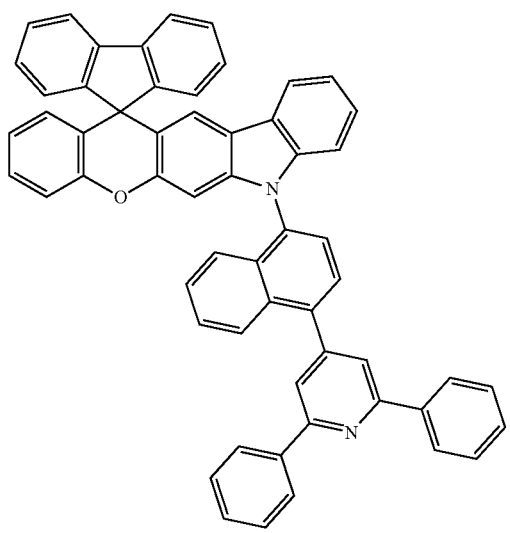
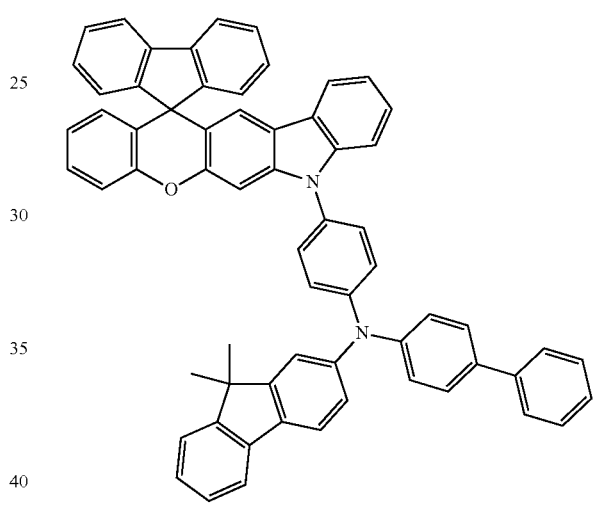
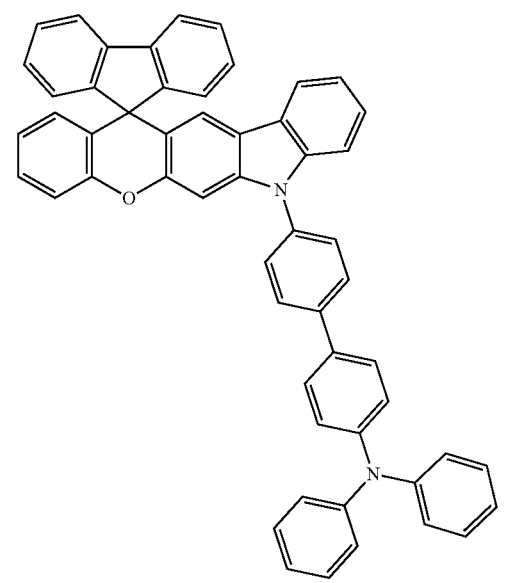
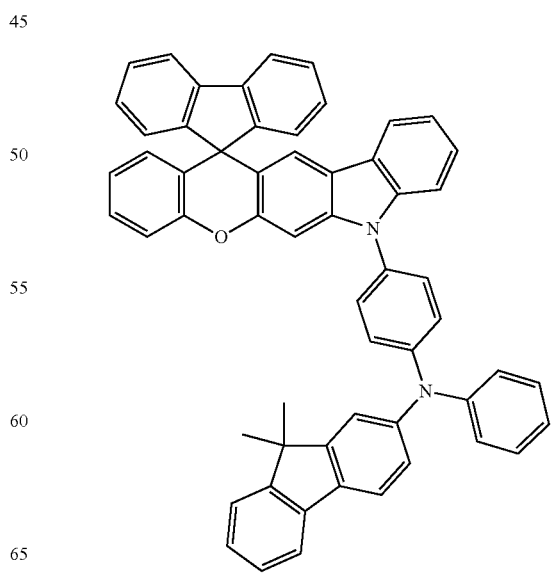

525
-continued
526
-continued
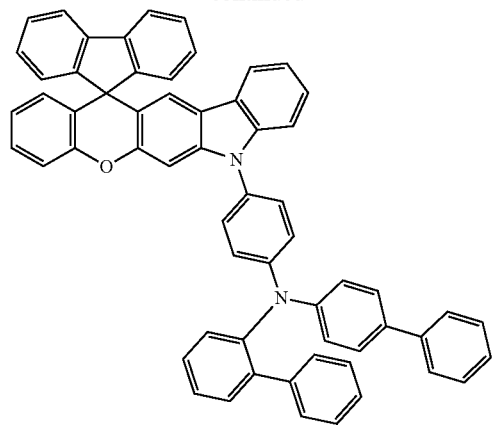
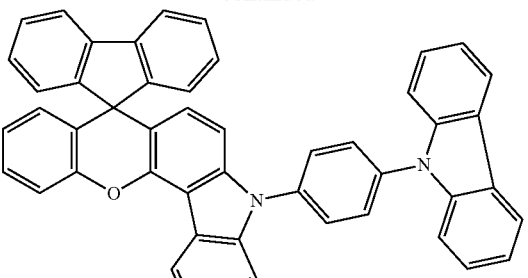
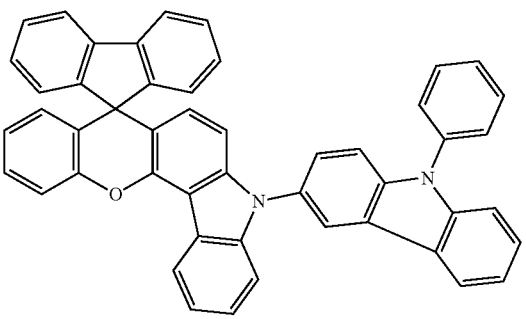
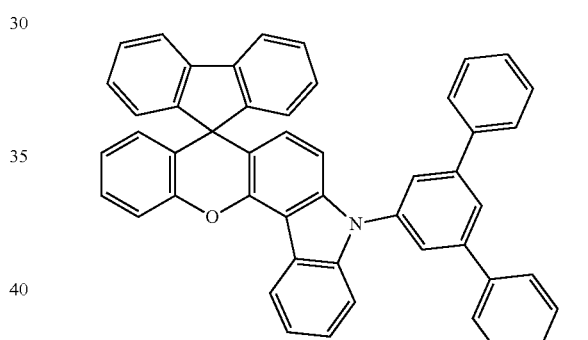
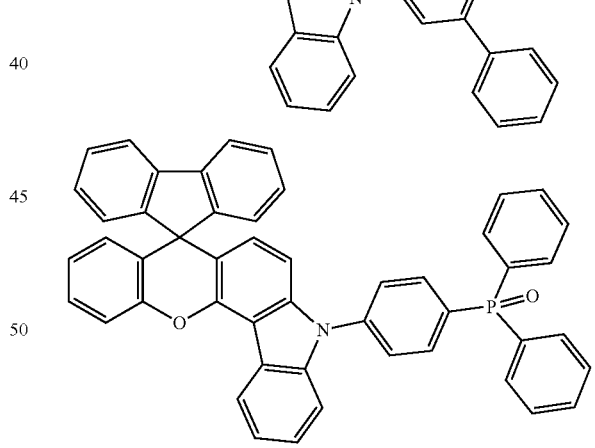
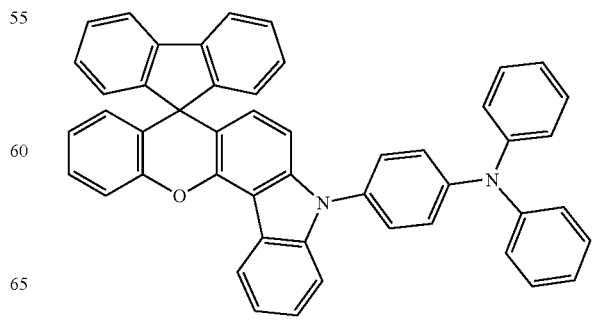

527
-continued
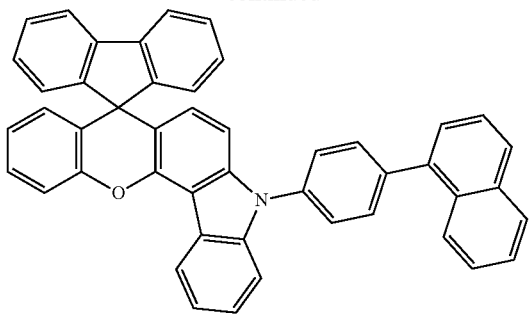
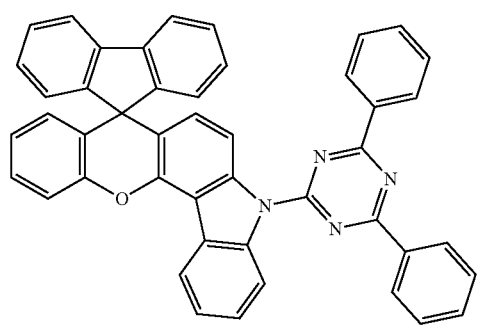
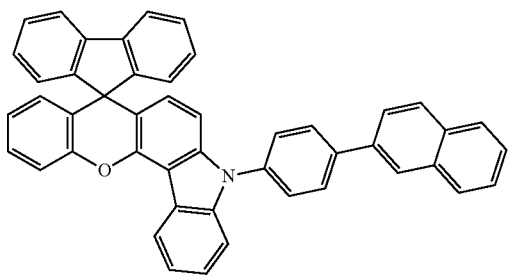
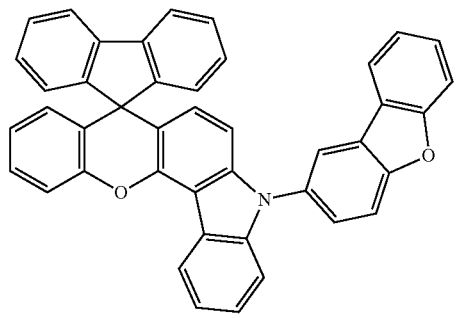
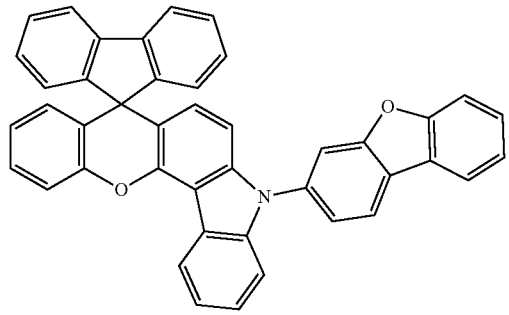
528
-continued
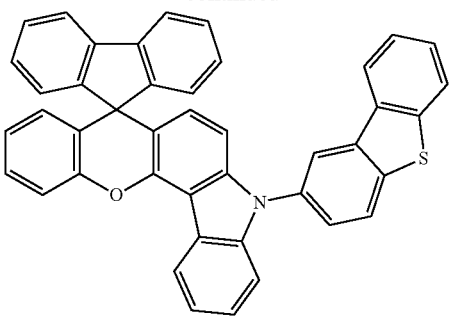
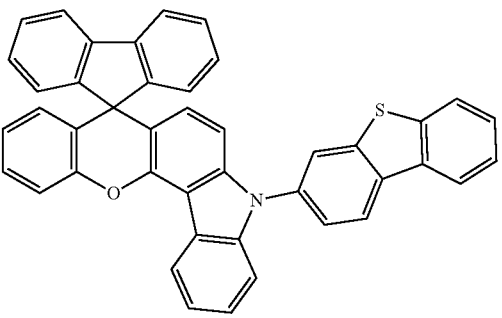
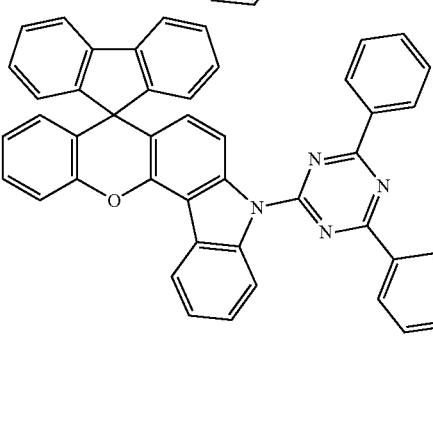
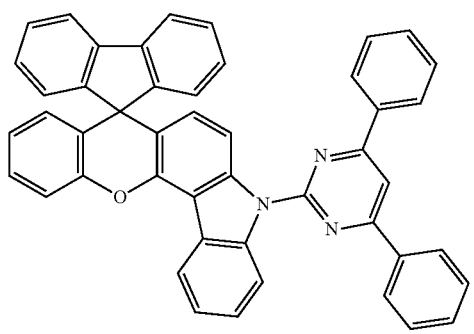
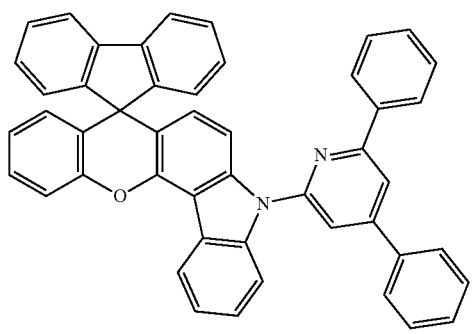

529
-continued
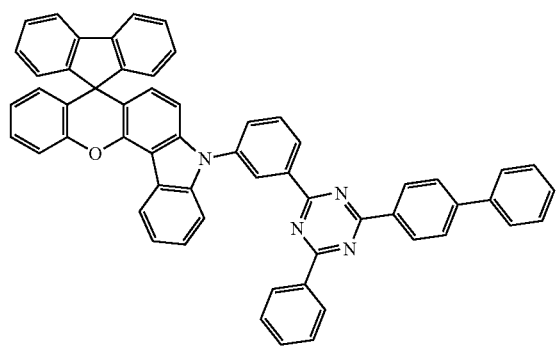
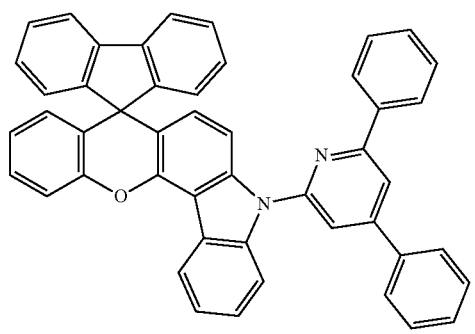
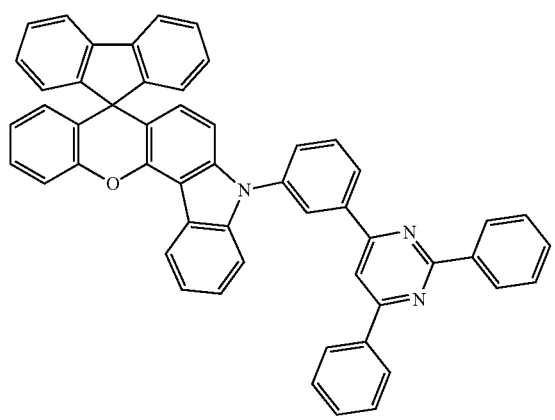
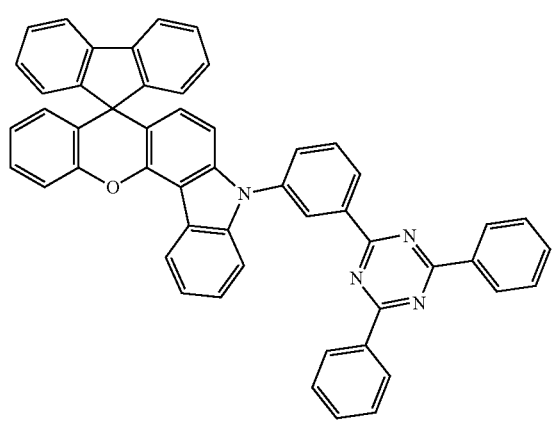
530
-continued
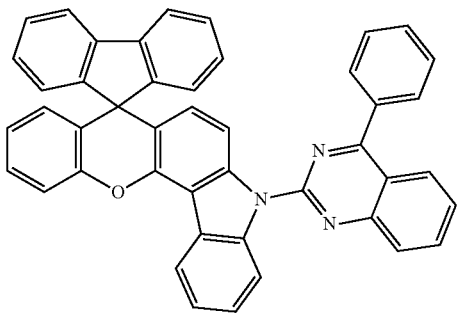
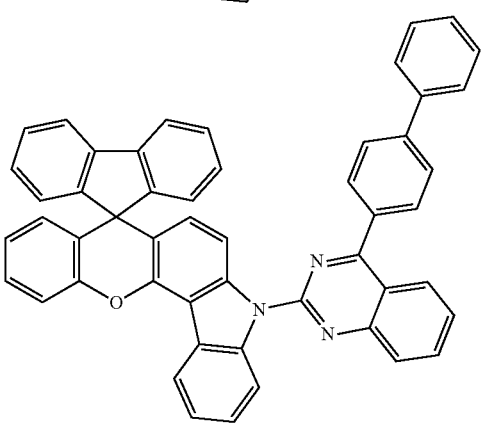
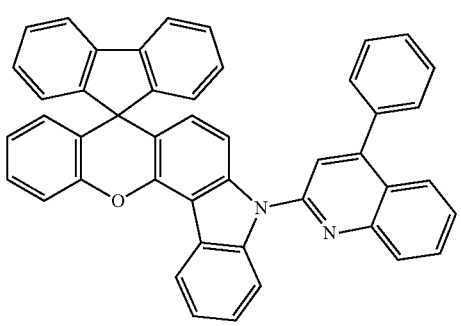
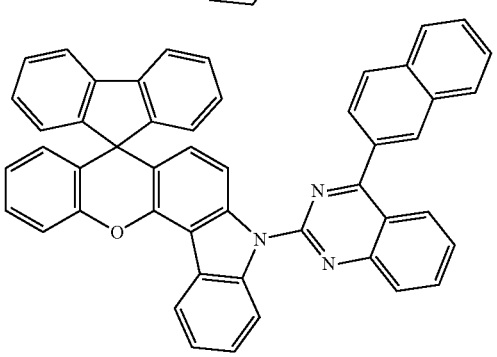
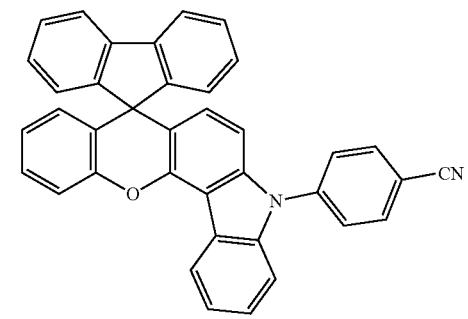

531
-continued
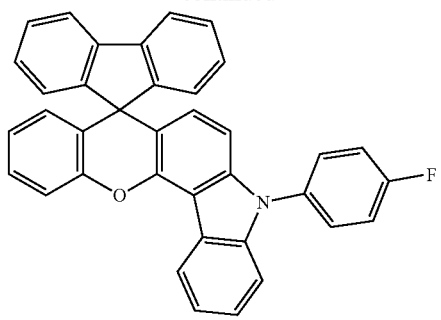
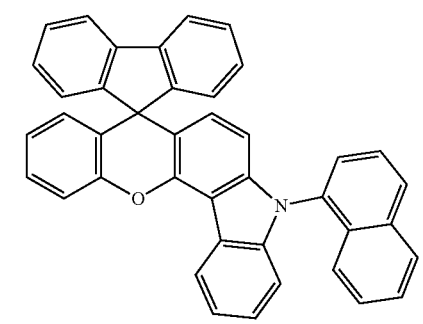
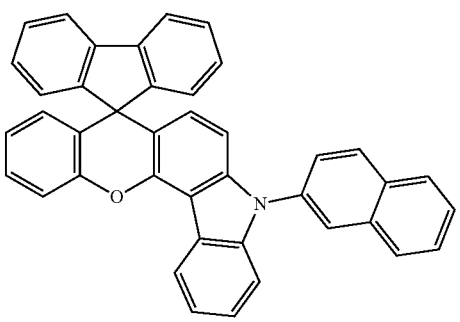
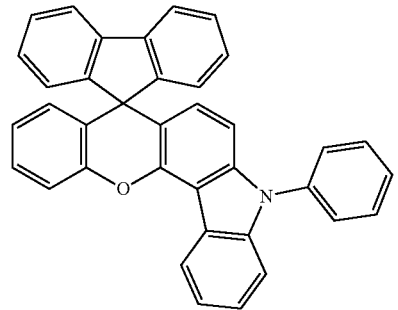
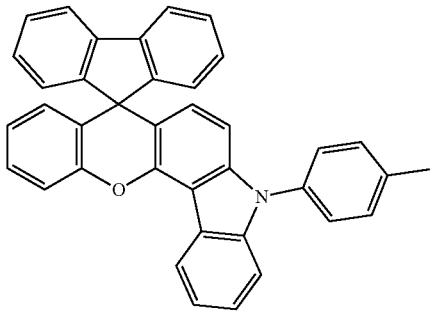
532
-continued
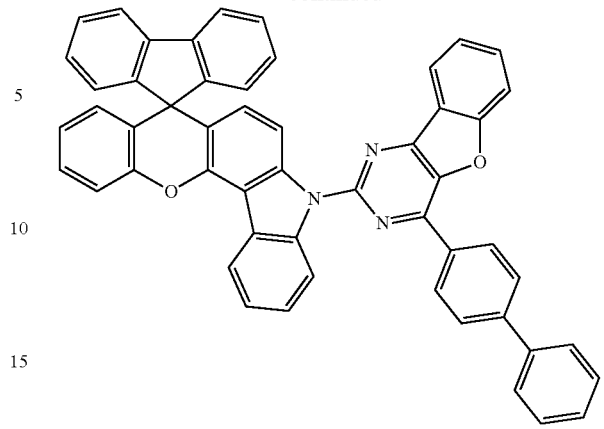
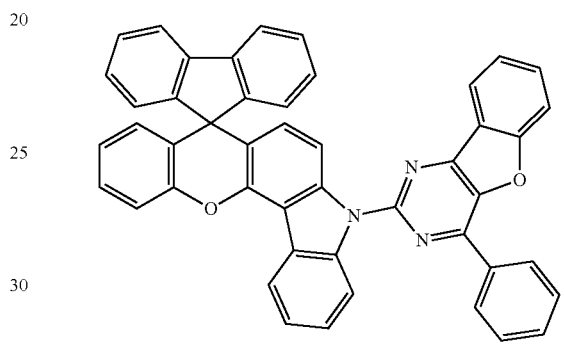
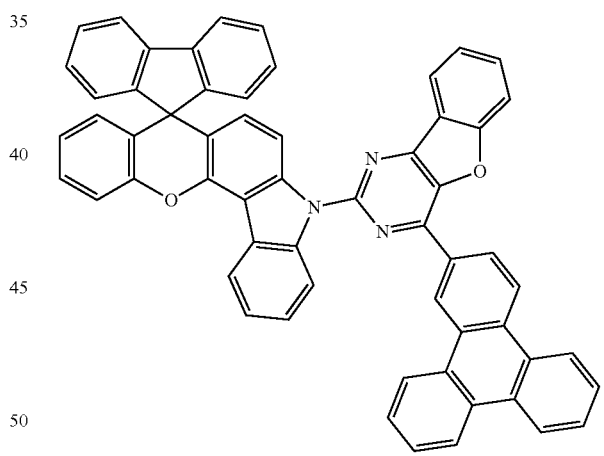
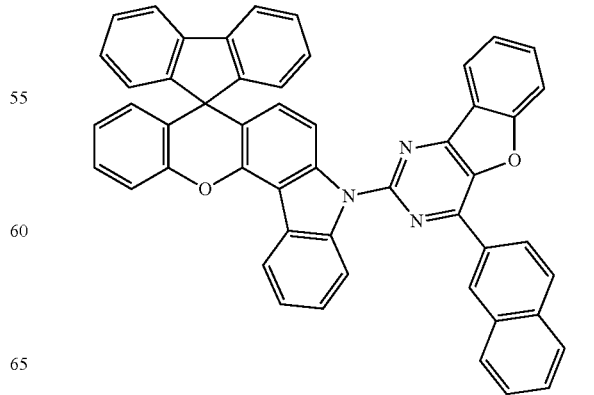

533
-continued
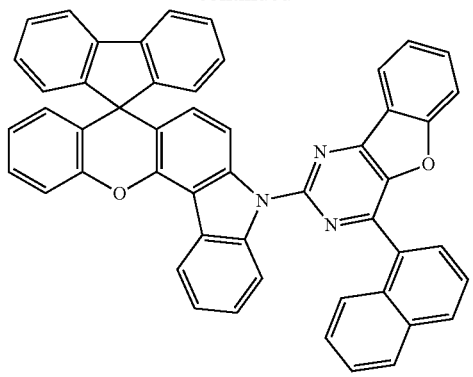
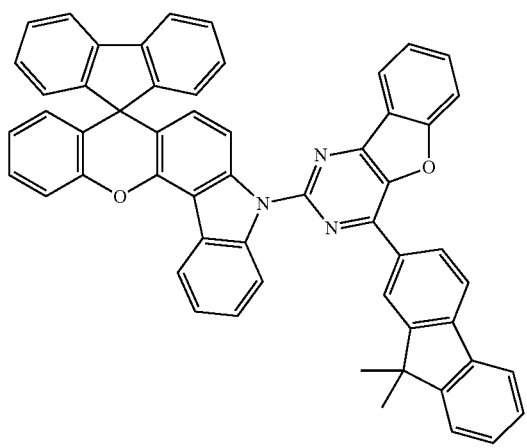
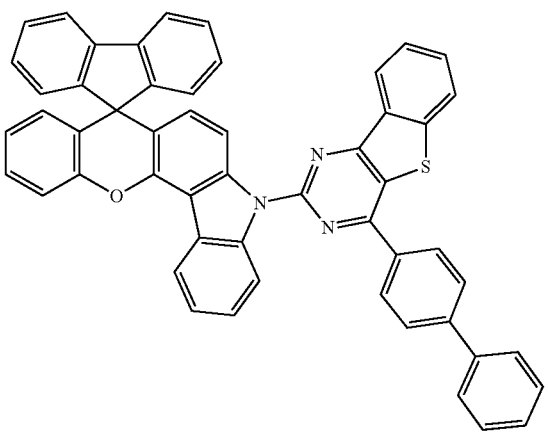
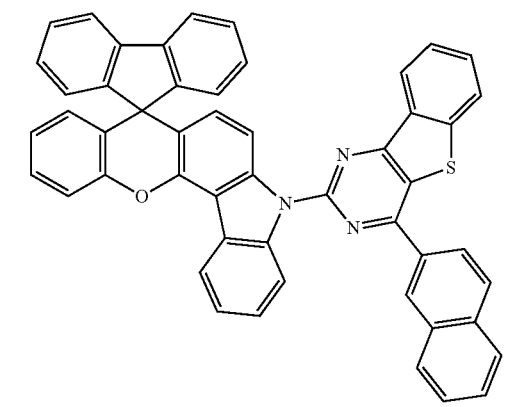
534
-continued
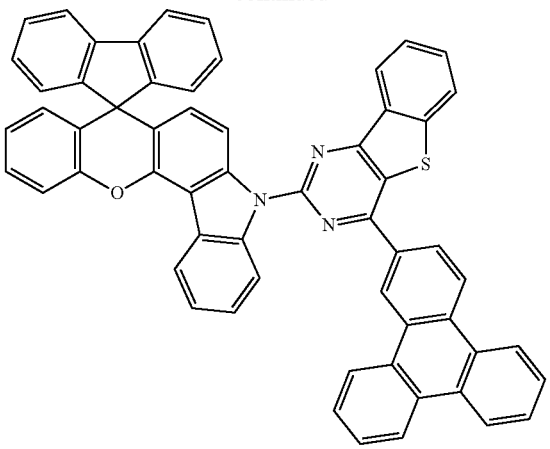
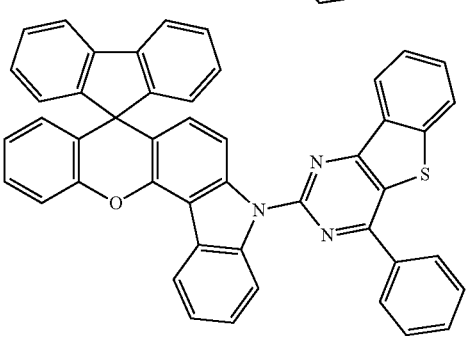
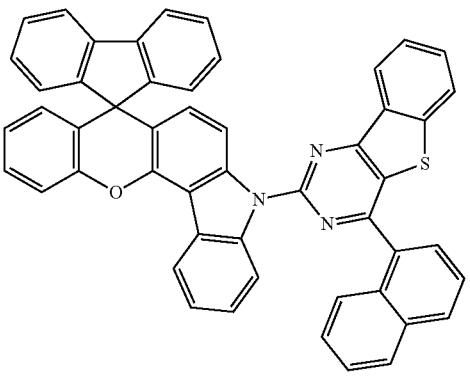
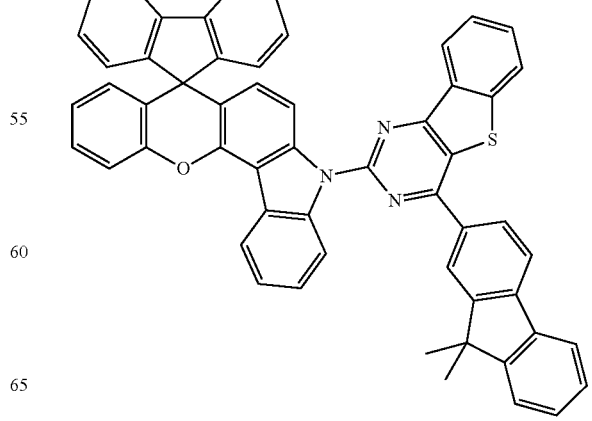

535
-continued
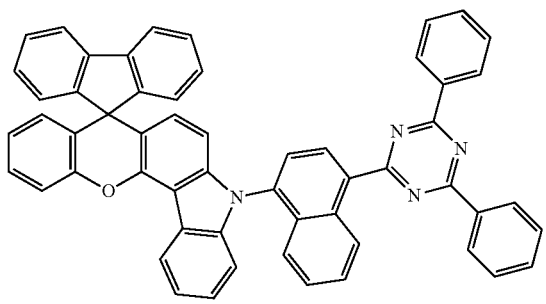
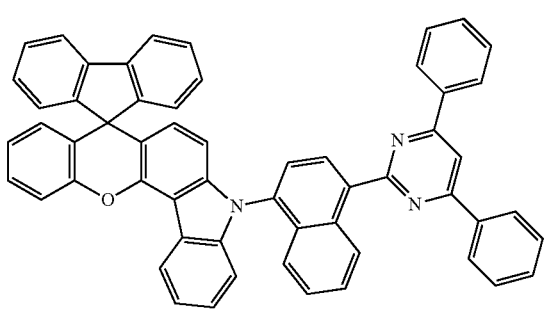
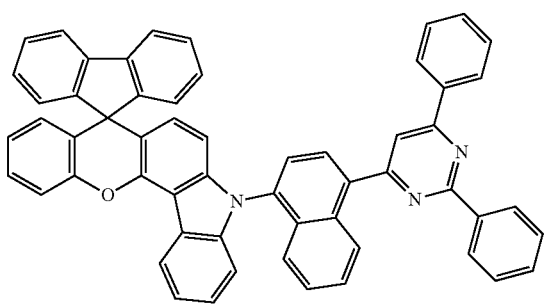
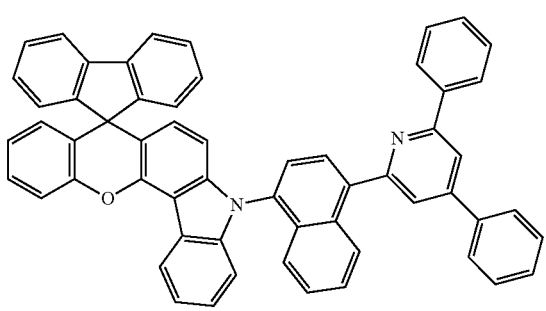
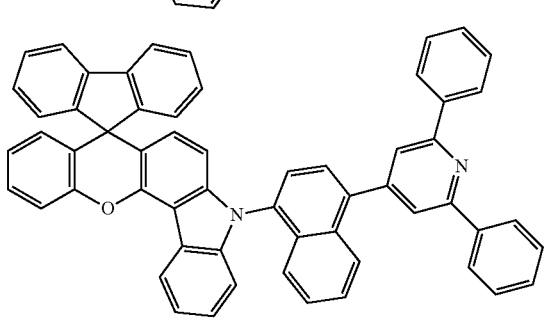
536
-continued
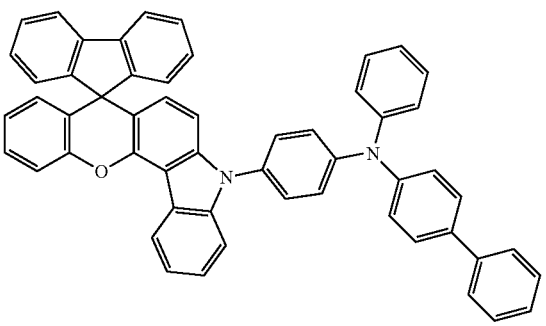
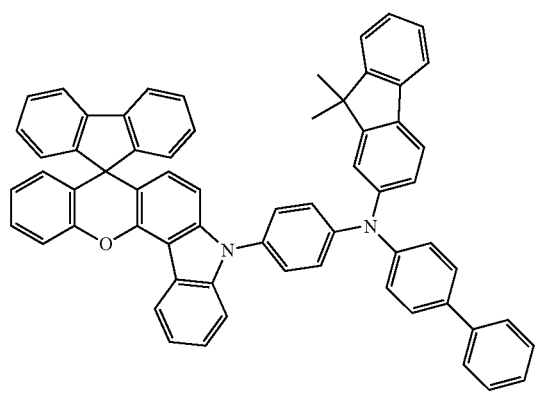
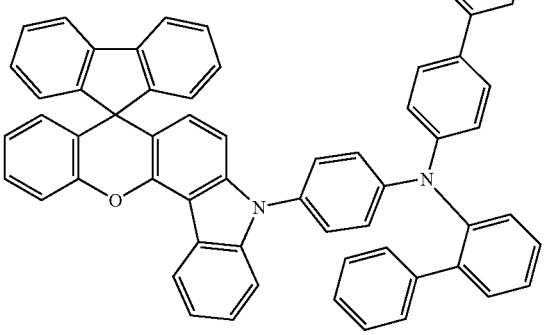
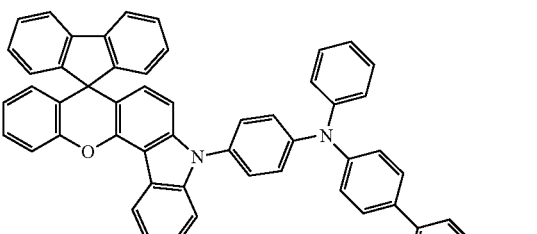
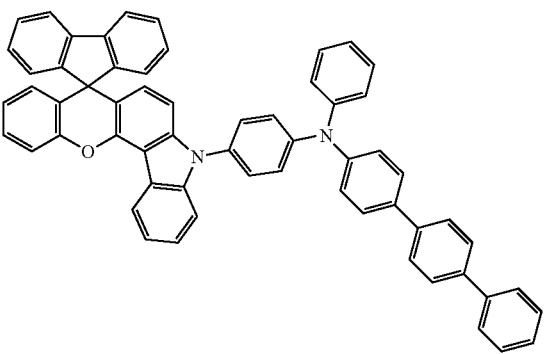

537
-continued
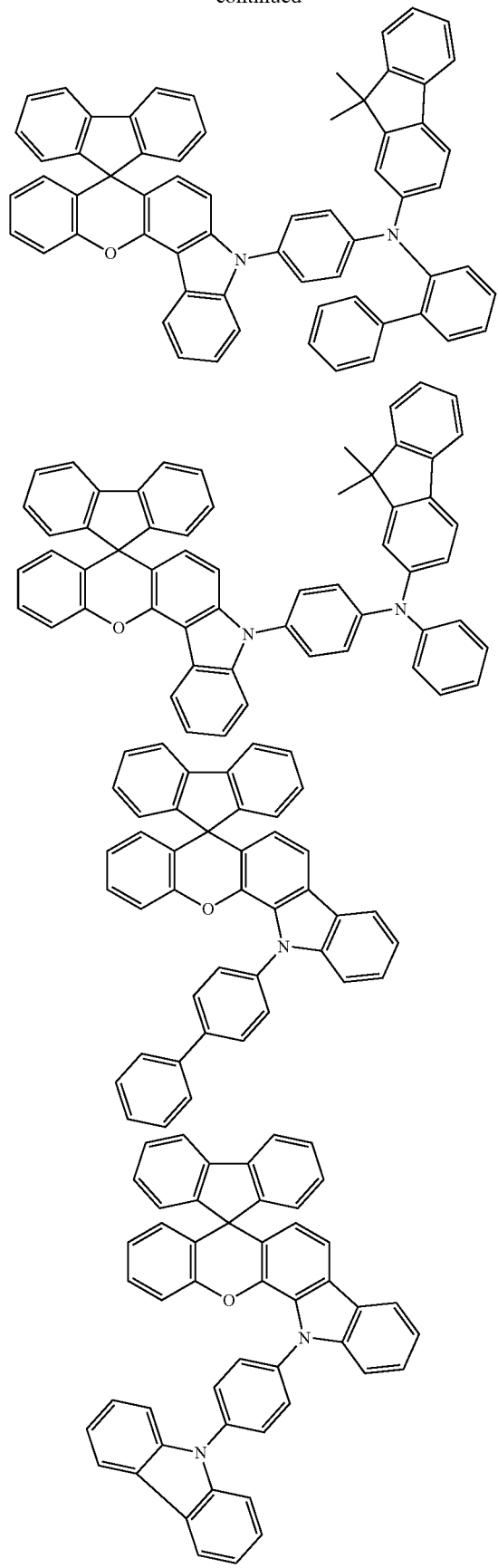
538
-continued
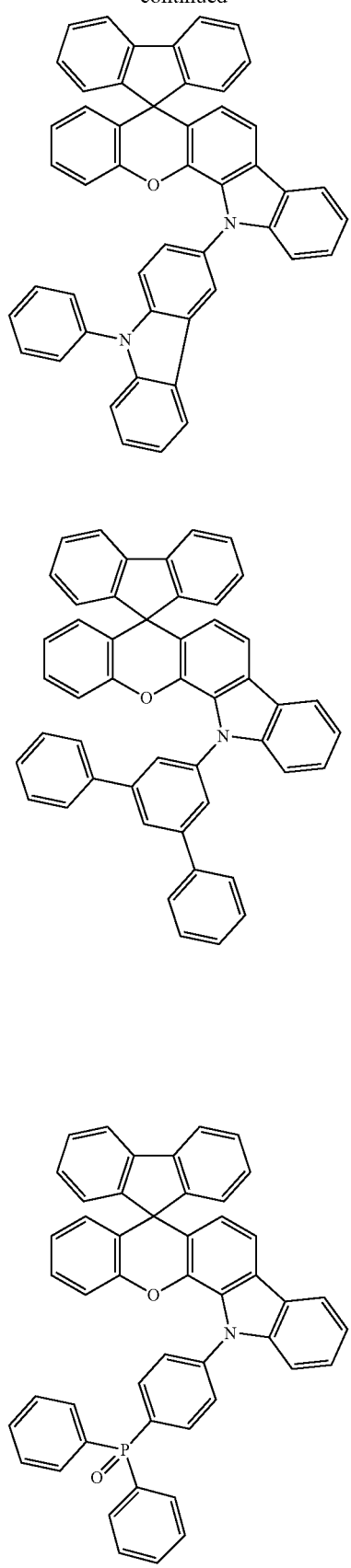

539
-continued
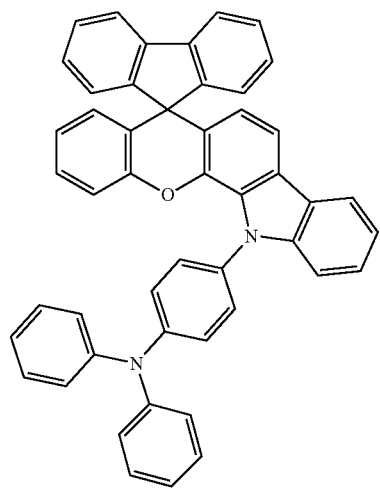
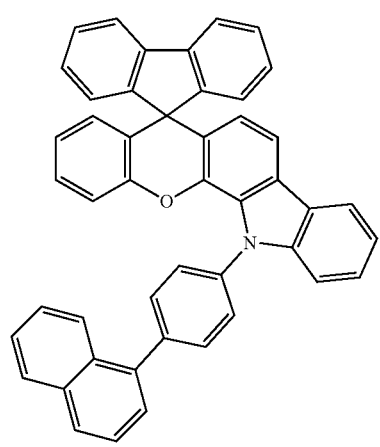
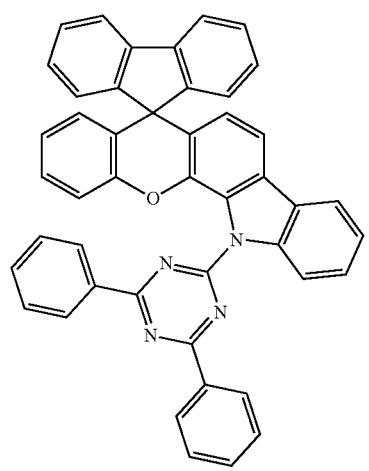
540
-continued
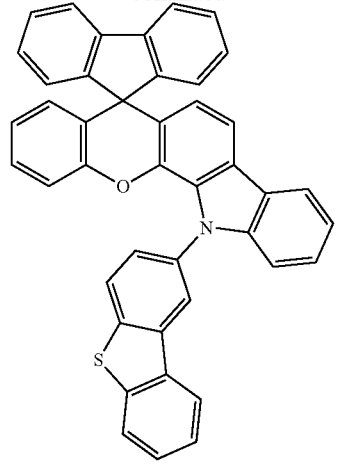
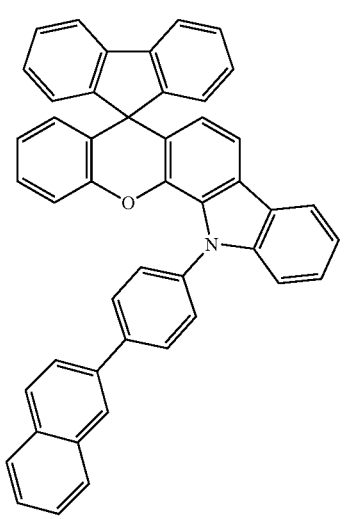
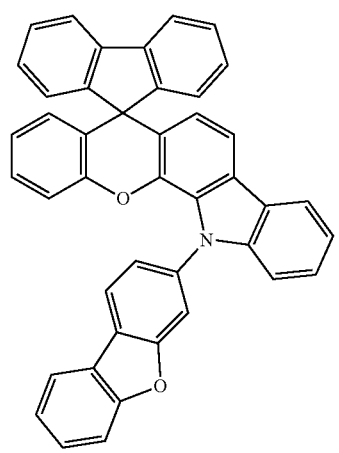

541
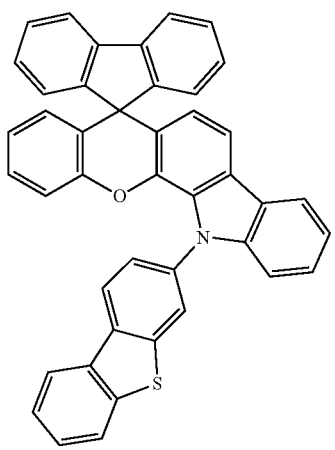
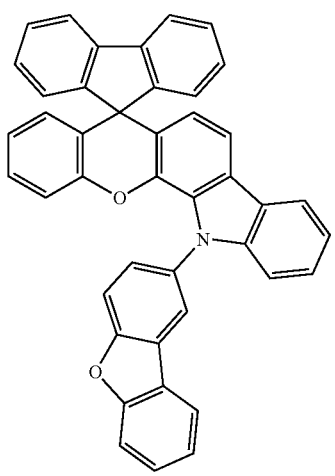
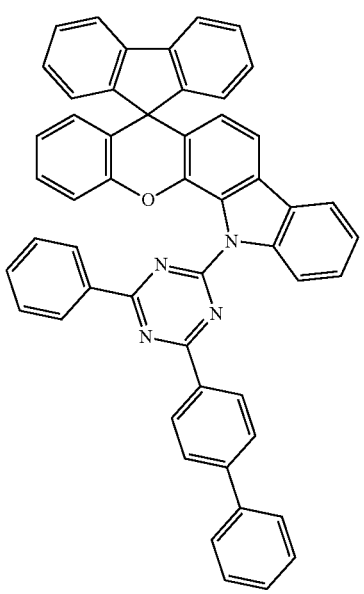
542
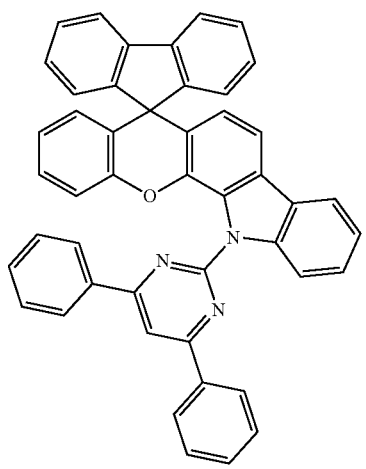
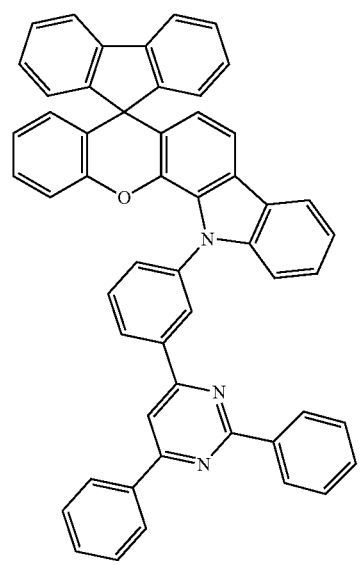
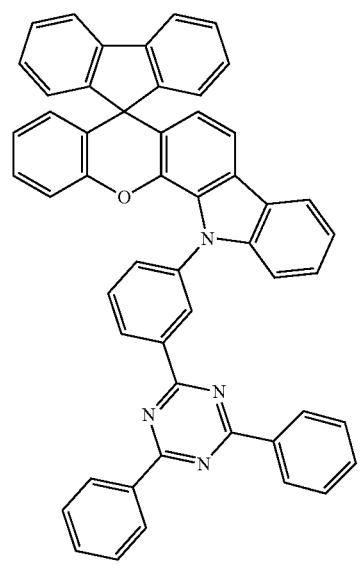

543
-continued
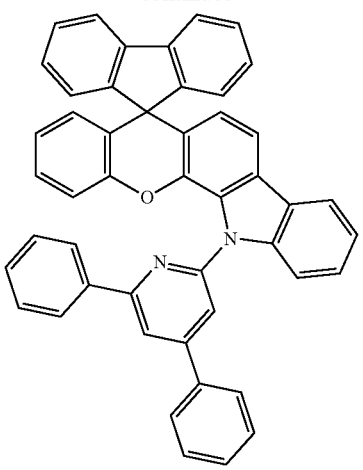
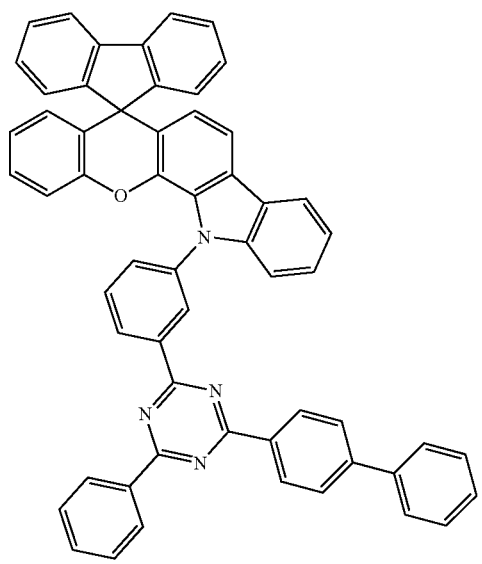
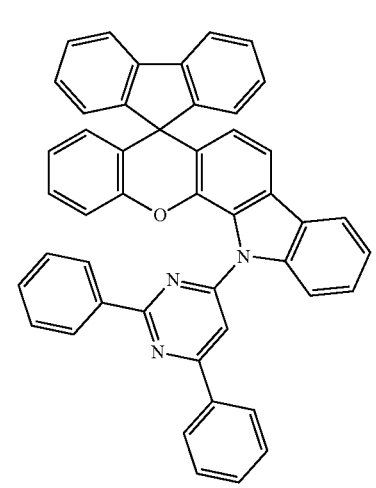
544
-continued
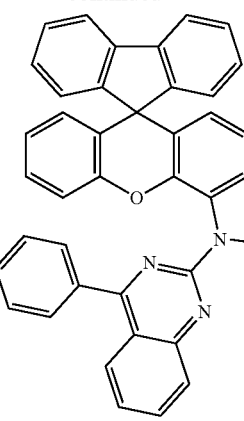
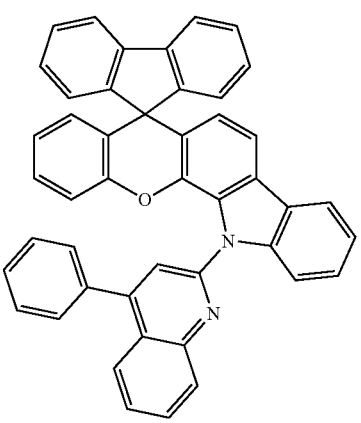
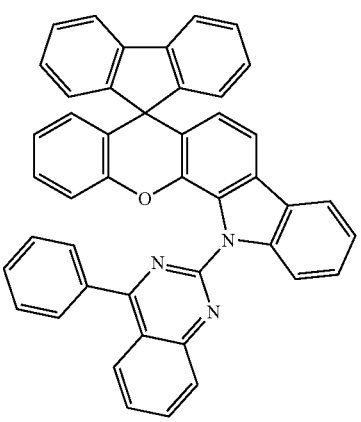
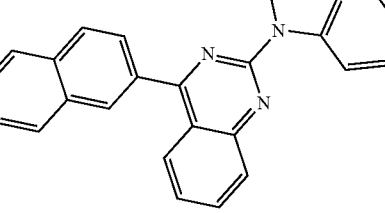

| 545 | 546 |
|---|---|
| -continued | -continued |
| 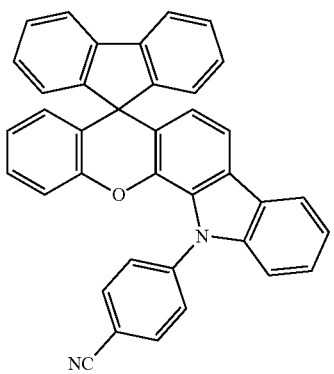 | 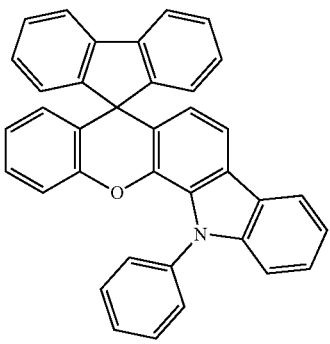 |
| 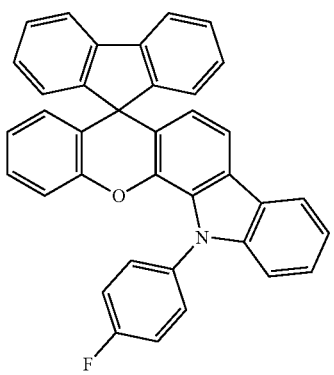 | 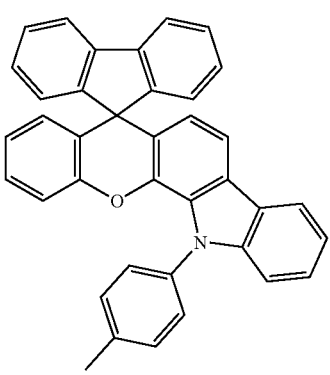 |
| 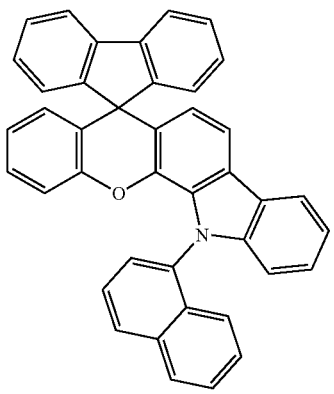 | 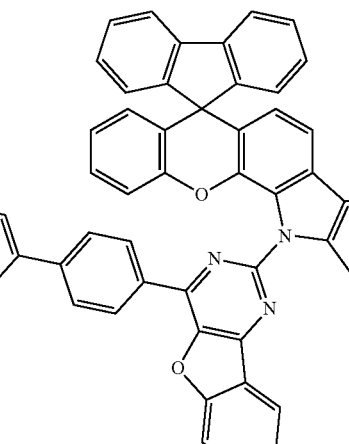 |
| 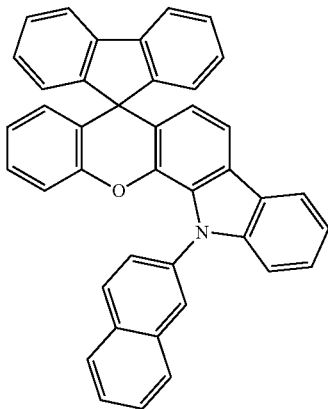 |  |

547
-continued
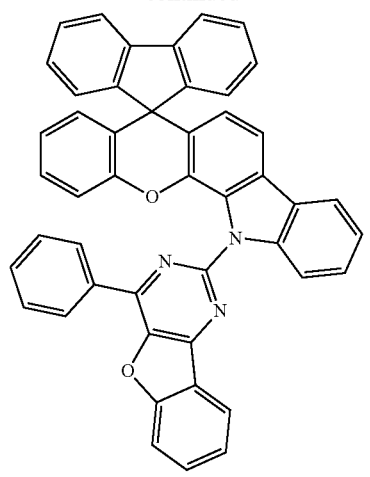
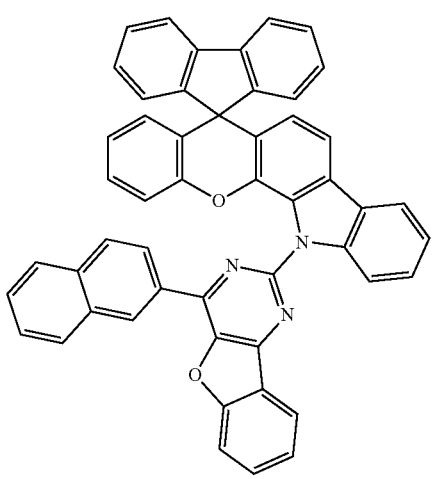
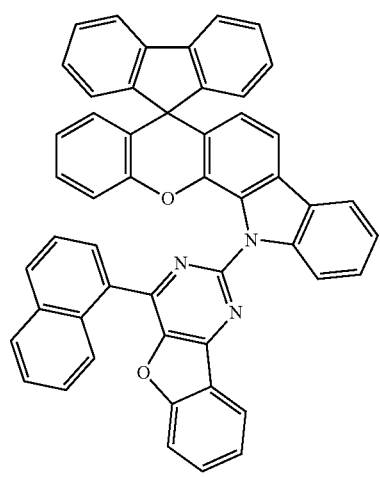
548
-continued
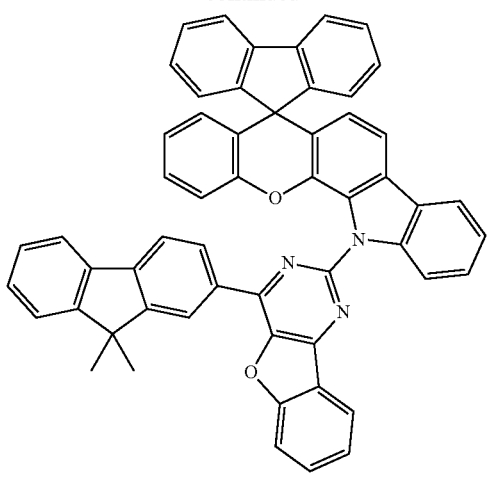
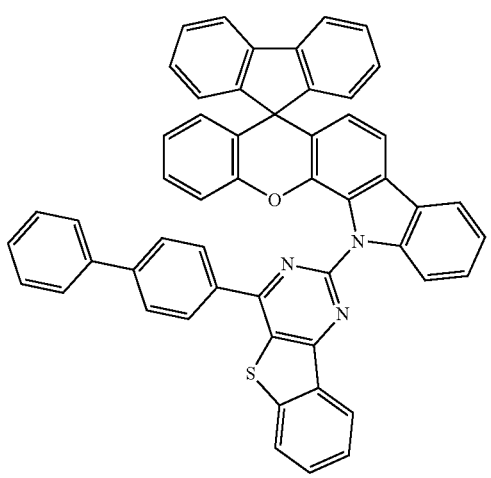
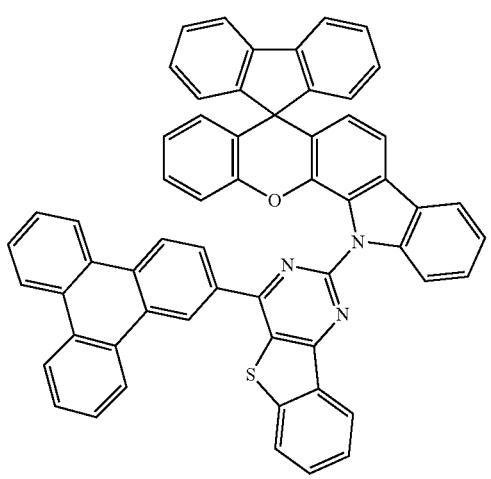

549
-continued
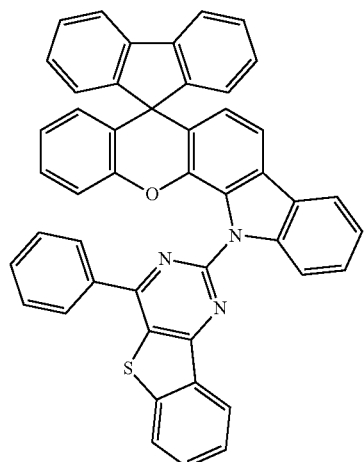
550
-continued
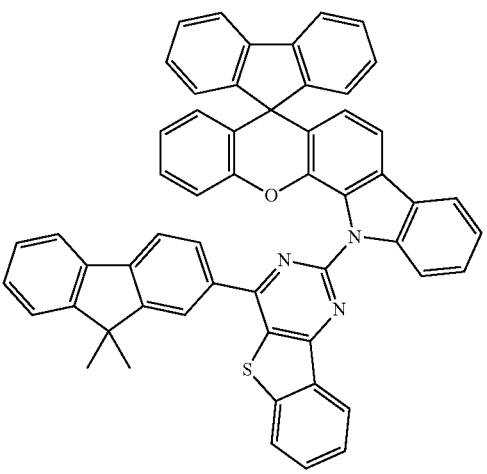
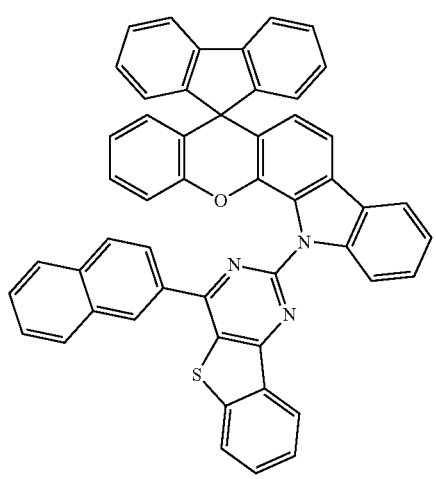
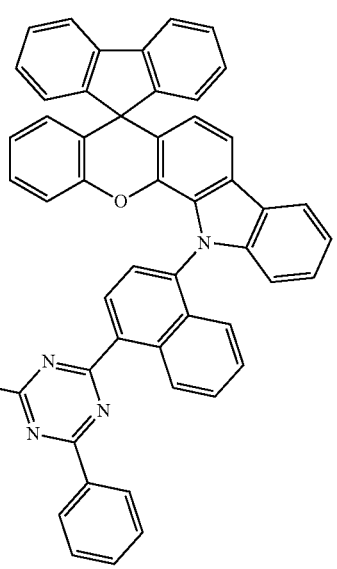
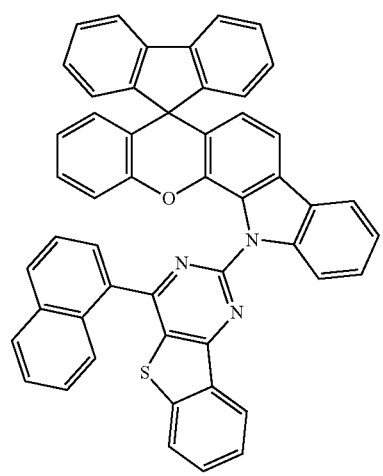

551
-continued
552
-continued
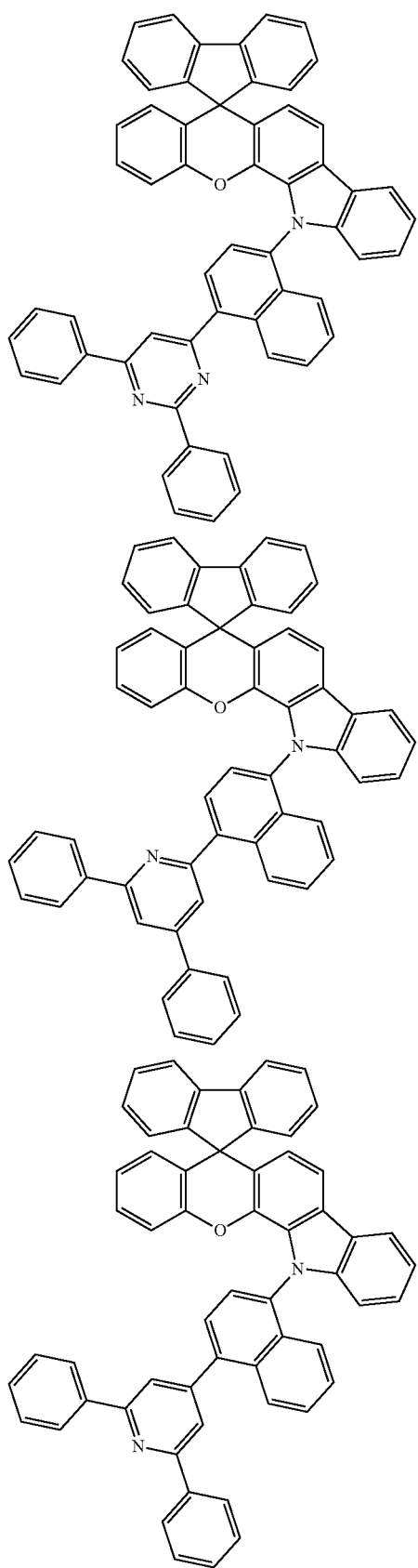

553
-continued
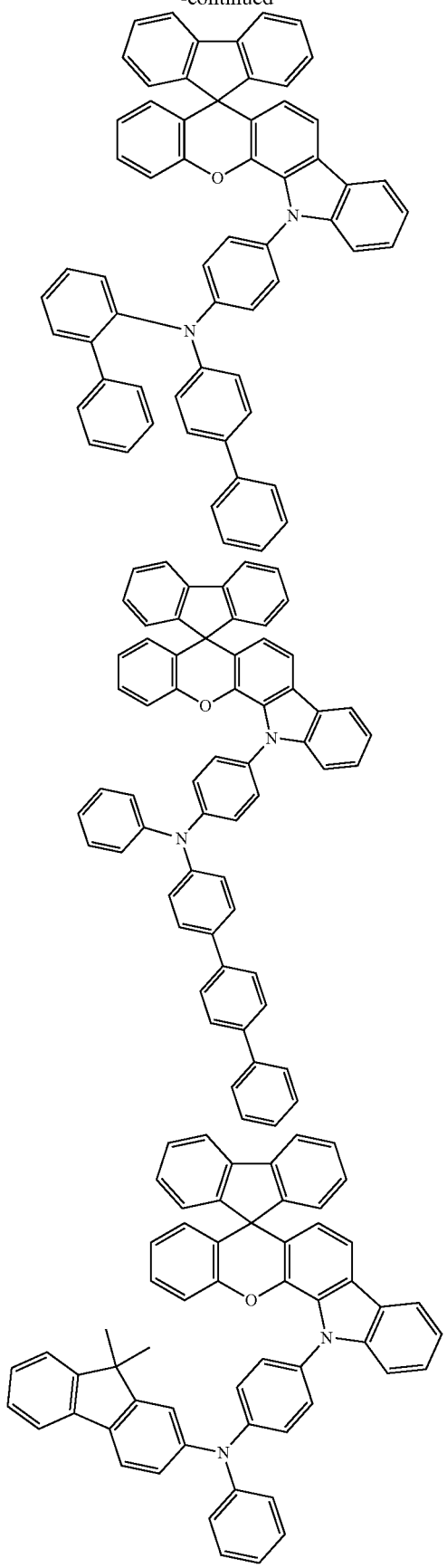
554
-continued
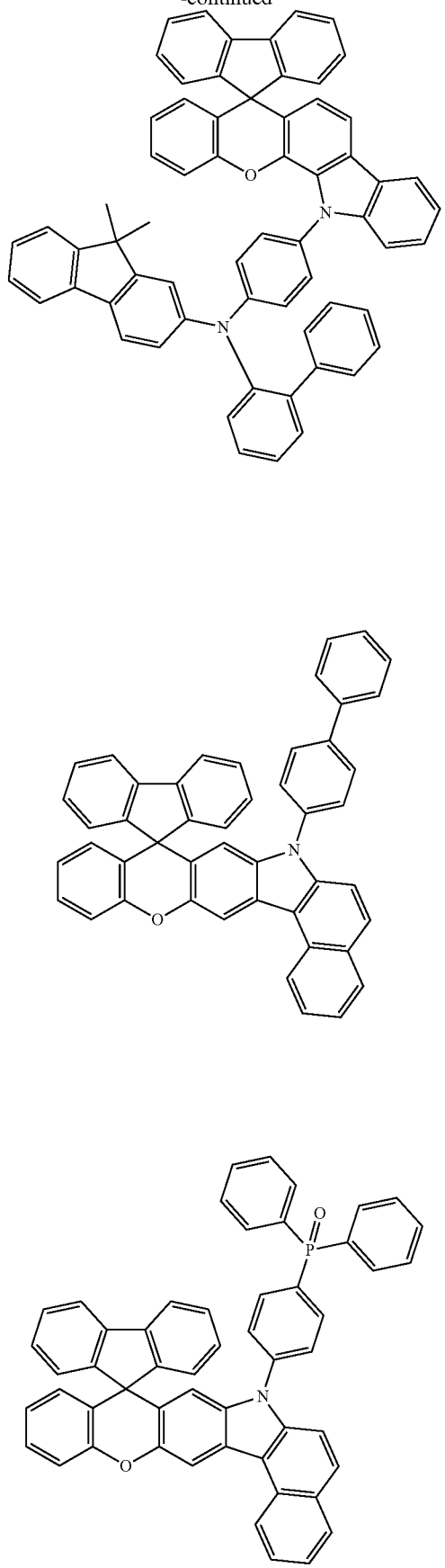

555
-continued
556
-continued
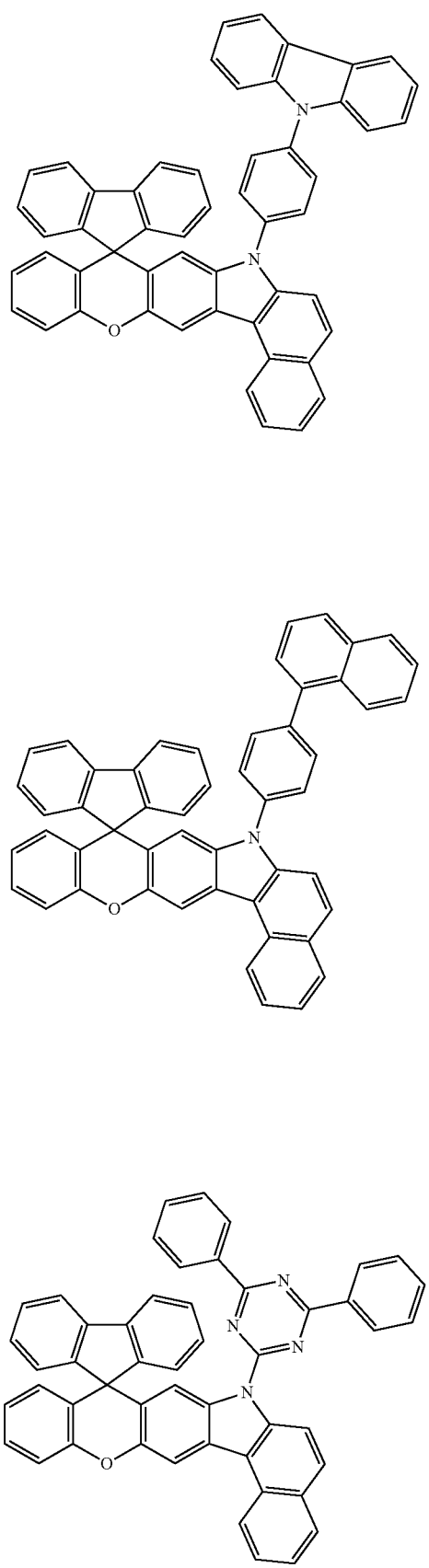
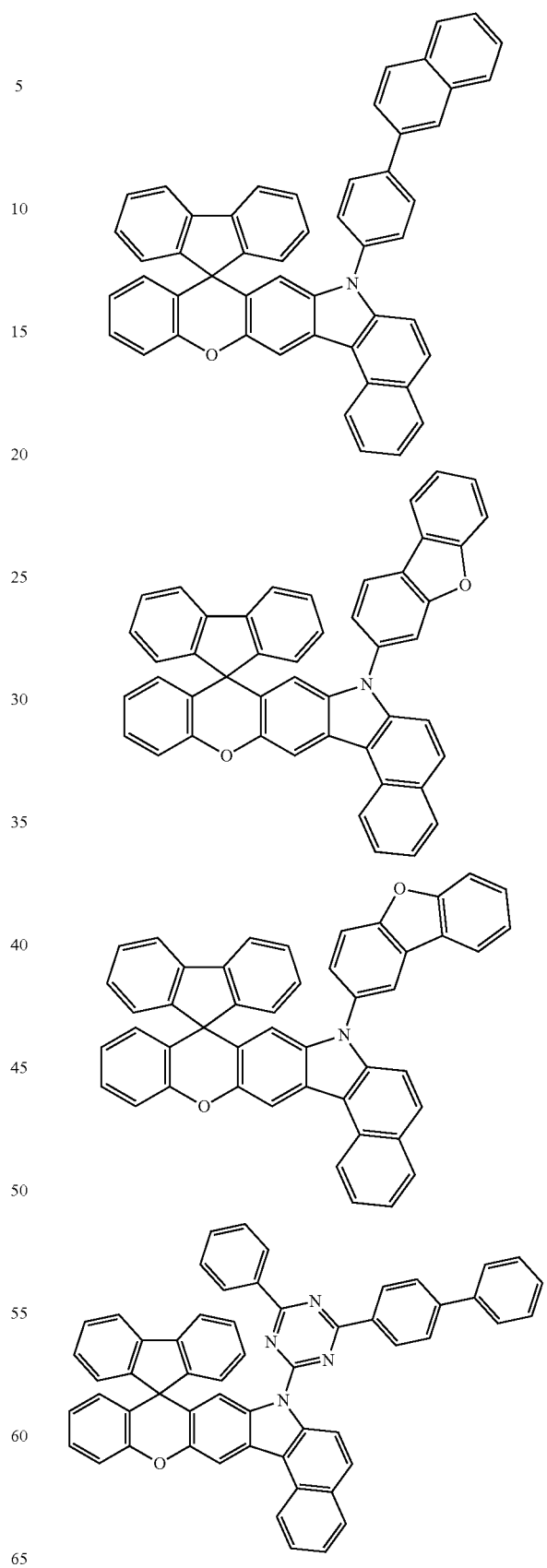

557
-continued
558
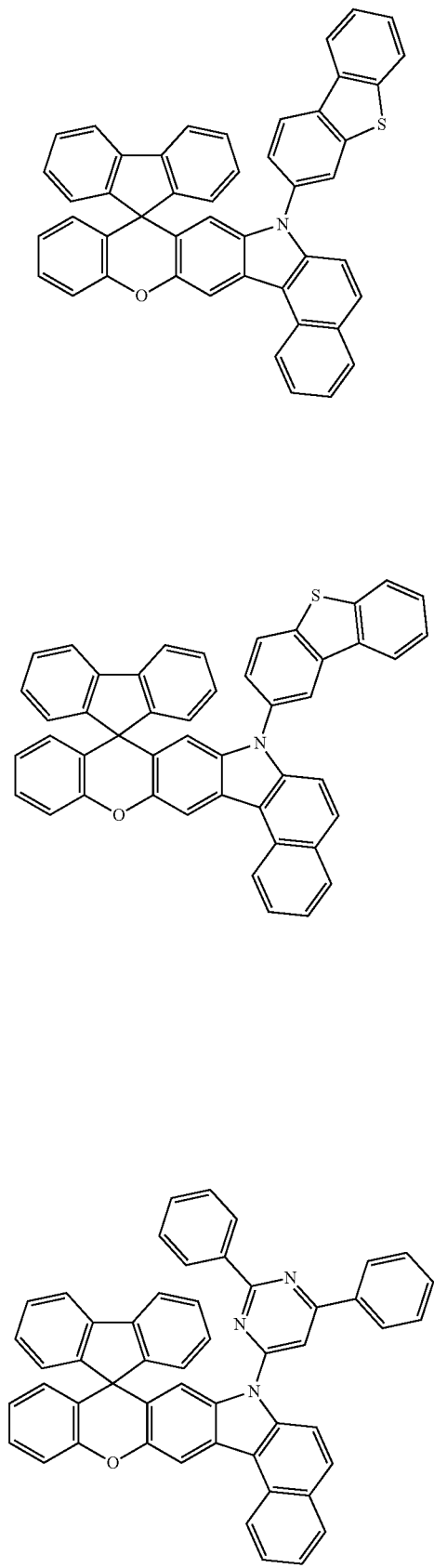
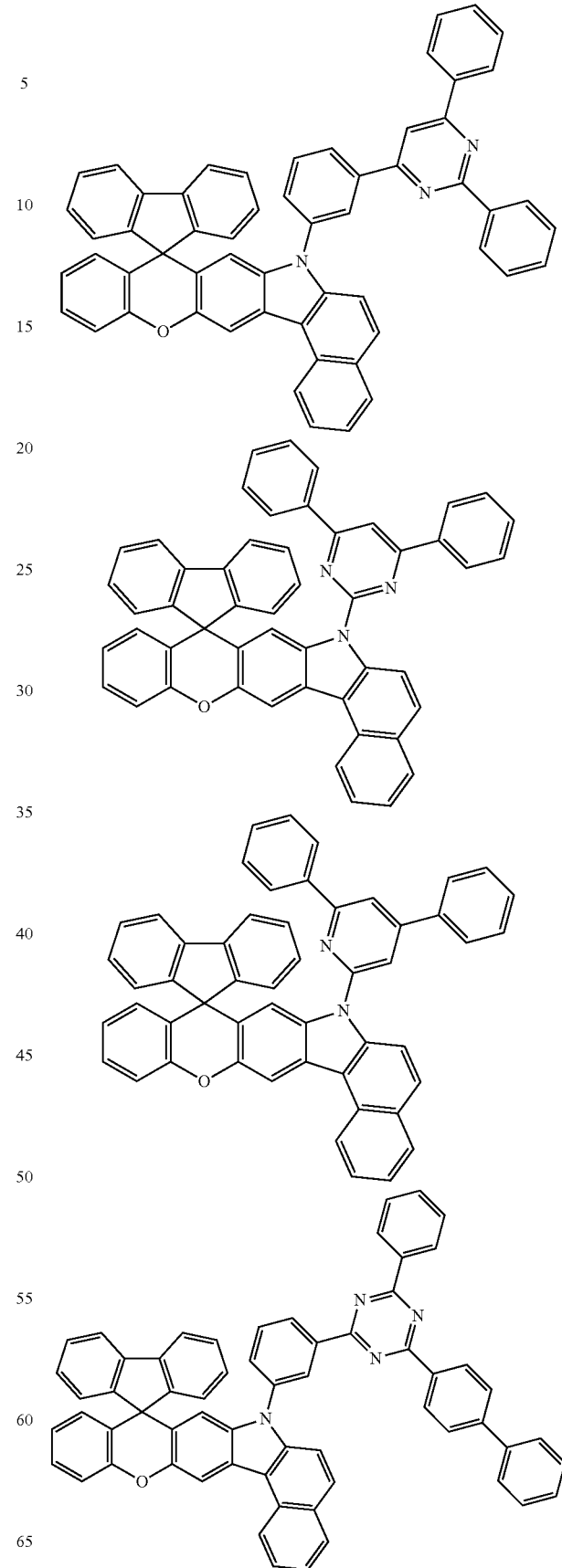

559
-continued
560
-continued
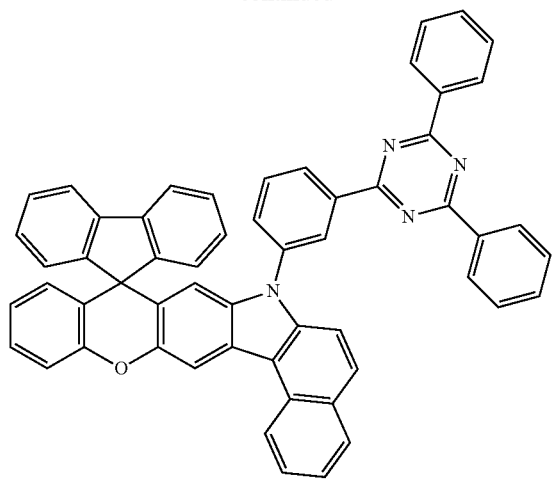
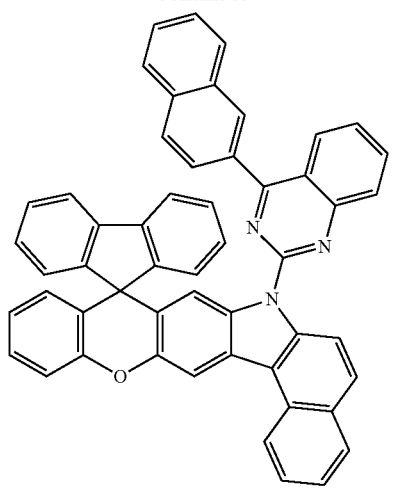
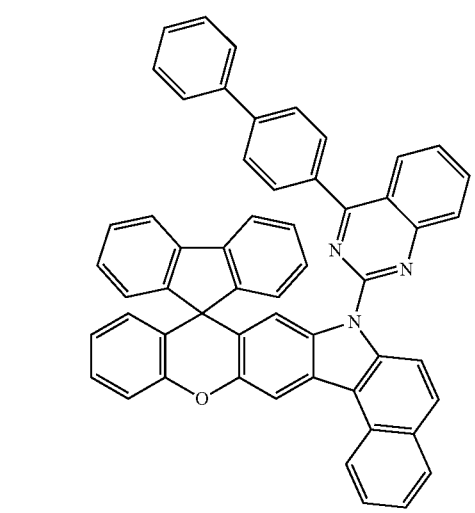
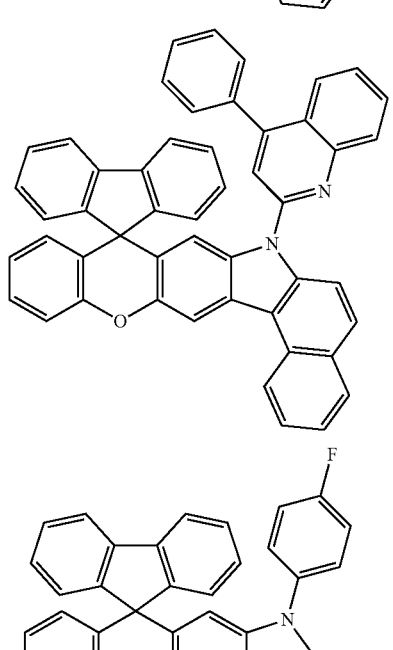
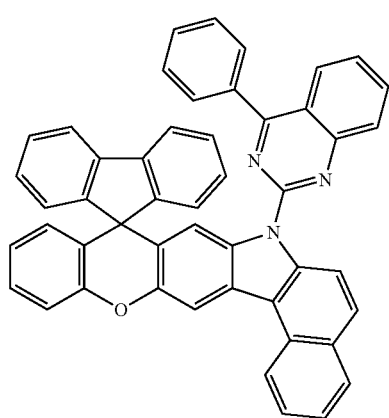
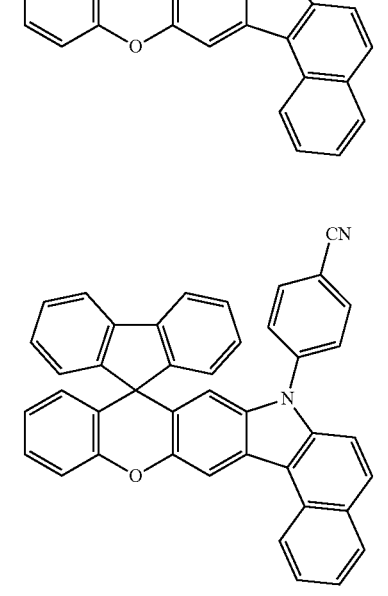

561
-continued
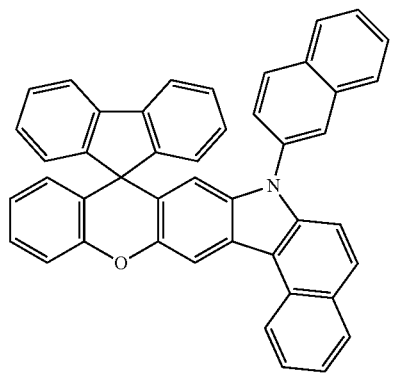
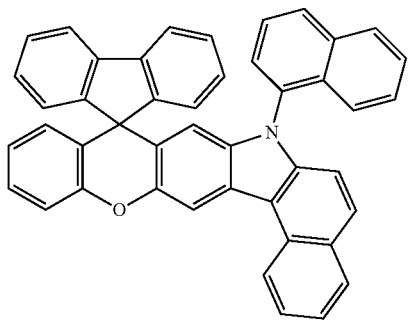
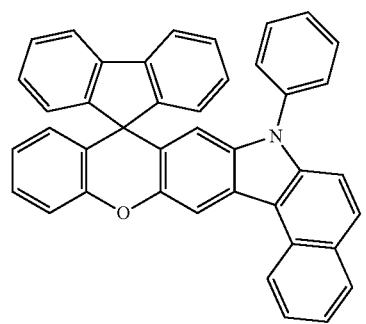
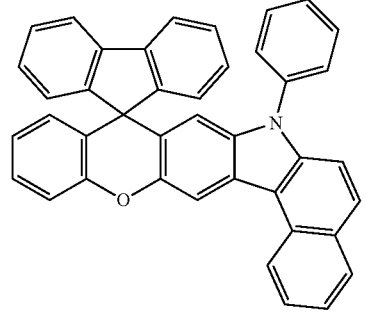
562
-continued
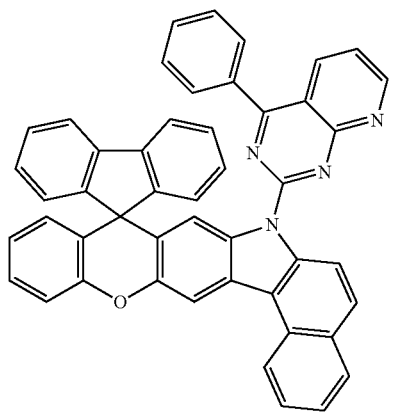
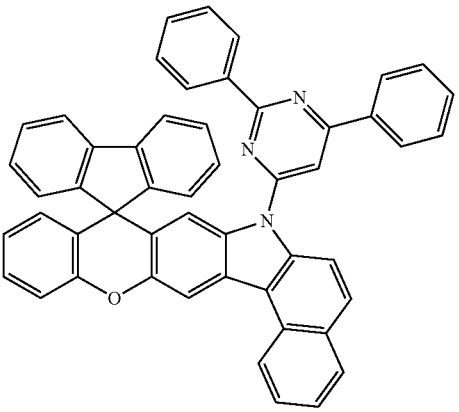
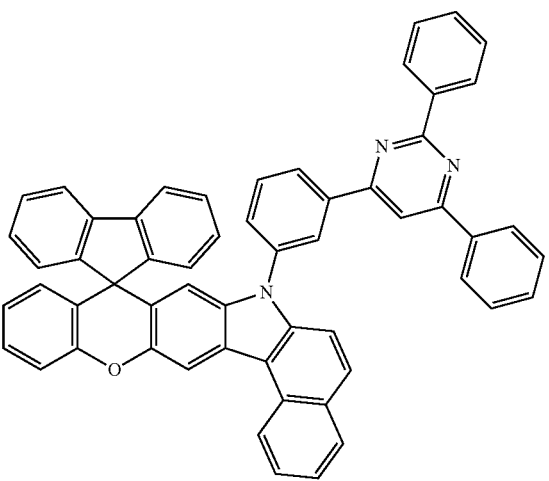

563
-continued
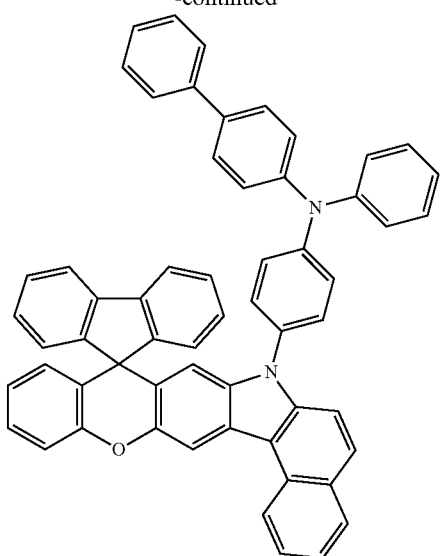
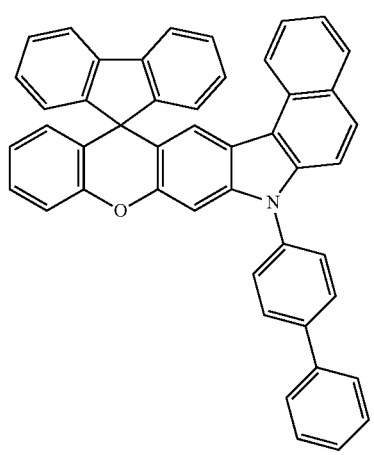
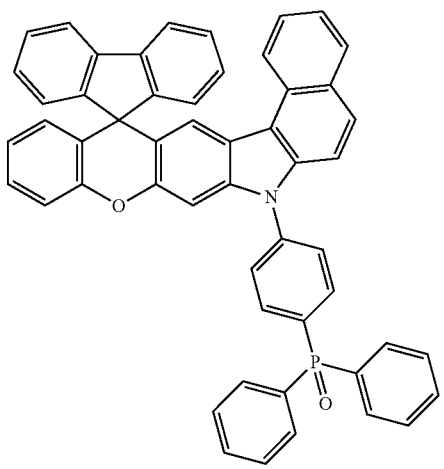
564
-continued
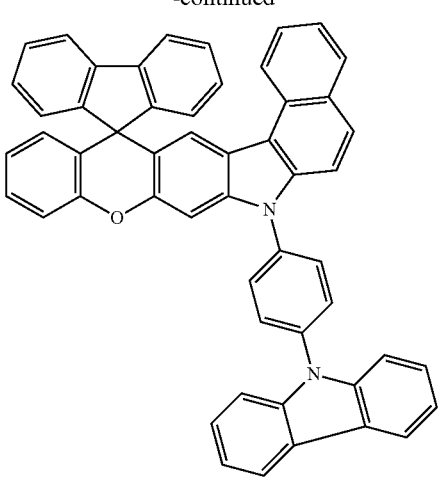
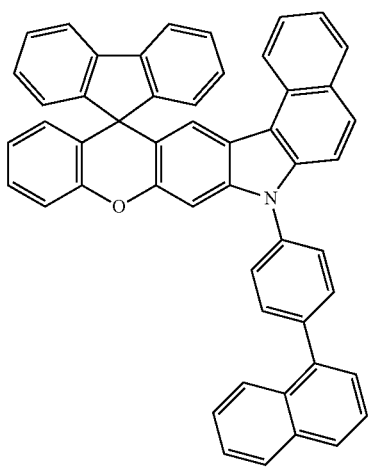
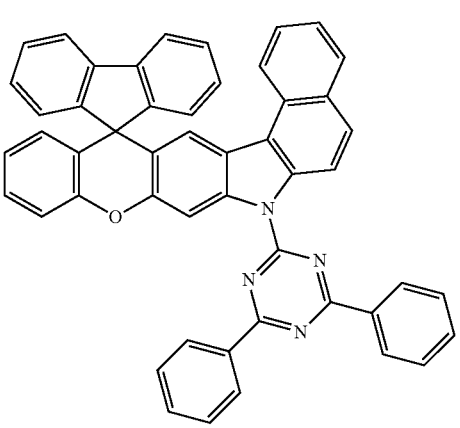

565
-continued
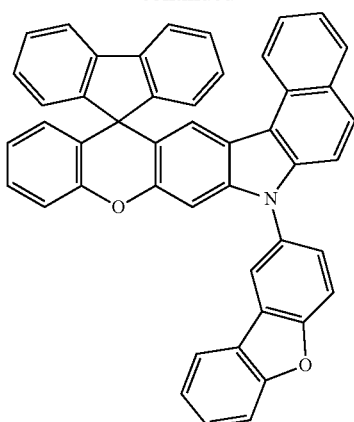
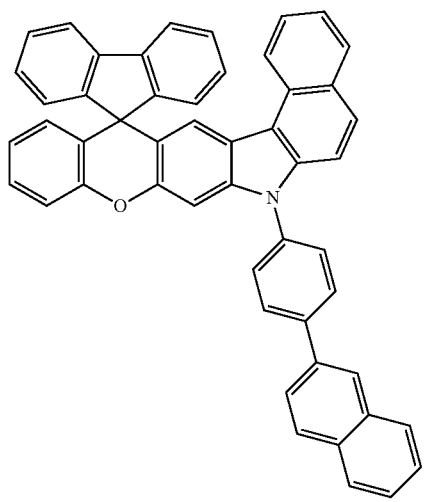
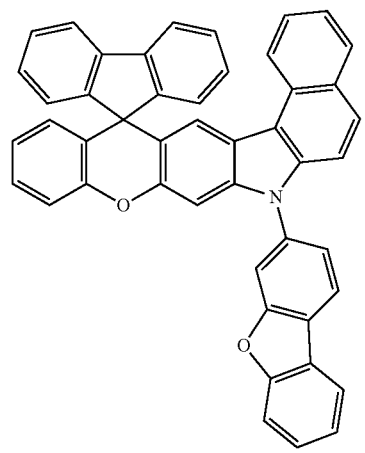
566
-continued
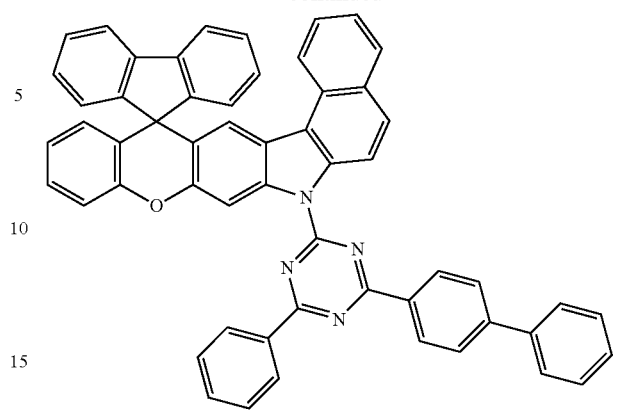
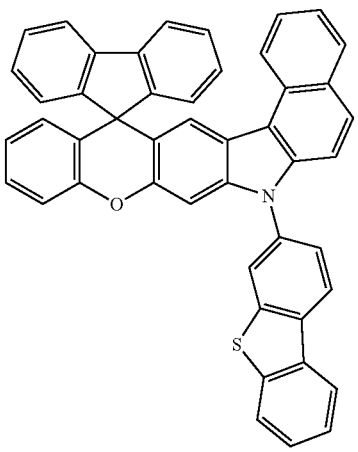
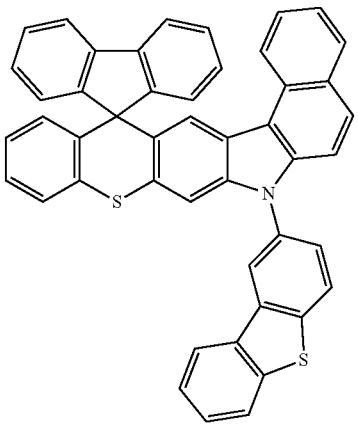

567
-continued
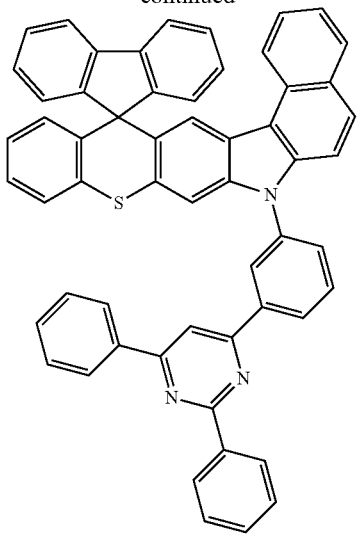
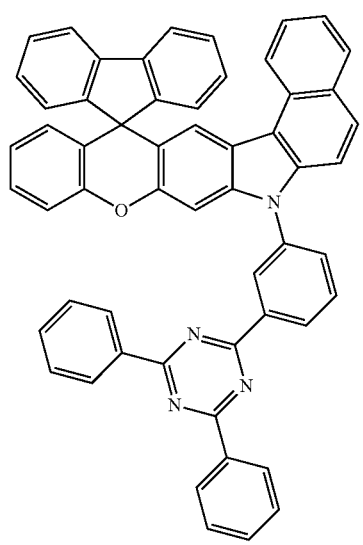
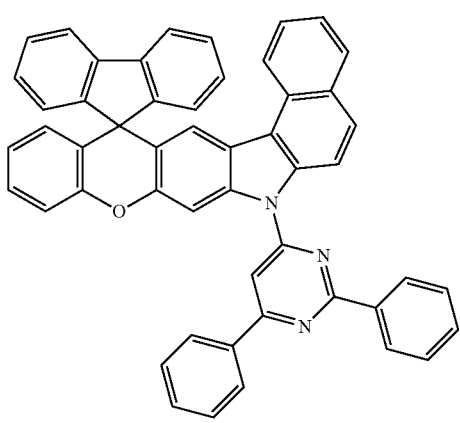
568
-continued
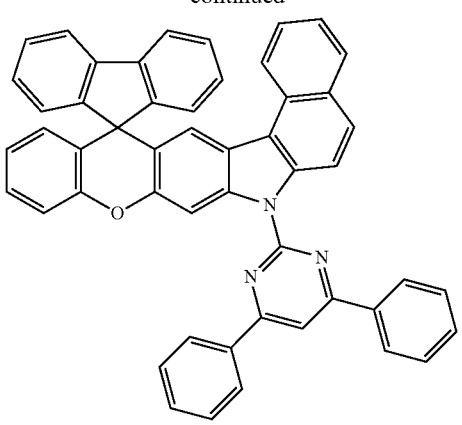
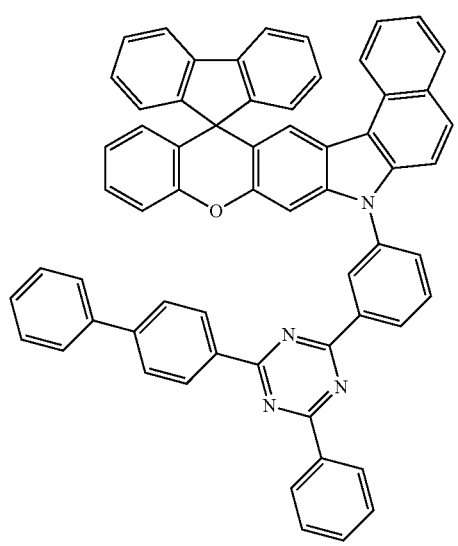
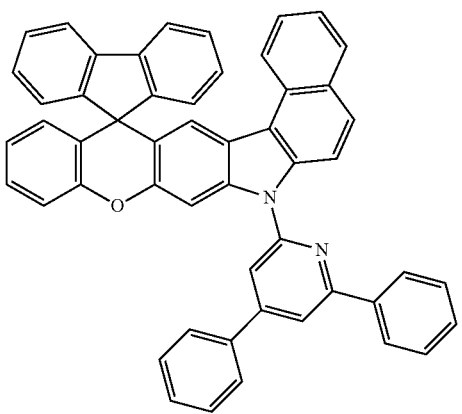

569
-continued
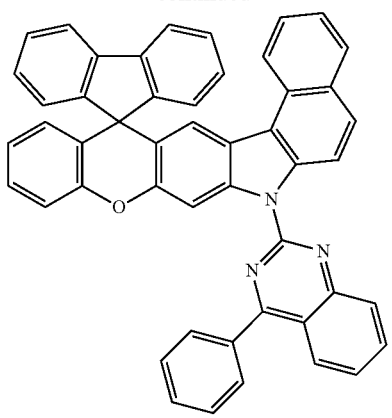
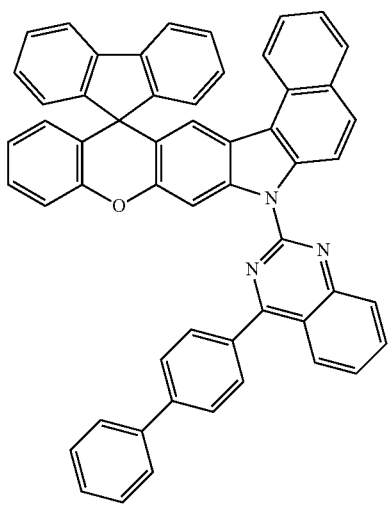
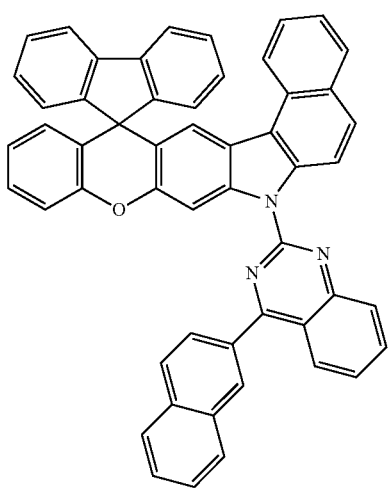
570
-continued
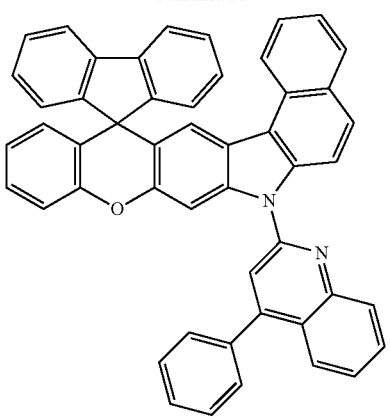
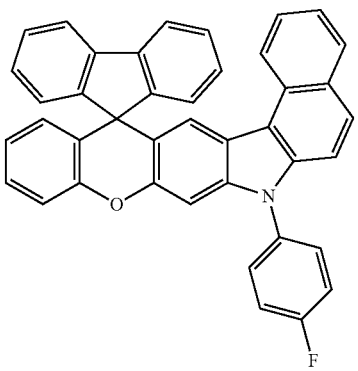
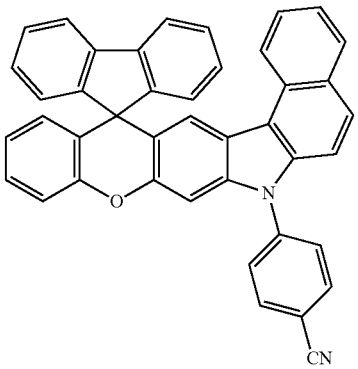
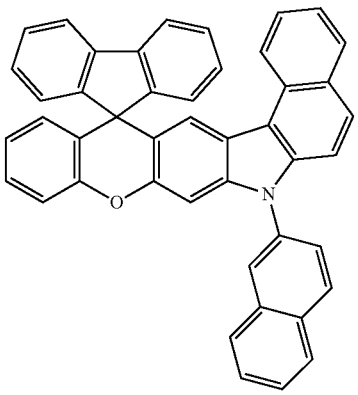

571
-continued
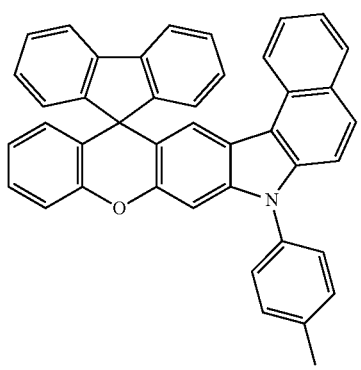
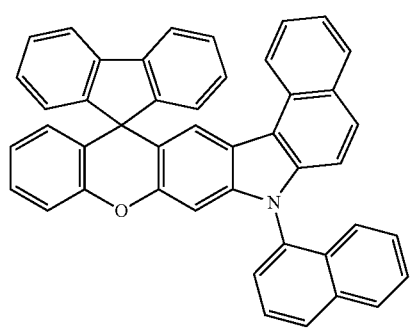
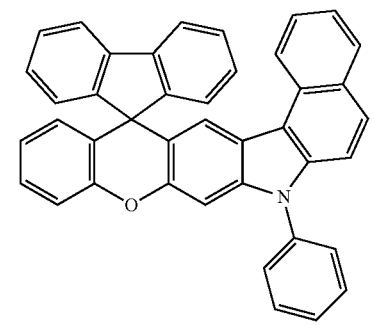
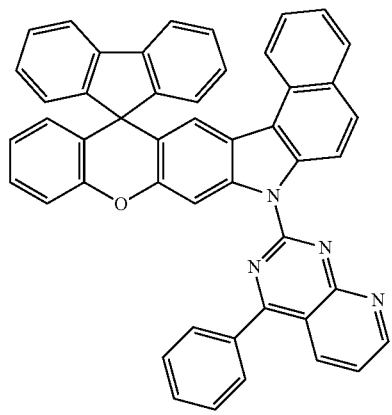
572
-continued
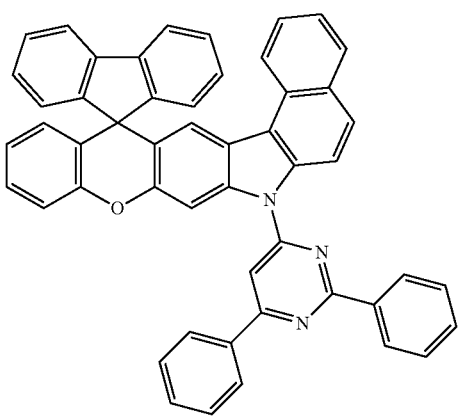
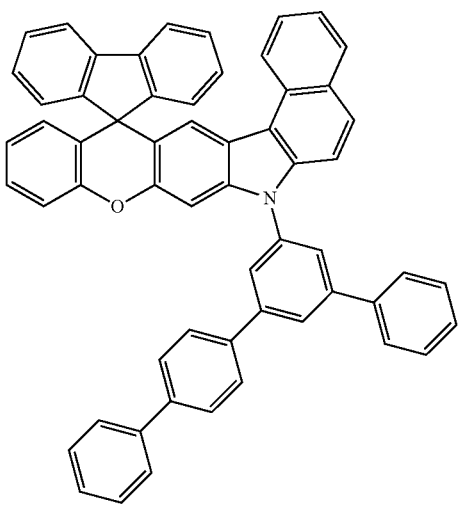
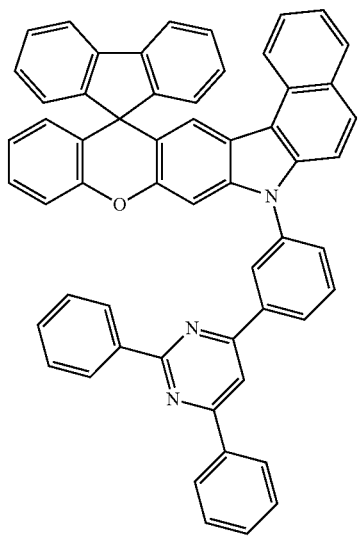

573
-continued
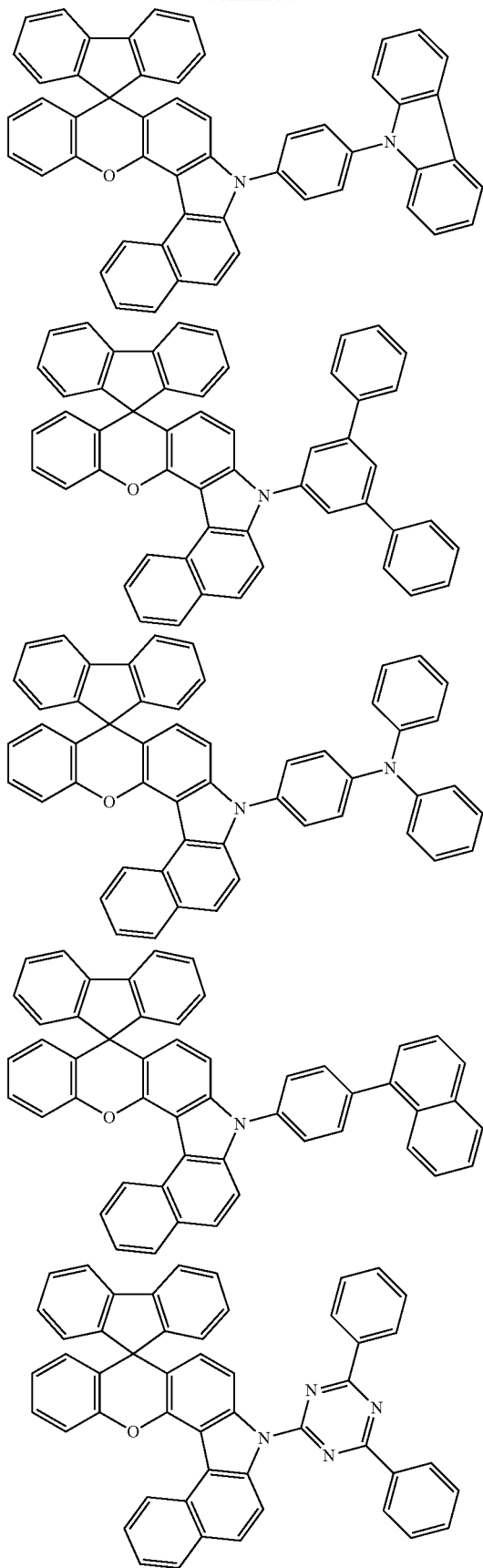
574
-continued
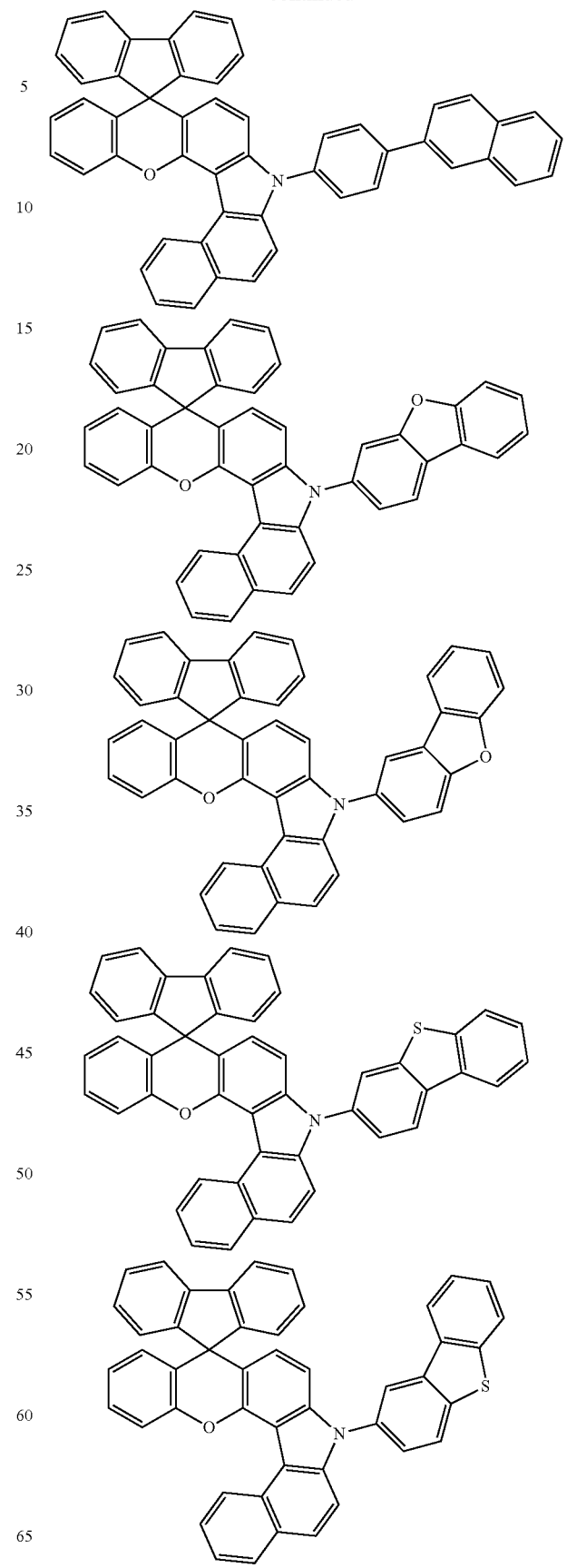

US 10,968,230 B2
575
-continued
576
-continued
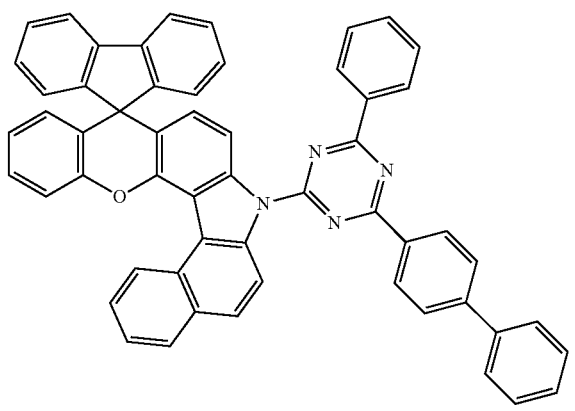
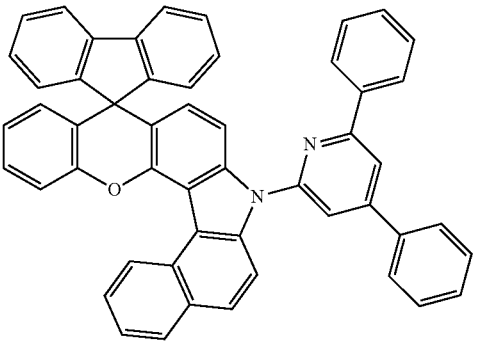
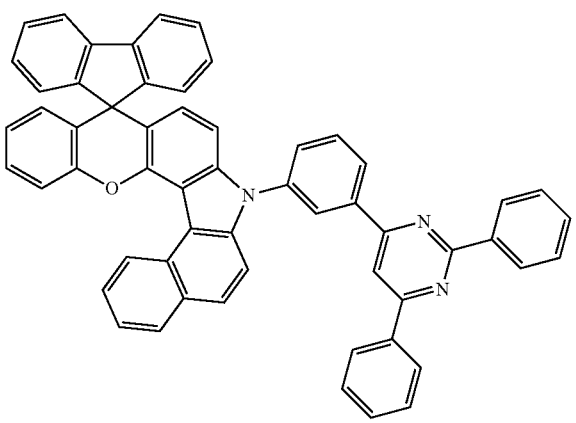
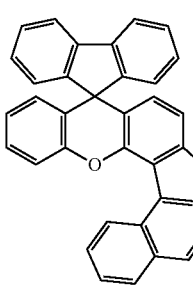
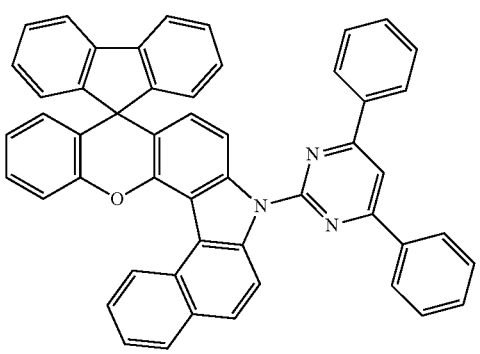
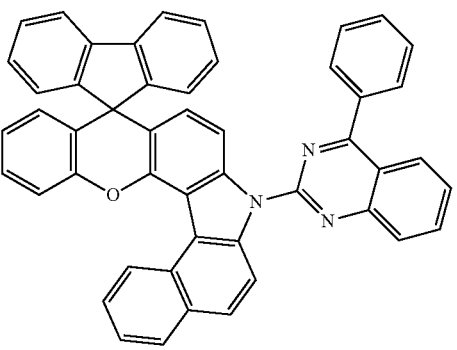
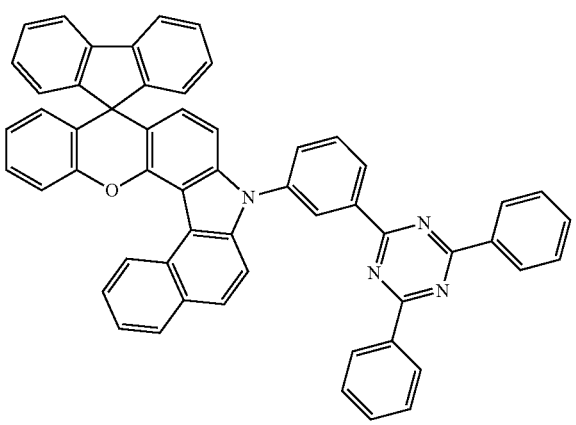
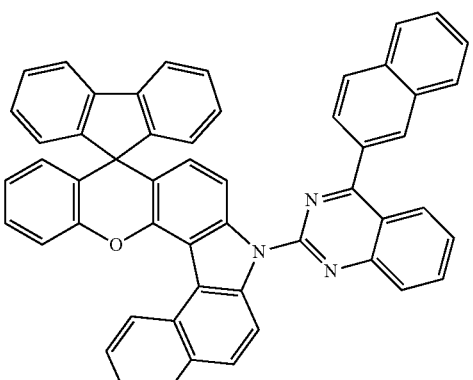

577
-continued
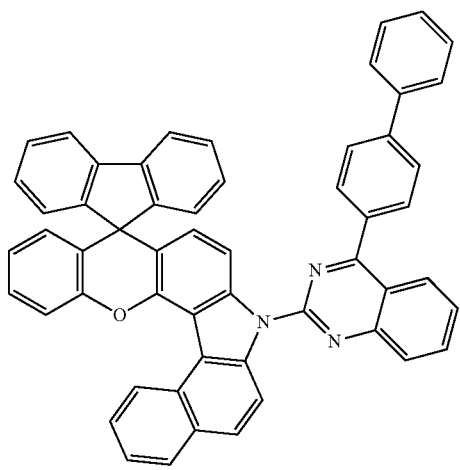
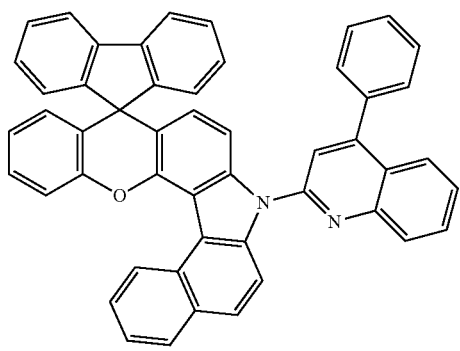
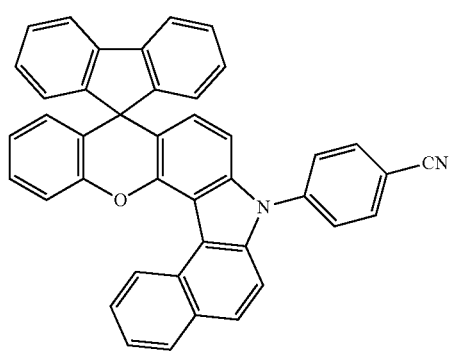
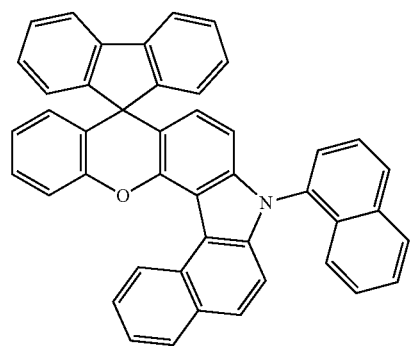
578
-continued
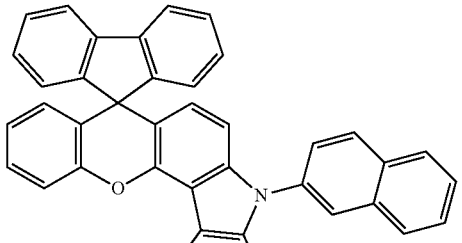
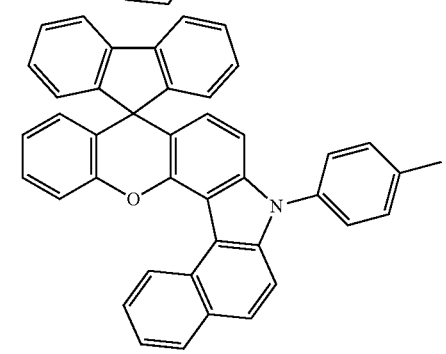
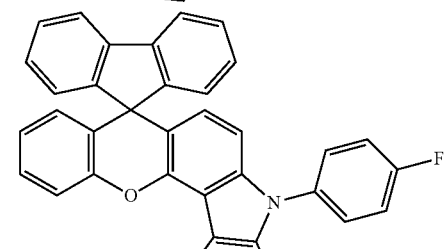
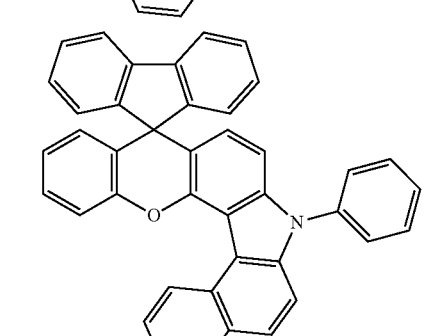
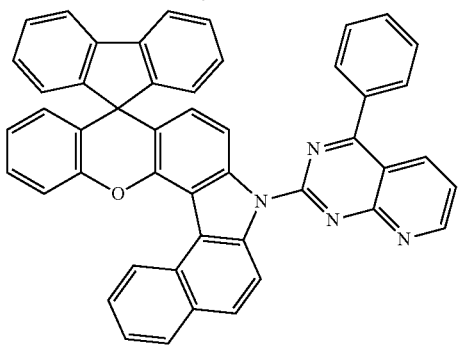

579
-continued
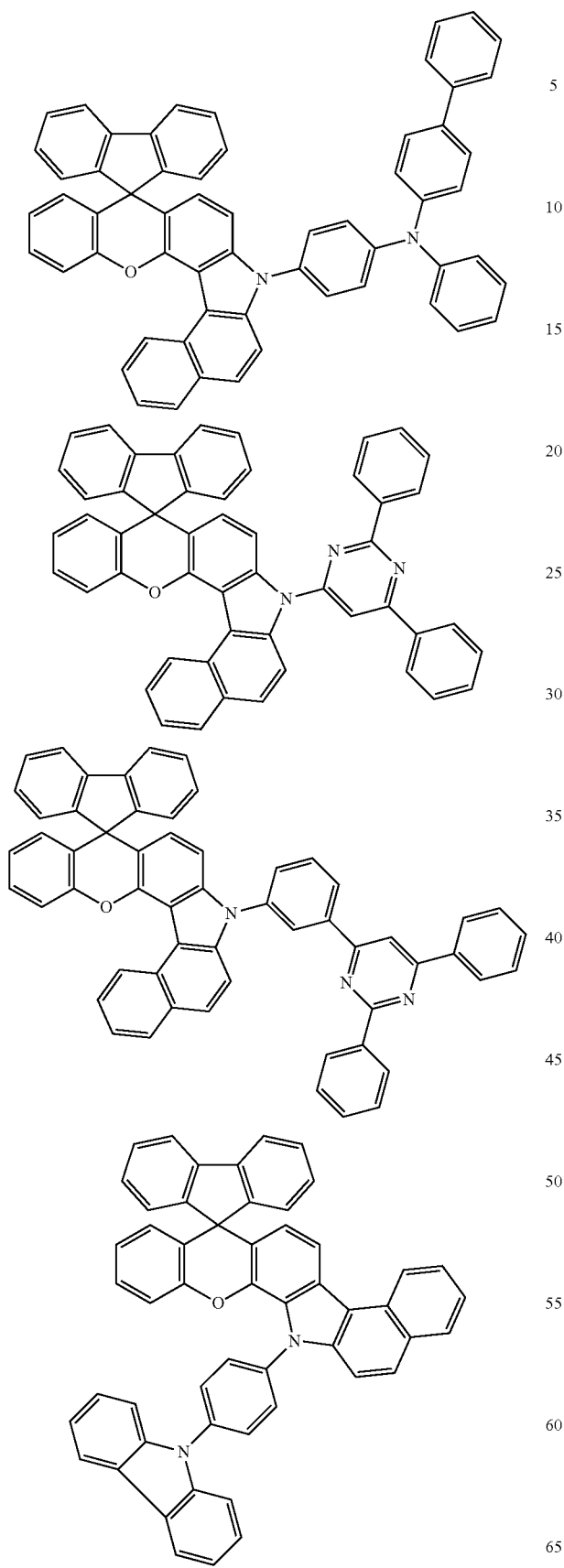
580
-continued
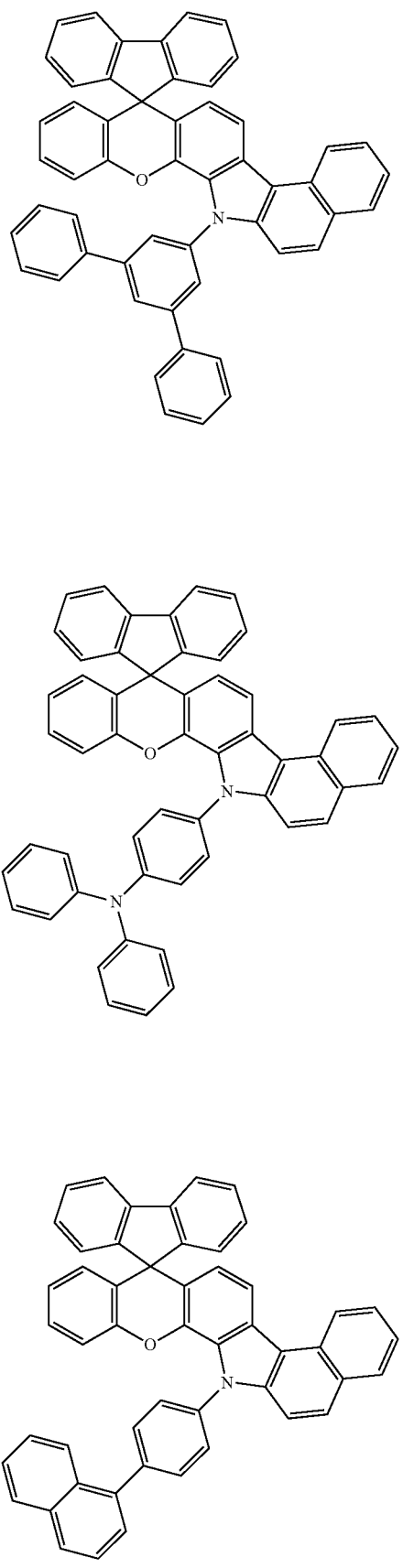

581
-continued
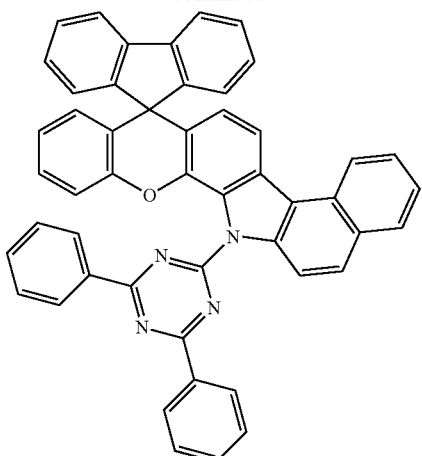
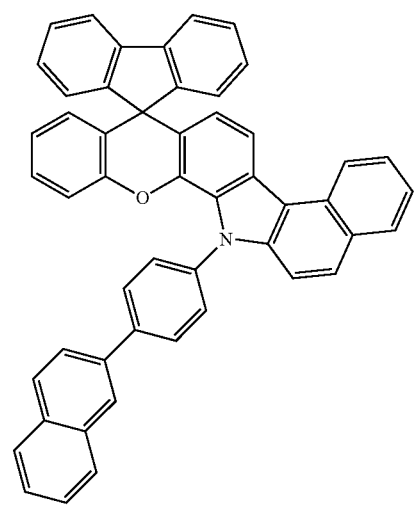
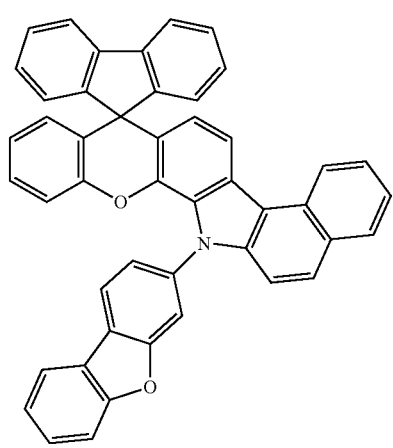
582
-continued
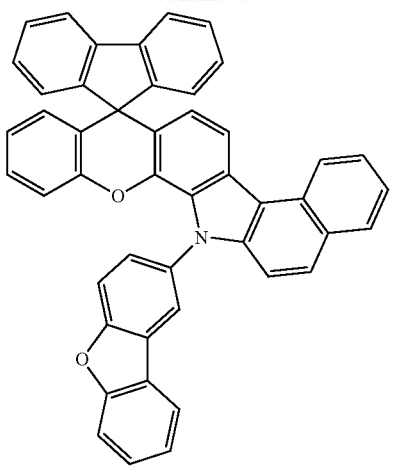
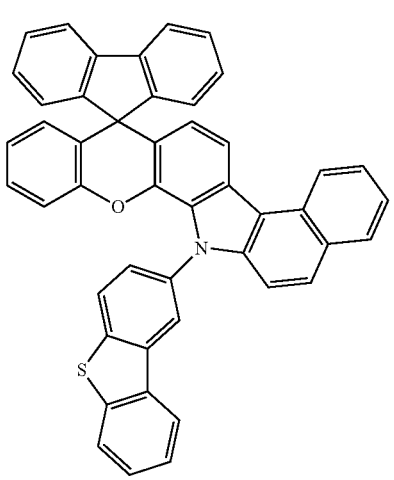
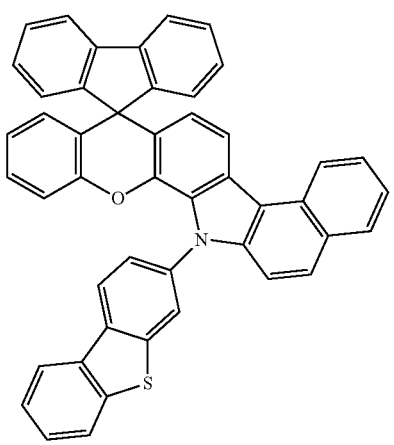

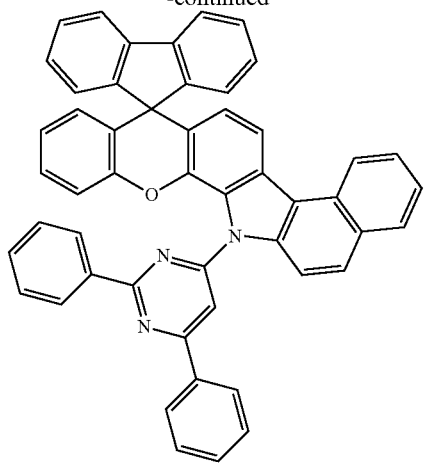
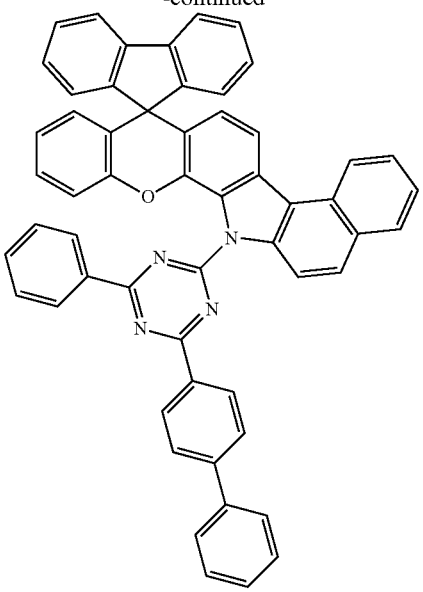
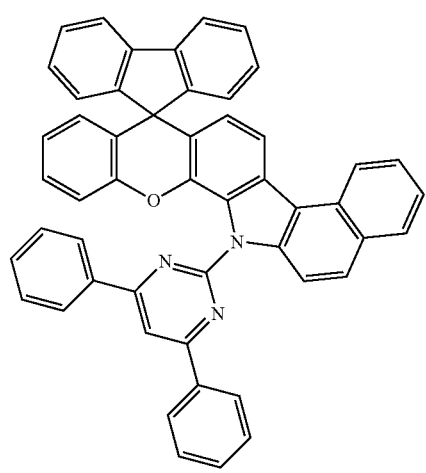
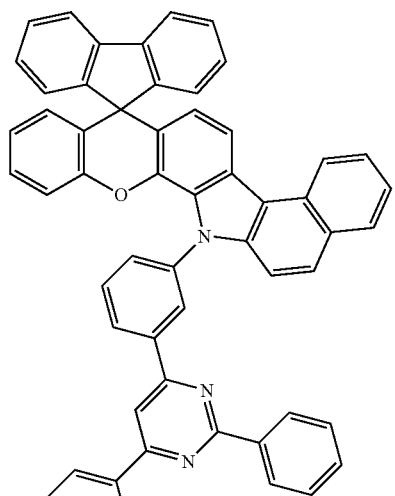
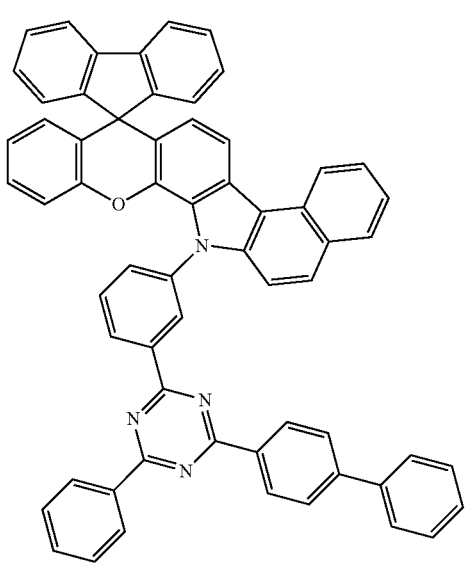

585
-continued
586
-continued
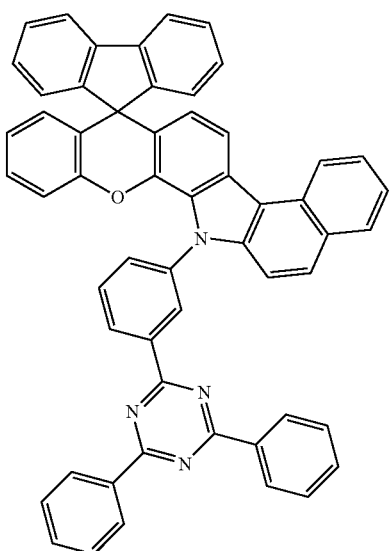
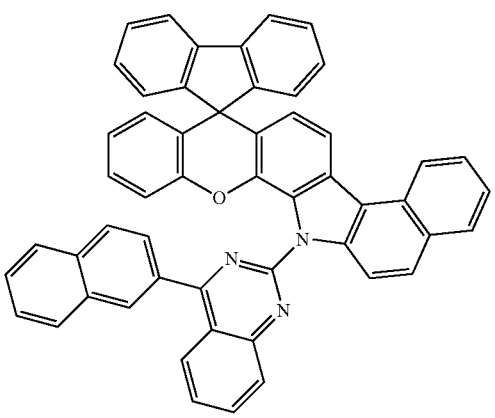
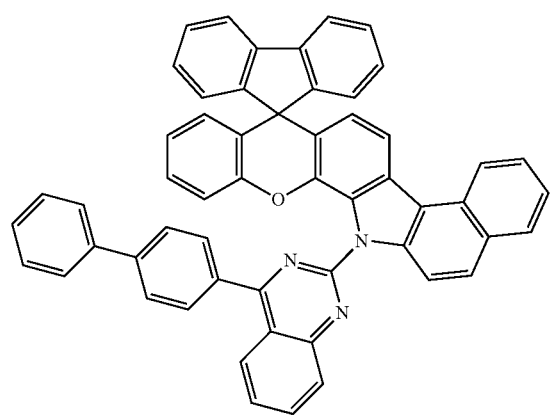
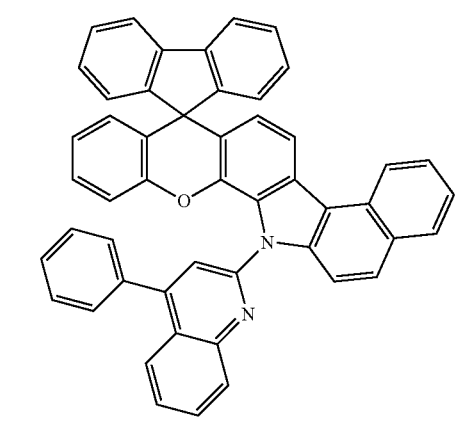
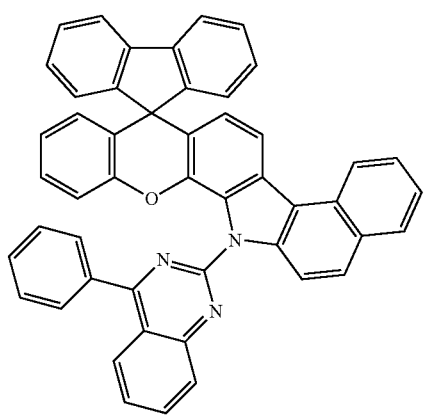
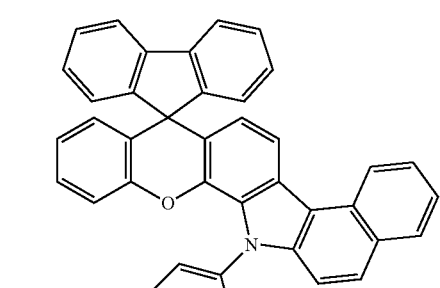
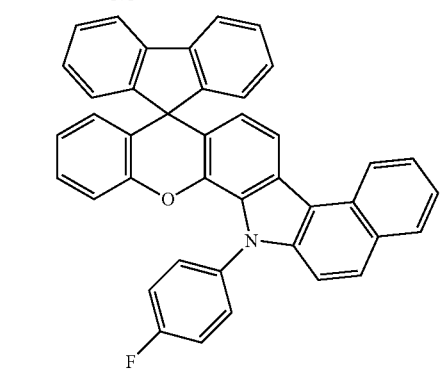

587
-continued
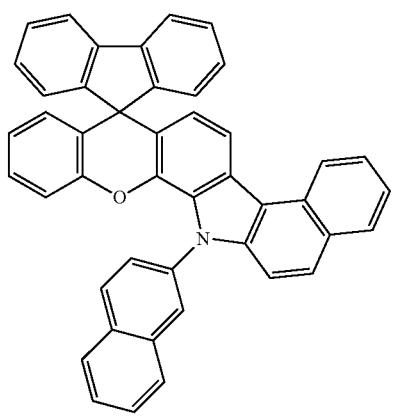
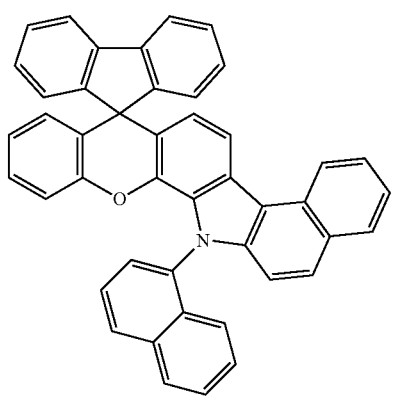
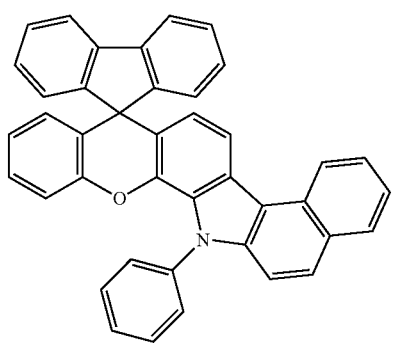
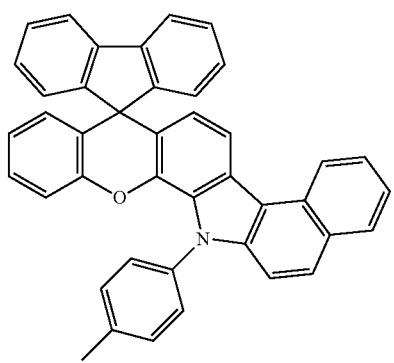
588
-continued
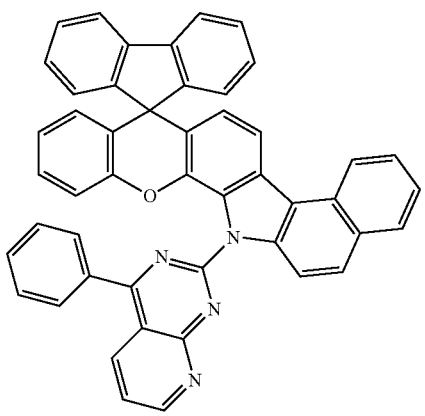
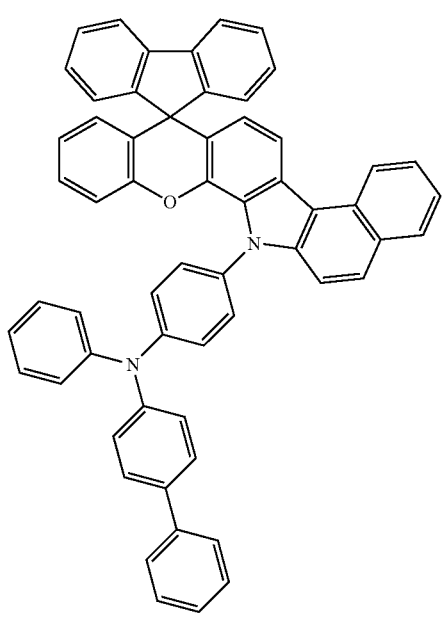
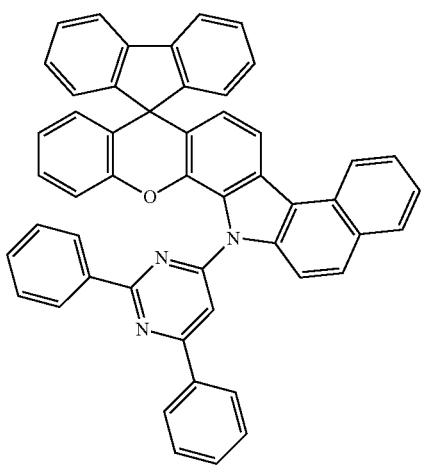

589
-continued
590
-continued
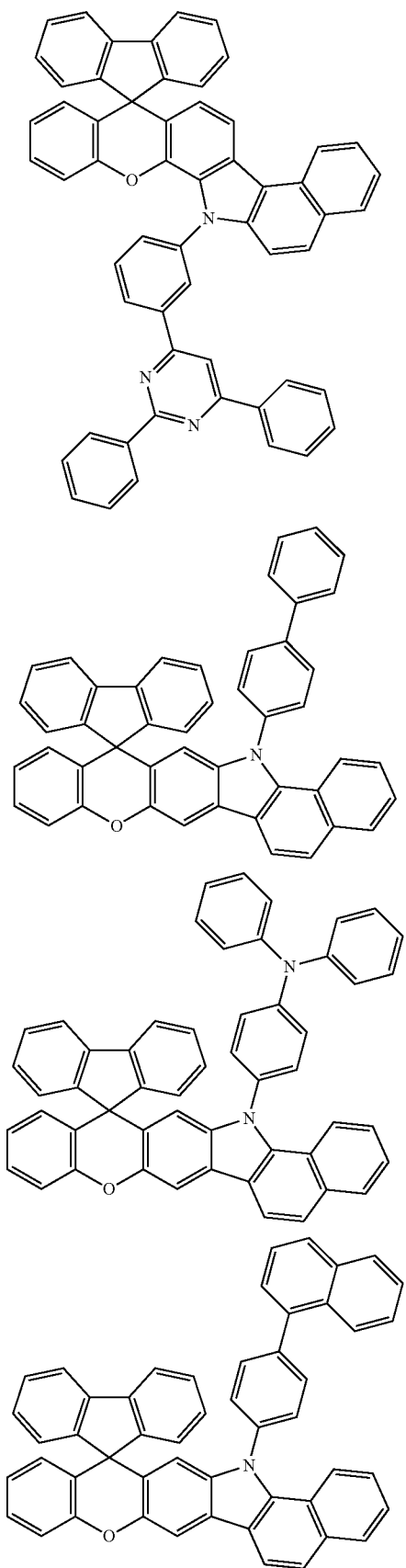
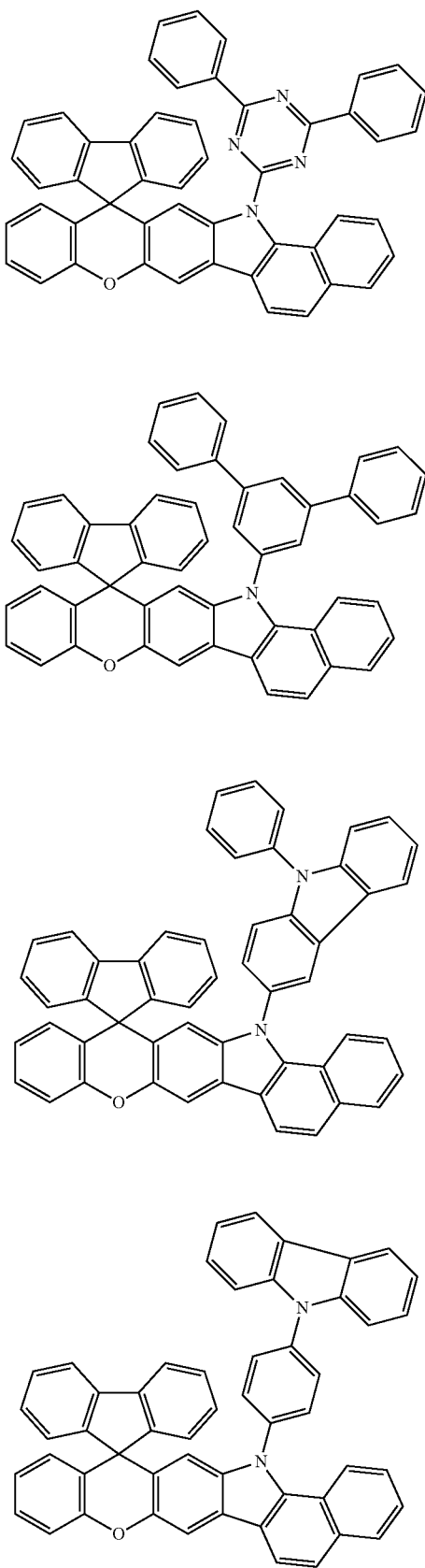

591
-continued
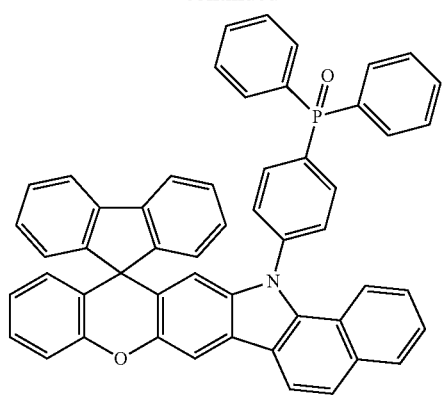
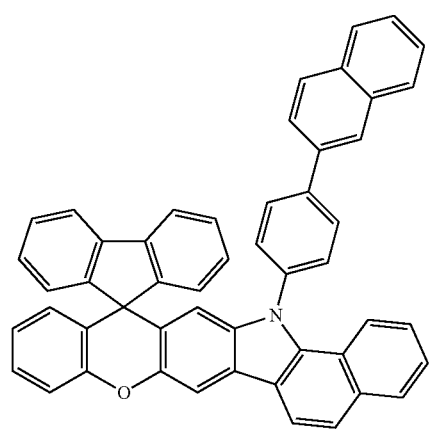
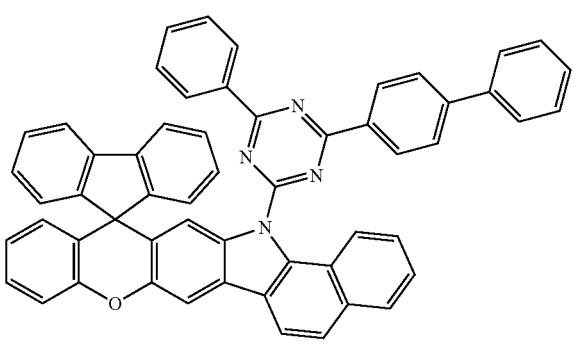
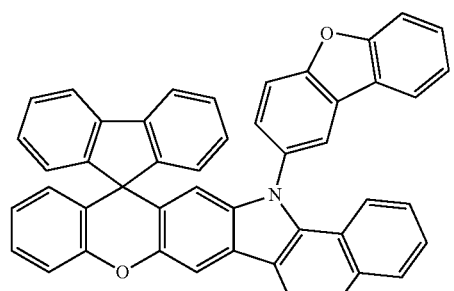
592
-continued
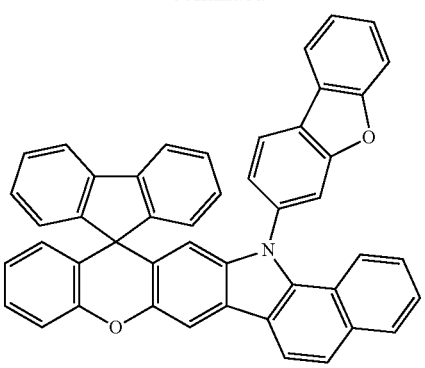
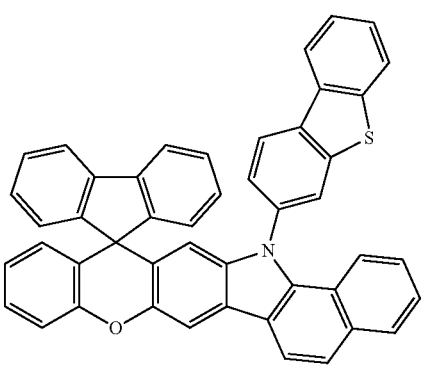
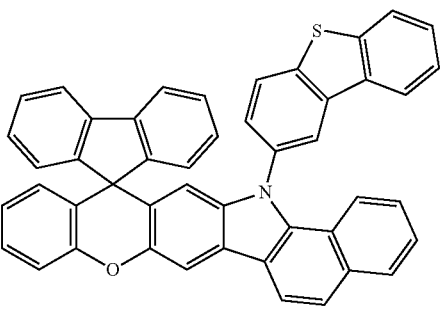
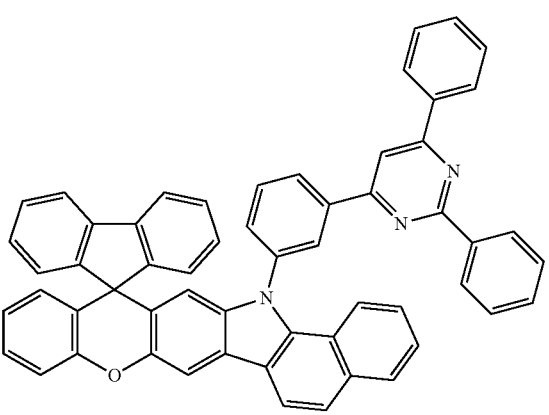

593
-continued
594
-continued
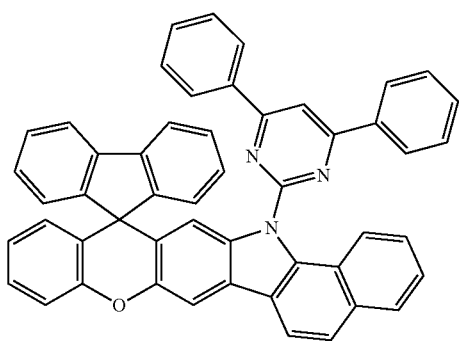
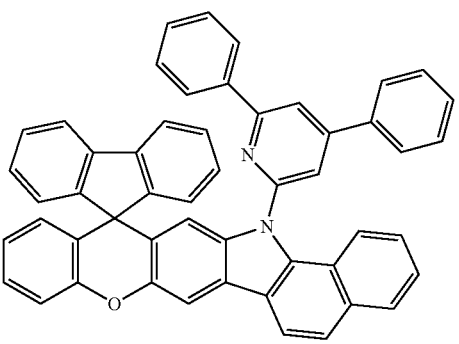
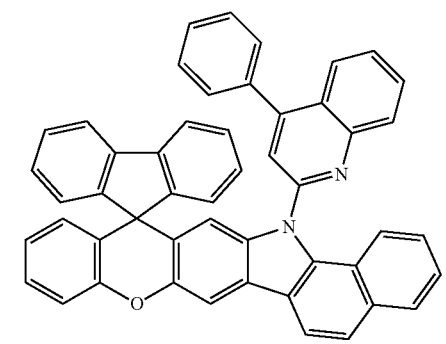
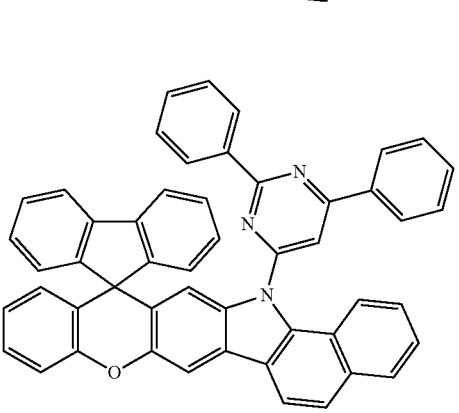
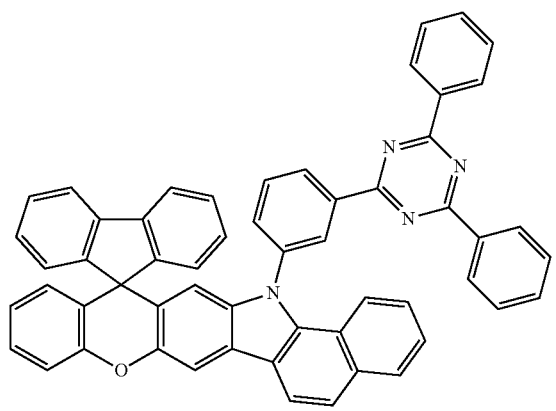
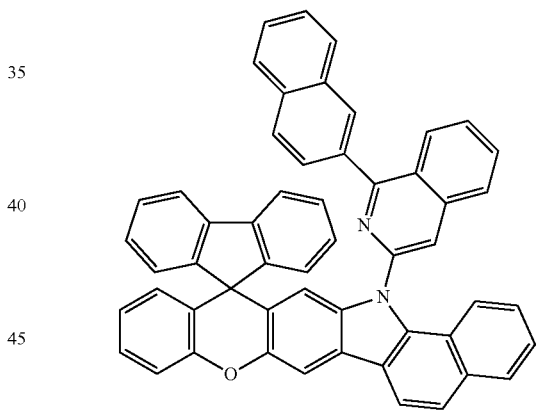
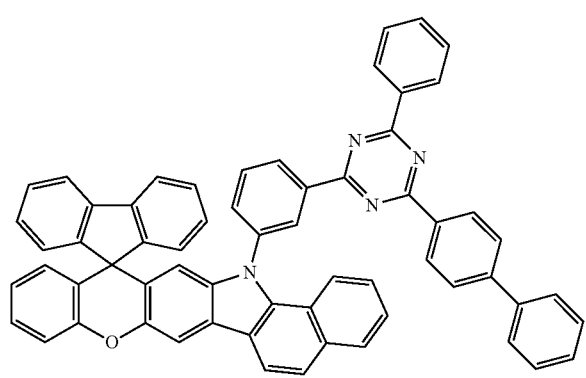
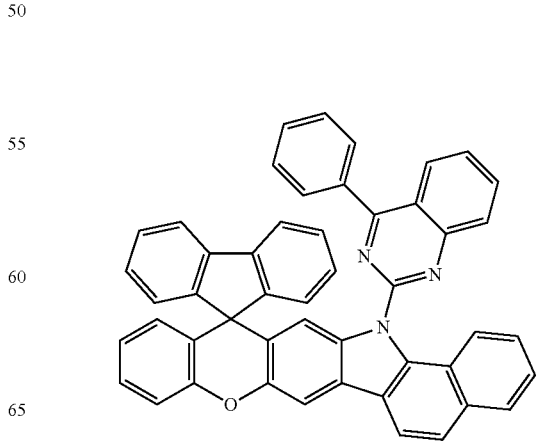

595
-continued
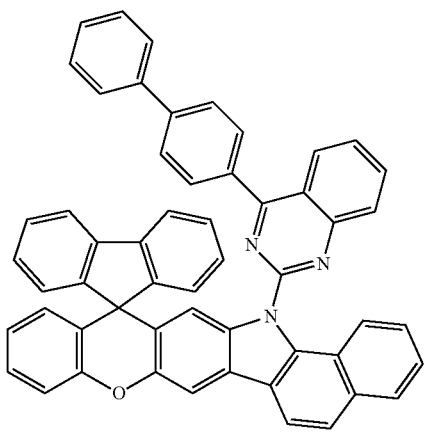
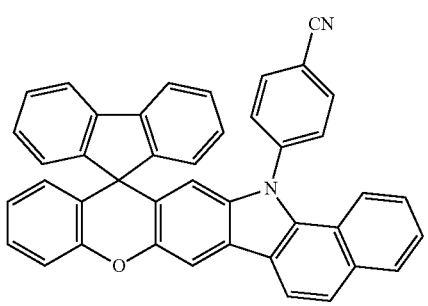
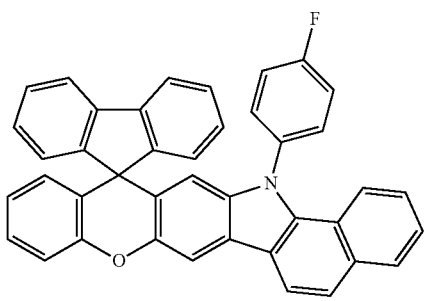
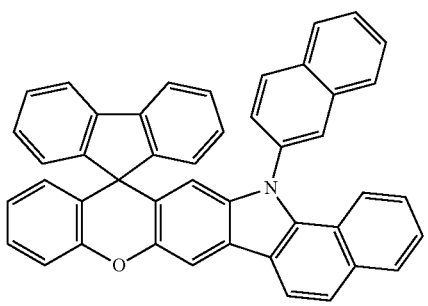
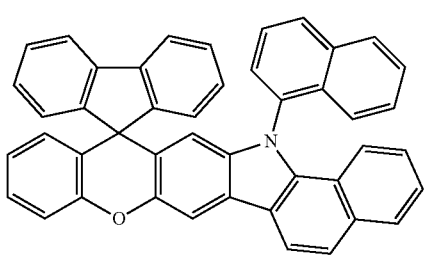
596
-continued
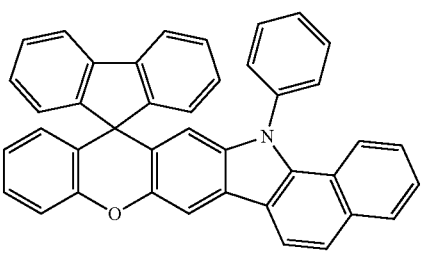
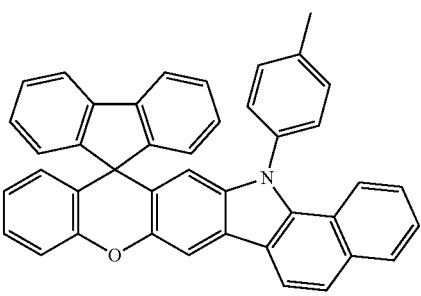
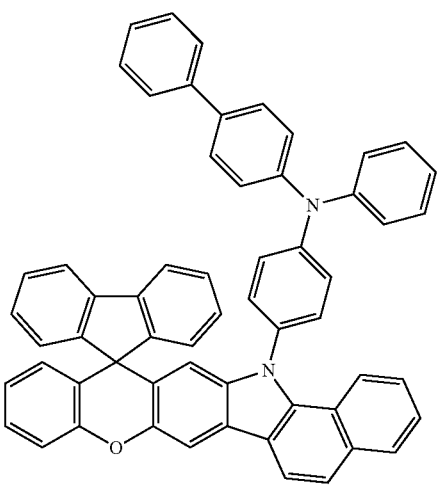
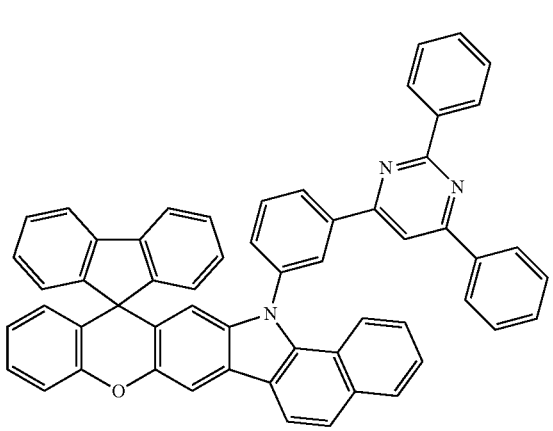

597
-continued
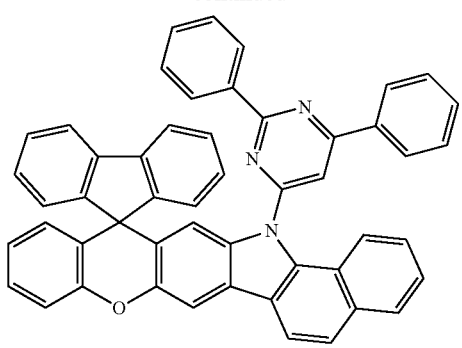
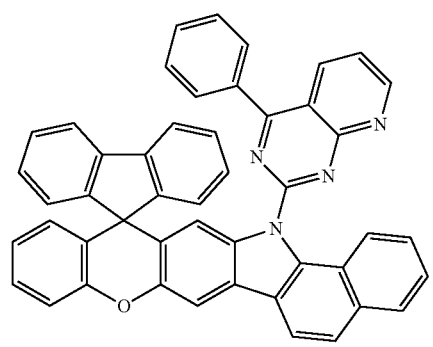
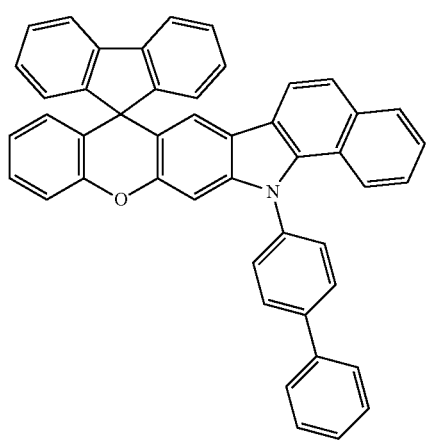
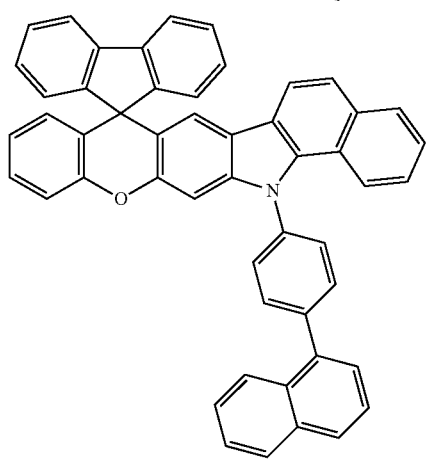
598
-continued
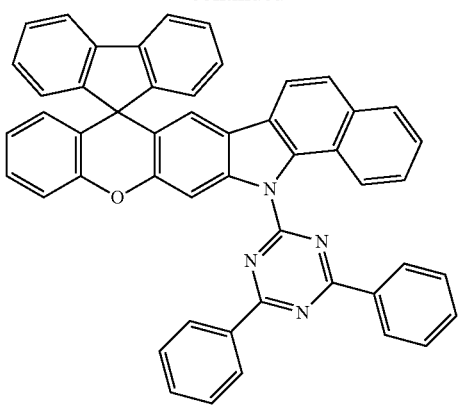
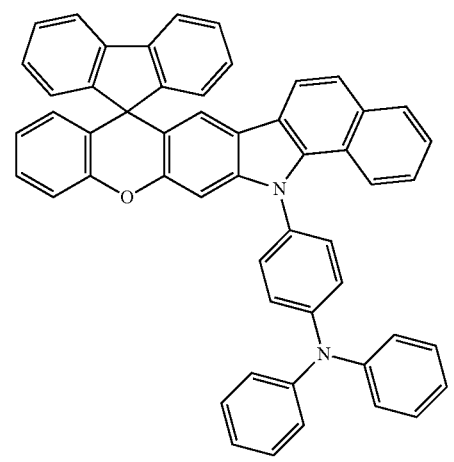
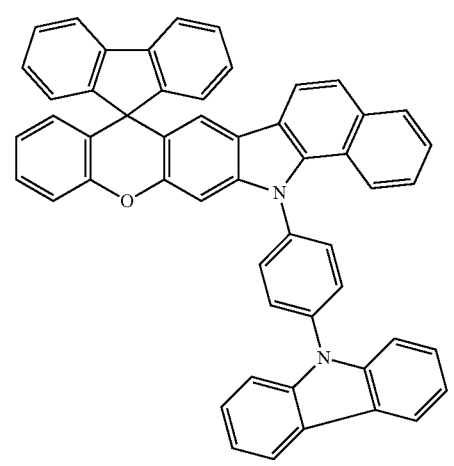

599
-continued
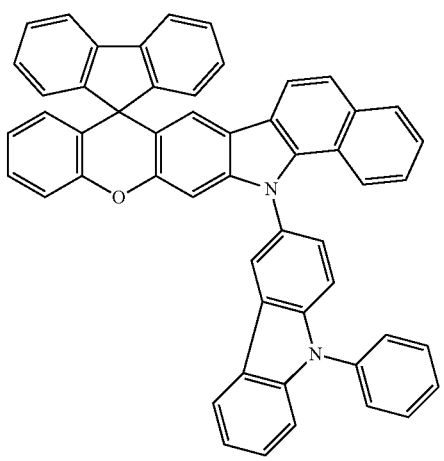
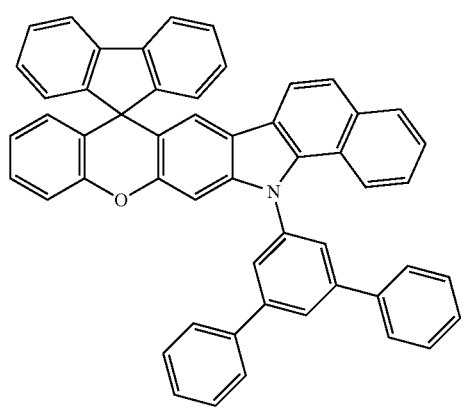
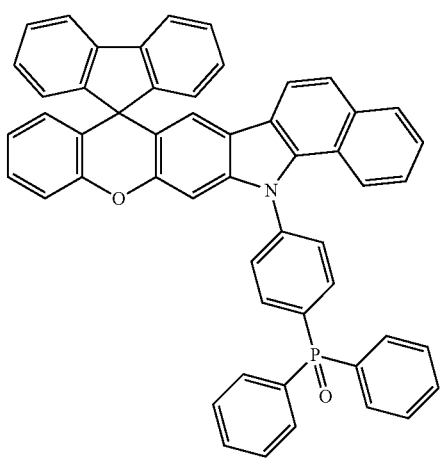
600
-continued
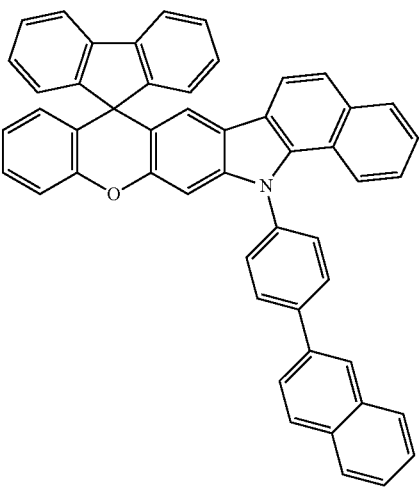
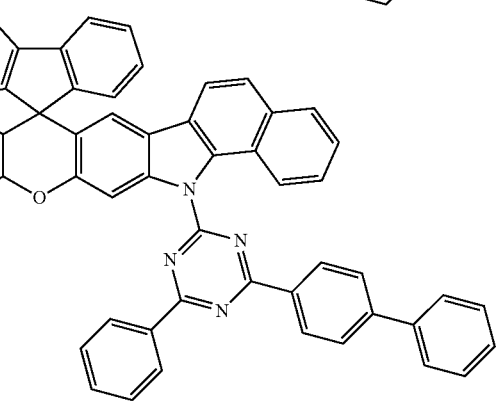
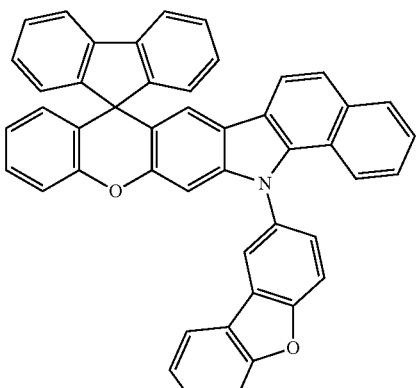
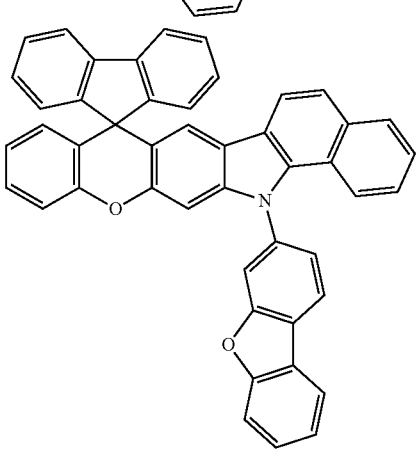

| 601 | 602 |
|---|---|
| 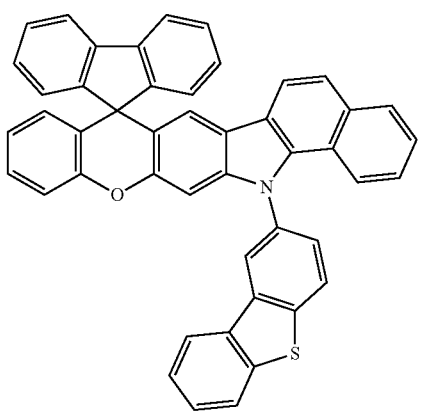 | 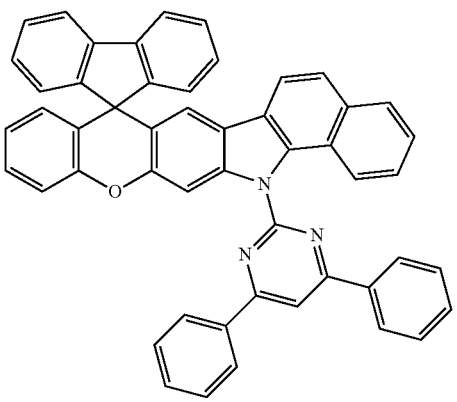 |
| 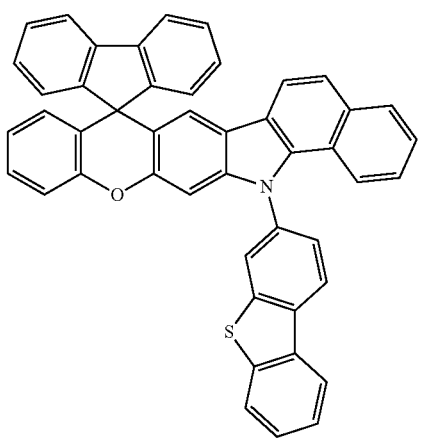 | 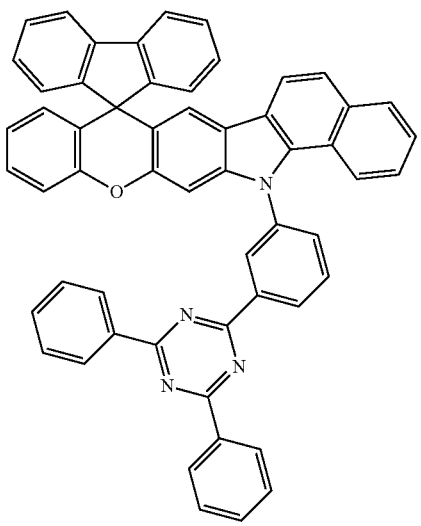 |
| 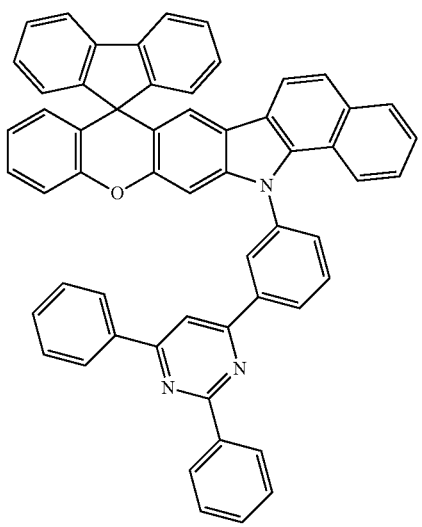 | 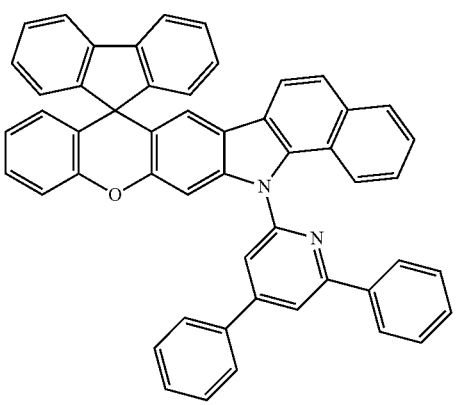 |

603
-continued
604
-continued
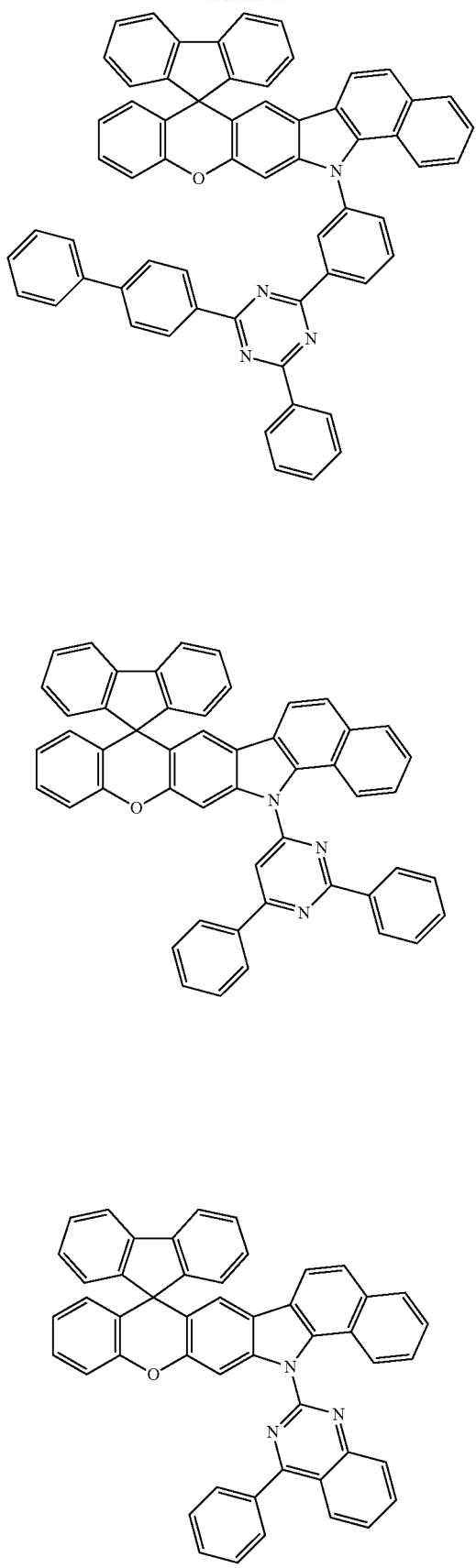
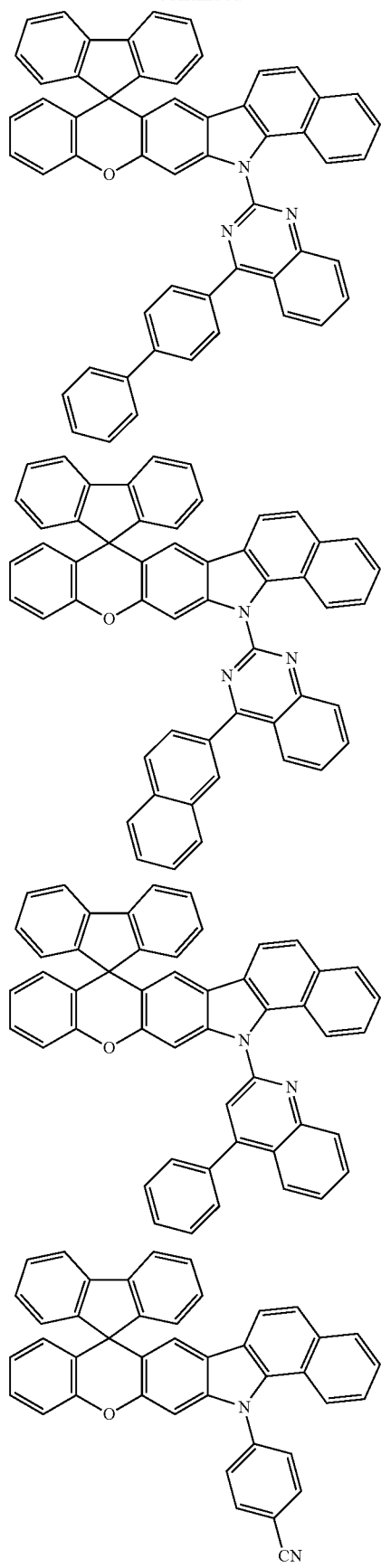

605
-continued
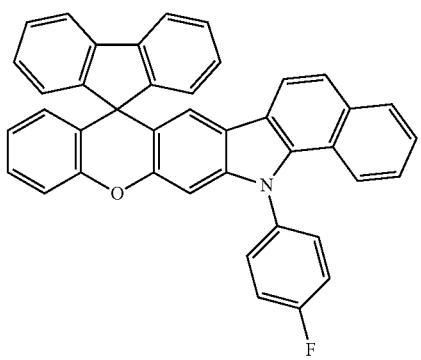
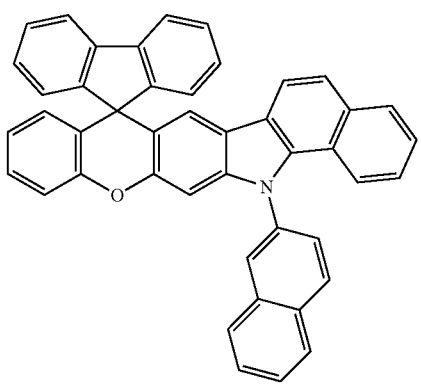
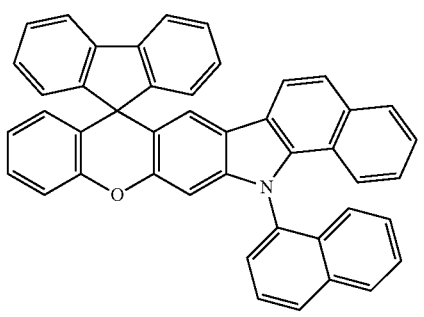
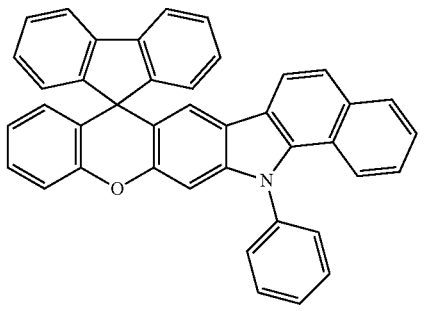
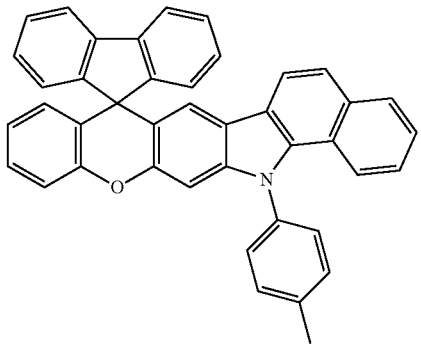
606
-continued
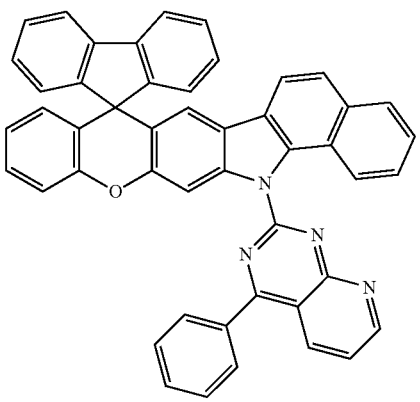
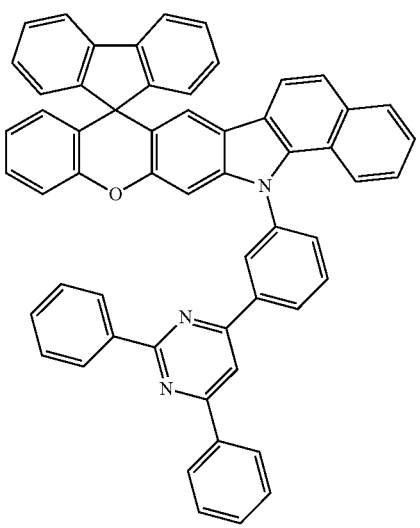
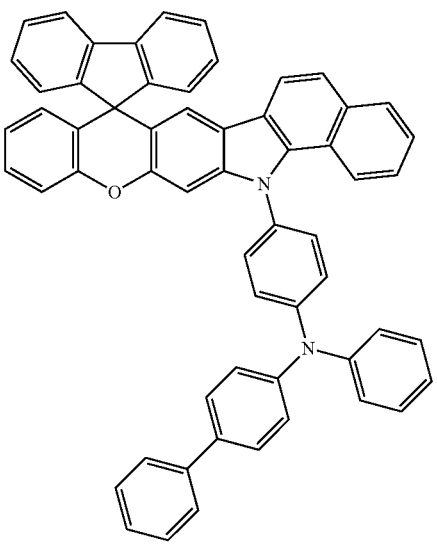

607
-continued
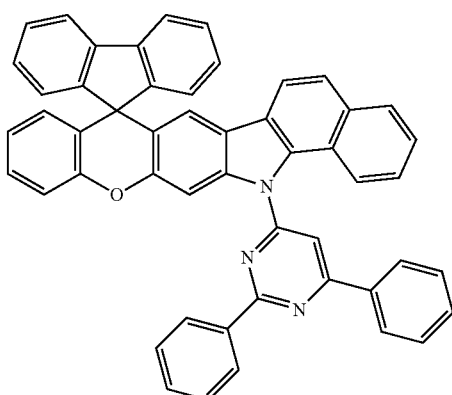
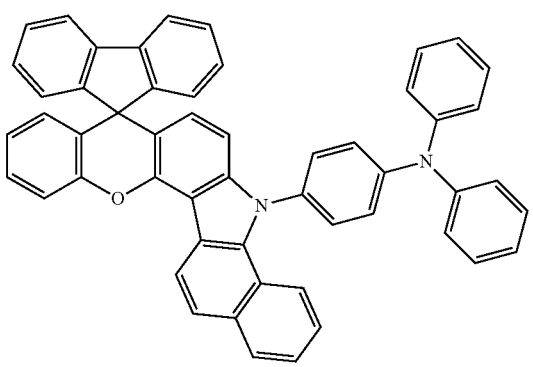
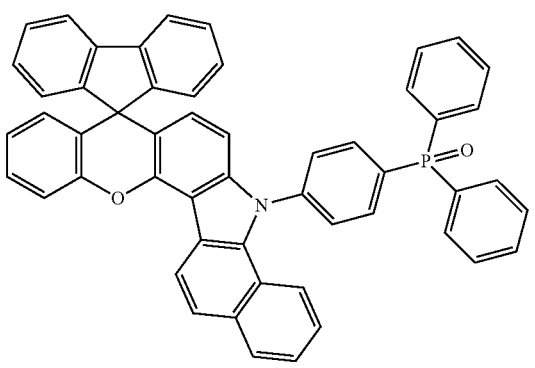
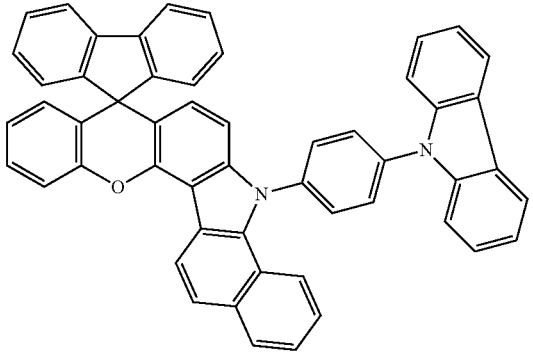
608
-continued
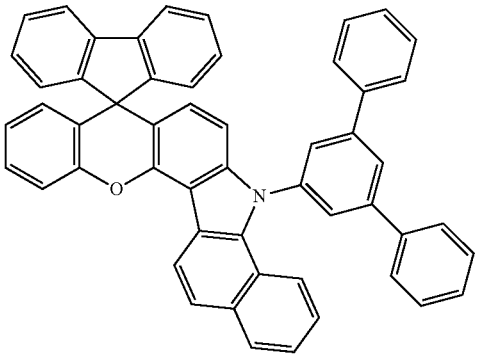
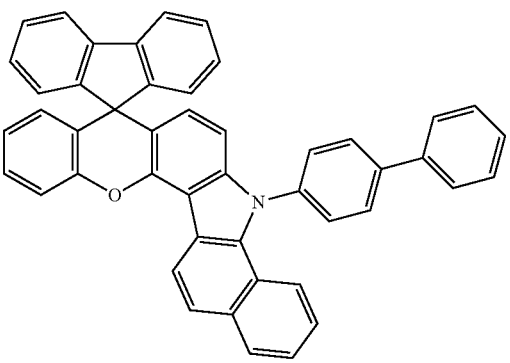
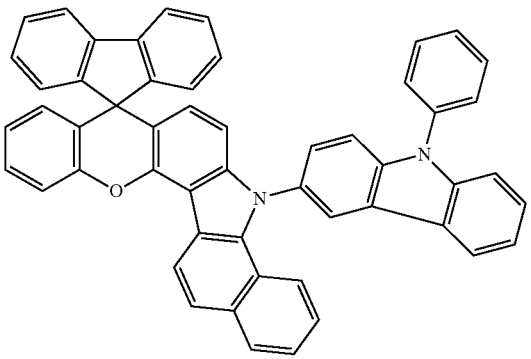
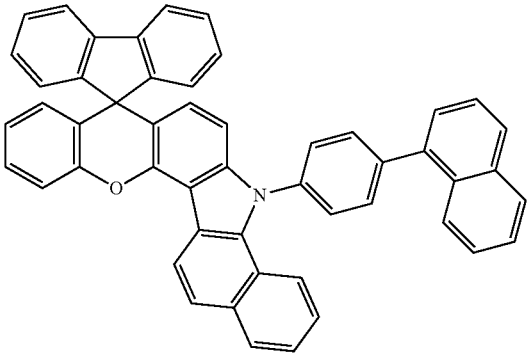

609
-continued
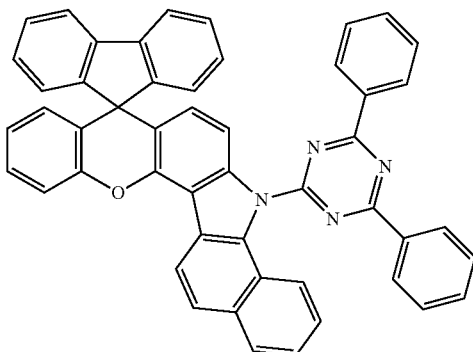
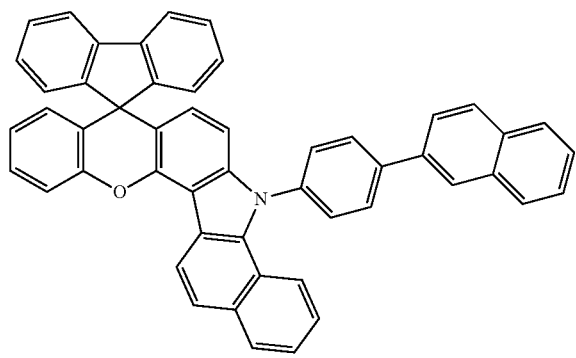
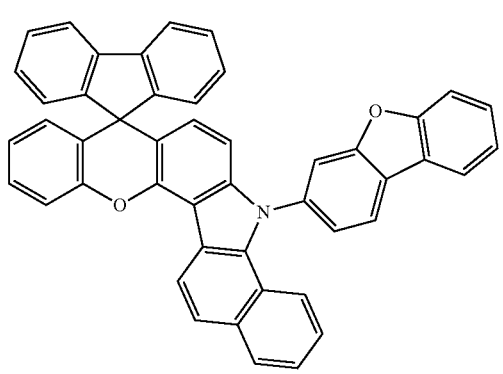
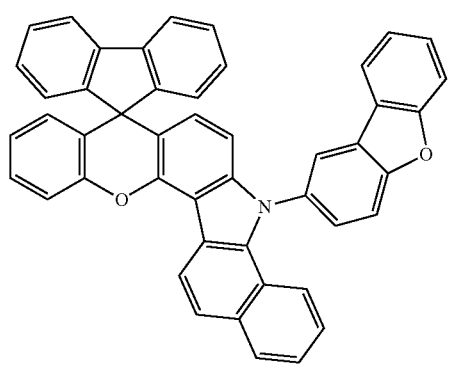
610
-continued
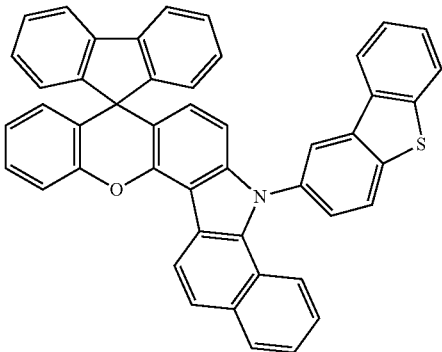
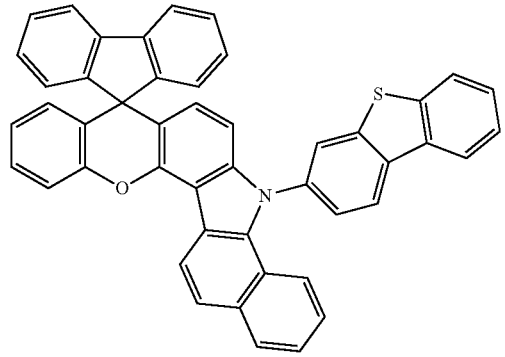
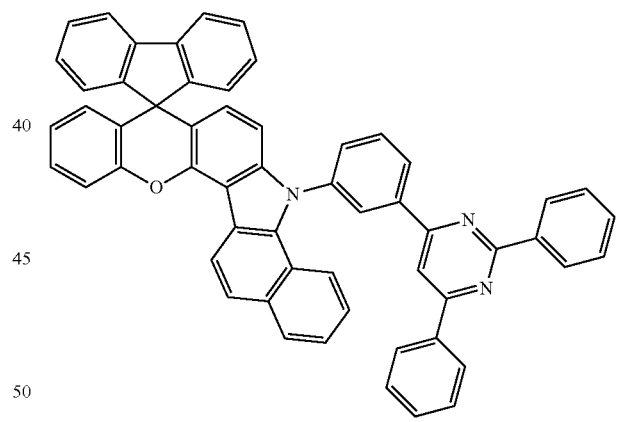
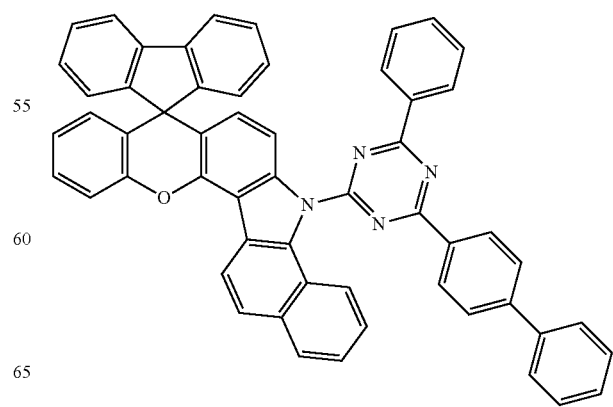

| 611 -continued | 612 -continued |
|---|---|
| 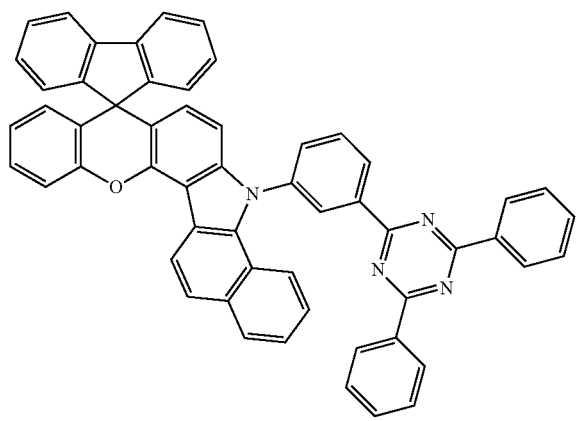 | 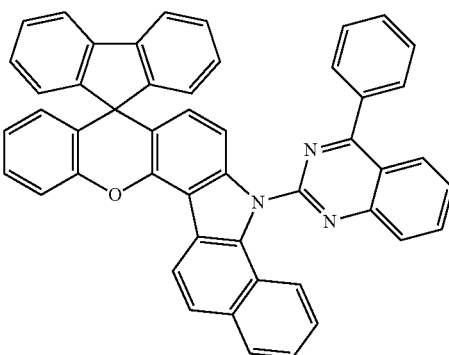 |
| 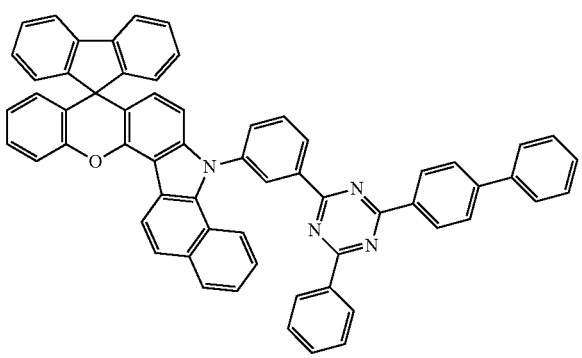 | 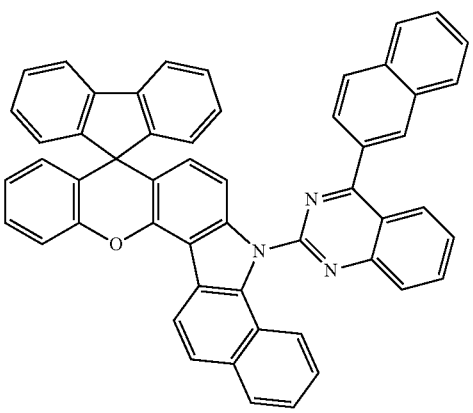 |
| 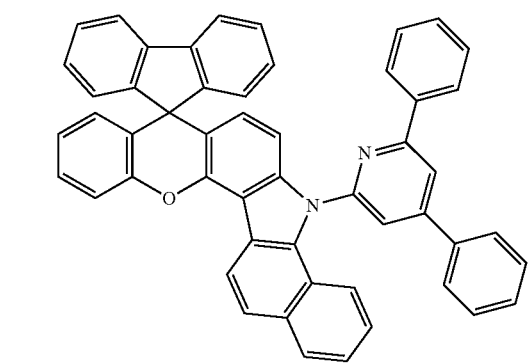 | 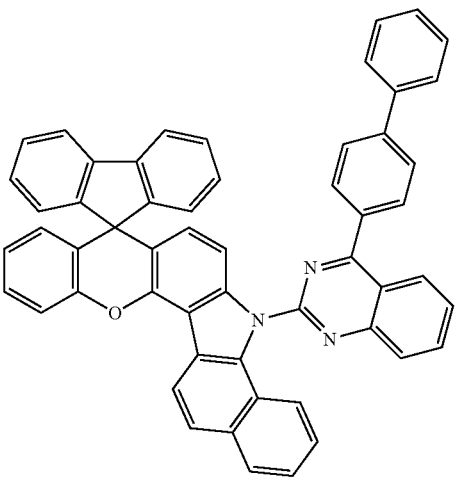 |
| 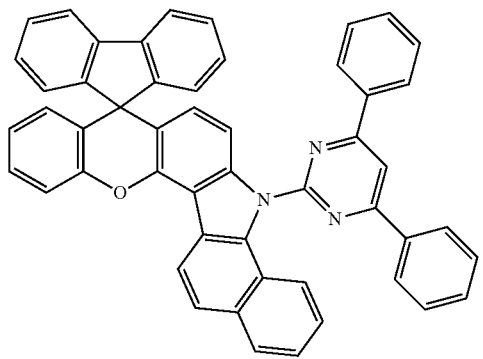 | 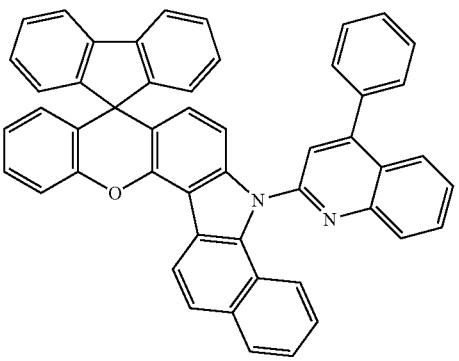 |

| 613 -continued | 614 -continued |
|---|---|
| 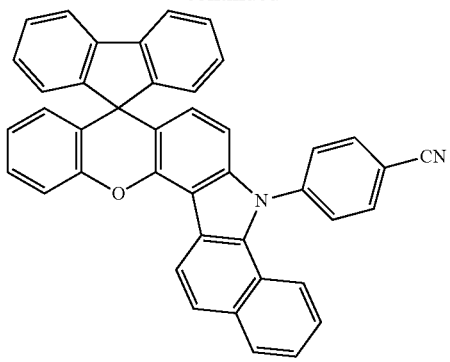 | 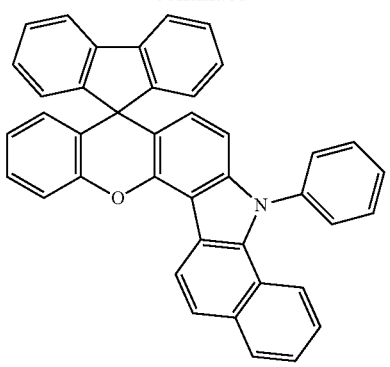 |
| 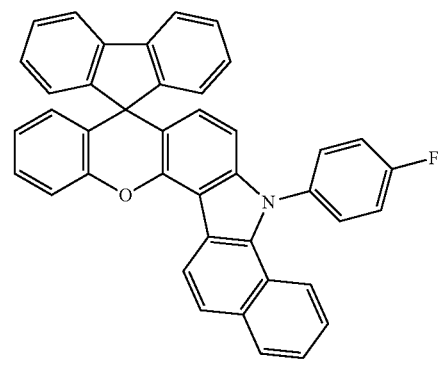 | 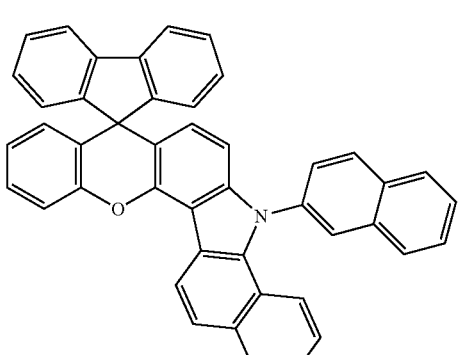 |
| 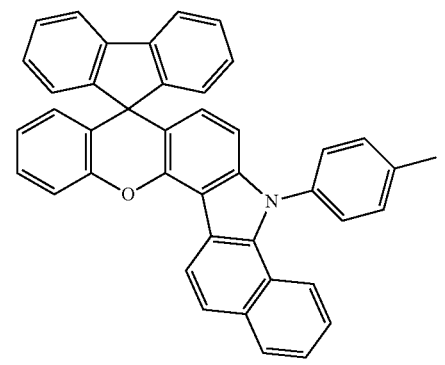 | 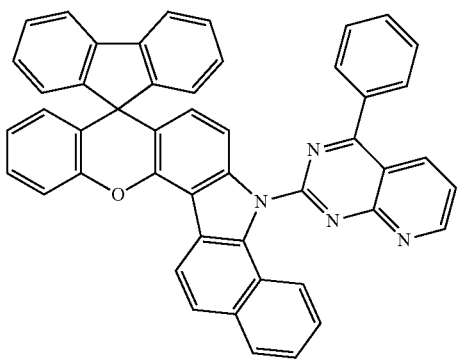 |
| 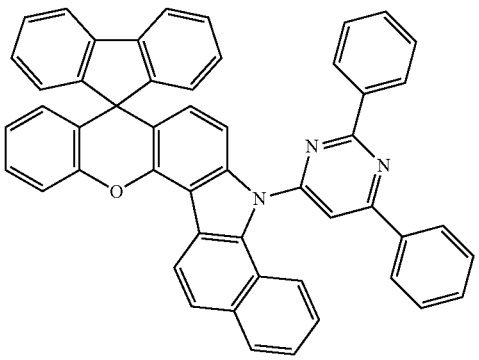 | 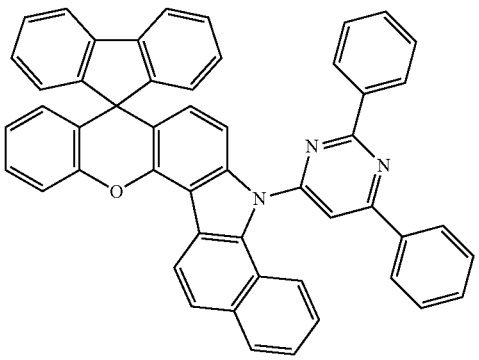 |

615
-continued
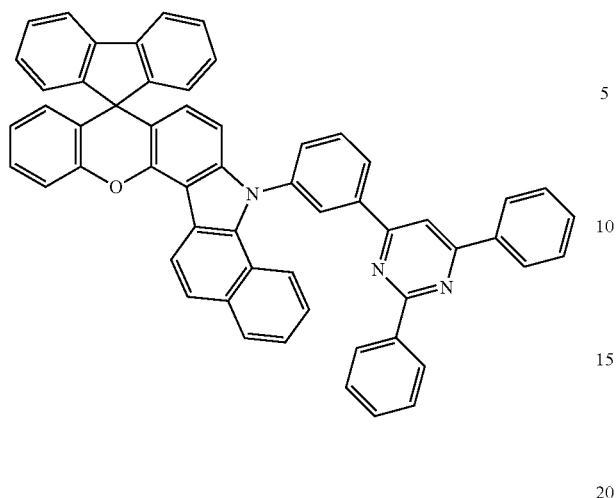
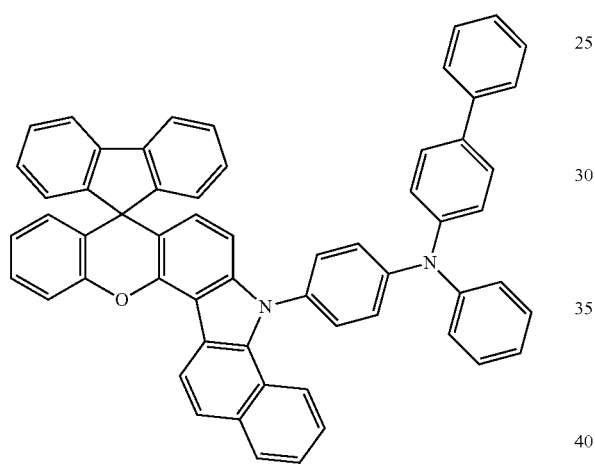
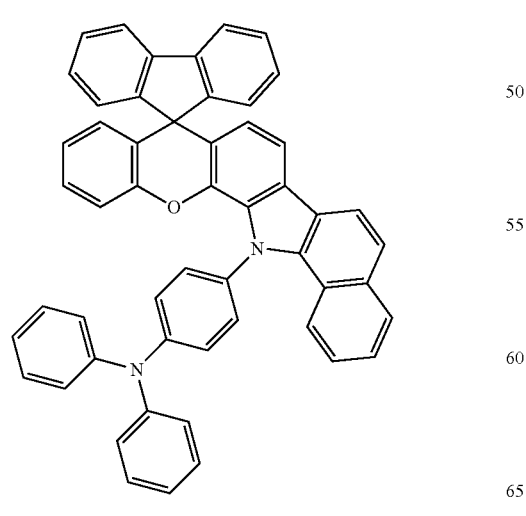
616
-continued
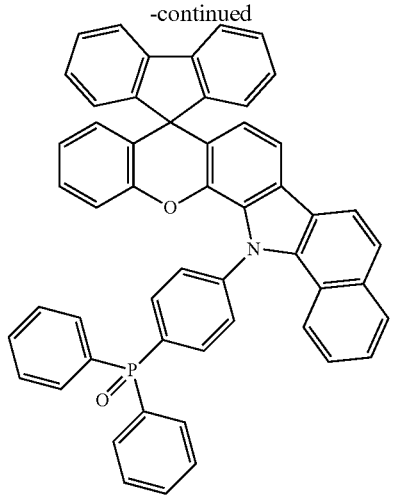
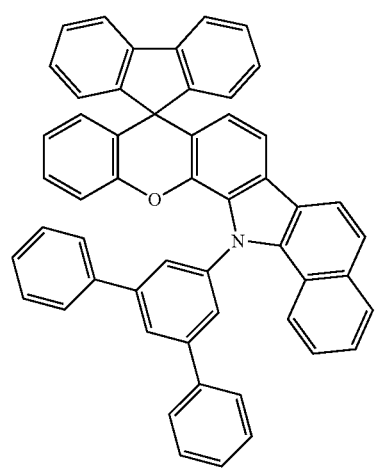
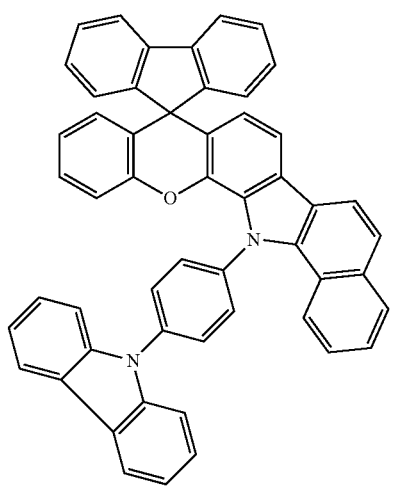

617
-continued
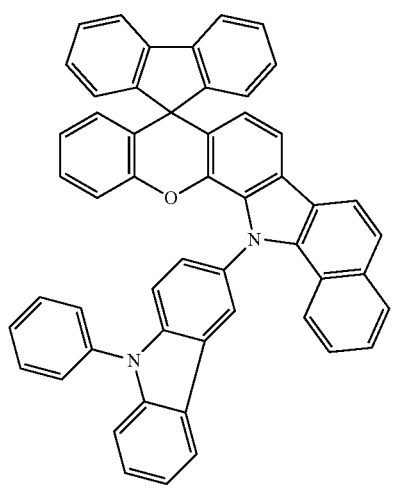
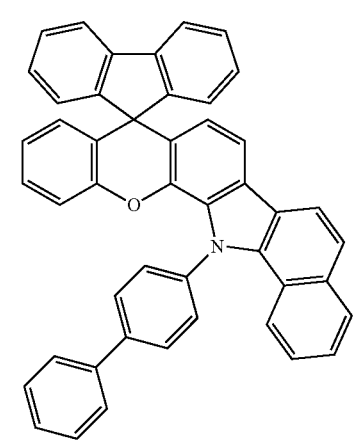
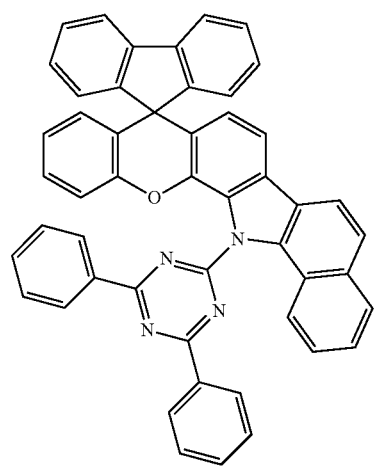
618
-continued
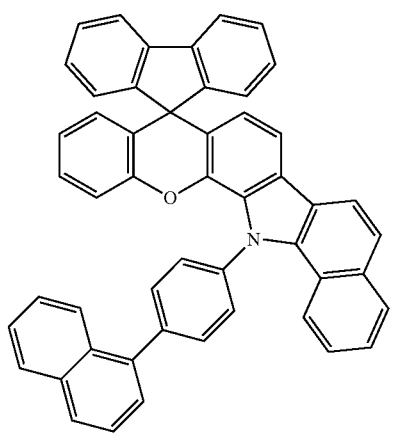
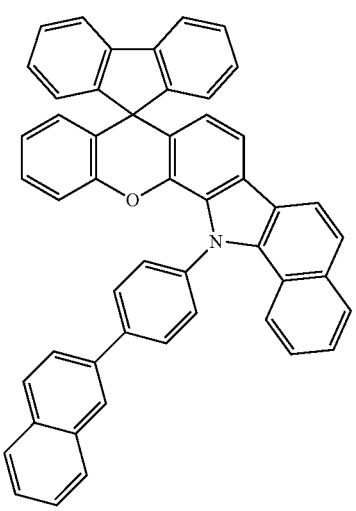
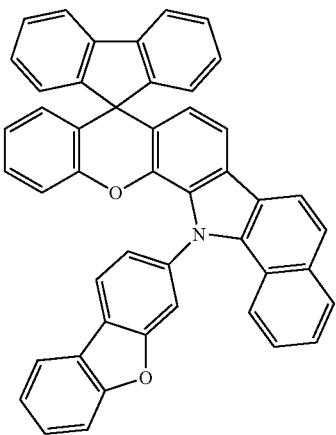

619
-continued
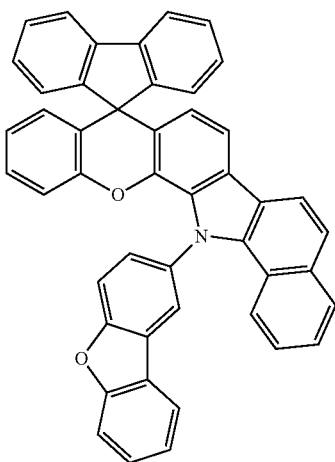
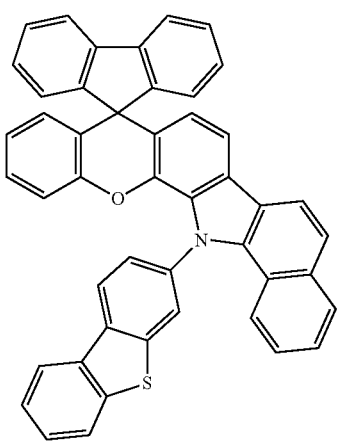
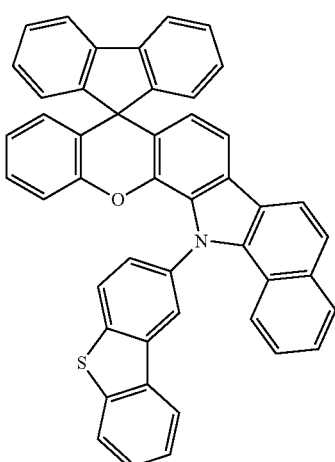
620
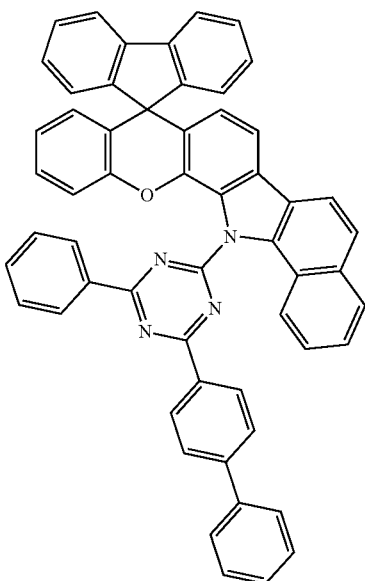
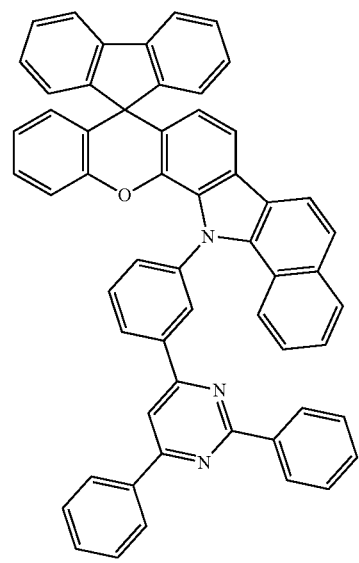
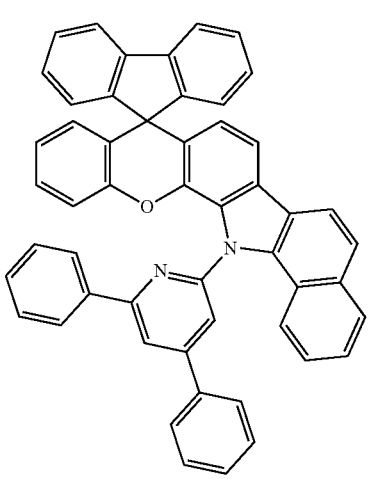

621
-continued
622
-continued
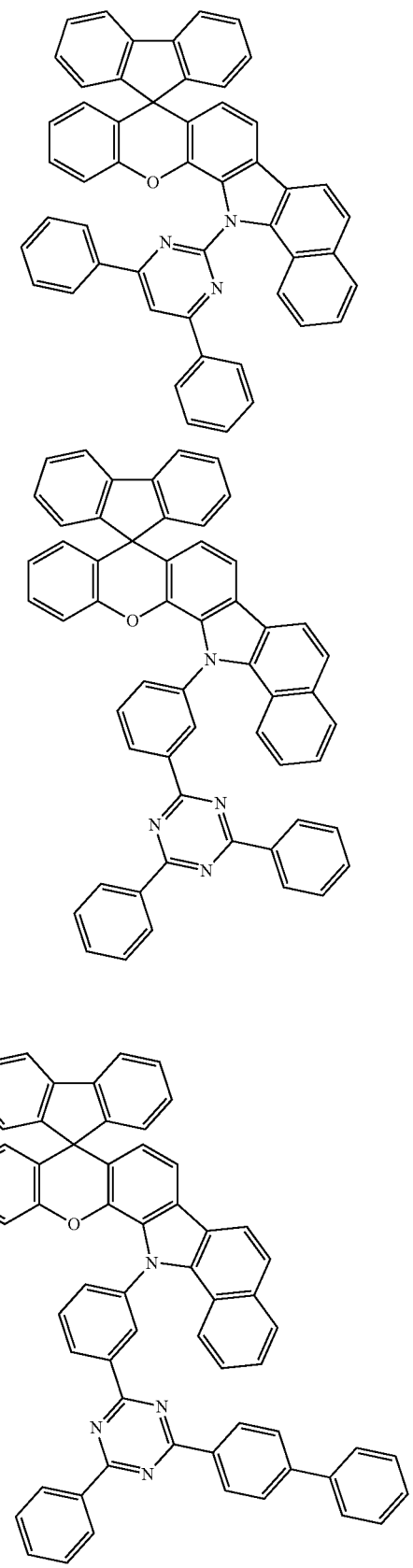
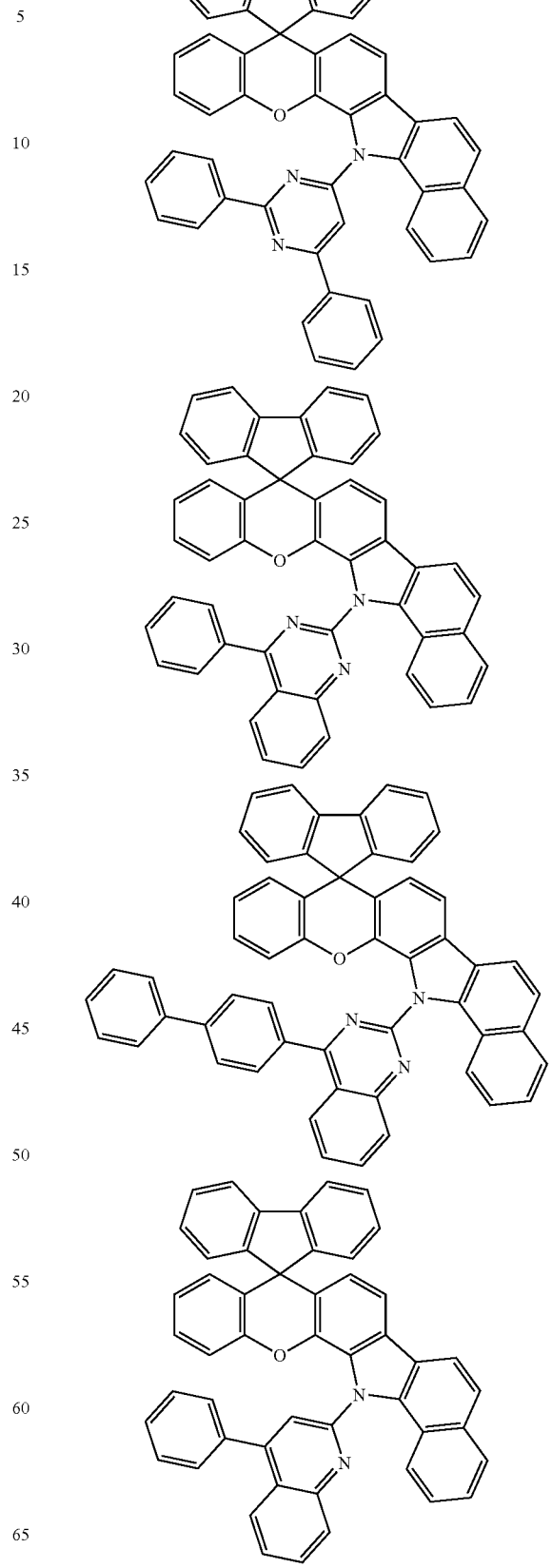

623
-continued
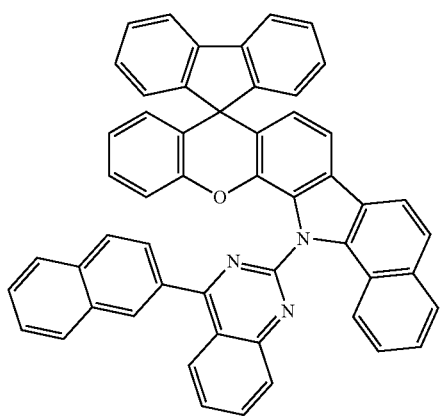
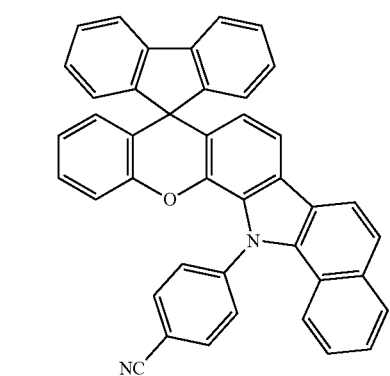
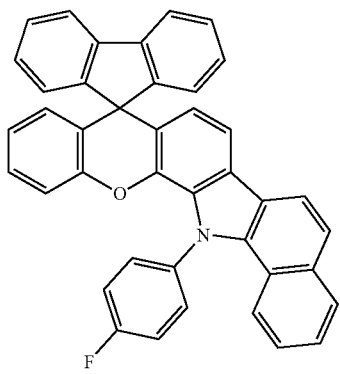
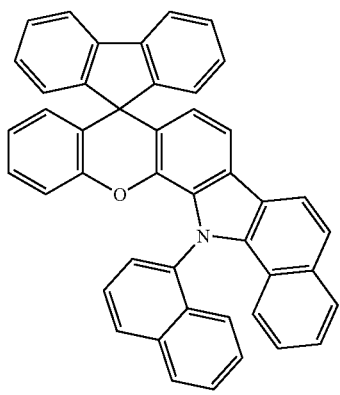
624
-continued
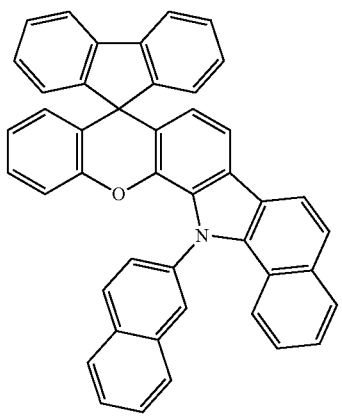
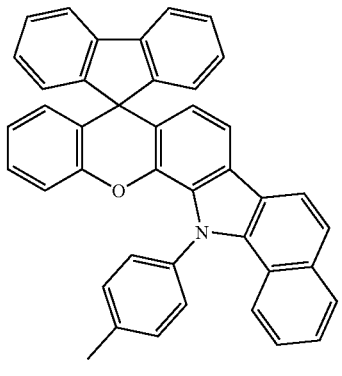
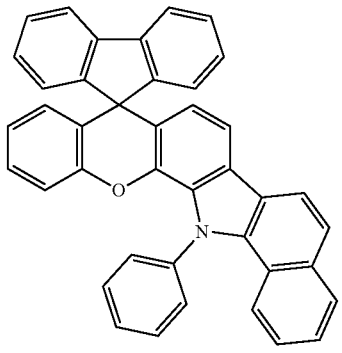
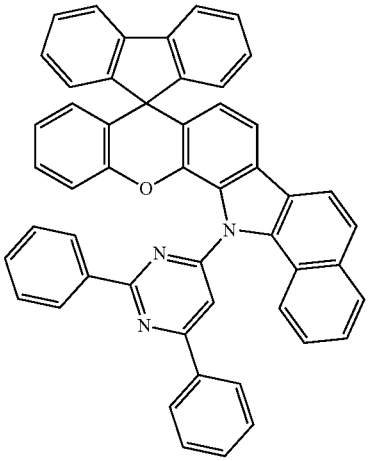

625
-continued
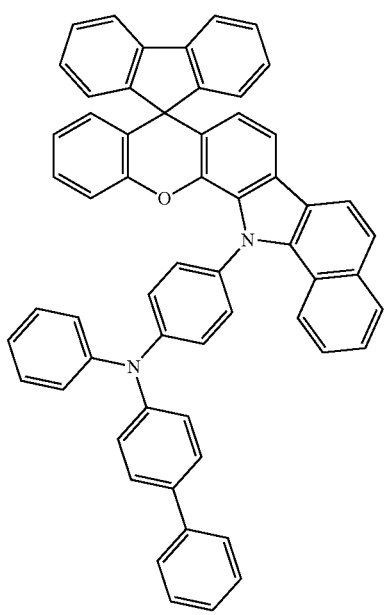
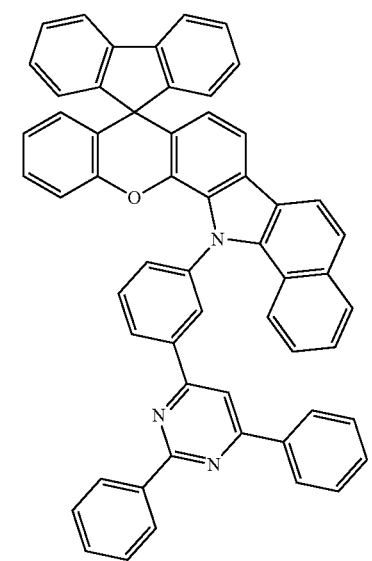
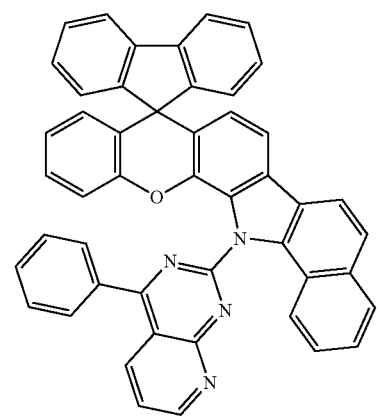
626
-continued
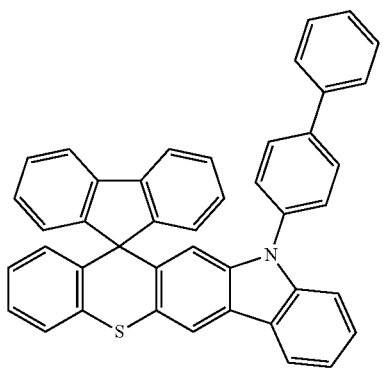
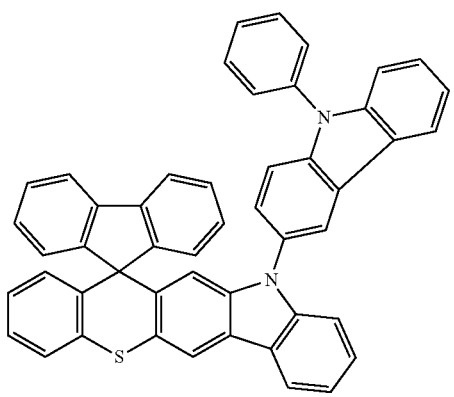
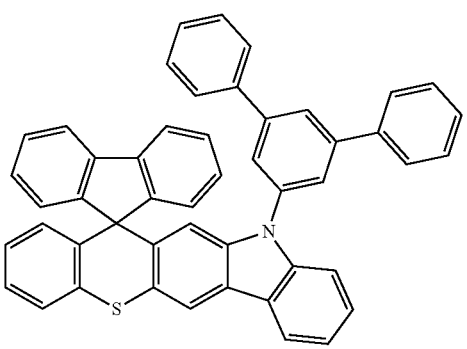
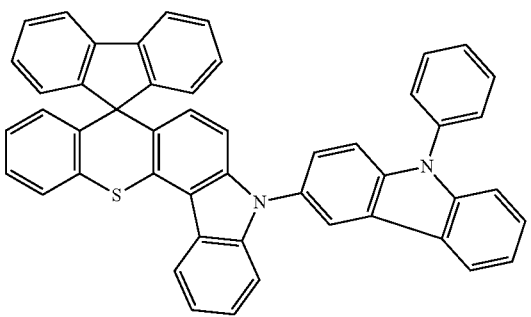

627
-continued
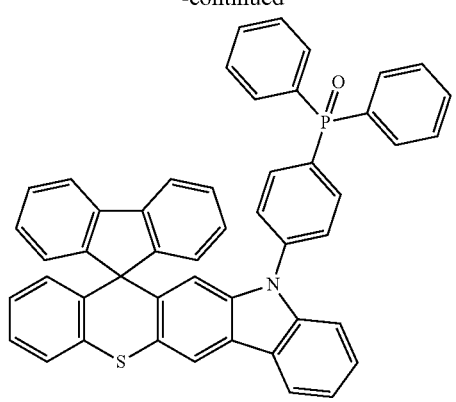
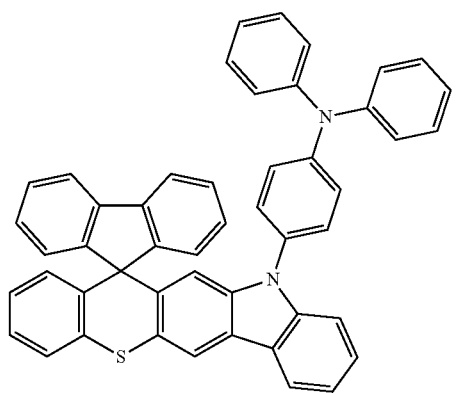
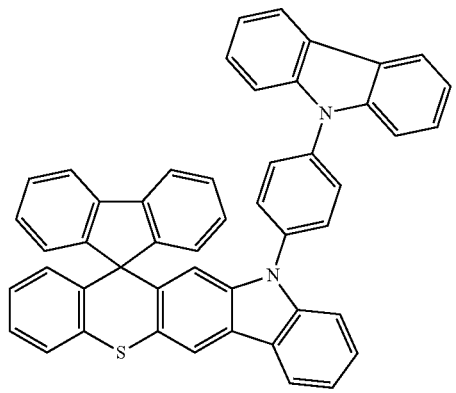
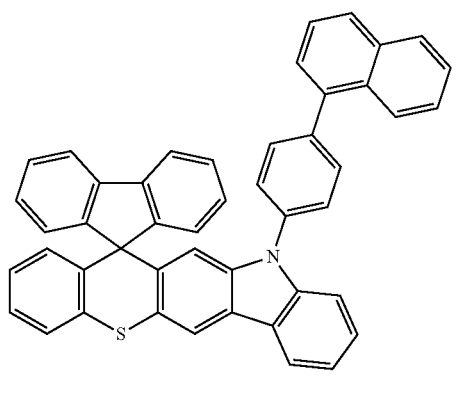
628
-continued
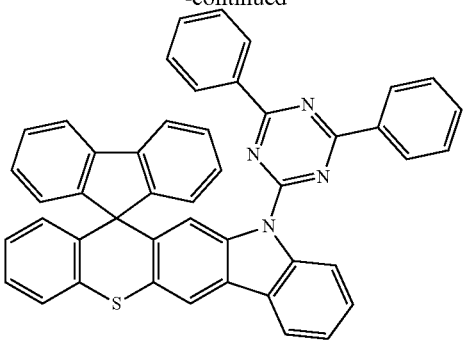
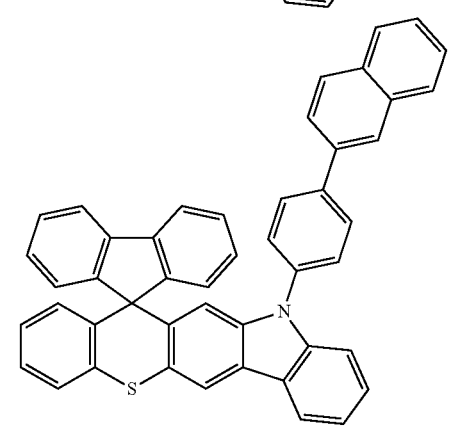
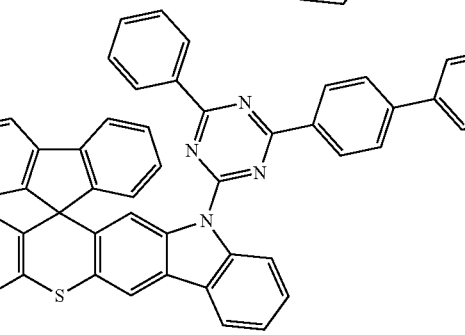
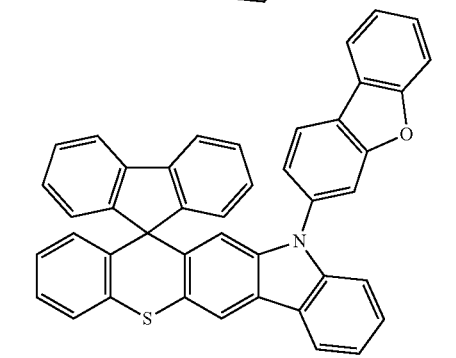
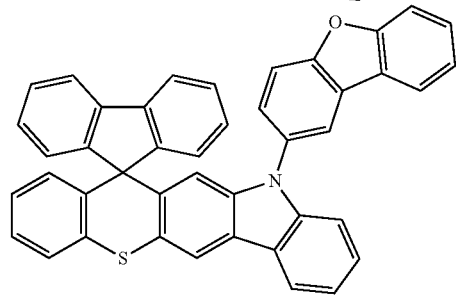

| 629 -continued | 630 -continued |
|---|---|
| 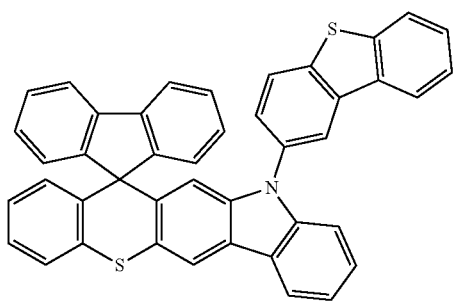 | 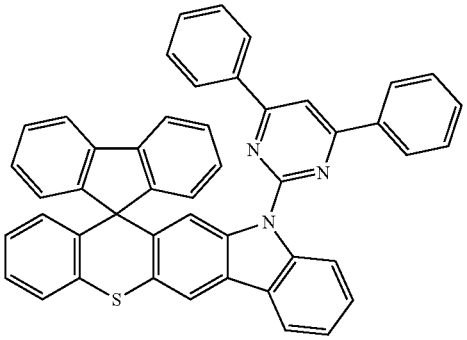 |
| 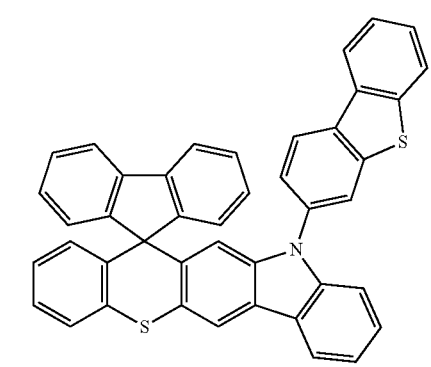 | 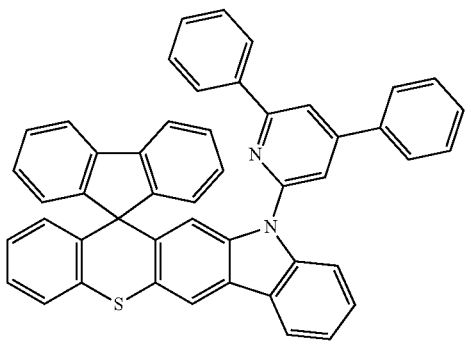 |
| 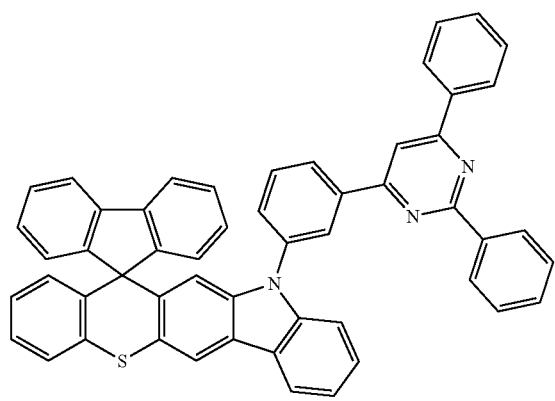 | 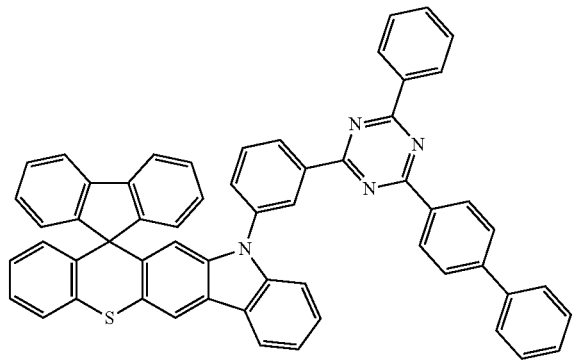 |
| | 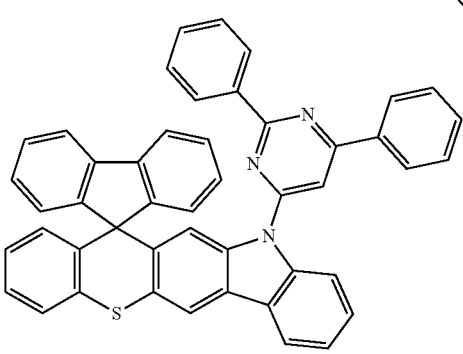 |
| 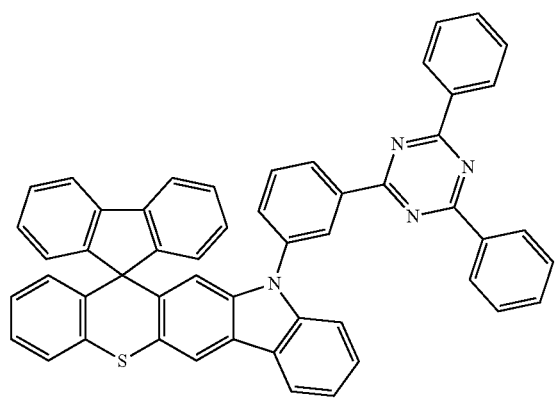 | 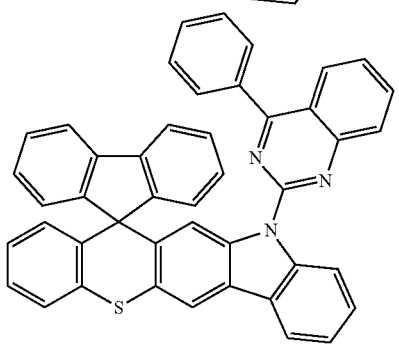 |

631
-continued
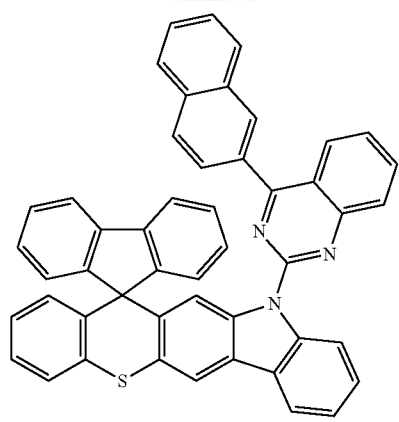
632
-continued
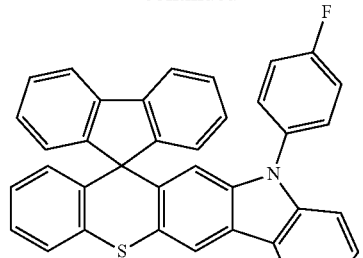
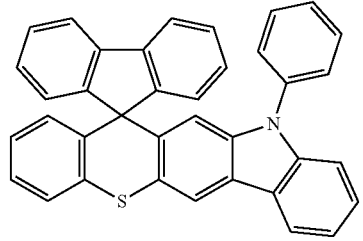
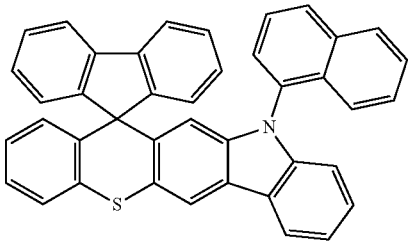
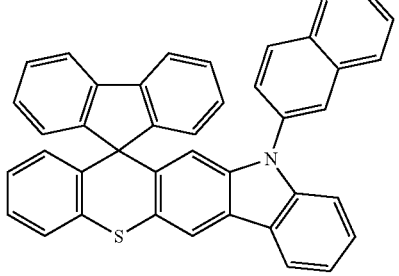
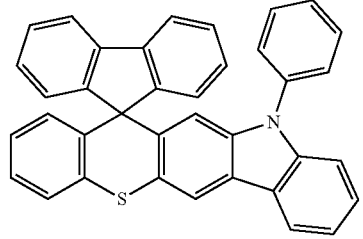
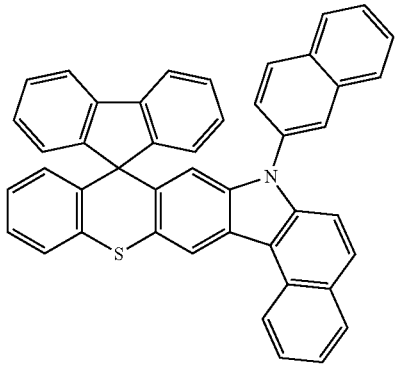

633
-continued
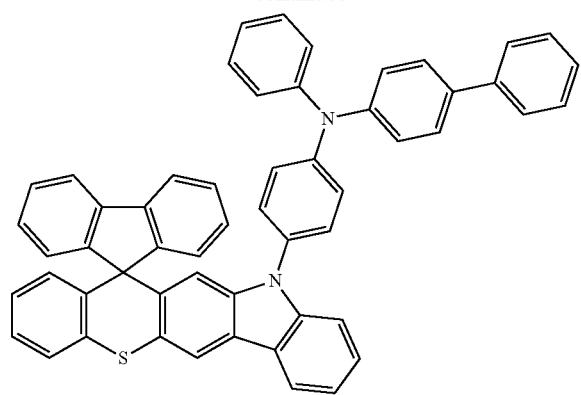
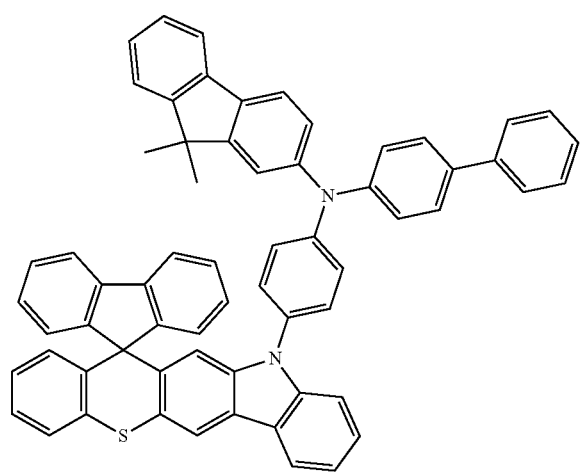
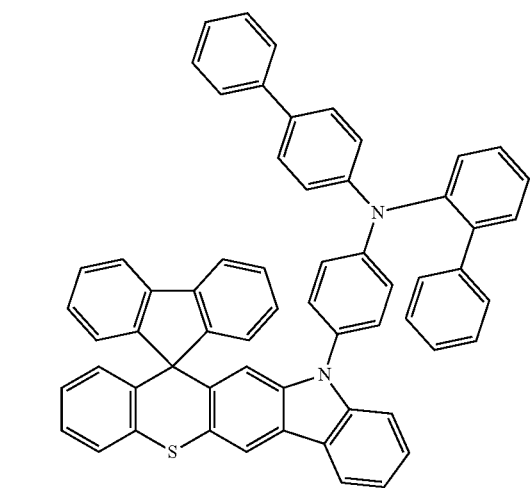
634
-continued
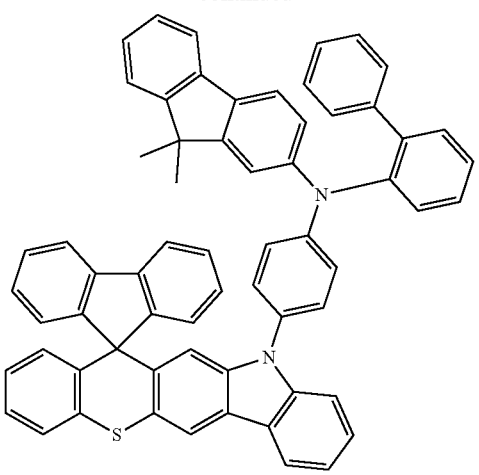
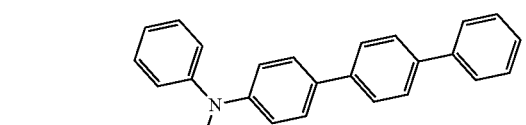
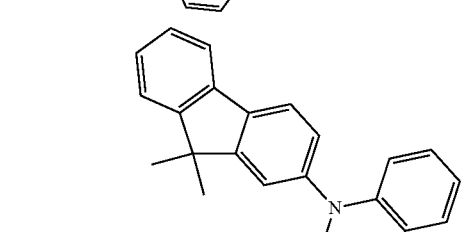
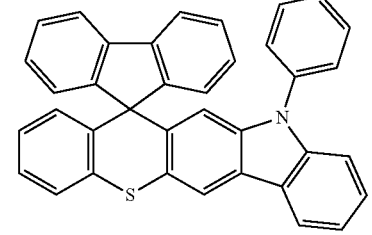
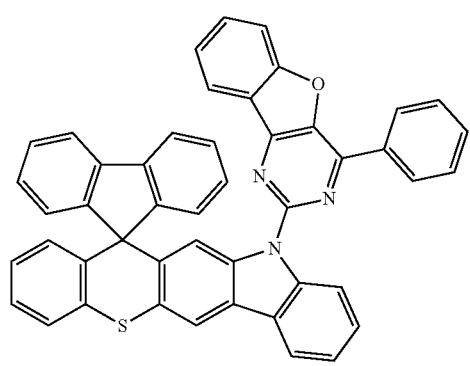

635
-continued
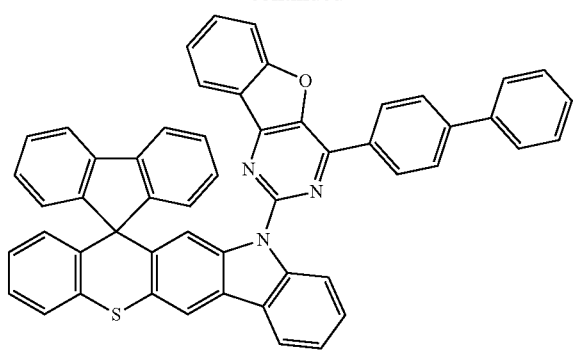
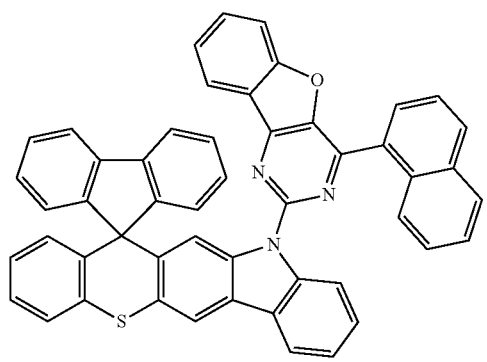
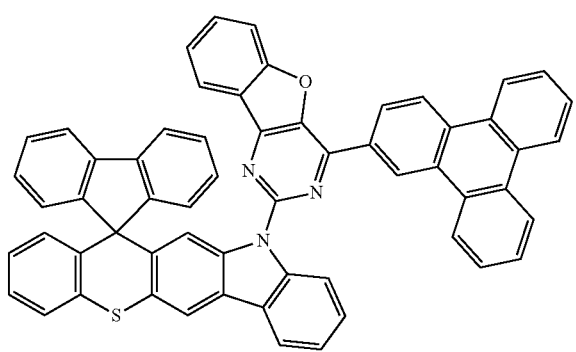
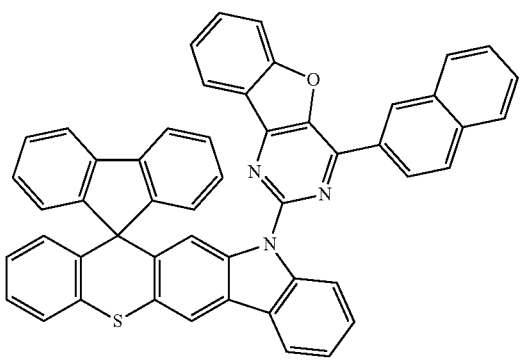
636
-continued
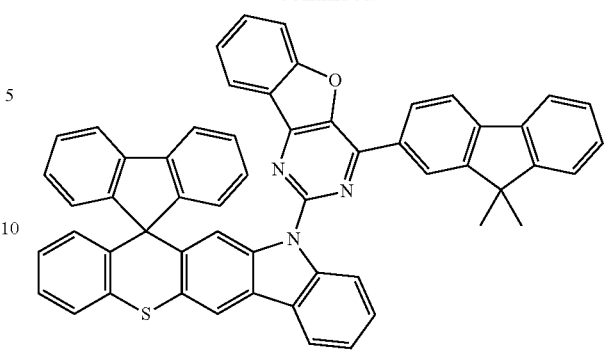
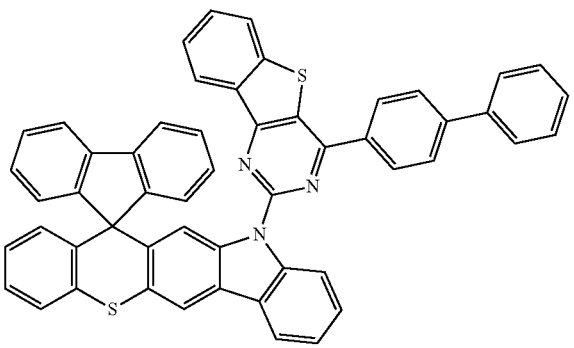
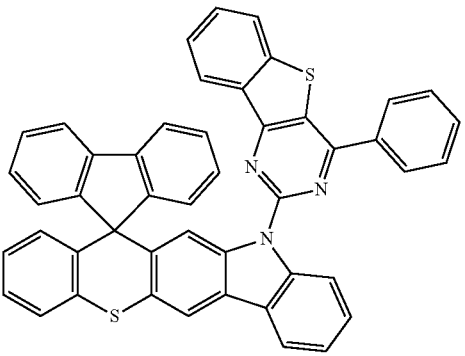
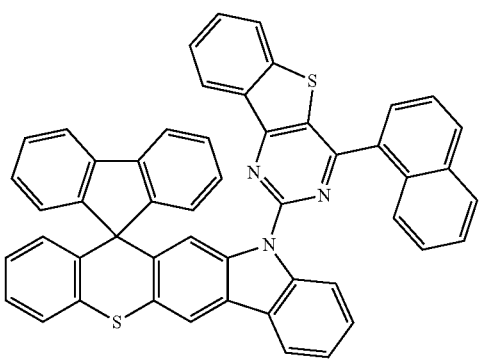

637
-continued
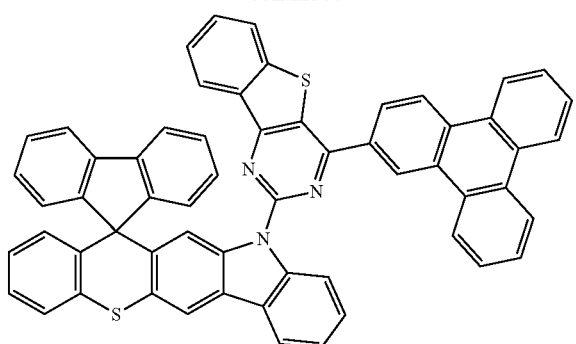
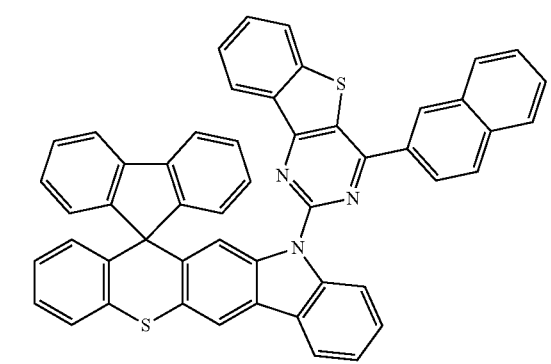
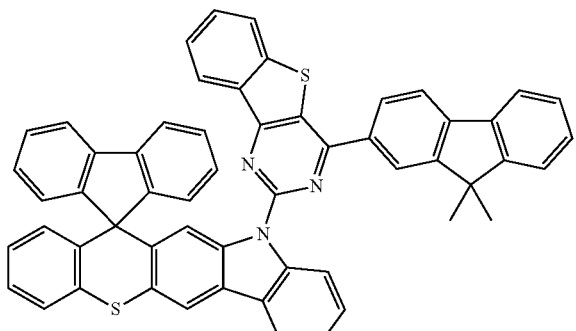
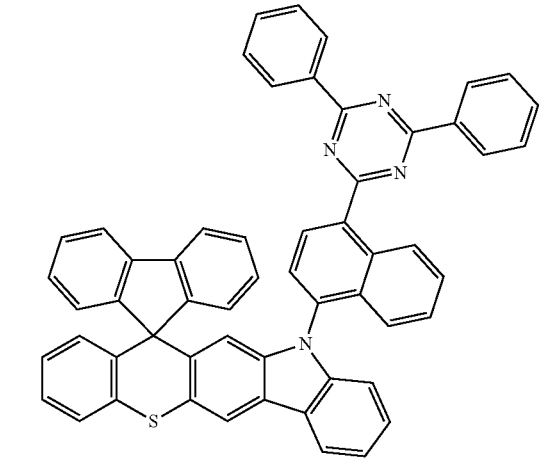
638
-continued
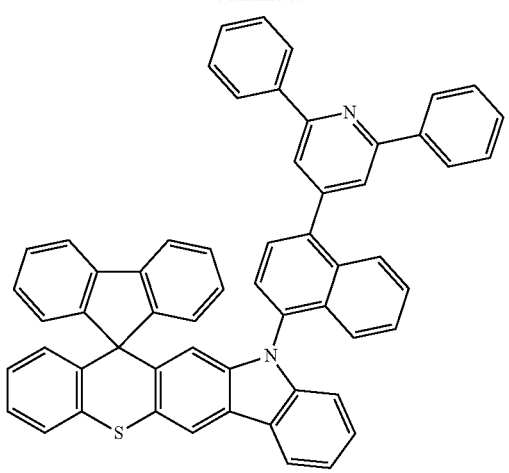
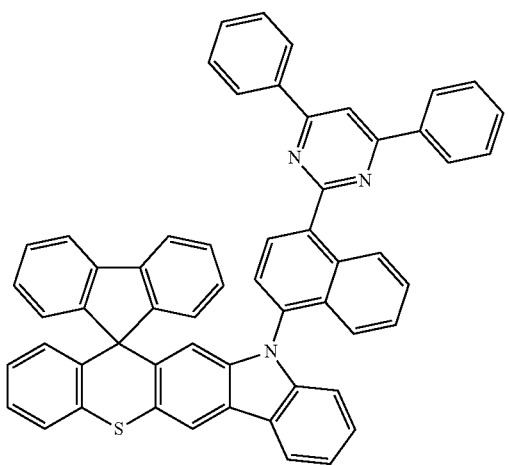
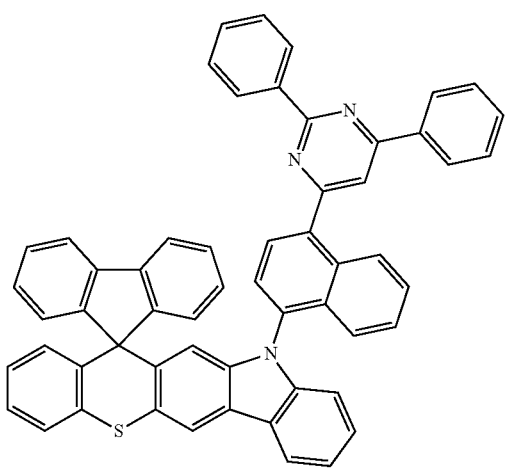

639
-continued
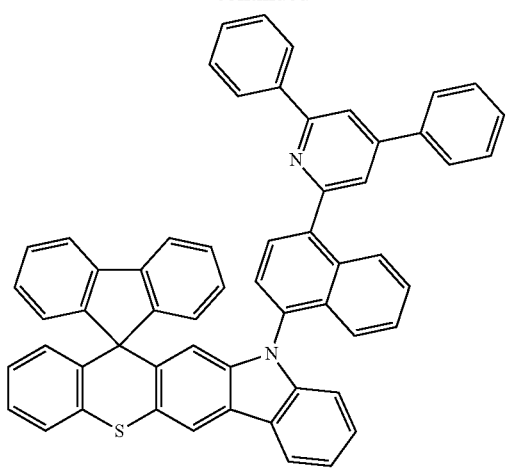
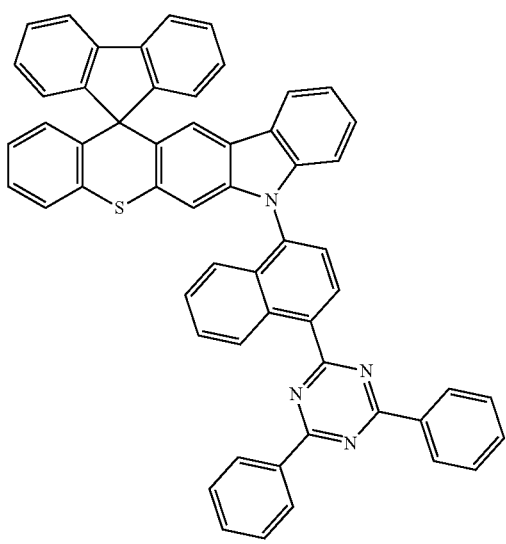
640
-continued
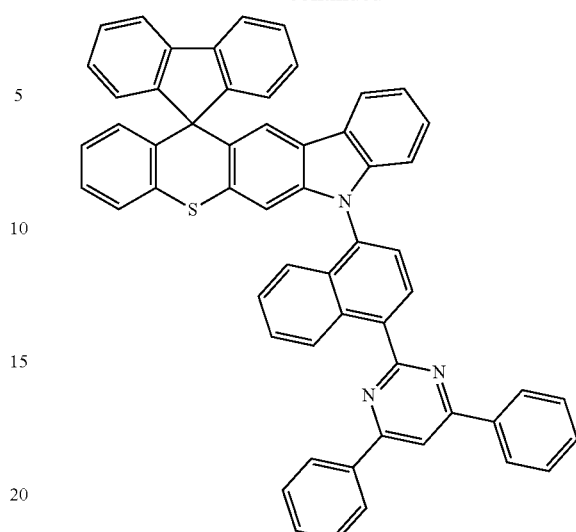
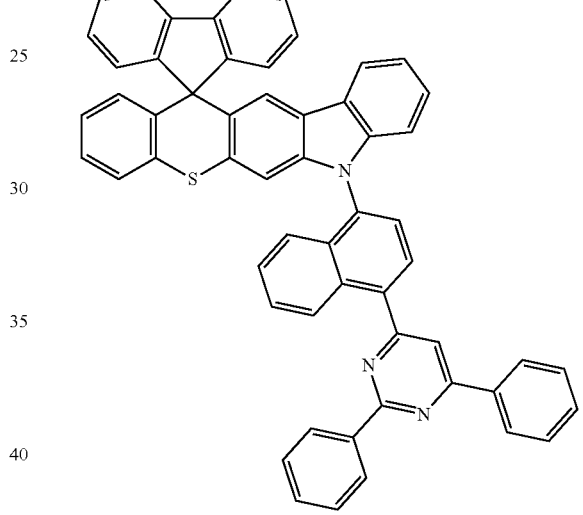
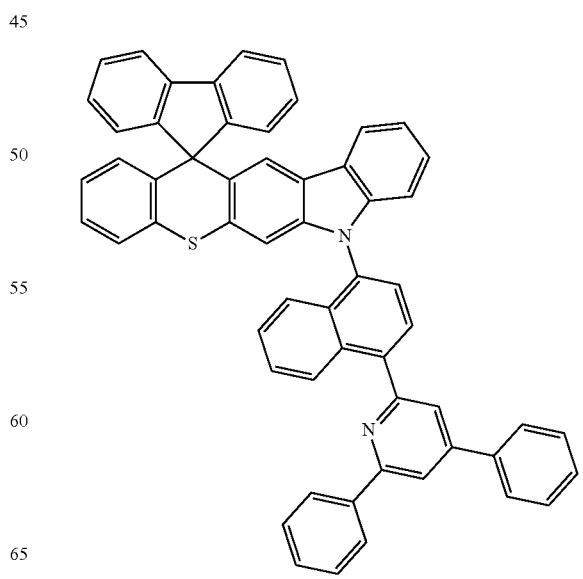

641
-continued
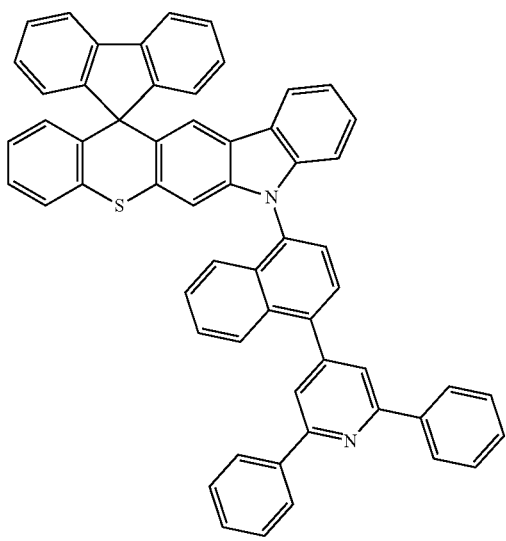
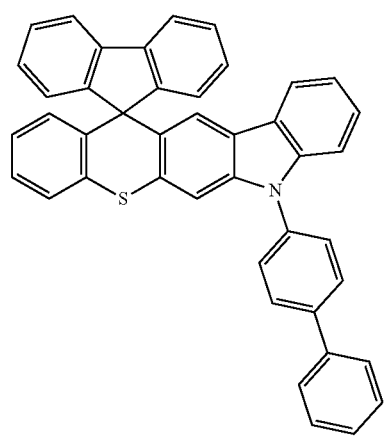
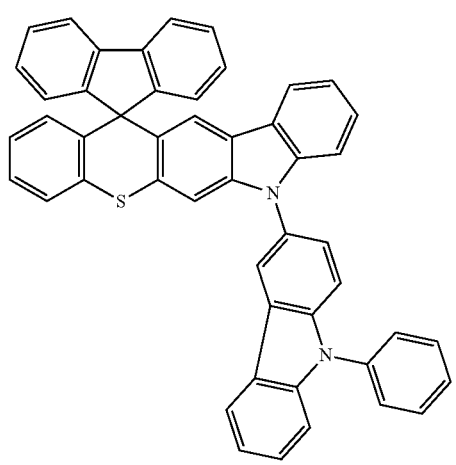
642
-continued
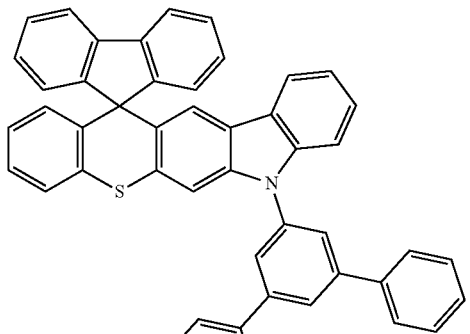
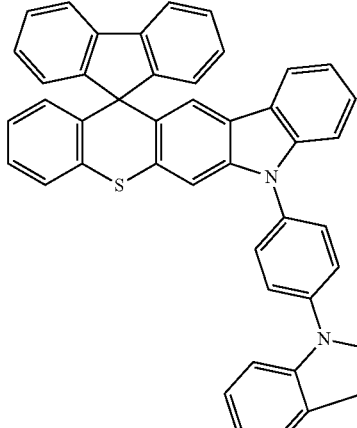
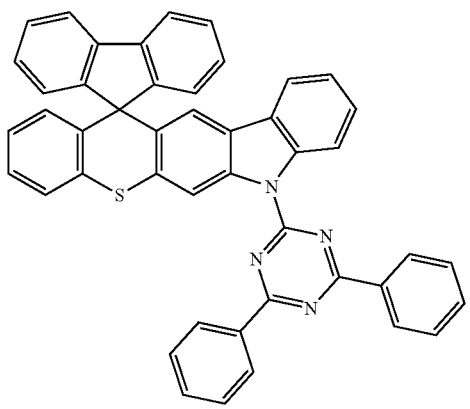
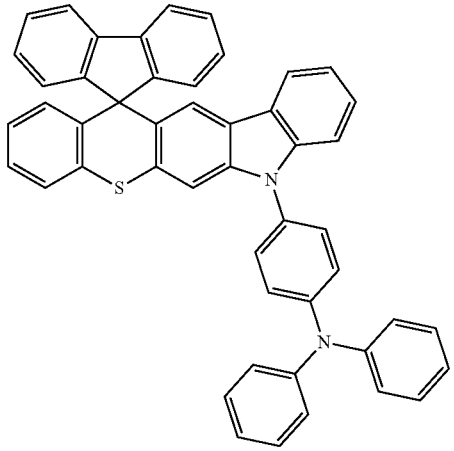

643
-continued
644
-continued
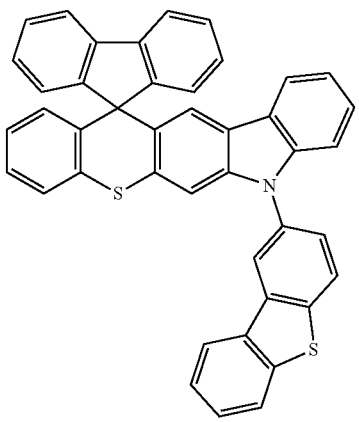
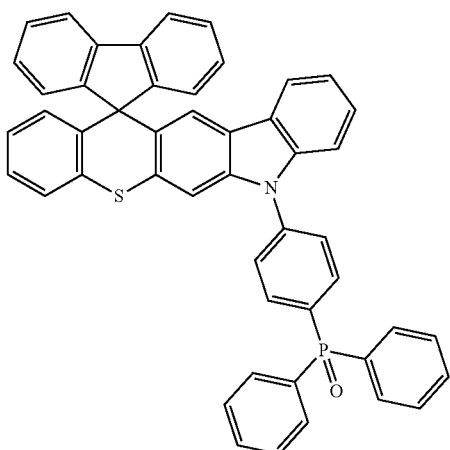
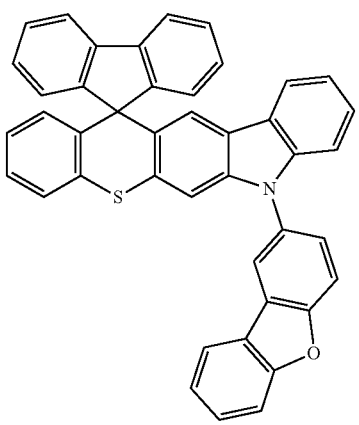
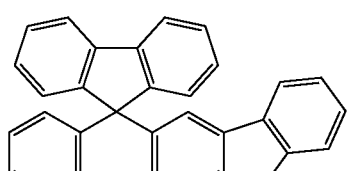
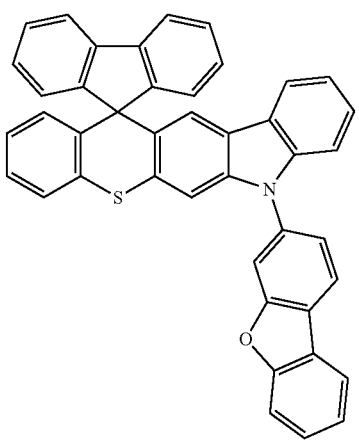
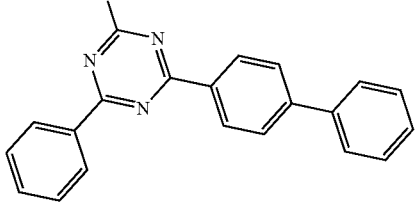

645
-continued
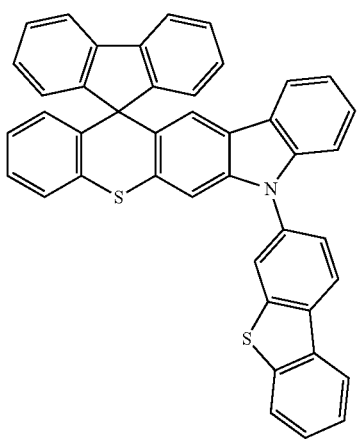
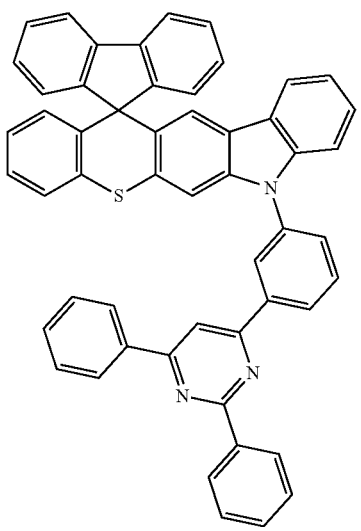
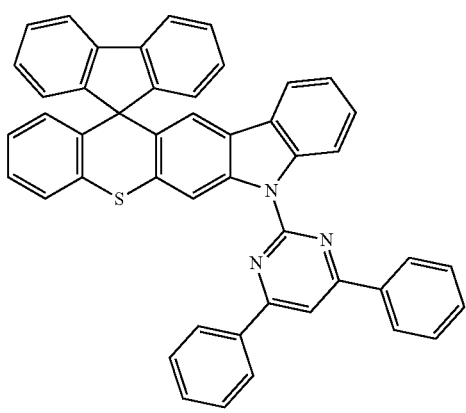
646
-continued
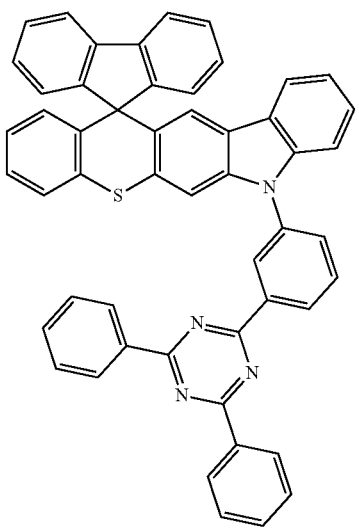
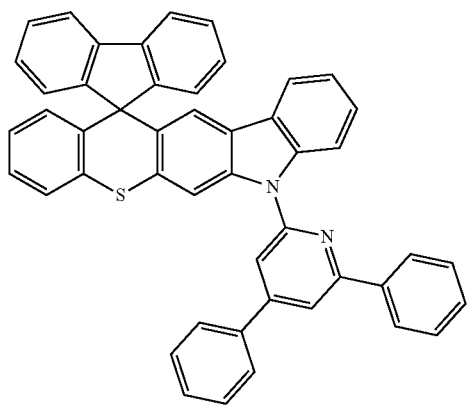
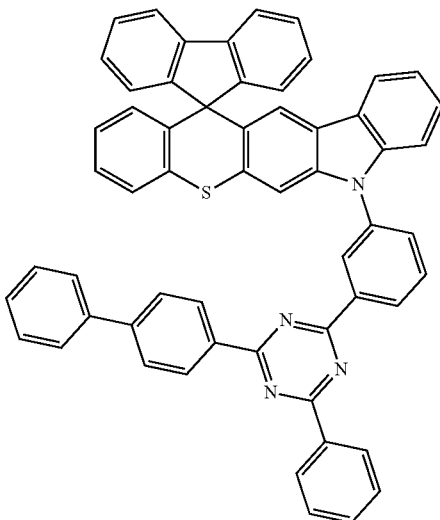

647
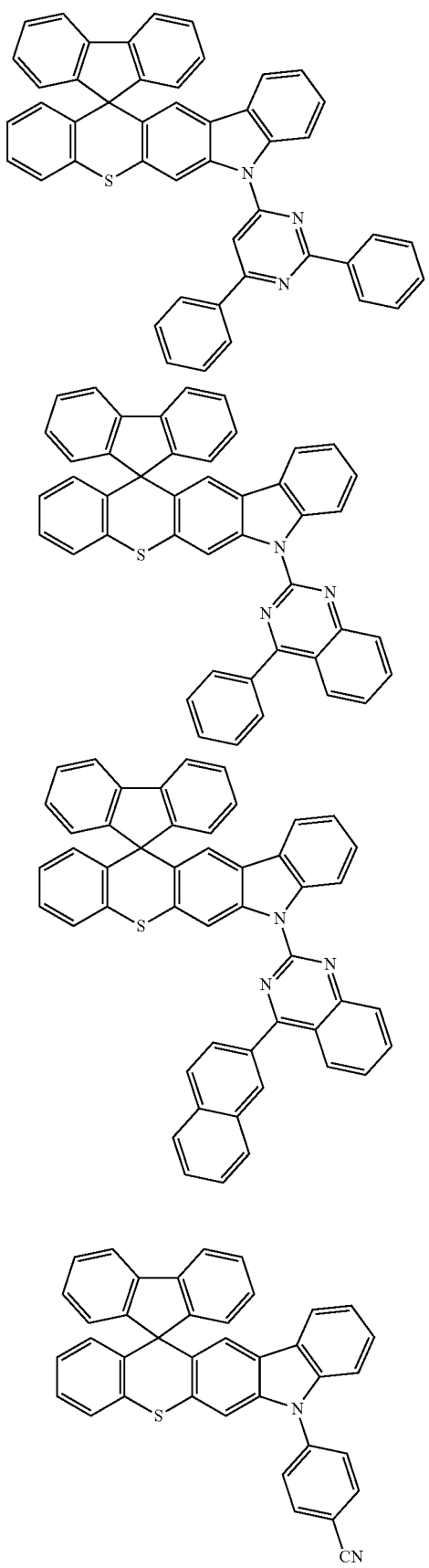
648
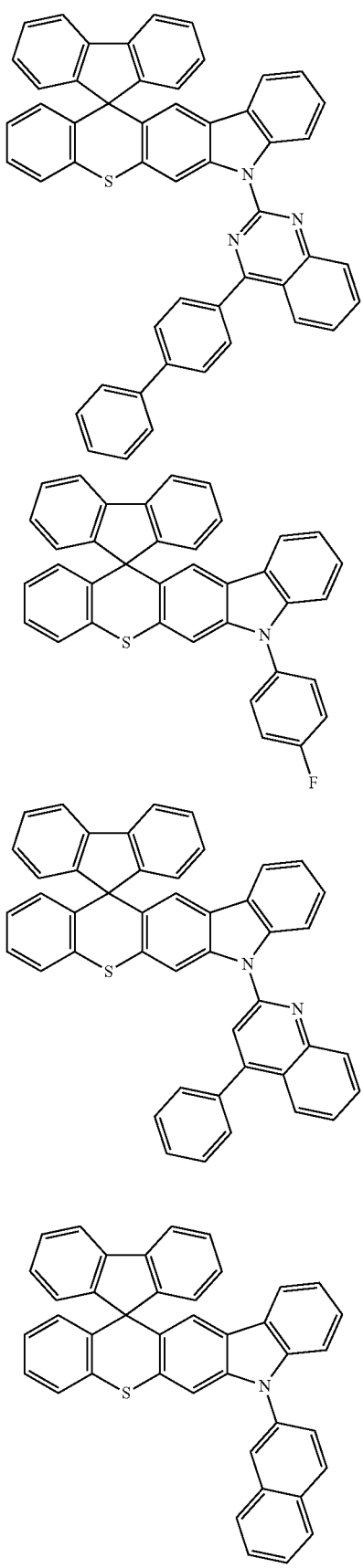

649
-continued
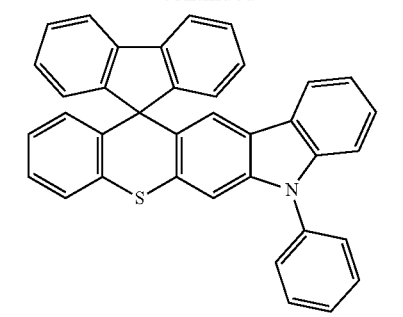
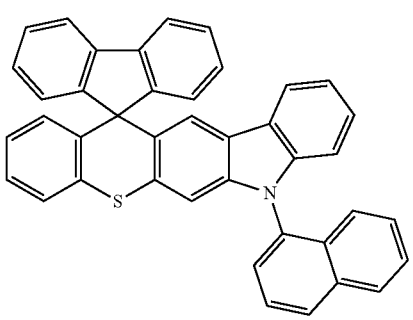
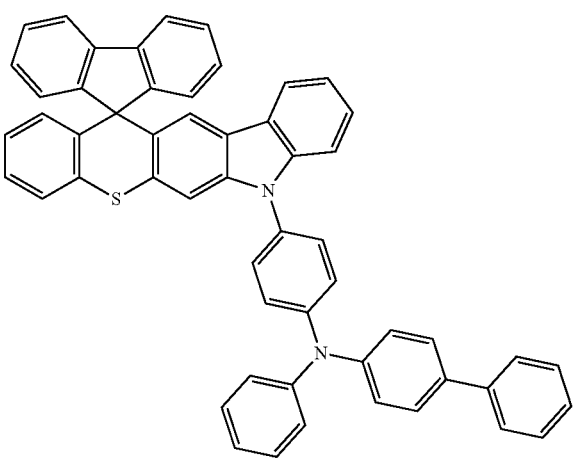
650
-continued
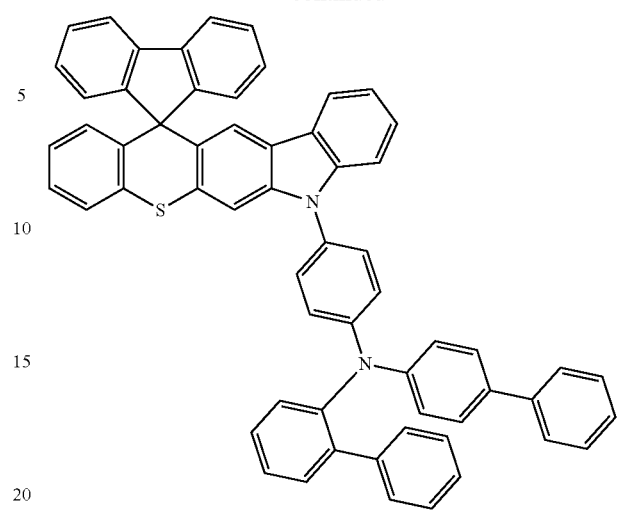
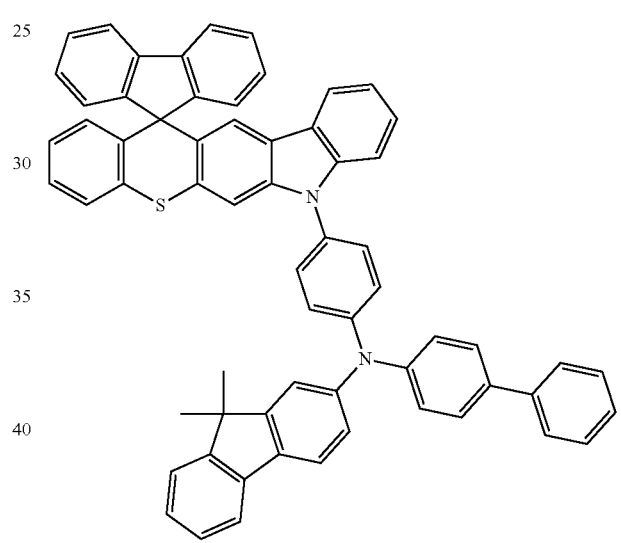
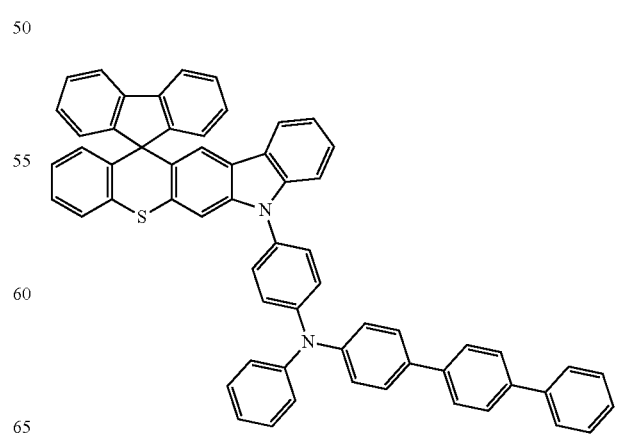

651
-continued
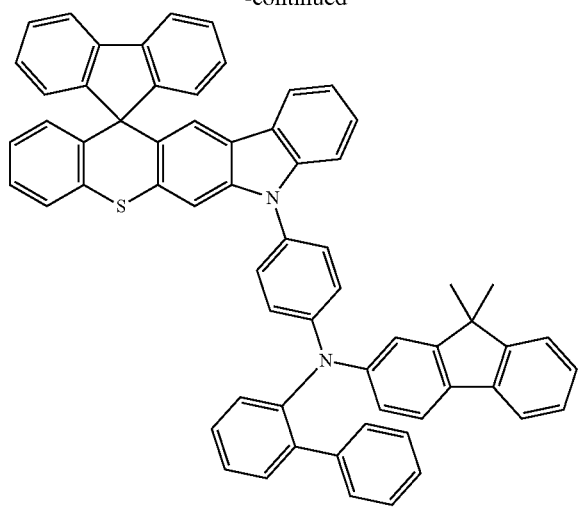
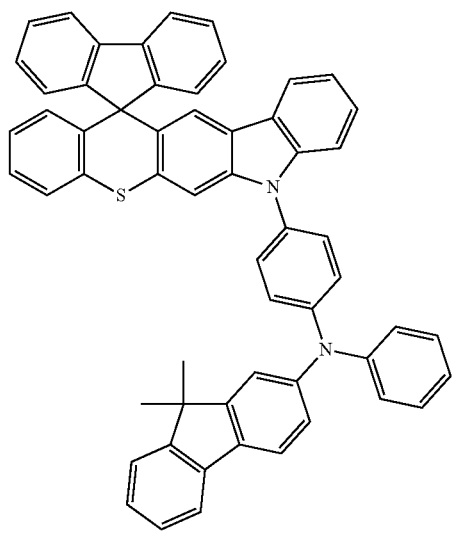
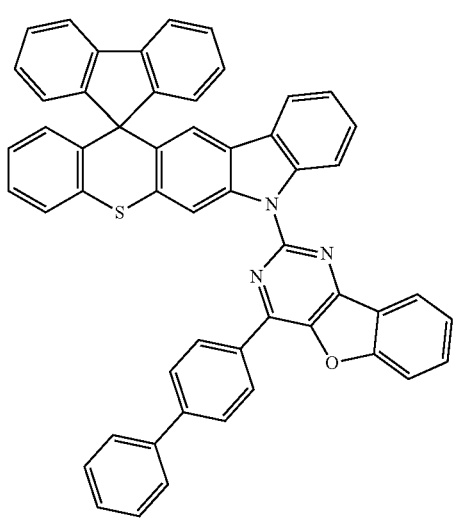
652
-continued
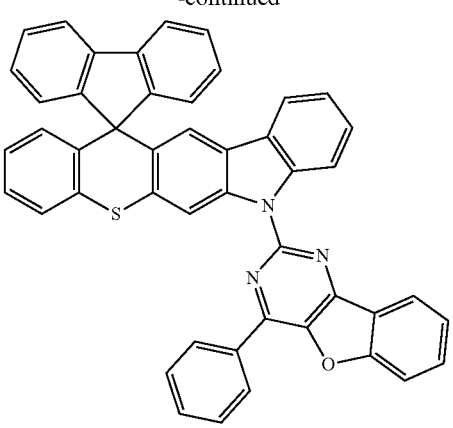
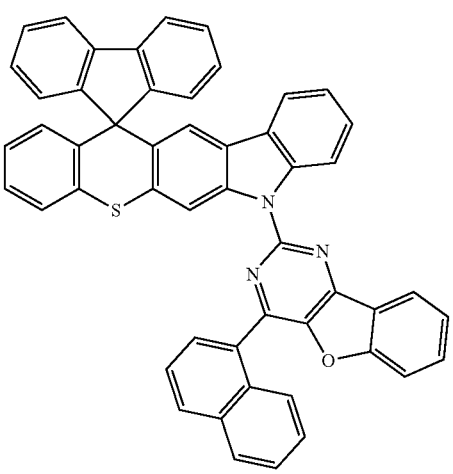
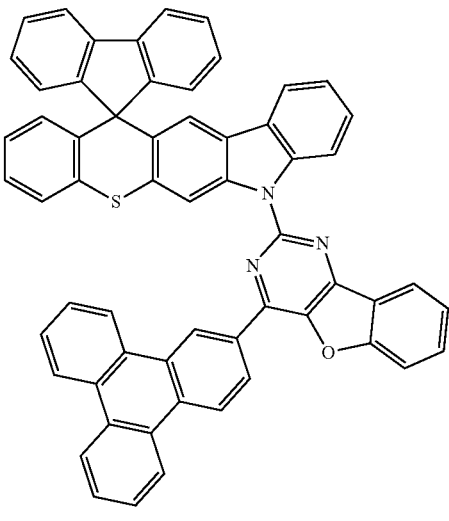

653
-continued
654
-continued
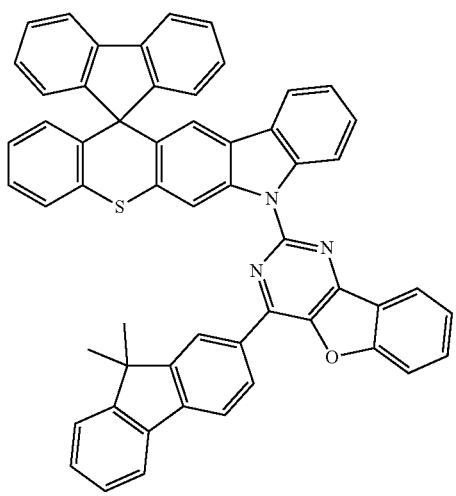
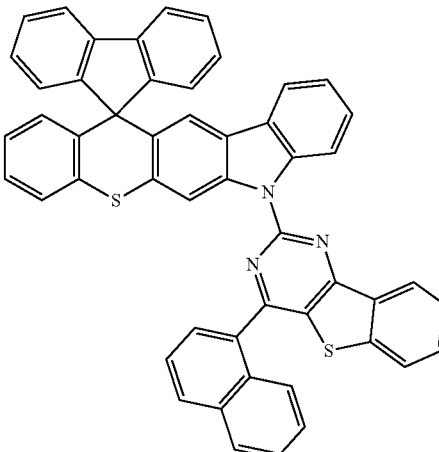
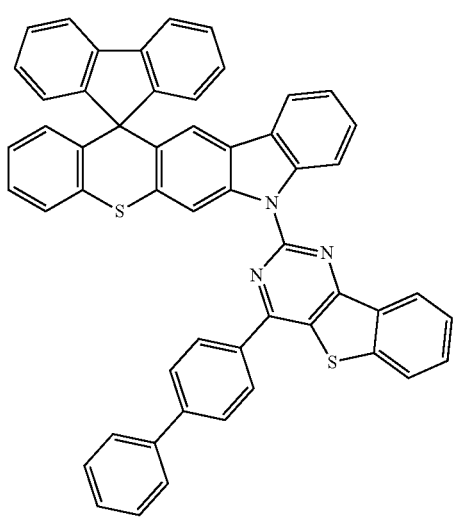
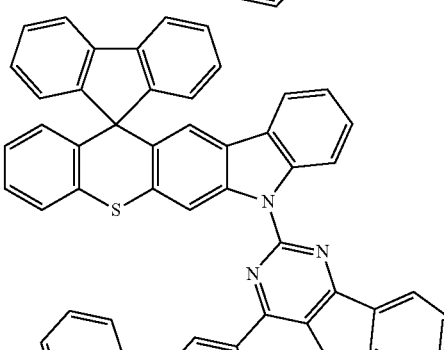
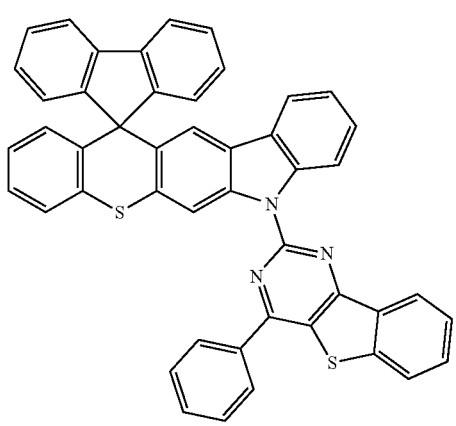
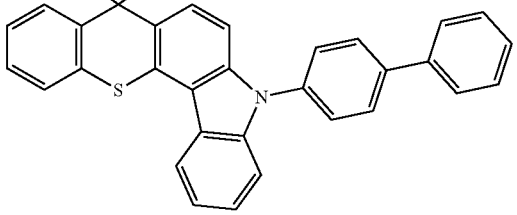

655
-continued
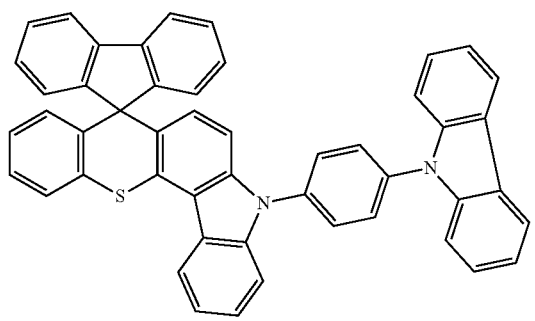
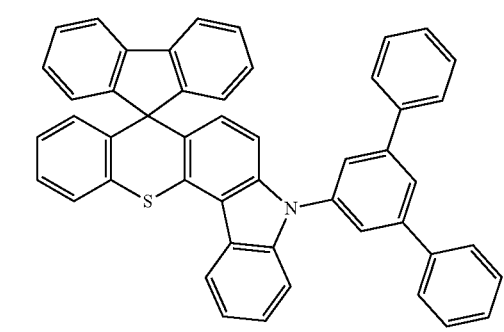
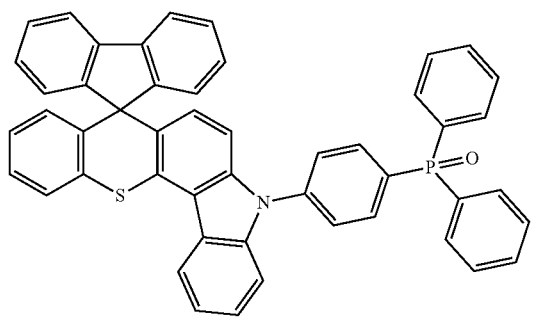
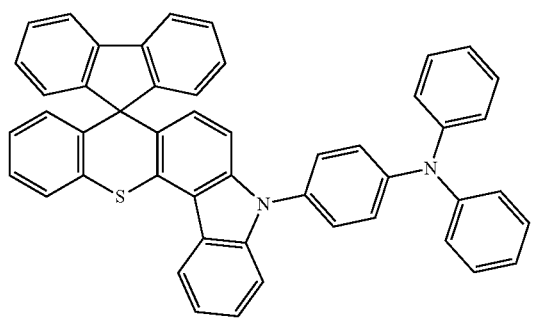
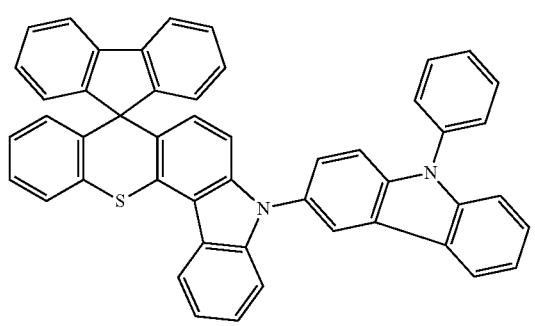
656
-continued
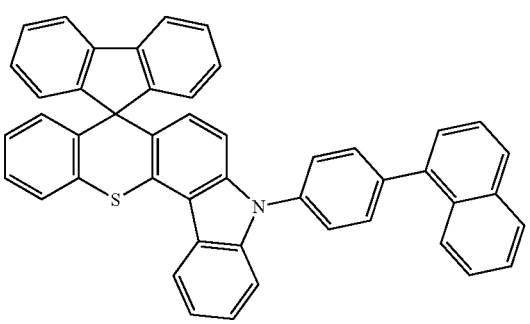
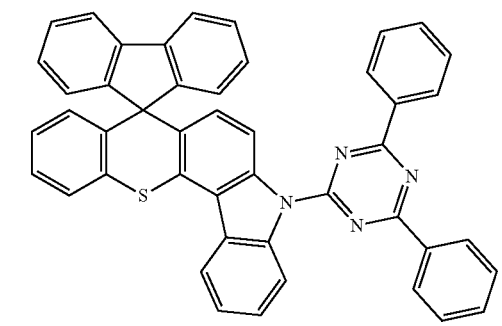
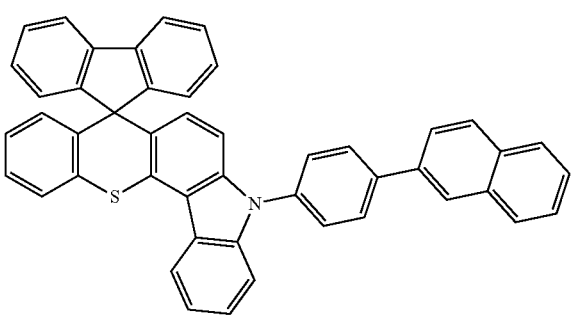
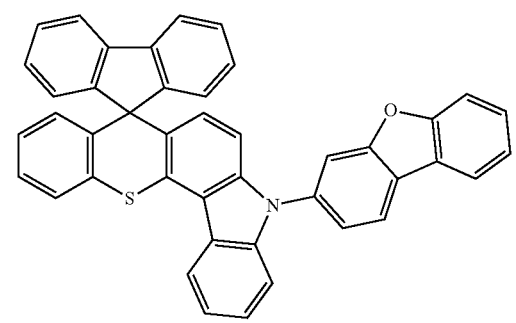
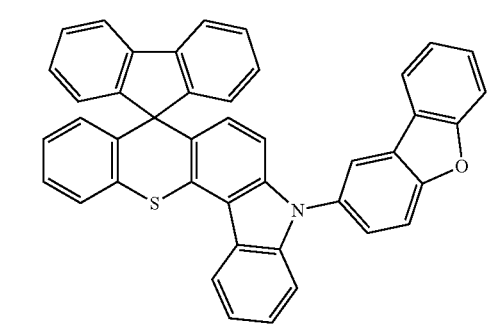

657
-continued
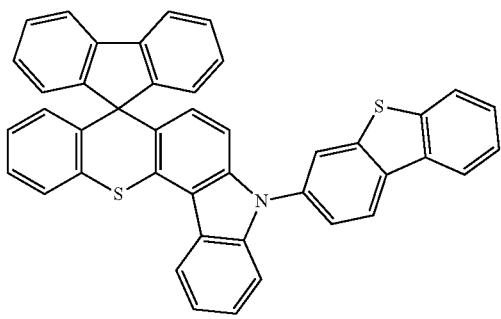
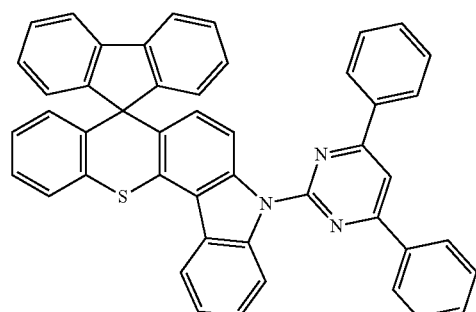
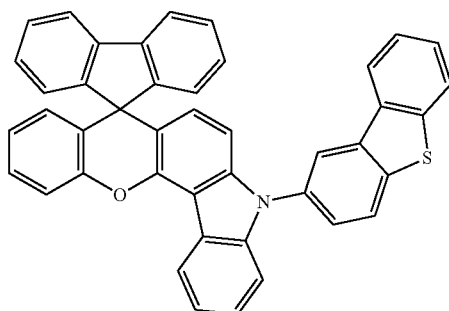
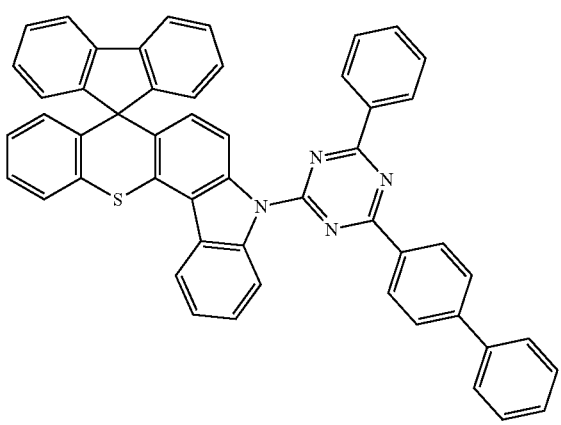
658
-continued
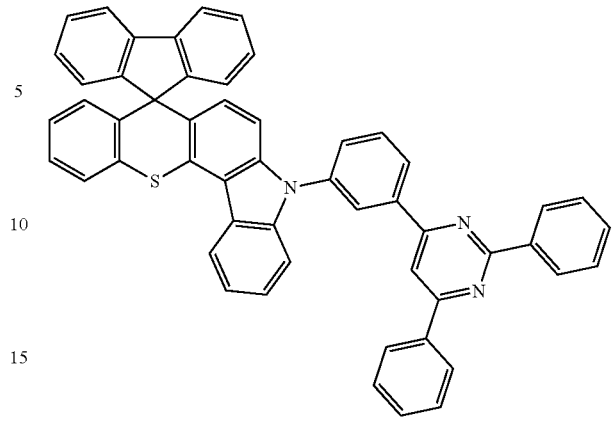
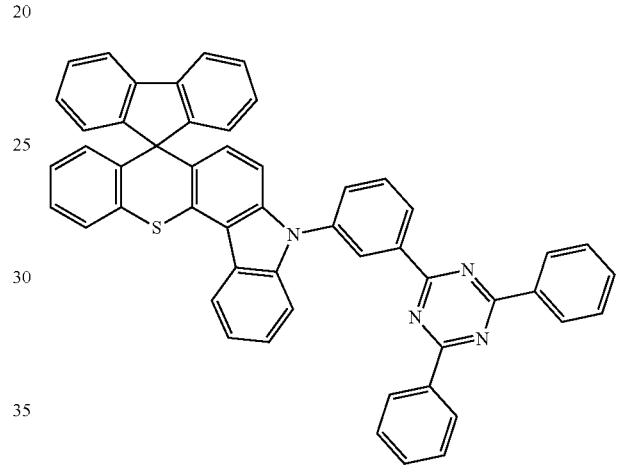
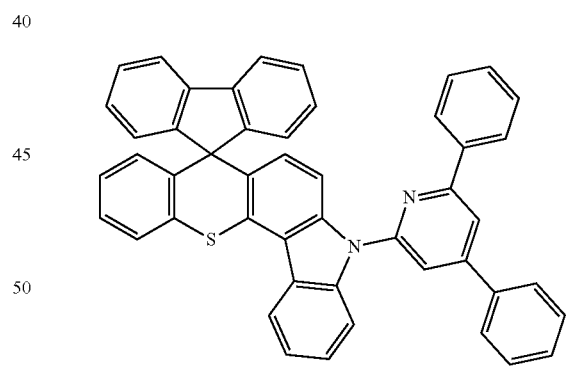
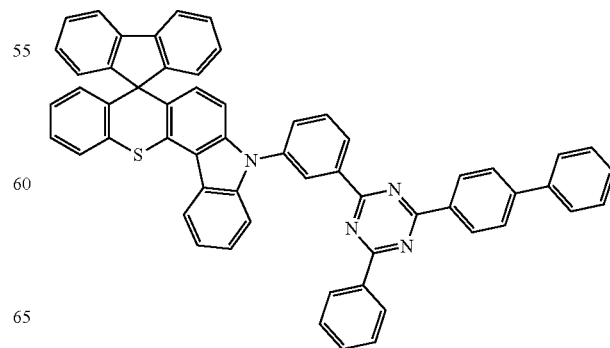

659
-continued
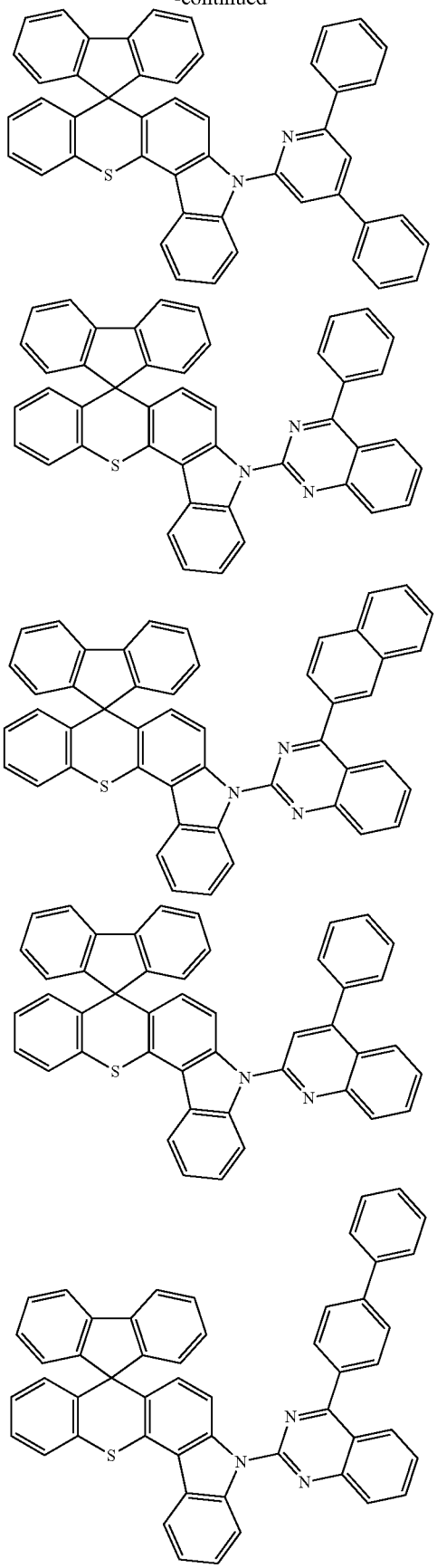
660
-continued
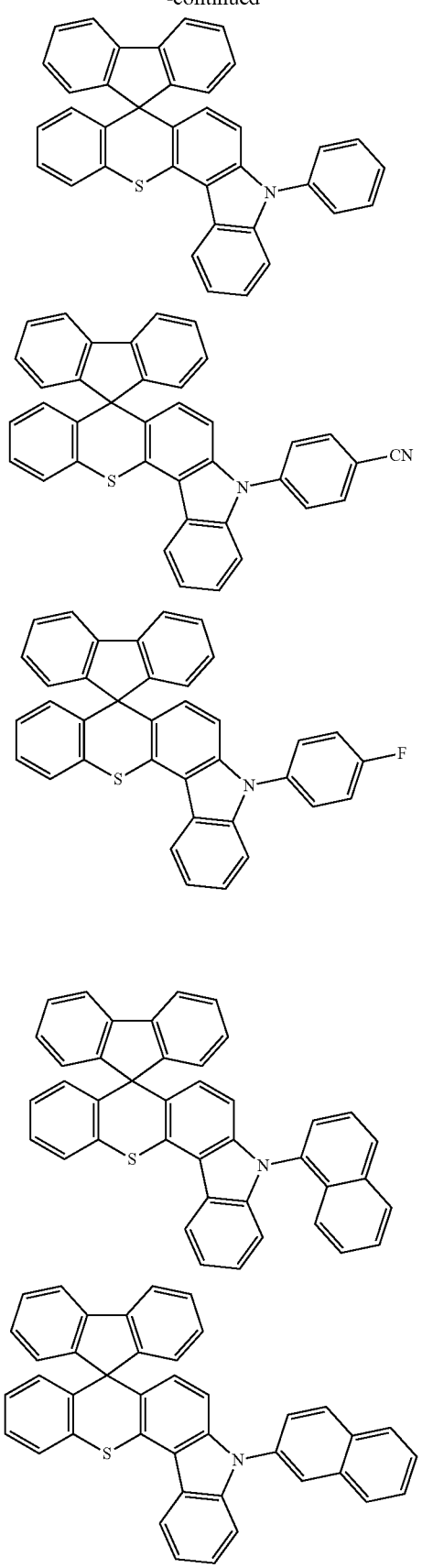

661
-continued
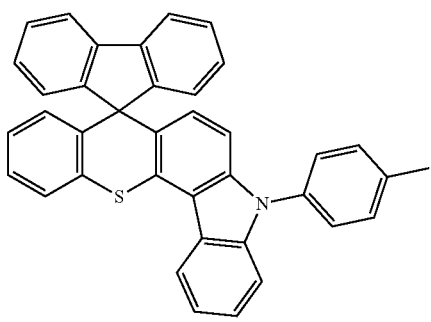
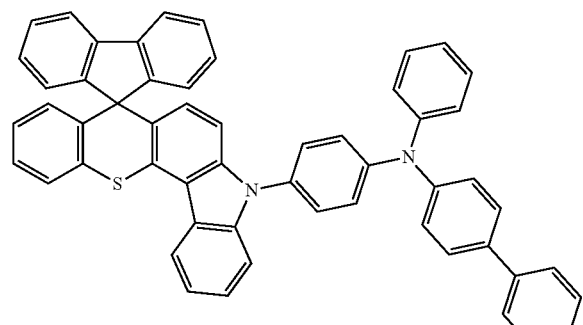
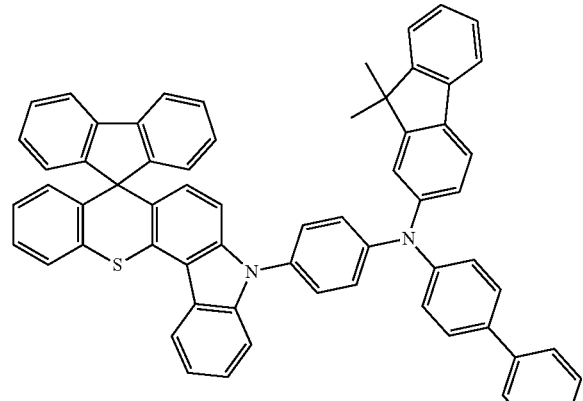
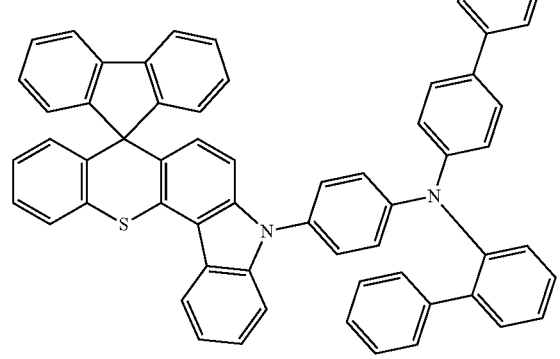
662
-continued
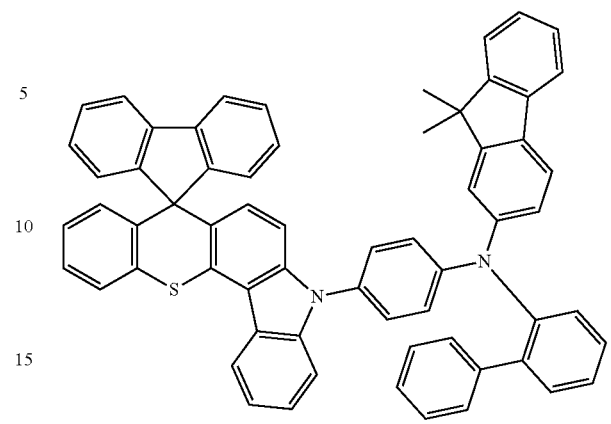
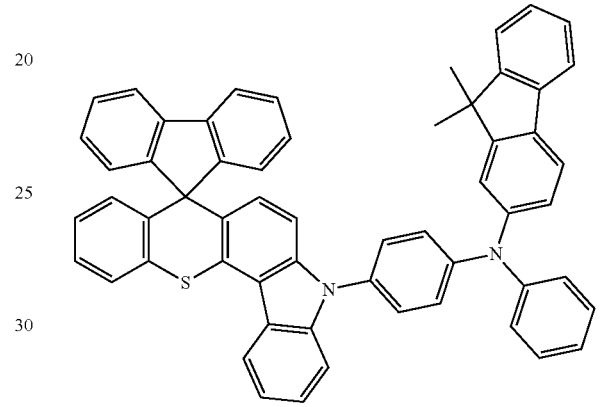
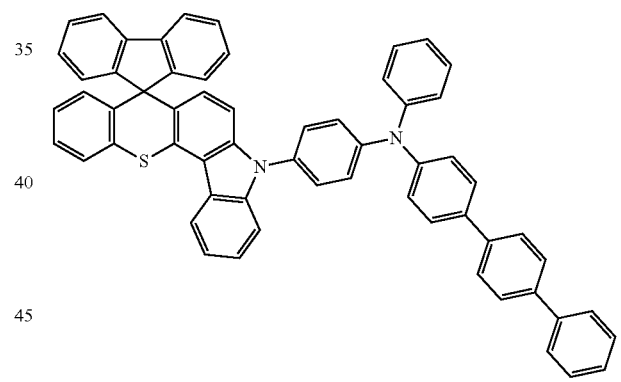
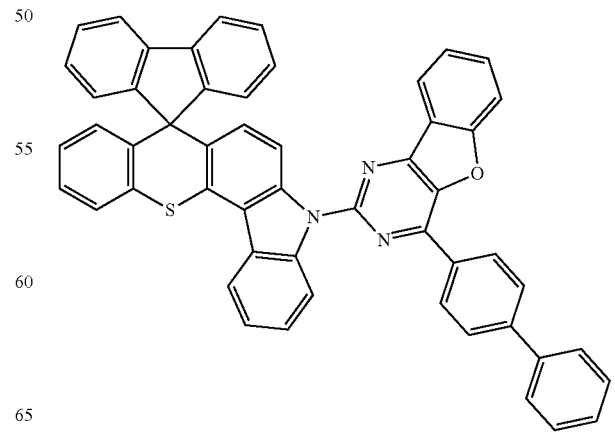

663
-continued
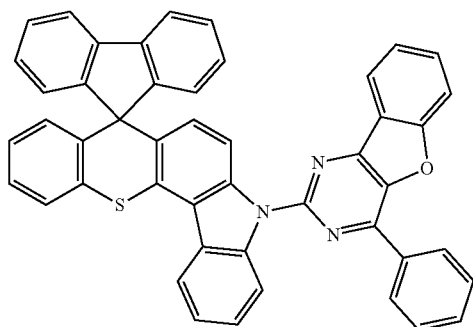
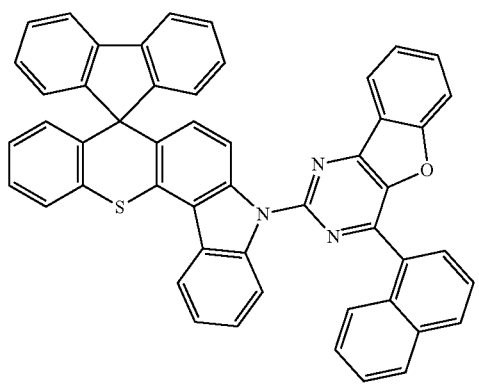
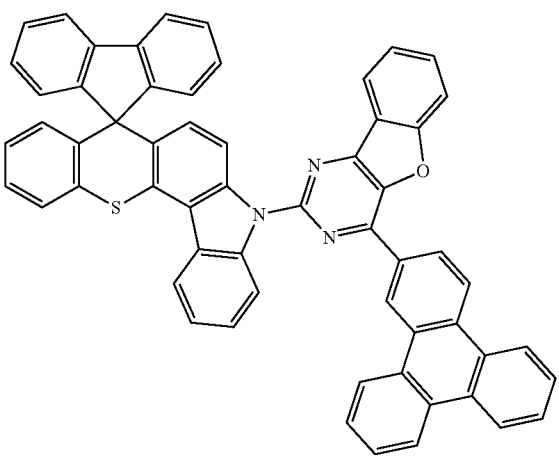
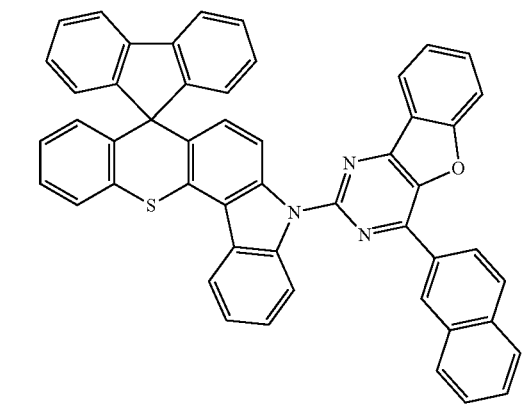
664
-continued
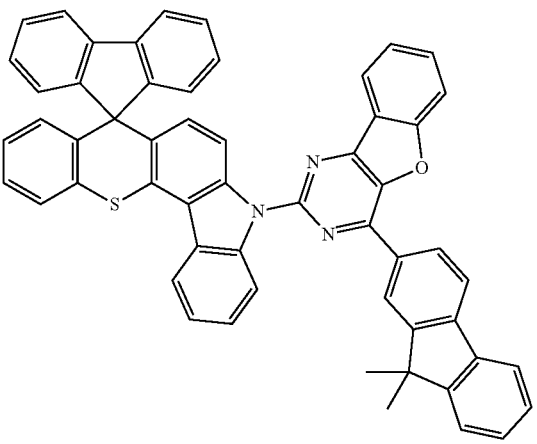
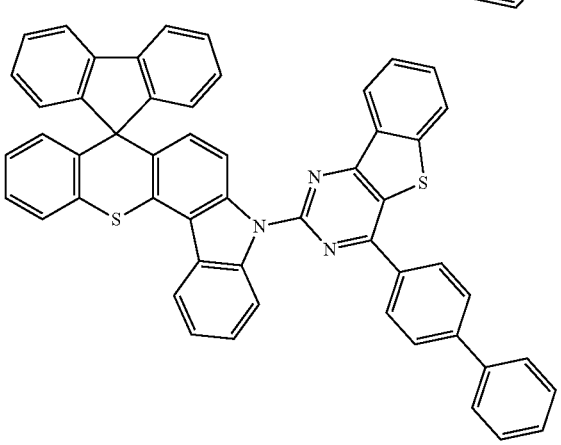
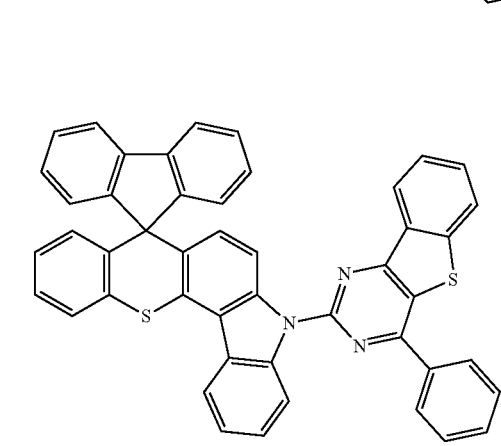
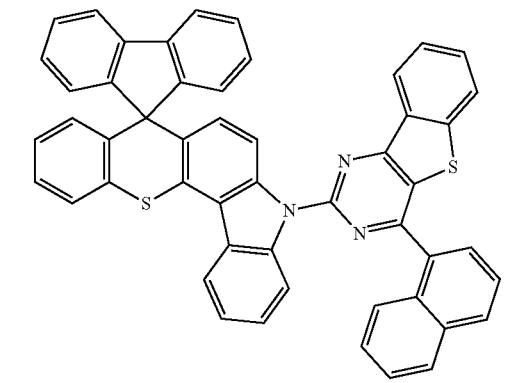

665
-continued
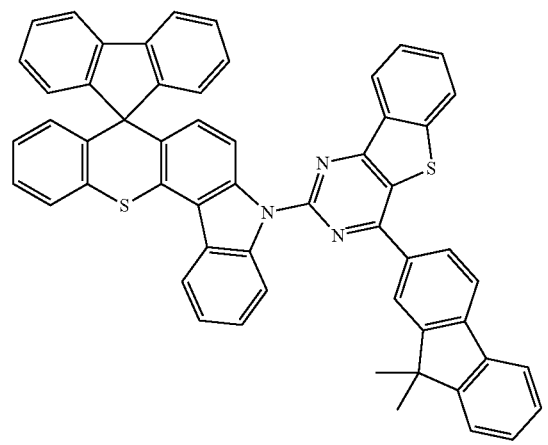
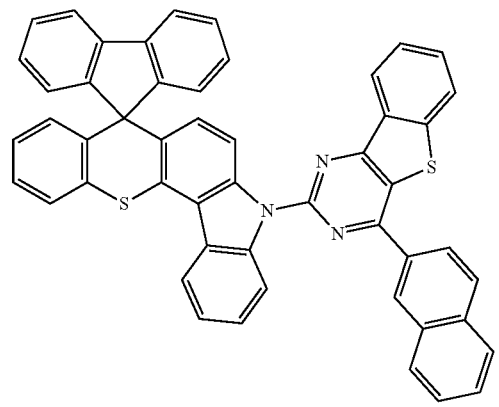
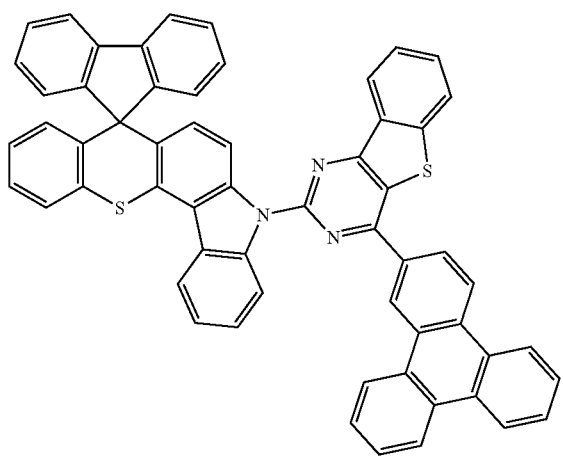
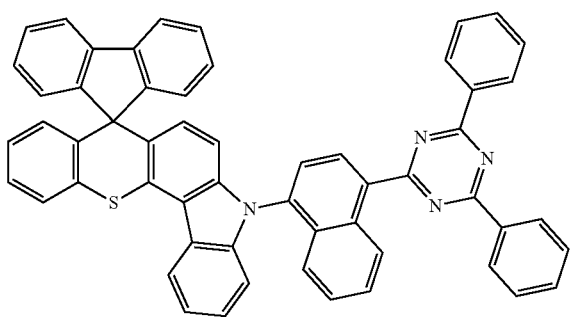
666
-continued
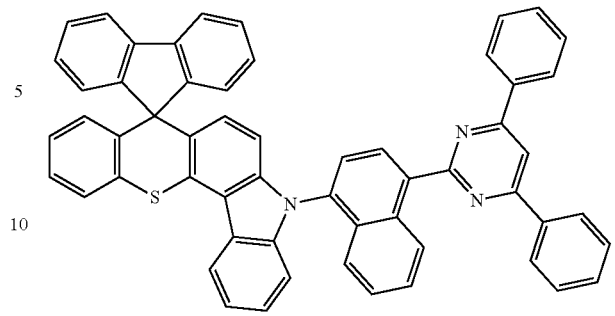
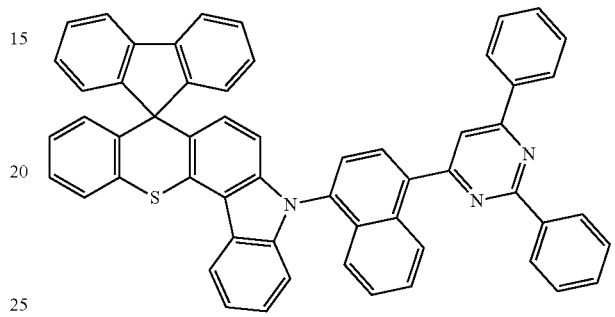
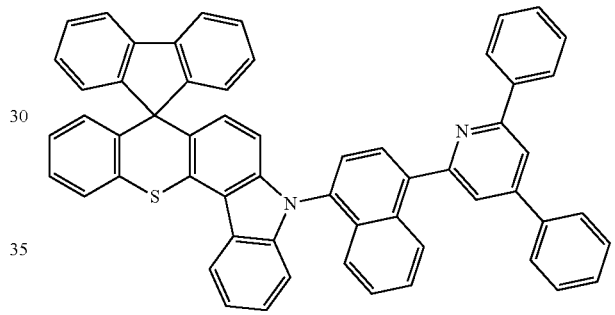
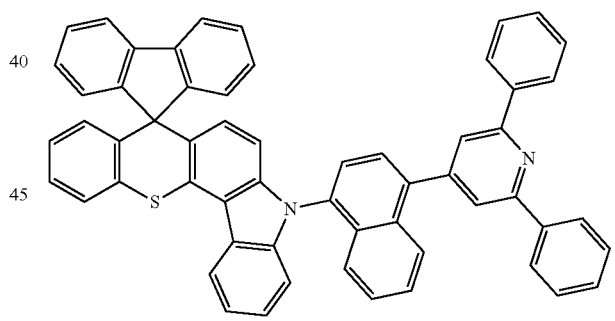
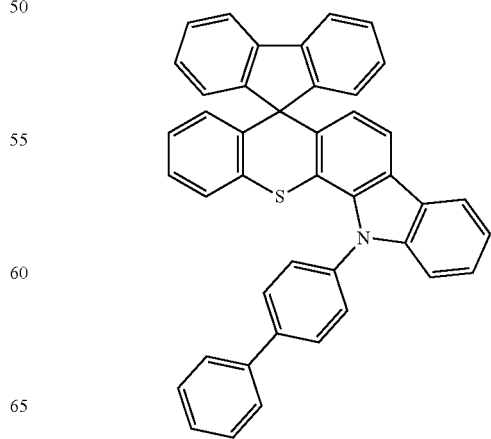

667
-continued

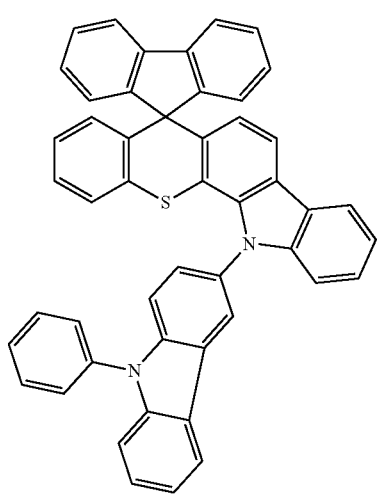
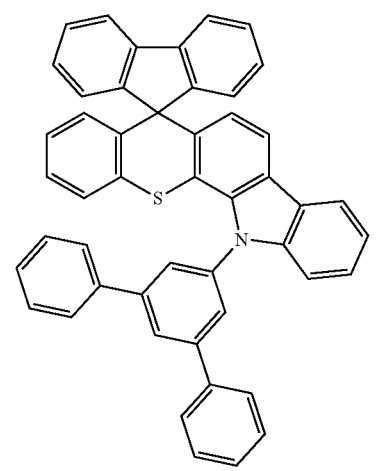
668
-continued
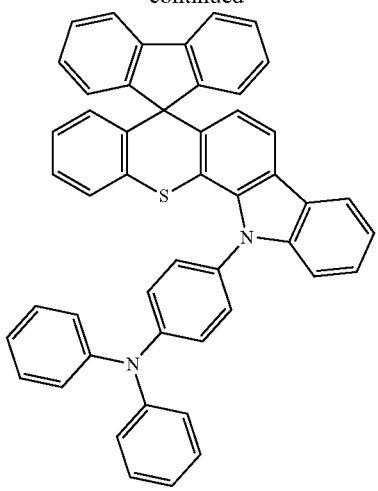
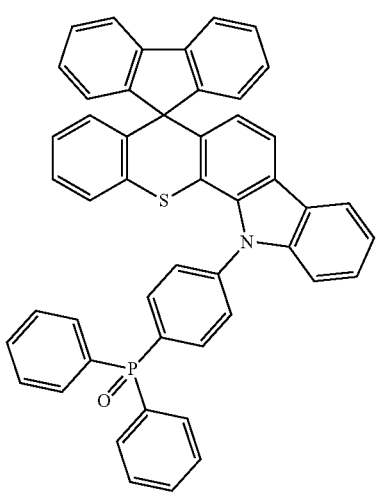
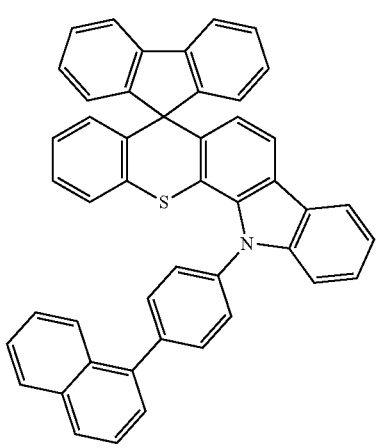

669
-continued
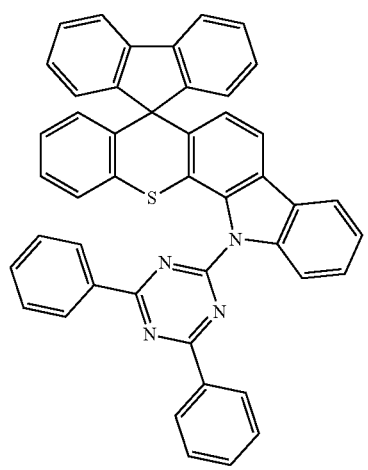
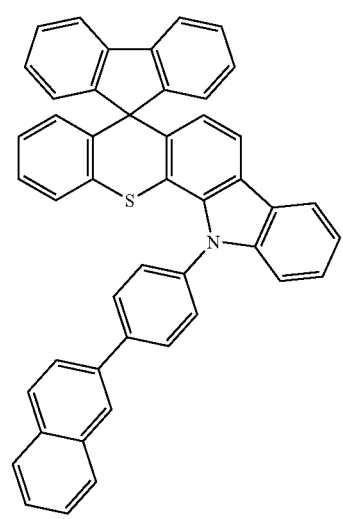
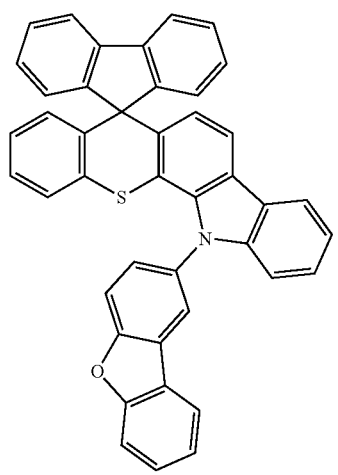
670
-continued
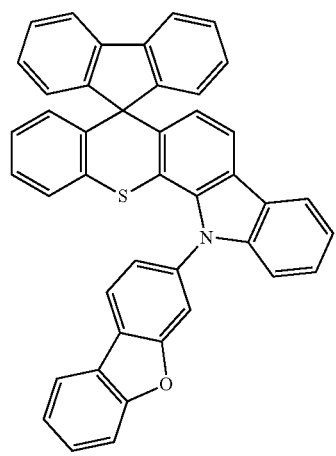
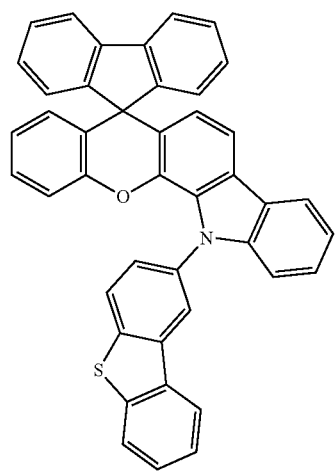
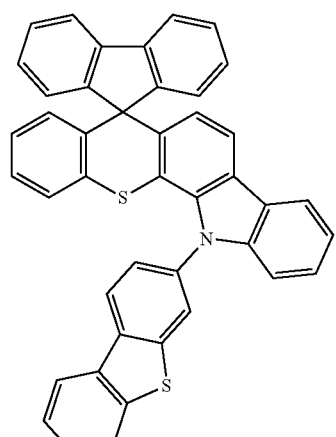

671
-continued
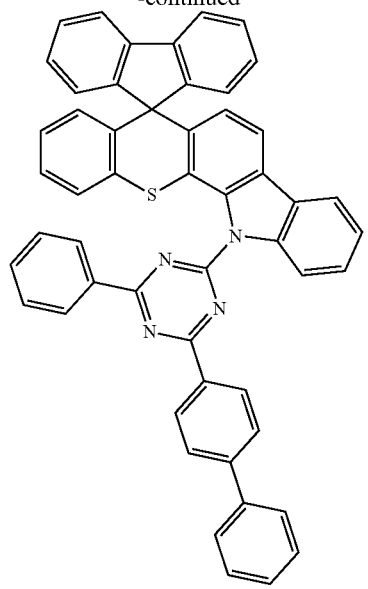
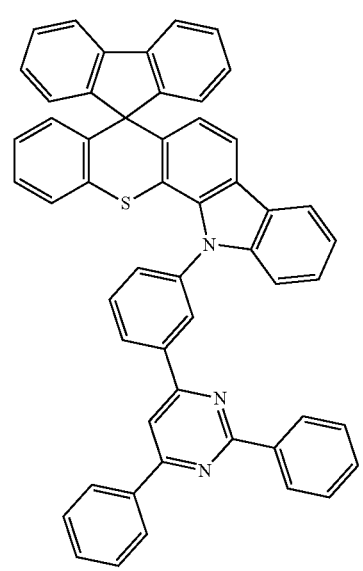
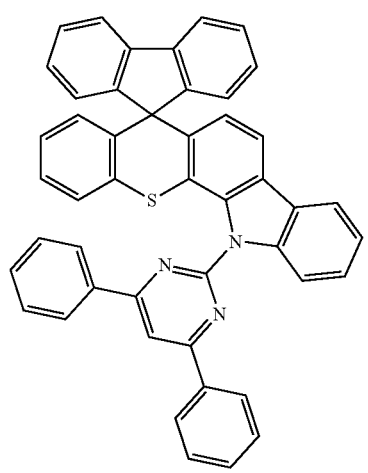
672
-continued
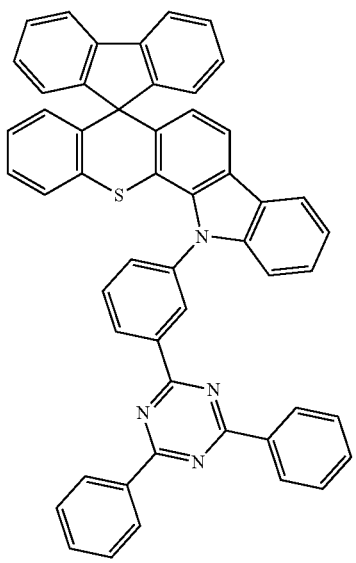
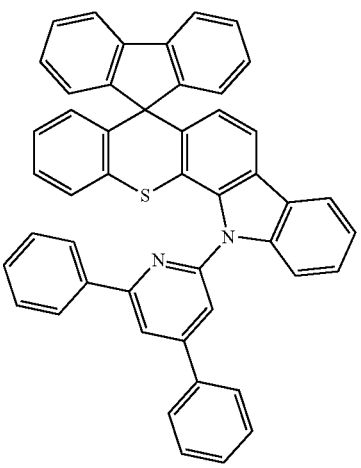
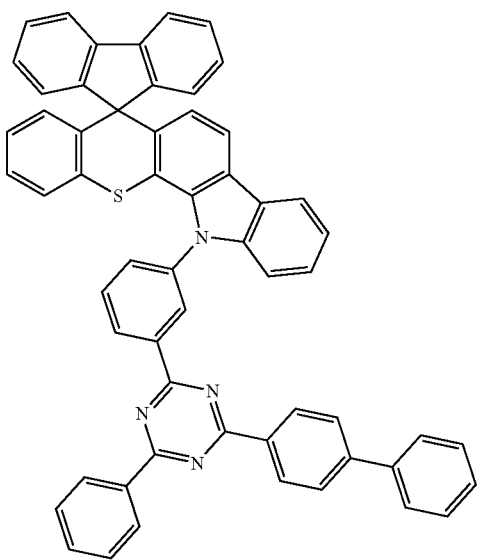

673
-continued
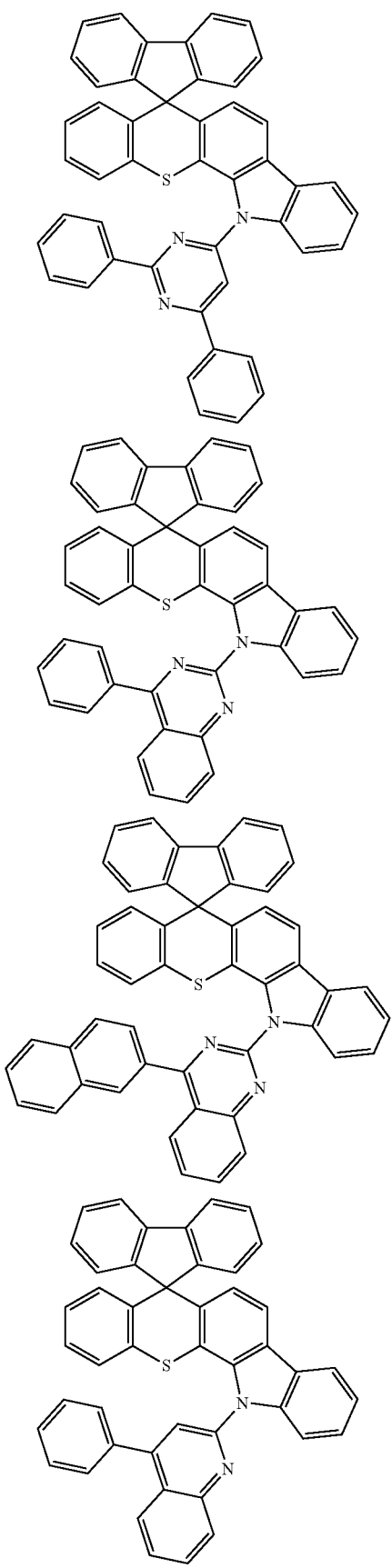
674
-continued
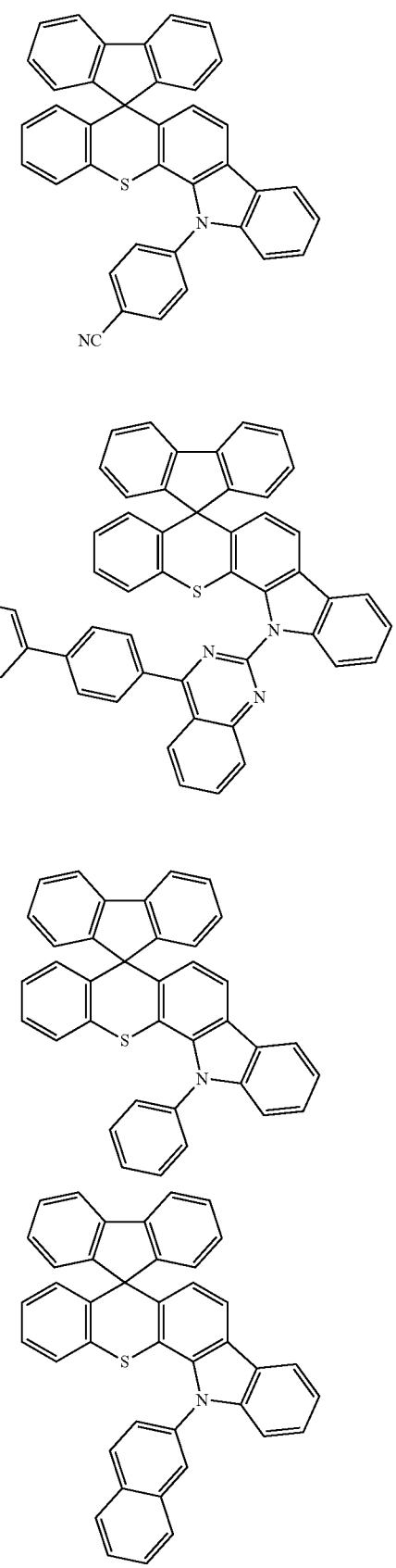

675
-continued
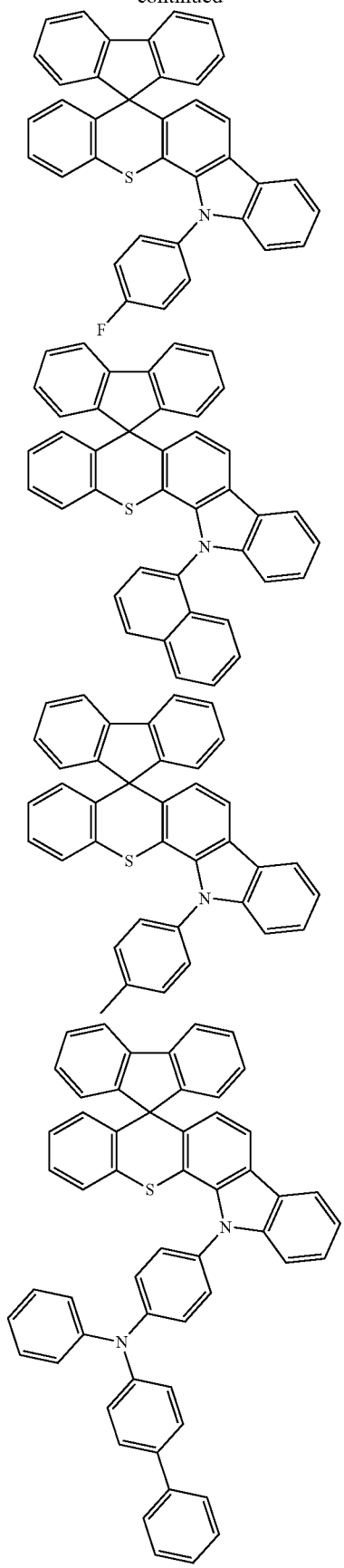
676
-continued
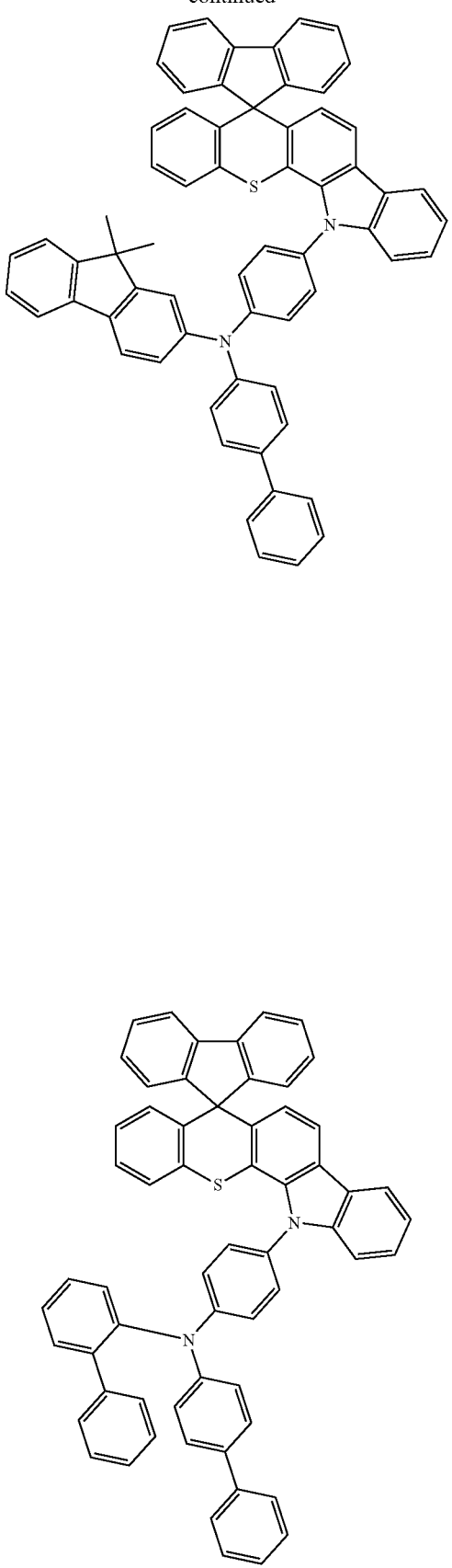

677
-continued
678
-continued
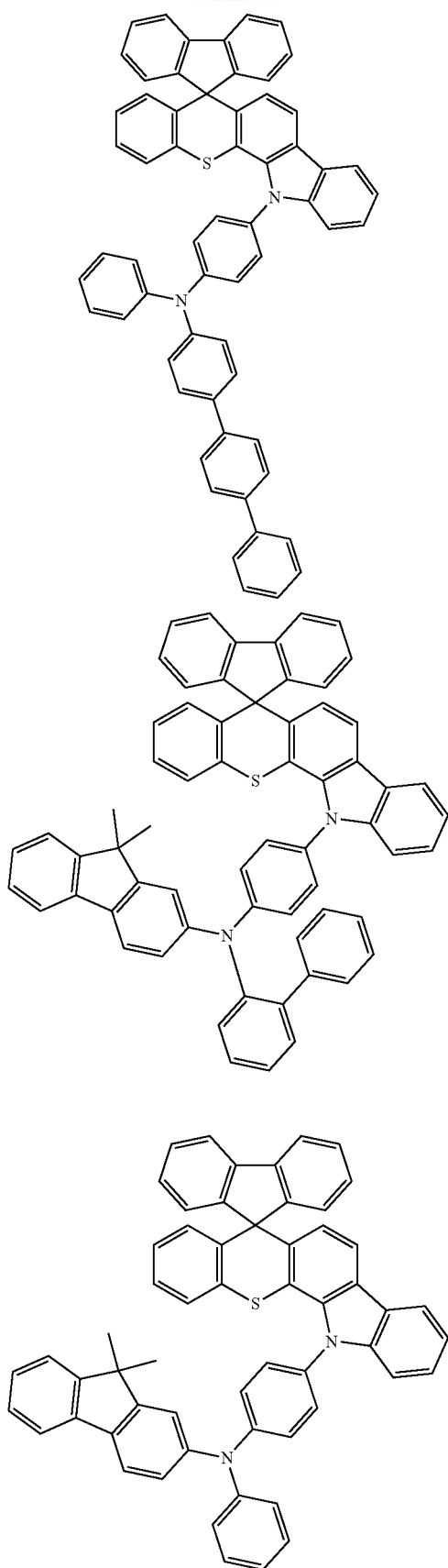
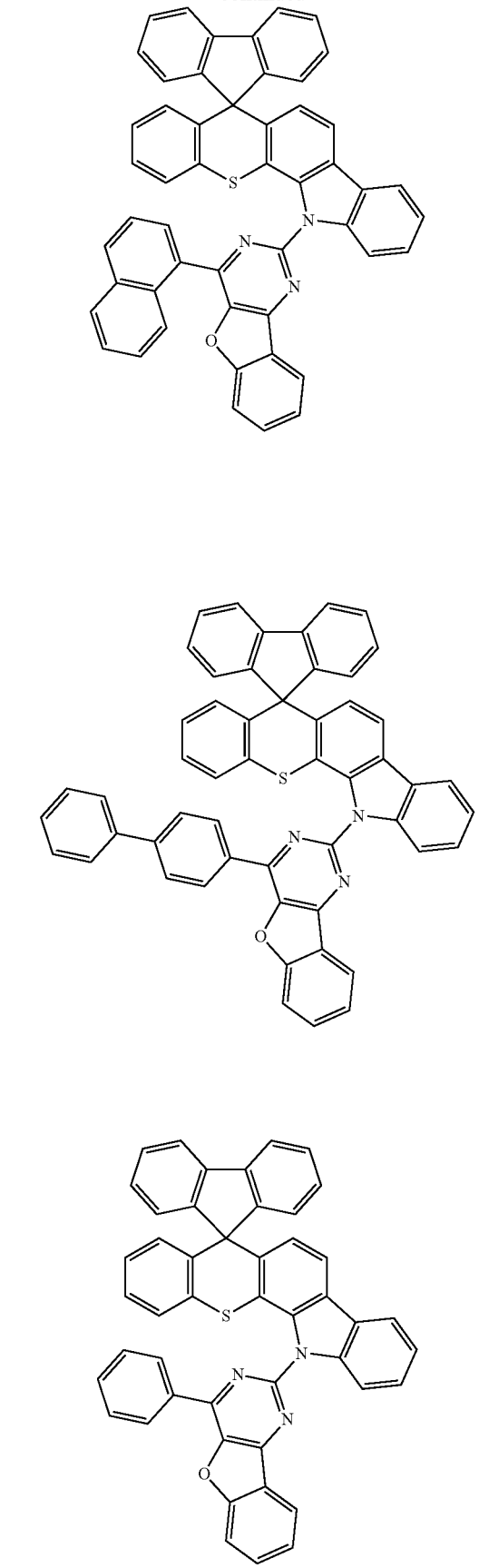

679
-continued
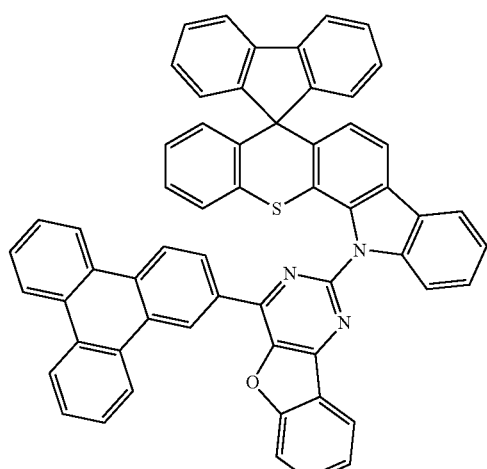
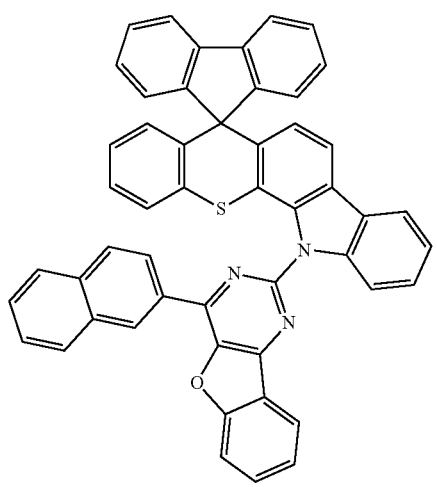
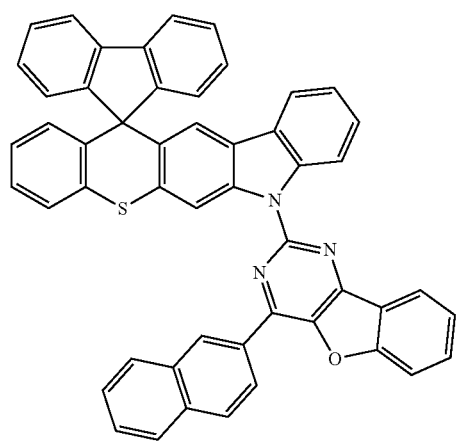
680
-continued
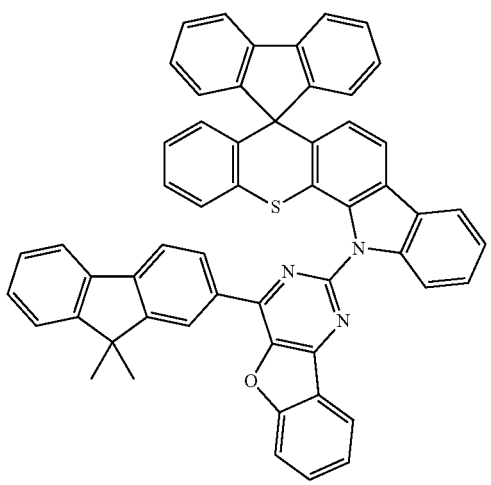
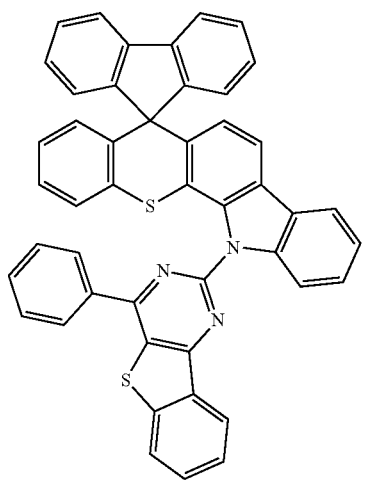
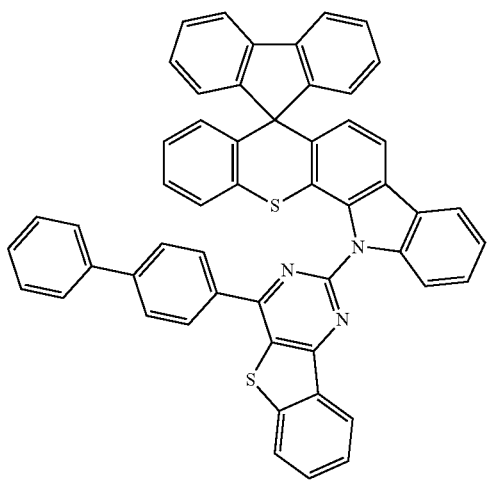

681
-continued
682
-continued
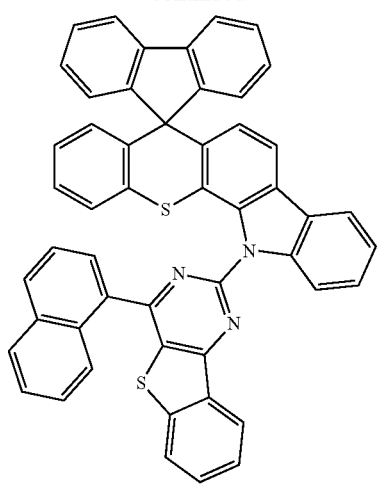
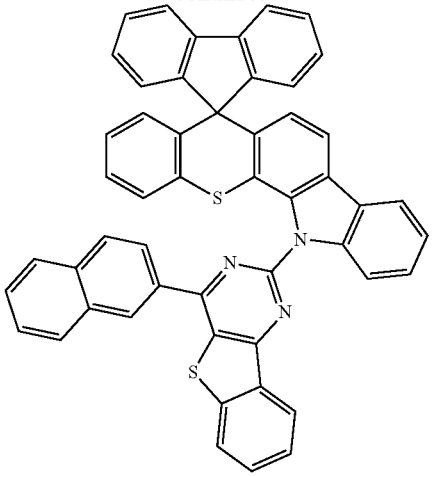
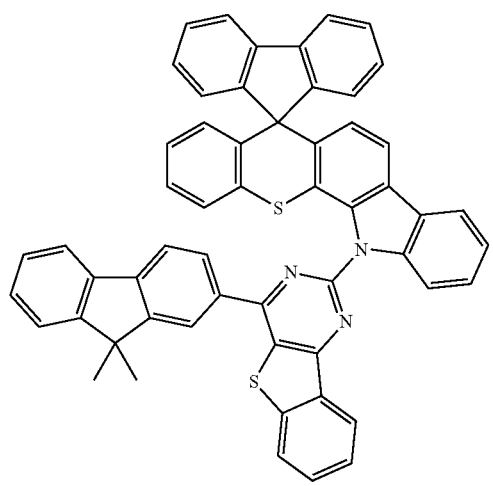
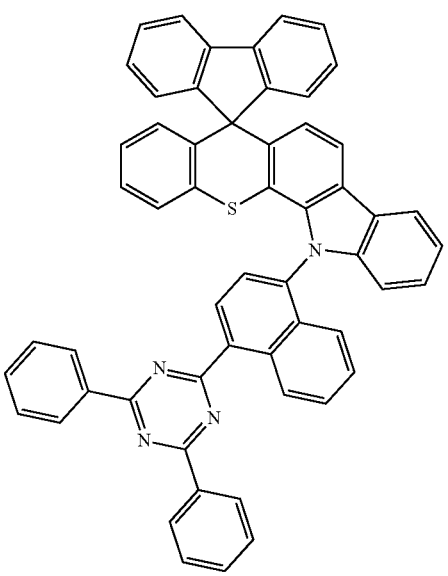

683
-continued
684
-continued
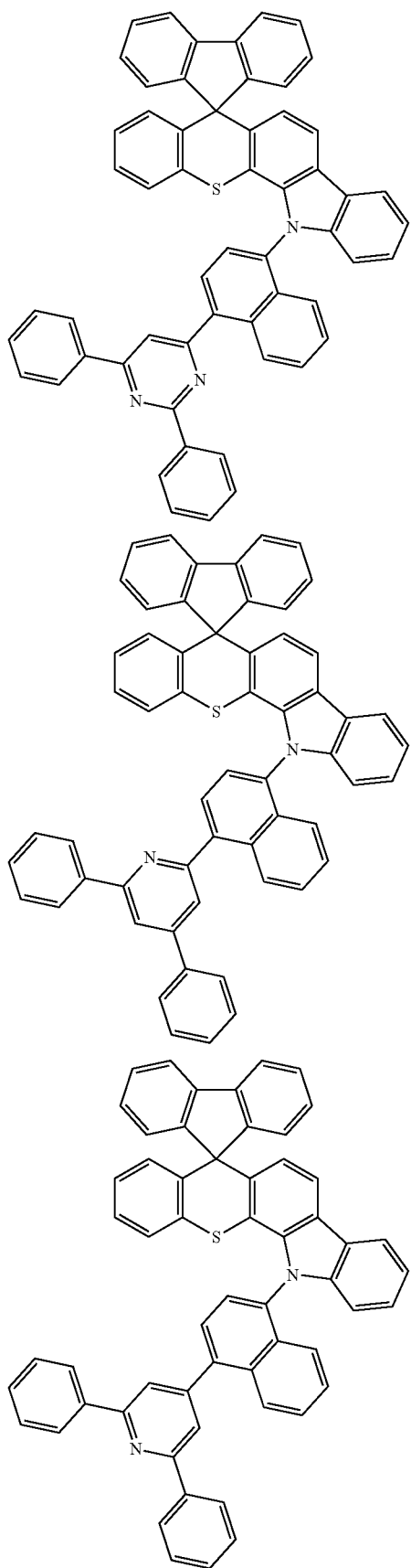
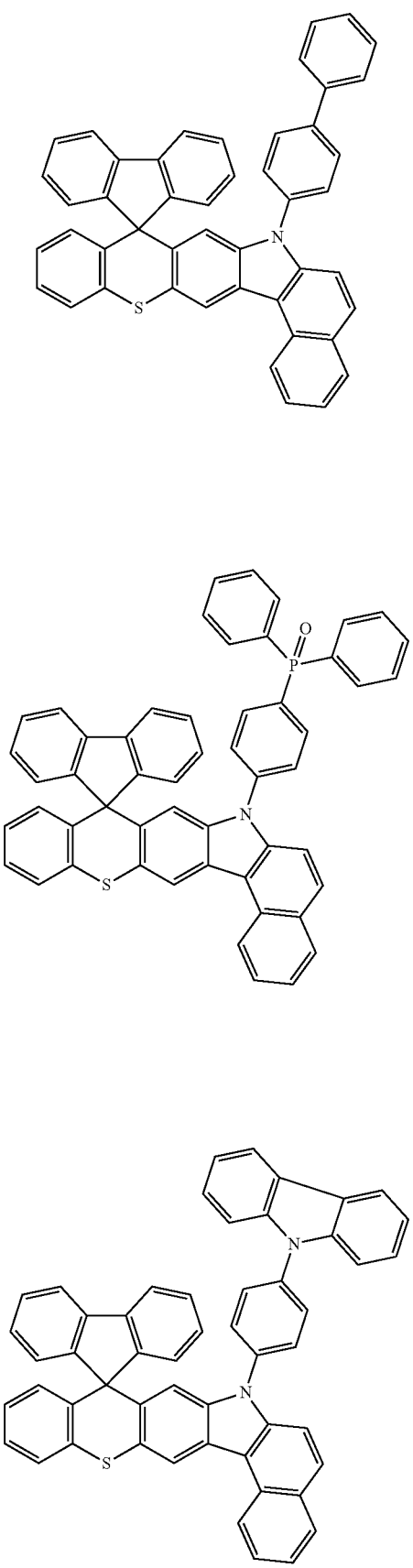

685
-continued
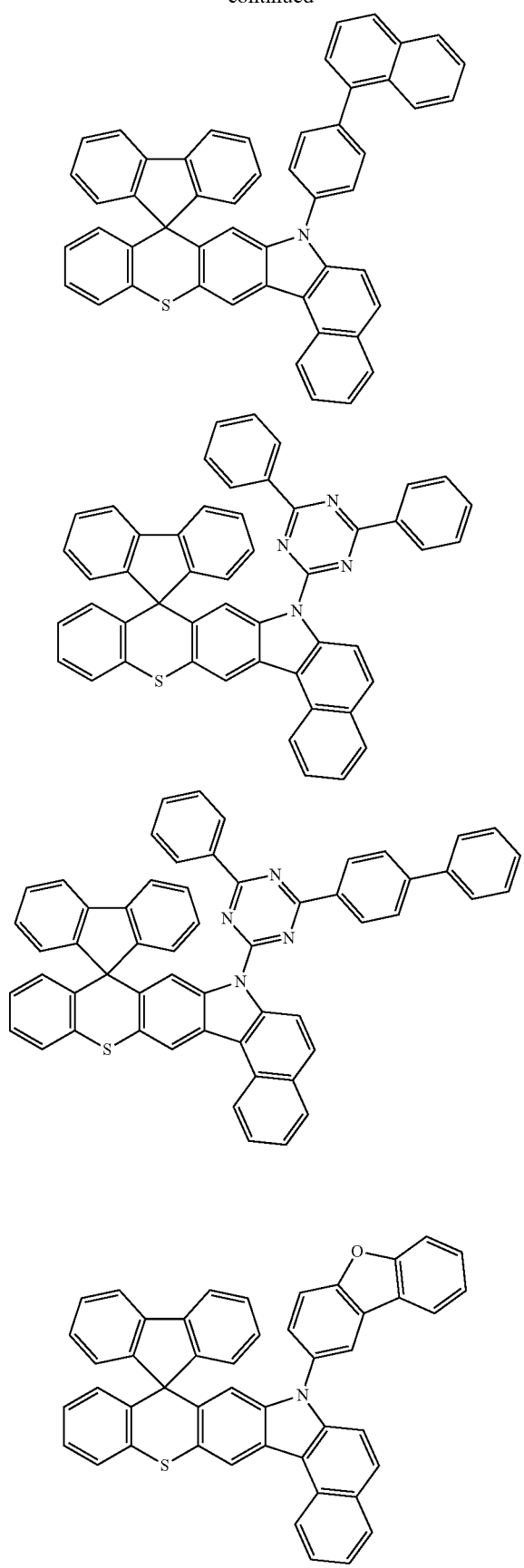
686
-continued
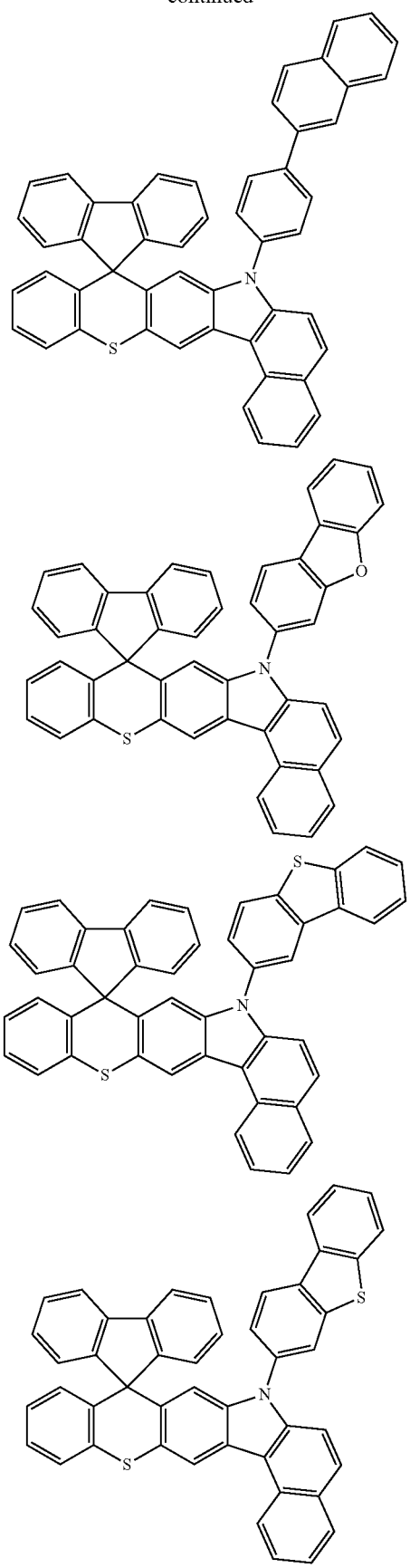

687
-continued
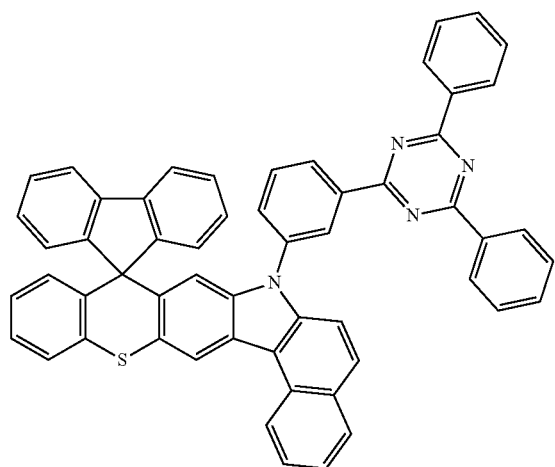 [SMILES: c1ccc(-c2nc(-c3ccccc3)nc(-c3cccc(-n4c5cc6c(cc5c5c7ccccc7ccc54)Sc4ccccc4C64c5ccccc5-c5ccccc54)c3)n2)cc1]
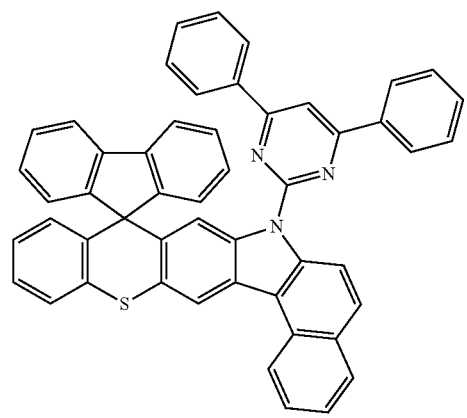
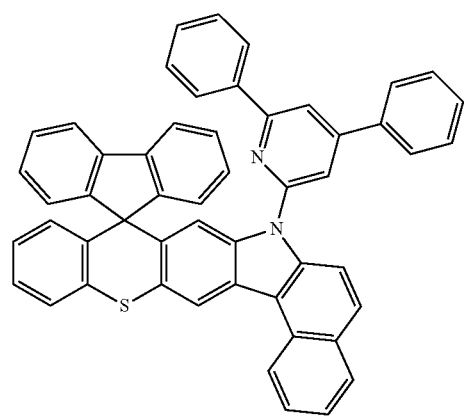
688
-continued
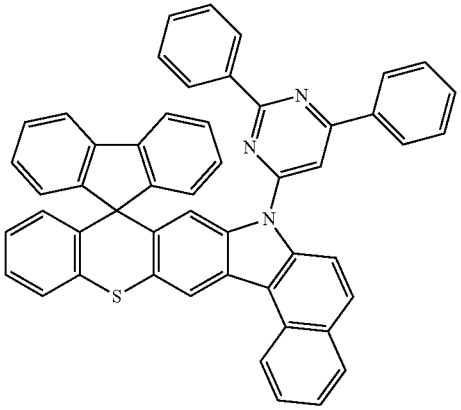
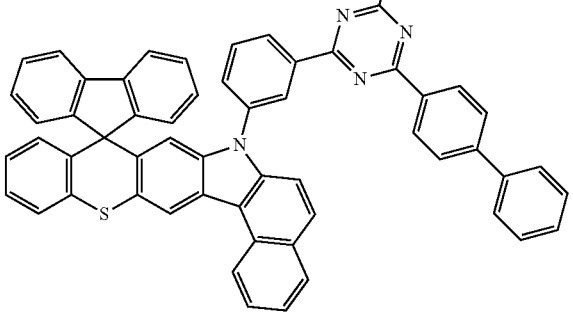
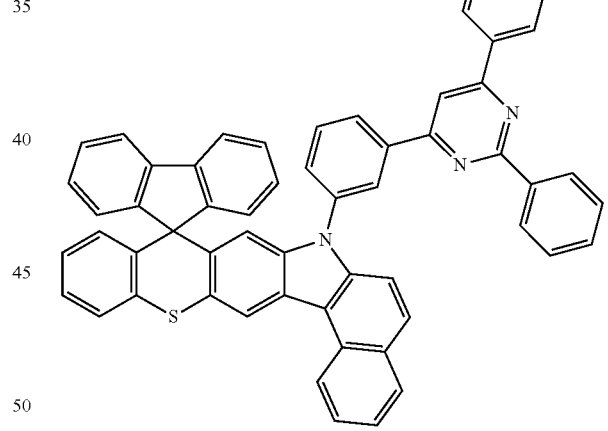
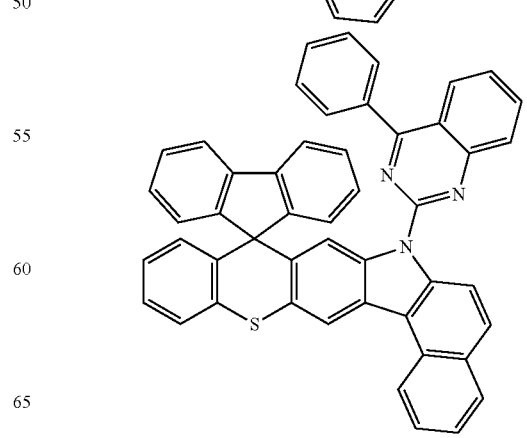

689
-continued
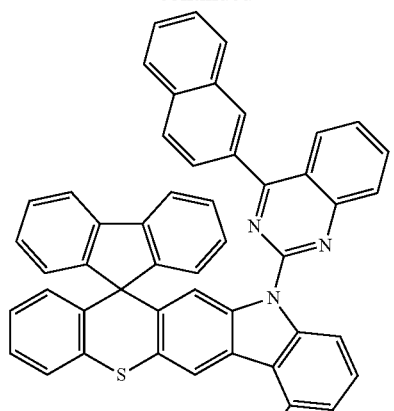
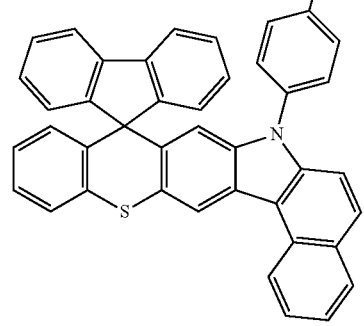
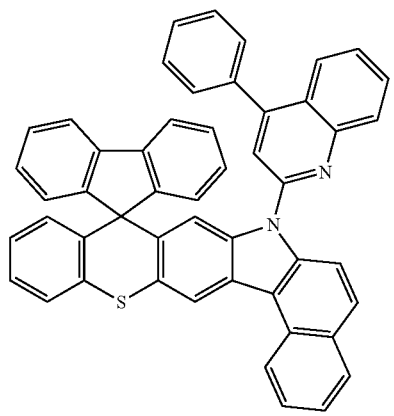
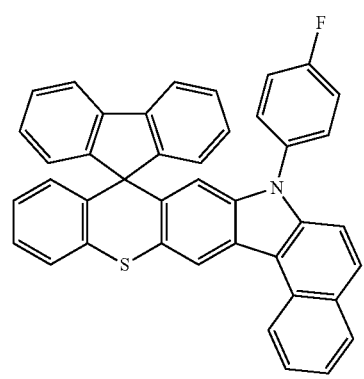
690
-continued
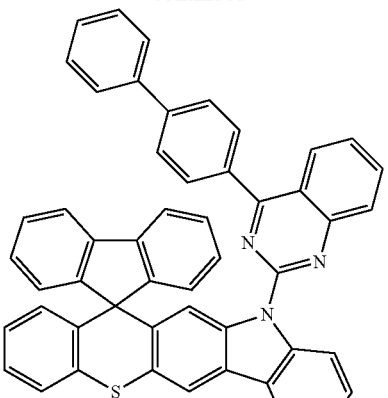
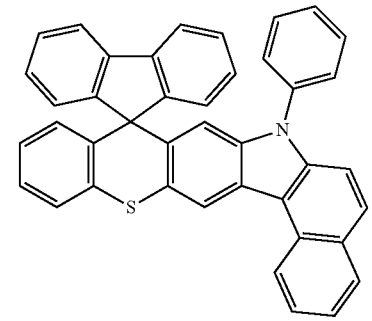
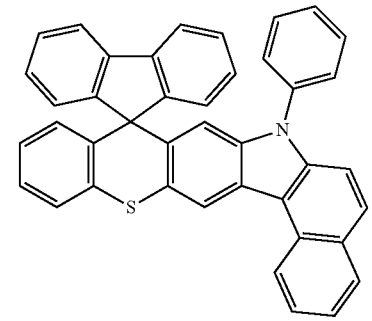
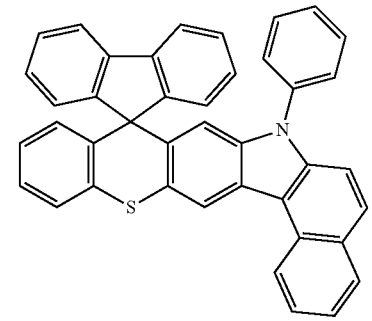

691
-continued
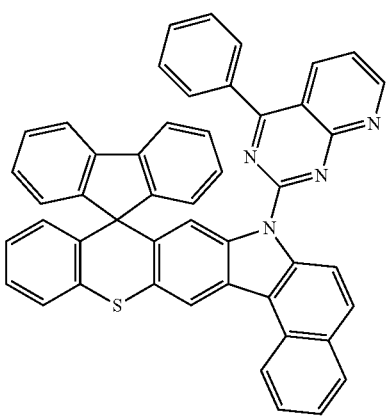
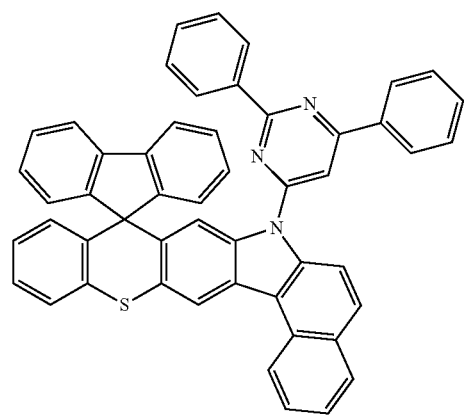
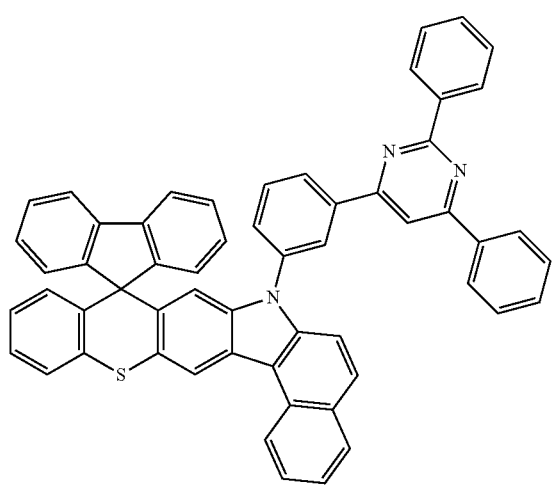
692
-continued
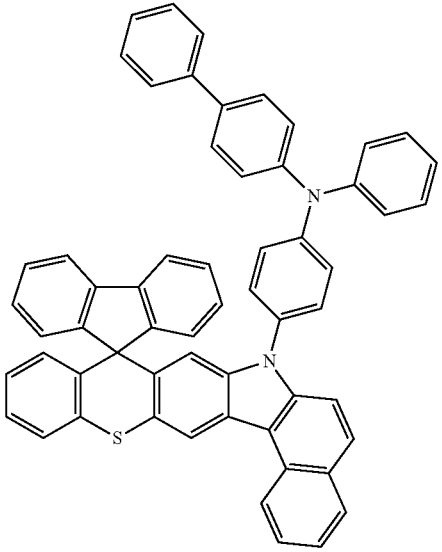
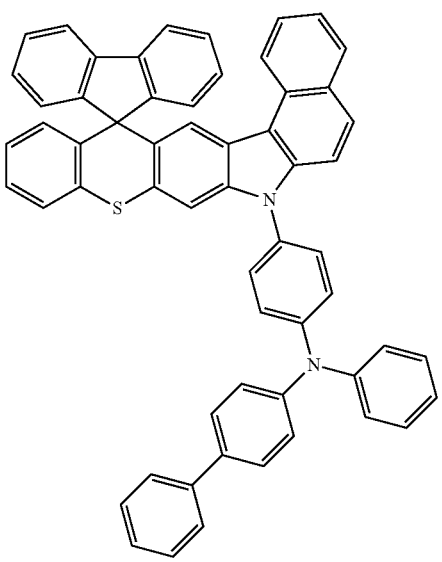
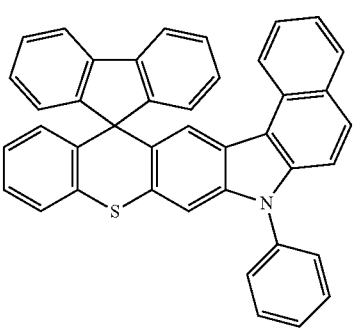

693
-continued
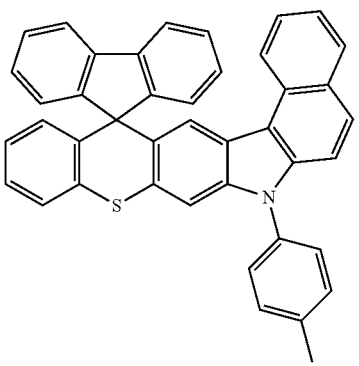
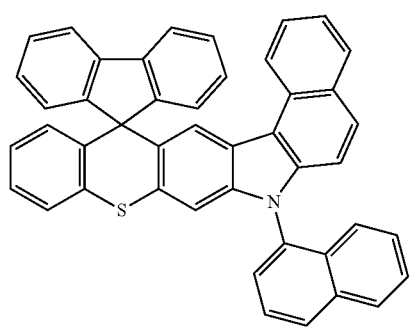
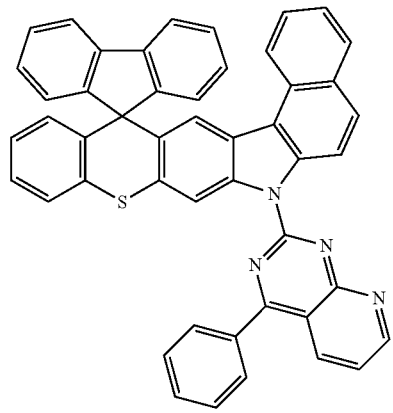
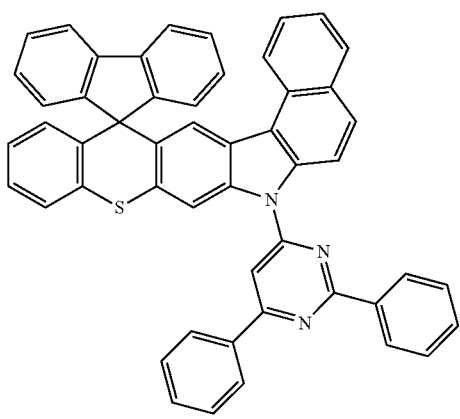
694
-continued
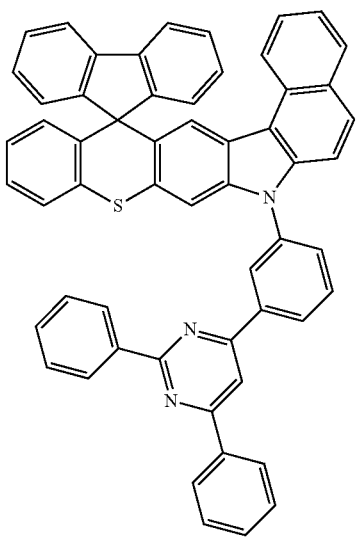
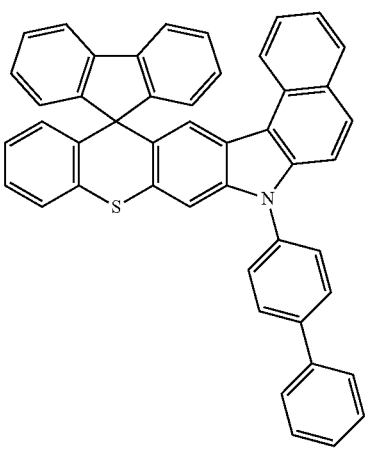
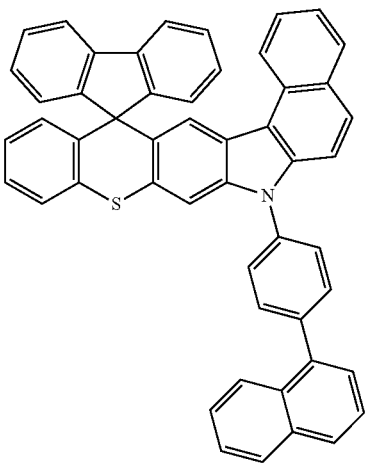

695
-continued
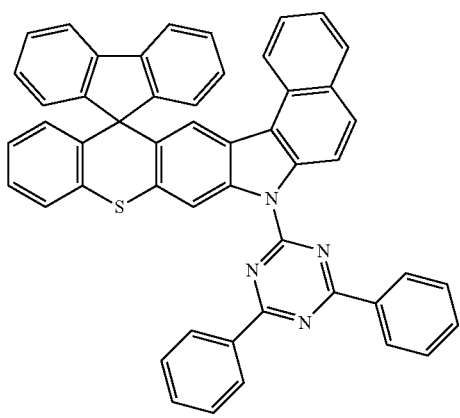
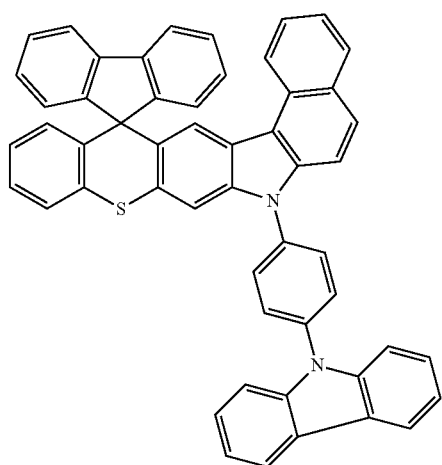
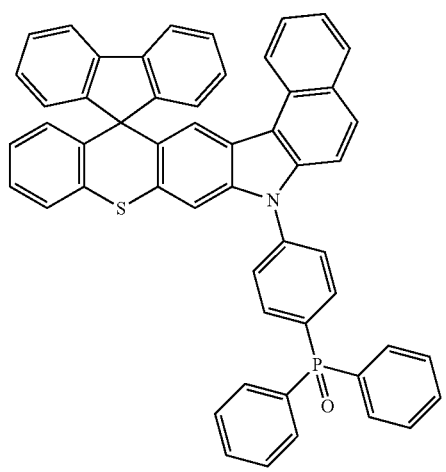
696
-continued
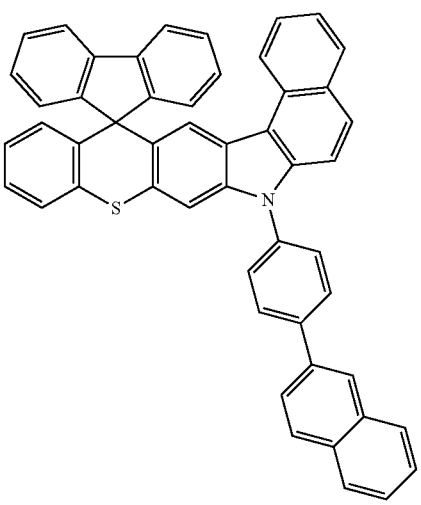
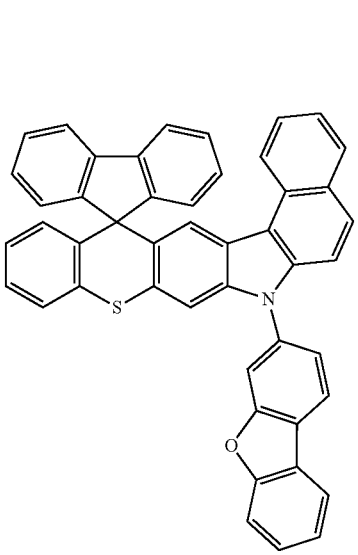

697
-continued
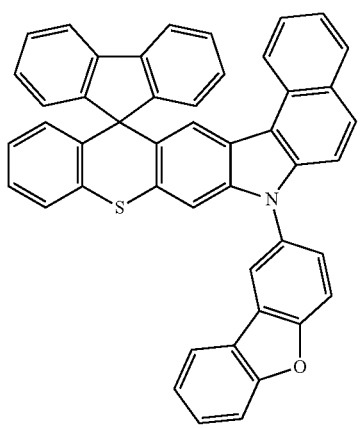
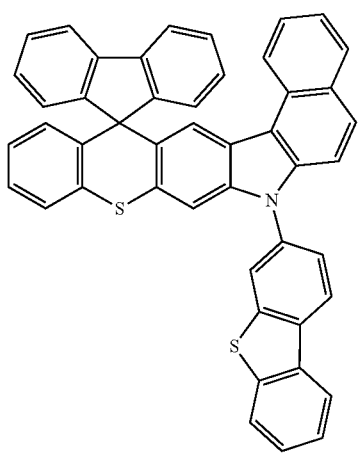
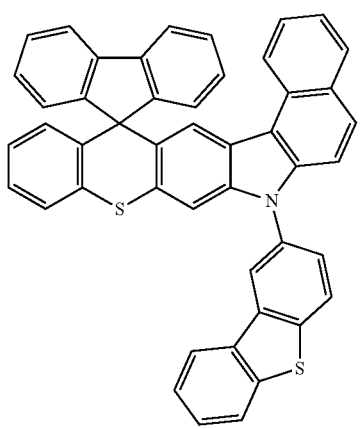
698
-continued
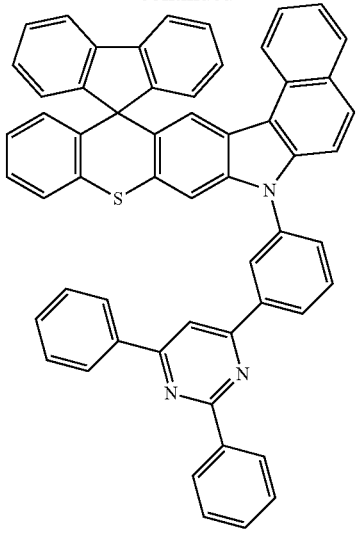
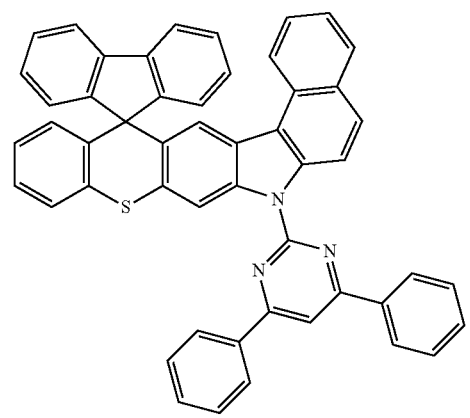
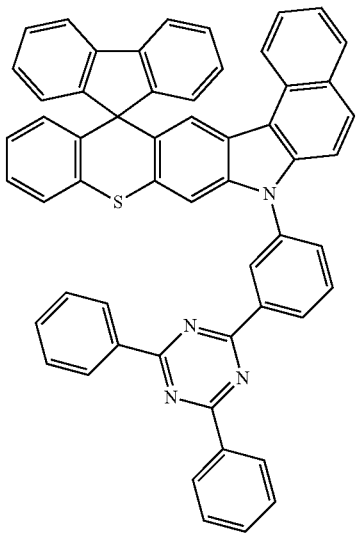

699
-continued
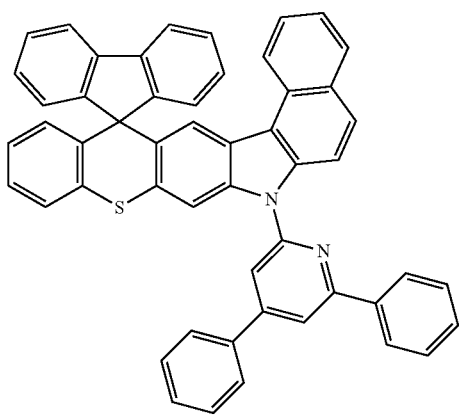
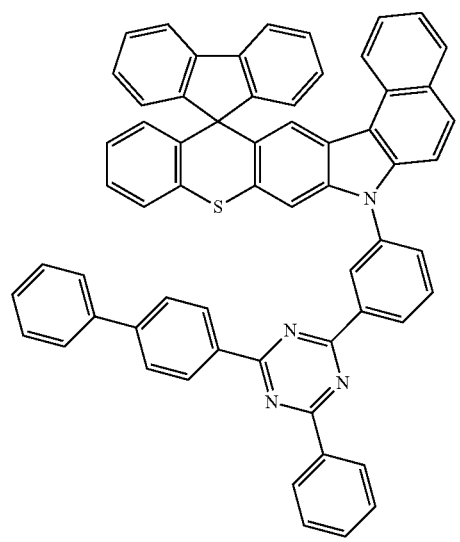
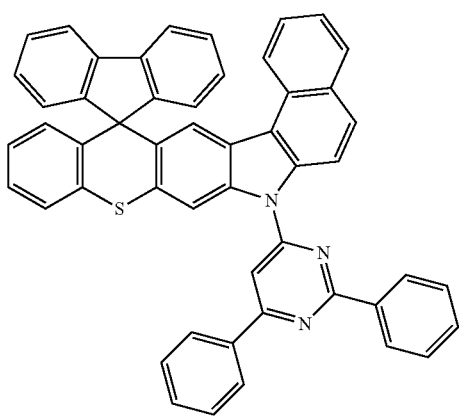
700
-continued
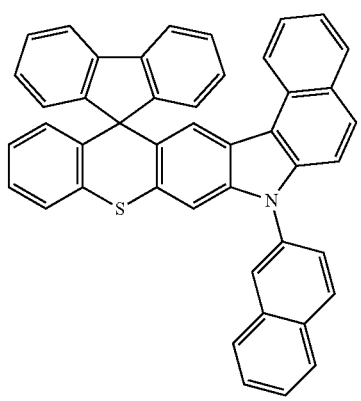
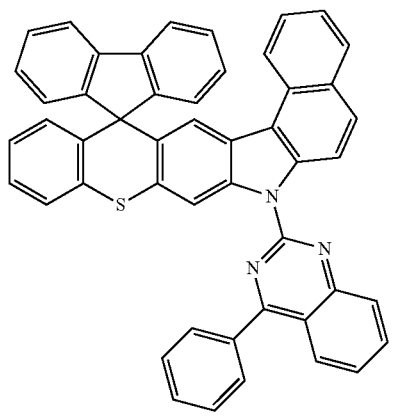
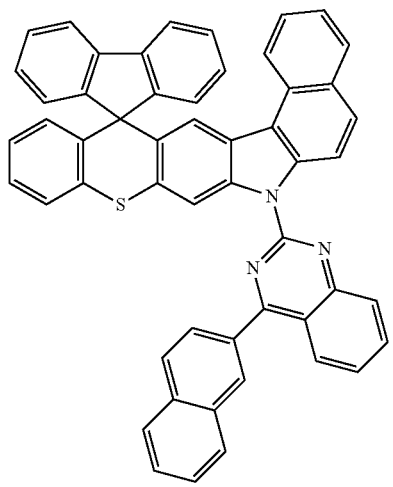
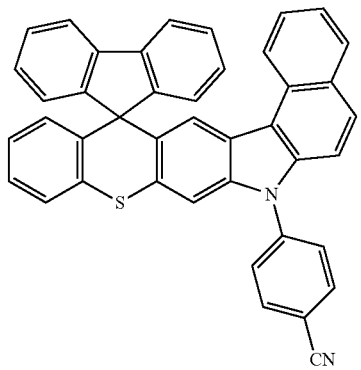

701
-continued
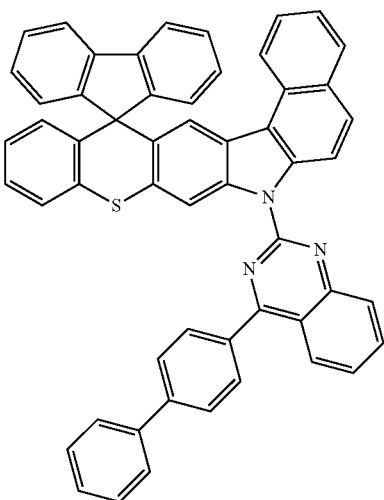
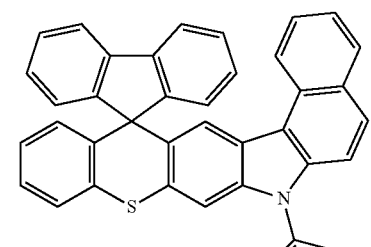
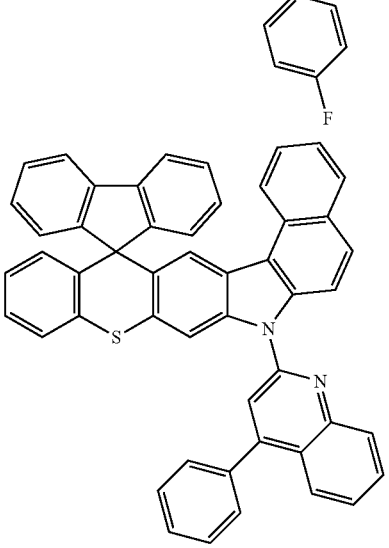
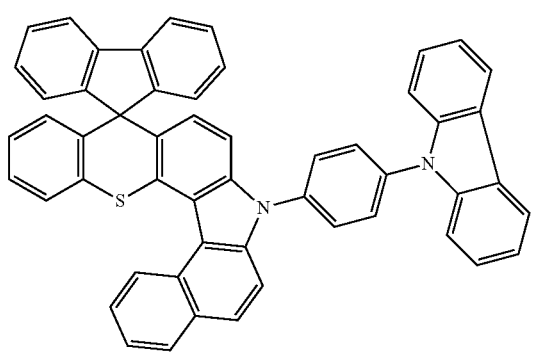
702
-continued
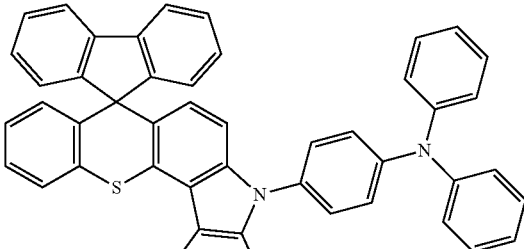
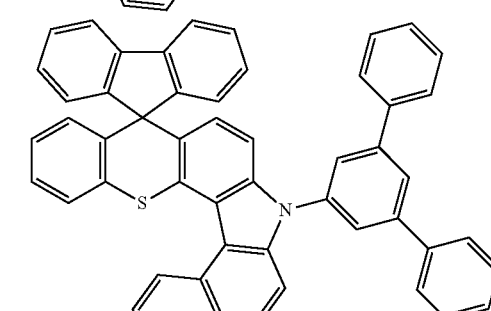
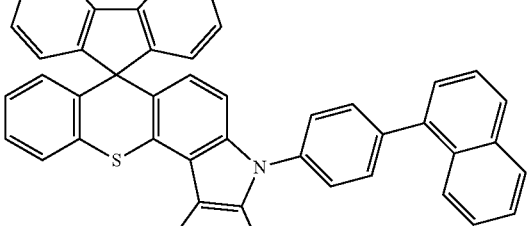
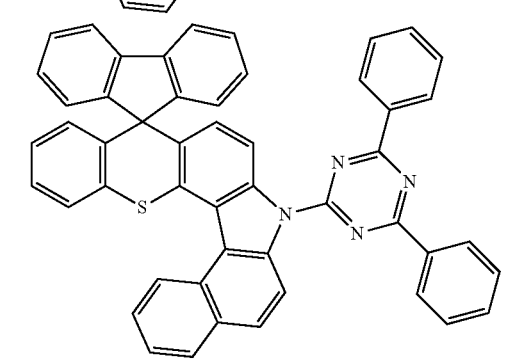
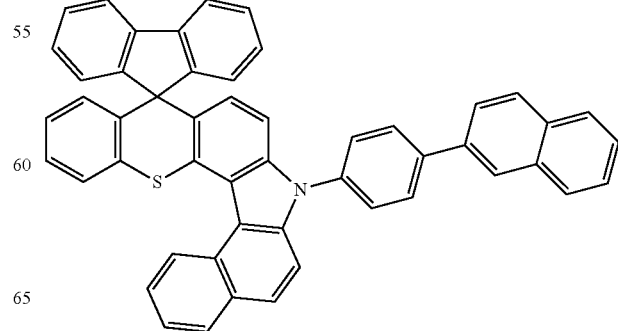

703
-continued
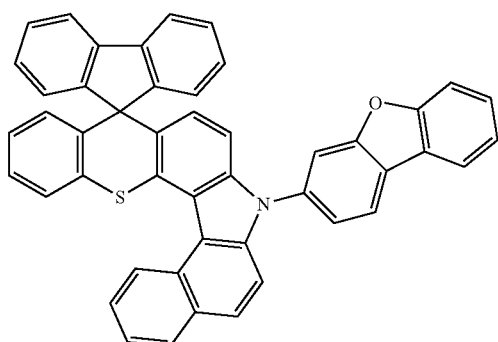
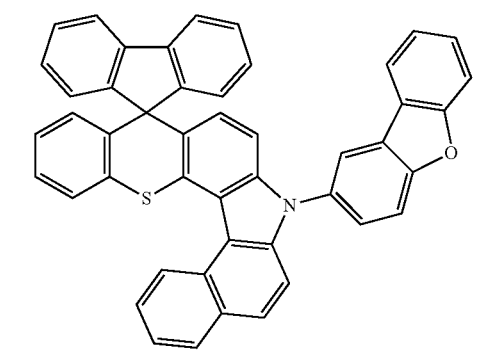
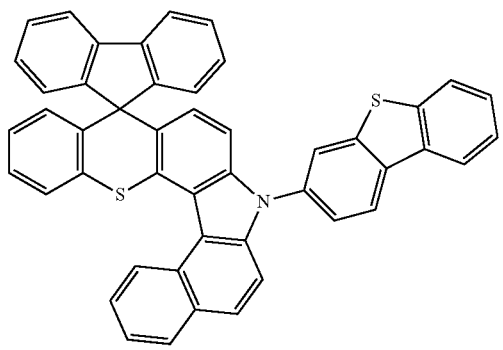
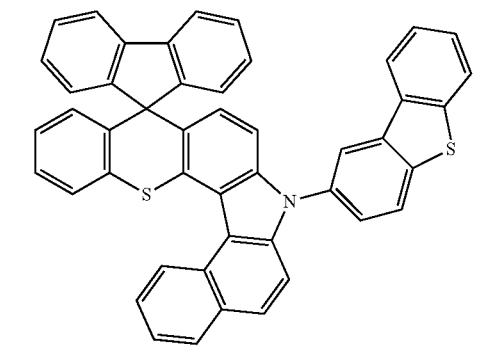
704
-continued
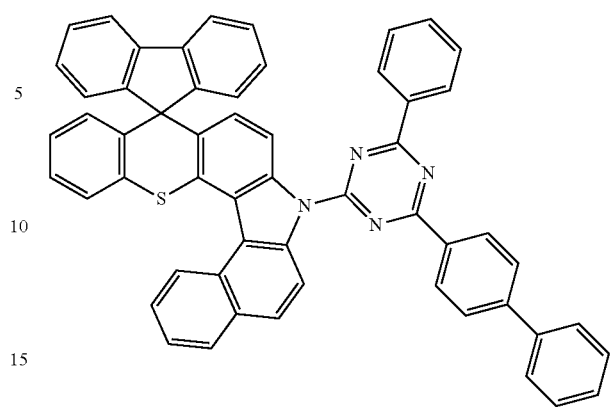
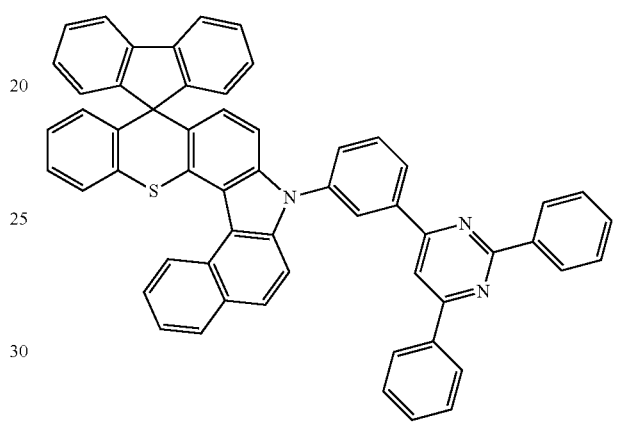
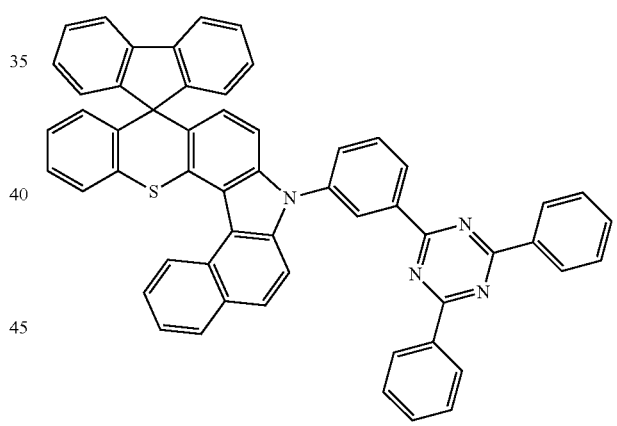
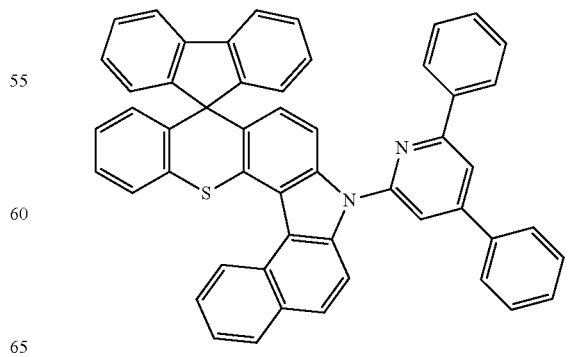

705
-continued
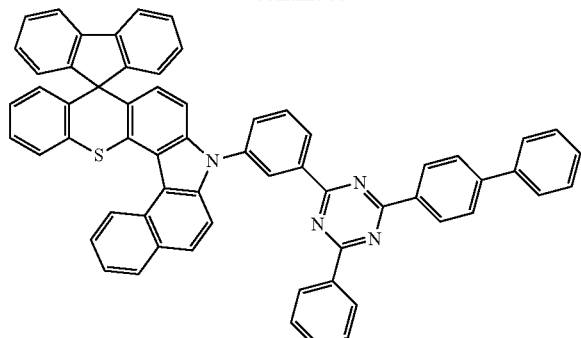
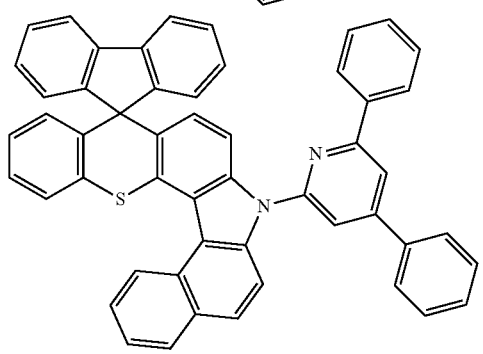
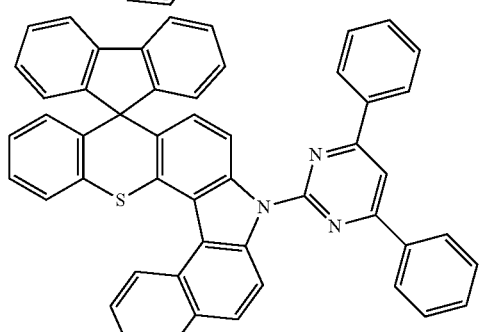
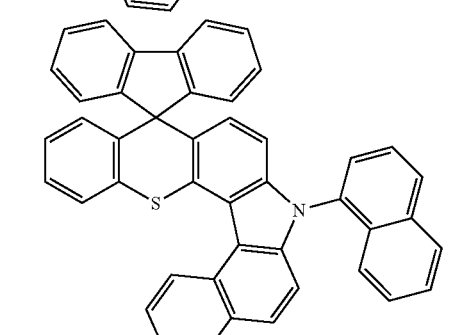
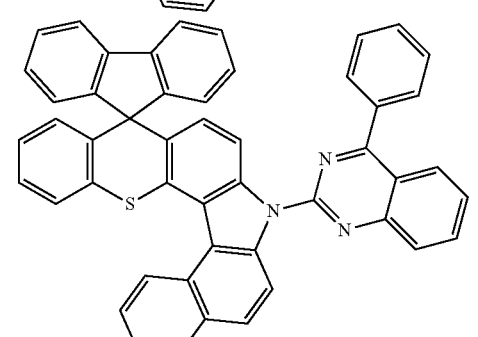
706
-continued
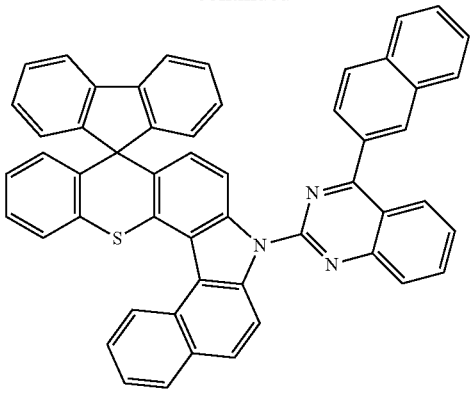
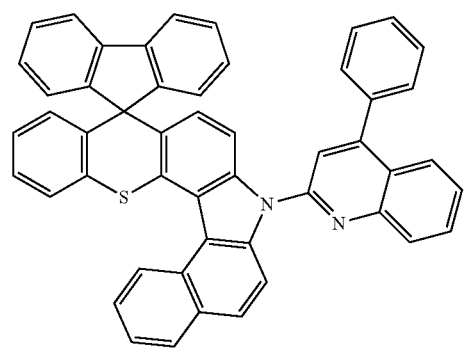
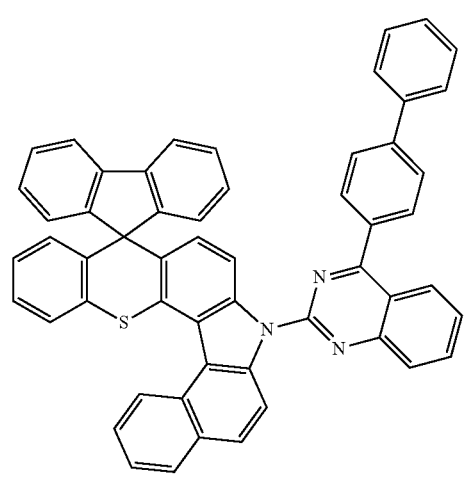
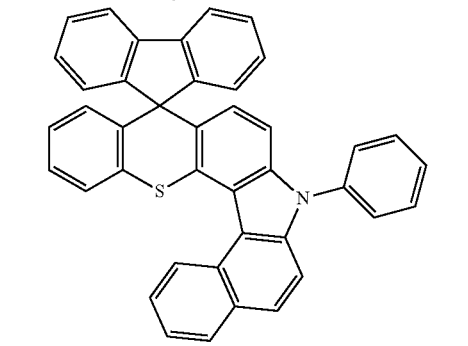

707
-continued
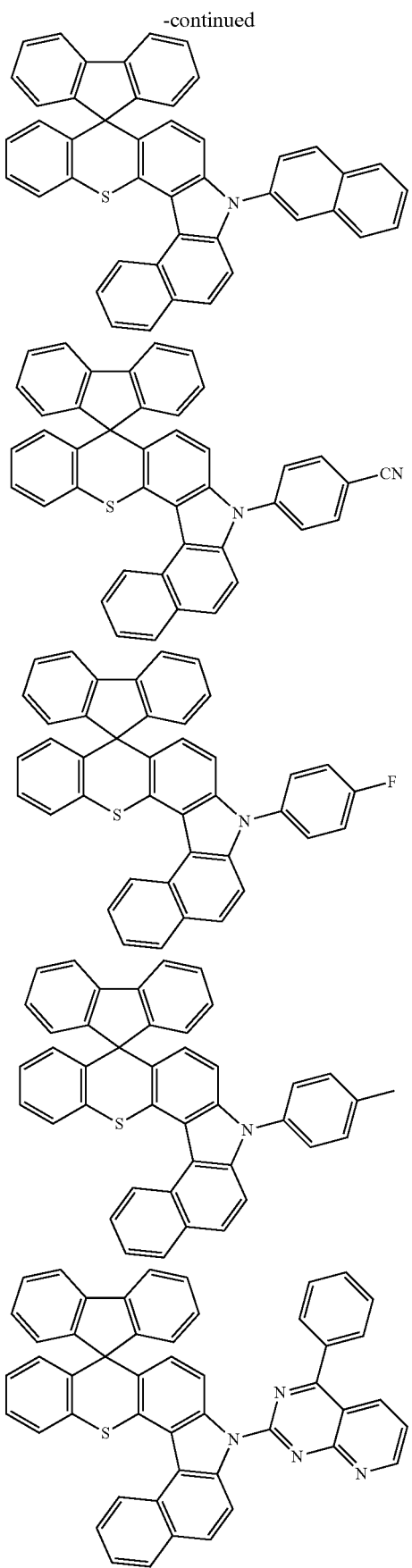
708
-continued
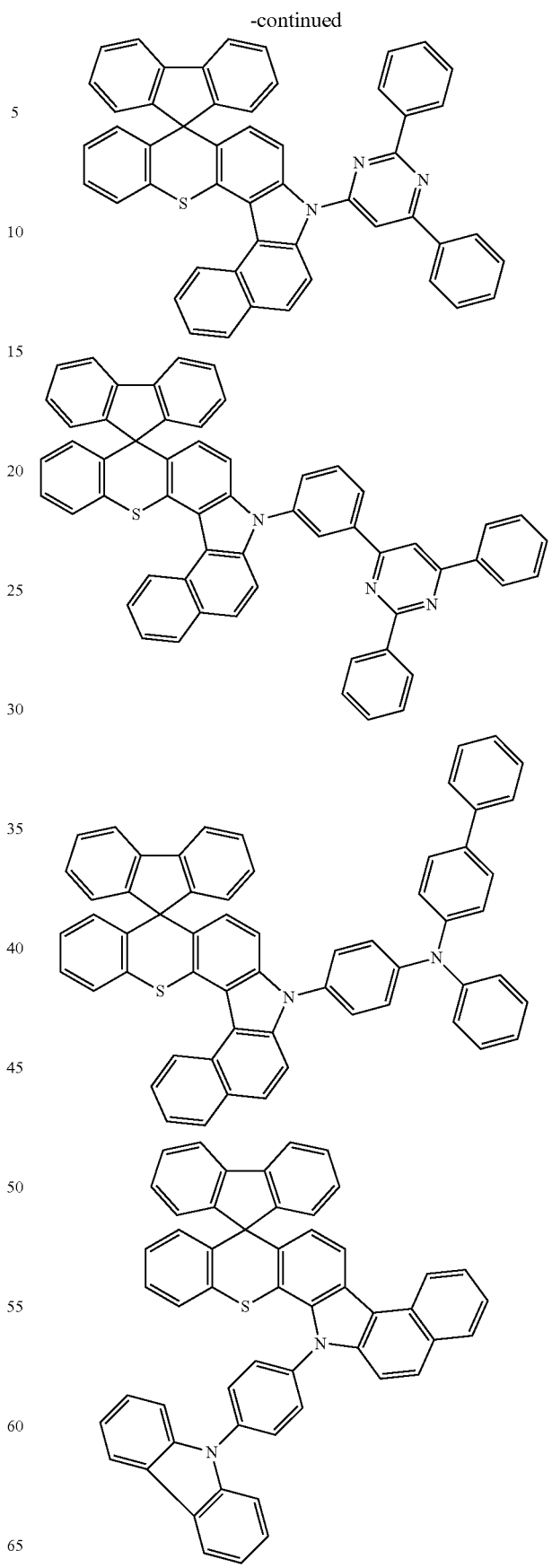

| 709 -continued | 710 -continued |
|---|---|
| 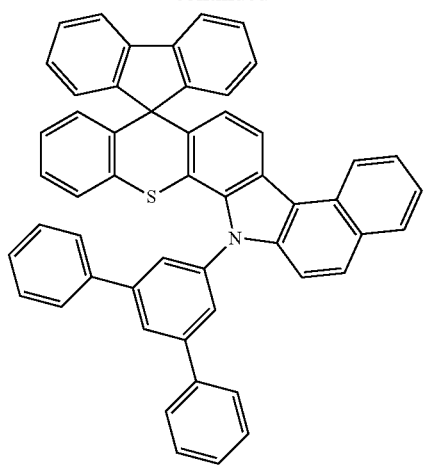 | 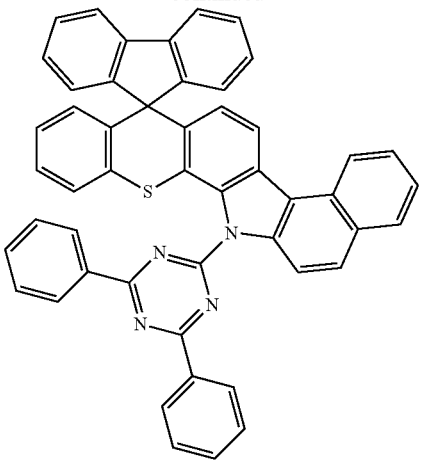 |
| 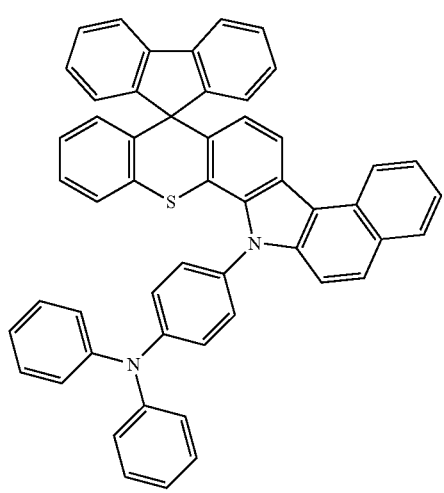 | 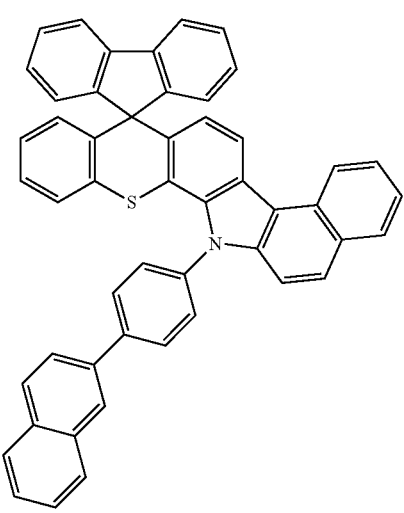 |
| 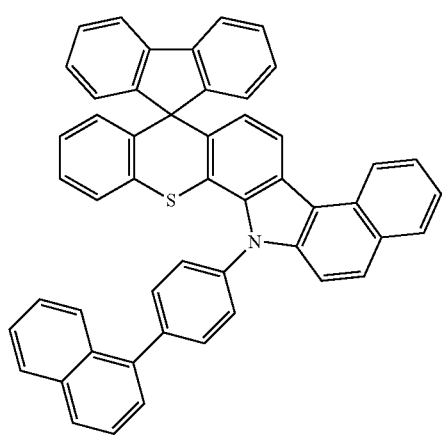 | 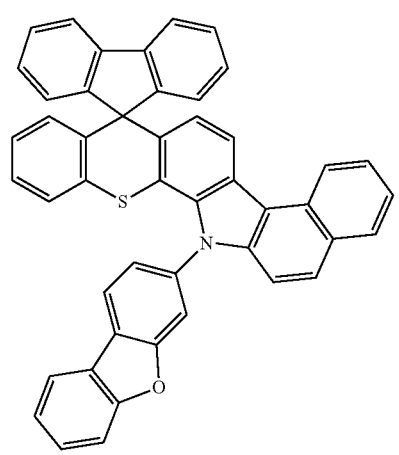 |

711
-continued
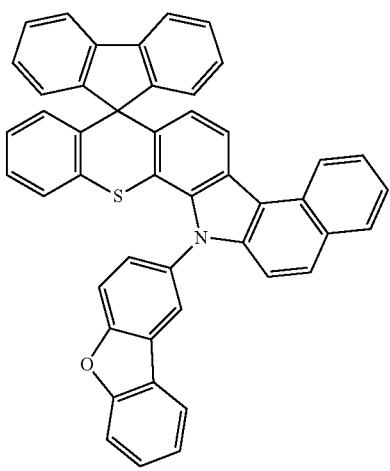
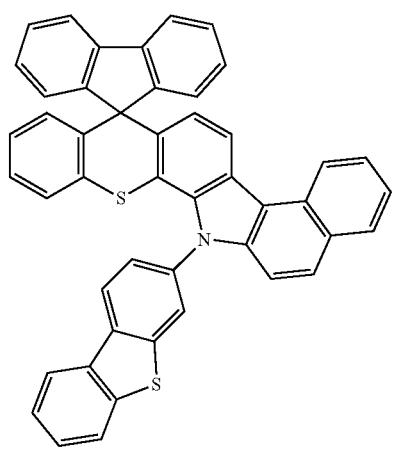
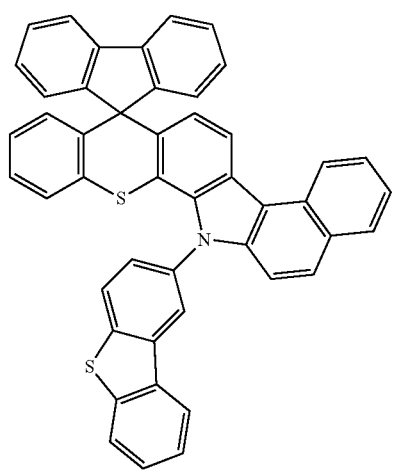
712
-continued
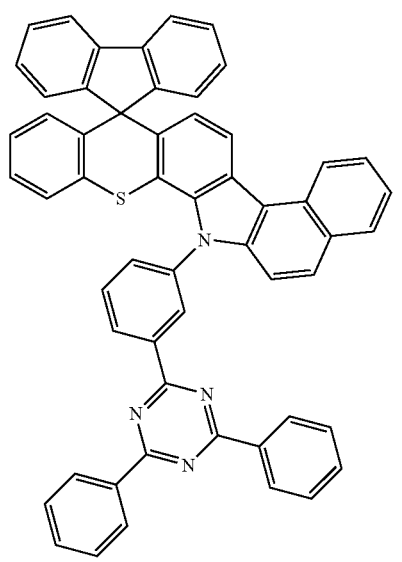
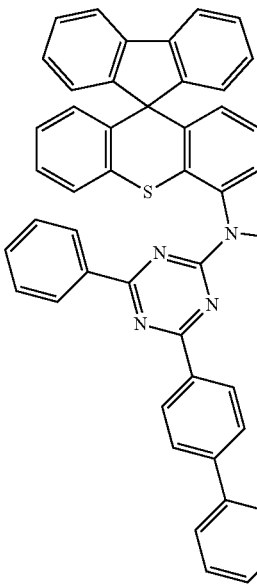
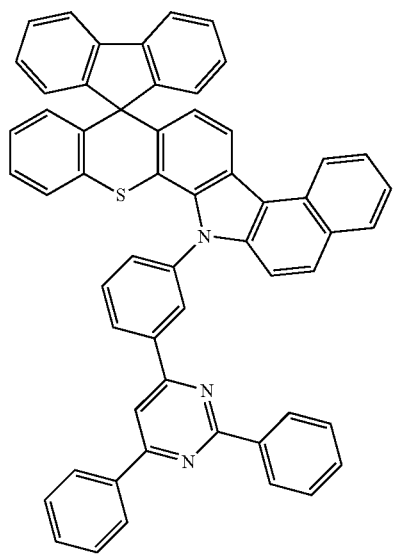

713
-continued
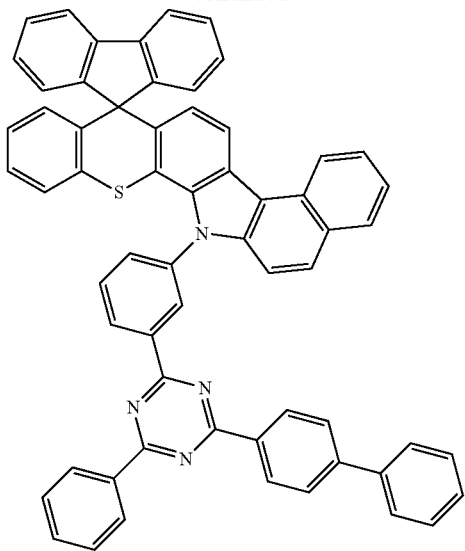
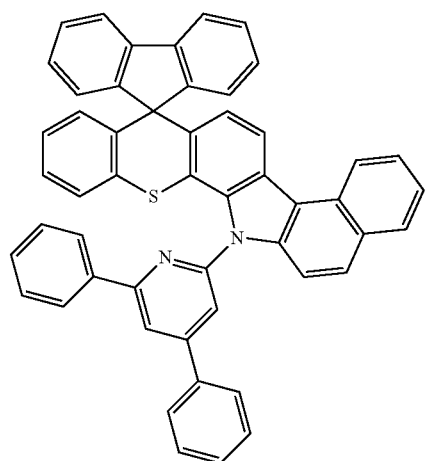
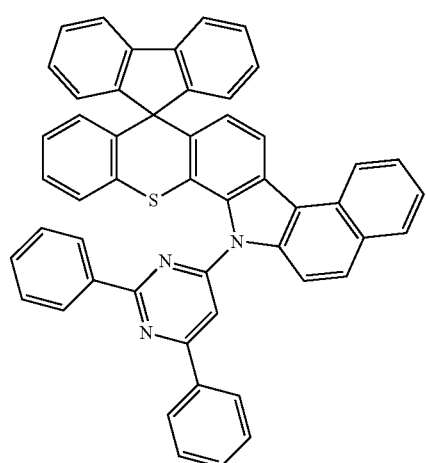
714
-continued
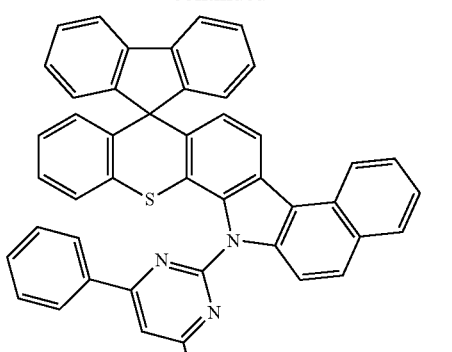
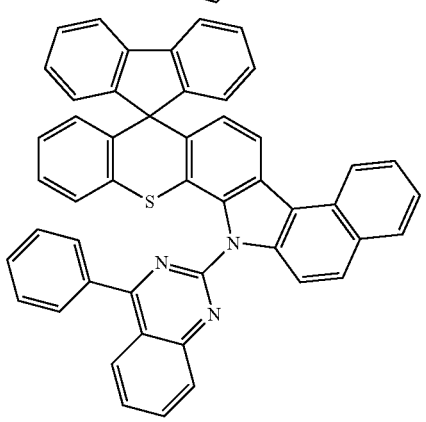
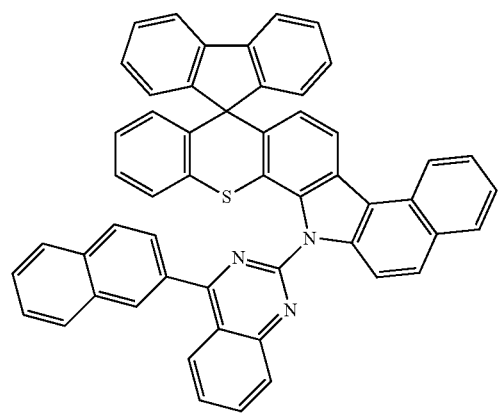
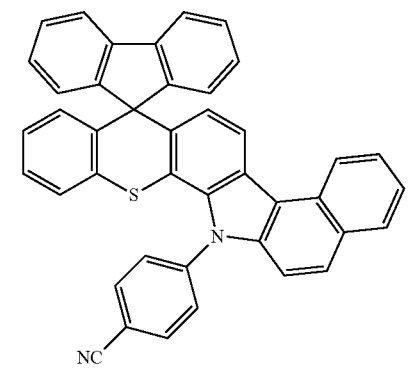

715
-continued
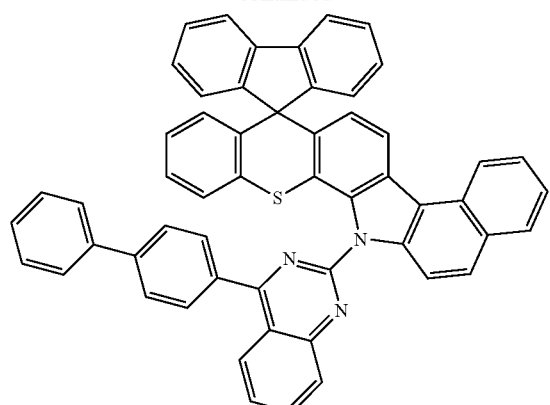
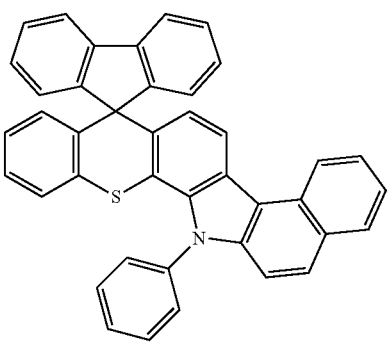
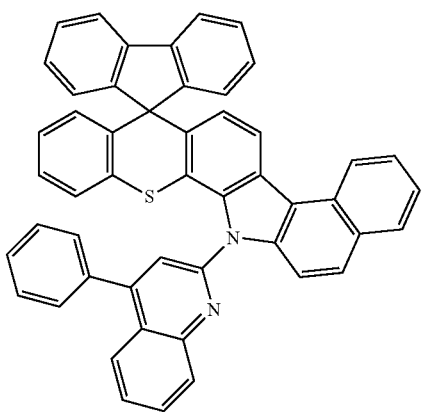
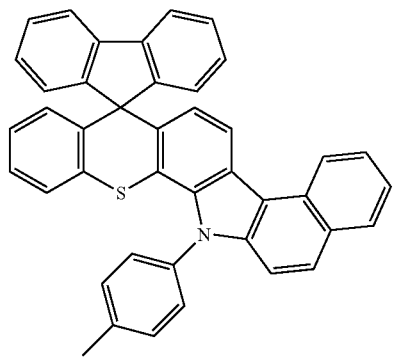
716
-continued
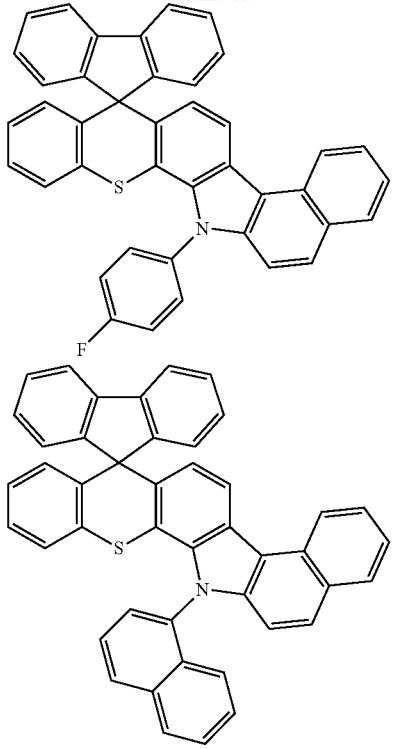
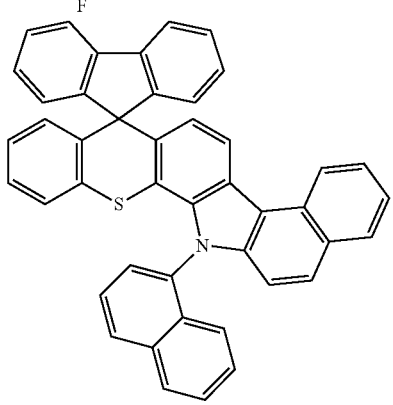
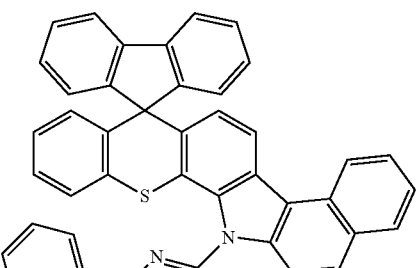
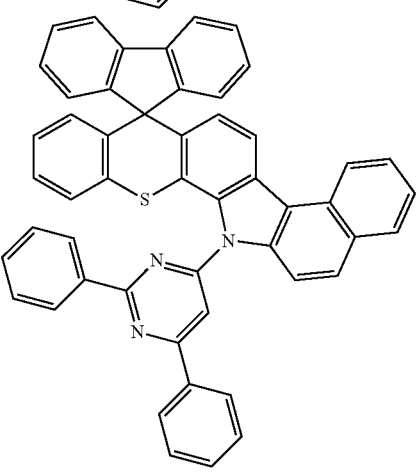

717
-continued
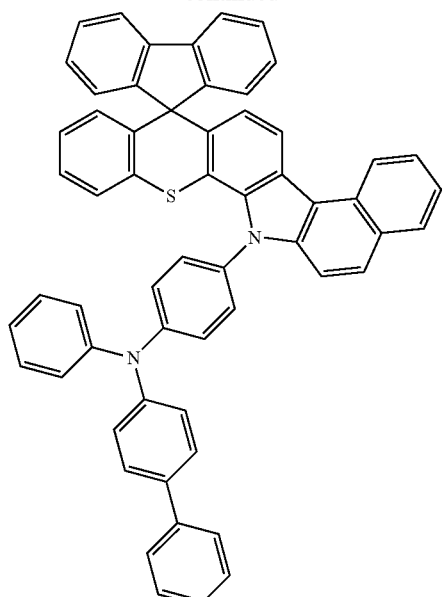
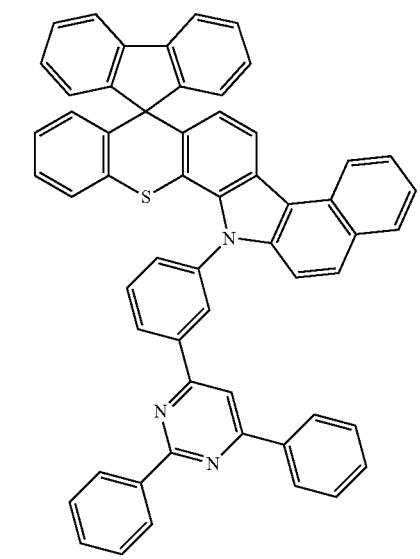
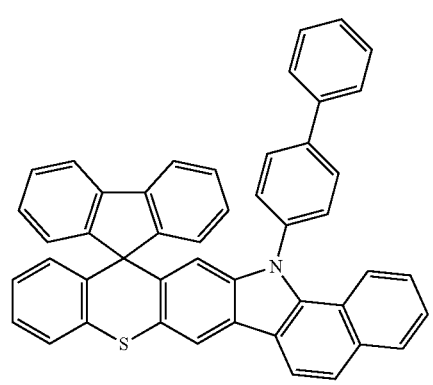
718
-continued
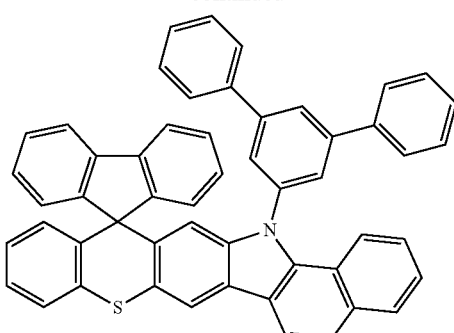
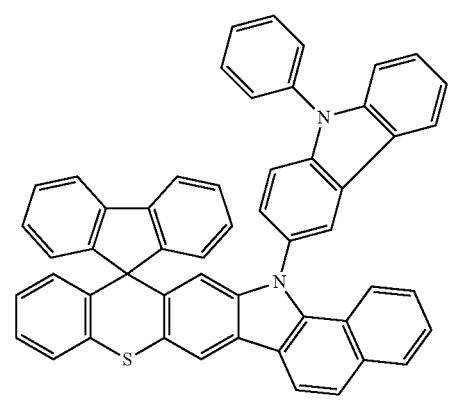
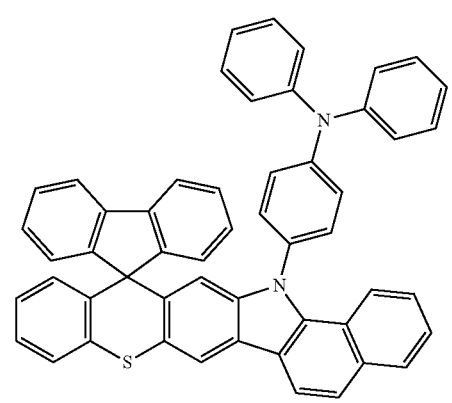
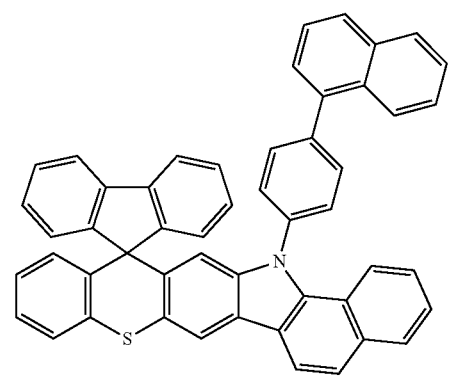

719
-continued
720
-continued
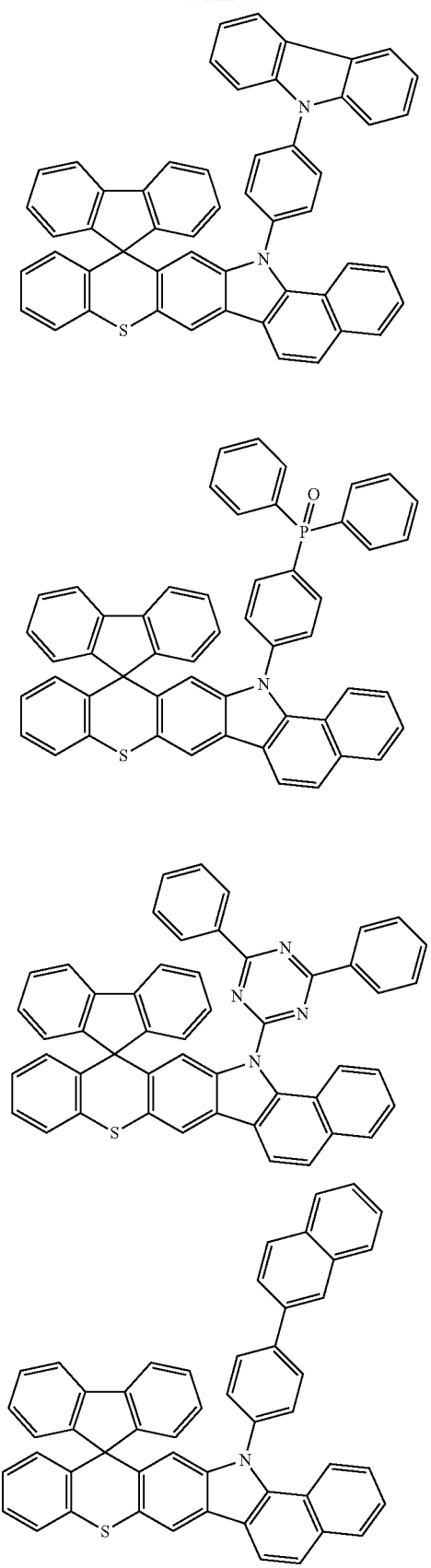
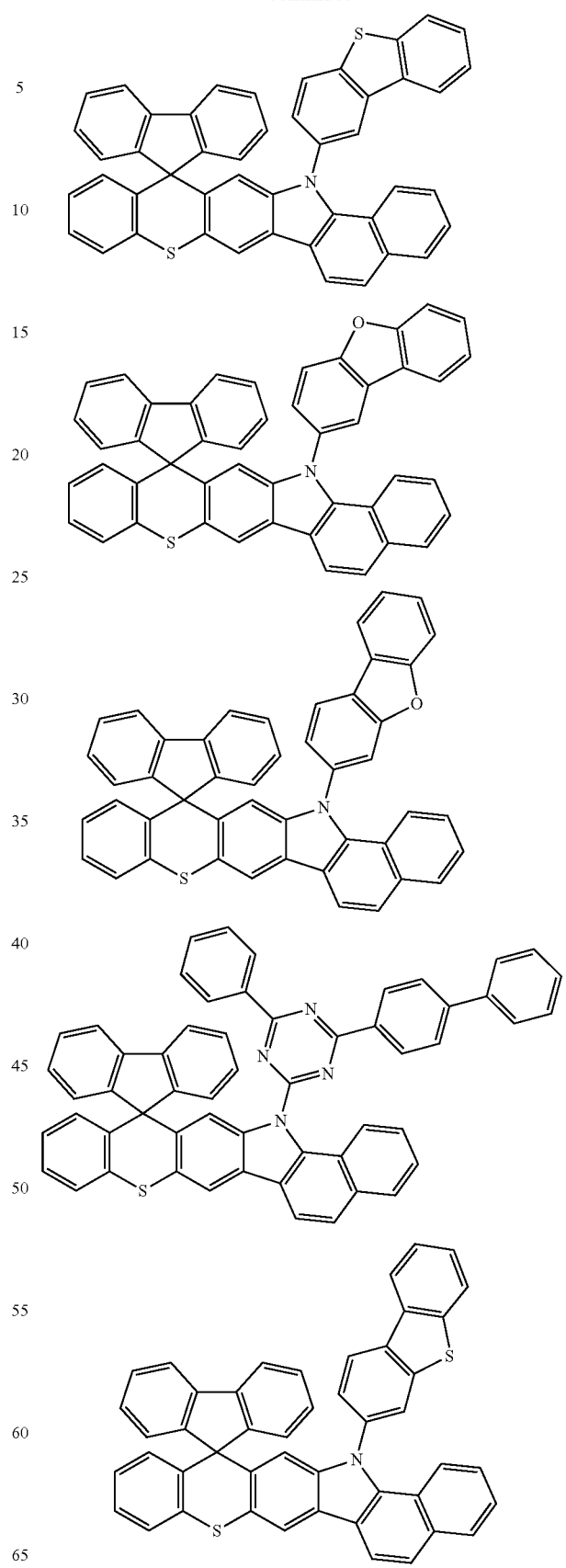

721
-continued
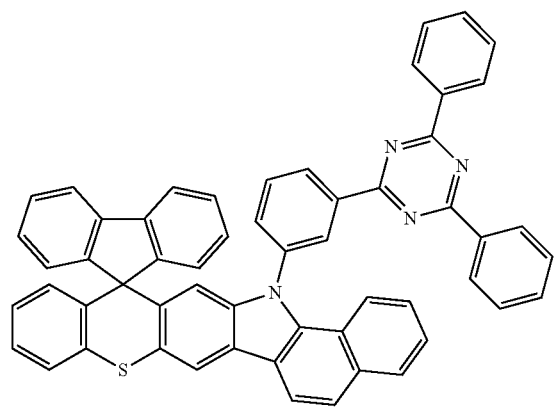
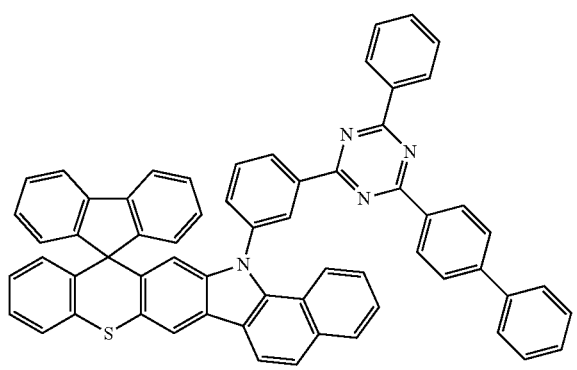
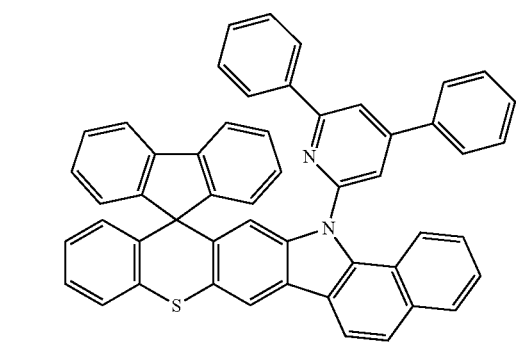
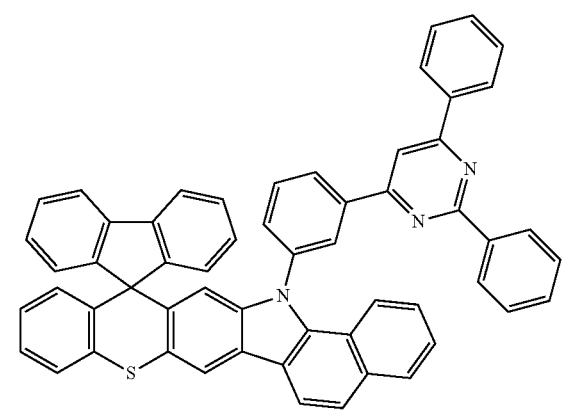
722
-continued
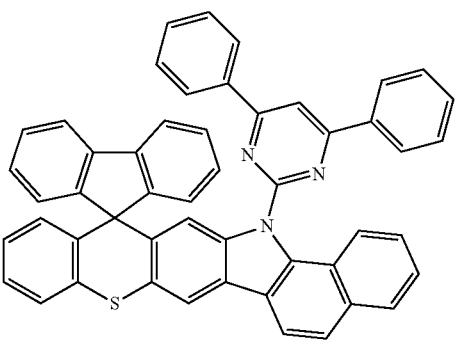
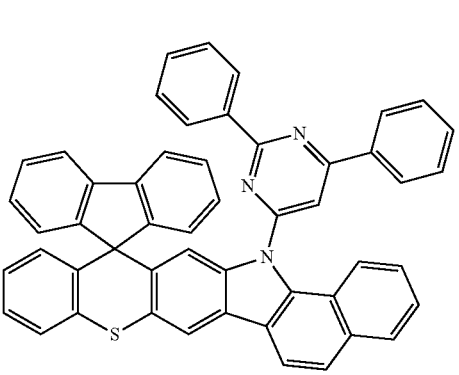
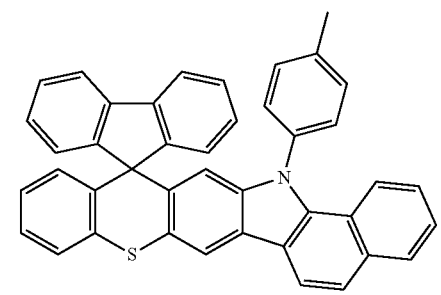
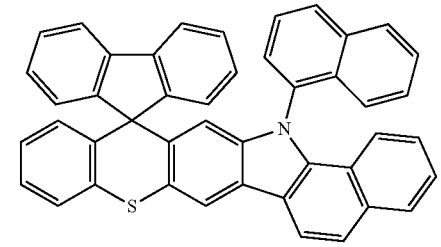
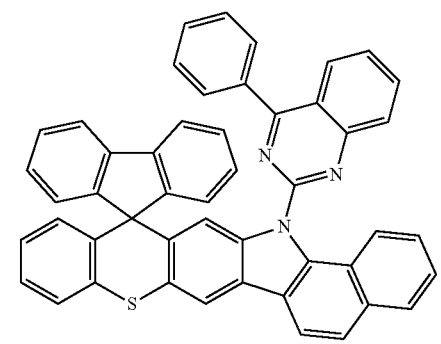

723
-continued
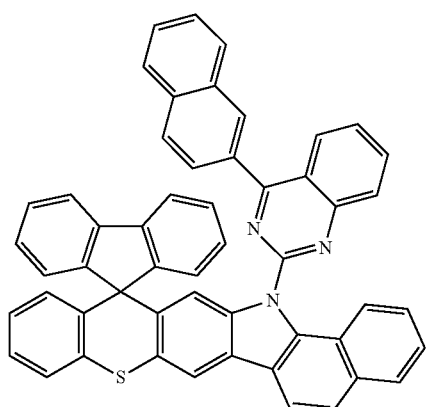
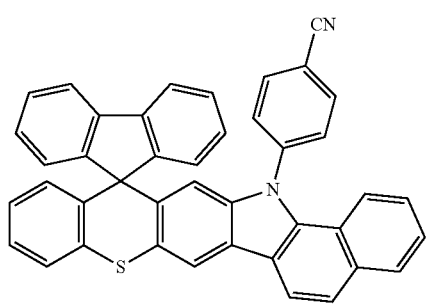
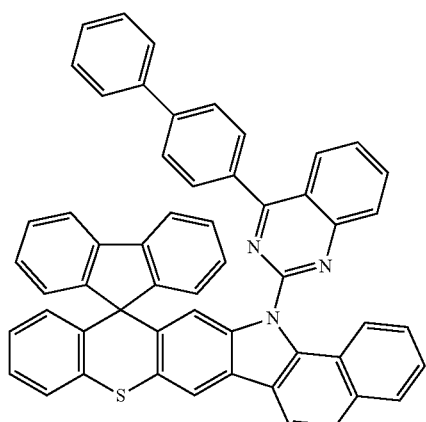
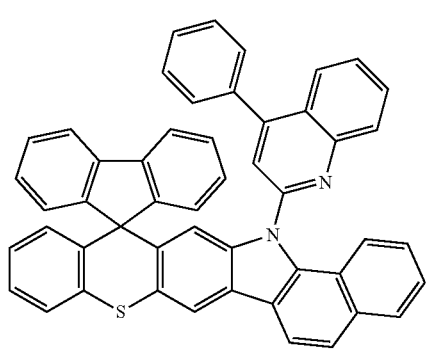
724
-continued
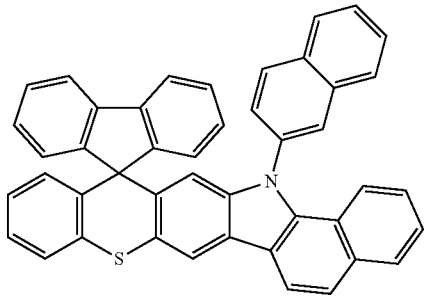
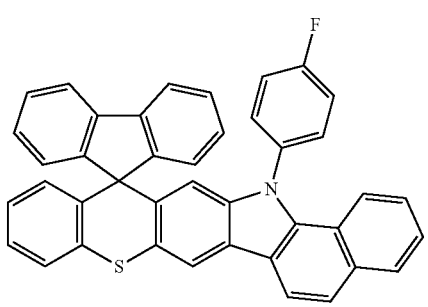
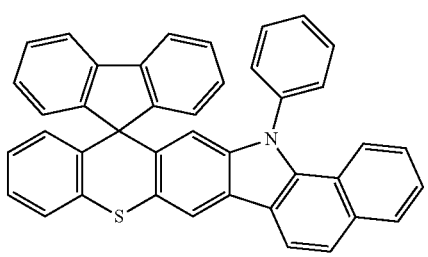
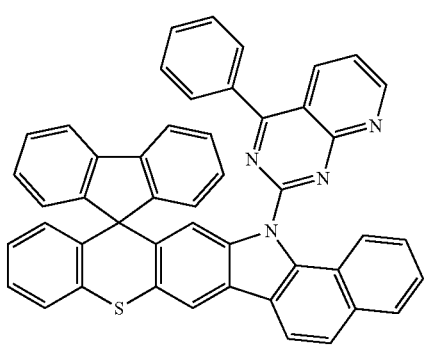
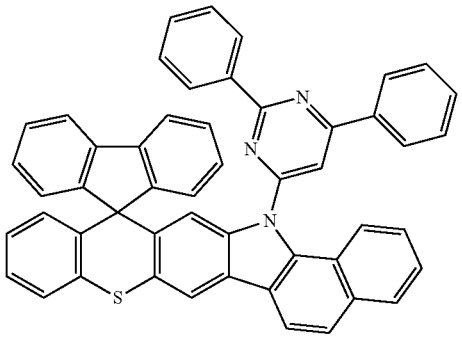

725
-continued
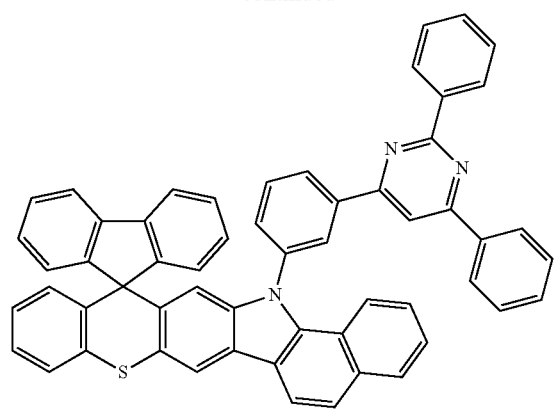
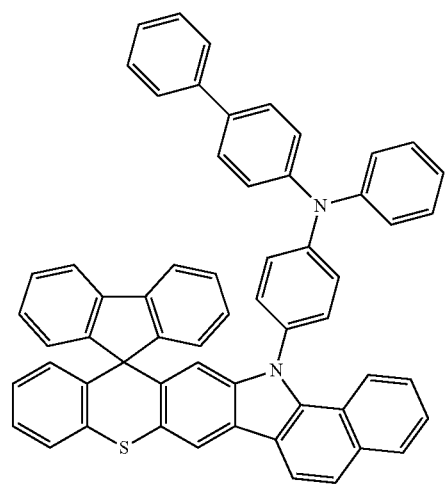
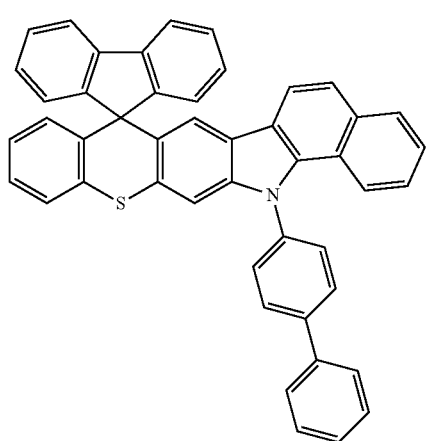
726
-continued
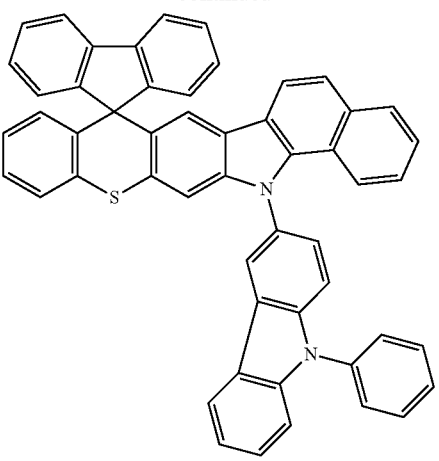
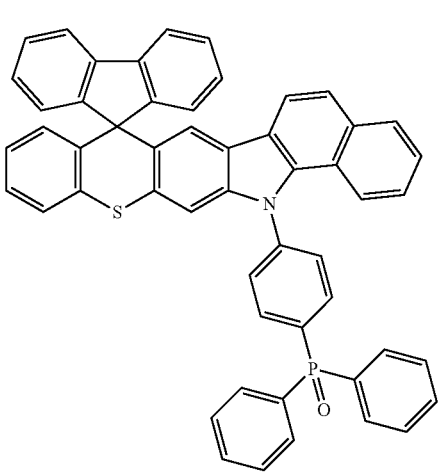
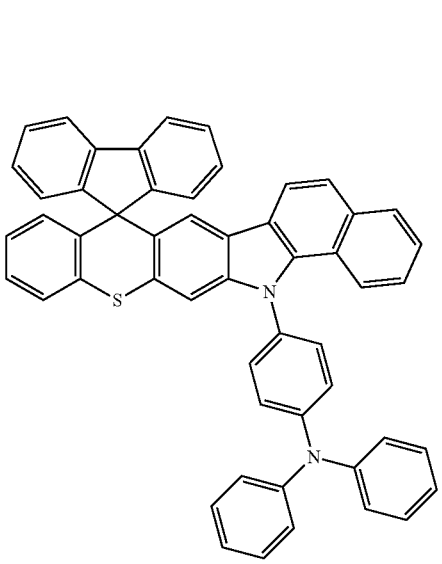

727
-continued
728
-continued
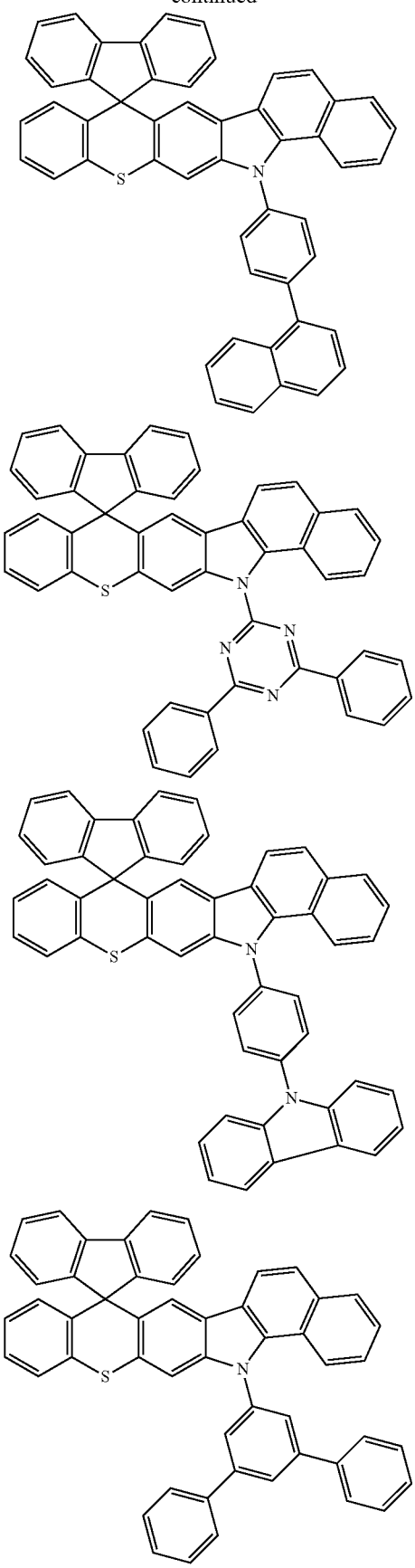
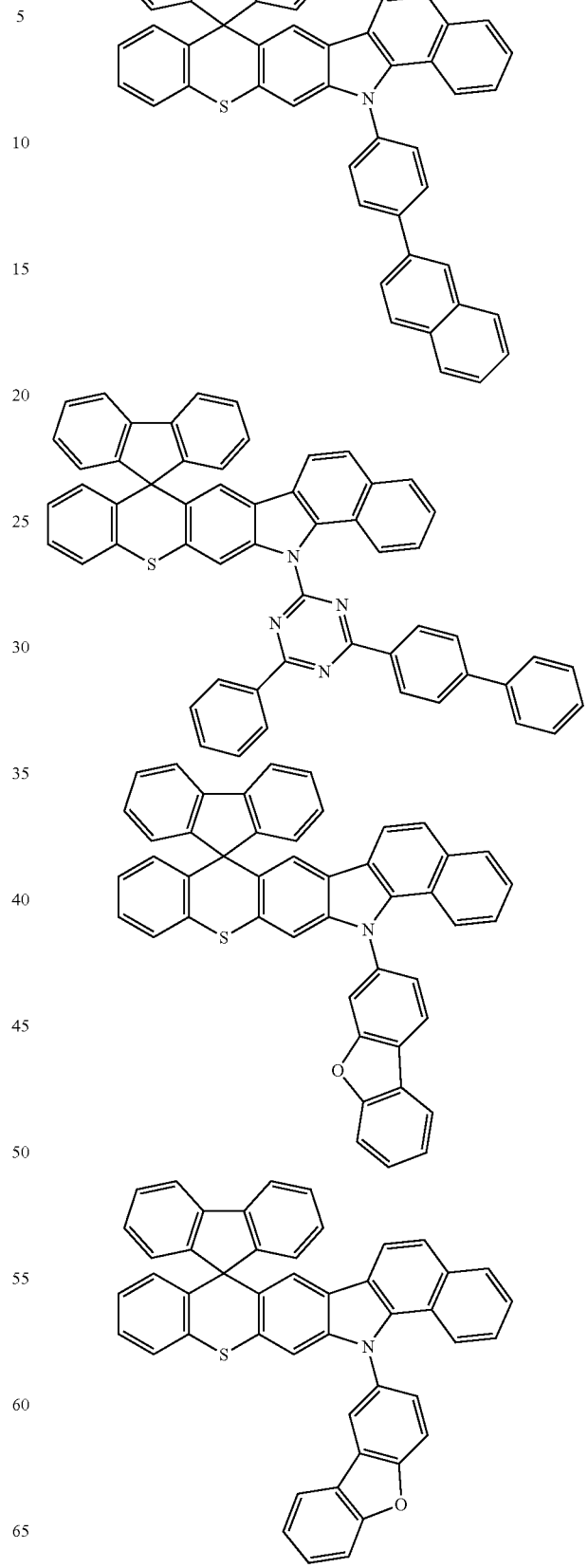

729
-continued
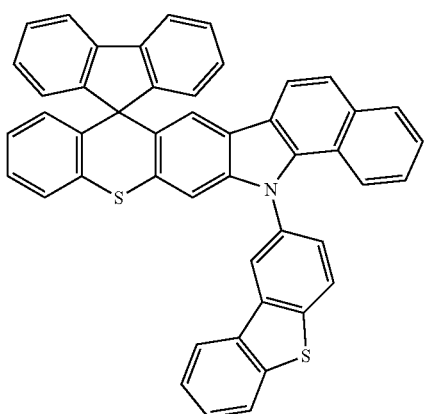
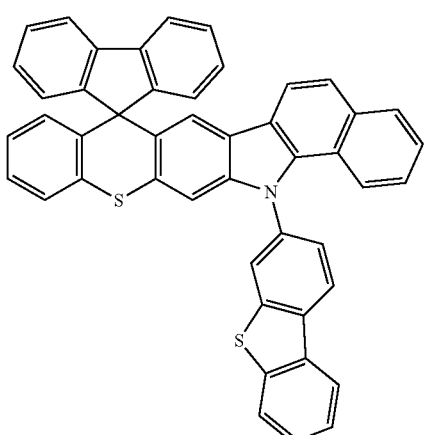
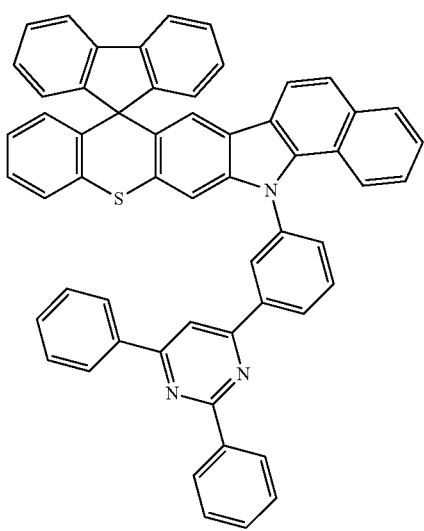
730
-continued
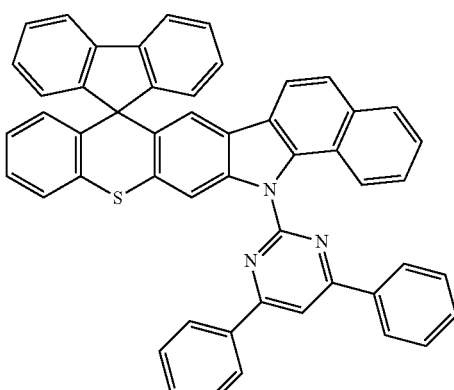
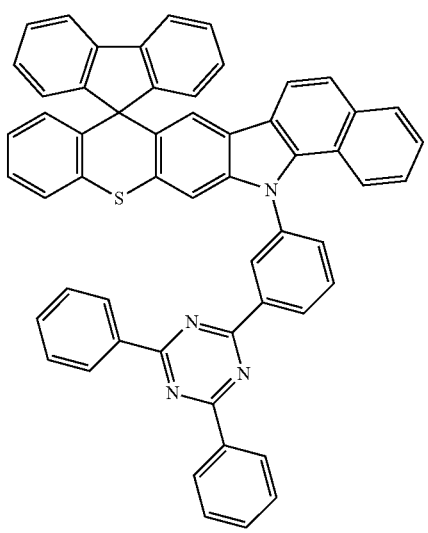
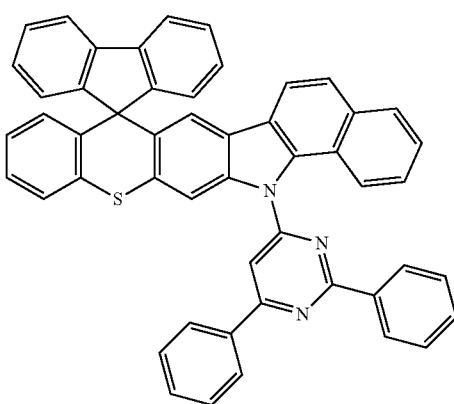

731
-continued
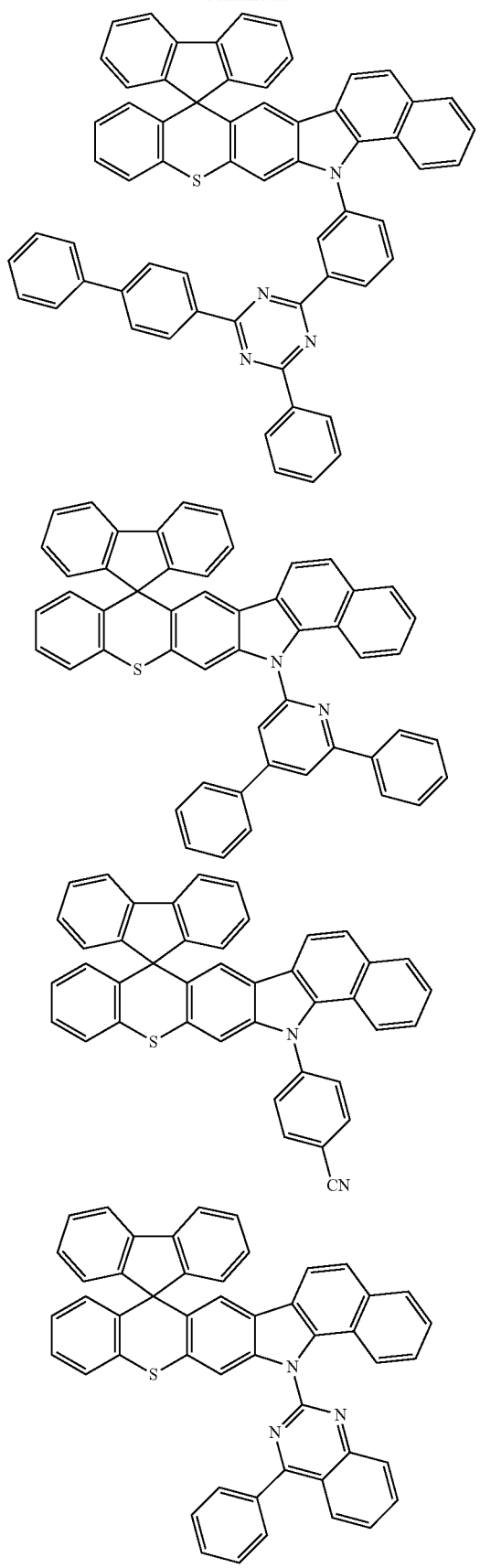
732
-continued
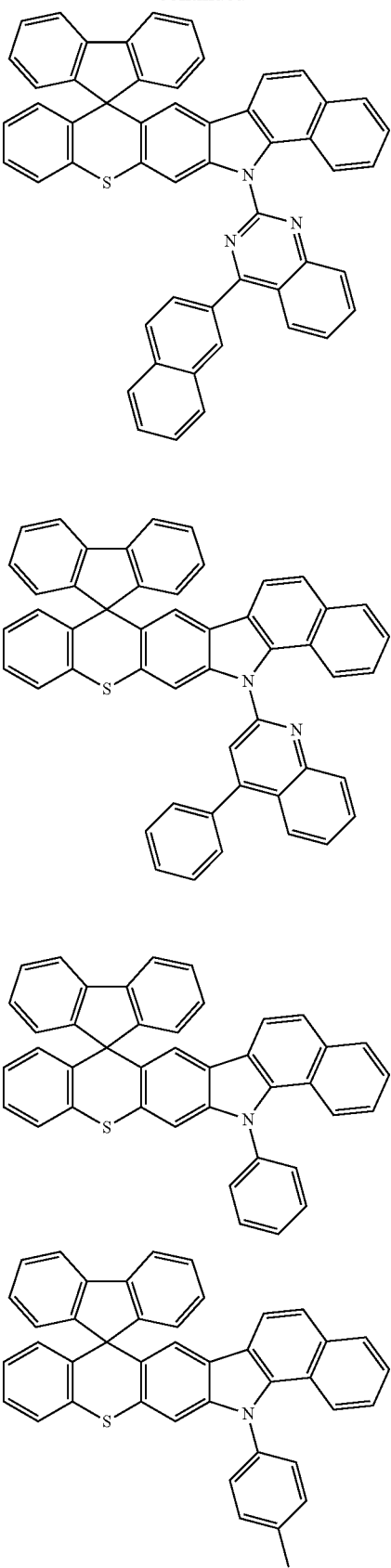

733
-continued

734
-continued

735
-continued
736
-continued
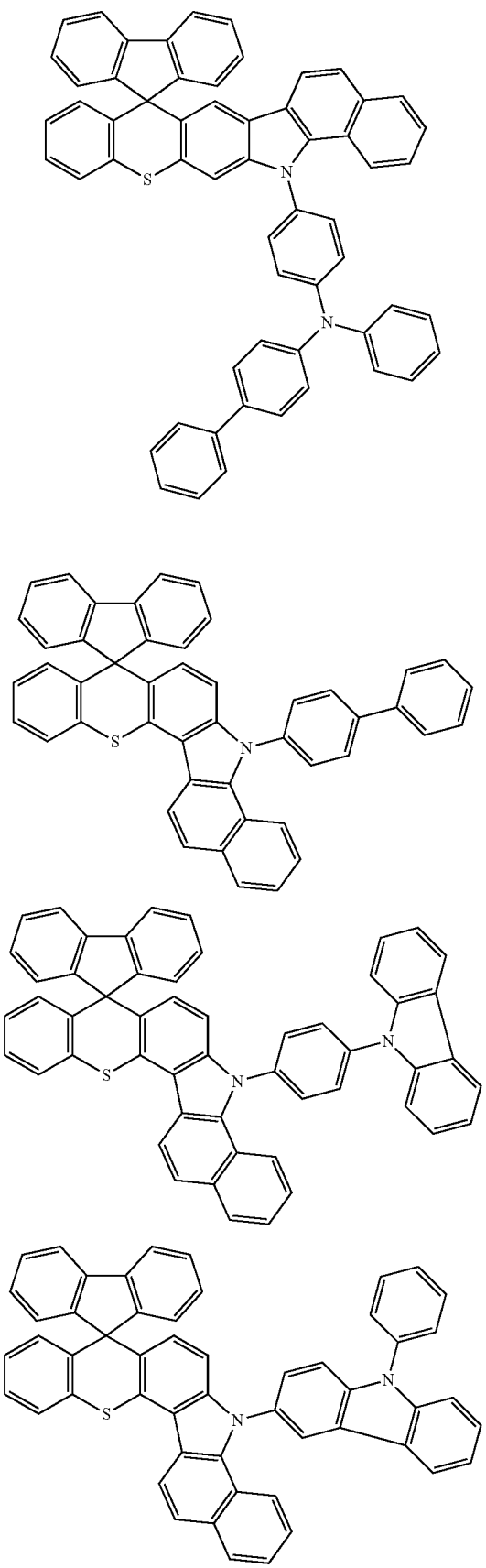
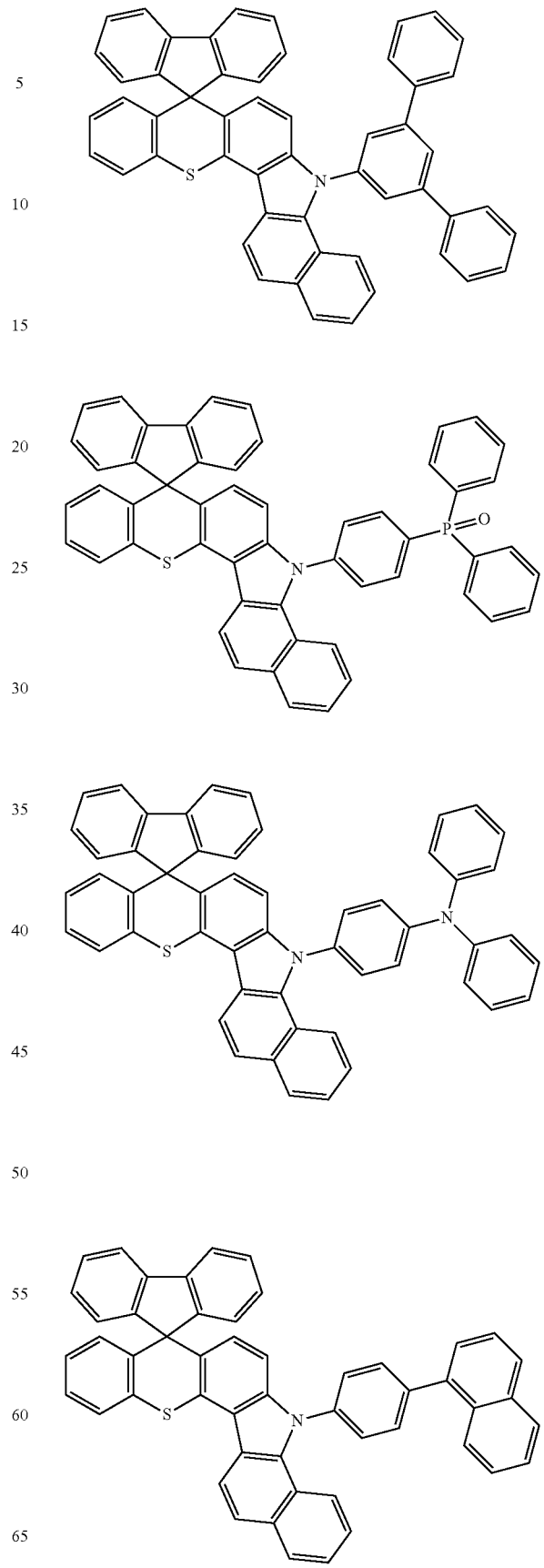

737
-continued
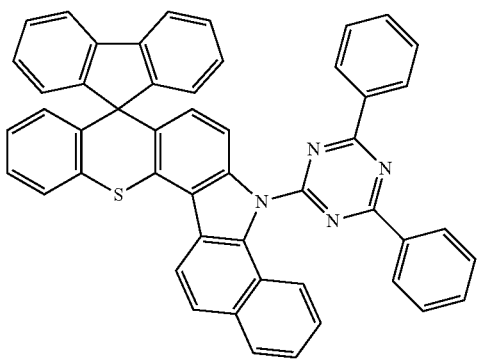
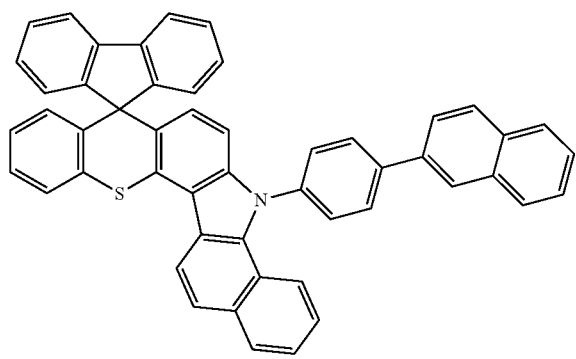
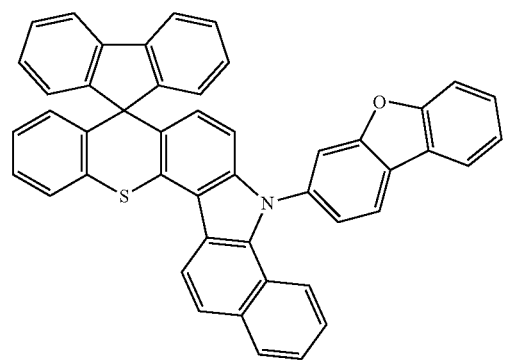
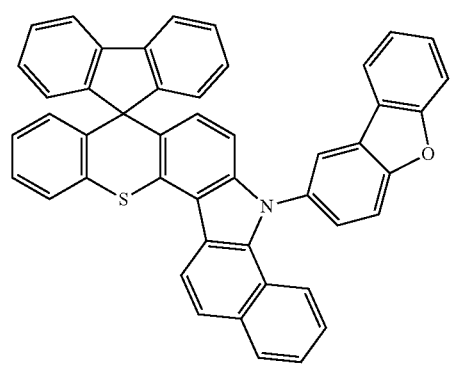
738
-continued
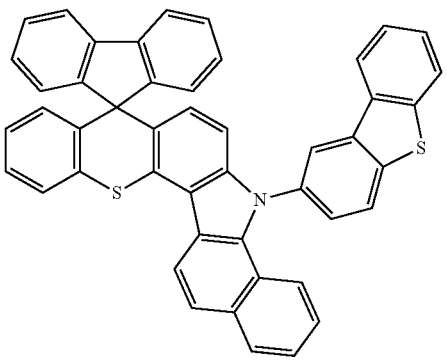
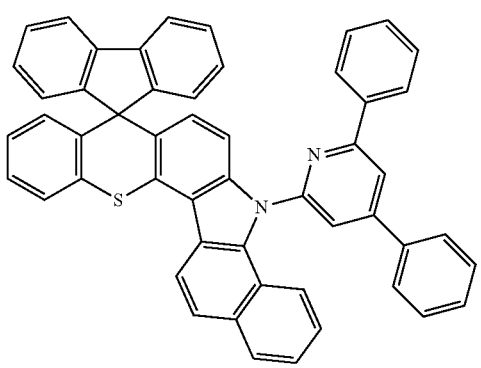
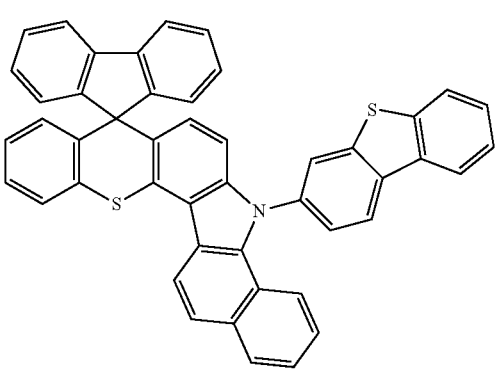
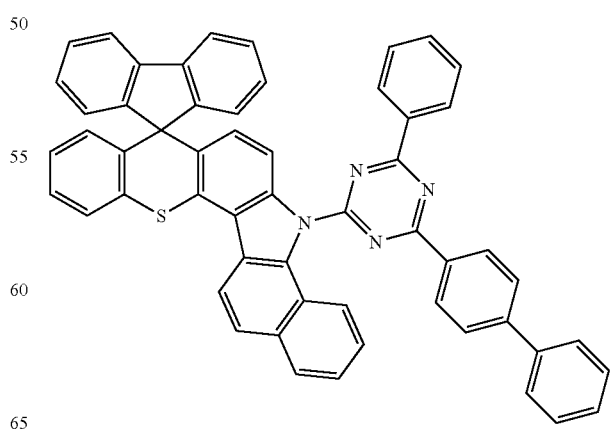

739
-continued
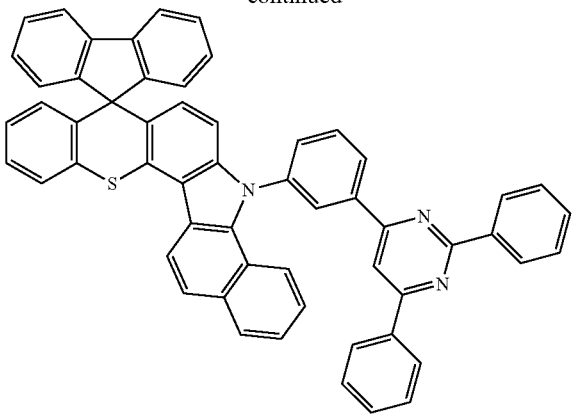
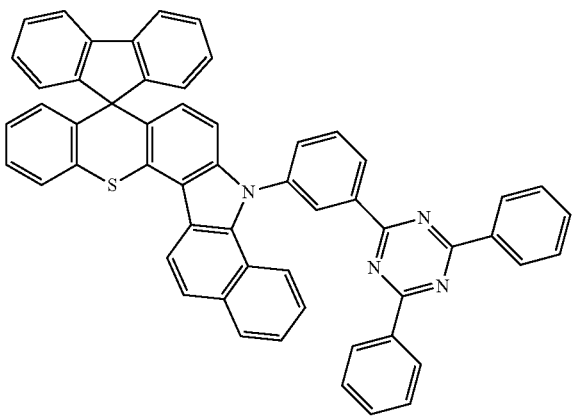
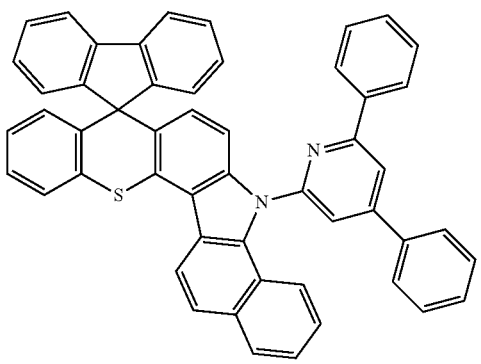
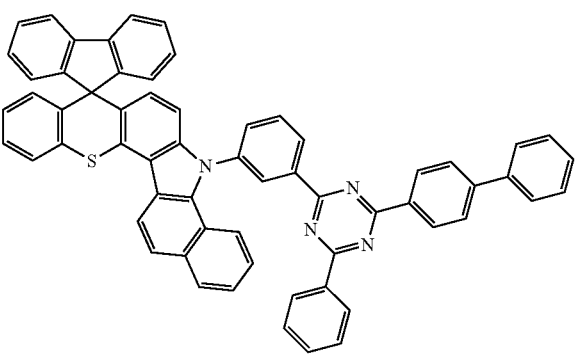
740
-continued
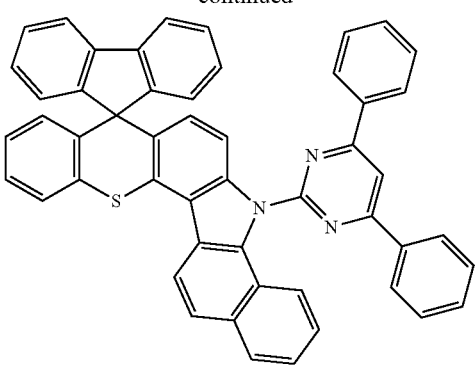
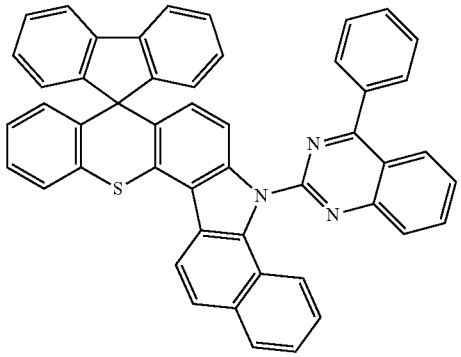
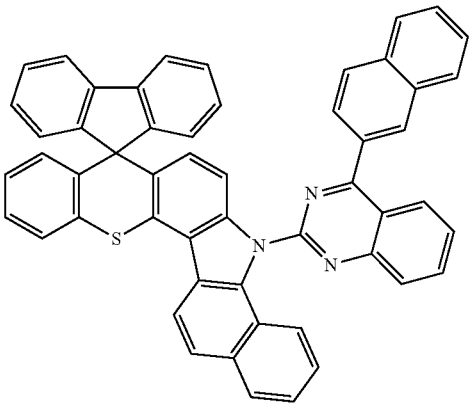
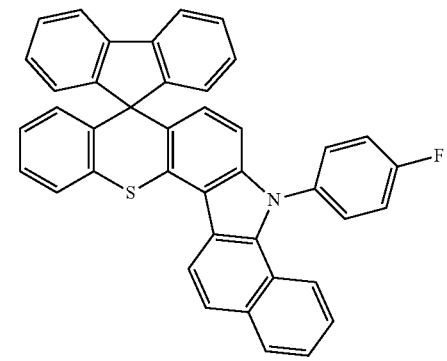

741
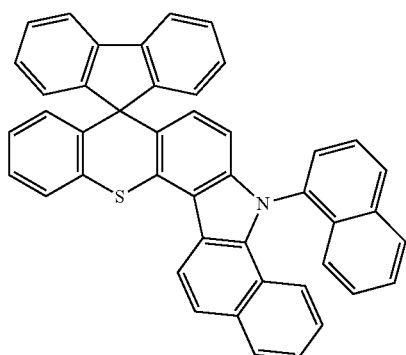
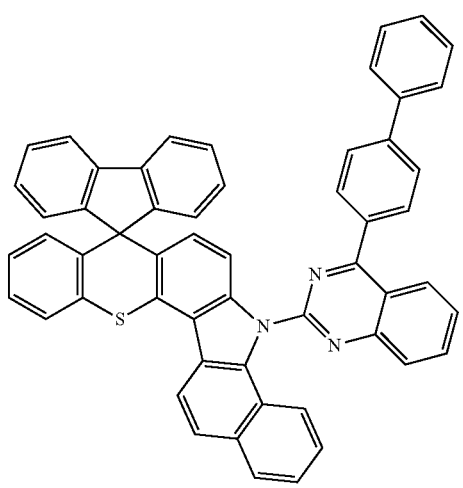
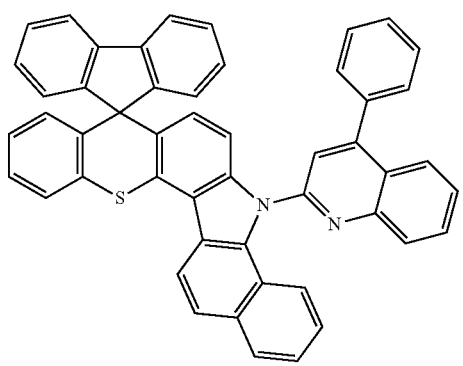
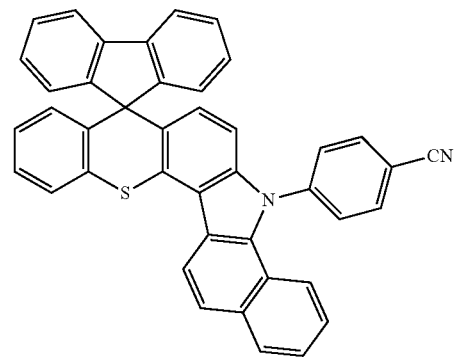
742
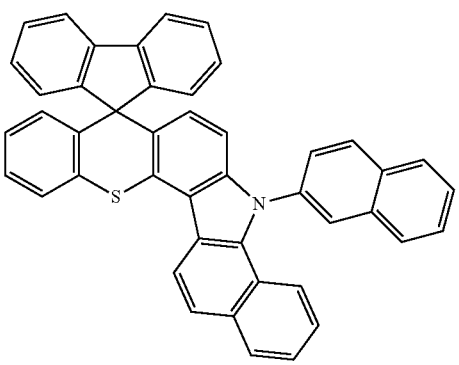
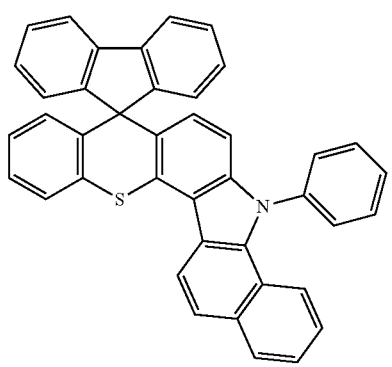
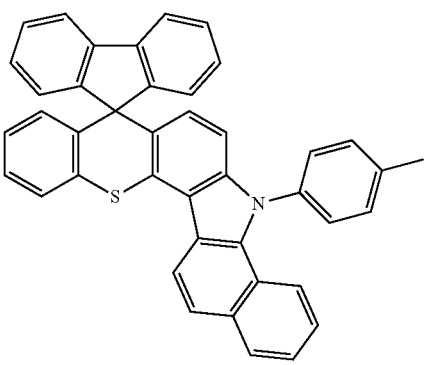
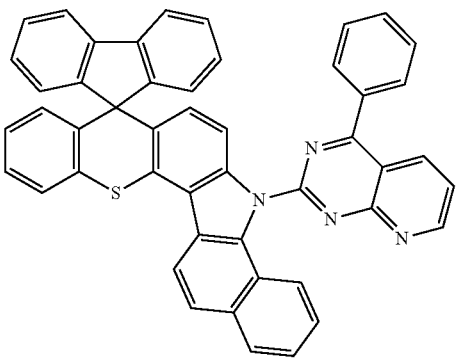

743
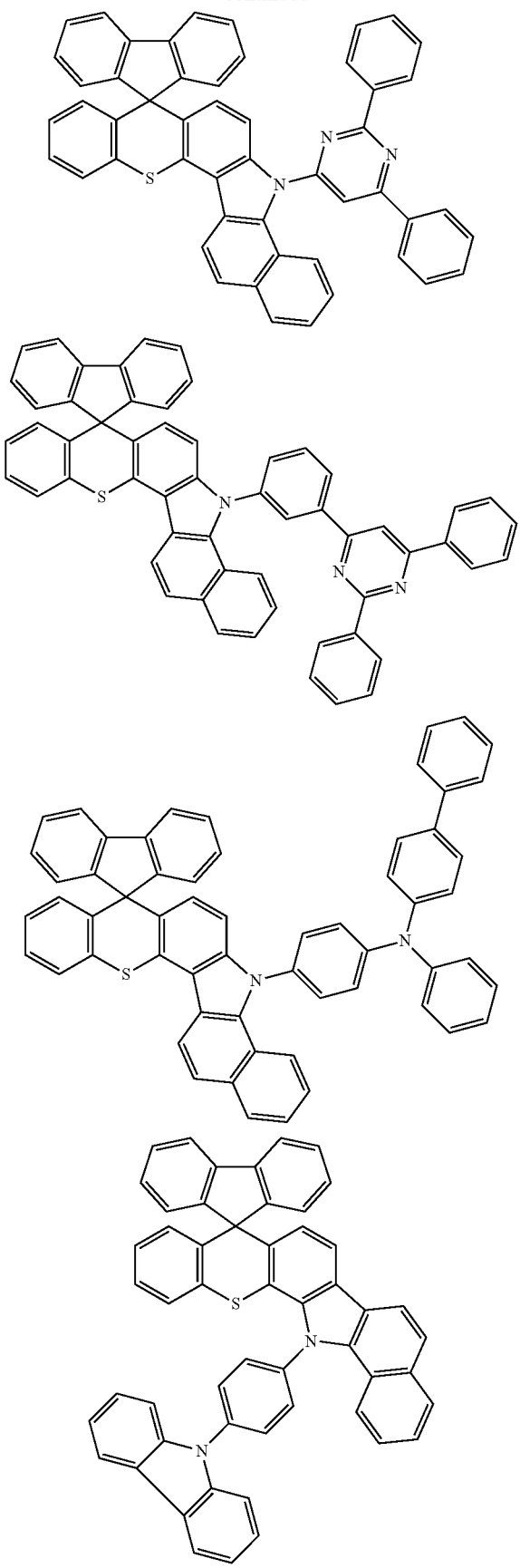
744
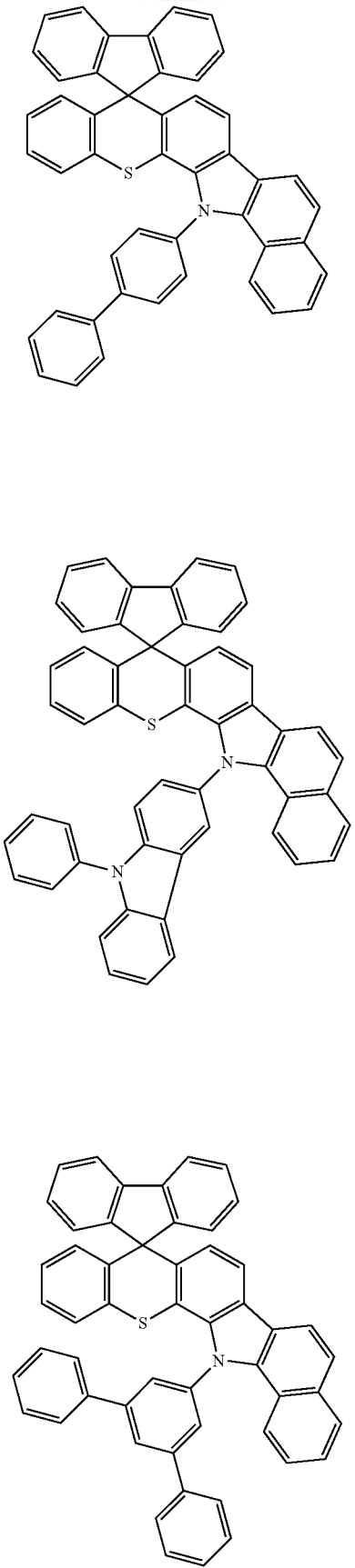

745
-continued
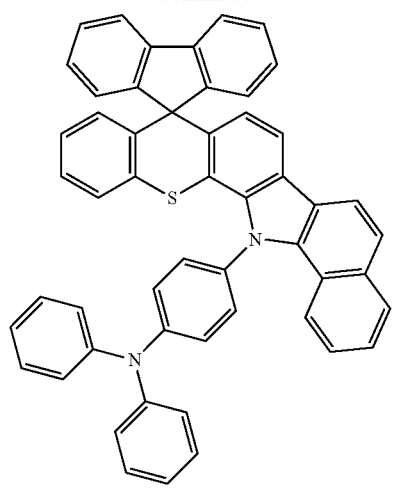
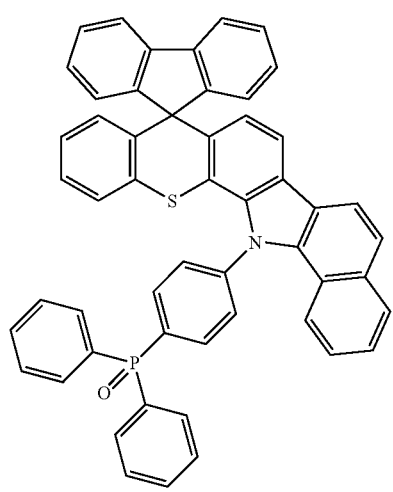
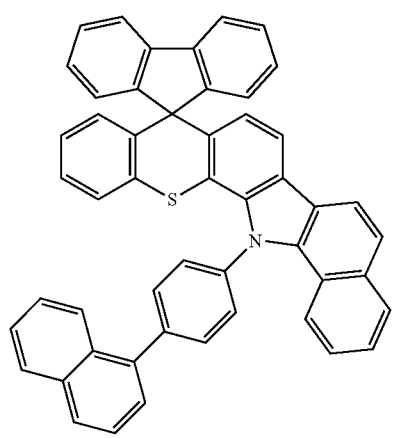
746
-continued
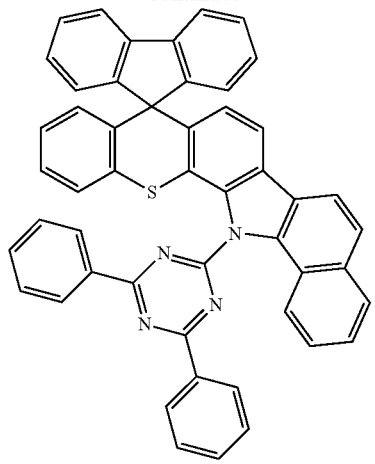
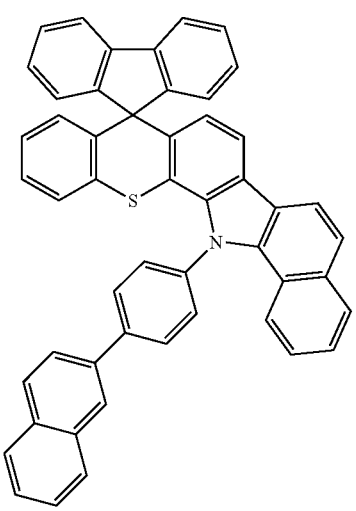
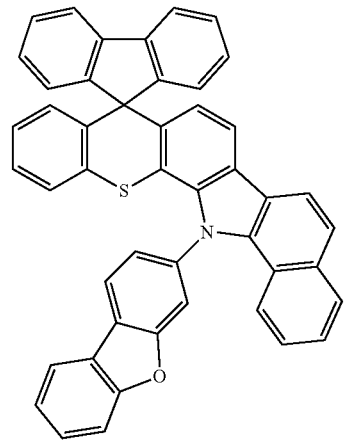

747
-continued
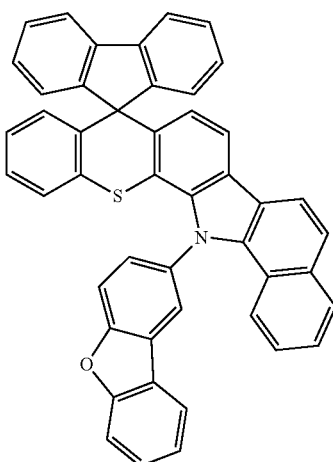
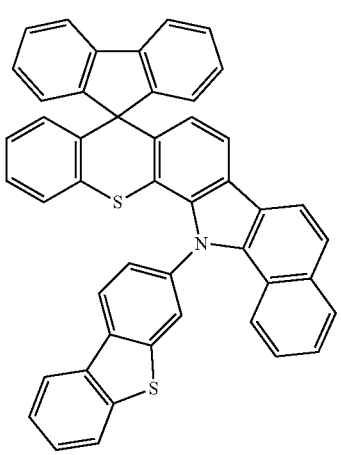
748
-continued
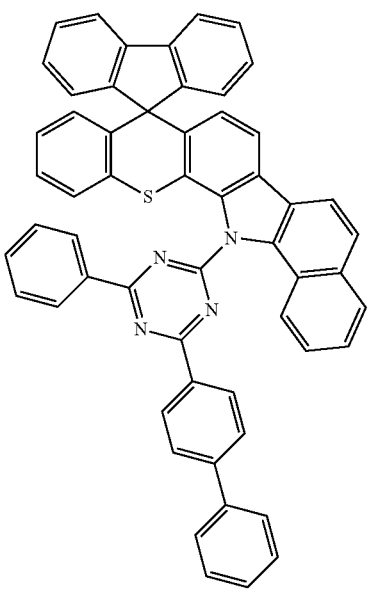
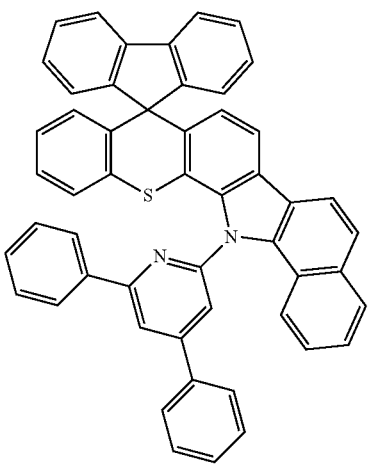
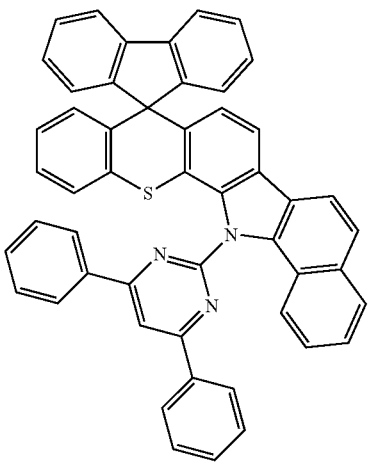

749
-continued
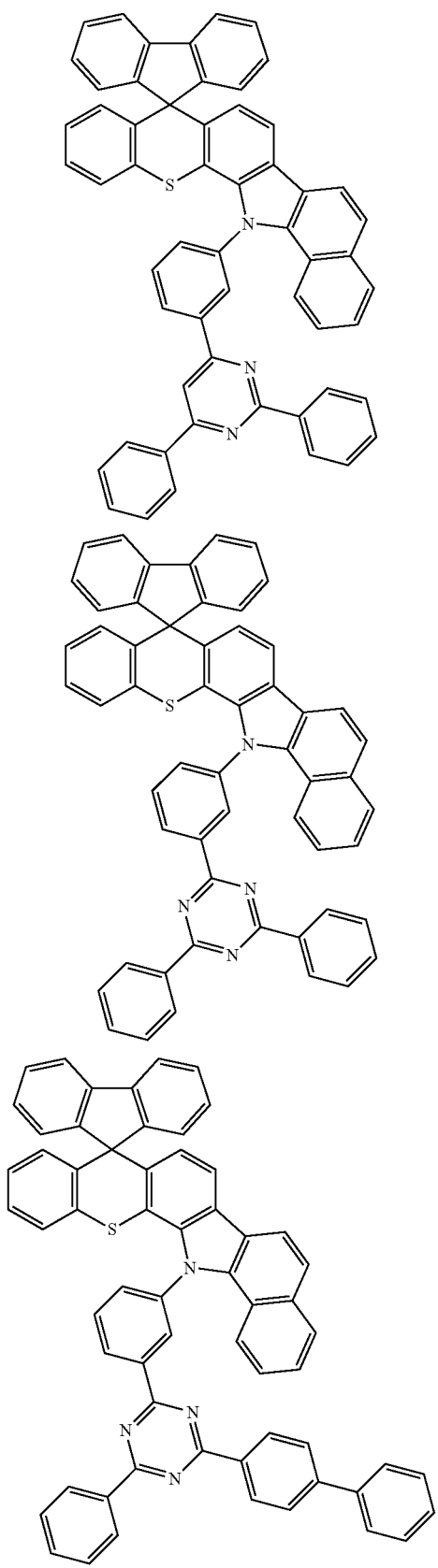
750
-continued
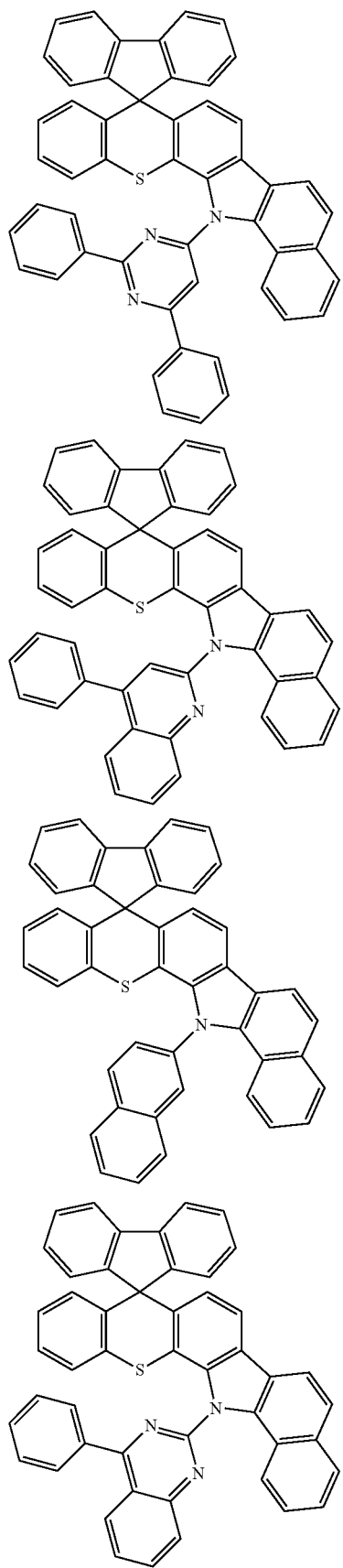

751
-continued
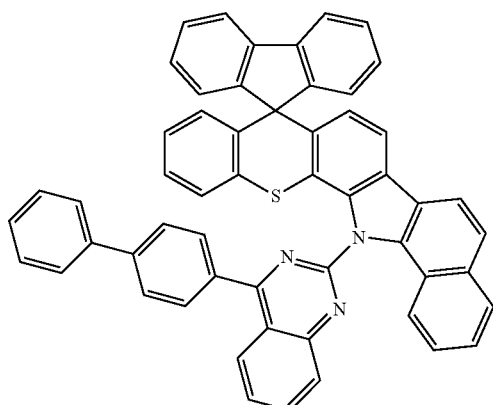
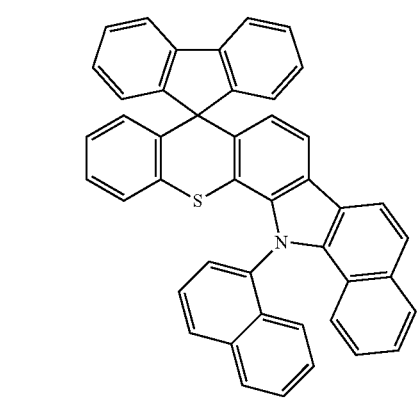
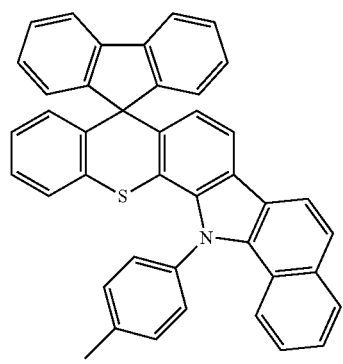
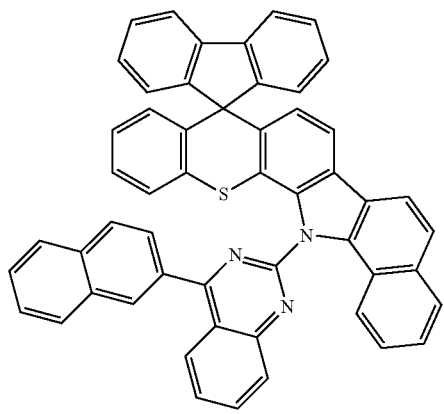
752
-continued
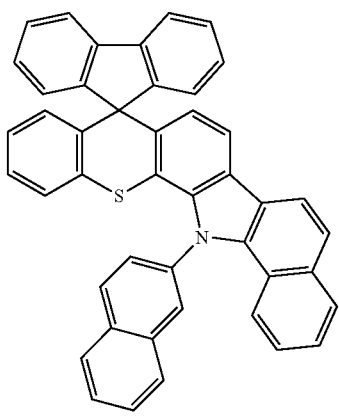
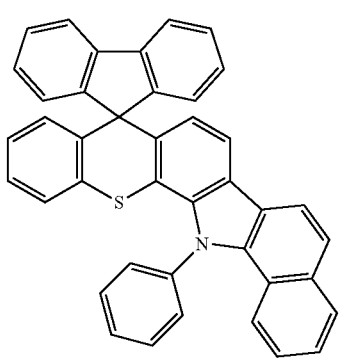
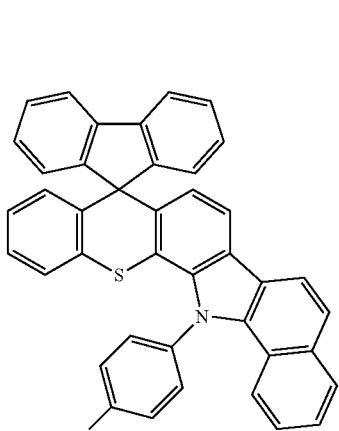
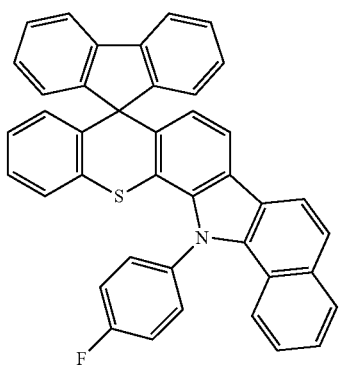

753
-continued
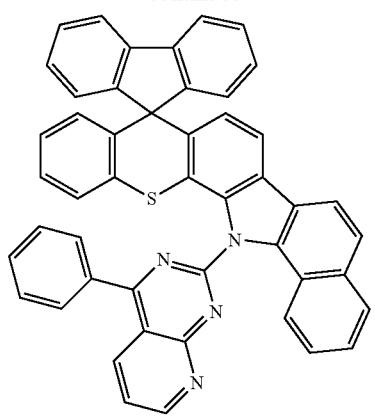
754
-continued
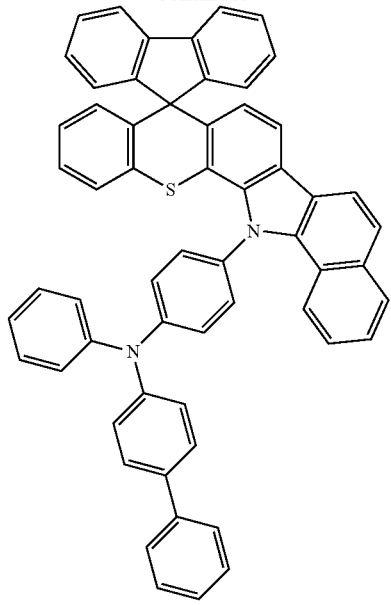
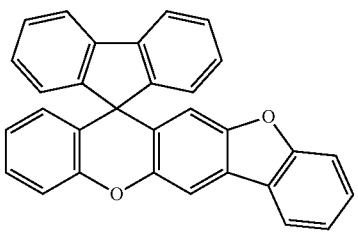
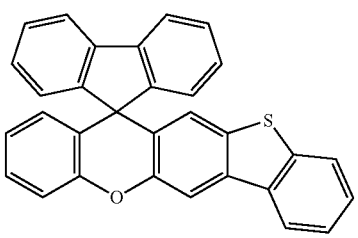
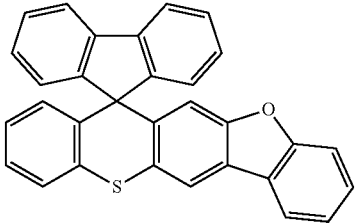
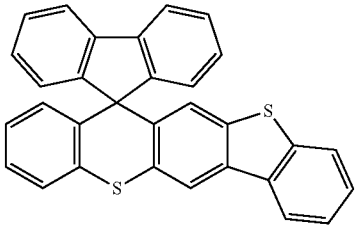

755
-continued
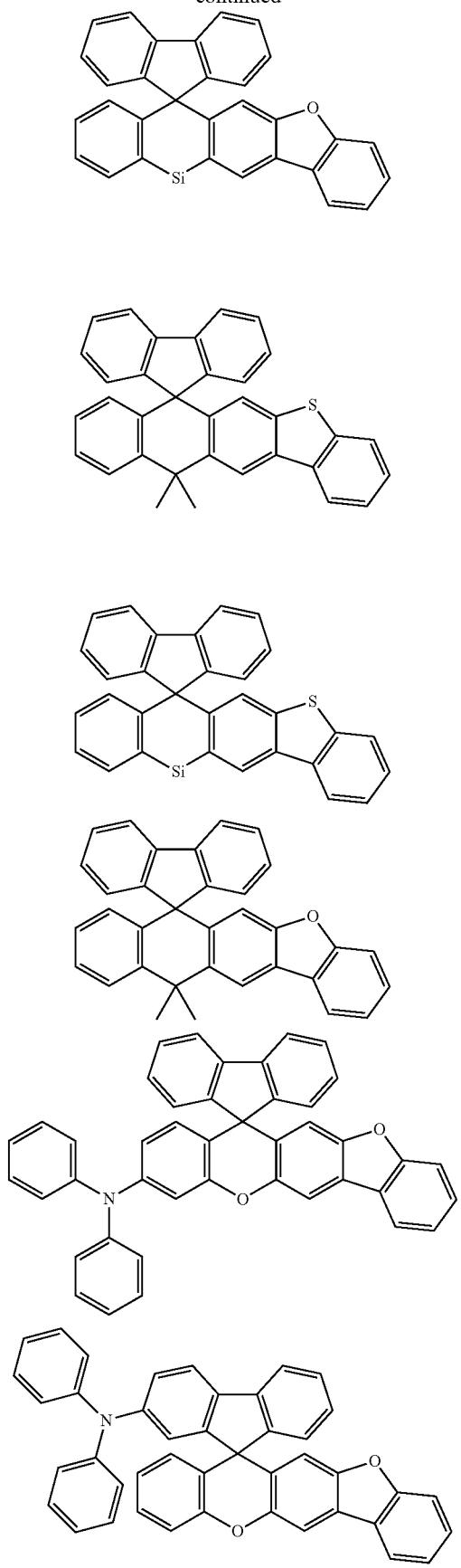
756
-continued
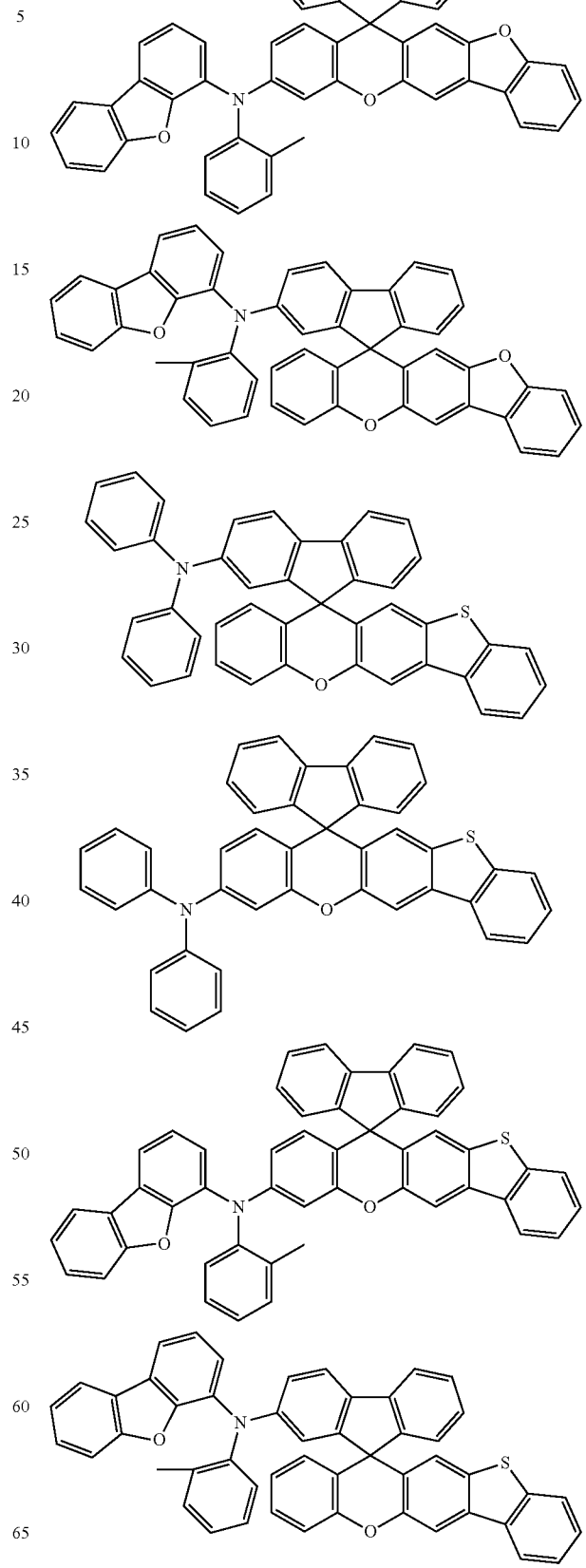

757
-continued
758
-continued
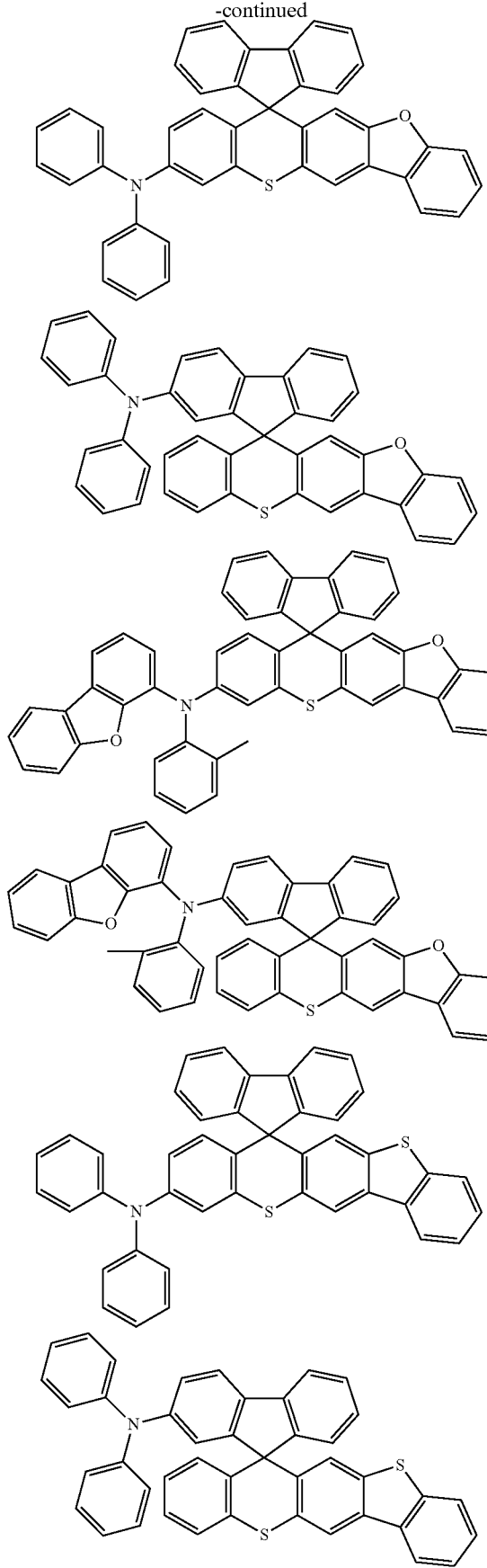
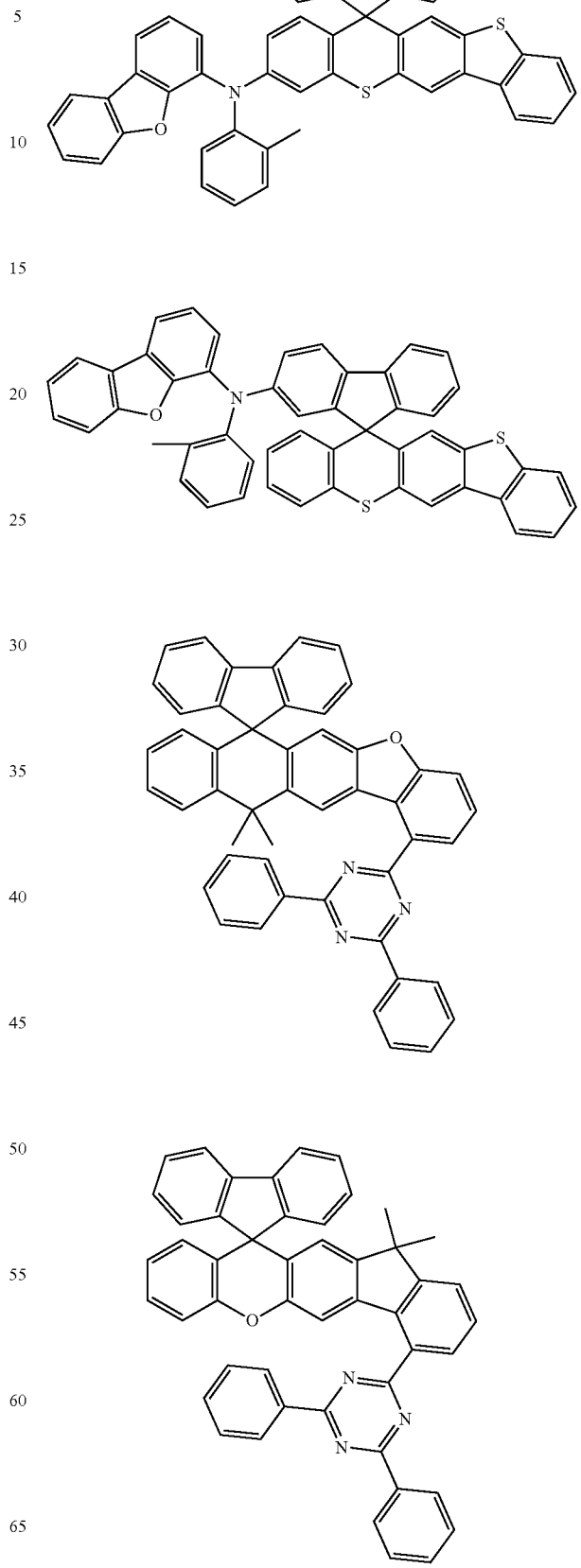

759
-continued
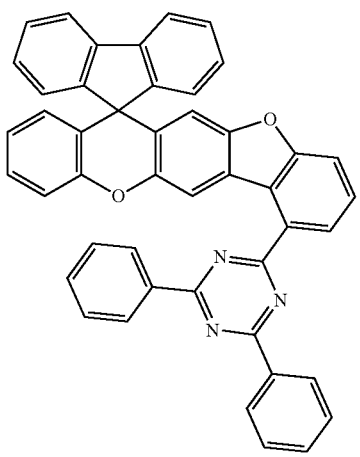
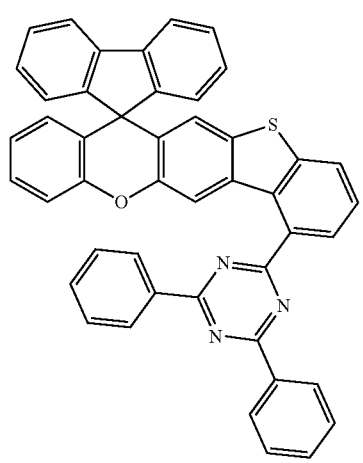
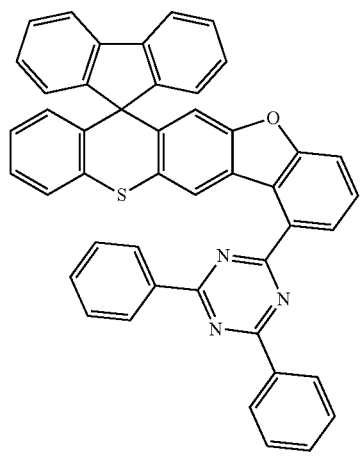
760
-continued
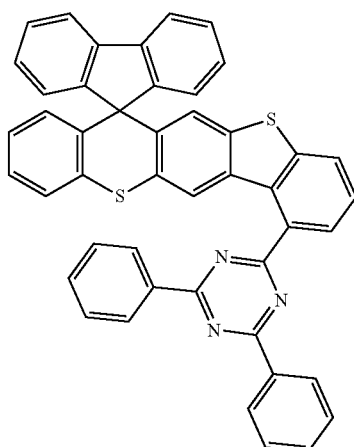
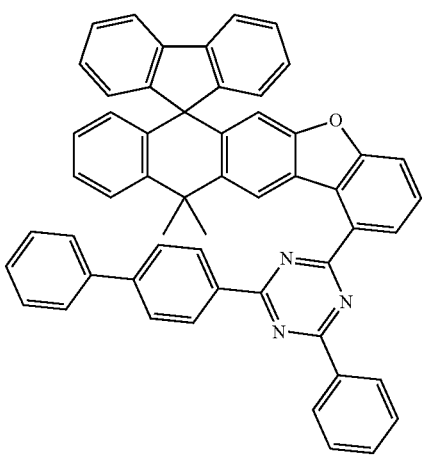
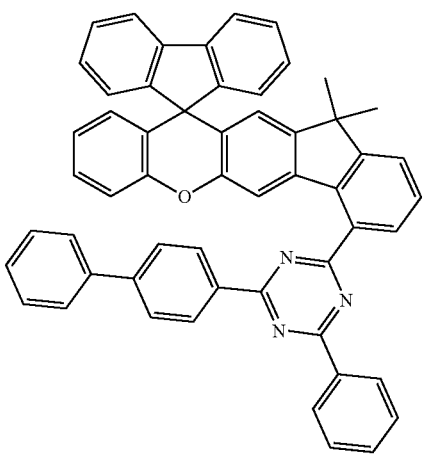

761
-continued
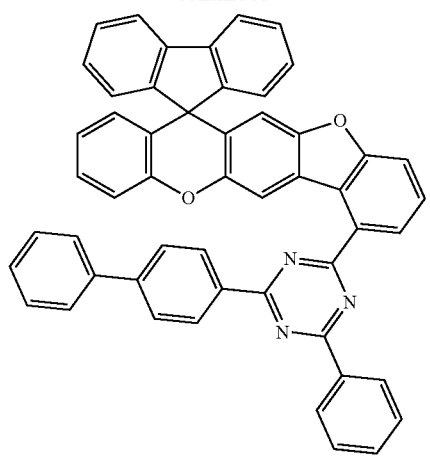
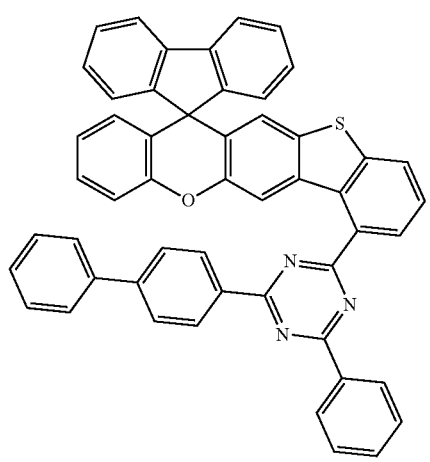
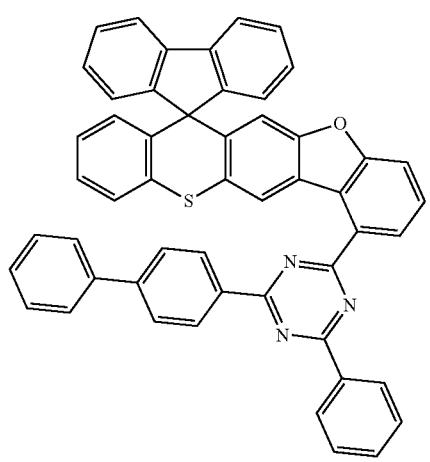
762
-continued
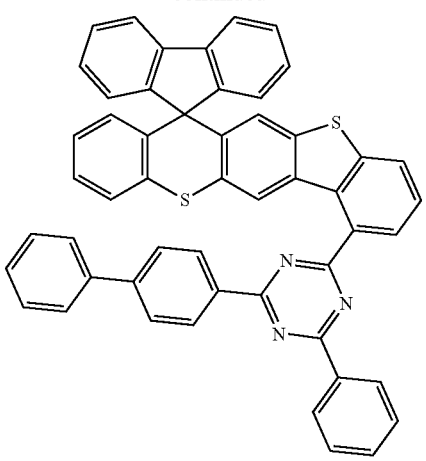
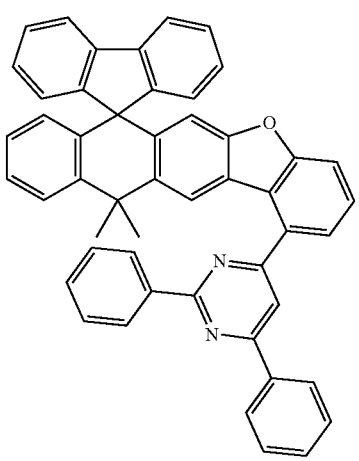
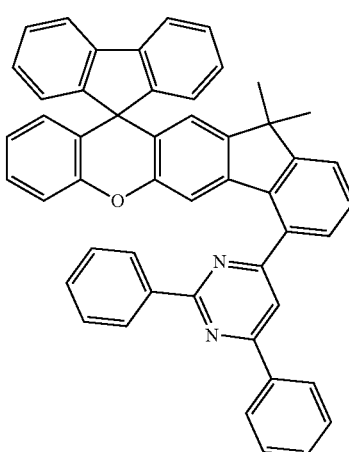

763
-continued
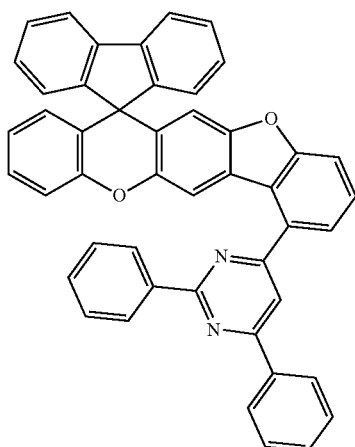
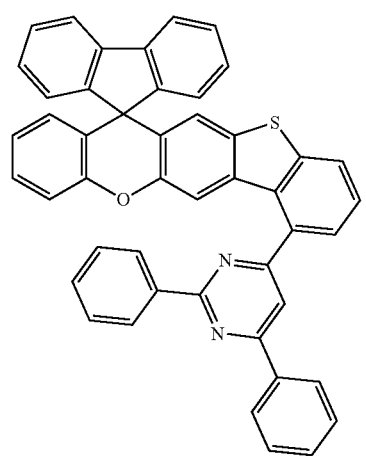
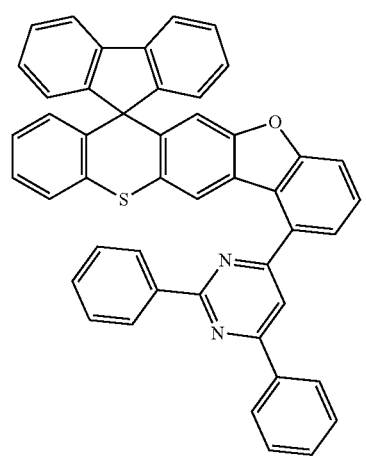
764
-continued
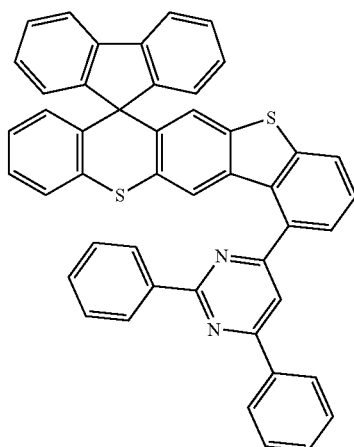
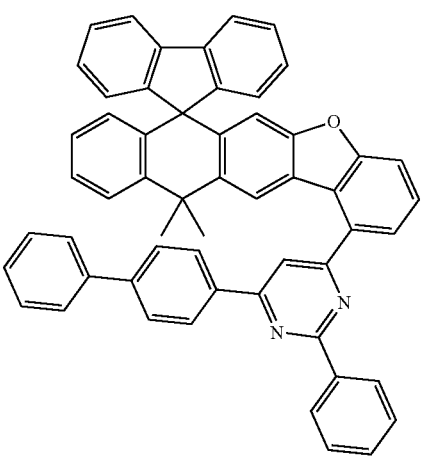
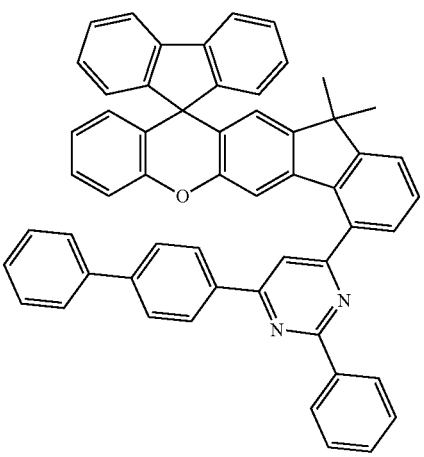

765
-continued
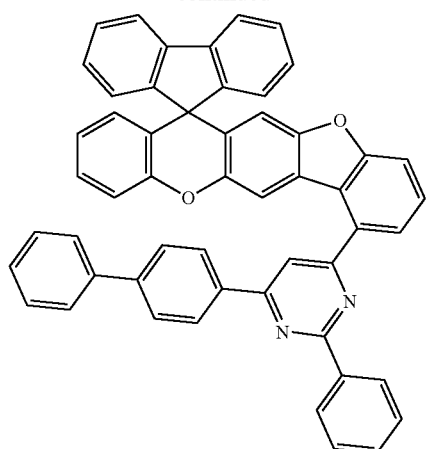
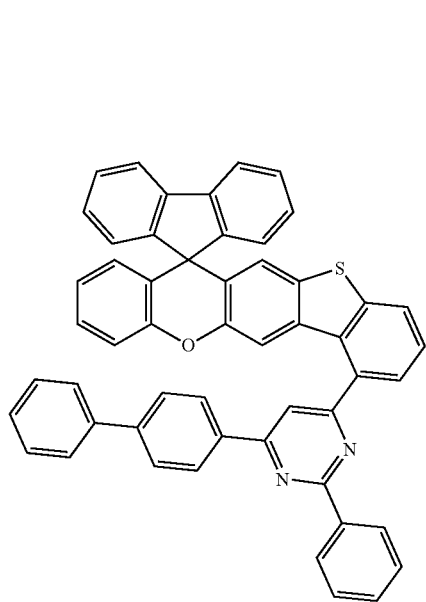
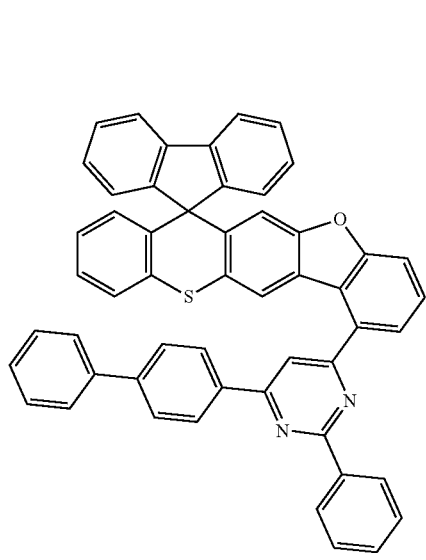
766
-continued
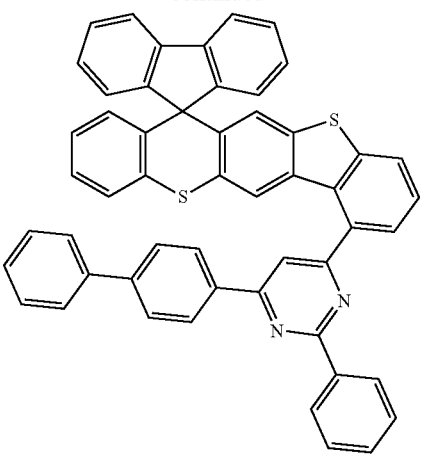
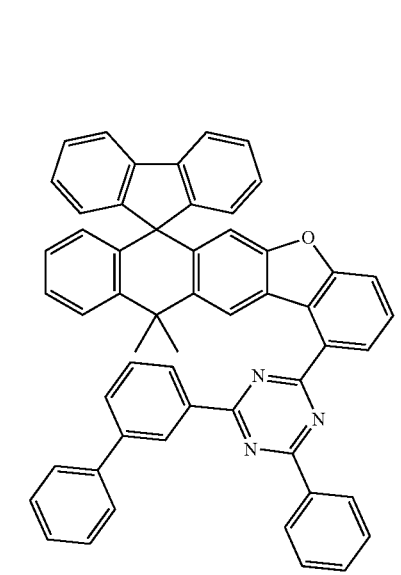
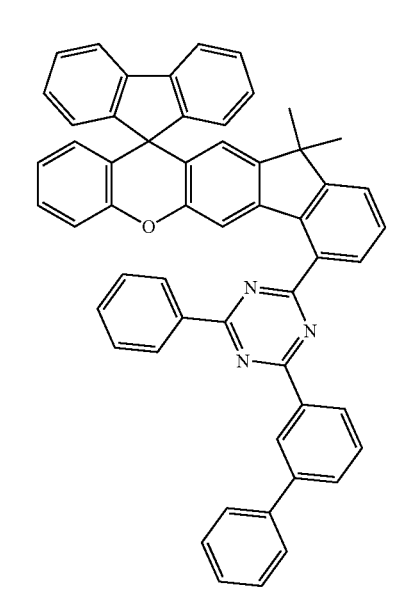

767
-continued
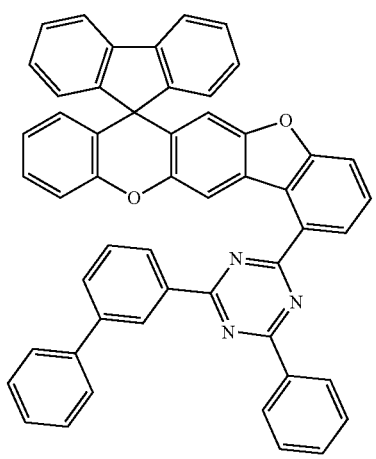
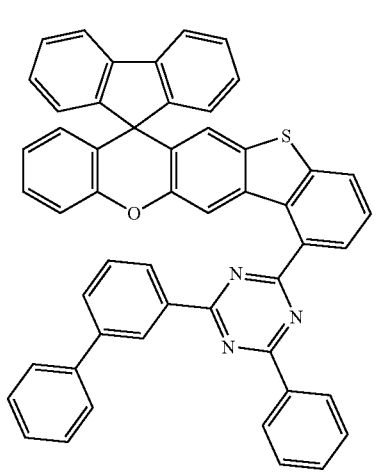
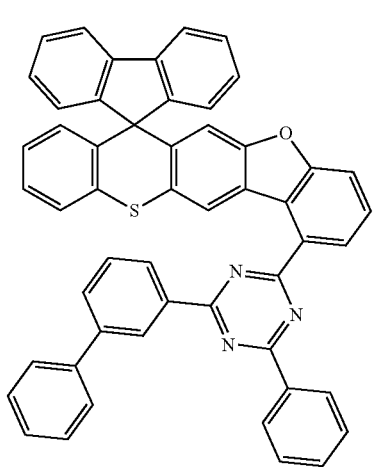
768
-continued
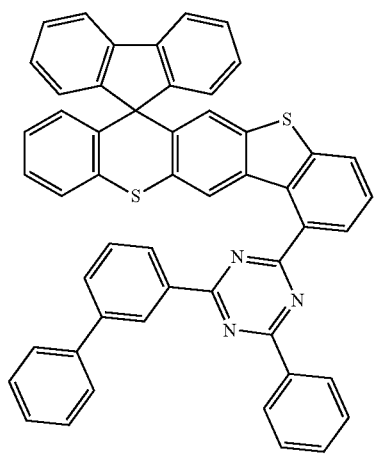
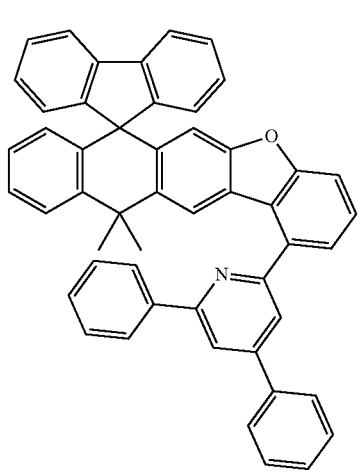
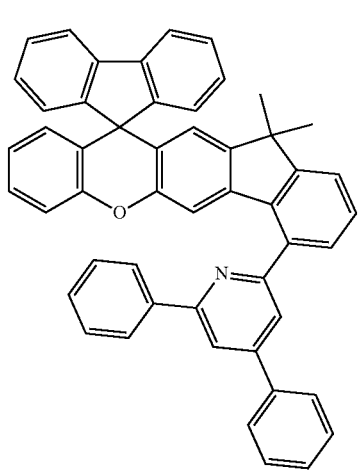

769
-continued
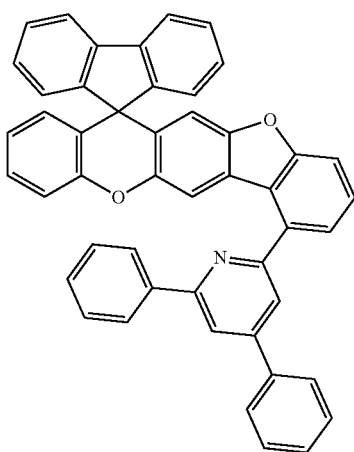
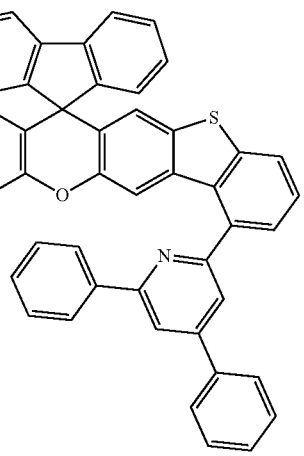
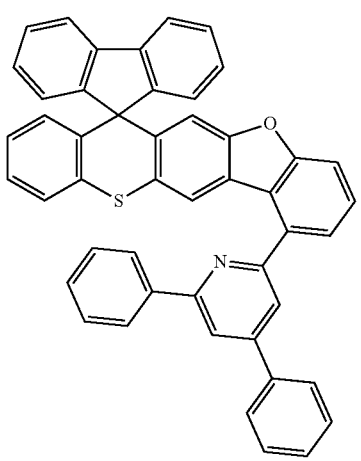
770
-continued
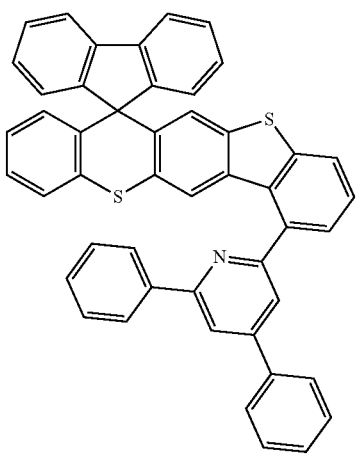
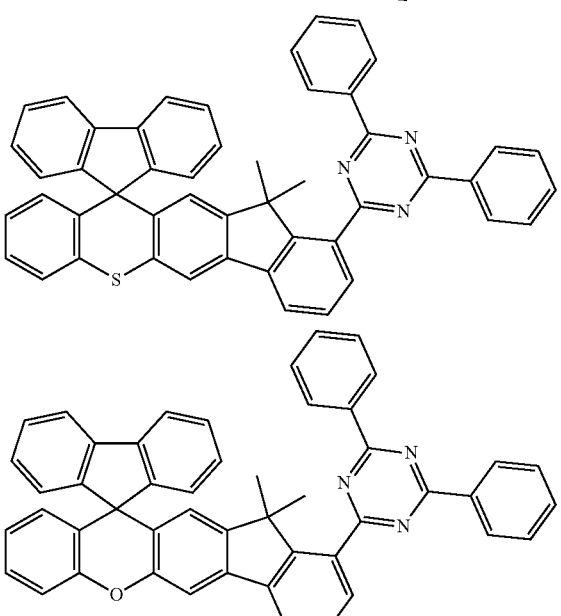
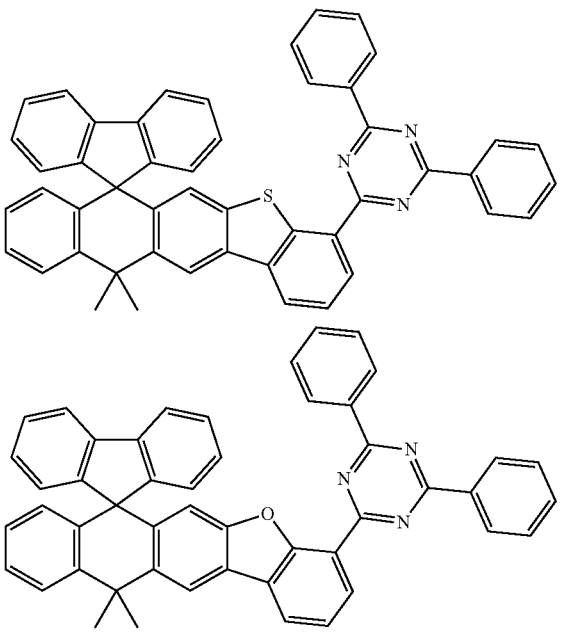

771
-continued
772
-continued
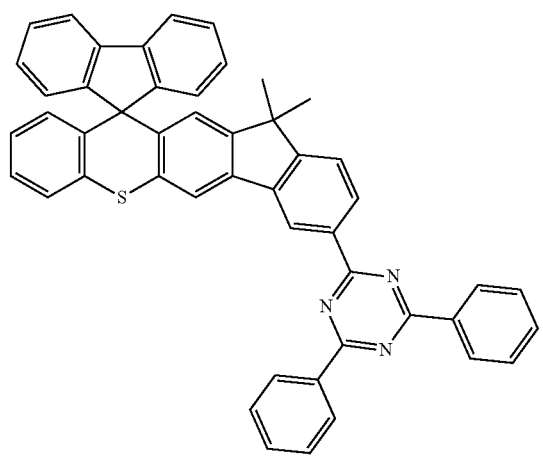
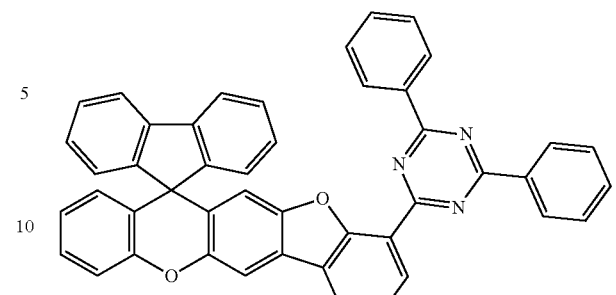
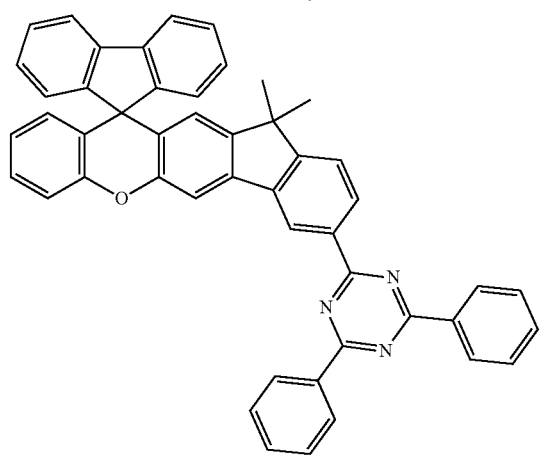
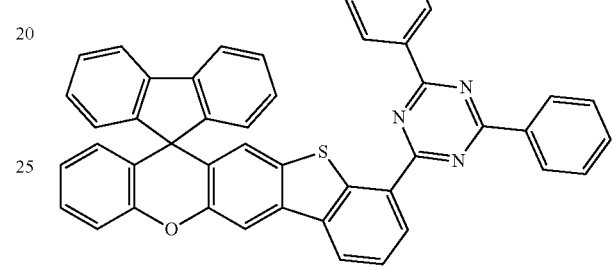
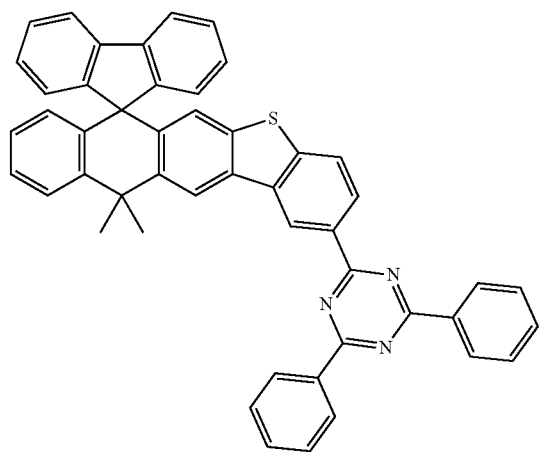
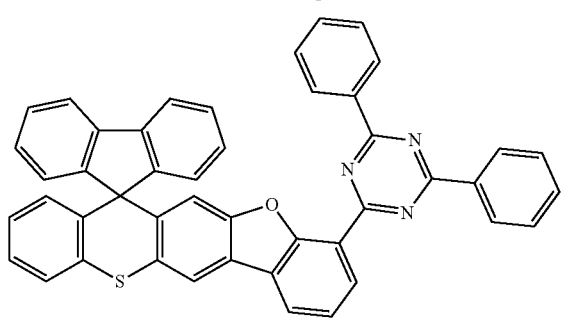
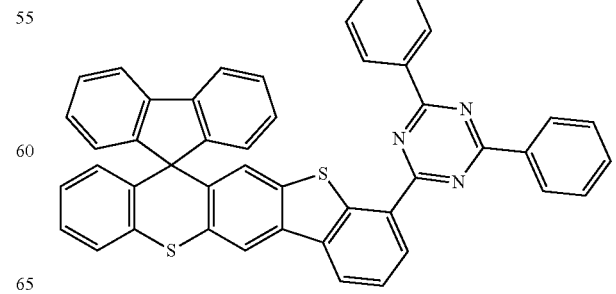

773
-continued
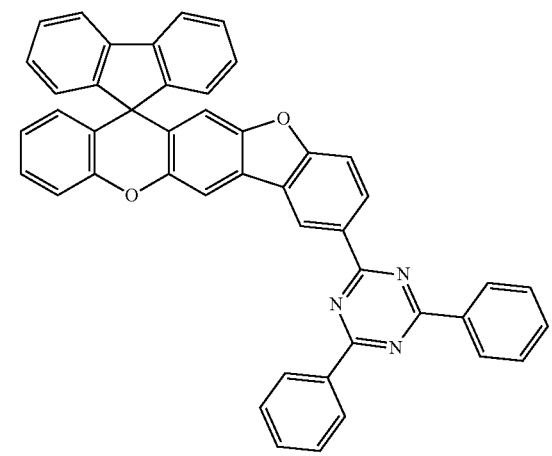
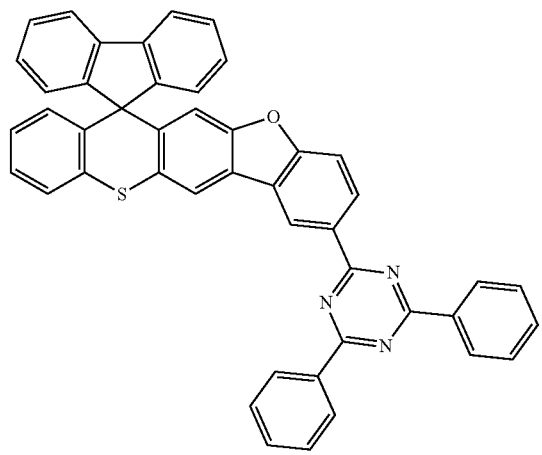
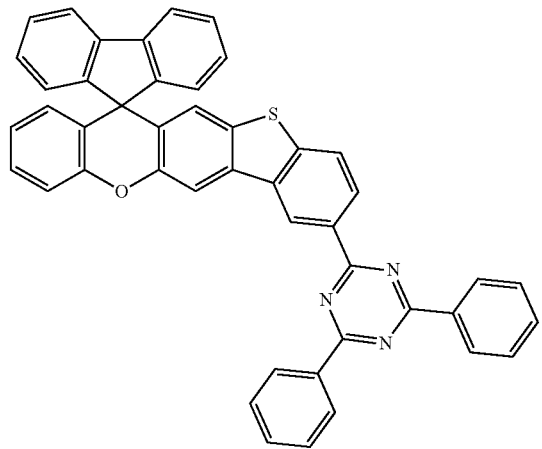
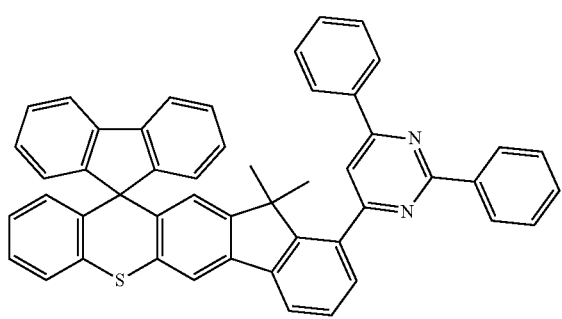
774
-continued
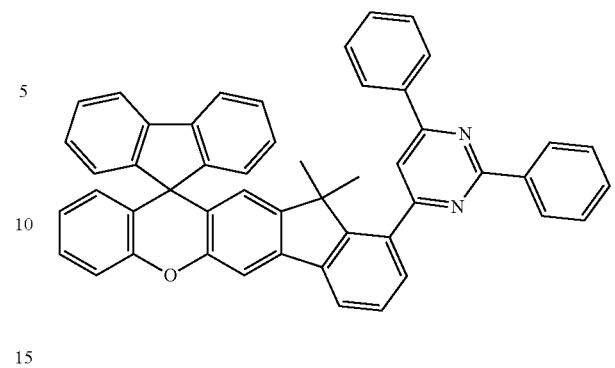
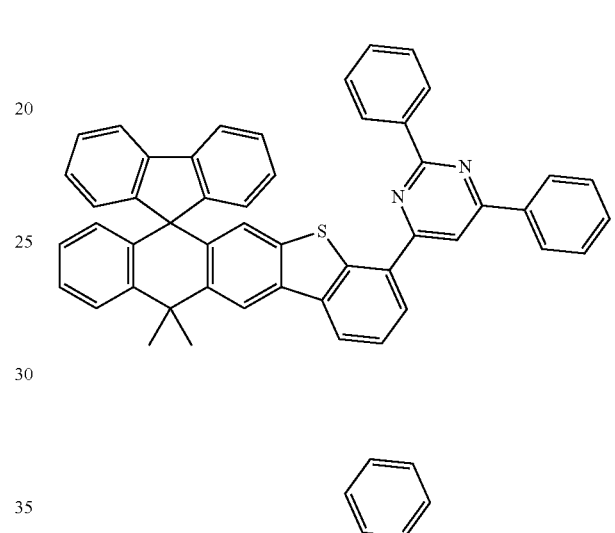
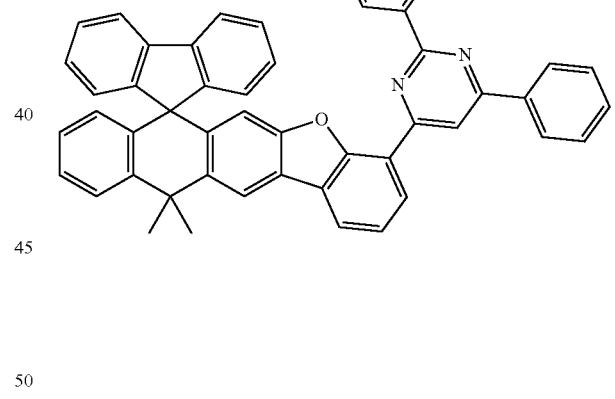
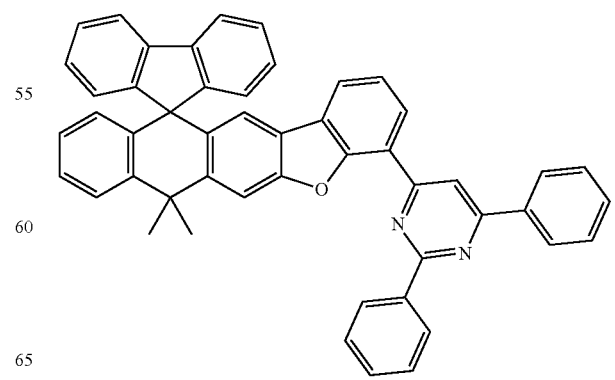

775
-continued
776
-continued
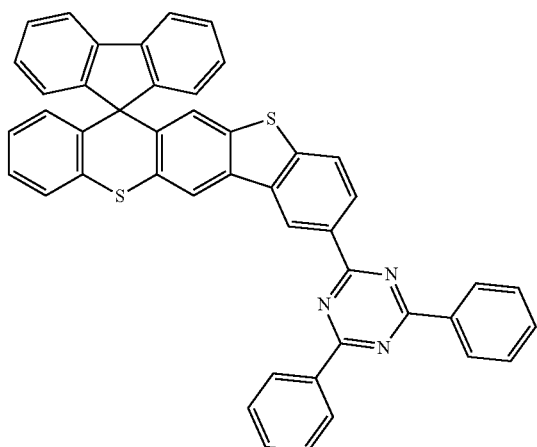
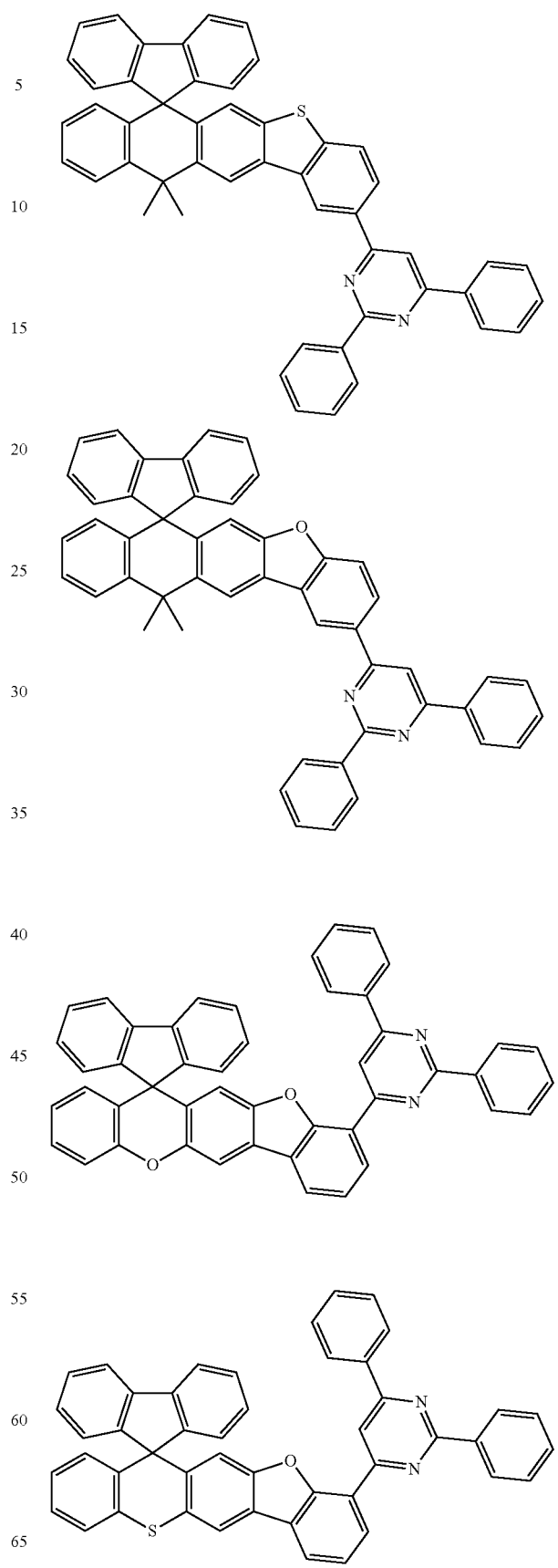

777
-continued
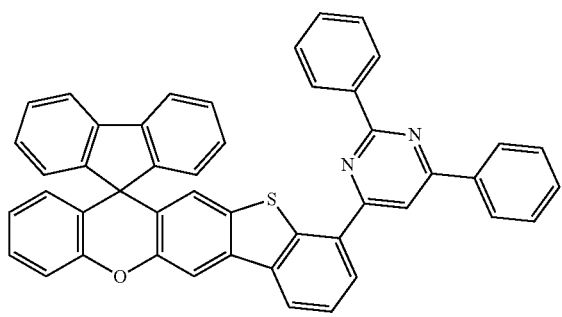
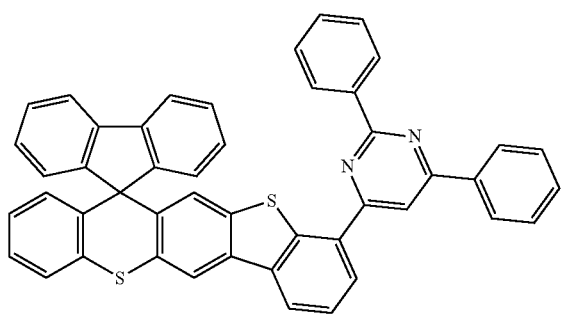
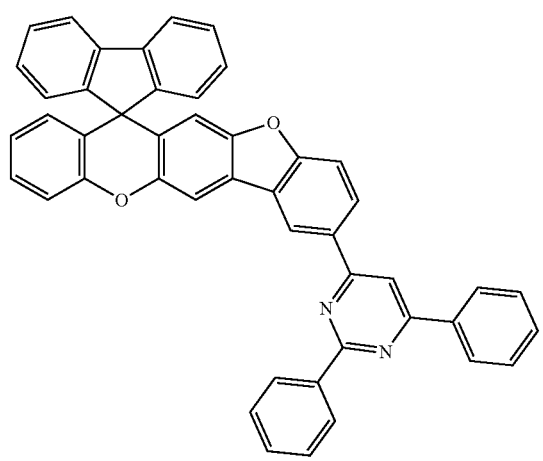
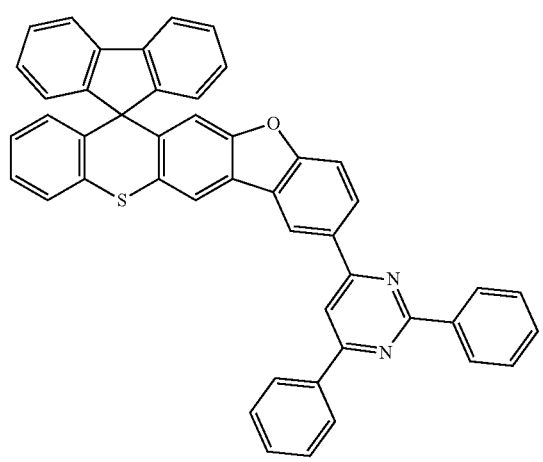
778
-continued
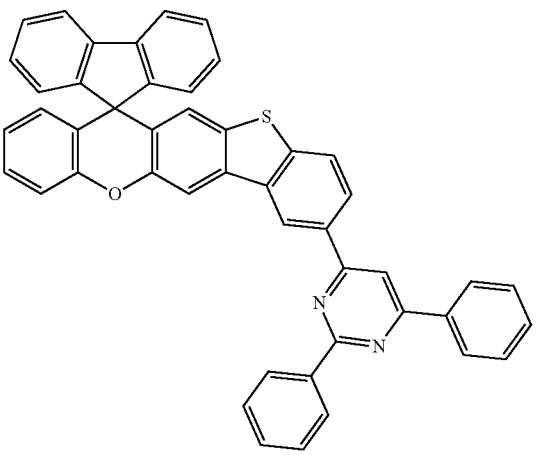
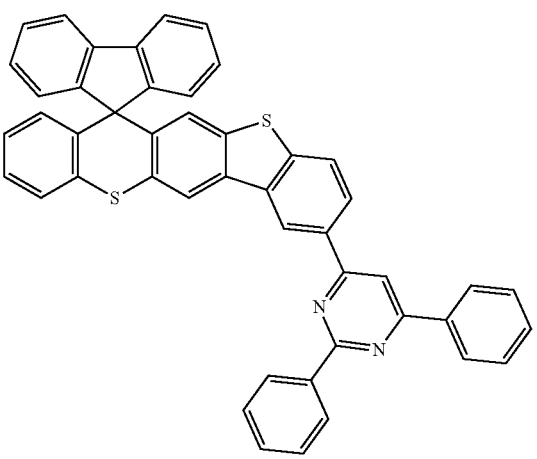
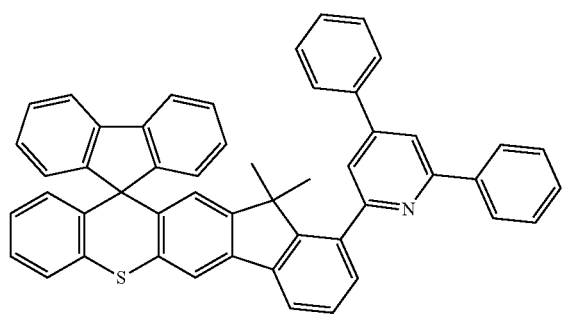
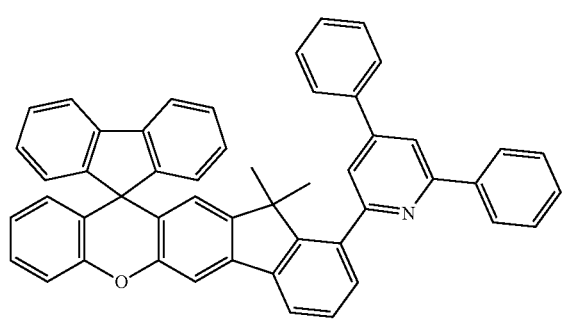

779
-continued
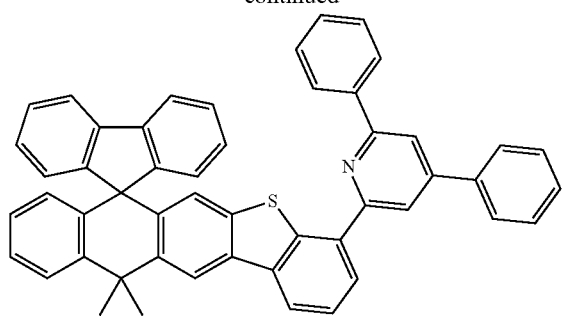
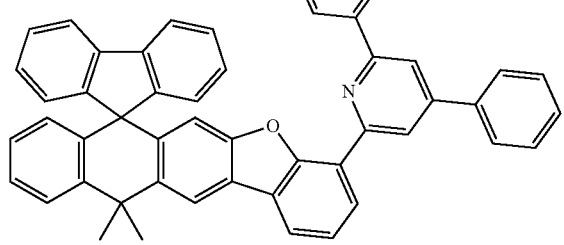
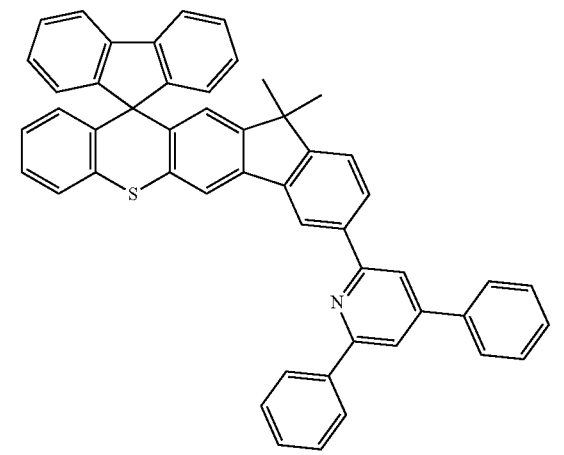
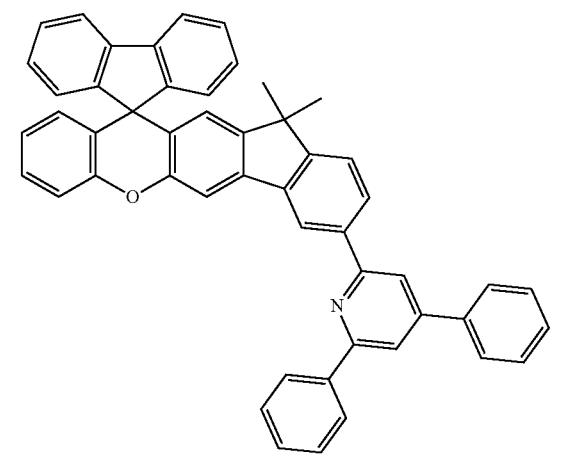
780
-continued
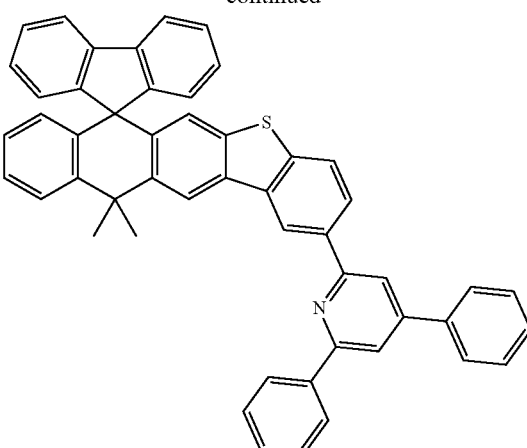
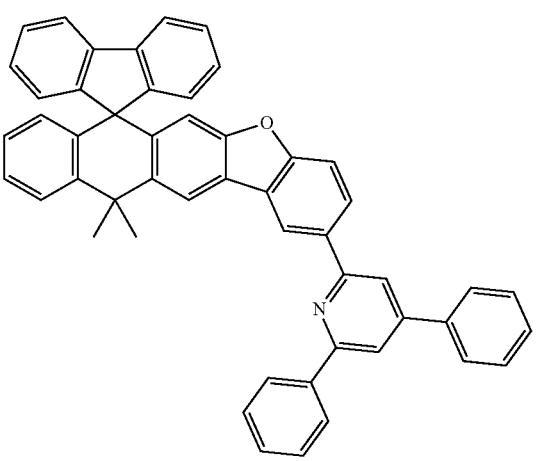
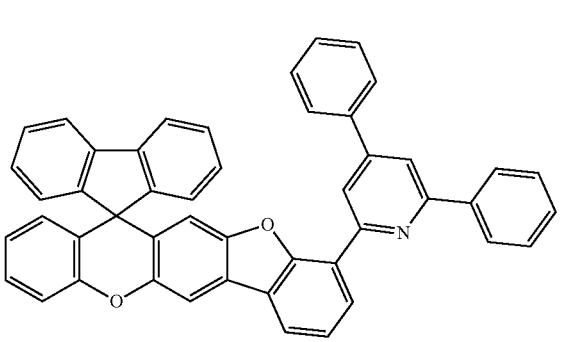
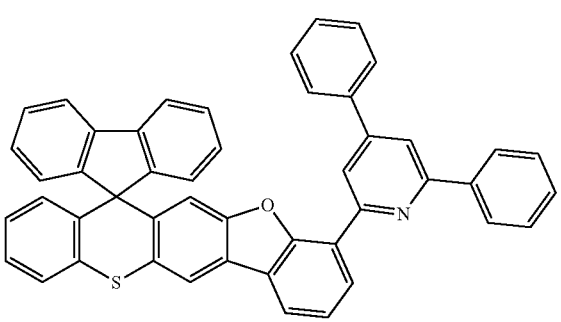

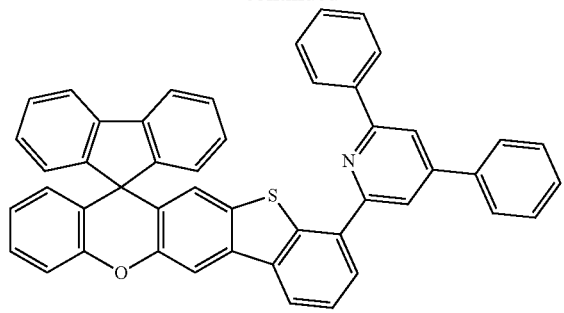
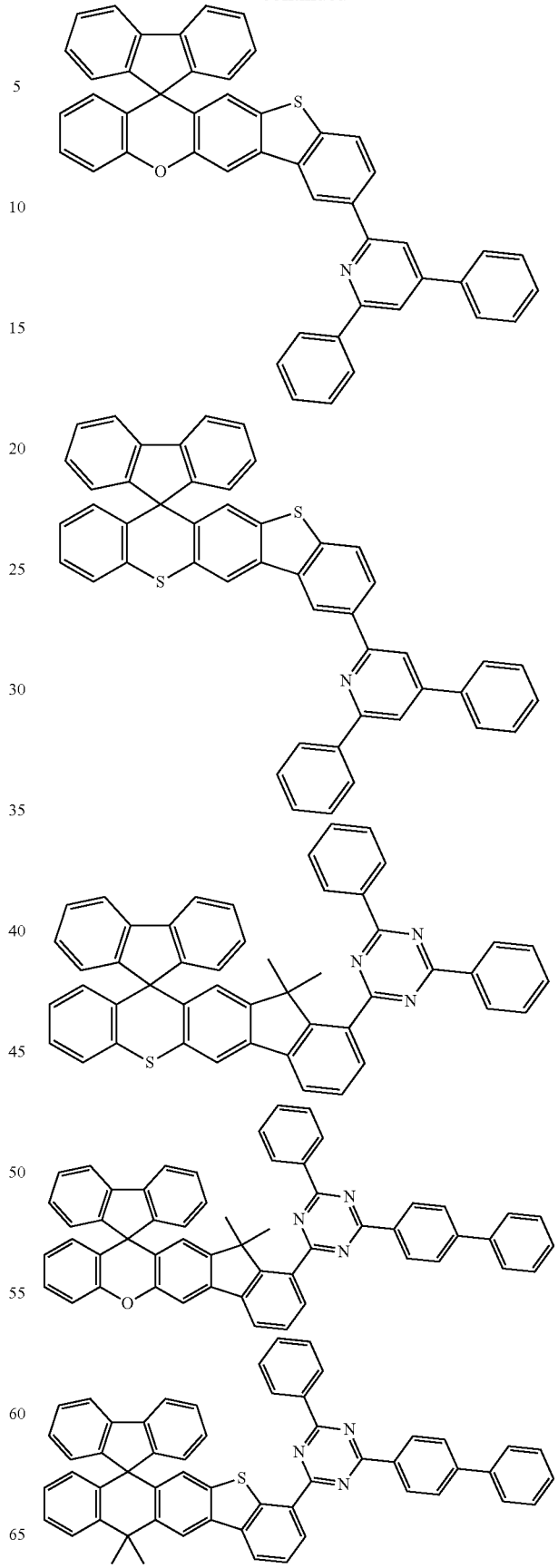

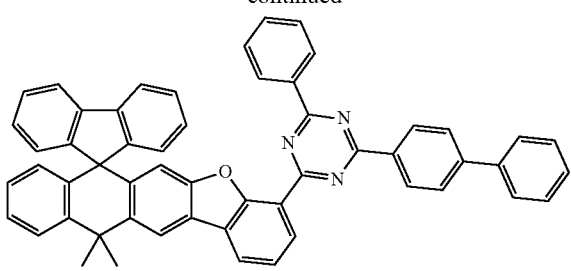
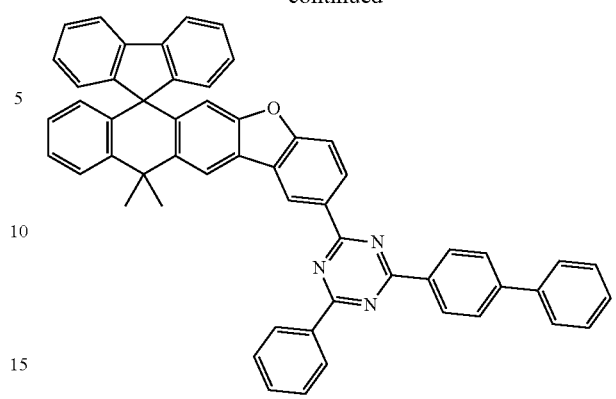
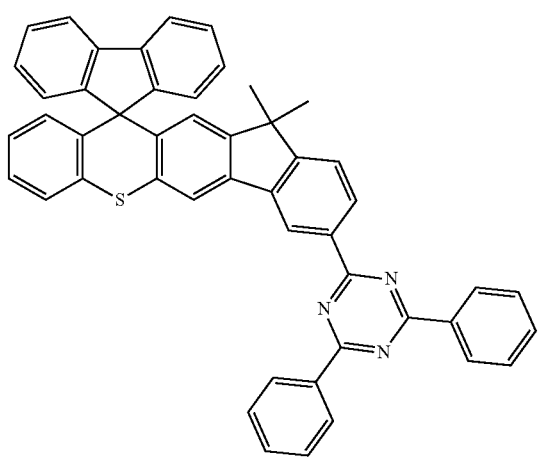
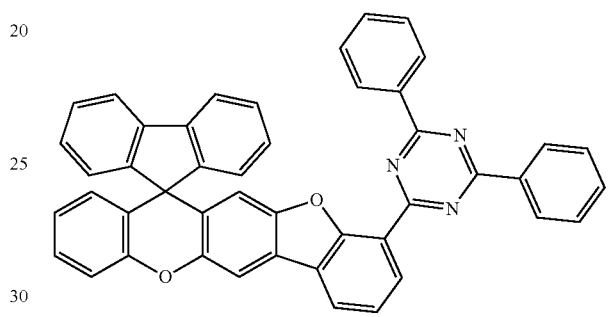
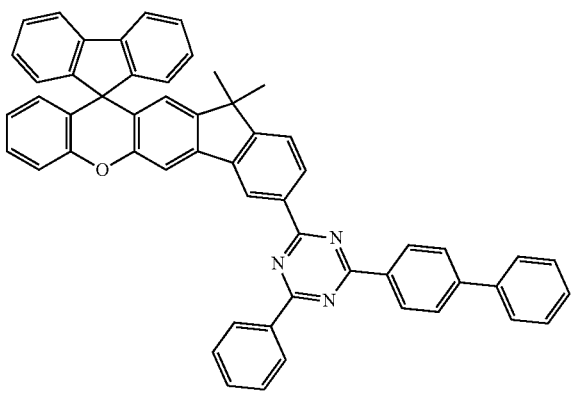
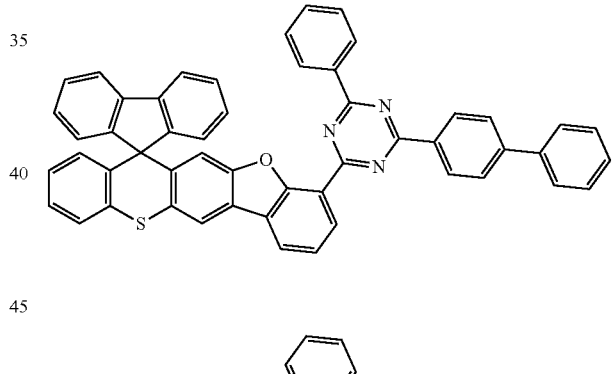
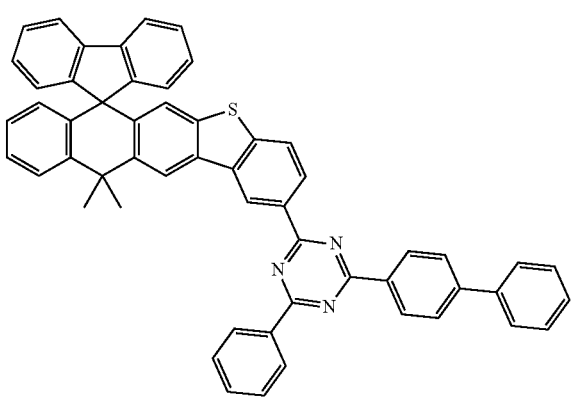
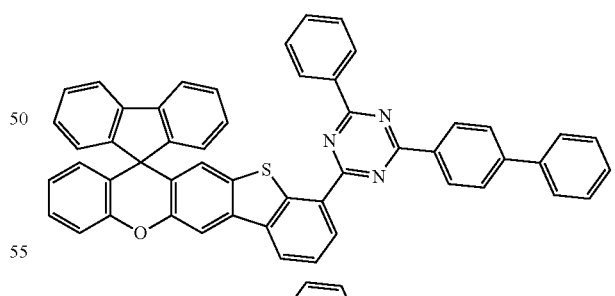
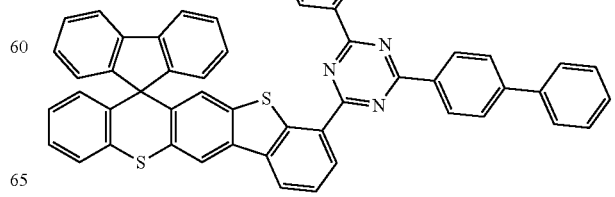

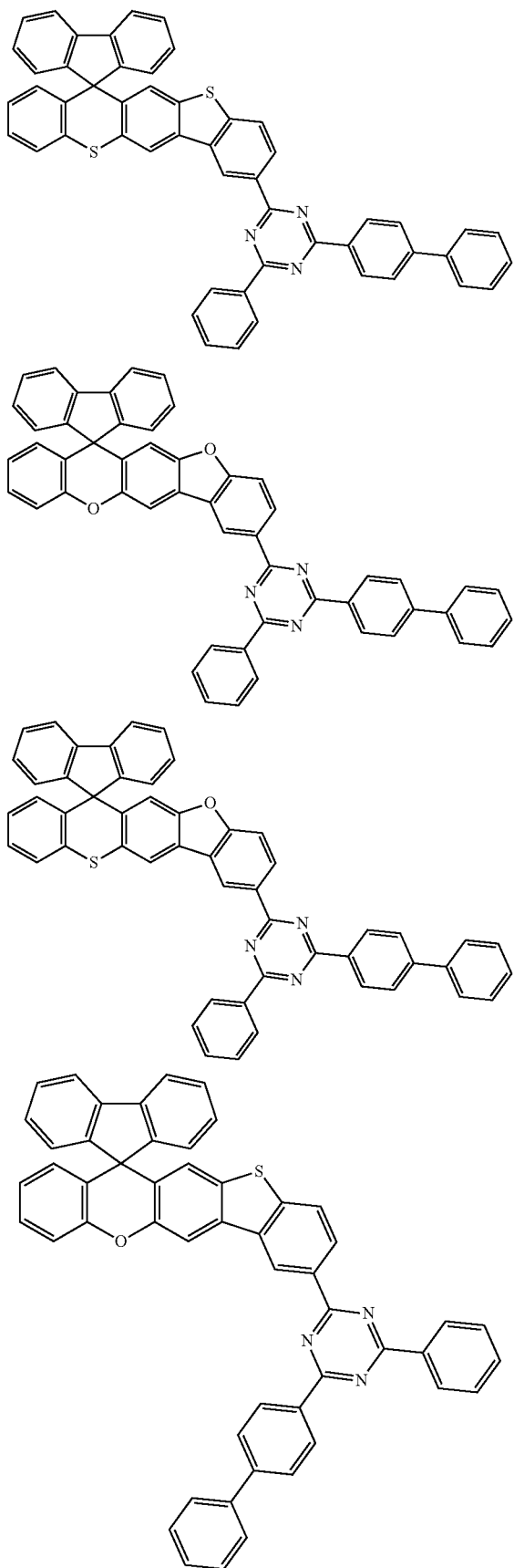
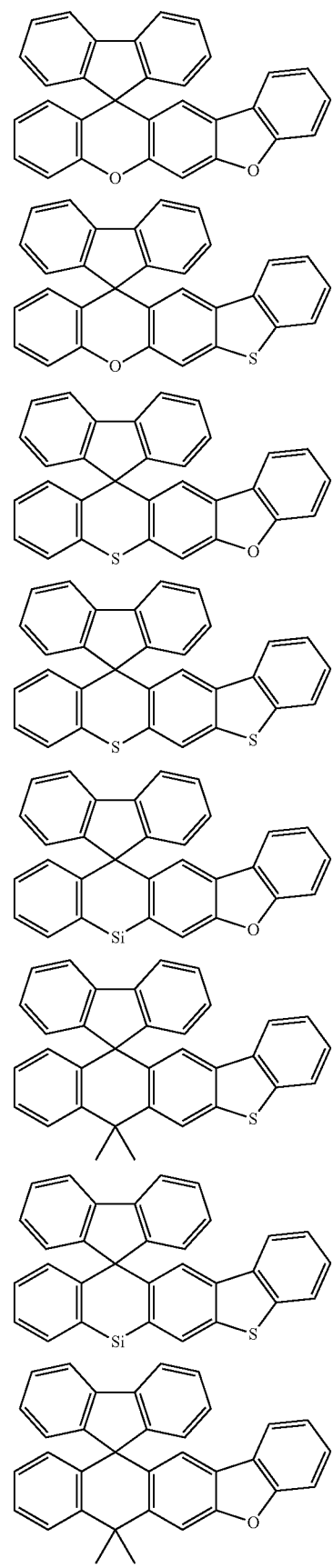

787
-continued
788
-continued
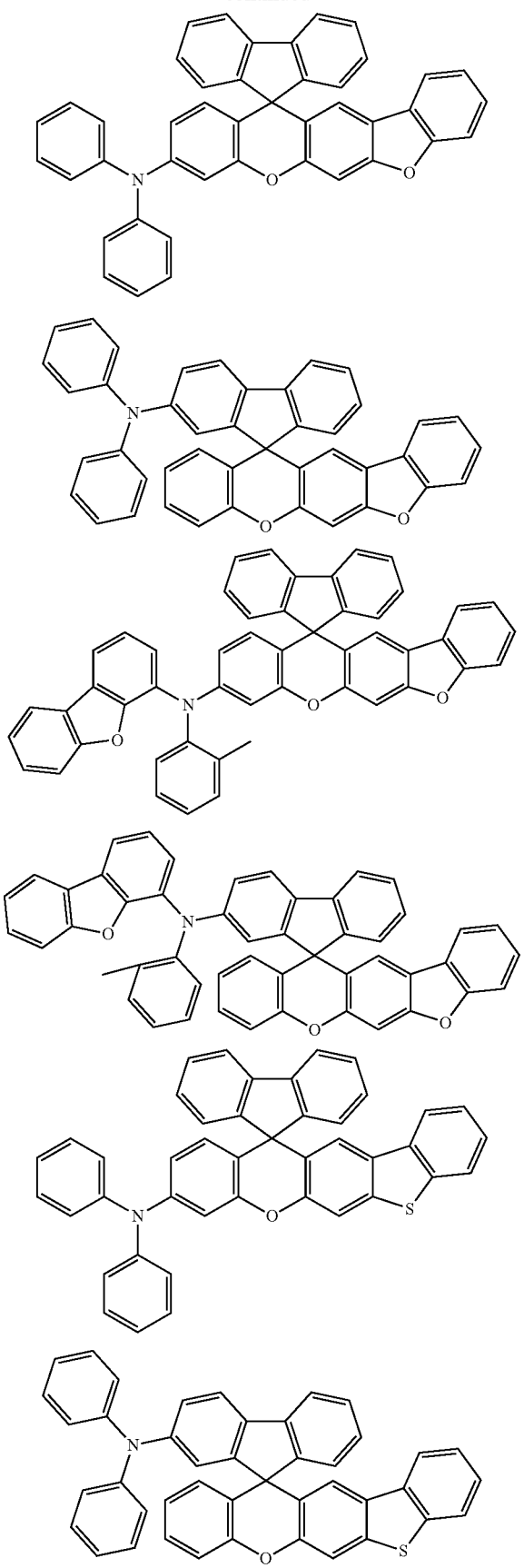
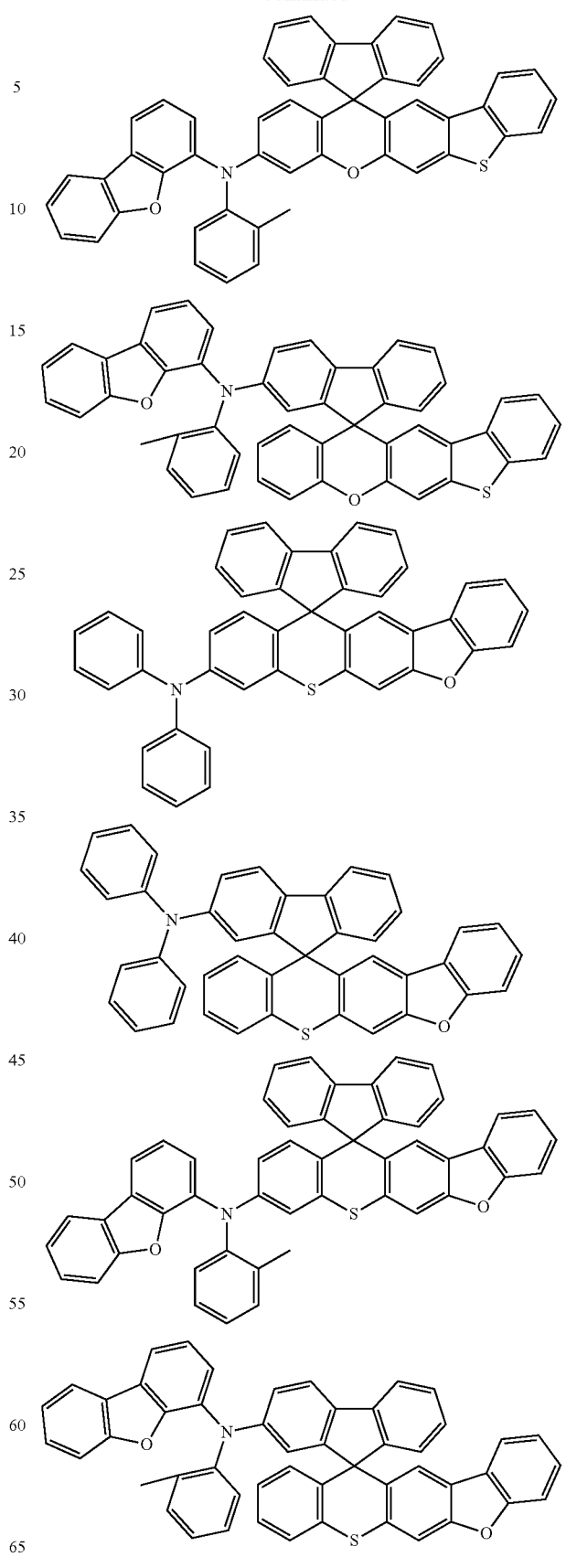

789
-continued
790
-continued
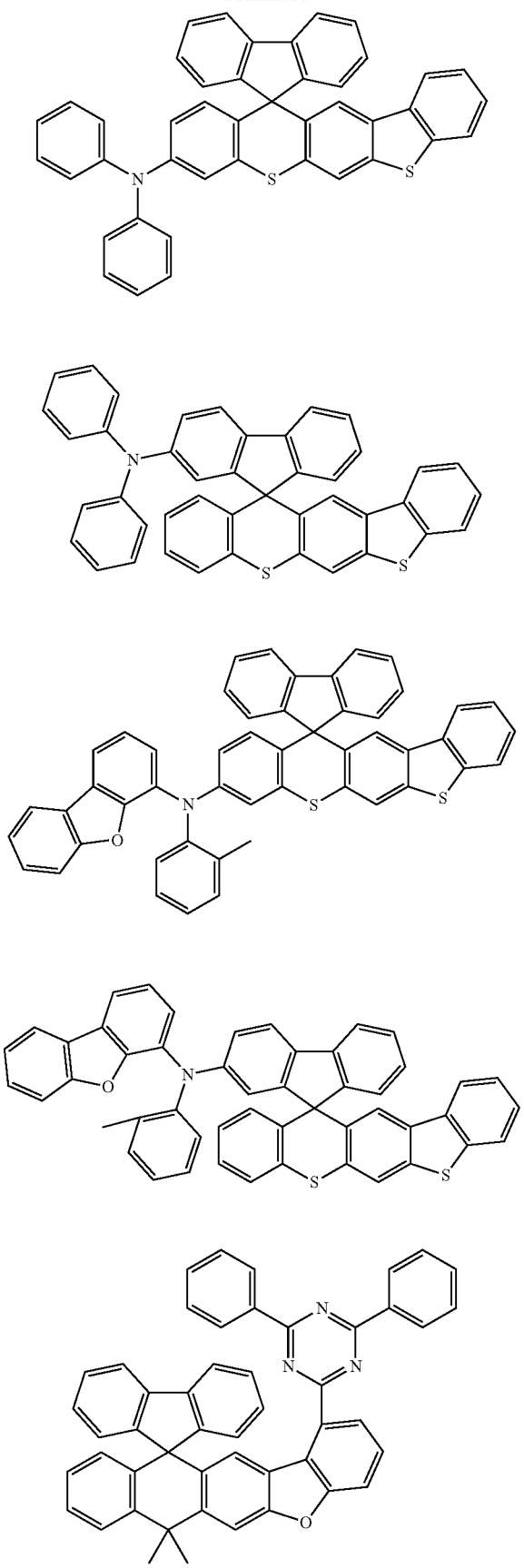
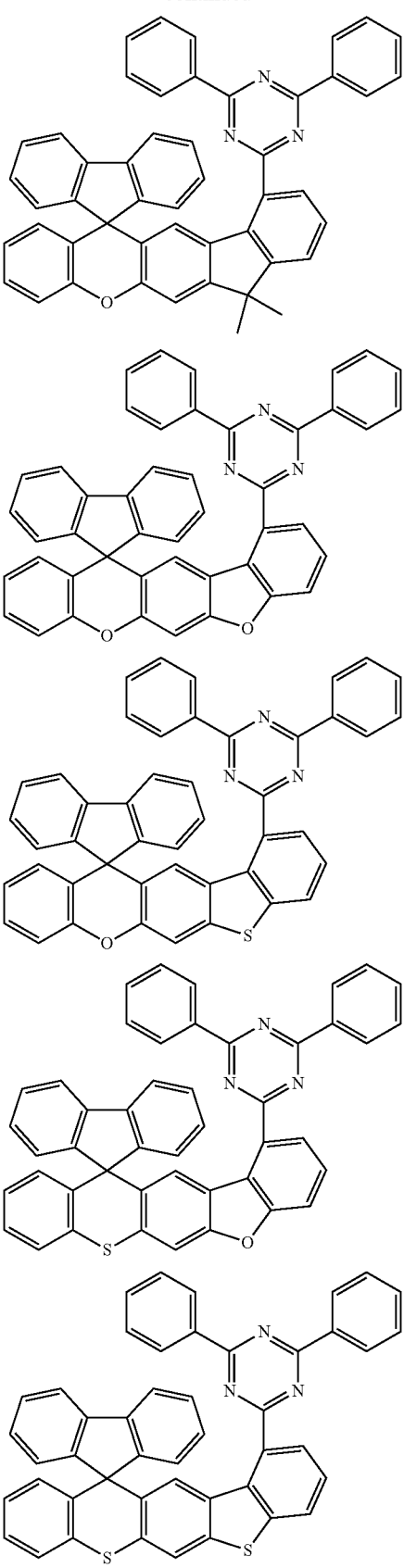

791
-continued
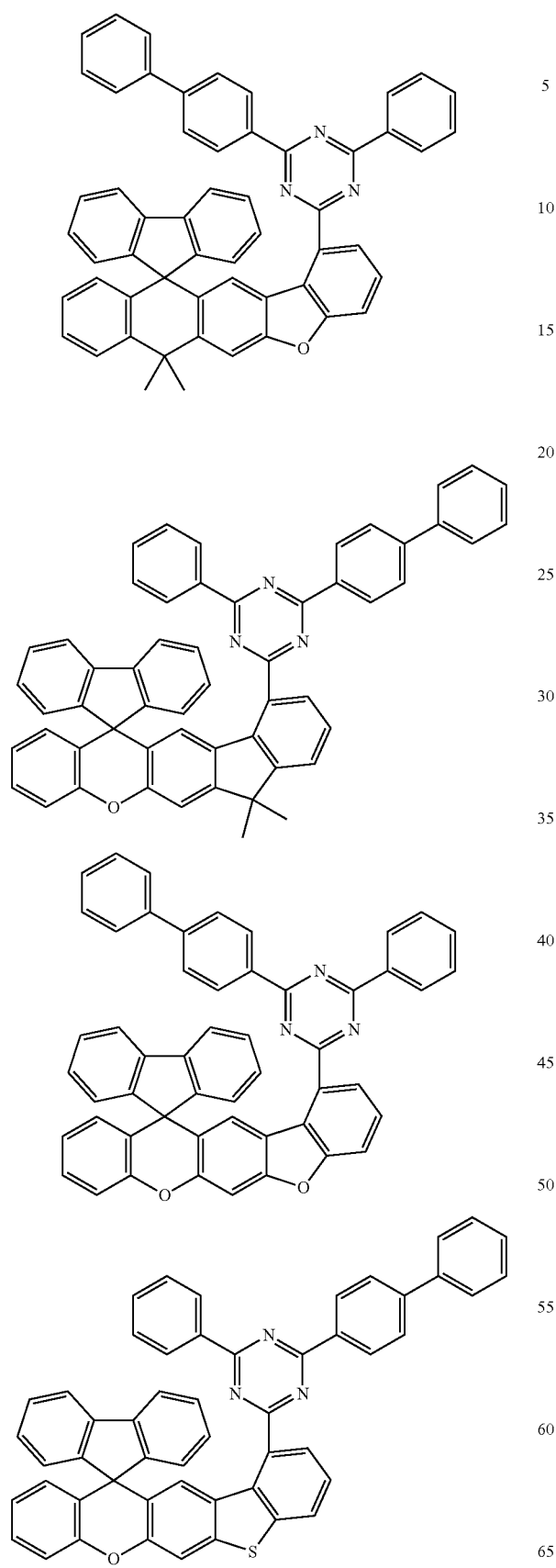
792
-continued
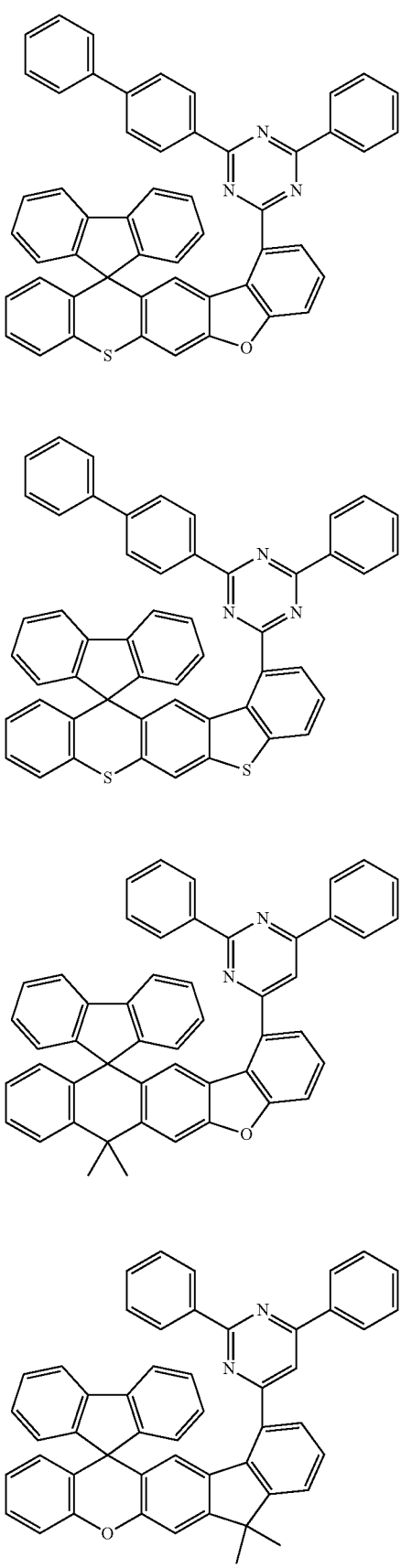

793
-continued
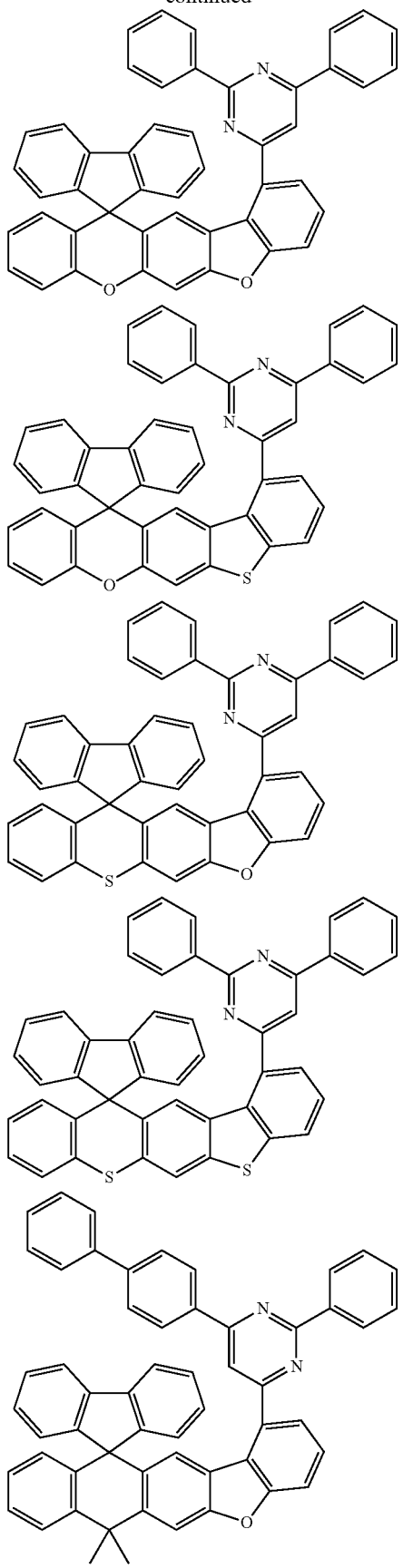
794
-continued
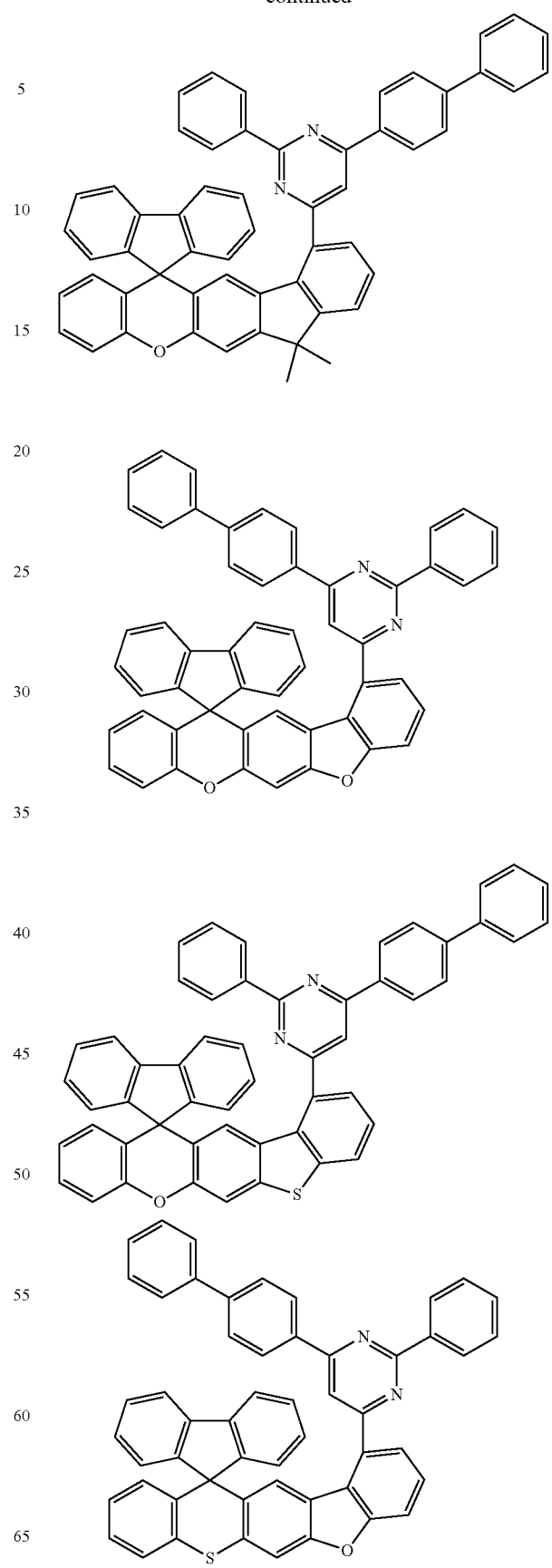

795
-continued
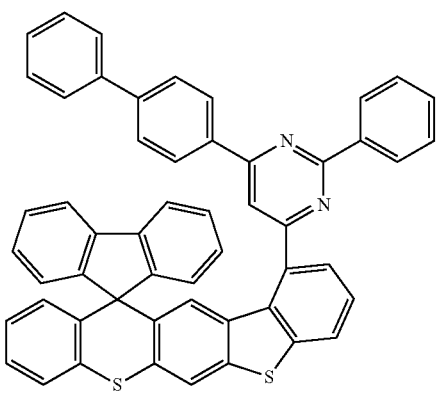
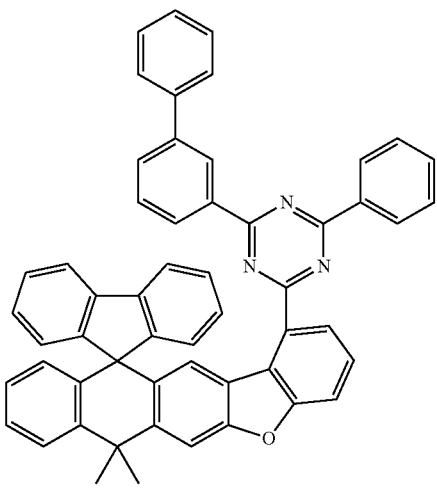
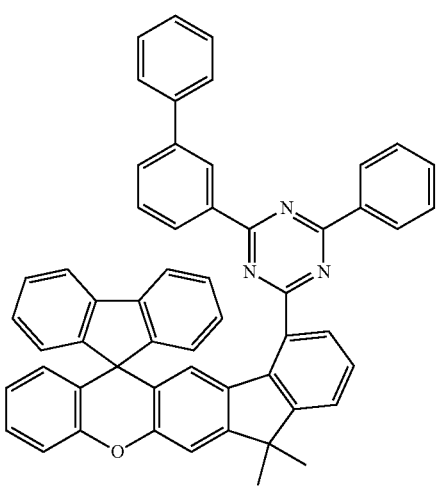
796
-continued
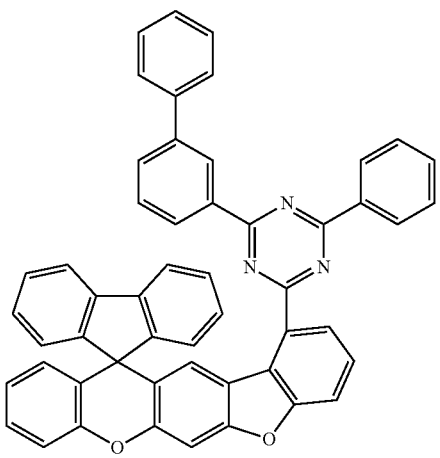
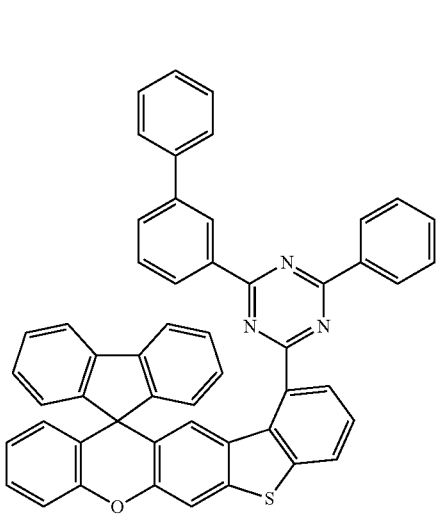
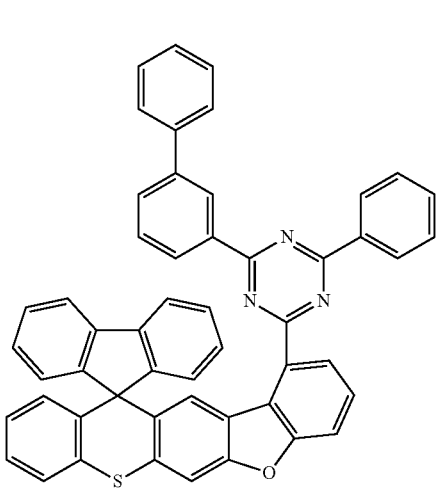

797
-continued
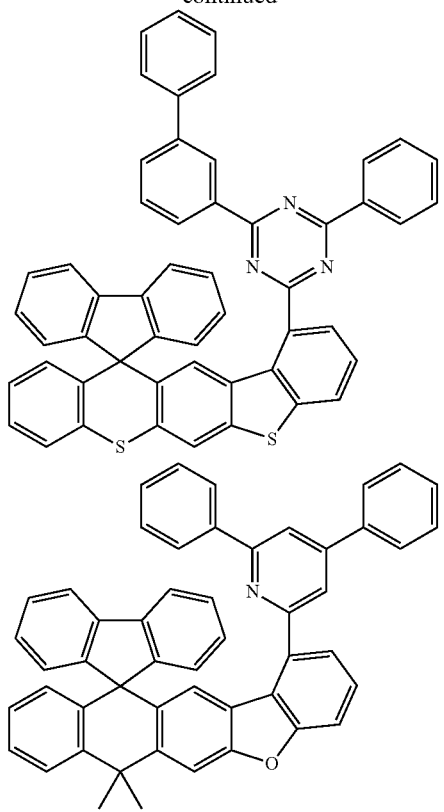
798
-continued
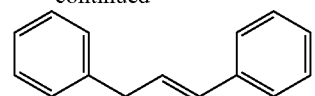
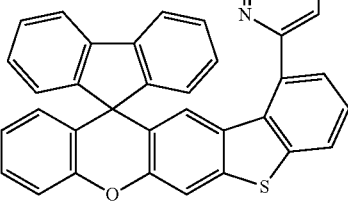
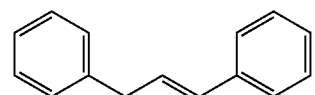
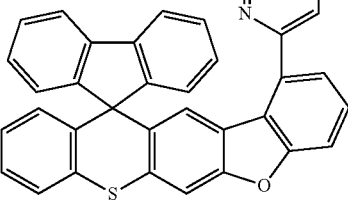
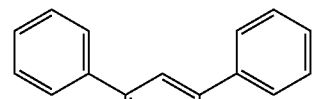
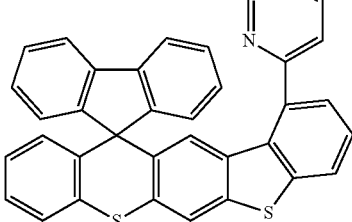
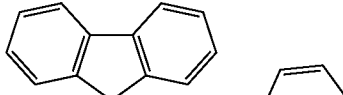
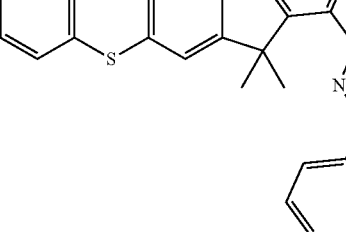
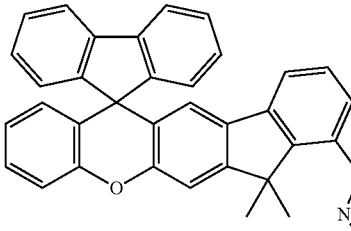

799
-continued
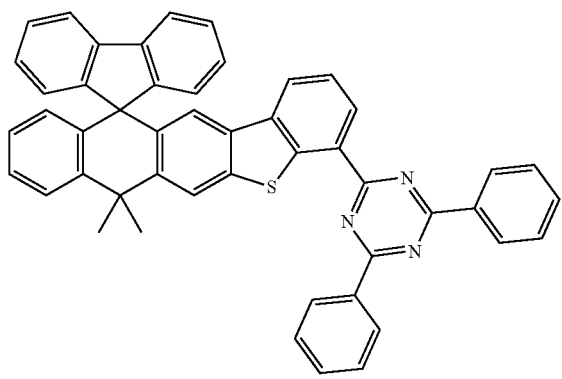
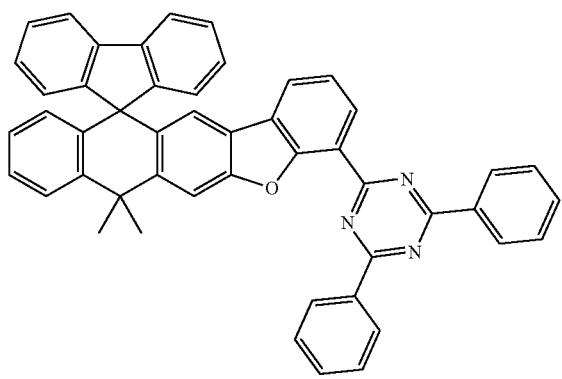
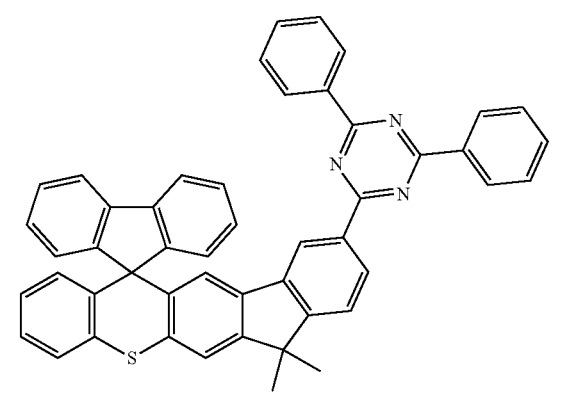
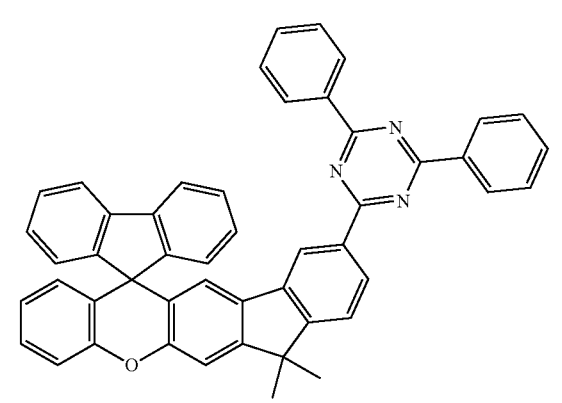
800
-continued
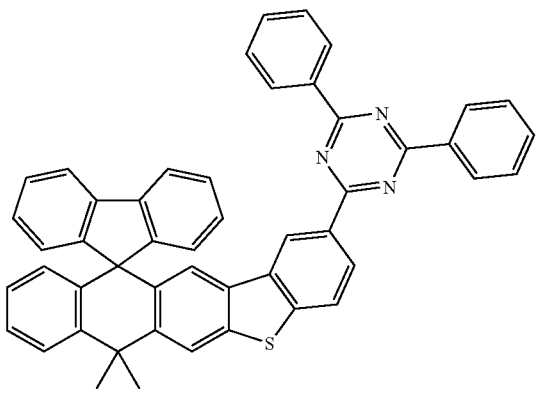
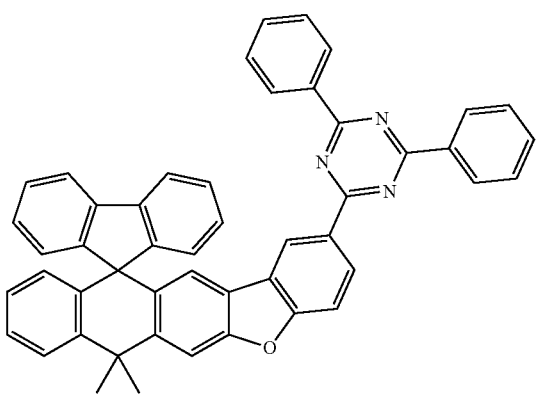
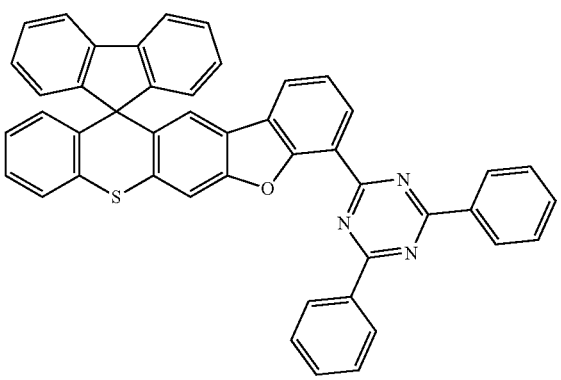
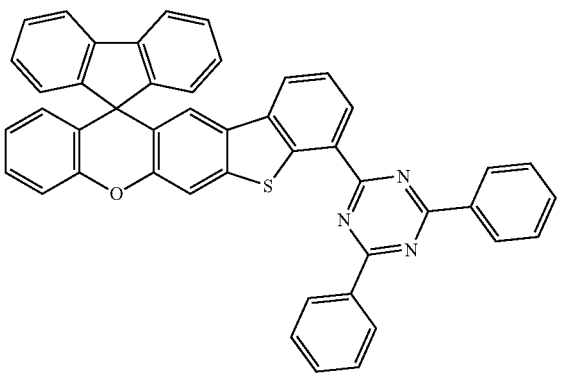

801
-continued
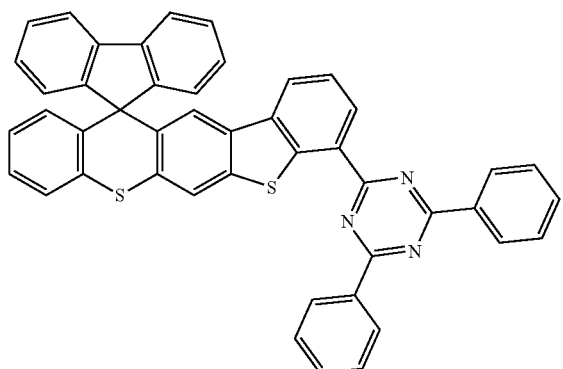
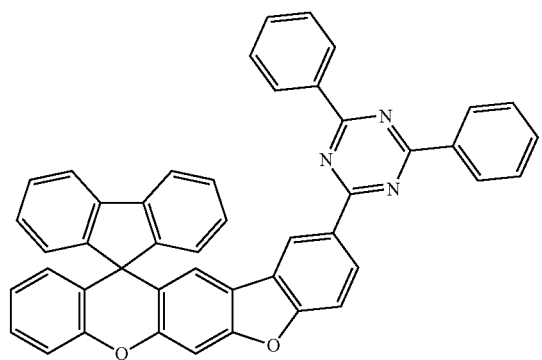
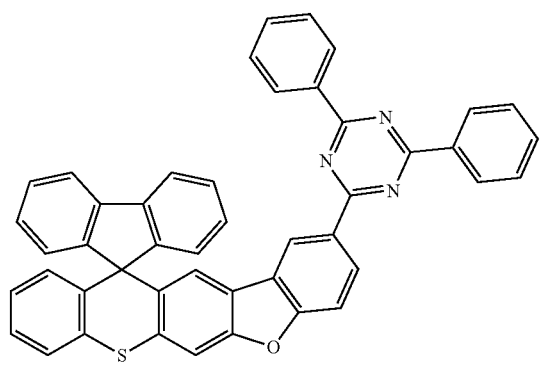
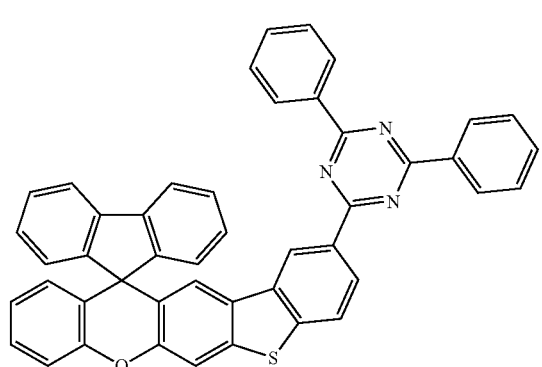
802
-continued
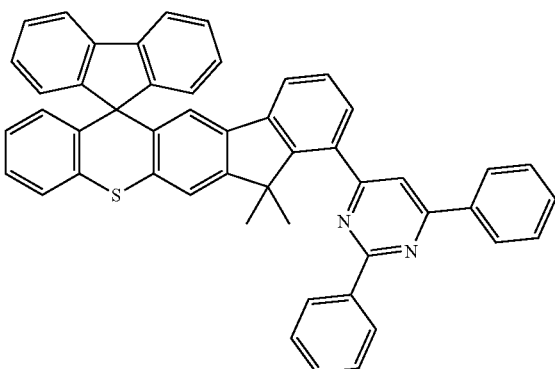
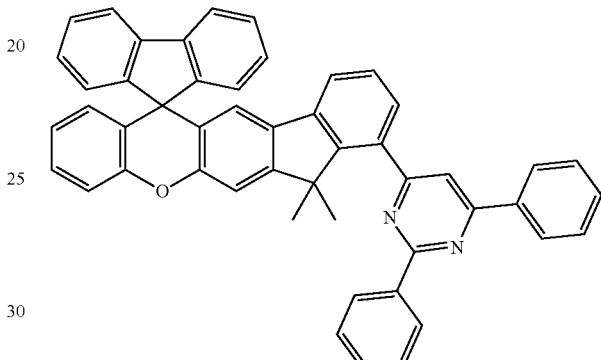
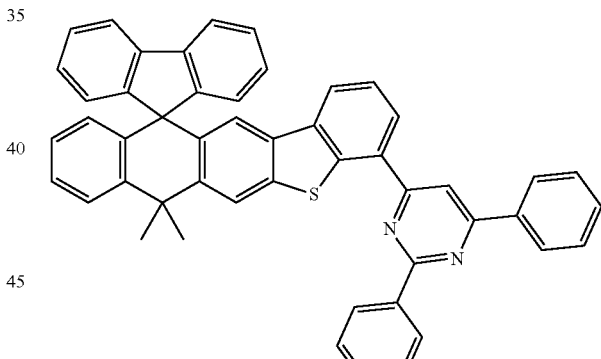
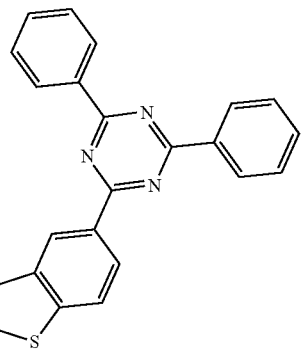

803
-continued
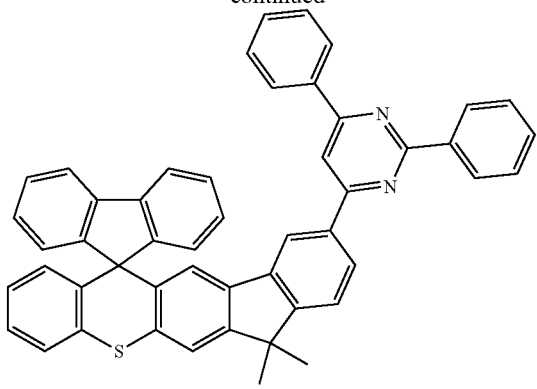
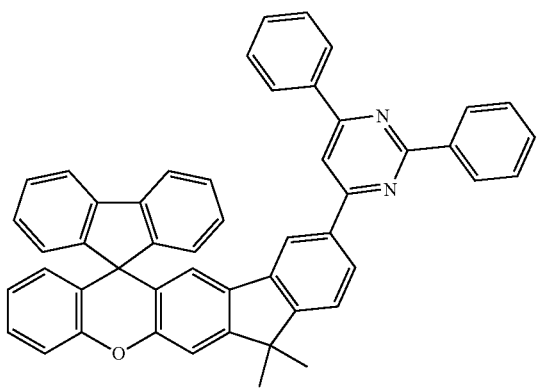
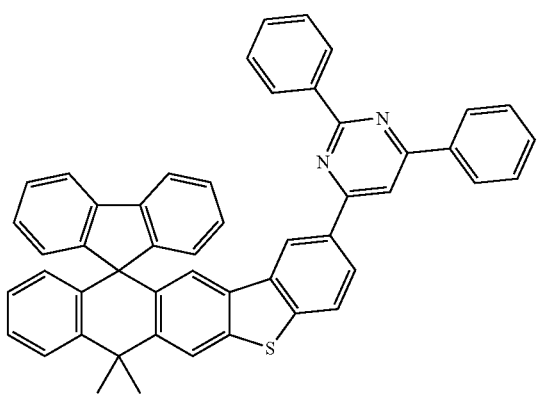
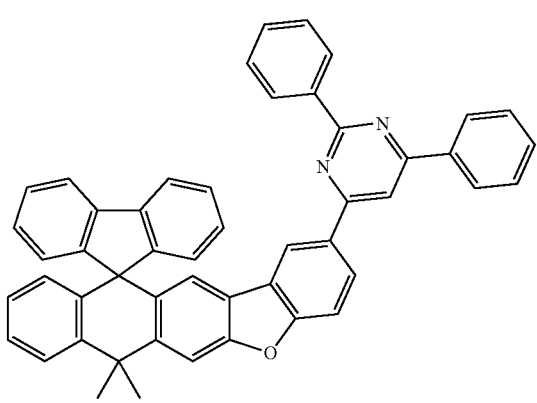
804
-continued
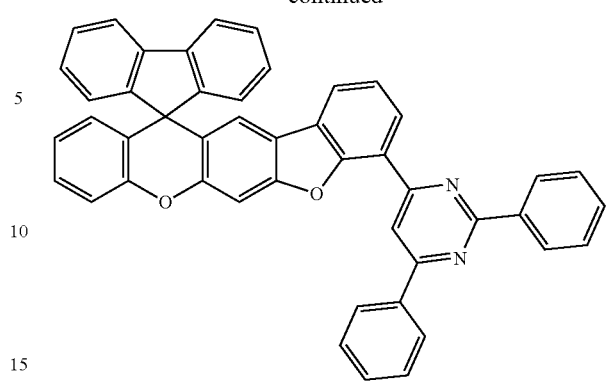
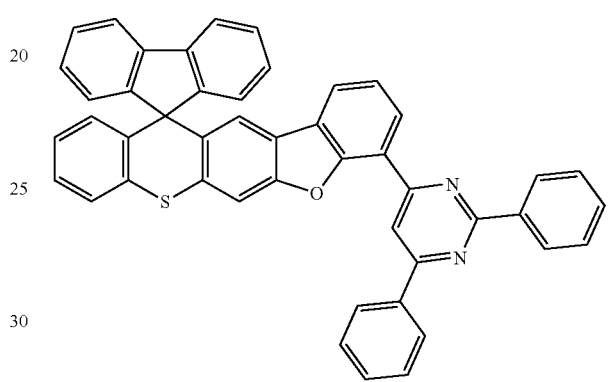
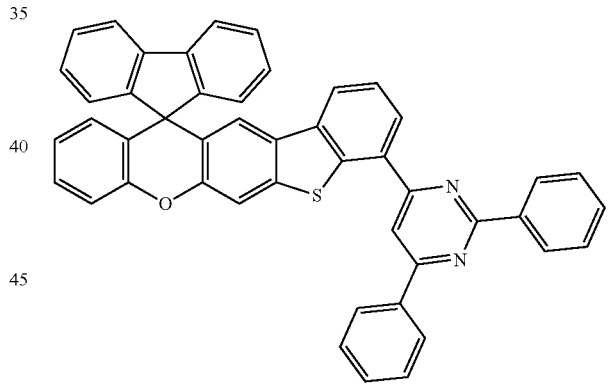
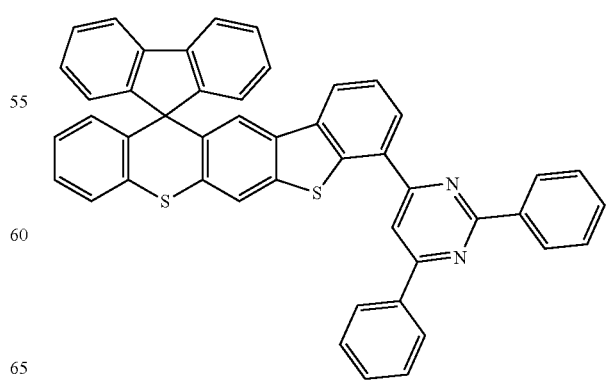

| 805 | 806 |
|---|---|
| 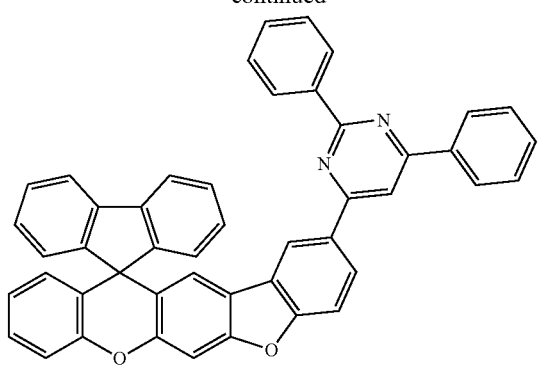 | 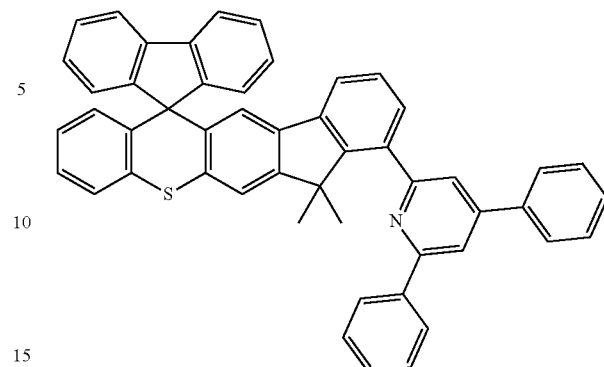 |
| 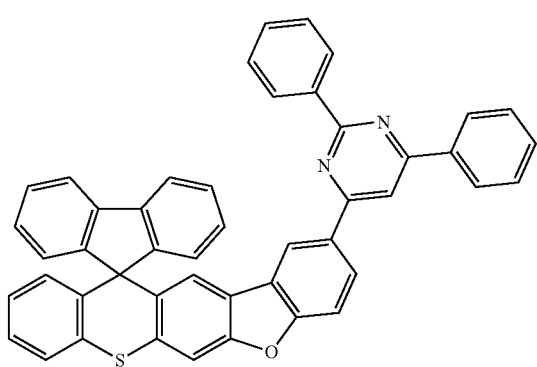 | 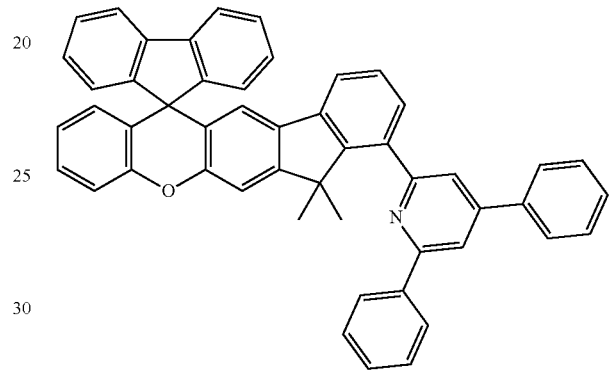 |
| 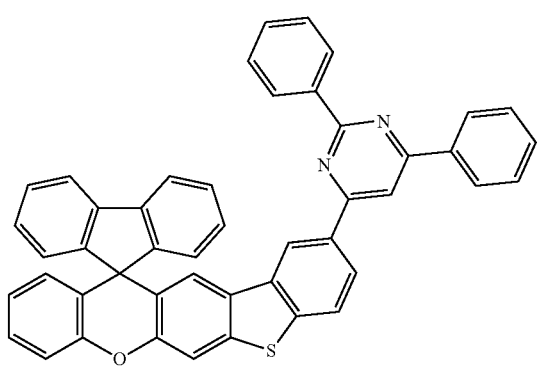 | 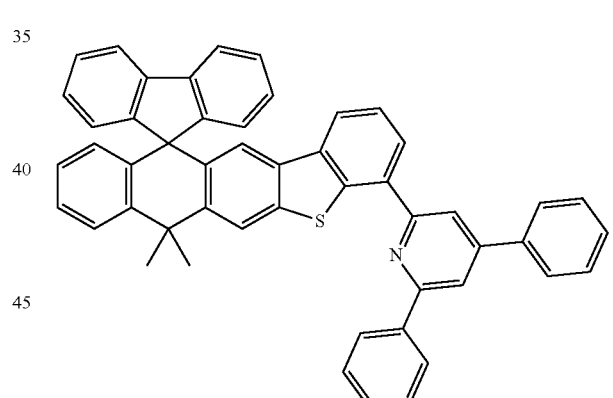 |
| 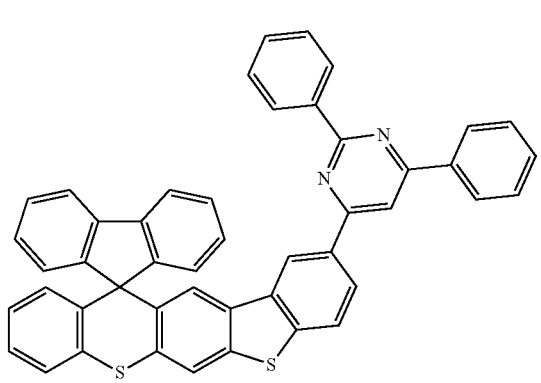 | 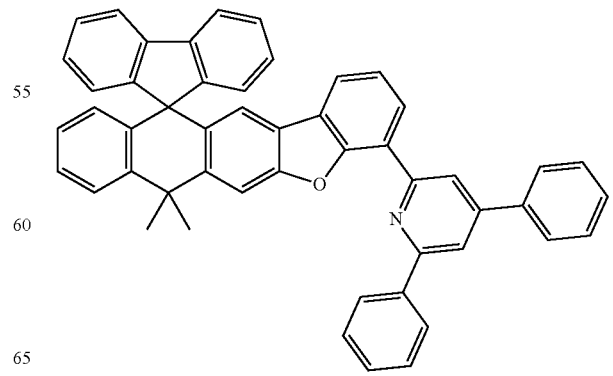 |

807
-continued
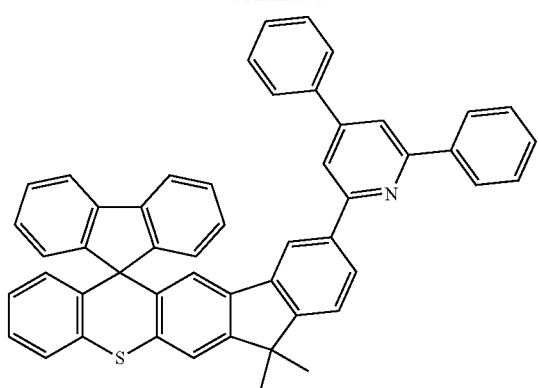
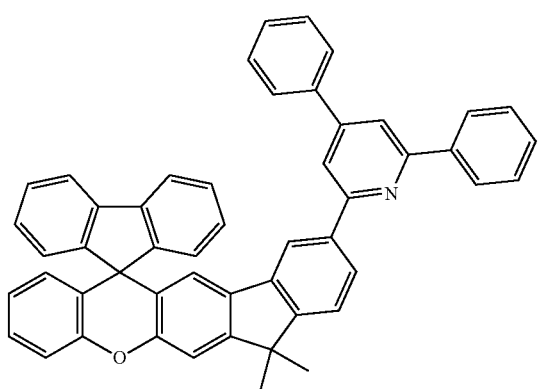
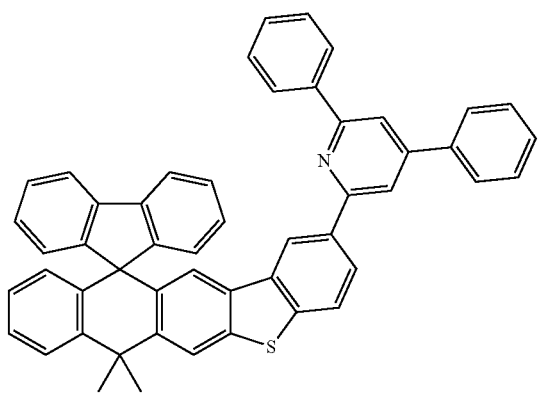
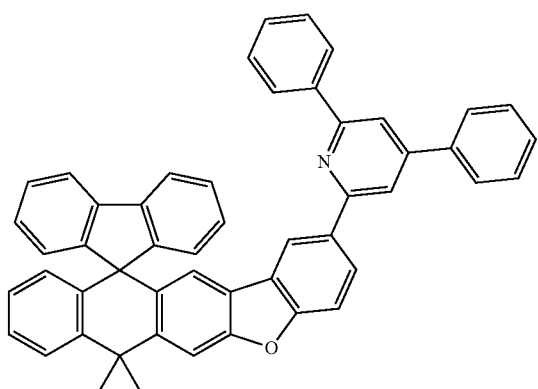
808
-continued
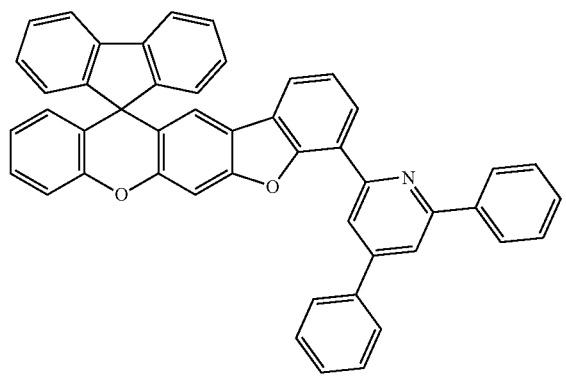
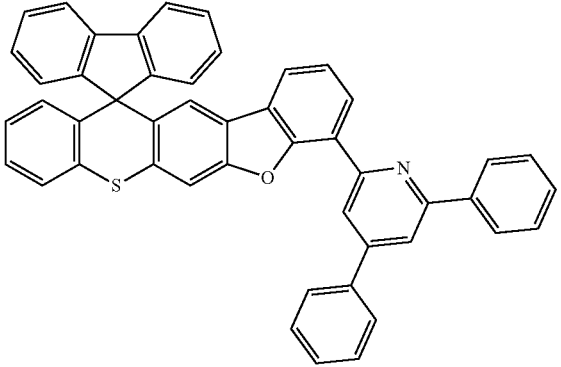
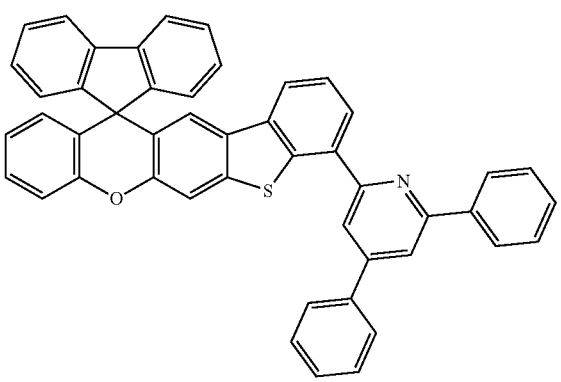
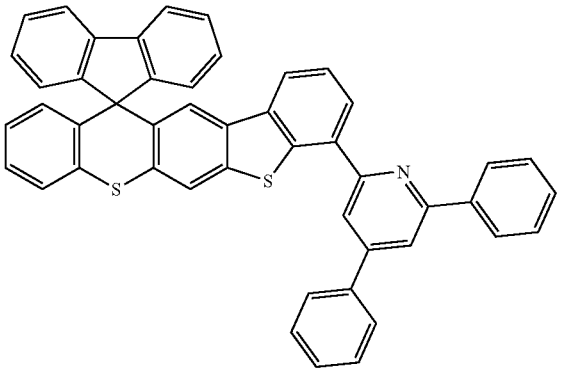

809
-continued
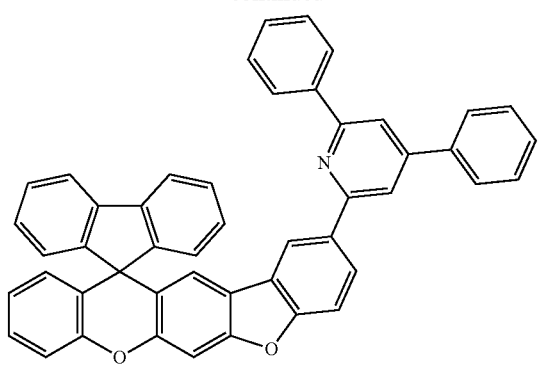
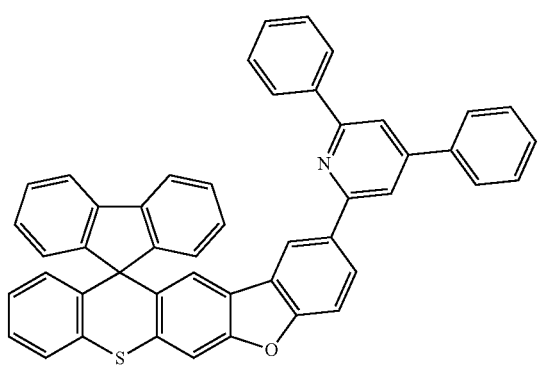
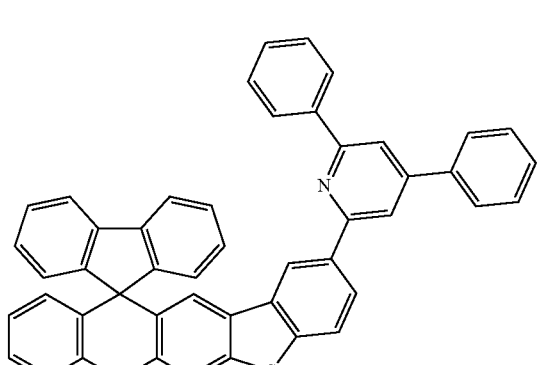
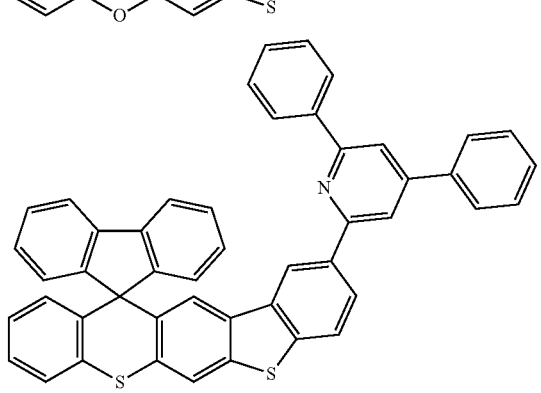
810
-continued
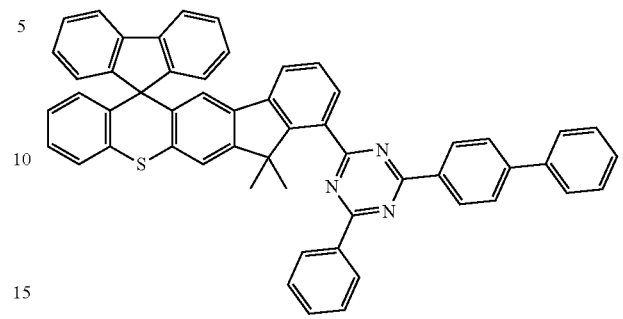
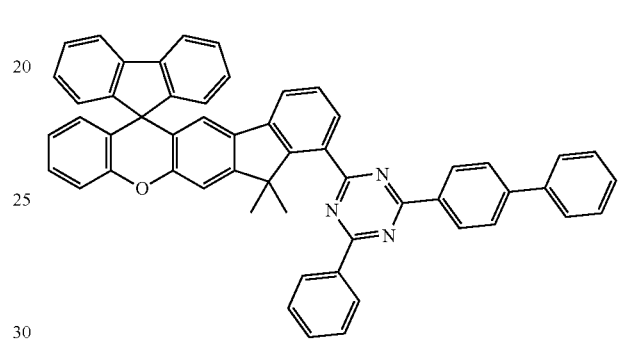
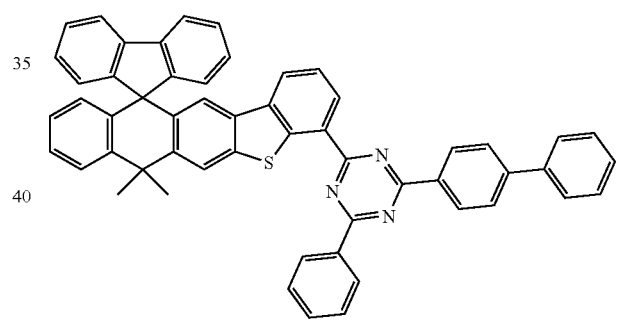
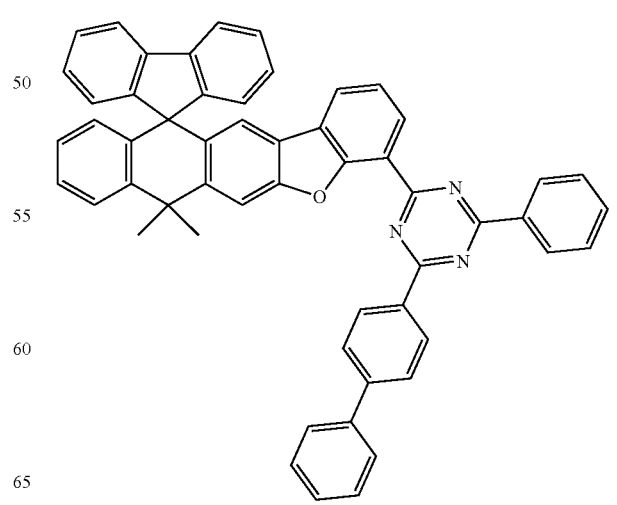

| 811 -continued | 812 -continued |
|---|---|
| 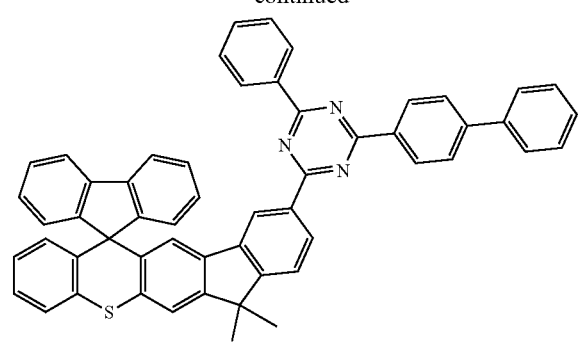 | 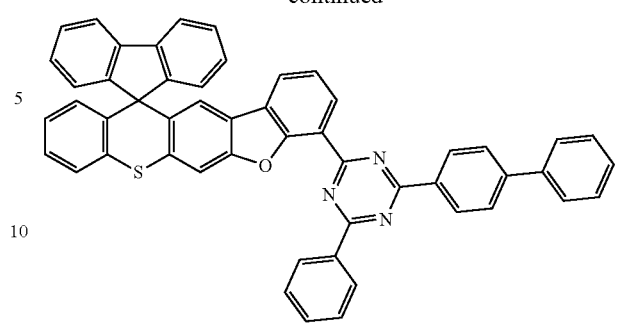 |
| 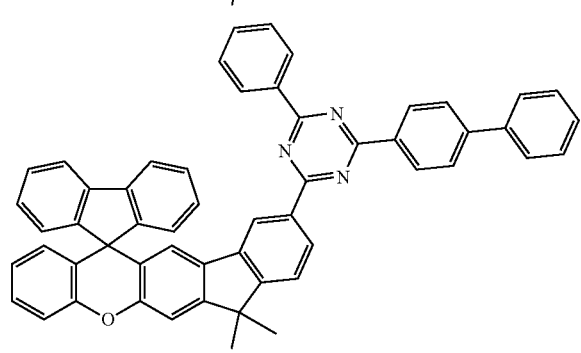 | 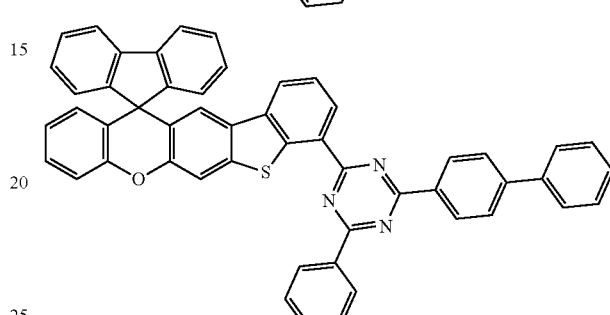 |
| 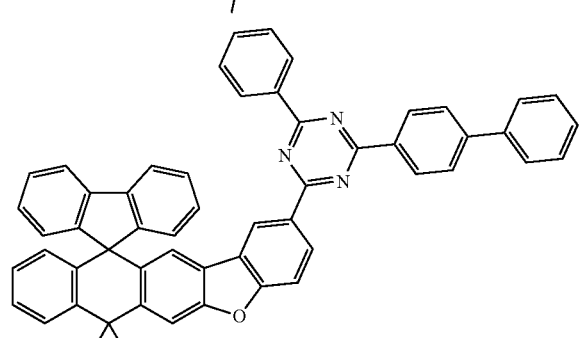 | 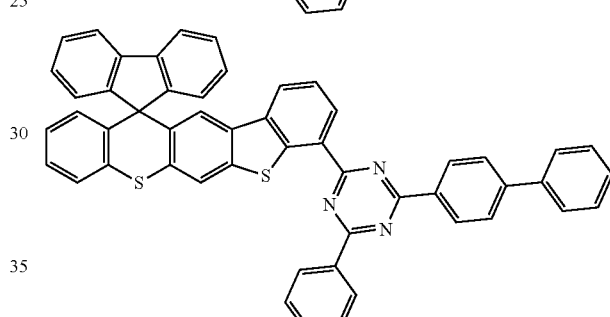 |
| 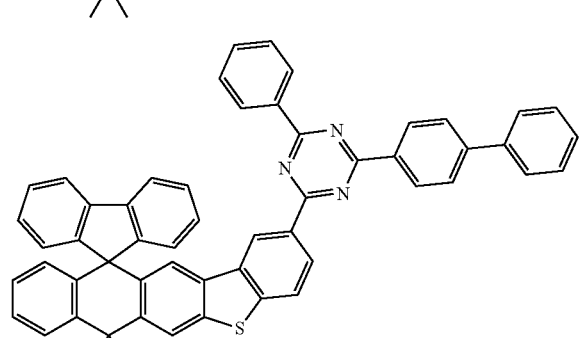 | 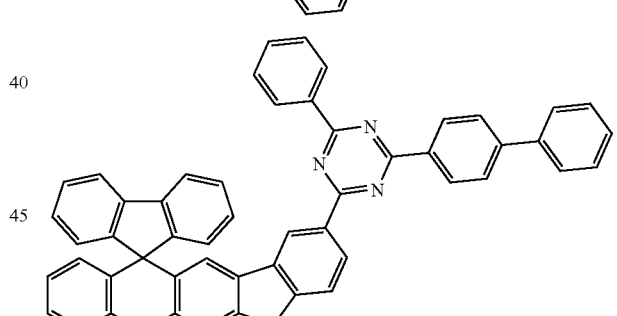 |
| 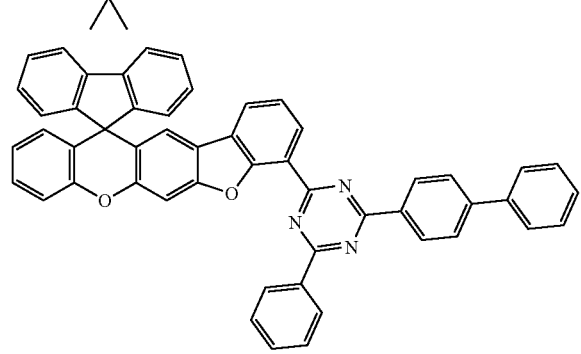 | 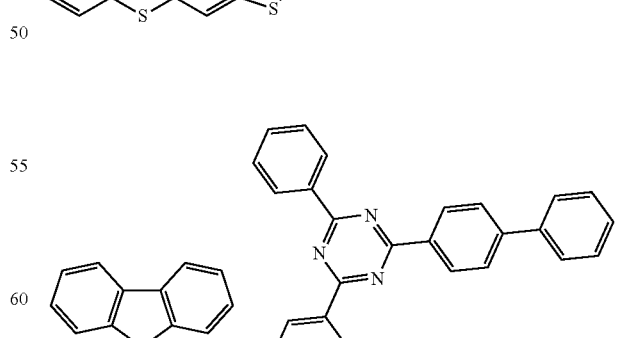 |

813
-continued
814
-continued
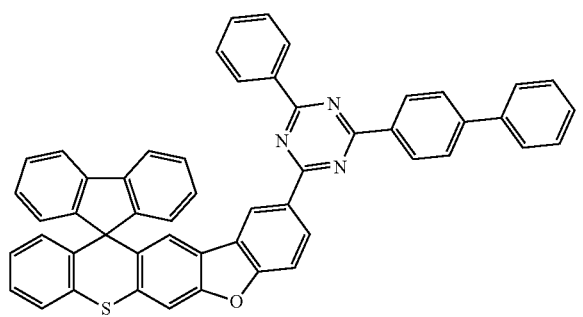
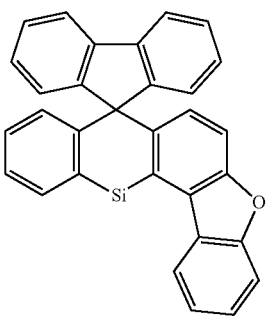
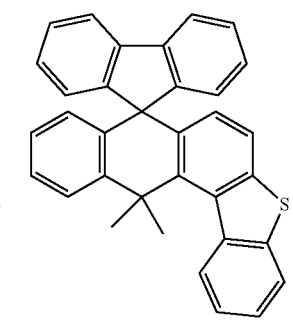
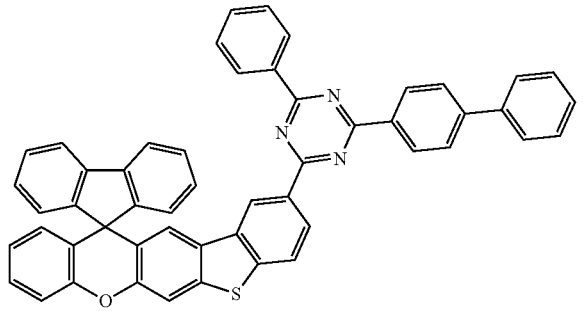
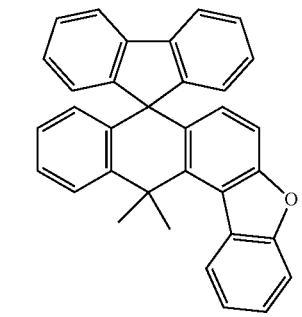
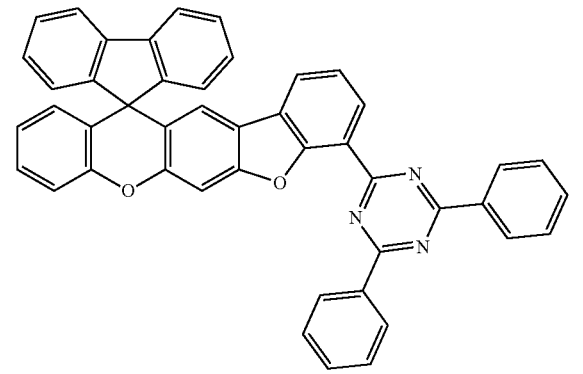
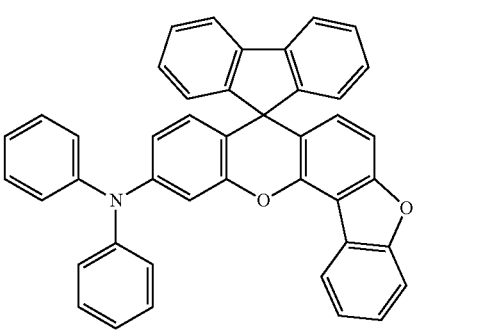
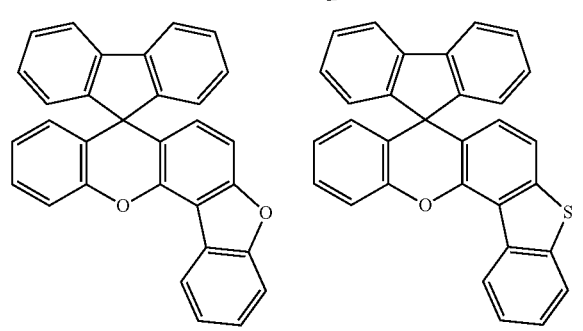
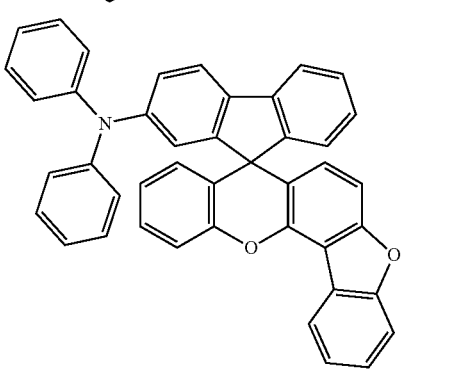
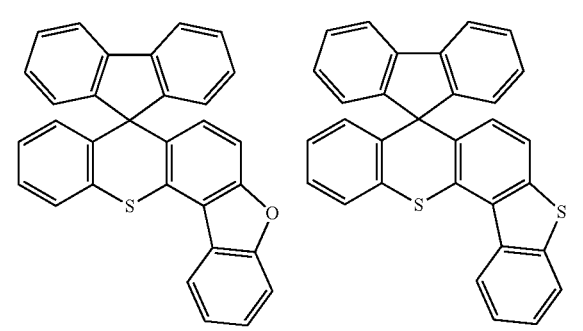
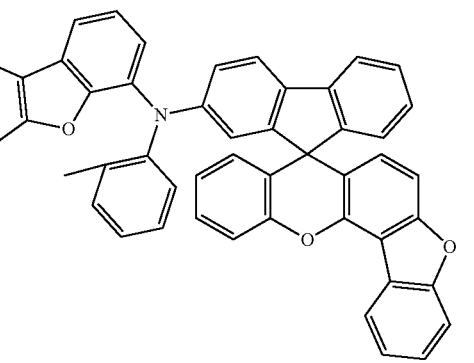

815
-continued
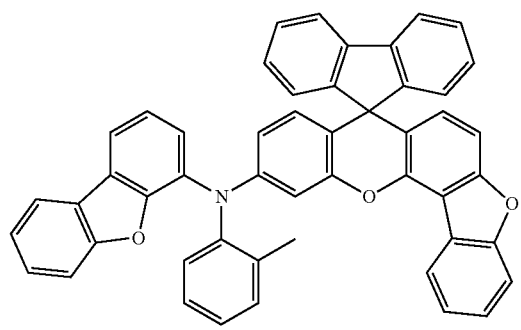
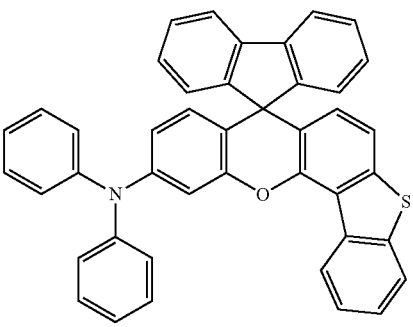
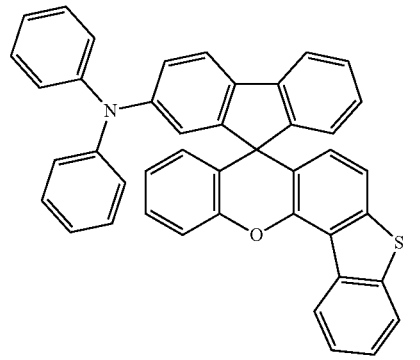
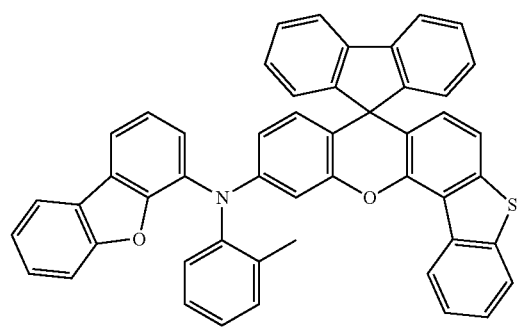
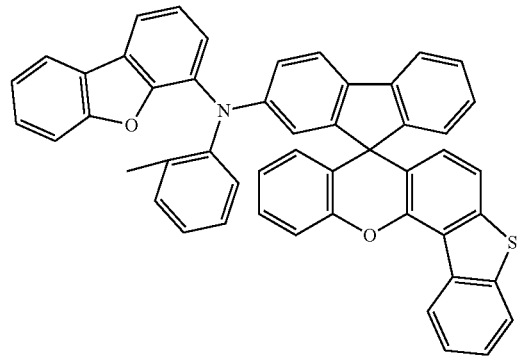
816
-continued
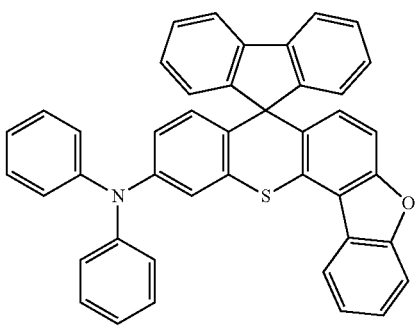
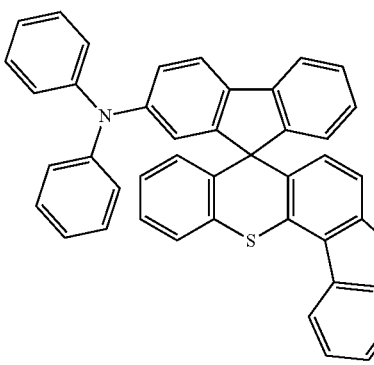
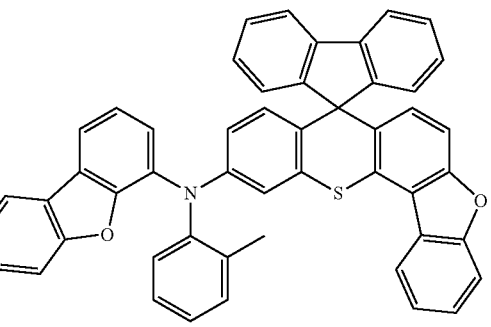
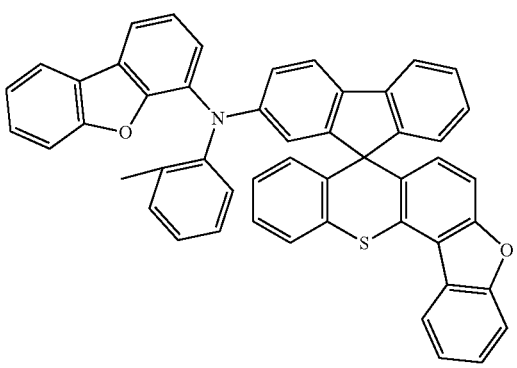
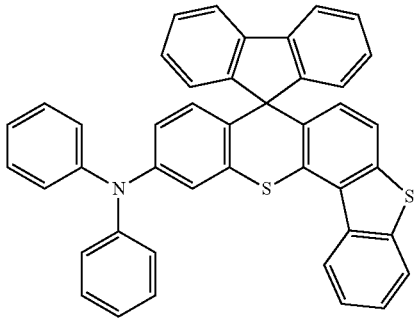

817
-continued
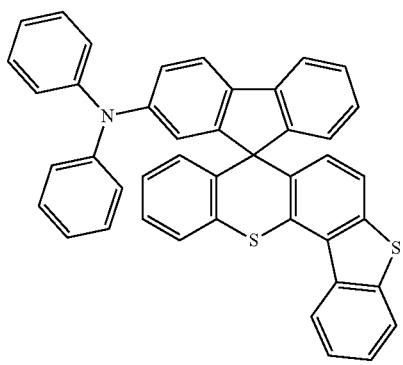
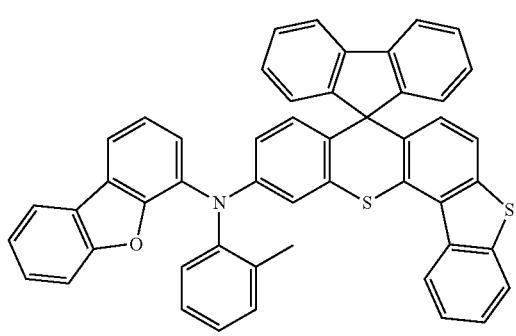
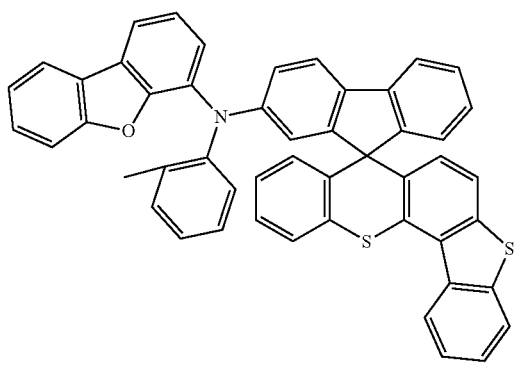
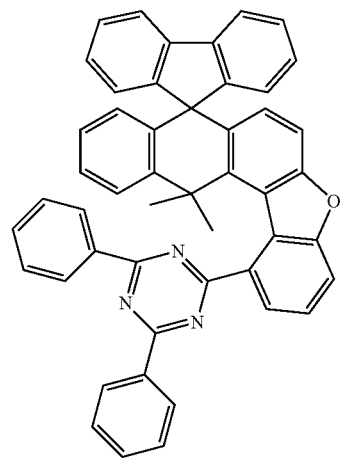
818
-continued
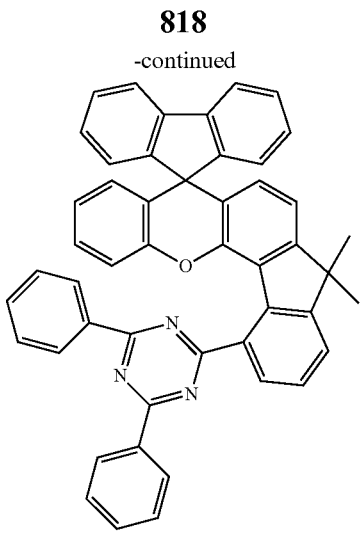
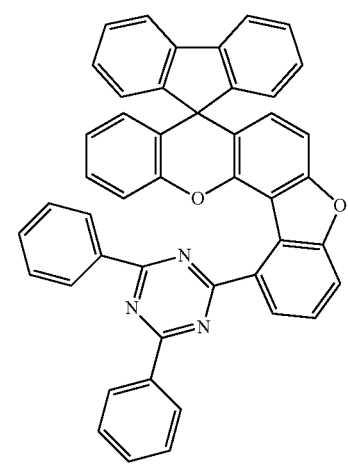
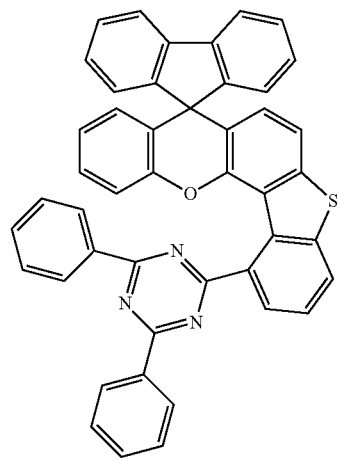

819
-continued
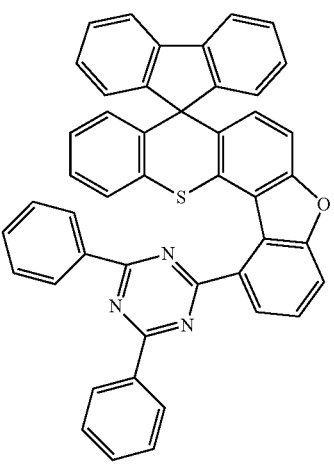
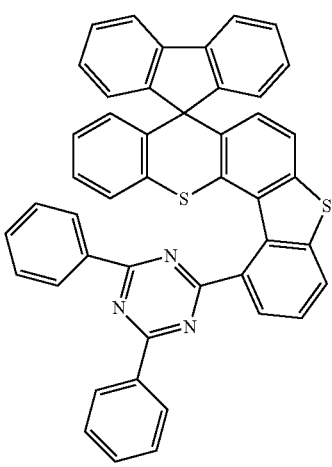
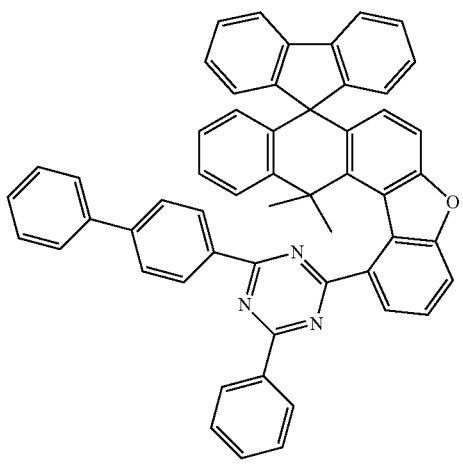
820
-continued
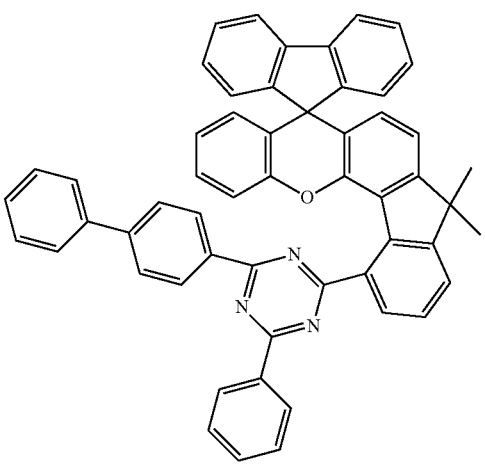
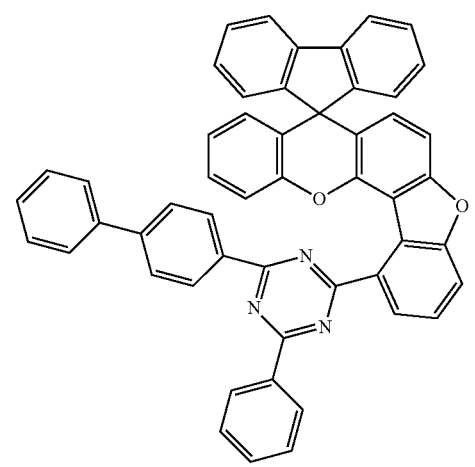
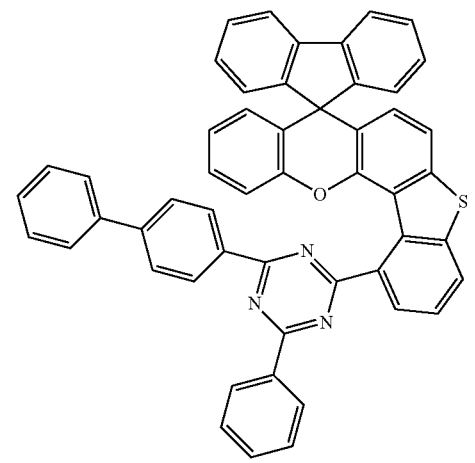

821
-continued
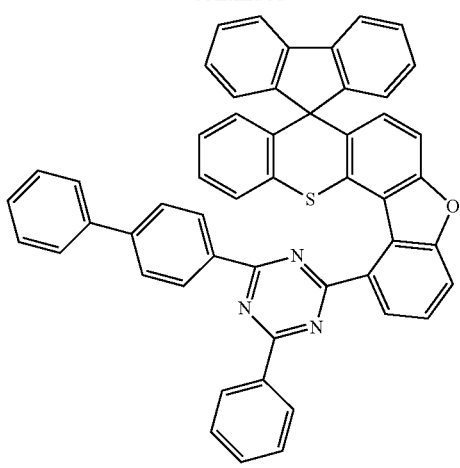
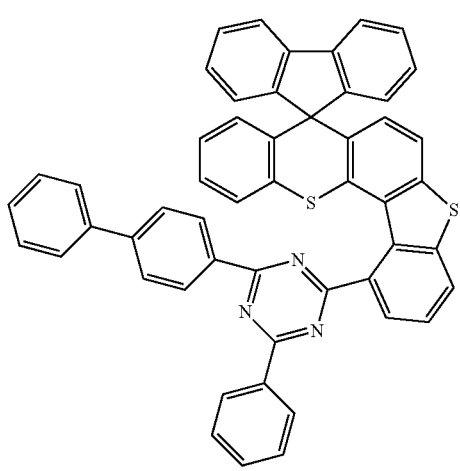
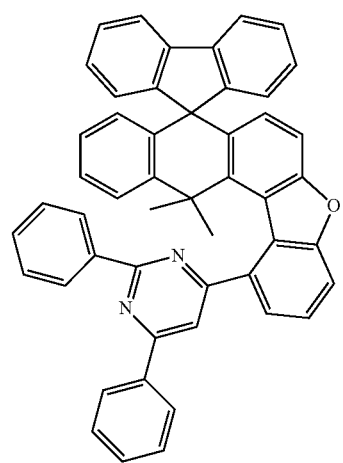
822
-continued
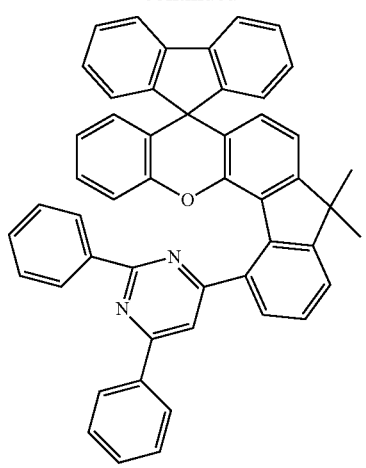
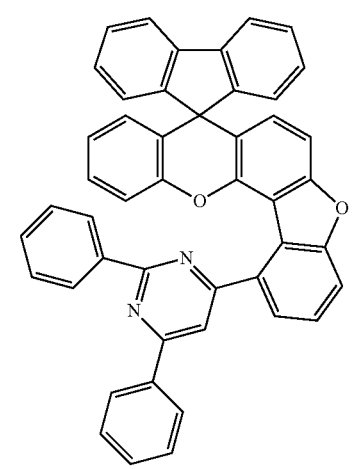
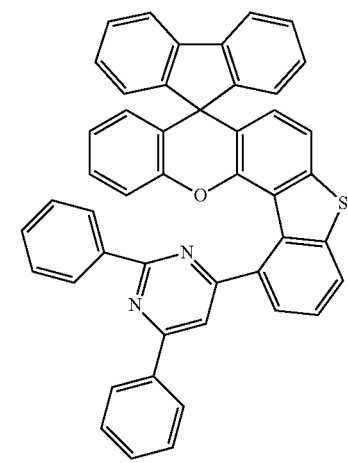

823
-continued
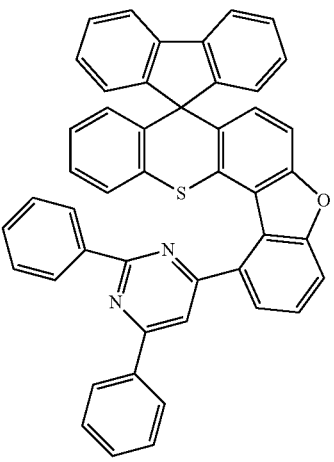
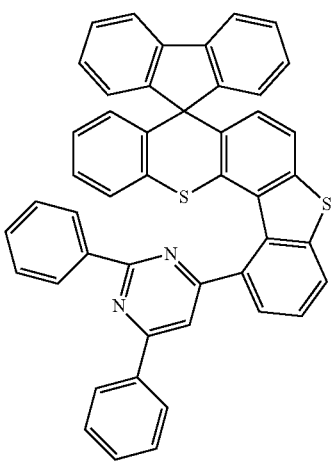
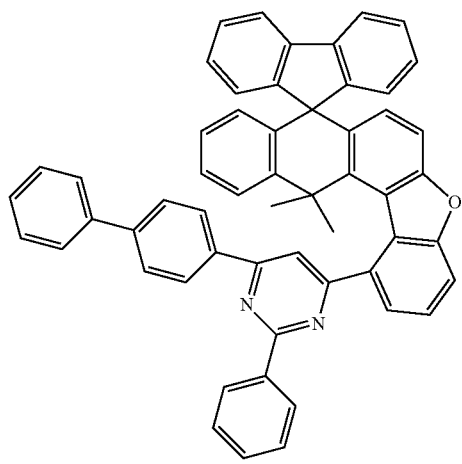
824
-continued
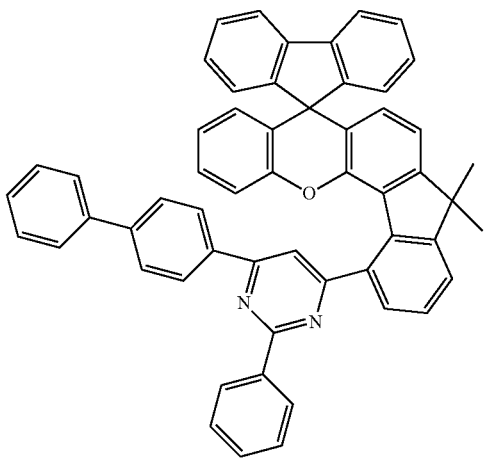
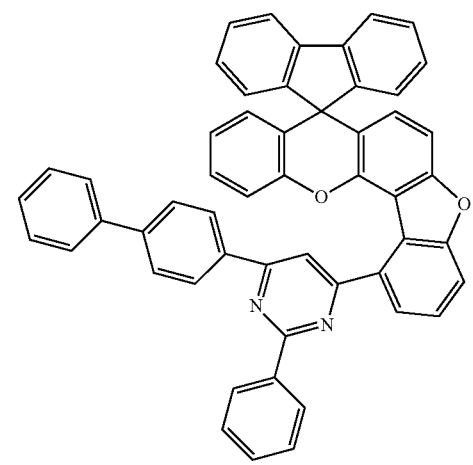
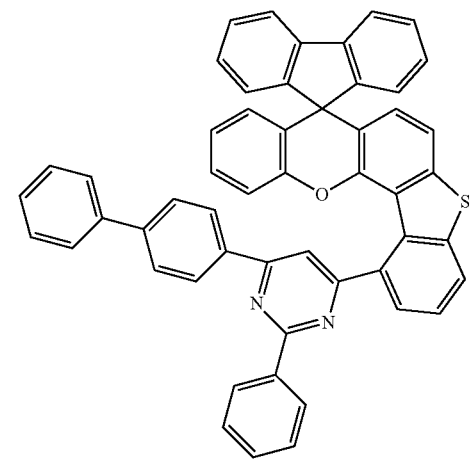

825
-continued
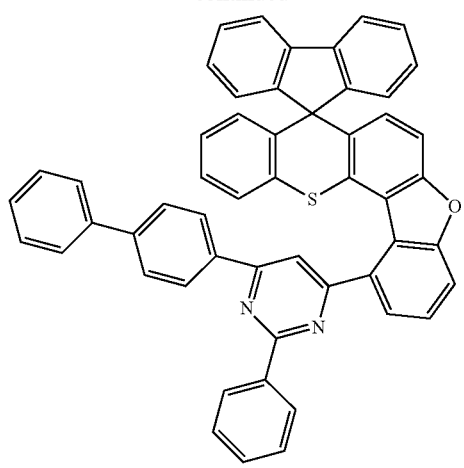
826
-continued
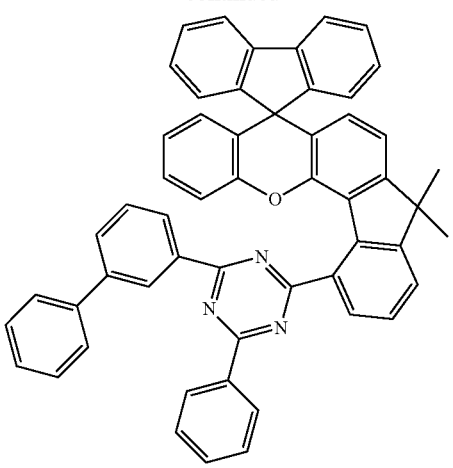
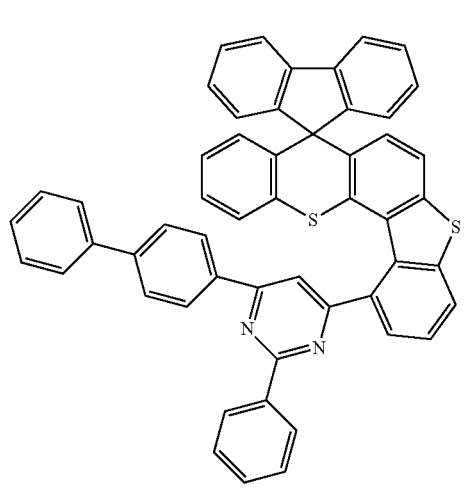
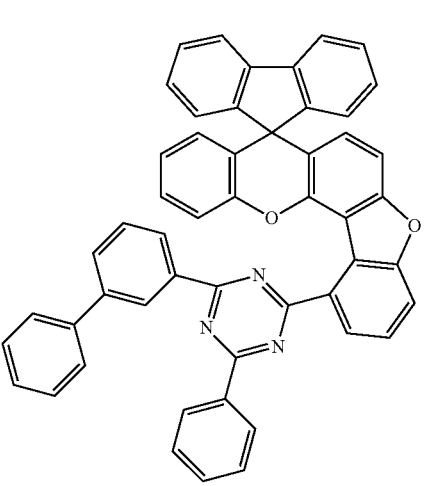
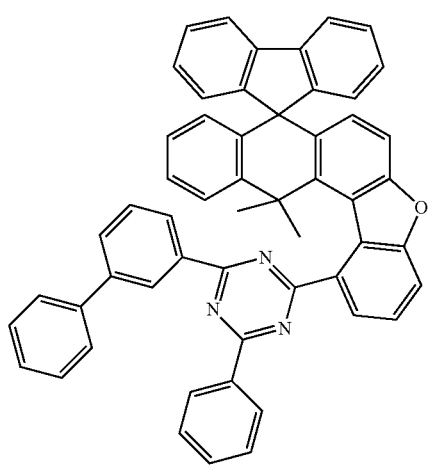
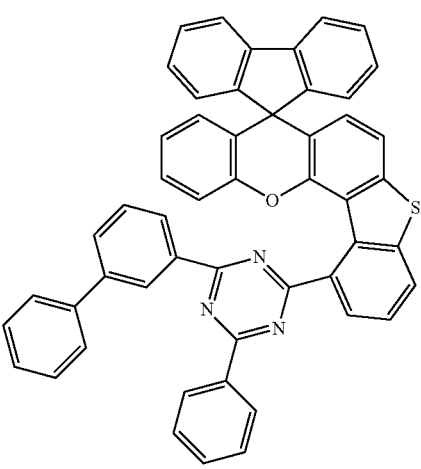

827
-continued
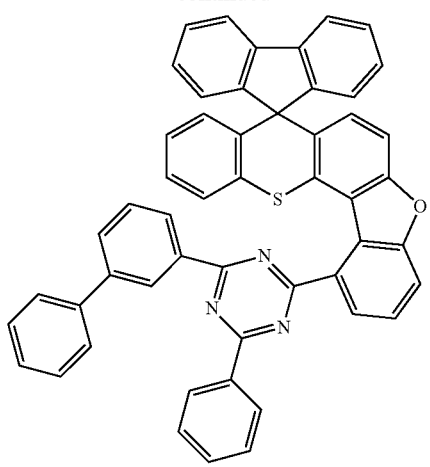
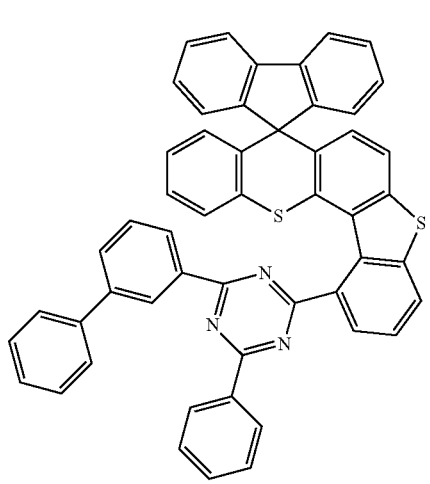
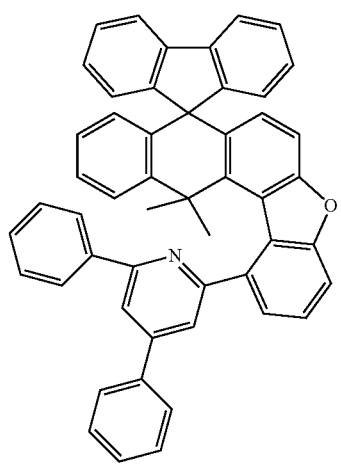
828
-continued
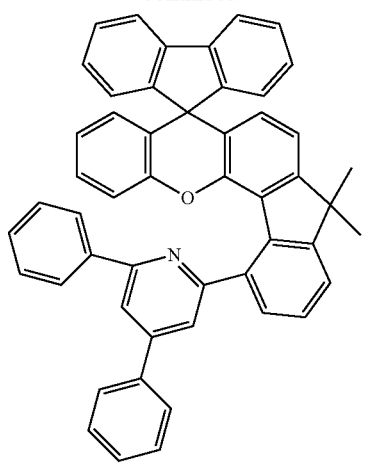
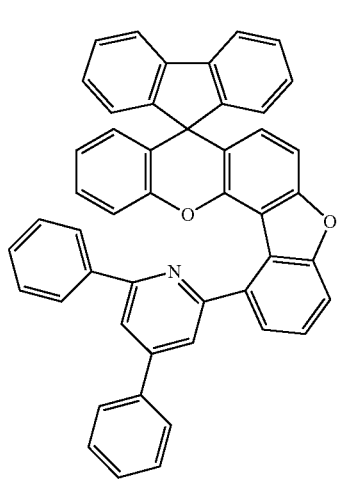
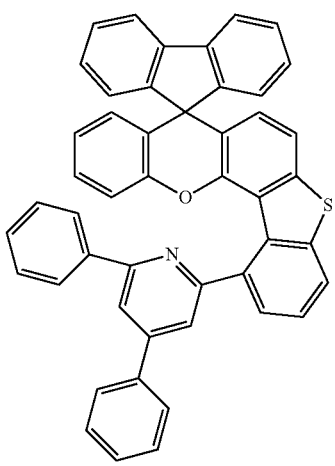

-continued
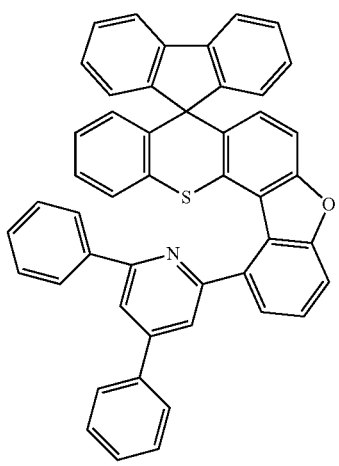
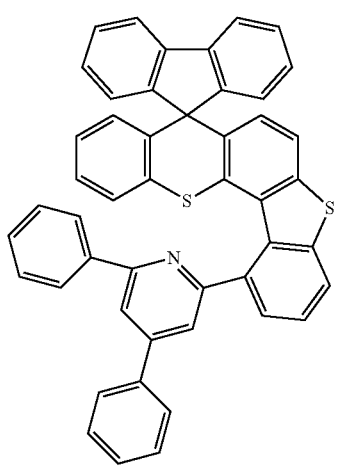
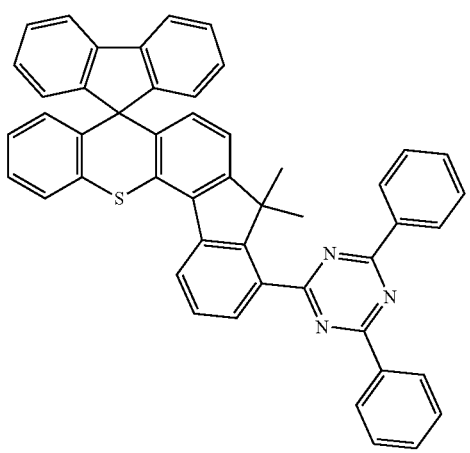
-continued
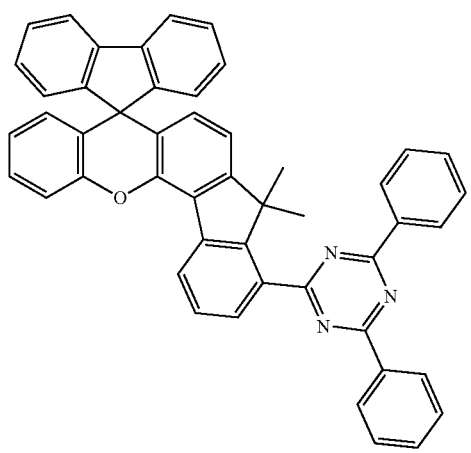
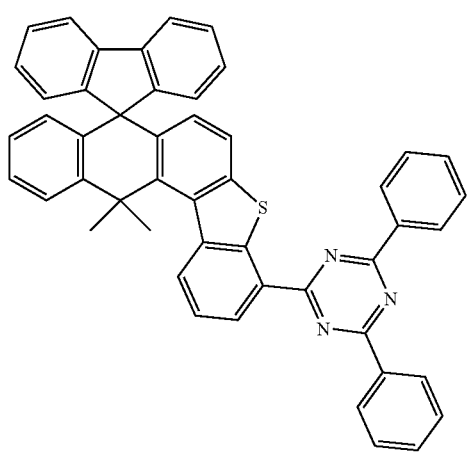
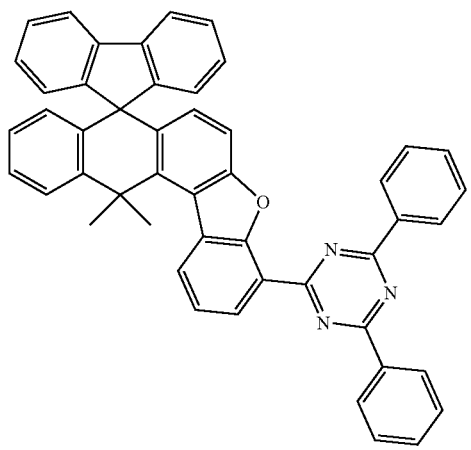

831
-continued
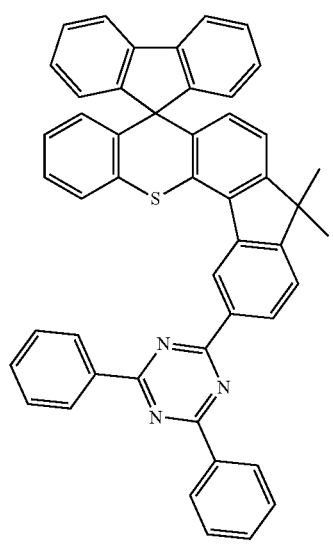
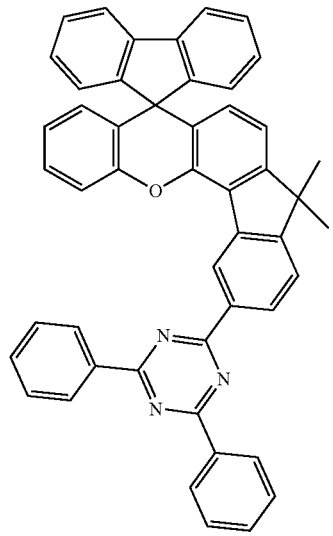
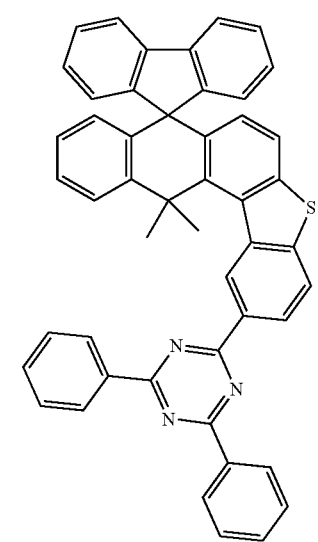
832
-continued
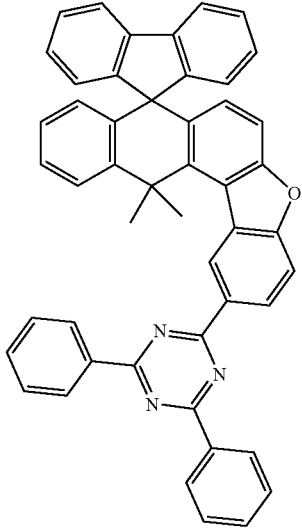
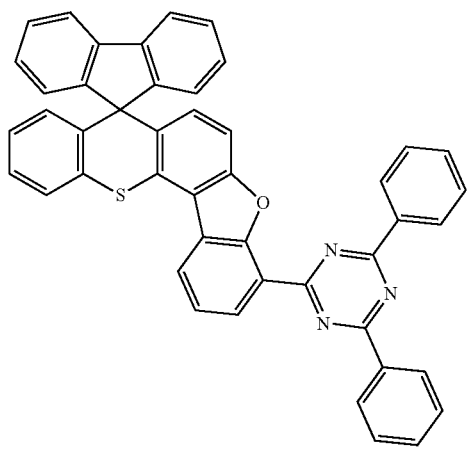
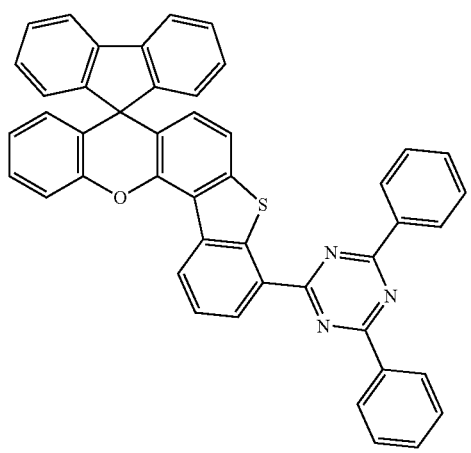

833
-continued
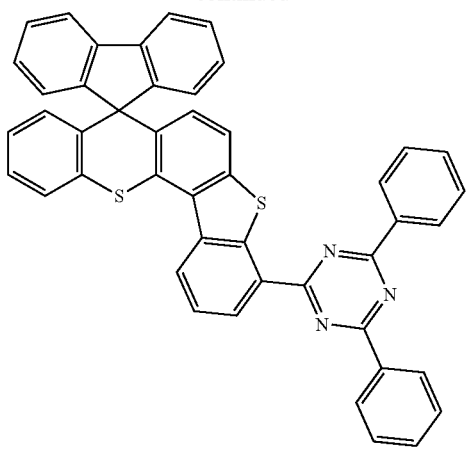
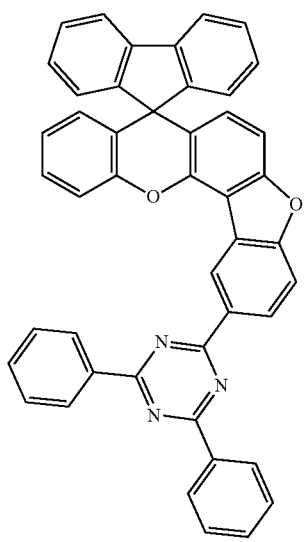
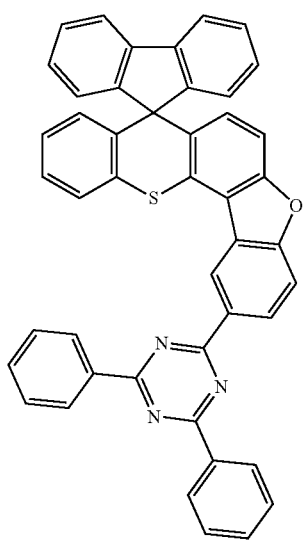
834
-continued
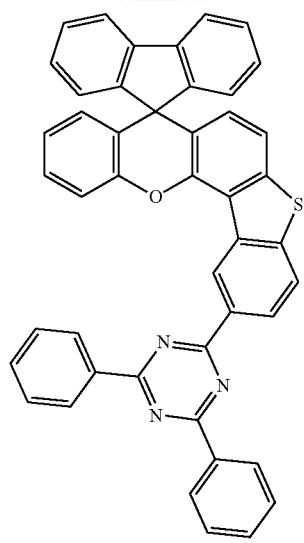
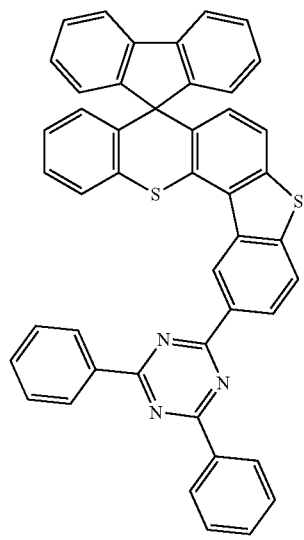
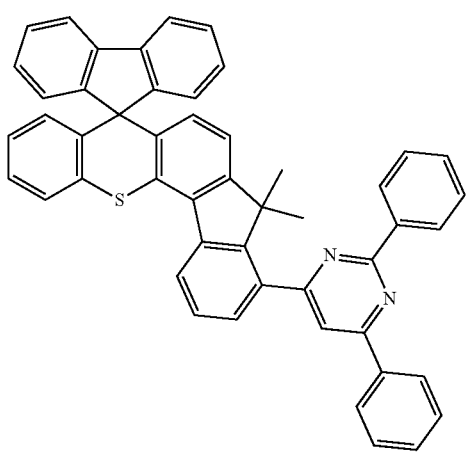

835
-continued
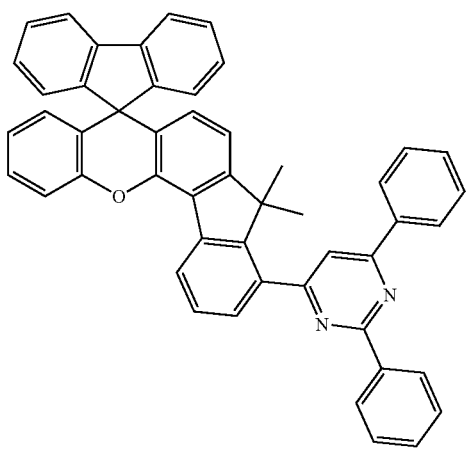
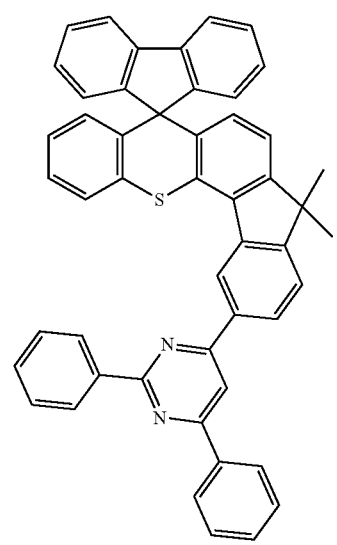
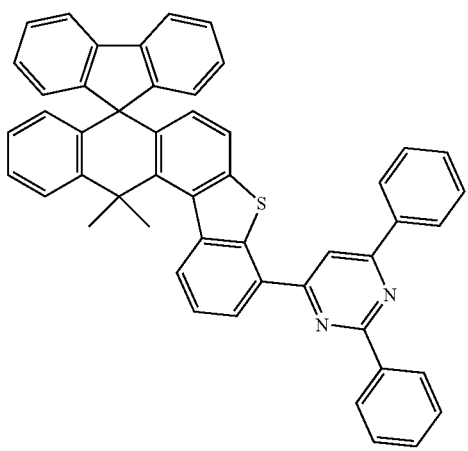
836
-continued
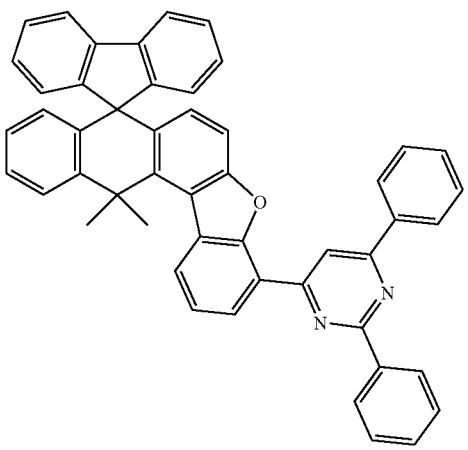
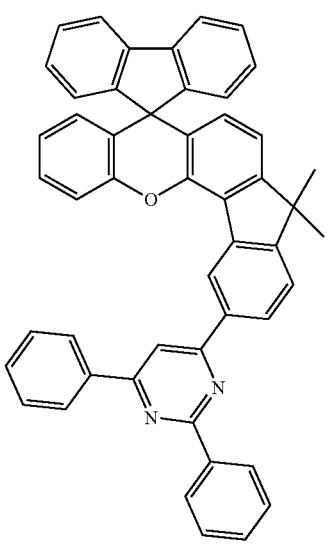
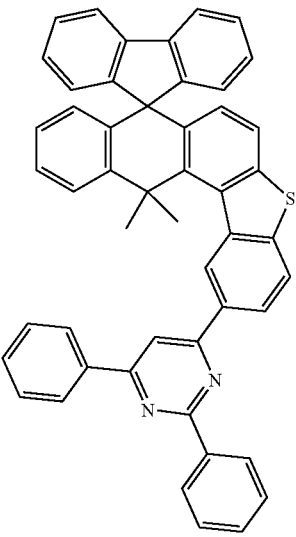

837
-continued
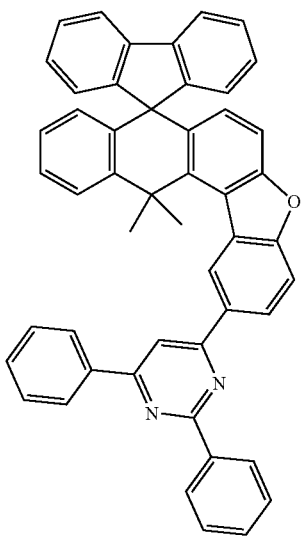
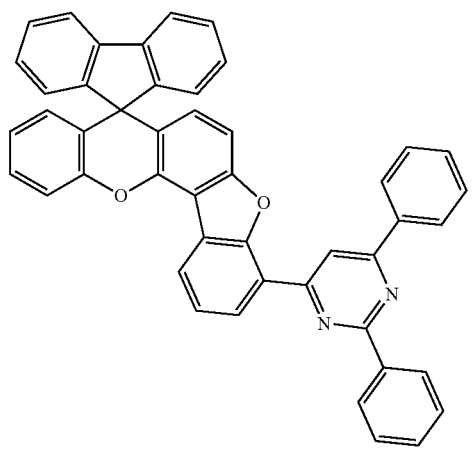
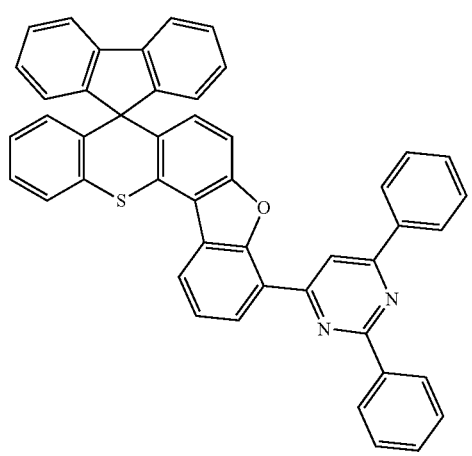
838
-continued
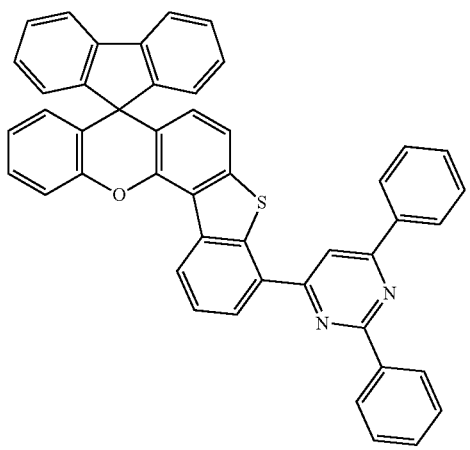
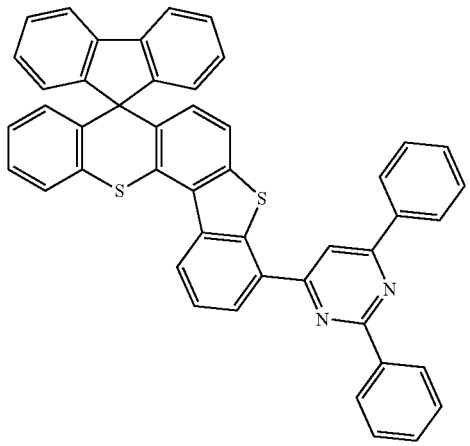
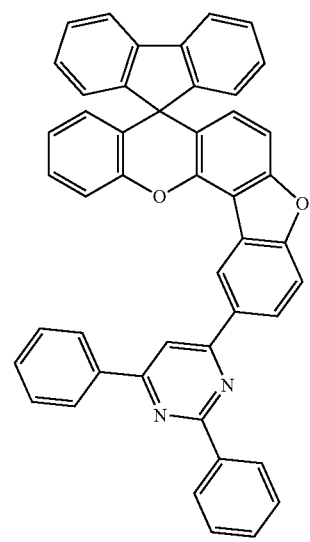

839                                    840
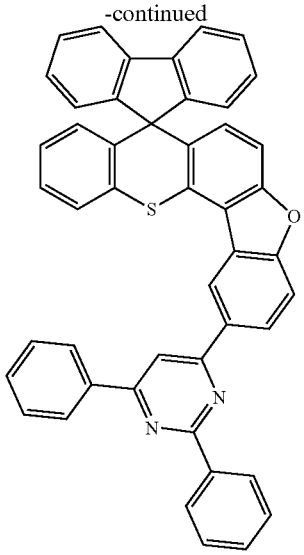
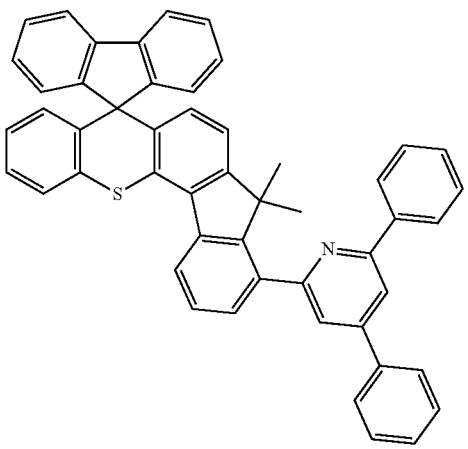
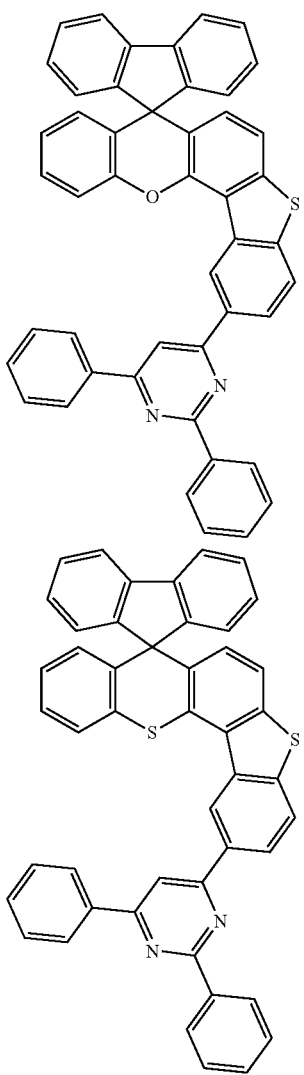
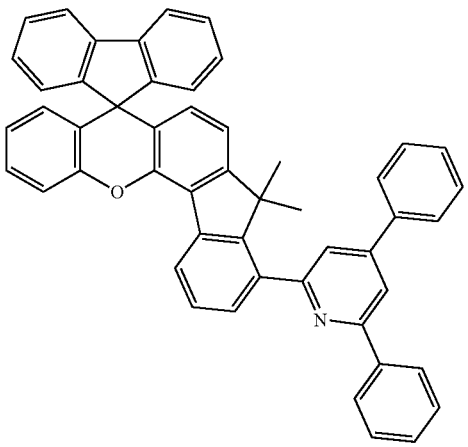
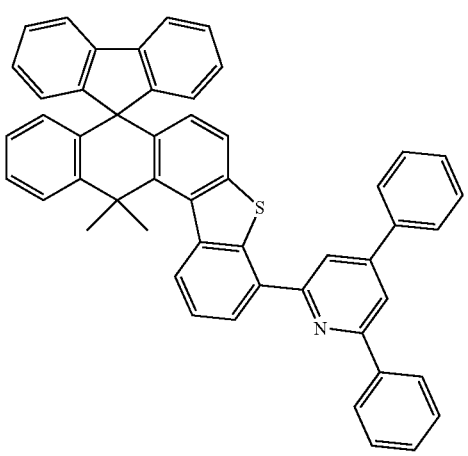

841
-continued
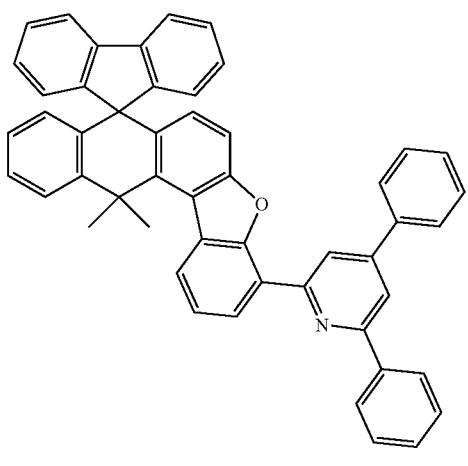
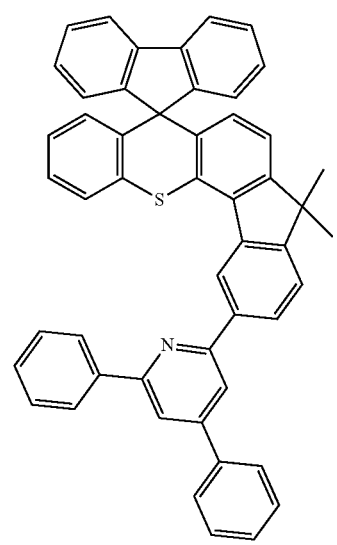
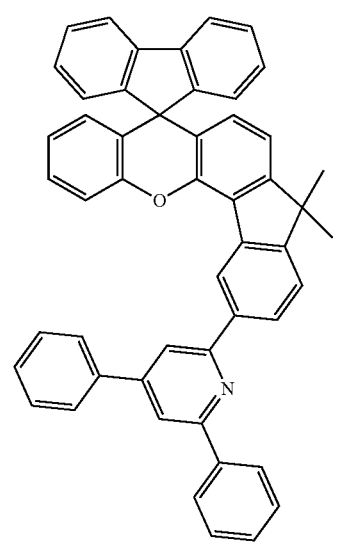
842
-continued
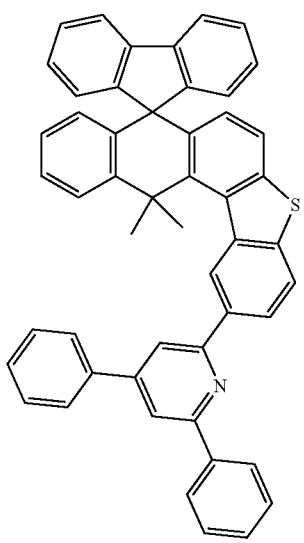
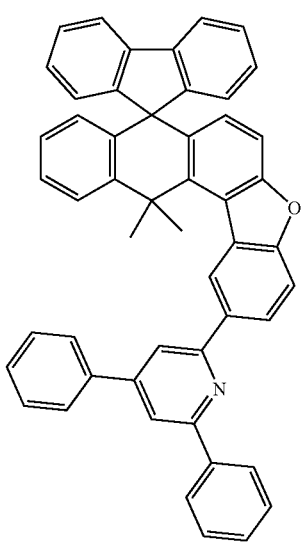
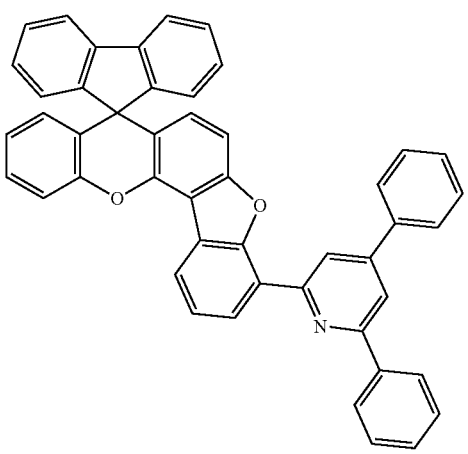

843
-continued
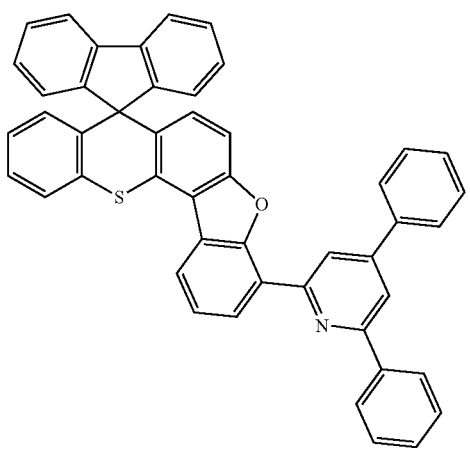
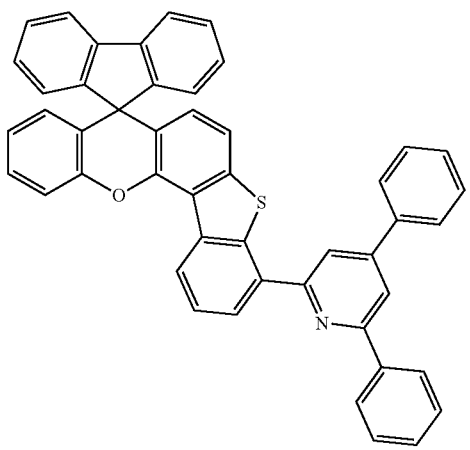
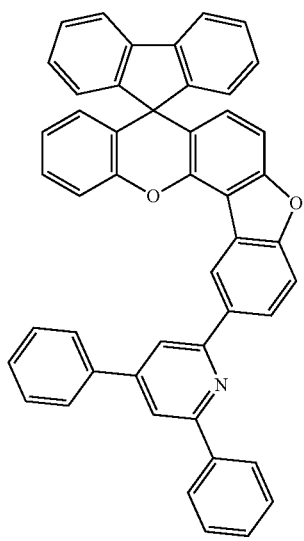
844
-continued
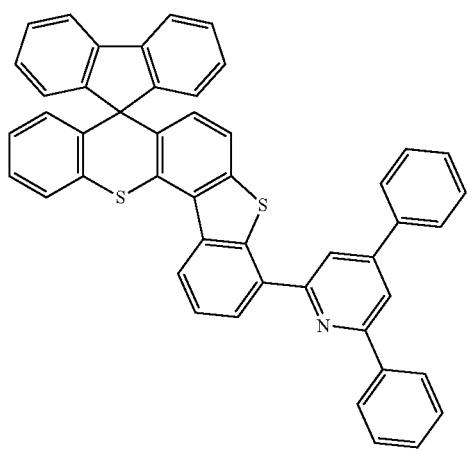
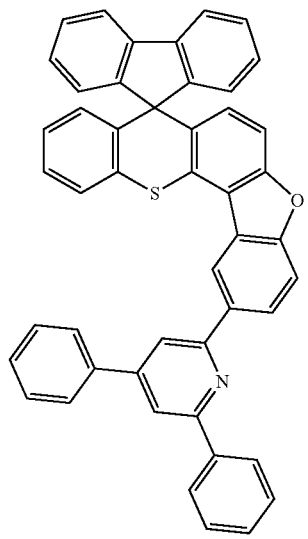
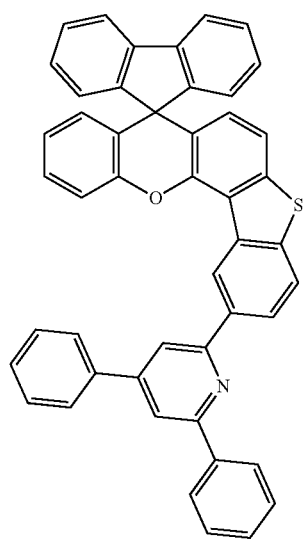

845
-continued
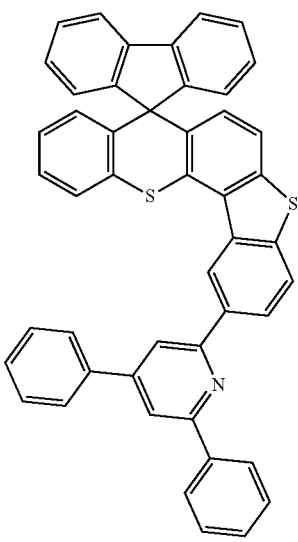
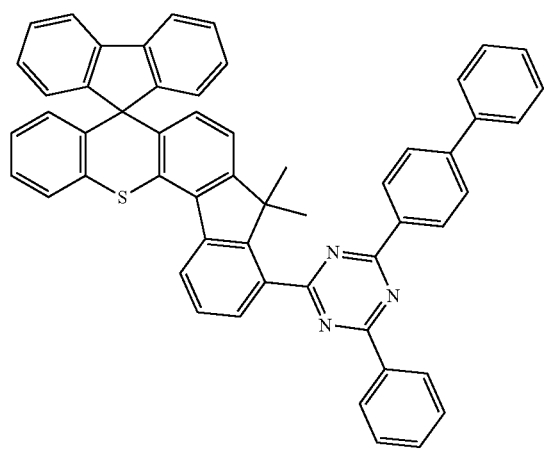
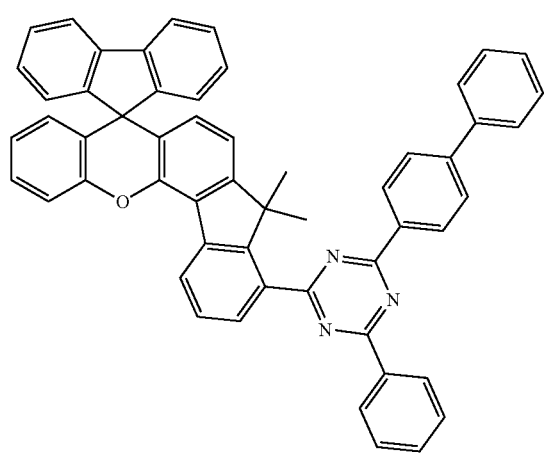
846
-continued
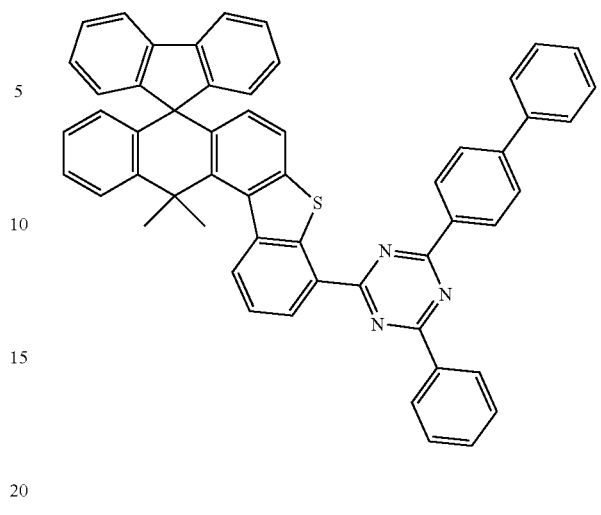
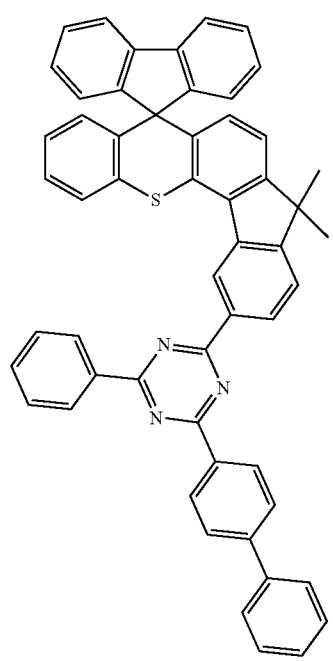

847
-continued
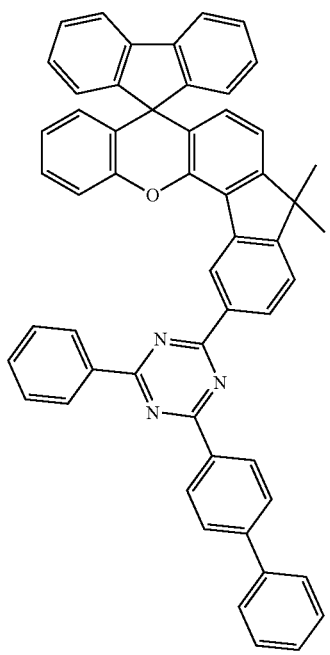
848
-continued
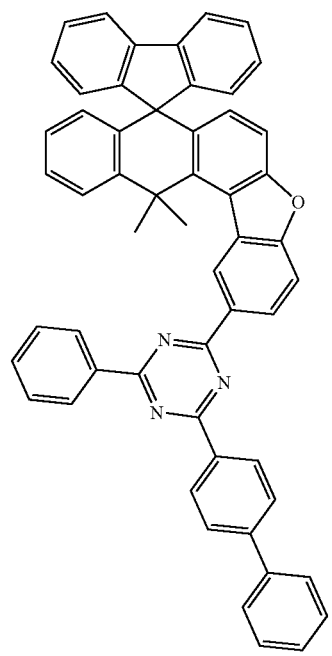 [SMILES: CC1(C)c2ccccc2C2(c3ccccc3-c3ccccc32)c2ccc3oc4ccc(-c5nc(-c6ccccc6)nc(-c6ccc(-c7ccccc7)cc6)n5)cc4c3c21]
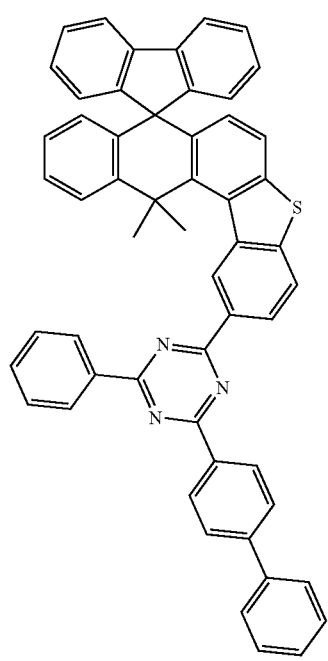
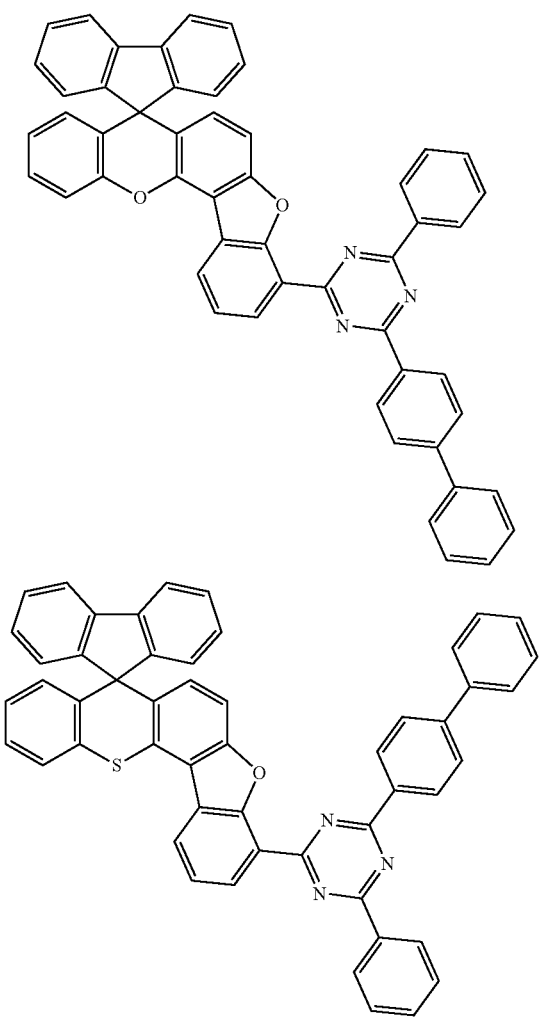

849
-continued
850
-continued
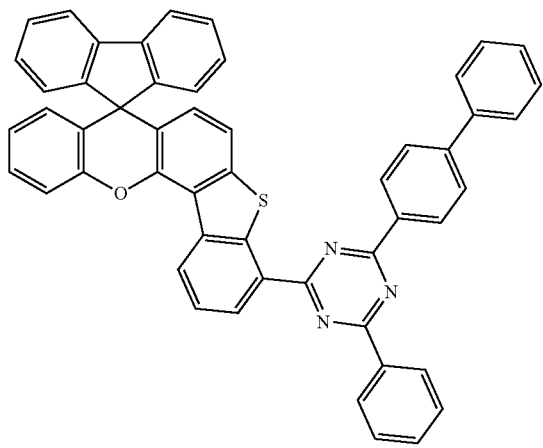
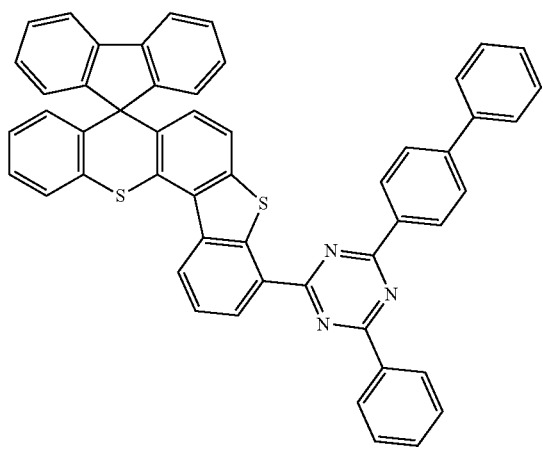
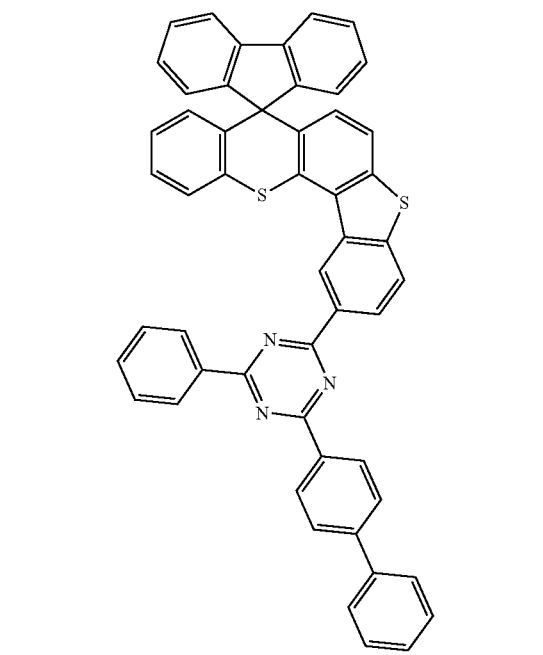
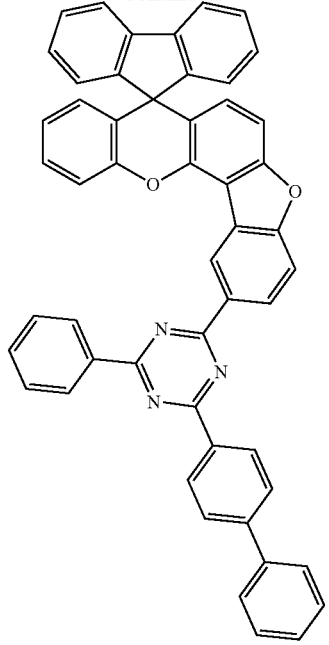
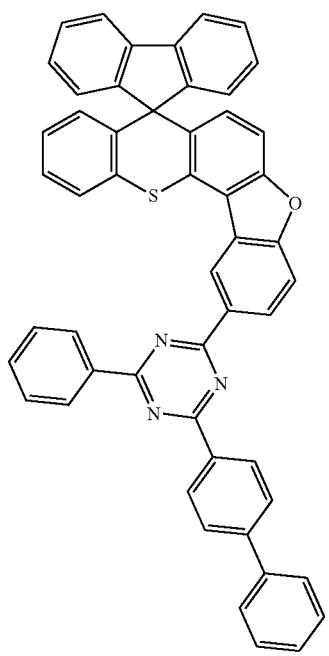

851
-continued
852
-continued
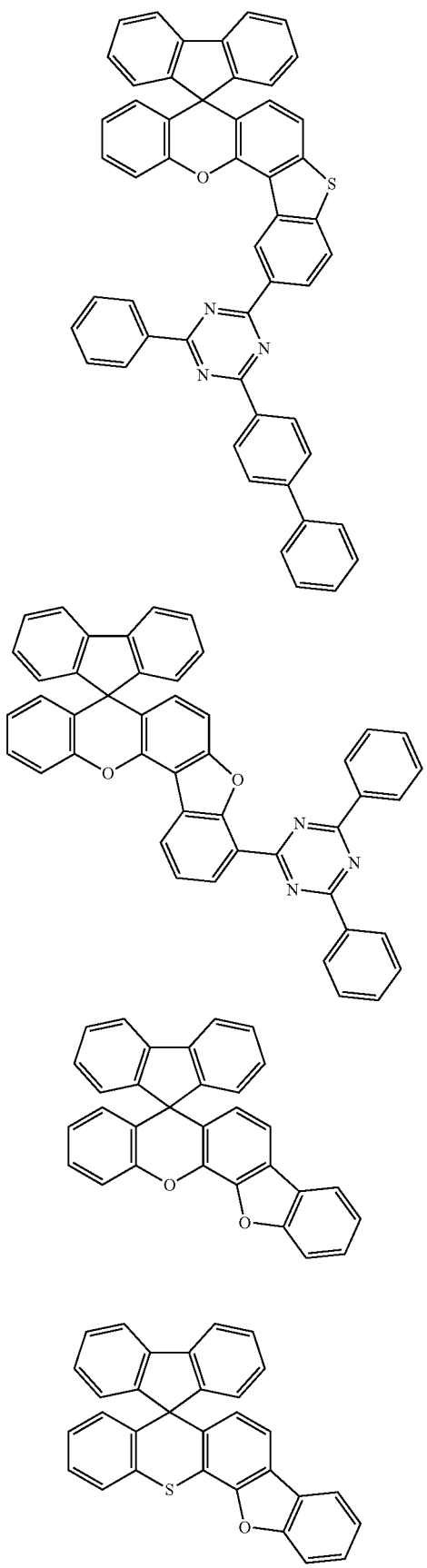
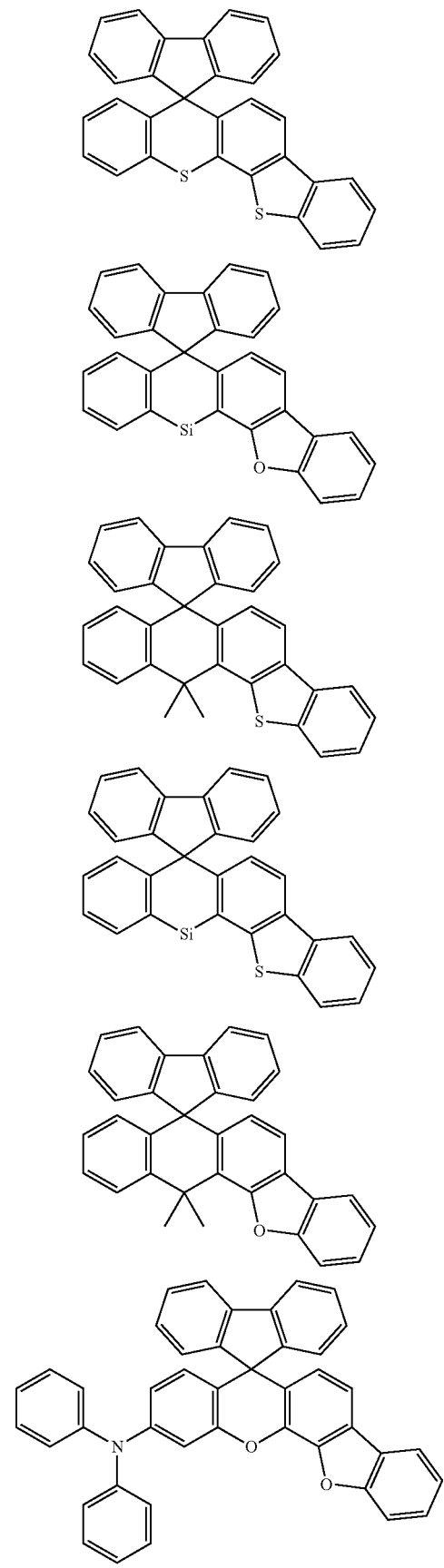

853
-continued
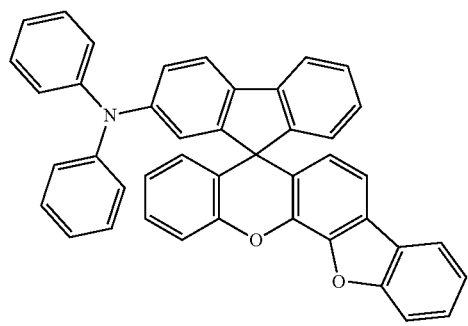
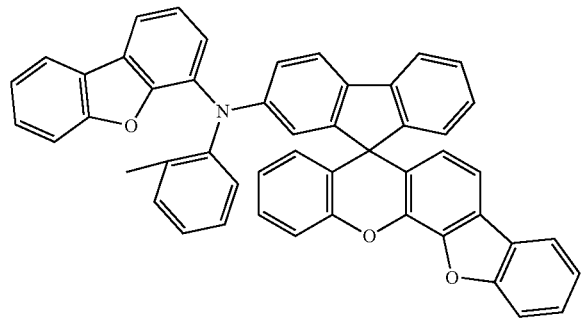
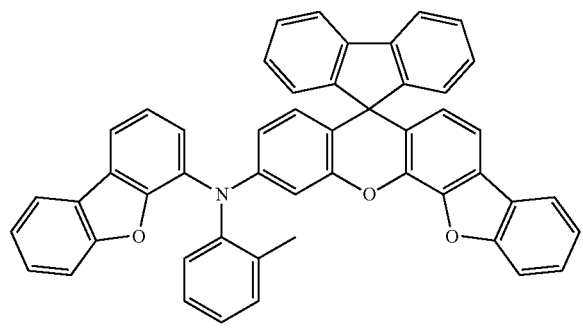 [SMILES: Cc1ccccc1N(c1ccc2c(c1)Sc1c(ccc3c1oc1ccccc13)C21c2ccccc2-c2ccccc21)c1cccc2c1oc1ccccc12]
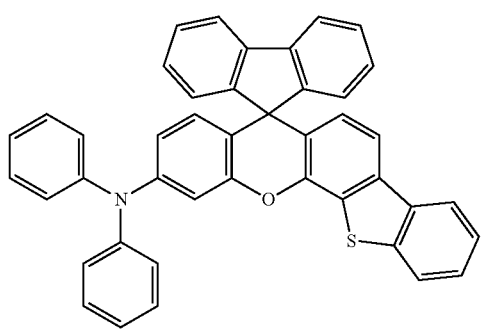
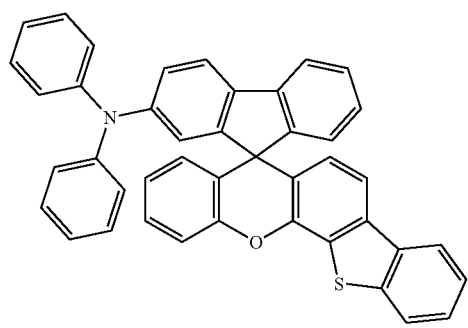
854
-continued
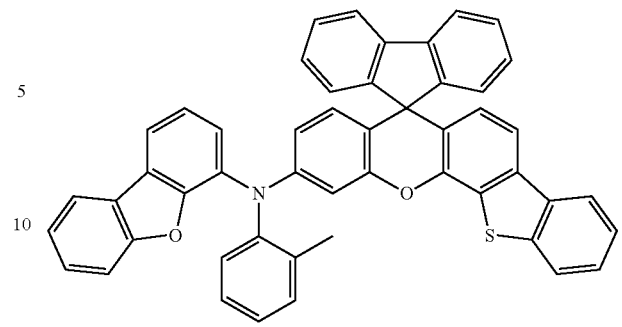
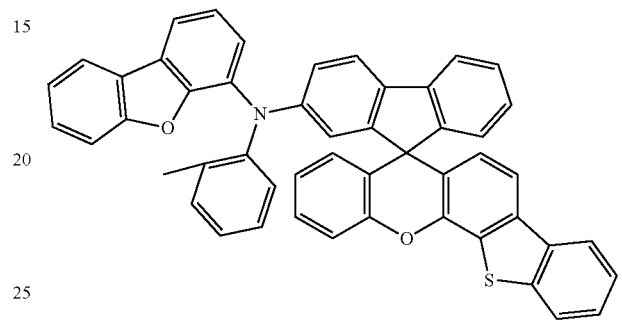
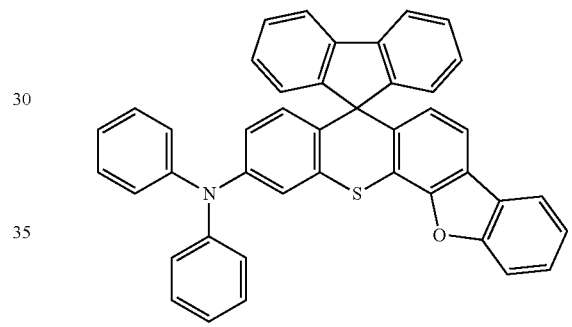
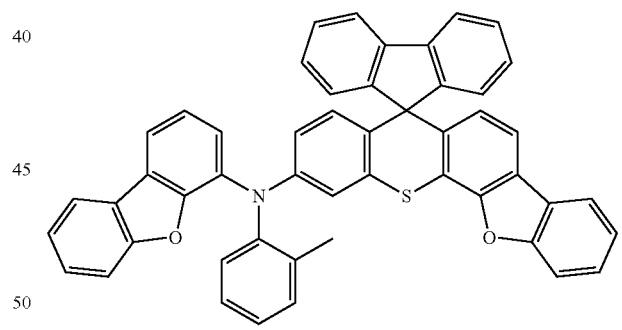
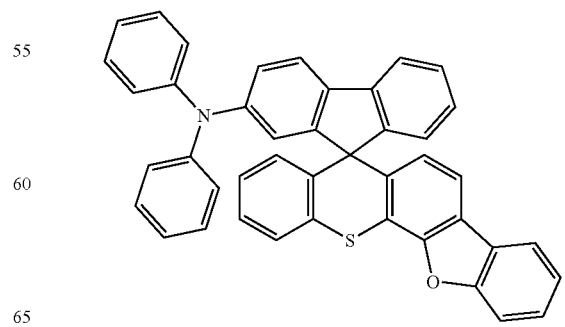

855
-continued
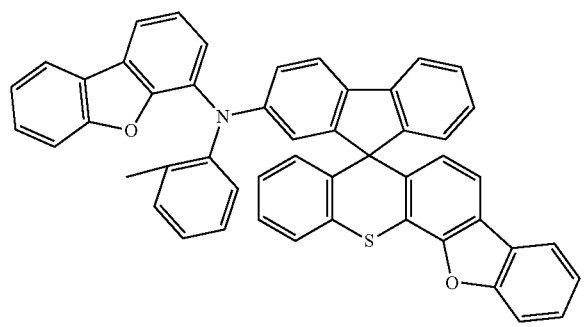
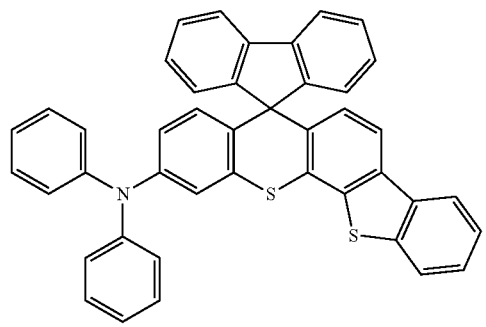
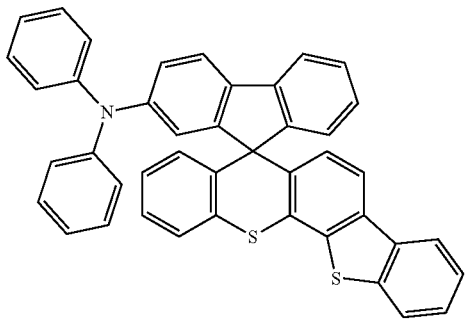
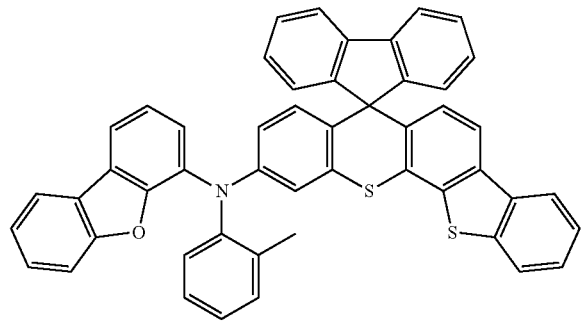
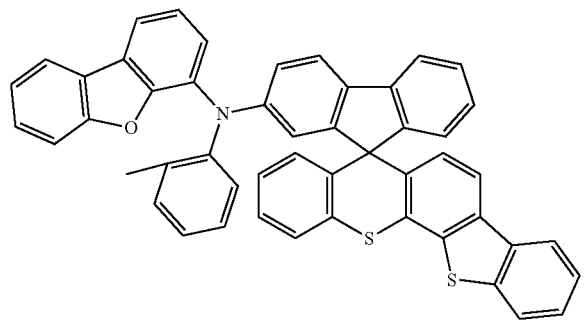
856
-continued
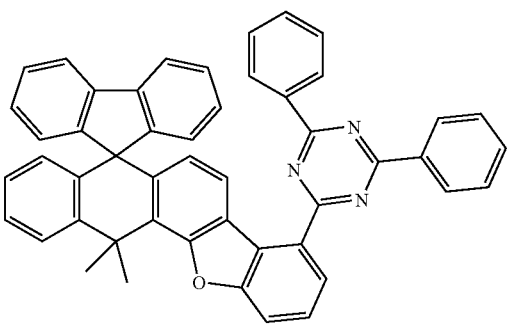
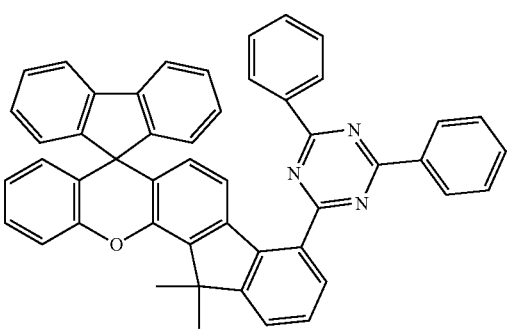
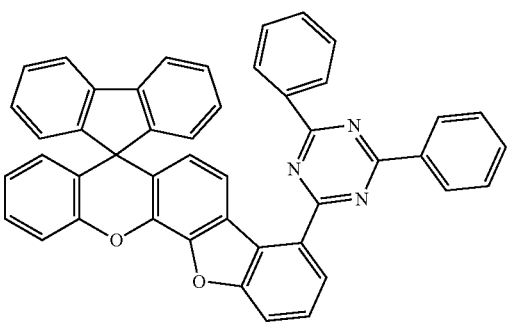
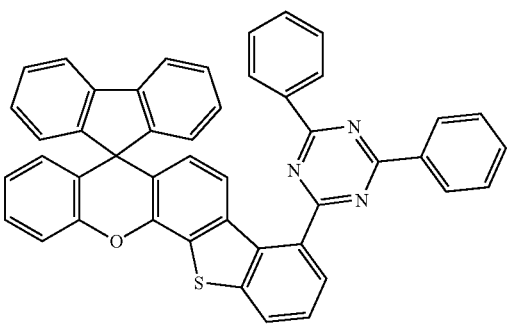
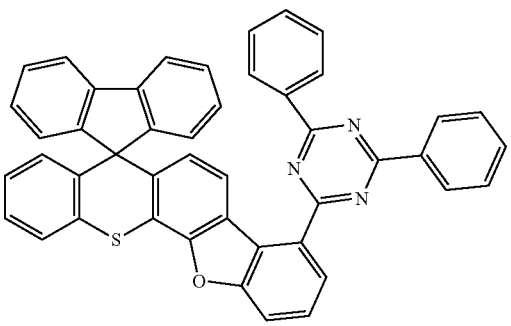

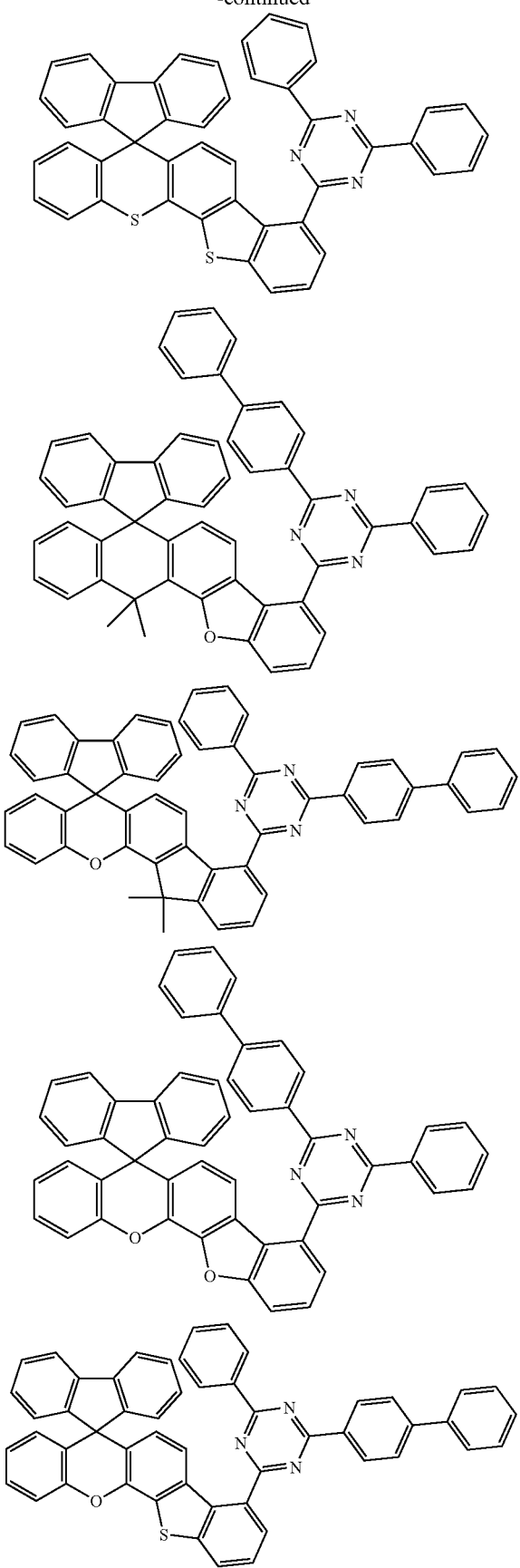
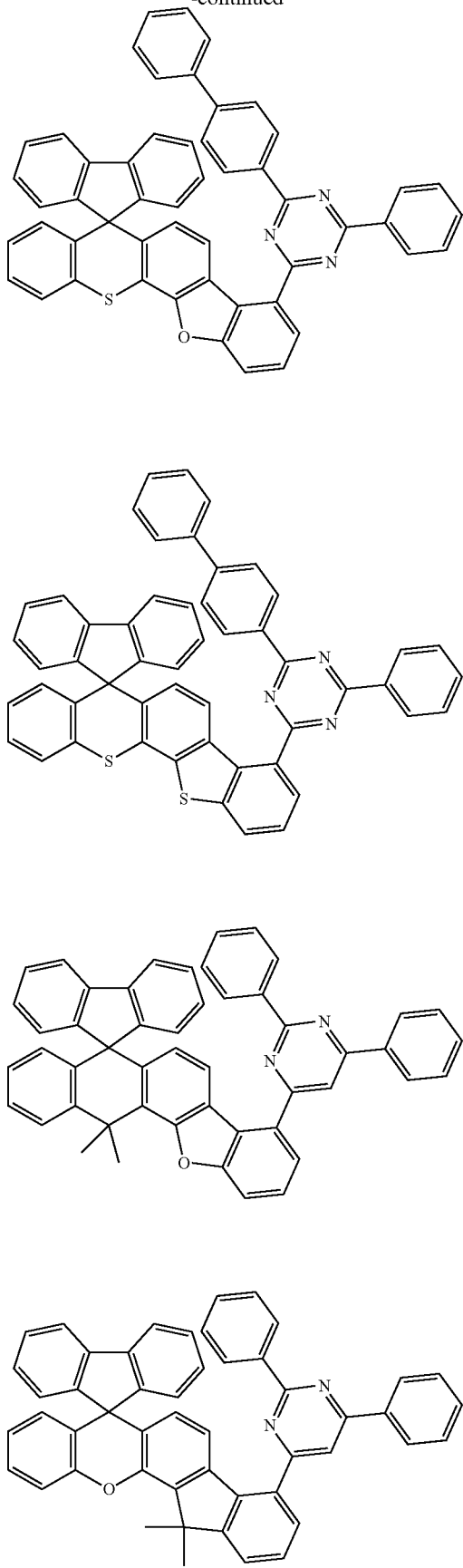

859
-continued
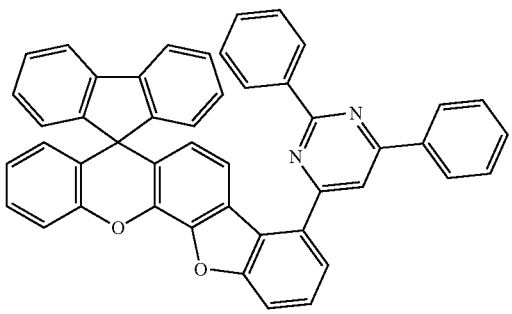
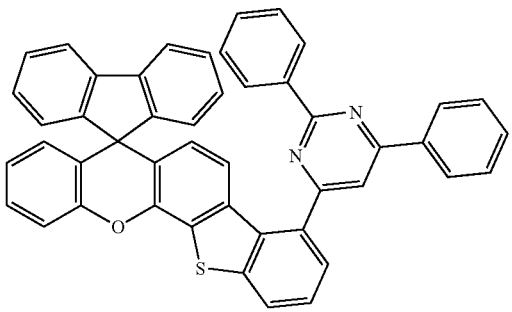
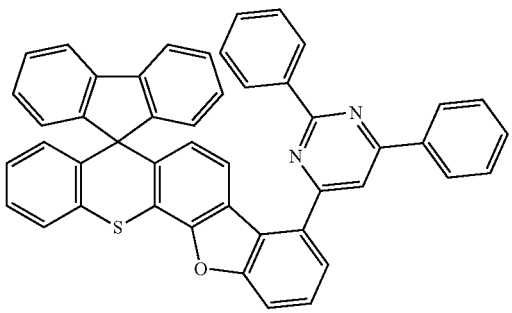
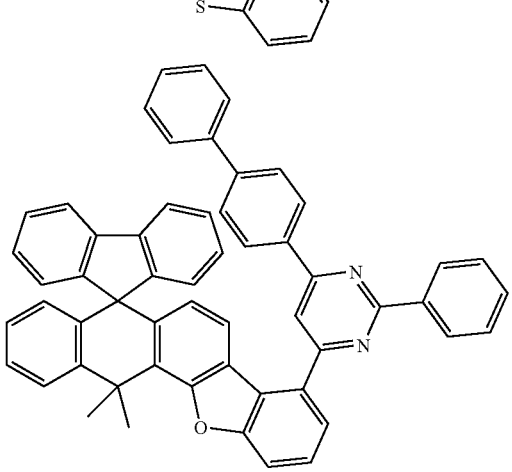
860
-continued
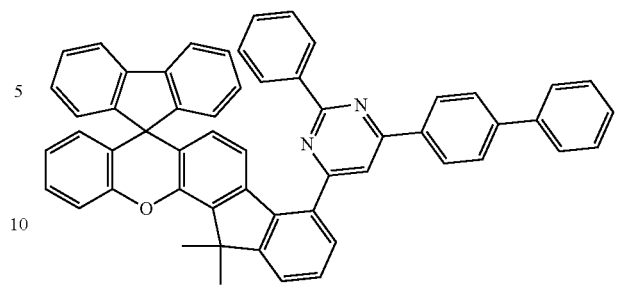
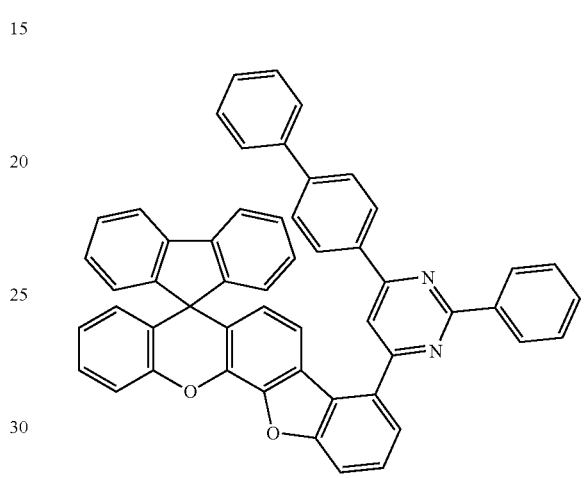
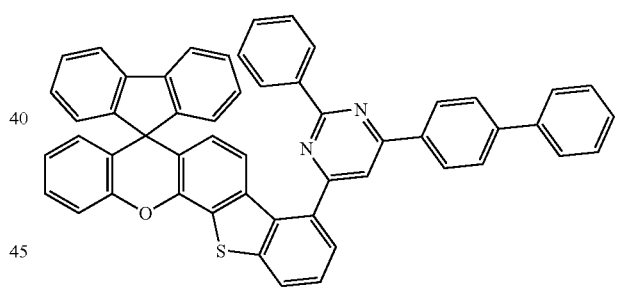
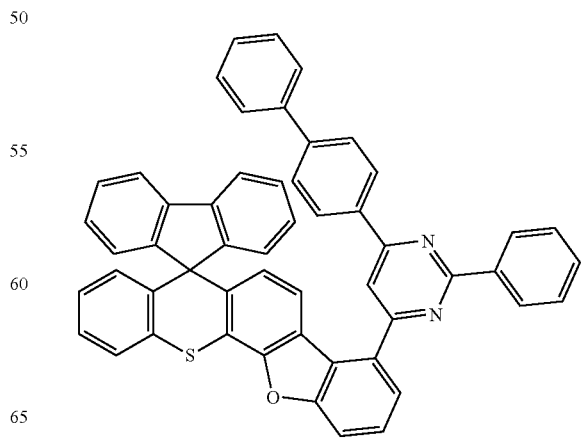

861
-continued
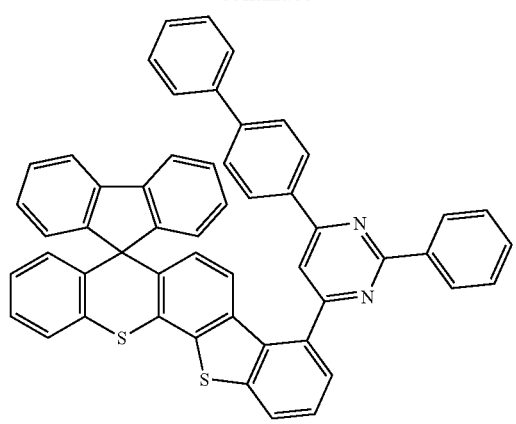
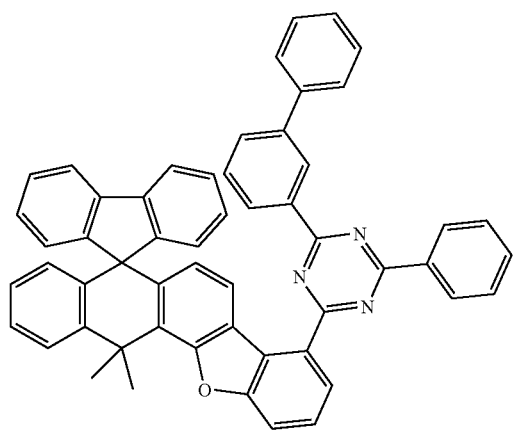
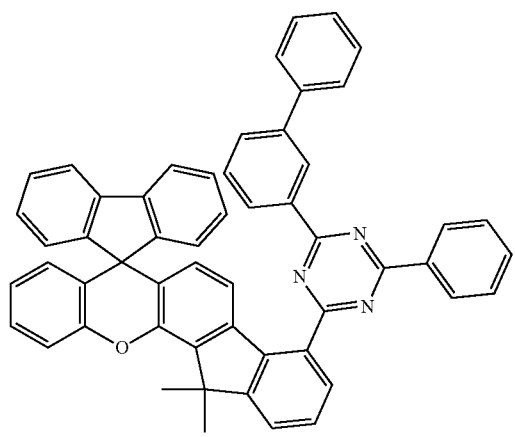 [SMILES: CC1(C)c2cccc(-c3nc(-c4ccccc4)nc(-c4cccc(-c5ccccc5)c4)n3)c2-c2ccc3c(c21)Oc1ccccc1C31c2ccccc2-c2ccccc21]
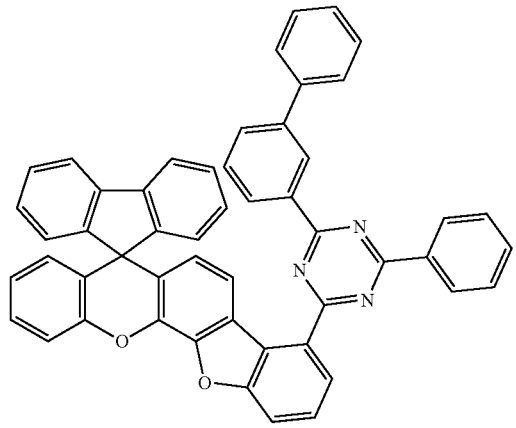
862
-continued
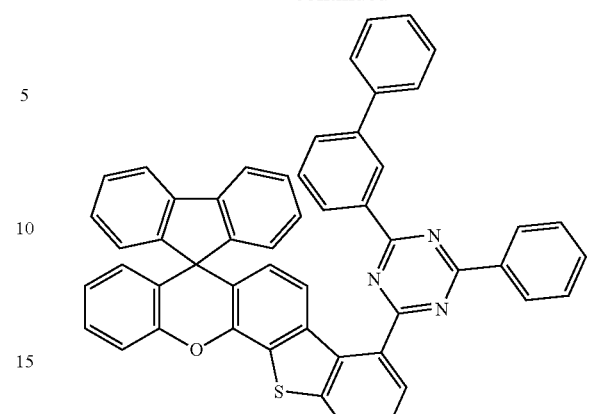
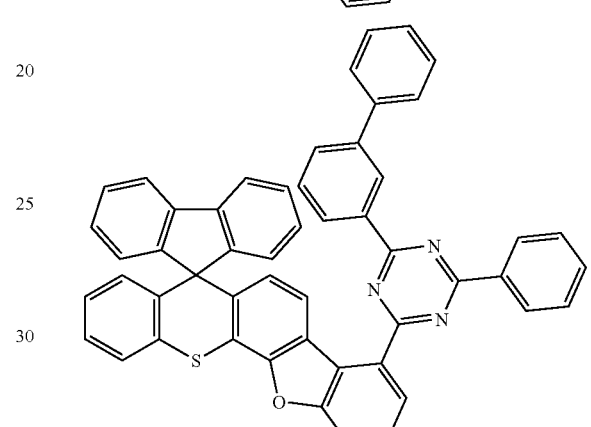
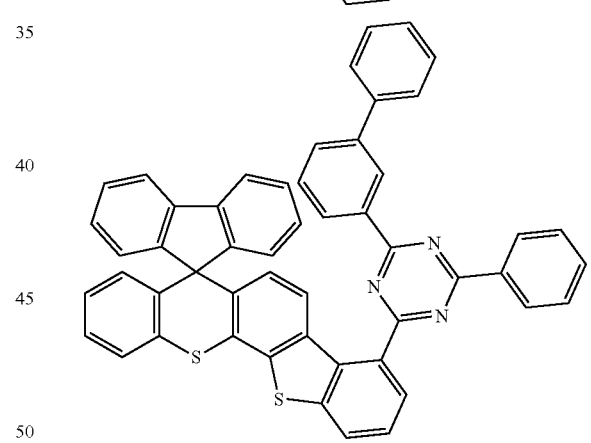
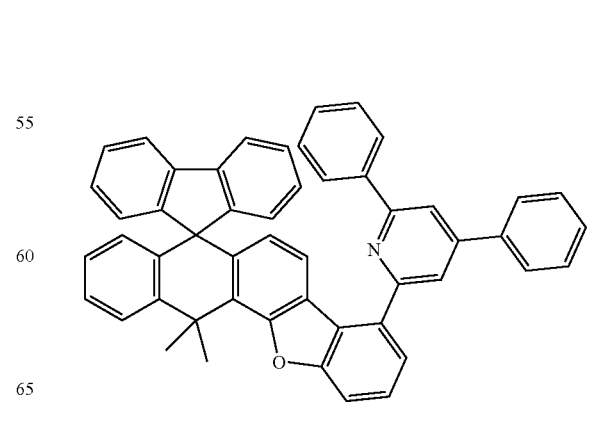

863
-continued
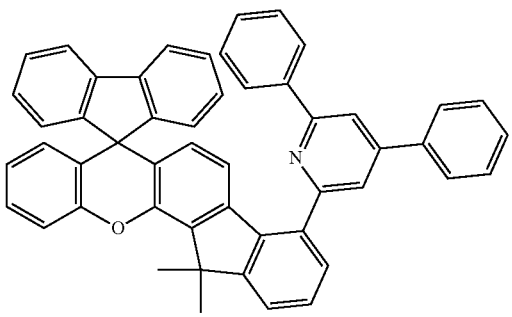
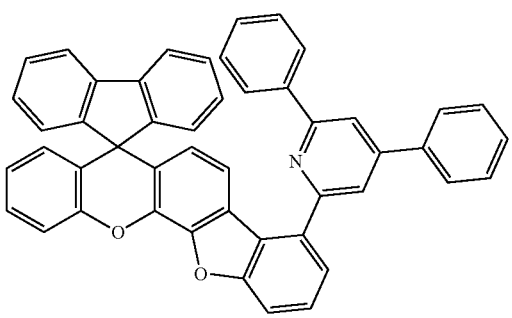
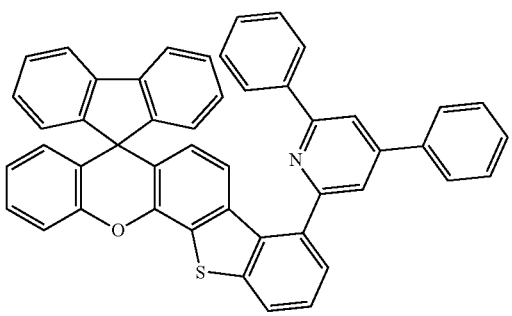
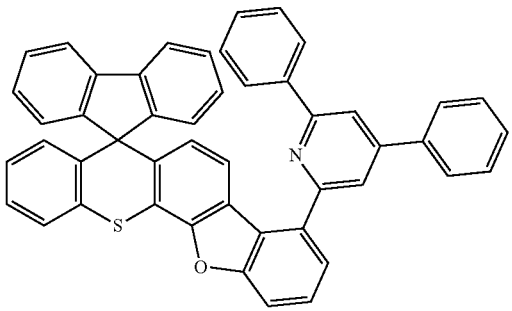
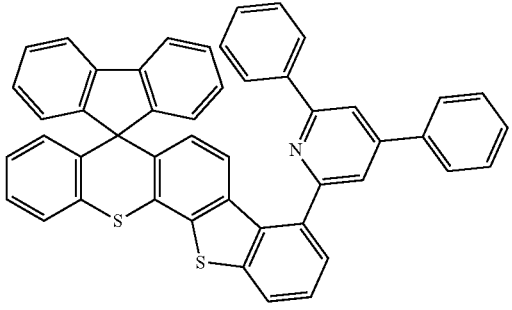
864
-continued
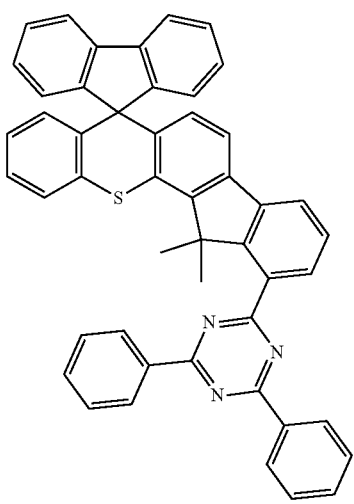
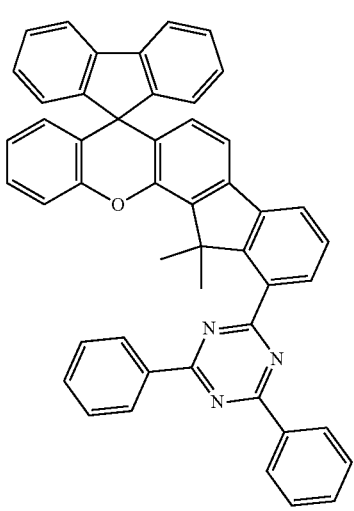
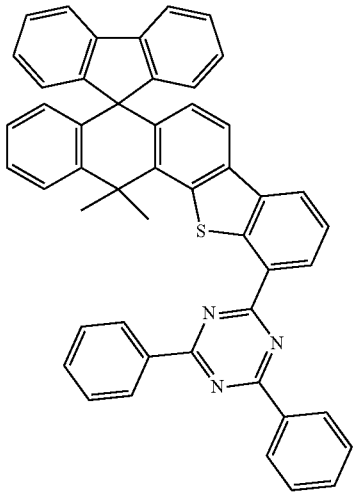

865
-continued
866
-continued
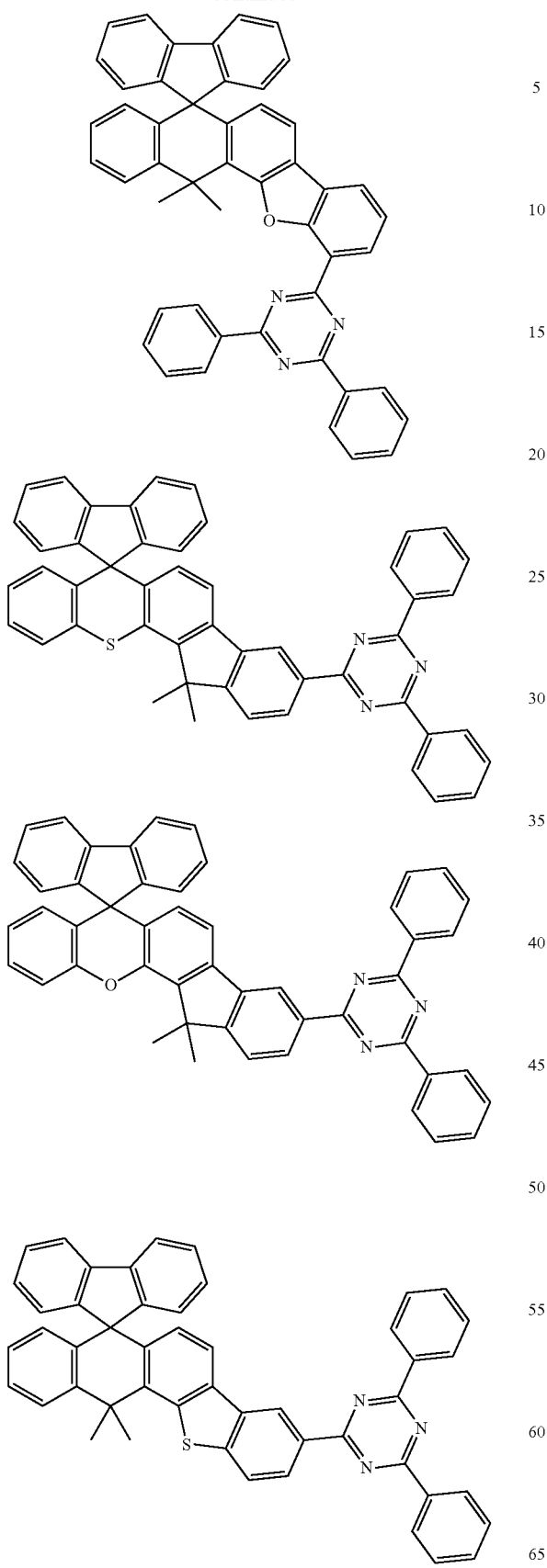
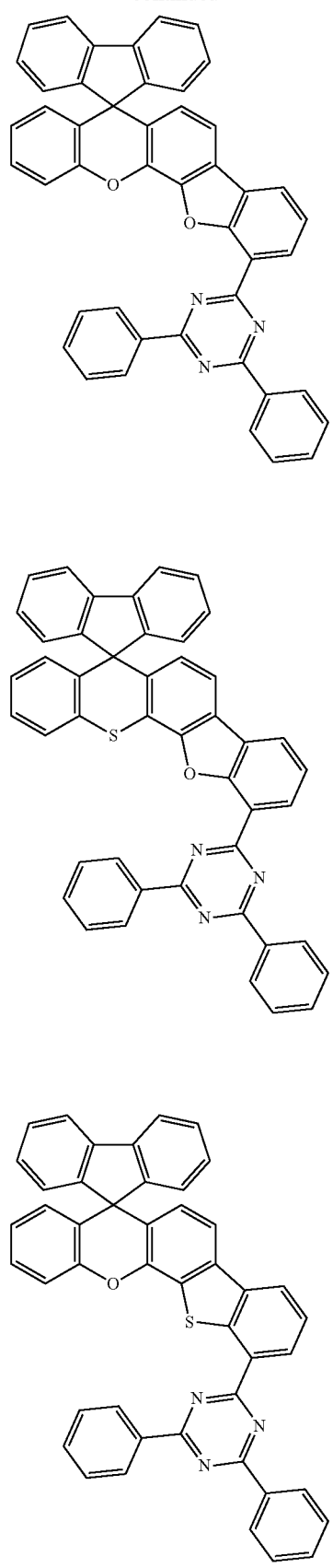

867
-continued
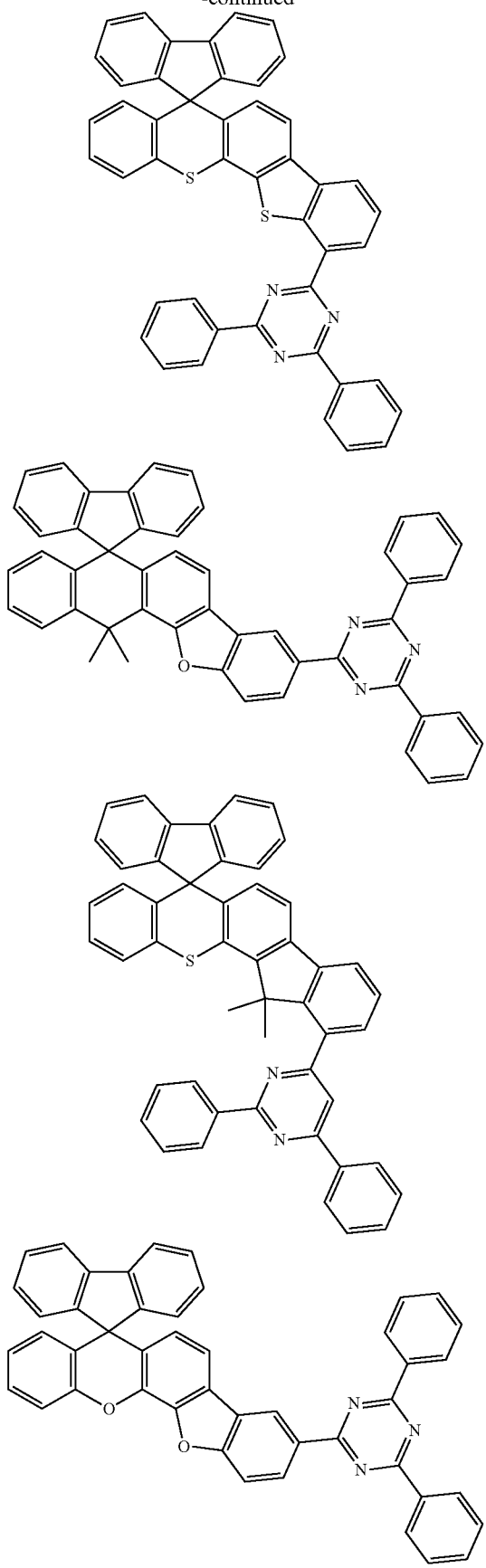
868
-continued
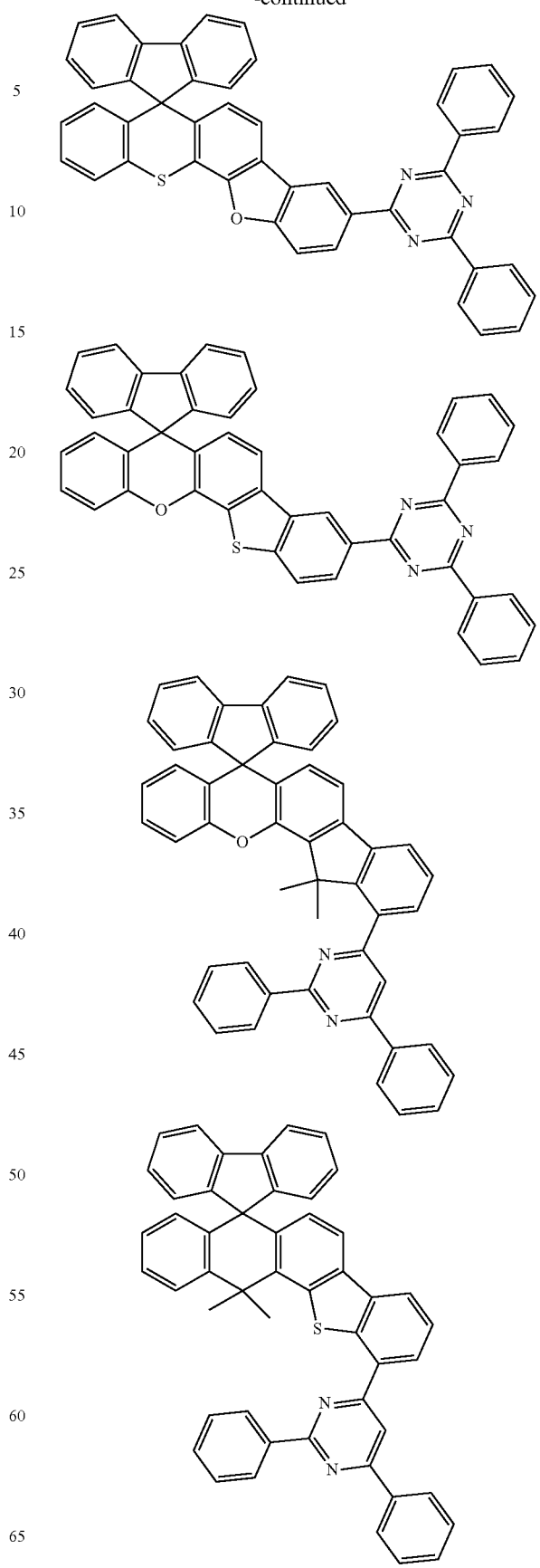

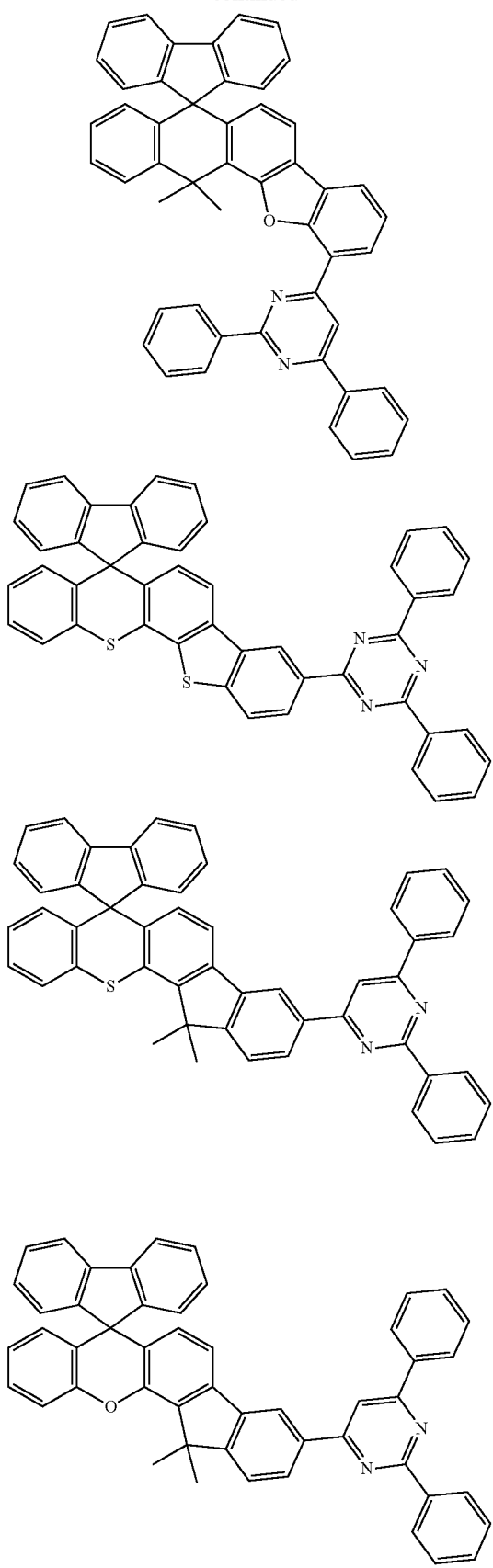
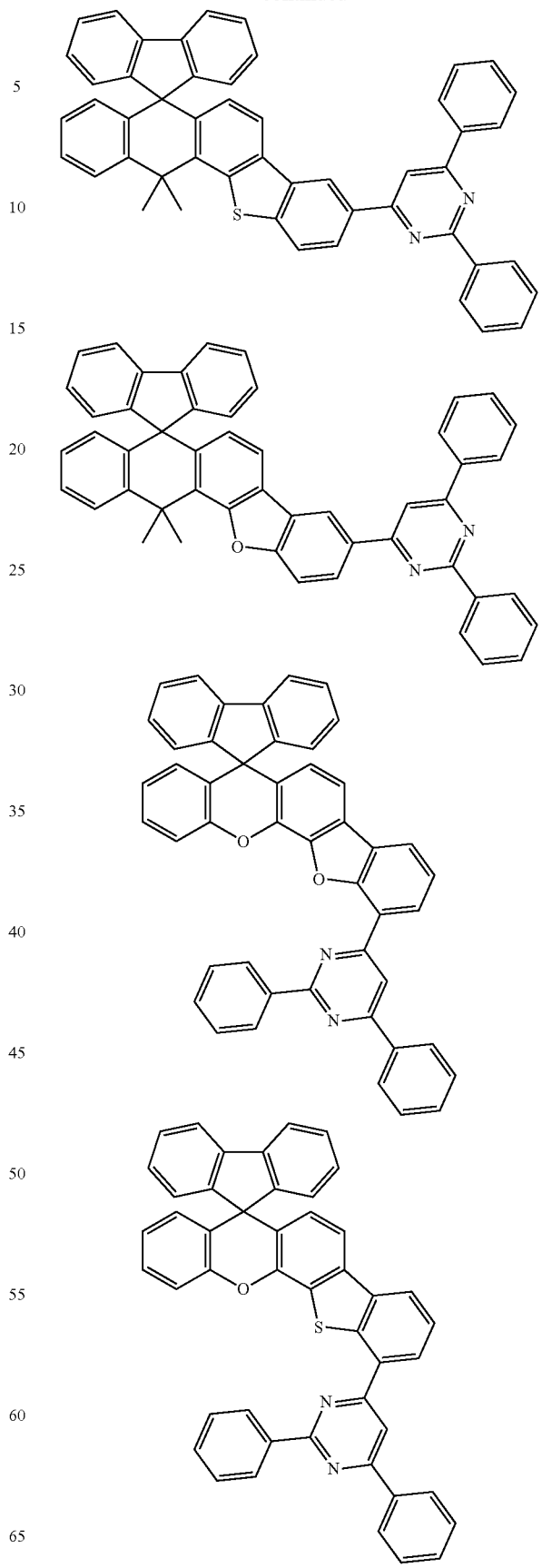

871
-continued
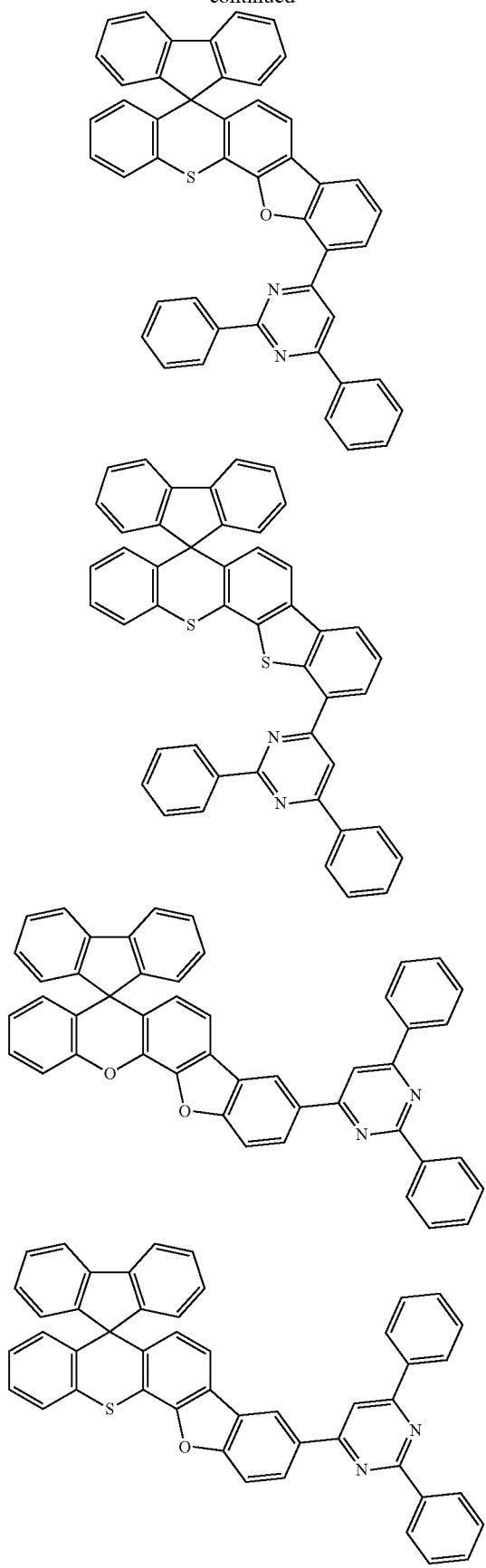
872
-continued
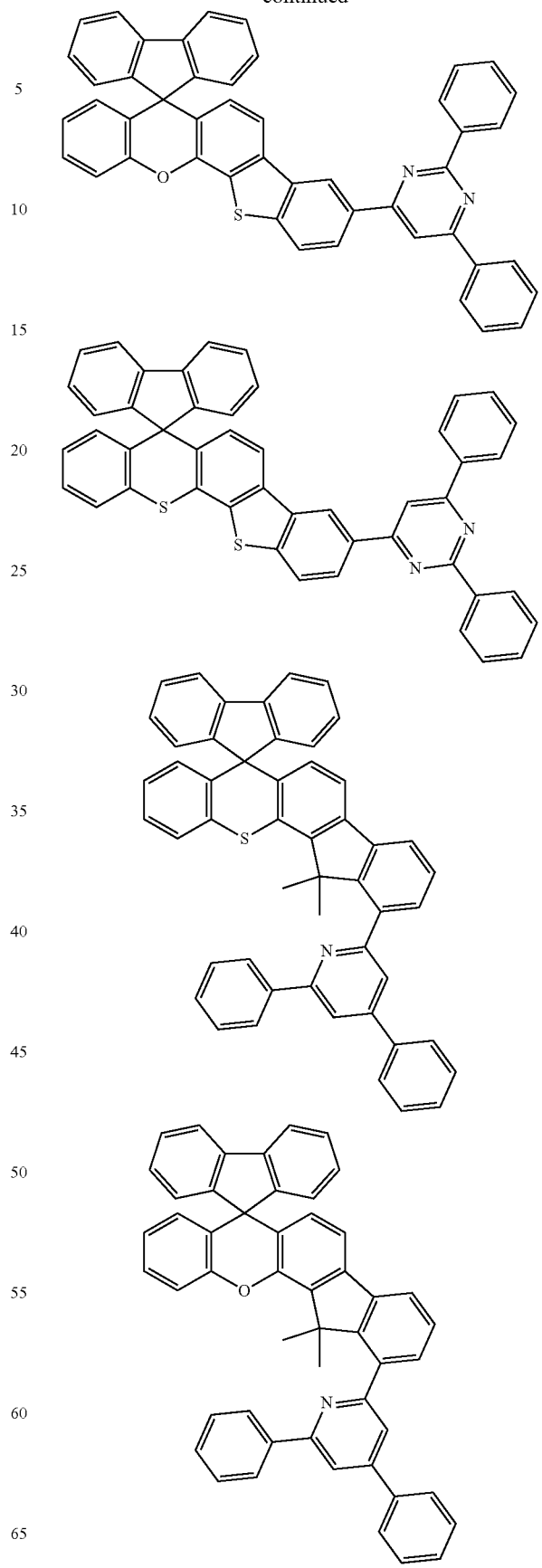

873
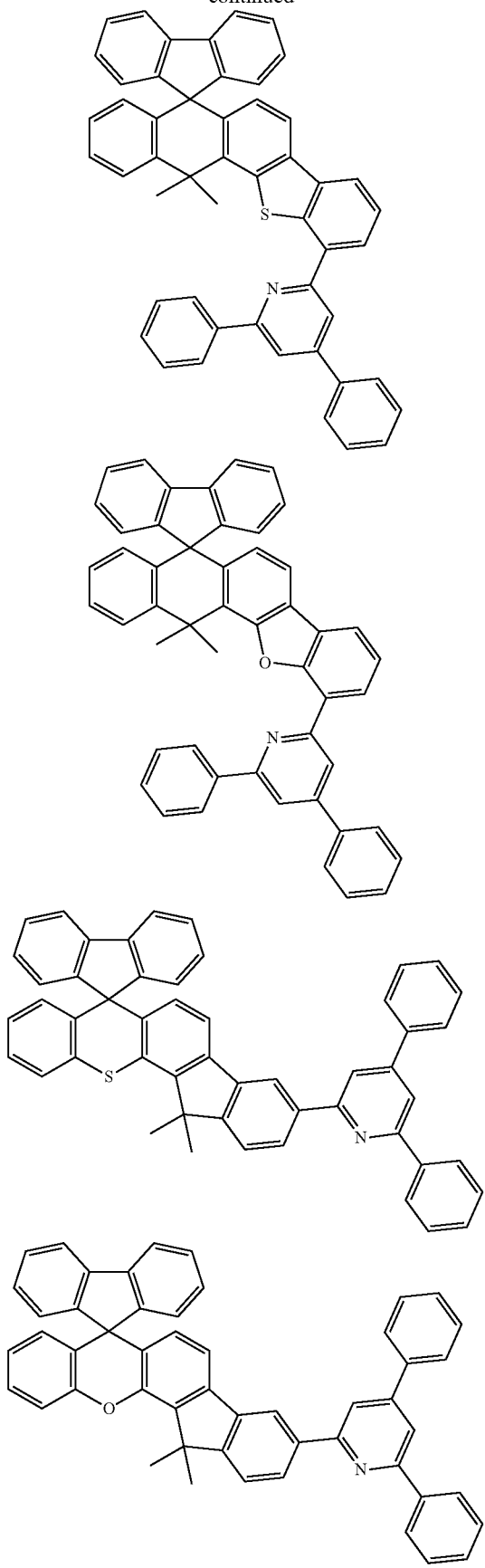
874
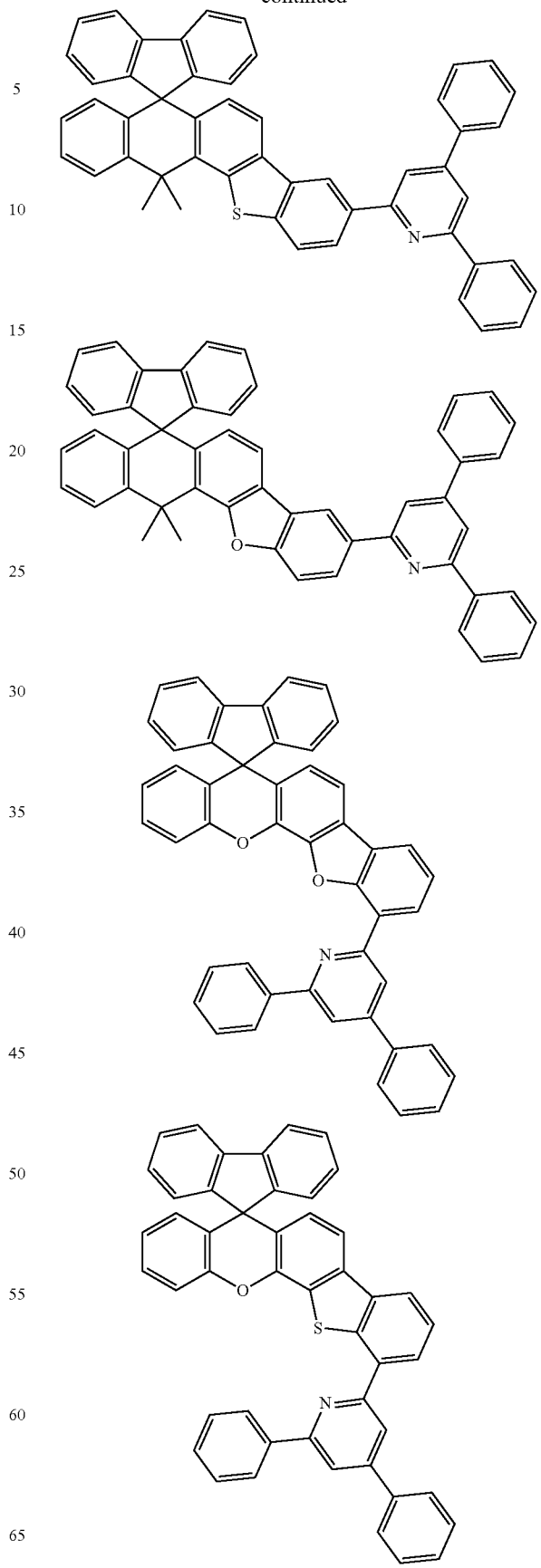

875
-continued
876
-continued
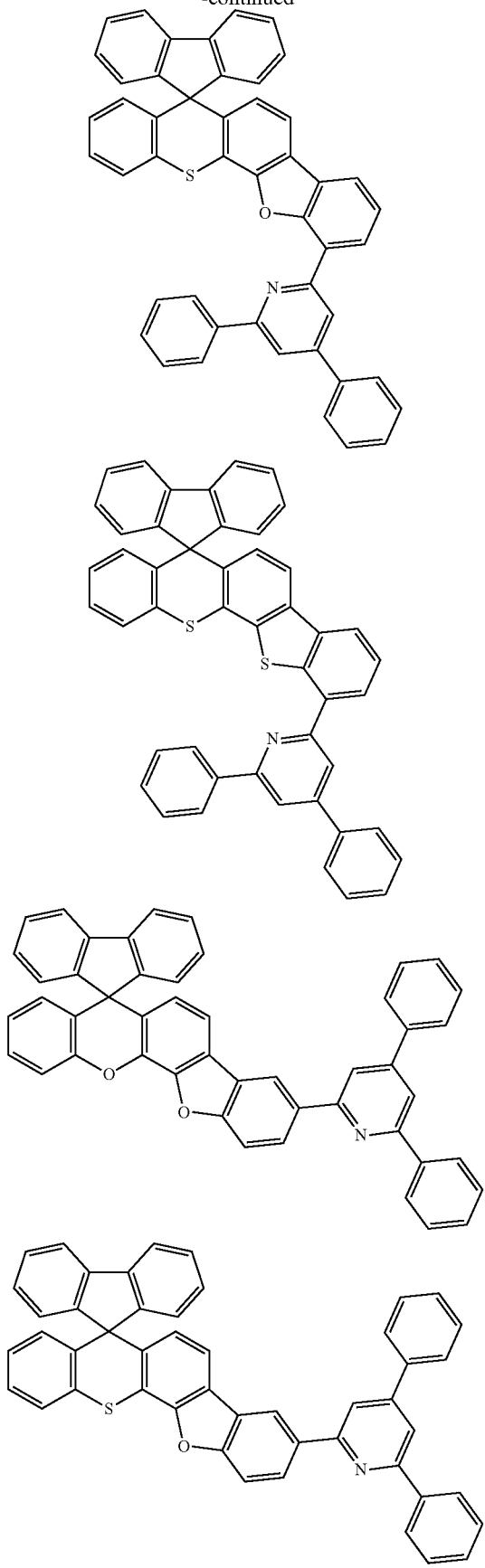
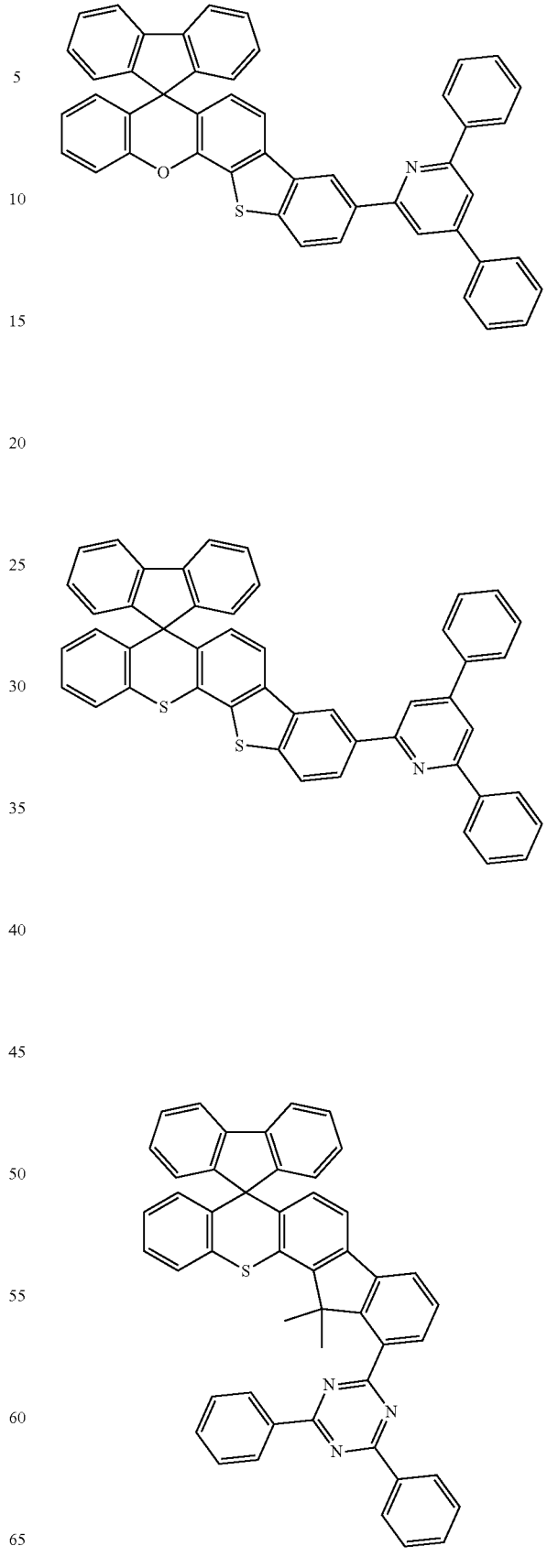

877
-continued
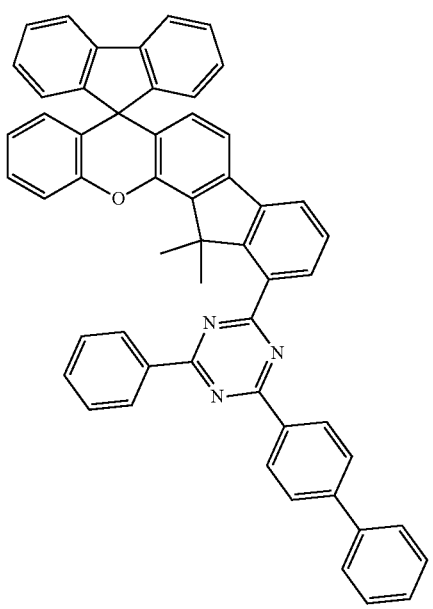 [SMILES: c1ccc(-c2ccc(-c3nc(-c4ccccc4)nc(-c4cccc5c4sc4c6c(ccc45)C4(c5ccccc5S6)c5ccccc5-c5ccccc54)n3)cc2)cc1]
878
-continued
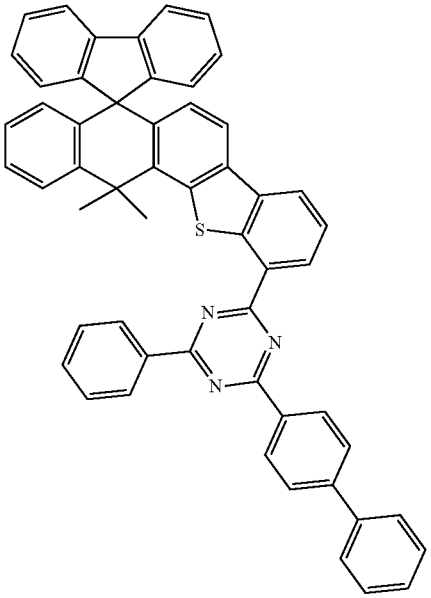
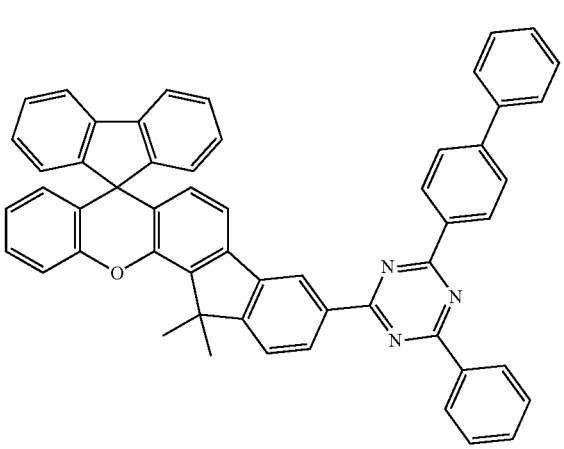
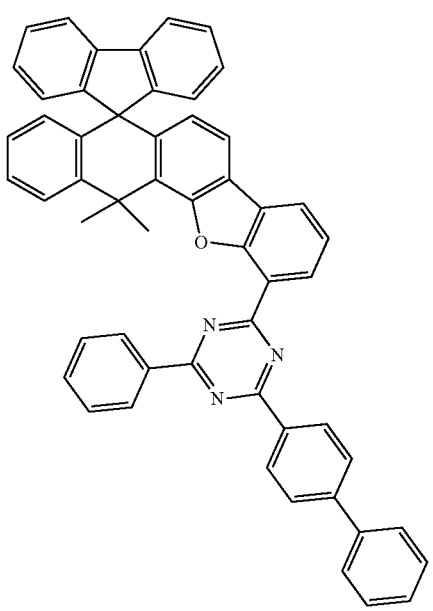

879
-continued
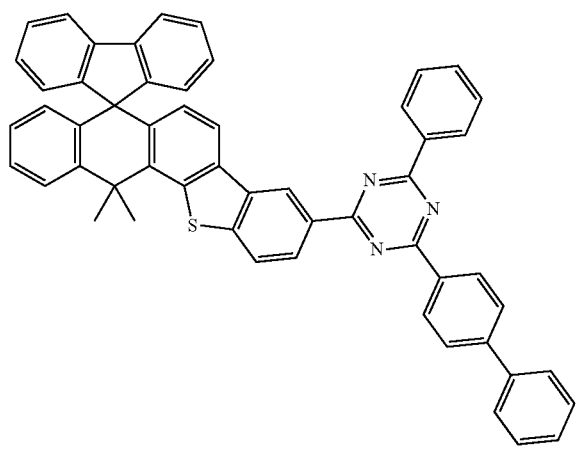 [SMILES: c1ccc(-c2ccc(-c3nc(-c4ccccc4)nc(-c4ccc5oc6c7c(ccc6c5c4)C4(c5ccccc5O7)c5ccccc5-c5ccccc54)n3)cc2)cc1]
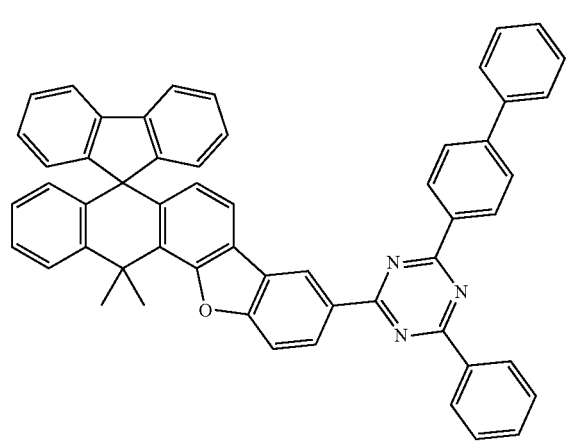
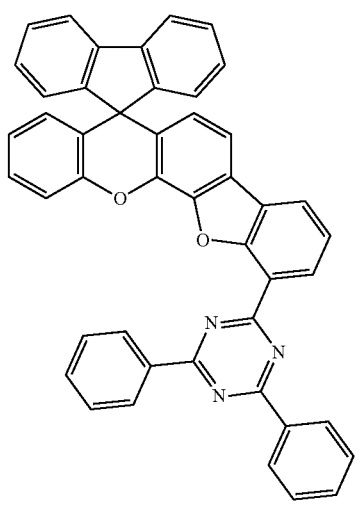
880
-continued
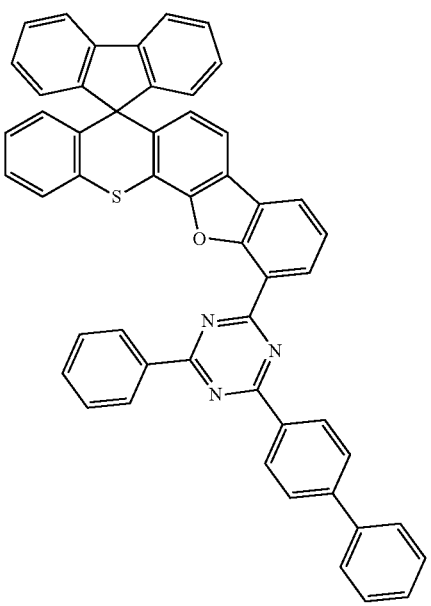
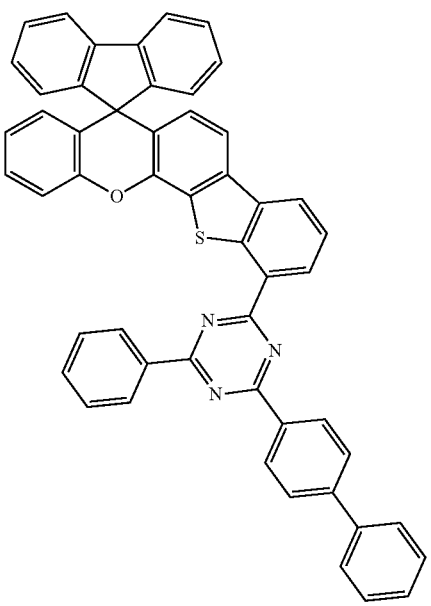

881
-continued

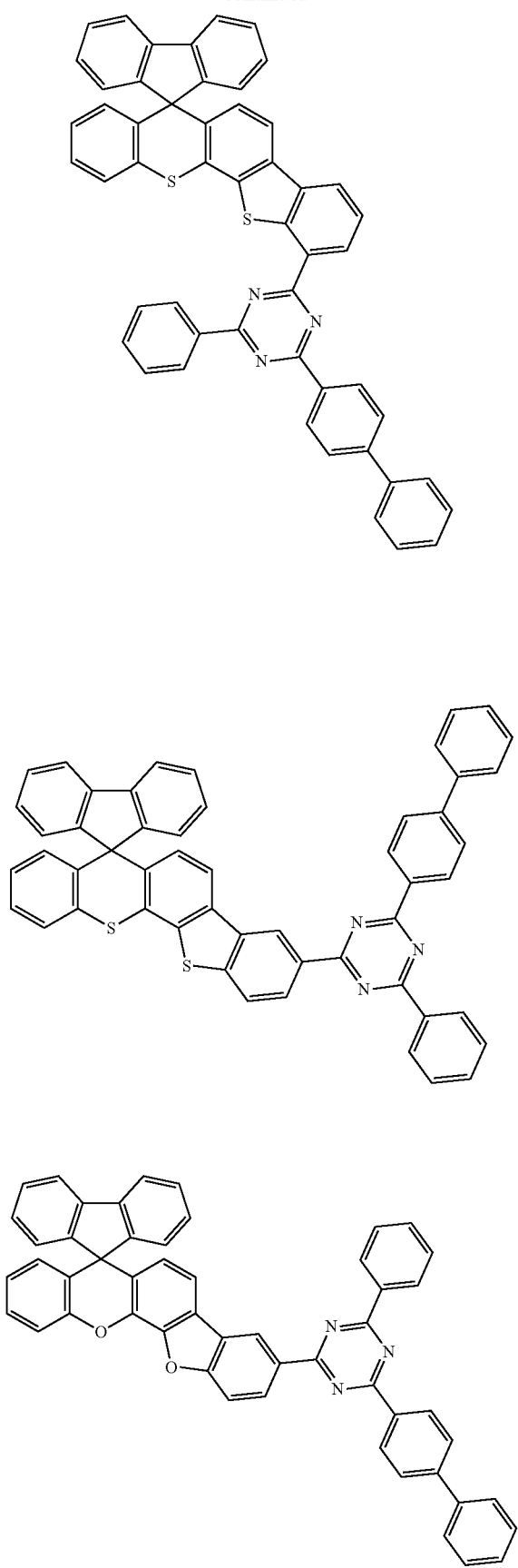

882
-continued

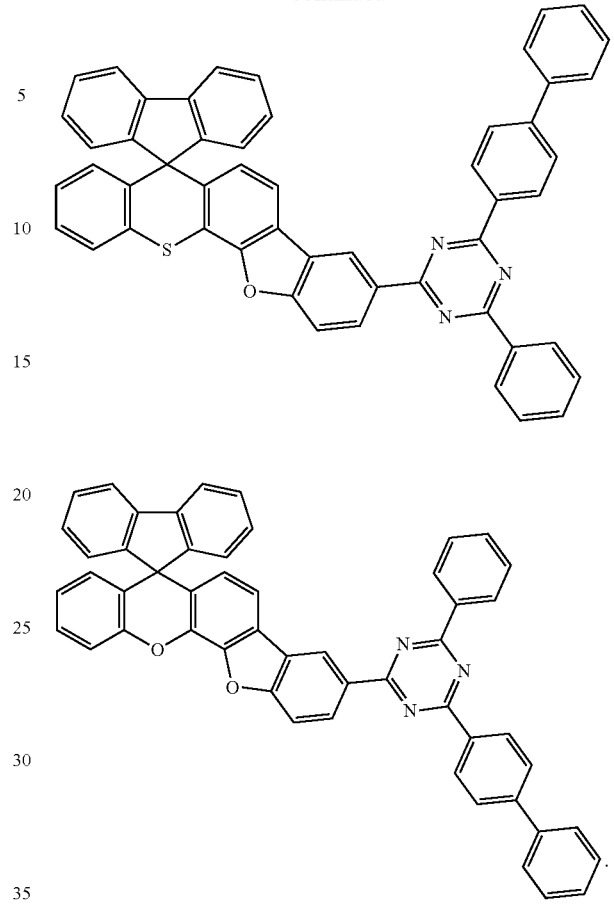

5. An organic electronic device comprising:
a first electrode;
a second electrode disposed to face the first electrode; and
an organic material layer having one or more layers disposed between the first electrode and the second electrode,
wherein the one or more layers of the organic material layer comprise the spiro compound of claim 1.

6. The organic electronic device of claim 5, wherein the organic material layer comprises a light emitting layer, and the light emitting layer comprises the spiro compound.

7. An organic electronic device comprising:
a first electrode;
a second electrode disposed to face the first electrode; and
an organic material layer having one or more layers disposed between the first electrode and the second electrode,
wherein the organic material layer comprises at least one of a hole injection layer, a hole transporting layer, an electron injection layer, an electron transporting layer, an electron blocking layer or a hole blocking layer, and the at least one of the hole injection layer, the hole transporting layer, the electron injection layer, the electron transporting layer, the electron blocking layer or the hole blocking layer comprises a spiro compound represented by the following Chemical Formula 1:

[Chemical Formula 1]

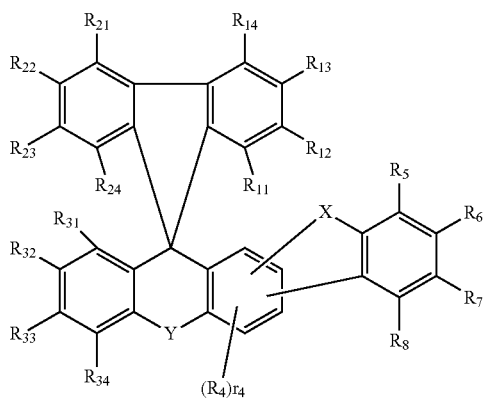

in Chemical Formula 1,
X is $NR_9$, O, S or $CR_{101}R_{102}$,
Y is O, S, $CR_{103}R_{104}$ or $SiR_{105}R_{106}$,
$R_9$ is $-L_1Ar_1$,
$L_1$ is a direct bond; a substituted or unsubstituted arylene group; or a substituted or unsubstituted heteroarylene group,
$R_4$ to $R_8$, $R_{11}$ to $R_{14}$, $R_{21}$ to $R_{24}$, $R_{31}$ to $R_{34}$, $R_{101}$ to $R_{106}$, and $Ar_1$ are the same as or different from each other, and are each independently hydrogen; deuterium; a halogen group; a cyano group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted amine group; a substituted or unsubstituted alkylamine group; a substituted or unsubstituted arylamine group; a substituted or unsubstituted heteroarylamine group; a substituted or unsubstituted phosphine oxide group; a substituted or unsubstituted aryl group; or a substituted or unsubstituted heteroaryl group, or are optionally bonded to an adjacent group to form a ring,
$r_4$ is an integer of 1 or 2, and
when $r_4$ is 2, $R_4$s are the same as or different from each other.

8. The organic electronic device of claim 5, wherein the organic material layer comprises an electron injection layer or an electron transporting layer, and the electron injection layer or the electron transporting layer comprises the spiro compound.

9. The organic electronic device of claim 5, wherein the organic material layer comprises an electron blocking layer or a hole blocking layer, and the electron blocking layer or the hole blocking layer comprises the spiro compound.

10. The organic electronic device of claim 5, wherein the organic electronic device further comprises one or two or more layers selected from the group consisting of a light emitting layer, a hole injection layer, a hole transporting layer, an electron injection layer, an electron transporting layer, an electron blocking layer, and a hole blocking layer.

11. The organic electronic device of claim 5, wherein the organic electronic device is selected from the group consisting of an organic light emitting device, an organic phosphorescent device, an organic solar cell, an organic photoconductor (OPC), and an organic transistor.

12. The organic electronic device of claim 5, wherein the organic material layer comprises a light emitting layer, and the light emitting layer comprises a compound represented by the following Chemical Formula A-1:

[Chemical Formula A-1]

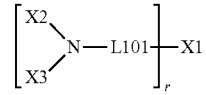

in Chemical Formula A-1,
X1 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L101 is a direct bond; a substituted or unsubstituted arylene group; or a substituted or unsubstituted heteroarylene group,
X2 and X3 are the same as or different from each other, and are each independently a substituted or unsubstituted aryl group; a substituted or unsubstituted silyl group; a substituted or unsubstituted alkyl group; a substituted or unsubstituted aralkyl group; or a substituted or unsubstituted heteroaryl group, or are optionally bonded to each other to form a substituted or unsubstituted ring,
r is an integer of 1 or more, and
when r is 2 or more, substituents in the parenthesis are the same as or different from each other.

13. The organic electronic device of claim 12, wherein L101 is a direct bond, X1 is a substituted or unsubstituted divalent pyrene group, X2 and X3 are the same as or different from each other, and are each independently an aryl group which is unsubstituted or substituted with a germanium group, and r is 2.

14. The organic electronic device of claim 5, wherein the organic material layer comprises a light emitting layer, and the light emitting layer comprises a compound represented by the following Chemical Formula A-2:

[Chemical Formula A-2]

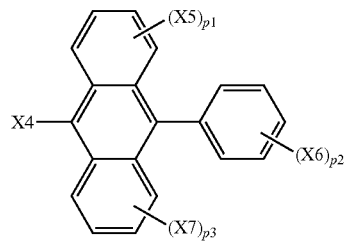

in Chemical Formula A-2,
X4 is a 1-naphthyl group, a 2-naphthyl group, a 1-anthracenyl group, a 2-anthracenyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

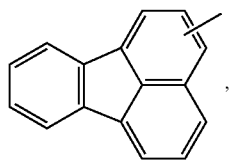
,

X6 is a phenyl group, a 1-naphtyl group, a 2-naphtyl group, a 1-anthracenyl group, a 2-anthracenyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthracenyl group, a 4-methylbiphenylyl group, a 4"-t-butyl-p-terphenyl-4-yl group, or a 3-fluoranthenyl group, X5 and X7 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, p2 is an integer from 1 to 5, p1 and p3 are each an integer from 1 to 4, and when p1 to p3 are each 2 or more, substituents in the parenthesis are the same as or different from each other.

15. The organic electronic device of claim 14, wherein X4 is a 1-naphthyl group, and X6 is a 2-naphthyl group.

16. The organic electronic device of claim 12, wherein the light emitting layer further comprises a compound represented by the following Chemical Formula A-2:

[Chemical Formula A-2]

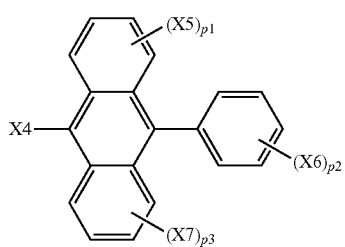

in Chemical Formula A-2,

X4 is a 1-naphthyl group, a 2-naphthyl group, a 1-anthracenyl group, a 2-anthracenyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

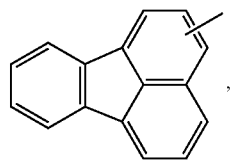
,

X6 is a phenyl group, a 1-naphtyl group, a 2-naphtyl group, a 1-anthracenyl group, a 2-anthracenyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthracenyl group, a 4-methylbiphenylyl group, a 4"-t-butyl-p-terphenyl-4-yl group, or a 3-fluoranthenyl group, X5 and X7 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, p2 is an integer from 1 to 5, p1 and p3 are each an integer from 1 to 4, and when p1 to p3 are each 2 or more, substituents in the parenthesis are the same as or different from each other.

17. The organic electronic device of claim 7, wherein the organic material layer comprises a hole injection layer or a hole transporting layer, and the hole injection layer or the hole transporting layer comprises the spiro compound.

18. The organic electronic device of claim 7, wherein the organic material layer comprises an electron injection layer or an electron transporting layer, and the electron injection layer or the electron transporting layer comprises the spiro compound.

19. The organic electronic device of claim 7, wherein the organic material layer comprises an electron blocking layer or a hole blocking layer, and the electron blocking layer or the hole blocking layer comprises the spiro compound.

* * * * *